US011518764B2

(12) United States Patent
Al-awar et al.

(10) Patent No.: US 11,518,764 B2
(45) Date of Patent: Dec. 6, 2022

(54) SUBSTITUTED HETEROARYLS AS INHIBITORS OF THE BCL6 BTB DOMAIN PROTEIN-PROTEIN INTERACTION

(71) Applicant: Ontario Institute for Cancer Research (OICR), Toronto (CA)

(72) Inventors: Rima Al-awar, Toronto (CA); Methvin Isaac, Brampton (CA); Anh My Chau, Toronto (CA); Ahmed Mamai, Mississauga (CA); Iain Watson, Toronto (CA); Gennady Poda, Toronto (CA); Pandiaraju Subramanian, Oakville (CA); Brian Wilson, Mississauga (CA); David Uehling, Toronto (CA); Michael Prakesch, Toronto (CA); Babu Joseph, Oakville (CA); Justin-Alexander Morin, Toronto (CA)

(73) Assignee: ONTARIO INSTITUTE FOR CANCER RESEARCH (OICR), Toronto (CA)

( * ) Notice: Subject to any disclaimer, the term of this patent is extended or adjusted under 35 U.S.C. 154(b) by 70 days.

(21) Appl. No.: 16/960,924

(22) PCT Filed: Feb. 6, 2019

(86) PCT No.: PCT/CA2019/050154
§ 371 (c)(1),
(2) Date: Jul. 9, 2020

(87) PCT Pub. No.: WO2019/153080
PCT Pub. Date: Aug. 15, 2019

(65) Prior Publication Data
US 2020/0331921 A1    Oct. 22, 2020

Related U.S. Application Data

(60) Provisional application No. 62/626,980, filed on Feb. 6, 2018.

(51) Int. Cl.
| *A61K 31/437* | (2006.01) |
| *A61K 31/519* | (2006.01) |
| *C07D 471/04* | (2006.01) |
| *C07D 487/04* | (2006.01) |
| *C07D 519/00* | (2006.01) |
| *A61K 45/06*  | (2006.01) |

(52) U.S. Cl.
CPC ......... *C07D 487/04* (2013.01); *C07D 471/04* (2013.01); *C07D 519/00* (2013.01); *A61K 45/06* (2013.01)

(58) Field of Classification Search
CPC .. A61K 31/437; A61K 31/519; C07D 487/04; C07D 471/04

USPC ......... 514/262.1, 265.1, 300; 544/262, 280; 546/113
See application file for complete search history.

(56) References Cited

FOREIGN PATENT DOCUMENTS

| WO | 0050013 A1 | 8/2000 | |
| WO | 2019119145 A1 | 6/2019 | |
| WO | WO-2019153080 A1 * | 8/2019 | ............. A61K 45/06 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Wolff, Manfred E., Ed. Burger's Medicinal Chemistry and Drug Discovery—Fifth Edition, vol. 1: Principles and Practice, New York: John Wiley & Sons, 1994, 975-977.*
International Search Report and Written Opinion for corresponding International Patent Application No. PCTCA2019/050154 dated Jun. 11, 2019, 7 pgs.
Kamada et al., "Discovery of a B-Cell Lymphoma 6 Protein-Protein Interaction Inhibitor by a Biophysics-Driven Fragment-Based Approach", J. Med. Chem., 2017, vol. 60, pp. 4358-4368.

(Continued)

*Primary Examiner* — Douglas M Willis
(74) *Attorney, Agent, or Firm* — Bereskin & Parr LLP/S.E.N.C.R.L., s.r.l.; Sandra Marone

(57) ABSTRACT

The present application relates to compounds of Formula I

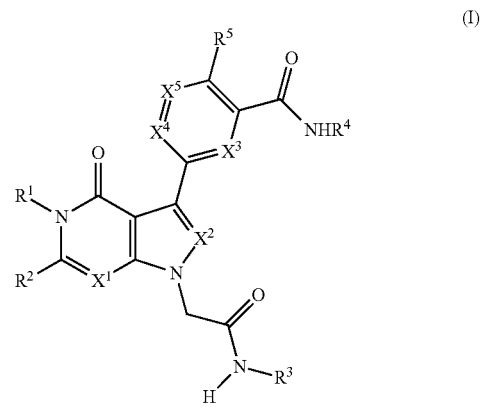

or pharmaceutically acceptable salts, solvates and/or prodrugs thereof, to compositions comprising these compounds or pharmaceutically acceptable salts, solvates and/or prodrugs thereof, and various uses in the treatment of diseases, disorders or conditions that are treatable by inhibiting interactions with BCL6 BTB, such as cancer.

18 Claims, No Drawings
Specification includes a Sequence Listing.

(56) References Cited

OTHER PUBLICATIONS

McCoull et al., "Discovery pf Pyrazolo [1,5-a] pyrimidine B-Cell Lymphoma 6 (BCL6) Binders and Optimization to High Affinity Marcocylic Inhibitors", J. Med. Chem., 2017, vol. 60, pp. 4386-4402.
Kerres et al., "Chemically Induced Degradation of the Oncogenic Transcription Factor BCL6", Cell Reports, Sep. 19, 2017, vol. 20, pp. 2860-2875.
Extended European Search Report of corresponding European Patent Application No. 19751282.5 dated Jun. 14, 2021, 8 pages.
Polo et al. "Specific peptide interference reveals BCL6 transcriptional and oncogenic mechanisms in B-cell lymphoma cells", Nat Med, 2004. 10(12): 1329-35.
Duy et al. "BCL6 enables Ph acute lymphoblastic leukemia cells to survive BCR-ABL1 kinase inhibition" Nature, 2011, 473(7347):384-8.

\* cited by examiner

SEQUENCE LISTING

<160> NUMBER OF SEQ ID NOS: 1

<210> SEQ ID NO 1
<211> LENGTH: 19
<212> TYPE: PRT
<213> ORGANISM: Artificial Sequence
<220> FEATURE:
<223> OTHER INFORMATION: Synthetic construct

<400> SEQUENCE: 1

```
Gly Ser Leu Val Ala Thr Val Lys Glu Ala Gly Arg Ser Ile His Glu
1               5                   10                  15
Ile Pro Ala
```

SUBSTITUTED HETEROARYLS AS INHIBITORS OF THE BCL6 BTB DOMAIN PROTEIN-PROTEIN INTERACTION

CROSS-REFERENCE TO RELATED APPLICATIONS

This application is a National Stage of co-pending International Application No. PCT/CA2019/050154 filed on Feb. 6, 2019 which claims the benefit of priority from U.S. Provisional Patent Application Ser. No. 62/626,980 filed on Feb. 6, 2018, the contents of both of which are incorporated herein by reference in their entirety.

INCORPORATION OF SEQUENCE LISTING

A computer readable form of the Sequence Listing "25308-P54823US01_SequenceListing.txt" (4,096 bytes), submitted via EFS-WEB and created on Oct. 1, 2020, is herein incorporated by reference.

FIELD

The present application relates to compounds, to processes for their preparation, to compositions comprising them, and to their use in therapy. More particularly, it relates to compounds useful in the treatment of diseases, disorders or conditions treatable by inhibiting or blocking the interaction of BCL6 BTB domain with its binding partners.

BACKGROUND

BCL6 (B Cell Lymphoma 6) is a member of the BTB/POZ (bric-á-brac, tramtrack, broad complex/pox virus zinc finger) family of transcription factors. The BCL6 gene was initially cloned by several groups in 1993 from a translocation occurring on chromosome 3q27 in diffuse large B-cell lymphoma (DLBCL) [*Histol Histopathol* 2004, 19:637-650]. Targeted disruption of the BCL6 gene revealed that BCL6 during normal B-cell development is a master regulator of antibody affinity maturation in germinal centers (GCs) [*Nat Rev Immunol* 2008, 8:22-33]. BCL6 is almost universally expressed in GC-derived B-cell lymphomas, including diffuse large B-cell lymphoma (DLBCL) and follicular lymphomas (FLs), regardless of translocations.

In normal lymphoid biology, BCL6 is required for naïve B cells to form GCs which are cellular compartments dedicated to the affinity maturation of antibodies. The GC is the site of two key molecular processes unique to B-cells: somatic hypermutation (SHM) and class switching recombination (CSR) [*Trends Biochem Sci* 2003, 28: 305-312]. Upon antigen-induced B-cell activation, B-cells proliferate and differentiate into either centroblasts or plasma cells [*Annu Rev Immunol* 1994 12: 117-139]. The centroblasts go through the dark zone of the GC where they rapidly proliferate, differentiate and revise their antigen receptors via SHM and CSR [*Cell* 1991 67: 1121-9; *Nature* 1991 354: 389-92; *Cell* 1981 27: 573-581]. SHM modulates the affinity of the antibodies to a specific antigen and, while not wishing to be limited by theory, it is believed that the mistargeting of SHM can result in the translocation of oncogenes.

BCL6 is a transcriptional repressor that reduces mRNA expression of its target genes by regulating survival and differentiation via distinct corepressor complexes [*Proc Natl Acad Sci USA,* 2007. 104(9): 3207-12; *Blood* 2007. 110(6): 2067-74; *Biochem Biophys Res Commun,* 2003. 300(2): 391-6]. BCL6 has six zinc fingers at its carboxyl terminus mediating sequence-specific DNA binding to regulatory sequences [*Nat Immunol,* 2007. 8(7): p. 705-14]. BCL6 binds to DNA as a homo-dimer and recruits, through its N-terminal domain, class I and II histone deacetylase complexes (HDACs) either directly or through corepressor molecules such as SMRT, NCOR1 and BCOR.

Different subsets of target genes appear to be repressed depending on which corepressors are engaged by BCL6 through the BTB domain [*Blood* 2007. 110(6): 2067-74]. The corepressors that bind to the BTB appear to be involved in the regulation of transcription associated with early stages of the GC process. Genome-wide studies indicate that BCL6 may, for example, target as many as 500 genes [*Blood* 2007. 110(6): 2067-74] mainly involved in cell cycle, gene transcription, DNA damage sensing, protein ubiquitylation and chromatin structure modification.

Direct BCL6 repressed target genes include ataxia telangectasia and Rad3 related (ATR), CHK1 checkpoint homolog (*S. pombe*) (CHEK1), tumor protein p53 (TP53) and cyclin dependent kinase inhibitor 1A or p21 (CDKN1A) [*Nat Immunol,* 2007. 8(7): 705-14]. These genes belong to survival pathways involved in DNA damage sensing and checkpoint activation. They are primarily regulated through the SMRT and NCOR corepressors. Both of these corepressors contain a highly conserved 17-residue BCL6 binding domain (BBD) that interacts with the homodimeric BTB domain [*Mol Cell,* 2003. 12(6): 11561-64] forming a promoter-localized protein complex. This complex represses the transcription of target genes such as ATR, TP53 and CDKN1A which in turn attenuates the DNA damage response and promote cell survival.

In addition to its role in survival, BCL6 also regulates differentiation through a specific BCL6 corepressor complex that represses B-lymphocyte-induced maturation protein1 or PRDM1 (BLIMP1), a transcription factor that promotes plasmacytic differentiation [*Cell,* 2004. 119(1): 75-86]. Maturation of GC B cells toward memory B-cells and plasma cells usually requires the down-regulation of BCL6. Such down-regulation of BCL6 function can occur via antigen-induced B cell receptor (BCR) mediated activation that subsequently leads to rapid BCL6 proteasomal degradation [*Genes Dev,* 1998. 12(13): 1953-61]. Alternatively, T-cell-mediated stimulation through the CD40 pathway leads to NF-κB driven induction of interferon regulatory factor 4 (IRF4), a regulator of plasma-cell development [*Science,* 1997. 275(5299): 540-3]. IRF4 leads to the transcriptional repression of BCL6 and to the transactivation of BLIMP1, which drives the regulatory program associated with plasmacytic differentiation and immunoglobulin (Ig) secretion [*Cell.* 1994; 77:297-306].

BCL6 has also been shown to play a role in the regulation of genes involved in the B-T cell interaction by regulating the expression levels of CD80 and CD274 (alias B7-H1, PDL1) [*J Exp Med.* 2003,198(2):211-2; *Proc Natl Acad Sci USA.* 2009,106(27):11294-9]. CD80 is expressed on B cells, and its interaction with CD28 is involved in T-cell activation, GC formation, and immunoglobulin class switching [*J Immunol.* 1997, 159(11):5336-44]. The B-T cell interaction is a step toward successful B-cell activation. Another gene for B-cell activation that is regulated by BCL6 is CD69. CD69 (a type II transmembrane glycoprotein) is an early activation marker in lymphocytes and is also a signal transmitter in inflammatory processes [*Life Sci.* 2012, 90(17-18):657-65]. The global BCL6-mediated repression of target genes such as CD69 and CD80 prevent premature activation of B cells during proliferative expansion. A number of other signaling pathways are modulated by BCL6 transcriptional repression. These include multiple interferon-types (e.g. interferon regulatory factor 7 or IRF7) and interleukin receptors as well as STAT (signal transducers and activators of transcription) family members including STAT1, STAT2 and STAT3 [*Adv Immunol.* 2010; 105:193-210; *Blood.* 2010, 115(5):975-84; *Blood* 2008, 111(3):1515-23]. Toll-like-receptor (TLR) signaling is also modulated by BCL6 via regulation of receptor expression (e.g. TLR7) as well as transduction of Toll-derived signals. The TLR pathway has also been shown to play a major role in the development and differentiation of memory B cells [Nature. 2005, 438(7066): 364-8; Adv Exp Med Biol. 2005; 560:11-8; J Exp Med. 2007, 204(13):3095-101].

Role of BCL6 in Cancers

The mechanisms that mediate the remodeling of antigen receptors in the GCs involve potentially mutagenic DNA double-strand breaks and suppression of the apoptotic machinery by BCL6. Failure to reactivate apoptosis upon exit from the GC has been established as a mechanism involved in lymphomagenesis, and has been specifically linked to diffuse large B cell lymphoma (DLBCL); an aggressive GC-derived malignancy that accounts for approximately 35% of all non-Hodgkin lymphoma (NHL) cases.

DLBCL is a heterogeneous disease with two major subtypes: the GC B cell-like (GCB) subtype characterized by an expression signature similar to normal GC B cells, and the activated B cell-like (ABC) subtype with gene expression pattern like in vitro BCR stimulation, which has a poorer prognosis [*Nature.* 2000. 403(6769): 503-11]. The most common genetic alterations in DLBCL affect the BCL6 promoter region and involve mutations in the 5' noncoding region and chromosomal translocations. Further experimental evidence that overexpression is sufficient for lymphomagenesis was provided by the production of transgenic mice in which BCL6 was driven by the immunoglobulin heavy chain (IgH) Iμ promoter [*Cancer. Cell.* 2005. 7(5): 445-55]. These mice developed a disease histologically similar to human DLBCL.

Gene rearrangements at 3q27 have been reported in 30-40% of DLBCL with a higher percentage being observed in the ABC subtype [*Oncogene.* 2001. 20(40): 5580-94]. These translocations place an intact BCL6 coding domain under the influence of heterologous promoter regions derived from a variety of alternative partner chromosomes (>20) including the immunoglobulin heavy and light chain genes resulting in deregulated expression of the normal BCL6 protein [*EMBO J.* 1995. 14(24): 6209-17]. In addition, while not wishing to be limited by theory, BCL6 may contribute to lymphomagenesis when its downregulation, which usually occurs after affinity maturation, is disrupted. One proposed mechanism for BCL6 downregulation disruption is the loss of IRF4 binding sites in the BCL6 gene. IRF4 expression is induced by sustained CD40 stimulation of the NF-κB pathway in germinal center cells. IRF4 usually binds to exon 1 and intron 1 of the BCL6 gene and represses BCL6 expression, but chromosome translocations or point mutations introduced during SHM (which commonly target the 5' non-coding promoter region of BCL6) may prevent this repressive effect [*Cancer. Cell.* 2007. 12(3): 280-92]. BCL6 promoter binding and gene repression has also been shown to vary between normal and malignant cells. BCL6 dependency has no correlation to the cell of origin (COO) classification system as dependency occurs in both ABC and GCB cell lines.

Studies have integrated genomic analysis and functional screens to provide a rationale for targeted therapies within defined populations of BCL6 driven DLBCL. Personalizing treatments by identifying patients with oncogenic dependencies via genotyping and specifically targeting the responsible drivers such as BCL6 may be useful for the treatment of DLBCL [*Clin. Cancer. Res,* 2012. 18(17): 4538-48].

Overexpression of BCL6 has been identified as a resistance mechanism arising during the targeted treatment of BCR-ABL1-positive leukemia and suggests a potential therapeutic opportunity to overcome this resistance. The BCR-ABL1 fusion gene is found in nearly all chronic myeloid leukemia (CMLs) and in about 25% of ALLs; the resulting oncogenic protein can be targeted by tyrosine kinase inhibitors (TKIs) such as imatinib, but the acute cellular response reveals protective feedback signaling leading to resistance. BCL6 expression appears to directly influence the response to imatinib as the authors found that modulation of BCL6 levels had the expected effects on the sensitivity of ALL cells to imatinib. A small molecule BCL6 BTB inhibitor may have utility in, for example, TKI-resistant Ph+ ALL patients, since TKI-resistance develops in most cases of Ph+ ALL [*Nature,* 2011. 473(7343): 384-388].

CML is induced by the oncogenic BCR-ABL1 tyrosine kinase and can be treated with TKIs. However, if CML patients do not receive life-long TKI treatment, leukemia will eventually recur. Such recurrence can be attributed to the failure of TKI treatment to eradicate leukemia-initiating cells (LICs). Recent studies demonstrated that forkhead box O (FoxO) transcription factors are critical for maintenance of CML-initiating cells. The BCL6 protooncogene was identified as a downstream effector of FoxO in self-renewal signaling of CML-initiating cells. BCL6 represses Arf and p53 in CML cells and is involved in colony formation and initiation of leukemia [*Curr Opin Immunol,* 2011. 13(2): 134-40]. Inhibition of BCL6 in human CML cells compromises colony formation and leukemia initiation in transplant recipients and selectively eradicates $CD34^+CD38^-$ LICs in patient-derived CML samples. Pharmacological inhibition of BCL6 may therefore eradicate LICs in CML, potentially limiting the duration of TKI treatment in CML patients, and substantially decrease the risk of blast crisis transformation.

X-ray crystallographic studies have shown that the BCL6 BTB domain forms a tight homodimer, and in solution the BCL6 BTB domain also appears to exist exclusively as a dimer, exhibiting a very low dissociation constant [*Mol Cell,* 2003. 12(6): 1551-64]. The BCL6 BTB domain interacts in a mutually exclusive manner with three corepressors: SMRT, NCOR1 and BCOR. Mutations that change the surface of the BCL6 lateral groove (without affecting the overall structure of the domain) no longer bind to the corepressor BBDs, and these mutations abrogate BCL6 BTB domain repressor activity. The above structural features suggest that the BCL6 BTB domain is druggable. Hence, agents that bind to the BCL6 BTB domain and compete for corepressor binding can reverse the repression activities of BCL6. Selective targeting of the BCL6 BTB domain could minimize toxicity compared to complete abrogation of BCL6 function. However, the length and complexity of the interface between the BBD and the BCL6 BTB binding groove are potential barriers toward developing effective small molecule inhibitors. Molecules such as BBD peptides, which contain many polar and charged amino acids, interact with an extended surface of the BCL6 BTB dimer, mostly through hydrogen bonds and multiple van der Waals contacts. Molecules large enough to fully occupy the lateral groove would be unlikely to readily penetrate cells as demonstrated by the peptide BPI, which has potency in the micromolar range and a short half-life in vivo [*Nat Med,*

2004. 10(12): 1329-35]. Several published articles reported the identification of chemical ligands for the BTB domain of BCL6, for example *J. Med. Chem.* 2017, 60, 4358-4368, *J. Med. Chem.* 2017, 60, 4386-4402 and *Cell Reports* 2017, 20, 2860-2875.

Considering the challenges generally associated with targeting protein-protein interactions, and the current need that exists to treat BCL6 dependent tumor types such as DLBCL, complementary approaches, namely virtual screening, traditional library screening and focused structure activity relationship studies, were used to identify compounds of the application which inhibit or block the interaction of the BCL6 BTB domain with its binding partners, such as the SMRT, NCOR2 and BCOR corepressors.

SUMMARY

The present application includes a compound of Formula I, or a pharmaceutically acceptable salt, solvate and/or prodrug thereof:

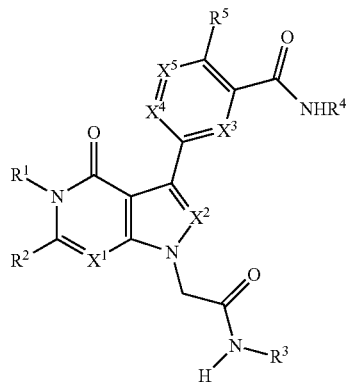

(I)

wherein
$X^1$, $X^2$ and $X^3$ are independently selected from $CR^6$ and N, $X^4$ is selected from $CR^7$ and N;
$X^5$ is selected from $CR^8$ and N;
$R^1$ is selected from H, $C_{1-6}$alkyl, $C_{1-6}$alkyleneOC$_{1-6}$alkyl, $C_{1-6}$alkyleneC$_{3-6}$cycloalkyl, $C_{1-6}$alkyleneC$_{3-6}$heterocycloalkyl, $C_{1-6}$alkyleneC$_{5-6}$heteroaryl, $C_{1-6}$alkylenephenyl, $C_{1-6}$alkyleneC(O)C$_{3-6}$cycloalkyl, $C_{1-6}$alkyleneC(O)C$_{3-6}$heterocycloalkyl, $C_{1-6}$alkyleneC(O)C$_{5-6}$heteroaryl, $C_{1-6}$alkyleneC(O)phenyl, $C_{2-6}$alkynyleneOC$_{1-6}$alkyl, $C_{2-6}$alkynyleneC$_{3-6}$cycloalkyl, $C_{2-6}$alkynyleneC$_{3-6}$heterocycloalkyl, $C_{2-6}$alkynyleneC$_{5-6}$heteroaryl, $C_{2-6}$alkynylenephenyl, $C_{2-6}$alkenyleneOC$_{1-6}$alkyl, $C_{2-6}$alkenyleneC$_{3-6}$cycloalkyl, $C_{2-6}$alkenyleneC$_{3-6}$heterocycloalkyl, $C_{2-6}$alkenyleneC$_{5-6}$heteroaryl and $C_{2-6}$alkenylenephenyl, and each cycloalkyl, heterocycloalkyl, heteroaryl and phenyl are optionally substituted with one to three substituents independently selected from halo and $C_{1-4}$alkyl;
$R^2$ is selected from H, $C_{1-6}$alkyl, OH, SH, $NH_2$, $NHC_{1-6}$alkyl, $N(C_{1-6}$alkyl)($C_{1-6}$alkyl), $OC_{1-6}$alkyl, halo, $Z^1C_{3-6}$cycloalkyl, $Z^1C_{3-6}$heterocycloalkyl, $Z^1C_{5-6}$heteroaryl, $Z^1$phenyl, $Z^1C_{1-6}$alkyleneOC$_{1-6}$alkyl, $Z^1C_{1-6}$alkyleneC$_{3-6}$cycloalkyl, $Z^1C_{1-6}$alkyleneC$_{3-6}$heterocycloalkyl, $Z^1C_{1-6}$alkyleneC$_{5-6}$heteroaryl, $Z^1C_{1-6}$alkylenephenyl, $Z^1C_{2-6}$alkynyleneOC$_{1-6}$alkyl, $Z^1C_{2-6}$alkynyleneC$_{3-6}$cycloalkyl, $Z^1C_{2-6}$alkynyleneC$_{3-6}$heterocycloalkyl, $Z^1C_{2-6}$alkynyleneC$_{5-6}$heteroaryl, $Z^1C_{2-6}$alkynylenephenyl, $Z^1C_{2-6}$alkenyleneOC$_{1-6}$alkyl, $Z^1C_{2-6}$alkenyleneC$_{3-6}$cycloalkyl, $Z^1C_{2-6}$alkenyleneC$_{3-6}$heterocycloalkyl, $Z^1C_{2-6}$alkenyleneC$_{5-6}$heteroaryl and $Z^1C_{2-6}$alkenylenephenyl, and each cycloalkyl, heterocycloalkyl, heteroaryl and phenyl is optionally substituted with one to three substituents independently selected from halo, OH, SH, $NH_2$, $NHC_{1-6}$alkyl and $N(C_{1-6}$alkyl)($C_{1-6}$alkyl); $Z^1$ is selected from a direct bond, O, NH, $NC_{1-6}$alkyl, S(O) and $SO_2$;
$R^3$ is selected from $C_{6-10}$aryl, $C_{6-10}$heteroaryl, $C_{6-10}$cycloalkyl and $C_{6-10}$heterocycloalkyl, each of which is optionally substituted with one to four substituents independently selected from halo, =O, $C_{1-6}$alkyl, CN, $NO_2$, $C_{2-6}$alkenyl, $C_{2-6}$alkynyl and $OC_{1-6}$alkyl and optionally substituted with one substituent selected from $Z^2R^9$;
$Z^2$ is selected from a direct bond, $C_{1-6}$alkylene, C(O), O, S, S(O) and $SO_2$;
$R^4$ is selected from H and $C_{1-6}$alkyl;
$R^5$ is OH;
$R^6$ is selected from H and halo;
$R^7$ and $R^8$ are independently selected from H, halo, $C_{1-6}$alkyl, $OC_{1-6}$alkyl, and $SO_2NH_2$, or
$R^7$ and $R^8$ are linked to form, together with the carbon atoms to which they are attached, a 3-8-membered heterocycloalkyl or heteroaromatic ring, both of which contain one to two additional heteroatoms selected from O, S, S(O), $SO_2$, NH and $NC_{1-6}$alkyl;
$R^9$ is selected from $C_{1-6}$alkyl, $NR^{10}R^{11}$, $C_{3-10}$cycloalkyl, $C_{3-10}$heterocycloalkyl, $C_{5-10}$heteroaryl and $C_{6-10}$aryl, the latter 4 groups being optionally substituted with one to six substituents independently selected from halo, CN, $C_{1-6}$alkyl and $OC_{1-6}$alkyl, and optionally substituted with one substituent selected from $C_{1-6}$alkyleneOC$_{1-6}$alkyl, $C_{1-6}$alkyleneOH, $C_{1-6}$alkylene(diOH), $SO_2C_{1-4}$alkyl, $Z^3C_{3-10}$cycloalkyl, $Z^3C_{3-10}$heterocycloalkyl, $Z^3C_{5-10}$heteroaryl and $Z^3C_{6-10}$aryl the latter four groups being optionally substituted with one to four substituents independently selected from halo and $C_{1-6}$alkyl;
$R^{10}$ and $R^{11}$ are independently selected from H, $C_{1-6}$alkyl, $C_{1-6}$alkyleneOH, $C_{1-6}$alkylene(diOH), $C_{1-6}$alkyleneOC$_{1-6}$alkyl, $SO_2C_{1-6}$alkyl, $Z^4C_{3-10}$cycloalkyl, $Z^4C_{3-10}$heterocycloalkyl, $Z^4C_{5-10}$heteroaryl and $Z^4C_{6-10}$aryl, the latter four groups being optionally substituted with one to six substituents independently selected from halo and $C_{1-6}$alkyl,
$Z^3$ and $Z^4$ are independently selected from a direct bond and $C_{1-6}$alkylene; and
all alkyl and alkylene groups are optionally fluoro-substituted and all available hydrogens are optionally replaced with deuterium.

The present application also includes a composition comprising one or more compounds of the application and a carrier. In an embodiment, the composition is a pharmaceutical composition comprising one or more compounds of the application and a pharmaceutically acceptable carrier.

The compounds of the application have been shown to have the potential to inhibit or block BCL6 BTB protein-protein interaction with its binding partners, in particular SMRT/NCOR and BCOR. Therefore the compounds of the application are useful for treating diseases, disorders or conditions that are treatable by inhibiting interactions with BCL6 BTB. Accordingly, the present application also includes a method of treating a disease, disorder or condition that is treatable by inhibiting interactions with BCL6 BTB, comprising administering a therapeutically effective amount of one or more compounds or compositions of the application to a subject in need thereof.

In some embodiments, the compounds of the application are used as medicaments. Accordingly, the application also includes one or more compounds of the application for use as a medicament.

The present application also includes a use of one or more compounds or compositions of the application for treatment of a disease, disorder or condition that is treatable by inhibiting interactions with BCL6 BTB as well as a use of one or more compounds or compositions of the application for the preparation of a medicament for treatment of a disease, disorder or condition that is treatable by inhibiting interactions with BCL6 BTB. The application further includes one or more compounds or compositions of the application for use in treating a disease, disorder or condition that is treatable by inhibiting interactions with BCL6 BTB.

In some embodiments, the disease, disorder or condition that is treatable by inhibiting interactions with BCL6 BTB, is a neoplastic disorder. In an embodiment, the treatment comprises administration or use of an amount of one or compounds or compositions of the application that is effective to ameliorate at least one symptom of the neoplastic disorder, for example, reduced cell proliferation or reduced tumor mass in a subject in need of such treatment.

In some embodiments, the disease, disorder or condition that is treatable by inhibiting interactions with BCL6 BTB, is cancer. In some embodiments, the cancer is selected from hematologic cancer, breast cancers, ovarian cancers and glioblastomas. In some embodiments the cancer is a B-cell lymphoma, such as diffuse large B-cell lymphoma (DLBCL) or follicular lymphomas.

In an embodiment, the disease, disorder or condition that is treatable by inhibiting interactions with BCL6 BTB, is a disease, disorder or condition associated with an uncontrolled and/or abnormal cellular activity affected directly or indirectly by the interaction of protein binding partners with the BCL6 BTB binding domain. In another embodiment, the uncontrolled and/or abnormal cellular activity that is affected directly or indirectly by the interaction of protein binding partners with the BCL6 BTB binding domain is proliferative activity in a cell.

The application also includes a method of inhibiting proliferative activity in a cell, comprising administering an effective amount of one or more compounds or compositions of the application to the cell.

In a further embodiment the disease, disorder or condition that is treatable by inhibiting interactions with BCL6 BTB, is cancer and the one or more compounds or compositions of the application are administered in combination with one or more additional cancer treatments. In another embodiment, the additional cancer treatment is selected from radiotherapy, chemotherapy, targeted therapies such as antibody therapies and small molecule therapies such as tyrosine-kinase inhibitors therapies, immunotherapy, hormonal therapy and anti-angiogenic therapies.

The application additionally provides a process for the preparation of compounds of the application. General and specific processes are discussed in more detail and set forth in the Examples below.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DETAILED DESCRIPTION

I. Definitions

Unless otherwise indicated, the definitions and embodiments described in this and other sections are intended to be applicable to all embodiments and aspects of the present application herein described for which they are suitable as would be understood by a person skilled in the art.

The present application refers to a number of chemical terms and abbreviations used by those skilled in the art. Nevertheless, definitions of selected terms are provided for clarity and consistency.

As used herein, the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process/method steps.

As used herein, the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "a compound" should be understood to present certain aspects with one compound or two or more additional compounds. In embodiments comprising an "additional" or "second" component, such as an additional or second compound, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

Unless otherwise indicated, the definitions and embodiments described in this and other sections are intended to be applicable to all embodiments and aspects of the application herein described for which they are suitable as would be understood by a person skilled in the art.

Unless otherwise specified within this application or unless a person skilled in the art would understand otherwise, the nomenclature used in this application generally follows the examples and rules stated in "Nomenclature of Organic Chemistry" (Pergamon Press, 1979), Sections A, B, C, D, E, F, and H. Optionally, a name of a compound may be generated using a chemical naming program: ACD/ChemSketch, Version 5.09/September 2001, Advanced Chemistry Development, Inc., Toronto, Canada.

The term "compound of the application" or "compound of the present application" and the like as used herein refers to a compound of Formula I, and pharmaceutically acceptable salts, solvates and/or prodrugs thereof.

The term "composition of the application" or "composition of the present application" and the like as used herein refers to a composition comprising one or more compounds the application and at least one additional ingredient.

The term "suitable" as used herein means that the selection of the particular compound or conditions would depend on the specific synthetic manipulation to be performed, and the identity of the species to be transformed, but the selection would be well within the skill of a person trained in the art. All method steps described herein are to be conducted under conditions sufficient to provide the desired product. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The compounds described herein may have at least one asymmetric center. Where compounds possess more than one asymmetric center, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (for example, less than 20%, suitably less than 10%, more suitably less than 5%) of compounds of the present application having alternate stereochemistry. It is intended that any optical isomers, as separated, pure or partially purified optical isomers or racemic mixtures thereof are included within the scope of the present application.

The compounds of the present application may also exist in different tautomeric forms and it is intended that any tautomeric forms which the compounds form are included within the scope of the present application.

The compounds of the present application may further exist in varying polymorphic forms and it is contemplated that any polymorphs which form are included within the scope of the present application.

The term "protecting group" or "PG" and the like as used herein refers to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J.F.W. Ed., Plenum Press, 1973, in Greene, T. W. and Wuts, P.G.M., "Protective Groups in Organic Synthesis", John Wiley & Sons, 3$^{rd}$ Edition, 1999 and in Kocienski, P. Protecting Groups, 3rd Edition, 2003, Georg Thieme Verlag (The Americas).

The term "cell" as used herein refers to a single cell or a plurality of cells and includes a cell either in a cell culture or in a subject.

The term "subject" as used herein includes all members of the animal kingdom including mammals, and suitably refers to humans. Thus the methods and uses of the present application are applicable to both human therapy and veterinary applications.

The term "pharmaceutically acceptable" means compatible with the treatment of subjects, for example humans.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to a subject.

The term "pharmaceutically acceptable salt" means either an acid addition salt or a base addition salt which is suitable for, or compatible with the treatment of subjects.

An acid addition salt suitable for, or compatible with, the treatment of subjects is any non-toxic organic or inorganic acid addition salt of any basic compound. Basic compounds that form an acid addition salt include, for example, compounds comprising an amine group. Illustrative inorganic acids which form suitable salts include hydrochloric, hydrobromic, sulfuric, nitric and phosphoric acids, as well as acidic metal salts such as sodium monohydrogen orthophosphate and potassium hydrogen sulfate. Illustrative organic acids which form suitable salts include mono-, di- and tricarboxylic acids. Illustrative of such organic acids are, for example, acetic, trifluoroacetic, propionic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, mandelic, salicylic, 2-phenoxybenzoic, p-toluenesulfonic acid and other sulfonic acids such as methanesulfonic acid, ethanesulfonic acid and 2-hydroxyethanesulfonic acid. Either the mono- or di-acid salts can be formed, and such salts can exist in either a hydrated, solvated or substantially anhydrous form. In general, acid addition salts are more soluble in water and various hydrophilic organic solvents, and generally demonstrate higher melting points in comparison to their free base forms. The selection criteria for the appropriate salt will be known to one skilled in the art. Other non-pharmaceutically acceptable salts such as but not limited to oxalates may be used, for example in the isolation of compounds of the application for laboratory use, or for subsequent conversion to a pharmaceutically acceptable acid addition salt.

A base addition salt suitable for, or compatible with, the treatment of subjects is any non-toxic organic or inorganic base addition salt of any acidic compound. Acidic compounds that form a basic addition salt include, for example, compounds comprising a carboxylic acid group. Illustrative inorganic bases which form suitable salts include lithium, sodium, potassium, calcium, magnesium or barium hydroxide as well as ammonia. Illustrative organic bases which form suitable salts include aliphatic, alicyclic or aromatic organic amines such as isopropylamine, methylamine, trimethylamine, picoline, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, EGFRaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. [See, for example, S. M. Berge, et al., "Pharmaceutical Salts," *J. Pharm. Sci.* 1977, 66, 1-19]. The selection of the appropriate salt may be useful so that an ester functionality, if any, elsewhere in a compound is not hydrolyzed. The selection criteria for the appropriate salt will be known to one skilled in the art.

Prodrugs of the compounds of the present application may be, for example, conventional esters formed with available hydroxy, thiol, amino or carboxyl groups. Some common esters which have been utilized as prodrugs are phenyl esters, aliphatic ($C_1$-$C_{24}$) esters, acyloxymethyl esters, carbamates and amino acid esters.

The term "solvate" as used herein means a compound, or a salt or prodrug of a compound, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate".

The term "inert organic solvent" as used herein refers to a solvent that is generally considered as non-reactive with the functional groups that are present in the compounds to be combined together in any given reaction so that it does not interfere with or inhibit the desired synthetic transformation. Organic solvents are typically non-polar and dissolve compounds that are non soluble in aqueous solutions.

The term "alkyl" as used herein, whether it is used alone or as part of another group, means straight or branched chain, saturated alkyl groups. The number of carbon atoms that are possible in the referenced alkyl group are indicated by the prefix "$C_{n1-n2}$". For example, the term $C_{1-6}$alkyl means an alkyl group having 1, 2, 3, 4, 5 or 6 carbon atoms. All alkyl groups are optionally fluorosubstituted unless otherwise stated.

The term "alkylene" as used herein, whether it is used alone or as part of another group, means a straight or branched chain, saturated alkylene group, that is, a saturated carbon chain that contains substituents on two of its ends. The number of carbon atoms that are possible in the referenced alkylene group are indicated by the prefix "$C_{n1-n2}$". For example, the term $C_{1-6}$alkylene means an alkylene group having 1, 2, 3, 4, 5 or 6 carbon atoms. All alkylene groups are optionally fluorosubstituted unless otherwise stated.

The term "alkenyl" as used herein, whether it is used alone or as part of another group, means straight or branched chain, unsaturated alkyl groups containing at least one double bond. The number of carbon atoms that are possible in the referenced alkenyl group are indicated by the prefix "$C_{n1-n2}$". For example, the term $C_{2-6}$alkenyl means an alkenyl group having 2, 3, 4, 5 or 6 carbon atoms and at least one double bond. All alkenyl groups are optionally fluorosubstituted unless otherwise stated.

The term "alkenylene" as used herein, whether it is used alone or as part of another group, means a straight or branched chain, unsaturated alkylene group, that is, an unsaturated carbon chain that contains substituents on two of its ends and at least one double bond. The number of carbon atoms that are possible in the referenced alkenylene group are indicated by the prefix "$C_{n1-n2}$". For example, the term $C_{2-6}$alkenylene means an alkenylene group having 2, 3, 4, 5 or 6 carbon atoms and at least one double bond. All alkenylene groups are optionally fluorosubstituted unless otherwise stated.

The term "alkynyl" as used herein, whether it is used alone or as part of another group, means straight or branched chain, unsaturated alkyl groups containing at least one triple bond. The number of carbon atoms that are possible in the referenced alkynyl group are indicated by the prefix "$C_{n1-n2}$". For example, the term $C_{2-6}$alkenyl means an alkynyl group having 2, 3, 4, 5 or 6 carbon atoms and at least one triple bond. All alkynyl groups are optionally fluorosubstituted unless otherwise stated.

The term "alkynylene" as used herein, whether it is used alone or as part of another group, means a straight or branched chain, unsaturated alkylene group, that is, an unsaturated carbon chain that contains substituents on two of its ends and at least one triple bond. The number of carbon atoms that are possible in the referenced alkynylene group are indicated by the prefix "$C_{n1-n2}$". For example, the term $C_{2-6}$alkynylene means an alkynylene group having 2, 3, 4, 5 or 6 carbon atoms and at least one triple bond. All alkynylene groups are optionally fluorosubstituted unless otherwise stated.

The term "cycloalkyl," as used herein, whether it is used alone or as part of another group, means a saturated carbocyclic group containing one or more rings. The number of carbon atoms that are possible in the referenced cycloalkyl group are indicated by the numerical prefix "$C_{n1-n2}$". For example, the term $C_{3-10}$cycloalkyl means a cycloalkyl group having 3, 4, 5, 6, 7, 8, 9 or 10 carbon atoms.

The term "aryl" as used herein, whether it is used alone or as part of another group, refers to carbocyclic groups containing at least one aromatic ring. In an embodiment of the application, the aryl group contains from 6, 9 or 10 carbon atoms, such as phenyl, indanyl or naphthyl.

The term "heterocycloalkyl" as used herein, whether it is used alone or as part of another group, refers to cyclic groups containing at least one non-aromatic ring in which one or more of the atoms are a heteroatom selected from O, S and N. Heterocycloalkyl groups are either saturated or unsaturated (i.e. contain one or more double bonds). When a heterocycloalkyl group contains the prefix $C_{n1-n2}$ this prefix indicates the number of carbon atoms in the corresponding carbocyclic group, in which one or more, suitably 1 to 5, of the ring atoms is replaced with a heteroatom as defined above.

The term "heteroaryl" as used herein refers to cyclic groups containing at least one aromatic ring and at least one a heteroatom selected from O, S and N. When a heteroaryl group contains the prefix $C_{n1-n2}$ this prefix indicates the number of carbon atoms in the corresponding carbocyclic group, in which one or more, suitably 1 to 5, of the ring atoms is replaced with a heteroatom as defined above.

All cyclic groups, including aryl, heteroaryl, heterocycloalkyl and cycloalkyl groups, contain one or more than one ring (i.e. are polycyclic). When a cyclic group contains more than one ring, the rings may be fused, bridged, or spirofused.

A first ring being "fused" with a second ring means the first ring and the second ring share two adjacent atoms there between.

A first ring being "bridged" with a second ring means the first ring and the second ring share two non-adjacent atoms there between.

A first ring being "spirofused" with a second ring means the first ring and the second ring share one atom there between.

The term "halo" as used herein refers to a halogen atom and includes fluoro, chloro, bromo and iodo.

The term "optionally substituted" refers to groups, structures, or molecules that are either unsubstituted or are substituted with one or more substituents.

The term "fluorosubstituted" refers to the substitution of one or more, including all, hydrogens in a referenced group with fluorine.

The symbol "∼" is used herein to represent the point of attachment of a group to the remainder of a molecule or chemical formula.

The term "protecting group" or "PG" and the like as used herein refers to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J.F.W. Ed., Plenum Press, 1973, in Greene, T. W. and Wuts, P.G.M., "Protective Groups in Organic Synthesis", John Wiley & Sons, $3^{rd}$ Edition, 1999 and in Kocienski, P. Protecting Groups, 3rd Edition, 2003, Georg Thieme Verlag (The Americas).

The term "atm" as used herein refers to atmosphere.

The term "MS" as used herein refers to mass spectrometry.

The term "aq." As used herein refers to aqueous.

The term "DCM" as used herein refers to dichloromethane.

The term "DIPEA" as used herein refers to N,N-diisopropyl ethylamine.

The term "DMF" as used herein refers to dimethylformamide.

The term "THF" as used herein refers to tetrahydrofuran.

The term "DMSO" as used herein refers to dimethylsulfoxide.

The term "EtOAc" as used herein refers to ethyl acetate.

The term "MeOH" as used herein refers to methanol.

The term "MeCN" or "ACN" as used herein refers to acetonitrile.

The term "HCl" as used herein refers to hydrochloric acid.

The term "TFA" as used herein refers to trifluoroacetic acid.

The term "CV" as used herein refers to column volume.

The term "Hex" as used herein refers to hexanes.

The term "PBS" as used herein refers to phosphate-based buffer.

The term "HBTU" as used herein refers to

The term "HATU" as used herein refers to

The term "RT" as used herein refers to room temperature.

The term "DIAD" as used herein refers to diisopropyl azodicarboxylate.

The term "TPP" as used herein refers to triphenylphosphine.

The term "TLC" as used herein refers to thin-layer chromatography.

The term "MOM-Cl" as used herein refers to methoxymethyl chloride.

The term "EDC-HCl" as used herein refers to N'-ethylcarbodiimide hydrochloride.

The term "TMEDA" as used herein refers to tetramethylethylenediamine.

The term "PyBOP" as used herein refers to benzotriazol-1-yl-oxytripyrrolidinophosphonium hexafluorophosphate.

The term "TEA" as used herein refers to triethylamine.

The term "mCPBA" as used herein refers to meta-chloroperoxybenzoic acid.

The term "TMSCl" as used herein refers to trimethylsilylchloride.

The term "NBS" as used herein refers to N-bromosuccinimide.

The term "DBAD" as used herein refers to di-tert-butyl azodicarboxylate.

The term "DPPA" as used herein refers to diphenylphosphoryl azide.

The term "NMP" as used herein refers to N-methyl-2-pyrrolidone.

The term "DiPA" as used herein refers to diisopropyl amine.

The term "NCS" as used herein refers to N-chloro succinimide.

The term "PMDTA" as used herein refers to N,N,N',N",N"-pentamethyldiethylenetriamine.

The term "DIMAP" as used herein refers to 4-Dimethylaminopyridine.

The term "treating" or "treatment" as used herein and as is well understood in the art, means an approach for obtaining beneficial or desired results, including clinical results. Beneficial or desired clinical results can include, but are not limited to alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. "Treating" and "treatment" as used herein also include prophylactic treatment. For example, a subject with early cancer can be treated to prevent progression, or alternatively a subject in remission can be treated with a compound or composition of the application to prevent recurrence. Treatment methods comprise administering to a subject a therapeutically effective amount of one or more of the compounds of the application and optionally consist of a single administration, or alternatively comprise a series of administrations. For example, in some embodiments, the compounds of the application may be administered at least once a week. In some embodiments, the compounds may be administered to the subject from about one time per three weeks, or about one time per week to about once daily for a given treatment. In another embodiment, the compounds are administered 2, 3, 4, 5 or 6 times daily. The length of the treatment period depends on a variety of factors, such as the severity of the disease, disorder or condition, the age of the subject, the concentration and/or the activity of the compounds of the application, and/or a combination thereof. It will also be appreciated that the effective dosage of the compound used for the treatment may increase or decrease over the course of a particular treatment regime. Changes in dosage may result and become apparent by standard diagnostic assays known in the art. In some instances, chronic administration may be required. For example, the compounds are administered to the subject in an amount and for duration sufficient to treat the patient.

"Palliating" a disease or disorder means that the extent and/or undesirable clinical manifestations of a disorder or a disease state are lessened and/or time course of the progression is slowed or lengthened, as compared to not treating the disorder.

The term "prevention" or "prophylaxis", or synonym thereto, as used herein refers to a reduction in the risk or probability of a patient becoming afflicted with a disease, disorder or condition treatable by inhibition of interactions with BCL6 BTB, or manifesting a symptom associated with a disease, disorder or condition treatable by inhibition of BCL6 BTB protein-protein interaction.

As used herein, the term "effective amount" or "therapeutically effective amount" means an amount of a compound, or one or more compounds, of the application that is effective, at dosages and for periods of time necessary to achieve the desired result. For example in the context of treating a disease, disorder or condition treatable by inhibition of interactions with BCL6 BTB, an effective amount is an amount that, for example, inhibits interactions with BCL6 BTB, compared to the inhibition without administration of the one or more compounds. Effective amounts may vary according to factors such as the disease state, age, sex and/or weight of the subject. The amount of a given compound that will correspond to such an amount will vary depending upon various factors, such as the given drug or compound, the pharmaceutical formulation, the route of administration, the type of condition, disease or disorder, the identity of the subject being treated, and the like, but can nevertheless be routinely determined by one skilled in the art. The effective amount is one that following treatment therewith manifests as an improvement in or reduction of any disease symptom. When the disease is cancer, amounts that are effective can cause a reduction in the number, growth rate, size and/or distribution of tumours.

The expression "inhibiting interactions with BCL6 BTB" as used herein refers to inhibiting, blocking and/or disrupting an interaction between a therapeutically relevant binding partner, such as a corepressor protein, with the BCL6 BTB binding domain in a cell, in particular a B-cell. The inhibiting, blocking and/or disrupting causes a therapeutic effect in the cell.

By "inhibiting, blocking and/or disrupting" it is meant any detectable inhibition, block and/or disruption in the presence of a compound compared to otherwise the same conditions, except for in the absence in the compound.

The term "BCL6 BTB" as used herein refers to the bric-e-brac, tramtrack, broad (BTB) domain of B-cell lymphoma 6 (BLC6) which comprises the amino acid sequence disclosed in *Mol. Cell* 2008, 29: 384-391.

The term "SMRT" as used herein refers to a corepressor protein that interacts with BCL6 BTB and this interaction results in the reduction of mRNA expression of target genes. SMRT (Gene ID: 9612) comprises the amino acid sequence disclosed in *Proc Natl Acad Sci* 1999, 96: 2639-2644 and *Proc Natl Acad Sci,* 1999 96: 3519-3524.

The term "NCOR" as used herein refers to a corepressor protein that interacts with BCL6 BTB and this interaction results in the reduction of mRNA expression of target genes. NCOR (Gene ID: 9611) comprises the amino acid sequence disclosed in *Proc Natl Acad Sci* 1999, 96: 2639-2644 and *Proc Natl Acad Sci,* 1999 96: 3519-3524 . . . .

The term "BCOR" as used herein as used herein refers to a corepressor protein that interacts with BCL6 BTB and this interaction results in the reduction of mRNA expression of target genes. BCOR (Gene ID: 54880) comprises the amino acid sequence disclosed in *Genes Dev.* 2000, 14, 1810-1823.

The term "administered" as used herein means administration of a therapeutically effective amount of a compound, or one or more compounds, or a composition of the application to a cell either in cell culture or in a subject.

The term "neoplastic disorder" as used herein refers to a disease, disorder or condition characterized by cells that have the capacity for autonomous growth or replication, e.g., an abnormal state or condition characterized by proliferative cell growth. The term "neoplasm" as used herein refers to a mass of tissue resulting from the abnormal growth and/or division of cells in a subject having a neoplastic disorder. Neoplasms can be benign (such as uterine fibroids and melanocytic nevi), potentially malignant (such as carcinoma in situ) or malignant (i.e. cancer).

II. Compounds

The present application includes a compound of Formula I, or a pharmaceutically acceptable salt, solvate and/or prodrug thereof:

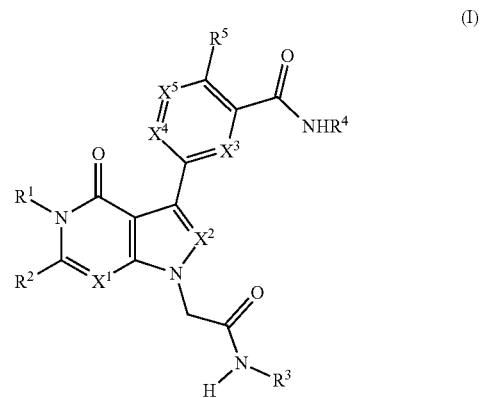

(I)

wherein
$X^1$, $X^2$ and $X^3$ are independently selected from $CR^6$ and N,
$X^4$ is selected from $CR^7$ and N;
$X^5$ is selected from $CR^8$ and N;
$R^1$ is selected from H, $C_{1-6}$alkyl, $C_{1-6}$alkyleneO$C_{1-6}$alkyl, $C_{1-6}$alkylene$C_{3-6}$cycloalkyl, $C_{1-6}$alkylene$C_{3-6}$heterocycloalkyl, $C_{1-6}$alkylene$C_{5-6}$heteroaryl, $C_{1-6}$alkylenephenyl, $C_{1-6}$alkyleneC(O)$C_{3-6}$cycloalkyl, $C_{1-6}$alkyleneC(O)$C_{3-6}$heterocycloalkyl, $C_{1-6}$alkyleneC(O)$C_{5-6}$heteroaryl, $C_{1-6}$alkyleneC(O)phenyl, $C_{2-6}$alkynyleneO$C_{1-6}$alkyl, $C_{2-6}$alkynylene$C_{3-6}$cycloalkyl, $C_{2-6}$alkynylene$C_{3-6}$heterocycloalkyl, $C_{2-6}$alkynylene$C_{5-6}$heteroaryl, $C_{2-6}$alkynylenephenyl, $C_{2-6}$alkenyleneO$C_{1-6}$alkyl, $C_{2-6}$alkenylene$C_{3-6}$cycloalkyl, $C_{2-6}$alkenylene$C_{3-6}$heterocycloalkyl, $C_{2-6}$alkenylene$C_{5-6}$heteroaryl and $C_{2-6}$alkenylenephenyl, and each cycloalkyl, heterocycloalkyl, heteroaryl and phenyl is optionally substituted with one to three substituents independently selected from halo and $C_{1-4}$alkyl;
$R^2$ is selected from H, $C_{1-6}$alkyl, OH, SH, $NH_2$, NH$C_{1-6}$alkyl, N($C_{1-6}$alkyl)($C_{1-6}$alkyl), O$C_{1-6}$alkyl, halo, $Z^1C_{3-6}$cycloalkyl, $Z^1C_{3-6}$heterocycloalkyl, $Z^1C_{5-6}$heteroaryl, $Z^1$phenyl, $Z^1C_{1-6}$alkyleneO$C_{1-6}$alkyl, $Z^1C_{1-6}$alkylene$C_{3-6}$cycloalkyl, $Z^1C_{1-6}$alkylene$C_{3-6}$heterocycloalkyl, $Z^1C_{1-6}$alkylene$C_{5-6}$heteroaryl, $Z^1C_{1-6}$alkylenephenyl, $Z^1C_{2-6}$alkynyleneO$C_{1-6}$alkyl, $Z^1C_{2-6}$alkynylene$C_{3-6}$cycloalkyl, $Z^1C_{2-6}$alkynylene$C_{3-6}$heterocycloalkyl, $Z^1C_{2-6}$alkynylene$C_{5-6}$heteroaryl, $Z^1C_{2-6}$alkynylenephenyl, $Z^1C_{2-6}$alkenyleneO$C_{1-6}$alkyl, $Z^1C_{2-6}$alkenylene$C_{3-6}$cycloalkyl, $Z^1C_{2-6}$alkenylene$C_{3-6}$heterocycloalkyl, $Z^1C_{2-6}$alkenylene$C_{5-6}$heteroaryl and $Z^1C_{2-6}$alkenylenephenyl, and each cycloalkyl, heterocycloalkyl, heteroaryl and phenyl, is optionally substituted with one to three substituents independently selected from halo, OH, SH, $NH_2$, NH$C_{1-6}$alkyl and N($C_{1-6}$alkyl)($C_{1-6}$alkyl);
$Z^1$ is selected from a direct bond, O, NH, N$C_{1-6}$alkyl, S(O) and $SO_2$;
$R^3$ is selected from $C_{6-10}$aryl, $C_{6-10}$heteroaryl, $C_{6-10}$cycloalkyl and $C_{6-10}$heterocycloalkyl, each of which is optionally substituted with one to four substituents independently selected from halo, =O, $C_{1-6}$alkyl, CN, $NO_2$, $C_{2-6}$alkenyl, $C_{2-6}$alkynyl and $OC_{1-6}$alkyl and optionally substituted with one substituent selected from $Z^2R^9$;

$Z^2$ is selected from a direct bond, $C_{1-6}$alkylene, C(O), O, S, S(O) and $SO_2$;

$R^4$ is selected from H and $C_{1-6}$alkyl;

$R^5$ is OH;

$R^6$ is selected from H and halo;

$R^7$ and $R^8$ are independently selected from H, halo, $C_{1-6}$alkyl, $OC_{1-6}$alkyl, and $SO_2NH_2$, or $R^7$ and $R^8$ are linked to form, together with the carbon atoms to which they are attached, a 3-8-membered heterocycloalkyl or heteroaromatic ring, both of which contain one to two additional heteroatoms selected from O, S, S(O), $SO_2$, NH and $NC_{1-6}$alkyl;

$R^9$ is selected from $C_{1-6}$alkyl, $NR^{10}R^{11}$, $C_{3-10}$cycloalkyl, $C_{3-10}$heterocycloalkyl, $C_{5-10}$heteroaryl and $C_{6-10}$aryl, the latter 4 groups being optionally substituted with one to six substituents independently selected from halo, CN, $C_{1-6}$alkyl and $OC_{1-6}$alkyl, and optionally substituted with one substituent selected from $C_{1-6}$alkyleneOC$_{1-6}$alkyl, $C_{1-6}$alkyleneOH, $C_{1-6}$alkylene(diOH), $SO_2C_{1-6}$alkyl, $Z^3C_{3-10}$cycloalkyl, $Z^3C_{3-10}$heterocycloalkyl, $Z^3C_{5-10}$heteroaryl and $Z^3C_{6-10}$aryl the latter four groups being optionally substituted with one to four substituents independently selected from halo and $C_{1-6}$alkyl;

$R^{10}$ and $R^{11}$ are independently selected from H, $C_{1-6}$alkyl, $C_{1-6}$alkyleneOH, $C_{1-6}$alkylene(diOH), $C_{1-6}$alkyleneOC$_{1-6}$alkyl, $SO_2C_{1-6}$alkyl, $Z^4C_{3-10}$cycloalkyl, $Z^4C_{3-10}$heterocycloalkyl, $Z^4C_{5-10}$heteroaryl and $Z^4C_{6-10}$aryl, the latter four groups being optionally substituted with one to six substituents independently selected from halo and $C_{1-6}$alkyl, $Z^3$ and $Z^4$ are independently selected from a direct bond and $C_{1-6}$alkylene; and all alkyl and alkylene groups are optionally fluoro-substituted and all available hydrogens are optionally replaced with deuterium.

In some embodiments, $X^1$ is N.

In some embodiments, $X^2$ is selected from N, CH and CF. In some embodiments, $X^2$ is CH.

In some embodiments, $X^3$ is selected from N, CH and CF. In some embodiments, $X^3$ is selected from CH and CF. In some embodiments, $X^3$ is CH.

In some embodiments, $X^4$ is $CR^7$. In some embodiments, $X^5$ is $CR^8$. In some embodiments, $R^7$ and $R^8$ are independently selected from H, F, Cl, $CH_3$, $CH_2CH_3$, $CF_3$, $OCH_3$, $OCF_3$ and $SO_2NH_2$. In some embodiments, $R^7$ and $R^8$ are both H. In some embodiments, $R^7$ and $R^8$ are linked to form, together with the carbon atoms to which they are attached, a 3-6-membered heterocycloalkyl or heteroaromatic ring, both of which contain one to two additional heteroatoms selected from O, S, NH and $NCH_3$. In some embodiments, $R^7$ and $R^8$ are linked to form, together with the carbon atoms to which they are attached, a 5-6-membered heterocycloalkyl ring, which contains one to two additional O.

In some embodiments, $R^1$ is selected from H, $C_{1-4}$alkyl, $C_{1-4}$alkyleneOC$_{1-4}$alkyl, $C_{1-4}$alkyleneC$_{3-6}$cycloalkyl, $C_{1-4}$alkyleneC$_{3-6}$heterocycloalkyl, $C_{1-4}$alkyleneC$_{5-6}$heteroaryl, $C_{1-4}$alkylenephenyl, $C_{1-4}$alkyleneC(O)C$_{3-6}$cycloalkyl, $C_{1-4}$alkyleneC(O)C$_{3-6}$heterocycloalkyl, $C_{1-4}$alkyleneC(O)C$_{5-6}$heteroaryl, $C_{1-4}$alkyleneC(O)phenyl, $C_{2-4}$alkynyleneOC$_{1-4}$alkyl, $C_{2-4}$alkynyleneC$_{3-6}$cycloalkyl, $C_{2-4}$alkynyleneC$_{3-6}$heterocycloalkyl, $C_{2-4}$alkynyleneC$_{5-6}$heteroaryl, $C_{2-4}$alkynylenephenyl, $C_{2-4}$alkenyleneOC$_{1-4}$alkyl, $C_{2-4}$alkenyleneC$_{3-6}$cycloalkyl, $C_{2-4}$alkenyleneC$_{3-6}$heterocycloalkyl, $C_{2-4}$alkenyleneC$_{5-6}$heteroaryl and $C_{2-4}$alkenylenephenyl, and each cycloalkyl, heterocycloalkyl, heteroaryl and phenyl is optionally substituted with one to two substituents independently selected from F, Cl, $CH_3$ and $CF_3$. In some embodiments, $R^1$ is selected from H, $CH_3$, $CF_3$, $CH_2OCH_3$, $CH_2OCF_3$, $CH_2C_{3-6}$cycloalkyl, $CH_2C_{3-6}$heterocycloalkyl, $CH_2C_{5-6}$heteroaryl, $CH_2$phenyl, $CH_2CH_2C(O)C_{3-6}$cycloalkyl, $CH_2CH_2C(O)C_{3-6}$heterocycloalkyl, $CH_2CH_2C(O)C_{5-6}$heteroaryl, $CH_2CH_2C(O)$phenyl, $CH_2C\equiv CC_{3-6}$cycloalkyl, $CH_2C\equiv CC_{3-6}$heterocycloalkyl, $CH_2C\equiv CC_{5-6}$heteroaryl and $CH_2C\equiv C$phenyl, and each cycloalkyl, heterocycloalkyl, heteroaryl and phenyl is optionally substituted with one to two substituents independently selected from F, Cl, $CH_3$ and $CF_3$. In some embodiments, $R^1$ is selected from H, $CH_3$, $CF_3$, $CH_2OCH_3$, $CH_2OCF_3$, $CH_2C_5$heteroaryl, $CH_2CH_2C(O)C_5$heteroaryl and $CH_2C\equiv CC_5$heteroaryl, and each heteroaryl is optionally substituted with one to two substituents independently selected from F, Cl, $CH_3$ and $CF_3$. In some embodiments, the heteroaryl of $R^1$ is a 5-membered heteroaryl containing one or 2 nitrogen atoms and is optionally substituted with one or two $CH_3$.

In some embodiments, $R^2$ is selected from H, $C_{1-4}$alkyl, OH, $NH_2$, $NHC_{1-4}$alkyl, $N(C_{1-4}$alkyl)($C_{1-4}$alkyl), $OC_{1-4}$alkyl, Cl, F, $Z^1C_{3-6}$cycloalkyl, $Z^1C_{3-6}$heterocycloalkyl, $Z^1C_{5-6}$heteroaryl, $Z^1$phenyl, $Z^1C_{1-4}$alkyleneOC$_{1-4}$alkyl, $Z^1C_{1-4}$alkyleneC$_{3-6}$cycloalkyl, $Z^1C_{1-4}$alkyleneC$_{3-6}$heterocycloalkyl, $Z^1C_{1-4}$alkyleneC$_{5-6}$heteroaryl, $Z^1C_{1-4}$alkylenephenyl, $Z^1C_{2-4}$alkynyleneOC$_{1-6}$alkyl, $Z^1C_{2-4}$alkynyleneC$_{3-6}$cycloalkyl, $Z^1C_{2-4}$alkynyleneC$_{3-6}$heterocycloalkyl, $Z^1C_{2-4}$alkynyleneC$_{5-6}$heteroaryl, $Z^1C_{2-4}$alkynylenephenyl, $Z^1C_{2-4}$alkenyleneOC$_{1-4}$alkyl, $Z^1C_{2-4}$alkenyleneC$_{3-6}$cycloalkyl, $Z^1C_{2-4}$alkenyleneC$_{3-6}$heterocycloalkyl, $Z^1C_{2-4}$alkenyleneC$_{5-6}$heteroaryl and $Z^1C_{2-4}$alkenylenephenyl, and each cycloalkyl, heterocycloalkyl, heteroaryl and phenyl, is optionally substituted with one to two substituents independently selected from Cl, F and $N(C_{1-4}$alkyl)($C_{1-4}$alkyl). In some embodiments, $R^2$ is selected from H, $CH_3$, $CF_3$, OH, $NH_2$, $N(CH_3)_2$, $N(CH_3)(CH_2CH_3)$, $(C_{1-4}$alkyl)($C_{1-4}$alkyl), $OCH_3$, Cl, F, $Z^1C_{3-6}$cycloalkyl, $Z^1C_{3-6}$heterocycloalkyl, $Z^1C_{5-6}$heteroaryl, $Z^1$phenyl, $Z^1C_{1-4}$alkyleneOC$_{1-4}$alkyl, $Z^1C_{1-4}$alkyleneC$_{3-6}$cycloalkyl, $Z^1C_{1-4}$alkyleneC$_{3-6}$heterocycloalkyl, $Z^1C_{1-4}$alkyleneC$_{5-6}$heteroaryl, $Z^1C_{1-4}$alkylenephenyl, $Z^1C_{2-4}$alkenyleneOC$_{1-4}$alkyl, $Z^1C_{2-4}$alkenyleneC$_{3-6}$cycloalkyl, $Z^1C_{2-4}$alkenyleneC$_{3-6}$heterocycloalkyl, $Z^1C_{2-4}$alkenyleneC$_{5-6}$heteroaryl and $Z^1C_{2-4}$alkenylenephenyl, and each cycloalkyl, heterocycloalkyl, heteroaryl and phenyl, is optionally substituted with one to two substituents independently selected from Cl, F and $N(CH_3)_2$. In some embodiments, $R^2$ is selected from H, $CH_3$, $CF_3$, OH, $NH_2$, $NHCH_3$, $N(CH_3)_2$, $N(CH_3)(CH_2CH_3)$, $OCH_3$, Cl, F, $Z^1C_{3-6}$cycloalkyl, $Z^1C_{3-6}$heterocycloalkyl, $Z^1C_{5-6}$heteroaryl, $Z^1$phenyl, $Z^1C_{1-2}$alkyleneOCH$_3$, $Z^1C_{1-2}$alkyleneC$_{3-6}$cycloalkyl, $Z^1C_{1-2}$alkyleneC$_{3-6}$heterocycloalkyl, $Z^1C_{1-4}$alkyleneC$_{5-6}$heteroaryl, $Z^1C_{1-4}$alkylenephenyl, $Z^1C_{2-3}$alkenyleneOC$_{1-4}$alkyl, $Z^1C_{2-3}$alkenyleneC$_{3-6}$cycloalkyl, $Z^1C_{2-3}$alkenyleneC$_{3-6}$heterocycloalkyl, $Z^1C_{2-3}$alkenyleneC$_{5-6}$heteroaryl and $Z^1C_{2-3}$alkenylenephenyl, and each cycloalkyl, heterocycloalkyl, heteroaryl and phenyl, is optionally substituted with one to two substituents independently selected from Cl, F and $N(CH_3)_2$. In some embodiments, $R^2$ is selected from H, $CH_3$, $CF_3$, $OCH_3$, $OCH_2CH_2OCH_3$, CH=CH-cyclopropyl, $NH_2$, $NHCH_2$cyclopropyl, $NHCH_2$-p-fluorophenyl, $NHCH_2CH_2CF_3$, phenyl, Cl, $N(CH_3)_2$, $NHCH_3$, $N(CH_3)(CH_2CH_3)$, OH, $C(CH_3)=CH_2$,

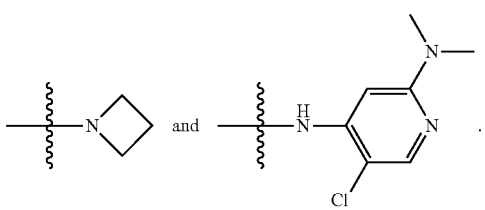 [SMILES: *N1CCC1 ; *Nc1cc(N(C)C)ncc1Cl]

In some embodiments, $R^2$ is H.

In some embodiments $Z^1$ is selected from a direct bond, O, NH and $N(CH_3)$. In some embodiments, $Z^1$ is selected from a direct bond, O and NH.

In some embodiments, $R^3$ is selected from $C_{6-10}$aryl, $C_{6-10}$heteroaryl, $C_{6-10}$cycloalkyl and $C_{6-10}$heterocycloalkyl, each of which is optionally substituted with one to four substituents independently selected from halo, =O, $C_{1-4}$alkyl, CN, $NO_2$, $C_{2-4}$alkenyl, $C_{2-4}$alkynyl and $OC_{1-4}$alkyl and optionally substituted with one substituent selected from $Z^2R^9$. In some embodiments, $R^3$ is selected from $C_{6-10}$aryl, $C_{6-10}$heteroaryl, $C_{6-10}$cycloalkyl and $C_{6-10}$heterocycloalkyl, each of which is optionally substituted with one to three substituents independently selected from Cl, F, =O, $C_{1-2}$alkyl, CN, $NO_2$, $C_{2-4}$alkenyl, $C_{2-4}$alkynyl and $OC_{1-2}$alkyl and is optionally substituted with one substituent selected from $Z^2R^9$. In some embodiments, $R^3$ is a mono or bicyclic $C_{6-10}$aryl or $C_{6-10}$heteroaryl, each of which is optionally substituted with one to three substituents independently selected from Cl, F, =O, $C_{1-2}$alkyl, CN, $NO_2$, $C_{2-4}$alkenyl, $C_{2-4}$alkynyl and $OC_{1-2}$alkyl and is optionally substituted with one substituent selected from $Z^2R^9$.

In some embodiments, $R^3$ is

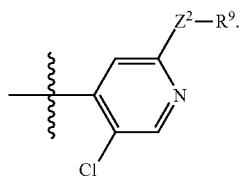

In some embodiments $Z^2$ is selected from a direct bond, $C_{1-4}$alkylene, C(O) and O.

In some embodiments, $R^4$ is selected from H and $CH_3$. In some embodiments, $R^4$ is H.

In some $R^6$ is selected from H and F.

In some embodiments, $R^9$ is selected from $C_{1-4}$alkyl, $NR^{10}R^{11}$, $C_{3-10}$cycloalkyl, $C_{3-10}$heterocycloalkyl, $C_{5-10}$heteroaryl and $C_{6-10}$aryl, the latter 4 groups being optionally substituted with one to six groups independently selected from halo, CN, $C_{1-4}$alkyl and $OC_{1-4}$alkyl, and optionally substituted with one group selected from $C_{1-4}$alkylene$OC_{1-4}$alkyl, $C_{1-4}$alkyleneOH, $C_{1-4}$alkylene(diOH), $SO_2C_{1-4}$alkyl, $Z^3C_{3-10}$cycloalkyl, $Z^3C_{3-10}$heterocycloalkyl, $Z^3C_{5-10}$heteroaryl and $Z^3C_{6-10}$aryl the latter 4 groups being optionally substituted with one to 4 groups independently selected from Cl, F and $C_{1-4}$alkyl.

In some embodiments, $Z^2$ is a direct bond and $R^9$ is:

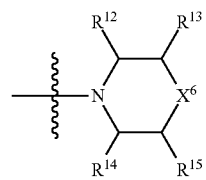

wherein $X^6$ is selected from O, NH, $NC_{1-4}$alkyl, $NC_{1-4}$alkylene$C_{3-6}$cycloalkyl, $NC_{1-4}$alkylene$C_{3-6}$heterocycloalkyl, $NC_{3-6}$heterocycloalkyl, $NC_{1-4}$alkyleneO$C_{1-4}$alkyl, $CH_2$, CHF, $CF_2$, $CHC_{1-4}$alkylene$C_{3-6}$cycloalkyl, $CHC_{1-4}$alkylene$C_{3-6}$heterocycloalkyl, $CHC_{3-6}$heterocycloalkyl, $CHC_{3-6}$cycloalkyl, $CHC_{1-4}$alkyleneO$C_{1-4}$alkyl, $CHC_{1-4}$alkyl and $C(C_{1-4}$alkyl)($C_{1-4}$alkyl);
$R^{12}$, $R^{13}$, $R^{14}$ and $R^{15}$ are independently selected from H, F, $C_{1-4}$alkyl, and $C_{1-4}$alkyleneO$C_{1-4}$alkyl, or
$R^{13}$ and $R^{15}$ are $C_{1-3}$alkylene linking the carbon atoms to which they are attached, or
$R^{12}$ and $R^{14}$ are $C_{1-3}$alkylene linking the carbon atoms to which they are attached; and each alkyl and alkylene group is optionally fluorosubstituted.

In some embodiment, $X^6$ is selected from O, NH, $NC_{1-4}$alkyl, $NC_{1-2}$alkylene$C_{3-6}$cycloalkyl, $NC_{1-2}$alkylene$C_{3-6}$heterocycloalkyl, $NC_{3-6}$heterocycloalkyl, $NC_{1-4}$alkyleneO$C_{1-4}$alkyl, $CH_2$, CHF, $CF_2$, $CHC_{1-2}$alkylene$C_{3-6}$cycloalkyl, $CHC_{1-2}$alkylene$C_{3-6}$heterocycloalkyl, $CHC_{3-6}$heterocycloalkyl, $CHC_{3-6}$cycloalkyl, $CHC_{1-2}$alkyleneO$C_{1-2}$alkyl, $CHC_{1-4}$alkyl and $C(C_{1-4}$alkyl)($C_{1-4}$alkyl). In some embodiments, $X^6$ is selected from O, NH, $NCH_3$, $NCH_2CH_3$, $NCH(CH_3)_2$, $NCH_2$cyclopropyl, $NCH_2$cyclobutyl, Ncyclopropyl, Ncyclobutyl, Noxetanyl, $NCH_2CH_2OCH_3$, $NCH(CH_3)$cyclopropyl, $CH_2$, CHF, $CF_2$, $CHCH_2$cyclopropyl and $CHCH_2$cyclobutyl.

In some embodiments, $R^{12}$, $R^{13}$, $R^{14}$ and $R^{15}$ are independently selected from H, F, $CH_3$, $CF_3$, and $C_{1-2}$alkyleneO$CH_3$.

In some embodiments $R^{13}$ and $R^{15}$ are $CH_2CH_2$ linking the carbon atoms to which they are attached.

In some embodiments, $R^{12}$ and $R^{14}$ are $CH_2CH_2$ linking the carbon atoms to which they are attached.

In some embodiments $R^{10}$ and $R^{11}$ are independently selected from H, $C_{1-4}$alkyl, $C_{1-4}$alkyleneOH, $C_{1-4}$alkylene(diOH), $C_{1-4}$alkyleneO$C_{1-6}$alkyl, $SO_2C_{1-4}$alkyl, $Z^4C_{3-10}$cycloalkyl, $Z^4C_{3-10}$heterocycloalkyl, $Z^4C_{5-10}$heteroaryl and $Z^4C_{6-10}$aryl, the latter 4 groups being optionally substituted with one to six groups independently selected from halo and $C_{1-4}$alkyl, In some embodiments, $Z^3$ and $Z^4$ are independently selected from a direct bond and $C_{1-4}$alkylene. In some embodiments, $Z^3$ and $Z^4$ are independently selected from a direct bond and $C_{1-2}$alkylene.

In some embodiments, when alkyl and alkylene groups are fluoro-substituted, such groups are selected from $CF_3$, $CF_2H$, $CFH_2$, $CH_2CF_3$, $CF_2CF_3$, —CHF— and —$CF_2$—.

In some embodiments, the compound of Formula I is selected from compound number 1 to 498 as shown in Tables 1 and 2, or a pharmaceutically acceptable salt, solvent and/or prodrug thereof.

The compounds of the present application are suitably formulated in a conventional manner into compositions using one or more carriers. Accordingly, the present application also includes a composition comprising one or more compounds of the application and a carrier. The compounds of the application are suitably formulated into pharmaceutical compositions for administration to subjects in a biologically compatible form suitable for administration in vivo. Accordingly, the present application further includes a pharmaceutical composition comprising one or more compounds of the application and a pharmaceutically acceptable carrier.

The compounds or compositions of the application may be administered to a subject in a variety of forms depending on the selected route of administration, as will be understood by those skilled in the art. Compounds or compositions of the application may be administered, for example, by oral, parenteral, buccal, sublingual, nasal, rectal, patch, pump or transdermal administration and the pharmaceutical compositions formulated accordingly. Administration can be by means of a pump for periodic or continuous delivery.

Parenteral administration includes intravenous, intra-arterial, intraperitoneal, subcutaneous, intramuscular, transepithelial, nasal, intrapulmonary (for example, by use of an aerosol), intrathecal, rectal and topical (including the use of a patch or other transdermal delivery device) modes of administration. Parenteral administration may be by continuous infusion over a selected period of time. Conventional procedures and ingredients for the selection and preparation of suitable compositions are described, for example, in *Remington's Pharmaceutical Sciences* (2000-20th edition) and in The United States Pharmacopeia: The National Formulary (USP 24 NF19) published in 1999.

Compounds or compositions of the application may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the compound may be incorporated with excipient and used in the form of ingestible tablets, buccal tablets, troches, capsules, caplets, pellets, granules, lozenges, chewing gum, powders, syrups, elixirs, wafers, aqueous solutions and suspensions, and the like. In the case of tablets, carriers that are used include lactose, corn starch, sodium citrate and salts of phosphoric acid. Pharmaceutically acceptable excipients include binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. In the case of tablets, capsules, caplets, pellets or granules for oral administration, pH sensitive enteric coatings, such as Eudragits™ designed to control the release of active ingredients are optionally used. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. Timed-release compositions can be formulated, e.g. liposomes or those wherein the active compound is protected with differentially degradable coatings, such as by microencapsulation, multiple coatings, etc. Liposome delivery systems include, for example, small unilamellar vesicles, large unilamellar vesicles and multilamellar vesicles. Liposomes can be formed from a variety of phospholipids, such as cholesterol, stearylamine or phosphatidylcholines. For oral administration in a capsule form, useful carriers or diluents include lactose and dried corn starch.

Liquid preparations for oral administration may take the form of, for example, solutions, syrups or suspensions, or they are suitably presented as a dry product for constitution with water or other suitable vehicle before use. When aqueous suspensions and/or emulsions are administered orally, the compound of the application is suitably suspended or dissolved in an oily phase that is combined with emulsifying and/or suspending agents. If desired, certain sweetening and/or flavoring and/or coloring agents may be added. Such liquid preparations for oral administration may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid). Useful diluents include lactose and high molecular weight polyethylene glycols.

It is also possible to freeze-dry the compounds of the application and use the lyophilizates obtained, for example, for the preparation of products for injection.

Compound or compositions of the application may also be administered parenterally. Solutions of a compound of the application can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. For parenteral administration, sterile solutions of the compounds of the application are usually prepared, and the pH of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or polyvinyl alcohol, preservatives such as sorbic acid, EDTA or benzyl chromium chloride, and the usual quantities of diluents or carriers. For pulmonary administration, diluents or carriers will be selected to be appropriate to allow the formation of an aerosol.

Compounds or compositions of the application may be formulated for parenteral administration by injection, including using conventional catheterization techniques or infusion. Formulations for injection may be presented in unit dosage form, e.g., in ampoules or in multi-dose containers, with an added preservative. The compositions may take such forms as sterile suspensions, solutions or emulsions in oily or aqueous vehicles, and may contain formulating agents such as suspending, stabilizing and/or dispersing agents. In all cases, the form must be sterile and must be fluid to the extent that easy syringability exists. Alternatively, the compounds of the application are suitably in a sterile powder form for reconstitution with a suitable vehicle, e.g., sterile pyrogen-free water, before use.

Compositions for nasal administration may conveniently be formulated as aerosols, drops, gels and powders.

For intranasal administration or administration by inhalation, the compounds or compositions of the application are conveniently delivered in the form of a solution, dry powder formulation or suspension from a pump spray container that is squeezed or pumped by the patient or as an aerosol spray presentation from a pressurized container or a nebulizer. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. Suitable propellants include but are not limited to dichlorodifluoromethane, trichlorofluoromethane, dichlorotetrafluoroethane, heptafluoroalkanes, carbon dioxide or another suitable gas. In the case of a pressurized aerosol, the dosage unit is suitably determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the application and a suitable powder base such as lactose or starch. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Suppository forms of the compounds of the application are useful for vaginal, urethral and rectal administrations. Such suppositories will generally be constructed of a mixture of substances that is solid at room temperature but melts at body temperature. The substances commonly used to create such vehicles include but are not limited to *theobroma* oil (also known as cocoa butter), glycerinated gelatin, other glycerides, hydrogenated vegetable oils, mixtures of polyethylene glycols of various molecular weights and fatty acid esters of polyethylene glycol. See, for example: *Remington's Pharmaceutical Sciences,* 16th Ed., Mack Publishing, Easton, Pa., 1980, pp. 1530-1533 for further discussion of suppository dosage forms.

Compounds of the application may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, compounds of the application may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The compounds of the application including pharmaceutically acceptable salts, solvates and prodrugs thereof are suitably used on their own but will generally be administered in the form of a pharmaceutical composition in which the one or more compounds of the application (the active ingredient) is in association with a pharmaceutically acceptable carrier. Depending on the mode of administration, the pharmaceutical composition will comprise from about 0.05 wt % to about 99 wt % or about 0.10 wt % to about 70 wt %, of the active ingredient (one or more compounds of the application), and from about 1 wt % to about 99.95 wt % or about 30 wt % to about 99.90 wt % of a pharmaceutically acceptable carrier, all percentages by weight being based on the total composition.

Compounds or composition of the application may be used alone or in combination with other known agents useful for treating diseases, disorders or conditions treatable by inhibiting interactions with BCL6 BTB. When used in combination with other agents useful in treating diseases, disorders or conditions that are treatable by inhibiting interactions with BCL6 BTB, it is an embodiment that the compounds of the application are administered contemporaneously with those agents. As used herein, "contemporaneous administration" of two substances to a subject means providing each of the two substances so that they are both biologically active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances. It is a further embodiment of the present application that a combination of agents is administered to a subject in a non-contemporaneous fashion. In an embodiment, a compound of the present application is administered with another therapeutic agent simultaneously or sequentially in separate unit dosage forms or together in a single unit dosage form. Accordingly, the present application provides a single unit dosage form comprising one or more compounds of the application (e.g. a compound of Formula I), an additional therapeutic agent, and a pharmaceutically acceptable carrier.

The dosage of compounds of the application can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the subject to be treated. One of skill in the art can determine the appropriate dosage based on the above factors. Compounds of the application may be administered initially in a suitable dosage that may be adjusted as required, depending on the clinical response. Dosages will generally be selected to maintain a serum level of compounds of the application from about 0.01 μg/cc to about 1000 μg/cc, or about 0.1 μg/cc to about 100 μg/cc. As a representative example, oral dosages of one or more compounds of the application will range between about 1 mg per day to about 1000 mg per day for an adult, suitably about 1 mg per day to about 500 mg per day, more suitably about 1 mg per day to about 200 mg per day. For parenteral administration, a representative amount is from about 0.001 mg/kg to about 10 mg/kg, about 0.01 mg/kg to about 10 mg/kg, about 0.01 mg/kg to about 1 mg/kg or about 0.1 mg/kg to about 1 mg/kg will be administered. For oral administration, a representative amount is from about 0.001 mg/kg to about 10 mg/kg, about 0.1 mg/kg to about 10 mg/kg, about 0.01 mg/kg to about 1 mg/kg or about 0.1 mg/kg to about 1 mg/kg. For administration in suppository form, a representative amount is from about 0.1 mg/kg to about 10 mg/kg or about 0.1 mg/kg to about 1 mg/kg. Compounds of the application may be administered in a single daily, weekly or monthly dose or the total daily dose may be divided into two, three or four daily doses.

To be clear, in the above, the term "a compound" also includes embodiments wherein one or more compounds are referenced.

III. Methods and Uses

The compounds of the application have been shown to be capable of inhibiting or blocking the interaction of BCL6 BTB binding domain with its corepressor binding partner SMRT/NCOR. The compounds have also been shown to inhibit tumor cell growth, specifically the Karpas-422 cell line.

Accordingly, the present application includes a method for inhibiting interactions with BCL6 BTB in a cell, either in a biological sample or in a patient, comprising administering an effective amount of one or more compounds or compositions of the application to the cell. The application also includes a use of one or more compounds of the application for inhibiting interactions with BCL6 BTB in a cell as well as a use of one or more compounds or compositions of the application for the preparation of a medicament for inhibiting interactions with BCL6 BTB interaction in a cell. The application further includes one or more compounds or compositions of the application for use in inhibiting interactions with BCL6 BTB protein.

As the compounds of the application have been shown to be capable of inhibiting interactions with BCL6 BTB, the compounds or compositions of the application are useful for treating diseases, disorders or conditions by inhibiting interactions with BCL6 BTB. Therefore the compounds of the present application are useful as medicaments. Accordingly, the present application includes a compound of the application for use as a medicament.

The present application also includes a method of treating a disease, disorder or condition that is treatable by inhibiting interactions with BCL6 BTB comprising administering a therapeutically effective amount of one or more compounds or compositions of the application to a subject in need thereof.

The present application also includes a use of one or more compounds or compositions of the application for treatment of a disease, disorder or condition that is treatable by inhibiting interactions with BCL6 BTB as well as a use of one or more compounds or compositions of the application for the preparation of a medicament for treatment of a disease, disorder or condition that is treatable by inhibiting interactions with BCL6 BTB. The application further includes one or more compounds or compositions of the application for use in treating a disease, disorder or condition that is treatable by inhibiting interactions with BCL6 BTB.

In an embodiment, the disease, disorder or condition is a neoplastic disorder. Accordingly, the present application also includes a method of treating a neoplastic disorder comprising administering a therapeutically effective amount of one or more compounds or compositions of the application to a subject in need thereof. The present application also includes a use of one or more compounds of the application for treatment of a neoplastic disorder as well as a use of one or more compounds of the application for the preparation of a medicament for treatment of a neoplastic disorder. The application further includes one or more compounds of the application for use in treating a neoplastic disorder. In an embodiment, the treatment is in an amount effective to ameliorate at least one symptom of the neoplastic disorder, for example, reduced cell proliferation or reduced tumor mass, among others, in a subject in need of such treatment.

Compounds of the application have been demonstrated to inhibit the growth of Karpas422 cells. Therefore in another embodiment of the present application, the disease, disorder or condition that is treatable by inhibiting interactions with BCL6 BTB is cancer. Accordingly, the present application also includes a method of treating cancer comprising administering a therapeutically effective amount of one or more compounds of the application to a subject in need thereof. The present application also includes a use of one or more compounds of the application for treatment of cancer as well as a use of one or more compounds of the application for the preparation of a medicament for treatment of cancer. The application further includes one or more compounds of the application for use in treating cancer. In an embodiment, the compound is administered for the prevention of cancer in a subject such as a mammal having a predisposition for cancer.

In an embodiment, the cancer is selected from hematologic cancers, breast cancers, ovarian cancers and glioblastomas. In some embodiments, the cancer is a B-cell lymphoma. In some embodiments, the cancer is a non-Hodgkins lymphoma or a follicular lymphoma. In some embodiments, the cancer is diffuse large B cell lymphoma (DLBCL). In some embodiments, the cancer is a leukemia. In some embodiments, the cancer is BCR-ABL1-positive leukemia. In some embodiments, the cancer is chronic myeloid leukemia (CML) or acute lymphoblastic leukemia (ALL).

In an embodiment, the disease, disorder or condition that is treatable by inhibiting interactions with BCL6 BTB is a disease, disorder or condition associated with an uncontrolled and/or abnormal cellular activity affected directly or indirectly by inhibiting interactions with BCL6 BTB. In another embodiment, the uncontrolled and/or abnormal cellular activity that is affected directly or indirectly by inhibiting interactions with BCL6 BTB is proliferative activity in a cell. Accordingly, the application also includes a method of inhibiting proliferative activity in a cell, comprising administering an effective amount of one or more compounds or compositions of the application to the cell. The present application also includes a use of one or more compounds of the application for inhibition of proliferative activity in a cell as well as a use of one or more compounds or compositions of the application for the preparation of a medicament for inhibition of proliferative activity in a cell. The application further includes one or more compounds or compositions of the application for use in inhibiting proliferative activity in a cell.

The present application also includes a method of inhibiting uncontrolled and/or abnormal cellular activities affected directly or indirectly by inhibiting interactions with BCL6 BTB in a cell, either in a biological sample or in a subject, comprising administering an effective amount of one or more compounds of the application to the cell. The application also includes a use of one or more compounds or compositions of the application for inhibition of uncontrolled and/or abnormal cellular activities affected directly or indirectly by inhibiting interactions with BCL6 BTB in a cell as well as a use of one or more compounds or compositions of the application for the preparation of a medicament for inhibition of uncontrolled and/or abnormal cellular activities affected directly or indirectly by inhibiting interactions with BCL6 BTB in a cell. The application further includes one or more compounds or compositions of the application for use in inhibiting uncontrolled and/or abnormal cellular activities affected directly or indirectly by inhibiting interactions with BCL6 BTB in a cell.

Accordingly, the present application also includes a method of treating a disease, disorder or condition that is treatable by inhibiting interactions with BCL6 BTB comprising administering a therapeutically effective amount of one or more compounds or compositions of the application in combination with another known agent useful for treatment of a disease, disorder or condition that is treatable by inhibiting interactions with BCL6 BTB to a subject in need thereof. The present application also includes a use of one or more compounds or compositions of the application in combination with another known agent useful for treatment of a disease, disorder or condition that is treatable by inhibiting interactions with BCL6 BTB for treatment of a disease, disorder or condition that is treatable by inhibiting interactions with BCL6 BTB, as well as a use of one or more compounds or compositions of the application in combination with another known agent useful for treatment of a disease, disorder or condition that is treatable by inhibiting interactions with BCL6 BTB for the preparation of a medicament for treatment of a disease, disorder or condition that is treatable by inhibiting interactions with BCL6 BTB. The application further includes one or more compounds or compositions of the application in combination with another known agent useful for treatment of a disease, disorder or condition that is treatable by inhibiting interactions with BCL6 BTB for use in treating a disease, disorder or condition that is treatable by inhibiting interactions with BCL6 BTB. In an embodiment, the disease, disorder or condition treatable by inhibiting interactions with BCL6 BTB is cancer.

In a further embodiment, the disease, disorder or condition that is treatable by inhibiting interactions with BCL6 BTB is cancer and the one or more compounds of the application are administered in combination with one or more additional cancer treatments. In another embodiment, the additional cancer treatment is selected from radiotherapy, chemotherapy, targeted therapies such as antibody therapies and small molecule therapies such as tyrosine-kinase inhibitors therapies, immunotherapy, hormonal therapy and anti-angiogenic therapies.

In some embodiments the interactions that are being inhibited are protein-protein interactions between BCL6 BTB and another protein. In some embodiments, the other protein is a corepressor BCL6 BTB binding protein. In some embodiments the protein is selected from SMRT, NCOR and BCOR.

In some embodiments, the subject is a mammal. In some embodiments, the subject is human.

IV. Methods of Preparation of Compounds of the Application

Compounds of the present application can be prepared by various synthetic processes. The choice of particular structural features and/or substituents may influence the selection of one process over another. The selection of a particular process to prepare a given compound of Formula I is within the purview of the person of skill in the art. Some starting materials for preparing compounds of the present application are available from commercial chemical sources. Other starting materials, for example as described below, are readily prepared from available precursors using straightforward transformations that are well known in the art.

The compounds of Formula I generally can be prepared according to the processes illustrated in the Schemes below. In the structural formulae shown below the variables are as defined in Formula I unless otherwise stated. A person skilled in the art would appreciate that many of the reactions depicted in the Schemes below would be sensitive to oxygen and water and would know to perform the reaction under an anhydrous, inert atmosphere if needed. Reaction temperatures and times are presented for illustrative purposes only and may be varied to optimize yield as would be understood by a person skilled in the art.

Accordingly in some embodiments, the compounds of Formula I are prepared as shown in Scheme 1.

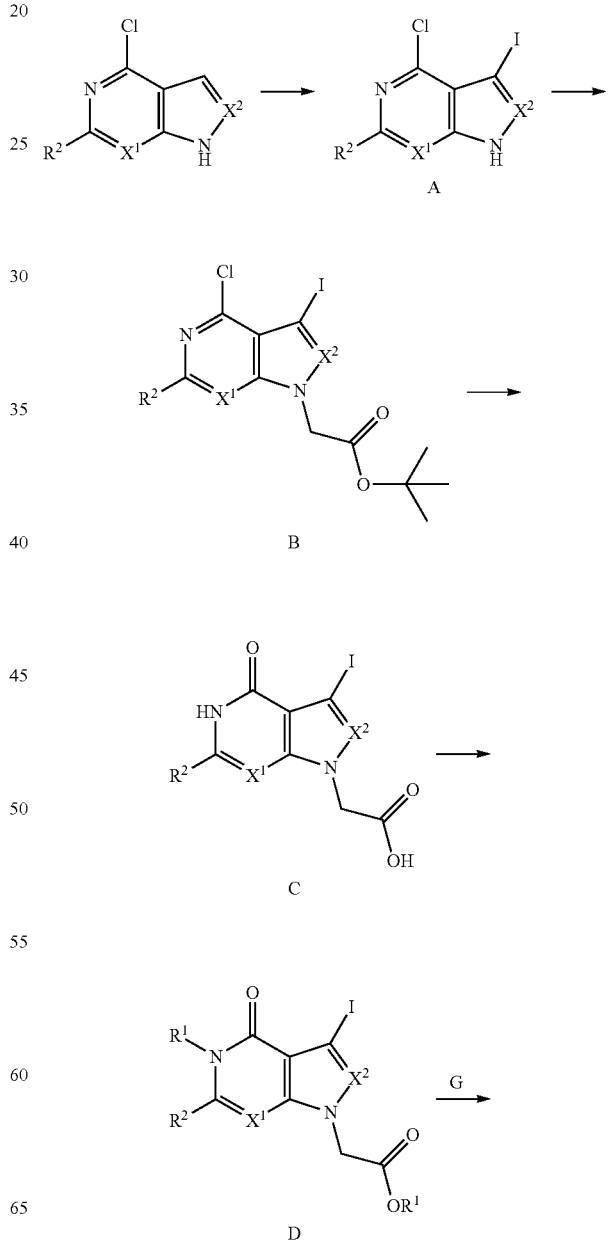

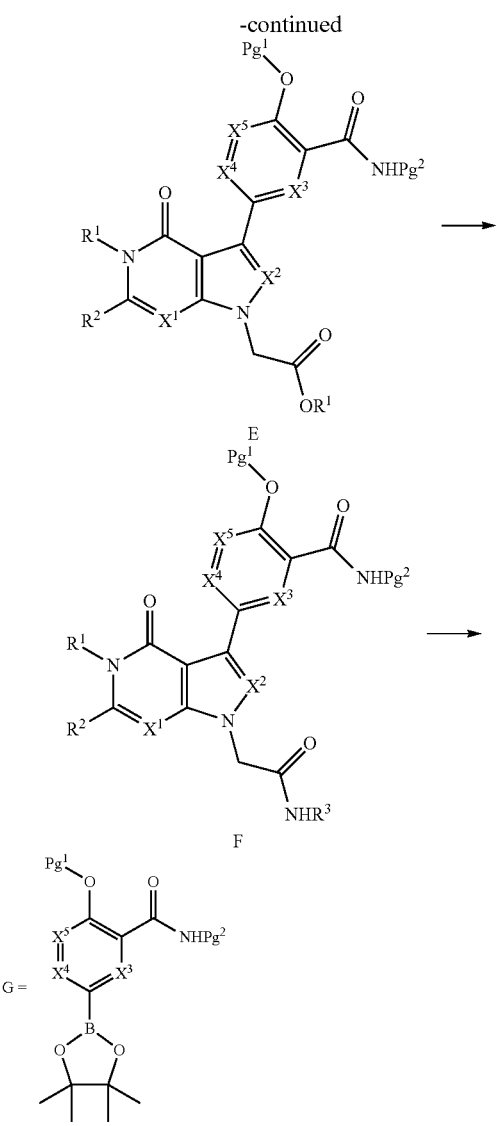

under base-mediated conditions gives the intermediate B. Hydrolysis of B in, for example, aqueous NaOH/Dioxane mixtures give the acid intermediate C. Alkylation of C with at least two equivalents of various alkylating agents ($R^1LG$, where LG represents a leaving group such as halogen, mesylate, tosylate etc.) provides D. Subsequent coupling of boronate ester G under Suzuki conditions provides ester E which upon Grignard-mediated coupling with various amines (e.g $R^3$—$NH_2$) affords intermediate F. Subjecting F to acid mediated deprotection conditions provides compounds of Formula I.

Alternatively, in some embodiments, compounds of Formula I may also be prepared from intermediate C via methyl ester D as shown in Scheme 2, in a similar manner according to Scheme 1.

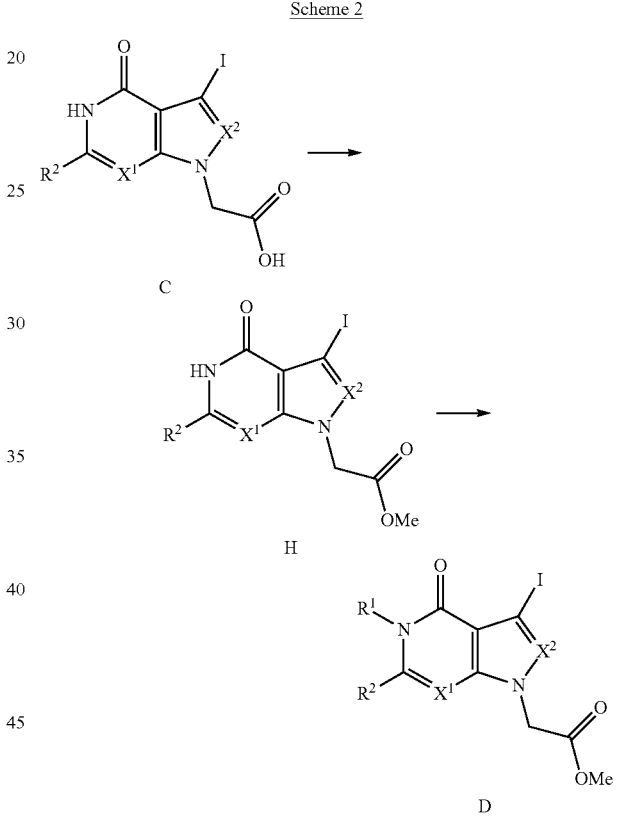

Therefore, compounds of Formula I may be readily prepared by treating agents such as 6-substituted 4-chloro-7H-pyrrolo[2,3-d]pyrimidine, 4-chloro-7H-pyrrolo[2,3-d]pyridine, 4-chloro-7H-pyrazolo[2,3-d]pyridine or 4-chloro-7H-pyrazolo[2,3-d]pyrimidine (some of which are commericially available) with a halogenating reagent such as N-halosuccinamides (e.g NIS or NBS) to give intermediate A (shown in Scheme 1 as iodinated with for example NIS). Subsequent treatment of A with t-butylbromoacetate In some embodiments, compounds of Formule I, wherein $R^2$=Aryl, Heteroaryl, vinyl, alkylamino, alkoxy, haloalkyl amino can be readily prepared according to Scheme 3.

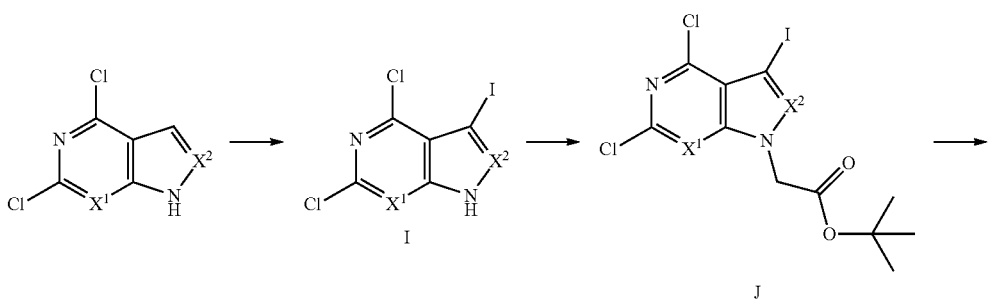

-continued

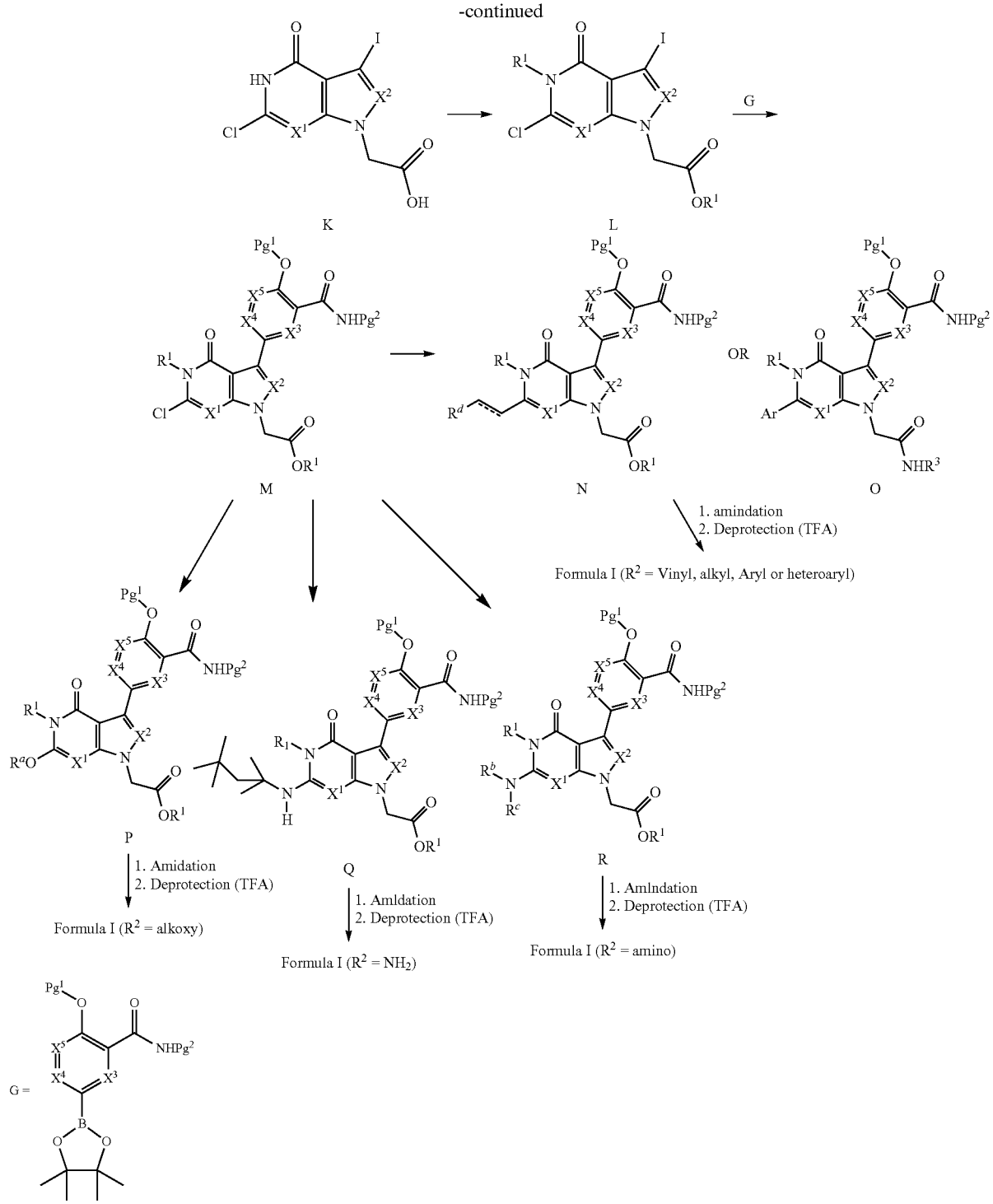

Therefore, in some embodiments, treatment of reagents such as i with t-butylbromoacetate under base-mediated conditions gives the intermediate J. Hydrolysis of J in, for example, aqueous NaOH/Dioxane mixtures provides the acid intermediate K. Alkylation of K with at least two equivalents of various alkylating agents (such as MeI, $R^1$=Me) provides L. Selective coupling of, for example, boronate ester G under Suzuki conditions give the versatile intermediate chloro ester M. Subsequent coupling of boronic acids or esters, alkoxides, amines under a variety of C—C, C—O and C—N coupling conditions provides intermediates N, O, P, Q or R which upon Grignard-mediated coupling with various amines (e.g $R^3$—$NH_2$) provides protected intermediates, which after acid-mediated deprotection (e.g. TFA), affords compounds of Formula I. Note that $R^a$, $R^b$, $R^c$ and $R^d$ are various functional groups that would allow intermediates N, O, P, Q and R to fall within the definition of $R^2$ in the compounds of Formula I.

In some embodiments, compounds of Formula I may also be prepared from D via Suzuki coupling to S followed by subsequent hydrolysis of S to give acid T, which upon coupling with various activating agents (e.g HATU, TBTU, alkylchloroformates) and amines, affords intermediate F. Acid mediated deprotection (e.g. TFA) of F provides the desired compounds of Formula I (Scheme 4).

example, TFA-mediated hydrolysis to give pyrimidone V which on base mediated alkylation affords intermediate W. Treatment of W with boronate esters or acids under Suzuki conditions gives the deacetylated intermediate X. Subsequent alkylation of X with various haloacetyl amides (prepared from haloacetyl halides and amines $R^3NH_2$) in the presence of a base (e.g. NaH, $Cs_2CO_3$, etc.) provides intermediate F. Subjecting F to acid mediated deprotection conditions provides compounds of Formula I (Scheme 5)

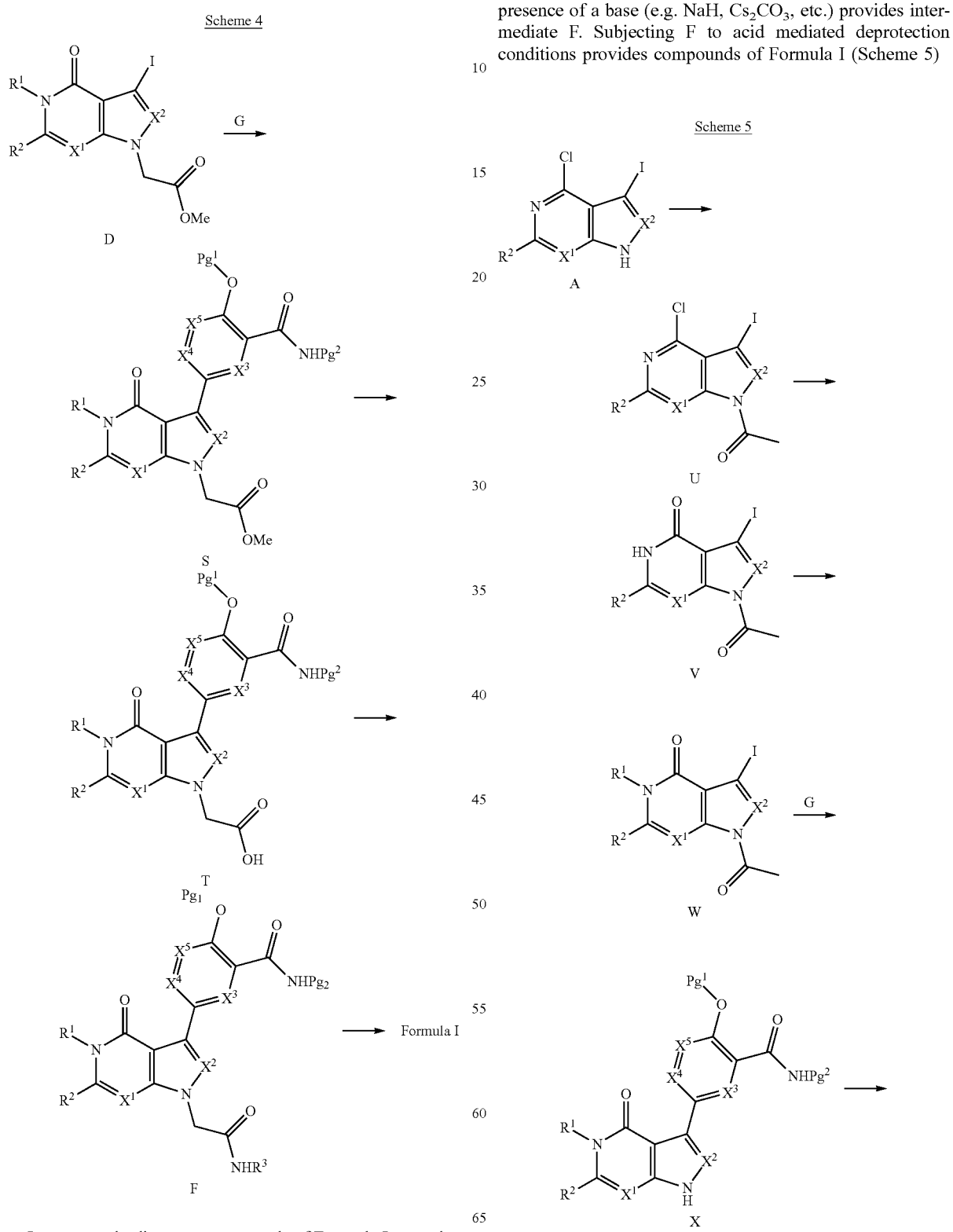

In some embodiments, compounds of Formula I may also be prepared from A via acetylation to U followed by, for

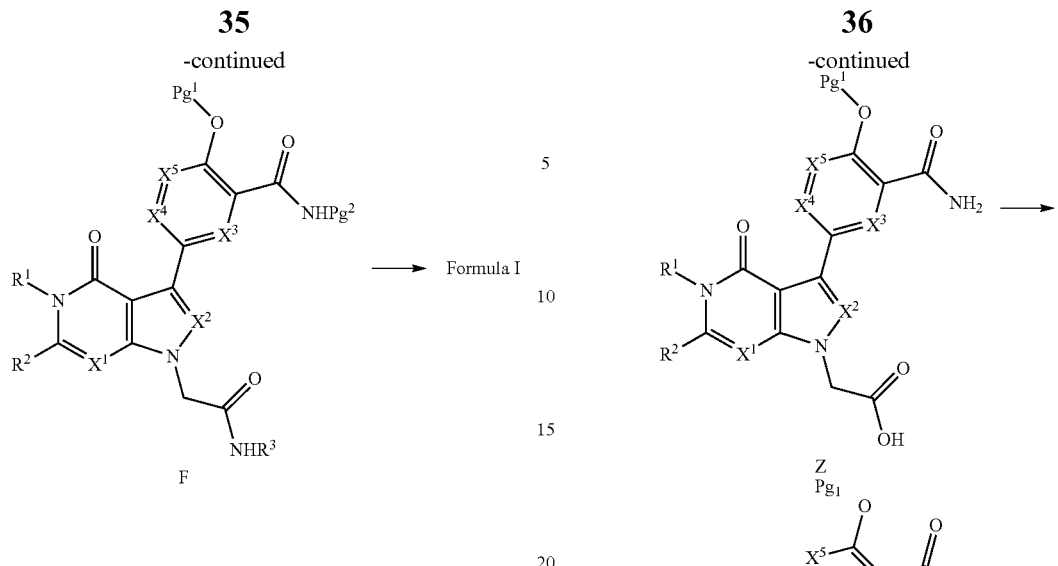

In some embodiments, compounds of Formula I may also be prepared by treating ester D with 2-hydroxy nitrile boronate esters or acids (G1) under Suzuki conditions to give intermediate Y. Subsequent hydrolysis of the nitrile-ester Y with peroxide under basic conditions provides the carboxamide acid Z. Re-esterification of Z with MeI or EtI in the presence of a base (e.g. $Na_2CO_3$, $Cs_2CO_3$, etc.) provides intermediate A1. Grignard mediated coupling of A1 with various amines (e.g $R^3$—$NH_2$) affords intermediate A2. Treatment of A2 under acid mediated deprotection conditions provides compounds of Formula I (Scheme 6).

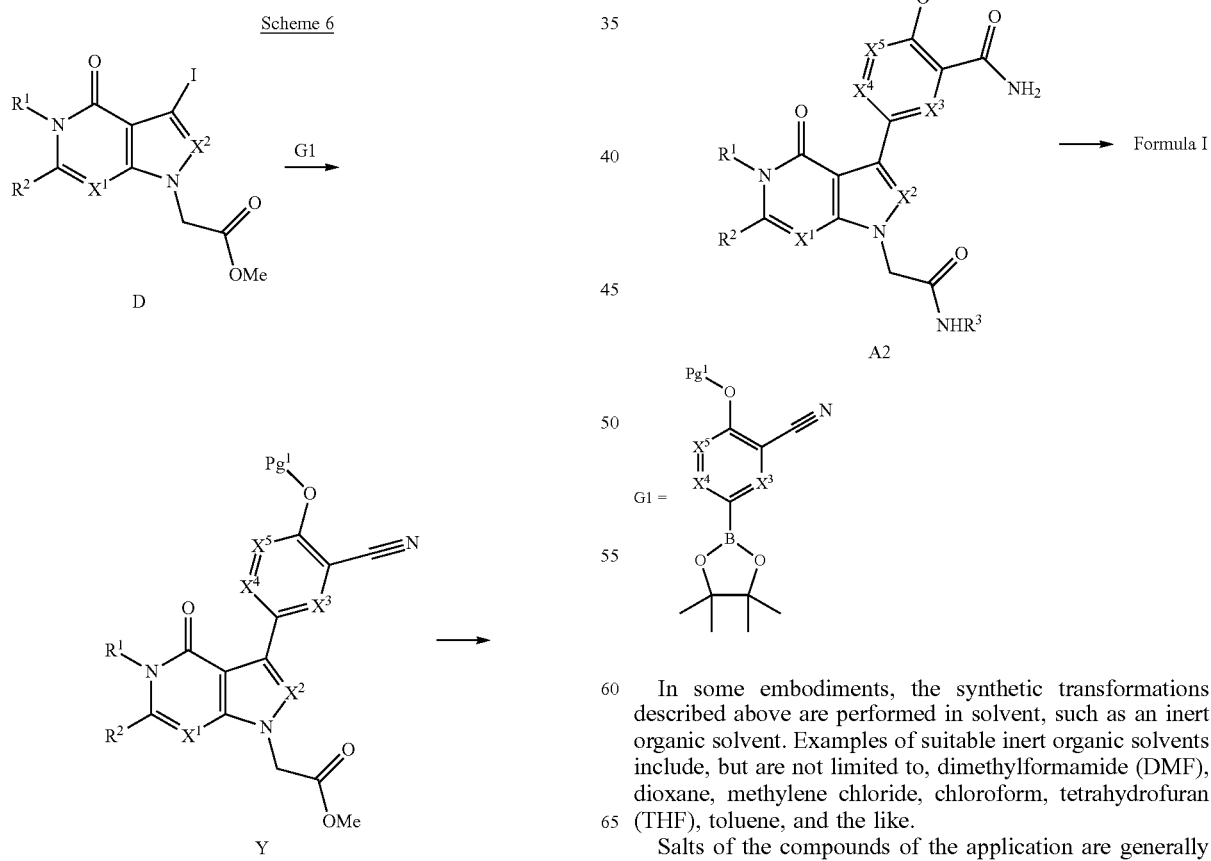

In some embodiments, the synthetic transformations described above are performed in solvent, such as an inert organic solvent. Examples of suitable inert organic solvents include, but are not limited to, dimethylformamide (DMF), dioxane, methylene chloride, chloroform, tetrahydrofuran (THF), toluene, and the like.

Salts of the compounds of the application are generally formed by dissolving the neutral compound in an inert organic solvent and adding either the desired acid or base and isolating the resulting salt by either filtration or other known means.

The formation of solvates of the compounds of the application will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

Prodrugs of the compounds of the present application may be, for example, conventional esters formed with available hydroxy, thiol, amino or carboxyl groups. For example, available hydroxy or amino groups may be acylated using an activated acid in the presence of a base, and optionally, in inert solvent (e.g. an acid chloride in pyridine).

The following non-limiting examples are illustrative of the present application:

EXAMPLES

Example 1: Synthesis and Characterization of Compounds

Synthesis of 4-chloro-5-iodo-7H-pyrrolo[2,3-d]pyrimidine (A-1)

To a suspension of 4-chloro-7H-pyrrolo [2,3-d]pyrimidine (17.00 g, 111 mmol) in N,N-dimethylformamide (DMF) (Volume: 50 ml) was added 1-iodopyrrolidine-2,5-dione (29.9 g, 133 mmol) and the mixture was stirred at room temperature over-night. The reaction was quenched with ice-cold water (~200 g) and extracted with EtOAc (500 mL×2). The organic layers were combined, dried over $Na_2SO_4$ and concentrated in vacuo. The crude residue was triturated with water (~1 L), filtered and the filter cake was vacuum dried to afford the desired product 4-chloro-5-iodo-7H-pyrrolo[2,3-d]pyrimidine (28 g, 88% yield). $[M+H]^+$ 279.85.

In a similar manner the following compounds were synthesized:

| | | |
|---|---|---|
| A-2 | 4-chloro-5-iodo-2-methyl-7H-pyrrolo[2,3-d]pyrimidine | 97% yield, LCMS $[M + H]^+$ 294 |
| A-3 | 4-chloro-5-iodo-2-(trifluoromethyl)-7H-pyrrolo[2,3-d]pyrimidine | 93% yield, LCMS $[M + H]^+$ 348 |
| A-4 (i-1) | 2,4-dichloro-5-iodo-7H-pyrrolo[2,3-d]pyrimidine | 100% yield, LCMS $[M + H]+$ 314 |

Synthesis of tert-butyl 2-(4-chloro-5-iodo-7H-pyrrolo[2,3-d]pyrimidin-7-yl)acetate (B-1)

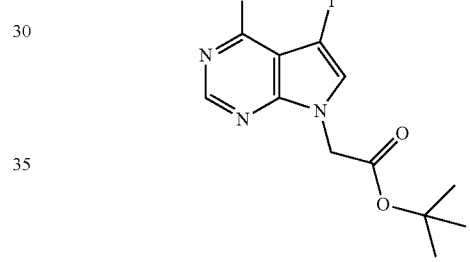

To a solution of the 4-chloro-5-iodo-7H-pyrrolo[2,3-d]pyrimidine (22 g, 79 mmol) in N,N-dimethylformamide (DMF) (Volume: 120 ml) was added cesium carbonate (51.3 g, 157 mmol). Tert-butyl 2-bromoacetate (16.07 ml, 110 mmol) was then added and the mixture was stirred at room temperature for two hours. The reaction was poured into ice-cold water (~200 ml) and stirred for an hour. Then precipitate was filtered and vacuum dried to afford the desired the product (27.10 g, 84% yield). $[M+H]^+$ 393.75.

In a similar manner the following compounds were synthesized:

| | | | |
|---|---|---|---|
| B-2 | | tert-butyl 2-(4-chloro-5-iodo-2-methyl-7H-pyrrolo[2,3-d]pyrimidin-7-yl)acetate | 84% yield, LCMS $[M + H]^+$ 408 |

| | | | |
|---|---|---|---|
| B-3 | 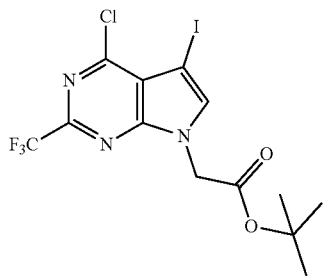 | tert-butyl 2-(4-chloro-5-iodo-2-(trifluoromethyl)-7H-pyrrolo[2,3-d]pyrimidin-7-yl)acetate | 100% yield, LCMS [M + H]+ 462 |
| J-1 | 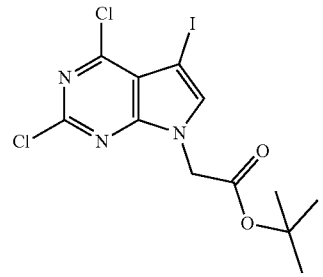 [SMILES: CC(C)(C)OC(=O)Cn1cc(I)c2c(Cl)nc(Cl)nc21] tert-butyl 2-(2,4-dichloro-5-iodo-7H-pyrrolo[2,3-d]pyrimidin-7-yl)acetate Exact Mass: 426.94 | | 94% yield, LCMS [M + H]+ 428 |

Synthesis of 2-(5-iodo-4-oxo-3H-pyrrolo[2,3-d]pyrimidin-7(4H)-yl)acetic Acid (C-1)

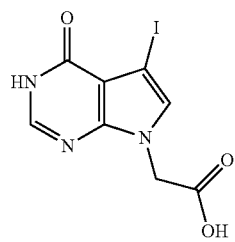 [SMILES: O=C(O)Cn1cc(I)c2c(=O)[nH]cnc21]

To a solution of tert-butyl 2-(4-chloro-5-iodo-7H-pyrrolo[2,3-d]pyrimidin-7-yl)acetate (27.1 g, 68.9 mmol) in water (Volume: 50 ml, Ratio: 1) and 1,4-dioxane (Volume: 50 ml, Ratio: 1.000) was added sodium hydroxide (12.81 g, 320 mmol) and the mixture was heated to reflux for 3 hrs. The reaction mixture was then cooled to room temperature, extracted with ether (200 mL×2) to remove dioxane and the aqueous layer was concentrated to dryness. The residue was then neutralized with ice cold 6M HCl (320 mmol HCl in 200 mL water) and the resulting precipitate was filtered and vacuum dried to afford the desired the product, 2-(5-iodo-4-oxo-3H-pyrrolo[2,3-d]pyrimidin-7(4H)-yl)acetic acid (21.5 g, 93% yield). [M+H]+ 319.85.

In a similar manner the following compounds were synthesized:

| | | | |
|---|---|---|---|
| C-2 | 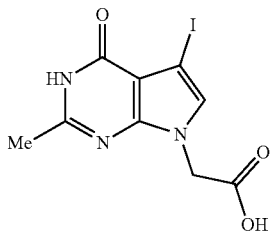 [SMILES: Cc1nc2c(c(I)cn2CC(=O)O)c(=O)[nH]1] | 2-(5-iodo-2-methyl-4-oxo-3H-pyrrolo[2,3-d]pyrimidin-7(4H)-yl)acetic acid | 96% yield, LCMS [M + H]+ 334 |
| C-3 | 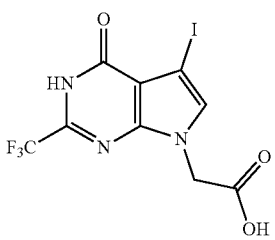 | 2-(5-iodo-4-oxo-2-(trifluoromethyl)-3H-pyrrolo[2,3-d]pyrimidin-7(4H)-yl)acetic acid | 87% yield, LCMS [M + H]+ 388 |

| | | | |
|---|---|---|---|
| K-1 | 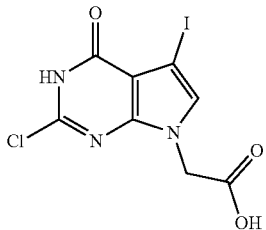 [SMILES: O=C(O)Cn1cc(I)c2c(=O)[nH]c(Cl)nc21] | 2-(2-chloro-5-iodo-4-oxo-3H-pyrrolo[2,3-d]pyrimidin-7(4H)-yl)acetic acid<br>Exact Mass: 352.91 | 95% yield, LCMS [M + H]+ 354 |

Synthesis of methyl 2-(5-iodo-3-methyl-4-oxo-3H-pyrrolo[2,3-d]pyrimidin-7(4H)-yl)acetate (D-1)

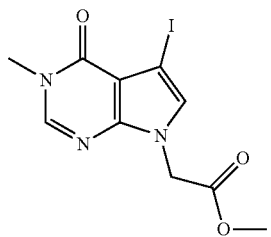

To a solution of the 2-(5-iodo-4-oxo-3H-pyrrolo[2,3-d]pyrimidin-7(4H)-yl)acetic acid (12.3 g, 38.6 mmol) in 40 mL of DMF was added Methyl iodide (12.17 ml, 193 mmol) followed by $Cs_2CO_3$ (25.1 g, 77 mmol). The reaction mixture was stirred at room temperature for 16 h. The mixture was filtered through celite and the filtrate was concentrated in vacuo. The residue was dissolved in $CH_2Cl_2$ (100 ml) followed by water extraction (2×50 ml). The organic layer was washed with brine and dried over $Na_2SO_4$ (anhydrous). The product mixture was filtered and the filtrate was concentrated to give 9 g of the title compound as a tan solid (64% yield); LCMS $[M+1]^+=348$ In a similar manner the following compounds were synthesized:

| | | | |
|---|---|---|---|
| D-2 | 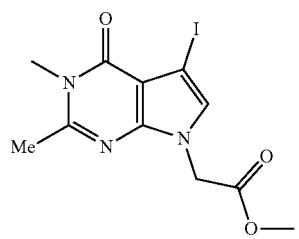 | methyl 2-(5-iodo-2,3-dimethyl-4-oxo-3H-pyrrolo[2,3-d]pyrimidin-7(4H)-yl)acetate | 93% yield, LCMS [M + H]+ 362 |
| D-3 | 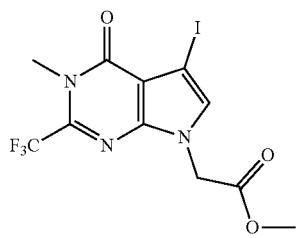 [SMILES: COC(=O)Cn1cc(I)c2c(=O)n(C)c(C(F)(F)F)nc21] | methyl 2-(5-iodo-3-methyl-4-oxo-2-(trifluoromethyl)-3H-pyrrolo[2,3-d]pyrimidin-7(4H)-yl)acetate | 23% yield, LCMS [M + H]+ 416 |
| D-4 | 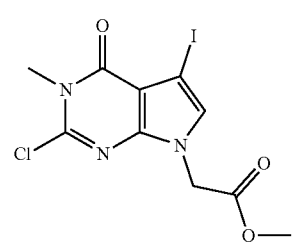 [SMILES: COC(=O)Cn1cc(I)c2c(=O)n(C)c(Cl)nc21] | methyl 2-(2-chloro-5-iodo-3-methyl-4-oxo-3H-pyrrolo[2,3-d]pyrimidin-7(4H)-yl)acetate<br>Exact Mass: 380.94 | 86% yield, LCMS [M + H]+ 382 |

Synthesis of methyl 2-(2-chloro-5-iodo-3-(methoxymethyl)-4-oxo-3,4-dihydro-7H-pyrrolo[2,3-d]pyrimidin-7-yl)acetate (L-1)

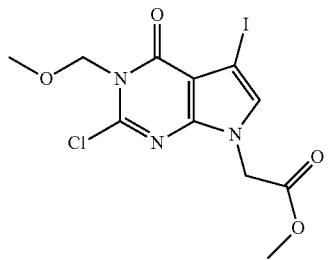 [SMILES: COCn1c(Cl)nc2c(c(I)cn2CC(=O)OC)c1=O]

To a solution of methyl 2-(2-chloro-5-iodo-4-oxo-3,4-dihydro-7H-pyrrolo[2,3-d]pyrimidin-7-yl)acetate (1.85 g, 5.03 mmol) in N,N-Dimethylformamide (DMF) (10 ml) at 23° C. Cesium carbonate (3.28 g, 10.07 mmol)-(suspension observed), followed by chloromethyl methyl ether (0.527 g, 6.54 mmol) were added dropwise over 10 min. This suspension was agitated at 23° C. over 30 min, after which the mixture was concentrated to dryness, quenched with ice-cold water, extracted with EtOAc and purified by ISCO (0-5-40% EA/Hex; 12 g column; 30 min) to give the desired product, methyl 2-(2-chloro-5-iodo-3-(methoxymethyl)-4-oxo-3,4-dihydro-7H-pyrrolo[2,3-d]pyrimidin-7-yl)acetate (2.77 mmol, 55.0% yield as white powder. LCMS [M+H]⁺ 412

Synthesis of 2-(5-iodo-2-methoxy-3-methyl-4-oxo-3H-pyrrolo[2,3-d]pyrimidin-7(4H)-yl)acetic Acid (D-5)

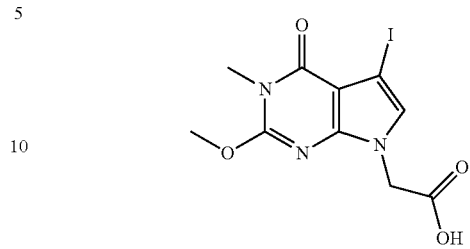

Methyl 2-(2-chloro-5-iodo-3-methyl-4-oxo-3H-pyrrolo[2,3-d]pyrimidin-7(4H)-yl)acetate (500 mg, 1.310 mmol) and sodium methoxide (95%, powder) (708 mg, 13.10 mmol) were charged in a microwave vial. MeOH was added to this mixture and the mixture was heated in the microwave for 30 min at 110° C. The mixture was acidified to ph~4 by HCl (1 N) solution. The methanol was evaporated and the resulting white solid was then washed with water, filtered and dried overnight under high vacuum to give the desired product as a white solid (209 mg, 44% yield); LCMS [M+1]⁺=364

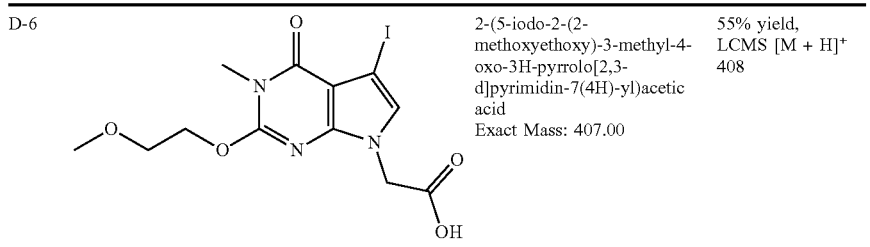

| D-6 | 2-(5-iodo-2-(2-methoxyethoxy)-3-methyl-4-oxo-3H-pyrrolo[2,3-d]pyrimidin-7(4H)-yl)acetic acid Exact Mass: 407.00 | 55% yield, LCMS [M + H]⁺ 408 |
| --- | --- | --- |

Synthesis of methyl 2-(5-iodo-2-methoxy-3-methyl-4-oxo-3H-pyrrolo[2,3-d]pyrimidin-7(4H)-yl)acetate (D-7)

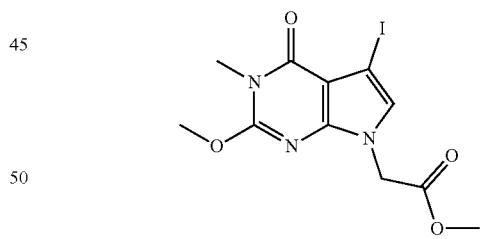

To a solution mixture of 2-(5-iodo-2-methoxy-3-methyl-4-oxo-3H-pyrrolo[2,3-d]pyrimidin-7(4H)-yl)acetic acid and Cesium carbonate (202 mg, 0.621 mmol) in DMF (Volume: 2.5 ml), was added dropwise, Iodomethane (0.037 ml, 0.593 mmol). The reaction was stirred at room temperature for 1 h. An additional 6 ul of MeI was added and the reaction was stirred for another 8 min. The DMF was evaporated and the residue was acidified with HCl (1 N). The residue was dissolved in CH₂Cl₂ followed by water extraction. The organic layer was washed with brine and dried over Na₂SO₄ (anhydrous). The crude product was purified by silica-gel column chromatography (4 g cartridge: Eluent 0%, 0-7% then 7% MeOH/DCM) to afford the right product as a white powder. (198 mg, 93% yield); LCMS [M+1]⁺=378

| D-8 | 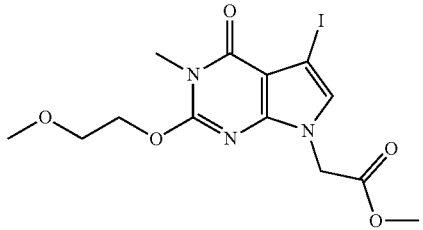 | methyl 2-(5-iodo-2-(2-methoxyethoxy)-3-methyl-4-oxo-3H-pyrrolo[2,3-d]pyrimidin-7(4H)-yl)acetate<br>Exact Mass: 421.01 | 14% yield, LCMS [M + H]⁺ 422 |

Synthesis of 2-(5-iodo-3-methyl-4-oxo-3H-pyrrolo[2,3-d]pyrimidin-7(4H)-yl)acetic Acid (D-9)

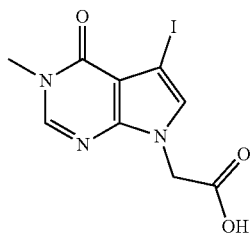 [SMILES: Cn1cnc2c(c(I)cn2CC(=O)O)c1=O]

To a solution of methyl 2-(5-iodo-3-methyl-4-oxo-3H-pyrrolo[2,3-d]pyrimidin-7(4H)-yl)acetate (9.00 g, 25.9 mmol) in tetrahydrofuran (THF) (Volume: 80 ml, Ratio: 1.000) was added a solution of lithium hydroxide monohydrate (5.60 g, 133 mmol in 80 ml of water) and the mixture was stirred at room temperature until judged complete by LCMS. The solvent was removed vacuum and ice cold-dilute 1 N HCl was added. The resulting precipitate was filtered vacuum dried to afford the desired the product (7.255 g, 80% yield). [M+H]⁺ 334.01.

Alternative synthesis of methyl 2-(5-iodo-3-methyl-4-oxo-3H-pyrrolo[2,3-d]pyrimidin-7(4H)-yl)acetate (D-1)

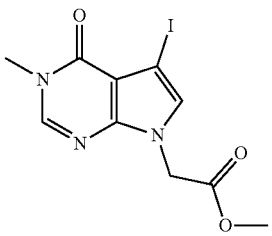

To a solution of the methyl 2-(5-iodo-4-oxo-3H-pyrrolo[2,3-d]pyrimidin-7(4H)-yl)acetate (10 g, 30.0 mmol) in 30 mL of DMF was added Methyl iodide (4.26 g, 30 mmol) followed by $Cs_2CO_3$ (11.7 g, 36 mmol). The reaction mixture was stirred at room temperature for 16 h. The mixture was filtered through celite and the filtrate was concentrated in vacuo. The residue was dissolved in $CH_2Cl_2$ (100 ml) followed by water extraction (2×50 ml). The organic layer was washed with brine and dried over $Na_2SO_4$ (anhydrous). The product mixture was filtered and the filtrate was concentrated to give 9 g of the title compound as a tan solid (9.84 g, 90% yield); LCMS [M+H]⁺348

In a similar manner the following compounds were synthesized:

| D-10 | 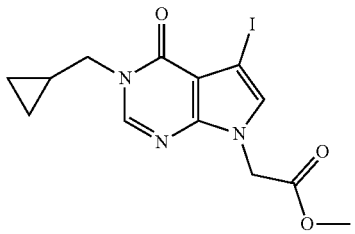 [SMILES: COC(=O)Cn1cc(I)c2c(=O)n(CC3CC3)cnc21] | methyl 2-(3-(cyclopropylmethyl)-5-iodo-4-oxo-3H-pyrrolo[2,3-d]pyrimidin-7(4H)-yl)acetate | 84% yield, LCMS [M + H]⁺ 388 |

| D-11 | 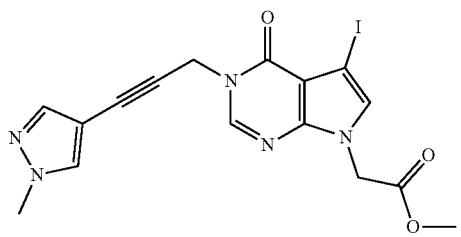 [SMILES: COC(=O)Cn1cc(I)c2c(=O)n(CC#Cc3cnn(C)c3)cnc21] | methyl 2-(5-iodo-3-(3-(1-methyl-1H-pyrazol-4-yl)prop-2-yn-1-yl)-4-oxo-3H-pyrrolo[2,3-d]pyrimidin-7(4H)-yl)acetate | 87% yield, LCMS [M + H]⁺ 452 |

Synthesis of N-(3-chloropyridin-4-yl)-2-(5-iodo-4-oxo-3H-pyrrolo[2,3-d]pyrimidin-7(4H)-yl)acetamide

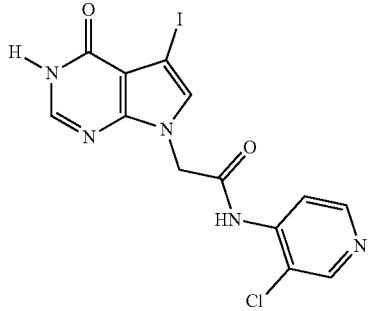 [SMILES: O=C(Cn1cc(I)c2c(=O)[nH]cnc21)Nc1ccncc1Cl]

To a 100 mL round bottom flask under N2 atmosphere was added 2-(5-iodo-4-oxo-3H-pyrrolo[2,3-d]pyrimidin-7(4H)-yl)acetic acid (4.625 g, 14.50 mmol), HATU (5.51 g, 14.50 mmol), 4-amino-3-chloropyridine (2.80 g, 21.74 mmol) and N,N-dimethylformamide (DMF) (Volume: 20 mL). The mixture was stirred at room temperature. After 10 minutes an additional 0.2 eqv HATU (1.102 g, 2.90 mmol) was added and the mixture was stirred overnight. Ether (300 mL) was added and the mixture agitated for about 10 minutes. Water (300 mL) was added and the mixture was vigorously stirred for 15 minutes. The resulting precipitate was filtered, dried under vacuum at 45-50° C. to afford the desired product (4.011 g, 59.3% yield). LCMS[M+H]$^+$ 431

Synthesis of methyl 2-(5-iodo-4-oxo-3H-pyrrolo[2,3-d]pyrimidin-7(4H)-yl)acetate (D-12)

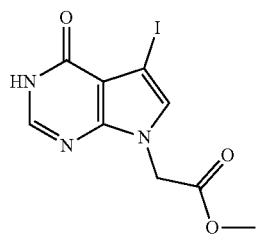 [SMILES: COC(=O)Cn1cc(I)c2c(=O)[nH]cnc21]

To a suspension of the 2-(5-iodo-4-oxo-3H-pyrrolo[2,3-d]pyrimidin-7(4H)-yl)acetic acid (1 g, 3.13 mmol) in Methanol (20 ml) was added a few drops of concentrated H$_2$SO$_4$. After stirring overnight, none of the desired methyl ester product was observed. Additional concentrated H$_2$SO$_4$ (3 ml) was added and the mixture was stirred at room temperature for an additional 2 h. Mixture was then filtered and the residue collected. The crude residue was dried to give an off white solid as the desired product (960 mg, 96% yield); LCMS [M+H]$^+$ 334

Synthesis of N-(3-chloropyridin-4-yl)-2-(5-iodo-3-methyl-4-oxo-3H-pyrrolo[2,3-d]pyrimidin-7(4H)-yl)acetamide

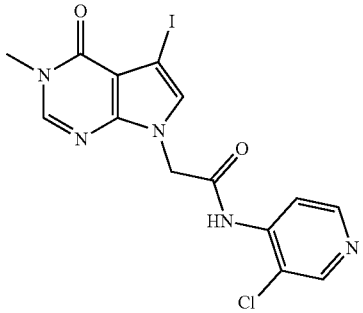 [SMILES: Cn1cnc2c(c(I)cn2CC(=O)Nc2ccncc2Cl)c1=O]

To a (100 mL) round bottom flask was added 2-(5-iodo-3-methyl-4-oxo-3H-pyrrolo[2,3-d]pyrimidin-7(4H)-yl)acetic acid (1.2 g, 3.60 mmol), HATU (1.370 g, 3.60 mmol) and 4-amino-3-chloropyridine (0.695 g, 5.40 mmol). N,N-dimethylformamide (DMF) (Volume: 7 mL) was added. The mixture was stirred at room temperature for 2 hrs after which an additional amount HATU (0.5 eqv) was added until reaction was judged complete by LCMS. A mixture of EtOAc/Hexanes (50 ml, 1:4) was added and the crude mixture stirred for an additional 5 minutes. The top layer was decanted and the resulting mixture was treated with 50 mL of water. The resulting precipitate was filtered, dried under vacuum at 45-50° C. to afford the desired product (1.582 g, 95% yield); LCMS [M+H]$^+$ 444.99.

Synthesis of 1-(4-chloro-5-iodo-7H-pyrrolo[2,3-d]pyrimidin-7-yl)ethanone (U-1)

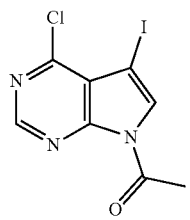

To a solution of 4-chloro-5-iodo-7H-pyrrolo[2,3-d]pyrimidine (0.98 g, 3.51 mmol) in Pyridine (Volume: 5 mL), was added acetic anhydride (1.074 g, 10.52 mmol). The mixture was agitated at 23° C. for 4 h. The reaction mixture was quenched with ice-cold HCl (2N, 20 mL), and the resulting suspension was filtered and the filter cake was washed with water and hexane (20 mL). The wet cake was vacuum oven dried to give the desired product, 1-(4-chloro-5-iodo-7H-pyrrolo[2,3-d]pyrimidin-7-yl)ethanone (0.82 g, 2.423 mmol, 69.1% yield), as a brown solid. LCMS [M+H]$^+$ 322.

Synthesis of 7-acetyl-5-iodo-3H-pyrrolo[2,3-d]pyrimidin-4(7H)-one (V-1)

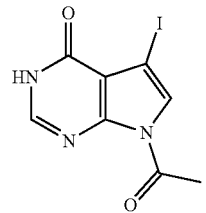

A suspension of 7-acetyl-5-iodo-3H-pyrrolo[2,3-d]pyrimidin-4(7H)-one (0.626 g, 1.964 mmol, 77% yield) in Acetonitrile (Volume: 8 mL, Ratio: 4.00) and Trifluoroacetic acid (TFA) (Volume: 2 mL, Ratio: 1.000) was agitated in a microwave for 60 min at 90° C. The reaction mixture was filtered and then washed with minimal DCM (10 mL). The wet cake thus obtained was vacuum dried to get the desired product, 7-acetyl-5-iodo-3H-pyrrolo[2,3-d]pyrimidin-4(7H)-one (0.626 g, 1.964 mmol, 77% yield) as a pale brown solid. LCMS [M+H]$^+$ 304

Synthesis of 7-acetyl-5-iodo-3-methyl-3H-pyrrolo[2,3-d]pyrimidin-4(7H)-one (W-1)

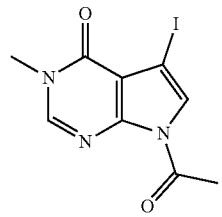

Iodomethane (0.616 ml, 9.90 mmol) was added dropwise to a stirring mixture of 7-acetyl-5-iodo-3H-pyrrolo[2,3-d]pyrimidin-4(7H)-one (2.5 g, 8.25 mmol) and and Cesium carbonate (2.96 g, 9.07 mmol) in DMF (Volume: 12 ml) at 0° C. After stirring for 10 minutes the ice bath was removed and the reaction was stirred at room temperature. After 1 h, LCMS analysis indicated clean methylation. The mixture was cooled to 0° C. and then neutralised with 1 N Aqueous HCl (4.95 ml, 4.95 mmol). The resulting colourless precipitate was collected by filtration and dried in vacuo overnight to afford 7-acetyl-5-iodo-3-methyl-3H-pyrrolo[2,3-d]pyrimidin-4(7H)-one (2.554 g, 8.05 mmol, 98% yield) as a colourless solid. 1H NMR (500 MHz, DMSO-d6) δ=8.46 (s, 1H), 7.76 (s, 1H), 3.48 (s, 3H), 2.82 (s, 3H); LCMS [M+H]+ 318

In a similar manner the following compounds were synthesized:

| | | | |
|---|---|---|---|
| W-2 | 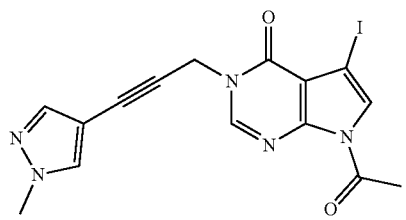 | 7-acetyl-5-iodo-3-(3-(1-methyl-1H-pyrazol-4-yl)prop-2-yn-1-yl)-3H-pyrrolo[2,3-d]pyrimidin-4(7H)-one | 63% yield, LCMS [M + H]$^+$ 559 |

Synthesis of 3-bromo-4-methoxy-1H-pyrazolo[3,4-d]pyrimidine (A-5)

To a suspension of 3-Bromo-4-chloro-1H-pyrazolo[3,4-d]pyrimidine in Methanol (10 mls) was added sodium methoxide (4.6 g, 86 mmol) and the mixture heated to 70° C. for 3 h. The crude residue was diluted with NH$_4$Cl (saturated), extracted with ethyl acetate (80 ml). The organic extract was then washed with brine and dried over Na$_2$SO$_4$ (anhydrous) and the solvent removed in vacuo. The residue was then triturated with cold hexane to give the desired product (1.7386 g, 89% yield) as a white solid. LCMS [M+1]+229

Synthesis of methyl 2-(3-bromo-4-methoxy-1H-pyrazolo[3,4-d]pyrimidin-1-yl)acetate (B-4)

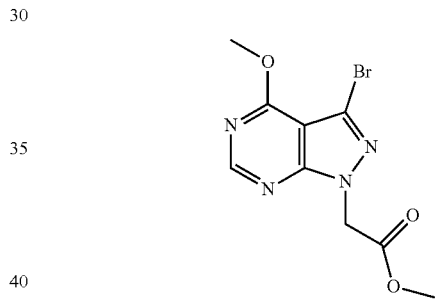

To a suspension of 3-bromo-4-methoxy-1H-pyrazolo[3,4-d]pyrimidine (1.3 g, 5.68 mmol, 1.0 equiv) in DMF (20 mL) was added Methyl Bromoacetate (0.645 ml, 6.81 mmol, 1.2 equiv). The reaction mixture was cooled to 0° C. and Cs$_2$CO$_3$ (3.70 g, 11.35 mmol, 2 equiv) was added and the reaction mixture was allowed to warm to rt and stirred for 3 h. The mixture diluted with DCM (30 ml) and then washed with water and brine. The organic phase was then dried over anhydrous Na$_2$SO$_4$ followed by removal of the solvent in vacuo. The crude residue was triturated with water, filtered and dried to give as an off white solid (1.5260 mg, 89%), which was used without further purification. LCMS [M+1]+ 301

51

Synthesis of methyl 2-(3-bromo-4-methoxy-1H-pyrazolo[3,4-d]pyrimidin-1-yl)acetate (C-4)

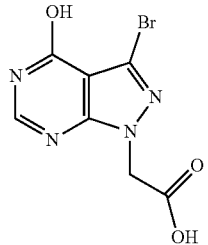 [SMILES: O=C(O)Cn1nc(Br)c2c(O)ncnc21]

To a solution of methyl 2-(3-bromo-4-methoxy-1H-pyrazolo[3,4-d]pyrimidin-1-yl)acetate (1200 mg, 3.99 mmol, 1.0 equiv) in Dioxane (10 mL) was added concentrated HCl (12 N, 10 ml, 120 mmol). The reaction mixture was heated to 90° C. for 1 hr. The reaction mixture was allowed to cool to rt and the solvent was removed in vacuo. The crude residue was triturated with ether, filtered and dried to give as an off white solid (795 mg, 73%) which was used without further purification. LCMS [M+1]+273

Synthesis of methyl 2-(3-bromo-5-methyl-4-oxo-4,5-dihydro-1H-pyrazolo[3,4-d]pyrimidin-1-yl)acetate (D-13)

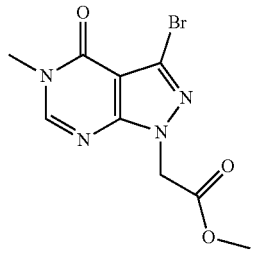

To a suspension of 3-bromo-4-methoxy-1H-pyrazolo[3,4-d]pyrimidine (1.3 g, 4.03 mmol, 1.0 equiv) in DMF (20 mL) was added Methyl Bromoacetate (0.552 ml, 8.86 mmol, 2.2 equiv). The reaction mixture was cooled to 0° C. and Cs$_2$CO$_3$ (2.63 g, 8.06 mmol, 2 equiv) was added and the reaction mixture was allowed to warm to rt and stirred for 3 h. The mixture was diluted with DCM (30 ml) and then washed with water and brine. The organic phase was then dried over anhydrous Na$_2$SO$_4$ followed by removal of the solvent in vacuo. The crude residue was triturated with water, filtered and dried to give as an off white solid (795 mg, 66%) which was used without further purification. LCMS [M+1]+301

52

Synthesis of methyl 2-(3-(3-chloro-5-((2,4,4-trimethylpentan-2-yl)carbamoyl)-4-(2-(trimethylsilyl)ethoxy)phenyl)-5-methyl-4-oxo-4,5-dihydro-1H-pyrazolo[3,4-d]pyrimidin-1-yl)acetate (E-1)

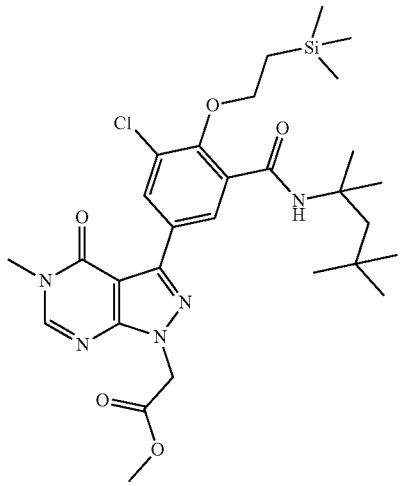 [SMILES: COC(=O)Cn1nc(-c2cc(Cl)c(OCC[Si](C)(C)C)c(C(=O)NC(C)(C)CC(C)(C)C)c2)c2c(=O)n(C)cnc21]

To a microwave vial charged with 3-chloro-5-(4,4,5,5-tetramethyl-1,3,2-dioxaborolan-2-yl)-N-(2,4,4-trimethylpentan-2-yl)-2-(2-(trimethylsilyl)ethoxy)benzamide (0.762, 1.495 mmol), methyl 2-(3-bromo-5-methyl-4-oxo-4,5-dihydro-1H-pyrazolo[3,4-d]pyrimidin-1-yl)acetate (0.300 g, 0.996 mmol), and K$_3$PO$_4$ (0.423, 1.993 mmol) was added dioxane (10 ml) and water (1 ml). The vial was flushed with nitrogen. Bis(di-tert-butyl(4-dimethylaminophenyl)phosphine)dichloropalladium(II) (0.106 g, 0.149 mmol) was added, the vial was sealed, and the mixture heated in a microwave reactor to 90° C. for 30 minutes. The mixture was neutralized with citric acid (1 N, 2 ml). The crude mixture was concentrated onto celite and purified using silica gel column chromatography (Hexane: EtOAc gradient 0-100%). The product was dried under vacuum to give the title compound as a light yellow solid (0.285 g, 47%).

Synthesis of 4-fluoro-3-methyl-5-(4,4,5,5-tetramethyl-1,3,2-dioxaborolan-2-yl)-2-(2-(trimethylsilyl)ethoxy)benzonitrile (G-1)

Scheme 7

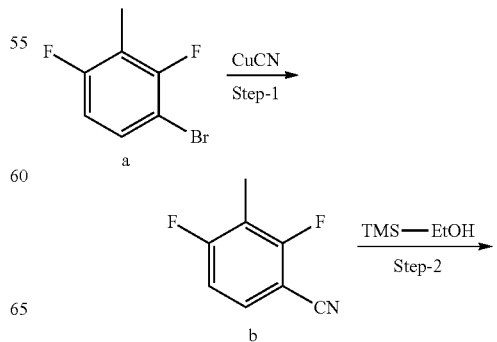

53

-continued

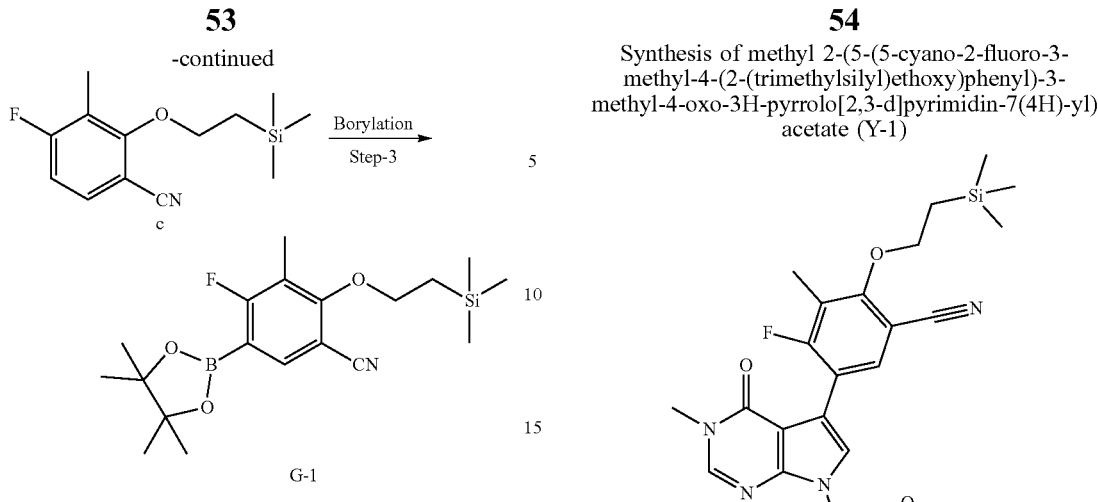

Step 1:
To a stirred solution of compound a (5 g, 24.27 mmol, 1 eq) in NMP (40 mL) was added CuCN (2.62 g, 29.12 mmol, 1.2 eq) and CuI (461 mg, 2.42 mmol, 0.1 eq) at RT. Then, the reaction mixture was heated to 140° C. in a sealed tube for 20 h. The reaction mixture was cooled to RT and diluted with water (50 mL) and EtOAc (50 mL), then filtered through celite pad and was washed with EtOAc (2×50 mL). The filtrate was extracted with EtOAc (2×50 mL) and was washed with sat.NaCl solution (50 mL). Then, the organic layer was dried over $Na_2SO_4$ and concentrated under reduced pressure to give a crude product. The crude product was purified by column chromatography (silica gel 100-200 mesh) using 0-3% EtOAc in petroleum ether as an eluent to give compound b (2 g, 53.9%) as color less oil.

Step 2:
To a stirred solution of 2-trimethylsilyl ethanol (2.31 mL, 15.68 mmol, 1.2 eq) in THF (40 mL) was added KHMDS (14.38 mL, 14.37 mmol, 1.1 eq) at RT under Argon atm and stirred for 30 min. Then, compound b (2 g, 13.67 mmol, 1 eq) was added slowly at RT and the resulting mixture was stirred for 16 h. TLC analysis indicated formation of a nonpolar spot. Then, the reaction mixture was quenched with water and diluted with EtOAc (100 mL). The organic layer was separated and the aqueous layer was extracted with EtOAc (2×50 mL). The combined organic layer was washed with sat.NaCl solution (1×100 mL), dried over $Na_2SO_4$ and concentrated under reduced pressure to give a crude product. The crude product was purified by column chromatography (silica gel 100-200 mesh) using 0-4% EtOAc in petroleum ether as an eluent to give compound c (1.7 g, 52.3%) as yellow liquid.

Step 3:
A stirred solution of compound c (2.4 g, 9.56 mmol, 1 eq) in Hexane (35 mL) in a sealed tube was degassed with Argon for 10 min. DTBPY (153 mg, 0.57 mmol, 0.06 eq), Bis (pinacolato) diborane (5.58 g, 21.99 mmol, 2.3 eq) and Iridium catalyst (190 mg, 0.28 mmol, 0.03 eq) were added to the solution of compound c at RT then heated to 60° C. for 3 h. TLC analysis indicated the formation of polar spot. The reaction mixture was cooled to RT, filtered through celite pad; and washed with EtOAc (2×10 mL). The filtrate was concentrated to obtain crude compound G-1. The crude product was purified by column chromatography (silica gel 100-200 mesh) using 0-2% EtOAc in petroleum ether as an eluent to obtain G-1 4-fluoro-3-methyl-5-(4,4,5,5-tetramethyl-1,3,2-dioxaborolan-2-yl)-2-(2-(trimethylsilyl)ethoxy) benzonitrile (2.55 g, 70.3%) as a white solid.

54

Synthesis of methyl 2-(5-(5-cyano-2-fluoro-3-methyl-4-(2-(trimethylsilyl)ethoxy)phenyl)-3-methyl-4-oxo-3H-pyrrolo[2,3-d]pyrimidin-7(4H)-yl) acetate (Y-1)

In a microwave vial with magnetic stir bar was placed methyl 2-(5-iodo-3-methyl-4-oxo-3H-pyrrolo[2,3-d]pyrimidin-7(4H)-yl)acetate (535 mg, 1.541 mmol), 4-fluoro-3-methyl-5-(4,4,5,5-tetramethyl-1,3,2-dioxaborolan-2-yl)-2-(2-(trimethylsilyl)ethoxy)benzonitrile (756 mg, 2.004 mmol), Bis(di-tert-butyl(4-dimethylaminophenyl)phosphine)dichloropalladium(II) (65.5 mg, 0.092 mmol), Potassium phosphate tribasic reagent grade, >=98% (1.186 mL, 1.541 mmol) then 1,4-Dioxane (Volume: 10.80 mL, Ratio: 9)/Water (Volume: 1.2 mL, Ratio: 1.000). The vial sealed, flushed with nitrogen, then heated in the microwave at 100° C. for 30 min when LCMS indicated complete. Reaction was quenched with dil. HCl on ice, then extracted with EtOAc. The collected organic fractions were concentrated and purified by flash chromatography ($SiO_2$, hexanes-EtOAc) to give the product as a brown solid; methyl 2-(5-(5-cyano-2-fluoro-3-methyl-4-(2-(trimethylsilyl) ethoxy)phenyl)-3-methyl-4-oxo-3H-pyrrolo[2,3-d]pyrimidin-7(4H)-yl)acetate (431 mg, 0.916 mmol, 59.4% yield).

Synthesis of 2-(5-(5-carbamoyl-2-fluoro-3-methyl-4-(2-(trimethylsilyl)ethoxy)phenyl)-3-methyl-4-oxo-3H-pyrrolo[2,3-d]pyrimidin-7(4H)-yl)acetic Acid Scheme 8

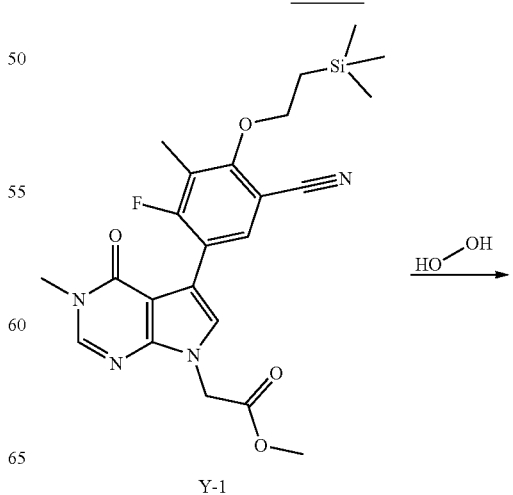

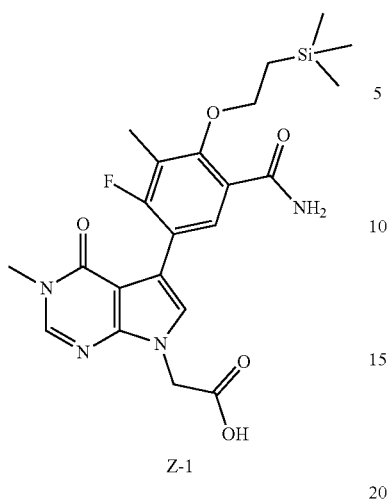

Z-1

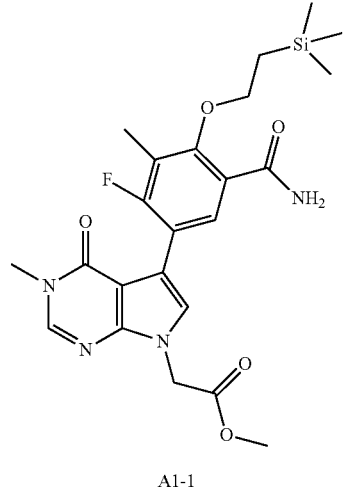

A1-1

In a large 250 mL flask was placed methyl 2-(5-(5-cyano-2-fluoro-3-methyl-4-(2-(trimethylsilyl)ethoxy)phenyl)-3-methyl-4-oxo-3H-pyrrolo[2,3-d]pyrimidin-7(4H)-yl)acetate (Y-1) (431 mg, 0.916 mmol), Ethanol (EtOH) (Volume: 10 mL), Hydrogen peroxide solution (0.091 mL, 0.916 mmol) and Sodium hydroxide pellets (430 mg, 10.75 mmol). This bubbling solution was allowed to stir at room temperature for 1 h when LCMS indicated complete reaction. The reaction was neutralized with Hydrochloric acid (ACS) (0.916 mL, 0.916 mmol) and the resultant solid filtered and collected as a white solid; 2-(5-(5-carbamoyl-2-fluoro-3-methyl-4-(2-(trimethylsilyl)ethoxy)phenyl)-3-methyl-4-oxo-3H-pyrrolo[2,3-d]pyrimidin-7(4H)-yl)acetic acid (Z-1) (182 mg, 0.384 mmol, 41.9% yield). The aqueous still showed product, so this was neutralized with dil. HCl and then extracted with DCM to give more product as a white solid; (642 mg, crude product which was used directly in the next step).

In a vial was placed 2-(5-(5-carbamoyl-2-fluoro-3-methyl-4-(2-(trimethylsilyl)ethoxy)phenyl)-3-methyl-4-oxo-3H-pyrrolo[2,3-d]pyrimidin-7(4H)-yl)acetic acid (Z-1) (182 mg, 0.384 mmol), Cesium carbonate (125 mg, 0.384 mmol), N,N-Dimethylformamide (DMF) (Volume: 2 mL) and Iodomethane (0.024 mL, 0.384 mmol). The solution was stirred for 15 min when LCMS indicated the reaction was incomplete. Stirring was continued for 4 h, when LCMS indicated the reaction was complete. The reaction was neutralized with 1M Hydrochloric acid (ACS) (0.384 mL, 0.384 mmol) on ice, then the solution was filtered. The filter cake was vacuum dried to get the desired product as a grey solid; methyl 2-(5-(5-carbamoyl-2-fluoro-3-methyl-4-(2-(trimethylsilyl)ethoxy)phenyl)-3-methyl-4-oxo-3H-pyrrolo[2,3-d]pyrimidin-7(4H)-yl)acetate (A1-1) (142 mg, 0.291 mmol, 76% yield).

Synthesis of 4-chloro-3-iodo-1H-pyrrolo[3,2-c]pyridine (A-6)

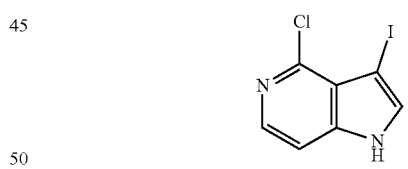

To a pale grey solution of commercially available 4-Choro-5-azaindole (3.34 g, 21.89 mmol) in DMF (Volume: 20 ml), was added N-iodosuccinimide (5.17 g, 22.98 mmol) in one portion at 20-23° C. The solution was agitated at 23 C for 2 h. The addition is slightly exothermic (+5° C.) and the mixture went from a white suspension to pale brown solution in 5 min. The mixture was poured onto ice cold water (2×250 mL) with agitation. After 30 min, the reaction was filtered and washed with water (2×1 L). The wet cake was diluted with acetonitrile (50 mL), agitated for 10 min in an ice bath, filtered and rinsed with 200 mL hexanes. The wet cake was dried under vacuum at 50° C. for 1 h followed by vacuum drying to give the desired product, 4-chloro-3-iodo-1H-pyrrolo[3,2-c]pyridine (A-6) (5.2 g, 17.74 mmol, 81% yield)—pale brown solid. 1H NMR (500 MHz, Synthesis of 2-(5-(5-carbamoyl-2-fluoro-3-methyl-4-(2-(trimethylsilyl)ethoxy)phenyl)-3-methyl-4-oxo-3H-pyrrolo[2,3-d]pyrimidin-7(4H)-yl)acetic Acid

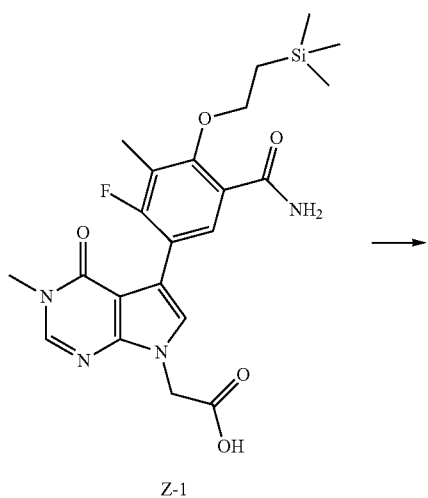

Z-1

DMSO-d6) δ=12.34 (br. s., 1H), 8.04 (d, J=5.6 Hz, 1H), 7.83 (d, J=2.3 Hz, 1H), 7.56 (d, J=5.6 Hz, 1H) LC-MS: m/z 393 (M+H).

Synthesis of tert-butyl 2-(4-chloro-3-iodo-1H-pyrrolo[3,2-c]pyridin-1-yl)acetate (B-5)

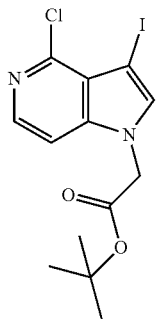 [SMILES: CC(C)(C)OC(=O)Cn1cc(I)c2c(Cl)nccc21]

To a solution of 4-chloro-3-iodo-1H-pyrrolo[3,2-c]pyridine (19.1 g, 68.6 mmol) and tert-Butyl bromoacetate (13.38 g, 68.6 mmol) in DMF (Volume: 50 ml, Ratio: 1.000), Cesium carbonate (24.58 g, 75 mmol) was added in one portion at 20-23° C. The resulting mixture was agitated at 23° C. for 2 h. The batch content was diluted with 100 ml DCM, filtered and washed with DCM. The combined filtrate was concentrated to dryness under vacuum. The filter cake and the concentrated residues were cautiously neutralized with ice-cold 2M HCl, and diluted with water. The precipitate thus formed was filtered and the filter cake was dried under vacuum in an oven at 50° C. for 2 h to give the desired product, tert-butyl 2-(4-chloro-3-iodo-1H-pyrrolo[3,2-c]pyridin-1-yl)acetate (28 g, 67.7 mmol, 99% yield) as a light brown solid. $^1$H NMR (500 MHz, DMSO-d6) δ=8.05 (d, J=5.7 Hz, 1H), 7.98-7.94 (m, 1H), 7.96 (s, 1H), 7.77 (s, 1H), 7.63 (d, J=5.7 Hz, 1H), 5.12 (s, 2H), 2.90 (s, 2H), 2.74 (s, 2H), 1.42 (s, 9H); LC-MS: m/z 393 (M+H);

Synthesis of 2-(3-iodo-4-methoxy-1H-pyrrolo[3,2-c]pyridin-1-yl)acetic Acid

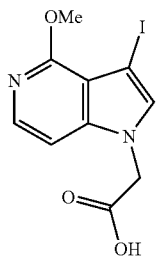 [SMILES: COc1nccc2c1c(I)cn2CC(=O)O]

Tert-butyl 2-(4-chloro-3-iodo-1H-pyrrolo[3,2-c]pyridin-1-yl)acetate (B-5) (28 g, 67.7 mmol, 99% yield) was suspended between 1,4-Dioxane (Volume: 200 ml, Ratio: 4.00) and Methanol (MeOH) (Volume: 200 ml, Ratio: 4.00). Sodium hydroxide pellets (19.20 g, 480 mmol) was added and the resulting mixture agitated at 130-140° C. (bath temp) for over 24 h to see >95% conversion to desired OMe-acid product. The reaction mixture was concentrated to dryness, acidified to pH 1 with ice cold 6M HCl, filtered and washed with water (100 ml). The wet cake thus obtained was dried in a vacuum oven at 50° C. overnight (or until to constant weight), to give the desired product, 2-(3-iodo-4-methoxy-1H-pyrrolo[3,2-c]pyridin-1-yl)acetic acid in quantitative yield as a beige colored solid—the product may contain small amounts of inorganic salt (NaCl). LC-MS: m/z 333 (M+H).

Synthesis of ethyl 2-(3-iodo-4-methoxy-1H-pyrrolo[3,2-c]pyridin-1-yl)acetate

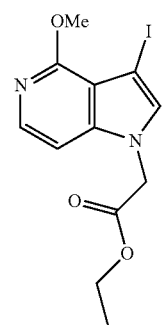 [SMILES: CCOC(=O)Cn1cc(I)c2c(OC)nccc21]

Acid mediated conditions: To a stirred thin suspension of 2-(3-iodo-4-methoxy-1H-pyrrolo[3,2-c]pyridin-1-yl)acetic acid (1.7 g, 5.12 mmol) in EtOH (Volume: 100 ml, Ratio: 25.00), Sulphuric acid (Volume: 4 ml, Ratio: 1.000) was added and agitated at room temperature overnight. 100 ml Et$_2$O was added. The resulting mixture was cooled to 0-5 for 30 min., filtered and washed with Et$_2$O (50 ml). The filter cake was dried under vacuum to get the desired product, ethyl 2-(3-iodo-4-methoxy-1H-pyrrolo[3,2-c]pyridin-1-yl)acetate (1.74 g, 4.59 mmol, 90% yield), as a white colored powder. LC-MS: m/z 361 (M+H).

Base mediated conditions: To a solution mixture of 2-(3-iodo-4-methoxy-1H-pyrrolo[3,2-c]pyridin-1-yl)acetic acid (28.26 g, 61.3 mmol), Iodoethane (9.56 g, 61.3 mmol) in N,N-Dimethylformamide (DMF) (Volume: 50 ml), Cesium carbonate (26.0 g, 80 mmol) was added at 23° C. the mixture was stirred at this temperature for 2 h. The mixture was concentrated to dryness under vacuum, neutralized with 1 M HCl (ice-cold), and filtered. The wet cake was washed with water and was dried at 70° C. under vacuum overnight. The crude material material was triturated from ACN (2-3 times, 50 ml) to get the desired product, ethyl 2-(3-iodo-4-oxo-4,5-dihydro-1H-pyrrolo[3,2-c]pyridin-1-yl)acetate (14.2 g, 40.2 mmol, 65.6% yield) as a white powder. LC-MS: m/z 361 (M+H);

Synthesis of ethyl 2-(4-hydroxy-3-iodo-1H-pyrrolo[3,2-c]pyridin-1-yl)acetate

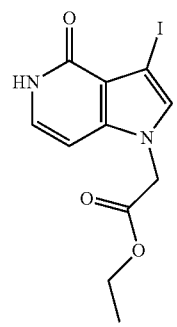 [SMILES: CCOC(=O)Cn1cc(I)c2c(=O)[nH]ccc21]

To a solution mixture of 2-(3-iodo-4-methoxy-1H-pyrrolo[3,2-c]pyridin-1-yl)acetic acid (28.26 g, 61.3 mmol), Iodoethane (9.56 g, 61.3 mmol) in N,N-Dimethylformamide (DMF) (Volume: 50 ml), Cesium carbonate (26.0 g, 80 mmol) was added at 23° C. The resulting mixture was stirred at this temperature for 2 h. The mixture was concentrated to dryness under vacuum, neutralized with 1 M HCl (ice-cold), and filtered. The wet cake was washed with water and was dried at 70° C. in vacuum overnight. The dried product was found to contain a product mixture as shown in the equation above at a ratio of 3/1. This could be due to residual HCl at 70° C. vac. oven temperature demethylated enolic ether. This material was triturated from ACN (2-3 times, 50 ml) to get the desired products, ethyl 2-(3-iodo-4-oxo-4,5-dihydro-1H-pyrrolo[3,2-c]pyridin-1-yl)acetate (2.74 g, 7.23 mmol, 11.80% yield), as a deep orange powder. 1H NMR (500 MHz, DMSO-d6) δ=11.13-10.77 (m, 1H), 7.24 (s, 1H), 7.03 (t, J=6.5 Hz, 1H), 6.48 (d, J=7.2 Hz, 1H), 5.05 (s, 2H), 4.16 (q, J=7.2 Hz, 2H), 1.22 (t, J=7.2 Hz, 3H) LC-MS: m/z 347 (M+H);

Synthesis of ethyl 2-(3-iodo-5-methyl-4-oxo-4,5-dihydro-1H-pyrrolo[3,2-c]pyridin-1-yl)acetate (D-14)

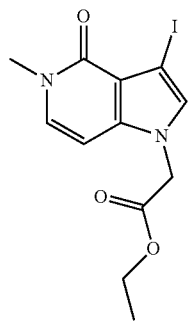 [SMILES: CCOC(=O)Cn1cc(I)c2c(=O)n(C)ccc21]

A solution mixture of ethyl 2-(3-iodo-4-oxo-4,5-dihydro-1H-pyrrolo[3,2-c]pyridin-1-yl)acetate (3 g, 8.67 mmol), iodomethane (1.230 g, 8.67 mmol) and Cesium carbonate (3.67 g, 11.27 mmol) in N,N-Dimethylformamide (DMF) (Volume: 10 ml) was agitated at 23° C. for 60 min. The reaction mixture was concentrated to dryness, neutralized with ice-cold 2M HCl, and extracted with ethyl acetate. The organic layer was dried over MgSO4, and concentrated to dryness to give the desired product, ethyl 2-(3-iodo-5-methyl-4-oxo-4,5-dihydro-1H-pyrrolo[3,2-c]pyridin-1-yl)acetate (D-14) (2.52 g, 6.65 mmol, 77% yield), as an orange colored solid. 1H NMR (500 MHz, DMSO-d6) δ=7.43 (d, J=7.5 Hz, 1H), 7.30 (s, 1H), 6.59 (d, J=7.5 Hz, 1H), 5.10 (s, 2H), 4.21 (q, J=7.1 Hz, 2H), 3.47 (s, 3H), 1.27 (t, J=7.1 Hz, 3H); LC-MS: m/z 361 (M+H).

Synthesis of 2-hydroxy-5-(4,4,5,5-tetramethyl-1,3,2-dioxaborolan-2-yl)benzamide

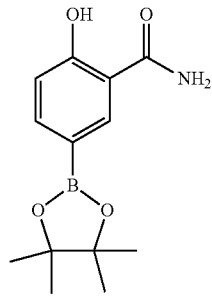 [SMILES: CC1(C)OB(c2ccc(O)c(C(N)=O)c2)OC1(C)C]

To a degassed suspension of Bis(pinacolato)diboron (2.351 g, 9.26 mmol) and 5-bromo-2-hydroxybenzamide (1.0 g, 4.63 mmol) in DMF (Volume: 8 mL) was added Bis(triphenylphosphine)palladium(II) dichloride (0.244 g, 0.347 mmol) followed by Potassium acetate (1.090 g, 11.11 mmol. The mixture was heated to 100° C. in a microwave for 45 min. Initial analysis indicated ~50% conversion hence the mixture was further heated in the microwave at 120° C. for 60 min. The mixture was concentrated in in vacuo, cool to 20-23° C. and quenched with ice-cold water (40 mL). The crude mixture was extracted with ethyl acetate (2×50 mL), dried over anhydrous MgSO4, concentrated and purified by flash column chromatography (0-10-50% EA/Hex as eluant, 24 g column) to give the desired product, 2-hydroxy-5-(4,4,5,5-tetramethyl-1,3,2-dioxaborolan-2-yl)benzamide (1.23 g, 2.81 mmol, 60.6% yield) as a yellow solid; Observed LCMS [M+H]$^+$ 264

Synthesis of 5-(7-(2-((3-chloropyridin-4-yl)amino)-2-oxoethyl)-3-methyl-4-oxo-4,7-dihydro-3H-pyrrolo[2,3-d]pyrimidin-5-yl)-2-hydroxybenzamide (Formula I-1)

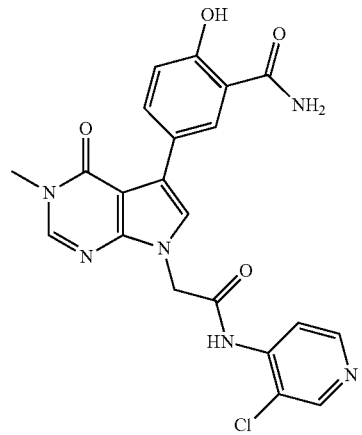 [SMILES: Cn1cnc2c(c(-c3ccc(O)c(C(N)=O)c3)cn2CC(=O)Nc2ccncc2Cl)c1=O]

To a vial containing a mixture of N-(3-chloropyridin-4-yl)-2-(5-iodo-3-methyl-4-oxo-3H-pyrrolo[2,3-d]pyrimidin-7(4H)-yl)acetamide (85 mg, 0.192 mmol) and 2-hydroxy-5-(4,4,5,5-tetramethyl-1,3,2-dioxaborolan-2-yl)benzamide (76 mg, 0.287 mmol) in Dioxane (Volume: 3 ml,) was added water (Volume: 0.65 ml). The mixture was degassed for 5 minutes and Bis(di-tert-butyl(4-dimethylaminophenyl)

phosphine)dichloropalladium(II) (8.14 mg, 0.011 mmol) was added followed by Potassium phosphate tribasic reagent grade, >=98% (61.0 mg, 0.287 mmol). The mixture was heated to 80° C. in a microwave for 30 min. The mixture was quenched with 1N HCl (3 mL). The crude mixture was extracted with DCM (2×15 mL). The organic layer was dried over anhydrous MgSO$_4$, and concentrated. The crude product mixture was purified by flash column chromatography (DCM/MeOH 0-10% as eluant, 12 g column) to give the desired product as a white solid (14 mg, 0.028 mmol, 14.84% yield). Observed LCMS [M+H]$^+$ 453.

Synthesis of
4-bromo-2-chloro-6-(methylcarbamoyl)phenyl
pivalate

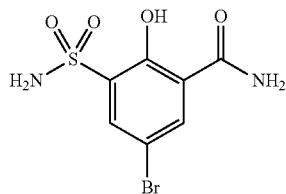 [SMILES: NC(=O)c1cc(Br)cc(S(N)(=O)=O)c1O]

CHLOROSULFONIC ACID (3875 μl, 57.9 mmol) was added to a microwave vial containing 5-bromo-2-hydroxybenzamide (250 mg, 1.157 mmol). The vial was capped and heated to 110° C. in an aluminum block. Any pressure build up was carefully vented by removing the vial from the reaction block and inserting a needle into the septum. The reaction was heated at 110° C. overnight. The reaction was pipetted into ice water in a separatory funnel and extracted into EtOAc. The organic extracts were dried over magnesium sulfate, and concentrated to dryness to afford a tan solid that did not appear to be the starting material (NMR analysis). The residue was taken up into acetone and NH$_4$OH was added. The mixture was concentrated to near dryness, no precipitate formed. Aqueous HCl was added and the mixture was extracted with DCM, followed by a CHCl$_3$/IPA mixture. The precipitate formed in the separatory funnel was collected and combined with the organic extracts to afford 167 mg of a solid that was a mixture of the desired product and the carboxylic acid. The crude product mixture was purified by silica gel flash chromatography [1-8% MeOH/DCM as eluant] to afford 5-bromo-2-hydroxy-3-sulfamoylbenzamide (0.060 g, 0.203 mmol, 17.57% yield) as a colourless solid. $^1$H NMR (500 MHz, DMSO-d6) δ 8.80 (br. s., 1H), 8.40 (br. s., 1H), 8.34-8.36 (m, 1H), 7.91-7.93 (m, 1H), 7.30 (s, 2H); Observed LCMS [M+H]$^+$ 295.

Synthesis of
4-bromo-2-chloro-6-(methylcarbamoyl)phenyl
pivalate

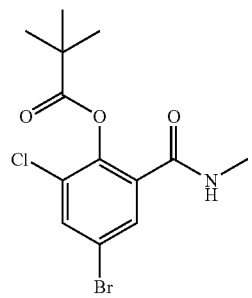 [SMILES: CNC(=O)c1cc(Br)cc(Cl)c1OC(=O)C(C)(C)C]

A solution of 5-bromo-3-chloro-2-hydroxybenzoic acid (3 g, 11.93 mmol) and N,N-Diisopropylethylamine (8.47 ml, 47.7 mmol) in THF was added to a stirred solution of Trimethylacetyl Chloride (4.32 g, 35.8 mmol) in DCM (Volume: 5 ml) at 23° C. The reaction mixture was then stirred overnight. The reaction mixture was concentrated to dryness, diluted with DCM and then treated with Methylamine Solution (2.0M/Methanol) (17.90 ml, 35.8 mmol) followed by N-ethyl-N-isopropylpropan-2-amine (6.17 g, 47.7 mmol). The resulting mixture was stirred at 55° C. overnight. The reaction was cooled to 23° C., quenched with 2M aqueous HCl and extracted EtOAc. The organic layer was concentrated and purified by silica gel chromatography (12 g column; 45 min; 0-20-30-70% EA/Hex) to give the desired product, 4-bromo-2-chloro-6-(methylcarbamoyl) phenyl pivalate, as a white solid (1.76 g, 4.29 mmol, 36.0% yield); Observed LCMS [M+H]$^+$ 348.

Synthesis of (3-chloro-4-hydroxy-5-(methylcarbamoyl)phenyl)boronic Acid

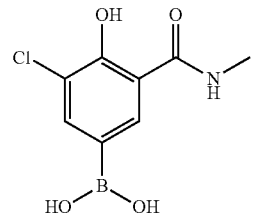

To a degassed suspension mixture of Bis(pinacolato) diboron (1.821 g, 7.17 mmol) and 4-bromo-2-chloro-6-(methylcarbamoyl)phenyl pivalate (1 g, 2.87 mmol) in DMF (Volume: 20 mL) Bis(triphenylphosphine)palladium(II) dichloride (0.201 g, 0.287 mmol) followed by Potassium acetate (1.126 g, 11.47 mmol) were added and sealed immediately. (Note: Reagents were added in that order). The mixture was heated at 120° C. for 45 min. The mixture was cooled to 20-23° C., concentrated to dryness. The mixture was quenched with saturated aqueous NH$_4$Cl and water followed by extraction with EtOAc (2×50 mL). The organic layer was dried over MgSO$_4$, concentrated onto celite and purified by silica-gel chromatography (0-5-20% EA/hex, 24 g column) to afford the desired product, as a crystalline yellow solid; Observed LCMS [M+H]$^+$ 230.

General Schemes for the Preparation of MOM-Protected Boronate Esters
Method A

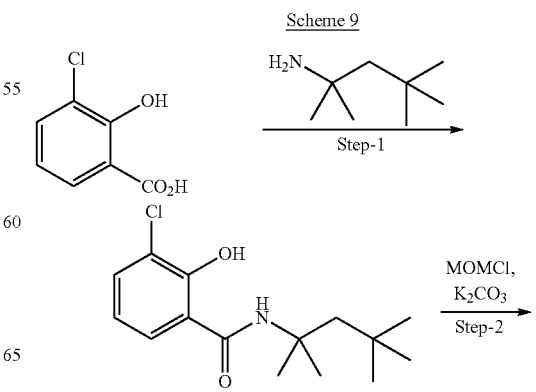

Scheme 9

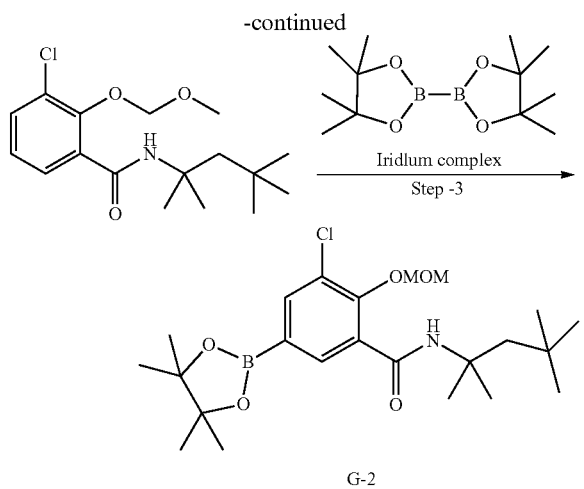

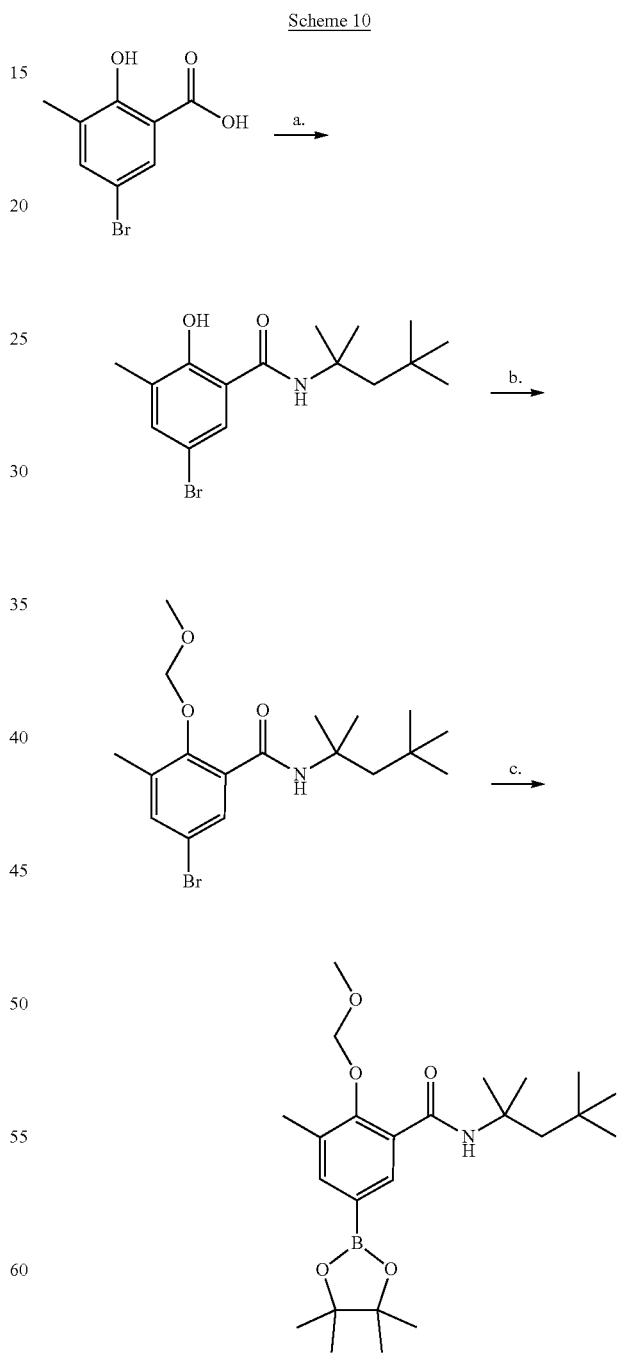

with n-hexane. Obtained filtrate was concentrated under reduced pressure to give crude residual oil, which was adsorbed on celite and purified by column chromatography (Silica gel 100-200 mesh) 0-5% EtOAc in petroleum ether as an eluent to afford 3-chloro-2-(methoxymethoxy)-5-(4,4,5,5-tetramethyl-1,3,2-dioxaborolan-2-yl)-N-(2,4,4-trimethylpentan-2-yl)benzamide (G-2) (10 g, 65.66%) as a pale yellow semi solid. Observed LCMS [M+H]$^+$ 454.

Method B

Step 1: To a stirred solution of compound 3-chloro-2-hydroxybenzoic acid (25 g, 145.3 mmol, 1 eq) in DMF (500 ml) was added EDC. HCl (33.3 g, 173.7 mmol, 1.2 eq) and HOBt (23.5 g, 173.7 mmol, 1.2 eq) at 0° C. under argon atmosphere followed by DiPEA (92 ml, 508.5 mmol, 3.5 eq) and stirred for 15 min at the same temp. Then, t-Octylamine (31.25 ml, 173.7 mmol, 1.2 eq) was added dropwise at 0° C. and allowed to warm up to RT over 16 h. TLC analysis indicated formation of less polar spot. The reaction mixture was diluted with water (4 L) and extracted with EtOAc (4×500 mL). The organic layer was washed with water (2×100 mL) and dried over Na$_2$SO$_4$ and concentrated under reduced pressure to give a crude product. Crude product was purified by column chromatography (silica gel 100-200 mesh) using 5-10% EtOAc in petroleum ether as an eluent to give 3-chloro-2-hydroxy-N-(2,4,4-trimethylpentan-2-yl)benzamide (18 g, 43.08%) as an off white solid. Observed LCMS [M+H]$^+$ 284.

Step 2: To a stirred solution of 3-chloro-2-hydroxy-N-(2,4,4-trimethylpentan-2-yl)benzamide (18 g, 63.6 mmol, 1 eq) in DMF (200 ml) was added K$_2$CO$_3$ (17.5 g, 127.2 mmol, 2 eq) at RT under argon atmosphere and continued for 30 min. Then, MOM-Cl (7.2 ml, 96 mmol, 1.5 eq) was added at RT and the reaction was continued for 16 h. TLC analysis indicated formation of polar spot. The reaction mixture was quenched in Ice water (2 L) and extracted with EtOAc (3×300 mL). The organic layer was dried over Na$_2$SO$_4$ and concentrated under reduced pressure to give a crude compound. The crude compound was purified by column chromatography (silica gel 100-200 mesh) using 5-10% EtOAc in petroleum ether as an eluent to provide 3-chloro-2-(methoxymethoxy)-N-(2,4,4-trimethylpentan-2-yl)benzamide (10 g, 71.87%) as an off-white solid. Observed LCMS [M+H]$^+$ 328.

Step 3: A solution of Bispinacolatodiboron (19.6 g, 77.3 mmol, 2.3 eq), DTBPY (540 mg, 2.01 mmol, 0.06 eq) in degassed dry n-hexane (200 ml) was degassed with argon for 10 min. After 10 min, Iridium complex (660 mg, 1 mmol, 0.03 eq) was added and stirred for 5 min (color change was observed from yellow to wine red). After 5 min, 3-chloro-2-(methoxymethoxy)-N-(2,4,4-trimethylpentan-2-yl)benzamide (11 g, 33.6 mmol, 1 eq) was added to above wine red solution at RT in sealed tube under Argon atm. Then, the sealed tube was immersed in preheated oil bath at 60° C. temp and the reaction stirred for 2 h. TLC analysis indicated formation of a nonpolar spot. Then, reaction mixture was cooled to RT and filter through celite, celite bed was washed a) i. SOCl$_2$, Et$_3$N, 70° C., ii. t-Octylamine, CH$_2$Cl$_2$; b) MOM-Cl, NaH, THF; c) Bispinacolatodiboron, PdCl$_2$(dppf)-CH2Cl2, Dioxane, 120° C.;

Synthesis of 2-(methoxymethoxy)-3-methyl-5-(4,4,5,5-tetramethyl-1,3,2-dioxaborolan-2-yl)-N-(2,4,4-trimethylpentan-2-yl)benzamide (G-3)

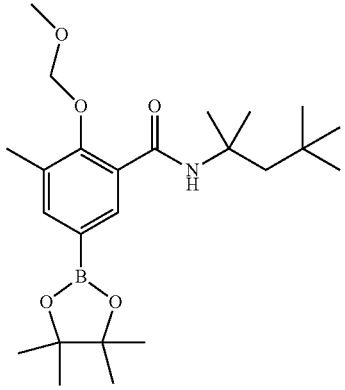 [SMILES: COCOc1c(C)cc(B2OC(C)(C)C(C)(C)O2)cc1C(=O)NC(C)(C)CC(C)(C)C]

Step 1: Synthesis of 5-bromo-2-hydroxy-3-methyl-N-(2,4,4-trimethylpentan-2-yl)benzamide

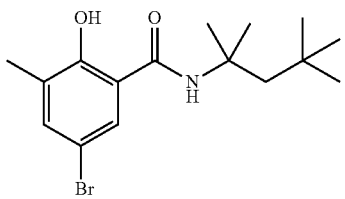 [SMILES: Cc1cc(Br)cc(C(=O)NC(C)(C)CC(C)(C)C)c1O]

To a flask charged with 5-Bromo-2-hydroxy-3-methyl-benzenecarboxylic acid (2 g, 8.66 mmol), was added Thionyl chloride (10 ml) followed triethylamine (0.5 ml) and the mixture was heated to 70° C. for 30 min. The thionyl chloride was removed in vacuo, the residue was dissolved in $CH_2Cl_2$ (10 ml) and the amine was added, and the mixture was stirred at room temperature overnight. The mixture was concentrated onto celite and purified by silica gel flash column chromatography (EA:Hexane 0-20% as eluant) to give the title compound as an off white solid (47%); Observed LCMS [M+H]+ 342

In a similar manner the following was prepared:

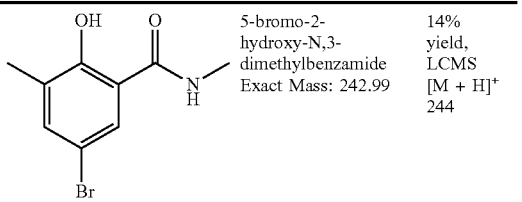

| | | |
|---|---|---|
| | 5-bromo-2-hydroxy-N,3-dimethylbenzamide Exact Mass: 242.99 | 14% yield, LCMS [M + H]+ 244 |

Step 2: Synthesis of 5-bromo-2-(methoxymethoxy)-3-methyl-N-(2,4,4-trimethylpentan-2-yl)benzamide

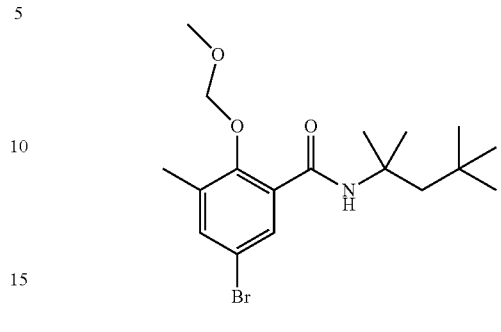

Step 2: Synthesis of 5-bromo-2-(methoxymethoxy)-3-methyl-N-(2,4,4-trimethylpentan-2-yl)benzamide To a solution of 5-bromo-2-hydroxy-3-methyl-N-(2,4,4-trimethylpentan-2-yl)benzamide (1.4 g, 4.09 mmol) in THF (25 ml) at 0° C. was added portionwise NaH (470 mg, 12.27 mmol). The mixture was stirred at room temperature for 30 min. To this mixture was added chloro (methoxy)methane (0.932 ml, 12.27 mmol) dropwise and the mixture was stirred at room temperature for an additional 2 h. The mixture was quenched with MeOH (1 ml), diluted with dichloromethane and washed with water (20 mL). The aqueous layer was extracted with dichloromethane (2×20 mL). The combined organic layer was dried ($Na_2SO_4$) and concentrated. The residue was purified by flash column chromatography [0-20% EtOAc/hexanes] to afford 5-bromo-2-(methoxymethoxy)-3-methyl-N-(2,4,4-trimethylpentan-2-yl)benzamide (1.5277 g, 97% yield) as a colourless oil; Observed LCMS [M+H]+ 386.

Step 3: Synthesis of 2-(methoxymethoxy)-3-methyl-5-(4,4,5,5-tetramethyl-1,3,2-dioxaborolan-2-yl)-N-(2,4,4-trimethylpentan-2-yl)benzamide (G-3)

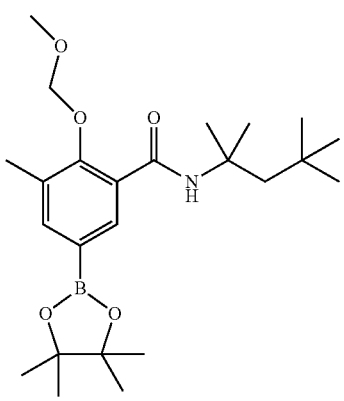 [SMILES: COCOc1c(C)cc(B2OC(C)(C)C(C)(C)O2)cc1C(=O)NC(C)(C)CC(C)(C)C]

To a stirred suspension of 5-bromo-2-(methoxymethoxy)-3-methyl-N-(2,4,4-trimethylpentan-2-yl)benzamide (1.5 g, 3.88 mmol), 4,4,4',4',5,5,5',5'-octamethyl-2,2'-bi-1,3,2-dioxaborolane (1.972 g, 7.77 mmol) and potassium acetate (1.524 g, 15.53 mmol) in Dioxane (35 mL) under nitrogen at room temperature was added $PdCl_2$(dppf)-$CH_2Cl_2$ adduct (193 mg, 0.237 mmol). The reaction vessel was sealed and heated at 110° C. for 3 h. After cooling the reaction, the reaction mixture was concentrated in vacuo and the residue was purified by silica-gel chromatography (EA:Hexane 0-20%) to give the the targeted boronate ester (G-3) as a white solid (65%); Observed LCMS [M+H]+ 434.

In a similar manner the following compounds were synthesized (Method in parentheses):

| | | | |
|---|---|---|---|
| G-4 (Method B) | | 2-(methoxymethoxy)-5-(4,4,5,5-tetramethyl-1,3,2-dioxaborolan-2-yl)-N-(2,4,4-trimethylpentan-2-yl)benzamide Exact Mass: 419.28 | 86% yield, LCMS [M + H]+ 420 |
| G-5 (Method A) | | 3-chloro-2-(methoxymethoxy)-5-(4,4,5,5-tetramethyl-1,3,2-dioxaborolan-2-yl)-N-(2,4,4-trimethylpentan-2-yl)benzamide Exact Mass: 453.25 | 95% yield, LCMS [M + H]+ 454 |
| G-6 (Method B) | | 3-fluoro-2-(methoxymethoxy)-5-(4,4,5,5-tetramethyl-1,3,2-dioxaborolan-2-yl)-N-(2,4,4-trimethylpentan-2-yl)benzamide Exact Mass: 437.27 | 61% yield, LCMS [M + H]+ 438 |
| G-7 (Method B) | | 4-fluoro-2-(methoxymethoxy)-5-(4,4,5,5-tetramethyl-1,3,2-dioxaborolan-2-yl)-N-(2,4,4-trimethylpentan-2-yl)benzamide Exact Mass: 437.27 | 66% yield, LCMS [M + H]+ 438 |

Synthesis of 4-chloro-2-(methoxymethoxy)-5-(4,4,5,5-tetramethyl-1,3,2-dioxaborolan-2-yl)-N-(2,4,4-trimethylpentan-2-yl)benzamide (G-8)

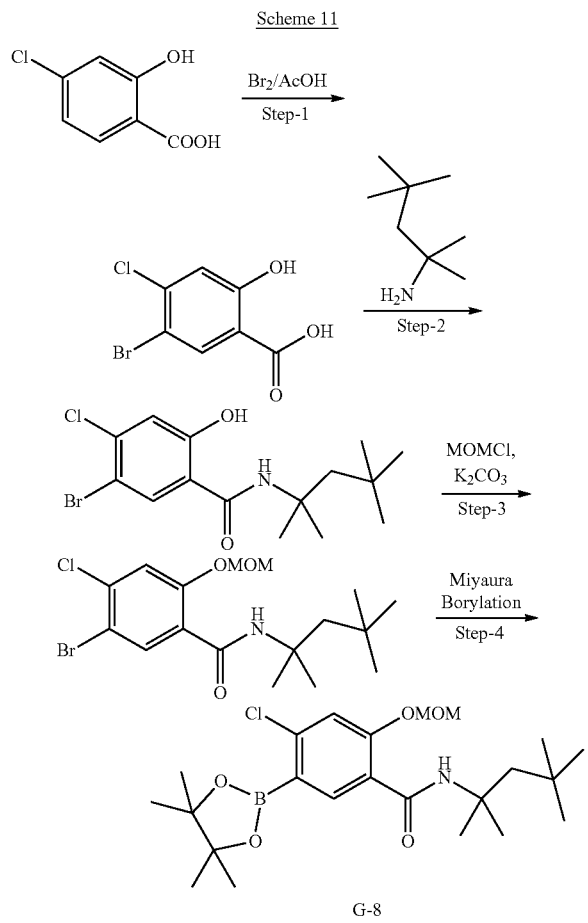

G-8

Step 1: To a stirred solution of compound 4-chloro-2-hydroxybenzoic acid (15 g, 86.9 mmol, 1 eq), a cooled solution of TEA (12.2 ml, 95.59 mmol, 1.1 eq) in DCM (300 ml) was added at −78° C. followed by addition of Bromine (5 ml, 86.9 mmol, 1 eq) in DCM (100 ml) at the same temp and the resulting mixture stirred for another 1 h. TLC analysis indicated formation of a nonpolar spot. Then, the reaction mixture was concentrated under reduced pressure to give a residue, which was redissolved in EtOAc (1 L) and washed with water and brine. The separated organic layer was dried over $Na_2SO_4$ and concentrated under reduced pressure to give a crude product. Crude product was washed with DCM to give analytically pure 5-bromo-4-chloro-2-hydroxybenzoic acid (10 g, 46.23%) as an off white solid.

Step 2: To a stirred solution of compound 5-bromo-4-chloro-2-hydroxybenzoic acid (2 g, 8.03 mmol, 1 eq) in DMF (20 ml) was added EDC. HCl (1.95 g, 9.63 mmol, 1.2 eq) and HOBt (1.3 g, 9.63 mmol, 1.2 eq) at 0° C. under argon atmosphere followed by DiPEA (5 ml, 28.10 mmol, 3.5 eq) and the resulting solution stirred for 15 min at the same temp. Then, t-Octylamine (1.6 ml, 9.61 mmol, 1.2 eq) was added dropwise at 0° C. and allowed to warm up to RT over 16 h. TLC analysis indicated formation of a less polar spot. The reaction mixture was diluted with water (200 mL) and extracted with EtOAc (3×50 mL). The organic layer was washed with water (2×20 mL), dried over $Na_2SO_4$ and concentrated under reduced pressure to give a crude product. The crude product was purified by column chromatography (silica gel 100-200 mesh) using 2% EtOAc in petroleum ether as an eluent to provide 5-bromo-4-chloro-2-hydroxy-N-(2,4,4-trimethylpentan-2-yl)benzamide (1.2 g, 42.86%) as an off white solid.

Step 3: To a stirred solution of 5-bromo-4-chloro-2-hydroxy-N-(2,4,4-trimethylpentan-2-yl)benzamide (5.5 g, 15.1 mmol, 1 eq) in DMF (60 ml) was added $K_2CO_3$ (4.2 g, 30.3 mmol, 2 eq) at RT under argon atmosphere. The resulting mixture was stirred for another 30 min. MOM-Cl (1.72 ml, 22.7 mmol, 1.5 eq) was then added at RT and the reaction was continued for 16 h. TLC analysis indicated formation of a polar spot. The reaction mixture was quenched in ice water (500 ml) and extracted with EtOAc (3×100 mL). The organic layer was dried over $Na_2SO_4$ and concentrated under reduced pressure to give a crude compound. The crude compound was purified by Combiflash™ chromatography using 100% petroleum ether as an eluent to give 5-bromo-4-chloro-2-(methoxymethoxy)-N-(2,4,4-trimethylpentan-2-yl)benzamide (5 g, 81.96%) as a pale yellow liquid; LCMS [M+H]+ 438.

Step 4: A stirred solution of 5-bromo-4-chloro-2-(methoxymethoxy)-N-(2,4,4-trimethylpentan-2-yl)benzamide (5 g, 12.3 mmol, 1 eq), Bis (pinacolato) diborane (4.7 g, 18.5 mmol, 1.5 eq), KOAc (3.62 g, 36.9 mmol, 3 eq) in 1,4-Dioxane (100 ml) was degassed with Ar for 20 min. Then, $PdCl_2$ (dppf).DCM complex (430 mg, 0.61 mmol, 0.05 eq) was added at RT and the reaction mixture was heated to 90-95° C. for 16 h in a sealed tube. TLC analysis indicated formation of a polar spot. The reaction mixture was cooled to RT then filtered through celite pad; celite pad was washed with EtOAc (2×10 ml). The filtrate was concentrated to give a crude product. The crude product was purified by column chromatography (silica gel 100-200 mesh) using 0-5% EtOAc in petroleum ether as an eluent to provide 4-chloro-2-(methoxymethoxy)-5-(4,4,5,5-tetramethyl-1,3,2-dioxaborolan-2-yl)-N-(2,4,4-trimethylpentan-2-yl)benzamide (2.5 g, 45.46%) as an off-white semi-solid.

General Scheme of
Borylation-Suzuki-Coupling/Amidation/Deprotection
Procedures (Scheme 12)

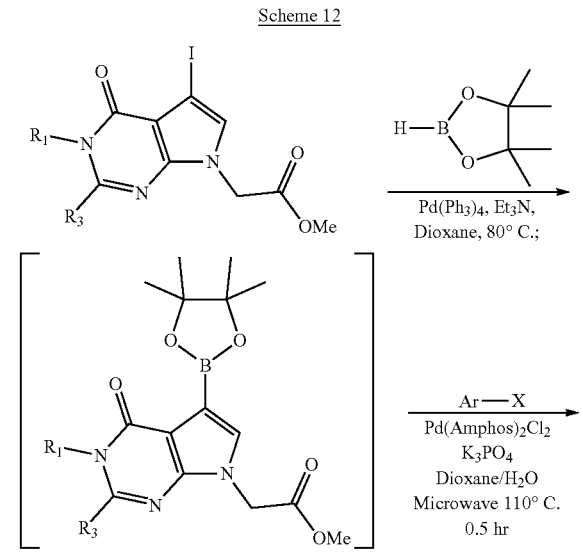

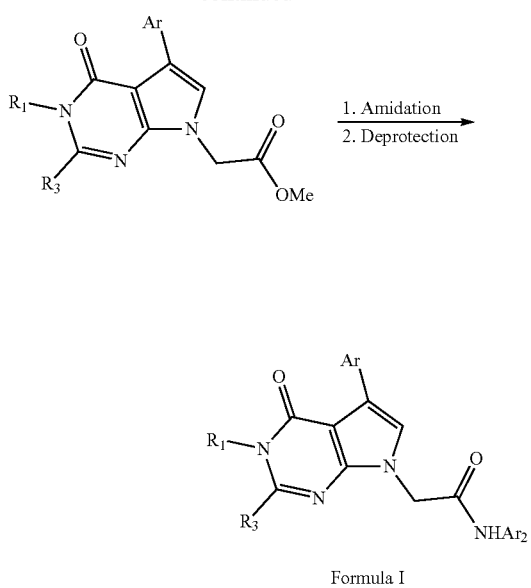

Formula I

Synthesis of (S)-7-(7-(2-((3-chloro-6-(2,4-dimethylpiperazin-1-yl)-2-fluoropyridin-4-yl)amino)-2-oxoethyl)-2,3-dimethyl-4-oxo-4,7-dihydro-3H-pyrrolo[2,3-d]pyrimidin-5-yl)-4-hydroxybenzo[d][1,3]dioxole-5-carboxamide (Compound I-311) Using Scheme 12

Scheme 13

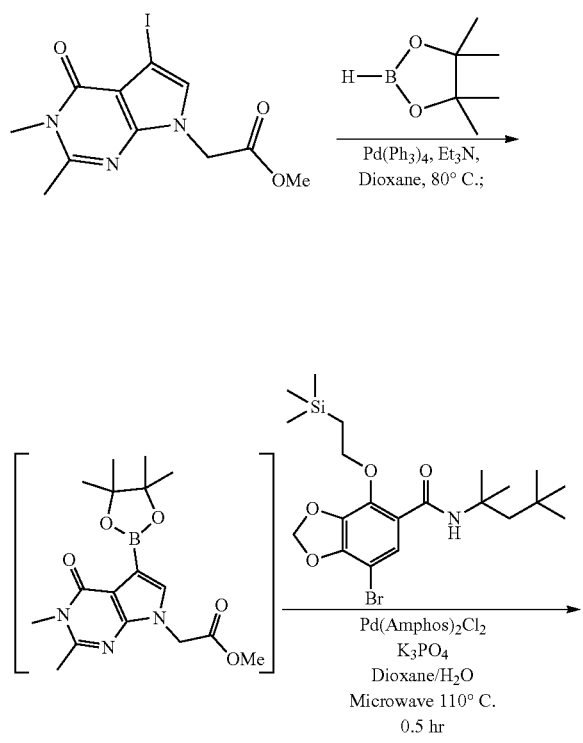

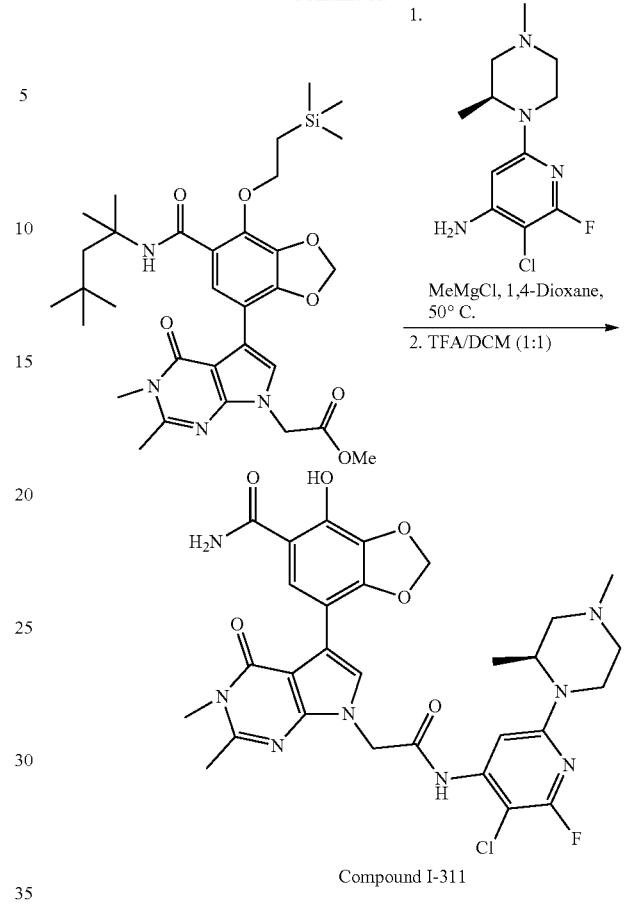

Compound I-311

Step 1: Preparation of methyl 2-(2,3-dimethyl-4-oxo-5-(6-((2,4,4-trimethylpentan-2-yl)carbamoyl)-7-(2-(trimethylsilyl)ethoxy)benzo[d][1,3]dioxol-4-yl)-3,4-dihydro-7H-pyrrolo[2,3-d]pyrimidin-7-yl)acetate
Exact Mass: 626.31

A microwave vial equipped with a magnetic stir bar was charged with methyl 2-(5-iodo-2,3-dimethyl-4-oxo-3H-pyrrolo[2,3-d]pyrimidin-7(4H)-yl)acetate (1.02 g, 2.82 mmol) and tetrakis(triphenylphosphine)palladium(0) (0.163 g, 0.141 mmol). The flask was sealed with a septum and was evacuated and flushed with N2 three times. Then 1,4-dioxane (12 mL), triethylamine (3.93 ml, 28.2 mmol) and 4,4,5,5-Tetramethyl-1,3,2-dioxaborolane (0.723 g, 5.65 mmol) were added to the flask, which was heated to 120° C. for 1 hour. LCMS analysis indicated complete the formation of the boronic acid instead of the desired boronate ester. The crude reaction mixture was cooled to RT, and used directly in the next step without further purification (quantitative conversion).

To a microwave vial charged with (7-(2-methoxy-2-oxoethyl)-2,3-dimethyl-4-oxo-4,7-dihydro-3H-pyrrolo[2,3-d]pyrimidin-5-yl)boronic acid (675 mg, 1.693 mmol) and 7-bromo-N-(2,4,4-trimethylpentan-2-yl)-4-(2-(trimethylsilyl)ethoxy)benzo[d][1,3]dioxole-5-carboxamide (500 mg, 1.058 mmol) in 1,4-Dioxane (12 ml), a solution of Potassium phosphate tribasic reagent grade, >=98% (449 mg, 2.116 mmol) in water (1.5 ml) followed by, Bis(di-tert-butyl(4-dimethylaminophenyl)phosphine)dichloropalladium(II) (37.5 mg, 0.053 mmol) was added. The vial was sealed, and the mixture heated in a microwave reactor to 120° C. for 45 minutes. The mixture was neutralized with citric acid (1 N, 1 ml). The crude mixture was concentrated onto celite and purified using by ISCO (12 g column, 0-5-35-100% EA/Hex; 30 min) to get the desired product, methyl 2-(2,3-dimethyl-4-oxo-5-(6-((2,4,4-trimethylpentan-2-yl)carbamoyl)-7-(2-(trimethylsilyl)ethoxy)benzo[d][1,3]dioxol-4-yl)-3,4-dihydro-7H-pyrrolo[2,3-d]pyrimidin-7-yl)acetate (447 mg, 60.6% yield), as a brown foamy solid. LCMS [M+H]+ 627.

Step 2: Preparation of (S)-7-(7-(2-((3-chloro-6-(2,4-dimethylpiperazin-1-yl)-2-fluoropyridin-4-yl)amino)-2-oxoethyl)-2,3-dimethyl-4-oxo-4,7-dihydro-3H-pyrrolo[2,3-d]pyrimidin-5-yl)-N-(2,4,4-trimethylpentan-2-yl)-4-(2-(trimethylsilyl)ethoxy)benzo[d][1,3]dioxole-5-carboxamide To a solution mixture of (S)-3-chloro-6-(2,4-dimethylpiperazin-1-yl)-2-fluoropyridin-4-amine (124 mg, 0.479 mmol) in 1,4-Dioxane (5 ml), methylmagnesium chloride (0.120 ml, 0.359 mmol) was added. After 5-10 min agitation, a dilute solution of methyl 2-(2,3-dimethyl-4-oxo-5-(6-((2,4,4-trimethylpentan-2-yl)carbamoyl)-7-(2-(trimethylsilyl)ethoxy)benzo[d][1,3]dioxol-4-yl)-3,4-dihydro-7H-pyrrolo[2,3-d]pyrimidin-7-yl)acetate (75 mg, 0.120 mmol) in 1,4-Dioxane (2.00 ml) was added. After 10 min. agitation at 55° C., two portions of methylmagnesium chloride (0.120 ml, 0.359 mmol in each portion) was added to see complete conversion to the desired product. The mixture was concentrated under vacuum to remove dioxane. The residue was quenched with sat. NH4Cl, satd. brine and EtOAc. The organic layer was concentrated and purified by reverse phase chromatography(ACN/water) to give the desired product, (S)-7-(7-(2-((5-chloro-2-(3-methylmorpholino)pyridin-4-yl)amino)-2-oxoethyl)-3-methyl-4-oxo-4,7-dihydro-3H-pyrrolo[2,3-d]pyrimidin-5-yl)-N-(2,4,4-trimethylpentan-2-yl)-4-(2-(trimethylsilyl)ethoxy)benzo[d][1,3]dioxole-5-carboxamide (34 mg, 0.038 mmol, 32% yield), as a brown solid.
The above, (S)-7-(7-(2-((5-chloro-2-(3-methylmorpholino)pyridin-4-yl)amino)-2-oxoethyl)-3-methyl-4-oxo-4,7-dihydro-3H-pyrrolo[2,3-d]pyrimidin-5-yl)-N-(2,4,4-trimethylpentan-2-yl)-4-(2-(trimethylsilyl)ethoxy)benzo[d][1,3]dioxole-5-carboxamide (34 mg, 0.038 mmol), was treated with DCM/TFA (4 mL/4 mL) and the reaction was stirred at 23° C. overnight. The mixture was concentrated under vacuum and purified by column chromatography (DCM/MeOH) to afford the desired product, (S)-7-(7-(2-((3-chloro-6-(2,4-dimethylpiperazin-1-yl)-2-fluoropyridin-4-yl)amino)-2-oxoethyl)-2,3-dimethyl-4-oxo-4,7-dihydro-3H-pyrrolo[2,3-d]pyrimidin-5-yl)-4-hydroxybenzo[d][1,3]dioxole-5-carboxamide, Trifluoroacetic Acid, NF3COOH [D](24 mg, 25% yield), as a beige colored solid; LCMS [M+H]+ 641 (Compound I-311).
General Schemes for the Preparation of trimethylsilylethyl (TMSE)-Protected Boronate Esters
Method 1

Scheme 14

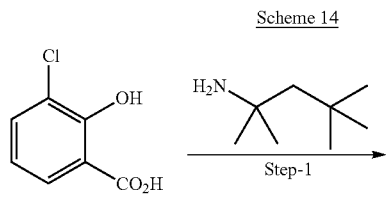

Step 1: To a stirred solution of compound 3-chloro-2-hydroxybenzoic acid (50 g, 290.6 mmol, 1 eq) in DMF (1000 ml) was added EDC. HCl (66.8 g, 348.7 mmol, 1.2 eq) and HOBt (47.11 g, 348.7 mmol, 1.2 eq) at 0° C. under argon atmosphere followed by DiPEA (180.12 ml, 1017.1 mmol, 3.5 eq). The resulting mixture was stirred for 15 min at the same temp. Then, t-Octylamine (58.8 ml, 248.7 mmol, 1.2 eq) was added dropwise at 0° C. and allowed to warm up to RT over 16 h. TLC analysis indicated formation of a less polar spot. The reaction mixture was diluted with water (5 L) and extracted with EtOAc (3×1 L). The organic layer was washed with water (2×1 L), dried over Na2SO4 and concentrated under reduced pressure to give a crude product. The crude product was purified by column chromatography (silica gel 100-200 mesh) using 5-10% EtOAc in petroleum ether as an eluent to provide 3-chloro-2-hydroxy-N-(2,4,4-trimethylpentan-2-yl)benzamide (30 g, 36.58%) as an off-white solid. LCMS [M+H]+ 284.

Step 2: To a solution of Triphenyl phosphine (18.51 g, 70.47 mmol, 2 eq) in Dry THF (350 ml), a solution of Diisopropyl azodicarboxylate (14.24 g, 70.47 mmol, 2 eq) was added dropwise over 30 min at 0° C. and stirred at the same temperature for 30 minutes. Then, a solution of 2-(Trimethylsilyl)ethanol (5.9 g, 70.47 mmol, 2 eq) was added followed by dropwise addition of 3-chloro-2-hydroxy-N-(2,4,4-trimethylpentan-2-yl)benzamide (10 g, 35.24 mmol, 1 eq) in Dry THF (70 ml) over 20 min at 0° C. and allowed to warm up to RT overnight under Argon atm. TLC analysis indicated formation of a non-polar spot. The reaction mixture was diluted with EtOAc (1 L), washed with water (2×2 50 ml) and sat. Brine (2×250). The separated organic layer was dried over Na2SO4 and concentrated under reduced pressure to give a crude product, which was purified by column chromatography (silica gel 100-200mesh) using 0-4% EtOAc in petroleum ether as an eluent to afford

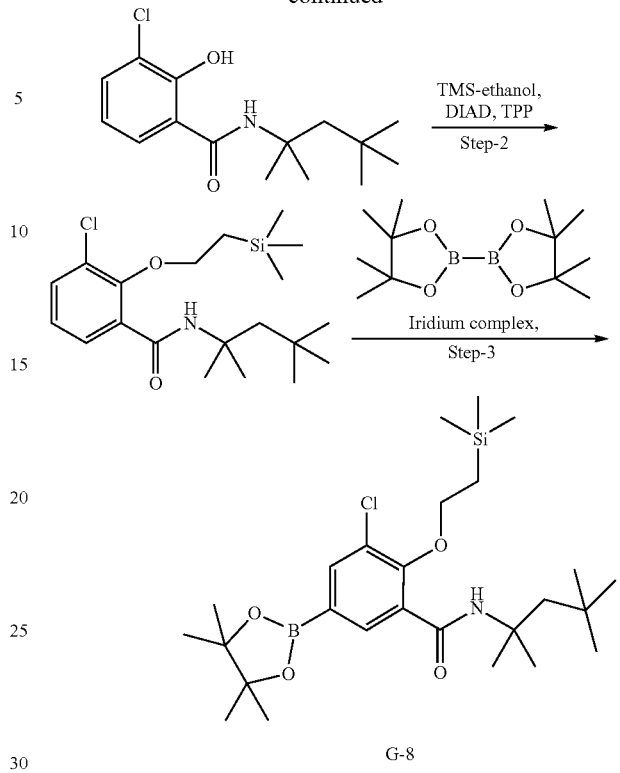

G-8

3-chloro-N-(2,4,4-trimethylpentan-2-yl)-2-(2-(trimethylsilyl)ethoxy)benzamide (8 g, 59.25%) as a reddish oil. LCMS [M+H]+ 384.

Step 3: To a solution of Bispinacolatodiboron (22.8 g, 90 mmol, 2.3 eq), DTBPY (620 mg, 2.34 mmol, 0.06 eq) in degassed dry n-hexane (450 ml) was degassed with argon for 30 min. After 10 min, Iridium complex (770 mg, 1.17 mmol, 0.03 eq) was added and stirred for 5 min (color change was observed from yellow to wine red). After 5 min, 3-chloro-N-(2,4,4-trimethylpentan-2-yl)-2-(2-(trimethylsilyl)ethoxy) benzamide (15 g, 33.6 mmol, 1 eq) was added to above wine red solution at RT under Argon atm. Then, the above round bottom flask was immersed in preheated oil bath at 65° C. and stirred for 1.5 h. TLC analysis indicated formation of a nonpolar spot. Then, reaction mixture was cooled to RT and filter through celite. The celite bed was washed with n-hexane. The obtained filtrate was concentrated under reduced pressure to give a crude residual oil, which was adsorbed on celite and purified by column chromatography (Silica gel 100-200 mesh) 5-10% EtOAc in petroleum ether as an eluent to afford 3-chloro-5-(4,4,5,5-tetramethyl-1,3,2-dioxaborolan-2-yl)-N-(2,4,4-trimethylpentan-2-yl)-2-(2-(trimethylsilyl)ethoxy)benzamide (12 g, 70.13%) as an off-white solid.
Method 2

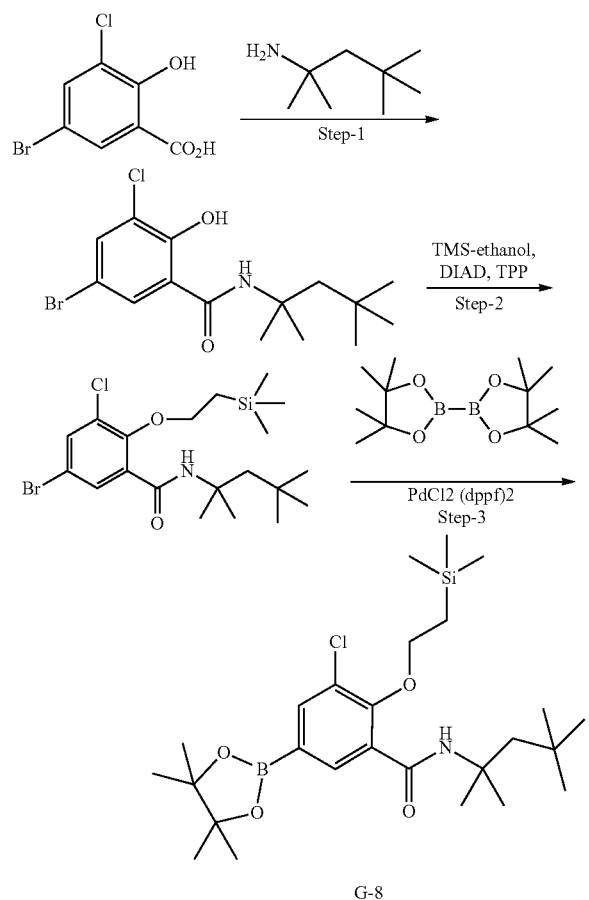

Scheme 15

G-8

Step 1: In a solution of 5-bromo-3-chloro-2-hydroxybenzoic acid (25.91 g, 103 mmol) in N,N-Dimethylformamide (DMF) (Volume: 250 ml) were added HBTU (42.93 g, 113 mmol) and N,N-Diisopropylethylamine (53.8 ml, 309 mmol). The reaction mixture was stirred for 10 minutes before adding tert-Octylamine (24.81 ml, 155 mmol). Then the reaction mixture was stirred at room temperature and followed via LCMS. After overnight, the reaction was partitioned between water and EtOAc. The layers were separated and the aqueous layer was extracted with EtOAc. The combined organic layers were washed with water and brine, and dried over magnesium sulfate. The crude material was loaded onto celite and purified by flash chromatography in 2 batches [5-50% EtOAc/hexanes] to give the desired 5-bromo-3-chloro-2-hydroxy-N-(2,4,4-trimethylpentan-2-yl)benzamide (35.1 g, 97 mmol, 94% yield) as a white solid.

Step 2: Di-tert-butyl azodicarboxylate 98% (1.071 g, 4.65 mmol) was added to a stirring solution of 5-bromo-3-chloro-2-hydroxy-N-(2,4,4-trimethylpentan-2-yl)benzamide (1.349 g, 3.72 mmol), 2-(Trimethylsilyl)ethanol (0.666 ml, 4.65 mmol) and Triphenylphosphine (1.219 g, 4.65 mmol) in Dichloromethane (DCM) (Volume: 35 ml) at room temperature. After stirring overnight, the mixture was concentrated, the residue was triturated with hexane and the filtrated was concentrated onto celite. The crude mixture was purified using flash chromatography [0-15% EtOAc/hexanes] to afford 5-bromo-3-chloro-N-(2,4,4-trimethylpentan-2-yl)-2-(2-(trimethylsilyl)ethoxy)benzamide (1.616 g, 3.49 mmol, 94% yield) as a viscous yellow oil. 1H NMR (500 MHz, DMSO-d6) δ=7.96 (s, 1H), 7.81 (d, J=2.4 Hz, 1H), 7.42 (d, J=2.4 Hz, 1H), 4.09-4.03 (m, 2H), 1.82 (s, 2H), 1.39 (s, 6H), 1.16-1.11 (m, 2H), 0.98 (s, 9H), 0.02 (s, 9H).

Step 3: A round bottom flask was charged with 5-bromo-3-chloro-N-(2,4,4-trimethylsilyl)ethoxy)benzamide (7.09 g, 15.32 mmol), Bis(pinacolato)diboron (7.94 g, 30.6 mmol), Potassium acetate (6.07 g, 61.3 mmol) and 1,4-Dioxane (Volume: 120 ml). The reaction mixture was degassed using argon for 15 minutes and [1,12-Bis(diphenylphosphino)ferrocene]dichloropalladium (II), DCM complex (1.251 g, 1.532 mmol) was finally added. The reaction mixture was heated to 110° C. and followed by LCMS.

After 2 hours, reaction mixture was concentrated onto celite and the crude compound was purified by flash chromatography [0-20% DCM/MeOH] to afford 3-chloro-5-(4,4,5,5-tetramethyl-1,3,2-dioxaborolan-2-yl)-N-(2,4,4-trimethylpentan-2-yl)-2-(2-(trimethylsilyl)ethoxy)benzamide (6.86 g, 13.45 mmol, 88% yield) as a slightly yellow oil that solidified on standing. 1H NMR (500 MHz, CHLOROFORM-d) δ=8.39 (d, J=1.5 Hz, 1H), 7.89 (d, J=1.5 Hz, 1H), 7.67 (s, 1H), 4.12-4.08 (m, 2H), 1.90 (s, 2H), 1.52 (s, 6H), 1.32 (s, 12H), 1.29-1.25 (m, 2H), 1.02 (s, 9H), 0.06 (s, 9H).
Method 3

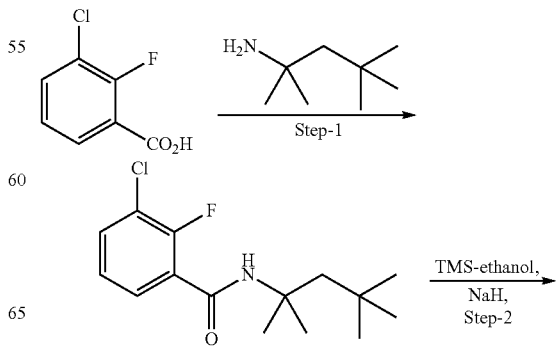

Scheme 16

-continued

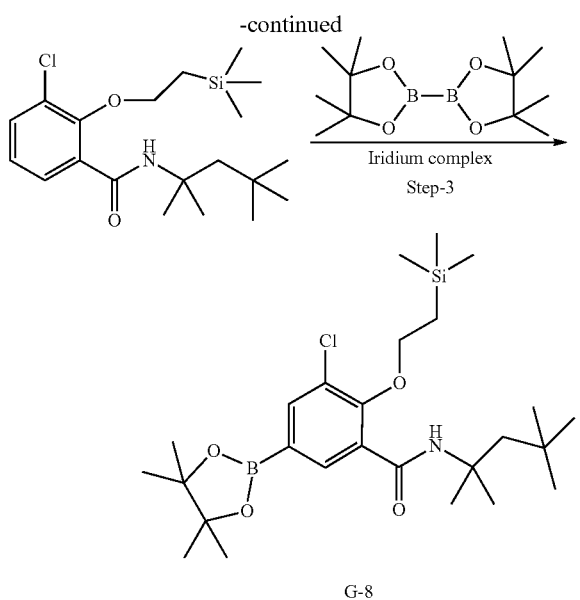

G-8

Step 1: Synthesis of 3-chloro-2-fluoro-N-(2,4,4-trimethylpentan-2-yl)benzamide

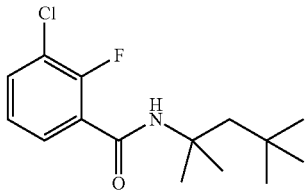 [SMILES: CC(C)(C)CC(C)(C)NC(=O)c1cccc(Cl)c1F]

To a flask charged with 3-Chloro-2-fluorobenzoic acid (2 g, 8.66 mmol), was added Thionyl chloride (10 ml) followed triethylamine (0.5 ml). The mixture was heated to 70° C. for 30 min. The thionyl chloride was removed in vacuo, the residue was dissolved in CH$_2$Cl$_2$ (10 ml) and tert-Octylamine was added, and the mixture was stirred at room temperature overnight. The mixture was concentrated onto celite and purified by silica gel flash column chromatography (EA:Hexane 0-20% as eluant) to give the title compound as a white solid (55%); Observed LCMS [M+H]$^+$ 286.

Step 2: Synthesis of 3-chloro-N-(2,4,4-trimethylpentan-2-yl)-2-(2-(trimethylsilyl)ethoxy)benzamide

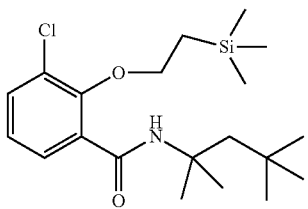 [SMILES: CC(C)(C)CC(C)(C)NC(=O)c1cccc(Cl)c1OCC[Si](C)(C)C]

To a flask charged with 2-(trimethylsilyl)ethanol as solvent (50.2 ml, 350 mmol), was added NaH (3.35 g, 87 mmol) and the mixture was heated to 80° C. for 30 min. The 3-chloro-2-fluoro-N-(2,4,4-trimethylpentan-2-yl)benzamide (10 g, 35 mmol) was added as a solid portion-wise and the resulting mixture was stirred for 10 min. LCMS analysis indicated that reaction was complete. The mixture was cooled, diluted with ether (150 ml) and then washed with NaOH (1 N, 75 ml) and brine. The organic layer was then dried over Na$_2$SO$_4$ (anhydrous) and concentrated onto celite and purified by silica gel flash column chromatography (EA:Hexane 0-10% as eluant) to give the title compound as a yellow oil (74%); 1H NMR (500 MHz, CHLOROFORM-d) δ=7.89 (dd, J=1.8, 7.9 Hz, 1H), 7.77 (s, 1H), 7.41 (dd, J=1.7, 7.9 Hz, 1H), 7.08 (t, J=7.9 Hz, 1H), 4.20-3.75 (m, 3H), 1.83 (s, 2H), 1.46 (s, 6H), 1.26-1.18 (m, 2H), 0.95 (s, 9H); Observed LCMS [M+Na]$^+$ 406.

Step 3: Synthesis of 3-chloro-5-(4,4,5,5-tetramethyl-1,3,2-dioxaborolan-2-yl)-N-(2,4,4-trimethylpentan-2-yl)-2-(2-(trimethylsilyl)ethoxy)benzamide (G-8)

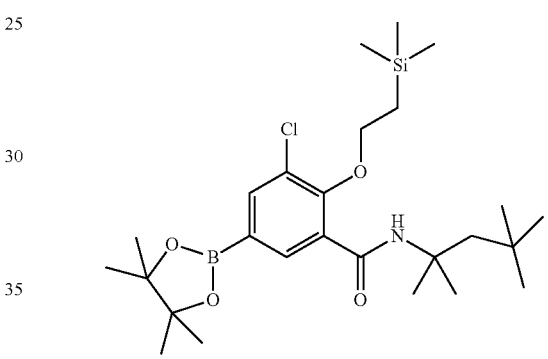

In a 250 mL round bottomed flask with magnetic stir bar was placed Bis(pinacolato)diboron (2.91 g, 11.46 mmol), Di-mu-methoxobis(1,5-cyclooctadiene)diiridium (I) (207 mg, 0.312 mmol) and 4,4'-Di-tert-butyl-2,2'-dipyridyl (168 mg, 0.625 mmol). The flask was evacuated and filled with nitrogen and then dry Hexane (Volume: 50 mL) was added via a syringe. This flask was stirred at rt for 5 min to activate the catalyst and dissolve the material. 3-chloro-N-(2,4,4-trimethylpentan-2-yl)-2-(2-(trimethylsilyl)ethoxy)benzamide (4 g, 10.42 mmol) was added and the reaction mixture was stirred for 2 h at 55° C. (LCMS indicated full conversion). The crude mixture was cooled to room temperature, concentrated onto celite and then purified by flash chromatography on ISCO (SiO2, hexanes-EtOAc 0-20%) to yield the product G-8 as a white solid (79% yield). 1H NMR (500 MHz, CHLOROFORM-d) δ=8.34 (d, J=1.3 Hz, 1H), 7.83 (d, J=1.3 Hz, 1H), 7.61 (s, 1H), 4.11-3.94 (m, 3H), 1.84 (s, 2H), 1.47 (s, 6H), 1.26 (s, 12H), 1.24-1.19 (m, 3H), 0.96 (s, 9H), 0.00 (s, 9H); Observed LCMS [M+Na]$^+$ 532.

Synthesis of 3-chloro-2-fluoro-6-(methoxymethoxy)-N-(2,4,4-trimethylpentan-2-yl)benzamide

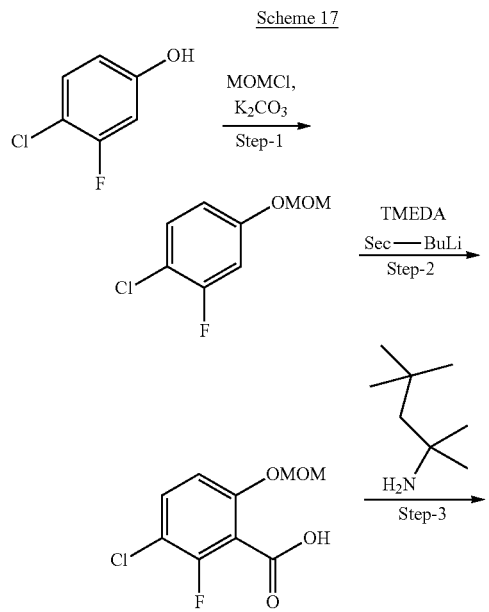

Step 1:
To a stirred solution of 4-chloro-3-fluorophenol (5 g, 34.118 mmol, 1 eq) in DMF (70 mL) was added DIPEA (12.16 mL, 68.236 mmol, 2 eq) at RT under argon atmosphere. The reaction was allowed to stir for 30 min. MOM-Cl (3.5 mL, 45.377 mmol, 1.33 eq) was then added at RT and the reaction was continued for 16 h. TLC analysis indicated formation of a non polar spot. The reaction mixture was quenched in Ice water (200 mL) and extracted with EtOAc (3×100 mL). The organic layer was dried over $Na_2SO_4$ and concentrated under reduced pressure to give a crude mixture. The crude mixture was purified by Combiflash chromatography using 5% EtOAc in petroleum ether as an eluent to provide the MOM-protected compound (5 g, 76.89%) as a colorless liquid.

Step 2:
To a stirred solution of TMEDA (5.9 mL, 39.349 mmol, 1.5 eq) in THF (602 mL) was added 1.6M Sec-BuLi in cyclohexane (28 mL, 39.349 mmol, 1.5 eq) slowly drop wise at −78° C. The reaction mass was stirred for 30 minutes at the same temperature followed by addition of MOM-protected 4-chloro-3-fluorophenol (5 g, 26.233 mmol, 1 eq) in THF (20 mL) at the same temp and stirring for another 30 min. Then the reaction mass was quenched with dry ice powder and allowed to warm up to RT over 16 h. TLC analysis indicated formation of a polar spot. The reaction mixture was diluted with water (200 mL) and its pH adjusted to approximately 5. Then the reaction was extracted with EtOAc (3×100 mL). The organic layer was dried over $Na_2SO_4$ and concentrated under reduced pressure to give the desired carboxylic acid (5 g, 81.23%) as an off-white solid. LCMS: m/z 233.01% (M+H).

Step 3:
To a stirred solution of the carboxylic acid from the Step 2 (5 g, 21.312 mmol, 1 eq) in DMF (50 mL) was added HATU (9.72 g, 25.754 mmol, 1.2 eq) at 0° C. under argon atmosphere followed by DiPEA (11.39 mL, 63.935 mmol, 1.2 eq) and the resulting mixture was stirred for 15 min at the same temp. Then, tert-Octylamine (4.29 mL, 25.574 mmol, 1.2 eq) was added drop wise at 0° C. and allowed to RT over 16 h. TLC analysis indicated formation of a non polar spot. The reaction mixture was diluted with ice water (500 mL) and extracted with EtOAc (2×100 mL). The organic layer was washed with water (2×50 mL), dried over $Na_2SO_4$ and concentrated under reduced pressure to give a crude product. The crude product was purified by Combiflash chromatography using 6% EtOAc in petroleum ether as an eluent providing 2-fluoro-6-(methoxymethoxy)-N-(2,4,4-trimethylpentan-2-yl)benzamide (3.25 g, 44.09%) as an off white solid. LCMS: m/z 346.42% (M+H).

Synthesis of 3-methoxy-5-(4,4,5,5-tetramethyl-1,3,2-dioxaborolan-2-yl)-N-(2,4,4-trimethylpentan-2-yl)-2-(2-(trimethylsilyl)ethoxy)benzamide (G-9)

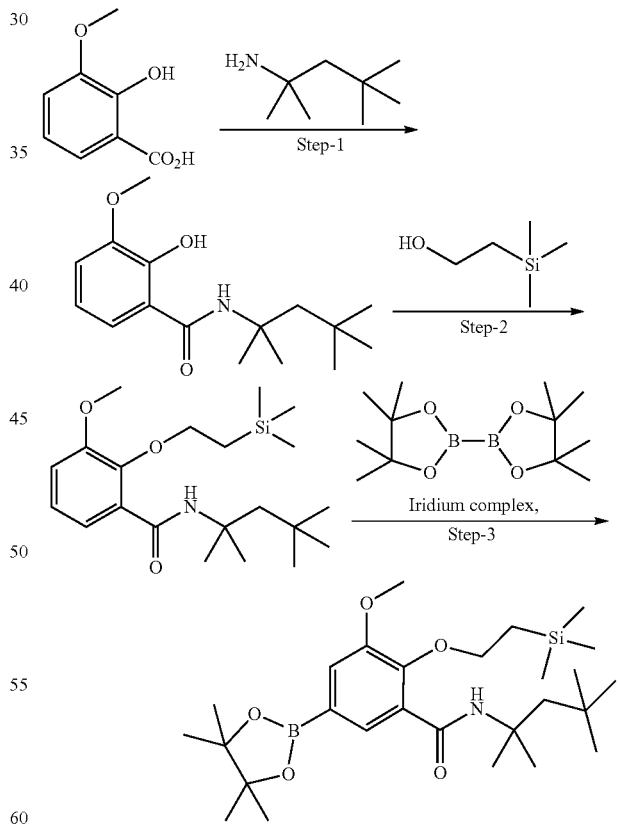

Step 1:
To a stirred solution of 2-hydroxy-3-methoxybenzoic acid (10 g, 59.5 mmol, 1 eq) in DMF (100 mL) was added EDC.HCl (17.10 g, 89.2 mmol, 1.5 eq) and HOBt (12.06 g, 89.2 mmol, 1.5 eq) at 0° C. under argon atmosphere followed by DiPEA (37.11 mL, 208.1 mmol, 3.5 eq) and the resulting mixture stirred for 15 min at the same temp. Then, 2,4,4-trimethylpentan-2-amine (11.97 mL, 71.4 mmol, 1.2 eq) was added dropwise at 0° C. and allowed to warm up to RT over 48 h. TLC analysis indicated formation of a less polar spot. The reaction mixture was diluted with water (500 mL) and extracted with EtOAc (2×200 mL). The organic layer was washed with water (2×100 mL), dried over $Na_2SO_4$ and concentrated under reduced pressure to give a crude product. The crude product was purified by column chromatography (silica gel 100-200 mesh) using 5% EtOAc in petroleum ether as an eluent to provide the desired compound (7 g, 42.14%) as an off white solid. LC-MS: m/z 280.28 (M+H).

Step 2:

To a solution of triphenyl phosphine (13.16 g, 50.1 mmol, 2 eq) in Dry THF (140 mL), a solution of Diisopropyl azodicarboxylate (9.9 mL, 50.1 mmol, 2 eq) was added drop wise at 0° C. and stirred for the same temp over 30 min. Then, a solution of 2-(trimethylsilyl)ethanol (4.16 mL, 50.1 mmol, 2 eq) was added followed by addition of the product from step 1 (7 g, 25.1 mmol, 1 eq) at 0° C. temp. Then, the reaction mixture was allowed to warm up to RT overnight. TLC analysis indicated formation of a non polar spot. The reaction mixture was concentrated under reduced pressure to give a crude residue, which was dissolved in EtOAc (300 mL) and washed with brine (2×100 mL) & water (2×100 mL). The separated organic layer was dried over $Na_2SO_4$ and concentrated under reduced pressure to result in a crude product, which was purified by column chromatography (silica gel 100-200mesh) using 2% EtOAc in petroleum ether as an eluent to give the desired product (8 g, 84.09%) as an pale yellow color liquid.

Step 3:

A solution of 4,4,4',4',5,5,5',5'-octamethyl-2,2'-bi(1,3,2-dioxaborolane) (12.31 g, 48.5 mmol, 2.3 eq), DTBPY (339 mg, 1.3 mmol, 0.06 eq) in degassed dry n-hexane (80 mL) was degassed with argon for 10 min. After 10 min, Iridium complex (419 mg, 0.63 mmol, 0.03 eq) was added and stirred for 5 min (color change was observed from yellow to wine red). After 5 min, the product from step 2 (8 g, 21.1 mmol, 1 eq) in n-hexane (20 mL) was added to above wine red solution at RT under Argon atm. Then, the reaction mass was immersed in preheated oil bath at 60° C. temp and stirred for 8 h. TLC analysis indicated formation of a polar spot. Then, reaction mixture was cooled to RT and filtered through celite. The celite bed was washed with n-hexane. The obtained filtrate was concentrated under reduced pressure gave crude residual oil, which was adsorbed on celite and purified by column chromatography (Silica gel 100-200 mesh) 0-5% EtOAc in petroleum ether as an eluent to afford 3-methoxy-5-(4,4,5,5-tetramethyl-1,3,2-dioxaborolan-2-yl)-N-(2,4,4-trimethylpentan-2-yl)-2-(2 (trimethylsilyl)ethoxy)benzamide (5.35 g, 50.21%) as an off white solid.

Synthesis of 3-ethoxy-5-(4,4,5,5-tetramethyl-1,3,2-dioxaborolan-2-yl)-N-(2,4,4-trimethylpentan-2-yl)-2-(2-(trimethylsilyl)ethoxy)benzamide (G-9)

Scheme 19

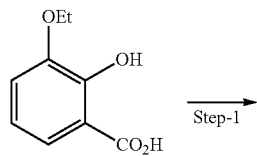

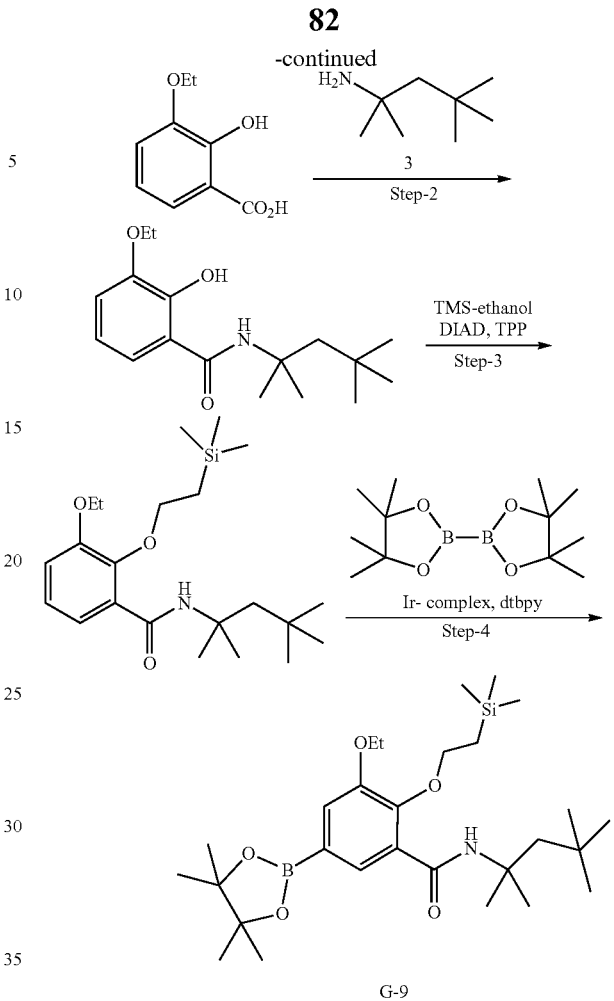

Step 1:

To a solution of 3-ethoxy-2-hydroxybenzaldehyde (5 g, 30.120 mmol, 1 eq) in 1,4-dioxane:$H_2O$ (4:2) (60 ml) was added sulfamic acid (4.4 g, 45.180, 1.5 eq), $NaH_2PO_4.H_2O$ (16.2 g, 117.46 mmol, 3.9 eq), and $NaClO_2$ (3.52 g, 39.15 mmol, 1.3 eq) at 0° C. The reaction mixture was allowed to warm up to RT then stirred for 2 h at rt. Then $Na_2SO_3$ (4.55 g, 36.144 mmol, 1.2 eq) was added at RT and stirred for 30 min at RT. TLC analysis indicated formation of a polar spot. The reaction mixture was acidified with Con.HCl (10 mL) and extracted with EtOAc (50 mL×3). The combined organic layer was dried over $Na_2SO_4$ and concentrated under reduced pressure to give a crude product. The crude product was purified by solvent wash to afforded analytically pure 3-ethoxy-2-hydroxybenzoic acid (5.3 g, 96.7%) as an off white solid. LC-MS: m/z 181.19 (M−H).

Step 2:

To a stirred solution of 3-ethoxy-2-hydroxybenzoic acid (10 g, 54.9 mmol, 1 eq) in DMF (100 ml) was added EDC.HCl (12.659 g, 65.88 mmol, 1.2 eq) and HOBt (8.92 g, 65.88 mmol, 1.2 eq) at 0° C. under argon atmosphere followed by DiPEA (46 ml, 129.24 mmol, 3.5 eq). The resulting mixture was stirred for 15 min at the same temp. Then, tert-octylamine (9.5 ml, 65.88 mmol, 1.2 eq) was added dropwise at 0° C. and allowed to warm up to RT over 16 h. TLC analysis indicated formation of a less polar spot. The reaction mixture was diluted with water (4 L) and extracted with EtOAc (4×500 mL). The organic layer was washed with water (2×200 mL), dried over $Na_2SO_4$ and concentrated under reduced pressure to give a crude product. The crude product was purified by column chromatography (silica gel 100-200 mesh) using 5-10% EtOAc in petroleum ether as an eluent to give 3-ethoxy-2-hydroxy-N-(2,4,4-trimethylpentan-2-yl)benzamide (8.5 g, 51.8%) as an off white solid. LC-MS: m/z 294.25 (M+H).

Step 3:

To a solution of Triphenyl phosphine (15 g, 56.65 mmol, 2 eq) in Dry THF (100 ml), a solution of Diisopropyl azodicarboxylate (11.2 ml, 56.65 mmol, 2 eq)) was added drop wise at 0° C. and stirred for the same temp over 30 min. Then, a solution of TMS-ethanol (4.6 ml, 56.65 mmol, 2 eq) was added followed by the addition of 3-ethoxy-2-hydroxy-N-(2,4,4-trimethylpentan-2-yl)benzamide (8.3 g, 28.327 mmol, 1 eq) at 0° C. temp. Then, the reaction mixture was allowed to warm up to RT overnight. TLC analysis indicated formation of a non polar spot. The reaction mixture was concentrated under reduced pressure gave crude residue which was dissolved in EtOAc (300 ml) and washed with brine (2×100 ml) & water (2×100 ml). Separated organic layer was dried over Na$_2$SO$_4$ and concentrated under reduced pressure to give a crude product; which was purified by column chromatography (silica gel 100-200mesh) using 0-5% petroleum ether as an eluent to give 3-ethoxy-N-(2,4,4-trimethylpentan-2-yl)-2-(2-(trimethylsilyl)ethoxy)benzamide (8.2 g, 73.87%) as an colorless liquid. LC-MS: m/z 394.12 (M+H).

Step 4:

To a solution of bispinacolato-diboron (25.96 g, 102.0 mmol, 2.3 eq), DTBPY (710 mg, 2.66 mmol, 0.06 eq) in degassed dry n-hexane (350 ml) was degassed with argon for 10 min. After 10 min, Iridium complex (880 mg, 1.33 mmol, 0.03 eq) was added and the resulting solution stirred for 5 min (color change was observed from yellow to wine red). After 5 min, 3-ethoxy-N-(2,4,4-trimethylpentan-2-yl)-2-(2-(trimethylsilyl)ethoxy)benzamide (17 g, 44.3 mmol, 1 eq) was added to above wine red solution at RT in sealed tube under Argon atm. Then, the sealed tube was immersed in preheated oil bath at 60° C. temp and stirred for 2 h. TLC analysis indicated formation of a non polar spot. Then, reaction mixture was cooled to RT and filter through celite, celite bed was washed with n-hexane. The obtained filtrate was concentrated under reduced pressure to give a crude residual oil, which was adsorbed on celite and purified by flash chromatography (Silica gel 100-200 mesh) 0-5% EtOAc in petroleum ether as an eluent to give 3-methoxy-5-(4,4,5,5-tetramethyl-1,3,2-dioxaborolan-2-yl)-N-(2,4,4-trimethylpentan-2-yl)-2-(2 (trimethylsilyl)ethoxy)benzamide (G-9) (6.4 g, 72.72%) as pale yellow thick liquid.

Synthesis of 4-fluoro-5-(4,4,5,5-tetramethyl-1,3,2-dioxaborolan-2-yl)-N-(2,4,4-trimethylpentan-2-yl)-2-(2-(trimethylsilyl)ethoxy)benzamide (G-10)

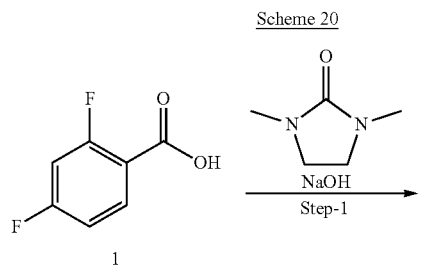

Scheme 20

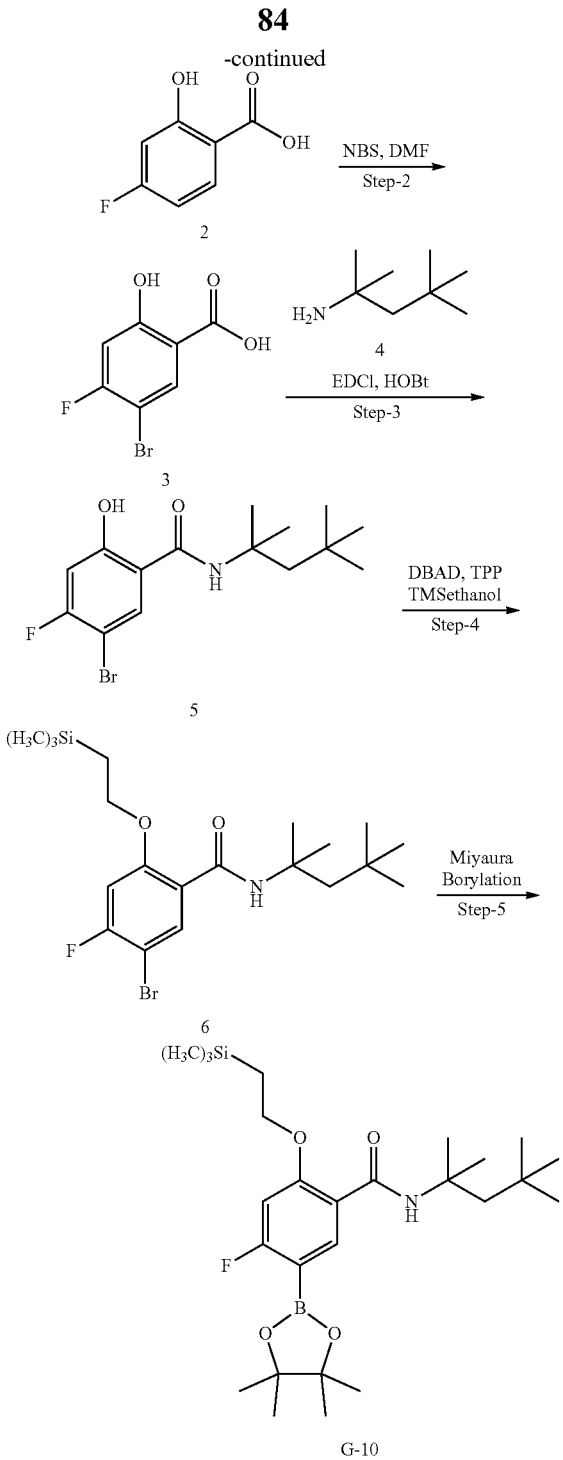

Compound numbers in text refer to structures shown in Scheme 20.

Step 1:

To a solution of compound 1 (15 g, 94.93 mmol, 1 eq) in 1,3-dimethyl-2-imidazolidinone (210 mL) was added NaOH (3.29 g, 332.27 mmol, 3.5 eq) at RT, then the reaction mixture was heated to 135° C. for 6 h. The reaction mixture was cooled to RT and quenched in ice cold water then acidified with 2N HCl at 0° C. The reaction mixture was filtered to give a solid compound under vacuum corresponding to compound 2 (10 g, 67.52%) as off-white solid. LC-MS: m/z 155.07 (M−H).

Step 2:

To a solution of compound 2 (1 g, 6.41 mmol, 1 eq) in DMF (15 mL) was added portion wise NBS (1.25 g, 7.051 mmol, 1.1 eq) at 0° C. The solution was allowed to warm up to RT for 1 h. Monitored by TLC, the reaction mixture was diluted with cold water then filtered to give a solid compound under vacuum corresponding to compound 3 (1.1 g, 73.33%) as off-white solid. LC-MS: m/z 235.03 (M–H).

Step 3:

To a solution of compound 3 (13 g, 55.55 mmol, 1 eq) in DMF (130 mL) was added HATU (31.66 g, 83.33 mmol, 1.5 eq), DIPEA (29.4 mL, 166.66 mmol, 3 eq) and compound 4 (13.96 mL, 83.33 mmol, 1.5 eq) at 0° C. The mixture was allowed to warm up to RT for 16 h. The reaction was monitored by TLC, then diluted with water and extracted with EtOAc (3×100 mL). The combined organic layer was washed with brine and dried over $Na_2SO_4$ and concentrated under reduced pressure to give a crude product. The crude compound was purified by column chromatography (silica gel 100-200 mesh) using 0-3% EtOAc in petroleum ether as an eluent to give compound 5 (8 g, 41.75%) as white solid. LC-MS m/z 348.19 (M+H).

Step 4:

To a stirred solution of TPP (21.0 g, 86.95 mmol, 3 eq) in THF (50 mL) was added slowly DBAD (20 g, 86.95 mmol, 3 eq) at 0° under Ar atmosphere, after 30 min. added TMS ethanol (4.6 mL, 57.97 mmol, 2 eq) and compound 5 (10 g, 28.98 mmol, 1 eq) at 0°. The reaction mixture was allowed to warm up to RT for 16 h. TLC analysis indicated formation of a polar spot. The reaction mixture was diluted with water and extracted with EtOAc (3×100 mL). The organic layer was washed with brine and dried over $Na_2SO_4$ and concentrated under reduced pressure to give a crude product. Crude product was purified by column chromatography (silica gel 100-200 mesh) using 0-1% EtOAc in petroleum ether as an eluent to give compound 6 (7 g, 54.30%) as white solid.

Step 5:

A stirred solution of compound 6 (6 g, 13.48 mmol, 1 eq) in dioxane (250 mL) was degassed with Ar for 20 min., then to it were added KOAc (3.96 g, 40.44 mmol, 3 eq), Bis (pinacolato) diboran (3.76 g, 14.83 mmol, 1.1 eq) and Pd (PPh$_3$)$_4$ (0.55 g, 1.34 mmol, 0.1 eq) at RT. The mixture was heated to 90° C. for 16 h. TLC analysis indicated formation of a polar spot. The reaction mixture was cooled to RT then filtered through celite pad; celite pad was washed with EtOAc (2×30 mL). The filtrate was concentrated to a crude product. The crude product was purified by column chromatography (silica gel 100-200 mesh) using 0-5% EtOAc in petroleum ether as an eluent to give 4-fluoro-5-(4,4,5,5-tetramethyl-1,3,2-dioxaborolan-2-yl)-N-(2,4,4-trimethylpentan-2-yl)-2-(2-(trimethylsilyl)ethoxy)benzamide (G-10) (4.5 g, 67.77%) as color less oil.

Synthesis of 3-fluoro-5-(4,4,5,5-tetramethyl-1,3,2-dioxaborolan-2-yl)-N-(2,4,4-trimethylpentan-2-yl)-2-(2-(trimethylsilyl)ethoxy)benzamide (G-11)

Scheme 21

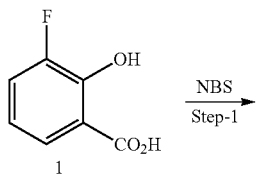

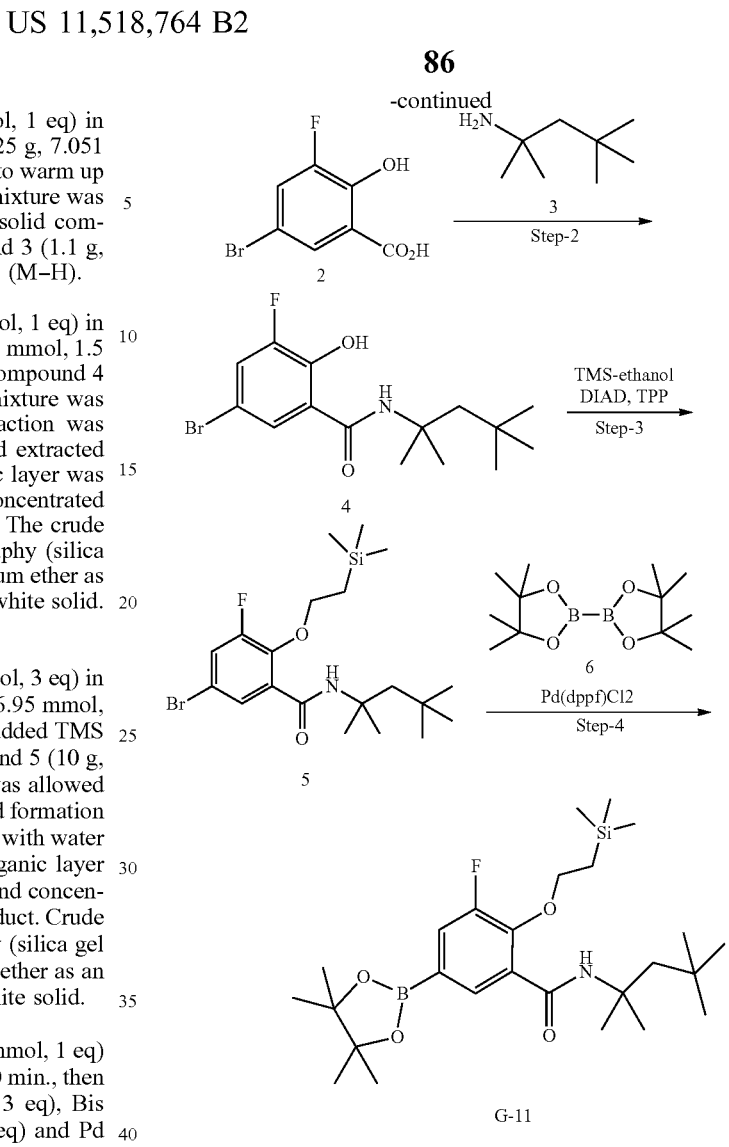

Compound numbers in text refer to structures shown in Scheme 21.

Step 1: Intermediate 2

To a stirred solution of compound 1 (10 g, 64.51 mmol, 1 eq) in ACN (200 ml) was added NBS (12.6 g, 70.96 mmol, 1.1 eq) at RT under argon atmosphere and then the reaction allowed to proceed for 2 h. TLC analysis indicated formation of a polar spot. The reaction mixture was concentrated under reduced pressure to obtain a crude residue, which was diluted with water and filtered to give a solid compound. The solid was washed with petroleum ether (2×30 mL) then dried under vacuum to afford compound 2 (13 g, 86.66%) as an off-white solid.

Step 2: Intermediate 4

To a stirred solution of compound 2 (13 g, 55.55 mmol, 1 eq) in DMF (150 mL) was added DIPEA (29.86 mL, 166.66 mmol, 3 eq) and HATU (25.33 g, 66.66 mmol, 1.2 eq) at RT under argon atmosphere. After 10 min., compound 3 (14.52 mL, 83.33 mmol, 1.5 eq) was added at RT and the reaction continued for 16 h. TLC analysis indicated formation of a less polar spot. The reaction mixture was diluted with water and extracted with EtOAc (3×100 mL). The organic layer was washed with water (2×150 mL), dried over $Na_2SO_4$ and concentrated under reduced pressure to give a crude product. The crude product was purified by column chromatography (silica gel 100-200 mesh) using 0-5% EtOAc in petroleum ether as an eluent to give compound 4 (11 g, 67.84%) as white solid. LC-MS: 346.32 (M+H).

Step 3: Intermediate 5

To a stirred solution of tetrakistriphenylphosphine (11.39 g, 43.47 mmol, 1.5 eq) in THF (150 mL) was added DIAD (11.71 g, 57.97 mmol, 2 eq) at 0° C. under argon atmosphere, after 30 min., added TMS-ethanol (8.55 mL, 57.97 mmol, 2 eq) followed by compound 4 (10 g, 28.98 mmol, 1 eq) at the same temperature. The reaction mixture was allowed to warm up to RT for 16 h. TLC analysis indicated formation of a less polar spot. The reaction mixture was diluted with water and extracted with EtOAc (3×150 mL). The combined organic layer was washed with water, dried over $Na_2SO_4$ and concentrated under reduced pressure to give a crude product. The crude compound was purified by column chromatography (100-200mesh) using 0-3% EtOAc in petroleum ether as eluent to afford compound 5 (9 g, 69.82%) as pale yellow oil.

Step 4: Preparation of 3-fluoro-5-(4,4,5,5-tetramethyl-1,3,2-dioxaborolan-2-yl)-N-(2,4,4-trimethylpentan-2-yl)-2-(2-(trimethylsilyl)ethoxy)benzamide A stirred solution of compound 5 (9 g, 20.22 mmol, 1 eq) in dioxane (100 mL) was degassed with Ar for 20 min. Then KOAc (5.94 g, 60.67 mmol, 3 eq), Bis (pinacolato) diboran (5.65 g, 22.24 mmol, 1.1 eq) and $PdCl_2$ (dppf) (1.65 g, 2.02 mmol, 0.1 eq) were added at RT and the mixture heated to 90° C. for 16 h. TLC analysis indicated formation of a polar spot. The reaction mixture was cooled to RT then filtered through celite pad; celite pad was washed with EtOAc (2×30 mL). The filtrate was concentrated to a crude compound. The crude product was purified by column chromatography (silica gel 100-200 mesh) using 0-4% EtOAc in petroleum ether as an eluent to give 3-fluoro-5-(4,4,5,5-tetramethyl-1,3,2-dioxaborolan-2-yl)-N-(2,4,4-trimethylpentan-2-yl)-2-(2(trimethylsilyl)ethoxy)benzamide (G-11) (7 g, 70.21%) as light yellow oil. 1H NMR (500 MHz, DMSO-d6) δ=7.85 (s, 1H), 7.62 (s, 1H), 7.42 (br d, J=11.4 Hz, 1H), 4.21-4.14 (m, 2H), 1.81 (s, 2H), 1.37 (s, 6H), 1.26 (s, 12H), 1.12-1.07 (m, 2H), 0.95 (s, 9H), 0.00 (s, 9H).

Synthesis of 3,4-difluoro-5-(4,4,5,5-tetramethyl-1,3,2-dioxaborolan-2-yl)-N-(2,4,4-trimethylpentan-2-yl)-2-(2-(trimethylsilyl)ethoxy)benzamide (G-12)

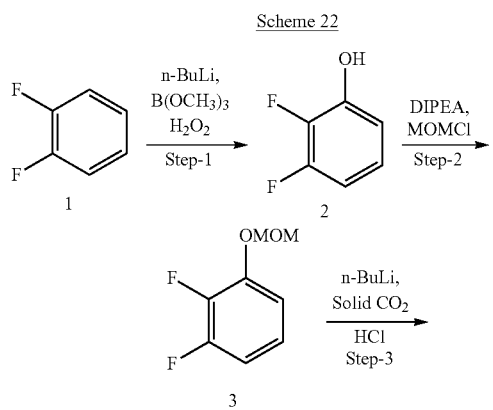

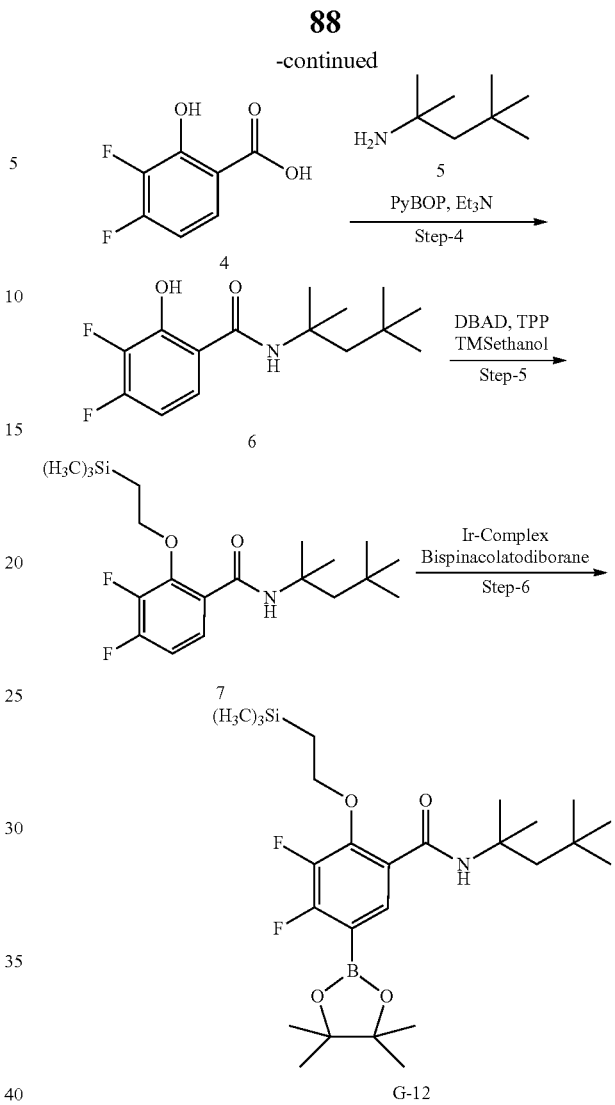

Compound numbers in text refer to structures shown in Scheme 22.

Step 1: Preparation of 2,3-Difluorophenol

To a suspension of compound 1 (20.0 g, 175.438 mmol, 1.0 eq) in dry THF (250 ml), cooled to −78° C. n-BuLi (80 mL, 1.1 eq, 1.6M) was added drop wise, then the reaction was stirred at −78° C. for 1 h. After 1 h, it was quenched with trimethylborate (30.0 mL, 263.157 mmol, 1.5 eq) then stirred for 16 h. TLC analysis indicated of a polar spot. The reaction was quenched with hydrogen peroxide(30%) solution (80 mL) then stirred for 3 h. TLC analysis indicated of a non-polar spot. The reaction mixture was diluted with diethyl ether (1 lt) and washed with water (500 mL). The separated organic layer was dried over with $Na_2So_4$ and concentrated under reduced pressure to give compound 2 (21.8 g, 93.96%) as a liquid compound.

Step 2: Preparation of MOM-protected 2,3-Difluorophenol

To a solution of compound 2 (18.0 g, 138.46 mmol, 1.0 eq) in DCM (250 ml), N,N-diisopropylamine (36.27 mL, 207.691 mmol, 1.5 eq) and MOM-Cl (15.7 mL, 207.691 mmol, 1.5 eq) were added at 0° C. and the reaction mixture was allowed to warm up to RT and stirred for 16 h. TLC analysis indicated formation of a non-polar spot. The reaction mixture was concentrated under reduced pressure to give a crude residue, which was dissolved in diethyl ether (500 mL) and washed with brine (2×200 mL) & water (2×100 mL). The separated organic layer was dried over with Na$_2$SO$_4$ and concentrated under reduced pressure to give crude product, which was purified by column chromatography (silica gel 100-200mesh) using 2% diethyl ether in petroleum ether as an eluent to give compound 3 (17 g, 70.83%) as a liquid compound.

Step 3: Synthesis of 3,4-difluoro-2-hydroxybenzoic acid

To a suspension of compound 3 (15.0 g, 86.206 mmol, 1.0 eq) in dry THF (160 ml), cooled to −78° C. n-BuLi (55 mL, 1.6 eq, 2.5M) was added drop wise, then the reaction mass stirred at −78° C. for 6 h. After 6 h, it was quenched with dry ice, then the reaction mixture was stirred at RT for 16 h. The reaction mixture was added to water (200 mL) and extract with diethyl ether (500 mL). The aqueous layer was adjusted to pH 1 with conc.HCl (50 mL) and extracted with diethyl ether (500 mL). The separated organic layer was dried over with Na$_2$SO$_4$ and concentrated under reduced pressure to give a crude compound, which was recrystallization from chloroform give to give compound 3,4-difluoro-2-hydroxybenzoic acid 4 (8.3 g, 55.33%) as a solid compound.

Alternative Synthesis of
3,4-difluoro-2-hydroxybenzoic Acid from
2,3,4-trifluorobenzoic Acid Scheme 23

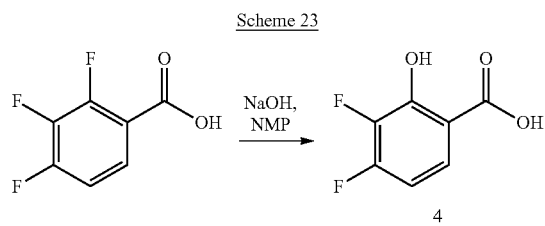 [SMILES: O=C(O)c1ccc(F)c(F)c1F ; O=C(O)c1ccc(F)c(F)c1O]

Compound numbers in text refer to structures shown in Scheme 23.

To a solution of 2,3,4-trifluorobenzoic acid (500 g, 2.84 mol) in NMP (3.5 L) under argon, is added Sodium hydroxide (459 g, 11.47 mol) in portions. Reaction mixture is refluxed at 188° C. under argon for 3 hrs. The progress of reaction is monitored by LCMS. Reaction is complete after 3 hrs. The reaction mixture is cooled to approx. 90-100° C. and NMP is removed by vacuum distillation at 112-115° C. using a rotary evaporator. The residue is diluted with water (16 L), cooled below 10° C. and acidified to pH 2 using pre-chilled 12N HCl. The precipitate was filtered, the solid was washed with cold water (1.5 L) and dried in vacuum oven at 45° C. for at least 18 hrs to obtain 617.92 g of 3,4-difluoro-2-hydroxybenzoic acid as a 1:1 mixture with NMP. Actual weight of Compound 4 is 393.6 g (80% yield).

Step 4: Preparation of 3,4-difluoro-2-hydroxy-N-(2,4,4-trimethylpentan-2-yl)benzamide To a suspension of compound 4 (5.5 g, 31.609 mmol, 1.0 eq) in dry THF (60 mL), triethylamine (4.32 mL, 31.609 mmol, 1.0 eq), PyBOP (16.34 g, 31.609 mmol, 1.5 eq) and compound 5 (3.41 mL, 20.861 mmol, 0.66 eq) were added. The reaction mixture was refluxed for 16 h. TLC analysis indicated formation of a non polar spot. The reaction mixture was concentrated under reduced pressure to give a crude residue, which was dissolved in diethyl ether (250 mL) and washed with brine (2×200 mL) & water (2×100 mL). The separated organic layer was dried over with Na$_2$SO$_4$ and concentrated under reduced pressure to give a crude product, which was purified by column chromatography (silica gel 100-200mesh) using 2% EtOAc in petroleum ether as an eluent to give compound 6 (3.5 g, 38.88%) as a solid compound.

Step 5: Preparation of 3,4-difluoro-N-(2,4,4-trimethylpentan-2-yl)-2-(2-(trimethylsilyl)ethoxy)benzamide To a solution of Triphenylphospine (8.65 g, 32.280 mmol, 2 eq) in Dry toluene (80 mL), Di-tertbutyl azodicarboxylate (13.0 g, 56.49 mmol, 3.5 eq) was added at room temp over 30 min. Then, a solution of compound TMSethanol (2.68 mL, 32.28 mmol, 2 eq) was added followed by addition of compound 6 (4.6 g, 16.140 mmol, 1.0 eq) at room temp. Then, the reaction mixture was stirred at RT overnight. TLC analysis indicated formation of a non polar spot. The reaction mixture was concentrated under reduced pressure to give a crude residue, which was dissolved in EtOAc (300 mL) and washed with brine (2×100 mL) & water (2×100 mL). The separated organic layer was dried over with Na$_2$SO$_4$ and concentrated under reduced pressure to give a crude product; which was purified by column chromatography (silica gel 100-200mesh) using 1-2% EtOAc in petroleum ether as an eluent to give compound 6 (5.8 g, 93.54%) as a solid compound.

Step 6: Preparation of 3,4-difluoro-5-(4,4,5,5-tetramethyl-1,3,2-dioxaborolan-2-yl)-N-(2,4,4-trimethylpentan-2-yl)-2-(2-(trimethylsilyl)ethoxy)benzamide To a Bispinacolatodiboron (9.25 g, 36.441 mmol, 2.3 eq), dtbpy (254 mg, 0.950 mmol, 0.06 eq) in degassed dry n-hexane (80 mL) was further degassed with argon for 20 min. After 20 min, Iridium complex (315 mg, 0.475 mmol, 0.03 eq) was added and stirred for 5 min (color change was observed from yellow to wine red). After 5 min, compound 6 (6.1 g, 15.844 mmol, 1.0 eq) in n-hexane (20 mL) was added to above wine red solution at RT under Argon atm. Then, the reaction mass was immersed in preheated oil bath at 60° C. temp and stirred for 16 h. TLC analysis indicated formation of a polar spot. Then, the reaction mixture was cooled to RT and filter through celite, celite bed was washed with n-hexane. The obtained filtrate was concentrated under reduced pressure to give a crude residual oil, which was adsorbed on celite and purified by column chromatography (Silica gel 100-200 mesh) 0.5-2% EtOAc in petroleum ether as an eluent to give 3,4-difluoro-5-(4,4,5,5-tetramethyl-1,3, 2-dioxaborolan-2-yl)-N-(2,4,4-trimethylpentan-2-yl)-2-(2-(trimethylsilyl)ethoxy)benzamide (G-12) (4.6 g, 61.33%) as off white solid.

Synthesis of 2,5-difluoro-3-(4,4,5,5-tetramethyl-1,3, 2-dioxaborolan-2-yl)-N-(2,4,4-trimethylpentan-2-yl)-6-(2-(trimethylsilyl)ethoxy)benzamide (G-13)

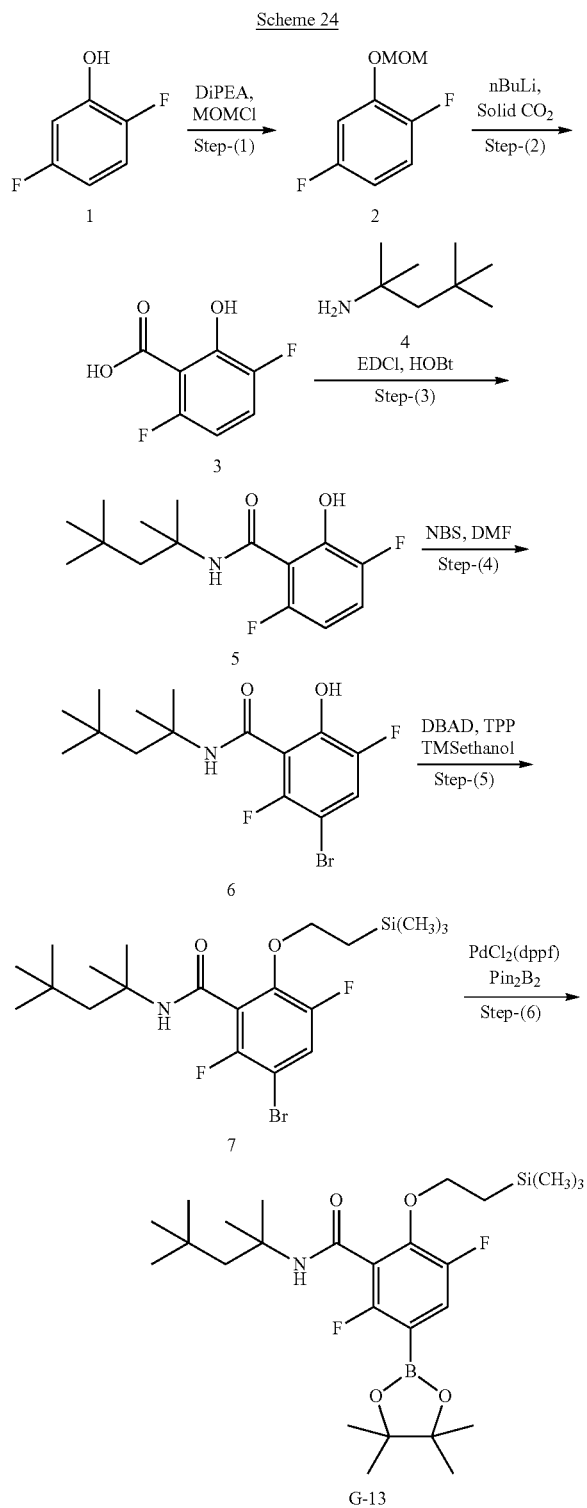

Compound numbers in text refer to structures shown in Scheme 24.

Step 1:

To a solution of compound 1 (23 g, 176.92 mmol, 1 eq) in DCM (140 mL) was added DIPEA (39.18 mL, 212.3 mmol, 1.2 eq) at 0° C. under Argon. The mixture was stirred for 30 mins. Then MOM-Cl (16.18 mL, 212.3 mmol, 1.2 eq) was added to it drop wise at the same temperature. The reaction mixture was slowly warmed to rt and stirred for 16 h. TLC analysis indicated formation of a non polar spot. Then, the reaction mixture was poured on ice-water (500 mL). The reaction mixture was extracted with DCM (2×200 mL); the combined organic layer was dried over $Na_2SO_4$ and concentrated under reduced pressure to give a crude product, which was purified by combiflash column chromatography using 0-10% EtOAc in petroleum ether as an eluent to give compound 2 (24 g, 77.97%) as a pale yellow liquid.

Step 2:

To a stirred solution of compound 2 (10 g, 57.47 mmol, 1 eq) in dry THF (200 mL), cooled to −78° C. was added n-BuLi (2.5M in hexane) (22.9 mL, 57.47 mmol, 1 eq) drop wise and the resulting reaction mixture was stirred at the same temperature for 3 h. Reaction mixture was quenched with crushed dry $CO_2$ and stirred at RT for 16 h. The reaction was monitored by TLC. TLC analysis indicated formation of a polar spot. The reaction mixture was diluted with water and ethyl acetate. The aqueous layer was acidified with 1 N HCl and extracted with ethyl acetate. The combined organic layer was dried over $Na_2SO_4$ and concentrated under reduced pressure to give Compound 3 (7 g, 56% yield) as an off white solid. LCMS: m/z 174.95 (M+H).

Step 3:

To a stirred solution of compound 3 (3.9 g, 22.41 mmol, 1 eq) in DMF (40 mL) was added DIPEA (10.07 mL, 56.02 mmol, 2.5 eq) and HATU (10.22 g, 26.89 mmol, 1.2 eq) at RT under argon atmosphere. After 10 min., compound 4 (5.5 mL, 33.61 mmol, 1.5 eq) was added at RT and the mixture heated to 90° C. for 16 h. TLC analysis indicated formation of a less polar spot. The reaction mixture was diluted with water and extracted with EtOAc (3×150 mL). The organic layer was washed with water (2×150 mL), dried over $Na_2SO_4$ and concentrated under reduced pressure to give a crude product. The crude product was purified by column chromatography (silica gel 100-200 mesh) using 0-5% EtOAc in petroleum ether as an eluent to give compound 5 (3.2 g, 62.86%) as a pale yellow solid. LCMS: m/z 286.04 (M+H).

Step 4:

To a stirred solution of compound 5 (5.5 g, 19.29 mmol, 1 eq) in DMF (80 mL), was added NBS (3.43 g, 19.29 mmol, 1 eq) at rt and the resulting mixture heated to 60° C. for 1 h. The reaction was monitored by TLC. TLC analysis indicated formation of a non-polar spot. The reaction mixture was diluted with water and extracted with EtOAc (3×50 mL). The organic layer was washed with water (2×50 mL), dried over $Na_2SO_4$ and concentrated under reduced pressure to give a crude product. The crude product was purified by column chromatography (silica gel 100-200 mesh) using 0-5% EtOAc in petroleum ether as an eluent to give compound 6 (6 g, 81.1%) as a pale yellow semi solid. LCMS: m/z 364.18 (M+H).

Step 5:

To a stirred solution of compound 6 (4 g, 10.38 mmol, 1 eq) TPP (8.16 g, 31.16 mmol, 3 eq) in THF 100 mL) was added TMS-ethanol (2.5 mL, 31.16 mmol, 3 eq) at rt −50° C. under argon atmosphere, added DBAD (7.16 g, 31.16 mmol, 3 eq) at same temperature for 4 h. TLC analysis indicated formation of a polar spot. Then concentrated under reduced pressure to give a crude product. The crude compound was purified by column chromatography (100-

200mesh) using 0-2% EtOAc in petroleum ether as eluent to afford compound 7 (1.5 g, 31.8%) as an off white solid.

Step 6:

A stirred solution of compound 7 (3 g, 6.47 mmol, 1 eq), Bis (pinacolato) diborane (1.8 g, 7.12 mmol, 1.1 eq), KOAc (1.9 g, 19.43 mmol, 3 eq) in 1,4-Dioxane (50 mL) was degassed with Ar for 20 min. Then, $PdCl_2$ (dppf).DCM complex (528 mg, 0.64 mmol, 0.1 eq) was added at RT and the reaction mixture was heated to 80-85° C. for 16 h in a sealed tube. TLC analysis indicated formation of a polar spot. The reaction mixture was cooled to RT then filtered through a celite pad; celite pad was washed with EtOAc (2×10 mL). The filtrate was concentrated to give a crude compound. The crude product was purified by column chromatography (silica gel 100-200 mesh) using 0-10% EtOAc in petroleum ether as an eluent to give 2,5-difluoro-3-(4,4,5,5-tetramethyl-1,3,2-dioxaborolan-2-yl)-N-(2,4,4-trimethylpentan-2-yl)-6-(2-(trimethylsilyl)ethoxy)benzamide (G-13) (920 mg, 27.79%) as an off white solid.

Synthesis of 4-fluoro-3-methoxy-5-(4,4,5,5-tetramethyl-1,3,2-dioxaborolan-2-yl)-N-(2,4,4-trimethylpentan-2-yl)-2-(2-(trimethylsilyl)ethoxy)benzamide (G-14)

Scheme 25

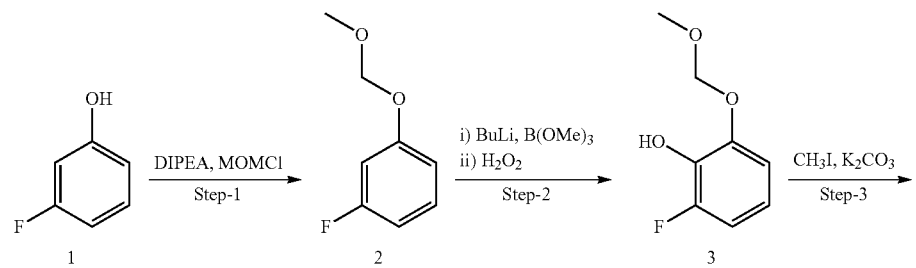

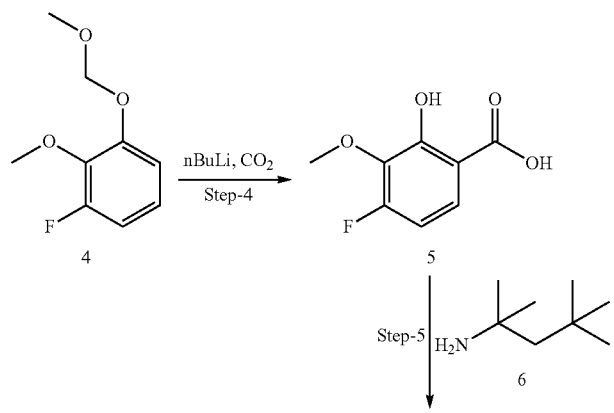

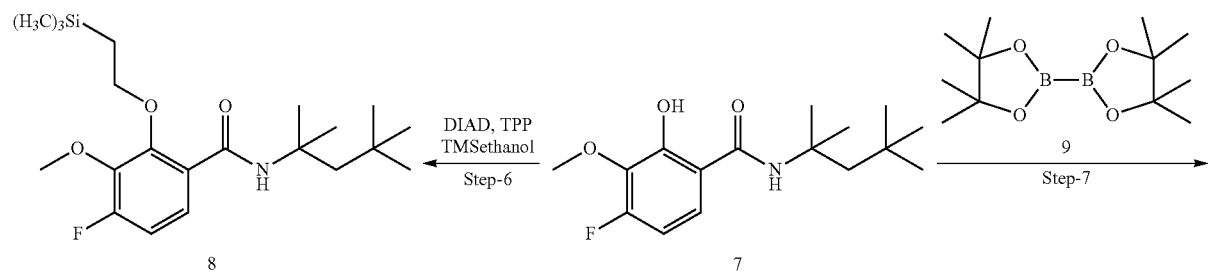

-continued

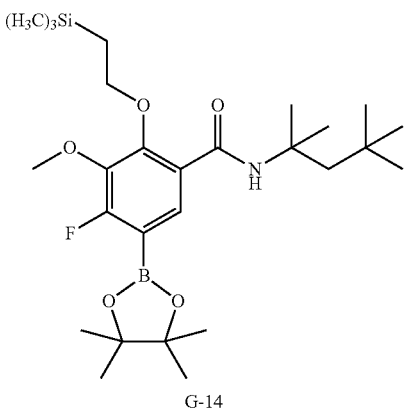

G-14

Compound numbers in text refer to structures shown in Scheme 25.

Step 1: Preparation of 1-fluoro-3-(methoxymethoxy)benzene

To a stirred solution of compound 1 (50 g, 446.030 mmol, 1 eq) in DCM (500 ml) was added DIPEA (159.02 ml, 892.060 mmol, 2 eq) at 0° C. under argon atmosphere and continued for 30 min. Then, MOM-Cl (40.65 ml, 535.236 mmol, 1.2 eq) was added at 0° C. and the reaction was allowed to warm up to RT for 16 h. TLC analysis indicated formation of a non polar spot. The reaction mixture was quenched in ice water (500 ml) and extracted with EtOAc (3×300 mL). The organic layer was dried over $Na_2SO_4$ and concentrated under reduced pressure to give a crude compound. The crude compound was purified by Combi flash chromatography using 1% EtOAC in petroleum ether as an eluent to give compound 2 (40 g, 57.47%) as a colorless liquid.

Step 2: Preparation of 2-fluoro-6-(methoxymethoxy)phenol

To a solution of n-BuLi (76.85 ml, 192.122 mmol, 1 eq) in THF (300 ml) was added TMEDA (29.89 ml, 99.807 mmol, 1.04 eq), the mixture was cooled to −78° C. and stirred for 1 h. Compound 2 (30 g, 192.122 mmol, 1 eq) in THF (75 ml) was added to it drop wise under argon, then reaction mass was stirred for 2 hr at −78° C., followed by addition of Trimethylborate at the same temperature. Then the mixture was slowly warmed to rt stirred for 16 h. Then the reaction mass was cooled to 0° C., then 30% $H_2O_2$ (18 ml) solution was added slowly drop wise. The reaction mass was warmed to rt and stirred at for 1 h. TLC analysis indicated formation of polar spot. The reaction mixture was dissolved in EtOAc (300 ml) and washed with brine (2×50 ml) & water (2×50 ml). The separated organic layer was dried over $Na_2SO_4$ and concentrated under reduced pressure to give a crude product; which was purified by column chromatography (silica gel 100-200mesh) using 8% petroleum ether as an eluent to give compound 3 (25 g, 75.55%) as a colorless oil.

Step 3: Preparation of 1-fluoro-2-methoxy-3-(methoxymethoxy)benzene

To a stirred solution of compound 3 (25 g, 145.222 mmol, 1 eq) in dry THF (250 ml) was added $K_2CO_3$ (30.11 g, 217.833 mmol, 1.5 eq) at 0° C. under argon atmosphere and the reaction continued for 30 min. After that methyl iodide (11.32 ml, 181.528 mmol, 1.25 eq) was added at 0° C. and the reaction was allowed to RT for 16 h. TLC analysis indicated formation of a non polar spot. The reaction mixture was quenched in ice water (500 ml) and extracted with EtOAc (3×300 mL). The organic layer was dried over $Na_2SO_4$ and concentrated under reduced pressure to give a crude compound. The crude compound was purified by Combi flash chromatography using 2% EtOAC in petroleum ether as an eluent to give compound 4 (25 g, 92.42%) as a colorless liquid.

Step 4: Preparation of 4-fluoro-2-hydroxy-3-methoxybenzoic Acid

To a solution of compound 4 (25 g, 134.279 mmol, 1.0 eq) in dry THF (500 ml) was added n-BuLi (53.71 mL, 134.279 mmol, 1.0 eq, 2.5M) drop wise at −78° C. under argon. The mixture was stirred for 2 h at the same temperature, then dry ice (saturated) was added to it portion wise at the same temperature. The mixture was slowly warmed to rt with stirring for overnight. TLC analysis indicated formation of a polar spot then the reaction mass was quenched with Con HCl (100 ml) solution up to pH 2; the quenched mixture was stirred for 1 h, the reaction mixture was dissolved in EtOAC (2×500 ml) and washed with brine (2×200 ml) & water (2×200 ml). The separated organic layer was dried over $Na_2SO_4$ and concentrated under reduced pressure to give a crude product; washed with pentane to give compound 5 (15 g, 60.06%) as an off white solid.

Step 5: Preparation of 4-fluoro-2-hydroxy-3-methoxy-N-(2,4,4-trimethylpentan-2-yl)benzamide To a stirred solution of compound 1 (14 g, 75.212 mmol, 1 eq) in THF (140 ml) was added triethylamine (31.49 ml, 225.636 mmol, 35 eq) and PYBOP (39.14 g, 75.212 mmol, 1 eq) at 0° C. under argon atmosphere and stirred for 15 min at the same temp. Then, compound 6 (15.14 ml, 90.255 mmol, 1.2 eq) was added dropwise at 0° C. and allowed to warm up to RT over 16 h. TLC analysis indicated formation of a non polar spot. The reaction mixture was diluted with water (200 ml) and extracted with EtOAc (2×200 mL). The organic layer was washed with water (2×100 mL), dried over $Na_2SO_4$ and concentrated under reduced pressure to give a crude product. The Crude product was purified by column chromatography (silica gel 100-200 mesh) using 4%

EtOAc in petroleum ether as an eluent to give compound 3 (10 g, 44.72%) as an off white solid. LC-MS: 298.21 (M+H).

Step 6: Preparation of 4-fluoro-3-methoxy-N-(2,4,4-trimethylpentan-2-yl)-2-(2-(trimethylsilyl)ethoxy)benzamide To a solution of Triphenylphosphine (17.67 g, 67.256 mmol, 2 eq) in Dry toluene (150 ml) was added Di-tert-butyl azodicarboxylate (23.23 g, 100.884 mmol, 3 eq) portion wise at RT and the resulting mixture stirred at the same temp over 30 min. Then, TMS ethanol (5.59 ml, 67.256 mmol, 2 eq) was added followed by addition of compound 7 (10 g, 33.628 mmol, 1 eq) in toluene (50 ml) at RT. Then, the reaction mixture was allowed to stir at RT overnight. TLC analysis indicated formation of a non polar spot. The reaction mixture was concentrated under reduced pressure to give a crude residue, which was dissolved in EtOAc (300 ml) and washed with brine (2×100 ml) & water (2×100 ml). The separated organic layer was dried over $Na_2SO_4$ and concentrated under reduced pressure to give a crude product, which was purified by column chromatography (silica gel 100-200mesh) using 3% EtOAC in petroleum ether as an eluent to give compound 5 (8 g, 59.83%) as a pale yellow color liquid.

Step 7: Preparation of 4-fluoro-3-methoxy-5-(4,4,5,5-tetramethyl-1,3,2-dioxaborolan-2-yl)-N-(2,4,4-trimethylpentan-2-yl)-2-(2-(trimethylsilyl)ethoxy)benzamide To a solution of compound 9 (11.75 g, 46.278 mmol, 2.3 eq), dtbpy (324 mg, 1.208 mmol, 0.06 eq) in degassed dry n-hexane (100 ml) was degassed with argon for 10 min. After 10 min, Iridium complex (159 mg, 0.604 mmol, 0.03 eq) was added and the mixture stirred for 5 min (color change was observed from yellow to wine red). After 5 min, compound 8 (8 g, 20.121 mmol, 1 eq) in n-hexane (20 ml) was added to above wine red solution at RT under Argon atm. Then, the reaction mass was immersed in preheated oil bath at 60° C. temp and stirred for 2 h. TLC analysis indicated formation of a polar spot. Then, reaction mixture was cooled to RT and filter through celite, celite bed was washed with n-hexane. The obtained filtrate was concentrated under reduced pressure to give a crude residual oil, which was adsorbed on celite and purified by column chromatography (Silica gel 100-200 mesh) 0-5% EtOAc in petroleum ether as an eluent to give 4-fluoro-3-methoxy-5-(4,4,5,5-tetramethyl-1,3,2-dioxaborolan-2-yl)-N-(2,4,4-trimethylpentan-2-yl)-2-(2-(trimethylsilyl)ethoxy)benzamide (G-14) (5 g, 47.46%) as a colorless liquid. $^1$H NMR (500 MHz, DMSO-d6) δ=7.88 (s, 1H), 7.68 (br d, J=6.5 Hz, 1H), 4.25-4.18 (m, 2H), 3.85 (s, 3H), 1.83 (s, 2H), 1.40 (s, 6H), 1.29 (s, 12H), 1.16-1.14 (m, 2H), 0.97 (s, 9H), 0.04 (s, 9H).

Synthesis of 3-chloro-4-fluoro-5-(4,4,5,5-tetramethyl-1,3,2-dioxaborolan-2-yl)-N-(2,4,4-trimethylpentan-2-yl)-2-(2-(trimethylsilyl)ethoxy)benzamide (G-15)

Scheme 26

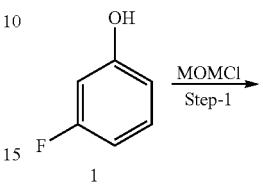

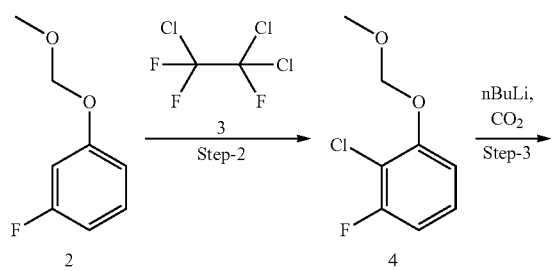

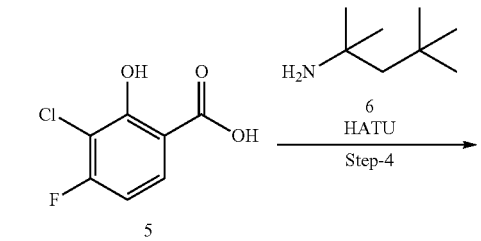

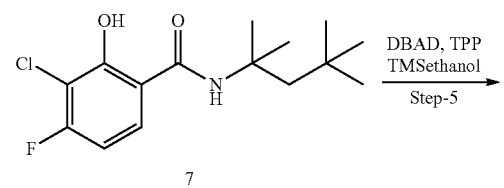

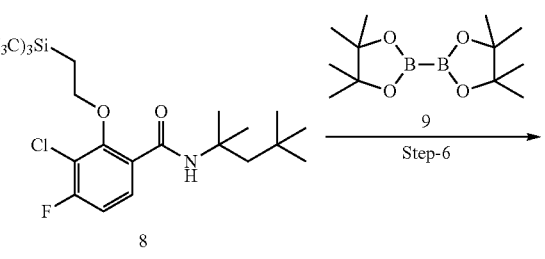

-continued

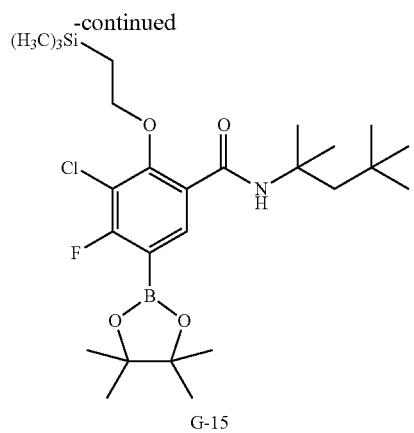

G-15

Compound numbers in text refer to structures shown in Scheme 26.

Step 1: Preparation of 1-fluoro-3-(methoxymethoxy)benzene

To a solution of compound 1 (27.3 g, 223.21 mmol, 1 eq) in Dry DCM (500 mL), was added Diisopropyl ethylamine (79.86 mL, 446.42 mmol, 2.0 eq) followed by MOM Chloride (20.18 mL, 267.85 mmol, 1.2 eq) drop wise at 0° C.-rt. The mixture was stirred for overnight. TLC analysis indicated formation of a non polar spot. The reaction mixture was dissolved in DCM (2×500 mL) and washed with brine (2×200 mL) & water (2×200 mL). The separated organic layer was dried over $Na_2SO_4$ and concentrated under reduced pressure to give a crude product; which was purified by column chromatography (silica gel 100-200mesh) using 100% petroleum ether as an eluent to give compound 2 (20 g, 57.97%) as a pale yellow color liquid.

Step 2: Preparation of 2-chloro-1-fluoro-3-(methoxymethoxy)benzene

To a solution of compound 2 (25 g, 130.2 mmol, 1.0 eq) in dry THF (250 mL) and dry cyclohexane (40 mL) was added sec-BuLi (121.82 mL, 195.3 mmol, 1.5 eq) drop wise at −78° C. under argon. The mixture was stirred for 2 h at the same temperature, then compound 3 (62 mL, 520.3 mmol, 4.0 eq) was added with stirring for 10 mins at the same temperature. TLC analysis indicated formation of a polar spot then the reaction mass was quenched with satd. $NH_4Cl$ solution; the reaction mixture was dissolved in ether (2×500 mL) and washed with brine (2×200 mL) & water (2×200 mL). The separated organic layer was dried over $Na_2SO_4$ and concentrated under reduced pressure to give a crude product; which was purified by column chromatography (silica gel 100-200mesh) using 1% EtOAc petroleum ether as an eluent to give compound 4 (20 g, 45.1%) as a pale yellow color liquid.

Step 3: Preparation of 3-chloro-4-fluoro-2-hydroxybenzoic Acid

To a solution of compound 4 (20 g, 104.7 mmol, 1.0 eq) in dry THF (400 mL) was added n-BuLi (41.8 mL, 104.7 mmol, 1.0 eq, 2.5M) drop wise at −78° C. under argon. The mixture was stirred for 4 h at the same temperature, then dry ice (saturated) was added to it portion wise at the same temperature. The mixture was slowly warmed to rt with stirring for overnight. TLC analysis indicated formation of a polar spot then the reaction mass was quenched with Conc. HCL (50 mL) solution up to pH 2 and stirred for 1 h. The reaction mixture was dissolved in EtOAc (2×500 mL) and washed with brine (2×200 mL) & water (2×200 mL). The separated organic layer was dried over $Na_2SO_4$ and concentrated under reduced pressure to give a crude product; washed with pentane to give compound 5 (20 g, 60.2%) as an off white solid.

Step 4: Preparation of 3-chloro-4-fluoro-2-hydroxy-N-(2,4,4-trimethylpentan-2-yl)benzamide To a stirred solution of compound 5 (13 g, 68.4 mmol, 1 eq) in DMF (250 mL) was added HATU (31.2 g, 82.1 mmol, 1.2 eq) at 0° C. under argon atmosphere followed by DiPEA (36.7 mL, 204.6 mmol, 3.0 eq) and stirred for 15 min at the same temp. Then, compound 6 (17.1 mL, 102.3 mmol, 1.5 eq) was added drop wise at 0° C. and allowed to warm up to RT over 16 h. TLC analysis indicated formation of a less polar spot. The reaction mixture was diluted with water (1 L) and extracted with EtOAc (2×500 mL). The organic layer was washed with water (2×200 mL) and dried over $Na_2SO_4$ and concentrated under reduced pressure to give a crude product. The crude product was purified by column chromatography (silica gel 100-200 mesh) using 5-10% EtOAc in petroleum ether as an eluent to give compound 7 (10 g, 56.42%) as an off white solid. LC-MS: m/z 302.01 (M+H).

Step 5: Preparation of 3-chloro-4-fluoro-N-(2,4,4-trimethylpentan-2-yl)-2-(2-(trimethylsilyl)ethoxy) benzamide To a solution of Triphenyl phosphine (17.4 g, 66.59 mmol, 2 eq) in Dry Toluene (200 mL), DBAD (22.92 g, 79.66 mmol, 3 eq) was added at RT and the mixture was stirred for over 30 min. Then, a solution of TMS ethanol (5.33 mL, 66.59 mmol, 2 eq) was added followed by addition of compound 7 (10 g, 33.22 mmol, 1 eq) at rt for overnight. TLC analysis indicated formation of a non polar spot. The reaction mixture was dissolved in EtOAc (300 mL) and washed with brine (2×200 mL) & water (2×200 mL). Separated organic layer was dried over $Na_2SO_4$ and concentrated under reduced pressure to give a crude product; which was purified by column chromatography (silica gel 100-200mesh) using 2% EtOAc petroleum ether as an eluent to give compound 8 (10.5 g, 76.92%) as a pale yellow color liquid.

Step 6: Preparation of 3-chloro-4-fluoro-5-(4,4,5,5-tetramethyl-1,3,2-dioxaborolan-2-yl)-N-(2,4,4-trimethylpentan-2-yl)-2-(2-(trimethylsilyl)ethoxy)benzamide A solution of compound 9 (15.29 g, 60.22 mmol, 2.3 eq), dtbpy (420 mg, 2.661.567 mmol, 0.06 eq) in degassed dry n-hexane (200 mL) was degassed with argon for 10 min. After 10 min, Iridium complex (520 mg, 0.78 mmol, 0.03 eq) was added and stirred for 5 min (color change was observed from yellow to wine red). After 5 min, compound 8 (10.5 g, 26.18 mmol, 1 eq) was added to above wine red solution at RT in sealed tube under Argon atm. Then, the sealed tube was immersed in preheated oil bath at 60° C. temp and stirred for 2 h. TLC analysis indicated formation of a polar spot. Then, the reaction mixture was cooled to RT and filter through celite, celite bed was washed with n-hexane. The obtained filtrate was concentrated under reduced pressure to give a crude residual oil, which was adsorbed on celite and purified by column chromatography (Silica gel 100-200 mesh) 0-5% EtOAc in petroleum ether as an eluent to give 3-chloro-4-fluoro-5-(4,4,5,5-tetramethyl-1,3,2-dioxaborolan-2-yl)-N-(2,4,4-trimethylpentan-2-yl)-2-(2-(trimethylsilyl)ethoxy)benzamide (G-15) (11 g, 84.61%) as an off white semi solid. 1H NMR (500 MHz, DMSO-d6) δ=7.89 (s, 1H), 7.66 (br d, J=6.5 Hz, 1H), 4.17-4.11 (m, 2H), 1.83 (s, 2H), 1.41 (s, 6H), 1.29 (s, 12H), 0.98 (s, 9H), 0.03 (s, 9H).

Synthesis of 7-bromo-N-(2,4,4-trimethylpentan-2-yl)-4-(2-(trimethylsilyl)ethoxy)benzo[d][1,3]dioxole-5-carboxamide (G-16)

poured into ice water and extracted with ethyl acetate. The combined organic layer was dried over Na$_2$SO$_4$ and concentrated under reduced pressure. The crude product was purified by column chromatography (silica 100-200) using 0-10% ethyl acetate in petroleum ether as an eluent to give Compound 2 (40 g, 73.69% yield) as white solid. LCMS: m/z 153.32 (M+H):

Step 2: Preparation of benzo[d][1,3]dioxol-4-ol

To a stirred solution of compound 2 (25 g, 164.4 mmol, 1 eq) in ACN (500 mL) cooled to 0° C. was added NaI (98.5 g, 657.8 mmol, 4 eq) followed by TMS-Cl (71.4 g, 657.8 mmol, 4 eq) and the resulting reaction mixture was heated at 75° C. for 8 h. The reaction was monitored by TLC. TLC

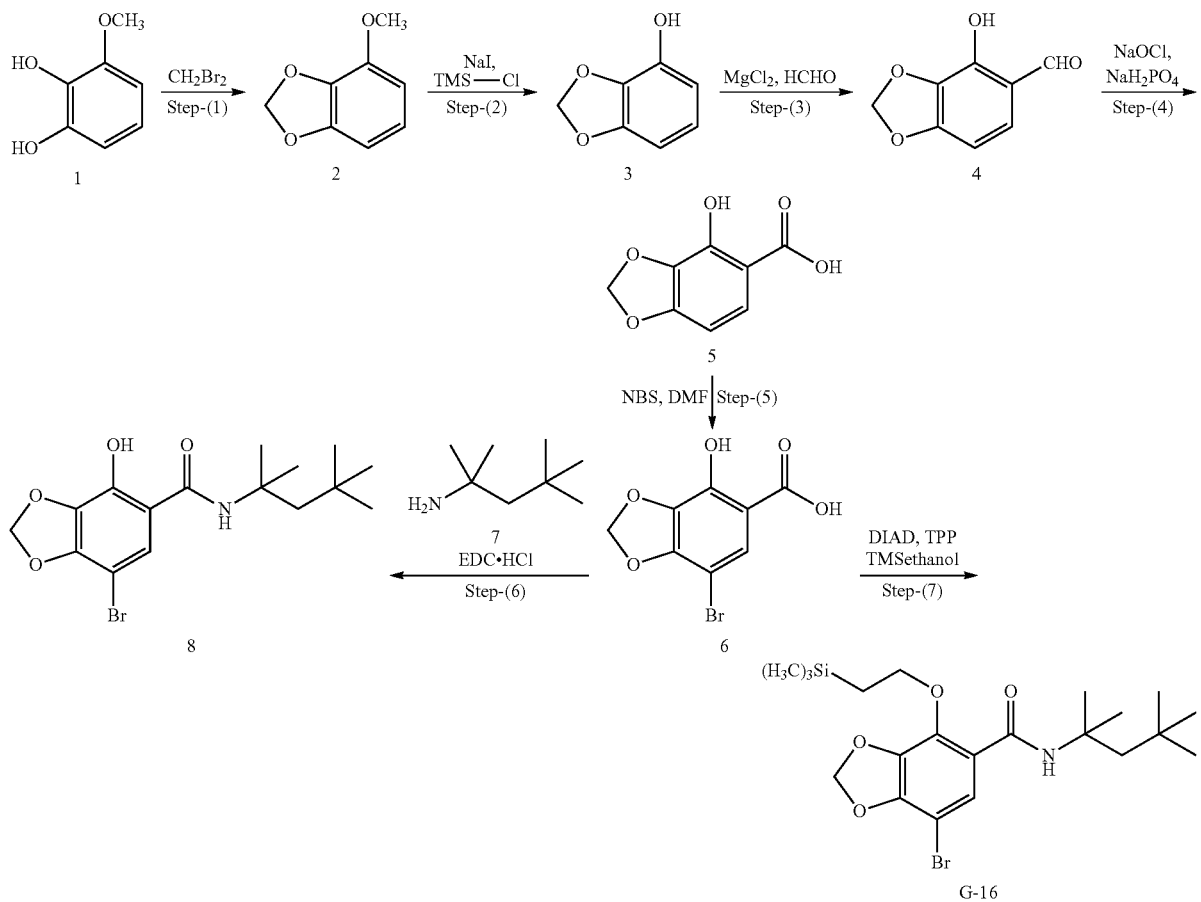

Scheme 27

Compound numbers in text refer to structures shown in Scheme 27.

Step 1: Preparation of 4-methoxybenzo[d][1,3]dioxole

To a stirred solution of compound 1 (50 g, 357.1 mmol, 1 eq) in DMF (500 mL), was added CuO (3.12 g, 39.2 mmol, 0.11 eq) followed by K$_2$CO$_3$ (60.1 g, 435.7 mmol, 1.22 eq) and dibromo methane (75.7 g, 435.7 mmol, 1.22 eq). The resulting reaction mixture was heated at 120° C. for 8 h. The reaction was monitored with TLC. TLC analysis indicated formation of a non-polar spot. The reaction mixture was analysis indicated formation of a polar spot. The reaction mixture was poured into ice water and extracted with ethyl acetate. The combined organic layer was dried over Na$_2$SO$_4$ and concentrated under reduced pressure. The crude product was purified by column chromatography (silica 230-400) using 20-30% ethyl acetate in petroleum ether as an eluent to give Compound 3 (16 g, 70.5% yield) as pale yellow solid. LCMS: m/z 139.31 (M+H):

Step 3: Preparation of 4-hydroxybenzo[d][1,3]dioxole-5-carbaldehyde

To a stirred solution of compound 3 (25 g, 183.8 mmol, 1 eq), in ACN (250 mL), was added TEA (89.2 mL, 680.1 mmol, 3.7 eq) followed by MgCl$_2$ (26.22 g, 275.7 mmol, 1.5 eq) at RT. The reaction mixture was cooled to 0° C. and para formaldehyde (37.22 g, 1240.8 mmol, 6.75 eq) was added and the resulting reaction mixture was refluxed for 4 h. The reaction was monitored by TLC. TLC analysis indicated formation of a non-polar spot. The reaction mixture was cooled to 0° C., acidified with aq 2N HCl solution and extracted with ethyl acetate. The combined organic layer was dried over Na$_2$SO$_4$ and concentrated under reduced pressure to give Compound 4 (21 g, 70% yield) as pale yellow solid. LCMS: m/z 167.29 (M+H):

Step 4: Preparation of 4-hydroxybenzo[d][1,3]dioxole-5-carboxylic Acid

To a stirred solution of compound 4 (30 g, 179.6 mol, 1 eq) in 1,4-dioxane: H$_2$O (3:1, 800 mL), was added sulfamic acid (26.1 g, 269.2 mol, 1.5 eq) followed by Na$_2$H$_2$PO$_4$.H$_2$O (99.16 g, 718.5 mol, 4 eq). The reaction mixture was cooled to 0° C. and added a solution of sodium chlorite (21.1 g, 233.5 mmol, 1.3 eq) in water (100 mL) drop wise and the resulting reaction mixture was stirred at RT for 1 h. The reaction was monitored by TLC. TLC analysis indicated formation of a polar spot. The reaction mixture was cooled to 0° C., quenched with sodium sulphite (27.16 g, 215.5 mmol, 1.2 eq) and stirred for 30 min at RT. Solvent was evaporated under reduced pressure, crude residue was cooled to 0° C. and acidified with aq 2N HCl. A solid precipitated was filtered and dried under vacuum to give Compound 5 (23 g, 69.9% yield) as pale yellow solid. LCMS: m/z 183.34 (M+H):

Step 5: Preparation of 7-Bromo-4-hydroxybenzo[d][1,3]dioxole-5-carboxylic Acid

To a stirred solution of compound 5 (20 g, 109.8 mmol, 1 eq) in ACN (200 mL), was added NBS (21.3 g, 120.8 mmol, 1.1 eq) and the resulting reaction mixture was stirred at RT for 3 h. The reaction was monitored by TLC. TLC analysis indicated formation of a non-polar spot. A solid precipitated was filtered and dried under vacuum. The filtered solid was triturated with n-pentane to give Compound 6 (12 g, 42.1% yield) as pale yellow solid. LCMS: m/z 259.17 (M−H):

Step 6: Preparation of 7-Bromo-4-hydroxy-N-(2,4,4-trimethylpentan-2-yl)benzo[d][1,3]dioxole-5-carboxamide To a stirred solution of compound 6 (20 g, 76.9 mmol, 1 eq) in DMF (200 mL), was added HATU (58.46 g, 253.8 mmol, 2 eq), DIPEA (42.5 mL, 230.6 mmol, 3 eq) followed by compound 7 (14.88 g, 115.3 mmol, 1.5 eq) and the resulting reaction mixture was stirred at RT for 48 h. The reaction was monitored by TLC. TLC analysis indicated formation of a non-polar spot. The reaction mixture was poured into ice water and extracted with ethyl acetate. The combined organic layer was dried over Na$_2$SO$_4$ and concentrated under reduced pressure. Crude product was purified by column chromatography (silica 100-200) using 10-20% ethyl acetate in petroleum ether as an eluent to give Compound 8 (20 g, 70.1% yield) as pale yellow solid. LCMS: m/z 372.28 (M+H):

Step 7: Preparation of 7-Bromo-N-(2,4,4-trimethylpentan-2-yl)-4-(2-(trimethylsilyl)ethoxy)benzo[d][1,3]dioxole-5-carboxamide To a stirred solution of TPP (28.2 g, 107.7 mmol, 2 eq) in THF (300 mL), cooled to 0° C. was added DIAD (21.2 mL, 107.7 mmol, 2 eq) and the resulting reaction mixture was stirred at the same temperature for 20 min. TMS-Ethanol (15.5 mL, 107.7 mmol, 2 eq) followed by a solution of compound 8 (20 g, 53.9 mmol, 1 eq) in THF (100 mL) was added and resulting reaction mixture was stirred at RT for 16 h. The reaction was monitored by TLC. TLC analysis indicated formation of a non-polar spot. The reaction mixture was quenched with ice water and extracted with ethyl acetate. The combined organic layer was dried over Na$_2$SO$_4$ and concentrated under reduced pressure. Crude product was purified by column chromatography (silica 100-200) using 0-5% ethyl acetate in petroleum ether as an eluent to give 7-Bromo-N-(2,4,4-trimethylpentan-2-yl)-4-(2-(trimethylsilyl)ethoxy)benzo[d][1,3]dioxole-5-carboxamide (G-16) (17 g, 67% yield) as off white solid. LCMS: m/z 471.98 (M+H):

Synthesis of 8-(4,4,5,5-tetramethyl-1,3,2-dioxaborolan-2-yl)-N-(2,4,4-trimethylpentan-2-yl)-5-(2-(trimethylsilyl)ethoxy)-2,3-dihydrobenzo[b][1,4]dioxine-6-carboxamide (G-17)

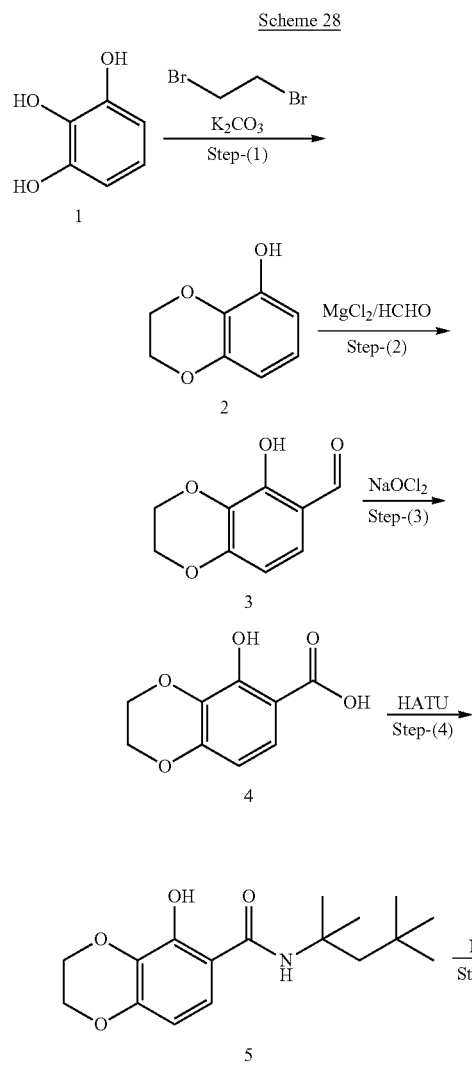

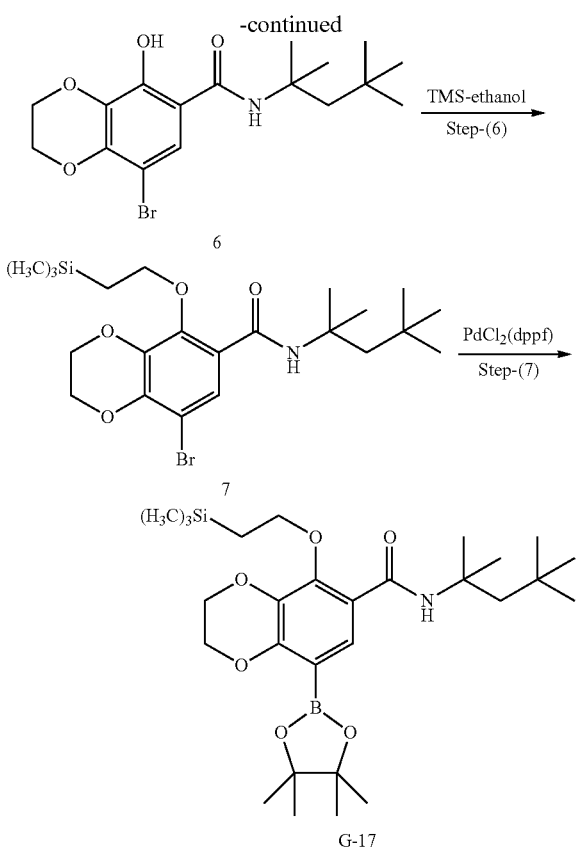

Compound numbers in text refer to structures shown in Scheme 28.

Step 1:

To a stirred solution of compound 1 (30 g, 238 mmol, 1 eq) in 2-butanolne (500 mL), was added K₂CO₃ (98 g, 714 mmol, 3 eq) and dibromo ethane (137 g, 714 mmol, 3 eq). The resulted reaction mixture was heated at 90° C. for 16 h. The reaction was monitored with TLC. TLC analysis indicated formation of a non-polar spot. The reaction mixture was poured into ice water and extracted with ethyl acetate. The combined organic layer was dried over Na₂SO₄ and concentrated under reduced pressure. The crude product was purified by column chromatography (silica 100-200) using 0-30% ethyl acetate in petroleum ether as an eluent to give Compound 2 (20 g, 56% yield) as a yellow oil. LCMS: m/z 153.32 (M+H):

Step 2:

To a stirred solution of compound 2 (10 g, 65.78 mmol, 1 eq), in ACN (200 mL), was added TEA (35 mL, 263 mmol, 4 eq) followed by MgCl₂ (9.3 g, 98.68 mmol, 1.5 eq) at RT. The reaction mixture was cooled to 0° C. and para formaldehyde (13.8 g, 460.5 mmol, 7 eq) was added and the resulting reaction mixture was refluxed for 4 h. The reaction was monitored by TLC. TLC analysis indicated formation of a non-polar spot. The reaction mixture was cooled to 0° C., acidified with aq 2N HCl solution and extracted with ethyl acetate. The combined organic layer was dried over Na₂SO₄ and concentrated under reduced pressure to give Compound 3 (7 g, 60% yield) as pale yellow liquid. LCMS: m/z 181.33 (M+H):

Step 3:

To a stirred solution of compound 3 (15 g, 83.3 mol, 1 eq) in 1,4-dioxane: H₂O (3:1, 800 mL), was added sulfamic acid (12 g, 124.9 mol, 1.5 eq) followed by Na₂H₂PO₄.H₂O (45.9 g, 333.3 mol, 4 eq). The reaction mixture was cooled to 0° C. and a solution of sodium chlorite (9.7 g, 108.3 mmol, 1.3 eq) in water (100 mL) was added drop wise. The resulting reaction mixture was stirred at RT for 1 h. The reaction was monitored by TLC. TLC analysis indicated formation of a polar spot. The reaction mixture was cooled to 0° C., quenched with sodium sulphite (27.16 g, 215.5 mmol, 1.2 eq) and stirred for 30 min at RT. Solvent was evaporated under reduced pressure, the crude residue was cooled to 0° C. and acidified with aq 2N HCl. A solid precipitated was filtered and dried under vacuum to give Compound 4 (8.5 g, 60% yield) as pale yellow solid. LCMS: m/z 197.35 (M+H):

Step 4:

To a stirred solution of compound 4 (8 g, 40.8 mmol, 1 eq) in DMF (200 mL), was added HATU (23.2 g, 61.2 mmol, 1.5 eq), DIPEA (21.06 mL, 122.4 mmol, 3 eq) followed by Amine (10.8 mL, 61.2 mmol, 1.5 eq) and the resulting reaction mixture was stirred at RT for 16 h. The reaction was monitored by TLC. TLC analysis indicated formation of a non-polar spot. The reaction mixture was poured into ice water and extracted with ethyl acetate. The combined organic layer was dried over Na₂SO₄ and concentrated under reduced pressure. The crude product was purified by column chromatography (silica 100-200) using 10-20% ethyl acetate in petroleum ether as an eluent to give Compound 5 (6 g, 50% yield) as pale yellow liquid. LCMS: m/z 308.52 (M+H):

Step 5:

To a stirred solution of compound 5 (4.5 g, 14.6 mmol, 1 eq) in DMF (450 mL), was added NBS (2.8 g, 16.1 mmol, 1.1 eq) and the resulting reaction mixture was stirred at 80° C. for 4 h. The reaction was monitored by TLC. TLC analysis indicated formation of a non-polar spot. The reaction mixture was poured into ice water and extracted with ethyl acetate. The combined organic layer was dried over Na₂SO₄ and concentrated under reduced pressure. The crude product was purified by column chromatography (silica 100-200) using 10-20% ethyl acetate in petroleum ether as an eluent to give Compound 6 (3 g, 54% yield) as pale yellow solid. LCMS: m/z 386.03 (M−H):

Step 6:

To a stirred solution of TPP (4.7 g, 18.18 mmol, 2 eq) in THF (100 mL), was cooled to 0° C. and added DIAD (3.6 mL, 18.18 mmol, 2 eq) and the resulting reaction mixture was stirred at the same temperature for 20 min. TMS-Ethanol (2.6 mL, 18.18 mmol, 2 eq) followed by a solution of compound 6 (3.5 g, 9.0 mmol, 1 eq) in THF (50 mL) was added and the resulting reaction mixture was stirred at RT for 16 h. The reaction was monitored by TLC. TLC analysis indicated formation of a non-polar spot. The reaction mixture was quenched with ice water and extracted with ethyl acetate. The combined organic layer was dried over Na₂SO₄ and concentrated under reduced pressure. Crude product was purified by column chromatography (silica 100-200) using 0-5% ethyl acetate in petroleum ether as an eluent to give 7 (3.3 g, 56% yield) as yellow gummy liquid. LCMS: m/z 486.55 (M+H):

Step 7:

A stirred solution of compound 7 (4.5 g, 9.27 mmol, 1 eq), Bis (pinacolato) diborane (3.5 g, 13.9 mmol, 1.5 eq), KOAc (2.7 g, 27.8 mmol, 3 eq) in DMF (50 ml) was degassed with Ar for 20 min. Then, PdCl₂ (dppf).DCM complex (759 mg, 0.9 mmol, 0.1 eq) was added at RT and the reaction mixture was heated to 80-85° C. for 16 h in a sealed tube. TLC analysis indicated formation of a polar spot. The reaction mixture was cooled to RT then filtered through celite pad;

celite pad was washed with EtOAc (2×10 ml). The filtrate was concentrated to a crude product. The crude product was purified by column chromatography (silica gel 100-200 mesh) using 0-10% EtOAc in petroleum ether as an eluent to give 8-(4,4,5,5-tetramethyl-1,3,2-dioxaborolan-2-yl)-N-(2,4,4-trimethylpentan-2-yl)-5-(2-(trimethylsilyl)ethoxy)-2,3-dihydrobenzo[b][1,4]dioxine-6-carboxamide (G-17) (2.4 g, 50%) as a pale yellow liquid. LCMS: m/z 534.75 (M+H). General Scheme of Suzuki-Coupling/Amidation/Deprotection Procedures Scheme 29

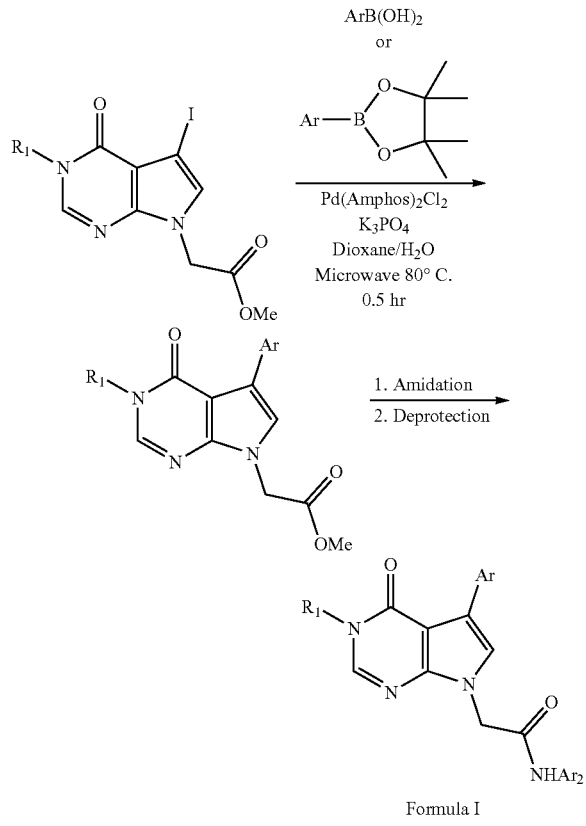

Formula I

Preparation of 5-(7-(2-((5-chloro-2-morpholinopyridin-4-yl)amino)-2-oxoethyl)-3-methyl-4-oxo-4,7-dihydro-3H-pyrrolo[2,3-d]pyrimidin-5-yl)-2-hydroxy-3-methylbenzamide (Compound I-4)

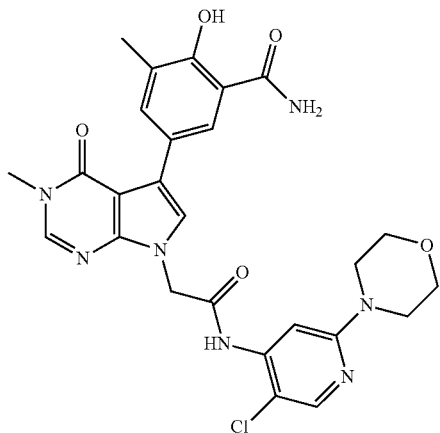 [SMILES: Cc1cc(-c2cn(CC(=O)Nc3cc(N4CCOCC4)ncc3Cl)c3ncn(C)c(=O)c23)cc(C(N)=O)c1O]

Step 1: Synthesis of methyl 2-(5-(4-(methoxymethoxy)-3-methyl-5-((2,4,4-trimethylpentan-2-yl)carbamoyl)phenyl)-3-methyl-4-oxo-3H-pyrrolo[2,3-d]pyrimidin-7(4H)-yl)acetate (E-1)

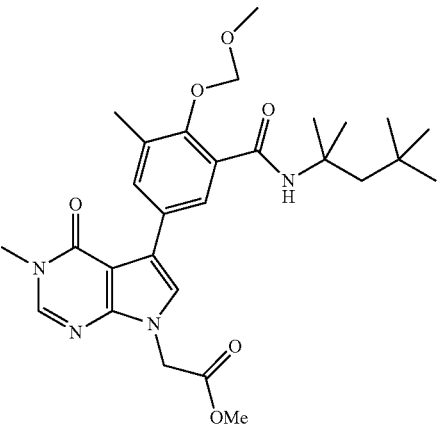 [SMILES: COCOc1c(C)cc(-c2cn(CC(=O)OC)c3ncn(C)c(=O)c23)cc1C(=O)NC(C)(C)CC(C)(C)C]

To a microwave vial charged with 2-(methoxymethoxy)-3-methyl-5-(4,4,5,5-tetramethyl-1,3,2-dioxaborolan-2-yl)-N-(2,4,4-trimethylpentan-2-yl)benzamide (350 mg, 0.807 mmol), methyl 2-(5-iodo-3-methyl-4-oxo-3H-pyrrolo[2,3-d]pyrimidin-7(4H)-yl)acetate (200 mg, 0.576 mmol) was added dioxane (8 ml) followed by $K_3PO_4$ (245 mg, 1.152 mmol) dissolved in water (1 ml) and the vial was flushed with nitrogen. Bis(di-tert-butyl(4-dimethylaminophenyl)phosphine)dichloropalladium(II) (41 mg, 0.058 mmol) was added and the vial was sealed, and the mixture heated in a microwave reactor to 110° C. for 30 minutes. The mixture was neutralized with citric acid (1N, 1.15 mls). The crude mixture was concentrated onto celite and purified by silica by flash column chromatography [0-100% EtOAc/hexanes] to give the desired product as a white solid (279 mg, 92% yield). 1H NMR (500 MHz, CHLOROFORM-d) δ=8.00 (d, J=2.1 Hz, 1H), 7.97 (d, J=2.2 Hz, 1H), 7.81 (s, 1H), 7.41 (s, 1H), 7.02 (s, 1H), 4.96 (s, 2H), 4.84 (s, 2H), 3.72 (s, 3H), 3.53 (s, 3H), 3.51 (s, 3H), 2.35 (s, 3H), 1.82 (s, 2H), 1.46 (s, 6H), 0.95 (s, 9H); Observed LCMS [M+H]$^+$ 527.

Step 2: Synthesis of 5-(7-(2-((5-chloro-2-morpholinopyridin-4-yl)amino)-2-oxoethyl)-3-methyl-4-oxo-4,7-dihydro-3H-pyrrolo[2,3-d]pyrimidin-5-yl)-2-(methoxymethoxy)-3-methyl-N-(2,4,4-trimethylpentan-2-yl)benzamide (F-1)

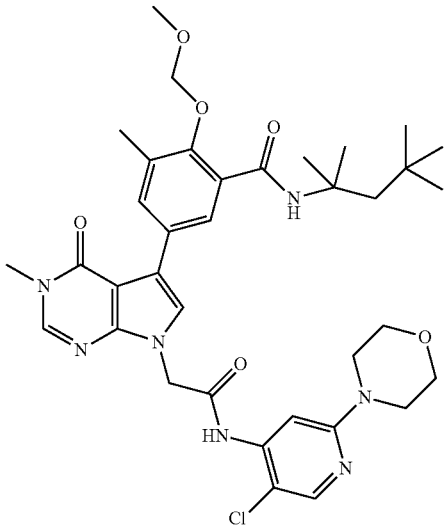 [SMILES: COCOc1c(C)cc(-c2cn(CC(=O)Nc3cc(N4CCOCC4)ncc3Cl)c3ncn(C)c(=O)c23)cc1C(=O)NC(C)(C)CC(C)(C)C]

To a vial of 5-chloro-2-morpholinopyridin-4-amine (203 mg, 0.949 mmol, 5 equiv) in Dioxane (8 ml) was added Methylmagnesium chloride (0.127 ml of 3 M soln, 0.380 mmol, 2 equiv). The reaction mixture was stirred at room temperature for 10 min after which methyl 2-(5-(4-(methoxymethoxy)-3-methyl-5-((2,4,4-trimethylpentan-2-yl)carbamoyl)phenyl)-3-methyl-4-oxo-3H-pyrrolo[2,3-d]pyrimidin-7(4H)-yl)acetate (100 mg, 0.190 mmol, 1 equiv) dissolved in dioxane (8 ml) was added and the reaction mixture was heated at 60° C. for 10 min. An additional amount of Methylmagnesium chloride (0.127 ml of 3 M soln, 0.380 mmol, 2 equiv) was added and the mixture was stirred for another 5 min. The mixture was quenched with methanol (20 ml), and the mixture was concentrated on celite and purified by reverse phase chromatography [AcCN Water 0-100% gradient] to give the title compound as a light purple solid (101 mg, 75%). Observed LCMS [M+H]$^+$ 708.

Step 3: Synthesis of 5-(7-(2-((5-chloro-2-morpholinopyridin-4-yl)amino)-2-oxoethyl)-3-methyl-4-oxo-4,7-dihydro-3H-pyrrolo[2,3-d]pyrimidin-5-yl)-2-hydroxy-3-methylbenzamide (I-4)

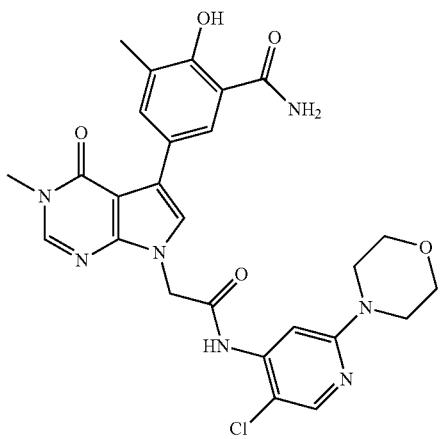 [SMILES: Cc1cc(-c2cn(CC(=O)Nc3cc(N4CCOCC4)ncc3Cl)c3ncn(C)c(=O)c23)cc(C(N)=O)c1O]

To a vial of 5-(7-(2-((5-chloro-2-morpholinopyridin-4-yl)amino)-2-oxoethyl)-3-methyl-4-oxo-4,7-dihydro-3H-pyrrolo[2,3-d]pyrimidin-5-yl)-2-(methoxymethoxy)-3-methyl-N-(2,4,4-trimethylpentan-2-yl)benzamide (100 mg, 0.077 mmol, 1 equiv) was added TFA/CH$_2$Cl$_2$ (2 ml of a 1:1 mixture). The reaction mixture was stirred at 60° C. for 30 min (Judged complete by LCMS). The solvent was removed in vacuo and the residue was triturated with ether to afford 79 mg of the title compound (I-4) (TFA. Salt) as an off-white solid (84% yield).

Preparation of 3-chloro-5-(7-(2-((5-chloro-2-morpholinopyridin-4-yl)amino)-2-oxoethyl)-3-methyl-4-oxo-4,7-dihydro-3H-pyrrolo[2,3-d]pyrimidin-5-yl)-2-hydroxy-N-methylbenzamide (Compound I-12)

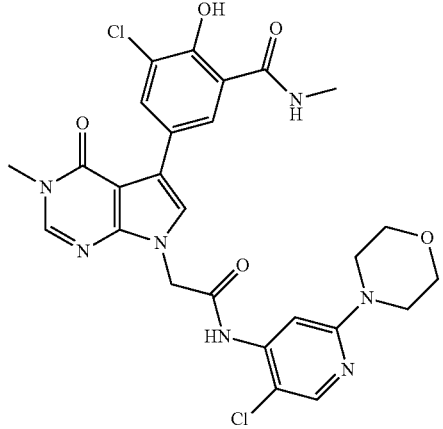 [SMILES: CNC(=O)c1cc(-c2cn(CC(=O)Nc3cc(N4CCOCC4)ncc3Cl)c3ncn(C)c(=O)c23)cc(Cl)c1O]

Step 1: Synthesis of methyl 2-(5-(3-chloro-4-hydroxy-5-(methylcarbamoyl)phenyl)-3-methyl-4-oxo-3H-pyrrolo[2,3-d]pyrimidin-7(4H)-yl)acetate (E-2)

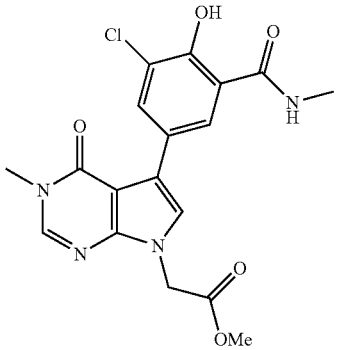

A mixture of methyl 2-(5-iodo-3-methyl-4-oxo-3H-pyrrolo[2,3-d]pyrimidin-7(4H)-yl)acetate (200 mg, 0.576 mmol) and 3-chloro-2-hydroxy-N-methyl-5-(4,4,5,5-tetramethyl-1,3,2-dioxaborolan-2-yl)benzamide (287 mg, 0.922 mmol) in Dioxane (Volume: 15 ml, Ratio: 15.00) was degassed for 10 min. Then, Bis(di-tert-butyl(4-dimethylaminophenyl)phosphine)dichloropalladium(II) (40.8 mg, 0.058 mmol) followed by an ice cold solution of Potassium phosphate tribasic reagent grade, >=98% (245 mg, 1.152 mmol) in water (Volume: 1 ml, Ratio: 1.000) was added. The mixture was heated at 100° C. for 90 minutes. The reaction mixture was concentrated under vacuum, washed with saturated aqueous NH$_4$Cl and extracted with EtOAc. The organic extract was concentrated onto celite and purified by ISCO (12 g column, 0-5-30-70-100% EA/Hex and switch to DCM/MeOH 0-5-15%, 30 min; product eluted DCM/MeOH gradients) to give the desired product, methyl 2-(5-(3-chloro-4-hydroxy-5-(methylcarbamoyl)phenyl)-3-methyl-4-oxo-3H-pyrrolo[2,3-d]pyrimidin-7(4H)-yl)acetate (207 mg, 0.486 mmol, 84% yield), as a pinkish white solid; Observed LCMS [M+H]$^+$ 405.

Step 2: Synthesis of 3-chloro-5-(7-(2-((5-chloro-2-morpholinopyridin-4-yl)amino)-2-oxoethyl)-3-methyl-4-oxo-4,7-dihydro-3H-pyrrolo[2,3-d]pyrimidin-5-yl)-2-hydroxy-N-methylbenzamide (I-12)

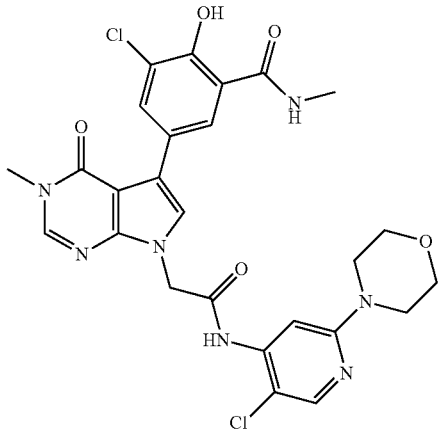 [SMILES: CNC(=O)c1cc(-c2cn(CC(=O)Nc3cc(N4CCOCC4)ncc3Cl)c3ncn(C)c(=O)c23)cc(Cl)c1O]

A solution of Methylmagnesium chloride, 3M (0.074 ml, 0.222 mmol) in THF was added to a stirred solution of 5-Chloro-2-morpholinopyridin-4-amine (47.5 mg, 0.222 mmol) in Dioxane (Volume: 3 ml, Ratio: 1.000) at 55° C. After 5 min, a dilute solution of methyl 2-(5-(3-chloro-4-hydroxy-5-(methylcarbamoyl)phenyl)-3-methyl-4-oxo-3H-pyrrolo[2,3-d]pyrimidin-7(4H)-yl)acetate (30 mg, 0.074 mmol) in 1,4-Dioxane (Volume: 3.00 ml, Ratio: 1.000) was added followed by the addition of another equiv. of Methylmagnesium chloride, 3M in THF (0.074 ml, 0.222 mmol) for 2 times at an interval of 5-10 min. LCMS analysis indicated the formation of the product. The reaction mixture was concentrated under vacuum, washed with saturated aqueous NH$_4$Cl and extracted with EtOAc. The organic extract was concentrated onto celite and and purified by ISCO (12 g column; 45 min; 0-20-30-70% EA/Hex) followed by reverse phase column (biotage, ACN/water, 10 g column) to give the desired product, 3-chloro-5-(7-(2-((5-chloro-2-morpholinopyridin-4-yl)amino)-2-oxoethyl)-3-methyl-4-oxo-4,7-dihydro-3H-pyrrolo[2,3-d]pyrimidin-5-yl)-2-hydroxy-N-methylbenzamide (I-12) (8.9 mg, 0.015 mmol, 20.07% yield), as a pale brown powder. Observed LCMS [M+H]$^+$ 586.

General Scheme of Suzuki-Coupling/Alkylation/Deprotection Procedures Preparation of 5-(7-(2-((5-chloro-2-(dimethylamino)pyridin-4-yl)amino)-2-oxoethyl)-3-methyl-4-oxo-4,7-dihydro-3H-pyrrolo[2,3-d]pyrimidin-5-yl)-2-hydroxy-3-methylbenzamide (Compound I-7)

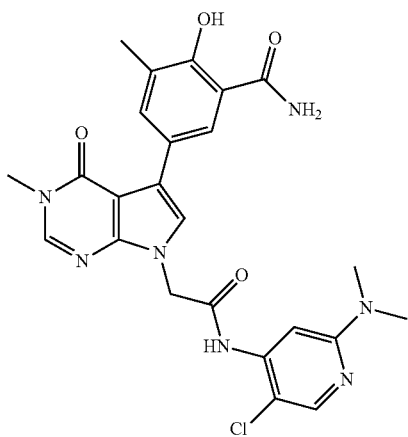

Step 1: Synthesis of 2-(methoxymethoxy)-3-methyl-5-(3-methyl-4-oxo-4,7-dihydro-3H-pyrrolo[2,3-d]pyrimidin-5-yl)-N-(2,4,4-trimethylpentan-2-yl)benzamide (X-1)

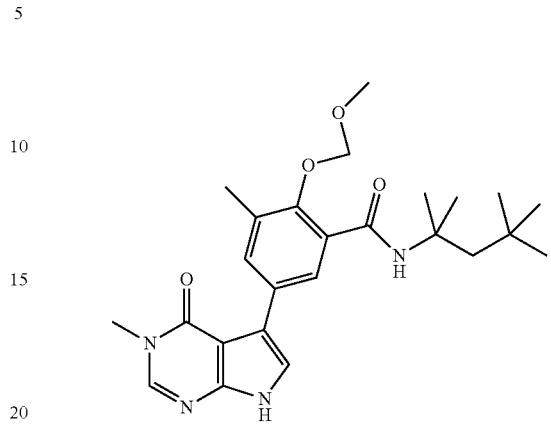

A microwave vial was charged with 7-acetyl-5-iodo-3-methyl-3H-pyrrolo[2,3-d]pyrimidin-4(7H)-one (0.040 g, 0.126 mmol), 2-(methoxymethoxy)-3-methyl-5-(4,4,5,5-tetramethyl-1,3,2-dioxaborolan-2-yl)-N-(2,4,4-trimethylpentan-2-yl)benzamide (0.057 g, 0.132 mmol) and Bis(di-tert-butyl(4-dimethylaminophenyl)phosphine)dichloropalladium(II) (8.93 mg, 0.013 mmol). The vial was capped, evacuated and backfilled with nitrogen gas. 1,4-Dioxane (Volume: 4 ml, Ratio: 5.33) was added followed by 0.75 mL of a 1.3 M solution of K$_3$PO$_4$. The reaction was irradiated to 110° C. for 90 minutes. LCMS analysis indicated very clean conversion to the desired product. The organic layer was separated and the aqueous layer was acidified with dilute citric acid and extracted with EtOAc. The combined organics were concentrated onto celite and purified by flash chromatography [40-100% EtOAc/hexanes] to afford 2-(methoxymethoxy)-3-methyl-5-(3-methyl-4-oxo-4,7-dihydro-3H-pyrrolo[2,3-d]pyrimidin-5-yl)-N-(2,4,4-trimethylpentan-2-yl)benzamide (0.043 g, 0.095 mmol, 75.0% yield); LCMS [M+H]+ 455.

Step 2: Synthesis of 5-(7-(2-((5-chloro-2-(dimethylamino)pyridin-4-yl)amino)-2-oxoethyl)-3-methyl-4-oxo-4,7-dihydro-3H-pyrrolo[2,3-d]pyrimidin-5-yl)-2-(methoxymethoxy)-3-methyl-N-(2,4,4-trimethylpentan-2-yl)benzamide (F-2)

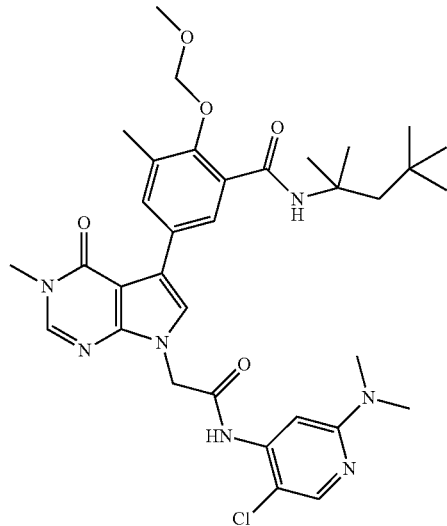 [SMILES: COCOc1c(C)cc(-c2cn(CC(=O)Nc3cc(N(C)C)ncc3Cl)c3ncn(C)c(=O)c23)cc1C(=O)NC(C)(C)CC(C)(C)C]

A mixture of 2-(methoxymethoxy)-3-methyl-5-(3-methyl-4-oxo-4,7-dihydro-3H-pyrrolo[2,3-d]pyrimidin-5-yl)-N-(2,4,4-trimethylpentan-2-yl)benzamide (0.043 g, 0.095 mmol), 2-chloro-N-(5-chloro-2-(dimethylamino)pyridin-4-yl)acetamide (0.028 g, 0.114 mmol) and $Cs_2CO_3$ (0.037 g, 0.114 mmol) in N,N-Dimethylformamide (DMF) (Volume: 3 ml) was stirred at room temperature overnight. The crude reaction mixture was loaded onto celite and purified by silica gel chromatography [50-100% EtOAc/hexanes] to afford 5-(7-(2-((5-chloro-2-(dimethylamino)pyridin-4-yl)amino)-2-oxoethyl)-3-methyl-4-oxo-4,7-dihydro-3H-pyrrolo[2,3-d]pyrimidin-5-yl)-2-(methoxymethoxy)-3-methyl-N-(2,4,4-trimethylpentan-2-yl)benzamide (0.041 g, 0.062 mmol, 65.1% yield); 1H NMR (500 MHz, DMSO-d6) δ=9.83 (br. s., 1H), 8.27 (s, 1H), 8.09 (s, 1H), 7.91 (d, J=2.2 Hz, 1H), 7.73-7.69 (m, 2H), 7.47 (s, 1H), 7.39 (s, 1H), 5.22 (s, 2H), 5.04 (s, 2H), 3.51 (s, 3H), 3.49 (s, 3H), 2.96 (s, 7H), 2.32 (s, 3H), 1.84 (s, 2H), 1.42 (s, 6H), 1.00 (s, 9H); LCMS [M+H]+ 666.

Step 3: Synthesis of 5-(7-(2-((5-chloro-2-(dimethylamino)pyridin-4-yl)amino)-2-oxoethyl)-3-methyl-4-oxo-4,7-dihydro-3H-pyrrolo[2,3-d]pyrimidin-5-yl)-2-hydroxy-3-methylbenzamide (I-7)

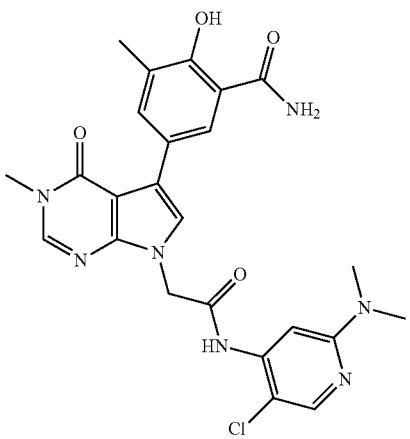

TFA (0.403 ml, 5.23 mmol) was added to a solution of 5-(7-(2-((5-chloro-2-(dimethylamino)pyridin-4-yl)amino)-2-oxoethyl)-3-methyl-4-oxo-4,7-dihydro-3H-pyrrolo[2,3-d]pyrimidin-5-yl)-2-(methoxymethoxy)-3-methyl-N-(2,4,4-trimethylpentan-2-yl)benzamide (0.041 g, 0.062 mmol) in Dichloromethane (DCM) (Volume: 2 ml) at room temperature. The reaction was warmed to 40° C. in an aluminum block for 1 h. LCMS analysis indicated complete removal of the MOM and near complete removal of the amide protecting group. Further heating for another 30 minutes and then concentrate to dryness. After removal of any residual TFA with a stream of compressed air, the residue was taken up in DCM and loaded onto celite. Flash RP on biotage [5-95% MeCN/water] to afford 5-(7-(2-((5-chloro-2-(dimethylamino)pyridin-4-yl)amino)-2-oxoethyl)-3-methyl-4-oxo-4,7-dihydro-3H-pyrrolo[2,3-d]pyrimidin-5-yl)-2-hydroxy-3-methylbenzamide (I-7) (0.015 g, 0.025 mmol, 40.6% yield) as a colourless solid; LCMS [M+H]+ 510.

General Scheme of Suzuki-Coupling/Alkylation/Deprotection Procedures

Scheme 30

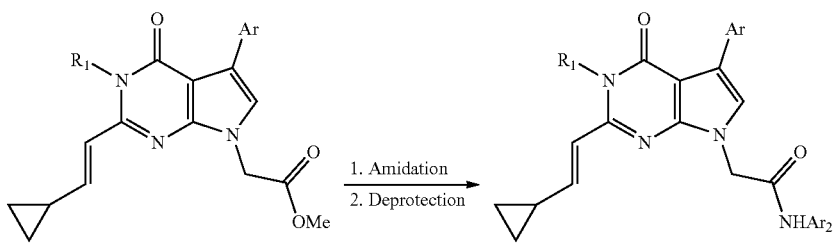

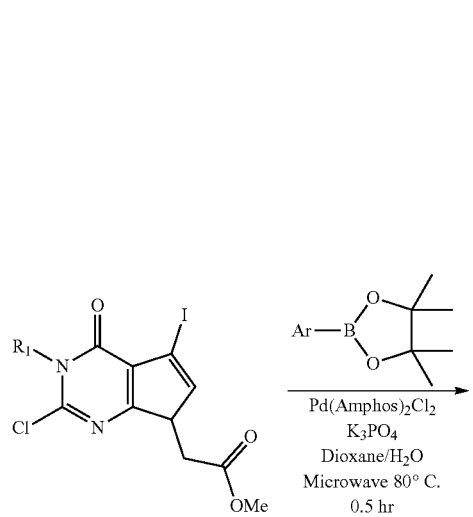
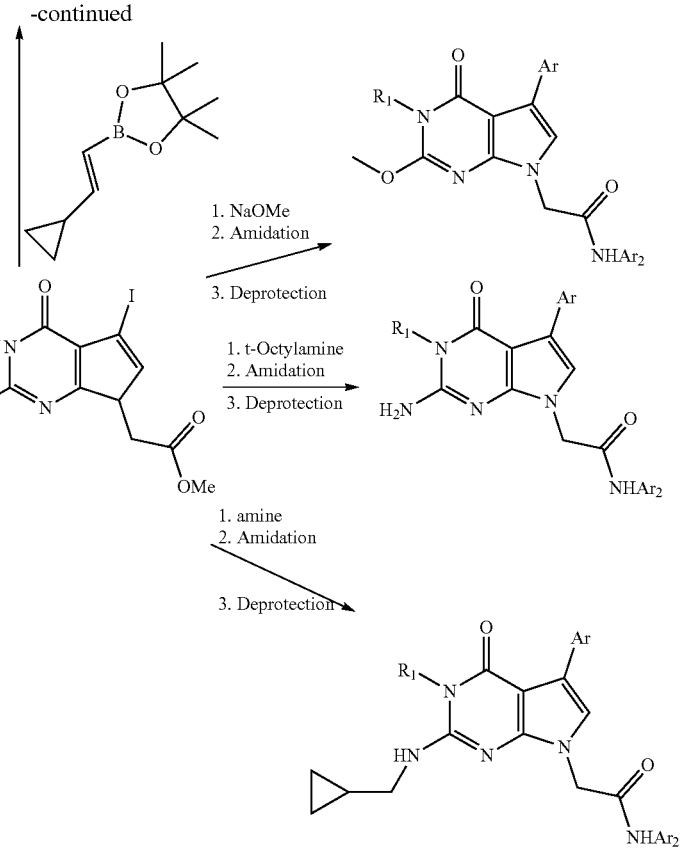

Preparation of (E)-3-chloro-5-(7-(2-((5-chloro-2-morpholinopyridin-4-yl)amino)-2-oxoethyl)-2-(2-cyclopropylvinyl)-3-methyl-4-oxo-4,7-dihydro-3H-pyrrolo[2,3-d]pyrimidin-5-yl)-2-hydroxybenzamide (Compound I-95)

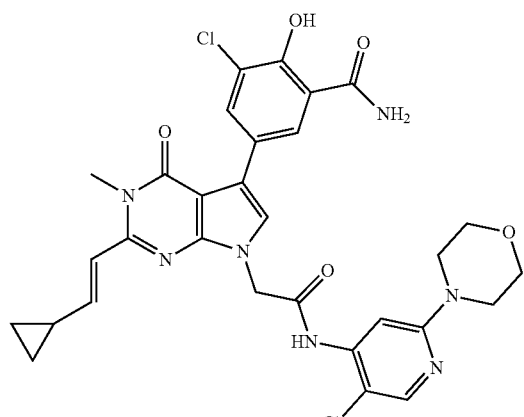

Step 1: Synthesis of methyl 2-(2-chloro-5-(3-chloro-5-((2,4,4-trimethylpentan-2-yl)carbamoyl)-4-(2-(trimethylsilyl)ethoxy)phenyl)-3-methyl-4-oxo-3H-pyrrolo[2,3-d]pyrimidin-7(4H)-yl)acetate (M-1)

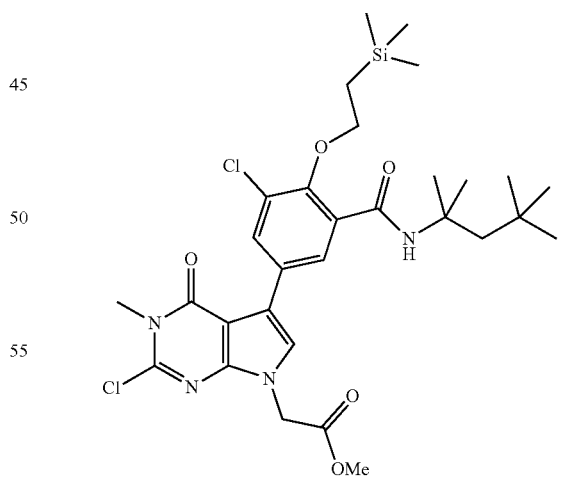

To a microwave vial charged with methyl 2-(2-chloro-5-iodo-3-methyl-4-oxo-3H-pyrrolo[2,3-d]pyrimidin-7(4H)-yl)acetate (1 g, 2.62 mmol), 3-chloro-5-(4,4,5,5-tetramethyl-1,3,2-dioxaborolan-2-yl)-N-(2,4,4-trimethylpentan-2-yl)-2-(2-(trimethylsilyl)ethoxy)benzamide (1.738 g, 3.41 mmol) and Bis(di-tert-butyl(4-dimethylaminophenyl)phosphine)dichloropalladium(II) (0.111 g, 0.157 mmol) was added dioxane (14 ml). Potassium phosphate tribasic reagent (1.113 g, 5.24 mmol) was dissolved in water (1.17 ml) and cooled. This solution was added to the mixture. The vial was sealed then heated in the microwave at 90° C. for 25 min.

The mixture was transferred to a separating funnel, citric acid (1 N) ~5.2 ml was added and the mixture was diluted with DCM and water. The organic extract was dried over Na₂SO₄, concentrated onto celite and purified by flash column silica gel chromatography (40 g cartridge: eluent 0%, 0-25% then 25%, EtOAc/Hexanes). The product was isolated as a pale brown foamy solid (1.385 g, 83% yield); LCMS [M+H]+ 637

Step 2: Synthesis of (E)-methyl 2-(5-(3-chloro-5-((2,4,4-trimethylpentan-2-yl)carbamoyl)-4-(2-(trimethylsilyl)ethoxy)phenyl)-2-(2-cyclopropylvinyl)-3-methyl-4-oxo-3H-pyrrolo[2,3-d]pyrimidin-7(4H)-yl)acetate (N-1) Exact Mass: 668.32

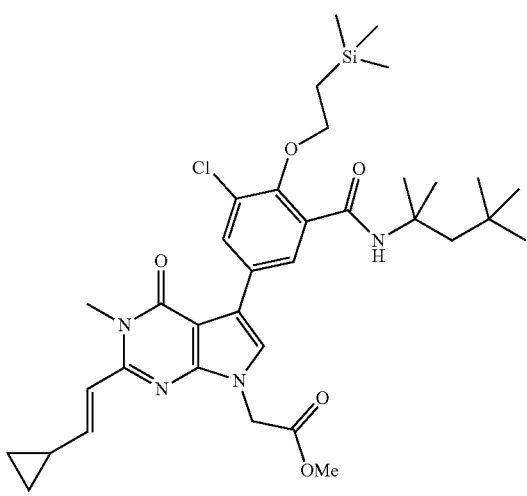 [SMILES: COC(=O)Cn1cc(-c2cc(Cl)c(OCC[Si](C)(C)C)c(C(=O)NC(C)(C)CC(C)(C)C)c2)c2c(=O)n(C)c(/C=C/C3CC3)nc21]

A microwave vial was charged with methyl 2-(2-chloro-5-(3-chloro-5-((2,4,4-trimethylpentan-2-yl)carbamoyl)-4-(2-(trimethylsilyl)ethoxy)phenyl)-3-methyl-4-oxo-3H-pyrrolo[2,3-d]pyrimidin-7(4H)-yl)acetate (100 mg, 0.157 mmol), (E)-2-Cyclopropylvinylboronic acid pinacol ester (42.6 mg, 0.220 mmol) Bis(di-tert-butyl(4-dimethylaminophenyl)phosphine)dichloropalladium(II) (11.10 mg, 0.016 mmol) and Dioxane (3 ml) was added. Potassium phosphate tribasic reagent grade (66.6 mg, 0.314 mmol) was dissolved in water (Volume: 1.000 ml, Ratio: 1) cooled and this K₃PO₄ solution was then added. The vial was then sealed and heated in the microwave at 110° C. for 25 min. The mixture was transferred to a separating funnel, citric acid (1 N) ~0.32 ml was added and the mixture was diluted with DCM and water. The organic extract was dried over Na₂SO₄, concentrated onto celite and purified by flash column silica gel chromatography (40 g cartridge: eluent 0%, 0-25% then 25%, EtOAc/Hexanes). The product was isolated as a yellow foamy solid (80 mg, 76% yield); LCMS [M+H]+ 669.

Step 3: Synthesis of (E)-3-chloro-5-(7-(2-((5-chloro-2-morpholinopyridin-4-yl)amino)-2-oxoethyl)-2-(2-cyclopropylvinyl)-3-methyl-4-oxo-4,7-dihydro-3H-pyrrolo[2,3-d]pyrimidin-5-yl)-N-(2,4,4-trimethylpentan-2-yl)-2-(2-(trimethylsilyl)ethoxy)benzamide (F-3)

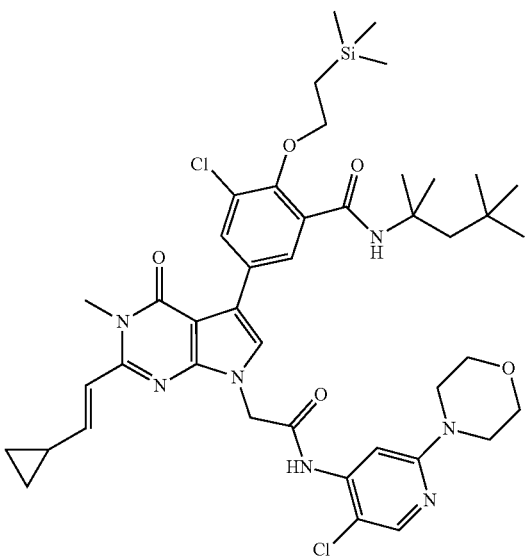 [SMILES: Cn1c(/C=C/C2CC2)nc2c(c(-c3cc(Cl)c(OCC[Si](C)(C)C)c(C(=O)NC(C)(C)CC(C)(C)C)c3)cn2CC(=O)Nc2cc(N3CCOCC3)ncc2Cl)c1=O]

To a solution of 5-Chloro-2-morpholinopyridin-4-amine in 3 ml of dioxane was added Methylmagnesium chloride (3M in THF). The reaction was allowed to stir at RT for 5 min. (E)-methyl 2-(5-(3-chloro-5-((2,4,4-trimethylpentan-2-yl)carbamoyl)-4-(2-(trimethylsilyl)ethoxy)phenyl)-2-(2-cyclopropylvinyl)-3-methyl-4-oxo-3H-pyrrolo[2,3-d]pyrimidin-7(4H)-yl)acetate (79 mg, 0.118 mmol) was added as a solution in 3 ml of dioxane. The mixture was stirred at 50° C. for 5 minutes after which an additional ~ 150 ul of MeMgCl was added. The reaction mixture was cooled, quenched with MeOH and concentrated onto celite. The crude mixture was purified by reverse phase silica gel chromatograpgy (Biotage, 12 g C18 cartridge: eluent 5%-100% then 100% water/acetonitrile). The product was isolated as as a mustard-colored foamy solid (0.065 g, 65% yield); LCMS [M+H]+ 850

Step 4: Synthesis of (E)-3-chloro-5-(7-(2-((5-chloro-2-morpholinopyridin-4-yl)amino)-2-oxoethyl)-2-(2-cyclopropylvinyl)-3-methyl-4-oxo-4,7-dihydro-3H-pyrrolo[2,3-d]pyrimidin-5-yl)-2-hydroxybenzamide (I-95) Exact Mass: 637.16

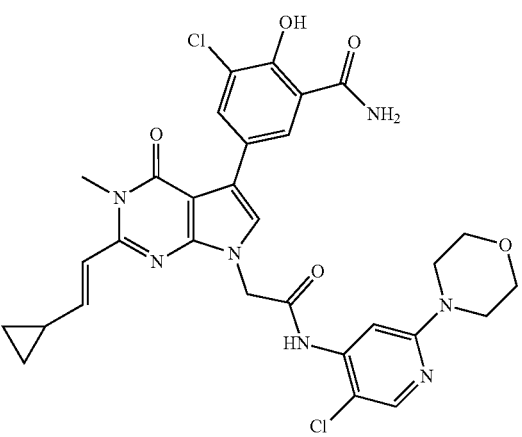 [SMILES: Cn1c(/C=C/C2CC2)nc2c(c(-c3cc(Cl)c(O)c(C(N)=O)c3)cn2CC(=O)Nc2cc(N3CCOCC3)ncc2Cl)c1=O]

(E)-3-chloro-5-(7-(2-((5-chloro-2-morpholinopyridin-4-yl)amino)-2-oxoethyl)-2-(2-cyclopropylvinyl)-3-methyl-4-oxo-4,7-dihydro-3H-pyrrolo[2,3-d]pyrimidin-5-yl)-N-(2,4,4-trimethylpentan-2-yl)-2-(2-(trimethylsilyl)ethoxy)benzamide (63.47 mg, 0.075 mmol) was dissolved in 1.5 ml of DCM. TFA (1.5 ml) was added the the mixture was heated at 50° C. for 1 h. The solvents were evaporated and the residue triturated with ether to give the desired compound as a pale yellow powder (0.046 g, 92% yield); LCMS [M+H]+ 638

In a similar sequence to compound I-95, the following analogs were prepared

I-247 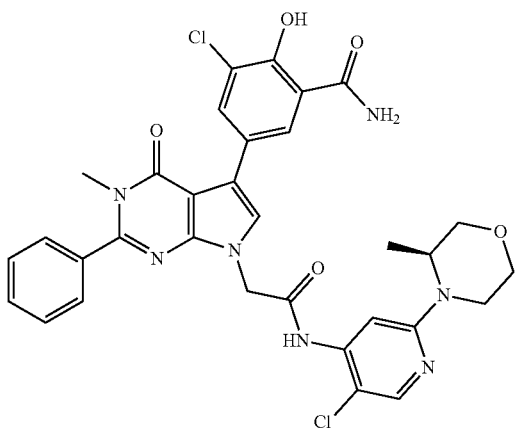 [SMILES: C[C@H]1COCCN1c1cc(NC(=O)Cn2cc(-c3cc(Cl)c(O)c(C(N)=O)c3)c3c(=O)n(C)c(-c4ccccc4)nc32)c(Cl)cn1] (S)-3-chloro-5-(7-(2-((5-chloro-2-(3-methylmorpholino)pyridin-4-yl)amino)-2-oxoethyl)-3-methyl-4-oxo-2-phenyl-4,7-dihydro-3H-pyrrolo[2,3-d]pyrimidin-5-yl)-2-hydroxybenzamide Exact Mass: 661.16 — 40% yield, LCMS [M + H]+ 662

I-260 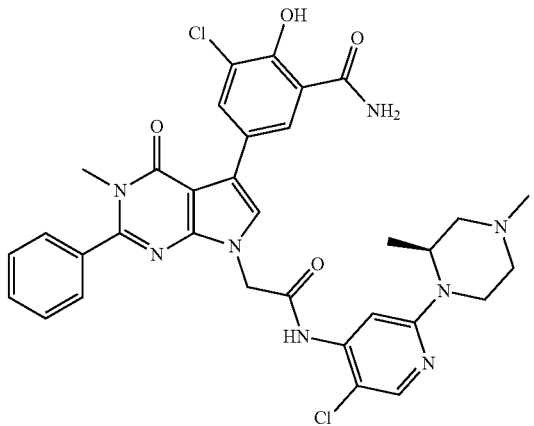 [SMILES: C[C@H]1CN(C)CCN1c1cc(NC(=O)Cn2cc(-c3cc(Cl)c(O)c(C(N)=O)c3)c3c(=O)n(C)c(-c4ccccc4)nc32)c(Cl)cn1] (S)-3-chloro-5-(7-(2-((5-chloro-2-(2,4-dimethylpiperazin-1-yl)pyridin-4-yl)amino)-2-oxoethyl)-3-methyl-4-oxo-2-phenyl-4,7-dihydro-3H-pyrrolo[2,3-d]pyrimidin-5-yl)-2-hydroxybenzamide Exact Mass: 674.19 — quantitative yield, LCMS [M + H]+ 675

I-261 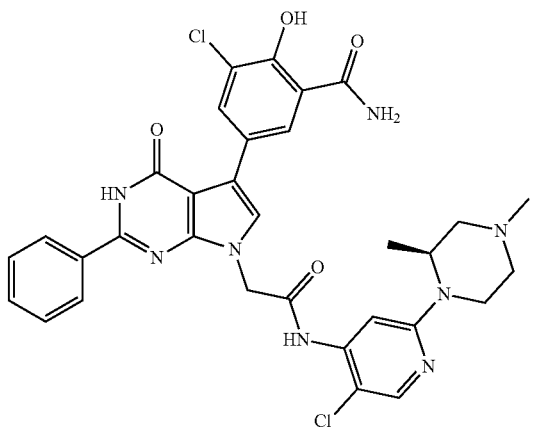 [SMILES: C[C@H]1CN(C)CCN1c1cc(NC(=O)Cn2cc(-c3cc(Cl)c(O)c(C(N)=O)c3)c3c(=O)[nH]c(-c4ccccc4)nc32)c(Cl)cn1] (S)-3-chloro-5-(7-(2-((5-chloro-2-(2,4-dimethylpiperazin-1-yl)pyridin-4-yl)amino)-2-oxoethyl)-4-oxo-2-phenyl-4,7-dihydro-3H-pyrrolo[2,3-d]pyrimidin-5-yl)-2-hydroxybenzamide Exact Mass: 660.18 — 64% yield, LCMS [M + H]+ 661

Preparation of methyl 2-(5-(3-chloro-5-((2,4,4-trimethylpentan-2-yl)carbamoyl)-4-(2-(trimethylsilyl)ethoxy)phenyl)-2-((cyclopropylmethyl)amino)-3-methyl-4-oxo-3,4-dihydro-7H-pyrrolo[2,3-d]pyrimidin-7-yl)acetate (R-1)

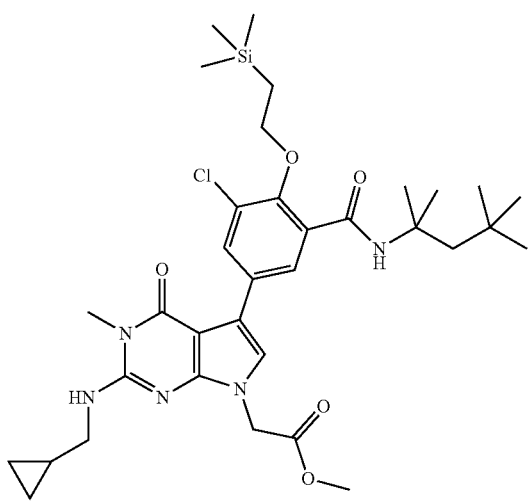 [SMILES: COC(=O)Cn1cc(-c2cc(Cl)c(OCC[Si](C)(C)C)c(C(=O)NC(C)(C)CC(C)(C)C)c2)c2c(=O)n(C)c(NCC3CC3)nc21]

To a 20 ml microwave vial was charged with methyl 2-(2-chloro-5-(3-chloro-5-((2,4,4-trimethylpentan-2-yl)carbamoyl)-4-(2-(trimethylsilyl)ethoxy)phenyl)-3-methyl-4-oxo-3H-pyrrolo[2,3-d]pyrimidin-7(4H)-yl)acetate (143 mg, 0.224 mmol) then 1,4-Dioxane (Volume: 10 ml, Ratio: 10.00) was added and the mixture was stirred at rt. Cyclopropylmethyl amine (Volume: 1 ml, Ratio: 1.000) was added. The vial was sealed and it was heated in the microwave at 110-130° C. for 30 min. LCMS showed formation of the desired product. The reaction mixture was concentrated under vacuum, loaded on celite, and purified by Isco (12 g cartridge: eluent 0%, 0-60% then 60%) to afford 2-(5-(3-chloro-5-((2,4,4-trimethylpentan-2-yl)carbamoyl)-4-(2-(trimethylsilyl)ethoxy)phenyl)-2-((cyclopropylmethyl)amino)-3-methyl-4-oxo-3,4-dihydro-7H-pyrrolo[2,3-d]pyrimidin-7-yl)acetate as semi foamy solid (98 mg, 65% yield); LCMS [M+H]$^+$ 672

In a similar manner the following compounds were synthesized:

| | | |
|---|---|---|
| R-2 | 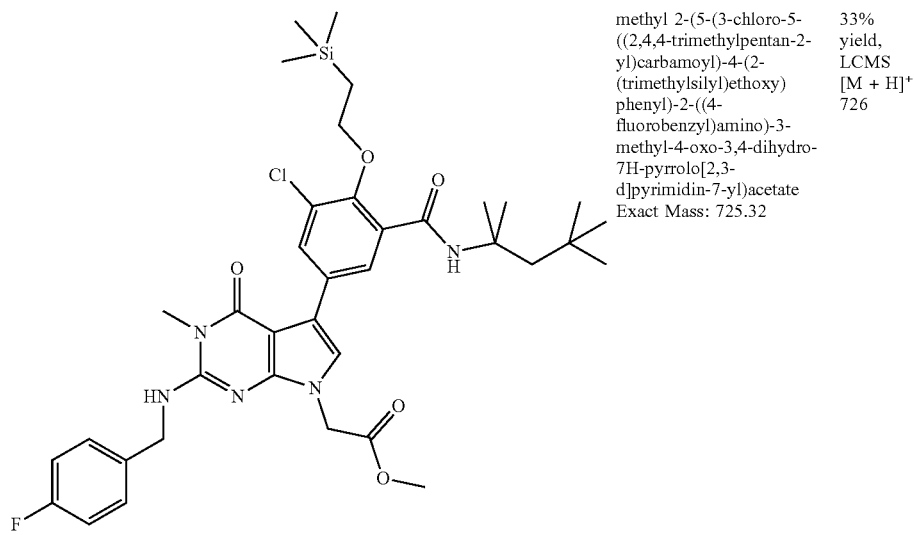 | methyl 2-(5-(3-chloro-5-((2,4,4-trimethylpentan-2-yl)carbamoyl)-4-(2-(trimethylsilyl)ethoxy)phenyl)-2-((4-fluorobenzyl)amino)-3-methyl-4-oxo-3,4-dihydro-7H-pyrrolo[2,3-d]pyrimidin-7-yl)acetate Exact Mass: 725.32 | 33% yield, LCMS [M + H]$^+$ 726 |

| | | |
|---|---|---|
| R-3 | 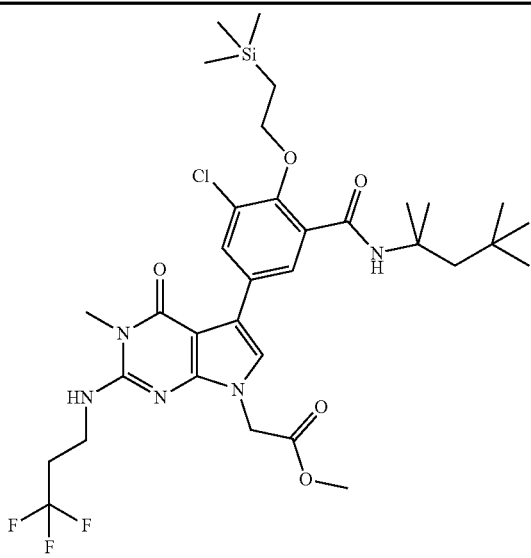 | methyl 2-(5-(3-chloro-5-((2,4,4-trimethylpentan-2-yl)carbamoyl)-4-(2-(trimethylsilyl)ethoxy) phenyl)-3-methyl-4-oxo-2-((3,3,3-trifluoropropyl)amino)-3,4-dihydro-7H-pyrrolo[2,3-d]pyrimidin-7-yl)acetate Exact Mass: 713.30    56% yield, LCMS [M + H]+ 714 |

Synthesis of (S)-3-chloro-5-(7-(2-((5-chloro-2-(3-methylmorpholino)pyridin-4-yl)amino)-2-oxoethyl)-2-(dimethylamino)-3-methyl-4-oxo-4,7-dihydro-3H-pyrrolo[2,3-d]pyrimidin-5-yl)-2-hydroxybenzamide (Compound I-263)

Scheme 31

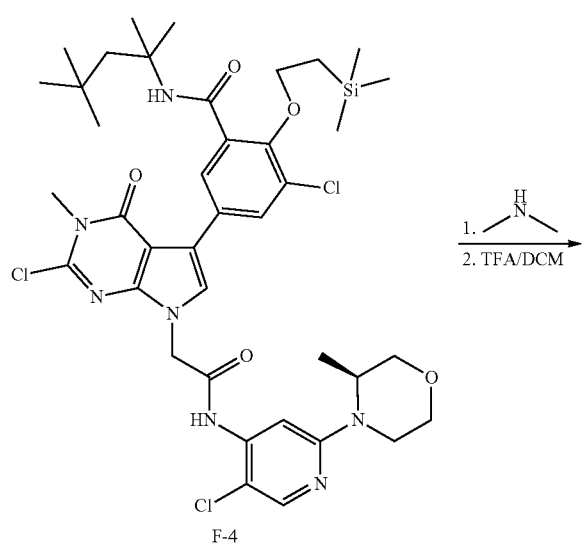

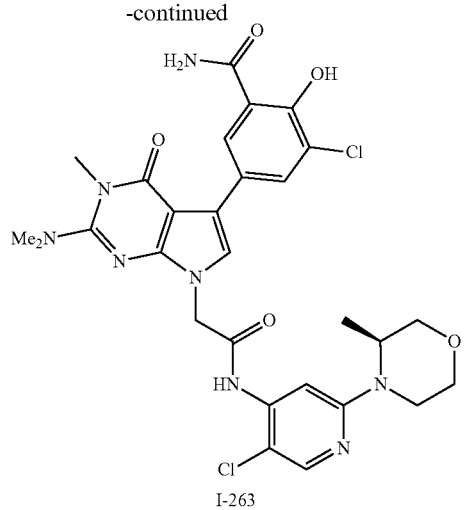

A solution of (S)-3-chloro-5-(2-chloro-7-(2-((5-chloro-2-(3-methylmorpholino)pyridin-4-yl)amino)-2-oxoethyl)-3-methyl-4-oxo-4,7-dihydro-3H-pyrrolo[2,3-d]pyrimidin-5-yl)-N-(2,4,4-trimethylpentan-2-yl)-2-(2-(trimethylsilyl) ethoxy)benzamide (F-4) (24 mg, 0.029 mmol) and Dimethylamine, 2.0M in THF (0.288 ml, 0.576 mmol) in 1,4-Dioxane (3 ml) was agitated at 110° C. (oil bath temp, microwave vial sealed tube) overnight. The reaction mixture was concentrated to dryness and dissolved in Dichloromethane (DCM) (1 ml) Trifluoroacetic acid (TFA) (1 ml) and agitated at 50° C. overnight.

The mixture was then concentrated onto celite and purified by ISCO (4 g column, DCM/MeOH 0-5-10%, 30 min) to get the desired product, (S)-3-chloro-5-(7-(2-((5-chloro-2-(3-methylmorpholino)pyridin-4-yl)amino)-2-oxoethyl)-2-(dimethylamino)-3-methyl-4-oxo-4,7-dihydro-3H-pyrrolo[2,3-d]pyrimidin-5-yl)-2-hydroxybenzamide (0.023 mmol, 79% yield); LCMS [M+H]+629.

In a similar manner the following compounds were synthesized:

| Example # | Structure | Name | Yield, LCMS |
|---|---|---|---|
| I-268 | 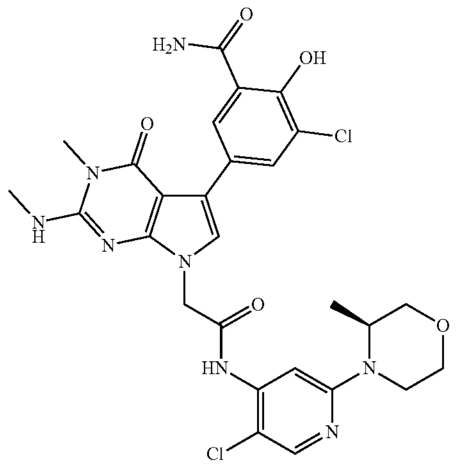 | (S)-3-chloro-5-(7-(2-((5-chloro-2-(3-methylmorpholino)pyridin-4-yl)amino)-2-oxoethyl)-3-methyl-2-(methylamino)-4-oxo-4,7-dihydro-3H-pyrrolo[2,3-d]pyrimidin-5-yl)-2-hydroxybenzamide | 33% yield, LCMS [M + H]$^+$ 726 |
| I-269 | 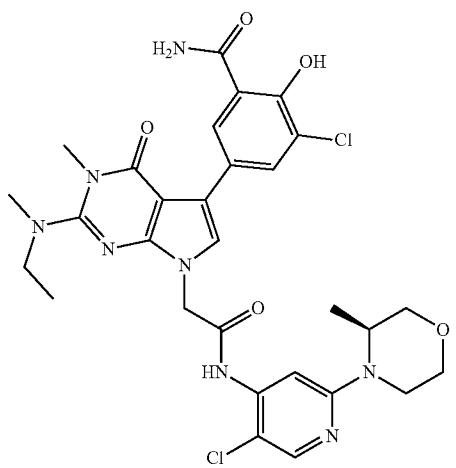 [SMILES: CCN(C)c1nc2c(c(-c3cc(Cl)c(O)c(C(N)=O)c3)cn2CC(=O)Nc2cc(N3CCOC[C@@H]3C)ncc2Cl)c(=O)n1C] | (S)-3-chloro-5-(7-(2-((5-chloro-2-(3-methylmorpholino)pyridin-4-yl)amino)-2-oxoethyl)-2-(ethyl(methyl)amino)-3-methyl-4-oxo-4,7-dihydro-3H-pyrrolo[2,3-d]pyrimidin-5-yl)-2-hydroxybenzamide | 63% yield, LCMS [M + H]$^+$ 643 |
| I-270 | 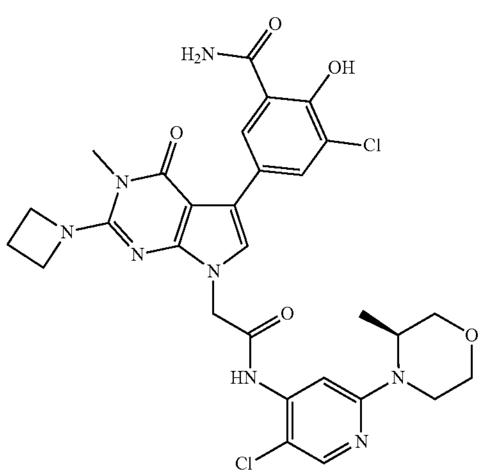 [SMILES: C[C@H]1COCCN1c1cc(NC(=O)Cn2cc(-c3cc(Cl)c(O)c(C(N)=O)c3)c3c(=O)n(C)c(N4CCC4)nc32)c(Cl)cn1] | (S)-5-(2-(azetidin-1-yl)-7-(2-((5-chloro-2-(3-methylmorpholino)pyridin-4-yl)amino)-2-oxoethyl)-3-methyl-4-oxo-4,7-dihydro-3H-pyrrolo[2,3-d]pyrimidin-5-yl)-3-chloro-2-hydroxybenzamide | 61% yield, LCMS [M + H]$^+$ 641 |

Synthesis of 3-chloro-5-(2-((5-chloro-2-(dimethyl-amino)pyridin-4-yl)amino)-7-(2-((5-chloro-2-(dimethylamino)pyridin-4-yl)amino)-2-oxoethyl)-3-methyl-4-oxo-4,7-dihydro-3H-pyrrolo[2,3-d]pyrimidin-5-yl)-2-hydroxybenzamide (I-291)

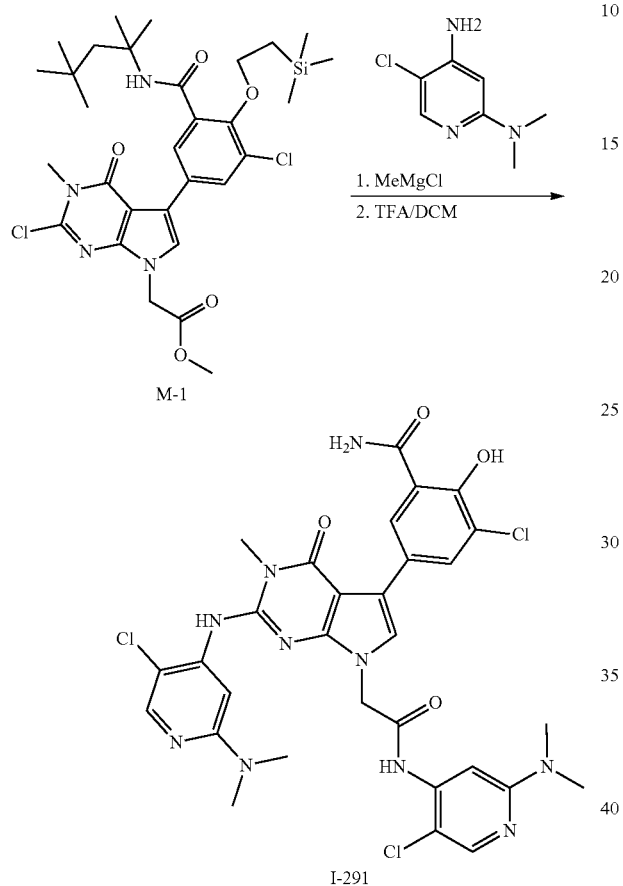

To a solution of 5-Chloro-N,N-dimethylpyridine-2,4-diamine (145 mg, 0.847 mmol) in 1,4-Dioxane (5 ml) at 70° C., Methylmagnesium chloride, 3M in THF (0.263 ml, 0.790 mmol) was added. After 10 min., a dilute solution of methyl 2-(2-chloro-5-(3-chloro-5-((2,4,4-trimethylpentan-2-yl)carbamoyl)-4-(2-(trimethylsilyl)ethoxy)phenyl)-3-methyl-4-oxo-3,4-dihydro-7H-pyrrolo[2,3-d]pyrimidin-7-yl)acetate (M-1) (180 mg, 0.282 mmol) in 1,4-Dioxane (5 ml) was added. After 10 min. agitation at 70° C., the mixture was charged with Methylmagnesium chloride, 3M in THF (0.263 ml, 0.790 mmol) two times at an interval 5 min. LCMS analysis indicated the formation desired product. The mixture was cooled to 23° C., extracted with sat.NH4Cl and EtOAc and the organic layer was concentrated. The crude mixture was then purified by biotage reverse phase chromatography (ACN/water) to give the desired disubstituted adduct, 3-chloro-5-(2-((5-chloro-2-(dimethylamino)pyridin-4-yl)amino)-7-(2-((5-chloro-2-(dimethylamino)pyridin-4-yl)amino)-2-oxoethyl)-3-methyl-4-oxo-4,7-dihydro-3H-pyrrolo[2,3-d]pyrimidin-5-yl)-N-(2,4,4-trimethylpentan-2-yl)-2-(2-(trimethylsilyl)ethoxy)benzamide (0.031 mmol, 11.07% yield), as a pasty brown solid. The adduct was dissolved in Dichloromethane (DCM) (1 ml), Trifluoroacetic acid (TFA) (1 ml) and agitated at 50° C. overnight. The mixture was then concentrated onto celite and purified by ISCO (4 g column, DCM/MeOH 0-5-10%, min) to get the desired product, 3-chloro-5-(2-((5-chloro-2-(dimethylamino)pyridin-4-yl)amino)-7-(2-((5-chloro-2-(dimethylamino)pyridin-4-yl)amino)-2-oxoethyl)-3-methyl-4-oxo-4,7-dihydro-3H-pyrrolo[2,3-d]pyrimidin-5-yl)-2-hydroxybenzamide (I-291) (12 mg, 7% yield over two step); LCMS [M+H]$^+$564.

Preparation of 5-(2-amino-7-(2-((5-chloro-2-morpholinopyridin-4-yl)amino)-2-oxoethyl)-3-methyl-4-oxo-4,7-dihydro-3H-pyrrolo[2,3-d]pyrimidin-5-yl)-3-chloro-2-hydroxybenzamide (I-120)

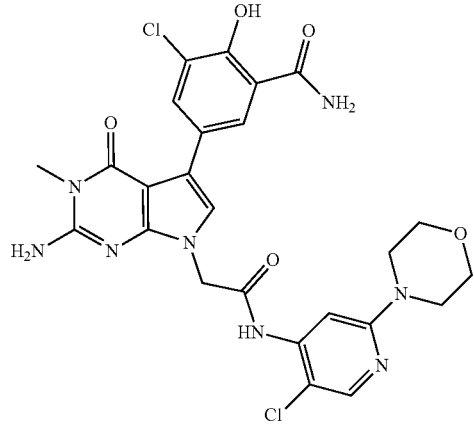 [SMILES: Cn1c(N)nc2c(c(-c3cc(Cl)c(O)c(C(N)=O)c3)cn2CC(=O)Nc2cc(N3CCOCC3)ncc2Cl)c1=O]

Step 1: Synthesis of methyl 2-(5-(3-chloro-5-((2,4,4-trimethylpentan-2-yl)carbamoyl)-4-(2-(trimethylsilyl)ethoxy)phenyl)-3-methyl-4-oxo-2-((2,4,4-trimethylpentan-2-yl)amino)-3H-pyrrolo[2,3-d]pyrimidin-7(4H)-yl)acetate (Q-1)

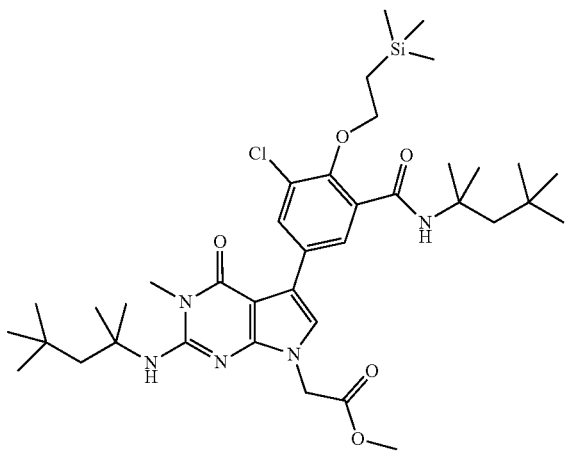 [SMILES: COC(=O)Cn1cc(-c2cc(Cl)c(OCC[Si](C)(C)C)c(C(=O)NC(C)(C)CC(C)(C)C)c2)c2c(=O)n(C)c(NC(C)(C)CC(C)(C)C)nc21]

A microwave vial was charged with methyl 2-(2-chloro-5-(3-chloro-5-((2,4,4-trimethylpentan-2-yl)carbamoyl)-4-(2-(trimethylsilyl)ethoxy)phenyl)-3-methyl-4-oxo-3H-pyrrolo[2,3-d]pyrimidin-7(4H)-yl)acetate (310 mg, 0.486 mmol) then tert-Octylamine (6244 μl, 38.9 mmol) was added. The vial was sealed and heated in the microwave at 160° C. for 5 h. The reaction mixture was concentrated in vacuo, and the crude residue was dissolved in DCM, loaded onto celite. The crude mixture was purified by silica gel chromatography (12 g cartridge: eluent 0, 0-20% then 20% EtOAc/Hexanes) to afford the product as a light purple foam (0.116 g, 33% yield); LCMS [M+H]+ 730.

Step 2: Synthesis of 3-chloro-5-(7-(2-((5-chloro-2-morpholinopyridin-4-yl)amino)-2-oxoethyl)-3-methyl-4-oxo-2-((2,4,4-trimethylpentan-2-yl)amino)-4,7-dihydro-3H-pyrrolo[2,3-d]pyrimidin-5-yl)-2-(2-(trimethylsilyl)ethoxy)benzamide (A2-1)

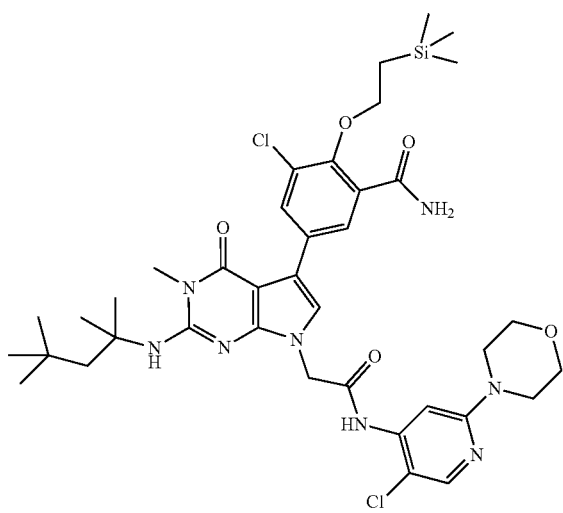 [SMILES: Cn1c(NC(C)(C)CC(C)(C)C)nc2c(c(-c3cc(Cl)c(OCC[Si](C)(C)C)c(C(N)=O)c3)cn2CC(=O)Nc2cc(N3CCOCC3)ncc2Cl)c1=O]

To a solution of 5-Chloro-2-morpholinopyridin-4-amine in 3 ml of dioxane was added Methylmagnesium chloride, (3M in THF). The reaction was allowed to stir at rt for 5 min. Methyl 2-(5-(3-chloro-5-((2,4,4-trimethylpentan-2-yl)carbamoyl)-4-(2-(trimethylsilyl)ethoxy)phenyl)-3-methyl-4-oxo-2-((2,4,4-trimethylpentan-2-yl)amino)-3H-pyrrolo[2,3-d]pyrimidin-7(4H)-yl)acetate was added as a solution in 4 ml of dioxane. The mixture was stirred at 50° C. for 5 minutes. After which, an additional ~150 µl of MeMgCl was added. The reaction mixture was cooled, quenched with MeOH and concentrated onto celite. The crude mixture was purified by reverse phase silica gel chromatograpgy (Biotage, 12 g C18 cartridge: eluent 5%-100% then 100% water/acetonitrile). The product was isolated as as a mustard-colored foamy solid (0.056 g, 41% yield); LCMS [M+H]+ 799.

Step 3: Synthesis of (E)-3-chloro-5-(7-(2-((5-chloro-2-morpholinopyridin-4-yl)amino)-2-oxoethyl)-2-(2-cyclopropylvinyl)-3-methyl-4-oxo-4,7-dihydro-3H-pyrrolo[2,3-d]pyrimidin-5-yl)-2-hydroxybenzamide (I-120) Exact Mass: 637.16

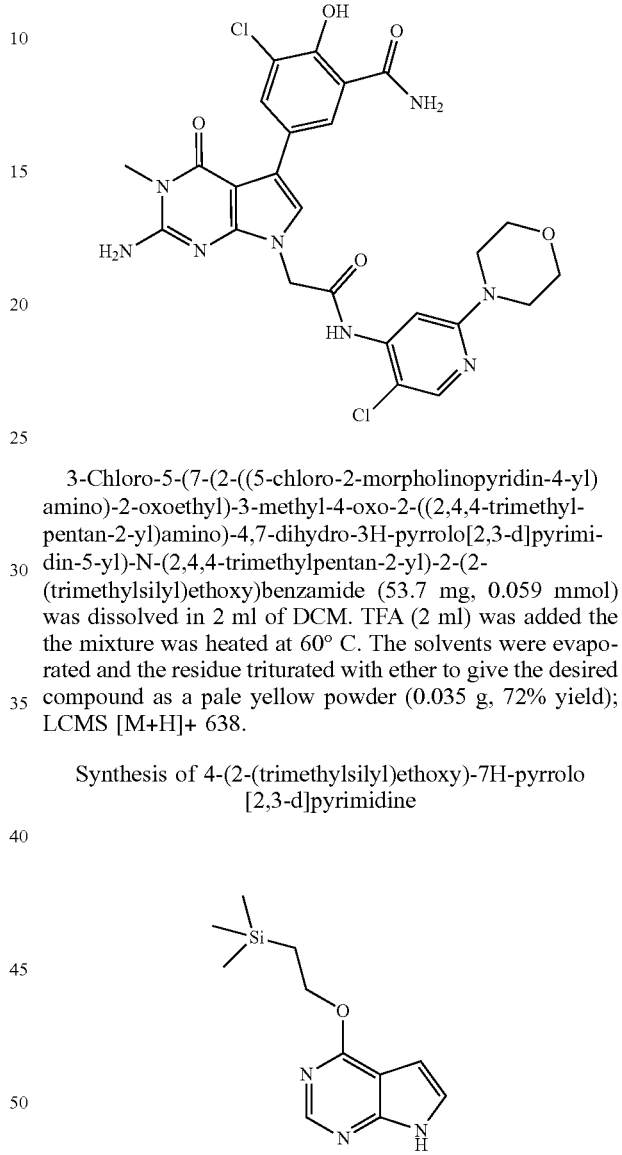

3-Chloro-5-(7-(2-((5-chloro-2-morpholinopyridin-4-yl)amino)-2-oxoethyl)-3-methyl-4-oxo-2-((2,4,4-trimethylpentan-2-yl)amino)-4,7-dihydro-3H-pyrrolo[2,3-d]pyrimidin-5-yl)-N-(2,4,4-trimethylpentan-2-yl)-2-(2-(trimethylsilyl)ethoxy)benzamide (53.7 mg, 0.059 mmol) was dissolved in 2 ml of DCM. TFA (2 ml) was added the the mixture was heated at 60° C. The solvents were evaporated and the residue triturated with ether to give the desired compound as a pale yellow powder (0.035 g, 72% yield); LCMS [M+H]+ 638.

Synthesis of 4-(2-(trimethylsilyl)ethoxy)-7H-pyrrolo[2,3-d]pyrimidine 2-(Trimethylsilyl)ethanol (44.8 ml, 313 mmol) was added to Sodium hydride, 60% in mineral oil (4.99 g, 130 mmol) in a round bottom flask under N2. Evolution of gas was observed. Then 4-chloro-7H-pyrrolo[2,3d]pyrimidine (8 g, 52.1 mmol) was added. The mixture was heated at 130° C. for 1 h. The reaction mixture was removed from the heating bath, cooled to room temperature, diluted with 150 mL EtOAc and then quenched with saturated NH₄Cl (aq) solution (150 ml). Water (100 ml) was added to get clear separation of phases. The organic phase was separated and the aqueous phase was extracted with EtOAc (100 ml). The combined organic phase was washed with water (2×150 ml), brine (150 ml), dried over Na₂SO₄ and concentrated under high vacuum to get the crude as a pale yellow solid. This was stirred at room temperature with 200 ml Hexanes for 15 min, then cooled in ice/water bathe for 15 min, the solid was filtered, the filter cake was washed with Hexanes and dried to afford pure desired product (10.6 g, 86%) as an off white solid; LCMS [M+H]+ 236.

Synthesis of 5-iodo-4-(2-(trimethylsilyl)ethoxy)-7H-pyrrolo[2,3-d]pyrimidine

Exact Mass: 361.01

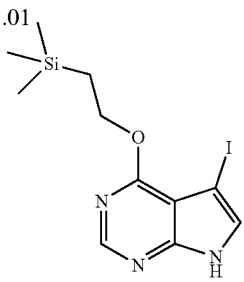

To a solution of the 4-(2-(trimethylsilyl)ethoxy)-7H-pyrrolo[2,3-d]pyrimidine (2.30 g, 9.77 mmol) in 10 mL of CH$_2$Cl$_2$ at 0° C. was added NIS (2.42 g, 10.75 mmol). The mixture was then allowed to warm to room temperature. The reaction mixture was stirred at RT for 1 h. The reaction is filtered through a short pad of silica and the solvent was removed in vacuo. The residue was triturated with hexane/ethylacetate (90:10) and the residue was filtered to give the title compound (3.14 g, 88% yield) as a light off-white solid; LCMS [M+H]+ 362.

The following compound 5-bromo-4-(2-(trimethylsilyl)ethoxy)-7H-pyrrolo[2,3-d]pyrimidine was prepared in a similar manner using NBS.

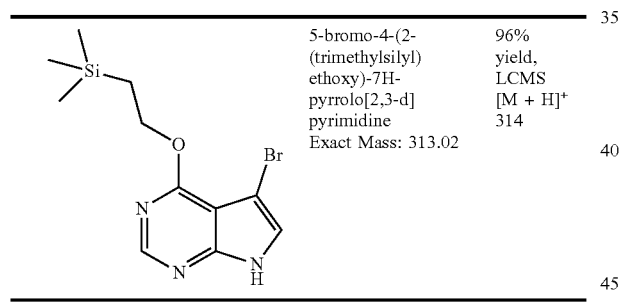

| | 5-bromo-4-(2-(trimethylsilyl)ethoxy)-7H-pyrrolo[2,3-d]pyrimidine Exact Mass: 313.02 | 96% yield, LCMS [M + H]+ 314 |
|---|---|---|

Synthesis of tert-butyl 5-bromo-4-(2-(trimethylsilyl)ethoxy)-7H-pyrrolo[2,3-d]pyrimidine-7-carboxylate
Exact Mass: 413.08

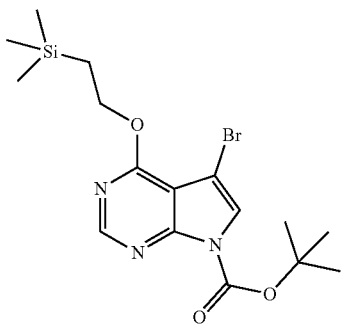 [SMILES: CC(C)(C)OC(=O)n1cc(Br)c2c(OCC[Si](C)(C)C)ncnc21]

To solution of 5-bromo-4-(2-(trimethylsilyl)ethoxy)-7H-pyrrolo[2,3-d]pyrimidine (6.6 g, 21.00 mmol) in N,N-Dimethylformamide (DMF) (Volume: 180 ml), under N2 in a 2-neck 500 mL RB flask, was added N,N-Diisopropylethylamine (10.97 ml, 63.0 mmol) and 4-(Dimethylamino)pyridine (0.257 g, 2.100 mmol). The reaction mixture was cooled to 0° C. (could be exotherm) and to this solution was added Di-tert-butyl dicarbonate (11.46 g, 52.5 mmol) in one portion. After 30 minutes in the ice bath, LCMS showed completion of the reaction. The reaction mix was mixed with 180 mL EtOAc and 180 ml water. The organic phase was separated, aqueous phase extracted with EtOAc (2×100 ml), the combined organic phase was washed with brine (100 ml), dried over Na$_2$SO$_4$ and concentrated under reduced pressure to get a brown residue. The residue was redissolved in DCM, adsorbed onto celite and purified on Isco column (120G), eluting with Hexanes containing 0-10% EtOAc. The desired product was isolated as a colourless oil, which on keeping under high vac, solidified to yield a white solid. (7.32 g, 84%); LCMS [M+H]+ 414.

Synthesis of methyl 2-(5-iodo-4-(2-(trimethylsilyl)ethoxy)-7H-pyrrolo[2,3-d]pyrimidin-7-yl)acetate

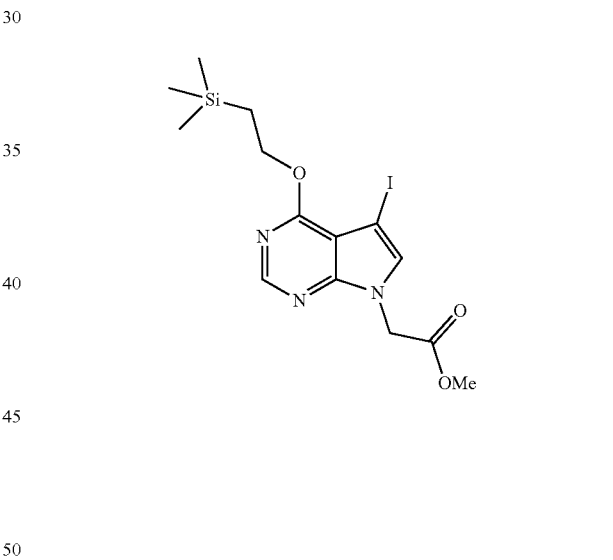

To a solution of the 5-iodo-4-(2-(trimethylsilyl)ethoxy)-7H-pyrrolo[2,3-d]pyrimidine (6.16 g, 17.05) in 10 mL of DMF at 0° C. was added Methyl bromoacetate (3.39 g, 22.17 mmol). The mixture was then allowed to stir at 0° C. for 0.5 hr. The reaction mixture was then allowed to warm to room temperature and stirred until judged complete by LCMS (1 hr). The reaction was diluted with CH$_2$Cl$_2$ (30 ml) and washed with water (10 ml). The organic phase was washed with brine and the dried over anhydrous Na$_2$SO$_4$. The solvent was removed in vacuo and the residue was dried and triturated to give the title compound (6.6 g, 89%) as an off-white solid; 1H NMR (500 MHz, DMSO-d$_6$) δ=8.39 (s, 1H), 7.60 (s, 1H), 5.09 (s, 2H), 4.64-4.58 (m, 2H), 3.68 (s, 3H), 1.23-1.17 (m, 2H), 0.08 (s, 9H).

Synthesis of (7-(tert-butoxycarbonyl)-4-(2-(trimethylsilyl)ethoxy)-7H-pyrrolo[2,3-d]pyrimidin-5-yl)boronic Acid

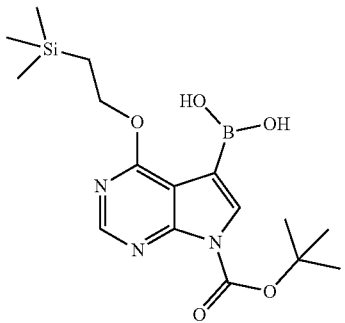 [SMILES: CC(C)(C)OC(=O)n1cc(B(O)O)c2c(OCC[Si](C)(C)C)ncnc21]

Butyllithium solution, 2.5 M in hexanes (7.72 ml, 19.31 mmol) was added dropwise to a stirred solution of tert-butyl 5-bromo-4-(2-(trimethylsilyl)ethoxy)-7H-pyrrolo[2,3-d]pyrimidine-7-carboxylate (4 g, 9.65 mmol) and 2-isopropoxy-4,4,5,5-tetramethyl-1,3,2-dioxaborolane (4.92 ml, 24.13 mmol) in Tetrahydrofuran (THF) (Volume: 125 ml) at −78° C. The reaction became a clear pale yellow solution. The reaction was maintained at −78° C. for 30 minutes and then warmed to room temperature. The clear yellow solution turned red and a little cloudy on warming. LCMS analysis indicated complete conversion to the pinacolate ester [m/z=462]. The reaction was quenched with an aqueous saturated NH$_4$Cl solution and the biphasic mixture was allowed to stir rapidly for an hour (LCMS indicated clean hydrolysis to the boronic acid). The layers were separated and the organic layer was added to ~300 mL of rapidly stirring ice cold hexanes. The resulting precipitate was collected by filtration and dried in the vacuum oven overnight to afford (7-(tert-butoxycarbonyl)-4-(2-(trimethylsilyl)ethoxy)-7H-pyrrolo[2,3-d]pyrimidin-5-yl)boronic acid (1.463 g, 3.66 mmol, 38.0% yield) as a colourless solid; LCMS [M+H]+ 380.

Synthesis of 2-bromo-5-(methoxymethoxy)-N-(2,4,4-trimethylpentan-2-yl)isonicotinamide

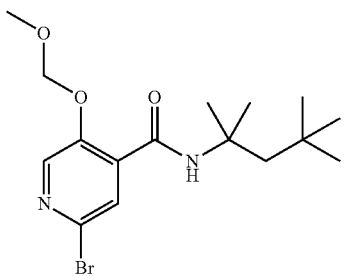 [SMILES: COCOc1cnc(Br)cc1C(=O)NC(C)(C)CC(C)(C)C]

Step 1: To a vial charged with 2-Bromo-5-hydroxy-isonicotinic acid (0.250 g, 1.147 mmol), N,N-Diisopropylethylamine (0.519 g, 4.01 mmol), t-Octylamine (0.178 g, 1.376 mmol), and HATU (0.532 g, 1.399 mmol) was added N,N-Dimethylformamide (DMF) (Volume: 4.0 ml). The reaction was stirred at RT overnight. LCMS showed no more SM. The reaction was concentrated under pressure. The residue was diluted with EtOAc and sat NH$_4$Cl (aq) solution. The organic phase was separated and the aqueous phase was further washed with EtOAc. The organic phases were combined, washed with water and concentrated onto celite. The crude was purified on the Biotage (silica gel) eluting with 0-20% EtOAc/Hexanes. The desired fractions were collected, concentrated and dried under vacuum to afford 6-bromo-3-hydroxy-N-(2,4,4-trimethylpentan-2-yl)picolinamide (0.468 g, 87% yield) as a beige solid; LCMS [M+H]+ 330

Step 2: To a solution of 2-bromo-5-hydroxy-N-(2,4,4-trimethylpentan-2-yl)isonicotinamide (464 mg, 0.987 mmol) in THF (Volume: 8 ml) in an ice/water bath, was added portionwise Sodium hydride (113 mg, 2.96 mmol). The mixture was stirred at room temperature for 20 min. To this mixture was added Chloromethyl methyl ether (0.225 ml, 2.96 mmol) dropwise and the mixture was stirred at room temperature for an additional 2 h. The mixture was quenched with MeOH (0.5 ml), diluted with dichloromethane and washed with water (10 mL). The aqueous layer was extracted with dichloromethane (2×10 mL). The combined organic layer was washed brine, dried (Na$_2$SO$_4$) and concentrated. The residue was purified by flash column chromatography [0-5% EtOAc/hexanes] to afford the title compound as a yellowish brown oil (307 mg, 83% yield); LCMS [M+H]+ 373

Synthesis of 6-bromo-3-(methoxymethoxy)-N-(2,4,4-trimethylpentan-2-yl)picolinamide

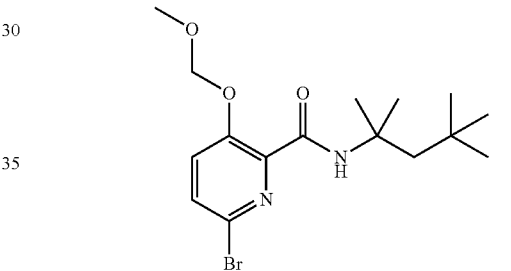

Step 1: To a vial charged with 6-Bromo-3-hydroxypicolinic acid (1.0 g, 4.59 mmol), N,N-Diisopropylethylamine (3.20 ml, 18.35 mmol), N,N-Diisopropylethylamine (3.20 ml, 18.35 mmol), and HATU (2.267 g, 5.96 mmol) was added N,N-Dimethylformamide (DMF) (Volume: 10.0 ml). The reaction was stirred at RT overnight. LCMS showed no more SM. The reaction was concentrated under pressure. The residue was diluted with EtOAc and sat NH$_4$Cl (aq) solution. The organic phase was separated and the aqueous phase was further washed with EtOAc. The organic phases were combined, washed with water and concentrated onto celite. The crude was purified on the Biotage (silica gel) eluting with 0-20% EtOAc/Hexanes. The desired fractions were collected, concentrated and dried under vacuum to afford 6-bromo-3-hydroxy-N-(2,4,4-trimethylpentan-2-yl)picolinamide (1.1 g, 3.34 mmol, 72.8% yield) as a black residue. 1H NMR (500 MHz, DMSO-d6) δ=12.46 (br. s., 1H), 7.95 (s, 1H), 7.70 (d, J=8.7 Hz, 1H), 7.41 (d, J=8.7 Hz, 1H), 1.81 (s, 2H), 1.49 (s, 6H), 1.00 (s, 9H)

Step 2: To a solution of 6-bromo-3-hydroxy-N-(2,4,4-trimethylpentan-2-yl)picolinamide (1.1 g, 3.34 mmol) in Tetrahydrofuran (THF) (Volume: 15 ml) at 0° C. was added portionwise Sodium hydride, 60% in mineral oil (0.384 g, 10.02 mmol). The mixture was allowed to warm to room temperature over 30 min. To this was added Chloromethyl methyl ether (0.761 ml, 10.02 mmol) dropwise and the mixture was stirred at RT for an additional 2 hours. LCMS showed complete conversion. The reaction slowly quenched with methanol then partitioned between water and DCM.

The organic layer was separated, and the aqueous layer was further washed with DCM (2×). The combined organic layers were dried over sodium sulfate and concentrated. The residue was purified on the Biotage (silica gel) eluting with 0-10% EtOAc/Hexanes. The desired fractions were collected, concentrated and dried on the h/v at RT to afford 6-bromo-3-(methoxymethoxy)-N-(2,4,4-trimethylpentan-2-yl)picolinamide (747 mg, 2.001 mmol, 59.9% yield) as an orange oil; LCMS [M+H]+ 373

Preparation of 2-(5-bromo-4-(2-(trimethylsilyl)ethoxy)-7H-pyrrolo[2,3-d]pyrimidin-7-yl)-N-(2-chlorophenyl)-N-(2,4-dimethoxybenzyl)acetamide

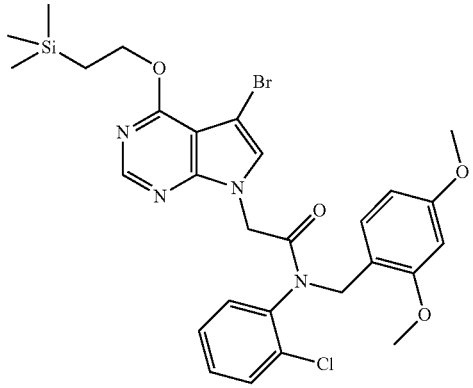 [SMILES: COc1ccc(CN(C(=O)Cn2cc(Br)c3c(OCC[Si](C)(C)C)ncnc32)c2ccccc2Cl)c(OC)c1]

A mixture of 5-bromo-4-(2-(trimethylsilyl)ethoxy)-7H-pyrrolo[2,3-d]pyrimidine (1.5 g, 4.8 mmol), 2-chloro-N-(2-chlorophenyl)-N-(2,4-dimethoxybenzyl)acetamide (1.9 g, 5.3 mmol) and Cs$_2$CO$_3$ (1.6 g, 5.0 mmol) in DMF (24 mL) was allowed to stir at 50° C. for 18 h. The inorganics were removed by filtration and the solvent was removed in vacuo. The residue was concentrated onto silica gel and purified by flash chromatography [0-30% EtOAc/Hexanes] to afford 2-(5-bromo-4-(2-(trimethylsilyl)ethoxy)-7H-pyrrolo[2,3-d]pyrimidin-7-yl)-N-(2-chlorophenyl)-N-(2,4-dimethoxybenzyl)acetamide (2.85 g, 90% yield). LCMS [M+H]+: 631.4.

Preparation of N-(2-chlorophenyl)-N-(2,4-dimethoxybenzyl)-2-(5-(4,4,5,5-tetramethyl-1,3,2-dioxaborolan-2-yl)-4-(2-(trimethylsilyl)ethoxy)-7H-pyrrolo[2,3-d]pyrimidin-7-yl)acetamide

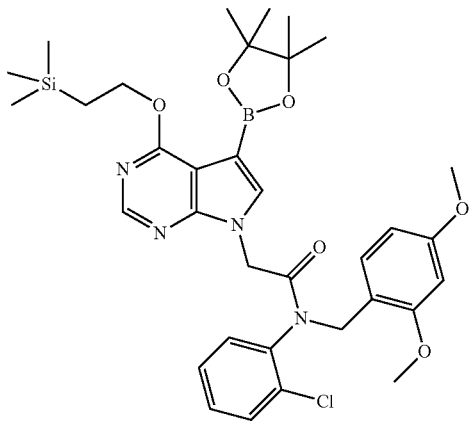 [SMILES: COc1ccc(CN(C(=O)Cn2cc(B3OC(C)(C)C(C)(C)O3)c3c(OCC[Si](C)(C)C)ncnc32)c2ccccc2Cl)c(OC)c1]

A vial was charged with 2-(5-bromo-4-(2-(trimethylsilyl)ethoxy)-7H-pyrrolo[2,3-d]pyrimidin-7-yl)-N-(2-chlorophenyl)-N-(2,4-dimethoxybenzyl)acetamide (1.5 g, 2.4 mmol), Tris(dibenzylideneacetone)dipalladium(0) (0.017 g, 0.024 mmol), and 2-dicyclohexylphosphino-2',4',6'-triisopropylbiphenyl (0.045 g, 0.095 mmol) and capped with a rubber septum. The vial was evacuated and backfilled with nitrogen. 1,4-Dioxane (12 mL) was added via syringe followed by triethylamine (0.58 mL, 4.2 mmol) and 4,4,5,5-tetramethyl-1,3,2-dioxaborolane (0.60 ml, 4.1 mmol). The vial was evacuated and backfilled with nitrogen an additional time and then heated at 100° C. for 50 min. After cooling to room temperature the reaction was quenched with water. The mixture was partitioned between DCM and water and the layers were separated. The aqueous layer was extracted with DCM and the combined organic extracts were dried over magnesium sulfate. After removal of the inorganics by filtration the filtrate was concentrated to dryness and the resulting residue was purified by flash chromatography [10-60% EtOAc/Hexanes] to afford N-(2-chlorophenyl)-N-(2,4-dimethoxybenzyl)-2-(5-(4,4,5,5-tetramethyl-1,3,2-dioxaborolan-2-yl)-4-(2-(trimethylsilyl)ethoxy)-7H-pyrrolo[2,3-d]pyrimidin-7-yl)acetamide (1.10 g, 68% yield) as a viscous oil. LCMS [M+H]+: 679.3.

Preparation of 5-(7-(2-((2-chlorophenyl)(2,4-dimethoxybenzyl)amino)-2-oxoethyl)-4-(2-(trimethylsilyl)ethoxy)-7H-pyrrolo[2,3-d]pyrimidin-5-yl)-2-hydroxy-3-sulfamoylbenzamide

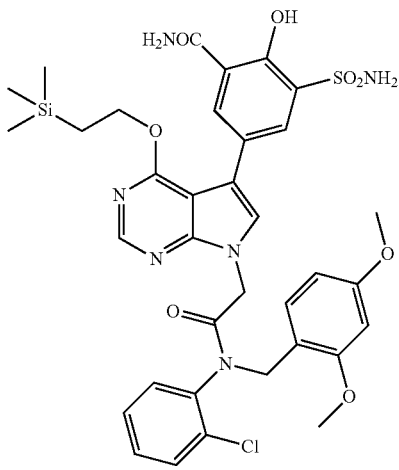 [SMILES: COc1ccc(CN(C(=O)Cn2cc(-c3cc(C(N)=O)c(O)c(S(N)(=O)=O)c3)c3c(OCC[Si](C)(C)C)ncnc32)c2ccccc2Cl)c(OC)c1]

A microwave vial was charged with N-(2-chlorophenyl)-N-(2,4-dimethoxybenzyl)-2-(5-(4,4,5,5-tetramethyl-1,3,2-dioxaborolan-2-yl)-4-(2-(trimethylsilyl)ethoxy)-7H-pyrrolo[2,3-d]pyrimidin-7-yl)acetamide (0.050 g, 0.074 mmol), 5-bromo-2-hydroxy-3-sulfamoylbenzamide (0.028 g, 0.096 mmol), and Pd(PPh$_3$)$_4$ (0.009 g, 7.4 μmol). The vial was capped, evacuated and backfilled with nitrogen. 1,4-Dioxane (3 mL) and 1 mL of a 2N (aq) Na$_2$CO$_3$ solution were added and the reaction was irradiated to 90° C. for 60 minutes. The reaction mixture was partitioned between DCM and dilute aqueous citric acid. The layers were separated and the aqueous layer was extracted with DCM and the combined organic extracts were dried over magnesium sulfate. After removal of the inorganics by filtration the filtrate was concentrated to dryness and the resulting residue was purified by flash chromatography [0-10% MeOH/EtOAc] to afford 5-(7-(2-((2-chlorophenyl)(2,4-dimethoxybenzyl)amino)-2-oxoethyl)-4-(2-(trimethylsilyl)ethoxy)-7H-pyrrolo[2,3-d]pyrimidin-5-yl)-2-hydroxy-3-sulfamoylbenzamide (0.025 g, 40% yield). LCMS [M+H]+: 767.4.

Preparation of 5-(7-(2-((2-chlorophenyl)amino)-2-oxoethyl)-4-oxo-4,7-dihydro-3H-pyrrolo[2,3-d]pyrimidin-5-yl)-2-hydroxy-3-sulfamoylbenzamide

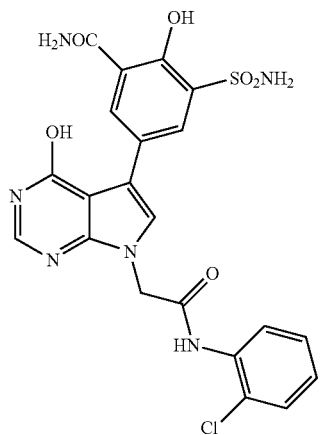 [SMILES: NC(=O)c1cc(-c2cn(CC(=O)Nc3ccccc3Cl)c3ncnc(O)c23)cc(S(N)(=O)=O)c1O]

A solution of 5-(7-(2-((2-chlorophenyl)(2,4-dimethoxybenzyl)amino)-2-oxoethyl)-4-(2-(trimethylsilyl)ethoxy)-7H-pyrrolo[2,3-d]pyrimidin-5-yl)-2-hydroxy-3-sulfamoylbenzamide (0.025 g, 0.033 mmol) and Ts—OH (0.022 g, 0.11 mmol) in 2,2,2-trifluoroethanol (2 mL) was heated to 55° C. for 15 hours. The reaction mixture was cooled to room temperature and neutralised with a saturated aqueous NaHCO₃ solution and then concentrated to dryness. The residue was purified by reverse phase [C18] chromatography [0-25% MeCN/water] to afford 5-(7-(2-((2-chlorophenyl)amino)-2-oxoethyl)-4-oxo-4,7-dihydro-3H-pyrrolo[2,3-d]pyrimidin-5-yl)-2-hydroxy-3-sulfamoylbenzamide (0.009 g, 43% yield, 80% purity). 1H NMR (500 MHz, DMSO-d6) δ 11.44-12.04 (m, 1H), 11.78 (br. s., 1H), 10.85 (d, J=5.87 Hz, 1H), 9.82 (br. s., 1H), 8.27 (d, J=2.57 Hz, 1H), 8.13 (d, J=2.57 Hz, 1H), 7.87 (s, 1H), 7.79 (d, J=7.95 Hz, 1H), 7.51 (d, J=8.07 Hz, 1H), 7.33 (t, J=7.83 Hz, 1H), 7.15-7.23 (m, 2H), 6.74-6.83 (m, 3H), 5.11 (s, 2H); LCMS [M+H]+: 517.0.

General Scheme of Suzuki-Coupling/Alkylation/Deprotection Procedures

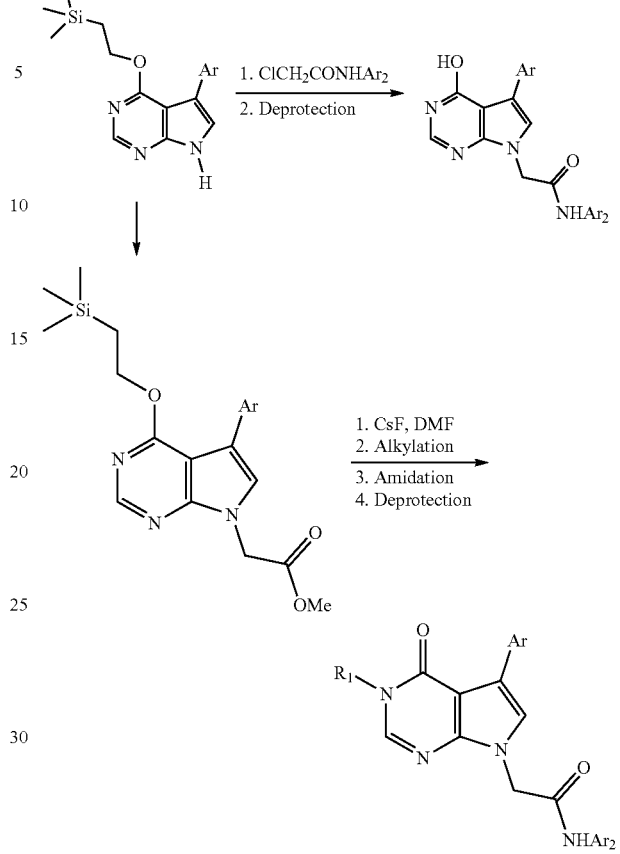

Preparation of 2-(7-(2-((5-chloro-2-morpholinopyridin-4-yl)amino)-2-oxoethyl)-3-methyl-4-oxo-4,7-dihydro-3H-pyrrolo[2,3-d]pyrimidin-5-yl)-5-hydroxyisonicotinamide (I-143)

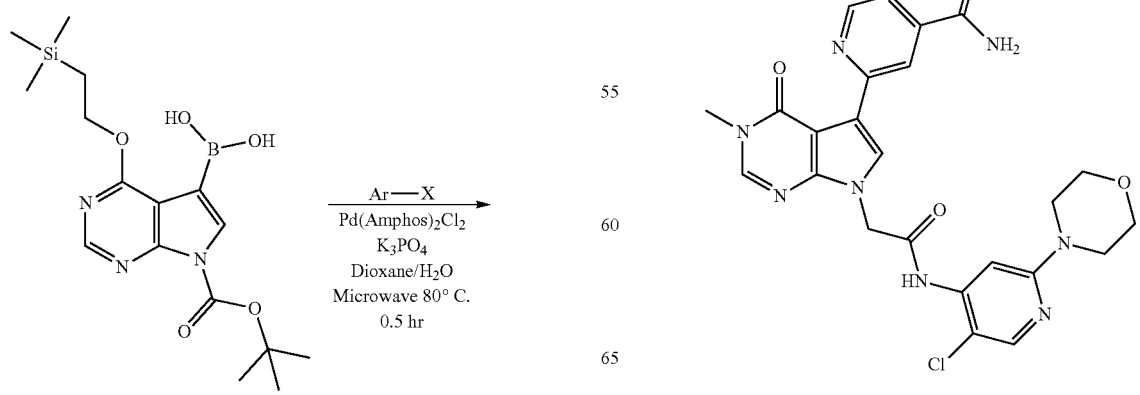

Scheme 33

Step 1: Synthesis of 5-(methoxymethoxy)-N-(2,4,4-trimethylpentan-2-yl)-2-(4-(2-(trimethylsilyl)ethoxy)-7H-pyrrolo[2,3-d]pyrimidin-5-yl)isonicotinamide Exact Mass: 527.29

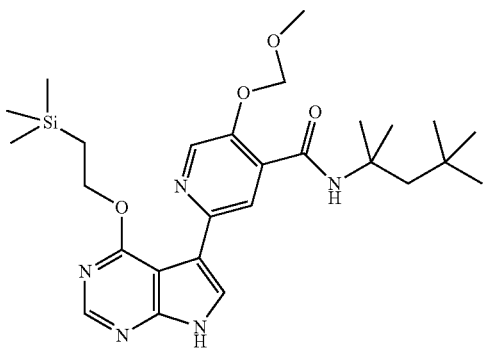 [SMILES: COCOc1cnc(-c2c[nH]c3ncnc(OCC[Si](C)(C)C)c23)cc1C(=O)NC(C)(C)CC(C)(C)C]

A microwave vial was charged with (7-(tert-butoxycarbonyl)-4-(2-(trimethylsilyl)ethoxy)-7H-pyrrolo[2,3-d]pyrimidin-5-yl)boronic acid (225 mg, 0.593 mmol), 2-bromo-5-(methoxymethoxy)-N-(2,4,4-trimethylpentan-2-yl)isonicotinamide (211 mg, 0.565 mmol), Tetrakis(triphenylphosphine)Palladium(0) (65.3 mg, 0.056 mmol). The vial was capped and flushed with nitrogen. 1,4-Dioxane (Volume: 6 ml), 2M Sodium carbonate solution (aq) (1.977 ml, 3.95 mmol) solution were added and the reaction was irradiated in the microwave at 110° C. for 45 minutes. LCMS analysis indicated clean conversion to the desired products. The reaction mixture was filtered, the filter cake was rinsed in with EtOAc (3×4 ml), the combined organic phase was washed with brined, dried over Na₂SO₄, adsorbed on celite and purified on Isco column (12G), eluting with hexanes containing 0-50% EtOAc. The product containing fractions were combined and concentrated to get the title compound as a yellow solid (212 mg, 71% yield); LCMS [M+H]+ 528.

Step 2: Synthesis of methyl 2-(5-(5-(methoxymethoxy)-4-((2,4,4-trimethylpentan-2-yl)carbamoyl)pyridin-2-yl)-4-(2-(trimethylsilyl)ethoxy)-7H-pyrrolo[2,3-d]pyrimidin-7-yl)acetate Exact Mass: 599.31

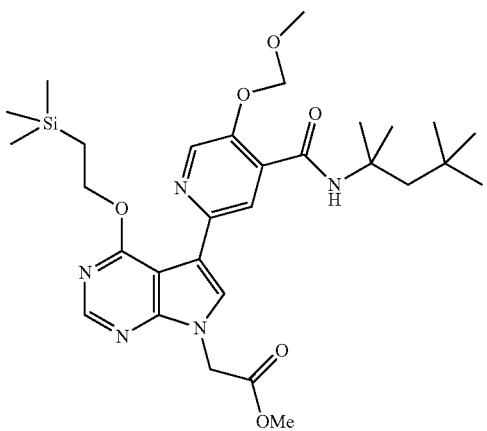 [SMILES: COCOc1cnc(-c2cn(CC(=O)OC)c3ncnc(OCC[Si](C)(C)C)c23)cc1C(=O)NC(C)(C)CC(C)(C)C]

To a suspension of 5-(methoxymethoxy)-N-(2,4,4-trimethylpentan-2-yl)-2-(4-(2-(trimethylsilyl)ethoxy)-7H-pyrrolo[2,3-d]pyrimidin-5-yl)isonicotinamide (200 mg, 0.379 mmol) and Cesium carbonate (247 mg, 0.758 mmol) in DMF (Volume: 2.0 ml) at RT, was added Methyl Bromoacetate (0.047 ml, 0.493 mmol) dropwise. The reaction mix was vigorously stirred at RT. LCMS after 2 hrs showed completion of the reaction. DCM (6 ml) and 10 ml of water were added to the reaction mixture. The organic layer was separated, aq phase was extracted with DCM (3×6 ml). The combined organic layer was washed with water, brine, dried over Na₂SO₄ and concentrated to give the desired product as a brown oil [327 mg, 94%]; LCMS [M+H]+ 600.

Step 3: Synthesis of methyl 2-(4-hydroxy-5-(5-(methoxymethoxy)-4-((2,4,4-trimethylpentan-2-yl)carbamoyl)pyridin-2-yl)-7H-pyrrolo[2,3-d]pyrimidin-7-yl)acetate (S-1) Exact Mass: 499.24

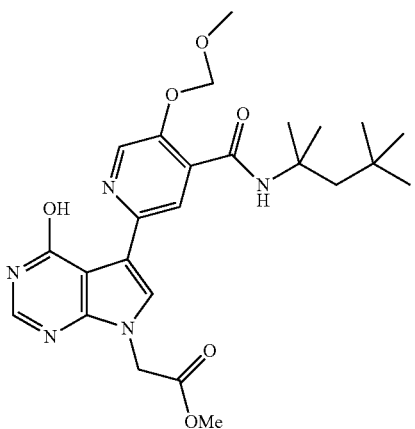 [SMILES: COCOc1cnc(-c2cn(CC(=O)OC)c3ncnc(O)c23)cc1C(=O)NC(C)(C)CC(C)(C)C]

A suspension of methyl 2-(5-(5-(methoxymethoxy)-4-((2,4,4-trimethylpentan-2-yl)carbamoyl)pyridin-2-yl)-4-(2-(trimethylsilyl)ethoxy)-7H-pyrrolo[2,3-d]pyrimidin-7-yl)acetate (317 mg, 0.344 mmol) and Cesium fluoride (78 mg, 0.515 mmol) in DMF (Volume: 1.5 ml) was heated in an oil bath at 60° C. LCMS after 1 h showed completion of the reaction. The reaction was allowed to cool down to RT. It was kept in ice and cold water was added to the reaction mixture. Formation of a yellowish brown solid was observed. This crude solid was used in the next step without further purification; LCMS [M+H]+ 500.

Step 4: Synthesis of methyl 2-(5-(5-(methoxymethoxy)-4-((2,4,4-trimethylpentan-2-yl)carbamoyl)pyridin-2-yl)-3-methyl-4-oxo-3H-pyrrolo[2,3-d]pyrimidin-7(4H)-yl)acetate (S-2) Exact Mass: 513.26

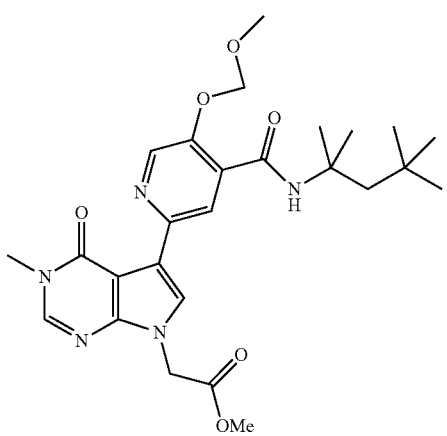 [SMILES: COCOc1cnc(-c2cn(CC(=O)OC)c3ncn(C)c(=O)c23)cc1C(=O)NC(C)(C)CC(C)(C)C]

Cesium carbonate (95 mg, 0.292 mmol) was added to a solution of methyl 2-(5-(5-(methoxymethoxy)-4-((2,4,4-trimethylpentan-2-yl)carbamoyl)pyridin-2-yl)-4-oxo-3H-pyrrolo[2,3-d]pyrimidin-7(4H)-yl)acetate (172 mg, 0.292 mmol) and Iodomethane (0.018 ml, 0.292 mmol) in DMF (Volume: 1.5 ml) cooled in ice/water. After 1 h in ice only 27% conversion was observed. Therefore, the cooling bath was removed and stirring was continued at RT. After 15 h at RT only 57% conversion was observed. Additional quantities of Iodomethane (0.018 ml, 0.292 mmol) and cesium carbonate (42.5 mg, 0.5 eq) were added and the mixture was stirred at RT until complete by LCMS. The mixture was diluted with DCM (6 ml) and washed with water (10 ml). The aqueous phase was extracted with DCM (2×6) and the combined organic phase was washed with water, brine, dried with $Na_2SO_4$ and concentrated onto celite. Purification by flash column chromatography on Isco (4G) column, eluting with DCM containing 0-3% MeOH afforded the title compound as an off white solid. (117 mg, 78% yield); LCMS [M+H]+ 514.

Step 5: Synthesis of 2-(7-(2-((5-chloro-2-morpholinopyridin-4-yl)amino)-2-oxoethyl)-3-methyl-4-oxo-4,7-dihydro-3H-pyrrolo[2,3-d]pyrimidin-5-yl)-5-(methoxymethoxy)-N-(2,4,4-trimethylpentan-2-yl)isonicotinamide (F-5) Exact Mass: 694.30

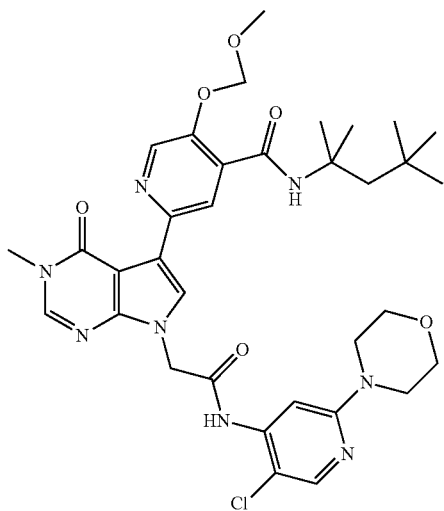 [SMILES: COCOc1cnc(-c2cn(CC(=O)Nc3cc(N4CCOCC4)ncc3Cl)c3ncn(C)c(=O)c23)cc1C(=O)NC(C)(C)CC(C)(C)C]

To a solution of methyl 5-Chloro-2-morpholinopyridin-4-amine (40.6 mg, 0.190 mmol) in 1,4-Dioxane (Volume: 3 ml, Ratio: 3.00) at 50° C. was added Methylmagnesium chloride, 3M in THF (0.097 ml, 0.292 mmol) dropwise under nitrogen. The reaction was allowed to stir at 50° C. for 15 min. A solution of methyl 2-(5-(5-(methoxymethoxy)-4-((2,4,4-trimethylpentan-2-yl)carbamoyl)pyridin-2-yl)-3-methyl-4-oxo-3H-pyrrolo[2,3-d]pyrimidin-7(4H)-yl)acetate (75 mg, 0.146 mmol) in 1,4-Dioxane (Volume: 1 ml, Ratio: 1.000) was slowly added and the mixture was stirred at 50° C. LCMS analysis of the reaction mixture after 10 minutes showed 30% conversion to the desired product. Additional Methylmagnesium chloride, 3M in THF (0.097 ml, 0.292 mmol) was added and the reaction mix was continuously stirred at 50° C. 20 minutes. The reaction mix was allowed to cool down to RT, quenched with saturated aq $NH_4Cl$ solution and extracted with EtOAc (2×6 ml). The combined organic phase was dried over $Na_2SO_4$, and concentrated to give the crude product which was adsorbed on celite and purified on Isco (4G), eluting with DCM containing 0-3% methanol. The desired product was isolated as a pale brown solid (35 mg, 31%); LCMS [M+H]+ 695

Step 6: Synthesis of 2-(7-(2-((5-chloro-2-morpholinopyridin-4-yl)amino)-2-oxoethyl)-3-methyl-4-oxo-4,7-dihydro-3H-pyrrolo[2,3-d]pyrimidin-5-yl)-5-hydroxyisonicotinamide (I-143)

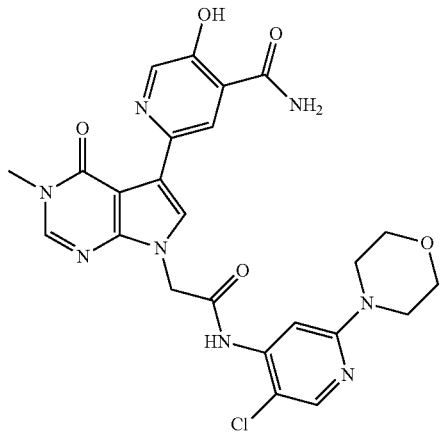 [SMILES: Cn1cnc2c(c(-c3cc(C(N)=O)c(O)cn3)cn2CC(=O)Nc2cc(N3CCOCC3)ncc2Cl)c1=O]

To a solution of the 2-(7-(2-((5-chloro-2-morpholinopyridin-4-yl)amino)-2-oxoethyl)-3-methyl-4-oxo-4,7-dihydro-3H-pyrrolo[2,3-d]pyrimidin-5-yl)-5-(methoxymethoxy)-N-(2,4,4-trimethylpentan-2-yl)isonicotinamide in DCM (2 ml) was added TFA (2 ml) at RT. The reaction mixture was stirred at 70° C. for 4 h. The reaction mix was concentrated and the residue was triturated with DCM/diethyl ether to afford the title compound as a dark yellow solid (29 mg, 67% yield); LCMS [M+H]+ 539

Preparation of 2-(7-(2-((5-chloro-2-morpholinopyridin-4-yl)amino)-2-oxoethyl)-3-methyl-4-oxo-4,7-dihydro-3H-pyrrolo[2,3-d]pyrimidin-5-yl)-5-hydroxyisonicotinamide (I-131)

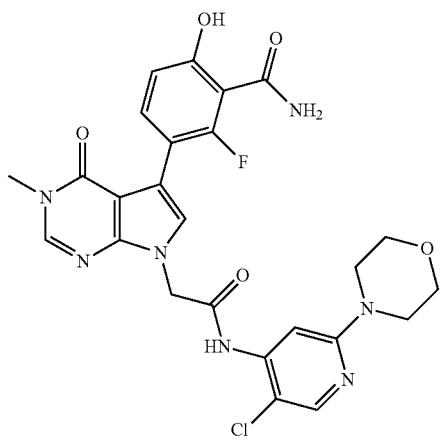 [SMILES: Cn1cnc2c(c(-c3ccc(O)c(C(N)=O)c3F)cn2CC(=O)Nc2cc(N3CCOCC3)ncc2Cl)c1=O]

Prepared in a manner similar to I-143.

Synthesis of (S)-5-(7-(2-((3-chloro-2-fluoro-6-(4-(3-hydroxy-2-(hydroxymethyl)propyl)-2-methylpiperazin-1-yl)pyridin-4-yl)amino)-2-oxoethyl)-3-methyl-4-oxo-4,7-dihydro-3H-pyrrolo[2,3-d]pyrimidin-5-yl)-3,4-difluoro-2-hydroxybenzamide (I-463)

Scheme 34

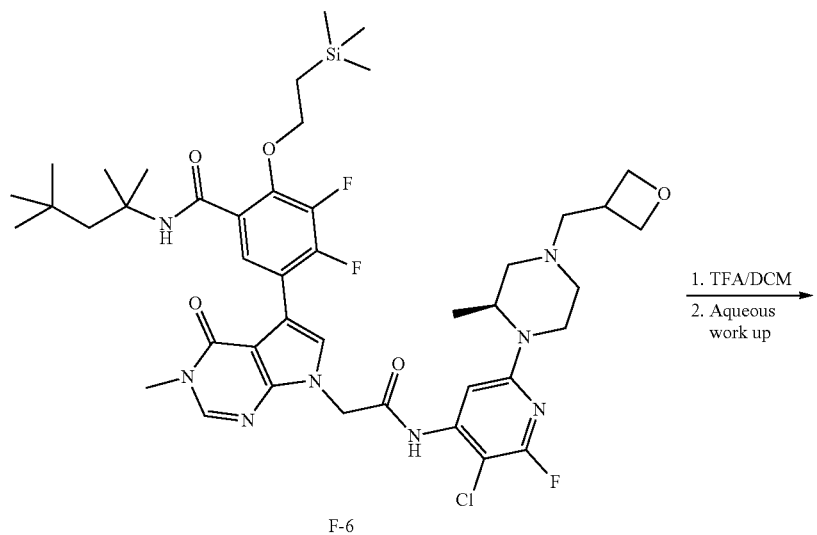

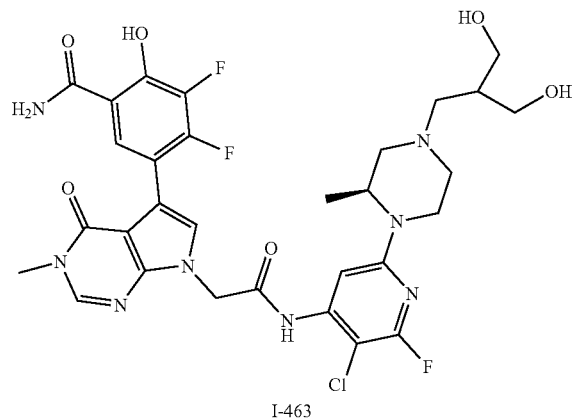

To a solution of (S)-5-(7-(2-((3-chloro-2-fluoro-6-(2-methyl-4-(oxetan-3-ylmethyl)piperazin-1-yl)pyridin-4-yl)amino)-2-oxoethyl)-3-methyl-4-oxo-4,7-dihydro-3H-pyrrolo[2,3-d]pyrimidin-5-yl)-3,4-difluoro-N-(2,4,4-trimethylpentan-2-yl)-2-(2-(trimethylsilyl)ethoxy)benzamide (F-6) (78 mg, 0.088 mmol) in Dichloromethane (DCM) (1.00 ml) was added Trifluoroacetic acid (0.760 ml, 9.92 mmol). The mixture was stirred at 40° C. for 1 hour. LCMS analysis showed no desired product—only ring-opened product with and without the octyl protecting group observed. The reaction was heated at 40° C. overnight. The reaction was concentrated in vacuo and purified on the Biotage (reverse phase silica gel) eluting with 0-80% ACN/H2O. The desired fractions were collected, concentrated in vacuo and dried under vacuum at RT to afford the diol (S)-5-(1-(2-((3-chloro-2-fluoro-6-(4-(3-hydroxy-2-(hydroxymethyl)propyl)-2-methylpiperazin-1-yl)pyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-2-hydroxybenzamide (I-463), 2Trifluoroacetic Acid, $CF_3COOH$ [D] (3.7 mg, 4% yield) as a beige solid.

145

Synthesis of (1R,2R)-2-(2-(5-(3-carbamoyl-5-chloro-4-hydroxyphenyl)-3-methyl-4-oxo-3,4-dihydro-7H-pyrrolo[2,3-d]pyrimidin-7-yl)acetamido)cyclohexyl 2,2,2-trifluoroacetate (I-254)

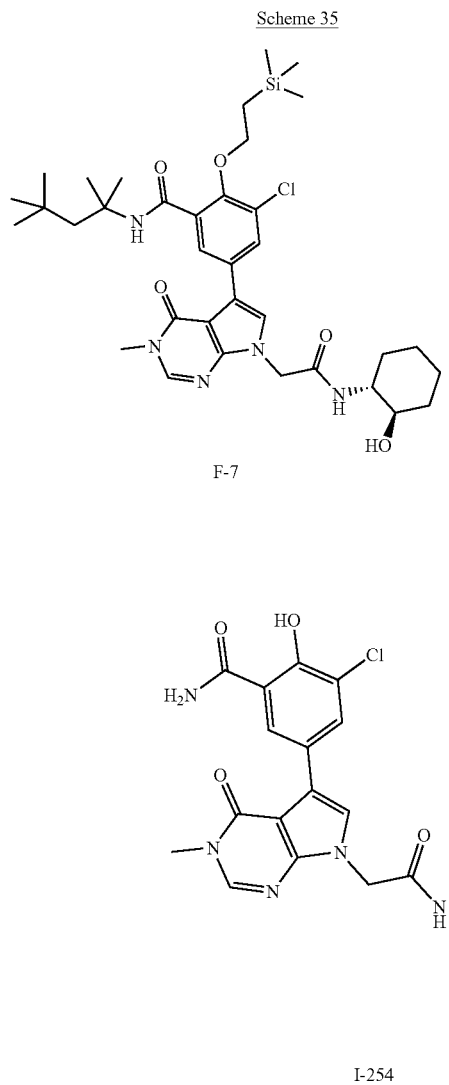

146

Synthesis of 5-(7-(2-((4-amino-2-chlorophenyl)amino)-2-oxoethyl)-3-methyl-4-oxo-4,7-dihydro-3H-pyrrolo[2,3-d]pyrimidin-5-yl)-3-chloro-2-hydroxybenzamide (I-10)

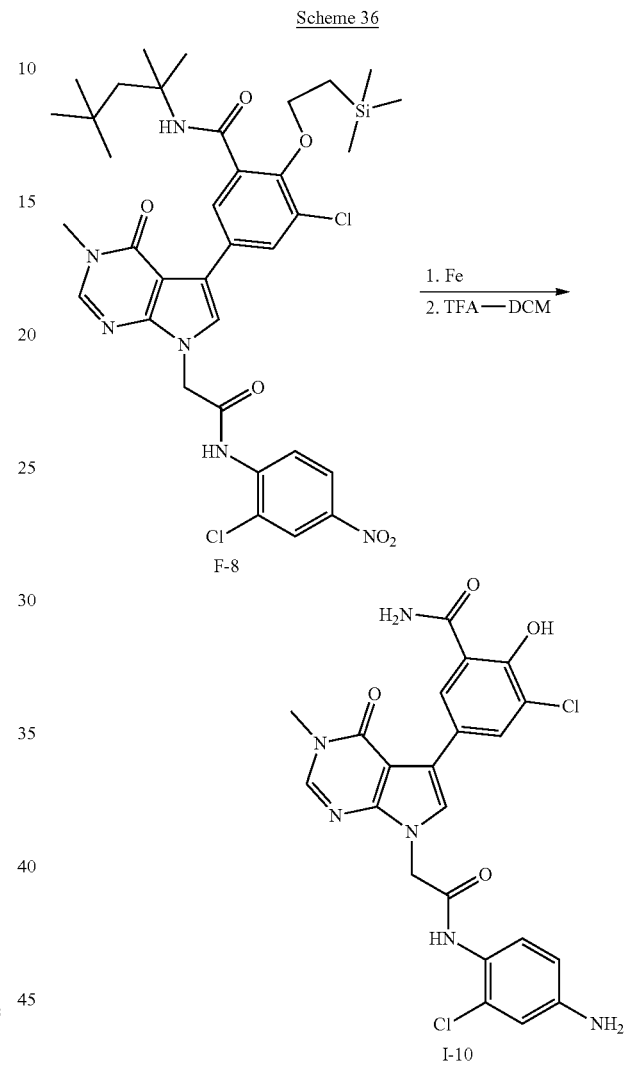

To a solution of 3-chloro-5-(7-(2-(((1R,2R)-2-hydroxycyclohexyl)amino)-2-oxoethyl)-3-methyl-4-oxo-4,7-dihydro-3H-pyrrolo[2,3-d]pyrimidin-5-yl)-N-(2,4,4-trimethylpentan-2-yl)-2-(2-(trimethylsilyl)ethoxy)benzamide (F-7) (37 mg, 0.054 mmol) in Dichloromethane (DCM) (0.5 ml) was added Trifluoroacetic acid (1.238 ml, 16.17 mmol) dropwise. The bright orange solution was warmed to RT then stirred at 50° C. overnight. The reaction was concentrated in vacuo, triturated from ether and dried under vacuum at RT to afford (1R,2R)-2-(2-(5-(3-carbamoyl-5-chloro-4-hydroxyphenyl)-3-methyl-4-oxo-3,4-dihydro-7H-pyrrolo[2,3-d]pyrimidin-7-yl)acetamido)cyclohexyl 2,2,2-trifluoroacetate, Trifluoroacetic Acid (I-254), CF$_3$COOH [D] (0.033 mmol, 61.2% yield) as a burgundy solid.). LCMS [M+1]+ 570

A solution of 3-chloro-5-(7-(2-((2-chloro-4-nitrophenyl)amino)-2-oxoethyl)-3-methyl-4-oxo-4,7-dihydro-3H-pyrrolo[2,3-d]pyrimidin-5-yl)-N-(2,4,4-trimethylpentan-2-yl)-2-(2-(trimethylsilyl)ethoxy)benzamide (F-8) (180 mg, 0.242 mmol) and Iron, powder (135 mg, 2.420 mmol) in Acetic acid (2 ml) was heated at 75° C. for 15 min., The reaction mixture became white slurry indicating completion of the reaction. The mixture was diluted with ethyl acetate (20 ml), filtered through celite, concentrated to dryness, and purified by ISCO (12 g column, DCM/MeOH, 0-5%, 30 min) to get the desired intermediate, 5-(7-(2-((4-amino-2-chlorophenyl)amino)-2-oxoethyl)-3-methyl-4-oxo-4,7-dihydro-3H-pyrrolo[2,3-d]pyrimidin-5-yl)-3-chloro-N-(2,4,4-trimethylpentan-2-yl)-2-(2-(trimethylsilyl)ethoxy)benzamide as a brown foamy solid. The silyl ether, 5-(7-(2-((4-amino-2-chlorophenyl)amino)-2-oxoethyl)-3-methyl-4-oxo-4,7-dihydro-3H-pyrrolo[2,3-d]pyrimidin-5-yl)-3-chloro-N-(2,4,4-trimethylpentan-2-yl)-2-(2-(trimethylsilyl)ethoxy)benzamide (40 mg) was treated with DCM/TFA (1 ml each) at 50° C. overnight. The mixture was concentrated to dryness to give the desired product 5-(7-(2-((4-amino-2-chlorophenyl)amino)-2-oxoethyl)-3-methyl-4-oxo-4,7-dihydro-3H-pyrrolo[2,3-d]pyrimidin-5-yl)-3-chloro-2-hydroxybenzamide (I-10), Trifluoroacetic Acid, CF$_3$COOH [D] (17 mg, 13% yield) as a light brown powder.). LCMS [M+1]+501

Preparation of (S)-5-(7-(2-((3-chloro-6-(2,4-dimethylpiperazin-1-yl)-2-fluoropyridin-4-yl)amino)-2-oxoethyl)-3-(3-(1-methyl-1H-pyrazol-4-yl)-3-oxopropyl)-4-oxo-4,7-dihydro-3H-pyrrolo[2,3-d]pyrimidin-5-yl)-3-fluoro-2-hydroxybenzamide (I-430)

Scheme 37

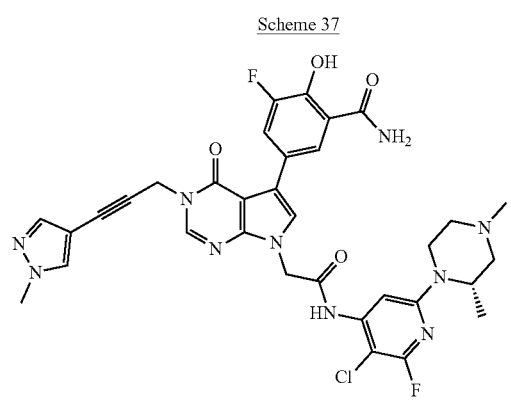

I-432

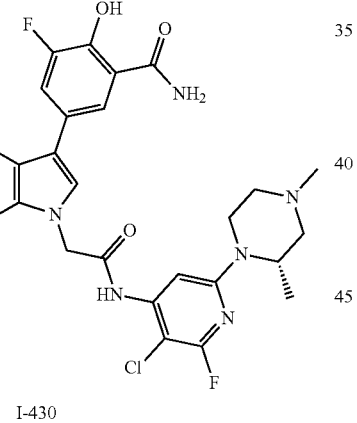

I-430

A 10 cc-2 g PoraPak Rxn RP columns was conditioned with 6 mL MeOH. Then sample; (S)-5-(7-(2-((3-chloro-6-(2,4-dimethylpiperazin-1-yl)-2-fluoropyridin-4-yl)amino)-2-oxoethyl)-3-(3-(1-methyl-1H-pyrazol-4-yl)prop-2-yn-1-yl)-4-oxo-4,7-dihydro-3H-pyrrolo[2,3-d]pyrimidin-5-yl)-3-fluoro-2-hydroxybenzamide (I-432, 64 mg, 0.091 mmol) was dissolved in MeOH (4 mL) and added to the cartridge, then they were each washed with MeOH (6 mL). The compound was then eluted from the cartridge with 6 mL of MeOH containing 3% NH$_4$OH and the collected solution was concentrated to give the product as a white solid. This material was then purified by prep-HPLC (MeCN—H$_2$O—NH$_4$CO$_3$); to give (S)-5-(7-(2-((3-chloro-6-(2,4-dimethylpiperazin-1-yl)-2-fluoropyridin-4-yl)amino)-2-oxoethyl)-3-(3-(1-methyl-1H-pyrazol-4-yl)-3-oxopropyl)-4-oxo-4,7-dihydro-3H-pyrrolo[2,3-d]pyrimidin-5-yl)-3-fluoro-2-hydroxybenzamide (I-430), Trifluoroacetic Acid, CF$_3$COOH [D] as an off-white (7 mg, 8.75% yield). LCMS [M+1]+723

Preparation of (S)-5-(7-(2-((5-chloro-2-(4-(2-hydroxyethyl)-2-methylpiperazin-1-yl)pyridin-4-yl)amino)-2-oxoethyl)-3-methyl-4-oxo-4,7-dihydro-3H-pyrrolo[2,3-d]pyrimidin-5-yl)-3,4-difluoro-2-hydroxybenzamide, 2Trifluoroacetic Acid, CF$_3$COOH [D] (I-452)

Scheme 38

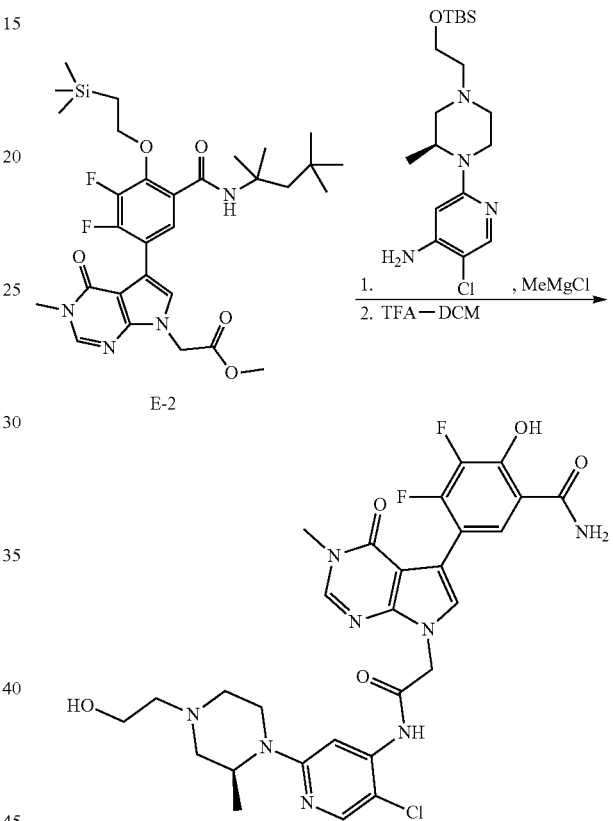

To a solution of (S)-2-(4-(2-((tert-butyldimethylsilyl)oxy)ethyl)-2-methylpiperazin-1-yl)-5-chloropyridin-4-amine (68.8 mg, 0.179 mmol) in 1,4-Dioxane (8.0 ml) was added Methylmagnesium chloride, 3M in THF (0.060 ml, 0.179 mmol) dropwise under nitrogen. The yellow suspension was allowed to stir at RT for 5 min. methyl 2-(5-(2,3-difluoro-5-((2,4,4-trimethylpentan-2-yl)carbamoyl)-4-(2-(trimethylsilyl)ethoxy)phenyl)-3-methyl-4-oxo-3H-pyrrolo[2,3-d]pyrimidin-7(4H)-yl)acetate (60 mg, 0.099 mmol) was slowly added and stirred at 40° C. for 10 min. Additional Methylmagnesium chloride, 3M in THF (0.060 ml, 0.179 mmol) was added. The mixture was stirred at 40° C. for 1 hour. The reaction was quenched with methanol and concentrated onto celite. The crude mixture was purified on the Biotage (reverse phase silica gel) eluting with 0-100% ACN/H$_2$O. The desired fractions were collected, concentrated and dried under vacuum to afford (S)-5-(7-(2-((2-(4-(2-((tert-butyldimethylsilyl)oxy)ethyl)-2-methylpiperazin-1-yl)-5-chloropyridin-4-yl)amino)-2-oxoethyl)-3-methyl-4-oxo-4,7-dihydro-3H-pyrrolo[2,3-d]pyrimidin-5-yl)-3,4-difluoro-N-(2,4,4-trimethylpentan-2-yl)-2-(2-(trimethylsilyl)ethoxy)benzamide (0.070 mmol, 70.5% yield) as a pale yellow residue. Carried onto next step. No 1H NMR taken.

To a solution of (S)-5-(7-(2-((2-(4-(2-((tert-butyldimethylsilyl)oxy)ethyl)-2-methylpiperazin-1-yl)-5-chloropyridin-4-yl)amino)-2-oxoethyl)-3-methyl-4-oxo-4,7-dihydro-3H-pyrrolo[2,3-d]pyrimidin-5-yl)-3,4-difluoro-N-(2,4,4-trimethylpentan-2-yl)-2-(2-(trimethylsilyl)ethoxy)benzamide in Dichloromethane (DCM) (1.00 ml) was added Trifluoroacetic acid (0.760 ml, 9.92 mmol). The mixture was stirred at 40° C. overnight. LCMS showed complete conversion. The reaction was concentrated in vacuo to remove the volatiles, followed by trituration with diethyl ether. The filtered solid was dried under vacuum at RT to afford (S)-5-(7-(2-((5-chloro-2-(4-(2-hydroxyethyl)-2-methylpiperazin-1-yl)pyridin-4-yl)amino)-2-oxoethyl)-3-methyl-4-oxo-4,7-dihydro-3H-pyrrolo[2,3-d]pyrimidin-5-yl)-3,4-difluoro-2-hydroxybenzamide (I-452), 2Trifluoroacetic Acid, CF₃COOH [D](57 mg, 66.9% yield) as a beige solid.

Synthesis of 5-(7-(2-((3-chloro-2-fluoro-6-((3-hydroxypropyl)amino)pyridin-4-yl)amino)-2-oxoethyl)-3-methyl-4-oxo-4,7-dihydro-3H-pyrrolo[2,3-d]pyrimidin-5-yl)-3,4-difluoro-2-hydroxybenzamide (I-481)

Scheme 39

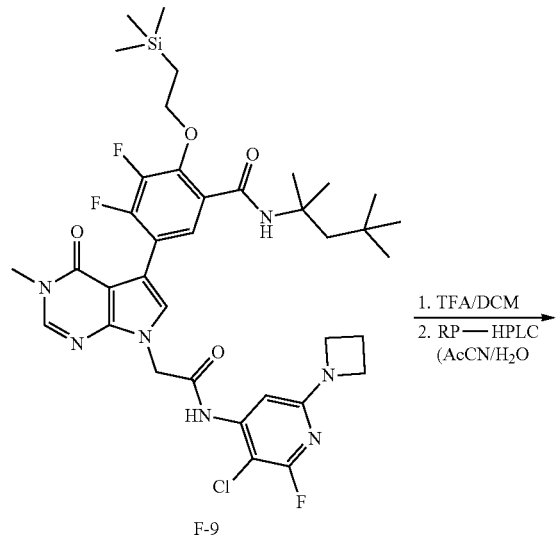

F-9

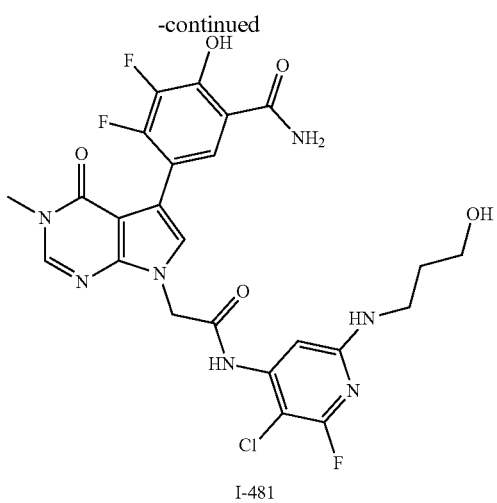

I-481

In a vial with magnetic stir bar was placed 5-(7-(2-((6-(azetidin-1-yl)-3-chloro-2-fluoropyridin-4-yl)amino)-2-oxoethyl)-3-methyl-4-oxo-4,7-dihydro-3H-pyrrolo[2,3-d]pyrimidin-5-yl)-3,4-difluoro-N-(2,4,4-trimethylpentan-2-yl)-2-(2-(trimethylsilyl)ethoxy)benzamide (F-9) (59 mg, 0.076 mmol), Dichloromethane (DCM) (2 mL) and Trifluoroacetic acid (2 mL, 26.1 mmol). The solution was heated to 50° C. for 6 h, followed by to 80° C. for 2 h. The crude mixture was then loaded onto Celite and purified by reverse phase chromatography (C₁₈, MeCN—H₂O) to isolate an azetidine opened material as a white solid; 5-(7-(2-((3-chloro-2-fluoro-6-((3-hydroxypropyl)amino)pyridin-4-yl)amino)-2-oxoethyl)-3-methyl-4-oxo-4,7-dihydro-3H-pyrrolo[2,3-d]pyrimidin-5-yl)-3,4-difluoro-2-hydroxybenzamide (I-481), Trifluoroacetic Acid, CF₃COOH [D] (11 mg, 18.72% yield). LCMS [M+1]+ 580

Preparation of 5-(7-(2-((3-chloro-6-((2S)-4-(2,4-dihydroxybutyl)-2-methylpiperazin-1-yl)-2-fluoropyridin-4-yl)amino)-2-oxoethyl)-3-methyl-4-oxo-4,7-dihydro-3H-pyrrolo[2,3-d]pyrimidin-5-yl)-3,4-difluoro-2-hydroxybenzamide (I-459) and 5-(7-(2-((3-chloro-2-fluoro-6-((2S)-2-methyl-4-(oxetan-2-ylmethyl)piperazin-1-yl)pyridin-4-yl)amino)-2-oxoethyl)-3-methyl-4-oxo-4,7-dihydro-3H-pyrrolo[2,3-d]pyrimidin-5-yl)-3,4-difluoro-2-hydroxybenzamide (I-460)

Scheme 40

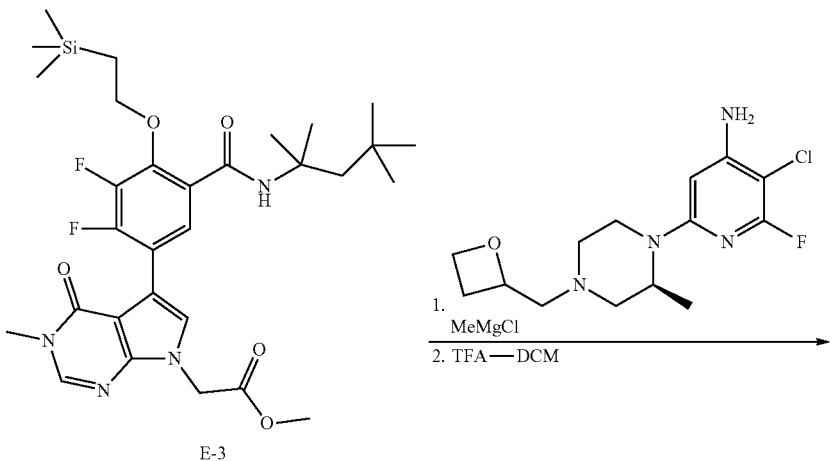

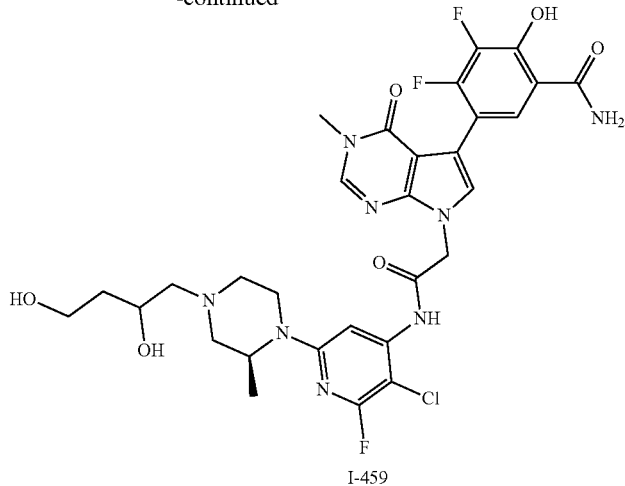

I-459

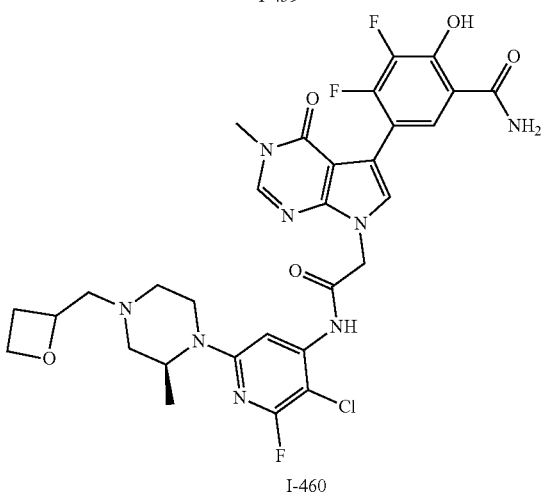

I-460

Methylmagnesium chloride, 3M in THF(0.069 ml, 0.208 mmol) dropwise under nitrogen. The yellow suspension was allowed to stir at RT for 5 min. Methyl 2-(5-(2,3-difluoro-5-((2,4,4-trimethylpentan-2-yl)carbamoyl)-4-(2-(trimethylsilyl)ethoxy)phenyl)-3-methyl-4-oxo-3H-pyrrolo[2,3-d]pyrimidin-7(4H)-yl)acetate (E-3) (70 mg, 0.116 mmol) was slowly added and stirred at 40° C. for 10 min. Additional Methylmagnesium chloride, 3M in THF (0.069 ml, 0.208 mmol) was added. The mixture was stirred at 40° C. for 1 hour. The reaction was quenched with methanol and concentrated onto celite. The crude mixture was purified on the Biotage (reverse phase silica gel) eluting with 0-100% ACN/H2O. The desired fractions were collected, concentrated and dried under vacuum to afford 5-(7-(2-(((3-chloro-2-fluoro-6-((2S)-2-methyl-4-(oxetan-2-ylmethyl)piperazin-1-yl)pyridin-4-yl)amino)-2-oxoethyl)-3-methyl-4-oxo-4,7-dihydro-3H-pyrrolo[2,3-d]pyrimidin-5-yl)-3,4-difluoro-N-(2,4,4-trimethylpentan-2-yl)-2-(2-(trimethylsilyl)ethoxy) benzamide (0.098 mmol, 85% yield) as a pale yellow residue. Carried onto next step.

To a solution of 5-(7-(2-((3-chloro-2-fluoro-6-((2S)-2-methyl-4-(oxetan-2-ylmethyl)piperazin-1-yl)pyridin-4-yl) amino)-2-oxoethyl)-3-methyl-4-oxo-4,7-dihydro-3H-pyrrolo[2,3-d]pyrimidin-5-yl)-3,4-difluoro-N-(2,4,4-trimethylpentan-2-yl)-2-(2-(trimethylsilyl)ethoxy) benzamide in Dichloromethane (DCM) (1.00 ml) was added Trifluoroacetic acid (0.886 ml, 11.57 mmol). The mixture was stirred at 35° C. for 2 hours. The reaction was concentrated in vacuo and purified by prep HPLC. The desired fractions were collected, concentrated in vacuo and dried under vacuum to afford the diol 5-(7-(2-(((3-chloro-6-((2S)-4-(2,4-dihydroxybutyl)-2-methylpiperazin-1-yl)-2-fluoro-pyridin-4-yl)amino)-2-oxoethyl)-3-methyl-4-oxo-4,7-dihydro-3H-pyrrolo[2,3-d]pyrimidin-5-yl)-3,4-difluoro-2-hydroxybenzamide (I-459), 2Trifluoroacetic Acid, CF3COOH [D] (9 mg, 8.16% yield) and oxetane 5-(7-(2-((3-chloro-2-fluoro-6-((2S)-2-methyl-4-(oxetan-2-ylmethyl)piperazin-1-yl)pyridin-4-yl)amino)-2-oxoethyl)-3-methyl-4-oxo-4,7-dihydro-3H-pyrrolo[2,3-d]pyrimidin-5-yl)-3,4-difluoro-2-hydroxybenzamide (I-460), 2Trifluoroacetic Acid, CF₃COOH [4 mg, 3.44% yield), both as beige solids.

General Scheme and Procedures for the Synthesis of 2-Substituted Amino-Pyridines

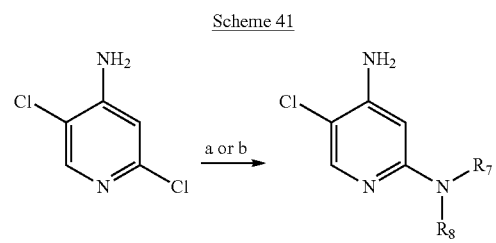

Scheme 41 a) HNR$_7$R$_8$ neat, 210° C., μW;
b) HNR$_7$R$_8$, EtNiPr$_2$, n-Butanol, 210° C., μW;

Method A (Nitrogen Analogues):

A microwave vial was charged with 2,5-dichloropyridin-4-amine dihydrochloride (860 mg, 4.31 mmol) and Morpholine (3771 μl, 43.1 mmol), and heated in the microwave at 210° C. until complete conversion as determined by LCMS. The reaction was partitioned between water and EtOAc. The water was extracted with EtOAc (2×). The combined organic layers were washed with brine, dried over Na$_2$SO$_4$, concentrated and dried under vacuum at RT to afford the titled compound. The product was carried onto the next step without further purification.

Method B (Nitrogen Analogues):

A microwave vial charged with 2,5-dichloropyridin-4-amine dihydrochloride (580 mg, 2.458 mmol), N,N-Diisopropylethylamine (1.713 ml, 9.83 mmol), [1,4]Oxazepane (995 mg, 9.83 mmol) in n-Butanol, was heated in the microwave at 210° C. until complete conversion as determined by LCMS. The mixture was concentrated in vacuo onto celite and the crude product was purified by reverse phase silica gel chromatography (0-50% ACN/H$_2$O) to give the title compound.

Method C (Oxygen Analogues):

To a microwave vial charged with 4-(2-Hydroxyethyl)morpholine (0.821 ml, 6.78 mmol) in 1,4-Dioxane (5.0 ml) was added Sodium hydride (260 mg, 6.78 mmol). The reaction was stirred at RT for 5 min, then 2,5-dichloropyridin-4-amine dihydrochloride (200 mg, 0.848 mmol) was added and heated at 150° C. in the microwave until complete conversion as determined by LCMS. The reaction was diluted with water and extracted with EtOAc (2×). The combined organic layers were washed with brine, dried over Na$_2$SO$_4$, concentrated. The crude product was carried onto the next step without further purification.

In a similar manner, the following compounds were prepared

| Method | Aniline | Name | Yield & Mass |
|---|---|---|---|
| A | (structure) | 5-chloro-2-morpholinopyridin-4-amine | 98% yield, LCMS [M]$^+$ 214.12 |
| A | (structure) | 5-chloro-2-(cis-2,6-dimethylmorpholino)pyridin-4-amine | 97% yield, LCMS [M]$^+$ 242.14 |
| B | (structure) | 5-chloro-2-((2R,5R)-2,5-dimethylmorpholino)pyridin-4-amine | 36% yield, LCMS [M]$^+$ 242.20 |

| Method | Aniline | Name | Yield & Mass |
|---|---|---|---|
| B | | 5-chloro-2-((2R,6R)-2,6-dimethylmorpholino)pyridin-4-amine | 87% yield, LCMS [M]+ 241.95 |
| B | | (S)-5-chloro-2-(2-methylmorpholino)pyridin-4-amine | 100% yield, LCMS [M]+ 228.22 |
| B | | (R)-5-chloro-2-(2-methylmorpholino)pyridin-4-amine | 100% yield, LCMS [M]+ 228.15 |
| A | | (S)-5-chloro-2-(3-methylmorpholino)pyridin-4-amine | 90% yield, LCMS [M]+ 228.22 |
| A | | (R)-5-chloro-2-(3-thylmorpholino)pyridin-4-amine | 96% yield, LCMS [M]+ 228.22 |
| B | | 5-chloro-2-(2,2-dimethylmorpholino)pyridin-4-amine | 97% yield, LCMS [M]+ 241.95 |
| B | | 5-chloro-2-(hexahydro-2H-benzo[b][1,4]oxazin-4(3H)-yl)pyridin-4-amine | 32% yield, LCMS [M]+ 268.23 |

| Method | Aniline | Name | Yield & Mass |
|---|---|---|---|
| A | (4-amino-5-chloro-2-(4-methylpiperazin-1-yl)pyridine structure) | 5-chloro-2-(4-methylpiperazin-1-yl)pyridin-4-amine | 70% yield, LCMS [M]⁺ 227.22 |
| A | (cis-3,5-dimethylpiperazinyl pyridine structure) | 5-chloro-2-(cis)-3,5-dimethylpiperazin-1-yl)pyridin-4-amine | 51% yield, LCMS [M]⁺ 241.20 |
| A | ((3R,5S)-3,4,5-trimethylpiperazinyl pyridine structure) | 5-chloro-2-((3R,5S)-3,4,5-trimethylpiperazin-1-yl)pyridin-4-amine | 32% yield, LCMS [M]⁺ 255.25 |
| B | ((S)-2,4-dimethylpiperazinyl pyridine structure) | (S)-5-chloro-2-(2,4-dimethylpiperazin-1-yl)pyridin-4-amine | 19% yield, LCMS [M]⁺ 241.26 |
| A | (4-(2,2,2-trifluoroethyl)piperazinyl pyridine structure) | 5-chloro-2-(4-(2,2,2-trifluoroethyl)piperazin-1-yl)pyridin-4-amine | 89% yield, LCMS [M]⁺ 295.18 |
| A | (pyrrolidin-1-yl pyridine structure) | 5-chloro-2-(pyrrolidin-1-yl)pyridin-4-amine | 100% yield, LCMS [M]⁺ 197.88 |

-continued

| Method | Aniline | Name | Yield & Mass |
|---|---|---|---|
| B | | 5-chloro-$N^2,N^2$-dimethylpyridine-2,4-diamine | 100% yield, LCMS $[M]^+$ 172.11 |
| B | | 5-chloro-2-(1,4-oxazepan-4-yl)pyridin-4-amine | 77% yield, LCMS $[M]^+$ 228.16 |
| B | | 5-chloro-2-(tetrahydro-1H-furo[3,4-c]pyrrol-5(3H)-yl)pyridin-4-amine | 77% yield, LCMS $[M]^+$ 240.20 |
| A | | 5-chloro-2-(tetrahydro-2H-furo[2,3-c]pyrrol-5(3H)-yl)pyridin-4-amine Exact Mass: 239.08 | 39% yield, LCMS $[M + H]^+$ 240 |
| A | | 5-chloro-2-(hexahydropyrazino[2,1-c][1,4]oxazin-8(1H)-yl)pyridin-4-amine Exact Mass: 268.11 | 61% yield, LCMS $[M + H]^+$ 269 |
| A | | 5-chloro-2-(3-oxa-9-azaspiro[5.5]undecan-9-yl)pyridin-4-amine Exact Mass: 281.13 | 55% yield, LCMS $[M + H]^+$ 282 |

-continued

| Method | Aniline | Name | Yield & Mass |
|---|---|---|---|
| A | (structure) | 5-chloro-2-(3,3,5,5-tetramethylpiperazin-1-yl)pyridin-4-amine Exact Mass: 268.15 | 55% yield, LCMS [M + H]+ 269 |
| A | (structure) | 2-(2-oxa-5-azabicyclo[2.2.1]heptan-5-yl)-5-chloropyridin-4-amine Exact Mass: 225.07 | 35% yield, LCMS [M]+ 226 |
| A | (structure) | 5-chloro-2-(5-oxa-8-azaspiro[3.5]nonan-8-yl)pyridin-4-amine Exact Mass: 253.10 | 100% yield, LCMS [M]+ 254 |
| A | (structure) | 5-chloro-2-(6-oxa-2-azaspiro[3.4]octan-2-yl)pyridin-4-amine Exact Mass: 239.08 | 100% yield, LCMS [M]+ 240 |
| A | (structure) | 2-(3-azabicyclo[3.1.0]hexan-3-yl)-5-chloropyridin-4-amine Exact Mass: 209.07 | 97% yield, LCMS [M]+ 210 |
| A | (structure) | 5-chloro-2-(9-oxa-2-azaspiro[5.5]undecan-2-yl)pyridin-4-amine Exact Mass: 281.13 | 44% yield, LCMS [M]+ 282 |

| Method | Aniline | Name | Yield & Mass |
|---|---|---|---|
| A | [structure: 5-chloropyridine with NH2, Cl, and 3,3,4,5,5-pentamethylpiperazin-1-yl] | 5-chloro-2-(3,3,4,5,5-pentamethylpiperazin-1-yl)pyridin-4-amine Exact Mass: 282.16 | 44% yield, LCMS [M]+ 283 |
| A | [structure: 5-chloropyridine with NH2, Cl, and (R)-3-methoxypyrrolidin-1-yl] | (R)-5-chloro-2-(3-methoxypyrrolidin-1-yl)pyridin-4-amine Exact Mass: 227.08 | 100% yield, LCMS [M]+ 228 |

General Scheme and Procedures for the Synthesis of 2-Substituted Amino-Pyridines Via Buchwald Coupling Reaction Scheme 42

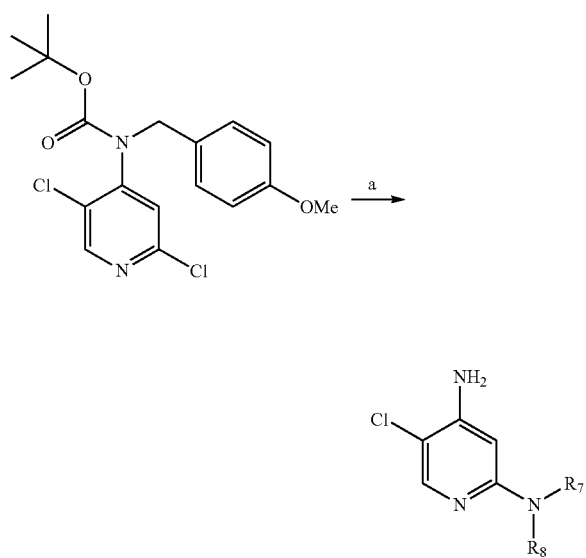

a) i. HNR7R8 RuPhos Pd G3, RuPhos, CsCO3, n-Butanol, μW;
ii) TFA, μW;

A microwave vial was charged with tert-butyl (2,5-dichloropyridin-4-yl)(4-methoxybenzyl)carbamate (780 mg, 2.035 mmol), 2,3-Dimethylmorpholine hydrochloride (401 mg, 2.65 mmol), Cs$_2$CO$_3$ (2652 mg, 8.14 mmol), RuPhos Pd G3 (30.9 mg, 0.041 mmol) and 2-Dicyclohexylphosphino-2',6'-di-i-propoxy-1,1'-biphenyl (38.0 mg, 0.081 mmol) (RuPhos). The system was flushed with nitrogen then t-BuOH (10 ml) was added. The system was flushed with nitrogen and heated at 100° C. to complete conversion as determined by LCMS. The reaction was concentrated onto celite, and purified by flash chromatography (silica gel) eluting with 0-10% MeOH/DCM+1% NH$_4$OH. The desired fractions were collected and dried under vacuum at RT to afford tert-butyl (5-chloro-2-(2,3-dimethylmorpholino)pyridin-4-yl)(4-methoxybenzyl)carbamate (598 mg, 1.294 mmol, 63.6% yield) as a yellow oil. To a stirring solution of tert-butyl (5-chloro-2-(2,3-dimethylmorpholino)pyridin-4-yl)(4-methoxybenzyl)carbamate (598 mg, 1.294 mmol) in Dichloromethane (1.0 ml) was added TFA (2.99 ml, 38.8 mmol) at room temperature.

Method A:

Upon completion of the reaction as judged by LCMS, the reaction was concentrated to dryness and purified on the Biotage (reverse phase silica gel) eluting with 0%-20% ACN/H$_2$O. The desired fractions were collected, dried on the h/v at RT to afford 5-chloro-2-(2,3-dimethylmorpholino)pyridin-4-amine trifluoroacetate (321 mg, 0.902 mmol, 69.7% yield) as a yellow residue.

Method B:

Upon completion of the reaction as judged by LCMS, the reaction was diluted with DCM and partitioned between DCM and water. The aqueous layer was neutralized with the addition of NaHCO$_3$ [both saturated solution and extra solid]. The layers were separated and the aqueous layer was extracted with DCM. The combined organics were dried over Na$_2$SO$_4$, filtered and concentrated in vacuo. The product used in next step without further purification.

| Method | Aniline | Name | Yield & Mass |
|---|---|---|---|
| A | (structure) | 5-chloro-2-(2,3-dimethylmorpholino)pyridin-4-amine | 44% yield over 2 steps 77% yield; LCMS [M + H]+ 242 |
| A | (structure) | 2-(2-azabicyclo[2.2.1]heptan-2-yl)-5-chloropyridin-4-amine Exact Mass: 223.09 | Quantitative yield over 2 steps, LCMS [M + H]+ 224 |
| A | (structure) | 2-((1s,4s)-7-azabicyclo[2.2.1]heptan-7-yl)-5-chloropyridin-4-amine Exact Mass: 223.09 | Quantitative yield over 2 steps, LCMS [M + H]+ 224 |
| A | (structure) | 5-chloro-2-(9-methyl-6-oxa-2,9-diazaspiro[4.5]decan-2-yl)pyridin-4-amine Exact Mass: 282.12 | Quantitative yield over 2 steps, LCMS [M + H]+ 283 |
| A | (structure) | 5-chloro-2-(2-methyl-6-oxa-2,9-diazaspiro[4.5]decan-9-yl)pyridin-4-amine Exact Mass: 282.12 | Quantitative yield over 2 steps, LCMS [M + H]+ 283 |
| A | (structure) | 5-chloro-N2-methyl-N2-(tetrahydro-2H-pyran-4-yl)pyridine-2,4-diamine Exact Mass: 241.10 | Quantitative yield over 2 steps, LCMS [M + H]+ 242 |

-continued

| Method | Aniline | Name | Yield & Mass |
|---|---|---|---|
| A | | 5-chloro-2-(3-morpholinoazetidin-1-yl)pyridin-4-amine<br>Exact Mass: 268.11 | Quantitative yield over 2 steps, LCMS [M + H]+ 269 |
| A | | 5-chloro-2-(8-methyl-3,8-diazabicyclo[3.2.1]octan-3-yl)pyridin-4-amine<br>Exact Mass: 252.11 | 28% × yield over 2 steps, LCMS [M + H]+ 253 |
| A | | 2-(8-oxa-3-azabicyclo[3.2.1]octan-3-yl)-5-chloropyridin-4-amine<br>Exact Mass: 239.08 | 36% × yield over 2 steps, LCMS [M + H]+ 240 |
| A | | 5-chloro-2-(2-oxa-7-azaspiro[4.4]nonan-7-yl)pyridin-4-amine<br>Exact Mass: 253.10 | 100 × yield over 2 steps, LCMS [M + H]+ 254 |
| A | | 5-chloro-2-(3-morpholinopyrrolidin-1-yl)pyridin-4-amine<br>Exact Mass: 282.12 | 100 × yield over 2 steps, LCMS [M + H]+ 282 |
| A | | 5-chloro-2-(3-morpholinopyrrolidin-1-yl)pyridin-4-amine<br>Exact Mass: 197.07 | 100 × yield over 2 steps, LCMS [M + H]+ 198 |
| A | | 2-(4-amino-5-chloropyridin-2-yl)hexahydropyrrolo[1,2-a]pyrazin-6(2H)-one<br>Exact Mass: 266.09 | 64% yield over 2 steps, LCMS [M + H]+ 267 |

-continued

| Method | Aniline | Name | Yield & Mass |
|---|---|---|---|
| A | | 7-(4-amino-5-chloropyridin-2-yl)hexahydro-3H-oxazolo[3,4-a]pyrazin-3-one<br>Exact Mass: 268.07 | 41% yield over 2 steps, LCMS [M + H]$^+$ 269 |
| A | | 7-(4-amino-5-chloropyridin-2-yl)-2-methylhexahydroimidazo[1,5-a]pyrazin-3(2H)-one<br>Exact Mass: 281.10 | 66% yield over 2 steps, LCMS [M + H]$^+$ 282 |
| A | | 2-(2-oxa-5-azabicyclo[4.1.0]heptan-5-yl)-5-chloropyridin-4-amine<br>Exact Mass: 225.07 | 33% yield over 2 steps, LCMS [M + H]$^+$ 226 |
| A | | 5-chloro-2-(8-oxa-5-azaspiro[3.5]nonan-5-yl)pyridin-4-amine<br>Exact Mass: 253.10 | 64% yield over 2 steps, LCMS [M + H]$^+$ 254 |
| A | | 5-chloro-2-(morpholino-d8)pyridin-4-amine<br>Exact Mass: 221.12 | 64% yield over 2 steps, LCMS [M + H]$^+$ 222 |
| A | | 5-chloro-2-(hexahydro-4H-furo[3,4-b][1,4]oxazin-4-yl)pyridin-4-amine<br>Exact Mass: 255.08 | 2% yield over 2 steps, LCMS [M + H]$^+$ 256 |

| Method | Aniline | Name | Yield & Mass |
|---|---|---|---|
| A | | 5-chloro-2-(hexahydrocyclopenta[b][1,4]oxazin-4(4aH)-yl)pyridin-4-amine<br>Exact Mass: 253.10 | 53% yield over 2 steps, LCMS [M + H]+ 254 |
| A | | 5-chloro-2-(4,4-difluorohexahydrocyclopenta[c]pyrrol-2(1H)-yl)pyridin-4-amine<br>Exact Mass: 273.08 | 18% yield over 2 steps, LCMS [M + H]+ 274 |
| A | | 2-(6-oxa-3-azabicyclo[3.1.1]heptan-3-yl)-5-chloropyridin-4-amine<br>Exact Mass: 225.07 | 53% yield over 2 steps, LCMS [M + H]+ 226 |
| A | | 2-(3-oxa-6-azabicyclo[3.1.1]heptan-6-yl)-5-chloropyridin-4-amine<br>Exact Mass: 225.07 | 36% yield over 2 steps, LCMS [M + H]+ 226 |
| A | | 2-(3-oxa-8-azabicyclo[3.2.1]octan-8-yl)-5-chloropyridin-4-amine<br>Exact Mass: 239.08 | 47% yield over 2 steps, LCMS [M + H]+ 240 |
| A | | 5-chloro-2-(3-(dimethylamino)azetidin-1-yl)pyridin-4-amine<br>Exact Mass: 226.10 | 62% yield over 2 steps, LCMS [M + H]+ 227 |

| Method | Aniline | Name | Yield & Mass |
|---|---|---|---|
| A | | 5-chloro-2-(4-methylhexahydropyrrolo[3,4-b][1,4]oxazin-6(2H)-yl)pyridin-4-amine<br>Exact Mass: 268.11 | 84% yield over 2 steps, LCMS [M + H]+ 269 |
| A | | (S)-5-chloro-2-(2-ethylmorpholino)pyridin-4-amine<br>Exact Mass: 241.10 | 39% yield over 2 steps, LCMS [M + H]+ 242 |
| A | | (R)-5-chloro-2-(2-ethylmorpholino)pyridin-4-amine<br>Exact Mass: 241.10 | 88% yield over 2 steps, LCMS [M + H]+ 242 |
| A | | (S)-5-chloro-2-(2-isopropylmorpholino)pyridin-4-amine<br>Exact Mass: 255.11 | 38% yield over 2 steps, LCMS [M + H]+ 256 |
| A | | (R)-5-chloro-2-(2-isopropylmorpholino)pyridin-4-amine<br>Exact Mass: 255.11 | 72% yield over 2 steps, LCMS [M + H]+ 256 |

Synthesis of 5-fluoro-2-morpholinopyridin-4-amine

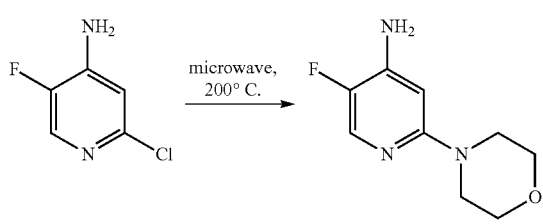

Scheme 43

A solution of 2-chloro-5-fluoropyridin-4-amine (900 mg, 6.41 mmol, 11 eq) in Morpholine (9 mL) was irradiated under microwave at 180° 0 for 90 min in 30 mL vial. TLC analysis indicated formation of polar spot. Then, the reaction mixture was cooled to RT and poured on ice-water to give a off white precipitate; which was purified by column chromatography (Silica gel 100-200mesh) using 40% EtOAc in petroleum ether as an eluent to give 5-fluoro-2-morpholinopyridin-4-amine (720 mg, 57.14% yield) as an off-white solid. LC-MS: m/z 198.0 (M+H).

The following compound was prepared in a similar manner.

| Aniline | Name | Yield & Mass |
|---|---|---|
| 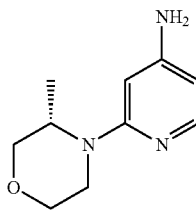 | (S)-5-fluoro-2-(3 methylmorpholino)pyridin-4-amine<br>Exact Mass: 211.11 | 86% yield, LCMS [M]+ 212 |

Synthesis of 5-chloro-2-methoxypyridin-4-amine

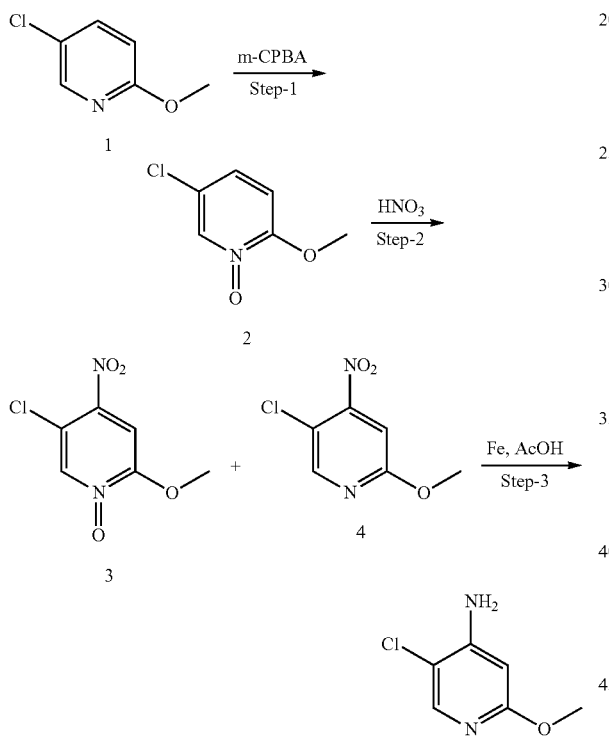

Compound numbers in text refer to structures shown in Scheme 44.

Step 1: Synthesis of 5-chloro-2-methoxypyridine 1-oxide

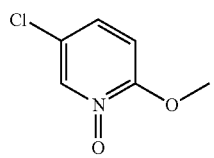

To a stirred solution of compound 5-chloro-2-methoxy-pyridine (40 g, 275.86 mmol, 1 eq) in DCM (300 ml) was added m-CPBA (142.3 g, 827.58 mmol, 3 eq) at RT and then the reaction continued at RT for 48 h. The reaction mixture was filtered and the filtrate was concentrated to obtain a crude mixture. The crude mixture was purified by column chromatography (100-200mesh) using 10-100% EtOAc in petroleum ether as an eluent to afford compound 2 (33 g, 74.20%) as off-white solid; LCMS [M+H]+ 160.

Step 2: Synthesis of 5-chloro-2-methoxy-4-nitropyridine 1-oxide and 5-chloro-2-methoxy-4-nitropyridine

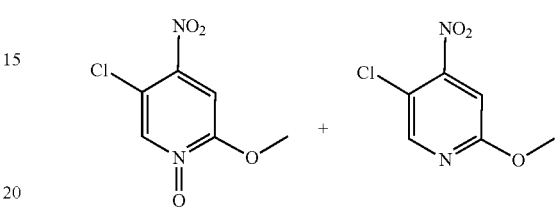

To a stirred solution of compound 5-chloro-2-methoxy-pyridine 1-oxide (3 g) in $H_2SO_4$ (10.8 mL) was slowly added $HNO_3$ (8.2 mL) at RT then heated to 70° C. for 20 h. TLC analysis indicated formation of two less polar spots. The reaction mixture was quenched in Ice water then basified with $Na_2CO_3$ and extracted with EtOAc (6×100 mL). The combined organic layer was dried over $Na_2SO_4$ and concentrated under reduced pressure to give a crude compound mixture (1.2 g) as light yellow semi-solid which was used without further purification; LCMS [M+H]+ 205.

Step 3: Synthesis of 5-chloro-2-methoxypyridin-4-amine

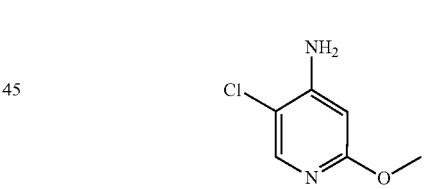

To a stirred solution of the mixture of 5-chloro-2-methoxy-4-nitropyridine 1-oxide and 5-chloro-2-methoxy-4-nitropyridine (3.3 g, 16.17 mmol, 1 eq) in AcOH (40 mL) was added Fe (5.4 g, 97.05 mmol, 6 eq) at RT and then heated to 80° C. for 1 h. TLC analysis indicated formation of polar spot. The reaction mixture was quenched in Ice and basified with $Na_2CO_3$ then filtered through celite bed, which is washed with EtOAc (4×50 mL). The filtrate was extracted with EtOAc (3×100 mL). The combined organic layer was dried over $Na_2SO_4$ and concentrated under reduced pressure to give a crude product. The crude product was washed and triturated with n-pentane (2×10 ml) to give the title compound (1.4 g) as a light green solid; LCMS [M+H]+ 159.

Synthesis of
5-chloro-3-fluoro-2-methoxypyridin-4-amine

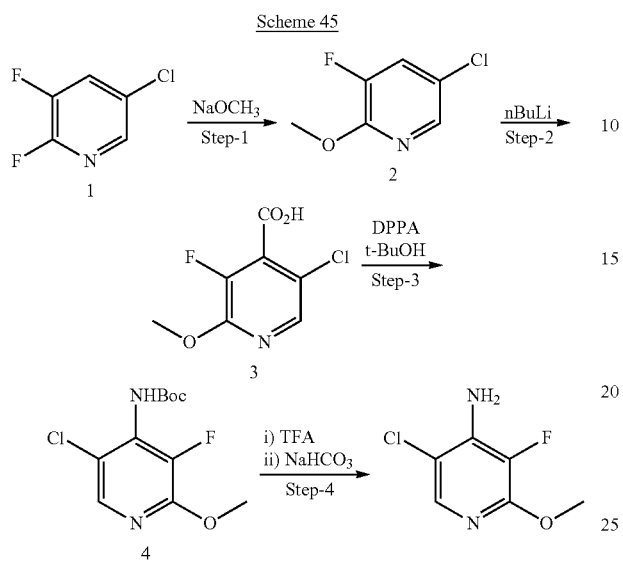

Compound numbers in text refer to structures shown in Scheme 45.

Step 1:
To a solution of compound 1 (1 g, 6.687 mmol, 1 eq) in Dry Methanol (5 mL), a solution of 30% NaOMe (1.8 mL, 10.03 mmol, 1.5 eq) was added dropwise and the reaction mixture was heated to 65° C. for 2 h (Reaction was monitored by 1HNMR and LCMS). Then, the reaction mixture was cooled to RT and concentrated under reduced pressure to give a residue. Residue was dissolved in EtOAc and washed with water. The separated organic layer was dried over $Na_2SO_4$ and concentrated under reduced pressure to give compound 2 (750 mg, 69.89%) as colorless liquid; which was sufficiently pure to use for next step.

Step 2:
To a solution of compound 2 (3.6 g, 17.56 mmol, 1 eq) in Dry THF (20 mL), a solution of nBuLi (1.6M in hexane, 1.5 eq) was added dropwise over 10 min at −78° C. and stirred 30 min at the same temp. After, 30 min crushed dry ice was added portion wise to the above solution at −78° C. Then, the reaction mixture was allowed to warm up to RT over 2 h. After 2 h, the reaction mixture was cooled to 0° C. and neutralized by conc.HCl. Then, the reaction mixture was concentrates under reduced pressure to give a crude product. The crude product was dissolved in 5M NaOH solution and washed with ether; the aqueous layer was cooled to 0° C. and acidified to pH 5-6 by conc. HCl. A precipitate formed. The precipitate was filtered and washed with ether to give compound 3 (2.7 g, 75.0%) as a white solid. LCMS: m/z 204.1 (M−1)

Step 3:
To a stirred solution of compound 3 (700 mg, 3.41 mmol, 1 eq) in tBuOH (28 mL), Triethyl amine (0.5 mL, 3.75 mmol, 1.1 eq) was added at RT. Then, a solution of DDPA (0.82 mL, 1.27 mmol, 1.12 eq) was added dropwise at RT. The reaction mixture was heated to 85-90° C. for 16 h. Then, the reaction mixture was cooled to RT and concentrated under reduced pressure to give a crude product. The crude product was purified by column chromatography (silica gel 100-200mesh) using 1-5% EtOAc in petroleum ether as an eluent to give a compound 4 as a white solid (650 mg, 68.71%). LCMS: m/z 277.22 (M+1)

Step 4:
To a precooled solution of compound 4 (1.8 g, 6.49 mmol, 1 eq) in dry DCM (20 mL), TFA (4.45 g, 38.98 mmol, 6 eq) was added and the reaction mixture was allowed to warm up to RT over 16 h. After 16 h, Reaction mixture was diluted with DCM (50 mL) and quenched with sat.$NaHCO_3$till to pH ~8. Combined organic layer was dried over $Na_2SO_4$ and concentrated under reduced pressure to give a crude compound; which was washed with n-pentane to give 5-chloro-3-fluoro-2-methoxypyridin-4-amine as a white solid (900 mg, 78.94%). LCMS: m/z 177.09 (M+1);

Synthesis of (S)-5-chloro-2-(2-methyl-4-(oxetan-3-yl)piperazin-1-yl)pyridin-4-amine Scheme 46

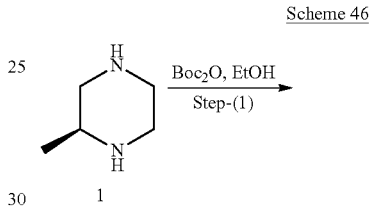

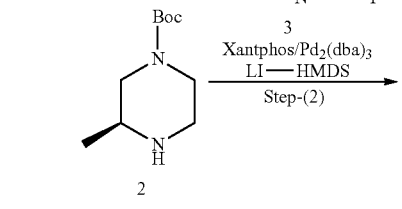

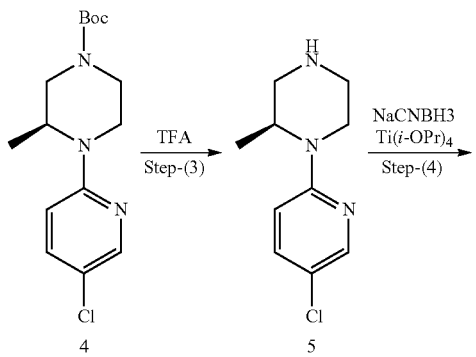

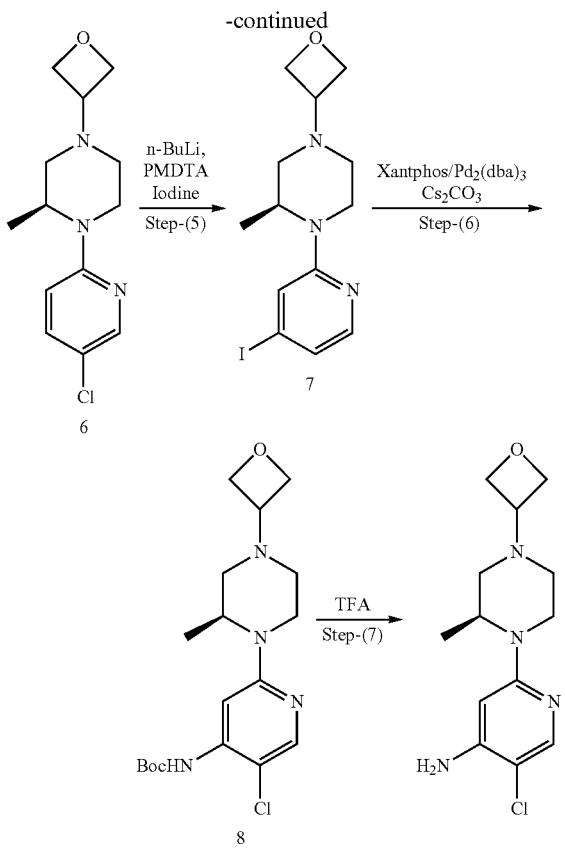

Compound numbers in text refer to structures shown in Scheme 46.

Step 1:

To a solution of compound 1 (10 g, 100 mmol, 1 eq) in EtOH (200 ml) was added DIPEA (43.58 mL, 250 mmol, 2.5 eq) and Boc$_2$O (21.8 mL, 100 mmol, 1 eq) at RT, then the reaction was continued for 16 h. TLC analysis indicated formation of a less polar spot. The reaction mixture was concentrated to crude compound, which is diluted with water and extracted with EtOAc (3×100 mL). The combined organic layer was dried over Na$_2$SO$_4$ then concentrated to give compound 2 (18 g, 90%) as a colorless oil.

Step 2:

To a stirred compound 2 (18 g, 90 mmol, 1 eq) was added compound 3 (23.58 g, 180 mmol, 2 eq), xantphos (1.56 g, 2.7 mmol, 0.03 eq), Pd$_2$(dba)$_3$ (2.47 g, 2.7 mmol, 0.03 eq) and Li-HMDS (450 mL, 450 mmol, 5 eq) at RT under argon atmosphere. Then, the reaction mixture was heated to 90° C. for 16 h. TLC analysis indicated formation of a less polar spot. The reaction mixture was cooled to RT then filtered through celite pad, which was washed with EtOAc (3 times). The filtrate was diluted with water and extracted with EtOAc (3×100 mL). The combined organic layer was dried over Na$_2$SO$_4$ then concentrated to crude compound. The crude compound was purified by column chromatography (silica gel, 100-200 mesh) using 0-10% EtOAc in petroleum ether as eluent to afford compound 4 (24 g, 85.74%) as a brown oil. LC-MS: m/z 312.17 (M+H);

Step 3:

To a stirred solution of compound 4 (24 g, 77.17 mmol, 1 eq) in DCM (250 mL) was added TFA (58.64 mL, 771.70 mmol, 10 eq) at 0° C. then allowed to warm up to RT for 16 h. TLC analysis indicated formation of a polar spot. The reaction mixture was concentrated to a crude residue, which is basified with aqueous NaHCO$_3$ solution then extracted with EtOAc (3×100 mL). The combined organic layer was dried over Na$_2$SO$_4$ then concentrated to give a crude compound. The crude compound was purified by column chromatography (silica gel, 100-200 mesh) using 0-2% MeOH in DCM as eluent to afford compound 5 (14 g, 85.99%) as a brown oil. LC-MS: m/z 212.12 (M+H).

Step 4:

To a stirred solution of compound 5 (4 g, 18.95 mmol, 1 eq) in MeOH (60 mL) was added oxetan-3-one (1.66 mL, 28.43 mmol, 1.5 eq) and Ti(i-OPr)$_4$ (8.4 mL, 28.43 mmol, 1.5 eq) at RT under argon atmosphere and continued for 2 h. NaCNBH$_3$ (2.39 g, 37.91 mmol, 2 eq) was then added at RT, and the reaction continued for another 2 h. TLC analysis indicated formation of a less polar spot. The reaction mixture was diluted with water and filtered through celite pad. The filtrate was extracted with EtOAc (3×90 mL). The combined organic layer was dried over Na$_2$SO$_4$ then concentrated to obtain a crude mixture. The crude mixture was purified by column chromatography (silica gel, 100-200 mesh) using 0-30% EtOAc in petroleum ether as eluent to afford compound 6 (2.8 g, 55%) as a brown oil. LC-MS: m/z 268.15 (M+H).

Step 5:

To a stirred solution of compound 6 (2.8 g, 10.48 mmol, 1 eq) in THF (60 mL) was added PMDTA (4.8 mL, 23.07 mmol, 2.2 eq) and n-BuLi (9.2 mL, 23.07 mmol, 2.2 eq, 2.5M in THF) at −78° C. under argon atmosphere. The reaction was continued for 2 h and a solution of 12 (5.32 g, 20.97 mmol, 2 eq, in THF) was added at −78° C. The mixture was then slowly allowed to warm up to RT for 16 h. TLC analysis indicated formation of a less polar spot. The reaction mixture was quenched in aqueous solution of sodium thiosulphate then extracted with EtOAc (3×80 mL). The combined organic layer was dried over Na$_2$SO$_4$ then concentrated under reduced pressure to give crude compound 7 (5 g, crude) as a brown oil. LC-MS: m/z 394.07 (M+H).

Step 6:

To a stirred solution of compound 7 (5 g, 12.72 mmol, 1 eq) in Toluene (80 mL) was added Cs$_2$CO$_3$ (8.2 g, 25.44 mmol, 2 eq) and NH$_2$Boc (1.77 g, 15.26 mmol, 1.2 eq) at RT. The reaction mixture was de-gassed with Argon for 5 min., then xantphos (220 mg, 0.38 mmol, 0.03 eq) and Pd$_2$(dba)$_3$ (350 mg, 0.38 mmol, 0.03 eq) were added at RT. The resulting reaction mixture was heated to 90° C. for 16 h. TLC analysis indicated formation of a polar spot. The reaction mixture was filtered through celite pad. The filtrate was concentrated to obtain a crude compound. The crude compound was purified by column chromatography (silica gel, 100-2000 mesh) using 0-1% MeOH in DCM as eluent to afford compound 8 (3.5 g, 87%, per two steps) as brown oil. LC-MS: m/z 383.23 (M+H).

Step 7:

To a stirred solution of compound 8 (3.5 g, 9.16 mmol, 1 eq) in DCM (30 mL) was added TFA (6.9 mL, 91.62 mmol, 10 eq) at RT and the reaction continued for 16 h. TLC analysis indicated formation of a polar spot. The reaction mixture was concentrated to a crude residue, which was basified by aqueous NaHCO$_3$ solution then extracted with EtOAc (3×60 mL). The combined organic layer was dried over Na$_2$SO$_4$ then concentrated under reduced pressure to obtain a crude compound. The crude compound was purified by column chromatography (silica gel, 100-200 mesh) using 0-2% MeOH in DCM as eluent to afford (S)-5-chloro-2-(2- methyl-4-(oxetan-3-yl)piperazin-1-yl)pyridin-4-amine (1.5 g 58%) as brown oil. LC-MS: m/z 283.0 (M+H).

Synthesis of
5-chloro-3-fluoro-2-morpholinopyridin-4-amine

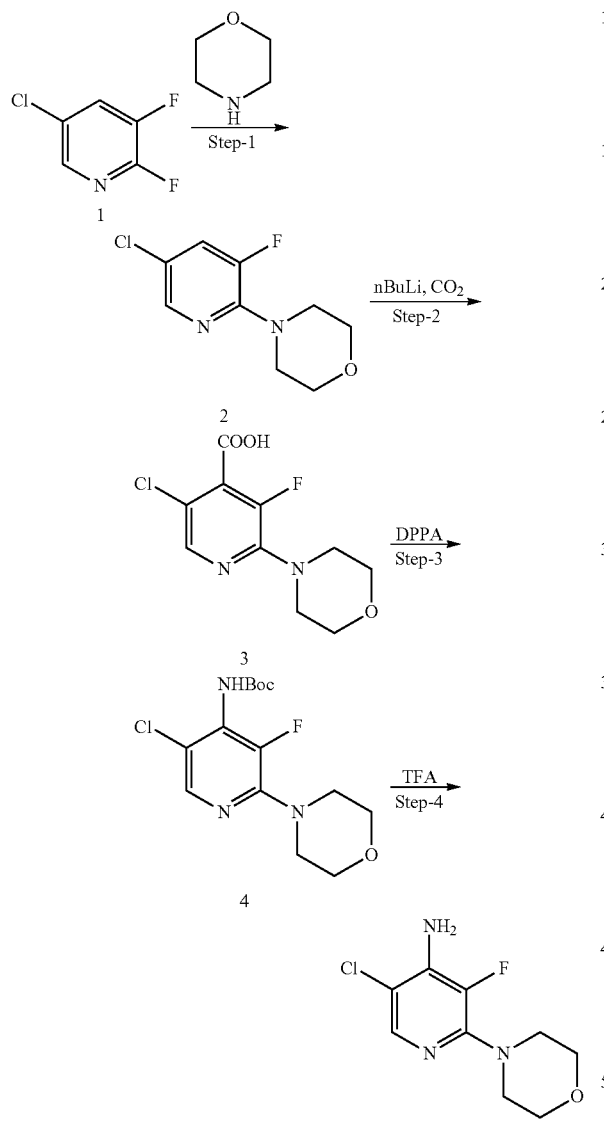

Compound numbers in text refer to structures shown Scheme 47.

Step 1:
To a solution of compound 1 (5 g, 33.5 mmol, 1 eq) in Dry DMF (37 mL) was added Morpholine (0.95 mL, 11 mmol, 0.33 eq) followed by DiPEA (10.2 mL, 56.9 mmol, 1.7 eq) at RT under Argon atmosphere. The mixture was heated to 100° C. for 16 h. Then, the reaction mixture was cooled to RT and poured on ice-water (300 mL). The reaction mixture was extracted with EtOAc (2×100 mL). The combined organic layer was dried over $Na_2SO_4$ and concentrated under reduced pressure to give a crude product. The crude product was purified by combiflash column chromatography using 10% EtOAc in petroleum ether as an eluent to give compound 2 (2.5 g, 34.73%) as an off-white solid.

Step 2:
To a solution of DiPA (3.1 mL, 21.7 mmol, 1.6 eq) in Dry THF (90 mL) was added n-BuLi (1.6M in n-hexane, 19.7 mL, 1.7 eq) at −78° C. and allowed to −30° C. for 30 min. So freshly prepared LDA was added to a solution of compound 2 (3 g, 13.8 mmol, 1 eq) in Dry THF (30 mL) at −78° C. under Argon atmosphere and the reaction maintained for 2 h at the same temp. Then, powder of dry ice was added slowly at the same temp. The reaction mixture was allowed to warm up to RT over 16 h. Then, the reaction mixture was quenched with sat.$NH_4Cl$ (50 mL) and washed with ether (2×20 mL). The aqueous layer was acidified with 1MHCl and extracted with EtOAc (4×50 mL). The combined organic layer was dried over $Na_2SO_4$ and concentrated under reduced pressure to give a crude product. The crude product was washed with n-pentane & ether to give compound 3 (3 g, 83.61%) as an off-white solid. LC-MS: m/z 261.31 (M+H).

Step 3:
To a solution of compound 3 (3 g, 11.49 mmol, 1 eq), TEA (1.75 mL, 12.5 mmol, 1.1 eq) in tBuOH (60 mL) at 5-10° C. temp, DPPA (2.8 mL, 12.87 mmol, 1.12 eq) was added in dropwise manner at the same temp. Then, the reaction mixture was heated to 85° C. for 16 h. TLC analysis indicated formation of a nonpolar spot. The reaction mixture was cooled to RT and concentrated under reduced pressure to give a residue; which was re-dissolved in EtOAc (60 mL) and washed with saturated brine. Separated organic layer was dried over $Na_2SO_4$ and concentrated under reduced pressure to give a crude product. The crude product was purified by combiflash column chromatography using 20% EtOAc in petroleum ether as an eluent to give compound 4 (1.5 g, 39.47% yield) as a pale yellow solid. LC-MS: m/z 332.36 (M+H).

Step 4:
To a solution of compound 4 (1.5 g, 4.63 mmol, 1 eq) in DCM (20 mL) was added Trifluoroacetic acid (4.3 mL, 5.42 mmol, 6.16 eq) in dropwise manner at 0° C. and the reaction was allowed to warm up to RT over 16 h. TLC analysis indicated formation of a polar spot. Then, the reaction mixture was concentrated under reduced pressure to give a TFA salt of the product; which was dissolved in water (20 mL), basified with sat.$NaHCO_3$ and extracted in EtOAc (3×30 mL). The combined organic layer was dried over $Na_2SO_4$ and concentrated under reduced pressure to give a crude product. Crude compound was purified by washing with n-pentane to give 5-chloro-3-fluoro-2-morpholinopyridin-4-amine (600 mg, 56.13%) as an off white solid. LC-MS: m/z 232.30 (M+H).

Synthesis of 5-chloro-3-fluoro-2-(4-methylpiperazin-1-yl)pyridin-4-amine

Scheme 48

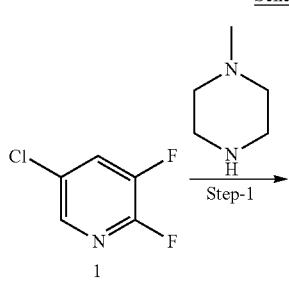

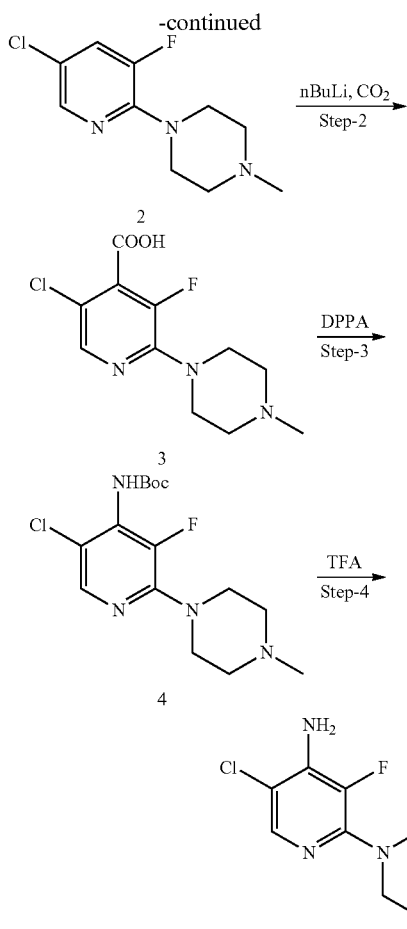

Compound numbers in text refer to structures shown in Scheme 48.

Step 1:

To a solution of compound 1 (5 g, 33.5 mmol, 1 eq) in Dry DMF (100 mL) was added 1-N-Methyl piperazine (1.7 mL, 13.4 mmol, 0.3 eq) followed by addition of DiPEA (10.2 mL, 56.9 mmol, 1.7 eq) at RT under Argon atmosphere and heated to 100° C. for 16 h. Then, the reaction mixture was cooled to RT and poured on ice-water (300 mL). The reaction mixture was extracted with EtOAc (2×100 mL); combined organic layer was dried over $Na_2SO_4$ and concentrated under reduced pressure to give a crude product. The crude product was purified by combiflash column chromatography using 10% EtOAc in petroleum ether as an eluent to give compound 2 (3.5 g, 45.63%) as a pale yellow solid. LC-MS: m/z 230.18 (M+H};

Step 2:

To a solution of DiPA (3.4 mL, 24.3 mmol, 1.6 eq) in Dry THF (90 mL) was added n-BuLi (1.6M in n-hexane, 16.2 mL, 25.9 mmol, 1.7 eq) at −78° C. and the mixture was allowed to warm up to −30° C. over 30 min. So freshly prepared LDA was added to a solution of compound 2 (3.5 g, 15.2 mmol, 1 eq) in Dry THF (30 mL) at −78° C. under Argon atmosphere and maintained for 2 h at the same temp. Then, powder of dry ice was added slowly at the same temp and the resulting mixture allowed to warm up to RT over 16 h. Then, the reaction mixture was quenched with sat.$NH_4Cl$ (50 mL) and washed with ether (2×20 mL). The aqueous layer was acidified with 1 M HCl and extracted with EtOAc (4×50 mL). The combined organic layer was dried over $Na_2SO_4$ and concentrated under reduced pressure to give a crude product. The crude product was washed with n-pentane & ether to give compound 3 (1.5 g, 37%) as an off-white solid.

Step 3:

To a solution of compound 3 (1.5 g, 5.74 mmol, 1 eq), TEA (0.88 mL, 6.23 mmol, 1.1 eq) in tBuOH (30 mL) at 5-10° C. temp, DPPA (1.89 g, 6.89 mmol, 1.2 eq) was added in a dropwise manner at the same temp. Then, the reaction mixture was heated to 85° C. for 16 h. TLC analysis indicated formation of a nonpolar spot. The reaction mixture was cooled to RT and concentrated under reduced pressure to give a residue, which was re-dissolved in EtOAc (60 mL) and washed with saturated brine. The separated organic layer was dried over $Na_2SO_4$ and concentrated under reduced pressure to give a crude product. The crude product was purified by combiflash column chromatography using 20% EtOAc in petroleum ether as an eluent to give compound 4 (0.8 g, 40% yield) as a pale yellow solid.

Step 4:

To a solution of compound 4 (0.8 g, 2.31 mmol, 1 eq) in DCM (10 mL) was added Trifluoroacetic acid (1.1 mL, 13.8 mmol, 6.0 eq) in a dropwise manner at 0° C. The resulting mixture was allowed to warm up to RT over 16 h. TLC analysis indicated formation of a polar spot. Then, the reaction mixture was concentrated under reduced pressure to give a TFA salt of the product, which was dissolved in water (20 mL), basified with sat.$NaHCO_3$ and extracted in EtOAc (3×30 mL). The combined organic layer was dried over $Na_2SO_4$ and concentrated under reduced pressure to give a crude product. The crude compound was purified by washing with n-pentane to give 5-chloro-3-fluoro-2-(4-methylpiperazin-1-yl)pyridin-4-amine (510 mg, 89.7%) as an off-white solid. LC-MS: m/z 245.1 (M+H);

Synthesis of (S)-5-chloro-2-(2-methyl-4-(2,2,2-trifluoroethyl)piperazin-1-yl)pyridin-4-amine Scheme 49

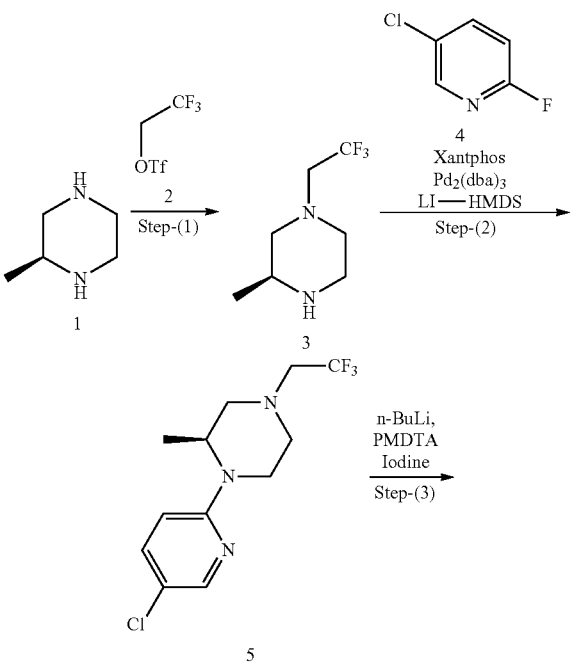

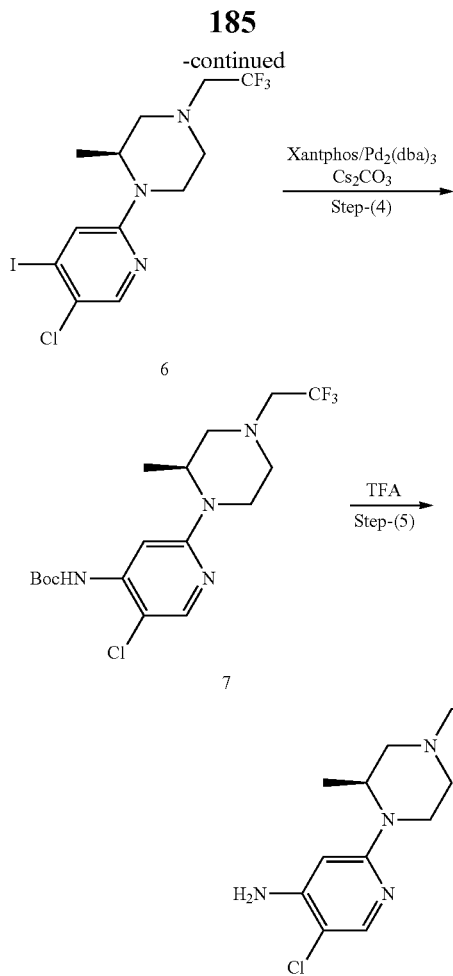

Compound numbers in text refer to structures shown in Scheme 49.

Step 1:

To a solution of compound 1 (4 g, 40.0 mmol, 1 eq) in EtOH (60 mL) was added DIPEA (17.4 mL, 100.0 mmol, 2.5 eq) and compound 2 (5.76 mL, 40.0 mmol, 1 eq) at RT, then the reaction mixture was continued for 16 h. The reaction mixture was concentrated to give a crude residue, which was diluted with EtOAc (100 mL) then washed with water (2×50 mL). The organic layer was dried over Na$_2$SO$_4$ then concentrated to give compound 3 (3 g, %) as a color less oil.

Step 2:

To a stirred mixture of compound 3 (3 g, 16.48 mmol, 1 eq) and compound 4 (4.31 g, 32.96 mmol, 2 eq) was added 1M Li-HMDS (164 mL, 164.83 mmol, 10 eq, in THF) at RT then added xantphos (571 mg, 0.989 mmol, 0.06 eq) and Pd$_2$(dba)$_3$ (452 mg, 0.494 mmol, 0.03 eq) at RT. The reaction mixture was heated to 80° C. for 16 h. TLC analysis indicated formation of a less polar spot. The reaction mixture was filtered through celite pad then the filtrate was concentrated to give a crude residue, which was diluted with EtOAc (100 mL) then washed with water (2×60 mL). The organic layer was dried over Na$_2$SO$_4$ then concentrated to a crude compound. The crude compound was purified by column chromatography (silica gel, 100-200 mesh) using 0-5% EtOAc in petroleum ether as eluent to afford compound 5 (3 g, %) as a color less oil. LC-MS: m/z 294.31 (M+H Step 3:

To a stirred solution of compound 5 (2.8 g, 9.55 mmol, 1 eq) in THF (30 mL) was added PMDTA (2.98 mL, 14.33 mmol, 1.5 eq) and n-BuLi (5.7 mL, 14.33 mmol, 1.5 eq) at −78° C. The reaction was continued for 1 h and a solution of 12 (4.85 g, 19.11 mmol, 2 eq, in THF) was added at −78° C. The mixture was then slowly allowed to warm up to RT for 16 h. TLC analysis indicated formation of a less polar spot. The reaction mixture was quenched with an aqueous solution of sodium thiosulphate then extracted with EtOAc (2×100 mL). The combined organic layer was dried over Na$_2$SO$_4$ then concentrated under reduced pressure to give compound 6 (2.6 g, %) as a pale brown oil. LC-MS: m/z 420.11 (M+H).

Step 4:

To a stirred solution of compound 6 (2.6 g, 6.20 mmol, 1 eq) in Toluene (30 mL) was added Cs$_2$CO$_3$ (4.0 g, 12.41 mmol, 2 eq) and NH$_2$Boc (863 mg, 7.44 mmol, 1.2 eq) at RT. The reaction mixture was de-gassed with Argon for 5 min., then xantphos (215 mg, 0.37 mmol, 0.06 eq) and Pd2(dba)3 (170 mg, 0.186 mmol, 0.03 eq) were added at RT. The reaction mixture was heated to 100° C. for 16 h. TLC analysis indicated formation of a polar spot. The reaction mixture was filtered through celite pad then filtrated was concentrated to crude compound. The crude compound was purified by column chromatography (silica gel, 100-2000 mesh) using 0-2% EtOAc in petroleum ether as eluent to afford compound 7 (2 g, %) as a color less oil. LC-MS: m/z 409.23 (M+H).

Step 5:

To a stirred solution of compound 7 (2.0 g, 4.90 mmol, 1 eq) in DCM (10 mL) was added TFA (3.75 mL, 49.01 mmol, 10 eq) at RT and the reaction continued for 16 h. TLC analysis indicated formation of a polar spot. The reaction mixture was concentrated to give a crude residue, which was basified by aqueous NaHCO$_3$ solution then extracted with EtOAc (3×50 mL). The combined organic layer was dried over Na$_2$SO$_4$ then concentrated under reduced pressure to give a crude compound. The crude compound was purified by column chromatography (silica gel, 100-200 mesh) using 0-15% EtOAc in petroleum ether as eluent to afford (S)-5-chloro-2-(2-methyl-4-(2,2,2-trifluoroethyl)piperazin-1-yl)pyridin-4-amine (1.3 g %) as a pale yellow solid. LC-MS: m/z 309.17 (M+H);

Synthesis of
3-chloro-2,5-difluoro-6-morpholinopyridin-4-amine

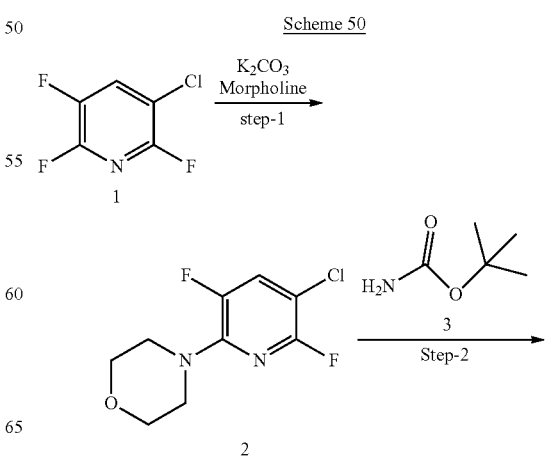

187

-continued

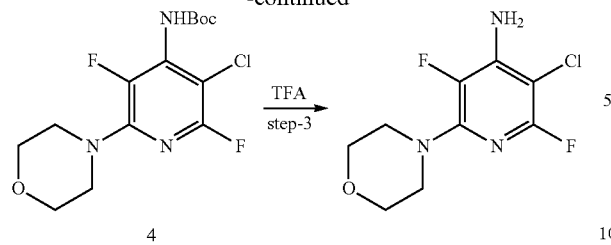

Compound numbers in text refer to structures shown in Scheme 50.

Step 1:

To a suspension of compound 1 (4.0 g, 23.9 mmol, 1.0 eq) in dry DMF (40 mL) cooled at −5° C., potassium carbonate (3.3 g, 23.9 mmol, 1.0 eq) and Morpholine (2.0 mL, 23.9 mmol, 1.0 eq) were added. The mixture was slowly warmed to RT for 3 h. TLC analysis indication formation of a polar spot. The reaction mixture was poured into ice cold water (2×500 mL) and extracted with EtOAc (2×250 mL). The separated organic layer was dried over with sodium sulfate and concentrated under reduced pressure to give a crude compound. The crude compound was purified by column chromatography by silica gel (100-200 mesh) using as an eluent 0-2% EtOAc in petroleum ether to give compound 2 (4.4 g, 78%).

Step 2:

To a suspension of compound 2 (4.9 g, 20.9 mmol, 1. eq) and compound 3 (2.44 g, 20.9 mmol, 1.0 eq) in LiHMDS (210 mL, 210.0 mmol, 10.0 eq), Xantphos (726 mg, 1.2 mmol, 0.06 eq) and Pd$_2$dba$_3$ (575 mg, 0.6 mmol, 0.03 eq) were added in a sealed tube. The reaction mixture was heated to 70° C. for 16 h. TLC analysis indicates the formation of a non-polar spot. The reaction mixture was diluted with EtOAc (200 mL) and washed with water (2×200 mL). The separated organic layer was dried over with sodium sulfate and concentrated under reduced pressure to give a crude compound. The Crude compound was purified by column chromatography by silica gel (100-200 mesh) using as an eluent 0-2% EtOAc in petroleum ether to give compound 4 (1.9 g, 27.53%)

Step 3:

To a solution of compound 3 (1.9 g, 5.7 mmol, 1.0 eq) in DCM (25 mL) was cooled to 0° C., TFA (6.0 mL, 68.8 mmol, 12 eq) was added drop wise and the reaction mixture was stirred at RT for 16 h. TLC analysis indicated formation of a polar spot. The reaction mass was concentrated under reduced pressure to give a crude residue. The crude residue was basified with satd. NaHCO$_3$ solution (200 mL) extracted with EtOAc (2×500 mL). The separated organic layer was dried over with Na$_2$SO$_4$ and concentrated under reduced pressure to give 3-chloro-2,5-difluoro-6-morpholinopyridin-4-amine (1.05 g, 80.8%) as a brown solid.

188

Synthesis of 5-fluoro-3-methyl-2-morpholinopyridin-4-amine

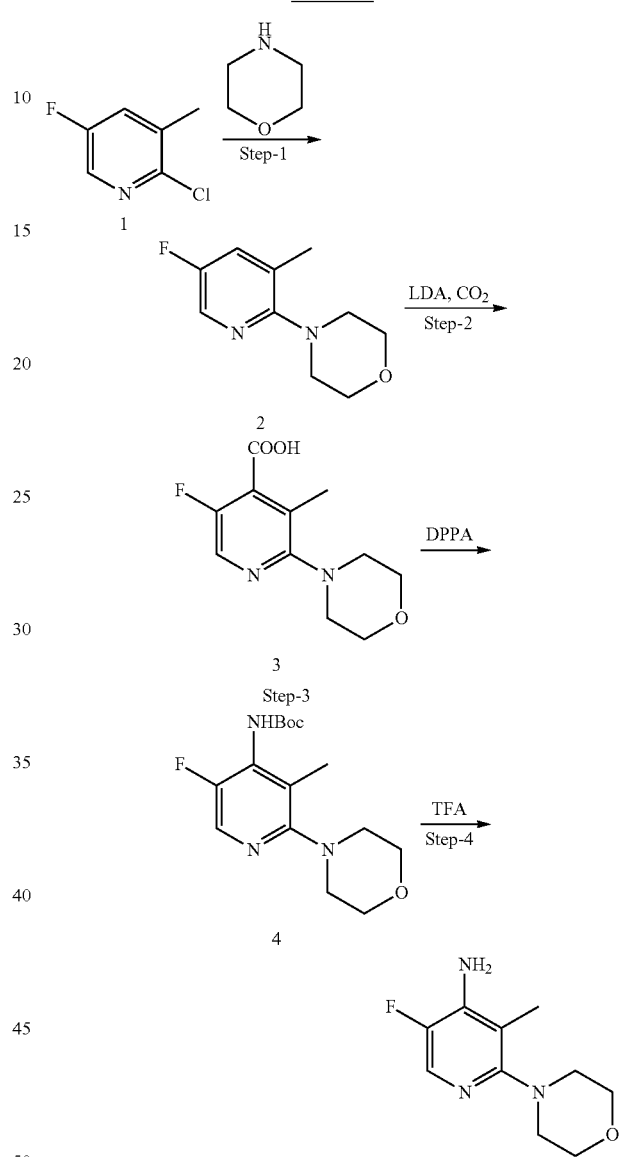

Compound numbers in text refer to structures shown in Scheme 51.

Step 1:

A solution of compound 1 (3 g, 20.6 mmol, 1 eq), Morpholine (1.78 mL, 20.6 mmol, 1 eq) and NaOtBu (3.97 g, 41.3 mmol, 2 eq) in Dry Toluene (30 mL) was degassed for 30 min, followed by the addition of Pd$_2$(dba)$_3$ (0.94 g, 1.03 mmol, 0.05 eq), and BINAP (0.64 g, 1.03 mmol, 0.05 eq). The reaction mixture was heated to 90-95° C. for 2 h in sealed tube. Then, the reaction mixture was cooled to RT and filtered through celite bed; celite bed was washed with EtOAc (10 mL). After solvent evaporation, the residue was purified by Combiflash column chromatography using 7% EtOAc in petroleum ether as an eluent to give compound 2 (2.5 g, 62.03%) as a pale yellow solid. LC-MS: m/z 197.30 (M+H);

Step 2:
To a solution of DiPA (3.65 mL, 20.4 mmol, 1.6 eq) in Dry THF (10 mL) was added n-BuLi (1.6M in n-hexane, 13.5 mL, 21.6 mmol, 1.7 eq) at −78° C. and the mixture allowed to warm up to −30° C. over 30 min. So freshly prepared LDA was added to a solution of compound 2 (2.5 g, 12.5 mmol, 1 eq) in Dry THF (50 mL) at −78° C. under Argon atmosphere and maintained for 4 h at the same temp. Then, powder of dry ice was added slowly at the same temp and the mixture allowed to warm up to RT over 16 h. Then, the reaction mixture was quenched with sat.NH$_4$Cl (50 mL) and washed with ether (2×20 mL). The aqueous layer was acidified with 1 M HCl and extracted with EtOAc (4×50 mL). The combined organic layer was dried over Na$_2$SO$_4$ and concentrated under reduced pressure to give a crude product. The crude product was washed with n-pentane and ether to give compound 3 (2.5 g, 83.34%) as a pale yellow solid. LC-MS: m/z 241 (M+H);

Step 3:
To a solution of compound 3 (2.5 g, 10.41 mmol, 1 eq), TEA (1.6 mL, 11.38 mmol, 1.1 eq) in tBuOH: Toluene (25 mL:25 mL) at 5-10° C. temp, DPPA (2.52 mL, 11.63 mmol, 1.12 eq) was added in a drop wise manner at the same temp. Then, the reaction mixture was heated to 85° C. for 16 h. TLC analysis indicated formation of a non polar spot. The reaction mixture was cooled to RT and concentrated under reduced pressure to give a residue, which was re-dissolved in EtOAc (100 mL) and washed with sat.brine. The separated organic layer was dried over Na$_2$SO$_4$ and concentrated under reduced pressure to give a crude product that was purified by combiflash column chromatography using 15% EtOAc in petroleum ether as an eluent to give compound 4 (2.7 g, 84.37% yield) as an off white solid. LC-MS: m/z 312.16 (M+H);

Step 4:
To a solution of compound 4 (2.7 g, 8.68 mmol, 1 eq) in DCM (30 mL) was added Trifluoroacetic acid (8.3 mL, 103.4 mmol, 12 eq) in a drop wise manner at 0° C. and allowed to warm up to RT over 6 h. TLC analysis indicated formation of a polar spot. Then, the reaction mixture was concentrated under reduced pressure to give a TFA salt of the product. The TFA salt was dissolved in water (20 mL), basified with sat.NaHCO$_3$ and extracted in EtOAc (3×50 mL). The combined organic layer was dried over Na$_2$SO$_4$ and concentrated under reduced pressure to give a crude product. The crude compound was purified by washing with n-pentane to give 5-fluoro-3-methyl-2-morpholinopyridin-4-amine (1.8 g, 100%) as an off white solid. LC-MS: m/z 212.40 (M+H);

Synthesis of
3,5-difluoro-2-morpholinopyridin-4-amine

Scheme 52

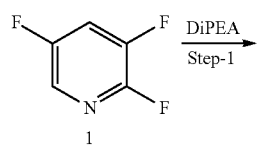

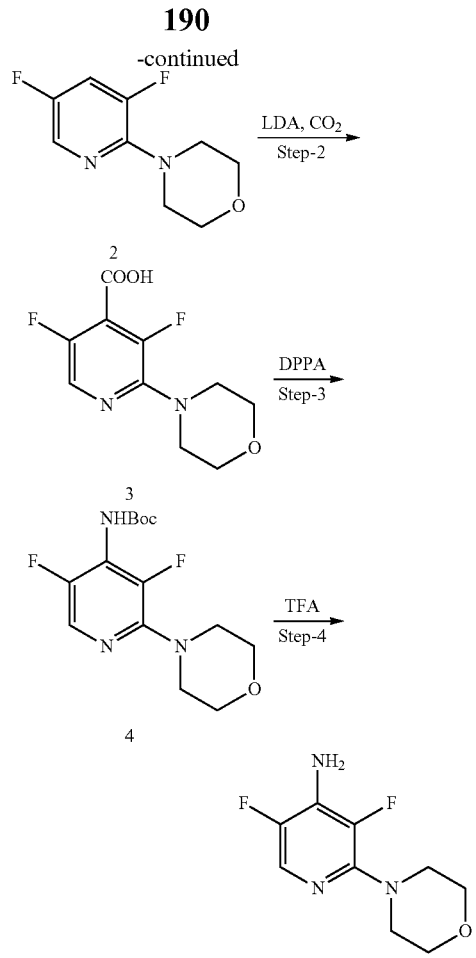

Compound numbers in text refer to structures shown Scheme 52.

Step 1:
To a solution of compound 1 (5 g, 33.5 mmol, 1 eq) in Dry DMF (50 mL) was added Morpholine (0.95 mL, 11 mmol, 0.3 eq) followed by addition of DiPEA (10.2 mL, 56.9 mmol, 1.7 eq) at RT under Argon atmosphere and heated to 80° C. for 5 h. Then, the reaction mixture was cooled to RT and poured in ice-water (300 mL). The reaction mixture was extracted with EtOAc (2×100 mL). The combined organic layer was dried over Na$_2$SO$_4$ and concentrated under reduced pressure to give a crude product. The crude product was purified by combiflash column chromatography using 3% EtOAc in petroleum ether as an eluent to give compound 2 (2.5 g, 37.31%) as an off white solid.

Step 2:
To a solution of DiPA (3.58 mL, 20 mmol, 1.6 eq) in Dry THF (250 mL) was added n-BuLi (1.6M in n-hexane, 13.3 mL, 1.7 eq) at −78° C. and allowed to −30° C. over 30 min. So freshly prepared LDA was added to a solution of compound 2 (2.5 g, 12.5 mmol, 1 eq) in Dry THF (50 mL) at −78° C. under Argon atmosphere and the reaction was maintained for 2 h at the same temp. Then, powder of dry ice was added slowly at the same temp and the mixture allowed to warm up to RT over 16 h. Then, the reaction mixture was quenched with sat.NH$_4$Cl (50 mL) and washed with ether (2×20 mL). The aqueous layer was acidified with 1 M HCl and extracted with EtOAc (4×50 mL). The combined organic layer was dried over Na$_2$SO$_4$ and concentrated under reduced pressure to give a crude product. The crude product was washed with n-pentane & ether to give compound 3 (1.5 g, 49.18%) as an off white solid. LCMS: m/z 245.01 (M+H):

Step 3:

To a solution of compound 3 (1.5 g, 6.14 mmol, 1 eq), TEA (0.93 mL, 6.73 mmol, 1.1 eq) in tBuOH: Toluene (10 mL:10 mL) at 5-10° C. temp, DPPA (1.5 mL, 6.87 mmol, 1.12 eq) was added in a drop wise manner at the same temp. Then, the reaction mixture was heated to 85° C. for 16 h. TLC analysis indicated formation of a non polar spot. The reaction mixture was cooled to RT and concentrated under reduced pressure to give a residue; which was re-dissolved in EtOAc (60 mL) and washed with sat.brine. The separated organic layer was dried over $Na_2SO_4$ and concentrated under reduced pressure to give a crude product was purified by combiflash column chromatography using 20% EtOAc in petroleum ether as an eluent to give compound 4 (1.5 g, 78.94% yield) as an off white solid. LCMS: m/z 316.29 (M+H):

Step 4:

To a solution of compound 4 (1.5 g, 4.76 mmol, 1 eq) in DCM (15 mL) was added Trifluoroacetic acid (4.54 mL, 57.0 mmol, 12 eq) in a drop wise manner at 0° C. and the mixture was allowed to warm up to RT over 6 h. TLC analysis indicated formation of a polar spot. Then, the reaction mixture was concentrated under reduced pressure to give a TFA salt of the product, which was dissolved in water (20 mL), basified with sat.$NaHCO_3$ and extracted in EtOAc (3×30 mL). The combined organic layer was dried over $Na_2SO_4$ and concentrated under reduced pressure to give a crude product. The crude compound was purified by washing with n-pentane to give 3,5-difluoro-2-morpholinopyridin-4-amine (1.02 g, 100%) as an off white solid. LCMS: m/z 216.23 (M+H):

Synthesis of 6-chloroimidazo[1,2-a]pyridin-7-amine

Scheme 53

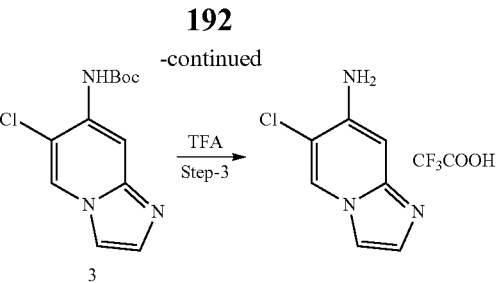

Compound numbers in text refer to structures shown Scheme 53.

Step 1:

To a solution of compound 1 (1 g, 3.8 mmol, 1 eq) in THF (15 mL) was added (2-biphenyl) dicyclohexylphopine (cyjhonphos) (108 mg, 0.305 mmol, 0.08 eq) at RT then degassed with argon for 10 min. $Pd_2(dba)_3$ (105 mg, 0.114 mmol, 0.03 eq) and LiHMDS (12 mL, 1M in THF, 12 mmol, 3.0 eq) were then added at RT in a sealed tube and the resulting mixture heated to 90° C. for 16 h. TLC analysis indicated formation of a polar spot. The reaction mixture was quenched with $NH_4Cl$ solution (100 mL) and extracted with EtOAc (50 mL×3). The combined organic layer was dried over $Na_2SO_4$ and concentrated under reduced pressure to give a crude product. The crude product was purified by combi flash using 0-30% EtOAc in petroleum ether as eluent to give analytically pure compound 2 (450 mg, 48.5%) as a light brown solid.

Step 2:

To a solution of compound 1 (1.5 g, 6.17 mmol, 1 eq) in EtOH (15 mL) was added chloroacetaldehyde 45% (9.6 mL, 61.75 mmol, 10 eq), $NaHCO_3$ (1.03 g, 12.34 mmol, 2.0 eq) at 0° C. then heated to 90° C. for 5 h. TLC analysis indicated formation of a polar spot. The reaction mixture was diluted with $H_2O$ (100 mL) and extracted with EtOAc (50 mL×3). The combined organic layer was dried over $Na_2SO_4$ and concentrated under reduced pressure to give a crude product. The crude product was purified by combi flash using 0-3% MeOH in DCM as eluent to give analytically pure compound 3 (1.3 g, 79%) as a light brown solid. LCMS: m/z 268.0% (M+H):

Step 3:

To a solution of compound 3 (1.3 g, 4.860 mmol, 1 eq) in DCM (15 mL) was added TFA (13 mL, 10 vol.) at 0° C. and then the reaction mixture was allowed to warm up to RT for 16 h. TLC analysis indicated formation of a polar spot. The reaction mixture was concentrated under vacuum pressure to give a crude compound. The crude compound was triturated with pentane: Diethyl ether (7:3) (3 mL×10 mL). As an eluent to give 6-chloroimidazo[1,2-a]pyridin-7-amine (1.2 g, 93.7%) as light green color solid. LCMS: m/z 168.1% (M+H): Synthesis of 6-chloro-1-methylindolin-5-amine Scheme 54

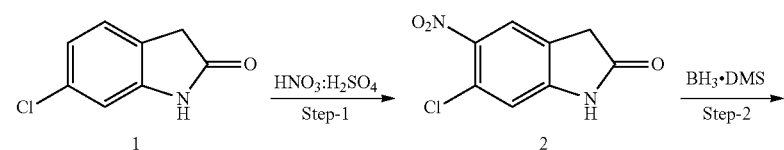

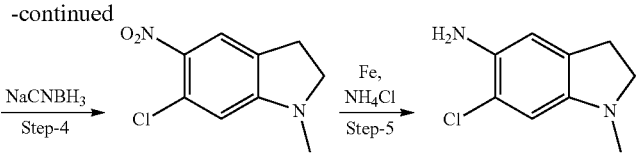

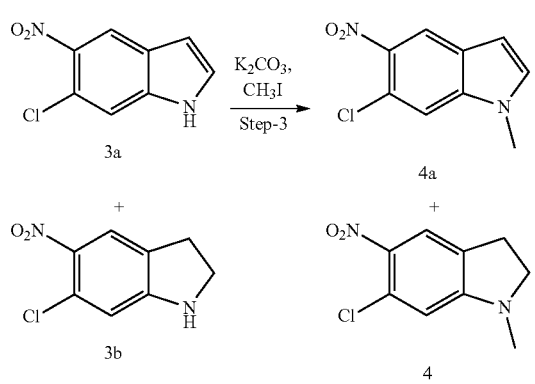

Compound numbers in text refer to structures shown in Scheme 54.

Step 1:

A solution of compound 1 (5 g, 29.83 mmol, 1 eq) in conc.H$_2$SO$_4$ (100 mL) was cooled to −10 to −15° C. (NaCl-ice mixture), followed by an dropwise addition of a pre-cooled (0° C.) solution of conc.HNO$_3$ (1.38 mL) in conc.H$_2$SO$_4$ (12.5 mL) at below −10° C. under vigorous stirring to avoid any rise in temp. The reaction was maintained for another 30 min. at the same temp. TLC analysis indicated formation of a polar spot. Then, the reaction mixture was slowly poured into ice-water with stirring to give a dark red precipitate, which was filtered off, washed with cold water and dried under vacuum. The crude product was purified by column chromatography (SiO$_2$) using 80% EtOAc in petroleum ether as an eluent to give compound 2 (3.6 g, 56.92%) as a red color solid.

Step 2:

To a solution of compound 2 (3.5 g, 16.46 mmol, 1 eq) in Dry THF (35 mL) at 0° C., a solution of BH$_3$.DMS (2M in THF, 14.82 mL, 29.63 mmol, 1.8 eq) was added dropwise under Argon atmosphere. Then, the reaction mixture was heated to reflux for 1 h. Then, the reaction mixture was cooled to 0° C., followed by quenching with MeOH (30 mL) and stirred for 16 h at RT. Then, reaction mixture was concentrated under reduced pressure to give a crude compound. The crude compound was purified by column chromatography using 10-12% EtOAc in petroleum ether as an eluent to give an inseparable mixture of compound 3a & 3b (2.5 g); LC-MS: m/z 197.25 (M+H).

Step 3:

To a solution of compound 3a & 3b (2 g, 12.71 mmol, 1 eq), K$_2$CO$_3$ (2.64 g, 19.07 mmol, 1.5 eq) in Dry DMF (25 mL) was added CH$_3$I (0.79 mL, 12.71 mmol, 1 eq) in a dropwise manner at RT and stirred for another 5 h. TLC analysis indicated formation of a nonpolar spot. Then, the reaction mixture was quenched with cold water (250 mL) and extracted with EtOAc (3×50 mL). The combined organic layer was dried over Na$_2$SO$_4$ and concentrated under reduced pressure to give a crude product. The crude product was washed with n-pentane to give an inseparable mixture of compound 4 &4a (2.5 g) as yellow solid. LC-MS: m/z 213.26 (M+H);

Step 4:

To a solution of compound 4 &4a (2.5 g, 11.86 mmol, 1 eq) in glacial acetic acid (25 mL) at RT, NaCNBH$_3$ (2.24 g, 35.60 mmol, 3 eq) was added at RT and stirred for 16 h. The reaction mixture was slowly neutralized with Sat.NaHCO$_3$ solution to pH7-8 and extracted with EtOAc (3×100 mL). The combined organic layer was dried over Na$_2$SO$_4$ and concentrated under reduced pressure to give 2.5 g of crude compound 5. Crude product was taken up for next step without any purification. LC-MS: m/z 213.10 (M+H);

Step 5:

A suspension of crude compound 5 (67.40% pure by LCMS analysis, 2.5 g, 11.75 mmol, 1 eq), NH$_4$Cl (2.64 g, 49.82 mmol, 4.2 eq) & Fe powder (2.76 g, 49.38 mmol, 4.2 eq) in a mixture of EtOH: Water (25 mL: 25.6 mL) was heated to 80° C. for 4 h. After 4 h, TLC analysis indicated formation of a polar spot (Ninhydrin positive). Then, the reaction mixture was cooled to RT and filtered through celite bed; celite bed was washed with EtOH (20 mL); the filtrate was concentrated under reduced pressure to give a crude product. The crude product was purified by Prep.HPLC to give 6-chloro-1-methylindolin-5-amine (535 mg, 37.15% yield) as an off white solid. LC-MS: m/z 183.1 (M+H);

Synthesis of 6-chloro-1-methyl-1H-indazol-5-amine and 6-chloro-2-methyl-2H-indazol-5-amine

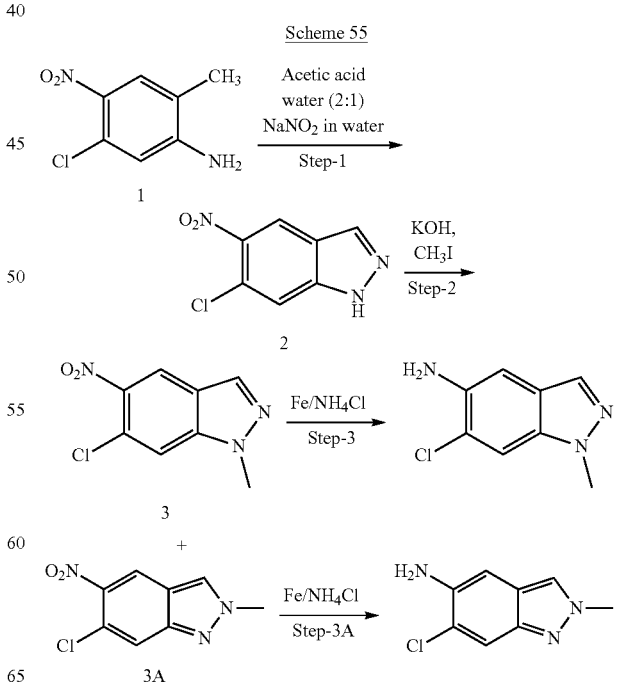

Compound numbers in text refer to structures shown Scheme 55.

Step 1:

To a solution of compound 1 (1 g, 5.36 mmol, 1 eq) in acetic acid: water (18 mL:9 mL), a solution of NaNO$_2$ (1.27 g, 18.42 mmol, 1.2 eq) in water (5 mL) was added at 0° C. and stirred for 6 h at 10° C. Then, the reaction mixture was quenched with Aq.NaOH solution (12 g, 300 mmol, 56 eq) in water (45 mL) and extracted with EtOAc (2×50 mL). The combined organic layer was dried over Na$_2$SO$_4$ and concentrated under reduced pressure to give a crude product, which was purified by column chromatography (silica gel 100-200mesh) using 10-20% EtOAc in petroleum ether as an eluent to give compound 2 (2 g, 38.46%) as a pale yellow solid.

Step 2:

To a precooled solution of compound 2 (2.5 g, 12.65 mmol, 1 eq) in dry DMF (50 mL) was added NaH (60%, 633 mg, 15.82 mmol, 1.25 eq) in a portion at 0° C. over 20 min. The reaction was stirred for 10 min, followed by addition of Methyl iodide (0.8 mL, 12.65 mmol, 1 eq) at the same temp. The reaction mixture was stirred for 30 min at 0° C. TLC analysis indicated formation of 2 new spots. Then, the reaction mixture was quenched with water (500 mL) and extracted with EtOAc (3×50 mL). The combined organic layer was dried over Na$_2$SO$_4$ and concentrated under reduced pressure to give a crude product, which was purified by column chromatography (silica gel 100-200mesh) using 15-30% EtOAc in petroleum ether as an eluent to give compound 3 (1.5 g, 56.39%) as pale yellow solid and another regeoisomer compound 3A (700 mg, 26.32%) as off white solid. LCMS: m/z 212.15% (M+H).

Step 3:

A suspension of compound 3 (1.5 g, 7.08 mmol, 1 eq), NH$_4$Cl (1.59 g, 29.77 mmol, 4.2 eq) & Fe powder (1.66 g, 29.77 mmol, 4.2 eq) in a mixture of EtOH: Water (15 mL: 15 mL) was heated to 80° C. for 6 h. After 6 h, TLC analysis indicated formation of a polar spot (Ninhydrin positive). Then, the reaction mixture was cooled to RT and filtered through celite bed; celite bed was washed with EtOH (50 mL); the combined filtrate was concentrated under reduced pressure to give a crude product. The crude product was purified by column chromatography (silica gel 100-200mesh) using 25% EtOAc in petroleum ether as an eluent to give 6-chloro-1-methyl-1H-indazol-5-amine (1.25 g, 97.65%) as an off-white solid. LCMS: m/z 182.04% (M+H):

Step 3A:

A suspension of compound 3 (700 mg, 3.31 mmol), NH$_4$Cl (1.59 g, 29.77 mmol) & Fe powder (1.66 g, 29.77 mmol) in a mixture of EtOH:Water (15 mL: 15 mL) was heated to 80° C. for 6 h. After 6 h, TLC analysis indicated formation of a polar spot (Ninhydrin positive). Then, the reaction mixture was cooled to RT and filtered through celite bed; celite bed was washed with EtOH (50 mL); filtrates was concentrated under reduced pressure to give a crude product. The crude product was purified by column chromatography (silica gel 100-200mesh) using 25% EtOAc in petroleum ether as an eluent to give 6-chloro-2-methyl-2H-indazol-5-amine (quantitative yield) as an off white solid. LCMS: m/z 182.04% (M+H):

Synthesis of 3-chloro-6-(4-methylpiperazin-1-yl)pyridin-2-amine

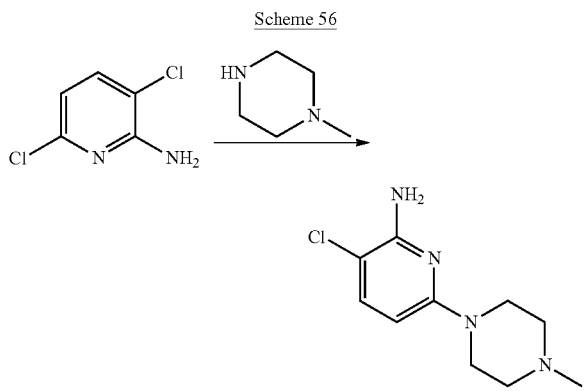

Scheme 56

In a microwave vial was placed 2-Amino-3,5,6-trichloropyridine (404 mg, 2.478 mmol), 1-Methylpiperazine (2.199 mL, 19.83 mmol) and Butan-1-ol (Volume: 5 mL). Then the reaction vial was sealed and heated in the microwave at 220° C. for 5 h to give a brown solution. The reaction mixture was concentrated (high vac) and purified by flash chromatography (SiO$_2$, DCM-MeOH, 1% NH$_4$OH) to give the product as a white-yellow solid; 3-chloro-6-(4-methylpiperazin-1-yl)pyridin-2-amine (502 mg, 2.104 mmol, 85% yield).

Synthesis of (S)-5-chloro-2-(4-isopropyl-2-methylpiperazin-1-yl)pyridin-4-amine

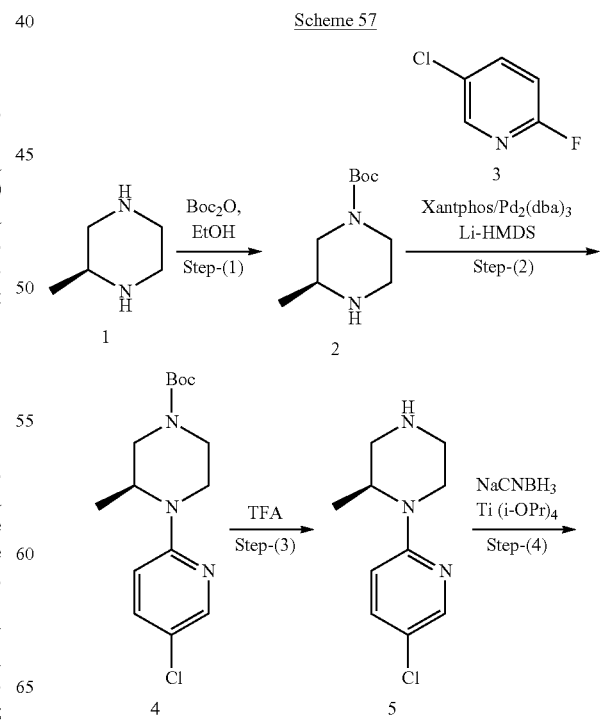

Scheme 57

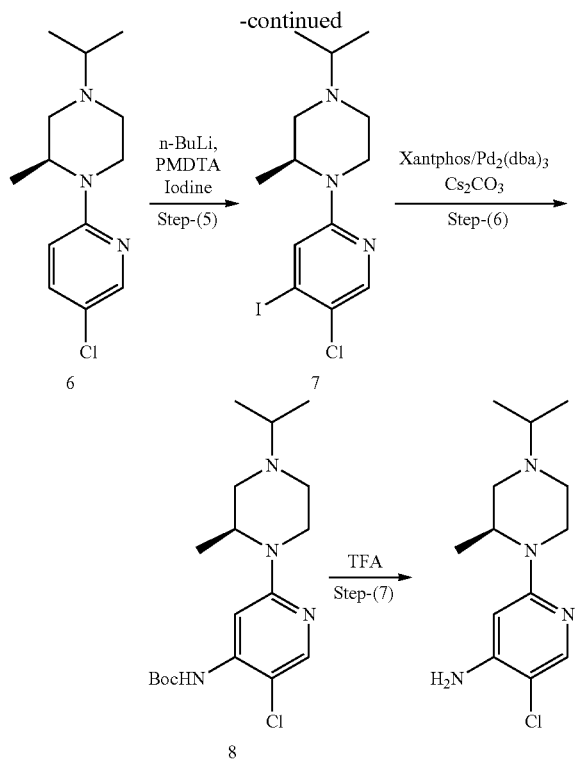

Compound numbers in text refer to structures shown in Scheme 57.

Step 1:

To a solution of compound 1 (10 g, 100 mmol, 1 eq) in EtOH (200 mL) was added DIPEA (43.58 mL, 250 mmol, 2.5 eq) and Boc$_2$O (21.8 mL, 100 mmol, 1 eq) at RT, then the reaction was continued for 16 h. TLC analysis indicated formation of a less polar spot. The reaction mixture was concentrated to a crude residue, which was diluted with water and extracted with EtOAc (3×100 mL). The combined organic layer was dried over Na$_2$SO$_4$ then concentrated to give compound 2 (18 g, 90%) as a colorless oil.

Step 2:

To a stirred solution of compound 2 (18 g, 90 mmol, 1 eq) was added compound 3 (23.58 g, 180 mmol, 2 eq), xantphos (1.56 g, 2.7 mmol, 0.03 eq), Pd$_2$(dba)$_3$ (2.47 g, 2.7 mmol, 0.03 eq) and Li-HMDS (450 mL, 450 mmol, 10 eq) at RT under argon atmosphere, then the reaction mixture was heated to 90° C. for 16 h. TLC analysis indicated formation of a less polar spot. The reaction mixture was cooled to RT then filtered through celite pad, which was washed with EtOAc (3times). The filtrate was diluted with water and extracted with EtOAc (3×100 mL). The combined organic layer was dried over Na$_2$SO$_4$ then concentrated to a crude residue. The crude residue was purified by column chromatography (silica gel, 100-200 mesh) using 0-10% EtOAc in petroleum ether as eluent to afford compound 4 (24 g, 85.74%) as brown oil. LC-MS: m/z 312.17 (M+H).

Step 3:

To a stirred solution of compound 4 (24 g, 77.17 mmol, 1 eq) in DCM (250 mL) was added TFA (58.64 mL, 771.70 mmol, 10 eq) at 0° C. then allowed to RT for 16 h. TLC analysis indicated formation of a polar spot. The reaction mixture was concentrated to a crude residue, which is basified with aqueous NaHCO$_3$solution then extracted with EtOAc (3×100 mL). The combined organic layer was dried over Na$_2$SO$_4$ then concentrated to a crude compound. The crude compound was purified by column chromatography (silica gel, 100-200 mesh) using 0-2% MeOH in DCM as eluent to afford compound 5 (14 g, 85.99%) as brown oil. LC-MS: with m/z 212.12 (M+H);

Step 4:

To a stirred solution of compound 5 (4 g, 18.95 mmol, 1 eq) in MeOH (40 mL) was added acetone (2.78 mL, 37.91 mmol, 2 eq) and Ti(i-OPr)$_4$ (8.4 mL, 28.43 mmol, 1.5 eq) at RT under argon atmosphere and the reaction continued for 2 h. NaCNBH$_3$ (2.39 g, 37.91 mmol, 2 eq) was then added at RT, and the mixture allowed to continue for 2 h. TLC analysis indicated formation of a less polar spot. The reaction mixture was diluted with water and filtered through celite pad and the filtrate was extracted with EtOAc (3×90 mL). The combined organic layer was dried over Na$_2$SO$_4$ then concentrated to obtain a crude compound. The crude compound was purified by column chromatography (silica gel, 100-200 mesh) using 0-2% MeOH in DCM as eluent to afford compound 6 (2.8 g, 58%) as brown oil. LC-MS: m/z 254.21 (M+H).

Step 5:

To a stirred solution of compound 6 (2.8 g, 11.06 mmol, 1 eq) in THF (30 mL) was added PMDTA (5.0 mL, 24.34 mmol, 2.2 eq) and n-BuLi (9.73 mL, 24.34 mmol, 2.2 eq, 2.5M in THF) at −78° C. under argon atmosphere then the reaction mixture was continued for 2 h. A solution of 12 (5.62 g, 22.13 mmol, 2 eq, in THF) was added at −78° C., and the mixture slowly allowed to warm up to RT for 16 h. TLC analysis indicated formation of a less polar spot. The reaction mixture was quenched in aqueous solution of sodium thiosulphate then extracted with EtOAc (3×80 mL). The combined organic layer was dried over Na$_2$SO$_4$ then concentrated under reduced pressure to give the crude compound 7 (4.2 g, crude) as a brown oil. LC-MS: m/z 380.14 (M+H);

Step 6:

To a stirred solution of compound 7 (4.2 g, 11.08 mmol, 1 eq) in Toluene (50 mL) was added Cs$_2$CO$_3$ (7.2 g, 22.16 mmol, 2 eq) and NH$_2$Boc (1.54 g, 13.29 mmol, 1.2 eq) at RT. The reaction mixture was de-gassed with Argon for 5 min., then xantphos (192 mg, 0.33 mmol, 0.03 eq) and Pd$_2$(dba)$_3$ (304 mg, 0.33 mmol, 0.03 eq) were added at RT. The reaction mixture was heated to 90° C. for 16 h. TLC analysis indicated formation of a polar spot. The reaction mixture was filtered through celite pad then the filtrate was concentrated to crude compound. The crude compound was purified by column chromatography (silica gel, 100-2000 mesh) using 0-1% MeOH in DCM as eluent to afford compound 8 (2.3 g, 56%, per two steps) as a brown oil. LC-MS: m/z 369.24 (M+H).

Step 7:

To a stirred solution of compound 8 (2.3 g, 6.30 mmol, 1 eq) in DCM (20 mL) was added TFA (4.78 mL, 63.01 mmol, 10 eq) at RT and the reaction continued for 16 h. TLC analysis indicated formation of a polar spot. The reaction mixture was concentrated to a crude residue, which was basified by aqueous NaHCO$_3$solution then extracted with EtOAc (3×60 mL). The combined organic layer was dried over Na$_2$SO$_4$ then concentrated under reduced pressure to give a crude compound. The crude compound was purified by column chromatography (silica gel, 100-200 mesh) using 0-2% MeOH in DCM as eluent to afford (S)-5-chloro-2-(4-isopropyl-2-methylpiperazin-1-yl)pyridin-4-amine (1.1 g 65%) as an off-white solid. LC-MS: 96.02% with m/z 269.2 (M+H);

Synthesis of (S)-5-chloro-2-(4-cyclopropyl-2-methylpiperazin-1-yl)pyridin-4-amine

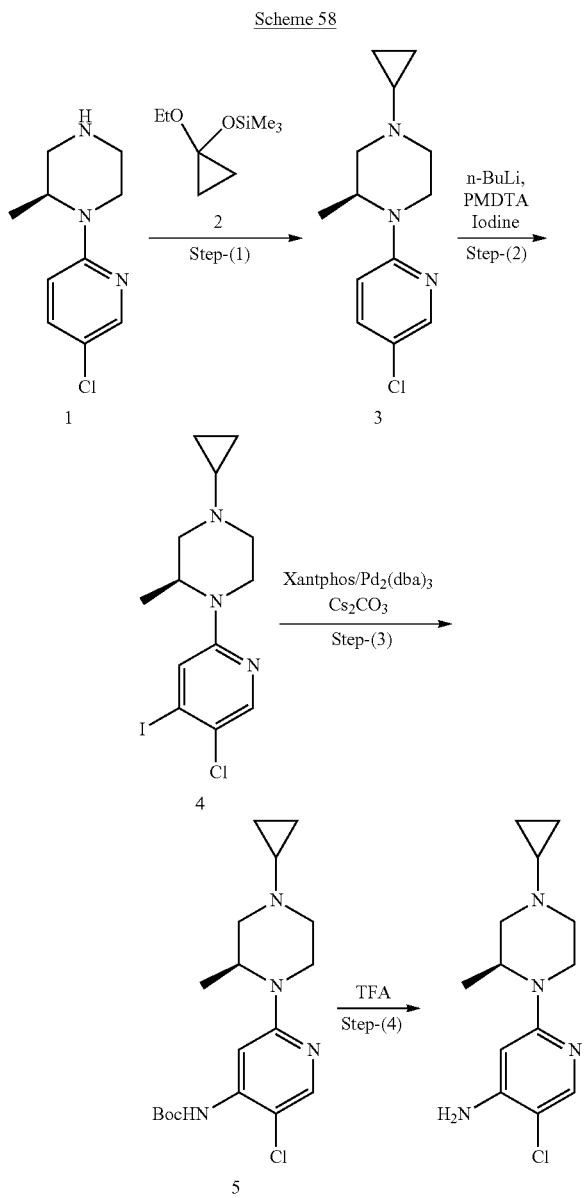

Scheme 58

Compound numbers in text refer to structures shown Scheme 58.

Step 1:

To a stirred solution of compound (S)-1-(5-chloropyridin-2-yl)-2-methylpiperazine (1, 4 g, 18.95 mmol, 1 eq) in MeOH (80 mL) was added compound 2 (18.95 mL, 94.78 mmol, 5 eq) and MS-4° (4 g) at RT. The mixture was then stirred for 10 min., followed by the addition of NaCNBH$_3$ (3.58 g, 56.87 mmol, 3 eq) at RT. The resulting mixture was heated to 70° C. for 4 h. TLC analysis indicated formation of a less polar spot. The reaction mixture was basified with aqueous NaHCO$_3$ solution and filtered through celite pad. The filtrate was extracted with EtOAc (3×90 mL). The combined organic layer was dried over Na$_2$SO$_4$ then concentrated to a crude compound. The crude compound was purified by column chromatography (silica gel, 100-200 mesh) using 0-10% EtOAc in petroleum ether as eluent to afford compound 3 (2.7 g, 56%) as a brown semi-solid.

Step 2:

To a stirred solution of compound 3 (3 g, 11.95 mmol, 1 eq) in THF (80 mL) was added PMDTA (5.48 mL, 26.29 mmol, 2.2 eq) and n-BuLi (10.5 mL, 26.29 mmol, 2.2 eq, 2.5M in THF) at −78° C. under argon atmosphere. The reaction mixture was continued for 2 h and was added a solution of 12 (6.07 g, 23.90 mmol, 2 eq, in THF) at −78° C. The resulting mixture was slowly allowed to warm to RT for 16 h. TLC analysis indicated formation of a less polar spot. The reaction mixture was quenched in aqueous solution of sodium thiosulphate then extracted with EtOAc (3×80 mL). The combined organic layer was dried over Na$_2$SO$_4$ then concentrated under reduced pressure to give crude compound 4 (4.5 g, crude) as a brown semi-solid. LC-MS: 91.73% with m/z 378.49 (M+H Step 3:

To a stirred solution of compound 4 (4.5 g, 11.93 mmol, 1 eq) in Toluene (100 mL) was added Cs$_2$CO$_3$ (7.75 g, 23.87 mmol, 2 eq) and NH$_2$Boc (1.66 g, 14.32 mmol, 1.2 eq) at RT. The reaction mixture was de-gassed with Argon for 5 min., then xantphos (206 mg, 0.35 mmol, 0.03 eq) and Pd$_2$(dba)$_3$ (328 mg, 0.35 mmol, 0.03 eq) were added at RT. The reaction mixture was heated to 90° C. for 16 h. TLC analysis indicated formation of polar spot. The reaction mixture was filtered through celite pad then the filtrate was concentrated to a crude compound. The crude compound was purified by column chromatography (silica gel, 100-2000 mesh) using 0-5% EtOAc in petroleum ether as eluent to afford compound 5 (2.5 g, 57%,) as a brown oil. LC-MS: m/z 367.36 (M+H).

Step 4:

To a stirred solution of compound 5 (2.5 g, 6.83 mmol, 1 eq) in DCM (20 mL) was added TFA (5.19 mL, 68.30 mmol, 10 eq) at RT and the reaction continued for 16 h. TLC analysis indicated formation of a polar spot. The reaction mixture was concentrated to a crude residue, which was basified by aqueous NaHCO$_3$ solution then extracted with EtOAc (3×80 mL). The combined organic layer was dried over Na$_2$SO$_4$ then concentrated under reduced pressure to crude compound. The crude compound was purified by column chromatography (silica gel, 100-200 mesh) using 0-1% MeOH in DCM as eluent to afford (S)-5-chloro-2-(4-cyclopropyl-2-methylpiperazin-1-yl)pyridin-4-amine (1.4 g 77%) as pale yellow semi-solid. LC-MS: m/z 267.0 (M+H);

Synthesis of (S)-5-chloro-2-(2-methyl-4-((1-methylcyclopropyl)methyl)piperazin-1-yl)pyridin-4-amine

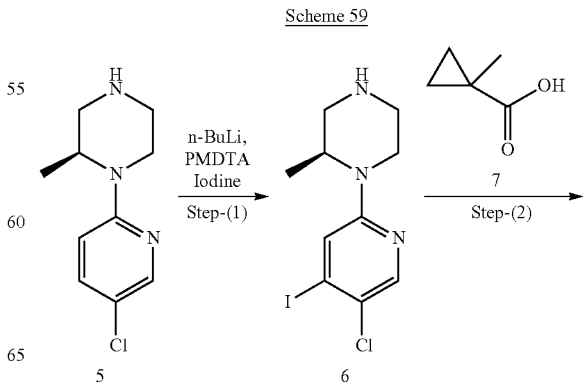

Scheme 59

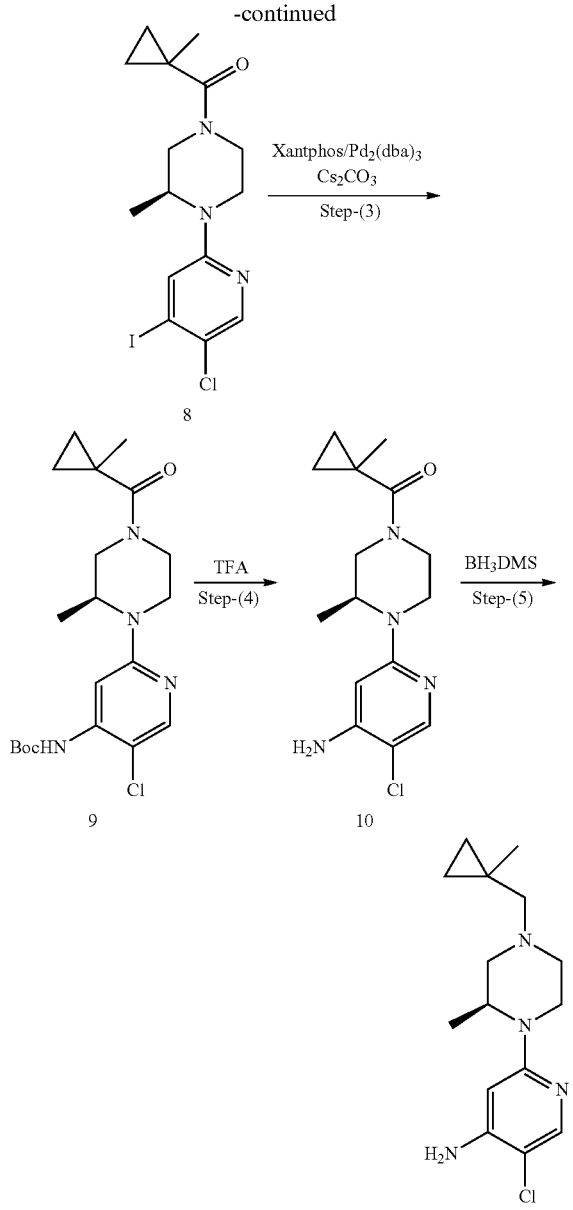

Compound numbers in text refer to structures shown Scheme 59.

Step 1:

To a stirred solution of compound 5 (10 g, 47.3 mmol, 1 eq) in THF (40 mL) was added NaH (1.36 g, 56.8 mmol, 1.2 eq) at 0° C. The solution was stirred for 30 mins, then cooled to −78° C. PMDTA (41.0 mL, 189.5 mmol, 4 eq) and n-BuLi (75.8 mL, 189.5 mmol, 4 eq, 2.5M in THF) was added at −78° C. under argon atmosphere. The reaction mixture was continued for 2 h and a solution of 12 (24.0 g, 94.7 mmol, 2 eq, in THF(100 mL)) was added at −78° C. that the reaction was slowly allowed to warm up to RT for 16 h. TLC analysis indicated formation of a less polar spot. The reaction mixture was quenched in aqueous solution of sodium thiosulphate, then extracted with EtOAc (2×200 mL). The combined organic layer was dried over Na₂SO₄ then concentrated under reduced pressure to give crude compound 6 (8 g, crude) as a brown oil. LC-MS: 59.86% with m/z 338.24 (M+H).

Step 2:

To a stirred solution of compound 6 (8 g, 23.8 mmol, 1 eq) in DCM:DMF (40:40 mL) and compound 7 (2.38 g, 23.8 mol, 1 eq) was added EDC. HCl (6.8 g, 35.7 mmol, 1.5 eq) and HOBt (4.82 g, 35.7 mmol, 1.5 eq) at 0° C. under argon atmosphere followed by DiPEA (12.2 mL, 71.4 mmol, 3 eq). The mixture was allowed to warm up to RT over 16 h. TLC analysis indicated formation of a less polar spot. The reaction mixture was diluted with water (500 mL) and extracted with EtOAc (2×200 mL). The organic layer was washed with water (2×200 mL), dried over Na₂SO₄ and concentrated under reduced pressure to give a crude product. The crude product was purified by column chromatography (silica gel 100-200 mesh) using 5-10% EtOAc in petroleum ether as an eluent to give compound 8 (3 g, 43.08%) as a pale yellow color liquid. LC-MS: 84.08% with m/z 419.84 (M+H).

Step 3:

To a stirred solution of compound 8 (3 g, 7.15 mmol, 1 eq) in Toluene (30 mL) was added $Cs_2CO_3$ (4.65 g, 14.31 mmol, 2 eq) and $NH_2Boc$ (1 g, 8.59 mmol, 1.2 eq) at RT. The reaction mixture was de-gassed with Argon for 5 min., then xantphos (240 mg, 0.42 mmol, 0.06 eq) and $Pd_2(dba)_3$ (190 mg, 0.21 mmol, 0.03 eq) were added at RT. The reaction mixture was then heated to 90° C. for 16 h. TLC analysis indicated formation of a polar spot. The reaction mixture was filtered through celite pad. The filtrate was concentrated to a crude compound. The crude compound was purified by column chromatography (silica gel, 100-2000 mesh) using 0-30% EtOAc in Petroleum ether as eluent to afford compound 9 (2.5 g, 87%) as a brown oil. LC-MS: 93.84% with m/z 408.96 (M+H).

Step 4:

To a stirred solution of compound 9 (3.5 g, 8.55 mmol, 1 eq) in DCM (30 mL) was added TFA (6.5 mL, 85.52 mmol, 10 eq) at RT and the reaction continued for 16 h. TLC analysis indicated formation of a polar spot. The reaction mixture was concentrated to give a crude residue, which was basified by aqueous $NaHCO_3$ solution then extracted with EtOAc (3×60 mL). The combined organic layer was dried over Na₂SO₄ then concentrated under reduced pressure to afford compound 10 (2.2 g 58%) as an off-white solid. LC-MS: 86.81% with m/z 308.92 (M+H).

Step 5:

To a stirred solution of compound 10 (2.2 g, 7.0 mmol, 1 eq) in THF (25 mL) was added $BH_3DMS$ (3.54 mL, 35.48 mmol, 10 eq) at 0° C.-RT and the reaction continued for 16 h. TLC analysis indicated formation of a less polar spot. The reaction mixture was cooled to 0° C. and quenched with methanol stirred at rt for another 16 h. TLC analysis indicated formation of a less polar spot. The mixture was concentrated to give a crude residue, which was then extracted with EtOAc (2×100 mL). The combined organic layer was dried over Na₂SO₄ then concentrated under reduced pressure. The crude compound was purified by column chromatography (silica gel, 100-2000 mesh) using 0-20% EtOAc in Petroleum ether as eluent to afford (S)-5-chloro-2-(2-methyl-4-((1-methylcyclopropyl)methyl)piperazin-1-yl)pyridin-4-amine (1.1 g, 87%) as an off-white solid. LC-MS: 97.48% with m/z 295.19 (M+H).

203
Synthesis of (S)-5-chloro-2-(4-cyclobutyl-2-methylpiperazin-1-yl)pyridin-4-amine

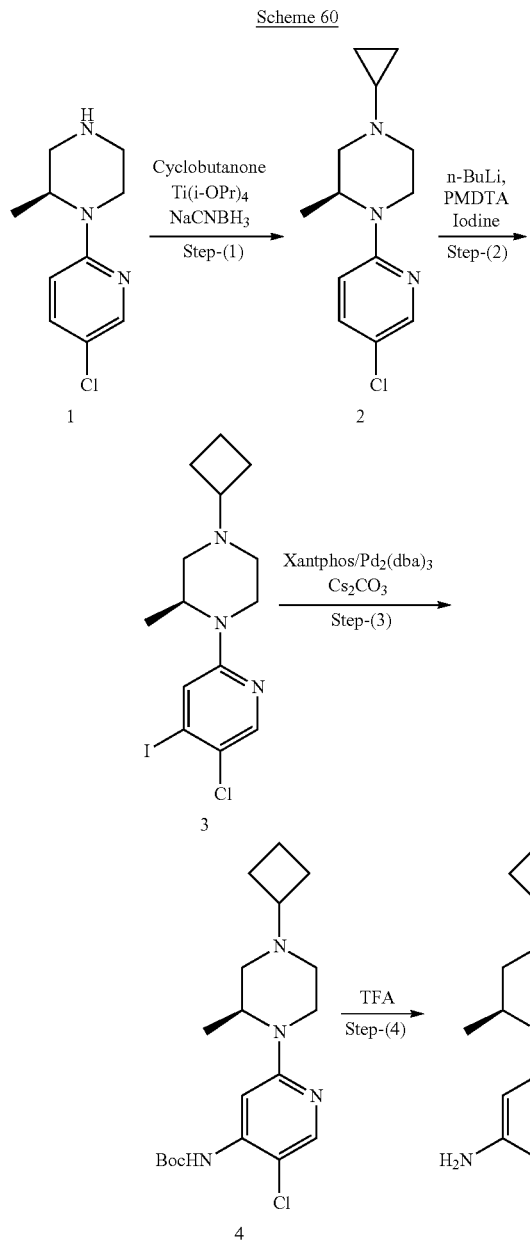

Compound numbers in text refer to structures shown in Scheme 60.

Step 1:

To a stirred solution of compound 1 (3 g, 14.21 mmol, 1 eq) in MeOH (60 mL) was added cyclobutanone (1.6 mL, 21.32 mmol, 1.5 eq), Ti(i-OPr)$_4$ (6.3 mL, 21.32 mmol, 1.5 eq) and STAB (6.0 g, 28.43 mmol, 2 eq) at 0° C. under argon atmosphere. The reaction mixture was allowed to warm up to RT for 16 h. NaCNBH$_3$ (1.8 g, 28.43 mmol, 2 eq) was then added at RT, again continued for 2 h. TLC analysis indicated formation of a less polar spot. The reaction mixture was diluted with water and filtered through celite pad and the filtrate was extracted with EtOAc (3×90 mL). The combined organic layer was dried over Na$_2$SO$_4$ then concentrated to a crude compound. The crude compound was purified by column chromatography (silica gel, 100-200 mesh) using 0-0.5% MeOH in DCM as eluent to afford compound 2 (2.4 g, 63%) as a brown semi-solid.

Step 2:

To a stirred solution of compound 2 (2.8 g, 10.56 mmol, 1 eq) in THF (60 mL) was added PMDTA (4.7 mL, 23.24 mmol, 2.2 eq) and n-BuLi (9.3 mL, 23.24 mmol, 2.2 eq, 2.5M in THF) at −78° C. under argon atmosphere. The reaction was continued for 2 h and a solution of 12 (5.36 g, 21.13 mmol, 2 eq, in THF) was added at −78° C. The mixture was slowly allowed to warm up to RT for 16 h. TLC analysis indicated formation of a less polar spot. The reaction mixture was quenched in aqueous solution of sodium thiosulphate then extracted with EtOAc (3×80 mL). The combined organic layer was dried over Na$_2$SO$_4$ then concentrated under reduced pressure to give crude compound 3 (4.1 g, crude) as a brown semi-solid. LC-MS: m/z 392.55 (M+H).

Step 3:

To a stirred solution of compound 3 (4.1 g, 10.48 mmol, 1 eq) in Toluene (100 mL) was added Cs$_2$CO$_3$ (6.81 g, 20.97 mmol, 2 eq) and NH$_2$Boc (1.45 g, 12.58 mmol, 1.2 eq) at RT. The reaction mixture was de-gassed with Argon for 5 min., then xantphos (181 mg, 0.31 mmol, 0.03 eq) and Pd$_2$(dba)$_3$ (288 mg, 0.31 mmol, 0.03 eq) were added at RT. The reaction mixture was then heated to 90° C. for 16 h. TLC analysis indicated formation of a polar spot. The reaction mixture was filtered through celite pad. The filtrate was concentrated to give a crude residue. The crude residue was purified by column chromatography (silica gel, 100-2000 mesh) using 0-1% MeOH in DCM as eluent to afford compound 4 (2.5 g, 62%, per two steps) as a brown oil. LC-MS: m/z 381.04 (M+H).

Step 4:

To a stirred solution of compound 4 (2.5 g, 6.57 mmol, 1 eq) in DCM (20 mL) was added TFA (5.0 mL, 65.78 mmol, 10 eq) at RT and the reaction continued for 16 h. TLC analysis indicated formation of a polar spot. The reaction mixture was concentrated to crude, which was basified by aqueous NaHCO$_3$ solution then extracted with EtOAc (3×80 mL). The combined organic layer was dried over Na$_2$SO$_4$ then concentrated under reduced pressure to give a crude residue. The crude residue was purified by column chromatography (silica gel, 100-200 mesh) using 0-1% MeOH in DCM as eluent to afford (S)-5-chloro-2-(4-cyclobutyl-2-methylpiperazin-1-yl)pyridin-4-amine (1.1 g 59%) as a pale yellow gummy. LC-MS: m/z 281.0 (M+H); Synthesis of (S)-5-chloro-2-(2-isopropyl-4-methylpiperazin-1-yl)pyridin-4-amine Scheme 61

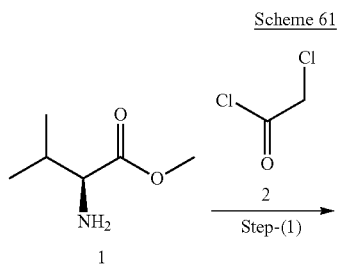

205
-continued

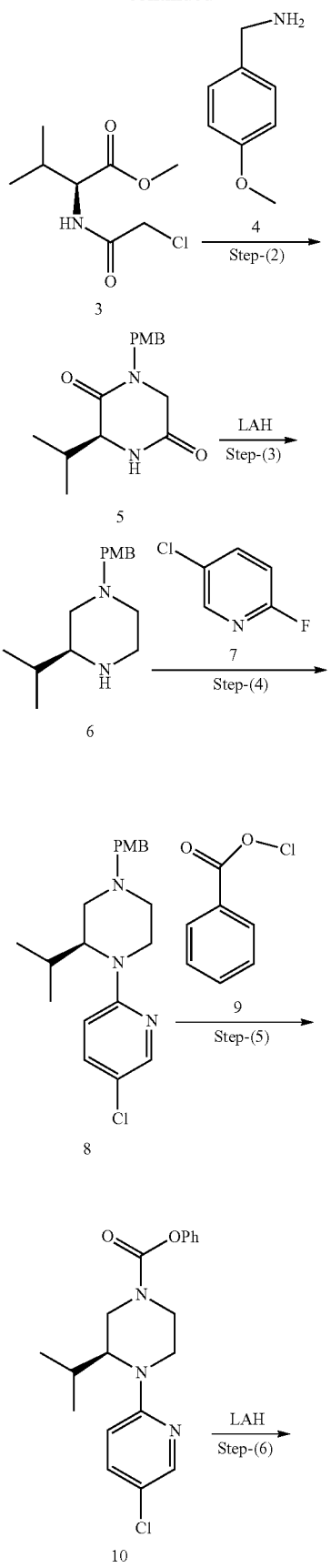

206
-continued

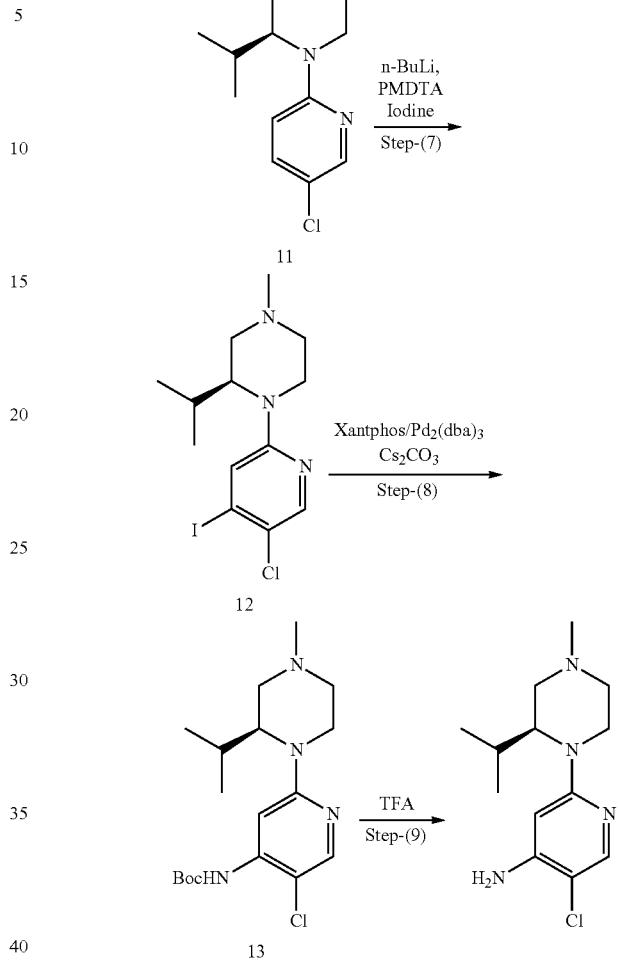

Compound numbers in text refer to structures shown in Scheme 61.

Step 1:

To a solution of compound 1 (34 g, 209.5 mmol, 1.0 eq) in DM Water (102 mL) was added NaHCO$_3$ (43 g, 519.0 mmol, 2 eq) at 5° C., then a solution of compound 2 (26.3 g, 233.5 mmol, 0.9 eq) in Toluene (68 mL) was added at the same temperature. The reaction mixture was allowed to warm up to RT and stirred for 18 h. TLC analysis indication of a less polar spot. The reaction mixture was diluted with water and extracted with EtOAc (3×300 mL). The combined organic layer was dried over Na$_2$SO$_4$ and concentrated under reduced pressure to give a crude compound, The crude mixture was purified by column chromatography (silica gel, 100-200 mesh) using 30% EtOAc in Hexane as eluent to afford compound 3 (32 g, 59.59%) as a white solid. LC-MS: m/z 208.09 (M+H).

Step 2:

To a stirred compound 3 (32 g, 154.5 mmol, 1 eq) in acetonitrile was added compound 4 (27.5 g, 200.9 mmol, 1.3 eq), TEA (15.6 g, 154.5 mmol, 1 eq) at RT under argon atmosphere, then the reaction mixture was heated to reflux for 16 h. TLC analysis indicated formation of a polar spot. The reaction mixture was cooled to RT and filtered. The filtrate was concentrated to get a crude compound. The crude compound was dissolved in 2-butanol (300 mL) and N-Methyl Morpholine (39.49 mL), ACOH(178 mL) were added at RT under argon atmosphere. The reaction mixture was heated to 100° C. for 16 h. TLC analysis indicated formation of a polar spot. The reaction mixture was concentrated and diluted with water and extracted with EtOAc (3×300 mL). The combined organic layer was dried over $Na_2SO_4$ then concentrated to give a crude compound, which was purified by column chromatography (silica gel, 100-200 mesh) using EtOAc is as eluent to afford compound 5 (25 g, 58.68%) as a white solid. LC-MS: m/z 277.17 (M+H).
Step 3:
To a stirred solution of LAH (24.9 g, 659.4 mmol, 7 eq) in THF (130 mL) was added a solution of compound 5 (26 g, 94.2 mmol, 1 eq) in THF (160 mL) at 0° C. The mixture was allowed to warm up to RT for 18 h. TLC analysis indicated formation of a polar spot. The reaction mixture was cool to 0° C. A solution of DM Water (25 mL) in THF (225 mL) was added, followed by a 2N NaOH Solution (50 mL) and DM Water (25 mL). Then the mixture was stirred for 30 min., and filtered. The filtrate was concentrated to give a crude mixture. The crude mixture was purified by column chromatography (silica gel, 100-200 mesh) using 0-5% MeOH in DCM as eluent to afford compound 6 (14 g, 85.99%) as a brown oil. LC-MS: m/z 249.28 (M+H);
Step 4:
To a stirred compound 6 (18 g, 72.58 mmol, 1 eq) was added compound 7 (19 g, 145.16 mmol, 2 eq), xantphos (1.25 g, 2.17 mmol, 0.03 eq), $Pd_2(dba)_3$ (1.98 g, 2.17 mmol, 0.03 eq) and Li-HMDS (725 mL, 725 mmol, 10 eq) at RT under argon atmosphere. The reaction mixture was heated to 90° C. for 16 h. TLC analysis indicated formation of a less polar spot. The reaction mixture was cooled to RT then filtered through celite pad, which was washed with EtOAc (3times). The filtrate was diluted with water and extracted with EtOAc (3×100 mL). The combined organic layer was dried over $Na_2SO_4$ then concentrated to give a crude residue. The crude residue was purified by column chromatography (silica gel, 100-200 mesh) using 0-10% EtOAc in petroleum ether as eluent to afford compound 8 (24 g, 85.74%) as a brown oil. LC-MS: m/z 360.30 (M+H);
Step 5:
To a solution of compound 8 (8 g, 22.28 mmol, 1 eq) and compound 9 (10.4 g, 66.85 mmol, 3 eq) in DCM was added $NaHCO_3$ (20.1 g, 77.98 mmol, 3.5 eq) at 5° C. The reaction mixture was allowed to warm up to RT and the reaction continued for 18 h. TLC analysis indicated formation of a polar spot. The reaction mixture was diluted with water and extracted with DCM (3×100 mL). The combined organic layer was dried over $Na_2SO_4$ then concentrated to give a crude compound. The crude compound was purified by column chromatography (silica gel, 100-200 mesh) using 0-10% MeOH in DCM as eluent to afford compound 10 (6 g,) as a brown oil. LC-MS: m/z 360.36 (M+H);
Step 6:
To a stirred solution of LAH (2.5 g, 66.85 mmol, 4 eq) in THF (30 mL) was added a solution of compound 10 (6 g. 16.71 mmol, 1 eq) in THF (30 mL) at 0° C. Then the mixture was allowed to warm up to RT for 18 h. TLC analysis indicated formation of a polar spot. The reaction mixture was cool to 0° C. and a solution of DM Water (2.5 mL) in THF (225 mL) was added, followed by a 2N NaOH Solution (5 mL), and DM Water (2.5 mL). Then the mixture was stirred for 30 min and filtered. The filtrate was concentrated to crude residue, The crude residue was purified by column chromatography (silica gel, 100-200 mesh) using 0-5% MeOH in DCM as eluent to afford compound 11 (4.5 g,) as brown oil. LC-MS: m/z 254.38 (M+H).
Step 7:
To a stirred solution of compound 11 (4.5 g, 17.78 mmol, 1 eq) in THF (9 mL) was added PMDTA (6.1 g, 35.57 mmol, 2 eq) and n-BuLi (14.2 mL, 35.57 mmol, 2 eq, 2.5M in THF) at −78° C. under argon atmosphere. The reaction was continued for 2 h and a solution of 12 (9 g, 35.57 mmol, 2 eq, in THF) was added at −78° C. The mixture was slowly allowed to reach RT for 16 h. TLC analysis indicated formation of a less polar spot. The reaction mixture was quenched in aqueous solution of sodium thiosulphate then extracted with EtOAc (3×100 mL). The combined organic layer was dried over $Na_2SO_4$ then concentrated under reduced pressure to give the crude compound 12(3.5 g, crude) as a brown semi-solid. LC-MS: m/z 380.27 (M+H).
Step 8:
To a stirred solution of compound 12(3.5 g, 9.23 mmol, 1 eq) in Toluene (50 mL) was added $Cs_2CO_3$ (5.9 g, 18.46 mmol, 2 eq) and $NH_2Boc$ (1.28 g, 11.08 mmol, 1.2 eq) at RT. The reaction mixture was de-gassed with Argon for 5 min., then xantphos (160 mg, 0.276 mmol, 0.03 eq) and $Pd_2(dba)_3$ (253 mg, 0.276 mmol, 0.03 eq) were added at RT. The reaction mixture was heated to 90° C. for 16 h. TLC analysis indicated formation of a polar spot. The reaction mixture was filtered through celite pad then the filtrate was concentrated to a crude compound. The crude compound was purified by column chromatography (silica gel, 100-200 mesh) using 0-1% MeOH in DCM as eluent to afford compound 8 (2.0 g, per two steps) as brown oil. LC-MS: m/z 369.38 (M+H).
Step 9:
To a stirred solution of compound 8 (2 g, 5.43 mmol, 1 eq) in DCM (10 mL) was added TFA (4.1 mL, 54.3 mmol, 10 eq) at RT and the reaction continued for 16 h. TLC analysis indicated formation of a polar spot. The reaction mixture was concentrated to crude, which was basified by aqueous $NaHCO_3$solution then extracted with EtOAc (3×80 mL). The combined organic layer was dried over $Na_2SO_4$ then concentrated under reduced pressure to a crude compound. The crude compound was purified by column chromatography (silica gel, 100-200 mesh) using 0-1% MeOH in DCM as eluent to afford (S)-5-chloro-2-(2-isopropyl-4-methylpiperazin-1-yl)pyridin-4-amine (600 mg 59%) as a pale yellow solid. LC-MS: m/z 269.36 (M+H).

Synthesis of 5-chloro-2-((3R,4S)-3-fluoro-4-methoxypyrrolidin-1-yl)pyridin-4-amine Scheme 62

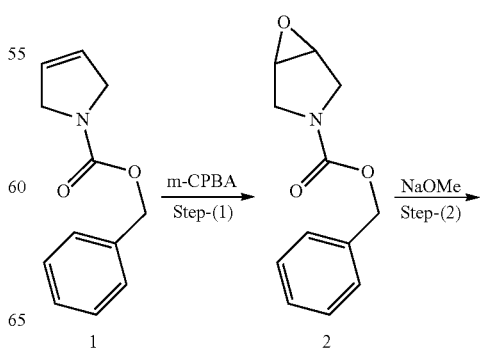

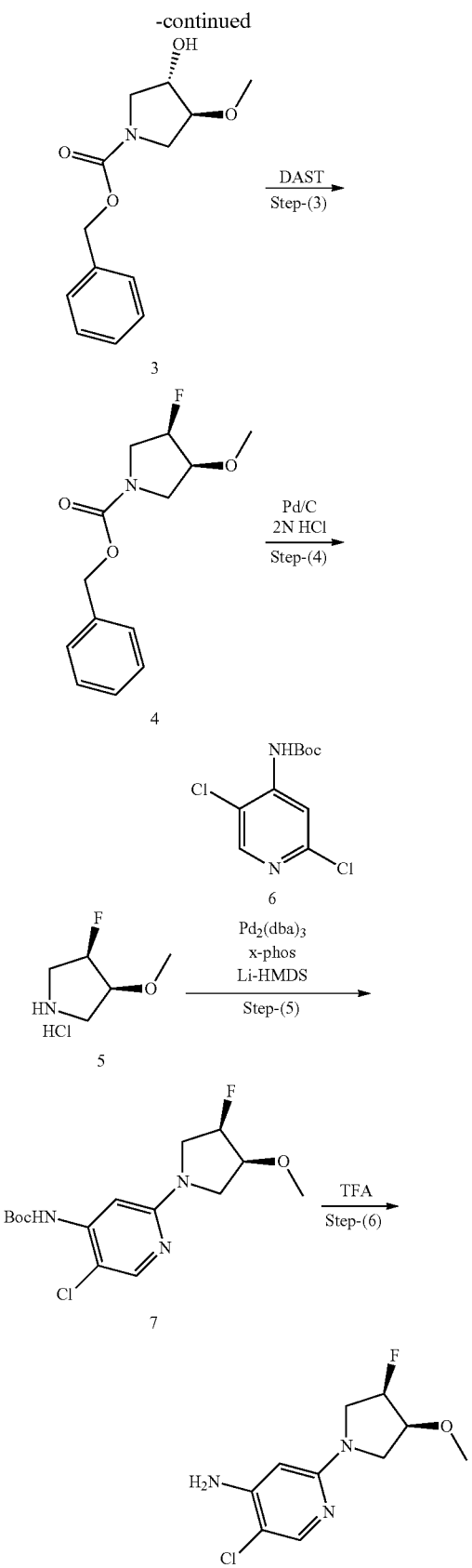

Compound numbers in text refer to structures shown Scheme 62.

Step 1:
To a stirred solution of compound 1 (15 g, 73.81 mmol, 1 eq) in DCM (300 mL) was added in m-CPBA (25.46 g, 147.63 mmol, 2 eq) then the resulting mixture was stirred for 48 h. TLC analysis indicated formation of a polar spot. The reaction mixture was basified with aqueous $NaHCO_3$ and extracted with EtOAc (3×100 mL). The combined organic layer was dried over $Na_2SO_4$ then concentrated to crude compound. The crude compound was purified by column chromatography (silica gel, 100-200 mesh) using 0-20% EtOAc in petroleum ether as eluent to afford compound 2 (15.2 g, 93%) as yellow color liquid.

Step 2:
To a stirred compound 2 (15.2 g, 69.406 mmol, 1 eq) in MeOH was added NaOMe (93.69 mL, 347.03 mmol, 5 eq, 20% in MeOH) at 0° C. The reaction mixture was allowed to warm up to RT for 48 h. TLC analysis indicated formation of a polar spot. The reaction mixture was neutralized with AcOH under ice cooling and extracted with EtOAc (3×100 mL). The combined organic layer was dried over $Na_2SO_4$ then concentrated to a crude compound. The crude compound was purified by column chromatography (silica gel, 100-200 mesh) using 0-30% EtOAc in petroleum ether as eluent to afford compound 3 (14.9 g, 85%) as yellow color liquid. LC-MS: m/z 208.19 (M+H);

Step 3:
To a stirred solution of compound 3 (14.9 g, 59.36 mmol, 1 eq) in DCM (300 mL) was added drop wise (15.6 mL, 118.72 mmol, 2 eq) at −78° C. then the mixture was stirred for 1 hr. The reaction mixture was allowed to warm to RT for 16 h. TLC analysis indicated formation of a less polar spot. The reaction mixture was basified with sat.$NaHCO_3$ solution then extracted with EtOAc (3×100 mL). The combined organic layer was dried over $Na_2SO_4$ then concentrated to a crude compound. The crude compound was purified by column chromatography (silica gel, 100-200 mesh) using 0-20% EtOAc in petroleum ether as eluent to afford compound 4 (7.6 g, 50%) as yellow liquid. LC-MS: m/z 254.10 (M+H);

Step 4:
To a stirred solution of compound 4 (7.5 g, 29.64 mmol, 1 eq) in EtOH (100 mL) was added 10% Pd/C (3.8 g) and 2N HCl (20 mL) at RT. The reaction mixture was stirred under H2 balloon pressure at RT for 16 h. TLC analysis indicated formation of a polar spot. The reaction mixture was filtered through celite. The filtrate was concentrated to a crude mixture. The crude mixture was triturated with ether to afford compound 5 (3.7 g, 80%) as a off-white solid.

Step 5:
To a stirred solution of compound 5 (3 g, 19.32 mmol, 1.5 eq) in dry THF (50 mL) was added compound 6 (3.3 g, 12.88 mmol, 1 eq),) at RT. The reaction mixture was de-gassed with argon for 15 min., then x-phos (368 mg, 0.77 mmol, 0.06 eq), $Pd_2(dba)_3$ (354 mg, 0.38 mmol, 0.03 eq) and Li-HMDS (64 mL, 64 mmol, 5 eq) were added at RT under argon atmosphere. The reaction mixture was heated to 90° C. for 16 h. TLC analysis indicated formation of a less polar spot. The reaction mixture was cooled to RT then filtered through celite pad, which was washed with EtOAc (3times). The filtrate was diluted with water and extracted with EtOAc (3×100 mL). The combined organic layer was dried over $Na_2SO_4$ then concentrated to crude compound. The crude compound was purified by column chromatography (silica gel, 100-200 mesh) using 0-10% EtOAc in petroleum ether as eluent to afford compound 7 (1.45 g, 21%) as a pale yellow oil. LC-MS: m/z 346.24 (M+H);

Step 6:

To a stirred solution of compound 7 (6.2 g, 17.97 mmol, 1 eq) in DCM (50 mL) was added TFA (13.3 mL, 179.7 mmol, 10 eq) at RT and the reaction continued for 16 h. TLC analysis indicated formation of a polar spot. The reaction mixture was concentrated to a crude residue, which was basified by aqueous NaHCO$_3$ solution then extracted with EtOAc (3×50 mL). The combined organic layer was dried over Na$_2$SO$_4$ then concentrated under reduced pressure to give a crude mixture. The crude mixture was purified by column chromatography (silica gel, 100-200 mesh) using 0-40% EtOAc in petroleum ether as eluent to afford 5-chloro-2-((3R,4S)-3-fluoro-4-methoxypyrrolidin-1-yl) pyridin-4-amine (3.3 g, 75%) as an off-white solid, which was purified by pre-SFC and isolated 550 mg of Isomer-1 and 530 mg of Isomer-2 as an off-white solid. LC-MS: m/z 246.12 (M+H).

Synthesis of 3-chloro-2-fluoro-6-((3R,4S)-3-fluoro-4-methoxypyrrolidin-1-yl)pyridin-4-amine

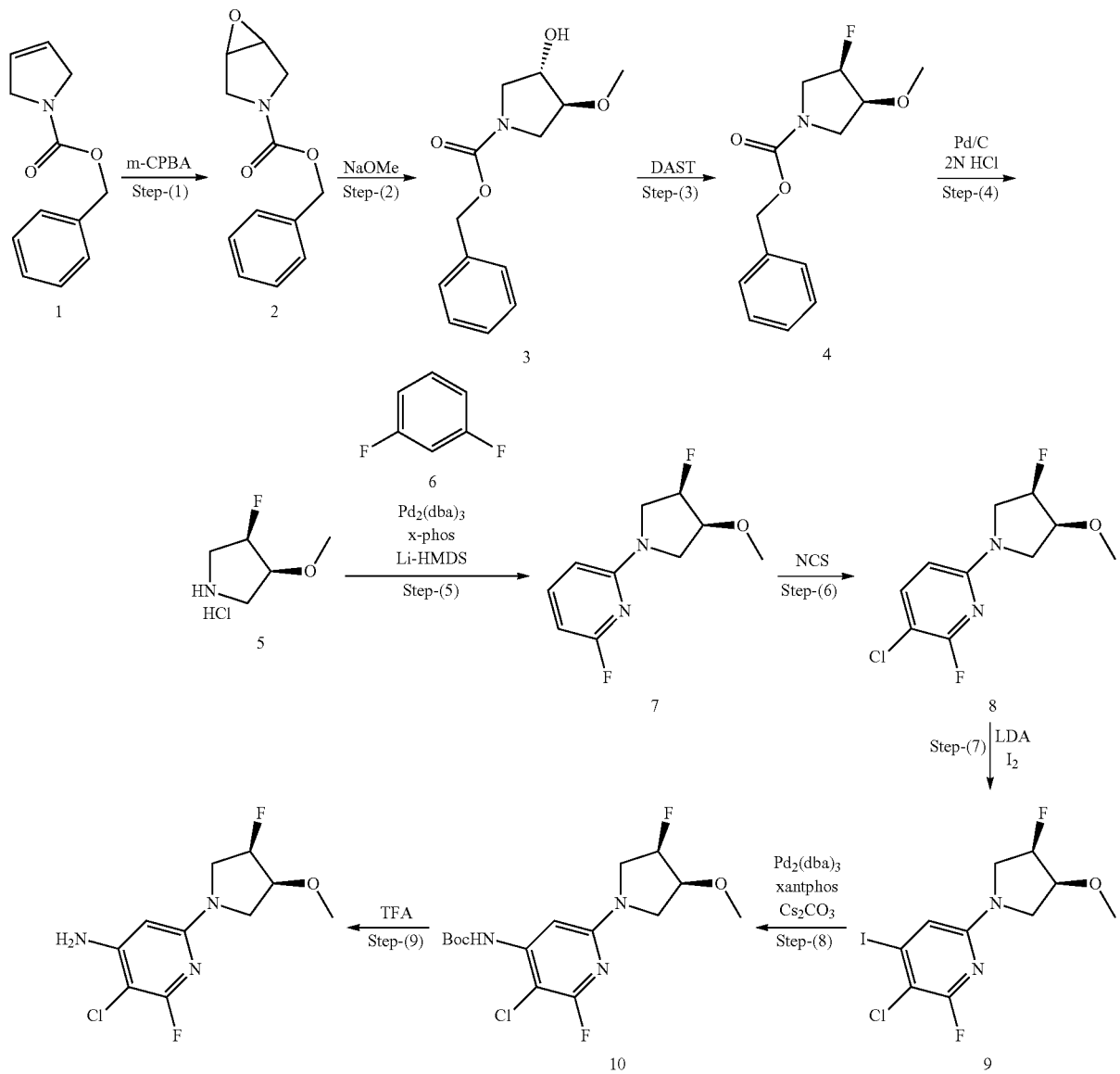

Compound numbers in text refer to structures shown in Scheme 63.

Step 1: To a stirred solution of compound 1 (15 g, 73.81 mmol, 1 eq) in DCM (300 mL) was added in m-CPBA (25.467 g, 147.63 mmol, 2 eq) at RT then the reaction mixture was stirred for 48 h. TLC analysis indicated formation of a polar spot. The reaction mixture was basified with aqueous NaHCO$_3$ and extracted with EtOAc (3×100 mL). The combined organic layer was washed with 2N NaOH and dried over Na$_2$SO$_4$ then concentrated to a crude compound. The crude compound was purified by column chromatography (silica gel, 100-200 mesh) using 0-20% EtOAc in petroleum ether as eluent to afford compound 2 (15.2 g, 93%) as yellow color liquid.

Step 2:

To a stirred solution of compound 2 (15.2 g, 69.406 mmol, 1 eq) in MeOH was added NaOMe (93.69 ml, 347.03 mmol, 5 eq, 20% in MeOH) at 0° C. The reaction mixture was allowed to warm up to RT for 48 h. TLC analysis indicated formation of polar spot. The reaction mixture was quenched in water and neutralized with AcOH under ice cooling then extracted with EtOAc (3×100 mL). The combined organic layer was dried over $Na_2SO_4$ and concentrated to crude compound. The crude compound was purified by column chromatography (silica gel, 100-200 mesh) using 0-30% EtOAc in petroleum ether as eluent to afford compound 3 (14.9 g, 85%) as yellow color liquid. LC-MS: m/z 252.14 (M+H);

Step 3:

To a stirred solution of compound 3 (14.9 g, 59.36 mmol, 1 eq) in DCM (300 mL) was drop wise added DAST (15.6 mL, 118.72 mmol, 2 eq) at −78° C. The mixture was stirred for 1 h. The reaction mixture was then allowed to warm up to RT for 16 h. TLC analysis indicated formation of a less polar spot. The reaction mixture was basified with sat.$NaHCO_3$solution then extracted with EtOAc (3×100 mL). The combined organic layer was dried over $Na_2SO_4$ then concentrated to a crude compound. The crude compound was purified by column chromatography (silica gel, 100-200 mesh) using 0-20% EtOAc in petroleum ether as eluent to afford compound 4 (7.6 g, 50%) as a yellow liquid. LC-MS: m/z 254.13 (M+H);

Step 4:

To a stirred solution of compound 4 (7.5 g, 29.64 mmol, 1 eq) in EtOH (100 mL) was added 10% Pd/C (3.8 g) and 2N HCl (20 mL) at RT. The reaction mixture was stirred under H2 balloon atmosphere at RT for 16 h. TLC analysis indicated formation of a polar spot. The reaction mixture was filtered through celite pad. The filtrate was concentrated to a crude compound. The crude compound was triturated with ether to afford compound 5 (3.79 g, 82%) as pale yellow solid. LCMS: m/z 120.10 (M+H).

Step 5:

To a stirred solution of compound 5 (5.9 g, 38.06 mmol, 1 eq) in dry THF (80 mL) was added compound 6 (5.4 g, 57.09 mmol, 1.5 eq) at RT. The reaction mixture was de-gassed with Argon for 15 min., then x-phos (1.08 g, 2.28 mmol, 0.06 eq), $Pd_2(dba)_3$ (1.046 g, 1.14 mmol, 0.03 eq) and Li-HMDS (190 mL, 190 mmol, 5 eq, 1 M in THF) were added at RT under argon atmosphere. The reaction mixture was heated to 90° C. for 16 h. TLC analysis indicated formation of a less polar spot. The reaction mixture was cooled to RT then quenched in water and filtered through celite pad. The filtrate was extracted with EtOAc (3times). The combined organic layer was dried over $Na_2SO_4$ then concentrated to crude compound. The crude compound was purified by column chromatography (silica gel, 100-200 mesh) using 0-5% EtOAc in petroleum ether as eluent to afford compound 7 (8 g, 98%) as a yellow oil. LC-MS: m/z 215.07 (M+H).

Step 6:

To a stirred solution of compound 7 (8 g, 37.38 mmol, 1 eq) in DMF (120 mL) was added NCS (4.99 g, 37.38 mmol, 1 eq) at RT. The reaction mixture was heated to 50° C. (pre heated) for 2 h. TLC analysis indicated formation of a polar spot. The reaction mixture was diluted in water and extracted with EtOAc (3×50 mL). The combined organic layer was dried over $Na_2SO_4$ then concentrated under reduced pressure to a crude compound. The crude compound was purified by column chromatography (silica gel, 100-200 mesh) using 0-5% EtOAc in petroleum ether as eluent to afford 8 (5.6 g, 60%) as a yellow oil. LC-MS: m/z 249.09 (M+H).

Step 7:

To a stirred solution of compound 8 (5.6 g, 22.58 mmol, 1 eq) in dry THF (100 mL) was added PMDTA (10.35 mL, 49.67 mmol, 2.2 eq) at RT. The reaction mixture was cooled to −78° C. and n-BuLi (19.87 mL, 49.67 mmol, 2.2 eq, 2.5M) was added drop wise. The resulting mixture was stirred at −78° C. for 2 h. A solution of 12 (11.47 g, 45.16 mmol, 2 eq, in THF) was added to the reaction mixture at −78° C. then the reaction mixture was allowed to warm up to RT for 16 h. TLC analysis indicated formation of a less polar spot. The reaction mixture diluted with sodium thio-sulphate solution and extracted in EtOAc (3×80 mL). The combined organic layer was dried over $Na_2SO_4$ then concentrated under reduced pressure to obtained crude compound 9 (10.3 g, crude) as yellow liquid. LCMS: m/z 375.26 (M+H).

Step 8:

To a stirred solution of compound 9 (10.3 g, 27.54 mmol, 1 eq) in toluene (150 mL) was added $NH_2Boc$ (3.83 g, 33.048 mmol, 1.2 eq) at RT. The reaction mixture was de-gassed with Argon for 15 min. $Cs_2CO_3$ (17.9 g, 55.08 mmol, 2 eq), xantphos (477.5 mg, 0.82 mmol, 0.03 eq) and $Pd_2(dba)_3$ (756 mg, 0.82 mmol, 0.03 eq) were added at RT under argon atmosphere. The reaction mixture was heated to 90° C. for 16 h. TLC analysis indicated formation of a polar spot. The reaction mixture was filtered through celite pad and the filtrate was concentrated to a crude compound. The crude compound was purified by column chromatography (silica gel, 100-200 mesh) using 0-3% EtOAc in petroleum ether as eluent to afford compound 10 (6.5 g, 79% after two steps) as yellow oil. LCMS: m/z 364.49 (M+H); Step 9:

To a stirred solution of compound 10 (6.5 g, 17.90 mmol, 1 eq) in DCM (50 mL) was added TFA (20.5 mL, 26.80 mmol, 15 eq) at RT and the reaction continued for 16 h. TLC analysis indicated formation of a polar spot. The reaction mixture was concentrated to a crude residue, which was basified by aqueous $NaHCO_3$solution then extracted with EtOAc (3×50 mL). The combined organic layer was dried over $Na_2SO_4$ then concentrated under reduced pressure to a crude compound. The crude compound was purified by column chromatography (silica gel, 100-200 mesh) using 0-10% EtOAc in petroleum ether as eluent to afford racemic 3-chloro-2-fluoro-6-((3R,4S)-3-fluoro-4-methoxypyrroli-din-1-yl)pyridin-4-amine (2.5 g, 53%) as an off-white solid. LC-MS: m/z 263.89 (M+H). The racemic compound was further purified by prep SFC to get Isomer-1 (983 mg) and Isomer-2 (850 mg).

Synthesis of 5-chloro-2-((1R,4R)-5-(2,2,2-trifluoro-ethyl)-2,5-diazbiyclo[2.2.1]heptan-2-yl)pyridin-4-amine

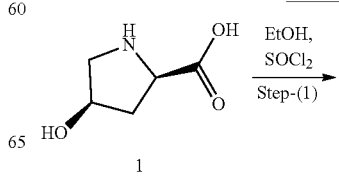

Scheme 64

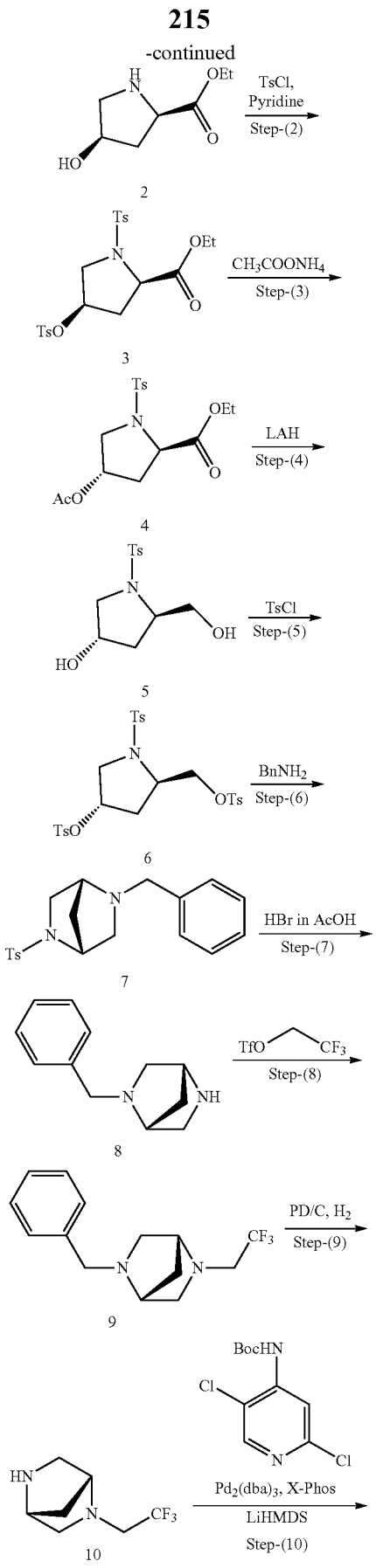

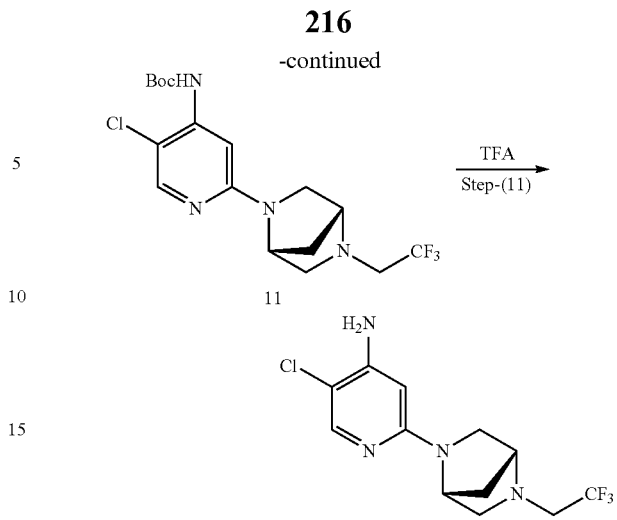

Compound numbers in text refer to structures shown in Scheme 64.

Step 1:

To a solution of compound 1 (30 g, 229 mmol, eq) in Ethanol (300 mL) was added SOCl$_2$ (16.7 mL, 229 mmol, 1 eq) drop wise at 0° C. The mixture was brought to reflux for 16 h. TLC analysis indicated formation of a less polar spot. The reaction mixture was cooled to 0° C. A solid was filtered and dried under vacuum to give compound 2 (30 g, 83%) as an off white solid.

Step 2:

To a solution of compound 2 (30 g, 188.6 mmol, 1 eq) in Pyridine (300 mL) was added TEA (98.9 mL, 754.4 mmol, 4 eq) cooled to 0° C. Tosyl chloride (143.3 g, 754.4 mmol, 4 eq) was added to it portion wise then the mixture slowly warmed to RT for 16 h. TLC analysis indicated formation of a less polar spot. The reaction mixture was poured into ice water. A solid precipitate was filtered and dried under vacuum to give compound 3 (35 g, 40%) as a pale yellow color solid. LCMS: 92.86% with m/z 468.24 (M+H):

Step 3:

To a solution of compound 3 (20 g, 42.8 mmol, 1.0 eq) in Toluene (200 mL) was added tetra methyl ammonium acetate (14.3 g, 54.8 mmol, 1.28 eq) at rt. The mixture was heated to reflux for 16 h. TLC analysis indicated formation of a polar spot. Then the reaction mass was extracted with EtOAc (2×200 mL) and washed with water (2×100 mL) and brine (2×100 mL). The organic layer was dried under reduced pressure. The residue (40 g) was taken up with 80 mL of 2-propanol. The mixture was stirred at 0° C. for 30 mins and the resulting Crystalline product was collected under dried under vacuum to give compound 4 (12 g, 68%) as a pale yellow color Solid. LCMS: 79.34% with m/z 356.24 (M+H):

Step 4:

To a solution of compound 4 (12 g, 33.8 mmol, eq) in dry THF (120 mL) was added Lithium borohydride (1.46 g, 67.3 mmol, 2 eq) at 0° C. The mixture was then slowly warmed to RT for 16 h. TLC analysis indicated formation of a polar spot. The reaction mixture was cooled to 0° C. and the pH was adjusted to 3 with 6N HCl solution. The solution was concentrated and the residue was triturated with cold water (150 mL). A solid precipitate was filtered and dried under vacuum to give compound 5 (7 g, 40%) as an off-white solid. LCMS: m/z 272.13 (M+H);

Step 5:

To a solution of compound 5 (7 g, 25 mmol, 1 eq) in Pyridine (70 mL) was added Tosyl chloride (17.1 g, 98.4 mmol, 4 eq) in one portion at 0° C. The temperature was raised to 50° C., then slowly lowered to RT stirred for 16 h. TLC analysis indicated formation of a less polar spot. The reaction mixture was poured into cold 2N HCl (200 mL) solution. A solid precipitate was filtered and dried under vacuum to give compound 6 (6 g, 40%) as a pale yellow color solid. LCMS: m/z 580.28 (M+H);

Step 6:

To a solution of compound 6 (6 g, 10.3 mmol, 1.0 eq) in Toluene (60 mL) was added benzyl amine (3.32 g, 30.84 mmol, 3 eq) at rt. The mixture was brought to reflux for 16 h. TLC analysis indicated formation of a polar spot. The reaction mixture was cooled and filtered. The residue was washed with toluene (50 mL). The combined organic layers were evaporated under reduced pressure and the resulting residue was taken up with 20 mL of 2-propanol. After cooling, the product was filtered, washed with diethyl ether to give compound 7 (3.4 g, 60% yield) as an off-white solid. LCMS: m/z 344.21 (M+H):

Step 7:

To a hot solution of hydro bromic acid (6.8 g, 1.0 eq) in acetic acid (34 mL) at 70° C. was added compound 7(3.4 g, 1 eq). Then the solution was stirred at same temperature for 16 h. TLC analysis indicated formation of a polar spot. The reaction mixture was cooled to RT. A solid precipitate was filtered under vacuum and washed with diethyl ether to give compound 8 (1.8 g, 60% yield) as an off-white solid.

Step 8:

To a solution of compound 8(1.8 g, 9.5 mmol, 1 eq) in ethanol was added DiPEA (3.43 mL, 19.1 mmol, 1.2 eq) was added compound 9 (1.6 mL, 11.4 mmol, 1.2 eq) at RT for 16 h. TLC analysis indicated formation of a less polar spot. The solvent was evaporated under reduced pressure, the residue was poured into ice water, extracted with EtOAc (2×50 mL) and washed with water (2×20 mL) and sat.brine (2×20 mL). The separated organic layer was dried over $Na_2SO_4$ and concentrated under reduced pressure to give crude compound 10 (2.4 g, 70% yield) as a pale yellow color liquid. LCMS: 91.29% with m/z 271.21 (M+H):

Step 9:

To a solution of compound 10 (2.4 g, 8.85 mmol, 1 eq) in ethanol was added 10% PdC (50 mg) under argon. The mixture was hydrogenated for 3 h under balloon pressure. TLC analysis indicated formation of a polar spot. The reaction mass was filtered through celite bed, which was washed with ethanol. The filtrate was evaporated under reduced pressure to give crude compound 11 (1.2 g (crude), 70.5% yield) as a pale yellow liquid.

Step 10:

To a suspension of compound 11 (1 g, 3.81 mmol, 1.0 eq) and compound 12 (0.82 g, 4.58 mmol, 1.2 eq) was added 2-dicyclohexylphospino-2,4,6-triisopropyl biphenyl (Xphos) (54 mg, 0.1 mmol, 0.03 eq) and $Pd_2(dba)_3$ (100 mg, 0.1 mmol, 0.03 eq) followed by LiHMDS (10 mL). The reaction mass was kept in a pre-heated oil bath for 1 h at 70° C. TLC analysis indicated the formation of a polar spot. The reaction mixture was quenched with saturated $NH_4Cl$ solution (20 mL) and extracted with EtOAc (2×50 mL) twice. The combined organic layer was dried over $Na_2SO_4$ and concentrated under reduced pressure to give a crude product, which was purified by column chromatography ($SiO_2$, 100-200 mesh) using 0-20% EtOAc in petroleum ether as an eluent to give compound 13 (1 g, 64.9% yield) as a pale yellow solid. LCMS: 96.73% with m/z 407.19 (M+H);

Step 11:

To a solution of compound 13 (1 g, 2.4 mmol, 1 eq) in DCM (10 mL) was added Trifluoro acetic acid (2.24 mL, 29.4 mmol, 12 eq) in drop wise manner at 0° C. and the mixture was allowed to reach RT over 16 h. TLC analysis indicated formation of a polar spot. Then, the reaction mixture was concentrated under reduced pressure to give a TFA salt of product, which was dissolved in water (20 mL), basified with sat.$NaHCO_3$and extracted in EtOAc (3×30 mL). The combined organic layer was dried over $Na_2SO_4$ and concentrated under reduced pressure to give a crude product. The crude compound was purified by combiflash column chromatography using 20% EtOAc in petroleum ether as an eluent to give compound 5-chloro-2-((1R,4R)-5-(2,2,2-trifluoroethyl)-2,5-diazabicyclo[2.2.1]heptan-2-yl) pyridin-4-amine (530 mg, 70.66% yield) as an off-white solid. LCMS: 96.20% with m/z 307.0 (M+H);

Synthesis of 5-chloro-2-((1R,5S)-3-(2,2,2-trifluoro-ethyl)-3,8-diazabicyclo[3.2.1]octan-8-yl)pyridin-4-amine

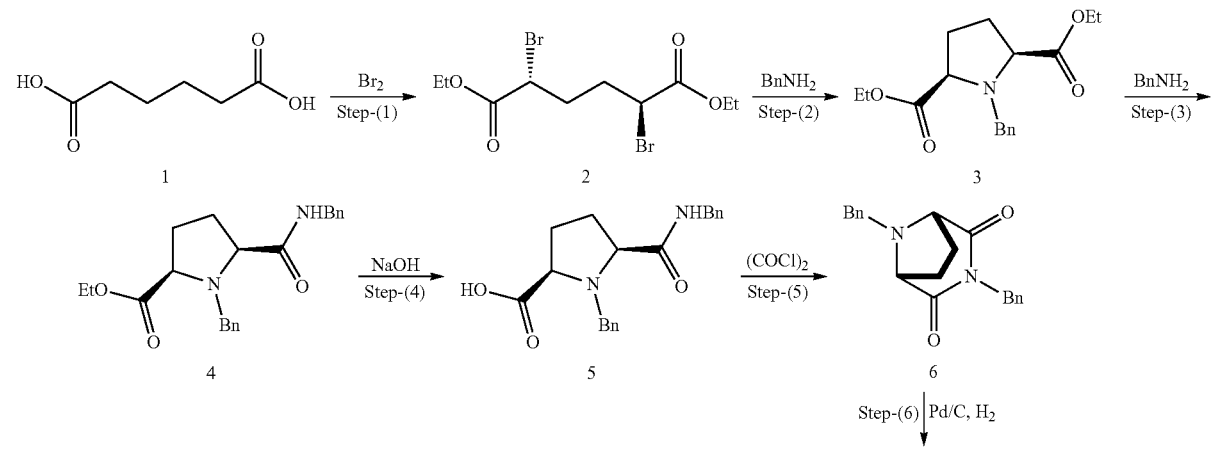

Scheme 65

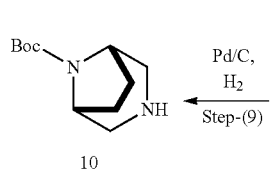
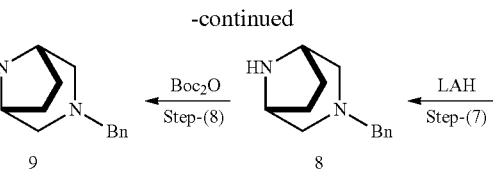
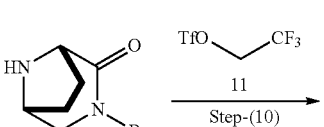
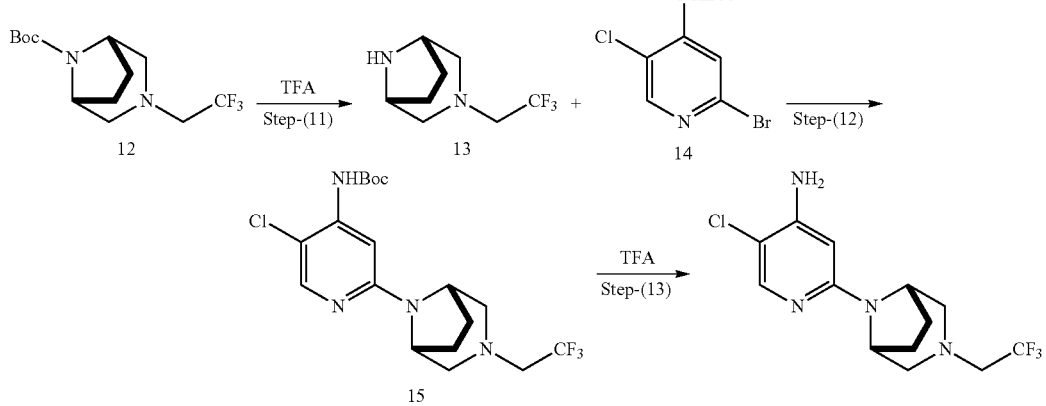

Compound numbers in text refer to structures shown in Scheme 65.

Step 1:

To compound 1 (300 g, 2054.7 mmol, 1 eq), SOCl$_2$ (600 mL, 8219.1 mmol, 4 eq) was added and the resulting reaction mixture was heated at 70° C. for 5 h. The reaction was monitored with TLC. TLC analysis indicated formation of a non-polar spot. The reaction mixture was concentrated under reduced pressure to get acid chloride crude product. The crude was heated to 80° C. Bromine (212.6 mL, 4120.8 mmol, 2.5 eq) was added drop wise at the same temperature. The resulted reaction mixture was heated at 80° C. for 4 h. The reaction was monitored with TLC. TLC analysis indicated formation of a non-polar spot. The reaction mixture was cooled to 0° C., degassed with nitrogen and quenched with ethanol (1 L). The resulted reaction mixture was stirred for 16 h at RT, solid formed was filtered and washed with cold ethanol to give compound 2 (200 g, 27.2% yield) as an off-white solid. LCMS: m/z 360.72 (M+2H).

Step 2:

To a stirred solution of compound 2 (400 g, 1117.6 mmol, 1 eq) in toluene (800 mL) was added benzyl amine (239 g, 2235.0 mmol, 2 eq) followed by K$_2$CO$_3$ (465 g, 3351 mmol, 3 eq) at RT and resulted reaction mixture was heated at 100° C. for 16 h. The reaction was monitored by TLC. TLC analysis indicated formation of a non-polar spot. The reaction mixture was diluted with ice water and extracted with ethyl acetate (2×800 mL). The combined organic layer was dried over Na$_2$SO$_4$ and concentrated under reduced pressure. The crude product was purified by column chromatography (silica 100-200) using 10% ethyl acetate in petroleum ether as an eluent to give compound 3 (160 g, 46.9% yield) as a colorless liquid. LCMS: m/z 305.93 (M):

Step 3:

To a stirred solution of compound 3 (100 g, 524.5 mmol, 1 eq) in xylene (1 L), was added benzyl amine (67 g, 629.5 mmol, 1.2 eq) at RT and the resulting reaction mixture was heated at 140° C. for 4 days. The reaction was monitored by TLC. TLC analysis indicated formation of a polar spot. The reaction mixture was concentrated under reduced pressure to get a crude product. The crude product was purified by column chromatography (silica 100-200) using ethyl acetate as an eluent to give Compound 4 (100 g, 83.4% yield) as a colorless liquid. LCMS: m/z 366.95 (M+H):

Step 4:

To a stirred solution of compound 4 (100 g, 273.2 mmol, 1 eq) in methanol (210 mL), was added drop wise a solution of NaOH (25.13 g, 628.4 mmol, 2.3 eq) in H2O (420 mL) and the resulting reaction mixture was stirred at RT for 5 h. The reaction was monitored by TLC. TLC analysis indicated formation of a polar spot. The reaction mixture was acidified with aq 6N HCl solution. A solid formed, and was filtered and washed with ethyl acetate to give Compound 5 (80 g, 86.6% yield) as an off-white solid. LCMS: m/z 339.57 (M+H):

Step 5:

In a steel vessel compound 5 (50 g, 147.9 mmol, 1 eq) in DCM (1 L), was cooled to 0° C. and oxalyl chloride (75 mL, 887.5 mmol, 6 eq) was added drop wise. The resulting reaction mixture was stirred at RT for 16 h. The reaction was monitored by TLC. TLC analysis indicated formation of a non-polar spot. The reaction mixture was concentrated under reduced pressure to give a crude product. The crude product was triturated with 2-propanol to give Compound 6 (40 g, 84.5% yield) as an off-white solid. LCMS: m/z 320.94 (M−H);

Step 6:

A solution of compound 6 (15 g, 46.87 mmol, 1 eq) in methanol (1.5 L) in par shaker was degassed for 20 min under nitrogen atmosphere. Pd/C (10% wt on carbon, 3 g) was added and the mixture stirred at RT for 16 h under hydrogen atmosphere. The reaction was monitored by TLC. TLC analysis indicated formation of a polar spot. The reaction mixture was filtered through celite, which was washed with methanol and DCM. The filtrate was concentrated under reduced pressure to give a crude product. The crude product was triturated with ethyl acetate to give Compound 7 (7.5 g, 70.09% yield) as off white solid. LCMS: m/z 230.76% (M+H);

Step 7:

To a stirred solution of compound 7 (28 g, 121.7 mmol, 1 eq) in THF (1.2 L) at 0° C. was added LAH (37 g, 973.9 mmol, 8 eq) portion wise. The resulting reaction mixture was heated at 70° C. for 36 h. The reaction was monitored by TLC. TLC analysis indicated formation of a polar spot. The reaction mixture was quenched with water (30 mL), filtered through celite, which was washed with ethyl acetate. The filtrate was extracted with ethyl acetate (2×750 mL), dried over $Na_2SO_4$ and concentrated under reduced pressure to give Compound 8 (16 g, 65% yield) as a yellow liquid.

Step 8:

To a stirred solution of compound 8 (16 g, 79.2 mmol, 1 eq) in DCM (160 mL) at 0° C. was added $(Boc)_2O$ (25.9 mL, 118.8 mmol, 1.5 eq) followed by TEA (22 mL, 158.4 mmol, 2 eq). The resulted reaction mixture was stirred at RT for 16 h. The reaction was monitored by TLC. TLC analysis indicated formation of a non-polar spot. Reaction mixture was diluted with ice water and extracted with DCM (2×500 mL). The combined organic layer was dried over $Na_2SO_4$ and concentrated under reduced pressure. The crude product was purified by column chromatography (silica 100-200) using 5% ethyl acetate in petroleum ether as an eluent to give Compound 9 (10 g, 41.8% yield) as a colour less liquid. LCMS: m/z 302.94 (M–H):

Step 9:

A stirred solution of compound 9 (14 g, 46.35 mmol, 1 eq) in methanol (500 mL) in par shaker was degassed for 20 min under nitrogen atmosphere. Pd/C (10% wt on carbon, 3 g) was added and the mixture stirred at RT for 16 h under hydrogen atmosphere. The reaction was monitored by TLC. TLC analysis indicated formation of a polar spot. The reaction mixture was filtered through celite, which was washed with methanol and DCM. The combined filtrate was concentrated under reduced pressure to give a crude product. The crude product was triturated with ethyl acetate to give Compound 10 (9 g, 91.8% yield) as an off-white solid.

Step 10:

To a stirred solution of compound 10 (4 g, 18.86 mmol, 1 eq) in ethanol (40 mL) was added compound 11 (5.47 g, 23.58 mmol, 1.25 eq) followed by DIPEA (8.6 mL, 47.15 mmol, 2.5 eq) and the resulting reaction mixture was stirred at RT for 16 h. The reaction was monitored by TLC. TLC analysis indicated formation of a non-polar spot. Reaction mixture was diluted with ice water and extracted with DCM (2×200 mL). The combined organic layer was dried over $Na_2SO_4$ and concentrated under reduced pressure. The crude product was purified by column chromatography (silica 100-200) using DCM as an eluent to give Compound 12 (2 g, 36.36% yield) as a colourless liquid. LCMS: m/z 295.42 (M–H):

Step 11:

To a stirred solution of compound 12 (4 g, 13.59 mmol, 1 eq) in DCM (20 mL), was added TFA (20 mL) drop wise and resulted reaction mixture was stirred at RT for 16 h. The reaction was monitored by TLC. TLC analysis indicated formation of a polar spot. The reaction mixture was concentrated under reduced pressure, basified with aq 2N NaOH solution and extracted with ethyl acetate (2×200 mL). The combined organic layer was dried over $Na_2SO_4$ and concentrated under reduced pressure to give Compound 13 (2.5 g, 95% yield) as an off-white solid.

Step 12:

To a stirred solution of compound 13 (1.4 g, 4.56 mmol, 1 eq) in THF (10 mL) at 0° C. was added $pd(dba)_3$ (0.417 g, 0.456 mmol, 0.1 eq), and xanthophos (0.108 g, 0.228 mmol, 0.05 eq) followed by compound 14 (1.06 g, 5.47 mmol, 1.2 eq). The resulting reaction mixture was stirred at 75° C. for 16 h. The reaction was monitored by TLC. TLC analysis indicated formation of a polar spot. The reaction mixture was quenched with ice water and extracted with ethyl acetate (2×200 mL). The combined organic layer was dried over $Na_2SO_4$ and concentrated under reduced pressure. The crude product was purified by column chromatography (silica 100-200) using 10-20% ethyl acetate in petroleum ether as an eluent to give Compound 15 (1.2 g, 39.6% yield) as a colourless liquid. LCMS m/z 422.05 (M–H):

Step 13:

To a stirred solution of compound 15 (1.2 g, 2.85 mmol, 1 eq) in DCM (20 mL), was added TFA (20 mL) drop wise and the resulting reaction mixture was stirred at RT for 16 h. The reaction was monitored by TLC. TLC analysis indicated formation of a polar spot. The reaction mixture was concentrated under reduced pressure, basified with aq 2N NaOH solution and extracted with ethyl acetate (2×50 mL). The combined organic layer was dried over $Na_2SO_4$ and concentrated under reduced pressure to give in 5-chloro-2-((1R,5S)-3-(2,2,2-trifluoroethyl)-3,8-diazabicyclo[3.2.1]octan-8-yl)pyridin-4-amine (0.8 g, 87.9% yield) as an off-white solid. LCMS: m/z 320.94 (M+H):

Synthesis of 5-chloro-2-((1R,5S)-8-(2,2,2-trifluoroethyl)-3,8-diazabicyclo[3.2.1]octan-3-yl)pyridin-4-amine Scheme 66

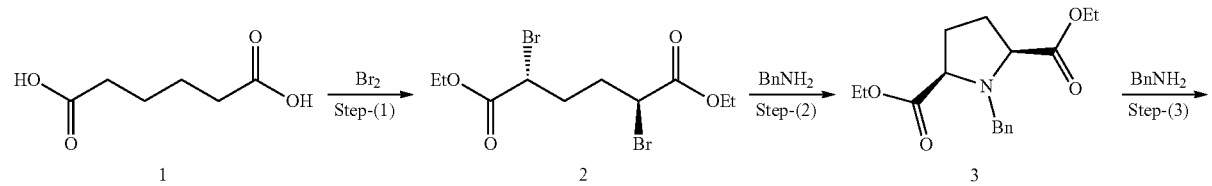

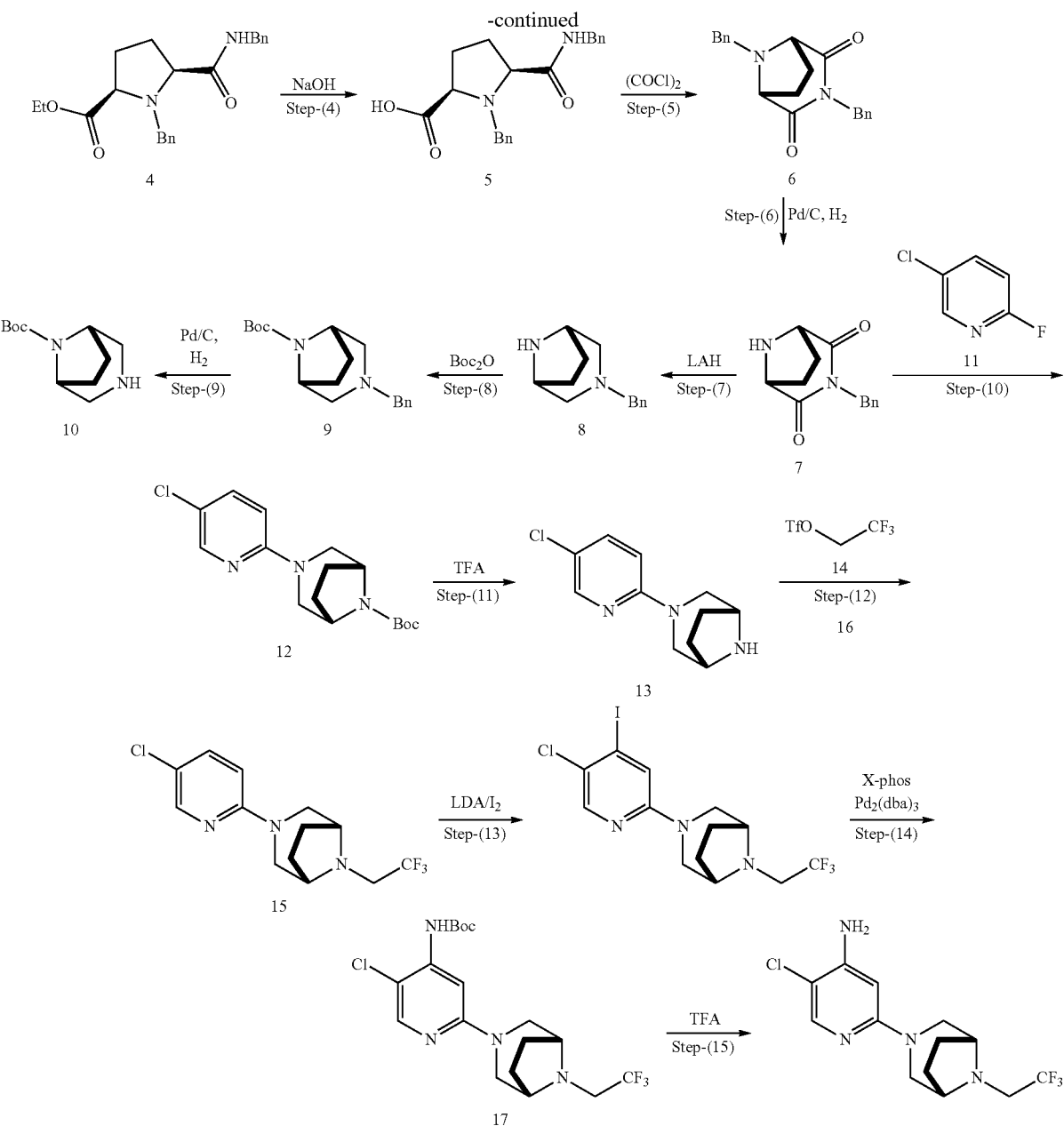

Compound numbers in text refer to structures shown in Scheme 66.

Step 1:

To compound 1 (300 g, 2054.7 mmol, 1 eq), SOCl₂ (600 mL, 8219.1 mmol, 4 eq) was added and the resulting reaction mixture was heated at 70° C. for 5 h. The reaction was monitored with TLC. TLC analysis indicated formation of a non-polar spot. The reaction mixture was concentrated under reduced pressure to get acid chloride crude product. Crude was heated to 80° C., was added bromine (212.6 mL, 4120.8 mmol, 2.5 eq) drop wise at same temperature. The resulting reaction mixture was heated at 80° C. for 4 h. The reaction was monitored with TLC. TLC analysis indicated formation of a non-polar spot. The reaction mixture was cooled to 0° C., degassed with nitrogen and quenched with ethanol (1 L). The resulting reaction mixture was stirred for 16 h at RT, solid formed was filtered and washed with cold ethanol to give Compound 2 (200 g, 27.2% yield) as an off-white solid. LCMS: 99.63% with m/z 360.72 (M+2H)

Step 2:

To a stirred solution of compound 2 (400 g, 1117.6 mmol, 1 eq) in toluene (800 mL) was added benzyl amine (239 g, 2235.0 mmol, 2 eq) followed by K₂CO₃ (465 g, 3351 mmol, 3 eq) at RT and the resulting reaction mixture was heated at 100° C. for 16 h. The reaction was monitored by TLC. TLC analysis indicated formation of a non-polar spot. Reaction mixture was diluted with ice water and extracted with ethyl acetate (2×800 mL). The combined organic layer was dried over Na₂SO₄ and concentrated under reduced pressure. The crude product was purified by column chromatography (silica 100-200) using 10% ethyl acetate in petroleum ether as an eluent to give in compound 3 (160 g, 46.9% yield) as a colorless liquid. LCMS: 94.17% with m/z 305.93 (M+H)

Step 3:

To a stirred solution of compound 3 (100 g, 524.5 mmol, 1 eq) in xylene (1 L), was added benzyl amine (67 g, 629.5 mmol, 1.2 eq) at RT and the resulting reaction mixture was heated at 140° C. for 4 days. The reaction mixture was concentrated under reduced pressure to get crude product. The crude product was purified by column chromatography (silica 100-200) using ethyl acetate as an eluent to give Compound 4 (100 g, 83.4% yield) as colorless liquid. LCMS: m/z 366.95 (M+H):

Step 4:

To a stirred solution of compound 4 (100 g, 273.2 mmol, 1 eq) in methanol (210 mL), was added a solution of NaOH (25.13 g, 628.4 mmol, 2.3 eq) in H2O (420 mL) drop wise and the resulting reaction mixture was stirred at RT for 5 h. The reaction was monitored by TLC. TLC analysis indicated formation of a polar spot. The reaction mixture was acidified with aq 6N HCl solution. A solid formed, and was filtered and washed with ethyl acetate to give Compound 5 (80 g, 86.6% yield) as an off-white solid. LCMS: m/z 339.57 (M+H):

Step 5:

In a steel vessel compound 5 (50 g, 147.9 mmol, 1 eq) in DCM (1 L), was cooled to 0° C. and oxalyl chloride (75 mL, 887.5 mmol, 6 eq) was added drop wise and the resulting reaction mixture was stirred at RT for 16 h. The reaction was monitored by TLC. TLC analysis indicated formation of a non-polar spot. Reaction mixture was concentrated under reduced pressure to give a crude product. The crude product was triturated with 2-propanol to give Compound 6 (40 g, 84.5% yield) as an off-white solid. LCMS: m/z 320.94 (M−H):

Step 6:

A solution of compound 6 (15 g, 46.87 mmol, 1 eq) in methanol (1.5 L) in par shaker was degassed for 20 min under nitrogen atmosphere. Pd/C (10% wt on carbon, 3 g) was added and the mixture stirred at RT for 16 h under hydrogen atmosphere. The reaction was monitored by TLC. TLC analysis indicated formation of a polar spot. The reaction mixture was filtered through celite, which was washed with methanol and DCM. The filtrate was concentrated under reduced pressure to give a crude product. The crude product was triturated with ethyl acetate to give Compound 7 (7.5 g, 70.09% yield) as an off-white solid. LCMS: 87.62% with m/z 230.76% (M+H):

Step 7:

To a stirred solution of compound 7 (28 g, 121.7 mmol, 1 eq) in THF (1.2 L) at 0° C. was added LAH (37 g, 973.9 mmol, 8 eq) portion wise and the resulting reaction mixture was heated at 70° C. for 36 h. The reaction was monitored by TLC. TLC analysis indicated formation of a polar spot. The reaction mixture was quenched with water (30 mL), filtered through celite, which was washed with ethyl acetate. Filtrate was extracted with ethyl acetate (2×750 mL), dried over $Na_2SO_4$ and concentrated under reduced pressure to give Compound 8 (16 g, 65% yield) as a yellow liquid. LCMS: m/z 203.48 (M−H):

Step 8:

To a stirred solution of compound 8 (16 g, 79.2 mmol, 1 eq) in DCM (160 mL) at 0° C. was added (Boc)2O (25.9 mL, 118.8 mmol, 1.5 eq) followed by TEA (22 mL, 158.4 mmol, 2 eq) and the resulting reaction mixture was stirred at RT for 16 h. The reaction was monitored by TLC. TLC analysis indicated formation of a non-polar spot. The reaction mixture was diluted with ice water and extracted with DCM (2×500 mL). The combined organic layer was dried over $Na_2SO_4$ and concentrated under reduced pressure. The crude product was purified by column chromatography (silica 100-200) using 5% ethyl acetate in petroleum ether as an eluent to give Compound 9 (10 g, 41.8% yield) as a colourless liquid. LCMS: m/z 302.94 (M−H):

Step 9:

To a stirred solution of compound 9 (14 g, 46.35 mmol, 1 eq) in methanol (500 mL) in par shaker was degassed for 20 min under nitrogen atmosphere. Pd/C (10% wt on carbon, 3 g) was added and stirred at RT for 16 h under hydrogen atmosphere. The reaction was monitored by TLC. TLC analysis indicated formation of a polar spot. The reaction mixture was filtered through celite, which was washed with methanol and DCM. Filtrate was concentrated under reduced pressure to give a crude product. The crude product was triturated with ethyl acetate to give Compound 10 (9 g, 91.8% yield) as an off-white solid.

Step 10:

To a stirred solution of compound 11 (5 g, 23.58 mmol, 1 eq) in DMSO (50 mL) was added $K_2CO_3$ (9.8 g, 70.mmol, 3 eq) followed by compound 10 (4.65 g, 35.37 mmol, 1.5 eq) and the resulting reaction mixture was heated at 100° C. for 16 h. The reaction was monitored by TLC. TLC analysis indicated formation of a polar spot. Reaction mixture was diluted with ice water and extracted with ethyl acetate (2×200 mL). The combined organic layer was dried over $Na_2SO_4$ and concentrated under reduced pressure. The crude product was purified by column chromatography (silica 100-200) using 5% ethyl acetate in petroleum ether as an eluent to give Compound 12 (5 g, 40.32% yield) as a colorless liquid. LCMS: m/z 324.00 (M+H):

Step 11:

To a stirred solution of compound 12 (5 g, 15.4 mmol, 1 eq) in DCM (50 mL), was added TFA (50 mL) drop wise and the resulting reaction mixture was stirred at RT for 16 h. The reaction was monitored by TLC. TLC analysis indicated formation of a polar spot. The reaction mixture was concentrated under reduced pressure, basified with aq 2N NaOH solution and extracted with ethyl acetate (2×300 mL). The combined organic layer was dried over $Na_2SO_4$ and concentrated under reduced pressure to give Compound 13 (3 g, 86.9% yield) as an off-white solid. LCMS: m/z 223.88 (M+H):

Step 12:

To a stirred solution of compound 13 (3.5 g, 15.69 mmol, 1 eq) in ethanol (35 mL) was added DIPEA (8.6 mL, 47.07 mmol, 3 eq) followed by compound 14 (4.5 mL, 31.39 mmol, 2 eq) and the resulting reaction mixture was stirred at RT for 16 h. The reaction was monitored by TLC. TLC analysis indicated formation of non-polar spot. Reaction mixture was diluted with ice water and extracted with DCM (2×200 mL). The combined organic layer was dried over $Na_2SO_4$ and concentrated under reduced pressure. The crude product was purified by column chromatography (silica 100-200) using DCM as an eluent to give Compound 15 (3 g, 63.8% yield) as a yellow liquid. LCMS: 97.25% with m/z 305.93 (M+H):

Step 13:

A stirred solution of compound 15 (3.1 g, 10.16 mmol, 1.0 eq), and PMDTA (4.2 mL, 20.32 mmol, 2 eq) in dry THF (30 mL) was cooled to −78° C. and n-BuLi (2.5M in hexane) (8.1 mL, 20.32 mmol, 2 eq) was added drop wise under argon atmosphere. Then, the resulting reaction mixture was stirred for 2 h at the same temperature. Then, a solution of iodine (5.16 g, 20.32 mmol, 2 eq) in THF (50 mL) was added drop wise at −78° C. and the resulting reaction mixture was allowed to RT for 16 h. The reaction was monitored by TLC. TLC analysis indicated formation of a non-polar spot. The reaction mixture was quenched with saturated aqueous solution of sodium thiosulfate and extracted with EtOAc (3×100 mL). The combined organic layer was dried over Na₂SO₄ and concentrated under reduced pressure to give compound 16 (4 g, 93% yield) as a red colored liquid. LC-MS: m/z 432.16 (M+H).

Step 14:

To a stirred solution of compound 16 (0.37 g, 0.86 mmol, 1 eq) in toluene (20 mL) was added Cs₂CO₃ (0.83 g, 2.58 mmol, 3 eq), compound 17 (0.119 g, 1.03 mmol, 1.2 eq) followed by xanthophos (0.02 g, 0.043 mmol, 0.05 eq) and the resulting reaction mixture was degassed with nitrogen for 15 min. Pd(dba)₃ (0.078 g, 0.086 mmol, 0.1 eq) was added and the resulting reaction mixture was refluxed for 16 h. The reaction was monitored by TLC. TLC analysis indicated formation of a polar spot. Reaction mixture was filtered through celite, washed with ethyl acetate and filtrate was concentrated under reduced pressure to get crude product. The crude product was purified by column chromatography (silica 100-200) using 20% ethyl acetate in petroleum ether as an eluent to give Compound 18 (0.2 g, 55.5% yield) as an off-white solid. LCMS: m/z 421.06 (M−H):

Step 15:

To a stirred solution of compound 18 (0.2 g, 0.476 mmol, 1 eq) in DCM (5 mL), was added TFA (5 mL) drop wise and the resulting reaction mixture was stirred at RT for 16 h. The reaction was monitored by TLC. TLC analysis indicated formation of a polar spot. The reaction mixture was concentrated under reduced pressure, basified with aq 2N NaOH solution and extracted with ethyl acetate (2×50 mL). The combined organic layer was dried over Na₂SO₄ and concentrated under reduced pressure to give 5-chloro-2-((1R,5S)-8-(2,2,2-trifluoroethyl)-3,8-diazabicyclo[3.2.1]octan-3-yl)pyridin-4-amine (0.12 g, 78.9% yield) as an off-white solid. LCMS: 96.29% with m/z 321.17 (M+H):

Synthesis of 5-chloro-2-((1R,4R)-5-methyl-2,5-diazabicyclo[2.2.1]heptan-2-yl)pyridin-4-amine Scheme 67

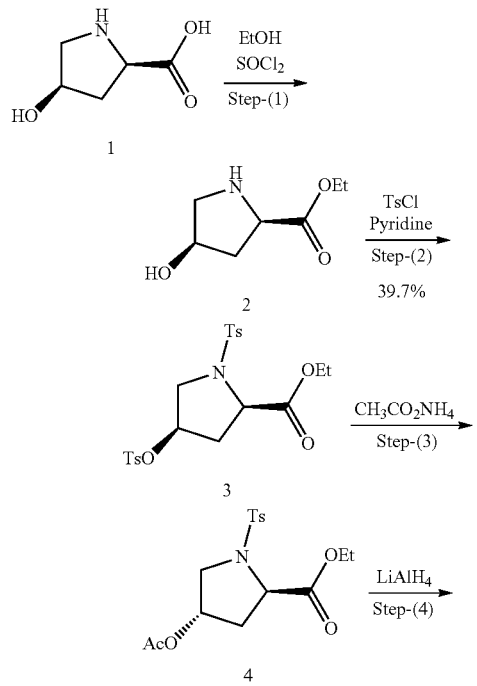

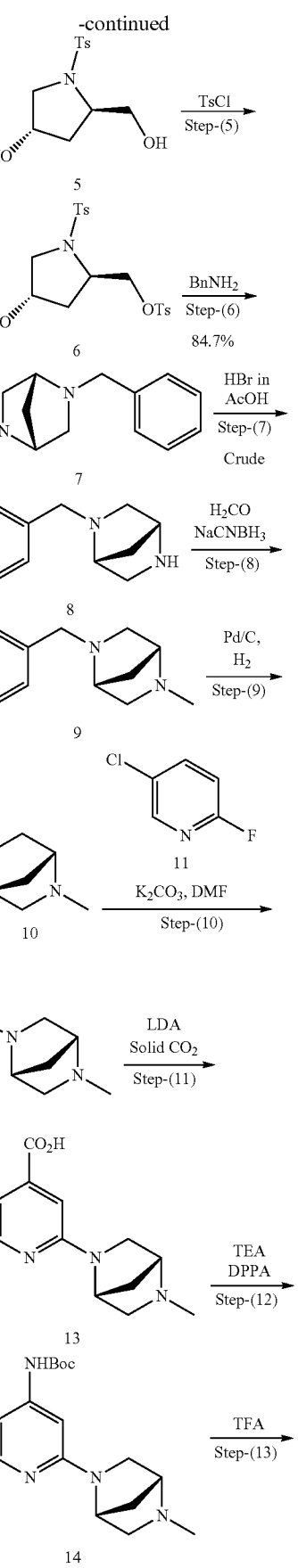

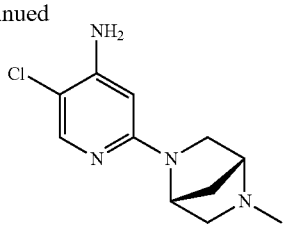

Compound numbers in text refer to structures shown in Scheme 67.

Step 1:

To a solution of compound 1 (30 g, 229 mmol, 1 eq) in Ethanol (300 mL) was added $SOCl_2$ (16.7 mL, 229 mmol, 1 eq) drop wise at 0° C. The mixture was brought to a reflux for 16 h. TLC analysis indicated formation of a less polar spot. The reaction mixture was cooled to 0° C. A solid was formed, filtered and dried under vacuum to give compound 2 (30 g, 82.4%) as an off-white solid.

Step 2:

To a solution of compound 2 (30 g, 188.6 mmol, 1 eq) in Pyridine (300 mL) was added TEA (98.9 mL, 754.4 mmol, 4 eq) cooled to 0° C. Tosyl chloride (143.3 g, 754.4 mmol, 4 eq) was added to it portion wise then the mixture was slowly warmed to RT for 16 h. TLC analysis indicated formation of less a polar spot. The reaction mixture was poured into ice water. A solid was formed, filtered and dried under vacuum to give compound 3 (35 g, 39.7%) as a pale yellow solid. LC-MS: 92.86% with m/z 468.24 (M+H+).

Step 3:

To a solution of compound 3 (30 g, 6.4 mmol, 1.0 eq) in Toluene (300 mL) was added tetra methyl ammonium acetate (33.5 g, 128.4 mmol, 2 eq) at rt then heated to reflux for 16 h. TLC analysis indicated formation of a polar spot. Then the reaction mass was extracted with EtOAc (2×200 ml), washed with water (2×100 ml) and brine (2×100 ml) and dried under reduced pressure. The residue (40 g) was taken up with 80 ml of 2-propanol. The mixture was stirred at 0° C. for 30 mins and the resulting Crystalline product was collected under dried under vacuum to give compound 4 (20 g, 87.7%) as a pale yellow solid.

Step 4:

To a solution of compound 4 (20 g, 56.3 mmol, 1 eq) in dry THF (200 mL) was added Lithium borohydride (2.44 g, 116.4 mmol, 2 eq) at 0° C. then slowly warmed to RT for 16 h. TLC analysis indicated formation of polar spot. The reaction mixture was cooled to 0° C. and the pH was adjusted to 3 with 6N HCl solution. The solution was concentrated and the residue was triturate with cold water (150 mL). A solid was formed, filtered and dried under vacuum to give compound 5 (10 g, 65.7%) as an off-white solid. LC-MS: 85.26% with m/z 271.83 (M+H+).

Step 5:

To a solution of compound 5 (10 g, 36.9 mmol, 1 eq) in Pyridine (100 mL) was added Tosyl chloride (24.5 g, 129.1 mmol, 4 eq) in one portion at 0° C. The temperature was raised to 50° C., then slowly lowered to RT stirred for 16 h. TLC analysis indicated formation of a less polar spot. The reaction mixture was poured into cold 2N HCl (200 mL) solution. A solid was formed, filtered and dried under vacuum to give compound 6 (15 g, 71.4%) as a pale yellow color solid. LC-MS: 84.09% with m/z 579.9 (M+H+).

Step 6:

To a solution of compound 6 (14 g, 24.1 mmol, 1.0 eq) in Toluene (140 mL) was added benzyl amine (5.17 g, 48.3 mmol, 3 eq) at rt. The mixture was brought to a reflux for 16 h. TLC analysis indicated formation of a polar spot. The reaction mixture was cooled and filtered. The residue was washed with toluene (50 mL). The combined organic layers were evaporated under reduced pressure and the resulting residue was taken up with 20 mL of 2-propanol. After cooling, the product was filtered, washed with diethyl ether to give compound 7 (7 g, 84.7% yield) as an off-white solid. LC-MS: 99.30% with m/z 343.58 (M+H+).

Step 7:

To a hot solution of hydro bromic acid (6.8 g, 2V) in acetic acid (34 mL) at 70° C. was added compound 7(3.4 g, 12.5 mmol, 1 eq). Then the solution was stirred at the same temperature for 16 h. TLC analysis indicated formation of a polar spot. The reaction mixture was cooled to RT. A solid was formed and filtered under vacuum washed with diethyl ether to give compound 8 (3 g, Crude) as an off-white solid.

Step 8:

To a solution of compound 8 (3 g, 17.0 mmol, 1 eq) in DCM: AcOH (32 mL+9 mL) was cooled to 0° C. and added 37% HCHO solution (3 mL, 68.08 mmol, 4 eq) drop wise at 0° C. under argon atmosphere. Then, the reaction mixture was allowed to warm to RT for 3 h. Reaction mixture was cooled to 0° C. and was added $NaCNBH_3$ (2.11 g, 34.0 mmol, 2 eq) slowly at 0° C. The mixture was allowed to warm up to RT for 2 h. The reaction was monitored by TLC. TLC analysis indicated formation of a less polar spot. The reaction was basified with sat.$NaHCO_3$solution and extracted with DCM (2×100 mL). The combined organic layer was dried over $Na_2SO_4$ then concentrated under reduced pressure to give compound 9 (3 g, Crude) as a pale yellow liquid. LC-MS: 77.28% with m/z 203.18 (M+H+).

Step 9:

A stirred solution of compound 9 (3 g, 14.8 mmol, 1 eq) in methanol (30 mL) and HCl (4M in Dioxane, 0.5 mL) was purged with nitrogen for 15 min. $Pd(OH)_2$ (20% wt on carbon, 600 mg, 0.15 times) was added. The mixture was hydrogenated under a balloon atmosphere of hydrogen gas for 16 h. The reaction was monitored by TLC. TLC analysis indicated formation of a polar spot. The reaction mixture was filtered through celite, which was washed with methanol: DCM. The filtrate was concentrated under reduced pressure to give crude compound 10 (1.5 g (crude), 70.5% yield) as a pale yellow liquid.

Step 10:

To a suspension of compound 10 (1.29 g, 11.5 mmol, 1.5 eq) and compound 11 (1 g, 7.6 mmol, 1.0 eq) in DMF (20 mL) was added $K_2CO_3$ (2.65 g, 19.2 mmol, 2.5 eq). The mixture was heated to 90° C. for 16 h. TLC analysis indicated the formation of a polar spot. The reaction mixture was extracted with EtOAc (2×150 ml) and washed with cold water (2×100 ml) and brine (2×100 ml) dried under reduced pressure. The combined organic layer was dried over $Na_2SO_4$ and concentrated under reduced pressure to give crude product, which was purified by column chromatography ($SiO_2$, 100-200 mesh) using 0-10% meOH in DCM as an eluent to give compound 12 (1 g, 39.0% yield) as a pale yellow liquid. LC-MS: 98.82% with m/z 223.81 (M+H);

Step 11:

To a solution of compound 12 (1 g, 4.4 mmol, 1.0 eq) in Dry THF (20 mL) was added PMDTA(3.1 g, 17.9 mmol, 4.0 eq) followed by n-BuLi (2.5M in n-hexane, 7.17 mL, 4.0 eq) at −78° C. for 4 h. Then, powder of dry ice was added slowly at the same temp and the mixture allowed to warm up to RT over 16 h. Then, the reaction mixture was quenched with Dioxane.HCl concentrated under reduced pressure to give a crude product, which was washed with n-pentane & ether to give crude compound 13 (1 g, crude) as a yellow color solid.

Step 12:

To a solution of compound 13 (1 g, 3.7 mmol, 1 eq), TEA (0.77 mL, 5.5 mmol, 1.5 eq) in Toluene:tBuOH (10:10 mL) at 5-10° C., DPPA (2.05 mL, 7.4 mmol, 2 eq) was added in drop wise manner at the same temperature. Then, the reaction mixture was heated to 85° C. for 16 h. TLC analysis indicated formation of a non polar spot. The reaction mixture was cooled to RT and concentrated under reduced pressure to give a residue, which was re-dissolved in EtOAc (60 mL) and washed with sat.brine. The separated organic layer was dried over $Na_2SO_4$ and concentrated under reduced pressure to give a crude product was purified by column chromatography using 0-10% MeOH in DCM as an eluent to give compound 14 (300 mg, 23.8% yield) as a brown gummy liquid.

Step 13:

To a solution of compound 14 (320 mg, 0.9 mmol, 1 eq) in Dioxane.HCl (10 mL) at 0° C.-RT for 16 h. TLC analysis indicated formation of polar spot. Then, the reaction mixture was concentrated under reduced pressure to give a TFA salt of product, which was washed with Diethyl ether to give 5-chloro-2-((1R,4R)-5-methyl-2,5-diazabicyclo[2.2.1]heptan-2-yl)pyridin-4-amine as a TFA salt (110 mg, 50%) as an off-white solid. LC-MS: 99.0% with m/z 239.1 (M+H+).

Synthesis of 5-chloro-2-((1R,5S)-6-methyl-3,6-diazabicyclo[3.1.1]heptan-3-yl)pyridin-4-amine Scheme 68

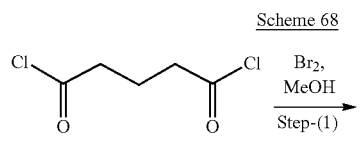

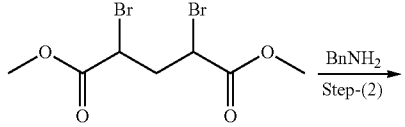

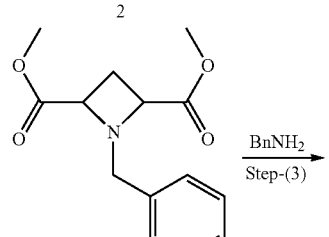

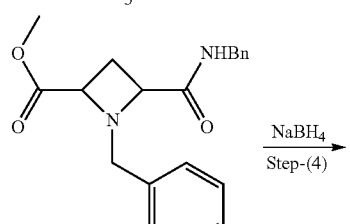

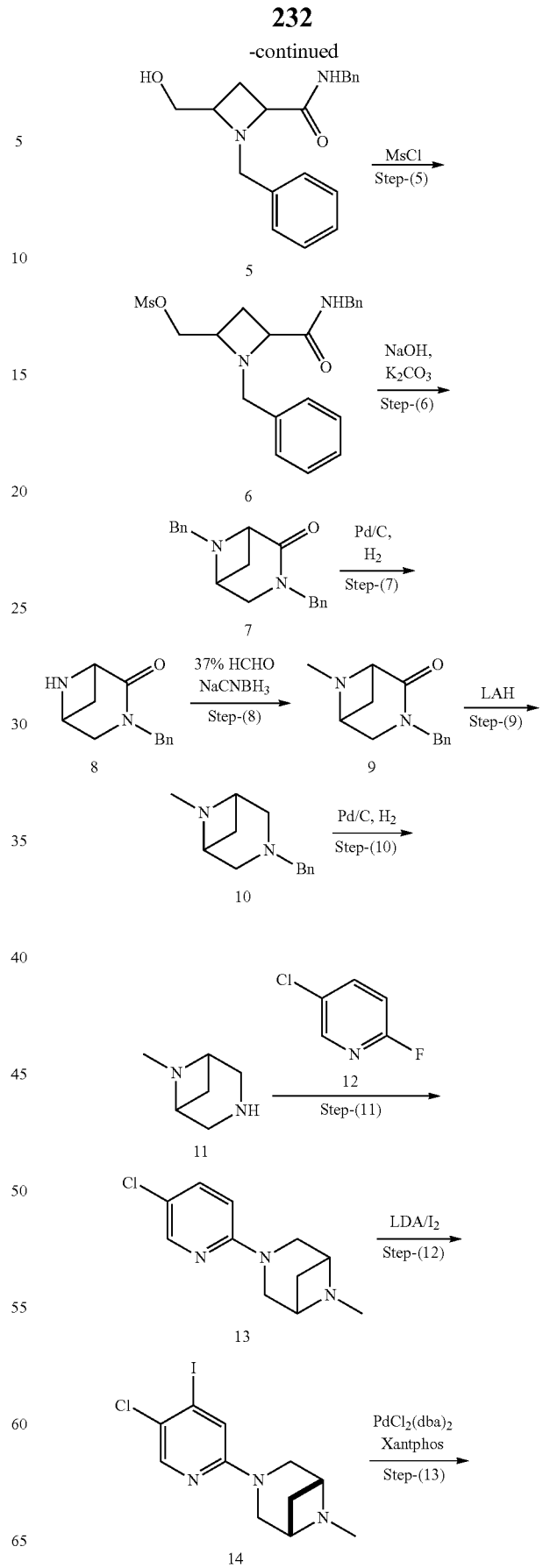

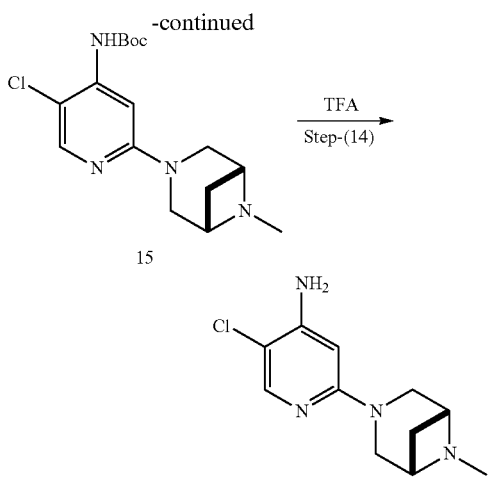

Compound numbers in text refer to structures shown Scheme 68.

Step 1:

To a stirred compound 1 (200 g, 1190 mmol, 1 eq) was added drop wise bromine (135 mL, 2619.0 mmol, 3.1 eq) under light (200W) condition at 90° C., the reaction mixture was continued at the same temp for 4 h. The reaction mixture was cooled to 0° C., then MeOH (1080 L, 15 eq) was added drop wise. Then the reaction mixture was allowed to warm up to RT for 16 h. The reaction was monitored by TLC. TLC analysis indicated formation of a nonpolar spot. The reaction mixture was basified with aq.NaHCO$_3$ and extracted with ethyl acetate (2×500 mL). The combined organic layer was washed with NaHSO$_4$ and dried over Na$_2$SO$_4$ then concentrated under reduced pressure to a crude compound. The crude compound was purified by downward distillation at 150° C. and 0.01 mmH vacuum pressure to afford compound 2 (300 g, 79.76% yield) as a colorless oil.

Step 2:

To a solution of compound 2 (175 g, 553.79 mmol, 1 eq) in DMF (1000 mL) was added BnNH$_2$ (181.4 mL, 1661.39 mmol, 3 eq) at RT, then the reaction mixture was heated to 90° C. for 4 h. The reaction was monitored by TLC. TLC analysis indicated formation of a polar spot. The reaction mixture was diluted with ethyl acetate (200 mL) and washed with H$_2$O (2×100 mL). The combined organic layer was dried over Na$_2$SO$_4$ then concentrated under reduced pressure to give crude compound. The crude compound was purified by column chromatography (silica gel, 100-200 mesh) using 0-60% ethyl acetate in petroleum ether as an eluent to afford compound 3 (60 g, 41.16% yield) as a brown liquid. LCMS: 49.6% with m/z 263.91 (M+1):

Step 3:

To a solution of compound 3 (55 g, 209 mmol, 1 eq) in toluene (500 mL) was added BnNH$_2$ (23 mL, 209 mmol, 1 eq) at RT, then the reaction mixture was heated to 110° C. for 60 h. the reaction was monitored by TLC. TLC analysis indicated formation of a polar spot. The reaction mixture was diluted with ethyl acetate (200 mL) and washed with H$_2$O (2×100 mL). The organic layer was dried over Na$_2$SO$_4$ then concentrated under reduced pressure to give a crude compound. The crude compound was purified by column chromatography (silica gel, 100-200mesh) using 0-60% ethyl acetate in petroleum ether as an eluent to afford compound 4 (23 g, 32.54% yield) as a brown liquid. LCMS: 47% with m/z 339.09 (M+1):

Step 4:

To a stirred solution of compound 4 (23 g, 68.04 mmol, 1 eq) in methanol (250 mL) was portion wise added NaBH$_4$ (10.29 g, 272.18 mmol, 4 eq) at 0° C., then the reaction mixture was allowed to RT for 16 h. The reaction was monitored by TLC. TLC analysis indicated formation of a polar spot. The reaction mixture was diluted with ethyl acetate (200 mL) and washed with H$_2$O (2×100 mL). The organic layer was dried over Na$_2$SO$_4$ then concentrated under reduced pressure to give crude compound. The crude compound was purified by column chromatography (silica gel, 100-200 mesh) using 0-70% ethyl acetate in petroleum ether as an eluent to afford compound 5 (20 g, 94.83% yield) as a brown liquid. LCMS: 78.35% with m/z 311.00 (M+1):

Step 5:

To a stirred solution of compound 5 (20 g, 64.5 mmol, 1 eq) in DCM (200 mL) was added TEA (27.15 mL, 193.5 mmol, 3 eq) at RT, then drop wise added mesyl-chloride (6.5 mL, 83.87 mmol, 1.3 eq) at 0° C. and the reaction mixture was stirred at 0° C. for 4 h. The reaction was monitored by TLC. TLC analysis indicated formation of a less polar spot. The reaction mixture was diluted with ethyl acetate (200 mL) and washed with H$_2$O (2×100 mL). The organic layer was dried over Na$_2$SO$_4$ then concentrated under reduced pressure to afford crude compound 6 (26 g, crude) as a brown liquid. LCMS: 56.43% with m/z 389.96 (M+1):

Step 6:

To a stirred solution of compound 6 (26 g, 66.98 mmol, 1 eq) in Toluene (300 mL) was added NaOH (9.37 g, 234.44 mmol, 3.5 eq), K$_2$CO$_3$ (18.51 g, 133.96 mmol, 2 eq) and (Bu$_4$N)HSO$_3$ (2.275 g, 6.698 mmol, 0.1 eq) at RT, then the reaction mixture was heated to 110° C. for 4 h, the reaction was monitored by TLC. TLC analysis indicated formation of a less polar spot. The reaction mixture was diluted with ethyl acetate (400 mL) and washed with H$_2$O (2×200 mL). The organic layer was dried over Na$_2$SO$_4$ then concentrated under reduced pressure to afford a crude residue, The crude compound was purified by column chromatography (silica gel, 100-200 mesh) using 0-50% ethyl acetate in petroleum ether as an eluent to afford compound 7 (13 g, 77% yield, After two steps) as a brown liquid. LCMS: 62.86% with m/z 293.04 (M+1):

Step 7:

To a stirred solution of compound 7 (25 g, 85.61 mmol, 1 eq) in EtOH (100 mL) was added 10% Pd/C (25 g) at RT under argon atmosphere, then the reaction mixture was heated to 70° C. in a autoclave condition under 70 psi of H2 pressure for 16 h. TLC analysis indicated formation of a polar spot. The reaction mixture was filtered through a celite pad and then filtrate was concentrated under vacuum to give a crude pale yellow solid, which was triturated with diethyl ether to afford compound 8 (15 g, 87.0% yield) as an off-white solid. LCMS: 67.52% with m/z 203.0 (M+1):

Step 8:

To a stirred solution of compound 8 (15 g, 74.25 mmol, 1 eq) in DCM (115 mL) and AcOH (45 mL) was added 37% HCHO (9.05 mL, 113.3 mmol, 1.5 eq) at RT and then the reaction continued for 2 h. NaCNBH$_3$ (9.3 g, 148 mmol, 2 eq) was added at 0° C. The mixture was allowed to warm up to RT for 2 h. TLC analysis indicated formation of a less polar spot. The reaction mixture was basified with aqueous NaHCO$_3$ solution then extracted with EtOAc (3×90 mL). The combined organic layer was dried over Na$_2$SO$_4$ then concentrated to crude compound. The crude compound was purified by column chromatography (silica gel, 100-200 mesh) using 0-70% EtOAc in petroleum ether as eluent to afford compound 9 (4.7 g, 29.3% yield) as a brown oil. LC-MS: 80.66% with m/z 216.93 (M+H).

Step 9:

To a stirred solution of compound 9 (16 g, 74.0 mmol, 1 eq) in THF (150 mL) was added LAH (16.8 g, 444.2 mmol, 6 eq) as portion wise at 0° C. then the mixture was allowed to warm up to RT and then slowly heated to 80° C. for 16 h. TLC analysis indicated formation of a less polar spot. The reaction mixture was slowly quenched with EtOAc (300 mL) at 0° C. to reduce the formation of bubbles, and further quenched with water (17 mL), 20% aqueous NaOH solution (17 mL) and water (52 mL). The reaction mixture was further stirred for 2 h at RT. The mixture was filtered through a celite pad and the filtrate was dried over $Na_2SO_4$ then concentrated to a crude compound. The crude compound was purified by column chromatography (silica gel, 100-200 mesh) using 10% MeOH in DCM as eluent to afford compound 10 (5.5 g, 37%) as brown oil. LC-MS: 94.63% with m/z 203.0 (M+H).

Step 10:

To a stirred solution of compound 10 (5.5 g, 27.20 mmol, 1 eq) in MeOH (100 mL) was added 10% $Pd(OH)_2$ (0.5 g) and 4M Dioxane in HCl (0.1 mL) at RT, then the reaction mixture was stirred in autoclave condition under 70 psi of H2 pressure at RT for 16 h. TLC analysis indicated formation of a polar spot. The reaction mixture filtered through a celite pad, then the filtrate was concentrated to afford compound 11 (2.5 g, 81.9%) as a pale yellow liquid. (As such forward to next step without any further purification)

Step 11:

To a stirred solution of compound 11 (3.0 g, 26.7 mmol, 1 eq) and 12 (7.4 g, 53.5 mmol, 2 eq) in DMF (10 mL) was added $K_2CO_3$ (11.0 g, 80.3 mmol, 3 eq) at RT under argon atmosphere. The reaction mixture was heated to 90° C. for 16 h. TLC analysis indicated formation of a less polar spot along with traces of un-reacted SM. The reaction mixture was diluted with ice-cold water then extracted with EtOAc (3×40 mL). The combined organic layer was dried over $Na_2SO_4$ then concentrated to give a crude compound. The crude compound was purified by column chromatography (silica gel, 100-200 mesh) using in 0-10% MeOH in DCM as eluent to afford compound 13 (1.5 g, 25.1%) as a light yellow oil. LC-MS: 97.34% with m/z 224.12 (M+H).

Step 12:

To a stirred solution of compound 13 (1.5 g, 6.70 mmol, 1 eq) in THF (20 mL) was added PMDTA (2.80 mL, 13.4 mmol, 2.0 eq) and n-BuLi (5.3 mL, 13.4 mmol, 2.0 eq, 2.5M in hexane) as drop wise at −78° C. under argon atmosphere. The reaction mixture was continued at the same temperature for 3 h. Then a solution of 12 (3.4 g, 13.4 mmol, 2 eq, in THF) was added at −78° C., after that slowly allowed to RT for 16 h. TLC analysis indicated formation of a less polar spot. The reaction mixture was quenched in aqueous solution of sodium thiosulphate then extracted with EtOAc (3×100 mL). The combined organic layer was dried over $Na_2SO_4$ then concentrated under reduced pressure to give crude compound 14 (2.0 g, crude) as a brown oil. (As such forward to next step without any farther purification). LC-MS: 95.78% with m/z 350.11 (M+H).

Step 13:

To a stirred solution of compound 14 (2 g, 8.03 mmol, 1 eq) in Toluene (50 mL) was added $Cs_2CO_3$ (5.26 g, 16.0 mmol, 2 eq) and $NH_2Boc$ (1.39 g, 12.0 mmol, 1.5 eq) at RT. The reaction mixture was de-gassed with argon for 20 min., then added xantphos (139 mg, 0.24 mmol, 0.03 eq) and $Pd_2(dba)_3$ (220 mg, 0.24 mmol, 0.03 eq) at RT, after that the reaction mixture was heated to 90° C. (pre-heated) for 16 h. TLC analysis indicated formation of a polar spot. The reaction mixture was filtered through celite pad then the filtrate was concentrated to a crude compound. The crude compound was purified by column chromatography (silica gel, 100-200 mesh) using 0-10% MeOH in DCM as eluent to afford compound 15 (1.3 g, 88.1% after two steps) as a pale yellow solid. LC-MS: 93.9% with m/z 339.23 (M+H).

Step 14:

To a stirred solution of compound 15 (2 g, 5.9 mmol, 1 eq) in DCM (50 mL) was added TFA (4.5 mL 59 mmol, 10 eq) at RT and the reaction continued for 16 h. TLC analysis indicated formation of a polar spot. The reaction mixture was basified by aqueous $NaHCO_3$ solution then extracted with EtOAc (3×150 mL). The combined organic layer was dried over $Na_2SO_4$ then concentrated under reduced pressure to a crude compound. The crude compound was purified by triturated with 1:1 pentane and diethyl ether to afford 5-chloro-2-((1R,5S)-6-methyl-3,6-diazabicyclo[3.1.1]heptan-3-yl)pyridin-4-amine (0.7 g, 49.7%) as an off-white solid. LCMS: m/z 239.11 (M+H).

Synthesis of 5-chloro-2-((1R,5S)-8-methyl-3,8-diazabicyclo[3.2.1]octan-3-yl)pyridin-4-amine

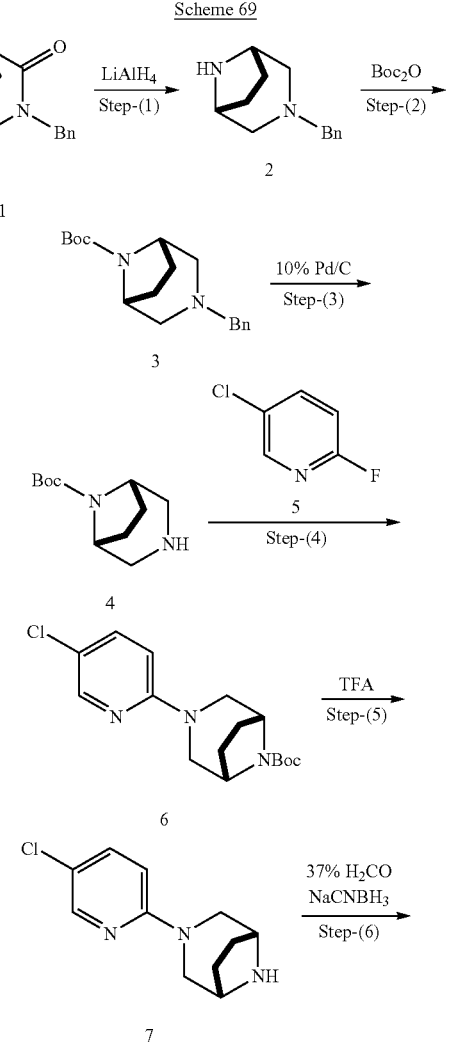

Scheme 69

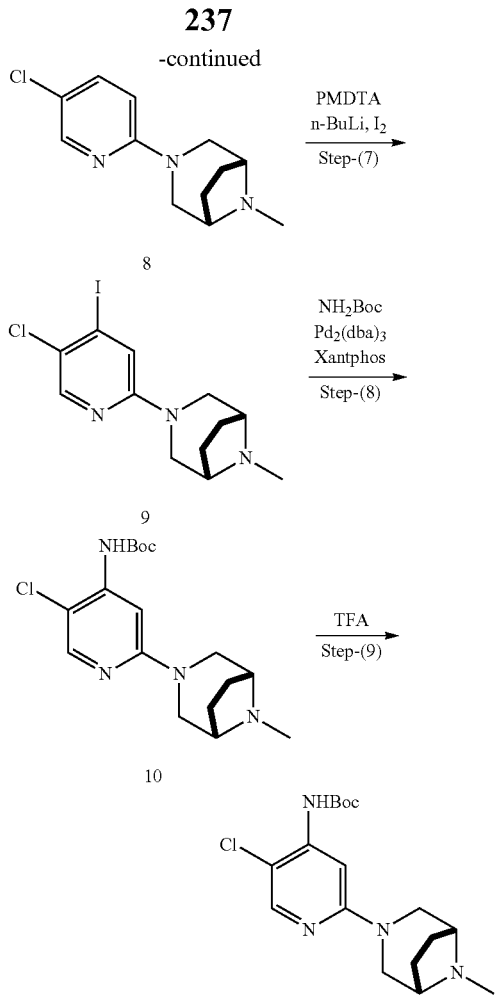

Compound numbers in text refer to structures shown in Scheme 69.

Step 1:

To a stirred solution of compound 1 (28 g, 121.7 mmol, 1 eq) in THF (1.2 L), was cooled to 0° C. and added LAH (37 g, 973.9 mmol, 8 eq) portion wise and the resulting reaction mixture was heated at 70° C. for 36 h. The reaction was monitored by TLC. TLC analysis indicated formation of a polar spot. The reaction mixture was quenched with water (30 mL), filtered through celite and washed with ethyl acetate. Filtrate was extracted with ethyl acetate (2×750 mL), dried over $Na_2SO_4$ and concentrated under reduced pressure to give Compound 2 (16 g, 65% yield) as a yellow liquid. LCMS: 73.70% with m/z 203.48 (M−H):

Step 2:

To a stirred solution of compound 2 (5 g, 24.75 mmol, 1.0 eq) in DCM (50 mL) were added triethyl amine (10.5 mL, 74.25 mmol, 3.0 eq) and $(Boc)_2O$ (6.0 mL, 37.12 mmol, 1.5 eq) at 0° C. and the reaction mixture was stirred under argon atm for 16 h. TLC analysis indication of a less polar spot. The reaction mixture was concentrated to give a crude compound, which was purified by column chromatography using silica gel (100-200 mesh) and as an eluent 5-10% EtOAc in petroleum ether to give compound 3 (5.5 g, 74.3%) as an off white solid compound. LC-MS: 97.91% with m/z 303.2 (M+H).

Step 3:

To a suspension of compound 3 (5.g, 27.22 mmol, 1.0 eq) in MeOH (60 mL), degassed for 20 min and was added 10% pd/c. The reaction mixture was stirred under H2 atm for 16 h. TLC analysis indication of a polar spot. The reaction mixture was filtered through celite and washed with methanol. The filtrate was dried over with $Na_2SO_4$ and concentrated under reduced pressure gave desired product 4 (3.5 g, 92.1%) as an off white solid.

Step 4:

To a solution of compound 4 (4 g, 29.7 mmol, 1.0 eq) in DMSO (50 mL) were added $K_2CO_3$ (7.82 g, 84.2 mmol, 3.0 eq) and compound 5 (3.7 g, 28.2 mmol, 1.5 eq) and the reaction mixture was heated to 90° C. under argon atmosphere for 16 h. TLC analysis indication of a less polar spot Then, the reaction mixture was cooled to RT. The reaction mixture was quenched with ice cold water (200 mL) and extracted with EtOAc (2×500 mL). The organic layer was dried over $Na_2SO_4$ and concentrated under reduced pressure to give a crude product, which was purified by column chromatography (silica gel 100-200 mesh) as an eluent 0-10% EtOAc in petroleum ether to give compound 6 (4.1 g, 68.3%) as a white solid. LC-MS: 82.53% with m/z 324.08 (M+H).

Step 5:

To a solution of compound 6 (3 g, 12.82 mmol, 1.0 eq) in DCM (50 mL) was cooled to 0° C. and TFA(14 mL, 153.8 mmol, 12.0 eq) was drop wise added and the reaction mixture was stirred at RT for 16 h. TLC analysis indicates the formation of a polar spot. TFA was concentrated under reduced pressure, basified with $NaHCO_3$ solution (200 mL) and extracted with EtOAc (2×500 mL). The combined organic layer dried over with $Na_2SO_4$ and concentrated under reduced pressure to give crude compound 7 (3.0 g, 96%) as an off white solid. LC-MS: 97.43% with m/z 223.89 (M+H).

Step 6:

To a solution of compound 6 (2.6 g, 11.65 mmol, 1.0 eq) in DCM:AcOH (7:3) (21 mL: 12 mL) 37% formaldehyde (1.62 mL, 20.17 mmol, 1.5 eq) was drop wise added and the reaction mixture was stirred at under argon atm RT for 2 h. $NaCNBH_3$ (1.7 g, 26.9 mmol, 2.0 eq) was added after that and the reaction mixture was stirred for 2 h. TLC analysis formation of less polar spot. The reaction was concentrated under reduced pressure and basified with $NaHCO_3$ solution (200 mL) and extracted with EtOAc (2×500 mL). The combined organic layer was dried over with $Na_2SO_4$ and concentrated under reduced pressure to give crude compound 8 (2.5 g, 92.5%) as an off white solid. LC-MS: 83.18% with m/z 238.14 (M+H).

Step 7:

To a suspension of compound 8 (1.5 g, 6.3 mmol, 1.0 eq) in dry THF (45 mL), cooled to −78° c. was added PMDTA (8.78 mL, 25.2 mmol, 4.0 eq) and n-BuLi (11 mL, 25.2 mmol, 4.0 eq, 2.5M in THF). The reaction mixture was stirred under argon atmosphere at the same temperature for 2 h. Iodine in THF(25 mL) (3.2 g, 16.2 mmol, 2.0 eq) was added and the mixture was slowly allowed to warm to rt for 16 h. TLC analysis indication of a less polar spot and the reaction mixture was quenched with hypo solution (100 mL) and extracted with EtOAc (2×500 mL). The combined organic layer dried over with $Na_2SO_4$ and concentrated under reduced pressure to give a crude compound, which was purified by column chromatography using silica gel (100-200 mesh) as an eluent with 0-5% MeOH in DCM to give compound 9 (1.2 g, 54.5%) as an off white semi solid. LC-MS: 94.53% with m/z 363.94(M+H).

Step 8:

To a mixture of compound 9 (2.6 g, 7.12 mmol, 1.0 eq), tert-butylcarbamate (1.0 g, 8.5 mmol, 1.2 eq) and cesiumcarbonate (2.32 g, 14.32 mmol, 2.0 eq) in toluene (30 mL) and degassed by argon atm for 20 min. then pd$_2$(dba)$_3$(650 mg, 0.716 mmol, 0.05 eq), Xantphos(210 mg, 0.35 mmol, 0.1 eq) were added and the reaction mixture was heated 100° c. for 16 h. TLC analysis of indication of a polar spot and the reaction mixture was filtered through celite and washed with EtOAc (200 mL). The filtrate was concentrated under reduced pressure to give a residue, which was purified by column chromatography by using silica gel (100-200 mesh) as an eluent 5-10% MeOH in DCM to to give desired compound 10 (1.9 g, 76%) as a gummy brown solid. LC-MS: 87.93% with m/z 353.32 (M+H).

Step 9:

To a suspension of compound 10(1.9 g, 5.39 mmol, 1.0 eq) in DCM (20 mL) cooled to 0° C. TFA (5.3 mL, 64.68 mmol, 12.0 eq) was drop wise added and the reaction mixture was stirred at RT for 16 h. TLC analysis indicated the formation of a polar spot and the mixture was concentrated under reduced pressure and basified with NH$_3$ in MeOH solution and concentrated under reduced pressure to give a crude compound, which was purified by column chromatography by using neutral alumina as an eluent 5-10% MeOH in DCM to give desired compound 5-chloro-2-((1R,5S)-8-methyl-3,8-diazabicyclo[3.2.1]octan-3-yl) pyridin-4-amine (520 mg, 40%) as an off white solid. LC-MS: 98.50% with m/z 253.16 (M+H).

Synthesis of (S)-5-chloro-2-(4-(cyclopropylmethyl)-2-methylpiperazin-1-yl) pyridin-4-amine

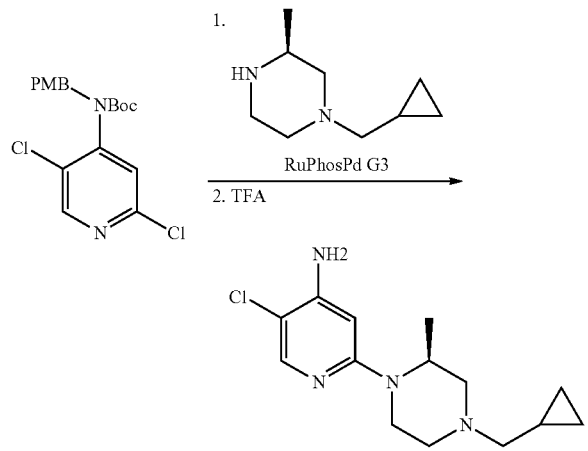

Scheme 70

Step 1: Preparation of tert-butyl (S)-(5-chloro-2-(4-(cyclopropylmethyl)-2-methylpiperazin-1-yl)pyridin-4-yl)(4-methoxybenzyl)carbamate To a round bottom flask was charged with tert-butyl (2,5-dichloropyridin-4-yl)(4-methoxybenzyl)carbamate (1700 mg, 4.44 mmol), (S)-1-(cyclopropylmethyl)-3-methylpiperazine dihydrochloride (1209 mg, 5.32 mmol), Cesium carbonate (6503 mg, 19.96 mmol) and t-BuOH (12 ml). The system was flushed with nitrogen then 2-Dicyclohexylphosphino-2',6'-di-i-propoxy-1,1'-biphenyl (83 mg, 0.177 mmol) and RuPhos Pd G3 (67.4 mg, 0.089 mmol) were added. The system was flushed with nitrogen and heated at 100° C. over the weekend. LCMS showed complete conversion. The reaction was loaded onto celite, and purified on the Biotage (silica gel) eluting with 0-10% MeOH/DCM. The desired fractions were collected and dried under vacuum to afford tert-butyl (S)-(5-chloro-2-(4-(cyclopropylmethyl)-2-methylpiperazin-1-yl)pyridin-4-yl)(4-methoxybenzyl)carbamate (2.2 g, 4.39 mmol, 99% yield) as an orange foam solid. The product was carried onto the next step.

Note: If the amine is neutralized in the previous deprotection step to generate the free base, then 2.5 equivalents of Cesium Carbonate can be used for the Buchwald reaction. Also, either SPhos (CAS No. 657408-07-6) or RuPhos (CAS No. 787618-22-8) can be used as a ligand for this reaction. LCMS RT=1.52 min, [M]+=501.5, Purity(UV 254)=90%

Step 2: Preparation of (S)-5-chloro-2-(4-(cyclopropylmethyl)-2-methylpiperazin-1-yl)pyridin-4-amine To a solution of tert-butyl tert-butyl (S)-(5-chloro-2-(4-(cyclopropylmethyl)-2-methylpiperazin-1-yl) pyridin-4-yl)(4 methoxybenzyl)carbamate (2.2 g, 4.39 mmol) in Dichloromethane (DCM) (1.0 ml)) was added Trifluoroacetic acid (3.36 ml, 43.9 mmol). The mixture was heated at 40° C. overnight. LCMS showed complete deprotection of Boc and PMB groups. The reaction was concentrated to dryness and partitioned between DCM and saturated NaHCO$_3$(aq). The aqueous layer was extracted with DCM and the combined organics were washed with water and brine. The organics were dried over magnesium sulfate, filtered and then concentrated to dryness to afford (S)-5-chloro-2-(4-(cyclopropylmethyl)-2-methylpiperazin-1-yl) pyridin-4-amine (4.20 mmol, 96% yield) as a sticky yellow foam solid. Product was used in the next step without further purification.

LCMS: RT=0.17 min, [M+1]+=281.4, Purity(UV 254)=~90%

In some cases, the product was purified by one of two methods described below.

Method A:

Upon completion of the reaction as judged by LCMS, the reaction was concentrated to dryness and purified on the Biotage (reverse phase silica gel) eluting with 0%-20% ACN/H$_2$O. The desired fractions were collected, dried under vacuum to afford the title compound.

Method B:

Upon completion of the reaction as judged by LCMS, the reaction was diluted with DCM and partitioned between DCM and water. The aqueous layer was neutralized with the addition of NaHCO$_3$ [both saturated solution and extra solid]. The layers were separated and the aqueous layer was extracted with DCM. The combined organics were dried over Na$_2$SO$_4$, filtered and concentrated in vacuo. The product used in the next step without further purification.

| Method | Aniline | Name | Yield & Mass |
|---|---|---|---|
| B | ![structure] | 5-chloro-2-(2,4,6-trimethylpiperazin-1-yl)pyridin-4-amine | 41% yield over 2 steps, LCMS [M]+ 255.6 |

Synthesis of (S)-3-chloro-2-fluoro-6-(2-methylpiperazin-1-yl)pyridin-4-amine

Scheme 71

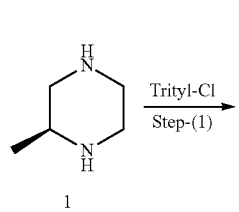

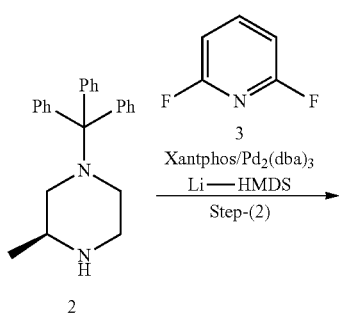

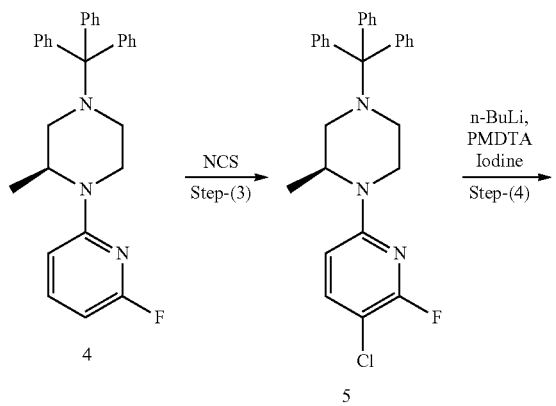

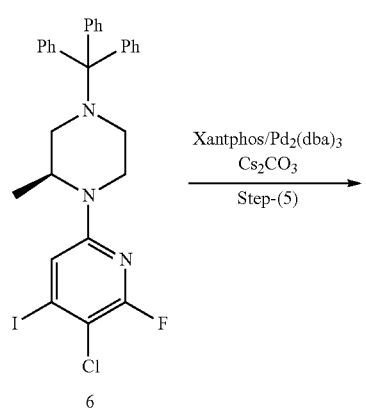

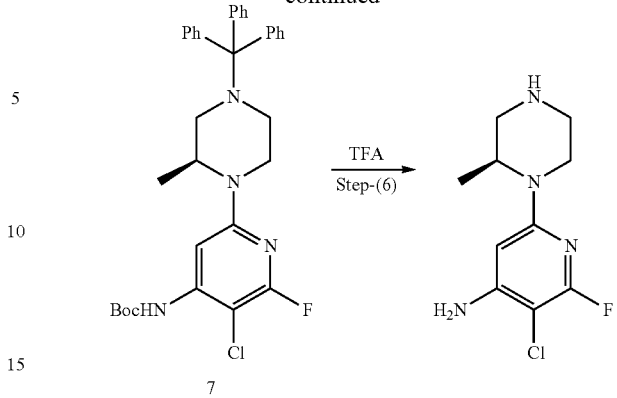

Compound numbers in text refer to structures shown in Scheme 71.

Step 1:

To a solution of compound 1 (1 g, 10 mmol, 1 eq) in DCM (30 ml) was added Trityl-Cl (2.78 g, 10 mmol, 1 eq) as portion wise at RT, then the reaction mixture was continued for 2 h. TLC analysis indicated formation of a less polar spot. The reaction mixture was quenched with water and extracted with EtOAc (3×50 mL). The combined organic layer was dried over $Na_2SO_4$ then concentrated to give compound 2 (3.3 g, 96%) as a colorless oil.

Step 2:

To a stirred solution of compound 2 (3 g, 8.77 mmol, 1 eq) was added compound 3 (1.51 g, 13.15 mmol, 1.5 eq), xantphos (152 mg, 0.026 mmol, 0.03 eq), $Pd_2(dba)_3$ (241 mg, 0.026 mmol, 0.03 eq) and Li-HMDS (43.8 mL, 43.85 mmol, 5 eq) at RT under argon atmosphere, then the reaction mixture was heated to 90° C. for 16 h. TLC analysis indicated formation of a less polar spot. The reaction mixture was cooled to RT then filtered through celite pad, which is washed with EtOAc (3×20). The filtrate was diluted with water and extracted with EtOAc (3×100 ml). The combined organic layer was dried over $Na_2SO_4$ then concentrated to give a crude compound. The crude compound was purified by column chromatography (silica gel, 100-200 mesh) using 0-2% EtOAc in petroleum ether as eluent to afford compound 4 (3 g, 78%) as a colorless oil.

Step 3:

To a stirred solution of compound 4 (3 g, 6.86 mmol, 1 eq) in DMF (40 mL) was added NCS (913 mg, 6.86 mmol, 1 eq) at RT then heated to 60° C. for 16 h. TLC analysis indicated formation of a less polar spot, which very close to SM and un-reacted SM. The reaction mixture was diluted with water then extracted with EtOAc (3×50 mL). The combined organic layer was dried over $Na_2SO_4$ then concentrated to crude compound. The crude compound was purified by column chromatography (silica gel, 100-200 mesh) using 0-2% EtOAc in petroleum ether as eluent to afford compound 5 (3 g, semi-pure) as a colorless oil.

Step 4:

To a stirred solution of compound 5 (3 g, 6.36 mmol, 1 eq) in THF (50 mL) was added PMDTA (2.65 mL, 12.73 mmol, 2 eq) and n-BuLi (5.0 mL, 12.73 mmol, 2 eq) at −78° C. The reaction mixture was continued for 2 h and a solution of 12 (3.23 g, 12.73 mmol, 2 eq, in THF) was added at −78° C. The mixture was slowly allowed to warm up to RT for 16 h. TLC analysis indicated formation of a less polar spot. The reaction mixture was quenched in aqueous solution of sodium thiosulphate then extracted with EtOAc (2×50 mL).

The combined organic layer was dried over Na₂SO₄ then concentrated under reduced pressure to give crude compound 6 (4.5 g, crude) as a brown oil.

Step 5:

To a stirred solution of compound 6 (4.5 g, 7.53 mmol, 1 eq) in Toluene (80 mL) was added Cs₂CO₃ (4.89 g, 15.07 mmol, 2 eq) and NH₂Boc (1.04 g, 9.04 mmol, 1.2 eq) at RT. The reaction mixture was de-gassed with Argon for 5 min., then xantphos (130 mg, 0.22 mmol, 0.03 eq) and Pd₂(dba)₃ (207 mg, 0.22 mmol, 0.03 eq) were added at RT. The reaction mixture was heated to 90° C. for 16 h. TLC analysis indicated formation of a polar spot. The reaction mixture was filtered through celite pad then the filtrate was concentrated to give a crude compound. The crude compound was purified by column chromatography (silica gel, 100-2000 mesh) using 0-3% EtOAc in petroleum ether as eluent to afford compound 7 (800 mg, 19% after three steps) as a pale yellow gummy liquid.

Step 6:

To a stirred compound 7 (800 mg, 1.36 mmol, 1 eq) was added TFA (5 mL) at RT and continued for 16 h. TLC analysis indicated formation of a polar spot. The reaction mixture was concentrated to crude, which was basified by aqueous NaHCO₃ solution then extracted with EtOAc (3×50 mL). The combined organic layer was dried over Na₂SO₄ then concentrated under reduced pressure to give a crude compound. The crude compound was purified by column chromatography (silica gel, 100-200 mesh) using 0-40% EtOAc in petroleum ether as eluent to afford (S)-3-chloro-2-fluoro-6-(2-methylpiperazin-1-yl)pyridin-4-amine (120 mg 36%) as a pale yellow semi-solid. LC-MS: m/z 245.01 (M+H+).

Representative Procedure for Aminopyridine Formation Via Alkylation

To a vial containing (S)-3-chloro-2-fluoro-6-(2-methylpiperazin-1-yl)pyridin-4-amine (322 mg, 1.316 mmol) in acetonitrile (1.0 ml) was added potassium carbonate (200 mg, 1.448 mmol) followed by 2-bromoethyl methyl ether (201 mg, 1.448 mmol). The reaction was stirred at RT overnight. Additional equivalents of potassium carbonate and 2-Bromoethyl methyl ether were added until the reaction was judged complete by LCMS. Methanol was added to the reaction then concentrated onto celite. The crude product was purified on the Biotage (reverse phase silica gel) eluting with 0-40% ACN/H₂O. The desired fractions were collected, concentrated and dried under vacuum to afford (S)-3-chloro-2-fluoro-6-(4-(2-m ethoxyethyl)-2-methylpiperazin-1-yl) pyridin-4-amine (0.796 mmol, 60.5% yield) as a yellow oil. In a similar manner, the following compounds were prepared

| Aniline | Name | Yield & Mass |
|---|---|---|
|  | (S)-5-chloro-2-(4-(2-methoxyethyl)-2-methylpiperazin-1-yl)pyridin-4-amine | 61% yield, LCMS [M]⁺ 303.5 |
|  | 3-chloro-2-fluoro-6-((S)-4-((S)-2-methoxypropyl)-2-methylpiperazin-1-yl)pyridin-4-amine | 38% yield, LCMS [M]⁺ 317.5 |
|  | (S)-3-chloro-2-fluoro-6-(2-methyl-4-(oxetan-3-ylmethyl)piperazin-1-yl)pyridin-4-amine | 56% yield, LCMS [M]⁺ 315.6 |
|  | (S)-3-chloro-6-(4-(2,2-difluoroethyl)-2-methylpiperazin-1-yl)-2-fluoropyridin-4-amine | 42% yield, LCMS [M]⁺ 309.4 |

Synthesis of (S)-3-chloro-6-(2,4-dimethylpiperazin-1-yl)-2-fluoropyridin-4-amine

Scheme 72

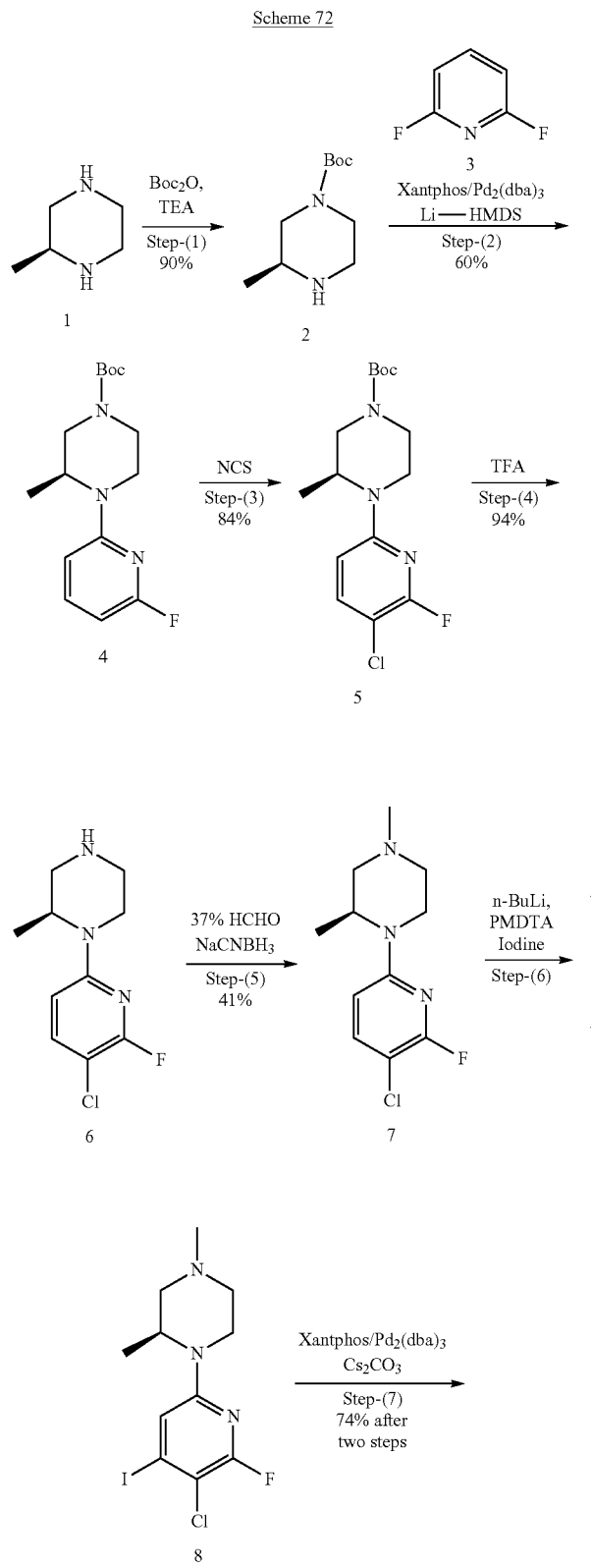

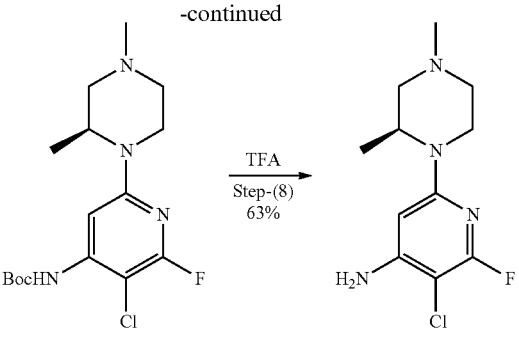

Compound numbers in text refer to structures shown in Scheme 72.

Step 1:

To a solution of compound 1 (10 g, 100 mmol, 1 eq) in EtOH (200 ml) was added DIPEA (43.58 mL, 250 mmol, 2.5 eq) and $Boc_2O$ (21.8 mL, 100 mmol, 1 eq) at RT, then the reaction mixture was continued for 16 h. TLC analysis indicated formation of a less polar spot. The reaction mixture was concentrated to give a crude residue, which is diluted with water and extracted with EtOAc (3×100 mL). The combined organic layer was dried over $Na_2SO_4$ then concentrated to give compound 2 (18 g, 90%) as colorless oil.

Step 2:

To a stirred solution of compound 2 (18 g, 90 mmol, 1 eq) was added compound 3 (20.7 g, 180 mmol, 2 eq), xantphos (1.56 g, 2.7 mmol, 0.03 eq), $Pd_2(dba)_3$ (2.47 g, 2.7 mmol, 0.03 eq) and Li-HMDS (450 mL, 450 mmol, 5 eq) at RT under argon atmosphere. The reaction mixture was heated to 90° C. for 16 h. TLC analysis indicated formation of a less polar spot. The reaction mixture was cooled to RT then filtered through celite pad, which is washed with EtOAc (3times). The filtrate was diluted with water and extracted with EtOAc (3×100 ml). The combined organic layer was dried over $Na_2SO_4$ then concentrated to give a crude compound. The crude compound was purified by column chromatography (silica gel, 100-200 mesh) using 0-1% MeOH in DCM as eluent to afford compound 4 (23 g, 86%) as a pale yellow oil. LC-MS: m/z 396.24 (M+H).

Step 3:

To a stirred solution of compound 4 (22 g, 74.57 mmol, 1 eq) in DMF (250 mL) was added NCS (9.91 g, 74.57 mmol, 1 eq) at RT then the mixture was heated to 60° C. (pre-heated) for 2 h. TLC analysis indicated formation of a polar spot, which was very close to SM. The reaction mixture was diluted with water then extracted with EtOAc (3×100 mL). The combined organic layer was dried over $Na_2SO_4$ then concentrated to give a crude compound. The crude compound was purified by column chromatography (silica gel, 100-200 mesh) using 0-5% EtOAc in petroleum ether as eluent to afford compound 5 (14 g, 57%) as a pale yellow oil. LC-MS: m/z 329.98 (M+H).

Step 4:

To a stirred solution of compound 5 (14 g, 42.55 mmol, 1 eq) in DCM (100 mL) was added TFA (32.34 mL, 425.53 mmol, 10 eq) at 0° C. then the mixture was allowed to reach RT for 16 h. TLC analysis indicated formation of a polar spot. The reaction mixture was concentrated to crude residue, which is basified with aqueous $NaHCO_3$ solution then extracted with EtOAc (3×100 mL). The combined organic layer was dried over Na₂SO₄ then concentrated to afford compound 6 (9 g, 92%) as a brown oil. LC-MS: m/z 230.34 (M+H).

Step 6: Reductive Amination or Alkylation a) Reductive Amination (Method A)

To a stirred solution of compound 6 (8 g, 34.93 mmol, 1 eq) in DCM (100 mL) was added 37% HCHO (4.25 mL, 52.40 mmol, 1.5 eq) and AcOH (30 mL) at RT then continued for 2 h, then added NaCNBH₃ (3.3 g, 52.40 mmol, 1.5 eq) at 0° C. then the reaction temperature was allowed to reach RT for 2 h. TLC analysis indicated formation of a less polar spot. The reaction mixture was basified with aqueous NaHCO₃ solution then extracted with EtOAc (3×90 mL). The combined organic layer was dried over Na₂SO₄ then concentrated to give a crude compound. The crude compound was purified by column chromatography (silica gel, 100-200 mesh) using 0-1% MeOH in DCM as eluent to afford compound 7 (5.4 g, 63%) as a brown oil. LC-MS: 73.12% with m/z 244.38 (M+H).

(b) General Procedure for Alkyation (Method B)

To a vial containing (S)-3-chloro-2-fluoro-6-(2-methylpiperazin-1-yl)pyridin-4-amine 6 (1 equivalent) in acetonitrile was added potassium carbonate (1.1 equivalent) followed by alkyl halide (1.1 equivalent). The reaction was stirred at RT overnight. Additional equivalents of potassium carbonate and alkyl halide were added until the reaction was judged complete by LCMS. Methanol was added to the reaction then concentrated onto celite. The crude product was purified on the Biotage (reverse phase silica gel) eluting with 0-40% ACN/H₂O. The desired fractions were collected, concentrated and dried under vacuum to afford the title compound 7.

Step 7:

To a stirred solution of compound 7 (5.4 g, 22.22 mmol, 1 eq) in THF (80 mL) was added PMDTA (10.19 mL, 48.88 mmol, 2.2 eq) and n-BuLi (19.55 mL, 48.88 mmol, 2.2 eq) at −78° C. The reaction was continued for 3 h and a solution of 12 (11.29 g, 44.44 mmol, 2 eq, in THF) was added at −78° C. The mixture was slowly allowed to reach RT for 16 h. TLC analysis indicated formation of a less polar spot. The reaction mixture was quenched with an aqueous solution of sodium thiosulphate then extracted with EtOAc (2×100 mL). The combined organic layer was dried over Na₂SO₄ then concentrated under reduced pressure to give the crude compound 8 (8 g, crude) as brown semi-solid. LC-MS: m/z 370.16 (M+H).

Step 8:

To a stirred solution of compound 8 (8 g, 21.68 mmol, 1 eq) in Toluene (100 mL) was added Cs₂CO₃ (14.1 g, 43.36 mmol, 2 eq) and NH₂Boc (3.01 g, 26.01 mmol, 1.2 eq) at RT. The reaction mixture was de-gassed with Argon for 5 min. Xantphos (376 mg, 0.65 mmol, 0.03 eq) and Pd₂(dba)₃ (595 mg, 0.65 mmol, 0.03 eq) were added at RT, after that reaction mixture was heated to 90° C. for 16 h. TLC analysis indicated formation of a polar spot. The reaction mixture was filtered through celite pad then the filtrate was concentrated to give a crude compound. The crude compound was purified by column chromatography (silica gel, 100-2000 mesh) using 0-1% MeOH in DCM as eluent to afford compound 9 (5 g, 62% per two steps) as a pale yellow gummy. LC-MS: m/z 359.59 (M+H).

Step 9:

To a stirred solution of compound 9 (5.0 g, 13.96 mmol, 1 eq) in DCM (50 mL) was added TFA (10.61 mL, 139.66 mmol, 10 eq) at RT and the reaction continued for 16 h. TLC analysis indicated formation of a polar spot. The reaction mixture was concentrated to give a crude residue, which was basified by aqueous NaHCO₃ solution then extracted with EtOAc (3×50 mL). The combined organic layer was dried over Na₂SO₄ then concentrated under reduced pressure to give a crude compound. The crude compound was purified by column chromatography (silica gel, 100-200 mesh) using 0-2% MeOH in DCM as eluent to afford (S)-3-chloro-6-(2,4-dimethylpiperazin-1-yl)-2-fluoropyridin-4-amine (2.6 g 72%) as a pale yellow gummy. 1H NMR (CDCl3, 400 MHz): δ 5.69 (s, 1H), 4.49 (brs, 2H), 4.30 (m, 1H), 3.76 (d, j=12.4 MHz, 1H), 3.10 (m, 1H), 2.85 (m, 1H), 2.68 (d, j=11.2 MHz, 1H), 2.27 (s, 3H), 2.20 (m, 1H), 2.02 (m, 1H), 1.21 (d, j=6.8 MHz, 3H). LC-MS: m/z 259.16 (M+H).

In a similar manner, the following compounds were prepared

| Method in Step 6 | Aniline | Name | Yield & Mass |
|---|---|---|---|
| B | (structure) | (S)-3-chloro-2-fluoro-6-(2-methyl-4-(oxetan-3-yl)piperazin-1-yl)pyridin-4-amine | 60% yield, LCMS [M]⁺ 301 |
| B | (structure) | (S)-5-chloro-2-(4-(2-ethoxyethyl)-2-methylpiperazin-1-yl)pyridin-4-amine Exact Mass: 298.16 | 61% yield, LCMS [M]⁺ 299 |

| Method in Step 6 | Aniline | Name | Yield & Mass |
|---|---|---|---|
| A | | (S)-3-chloro-2-fluoro-6-(4-(2-methoxyethyl)-2-methylpiperazin-1-yl)pyridin-4-amine | 57% yield, LCMS [M]+ 303 |
| A | | 3-chloro-2-fluoro-6-((S)-2-((S)-2-methoxypropyl)-2-methylpiperazin-1-yl)pyridin-4-amine | 38% yield, LCMS [M]+ 317 |
| B | | 3-chloro-6-(4-(cyclopropylmethyl)piperazin-1-yl)-2-fluoropyridin-4-amine | 69% yield, LCMS [M]+ 285 |
| A | | (S)-3-chloro-6-(4-ethyl-2-methylpiperazin-1-yl)-2-fluoropyridin-4-amine | 56% yield, LCMS [M]+ 273 |

Synthesis of 3-chloro-2-fluoro-6-((1R,5S)-8-methyl-3,8-diazabicyclo[3.2.1]octan-3-yl)pyridin-4-amine

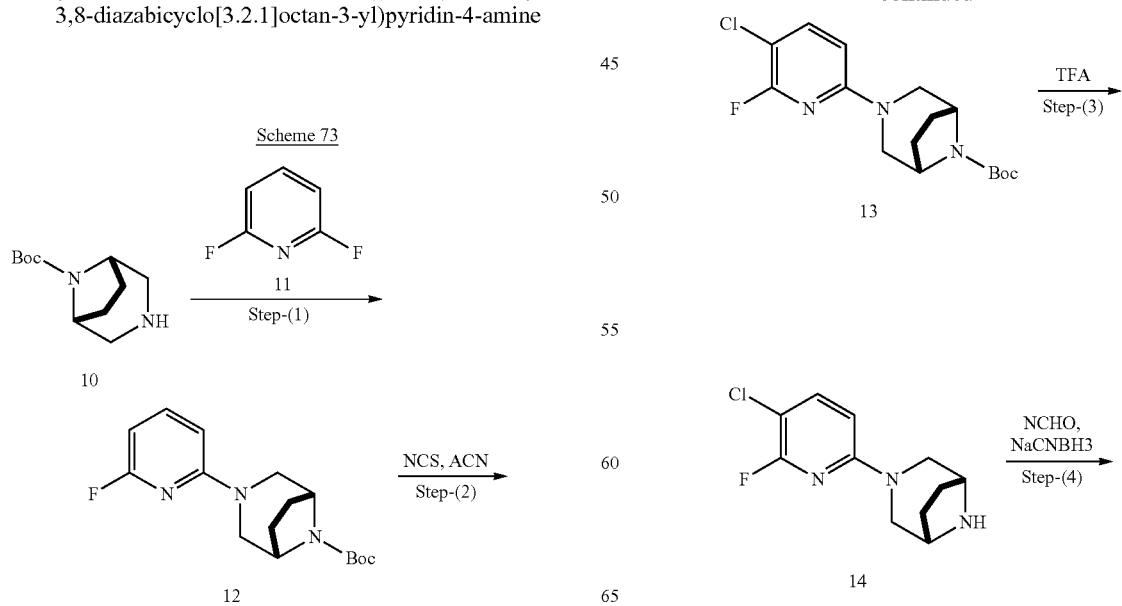

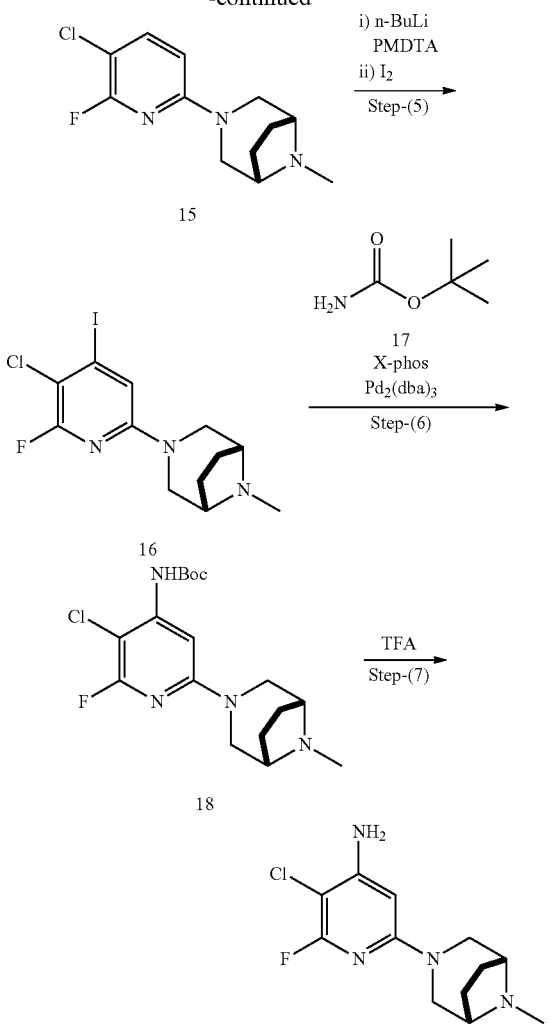

Compound numbers in text refer to structures shown in Scheme 73.

Step 1:

To a stirred solution of compound 10 (4 g, 19.3 mmol, 1 eq) in DMSO (50 mL) was added K$_2$CO$_3$ (8 g, 57.9 mmol, 3 eq) followed by compound 11 (3.7 mL, 38.6 mmol, 2 eq) and the resulting reaction mixture was heated at 90° C. for 16 h. The reaction was monitored by TLC. TLC analysis indicated formation of a non-polar spot. Reaction mixture was diluted with ice water and extracted with ethyl acetate (2×200 mL). The combined organic layer was dried over Na$_2$SO$_4$ and concentrated under reduced pressure. The crude product was purified by column chromatography (silica 100-200) using 0-20% ethyl acetate in petroleum ether as an eluent to give compound 12 (4.5 g, 77.7% yield) as a colourless liquid. LCMS: 77.91% with m/z 308.45 (M+H):

Step 2:

To a stirred solution of compound 12 (1 g, 3.25 mmol, 1 eq) in ACN (25 mL), was added NCS (0.52 g, 3.9 mmol, 1.2 eq) and the resulting reaction mixture was heated at 75° C. for 1.5 h in a preheated oil bath. The reaction was monitored by TLC. TLC analysis indicated formation of a polar spot. The reaction mixture was diluted with ice water and extracted with ethyl acetate (2×100 mL). The combined organic layer was dried over Na$_2$SO$_4$ and concentrated under reduced pressure. The crude product was purified by column chromatography (silica 230-400) using 0-20% ethyl acetate in petroleum ether as an eluent to give Compound 13 (0.5 g, 64.1% yield) as a pale yellow liquid. LCMS: 60.03% with m/z 342.51 (M+H):

Step 3:

To a stirred solution of compound 13 (1.5 g, 4.4 mmol, 1 eq) in DCM (15 mL), was added TFA (4.4 mL, 52.7 mmol, 12 eq) drop wise and the resulting reaction mixture was stirred at RT for 16 h. The reaction was monitored by TLC. TLC analysis indicated formation of a polar spot. The reaction mixture was concentrated under reduced pressure, basified with aq 2N NaHCO$_3$ solution and extracted with ethyl acetate (2×100 mL). The combined organic layer was dried over Na$_2$SO$_4$ and concentrated under reduced pressure to give Compound 14 (0.9 g, crude yield) as an off-white solid. LCMS: 67.45% with m/z 242.46 (M+H):

Step 4:

To a stirred solution of compound 14 (1.8 g, 7.4 mmol, 1 eq) in DCM:AcOH (2:1, 14 mL) was added 37% HCHO (2.43 mL, 29.8 mmol, 4 eq) and the resulting reaction mixture was stirred at RT for 2 h. Reaction mixture was cooled to 0° C., NaCNBH$_3$ (0.94, 15.0 mmol, 2 eq) was added and the mixture stirred at RT for 16 h. The reaction was monitored by TLC. TLC analysis indicated formation of a non-polar spot. Reaction mixture was concentrated under reduced pressure, basified with aq 2N NaHCO$_3$ solution and extracted with DCM (2×100 mL). The combined organic layer was dried over Na$_2$SO$_4$ and concentrated under reduced pressure to give Compound 15 (1.75 g, 92.1% yield) as a yellow liquid. LCMS: 61.65% with m/z 256.19 (M+H):

Step 5:

To a stirred solution of compound 15 (1.7 g, 6.66 mmol, 1 eq), and PMDTA (6 mL, 26.6 mmol, 4 eq) in dry THF (25 mL) cooled to −78° C. was added n-BuLi (12 mL, 26.6 mmol, 4 eq, 2.5M in hexane) drop wise under argon atmosphere. Then, the resulting reaction mixture was stirred for 2 h at the same temperature. Then, a solution of iodine (3.4 g, 13.2 mmol, 2 eq) in THF (10 mL) was added drop wise at −78° C. and the resulting reaction mixture was stirred for 5 min. The reaction was monitored by TLC. TLC analysis indicated formation of a non-polar spot. The reaction mixture was quenched with saturated aqueous solution of sodium thiosulfate and extracted with EtOAc (3×100 mL). The combined organic layer was dried over Na$_2$SO$_4$ and concentrated under reduced pressure to give Compound 16 (2.4 g, 96% yield) as a pale brown solid. LC-MS: 77.59% with m/z 382.07 (M+H).

Step 6:

To a stirred solution of compound 16 (2.5 g, 6.57 mmol, 1 eq) in 1,4-dioxane (25 mL) was added Cs$_2$CO$_3$ (4.25 g, 13.14 mmol, 2 eq), and compound 17 (0.84 g, 7.22 mmol, 1.1 eq) followed by xanthophos (0.38 g, 0.69 mmol, 0.1 eq). The resulting reaction mixture was degassed with nitrogen for 15 min. Pd(OAc)$_2$ (0.073 g, 0.32 mmol, 0.05 eq) was added and the resulting reaction mixture was heated at 85° C. for 16 h. The reaction was monitored by TLC. TLC analysis indicated formation of a polar spot. Reaction mixture was filtered through celite, washed with ethyl acetate and filtrate was concentrated under reduced pressure to get a crude product. The crude product was purified by column chromatography (silica 230-400) using 0-5% methanol in DCM as an eluent to give Compound 18 (1.2 g, 50% yield) as a brown solid. LCMS: 89.84% with m/z 371.27 (M+H);

Step 7:

To a stirred solution of compound 18 (1.1 g, 2.97 mmol, 1 eq) in DCM (20 mL), was added TFA (3.2 mL, 35.6 mmol, 12 eq) drop wise and the resulting reaction mixture was stirred at RT for 16 h. The reaction was monitored by TLC. TLC analysis indicated formation of a polar spot. The reaction mixture was concentrated under reduced pressure, basified with aq 2N NaOH solution and extracted with ethyl acetate (2×50 mL). The combined organic layer was dried over Na₂SO₄ and concentrated under reduced pressure. The crude product was purified by column chromatography (silica 230-400) using 0-90% methanol in DCM as an eluent to give 3-chloro-2-fluoro-6-((1R,5S)-8-methyl-3,8-diazabicyclo[3.2.1]octan-3-yl)pyridin-4-amine (0.52 g, 65% yield) as a brown solid. LCMS: 97.99% with m/z 271.47 (M+1):
Synthesis of 5-chloro-2-(6-methyl-2,6-diazaspiro[3.4]octan-2-yl)pyridin-4-amine Scheme 74

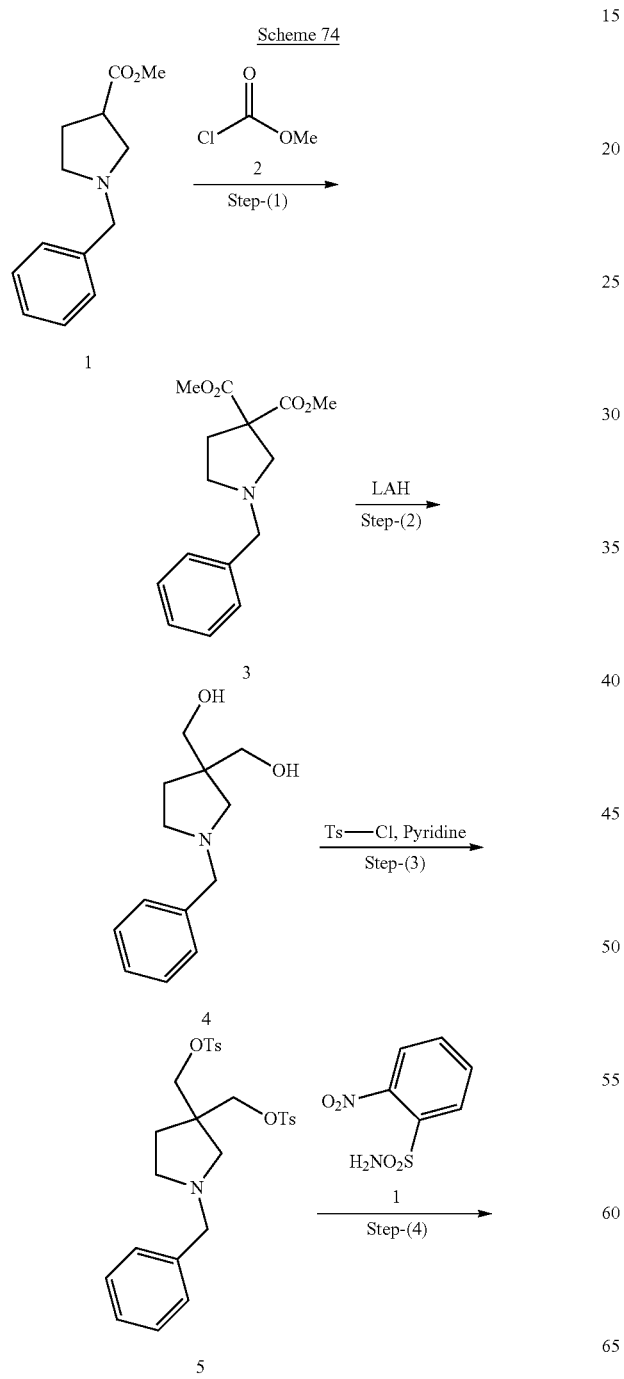

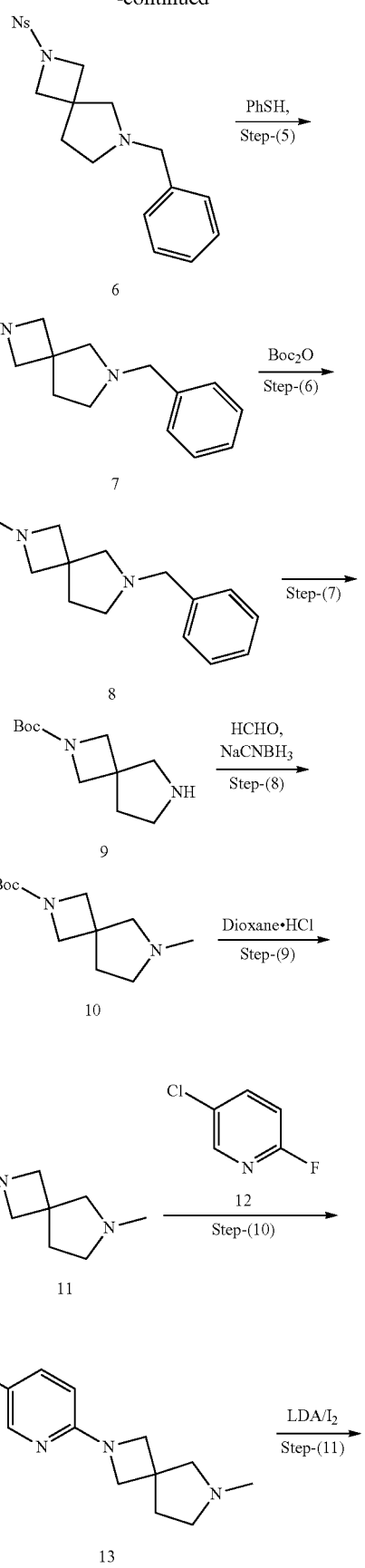

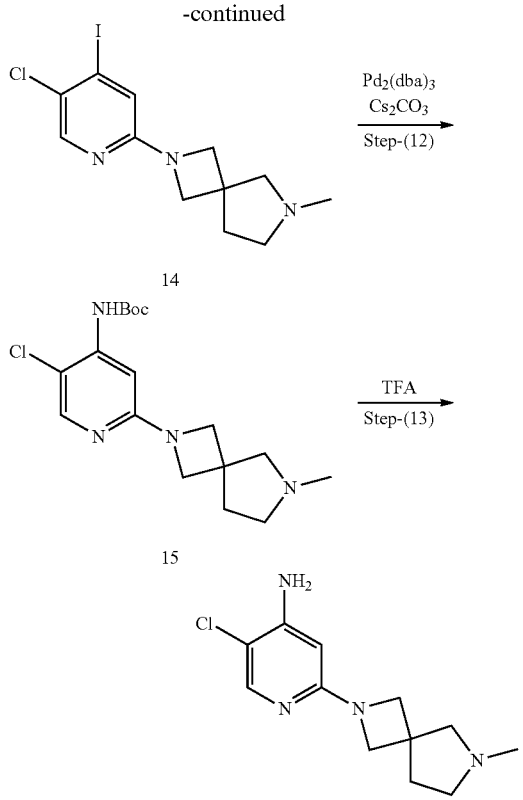

Compound numbers in text refer to structures shown in Scheme 74.

Step 1:

To a solution of DIPA (48.0 mL, 342.46 mmol, 3 eq) in THF (350 mL) was added n-BuLi (136.9 mL, 342.46 mmol, 3 eq) at −70° C., then the reaction mixture was stirred for 30 min., after that added a solution of compound 1 (25 g, 114.155 mmol, 1 eq, in 50 mL of THF) at −78° C. and stirred for 90 min., then at −40° C. for 2 h. The reaction mixture was again cooled to −78° C. and added a solution of compound 2 (26.96 mL, 342.46 mmol, 3 eq, in 50 mL of THF) then allowed to warm up to RT for 16 h. TLC analysis indicated formation of a less polar spot. The reaction mixture was cooled to 0° C. then quenched with sat.NH$_4$Cl solution then extracted with EtOAc (3×200 mL). The combined organic layer was dried over Na$_2$SO$_4$ then concentrated to crude compound. The crude compound was purified by column chromatography (silica gel, 100-200 mesh) using 0-10% EtOAc in petroleum ether as eluent to afford compound 3 (23 g, 72%) as a pale yellow liquid. LC-MS: m/z 278.03 (M+H).

Step 2:

To a solution of compound 3 (29 g, 104.69 mmol, 1 eq) in THF (500 mL) was added LAH (15.91 g, 418.77 mmol, 4 eq) as portion wise at 0° C. then the mixture was allowed to reach RT for 16 h. Monitored by TLC, the reaction mixture was cooled to 0° C. then added slowly quenched with saturated Na$_2$SO$_4$ solution (50 mL) and filtered through celite pad and washed with EtOAc (2×100 mL). The filtrate was dried over Na$_2$SO$_4$ then concentrated under reduced pressure to crude compound 4 (20 g, 86%) as a colorless oil. LC-MS: 89.50% with m/z 222.01 (M+H).

Step 3:

To a solution of compound 4 (20 g, 90.49 mmol, 1 eq) in pyridine (200 mL) was added Tosyl-Chloride (68.77 g, 361.99 mmol, 4 eq) at 0° C. as portion wise then allowed to RT for 16 h. Monitored by TLC, the reaction mixture was diluted with cold water then filtered the solid compound under vacuum to give compound 5 (45 g, 94%) as an off-white solid. LC-MS: 98.0% with m/z 530.11 (M+H).

Step 4:

To a solution of compound 2 (45 g, 85.06 mmol, 1 eq) in DMF (500 mL) was added 2-nitrobenzenesulfonamide (20.6 g, 102.07 mmol, 1.2 eq) and K$_2$CO$_3$ (41.08 g, 297.73 mmol, 3.5 eq) at RT then the reaction mixture was heated to 100° C. for 16 h. Monitored by TLC, the reaction mixture was diluted with cold water then extracted with EtOAc (3×200 mL). The combined organic layer was dried over Na$_2$SO$_4$ then concentrated to give a crude compound. The crude compound was purified by column chromatography (silica gel, 100-200 mesh) using 0-30% EtOAc in petroleum ether as eluent to afford compound 6 (22 g, 66%) as a colorless liquid. LC-MS: m/z 388.01 (M+H).

Step 5:

To a solution of compound 6 (22 g, 56.84 mmol, 1 eq) in ACN (300 mL) was added Cs$_2$CO$_3$ (27.7 g, 85.27 mmol, 1.5 eq) and benzenethiol (6.87 mL, 62.53 mmol, 1.1 eq) at RT and then reaction mixture was stirred for 16 h. Monitored by TLC, the reaction mixture was diluted with DCM and then filtered through celite pad and washed with DCM (2×100 mL). The filtrate was concentrated to crude compound. The crude compound was purified by column chromatography (silica gel, 100-200 mesh) using 0-20% MeOH in DCM as eluent to afford compound 7 (9 g, 78%) as a colorless liquid. LC-MS: m/z 202.96 (M+H).

Step 6:

To a solution of compound 7 (6 g, 29.70 mmol, 1 eq) in DCM (100 mL) was added TEA (12.16 mL, 89.10 mmol, 3 eq) and then slowly Boc$_2$O (9.7 mL, 44.55 mmol, 1.5 eq) at 0° C. The mixture was allowed to reach RT for 16 h. Monitored by TLC, the reaction mixture was diluted with cold water then extracted with EtOAc (3×100 mL). The combined organic layer was dried over Na$_2$SO$_4$ then concentrated to give a crude compound. The crude compound was purified by column chromatography (silica gel, 100-200 mesh) using 0-30% EtOAc in petroleum ether as eluent to afford compound 8 (6 g, 66%) as a pale yellow liquid. LC-MS: m/z 303.12 (M+H).

Step 7:

To a solution of compound 8 (6 g, 19.86 mmol, 1 eq) in EtOH (100 mL) was added 10% Pd/C (1.5 g) at RT and then stirred under 100 psi of H2 pressure at RT for 16 h. Monitored by TLC, the reaction mixture was filtered through celite pad and washed with EtOAc (3×50 mL). The filtrate was concentrated under vacuum to give compound 9 (4 g, 95%) as a colorless oil. LC-MS: m/z 213.40 (M+H).

Step 8:

To a solution of compound 9 (7 g, 33.1 mmol, 1 eq) in DCM:AcOH (140 mL, 7: 3) was added 37% HCHO (4.0 mL, 49.7 mmol, 1.5 eq) at RT and continued for 2 h, then added NaCNBH$_3$ (4.16 g, 66.35 mmol, 2 eq) at RT and the reaction continued for 16 h. Monitored by TLC, the reaction mixture was basified with saturated NaHCO$_3$ solution and then extracted with EtOAc (3×100 mL). The combined organic layer was dried over Na$_2$SO$_4$ then concentrated to afford compound 10 (5 g, 67%) as a pale yellow liquid.

Step 9:

To a stirred solution of compound 10 (4.5 g, 19.91 mmol, 1 eq) in 1,4-dioxane (10 mL) was added dioxane.HCl (15 mL, 4M) at 0° C. then allowed to RT for 16 h. Monitored by TLC, the reaction mixture was concentrated under vacuum to give crude compound 11 (3 g, crude) as a colorless oil. (Note: Based on TLC proceeded to next step)

Step 10:

To a solution of compound 11 (140 mg, 0.86 mmol, 1 eq) in DMSO (05 mL) was added compound 12 (226 mg, 1.76 mmol, 2 eq) and K$_2$CO$_3$ (477 mg, 3.45 mmol, 4 eq) at RT and then the solution was heated to 90° C. and the reaction continued for 16 h. Monitored by TLC, the reaction mixture was diluted with water and extracted with EtOAc (3×50 mL). The combined organic layer was dried over Na$_2$SO$_4$ then concentrated to give a crude compound. The crude compound was purified by column chromatography (silica gel, 100-200 mesh) using 0-5% MeOH in DCM as eluent to afford compound 13 (90 mg, 44%) as an off-white semi-solid. LC-MS: m/z 237.96 (M+H).

Step 11:

To a solution of compound 14 (1.5 g, 6.32 mmol, 1 eq) in THF (30 mL) was added PMDTA (3.95 mL, 18.98 mmol, 3 eq) at RT. The mixture was then cooled to −78° C. and n-BuLi (7.6 mL, 18.98 mmol, 3 eq, 2.5M in THF) was added at −78° C. The reaction was continued for 2 h, then 12 solution (3.21 g, 12.65 mmol, 2 eq) was added and the mixture allowed to stir RT for 16 h. Monitored by TLC, the reaction mixture was quenched with saturated sodium thiosulphate solution and extracted with EtOAc (3×50 mL). The combined organic layer was dried over Na$_2$SO$_4$ then concentrated to afford crude compound 14 (2.2 g, crude) as a brown solid. LC-MS: m/z 364.132 (M+H).

Step 12:

To a stirred solution of compound 14 (2.2 g, 6.06 mmol, 1 eq) in Toluene (30 mL) was added Cs$_2$CO$_3$ (3.93 g, 12.12 mmol, 2 eq) and NH$_2$Boc (843 mg, 7.27 mmol, 1.2 eq) at RT. The reaction mixture was de-gassed with Argon for 15 min., then xantphos (105 mg, 0.18 mmol, 0.03 eq) and Pd$_2$(dba)$_3$ (166 mg, 0.18 mmol, 0.03 eq) were added at RT. The reaction mixture was then heated to 90° C. for 16 h. Monitored by TLC, the reaction mixture was filtered through celite pad then the filtrate was concentrated to give a crude compound. The crude compound was purified by column chromatography (silica gel, 100-2000 mesh) using 0-10% MeOH in DCM as eluent to afford compound 15 (1.6 g, 72% per two steps) as a brown oil. LC-MS: m/z 353.32 (M+H).

Step 13:

To a stirred solution of compound 15 (1.6 g, 4.54 mmol, 1 eq) in DCM (10 mL) was added TFA (3.48 mL, 45.45 mmol, 10 eq) at RT and the reaction was continued for 16 h. Monitored by TLC, the reaction mixture was concentrated to crude, which was basified by aqueous NaHCO$_3$ solution then extracted with EtOAc (3×60 mL). The combined organic layer was dried over Na$_2$SO$_4$ then concentrated under reduced pressure to give a crude compound. The crude compound was purified by column chromatography (silica gel, 100-200 mesh) using 0-15% MeOH in DCM as eluent to afford 5-chloro-2-(6-methyl-2,6-diazaspiro[3.4]octan-2-yl)pyridin-4-amine (620 mg 54%) as a pale brown semi-solid. LC-MS: m/z 253.0 (M+H).

Synthesis of (R)-3-chloro-2-fluoro-6-(3-fluoropyrrolidin-1-yl)pyridin-4-amine

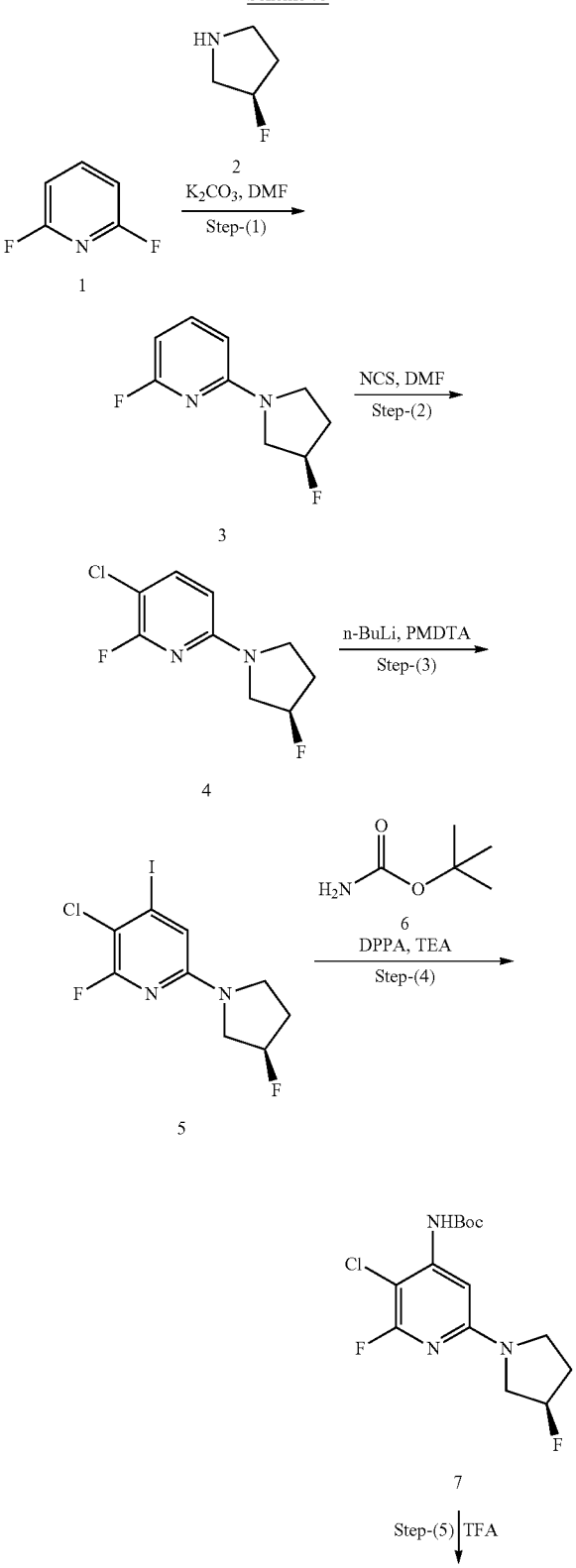

-continued

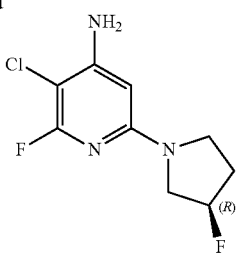

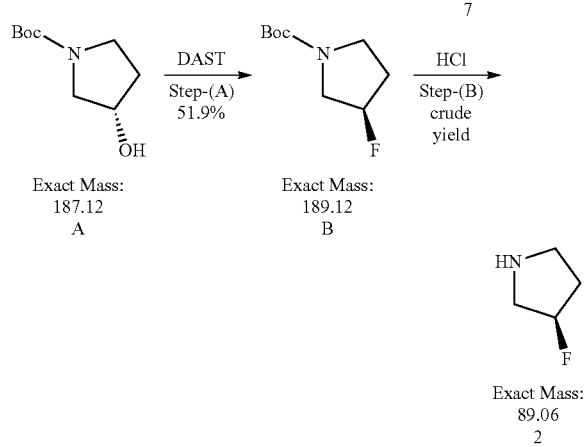

Compound numbers in text refer to structures shown in Scheme 75.

Step A:

To a stirred solution of compound A (20 g, 107.1 mmol, 1 eq) in dry DCM (300 mL) cooled to −78° C. was added DAST (14.22 mL, 107.1 mmol, 1 eq) drop wise and the resulting reaction mixture was stirred at RT for 16 h. Reaction was monitored with TLC, TLC indicated formation of a non-polar spot. The reaction mixture was concentrated under reduced pressure, basified with sat NaHCO$_3$ solution and extracted with ethyl acetate (2×500 mL). The combined organic layer was washed with water (200 mL) followed by brine solution (200 mL), dried over Na$_2$SO$_4$ and concentrated under reduced pressure to give a crude product. The crude product was purified by column chromatography (silica gel 100-200) using 0-10% ethyl acetate in petroleum ether as an eluent to give Compound B (10.5 g, 51.9% yield) as an off-white liquid.

Step B:

To compound B (10.5 g, 55.5 mmol, 1 eq), cooled to 0° C., was added 1,4-dioxane.HCl (4M) (100 mL) and resulting reaction mixture was stirred at RT for 2 h. The reaction was monitored by TLC. TLC analysis indicated formation of a polar spot. The reaction mixture was concentrated under reduced pressure to get a crude product. The crude product was triturated with n-pentane to give Compound 2 (6.5 g, crude yield) as an off-white solid. LCMS: 99.23% with m/z 90.19 (M+H):

Step 1:

To a stirred solution of compound 1 (10.5 g, 84 mmol, 1 eq) in DMF (200 mL) was added K$_2$CO$_3$ (40.6 g, 294 mmol, 2.5 eq) followed by compound 2 (27 g, 126 mmol, 1.5 eq) at RT. The resulting reaction mixture was heated at 90° C. for 16 h. The reaction was monitored by TLC. TLC analysis indicated formation of a non-polar spot. Reaction mixture was quenched with ice water and extracted with ethyl acetate (2×300 mL). The combined organic layer was dried over Na$_2$SO$_4$ and concentrated under reduced pressure. The crude product was purified by column chromatography (silica 100-200) using 0-15% ethyl acetate in petroleum ether as an eluent to give Compound 3 (14.5 g, 86.3% yield) as colour less liquid. LCMS: 98.24% with m/z 185.09 (M+H Step 2:

To a stirred solution of compound 3 (15 g, 21.52 mmol, 1 eq) in DMF (200 mL), was added NCS (13.1 g, 97.82 mmol, 1.2 eq) and the resulting reaction mixture was heated at 75° C. for 30 min., in a preheated oil bath. The reaction was monitored by TLC. TLC analysis indicated formation of a polar spot. Reaction mixture was quenched with ice water and extracted with ethyl acetate (2×300 mL). The combined organic layer was dried over Na$_2$SO$_4$ and concentrated under reduced pressure. The crude product was purified by column chromatography (silica 230-400) using 0-10% ethyl acetate in petroleum ether as an eluent to give Compound 4 (7 g, 39.5% yield) as an off-white solid. LCMS: 98.30% with m/z 219.01 (M+H):

Step 3:

To a stirred solution of compound 4 (5.6 g, 25.6 mmol, 1.0 eq), and PMDTA (21 mL, 102.7 mmol, 4 eq) in dry THF (60 mL) cooled to −78° C. was added n-BuLi (41 mL, 102.7 mmol, 4 eq, 2.5M in hexane) drop wise under argon atmosphere. The resulting reaction mixture was stirred for 2 h at the same temperature. Then, a solution of iodine (13 g, 51.3 mmol, 2 eq) in THF (60 mL) was added drop wise at −78° C. and the resulting reaction mixture was allowed to RT for 2 h. The reaction was monitored by TLC. TLC analysis indicated formation of a non-polar spot. The reaction mixture was quenched with saturated aqueous solution of sodium thiosulfate and extracted with EtOAc (3×200 mL). The combined organic layer was dried over Na$_2$SO$_4$ and concentrated under reduced pressure. The crude product was purified by column chromatography (silica 100-200) using 0-10% ethyl acetate in petroleum ether as an eluent to give Compound 5 (5.4 g, 61.3% yield) as a pale yellow liquid. LCMS: 70.66% with m/z 345.01 (M+H).

Step 4:

To a stirred solution of compound 5 (5.5 g, 16.03 mmol, 1 eq) in 1,4-dioxane (60 mL) was added Cs$_2$CO$_3$ (10.4 g, 32 mmol, 2 eq), and compound 6 (2 g, 17.6 mmol, 2 eq) followed by xanthophos (0.92 g, 1.6 mmol, 0.1 eq) and the resulting reaction mixture was degassed with nitrogen for 15 min. Pd(OAc)$_2$ (0.18 g, 0.8 mmol, 0.05 eq) was added and the the resulting reaction mixture was heated at 100° C. for 16 h. The reaction was monitored by TLC. TLC analysis indicated formation of a polar spot. Reaction mixture was filtered through celite, washed with ethyl acetate and the filtrate was concentrated under reduced pressure to get crude product. The crude product was purified by column chromatography (silica 100-200) using 0-10% ethyl acetate in petroleum ether as an eluent to give compound 7 (4.2 g, 79.2% yield) as an off white solid. LCMS: 81.53% with m/z 333.99 (M+H):

Step 5:

To a stirred solution of compound 7 (4.3 g, 12.9 mmol, 1 eq) in DCM (60 mL), was added TFA (12.5 mL, 12.0 mmol, 12 eq) drop wise and the the resulting reaction mixture was stirred at RT for 16 h. The reaction was monitored by TLC. TLC analysis indicated formation of a polar spot. The reaction mixture was concentrated under reduced pressure, basified with aq NaHCO$_3$ solution and extracted with ethyl acetate (2×50 mL). The combined organic layer was dried over Na$_2$SO$_4$ and concentrated under reduced pressure. The crude product was purified by column chromatography (silica 100-200) using 0-20% ethyl acetate in petroleum ether as an eluent to give (R)-3-chloro-2-fluoro-6-(3-fluoropyrrolidin-1-yl)pyridin-4-amine (1.4 g, 46.6% yield) as an off white solid. LCMS: 99.72% with m/z 234.43 (M+H):

Synthesis of 3-chloro-2-fluoro-6-(pyrrolidin-1-yl)pyridin-4-amine

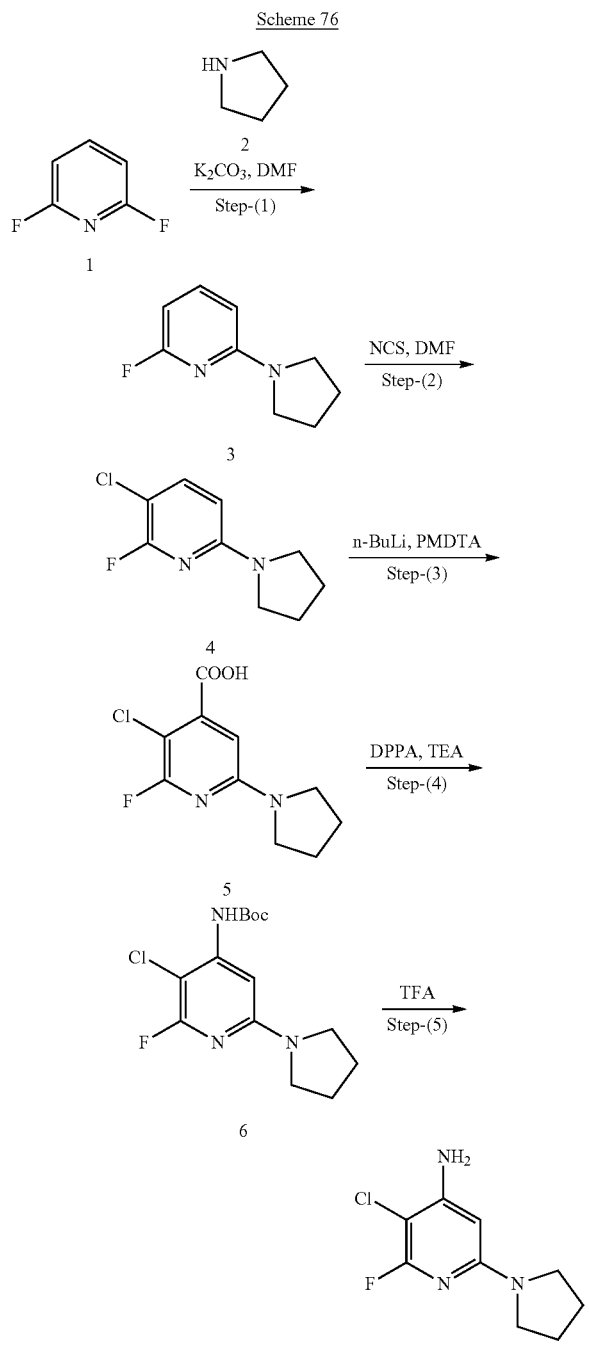

Compound numbers in text refer to structures shown Scheme 76.

Step 1:

To a stirred solution of compound 1 (10 g, 86.9 mmol, 1 eq) in DMF (100 mL) was added K₂CO₃ (24 g, 173.9 mmol, 2 eq) followed by compound 2 (10.7 mL, 130.4 mmol, 1.5 eq) at RT and the resulting reaction mixture was heated at 90° C. for 16 h. The reaction was monitored by TLC. TLC analysis indicated formation of a polar spot. Reaction mixture was quenched with ice water and extracted with ethyl acetate (2×200 mL). The combined organic layer was dried over Na₂SO₄ and concentrated under reduced pressure. The crude product was purified by column chromatography (silica 100-200) using 0-4% ethyl acetate in petroleum ether as an eluent to give Compound 3 (9 g, 62.5% yield) as a pale yellow liquid. LCMS: m/z 167.36 (M+H).

Step 2:

To a stirred solution of compound 3 (10 g, 60.24 mmol, 1 eq) in DMF (200 mL), was added NCS (8.8 g, 66.2 mmol, 1.1 eq) and the resulting reaction mixture was heated at 60° C. for 2 h. The reaction was monitored by TLC. TLC analysis indicated formation of a non-polar spot. Reaction mixture was quenched with ice water and extracted with ethyl acetate (2×500 mL). The combined organic layer was dried over Na₂SO₄ and concentrated under reduced pressure. The crude product was purified by column chromatography (silica 230-400) using 0-10% ethyl acetate in petroleum ether as an eluent to give Compound 4 (8 g, 67.2% yield) as off white solid. LCMS: m/z 201.34 (M+H):

Step 3:

To a stirred solution of compound 4 (8 g, 40.2 mmol, 1 eq) in dry THF (160 mL) cooled to −78° C. was added PMDTA (33.57 mL, 160.8 mmol, 4 eq) followed by n-BuLi (2.5M in hexane) (64.3 mL, 160.8 mmol, 4 eq) drop wise and the resulting reaction mixture was stirred at same temperature for 3 h. The reaction mixture was quenched with crushed dry CO₂ and stirred at RT for 16 h. The reaction was monitored by TLC. TLC analysis indicated formation of a polar spot. The reaction mixture was diluted with water and ethyl acetate, the aqueous layer was acidified with 1 N HCl and extracted with ethyl acetate. The combined organic layer was dried over Na₂SO₄ and concentrated under reduced pressure to give Compound 5 (8 g, 81.6% yield) as a pale yellow solid. LCMS: m/z 245.34% (M+H):

Step 4:

To a stirred solution of compound 5 (8 g, 32.7 mmol, 1 eq) in t-BuOH:toluene (1:1) (160 mL), was cooled to 0° C. and added TEA (3.8 mL, 49.18 mmol, 1.5 eq) followed by DPPA (18.7 mL, 49.18 mmol, 1.5 eq) and the resulting reaction mixture was heated at 85° C. for 16 h. The reaction was monitored by TLC. TLC analysis indicated formation of non-polar spot. Solvent was concentrated under reduced pressure to get crude product. The crude was diluted with ethyl acetate (300 mL) and washed with saturated brine solution. The combined organic layer was dried over Na₂SO₄ and concentrated under reduced pressure. The crude product was purified by column chromatography (silica 230-400mesh) using 0-20% ethyl acetate in petroleum ether as an eluent to give Compound 6 (5 g, 48.5% yield) as pale yellow solid. LCMS: m/z 316.40 (M+H):

Step 5:

To a stirred solution of compound 6 (5 g, 15.87 mmol, 1 eq) in DCM (50 mL), was added TFA (12.9 mL, 158.7 mmol, 10 eq) drop wise and the resulting reaction mixture was stirred at RT for 16 h. The reaction was monitored by TLC. TLC analysis indicated formation of polar spot. The reaction mixture was concentrated under reduced pressure, basified with saturated aq NaHCO₃ solution and extracted with ethyl acetate (2×200 mL). The combined organic layer was dried over Na₂SO₄ and concentrated under reduced pressure. The crude was triturated with n-pentane to afford 3-chloro-2-fluoro-6-(pyrrolidin-1-yl)pyridin-4-amine (3 g, 88.2% yield) as a pale brown solid. LCMS: m/z 216.36 (M+H).

Synthesis of 3-chloro-2-fluoro-6-(5-methylhexahydropyrrolo[3,4-c]pyrrol-2(1H)-yl)pyridin-4-amine

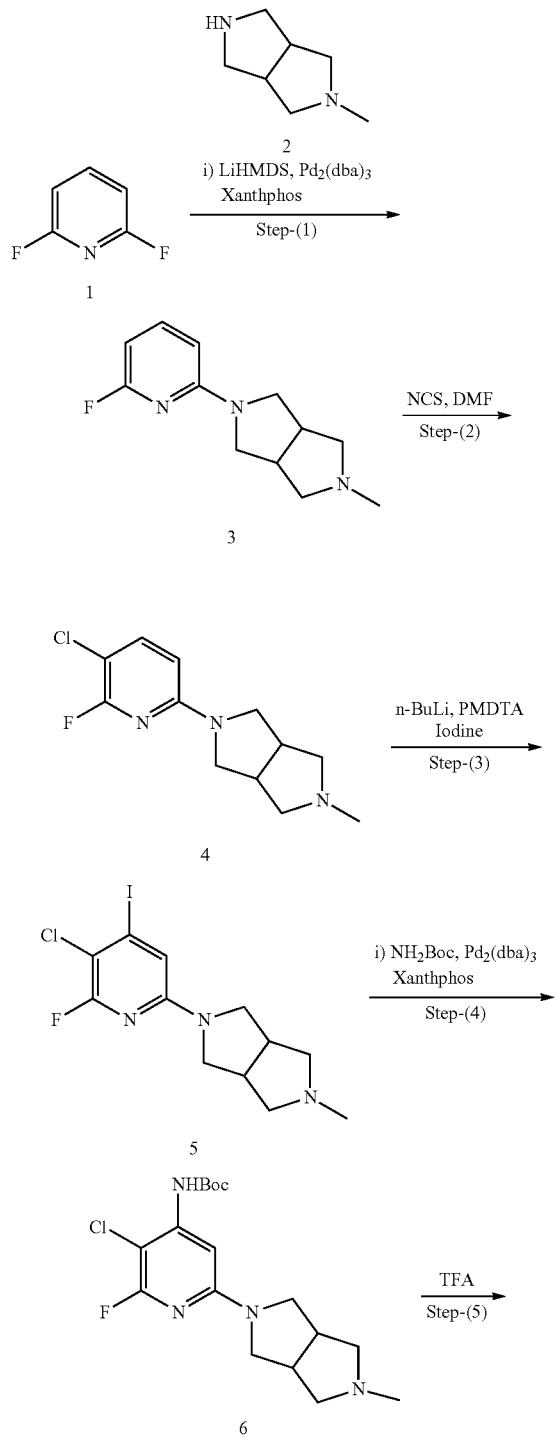

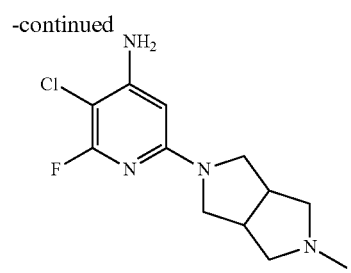

Compound numbers in text refer to structures shown in Scheme 77.

Step 1:

To a stirred solution of compound 2 (5 g, 39.64 mmol, 1 eq) in LiHMDS (50 mL) was cooled to 0° C. and added compound 1 (5.7 mL, 59.46 mmol, 1.5 eq), and xanthophos (2.2 g, 3.96 mmol, 0.1 eq) followed by $Pd_2(dba)_3$ (3.6 g, 3.96 mmol, 0.1 eq). The resulting reaction mixture was heated at 75° C. for 16 h. The reaction was monitored by TLC. TLC analysis indicated formation of a non-polar spot. Reaction mixture was diluted with ethyl acetate and filtered through celite, which was washed with ethyl acetate. The filtrate was dried over $Na_2SO_4$ and concentrated under reduced pressure. The crude product was purified by column chromatography (silica 100-200mesh) using 0-10% methanol in DCM as an eluent to give Compound 3 (8.0 g, 90% yield) as a colorless gummy liquid. LCMS: 67.67% with m/z 222.31 (M+H).

Step 2:

To a stirred solution of compound 3 (3.5 g, 15.829 mmol, 1 eq) in ACN (35 mL), was added NCS (2.5 g, 18.99 mmol, 1.2 eq) and the resulting reaction mixture was heated at 75° C. for 3.5 h in a preheated oil bath. The reaction was monitored by TLC. TLC analysis indicated formation of a non-polar spot. Reaction mixture was concentrated under reduced pressure. The crude product was purified by column chromatography (silica 230-400) using 0-10% methanol in DCM as an eluent to give Compound 4 (1.4 g, 35% yield) as a colourless liquid. LCMS: 71.63% with m/z 256.43 (M+H):

Step 3:

To a stirred solution of compound 4 (1.0 g, 3.92156 mmol, 1.0 eq), and PMDTA (3.2 mL, 15.6862 mmol, 4 eq) in dry THF (20 mL) cooled to −78° C. was added n-BuLi (10 mL, 15.6862 mmol, 4 eq, 1.5M in hexane) drop wise under argon atmosphere. The resulting reaction mixture was stirred for 2 h at the same temperature. Then, a solution of iodine (2.0 g, 7.8431 mmol, 2 eq) in THF (10 mL) was added drop wise at −78° C. and the resulting reaction mixture was allowed to warm to RT for 2 h. The reaction was monitored by TLC. TLC analysis indicated formation of a non-polar spot. The reaction mixture was quenched with saturated aqueous solution of sodium thiosulfate and extracted with EtOAc (3×100 mL). The combined organic layer was dried over $Na_2SO_4$ and concentrated under reduced pressure to give Compound 5 (1.2 g, 80.0% yield) as a pale yellow liquid. LCMS: 89.69% with m/z 382.22 (M+H):

Step 4:

To a stirred solution of compound 5 (650 mg, 1.706 mmol, 1 eq) in Toluene (6.5 mL) was added $Cs_2CO_3$ (1.1 g, 3.41206 mmol, 2 eq), $NH_2Boc$ (240 mg, 2.0472 mmol, 1.2 eq) followed by xantphos (60 mg, 0.1023 mmol, 0.06 eq) and the resulting reaction mixture was degassed with nitrogen for 15 min. $Pd_2(dba)_3$ (0.047 g, 0.0511 mmol, 0.03 eq) was added and the resulting reaction mixture was heated at 85° C. for 16 h. The reaction was monitored by TLC. TLC analysis indicated formation of a polar spot. Reaction mixture was filtered through celite, washed with ethyl acetate and filtrate was concentrated under reduced pressure to get a crude product. The crude product was purified by column chromatography (silica 230-400) using 0-40% ethyl acetate in petroleum ether as an eluent to give Compound 6 (320 mg, 50.79% yield) as an off-white semi solid. LCMS: 91.56% with m/z 371.34 (M+H):

Step 5:

To a stirred solution of compound 6 (0.9 g, 2.4317 mmol, 1 eq) in DCM (20 mL), was added TFA (2 mL, 24.3177 mmol, 10 eq) drop wise and the resulting reaction mixture was stirred at RT for 16 h. The reaction was monitored by TLC. TLC analysis indicated formation of polar spot. The reaction mixture was concentrated under reduced pressure, basified with aq NaHCO$_3$ solution and extracted with ethyl acetate (2×50 mL). The combined organic layer was dried over Na$_2$SO$_4$ and concentrated under reduced pressure. The crude product was triturated with n-pentane to give 3-chloro-2-fluoro-6-(5-methylhexahydropyrrolo[3,4-c]pyrrol-2(1H)-yl)pyridin-4-amine (600 mg, 91.4% yield) as an off white solid. LCMS: 94.79% with m/z 271.07 (M+H):

Synthesis of 3-chloro-2-fluoro-6-(1-methylhexahydropyrrolo[3,4-b]pyrrol-5(1H)-yl)pyridin-4-amine Scheme 78

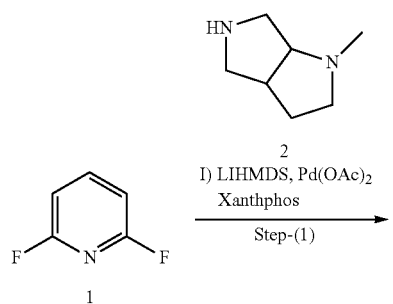

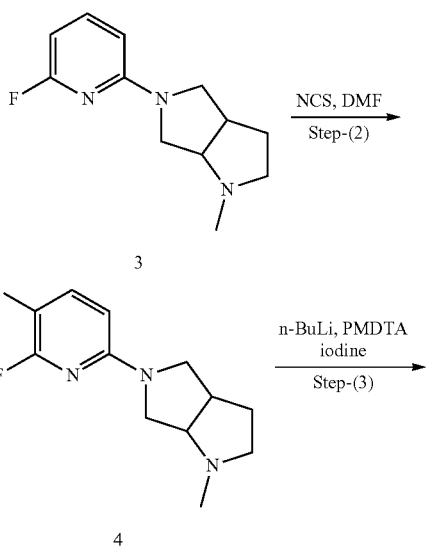

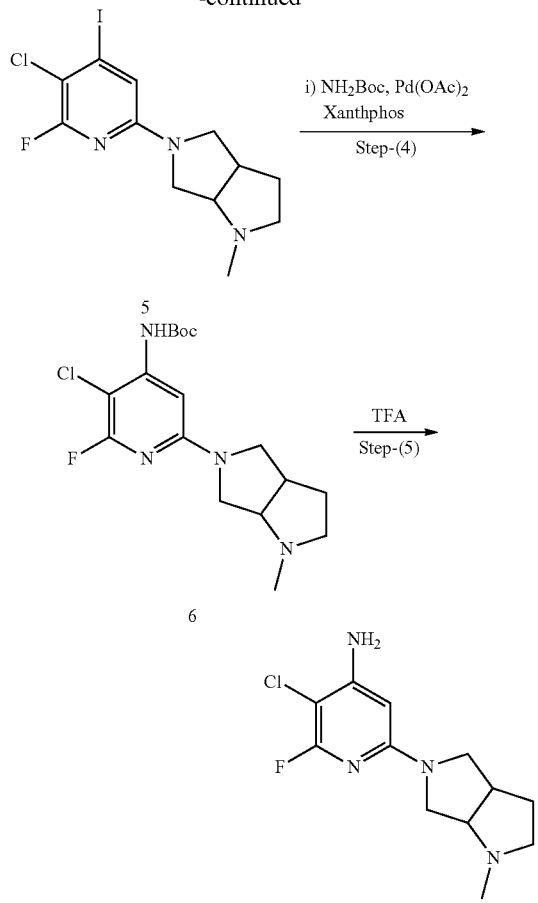

Compound numbers in text refer to structures shown in Scheme 78.

Step 1:

To a stirred solution of compound 1 (5 g, 39.63 mmol, 1 eq) in LiHMDS (60 mL) cooled to 0° C. was added compound 2 (9.1 g, 79.26 mmol, 2 eq), xanthophos (2.3 g, 3.96 mmol, 0.1 eq) followed by Pd(OAc)$_2$ (0.44 g, 1.98 mmol, 0.05 eq). The resulting reaction mixture was heated at 75° C. for 16 h. The reaction was monitored by TLC. TLC analysis indicated formation of a non-polar spot. Reaction mixture was diluted with ethyl acetate and filtered through celite, which was washed with ethyl acetate. The filtrate was dried over Na$_2$SO$_4$ and concentrated under reduced pressure. The crude product was purified by column chromatography (silica 100-200) using 0-10% methanol in DCM as an eluent to give Compound 3 (5.8, 60.4% yield) as a colorless liquid. LCMS: 91.4% with m/z 222.30 (M+H).

Step 2:

To a stirred solution of compound 3 (2.5 g, 11.36 mmol, 1 eq) in ACN (30 mL), was added NCS (2 g, 14.77 mmol, 1.3 eq) and the resulting reaction mixture was heated at 75° C. for 3.5 h in a preheated oil bath. The reaction was monitored by TLC. TLC analysis indicated formation of a non-polar spot. The reaction mixture was concentrated under reduced pressure. The crude product was purified by column chromatography (silica 230-400) using 0-10% methanol in DCM as an eluent to give Compound 4 (1 g, 34.7% yield) as a colorless liquid. LCMS: 65.02% with m/z 256.32 (M+H):

Step 3:

To a stirred solution of compound 4 (1.1 g, 4.31 mmol, 1.0 eq), and PMDTA (3.6 mL, 17.25 mmol, 4 eq) in dry THF (15 mL) cooled to −78° C. was added n-BuLi (7 mL, 17.25 mmol, 4 eq, 2.5M in hexane) drop wise under argon atmosphere. The resulting reaction mixture was stirred for 2 h at the same temperature. Then, a solution of iodine (2.1 g, 8.62 mmol, 2 eq) in THF (10 mL) was added drop wise at −78° C. and the resulting reaction mixture was allowed to warm to RT for 2 h. The reaction was monitored by TLC. TLC analysis indicated formation of a non-polar spot. The reaction mixture was quenched with saturated aqueous solution of sodium thiosulfate and extracted with EtOAc (3×100 mL). The combined organic layer was dried over $Na_2SO_4$ and concentrated under reduced pressure to give Compound 5 (0.64 g, 40.3% yield) as a pale yellow liquid. LCMS: 87.81% with m/z 382.31 (M+H):

Step 4:

To a stirred solution of compound 5 (1.7 g, 4.46 mmol, 1 eq) in 1,4-dioxane (25 mL) was added $Cs_2CO_3$ (2.9 g, 8.92 mmol, 2 eq), $NH_2Boc$ (0.57 g, 4.9 mmol, 1.1 eq) followed by xanthophos (0.25 g, 0.44 mmol, 0.1 eq) and the resulting reaction mixture was degassed with nitrogen for 15 min. $Pd(OAc)_2$ (0.05 g, 0.22 mmol, 0.05 eq) was added and the resulting reaction mixture was heated at 85° C. for 16 h. The reaction was monitored by TLC. TLC analysis indicated formation of a polar spot. Reaction mixture was filtered through celite, washed with ethyl acetate and filtrate was concentrated under reduced pressure to get a crude product. The crude product was purified by column chromatography (silica 230-400) using 0-40% ethyl acetate in petroleum ether as an eluent to give Compound 6 (1.3 g, 81.2% yield) as an off-white semi solid. LCMS: 91.73% with m/z 371.22 (M+H):

Step 5:

To a stirred solution of compound 6 (1.3 g, 3.51 mmol, 1 eq) in DCM (20 mL), was added TFA (3.5 mL, 42.1 mmol, 12 eq) drop wise and the resulting reaction mixture was stirred at RT for 16 h. The reaction was monitored by TLC. TLC analysis indicated formation of a polar spot. The reaction mixture was concentrated under reduced pressure, basified with aq $NaHCO_3$ solution and extracted with ethyl acetate (2×50 mL). The combined organic layer was dried over $Na_2SO_4$ and concentrated under reduced pressure. The crude product was triturated with n-pentane resulting in 3-chloro-2-fluoro-6-(1-methylhexahydropyrrolo[3,4-b]pyrrol-5(1H)-yl)pyridin-4-amine (0.7 g, 74.4% yield) as an off-white solid. LCMS: 96.77% with m/z 271.44 (M+H);

Synthesis of 3-chloro-2-fluoro-6-(4-methyl-1,4-diazepan-1-yl)pyridin-4-amine

Scheme 79

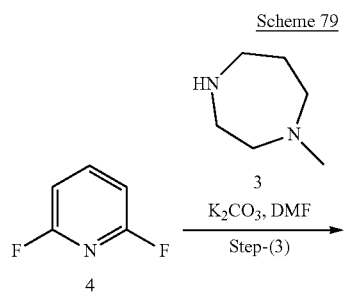

Preparation of Inetermediate 3:

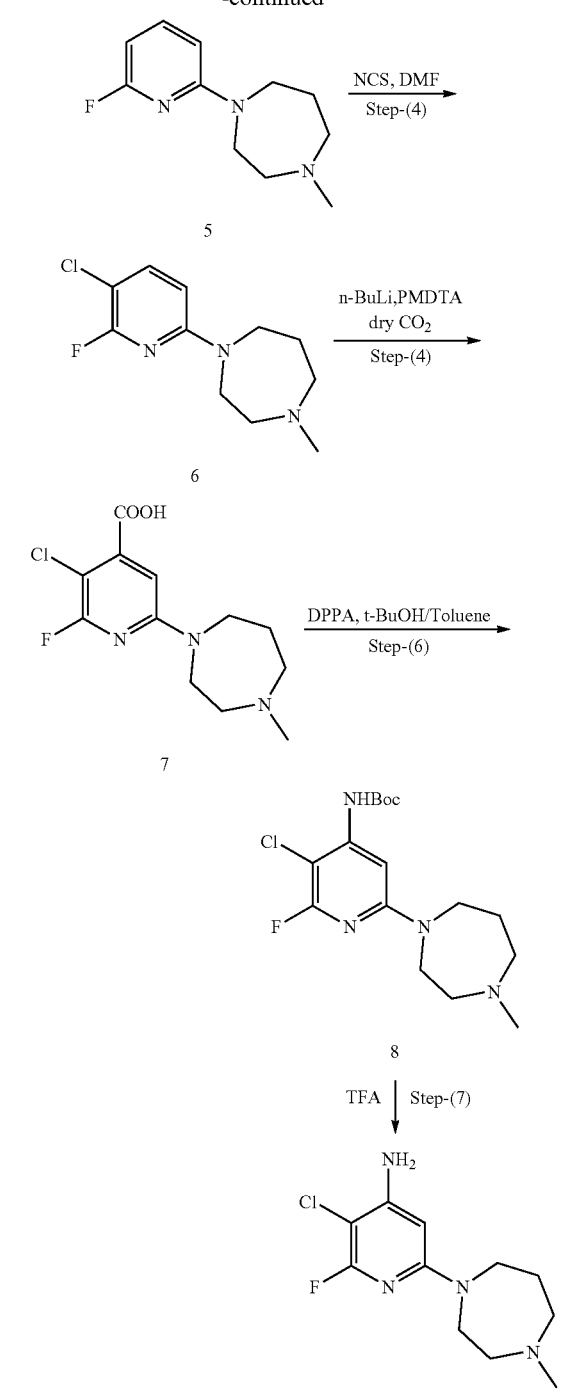

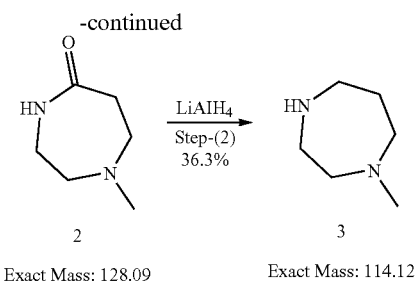

Compound numbers in text refer to structures shown in Scheme 79.

Step 1:

To a stirred solution of compound 1 (5 g, 44.18 mmol, 1 eq) in $CHCl_3$ (75 mL), cooled to −5° C. was added drop wise con. $H_2SO_4$ (13.9 mL, 260.6 mmol, 5.9 eq) followed by $NaN_3$ (5.75 g, 88.37 mmol, 2 eq) and the resulting reaction mixture was heated at 70° C. for 2 h. The reaction was monitored with TLC. TLC analysis indicated formation of a polar spot. The reaction mixture was quenched with ice water, basified with $K_2CO_3$ followed by 60% aq KOH solution and stirred for 15 min. Filtered through celite, layers were separated and the aqueous layer was extracted with DCM. The combined organic layer was dried over $Na_2SO_4$ and concentrated under reduced pressure to give compound 2 (5.2 g, 92.8% yield) as a brown semi solid. LCMS: 98.86% with m/z 129.31 (M+2H).

Step 2:

To a stirred solution of compound 2 (5 g, 39.03 mmol, 1 eq) in THF (100 mL) cooled to 0° C. was added LAH (2.96 g, 78.06 mmol, 2 eq) portion wise and the resulting reaction mixture was stirred at RT for 16 h. The reaction was monitored by TLC. TLC analysis indicated formation of a polar spot. The reaction mixture was quenched with ice water (5 mL) followed by 50% aq NaOH solution (10 mL) and stirred for 30 min. The reaction mixture was filtered through celite, dried over $Na_2SO_4$ and concentrated under reduced pressure. Crude was co-distilled with toluene (2×40 mL) to give compound 3 (1.6 g, 36.3% yield) as a pale yellow liquid. LCMS (ELSD): 98.5% with m/z 115.30 (M+H)

Step 3:

To a stirred solution of compound 3 (3.8 g, 33.3 mmol, 1 eq) in DMF (38 mL), was added $K_2CO_3$ (6.9 g, 49.95 mmol, 1.5 eq) followed by compound 4 (7.6 mL, 83.2 mmol, 2.5 eq) at RT and the resulting reaction mixture was heated at 80° C. for 2 h. The reaction was monitored by TLC. TLC analysis indicated formation of a non-polar spot. The reaction mixture was diluted with ice water and extracted with ethyl acetate (2×500 mL). The combined organic layer was dried over $Na_2SO_4$ and concentrated under reduced pressure. The crude product was purified by column chromatography (silica 230-400) using 10% methanol in DCM as an eluent to give compound 5 (3.8 g, 55.07% yield) as a pale brown liquid. LCMS: 96.17% with m/z 210.36 (M+H):

Step 4:

To a stirred solution of compound 5 (1 g, 4.78 mmol, 1 eq) in ACN (20 mL), was added NCS (0.64 g, 4.78 mmol, 1 eq) and the resulting reaction mixture was heated at 50° C. for 3.5 h in a preheated oil bath. The reaction was monitored by TLC. TLC analysis indicated formation of a non-polar spot. Solvent was concentrated under reduced pressure to get a crude product. The crude product was purified by column chromatography (silica 230-400) using 0-5% methanol in DCM as an eluent to give compound 6 (0.5 g, 43.1% yield) as a pale brown liquid. LCMS: 85.5% with m/z 244.44 (M+H):

Step 5:

To a stirred solution of compound 6 (1.2 g, 4.92 mmol, 1 eq) in THF (48 mL), cooled to −78° C. was added PMDTA (4.11 mL, 19.69 mmol, 4 eq) followed by n-BuLi (2.5M in hexane) (7.88 mL, 19.69 mmol, 4 eq) drop wise and the resulting reaction mixture was stirred at same temperature for 2 h. Reaction mixture was quenched with crushed dry $CO_2$ and stirred at RT for 16 h. The reaction was monitored by TLC. TLC analysis indicated formation of a polar spot. The reaction mixture was acidified with 4M dioxane in HCl. The solid precipitate formed was filtered and washed with ethyl acetate to give compound 7 (1.2 g, 85.7% yield) as pale yellow sticky solid. LCMS: 19.12% with m/z 288.07% (M+H):

Step 6:

To a stirred solution of compound 7 (2.3 g, 7.99 mmol, 1 eq) in t-BuOH:toluene (1:1) (46 mL), was added TEA (2.8 mL, 19.98 mmol, 2.5 eq) followed by DPPA (2.6 mL, 11.99 mmol, 1.5 eq) and the resulting reaction mixture was heated at 100° C. for 48 h. The reaction was monitored by TLC. TLC analysis indicated formation of a non-polar spot. Solvent was concentrated under reduced pressure to get a crude product. The crude product was diluted with ethyl acetate (100 mL) and washed with saturated brine solution. The combined organic layer was dried over $Na_2SO_4$ and concentrated under reduced pressure. The crude product was purified by column chromatography (silica 230-400) using 5% methanol in DCM as an eluent to give compound 8 (350 mg, 12.5% yield) as a pale brown liquid. LCMS: 73.26% with m/z 359.11 (M+H):

Step 7:

To a stirred solution of compound 8 (350 mg, 0.97 mmol, 1 eq) in DCM (7 mL), was added TFA (0.76 mL, 9.97 mmol, 10 eq) drop wise and the resulting reaction mixture was stirred at RT for 16 h. The reaction was monitored by TLC. TLC analysis indicated formation of a polar spot. The reaction mixture was concentrated under reduced pressure, basified with aq 2N $NH_3OH$ solution and extracted with ethyl acetate (2×50 mL). The combined organic layer was dried over $Na_2SO_4$ and concentrated under reduced pressure to give in 3-chloro-2-fluoro-6-(4-methyl-1,4-diazepan-1-yl)pyridin-4-amine (110 mg, 43.6% yield) as a brown liquid. LCMS: 93.04% with m/z 259.19 (M+H):

Synthesis of 6-(azetidin-1-yl)-3-chloro-2-fluoropyridin-4-amine

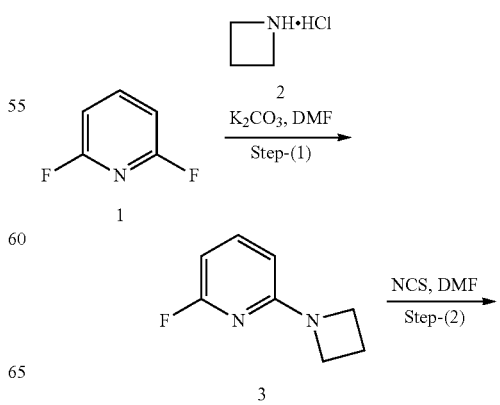

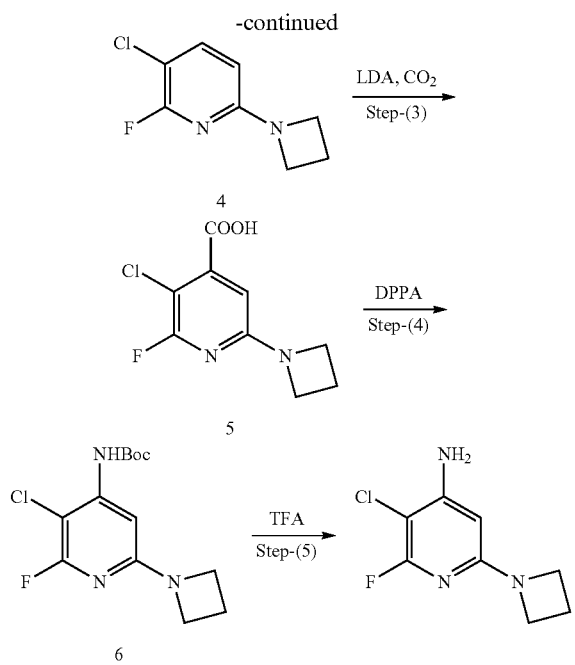

Compound numbers in text refer to structures shown in Scheme 80.

Step 1:

In a seal tube compound 1 (5 g, 43.47 mmol, 1 eq) in DMF (50 mL), was added K₂CO₃ (12 g, 86.95 mmol, 2 eq) followed by compound 2 (4.88 g, 52.1 mmol, 1.2 eq) and the resulting reaction mixture was heated at 85° C. for 16 h. The reaction was monitored by TLC. TLC analysis indicated formation of a polar spot. The reaction mixture was quenched with ice cold water and extracted with ethyl acetate. The combined organic layer was dried over $Na_2SO_4$ and concentrated under reduced pressure. Crude product was purified by column chromatography (silica 100-200) using 3% ethyl acetate in petroleum ether as an eluent to give compound 3 (3 g, 45.45% yield) as a pale yellow liquid. LCMS: 89.42% with m/z 153.05 (M+H):

Step 2:

To a stirred solution of compound 3 (3 g, 19.7 mmol, 1 eq) in DMF (30 mL), was added NCS (2.88 g, 21.6 mmol, 1.1 eq) and the resulting reaction mixture was heated at 70° C. for 1 h in a preheated oil bath. The reaction was monitored by TLC. TLC analysis indicated formation of a non-polar spot. The reaction mixture was quenched with ice cold water and extracted with ethyl acetate. The combined organic layer was washed with brine solution, dried over $Na_2SO_4$ and concentrated under reduced pressure. The crude product was purified by column chromatography (silica 100-200) using 2% ethyl acetate in petroleum ether as an eluent to give compound 4 (2 g, 55.5% yield) as a pale yellow liquid. LCMS: 98.55% with m/z 187.34 (M+1):

Step 3:

To a stirred solution of compound 4 (2 g, 10.3 mmol, 1 eq) in THF (40 mL), cooled to −78° C. was added PMDTA (8.9 mL, 43.01 mmol, 4 eq) followed by n-BuLi (2.5M in hexane) (17.2 mL, 43.01 mmol, 4 eq) drop wise and the resulting reaction mixture was stirred at the same temperature for 3 h. The reaction mixture was quenched with crushed dry $CO_2$ and the resulting reaction mixture was stirred at RT for 16 h. The reaction was monitored by TLC. TLC analysis indicated formation of a non-polar spot. Reaction mixture was quenched with ice cold water, acidified (pH−2) with aq 2N HCl solution and extracted with ethyl acetate. The combined organic layer was dried over $Na_2SO_4$ and concentrated under reduced pressure. The crude product was triturated with n-pentane followed by diethyl ether to give compound 5 (1.5 g, 62.5% yield) as a pale brown liquid. LCMS: 92.38% with m/z 231.30 (M+H):

Step 4:

To a stirred solution of compound 5 (1.5 g, 6.55 mmol, 1 eq) in toluene:t-butanol (1:1, 30 mL), was added TEA (1.28 mL, 9.81 mmol, 1.5 eq) followed by DPPA (2.11 mL, 9.81 mmol, 1.5 eq) and the resulting reaction mixture was heated at 90° C. for 16 h. The reaction was monitored by TLC. TLC analysis indicated formation of a non-polar spot. Solvent was evaporated under reduced pressure; crude was diluted with water and extracted with ethyl acetate. The combined organic layer was dried over $Na_2SO_4$ and concentrated under reduced pressure. The crude product was purified by column chromatography (silica 230-400) using 5% ethyl acetate in petroleum ether as an eluent to give compound 6 (1 g, 51% yield) as a pale yellow solid. LCMS: 98.40% with m/z 302.36 (M+H):

Step 5:

To a stirred solution of compound 6 (1 g, 3.32 mmol, 1 eq) in DCM (20 mL), was added TFA (2.2 mL, 33.2 mmol, 10 eq) drop wise and the resulting reaction mixture was stirred at RT for 16 h. The reaction was monitored by TLC. TLC analysis indicated formation of a polar spot. The reaction mixture was concentrated under reduced pressure, basified with aq saturated $NaHCO_3$ solution and extracted with ethyl acetate (2×50 mL). The combined organic layer was dried over $Na_2SO_4$ and concentrated under reduced pressure. The crude product was purified by column chromatography (neutral alumina) using 20% ethyl acetate in petroleum ether as an eluent to give 6-(azetidin-1-yl)-3-chloro-2-fluoropyridin-4-amine (0.65 g, 98.48% yield) as a pale brown solid. LCMS: 99.06% with m/z 202.32 (M+H);

Synthesis of 3-chloro-2-fluoro-6-((2R,6S)-2,4,6-trimethylpiperazin-1-yl)pyridin-4-amine

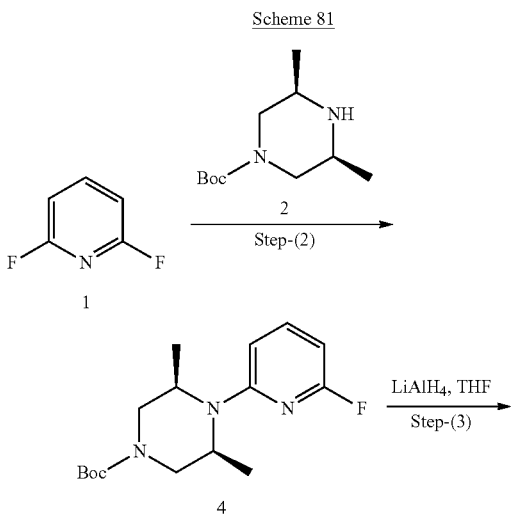

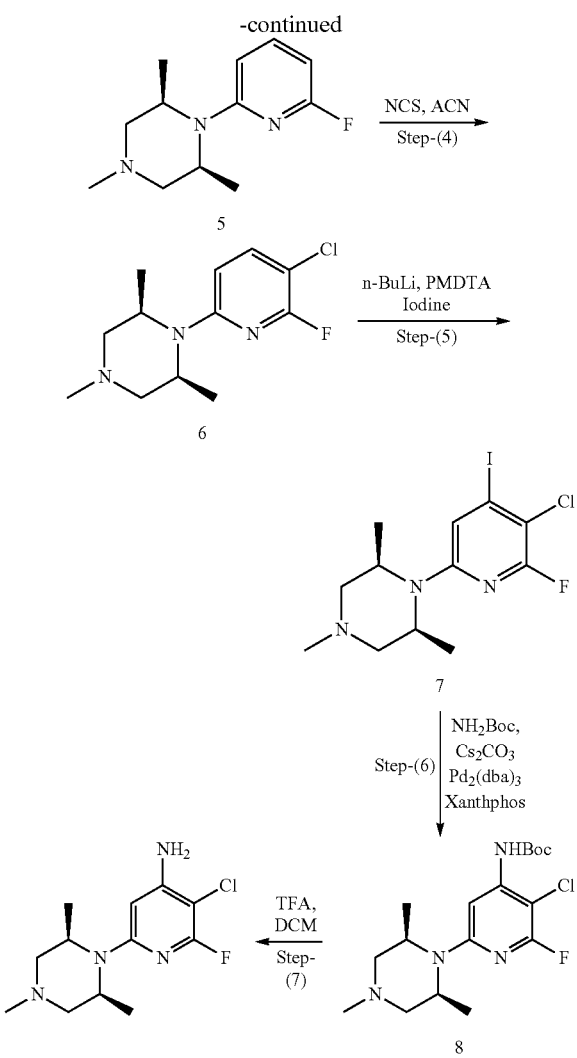

Preparation of Int-2:

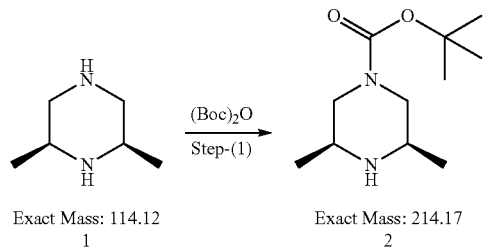

Compound Numbers in Text Refer to Structures Shown in Scheme 81.

Step 1:

To a stirred solution of compound 1 (25 g, 219.1 mmol, 1 eq) in DCM (250 mL) cooled to 0° C. was added (Boc)2O (55.36 mL, 241.01 mmol, 1.1 eq) and the resulting reaction mixture was stirred for overnight at room temperature. The reaction was monitored with TLC, TLC indicated formation of a non-polar spot. The reaction mixture was diluted with water (100 mL) and extracted with EtOAc (3×300 mL). The combined organic layer was dried over $Na_2SO_4$, concentrated under reduced pressure to give a crude product. The crude product was purified by filtered column chromatography (silica gel 230-400 mesh) using 0-5% Methanol in DCM as an eluent to give Compound 2 (37 g, 78.89% yield) as a pale brown semisolid.

Step 2:

To a stirred solution of compound 2 (20 g, 93.0 mmol, 1 eq) in LiHMDS (200 mL) cooled to 0° C. was added compound 3 (26.8 mL, 280.3 mmol, 3 eq), xanthophos (3.24 g, 5 mmol, 0.06 eq) followed by $Pd_2(dba)_3$ (2.5 g, 2.7 mmol, 0.03 eq). Then, the resulting reaction mixture was stirred for overnight at 80° C. The reaction was monitored with TLC, TLC indicated formation of a non-polar spot. The reaction mixture was quenched with ice water (100 mL), filtered through celite and washed with ethyl acetate. Layers were separated, the aqueous layer was extracted with ethyl acetate (2×150 mL) and washed with brine solution (1×100 mL). The combined organic layer was dried over $Na_2SO_4$, concentrated under reduced pressure to give a crude product. The crude product was purified by column chromatography (silica gel 100-200 mesh) using 0-5% ethyl acetate in petroleum ether as an eluent to give compound 4 (20 g, 37.73% yield) as a brown liquid. LCMS: m/z 310.54 (M+H):

Step 3:

To a stirred solution of compound 4 (10 g, 32.36 mmol, 1 eq) in THF (90 mL) cooled to 0° C. was added LAH (4.91 g, 129.4 mmol, 4 eq) portion wise. Then the reaction mass was stirred for overnight at room temperature. The reaction was monitored by TLC. TLC analysis indicated formation of a polar spot. The reaction mixture was quenched with $H_2O$ (10 mL), Aq. 2N NaOH solution (5 mL) and the resulting suspension was stirred for 15 min. Filtered through celite and washed with ethyl acetate. Layers were separated, the organic layer was dried over $Na_2SO_4$ and concentrated under reduced pressure to give a crude product. The crude product was purified by column chromatography (silica gel 100-200 mesh) using 15-20% ethyl acetate in petroleum ether as an eluent to give compound 5 (6.13 g, 85% yield) as a brown liquid. LCMS: m/z 224.46 (M+H Step 4:

To a stirred solution of compound 5 (5 g, 22.42 mmol, 1 eq) in ACN (100 mL) was added NCS (3.3 g, 24.66 mmol, 1.1 eq) and the resulting reaction mixture was heated at 75° C. for 3-4 h in preheated oil bath. The reaction was monitored by TLC. TLC analysis indicated formation of a non-polar spot. Solvent was concentrated under reduced pressure to give a crude product. The crude product was purified by column chromatography (silica gel 2300-400 mesh) using 0-5% methanol in DCM as an eluent to give compound 6 (4 g, 71.42% yield) as a pale brown liquid. LCMS: m/z 258.44 (M+H):

Step 5:

To a stirred solution of compound 6 (10 g, 38.8 mmol, 1 eq) in Dry THF (400 mL) was added PMDTA (30 mL, 155.2 mmol, 4 eq), the mixture was cooled to −78° C. and n-BuLi (2.5M in hexane) (60 mL, 155.2 mmol, 4 eq) was added drop wise. Then the resulting reaction mixture was stirred for 2 h at the same temperature. To reaction mixture was added a solution of Iodine (19.7 g, 77.6 mmol, 2 eq) in dry THF (200 mL) at −78° C. and stirred for 10 min. The reaction was monitored by TLC. TLC analysis indicated formation of a non-polar spot. The reaction was quenched with hypo solution (100 mL), extracted with ethyl acetate (2×200 mL) and washed with brine solution (1×100 mL). The combined organic layer was dried over $Na_2SO_4$, concentrated under reduced pressure to give a crude product. The crude product was purified by column chromatography (silica gel 100-200 mesh) using 10-20% ethyl acetate in petroleum ether as an eluent to give compound 7 (7.3 g, 48.99% yield) as a pale yellow liquid. LCMS: m/z 384.1 (M+H):

Step 6:

To a stirred solution of compound 7 (7.3 g, 19.06 mmol, 1 eq) in toluene (70 mL) was added NH₂Boc (2.67 g, 22.3 mmol, 1.2 eq), and Cs₂CO₃ (12.38 g, 38.4 mmol, 2 eq) followed by xantphos (0.66 g, 1.1 mmol, 0.06 eq). Then, the resulting reaction mixture was degassed under nitrogen atmosphere for 20 min, was added Pd₂(dba)₃ (0.52 g, 0.52 mmol, 0.03 eq). Then, the resulting reaction mixture was stirred for overnight at 95° C. Reaction was monitored with TLC, TLC indicated formation of polar spot. The reaction mixture was filtered through celite and washed with ethyl acetate. Filtrate was dried over Na₂SO₄ and concentrated under reduced pressure to give a crude product. The crude product was purified by column chromatography (silica gel 100-200 mesh) using 0-1% methanol in DCM as an eluent to give compound 8 (5 g, 70.52% yield) as a pale brown liquid. LCMS: m/z 373.54 (M+H):

Step 7:

To a stirred solution of compound 8 (5 g, 13.4 mmol, 1 eq) in DCM (100 mL) cooled to 0° C. was added TFA (15.6 mL, 134.0 mmol, 10 eq). Then the resulting reaction mixture was stirred for overnight at room temperature. The reaction was monitored by TLC. TLC analysis indicated formation of a polar spot. Solvent was concentrated under reduced pressure and the crude was basified (pH~8) with aq NaHCO₃ solution and extracted with ethyl acetate (2×100 mL). The combined organic layer was dried over Na₂SO₄, concentrated under reduced pressure to give a crude product. The crude product was washed with pentane and diethyl ether, filtered and dried ao afford 3-chloro-2-fluoro-6-((2R,6S)-2,4,6-trimethylpiperazin-1-yl)pyridin-4-amine (2.1 g, 57.53% yield) as a pale brown solid. LCMS: m/z 273.05 (M+H):

Synthesis of 3-chloro-2-fluoro-6-((2S,6S)-2,4,6-trimethylpiperazin-1-yl)pyridin-4-amine

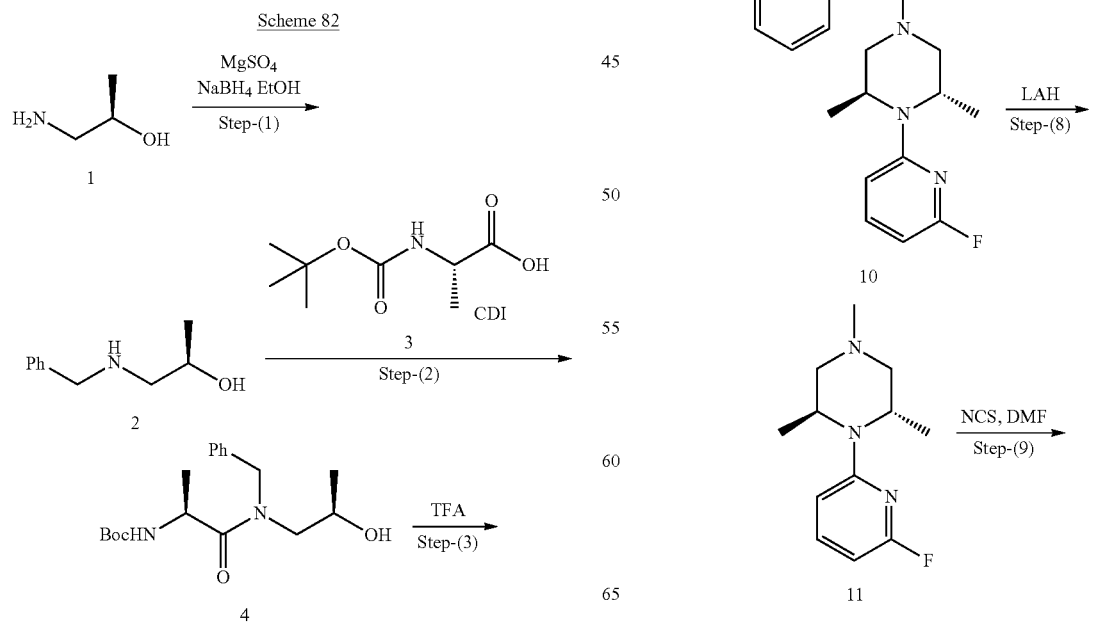

-continued

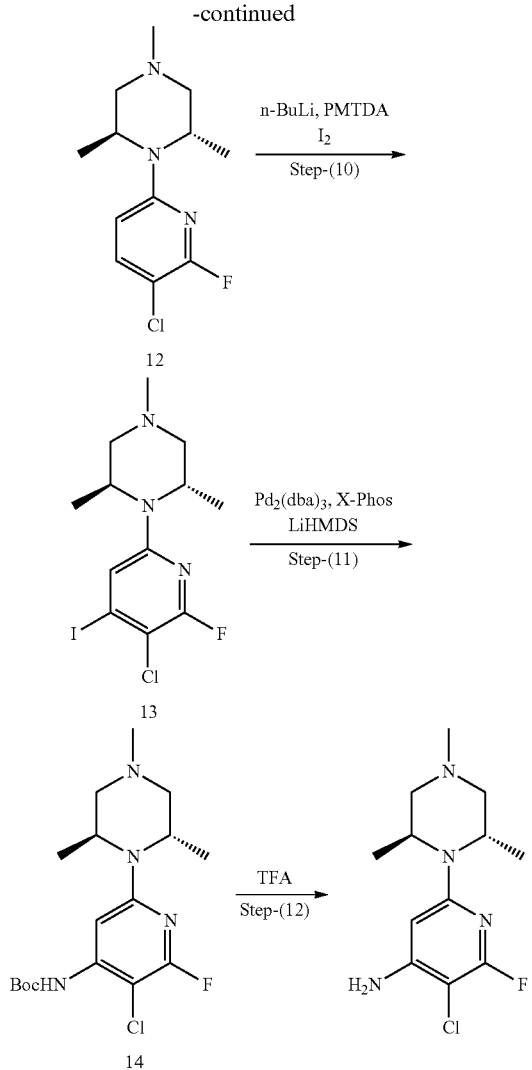

Compound numbers in text refer to structures shown in Scheme 82.

Step 1:

To a stirred solution of compound 1 (50 g, 665 mmol, 1 eq) in THF (1680 mL), cooled to 0° C. was added MgSO₄ (41 h, 340 mmol, 0.5 eq) followed by benzaldehyde (81.5 mL, 798 mmol, 1.5 eq) drop wise and the resulting reaction mixture was stirred at RT for 4 h. The reaction mixture was filtered, the filtrate was concentrated under reduced pressure. The crude residue was diluted with ethanol (1680 mL), cooled to 0° C. NaBH₄ (8.4 g, 222 mmol, 0.325 eq) was added and the resulting reaction mixture was stirred at RT for 2 h. Further NaBH₄ (8.4 g, 222 mmol, 0.325 eq) was added at 0° C. and the mixture was slowly warmed to rt and stirred for 72 h. The reaction was monitored with TLC. TLC analysis indicated formation of a non-polar spot. Solvent was evaporated under reduced pressure; crude was diluted with ethyl acetate and extracted with aq 2N HCl solution. The aqueous layer was basified with saturated NaHCO₃solution and extracted with 5% methanol:DCM. The combined organic layer was dried over Na₂SO₄ and concentrated under reduced pressure to give compound 2 (91 g, 82.7% yield) as a brown semi solid.

Step 2:

To a stirred solution of compound 3 (104.5 g, 551.5 mmol, 1 eq) in DCM (1820 mL) was added CDI (89.43 g, 551.5 mmol, 1 eq) and the resulting reaction mixture was stirred at RT for 1 h. Compound 2 (91 g, 551.5 mmol, 1 eq) was added and the resulting reaction mixture was stirred at RT for 16 h. The reaction was monitored by TLC. TLC analysis indicated formation of a polar spot. Reaction mixture was concentrated under reduced pressure and the crude residue was purified by column chromatography (silica 100-200) using 20%-50% ethyl acetate in petroleum ether as an eluent to give compound 4 (98 g, 52.9% yield) as a pale brown liquid. LCMS m/z 337.32 (M+H):

Step 3:

To a stirred solution of compound 4 (98 g, 291 mmol, 1 eq) in DCM (980 mL), was added TFA (490 mL, 6403 mmol, 5 eq) drop wise and the resulting reaction mixture was stirred at RT for 30 min. The reaction was monitored by TLC. TLC analysis indicated formation of a polar spot. The reaction mixture was concentrated under reduced pressure, basified with saturated aq NaHCO₃solution and extracted with 5% Methanol:DCM (2×500 mL). The combined organic layer was dried over Na₂SO₄ and concentrated under reduced pressure to give compound 5 (67 g, 97.3% yield) as a pale brown liquid. LCMS: m/z 237.05 (M+H);

Step 4:

To a stirred solution of compound 5 (30 g, 127 mmol, 1 eq) in THF (570 mL), cooled to 0° C. was added Borane DMS (44.4 mL, 444 mmol, 3.5 eq) and the resulting reaction mixture was stirred at RT for 16 h. The reaction mixture was quenched with 20% Aq HCl (100 mL) followed by a solution of KOH (200 g) in H₂O (400 mL) and the resulting reaction mixture was heated at 70° C. for 24 h. The reaction mixture was cooled to 0° C., methanol (100 mL) was added and the resulting reaction mixture was refluxed at 75° C. for 24 h. The reaction was monitored by TLC. TLC analysis indicated formation of a non-polar spot. The solvent was removed under reduced pressure to get a crude residue. The crude residue was diluted with water and extracted with DCM. The combined organic layer was dried over Na₂SO₄ and concentrated under reduced pressure. The crude product was purified by column chromatography (neutral alumina) using 5-10% methanol in DCM as an eluent to give compound 6 (16.5 g, 58.5% yield) as a pale brown liquid. LCMS: m/z 223.26 (M+H);

Step 5:

To a stirred solution of compound 6 (14 g, 63 mmol, 1 eq) in THF (560 mL)cooled to 0° C. was added TPP (33 g, 126 mmol, 2 eq) followed by DIAD (25 mL, 126 mmol, 2 eq) drop wise and the resulting reaction mixture was stirred at RT for 16 h. The reaction was monitored by TLC. TLC analysis indicated formation of a non-polar spot. Solvent was concentrated under reduced pressure to get a crude product. The crude product was purified by column chromatography (silica 230-400) using 5-8% methanol in DCM as an eluent to give compound 7 (4.7 g, 36.7% yield) as a pale yellow liquid. LCMS: 76.55% with m/z 205.24% (M+H):

Step 6:

In a seal tube compound 7 (2 g, 9.7 mmol, 1 eq) in LiHMDS (20 mL), was added compound 8 (2.66 mL, 29.3 mmol, 3 eq), Pd(OAc)₂ (0.22 g, 0.97 mmol, 0.1 eq) followed by BINAP (0.65 g, 0.97 mmol, 0.1 eq) and the resulting reaction mixture was heated at 250° C. for 16 h. The reaction was monitored by TLC. TLC analysis indicated formation of non-polar spot. The reaction mixture was quenched with ice cold water, filtered through celite, which was washed with ethyl acetate. Filtrate was dried over Na₂SO₄ and concentrated under reduced pressure to give compound 9 (770 mg, 26.2% yield) as a pale yellow liquid. LCMS: m/z 300.34 (M+H):

Step 7:

To a stirred solution of compound 9 (2.15 g, 7.1 mmol, 1 eq) in DCM (43 mL), was added phenyl chloroformate (2.7 mL, 21.5 mmol, 3 eq) followed by sodium bicarbonate (1.81 g, 21.5 mmol, 3 eq) and the resulting reaction mixture was stirred at RT for 16 h. The reaction was monitored by TLC. TLC analysis indicated formation of a polar spot. The reaction mixture was diluted with water and extracted with DCM. The combined organic layer was dried over $Na_2SO_4$ and concentrated under reduced pressure. The crude product was purified by column chromatography (neutral alumina) using 4% ethyl acetate in petroleum ether as an eluent to give compound 10 (1.71 g, 72.45% yield) as an off-white solid. LCMS: m/z 330.24 (M+H):

Step 8:

To a stirred solution of compound 10 (1.71 g, 5.1 mmol, 1 eq) in THF (35 mL) cooled to 0° C. was added LAH (0.39 g, 10.3 mmol, 2 eq) portion wise and the resulting reaction mixture was stirred at RT for 16 h. The reaction was monitored by TLC. TLC analysis indicated formation of a polar spot. Reaction mixture was quenched with saturated aq sodium sulphate and stirred for 30 min. The reaction mixture was filtered through celite, the filtrate was dried over $Na_2SO_4$ and concentrated under reduced pressure to give compound 11 (1 g, 86.9% yield) as a pale yellow liquid. LCMS: m/z 224.27 (M+H):

Step 9:

To a stirred solution of compound 11 (1 g, 4.4 mmol, 1 eq) in DMF (10 mL), was added NCS (0.717 g, 5.3 mmol, 1.2 eq) and the resulting reaction mixture was heated at 50° C. for 1 h in a preheated oil bath. The reaction was monitored by TLC. TLC analysis indicated formation of a non-polar spot. The reaction mixture was quenched with ice cold water and extracted with ethyl acetate. The combined organic layer was washed with brine solution, dried over $Na_2SO_4$ and concentrated under reduced pressure. The crude product was purified by column chromatography (neutral alumina) using 10-30% ethyl acetate in petroleum ether as an eluent to give compound 12 (0.8 g, 69.5% yield) as a pale yellow liquid. LCMS: m/z 257.98 (M+H):

Step 10:

To a stirred solution of compound 12 (1 g, 3.88 mmol, 1 eq) in THF (60 mL) cooled to −78° C. was added PMDTA (2.68 g, 15.52 mmol, 4 eq) followed by n-BuLi (2.5M in hexane) (6.2 mL, 15.52 mmol, 4 eq) drop wise and the resulting reaction mixture was stirred at same temperature for 2 h. A solution of iodine (1.96 g, 7.76 mmol, 2 eq) in THF (30 mL) was added at −78° C. and the resulting reaction mixture was stirred for 15 min. The reaction was monitored by TLC. TLC analysis indicated formation of a non-polar spot. Reaction mixture was quenched with ice cold water and extracted with ethyl acetate. The combined organic layer was dried over $Na_2SO_4$ and concentrated under reduced pressure to give compound 13 (1.2 g, 80.59% yield) as a pale brown liquid. LCMS: m/z 383.94% (M+H):

Step 11:

To a stirred solution of compound 13 (1 g, 3.1 mmol, 1 eq) in toluene (48 mL), was added $Cs_2CO_3$ (1.69 g, 5.2 mmol, 2 eq), and Boc amine (440 mg, 3.7 mmol, 1.2 eq) followed by xanthophos (91 mg, 0.15 mmol, 0.06 eq) and the resulting reaction mixture was degassed for 15 min under nitrogen atmosphere. $Pd_2(dba)_3$ (72 mg, 0.07 mmol, 0.03 eq) was added and the resulting reaction mixture was stirred at 110° C. for 16 h. The reaction was monitored by TLC. TLC analysis indicated formation of a non-polar spot. The reaction mixture was filtered through celite and washed with ethyl acetate. The combined organic layer was dried over $Na_2SO_4$ and concentrated under reduced pressure. The crude product was purified by column chromatography (silica 230-400) using 1-10% methanol in DCM as an eluent to give compound 14 (0.87 g, 90% yield) as a pale yellow liquid. LCMS: m/z 373.09 (M+H):

Step 12:

To a stirred solution of compound 14 (0.5 g, 1.34 mmol, 1 eq) in DCM (10 mL), was added TFA (1.03 mL, 13.4 mmol, 10 eq) drop wise and the resulting reaction mixture was stirred at RT for 16 h. The reaction was monitored by TLC. TLC analysis indicated formation of a polar spot. The reaction mixture was concentrated under reduced pressure. The crude residue was diluted with water and washed with ethyl acetate. Aqueous layer was basified with aq saturated $NaHCO_3$ solution and extracted with ethyl acetate (2×50 mL). The combined organic layer was dried over $Na_2SO_4$ and concentrated under reduced pressure. The crude product was purified by column chromatography (neutral alumina) using 1-10% methanol in DCM as an eluent to give 3-chloro-2-fluoro-6-((2S,6S)-2,4,6-trimethylpiperazin-1-yl) 308yridine-4-amine (0.185 g, 50.6% yield) as a pale yellow liquid. LCMS: m/z 273.42 (M+H):

In a similar manner, the following was prepared

| Aniline | Name | Yield & Mass |
|---|---|---|
| 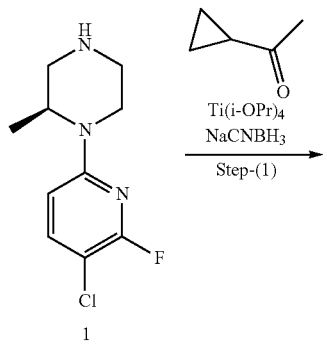 | 5-chloro-2-((2S,6S)-2,4,6-trimethylpiperazin-1-yl)pyridin-4-amine | 51% yield, LCMS [M]+ 273.6 |

Synthesis of 3-chloro-6-((S)-4-((S)-1-cyclopropylethyl)-2-methylpiperazin-1-yl)-2-fluoropyridin-4-amine and 3-chloro-6-((S)-4-((R)-1-cyclopropylethyl)-2-methylpiperazin-1-yl)-2-fluoropyridin-4-amine Scheme 83

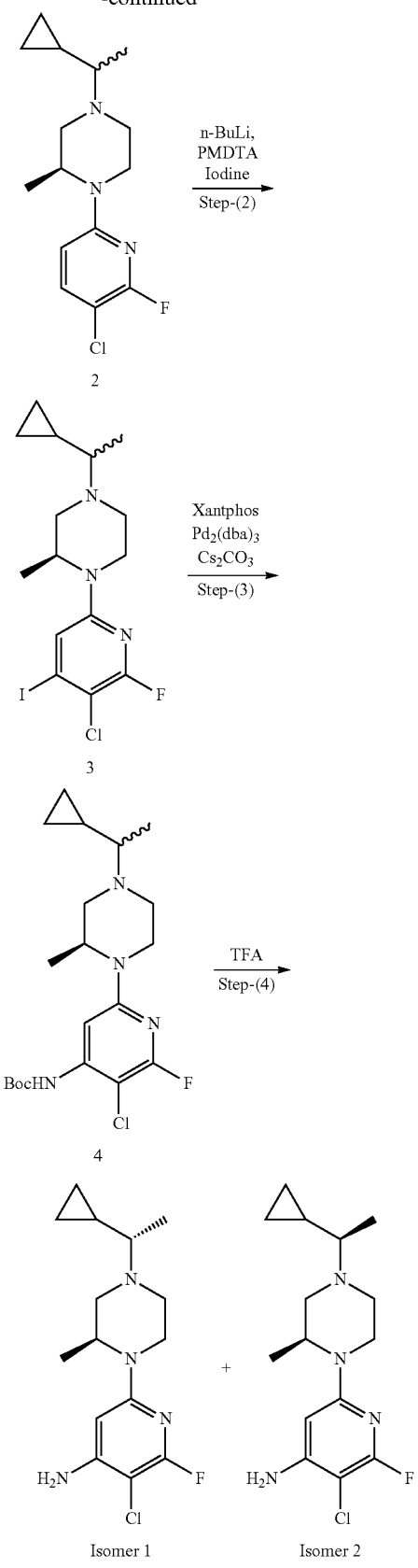

Compound numbers in text refer to structures shown in Scheme 83.

Step 1:

To a stirred solution of compound 1 (5 g, 21.83 mmol, 1 eq) in MeOH (100 mL) was added cyclopropyl methyl ketone (2.75 g, 32.75 mmol, 1.5 eq) and Ti(i-OPr)$_4$ (9.68 mL, 32.75 mmol, 1.5 eq) and Na(OAc)$_3$BH (9.25 g, 43.66 mmol, 2 eq) at RT under argon atmosphere and the reaction was continued for 2 h. NaCNBH$_3$ (2.75 g, 43.66 mmol, 2 eq) was added at RT and the reaction was continued for another 2 h. Further cyclopropyl methyl ketone (2.75 g, 32.75 mmol, 1.5 eq) and NaCNBH$_3$ (2.75 g, 43.66 mmol, 2 eq) were added and the reaction was continued for another 16 h. TLC analysis indicated formation of a less polar spot. The reaction mixture was diluted with water and filtered through celite pad and the filtrate was extracted with EtOAc (3×100 mL). The combined organic layer was dried over Na$_2$SO$_4$ then concentrated to crude compound. The crude compound was purified by column chromatography (silica gel, 100-200 mesh) using 0-20% EtOAc in petroleum ether as eluent to afford compound 2 (2.5 g, 38.5%) as a pale yellow oil. LCMS: m/z 298.08 (M+H).

Step 2:

To a stirred solution of compound 2 (700 mg, 2.35 mmol, 1 eq) in THF (15 mL) was added PMDTA (0.98 mL, 4.71 mmol, 2 eq) and n-BuLi (1.88 mL, 4.71 mmol, 2 eq, 2.5M in THF) at −78° C. under argon atmosphere then the reaction mixture was continued for 2 h. A solution of I$_2$ (1.19 g, 4.71 mmol, 2 eq, in THF) was added at −78° C. The reaction mixture was slowly allowed to reach RT for 16 h. TLC analysis indicated formation of a less polar spot. The reaction mixture was quenched in aqueous solution of sodium thiosulphate then extracted with EtOAc (3×50 mL). The combined organic layer was dried over Na$_2$SO$_4$ then concentrated under reduced pressure to give the crude compound 3 (950 mg, crude) as a brown oil. LC-MS: m/z 423.94 (M+H).

Step 3:

To a stirred solution of compound 3 (950 mg, 2.24 mmol, 1 eq) in Toluene (15 mL) was added Cs$_2$CO$_3$ (1.45 g, 4.49 mmol, 2 eq) and NH$_2$Boc (312 mg, 2.69 mmol, 1.2 eq) at RT. The reaction mixture was de-gassed with Argon for 20 min. Xantphos (39 mg, 0.067 mmol, 0.03 eq) and Pd$_2$(dba)$_3$ (61.7 mg, 0.067 mmol, 0.03 eq) were added at RT. The resulting reaction mixture was heated to 90° C. for 16 h. TLC analysis indicated formation of a polar spot. The reaction mixture was filtered through celite pad. The filtrate was concentrated to crude compound. The crude compound was purified by column chromatography (silica gel, 100-2000 mesh) using 0-5% EtOAc in petroleum ether as eluent to afford compound 4 (600 mg, 61.7% per two steps) as a light yellow oil. LC-MS: m/z 413.10 (M+H).

Step 4:

To a stirred solution of compound 4 (6 g, 14.56 mmol, 1 eq) in DCM (60 mL) was added TFA (11.16 mL, 145.63 mmol, 10 eq) at RT and continued for 16 h. TLC analysis indicated formation of a polar spot. The reaction mixture was concentrated to crude, which was basified by aqueous NaHCO$_3$ solution then extracted with EtOAc (4×100 mL). The combined organic layer was dried over Na$_2$SO$_4$ then concentrated under reduced pressure to give a crude compound. The crude compound was purified by column chromatography (silica gel, 100-200 mesh) using 0-20% EtOAc in petroleum ether as eluent to afford mixture of isomer 1/isomer 2 (3.9 g, 85.9%) as an off-white semi-solid. This mixture of isomers are separated by chiral SFC and isolated to afford 1.4 g of Isomer 1 as an off-white solid [LC-MS: m/z 313.32 (M+H)] and 1.8 g of Isomer 2 as a brown oil. LC-MS: m/z 313.32 (M+H).

Synthesis of (S)-3-chloro-2-fluoro-6-(3-methylmorpholino)pyridin-4-amine

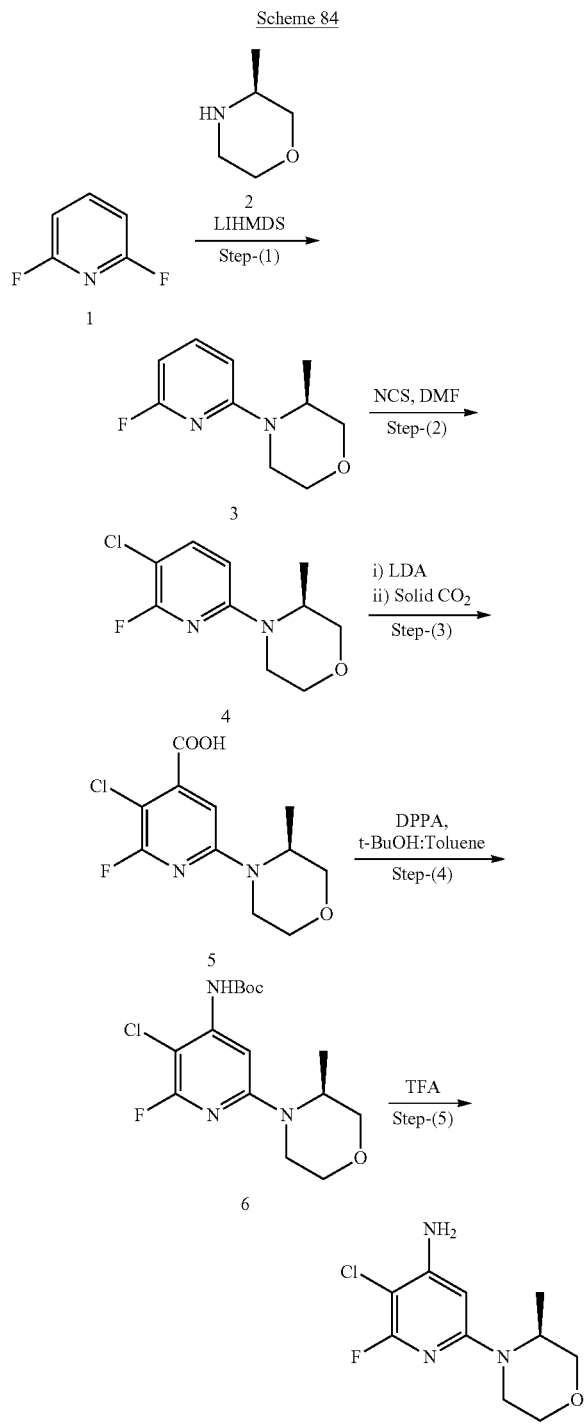

Compound numbers in text refer to structures shown Scheme 84.

Step 1:

To a solution of compound 1 (25 g, 217.3 mmol, 1.0 eq) and compound 2 (26.3 g, 260 mmol, 1.2 eq), Xanthphos (3.76 g, 6.52 mmol, 0.03 eq) then $Pd_2(dba)_3$ (5.97 g, 6.52 mmol, 0.03 eq) at RT under argon atmosphere and degassed for 5 min., and LiHMDS (250 mL, 10V) were added at RT and the total reaction mass was refluxed for 16 h. TLC analysis indicated the formation of a polar spot. The reaction mixture was quenched with saturated $NH_4Cl$ solution (250 mL) and extracted with EtOAc (2×500 mL) twice. The combined organic layer was dried over $Na_2SO_4$ and concentrated under reduced pressure to give a crude product, which was purified by column chromatography ($SiO_2$, 100-200 mesh) using 0-10% EtOAc in petroleum ether as an eluent to give compound 4(27 g, 63.38% yield) as a pale yellow liquid. LC-MS: m/z 197.14 (M+H).

Step 2:

To a solution of compound 3 (27 g, 137.7 mmol, 1 eq) in DMF (550 mL) was added NCS (18.39 g, 137.7 mmol, 0.8 eq) at 0° C. The mixture was heated to 50° C. for 2 h. TLC analysis indicated formation of a polar spot. Then, the reaction mixture was cooled to RT and poured on ice-water (300 mL). The reaction mixture was extracted with EtOAc (2×200 mL); combined organic layer was dried over $Na_2SO_4$ and concentrated under reduced pressure to give a crude product, which was purified by combiflash column chromatography using 0-10% EtOAc in petroleum ether as an eluent to give compound 4 (13 g, 45%) as a pale yellow color liquid. LC-MS: m/z 231.02 (M+H).

Step 3:

To a mixture of DiPA (18.2 mL, 130.4 mmol, 2 eq) and LiCl (2.73 g, 65.2 mmol, 1.0 eq) in Dry THF (150 mL) was added n-BuLi (1.6M in n-hexane, 81.5 mL, 130.4 mmol, 2 eq) at −78° C. and allowed to warm to −30° C. over 30 min. So freshly prepared LDA was added a solution of compound 4 (15 g, 65.2 mmol, 1 eq) in Dry THF (350 mL) at −78° C. under Argon atmosphere and maintained for 4 h at the same temp. Then, powder of dry ice was added slowly at the same temp and the mixture allowed to warm up to RT over 16 h. TLC analysis indicated formation of a polar spot. Then, the reaction mixture was quenched with sat.$NH_4Cl$ (150 mL) and washed with ether (2×150 mL); aqueous layer was acidified with 1MHCl and extracted with EtOAc (4×200 mL). Combined organic layer was dried $Na_2SO_4$ and concentrated under reduced pressure to give a crude product, which was washed with n-pentane & ether to give compound 5 (10 g, 76.9%) as a Brown color liquid. LC-MS: m/z 275.23 (M+H).

Step 4:

To a solution of compound 5 (25 g, 91.2 mmol, 1 eq), TEA (14 mL, 100.3 mmol, 1.1 eq) in tBuOH:Toluene (250 mL:250 mL) at 5-10° C. temp, DPPA (31.95 mL, 102.1 mmol, 1.12 eq) was added in dropwise manner at the same temp. Then, the reaction mixture was heated to 85° C. for 16 h. TLC analysis indicated formation of a nonpolar spot. The reaction mixture was cooled to RT and concentrated under reduced pressure to give a residue; which was re-dissolved in EtOAc (200 mL) and washed with saturated brine. Separated organic layer was dried over $Na_2SO_4$ and concentrated under reduced pressure to give a crude product, which was purified by combiflash column chromatography using 0-20% EtOAc in petroleum ether as an eluent to give compound 6 (21 g, 80% yield) as an off white solid.

Step 5:

To a solution of compound 6 (21 g, 60.8 mmol, 1 eq) in DCM (210 mL) was added Trifluoro acetic acid (55.5 mL, 730.4 mmol, 12 eq) in drop wise manner at 0° C. and the mixture allowed to warm up to RT over 16 h. TLC analysis indicated formation of a polar spot. Then, the reaction mixture was concentrated under reduced pressure to give a TFA salt of product, which was dissolved in water (100 mL), basified with sat.NaHCO$_3$ and extracted in EtOAc (3×100 mL). Combined organic layer was dried over Na$_2$SO$_4$ and concentrated under reduced pressure to give a crude product. Crude compound was purified by washing with n-pentane to give (S)-3-chloro-2-fluoro-6-(3-methylmorpholino)pyridin-4-amine (13.5 g, 93.1%) as an off white solid. LC-MS: m/z 246.0 (M+H).

Synthesis of tert-butyl (2,5-dichloropyridin-4-yl)carbamate

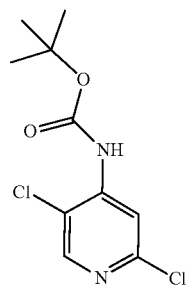 [SMILES: CC(C)(C)OC(=O)Nc1cc(Cl)ncc1Cl]

To a solution of 2,5-Dichloroisonicotinic acid (10.0 g, 52.1 mmol) in tert-Butanol (199 ml, 2083 mmol) was added Triethylamine (8.71 ml, 62.5 mmol) and Diphenylphosphoryl azide, 97% (12.35 ml, 57.3 mmol). The mixture was heated at 90° C. over the weekend. LCMS analysis shows complete conversion of the SM with ~24% de-Boc product. The mixture was evaporated and the residue was partitioned between ethyl acetate and water. The organic phase was washed with water, NaHCO$_3$(aq), dried over MgSO$_4$ and evaporated to obtain tert-butyl (2,5-dichloropyridin-4-yl)carbamate (13.4 g, 50.9 mmol, 98% yield) as a white solid. The product was carried onto the next step as a mixture without further purification. LCMS [M+1]+=263

Synthesis of 5-chloro-2-(prop-1-en-2-yl)pyridin-4-amine

A microwave vial with magnetic stir bar was charged with Isopropenylboronic acid pinacol ester, 2-Bromo-5-chloro-pyridin-4-ylamine HCl, Bis(di-tert-butyl(4 dimethylaminophenyl)phosphine)dichloropalladium(II) and Potassium phosphate tribasic reagent grade, >=98%. 1,4-Dioxane (Volume: 12.0 ml, Ratio: 9.000)/Water (Volume: 4.000 ml, Ratio: 1.000) were added. The vial was sealed and heated in the microwave at 100° C. for 45 min, LCMS showed partial progress. It was heated for an extra 90 min at 100° C. upon which LCMS showed complete conversion of starting material. The reaction was partitioned between DCM and water The aqueous layer was extracted with DCM, dried over Na$_2$SO$_4$ and concentrated down. The crude was purified by Isco (24 g cartridge, eluent: ((EtOAc/DCM;1/1)/Hexanes: 05 then 0-100% then 100%) to afford 5-chloro-2-(prop-1-en-2-yl)pyridin-4-amine as an light yellow powder (403 mg, 75%).

In a similar manner, the following was prepared

| Aniline | Name | Yield & Mass |
|---|---|---|
| ![NH2, Cl pyridine with vinyl] | 5-chloro-2-vinylpyridin-4-amine Exact Mass: 154.03 | yield not determined LCMS [M]+ 155 |

Scheme 85

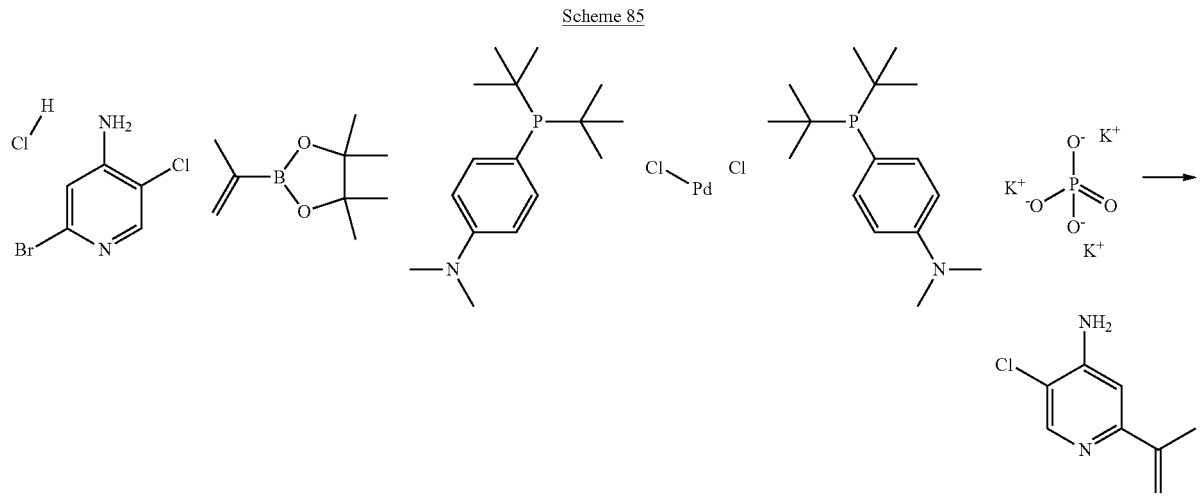

Synthesis of 5-chloro-2-(prop-1-en-2-yl)pyridin-4-amine

Scheme 86

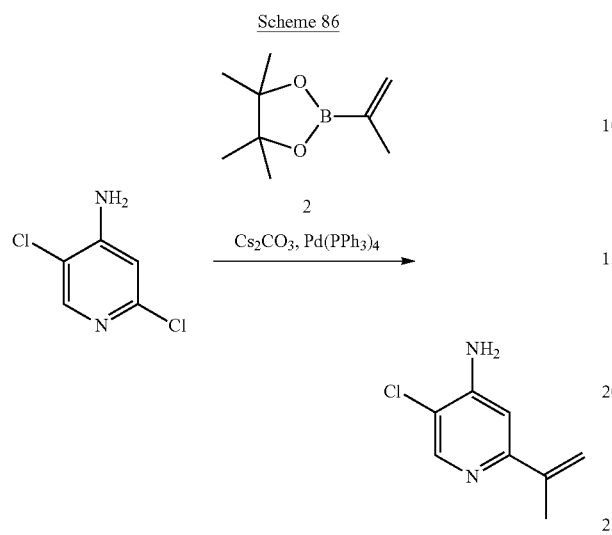

A stirred solution of compound 1 (3 g, 18.51 mmol, 1 eq), and compound 2 (4.2 mL, 22.22 mmol, 1.2 eq) in Dry DMF (30 mL) was degassed with argon for 20 min followed by the addition of Pd (PPh$_3$)$_4$ (370 mg, 0.320 mmol, 0.025 eq) and Cs$_2$CO$_3$ (1.2 eq) at RT then heated to 90° C. in a sealed tube for 16 h. Then, the reaction mixture was cooled to RT and quenched with ice-water (300 mL) and diluted with EtOAc (200 mL), which was filtered through a celite bed; celite bed was washed with EtOAc (2×20 mL). The combined organic layer was dried over Na$_2$SO$_4$ and concentrated under reduced pressure to give a crude product. The crude compound was purified by column chromatography (silica gel 100-200 mesh) using 10%% EtOAc in petroleum ether as an eluent to give 5-chloro-2-(prop-1-en-2-yl)pyridin-4-amine (1.7 g, 54.83%) as an off white solid. LCMS: m/z 169.0% (M+H):

Synthesis of 5-chloro-2-(2,2,4-trimethylpiperazin-1-yl)pyridin-4-amine

Scheme 87

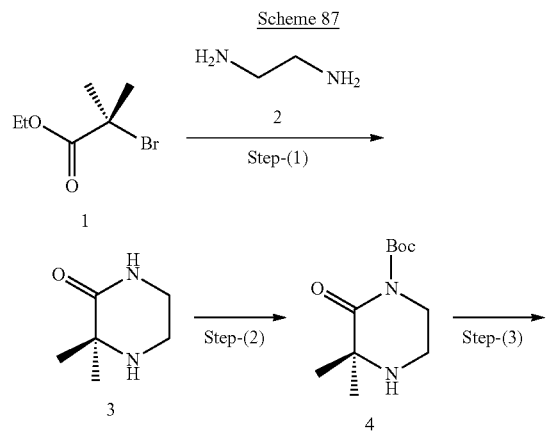

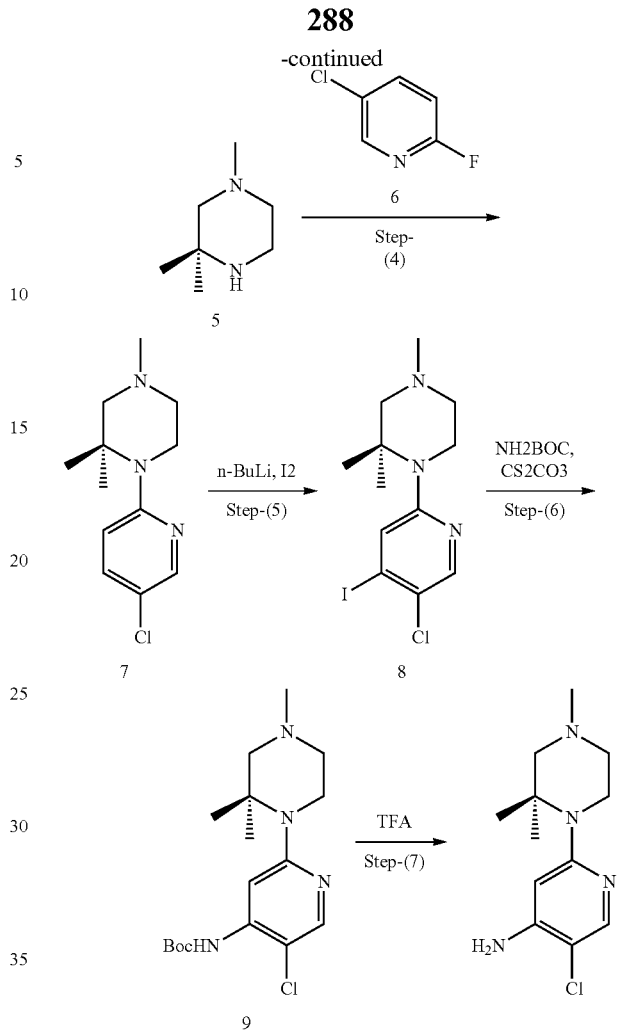

Compound numbers in text refer to structures shown Scheme 87.

Step 1:
To a solution of Compound 1 (30 g, 153 mmol, 1 eq) in THF (500 mL) was added K$_2$CO$_3$ (23.39 g, 169 mmol, 1.1 eq) at rt stirred for 10 min., after that added a solution of compound 2 (60.08 g, 998 mmol, 6.5 eq) at rt. then heated to 120° C. for 24 h. TLC analysis indicated formation of a polar spot. The reaction mixture was cooled to 0° C. and filtered. The filtrate was concentrated under reduced pressure washed with diethyl ether to afford compound 3 (9 g, 48%) as an off white solid. LC-MS: m/z 128.83 (M+H).

Step 2:
To a solution of compound 3 (9 g, 70.3 mmol, 1 eq) in DCM (210 mL) was added BOC-anhydride (18 mL, 77.3 mol, 1.1 eq) followed by DMAP(0.85 g, 6.96 mmol, 0.1 eq) at rt for 16 h. TLC analysis indicated formation of a less polar spot. The reaction mixture was quenched with saturated NaHCO$_3$ solution and extracted with DCM (2×200 mL). The combined organic layer was dried over Na$_2$SO$_4$ and concentrated under reduced pressure to give Compound 4 (8 g, 50% yield) as a pale yellow semi solid. LC-MS: m/z 229.19 (M+H).

Step 3:
To a solution of compound 4 (8 g, 35.0 mmol, 1 eq) in THF (200 mL) was added LAH (7.8 g, 210.0 mmol, 6 eq) as portion wise at 0° C. then allowed to 50° C. for 4 h. Monitored by TLC. TLC analysis indicated formation of a polar spot. The reaction mixture was cooled to 0° C. quenched with 6N NaOH solution and filtered through celite bed, which was washed with EtOAc, then the filtrate was concentrated under reduced pressure to afford Compound 5 (7 g crude) as a pale brown liquid.

Step 4:

To a stirred compound 5 (2 g, 8.77 mmol, 1 eq) was added compound 6 (2.29 g, 17.48 mmol, 2 eq), x-phos (0.3 g, 0.51 mmol, 0.06 eq), Pd$_2$(dba)$_3$ (0.24 g, 0.26 mmol, 0.06 eq) and Li-HMDS (87 mL, 10V) at RT under argon atmosphere, then the reaction mixture was heated to 90° C. for 16 h. TLC analysis indicated formation of a less polar spot. The reaction mixture was cooled to RT then filtered through a celite pad, which was washed with EtOAc (200 mL). The filtrate was diluted with water and extracted with EtOAc (3×100 mL). The combined organic layer was dried over Na$_2$SO$_4$ then concentrated to crude compound. The crude compound was purified by column chromatography (silica gel, 100-200 mesh) using 30-60% EtOAc in petroleum ether as eluent to afford compound 7 (0.6 g, 20% yield) as a brown oil. LC-MS: m/z 240.15 (M+H).

Step 5:

To a stirred solution of compound 7 (1.7 g, 7.11 mmol, 1 eq), was added PMDTA (3.26 mL, 15.64 mmol, 2.2 eq) in dry THF (30 mL) and added n-BuLi (6.25 mL, 15.64 mmol, 2.2 eq, 2.5M in hexane) drop wise at −78° C. under argon atmosphere. Then, the resulting reaction mixture was stirred for 2 h at the same temperature. Then, a solution of iodine (3.61 g, 14.22 mmol, 2 eq) in THF (10 mL) was added drop wise at −78° C. and the resulting reaction mixture was slowly warmed to rt, and stirred for 16 h. The reaction was monitored by TLC. TLC analysis indicated formation of a non-polar spot. The reaction mixture was quenched with saturated aqueous solution of sodium thiosulfate and extracted with EtOAc (3×50 mL). The combined organic layer was dried over Na$_2$SO$_4$ and concentrated under reduced pressure to give Compound 8 (2.5 g, 80% yield) as a pale brown solid. LC-MS: m/z 366.14 (M+H).

Step 6:

To a stirred solution of compound 8 (2.5 g, 59 mmol, 1 eq) in Toluene (35 mL) was added Cs$_2$CO$_3$ (4.28 g, 13.19 mmol, 1.22 eq), NH$_2$Boc (0.91 g, 7.91 mmol, 1.2 eq) followed by xanthophos (0.11 g, 0.19 mmol, 0.03 eq) and the resulting reaction mixture was degassed with nitrogen for 15 min. Pd$_2$(dba)$_3$ (0.18 g, 0.19 mmol, 0.03 eq) was added and the resulting reaction mixture was heated at 95° C. for 16 h. The reaction was monitored by TLC. TLC analysis indicated formation of a polar spot. Reaction mixture was filtered through celite, which was washed with ethyl acetate and the filtrate was concentrated under reduced pressure to get a crude product. The crude product was purified by column chromatography (silica 100-200) using 0-10% methanol in DCM as an eluent to give Compound 9 (2.1 g, 50% yield) as a brown solid. LCMS: m/z 355.25 (M+H):

Step 7:

To a stirred solution of compound 9 (2.1 g, 5.93 mmol, 1 eq) in DCM (20 mL), was added TFA (4.5 mL, 59.32 mmol, 10 eq) drop wise and the resulting reaction mixture was stirred at RT for 16 h. The reaction was monitored by TLC. TLC analysis indicated formation of a polar spot. The reaction mixture was concentrated under reduced pressure, basified with aq 2N NaHCO$_3$solution and extracted with ethyl acetate (2×50 mL). The combined organic layer was dried over Na$_2$SO$_4$ and concentrated under reduced pressure. The crude product was purified by column chromatography (silica 100-200) using 0-2% methanol in DCM as an eluent to give 5-chloro-2-(2,2,4-trimethylpiperazin-1-yl)pyridin-4-amine (1.3 g, 50% yield) as a brown color liquid. LCMS: m/z 255.2 (M+H):

Synthesis of 5-chloro-2-(4-fluoro-1-methylpiperidin-4-yl)pyridin-4-amine

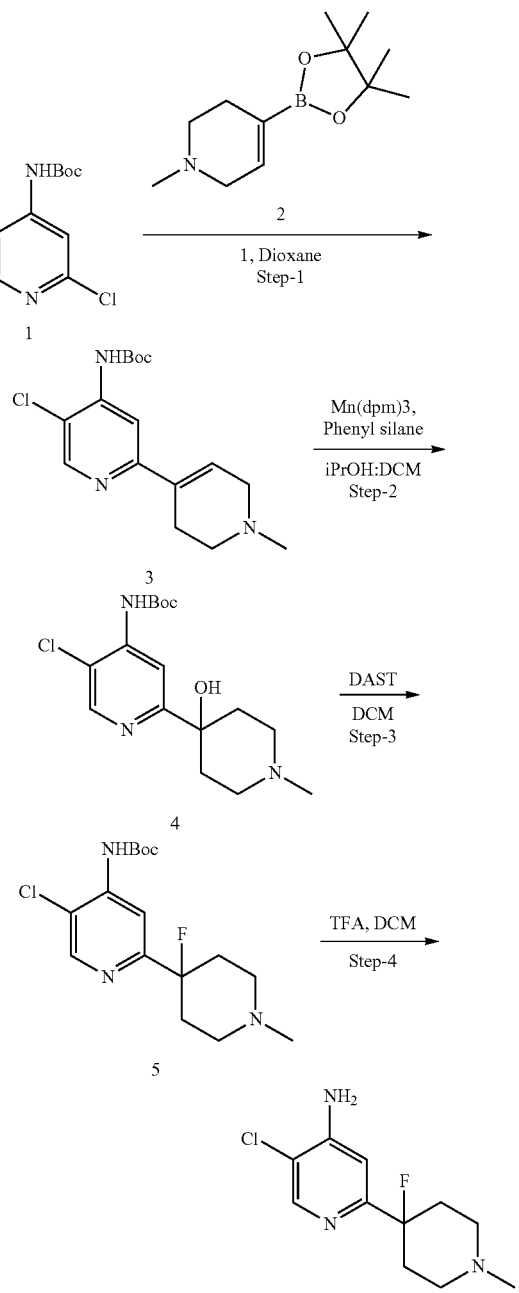

Compound numbers in text refer to structures shown in Scheme 88.

Step 1: Synthesis of tert-butyl (5-chloro-1'-methyl-1',2',3',6'-tetrahydro-[2,4'-bipyridin]-4-yl)carbamate To a stirred solution of compound tert-butyl (2,5-dichloropyridin-4-yl)carbamate (2.0 g, 7.66 mmol, 1.5 eq), 1-methyl-4-(4,4,5,5-tetramethyl-1,3,2-dioxaborolan-2-yl)-1,2,3,6-tetrahydropyridine (2.56 g, 11.49 mmol, 1.5 eq) in 1,4-dioxane (40 mL) and water (5 mL) was added $K_2CO_3$ (3.17 g, 22.9 mmol, 3 eq) at RT. The mixture was then degassed with argon for 20 min followed by an addition of Pd $(PPh_3)_4$ (560 mg, 0.38 mmol, 0.05 eq) at RT. The resulting mixture was then heated to 90° C. in a sealed tube for 16 h. The reaction mixture was cooled to RT and filtered through celite bed; celite bed was washed with EtOAc (2×20 ml); the filtrate was extracted with EtOAc (2×50 mL). The combined organic layer was dried over $Na_2SO_4$ and concentrated under reduced pressure to give a crude product. The crude compound was purified by Combi flash chromatography using 3% of methanol in DCM as an eluent to give the title compound (1.5 g, 40.6%) as a pale yellow solid; LCMS $[M+H]^+$ 324.

Step 2: Synthesis of tert-butyl (5-chloro-2-(4-hydroxy-1-methylpiperidin-4-yl)pyridin-4-yl)carbamate To a stirred solution of tert-butyl (5-chloro-1'-methyl-1',2',3',6'-tetrahydro-[2,4'-bipyridin]-4-yl)carbamate (2.0 g, 6.19 mmol, 1.0 eq), in iPrOH:DCM (18:2 ml) was added Mn $(dpm)_3$ (0.08 g, 0.13 mmol, 0.022 eq) followed by phenyl silane (1.33 g, 12.38 mmol, 2.0 eq) at 0° C. then the mixture was slowly warmed to rt stirred for 16 h. Then the reaction mass was extracted with DCM (2×50 mL). The combined organic layer was dried over $Na_2SO_4$ and concentrated under reduced pressure to give a crude product. The crude compound was purified by Combi flash chromatography using 10% of methanol in DCM as an eluent to give the title compound (1.4 g, 66.6%) as a pale yellow solid; LCMS $[M+H]^+$ 342.

Step 3: Synthesis of tert-butyl (5-chloro-2-(4-fluoro-1-methylpiperidin-4-yl)pyridin-4-yl)carbamate To a stirred solution of compound (5-chloro-2-(4-hydroxy-1-methylpiperidin-4-yl)pyridin-4-yl)carbamate (1.4 g, 4.10 mmol, 1.0 eq), in dry DCM (20 ml) was added DAST (1.08 ml, 8.19 mmol, 2.0 eq) −78° C. then slowly warmed to rt stirred for 2 h. After 2 h reaction mass was quenched with Satd.$NaHCO_3$ solution extracted with DCM washed with water and brine The combined organic layer was dried over $Na_2SO_4$ and concentrated under reduced pressure to give a crude product. The crude compound was purified by Combi flash chromatography then followed by SFC eluent to give the title compound (0.97 g, 66.6%) as a pale yellow solid; LCMS $[M+H]^+$ 344.

Step 4: Synthesis of 5-chloro-2-(4-fluoro-1-methylpiperidin-4-yl)pyridin-4-amine To a stirred solution of compound 5 (0.95 g, 2.82 mmol, 1 eq) in DCM (20 ml) was added TFA (2.7 ml, 33.9 mmol, 12 eq) at RT for 16 h. After 16 h, the solvent was evaporated under reduced pressure, and the residue neutralized with Satd.$NaHCO_3$ solution and extracted with EtOAc (2×10 ml). The organism layer was washed with water and brine. The combined organic layer was dried over $Na_2SO_4$ and concentrated under reduced pressure to give a crude product. The crude compound was purified by washed with pentane to give the title compound (650 mg, 98.4%) as an off white solid; LCMS $[M+H]^+$ 244.

| # | Structure | Name | Source |
|---|---|---|---|
| 1 | 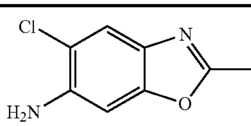 | 5-chloro-2-(1-(2,2,2-trifluoroethyl)piperidin-4-yl)pyridin-4-amine | Commercial |
| 2 | 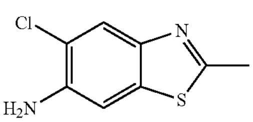 | 2-chloro-5-(isoxazol-3-yl)aniline | Commercial |
| 3 | 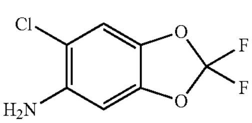 [SMILES: Nc1cc2c(cc1Cl)OC(F)(F)O2] | 2-chloro-5-(1,3,4-oxadiazol-2-yl)aniline | Commercial |
| 4 | 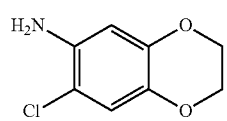 [SMILES: Nc1cc2c(cc1Cl)OCCO2] | 6-amino-7-chloro-4-(2-morpholinoethyl)-2H-benzo[b][1,4]oxazin-3(4H)-one | Commercial |
| 5 | 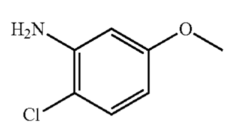 | 2-chloro-5-methoxyaniline | Commercial |
| 6 | 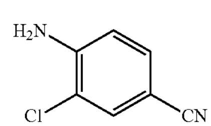 | 4-amino-3-chlorobenzonitrile | Commercial |

| | | | |
|---|---|---|---|
| 7 | H₂N–(2-Cl,4-NO₂-phenyl) | 2-chloro-4-nitroaniline | Commercial |
| 8 | H₂N–(2-Cl,4-F-phenyl) | 2-chloro-4-fluoroaniline | Commercial |
| 9 | H₂N–(3-Br-pyridin-4-yl) | 3-bromopyridin-4-amine | Commercial |
| 10 | H₂N–(5-Cl-2-methylpyridin-4-yl) | 5-chloro-2-methylpyridin-4-amine | Commercial |
| 11 | H₂N–(5,6,7,8-tetrahydroquinolin-5-yl) | 5,6,7,8-tetrahydroquinolin-5-amine | Commercial |
| 12 | H₂N–(5,6,7,8-tetrahydroisoquinolin-8-yl) | 5,6,7,8-tetrahydroisoquinolin-8-amine | Commercial |
| 13 | (1S,2S)-2-fluorocyclohexan-1-amine | (1S,2S)-2-fluorocyclohexan-1-amine | Commercial |
| 14 | (1S,2S)-2-hydroxycyclohexan-1-amine | (1S,2S)-2-fluorocyclohexan-1-amine | Commercial |
| 15 | cyclohexan-1-amine | (1S,2S)-2-fluorocyclohexan-1-amine | Commercial |
| 16 | H₂N–(3-Cl-2,5,6-trifluoropyridin-4-yl) | 3-chloro-2,5,6-trifluoropyridin-4-amine | Commercial |
| 17 | H₂N–(2-Cl-phenyl) | 2-chloroaniline | Commercial |

General Procedure for Pyridylchloro Aniline Formation Via Microwave

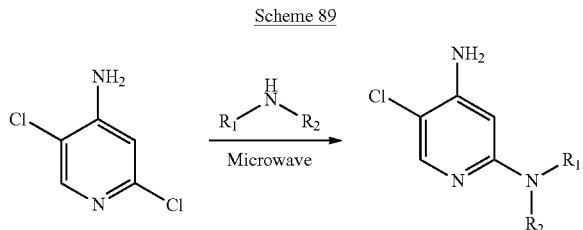

Scheme 89

A microwave vial charged with 2,5-dichloropyridin-4-amine (1.0 eq), N,N-diisopropylethylamine (3.0 eq) and desired amine (2-20 eq) were heated in the microwave at 200-230° C. for 15 hours, as judged complete by LCMS.

Method A:

Upon completion of the reaction as judged by LCMS, the reaction was concentrated onto celite and purified on the Biotage (reverse phase silica gel) eluting with 0-50% ACN/$H_2O$. The desired fractions were collected, concentrated and dried under vacuum to afford the desired product.

Method B:

Upon completion of the reaction as judged by LCMS, the reaction was diluted with ethyl acetate and partitioned between ethyl acetate and water. The layers were separated and the aqueous layer was extracted with ethyl acetate (2×). The combined organic extracts were dried over $Na_2SO_4$, filtered, concentrated and dried under high vacuum. The material was carried onto the next step without further purification.

| Method | Aniline | Name | Yield & Mass |
|---|---|---|---|
| A | (structure) | 5-chloro-2-(3,3-dimethylmorpholino)pyridin-4-amine | 97% yield, LCMS $[M]^+$ 241.9 |
| A | (structure) | 5-chloro-2-(2-((dimethylamino)methyl)morpholino)pyridin-4-amine | 54% yield, LCMS $[M]^+$ 271.2 |
| A | (structure) | (S)-2-((4-amino-5-chloropyridin-2-ylamino)propan-1-ol | 68% yield, LCMS $[M]^+$ 202.4 |
| B | (structure) | 5-chloro-2-(pyrrolidin-1-yl)pyridin-4-amine | 99% yield, LCMS $[M]^+$ 197.9 |
| B | (structure) | 5-chloro-2-(tetrahydro-1H-furo[3,4-c]pyrrol-5(3H)-yl)pyridin-4-amine | 77% yield, LCMS $[M]^+$ 240.2 |

-continued

| Method | Aniline | Name | Yield & Mass |
|---|---|---|---|
| B | (structure) | 5-chloro-2-(4-methyl-1,4-diazepan-1-yl)pyridin-4-amine | 52% yield, LCMS $[M]^+$ 241.3 |
| A | (structure) | 5-chloro-2-((3R,5S)-3,4,5-trimethylpiperazin-1-yl)pyridin-4-amine | 81% yield, LCMS $[M]^+$ 255.3 |

General Procedure for Pyridylchloro Aniline Formation Via Buchwald Coupling Reaction

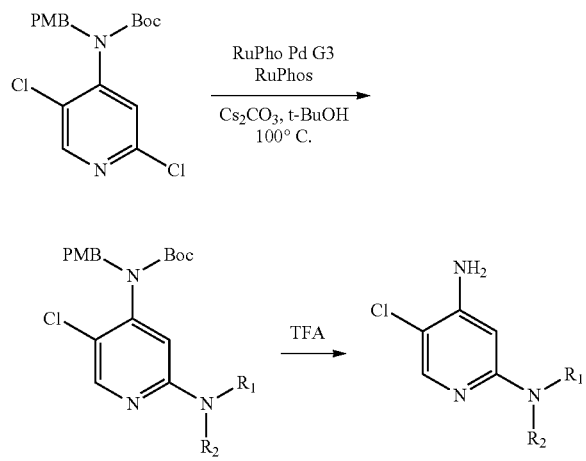

Scheme 90

A microwave vial was charged with tert-butyl (2,5-dichloropyridin-4-yl)(4-methoxybenzyl)carbamate (1.0 eq, 2.0 mmol), 2,3-dimethylmorpholine hydrochloride (1.3 eq), $Cs_2CO_3$ (4 eq), RuPhos Pd G3 (0.02 eq) and 2-dicyclohexylphosphino-2',6'-di-i-propoxy-1,1'-biphenyl (0.04 eq) (RuPhos). The system was flushed with nitrogen then t-butanol (10 ml) was added. The system was flushed with nitrogen and heated at 100° C. to complete conversion as determined by LCMS. The reaction was concentrated onto celite, and purified by flash chromatography (silica gel) eluting with 0-10% MeOH/DCM+1% $NH_4OH$. The desired fractions were collected and dried under high vacuum at RT to afford the PMB-Boc-protected intermediate as a yellow oil. To a stirring solution of the PMB-Boc-protected intermediate (1.0 eq, 1.3 mmol) in dichloromethane (1.0 ml) was added TFA (30 eq) at room temperature.

Method A:

Upon completion of the reaction as judged by LCMS, the reaction was concentrated to dryness and purified on the Biotage (reverse phase silica gel) eluting with 0%-50% $ACN/H_2O$. The desired fractions were collected, dried under high vacuum at RT to afford the desired aniline as a trifluoroacetate salt.

Method B:

Upon completion of the reaction as judged by LCMS, the reaction was diluted with DCM and partitioned between DCM and water. The aqueous layer was neutralized with the addition of $NaHCO_3$ [both saturated solution and extra solid]. The layers were separated and the aqueous layer was extracted with DCM. The combined organics were dried over $Na_2SO_4$, filtered and concentrated in vacuo onto celite. The crude material was purified on the Biotage (reverse phase silica gel) eluting with 0%-50% $ACN/H_2O$. The desired fractions were collected, dried under high vacuum at RT to afford the desired product.

Method C:

Upon completion of the reaction as judged by LCMS, the reaction was diluted with DCM and partitioned between DCM and water. The aqueous layer was neutralized with the addition of $NaHCO_3$ [both saturated solution and extra solid]. The layers were separated and the aqueous layer was extracted with DCM. The combined organics were dried over $Na_2SO_4$, filtered, concentrated in vacuo and dried under high vacuum. The material was used in the next step without further purification.

| Method | Aniline | Name | Yield & Mass |
|---|---|---|---|
| B | | (R)-5-chloro-2-(3-(methoxymethyl)morpholino)pyridin-4-amine | 77% yield over 2 steps, LCMS [M]+ 258.6 |
| B | | (S)-5-chloro-2-(3-(methoxymethyl)morpholino)pyridin-4-amine | 79% yield over 2 steps, LCMS [M]+ 258.7 |
| B | | 5-chloro-2-(1,3-dihydro-2H-pyrrolo[3,4-c]pyridin-2-yl)pyridin-4-amine | 74% yield over 2 steps, LCMS [M]+ 247.6 |
| B | | 5-chloro-2-(2-(trifluoromethyl)-5,6-dihydroimidazo[1,2-a]pyrazin-7(8H)-yl)pyridin-4-amine | 33% yield over 2 steps, LCMS [M]+ 318.3 |
| A | | 5-chloro-2-((3R,5R)-3,5-dimethylmorpholino)pyridin-4-amine, trifluoroacetate | 34% yield over 2 steps, LCMS [M]+ 242.6 |
| B | | 5-chloro-2-((3S,5R)-3,5-dimethylmorpholino)pyridin-4-amine | 51% yield over 2 steps, LCMS [M]+ 242.5 |

-continued

| Method | Aniline | Name | Yield & Mass |
|---|---|---|---|
| C | | 5-chloro-2-(1-methylhexahydropyrrolo[3,4-b]pyrrol-5(1H)-yl)pyridin-4-amine | 87% yield over 2 steps, LCMS [M]$^+$ 253.6 |
| C | | 5-chloro-2-(5-methylhexahydropyrrolo[3,4-c]pyrrol-2(1H)-yl)pyridin-4-amine | 67% yield over 2 steps, LCMS [M]$^+$ 258.6 |
| C | | (R)-5-chloro-2-(2,4-dimethylpiperazin-1-yl)pyridin-4-amine | 72% yield over 2 steps, LCMS [M]$^+$ 241.5 |
| C | | (S)-2-(4-benzyl-2-methylpiperazin-1-yl)-5-chloropyridin-4-amine | 78% yield over 2 steps, LCMS [M]$^+$ 317.6 |
| C | | 5-chloro-2-(3-((dimethylamino)methyl)morpholino)pyridin-4-amine | 60% yield over 2 steps, LCMS [M]$^+$ 271.7 |
| C | | (S)-5-chloro-2-(4-ethyl-2-methylpiperazin-1-yl)pyridin-4-amine | 53% yield over 2 steps, LCMS [M]$^+$ 255.6 |

-continued

| Method | Aniline | Name | Yield & Mass |
|---|---|---|---|
| A | 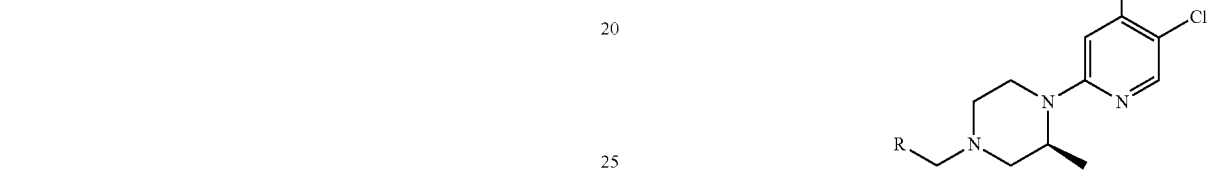 | 5-chloro-2-((2S)-4-(1-cyclopropylethyl)-2-methylpiperazin-1-yl)pyridin-4-amine, trifluoroacetate | 28% yield over 2 steps, LCMS [M]+ 295.4 |

General Procedure for Pyridylchloro Aniline Formation Via Alkylation

Scheme 91

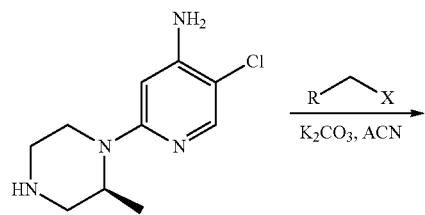

-continued

To a vial containing (S)-3-chloro-2-fluoro-6-(2-methyl piperazin-1-yl)pyridin-4-amine (1.0 eq, 1.3 mmol) in acetonitrile (1.0 ml) was added potassium carbonate (1.1 eq) followed by 2-bromoethyl methyl ether (1.1 eq). The reaction was stirred at RT overnight. Additional equivalents of potassium carbonate and 2-Bromoethyl methyl ether were added until the reaction was judged complete by LCMS. Methanol was added to the reaction then concentrated onto celite. The crude product was purified on the Biotage (reverse phase silica gel) eluting with 0-40% ACN/H$_2$O. The desired fractions were collected, concentrated and dried under high vacuum at room temperature to afford the desired aniline.

| Aniline | Name | Yield & Mass |
|---|---|---|
| | (S)-5-chloro-2-(4-(2-methoxyethyl)-2-methylpiperazin-1-yl)pyridin-4-amine | 62% yield, LCMS [M]+ 285.5 |
| | (S)-3-chloro-2-fluoro-6-(4-(2-methoxyethyl)-2-methylpiperazin-1-yl)pyridin-4-amine | 61% yield, LCMS [M]+ 303.5 |

-continued

| Aniline | Name | Yield & Mass |
|---|---|---|
| | (S)-5-chloro-2-(4-(cyclobutylmethyl)-2-methylpiperazin-1-yl)pyridin-4-amine | 17% yield, LCMS [M]+ 295.5 |
| | (S)-3-chloro-6-(4-(cyclopropylmethyl)-2-methylpiperazin-1-yl)-2-fluoropyridin-4-amine | 72% yield, LCMS [M]+ 299.5 |
| | (S)-2-(4-(2-((tert-butyldimethylsilyl)oxy)ethyl)-2-methylpiperazin-1-yl)-5-chloropyriidn-4-amine | 76% yield, LCMS [M]+ 385.6 |
| | (S)-3-chloro-2-fluoro-6-(4-isobutyl-2-methylpiperazin-1-yl)pyridin-4-amine | 63% yield, LCMS [M]+ 301.5 |
| | 3-chloro-2-fluoro-6-((2S)-2-methyl-4-(oxetan-2-ylmethyl)piperazin-1-yl)pyridin-4-amine | 52% yield, LCMS [M]+ 315.5 |

General Procedure for Pyridylchloro Aniline Formation Via Reductive Amination

Scheme 92

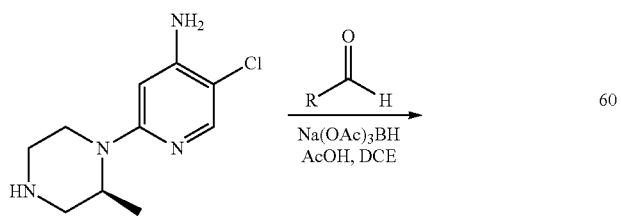

-continued

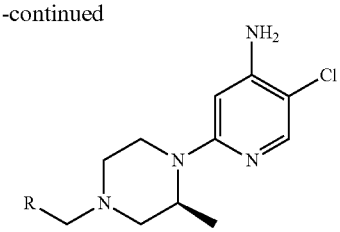

To a screw-cap vial was added the aldehyde (1.0 eq) and (S)-5-chloro-2-(2-methylpiperazin-1-yl)pyridin-4-amine (0.882 mmol, 1.0 eq) in 1,2-dichloroethane (DCE) (1.0 ml) followed by acetic acid (5.0 ml) and sodium triacetoxyborohydride (3.0 eq). The reaction was stirred at RT for 2 hours.

Method A:
 Upon completion of the reaction as judged by LCMS, the reaction was concentrated to dryness and purified on the Biotage (reverse phase silica gel) eluting with 0%-50% ACN/H₂O. The desired fractions were collected, concentrated in vacuo and dried under high vacuum overnight at RT to afford the desired product.

Method B:
 Upon completion of the reaction as judged by LCMS, the reaction was diluted with DCM and partitioned between DCM and water. The aqueous layer was neutralized with the addition of NaHCO₃ [both saturated solution and extra solid]. The layers were separated and the aqueous layer was extracted with DCM. The combined organics were dried over Na₂SO₄, filtered and concentrated in vacuo. The crude material was purified on the Biotage (reverse phase silica gel or silica gel) eluting with 0-80% ACN/H₂O or 0-5% MeOH/DCM+1% NH₄OH respectively. The desired fractions were collected, concentrated and dried under high vacuum at room temperature to afford the desired product.

Method C:
 Upon completion of the reaction as judged by LCMS, the reaction was diluted with DCM and partitioned between DCM and water. The aqueous layer was neutralized with the addition of NaHCO₃ [both saturated solution and extra solid]. The layers were separated and the aqueous layer was extracted with DCM. The combined organics were dried over Na₂SO₄, filtered, concentrated in vacuo and dried under high vacuum. The material was used in the next step without further purification.

| Method | Aniline | Name | Yield & Mass |
|---|---|---|---|
| A | | (S)-5-chloro-2-(2-methyl-4-(3,3,3-trifluoropropyl)piperazin-1-yl)pyridin-4-amine, acetate | 22% yield, LCMS [M]⁺ 323.5 |
| B | | (S)-3-chloro-2-fluoro-6-(2-methyl-4-(3,3,3-trifluoropropyl)piperazin-1-yl)pyridin-4-amine | 22% yield, LCMS [M]⁺ 341.5 |
| B | | (S)-5-chloro-2-(2-methyl-4-propylpiperazin-1-yl)pyridin-4-amine | 80% yield, LCMS [M]⁺ 269.4 |
| C | | (S)-5-chloro-2-(4-(furan-2-ylmethyl)-2-methylpiperazin-1-yl)pyridin-4-amine | 84% yield, LCMS [M]⁺ 307.4 |
| B | | (S)-5-chloro-2-(2-methyl-4-((5-methylthiophen-2-yl)methyl)piperazin-1-yl)pyridin-4-amine | 42% yield, LCMS [M]⁺ 337.4 |

-continued

| Method | Aniline | Name | Yield & Mass |
|---|---|---|---|
| A | (structure) | (S)-1-((4-(4-amino-5-chloropyridin-2-yl)-3-methylpiperazin-1-yl)methyl)cyclopropane-1-carbonitrile, acetate | 39% yield, LCMS [M]+ 306.4 |
| A | (structure) | (S)-5-chloro-2-(2-methyl-4-((1-(trifluoromethyl)cyclopropyl)methyl)piperazin-1-yl)pyridin-4-amine | 78% yield, LCMS [M]+ 349 |

Synthesis of 2-chloro-4-fluoro-5-morpholinoaniline

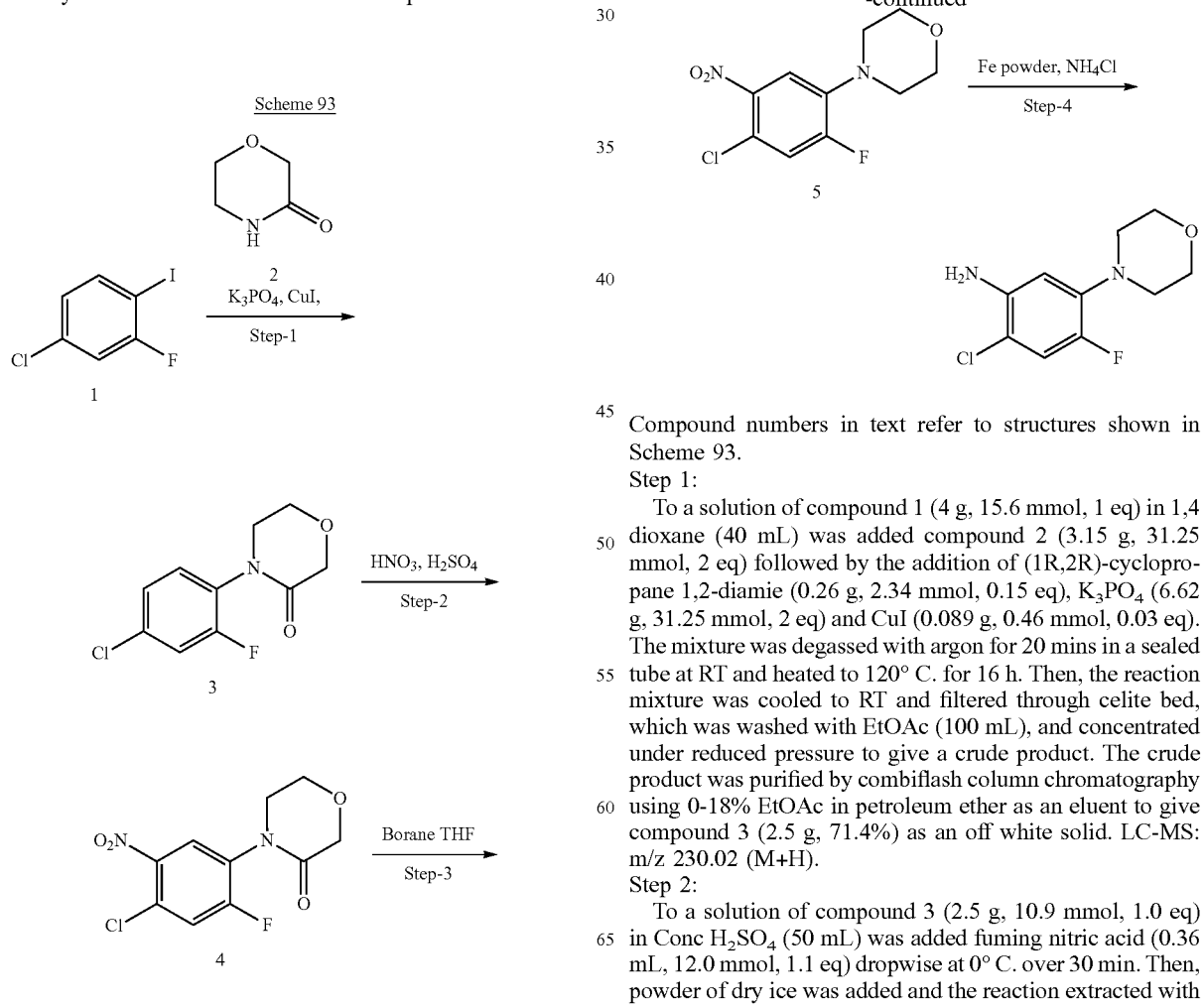

Compound numbers in text refer to structures shown in Scheme 93.

Step 1:

To a solution of compound 1 (4 g, 15.6 mmol, 1 eq) in 1,4 dioxane (40 mL) was added compound 2 (3.15 g, 31.25 mmol, 2 eq) followed by the addition of (1R,2R)-cyclopropane 1,2-diamie (0.26 g, 2.34 mmol, 0.15 eq), $K_3PO_4$ (6.62 g, 31.25 mmol, 2 eq) and CuI (0.089 g, 0.46 mmol, 0.03 eq). The mixture was degassed with argon for 20 mins in a sealed tube at RT and heated to 120° C. for 16 h. Then, the reaction mixture was cooled to RT and filtered through celite bed, which was washed with EtOAc (100 mL), and concentrated under reduced pressure to give a crude product. The crude product was purified by combiflash column chromatography using 0-18% EtOAc in petroleum ether as an eluent to give compound 3 (2.5 g, 71.4%) as an off white solid. LC-MS: m/z 230.02 (M+H).

Step 2:

To a solution of compound 3 (2.5 g, 10.9 mmol, 1.0 eq) in Conc $H_2SO_4$ (50 mL) was added fuming nitric acid (0.36 mL, 12.0 mmol, 1.1 eq) dropwise at 0° C. over 30 min. Then, powder of dry ice was added and the reaction extracted with EtOAc (2×100 mL). Combined organic layer was dried over Na$_2$SO$_4$ and concentrated under reduced pressure to give a crude product. The crude product was washed with n-pentane & ether to give compound 4 (1.7 g, 58.6%) as an off white solid.

Step 3:

To a solution of compound 4 (1.7 g, 6.2 mmol, 1 eq), in dry THF (40 mL) was added Borane THF (17.3 mL, 17.3 mmol, 2.8 eq, 1M in THF) at 0° C. The mixture was stirred at rt for 3 h. TLC analysis indicated formation of a nonpolar spot. The reaction mixture was slowly quenched with methanol at 0° C. and concentrated under reduced pressure to give a residue; which was washed with pentane to give compound 5 (1.1 g, 68.3% yield) as a pale yellow solid. LC-MS: m/z 260.94 (M+H).

Step 4:

To a solution of compound 5 (1.1 g, 4.23 mmol, 1 eq) in EtOH:H$_2$O (16:4 mL) was added Iron powder (0.93 g, 16.92 mmol, 4.0 eq) and NH$_4$Cl (0.89 g, 16.92 mmol, 4.0 eq) at RT. The mixture was heated to 75° C. over 1 h. TLC analysis indicated formation of a polar spot. Then, the reaction mixture was cooled to RT and filtered through celite bed. The filtrate was concentrated under reduced pressure and was then extracted in EtOAc (3×50 mL), washed with water (2×50 mL) and brine (2×50 mL). The combined organic layer was dried over Na$_2$SO$_4$ and concentrated under reduced pressure to give a crude product. The crude compound was purified by washing with n-pentane to give 2-chloro-4-fluoro-5-morpholinoaniline (0.8 g, 82.4%) as a brown color solid. LC-MS: m/z 231.04 (M+H).

Synthesis of 2,3,6-trifluoropyridin-4-amine

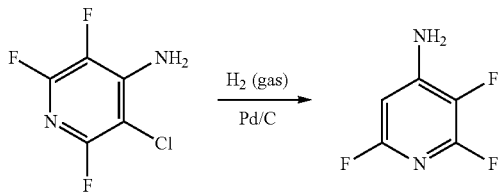

Scheme 94

A solution mixture of 4-Amino-3-chloro-2,5,6-trifluoro-pyridine (1 g, 5.48 mmol) in Methanol (50 ml) and Triethylamnine (5 ml) was subjected to hydrogenolysis using H-Cube (Pd/C) at the 50 psi H2 atmosphere and at 60° C. overnight. The batch content was concentrated. Worked up with EtOAc/water (to remove Et$_3$NHCl) to get the desired product, 2,3,6-trifluoropyridin-4-amine (684 mg, 80% yield), as a white powder. LC-MS: m/z 149 (M+H).

Synthesis of 5-chloro-6-fluoro-N2,N2-dimethylpyridine-2,4-diamine

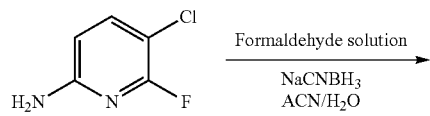

Scheme 95

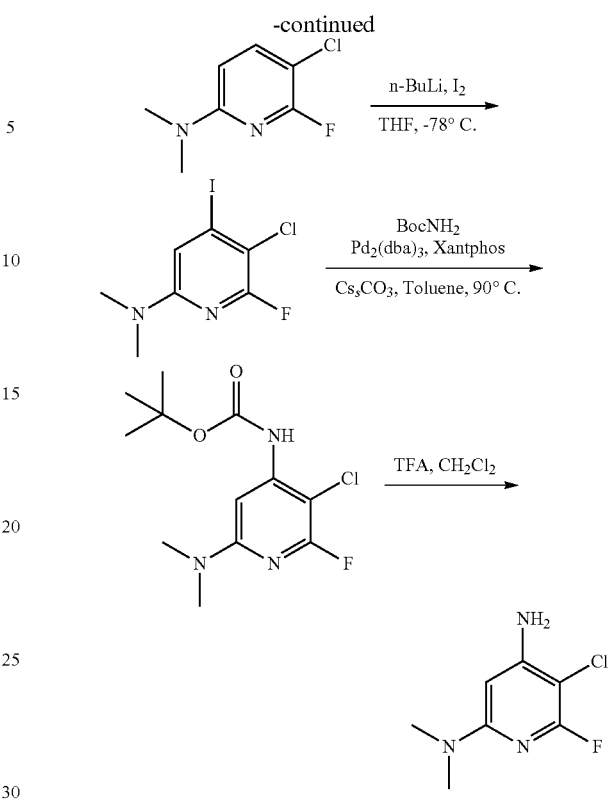

5-chloro-6-fluoro-N,N-dimethylpyridin-2-amine. To an ice-cold mixture of 5-chloro-6-fluoro-pyridin-2-ylamine (2.0 g, 13.65 mmol) in acetonitrile (60 ml) was added sequentially water (10 ml) followed by formaldehyde solution, 37% wt in water (20.32 ml, 273 mmol) and sodium cyanoborohydride (4.29 g, 68.2 mmol). The resulting reaction was stirred at 0° C. for 10 min followed by drop wise addition of acetic acid (5.0 ml). The reaction mixture was then allowed to stir at RT overnight. Additional formaldehyde solution, 37% wt in water (20.32 ml, 273 mmol), sodium cyanoborohydride (4.29 g, 68.2 mmol) and acetic acid (5.0 ml) were added. The reaction was allowed to stir overnight. The solvent was evaporated and the residue was treated with 1 N NaOH$_{(aq)}$ solution and extracted three times with EtOAc. The combined organic layers were dried with Na$_2$SO$_4$, filtered and concentrated. The residue was purified on the Biotage eluting with 0-5% EtOAc/Hexane to give 5-chloro-6-fluoro-N,N-dimethylpyridin-2-amine (5.74 mmol, 42.1% yield). $^1$H NMR (500 MHz, DMSO-d6) δ=8.12 (dd, J=8.9, 9.7 Hz, 1H), 6.93 (d, J=8.8 Hz, 1H), 3.41 (s, 6H); LCMS (m/z): 175.3 [M+1]*.

5-chloro-6-fluoro-4-iodo-N,N-dimethylpyridin-2-amine. To −78° C. solution of 5-chloro-6-fluoro-N,N-dimethylpyridin-2-amine (1.00 g, 5.74 mmol) in anhydrous tetrahydrofuran (15 ml) was added 1,1,4,7,7-pentamethyldiethylenetriamine (2.64 ml, 12.63 mmol) and n-butyllithium solution, 2.5 M in hexanes (5.05 ml, 12.63 mmol). The reaction was stirred at −78° C. for 1.5 h and then a solution of iodine (resublimed) (2.92 g, 11.49 mmol) in tetrahydrofuran (3.0 ml) was added, followed by warming up to RT overnight. The reaction mixture was quenched with a saturated aqueous solution of sodium thiosulfate then extracted with EtOAc (2×). The combined organic layers were dried over Na$_2$SO$_4$ then concentrated and dried on the h/v overnight to give 5-chloro-6-fluoro-4-iodo-N,N-dimethylpyridin-2-amine (5.37 mmol, 93% yield) as a brown solid. The crude product was carried onto the next step without purification. LCMS (m/z): 301.2 [M+1]+.

tert-butyl (3-chloro-6-(dimethylamino)-2-fluoropyridin-4-yl)carbamate. To a stirred solution of 5-chloro-6-fluoro-4-iodo-N,N-dimethylpyridin-2-amine (1.376 g, 4.58 mmol) in toluene (20 ml) was added cesium carbonate (2.98 g, 9.16 mmol) and tert-butyl carbamate (0.644 g, 5.49 mmol). The system was flushed with nitrogen for 5 minutes, then Xantphos (0.159 g, 0.275 mmol) and tris(dibenzylideneacetone)dipalladium(0) (0.252 g, 0.275 mmol) were added. The system was flushed with nitrogen then heated at 90° C. for 16 h. The reaction mixture was concentrated onto celite and purified by column chromatography (silica gel) eluting with 0-5% MeOH/DCM. The desired fractions were collected, concentrated, and dried under high vacuum to afford tert-butyl (3-chloro-6-(dimethylamino)-2-fluoropyridin-4-yl)carbamate (4.18 mmol, 91% yield). $^1$H NMR (500 MHz, DMSO-d6) δ=8.69-8.66 (m, 1H), 7.02 (s, 13H), 2.97 (s, 6H), 1.48 (s, 9H); LCMS (m/z): 290.4 [M+1]+.

5-chloro-6-fluoro-N2,N2-dimethylpyridine-2,4-diamine. To a solution of tert-butyl (3-chloro-6-(dimethylamino)-2-fluoropyridin-4-yl)carbamate (1.211 g, 4.18 mmol) in dichloromethane (1 ml) was added trifluoroacetic acid (3.20 ml, 41.8 mmol) and the mixture stirred at room temperature for 1 h.

Upon completion of the reaction as judged by LCMS, the reaction was concentrated to remove the volatiles. The reaction was diluted with EtOAc and partitioned between EtOAc and water. The aqueous layer was neutralized with the addition of NaHCO$_3$ [both saturated solution and extra solid]. The layers were separated and the aqueous layer was extracted with EtOAc. The combined organics were dried over Na$_2$SO$_4$, filtered and concentrated in vacuo. The crude compound was purified on the Biotage (reverse phase silica gel) eluting with 0-40% ACN/H$_2$O. The fractions were collected, concentrated, and dried under high vacuum to afford 5-chloro-6-fluoro-N2,N2-dimethylpyridine-2,4-diamine (2.73 mmol, 65.2% yield) as a white solid.

Synthesis of (S)-5-fluoro-2-(3-methylmorpholino)pyridin-4-amine

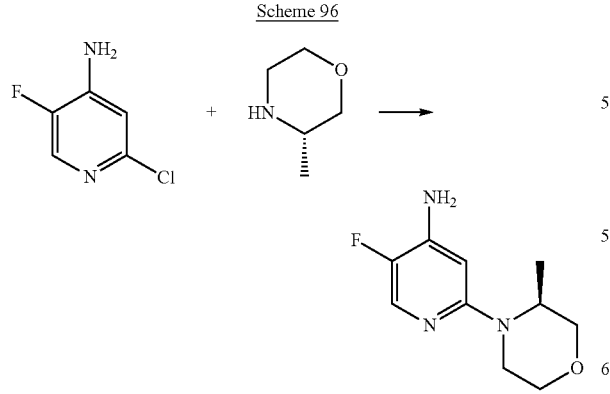

Scheme 96

A microwave vial charged with 2-Chloro-5-fluoropyridin-4-amine (500 mg, 3.41 mmol) and (S)-3-Methylmorpholine (3102 μl, 27.3 mmol) was heated in the microwave at 210° C. for 52 hours. The crude product was concentrated onto celite and purified on the Biotage (reverse phase silica gel) eluting with 0-50% ACN/H$_2$O. The desired fractions were collected, concentrated and dried under high vacuum at RT to afford (S)-5-fluoro-2-(3-methylmorpholino)pyridin-4-amine (2.94 mmol, 86% yield) as a sticky brown solid. $^1$H NMR (500 MHz, DMSO-d6) δ=7.70 (d, J=3.1 Hz, 1H), 5.96 (d, J=6.4 Hz, 1H), 5.85 (s, 2H), 4.11-4.05 (m, 1H), 3.87 (dd, J=3.5, 11.1 Hz, 1H), 3.68-3.64 (m, 1H), 3.61-3.56 (m, 1H), 3.51 (dd, J=2.1, 12.8 Hz, 1H), 3.43 (dt, J=3.1, 11.6 Hz, 1H), 2.92 (dt, J=3.7, 12.4 Hz, 1H), 1.02 (d, J=6.6 Hz, 3H); LCMS (m/z): 212.4 [M+1]+.

Synthesis of (S)-5-chloro-2-(4-((cyclopropyl-1-d)methyl-d2)-2-methylpiperazin-1-yl)pyridin-4-amine

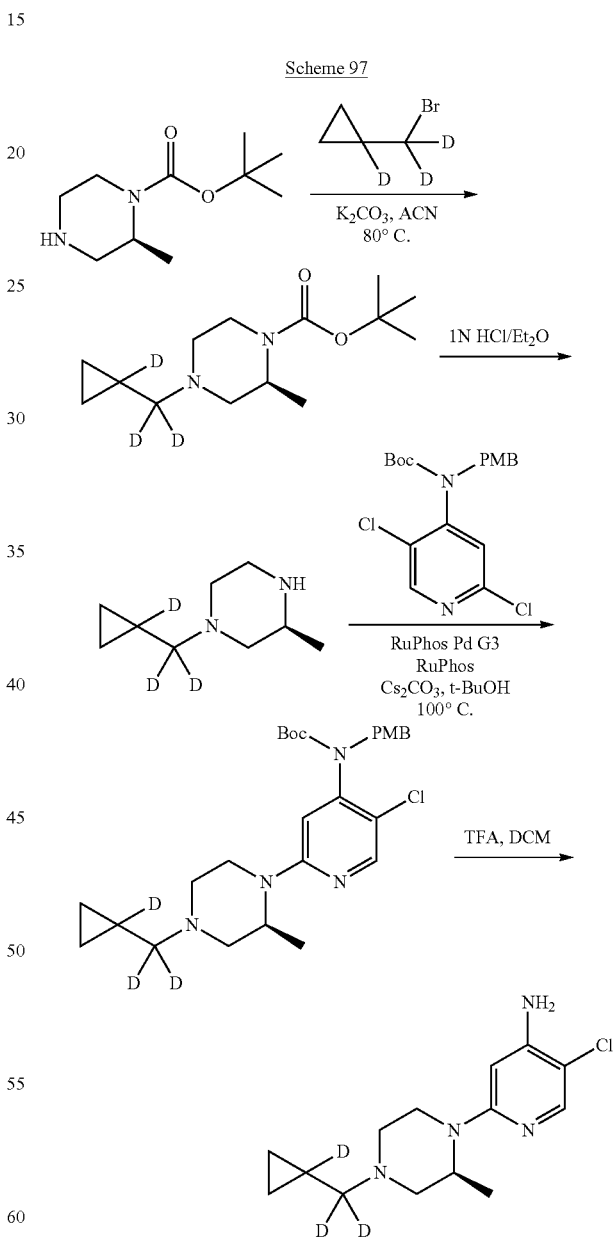

Scheme 97 tert-butyl (S)-4-((cyclopropyl-1-d)methyl-d2)-2-methylpiperazine-1-carboxylate. To (S)-1-N-Boc-2-methyl piperazine (310 mg, 1.548 mmol) in acetonitrile (3.0 ml) was added potassium carbonate (257 mg, 1.857 mmol) followed by (bromomethyl-d2)cyclopropane-1-d1 (235 mg, 1.703 mmol). The mixture was heated at 80° C. over the 2 days. The solvent was removed in vacuo, and the residue was taken up in water and extracted with DCM. The organic extract was dried over sodium sulfate, and the solvent removed in vacuo to afford tert-butyl (S)-4-((cyclopropyl-1-d)methyl-d2)-2-methylpiperazine-1-carboxylate as a colourless oil. LCMS (m/z): 258.5 [M+1]$^+$.

To a 0° C. solution of tert-butyl (S)-4-((cyclopropyl-1-d)methyl-d2)-2-methylpiperazine-1-carboxylate in ether (10 ml) was added hydrogen chloride, 2M in diethyl ether (3.87 ml, 7.74 mmol). The mixture was allowed to warm up to room temperature and stirred at RT overnight. The white suspension was concentrated in vacuo, triturated from ether and dried under high vacuum at RT to afford (S)-1-((cyclopropyl-1-d)methyl-d2)-3-methylpiperazine, hydrochloride (1.525 mmol, 99% yield) as a pale yellow solid. LCMS (m/z): 158.3 [M+1]$^+$.

tert-butyl (S)-(5-chloro-2-(4-((cyclopropyl-1-d)methyl-d2)-2-methylpiperazin-1-yl)pyridin-4-yl)(4-methoxybenzyl)carbamate. A microwave vial was charged with tert-butyl (2,5-dichloropyridin-4-yl)(4-methoxybenzyl)carbamate (480 mg, 1.252 mmol), (S)-1-((cyclopropyl-1-d)methyl-d2)-3-methylpiperazine, hydrochloride (346 mg, 1.503 mmol), cesium carbonate (1836 mg, 5.64 mmol) and t-BuOH (8 ml). The system was flushed with nitrogen then 2-dicyclohexylphosphino-2',6'-di-i-propoxy-1,1'-biphenyl (23.38 mg, 0.050 mmol) and RuPhos Pd G3 (19.04 mg, 0.025 mmol) were added. The system was flushed with nitrogen and heated at 100° C. over 2 days. The reaction was loaded onto celite, and purified on the Biotage (silica gel) eluting with 0-10% MeOH/DCM. The desired fractions were collected and dried under high vacuum at RT to obtain (S)-(5-chloro-2-(4-((cyclopropyl-1-d)methyl-d2)-2-methylpiperazin-1-yl)pyridin-4-yl)(4-methoxybenzyl)carbamate as a yellow foam solid. LCMS (m/z): 504.3 [M+1]$^+$.

(S)-5-chloro-2-(4-((cyclopropyl-1-d)methyl-d2)-2-methylpiperazin-1-yl)pyridin-4-amine. To a solution of tert-butyl (S)-(5-chloro-2-(4-((cyclopropyl-1-d)methyl-d2)-2-methylpiperazin-1-yl)pyridin-4-yl)(4-methoxybenzyl)carbamate in dichloromethane (1.0 ml) was added trifluoroacetic acid (1428 mg, 12.52 mmol) and the mixture stirred at RT overnight. The reaction was concentrated onto celite and purified on the Biotage (reverse phase silica gel) eluting with 0-60% ACN/H$_2$O. The desired fractions were collected, concentrated and dried under high vacuum at RT to afford (S)-5-chloro-2-(4-((cyclopropyl-1-d)methyl-d2)-2-methylpiperazin-1-yl)pyridin-4-amine, trifluoroacetic acetate (0.135 mmol, 11% yield over 2 steps). LCMS (m/z): 284.4 [M+1]$^+$.

General Procedures for the Preparation of Chloromethylacetamide Derivatives
Method B Scheme 98

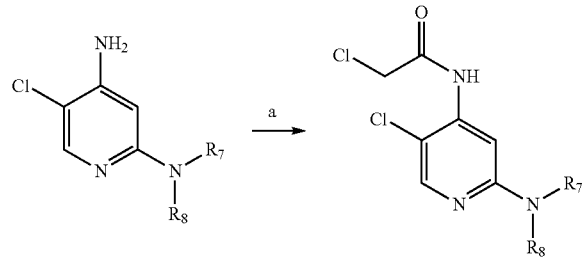

a) ClCH$_2$COCl, EtNiPr$_2$, CH$_2$Cl$_2$

Method C

Scheme 99

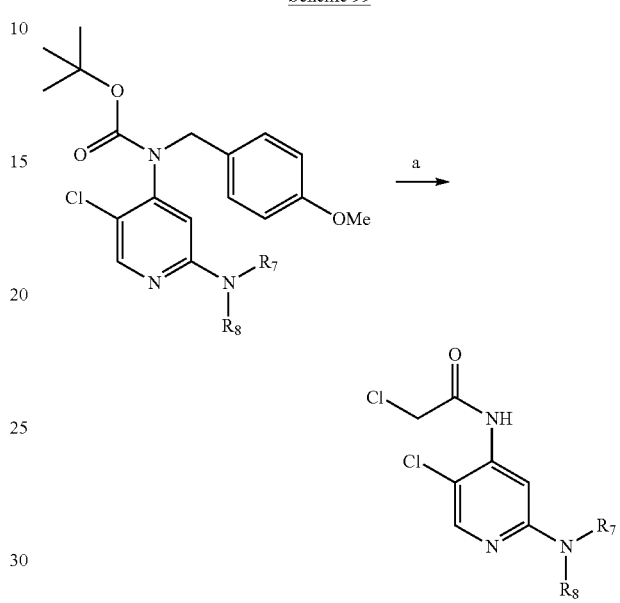

a) i. TsOH, TFA; ii) ClCH$_2$COCl, EtNiPr$_2$, CH$_2$Cl$_2$;

p-Toluenesulfonic acid monohydrate (9.47 mg, 0.050 mmol) was added to a stirring solution of (S)-tert-butyl (5-chloro-2-(3-fluoropyrrolidin-1-yl)pyridin-4-yl)(4-methoxybenzyl)carbamate (0.217 g, 0.498 mmol) in TFA (3.26 ml, 42.3 mmol) at room temperature. After stirring for 2 h LCMS indicated clean deprotection. The reaction was diluted with DCM and partioned between DCM and water. The aqueous layers was neutralised with the addition of NaHCO$_3$[both saturated solution and extra solid]. The layers were separated and the aqueous layer was extracted with DCM. The combined organic extract was dried, filtered and concentrated to dryness to afford (S)-5-chloro-2-(3-fluoropyrrolidin-1-yl)pyridin-4-amine as a solid.

The crude deprotected amino-pyridine was dissolved in Dichloromethane (DCM) (Volume: 6 ml). DIEA (0.109 ml, 0.622 mmol) and Chloroacetyl chloride (0.049 ml, 0.622 mmol) were added and the reaction was allowed to stir at room temperature for 3 h. LCMS indicated about 50% conversion. Additional reagents were added and the reaction was allowed to stir for an addition 2 h. LCMS indicated improved conversion (still not 100% but only need ~20mgs to make the target analog) so the reaction mixture was loaded onto celite. Flash [0-5% MeOH/DCM] to give (S)-2-chloro-N-(5-chloro-2-(3-fluoropyrrolidin-1-yl)pyridin-4-yl)acetamide (0.104 g, 0.356 mmol, 71.5% yield) as an amber film that was pure enough by LCMS and NMR to carry forward to the next step.

In a similar manner the following compounds were synthesized (Method in parentheses):

| | | |
|---|---|---|
| 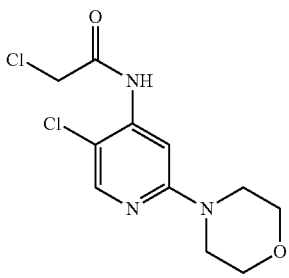 [SMILES: O=C(CCl)Nc1cc(N2CCOCC2)ncc1Cl] | 2-chloro-N-(5-chloro-2-morpholinopyridin-4-yl)acetamide | 77% yield; LCMS [M + H]+ 290 |
| 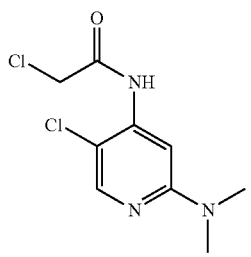 | 2-chloro-N-(5-chloro-2-(dimethylamino)pyridin-4-yl)acetamide | 81% yield; LCMS [M + H]+ 248 |
| 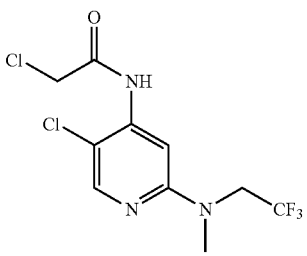 [SMILES: CN(CC(F)(F)F)c1cc(NC(=O)CCl)c(Cl)cn1] | 2-chloro-N-(5-chloro-2-(methyl(2,2,2-trifluoroethyl)amino)pyridin-4-yl)acetamide | 26% yield; LCMS [M + H]+ 316 |
| 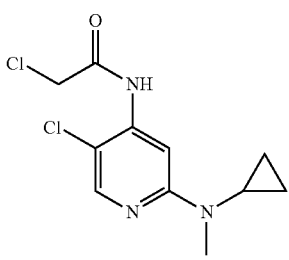 [SMILES: CN(c1cc(NC(=O)CCl)c(Cl)cn1)C1CC1] | 2-chloro-N-(5-chloro-2-(cyclopropyl(methyl)amino)pyridin-4-yl)acetamide | 34% yield; LCMS [M + H]+ 274 |
| 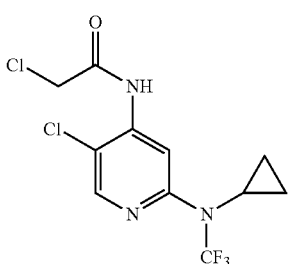 | 2-chloro-N-(5-chloro-2-(cyclopropyl(trifluoromethyl)amino)-pyridin-4-yl)acetamide Exact Mass: 327.02 | 52% yield; LCMS [M + H]+ 328 |
| 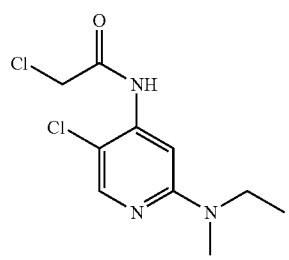 [SMILES: CCN(C)c1cc(NC(=O)CCl)c(Cl)cn1] | 2-chloro-N-(5-chloro-2-(ethyl(methyl)amino)pyridin-4-yl)acetamide | 43% yield; LCMS [M + H]+ 262 |

-continued

| | | |
|---|---|---|
| 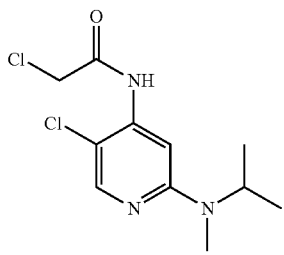 [SMILES: CC(C)N(C)c1cc(NC(=O)CCl)c(Cl)cn1] | 2-chloro-N-(5-chloro-2-(isopropyl(methyl)amino)pyridin-4-yl)acetamide | 24% yield; LCMS [M + H]+ 276 |
| 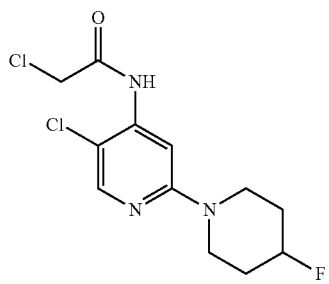 [SMILES: O=C(CCl)Nc1cc(N2CCC(F)CC2)ncc1Cl] | 2-chloro-N-(5-chloro-2-(4-fluoropiperidin-1-yl)pyridin-4-yl)acetamide Exact Mass: 305.05 | 30% yield; LCMS [M + H]+ 306 |
| 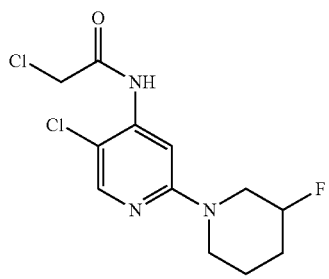 [SMILES: O=C(CCl)Nc1cc(N2CCCC(F)C2)ncc1Cl] | 2-chloro-N-(5-chloro-2-(4-fluoropiperidin-1-yl)pyridin-4-yl)acetamide Exact Mass: 305.05 | 76% yield; LCMS [M + H]+ 306 |
| 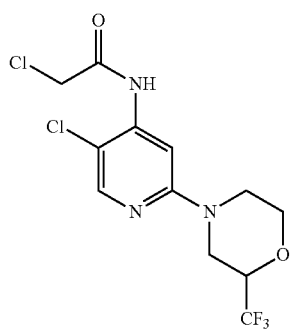 [SMILES: O=C(CCl)Nc1cc(N2CCOC(C(F)(F)F)C2)ncc1Cl] | 2-chloro-N-(5-chloro-2-(2-(trifluoromethyl)morpholino)pyridin-4-yl)acetamide Exact Mass: 357.03 | 55% yield; LCMS [M + H]+ 358 |
| 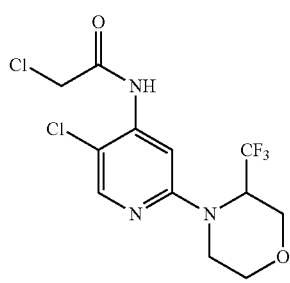 [SMILES: O=C(CCl)Nc1cc(N2CCOCC2C(F)(F)F)ncc1Cl] | 2-chloro-N-(5-chloro-2-(3-(trifluoromethyl)morpholino)pyridin-4-yl)acetamide Exact Mass: 357.03 | 36% yield; LCMS [M + H]+ 358 |

| | | |
|---|---|---|
| 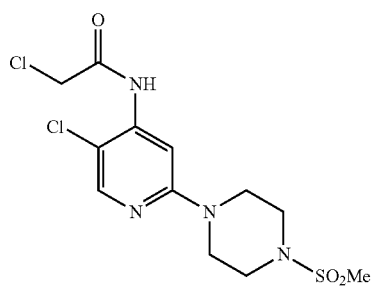 [SMILES: CS(=O)(=O)N1CCN(c2cc(NC(=O)CCl)c(Cl)cn2)CC1] | 2-chloro-N-(5-chloro-2-(4-(methylsulfonyl)piperazin-1-yl)pyridin-4-yl)acetamide<br>Exact Mass: 366.03 | 23% yield; LCMS [M + H]+ 367 |
| 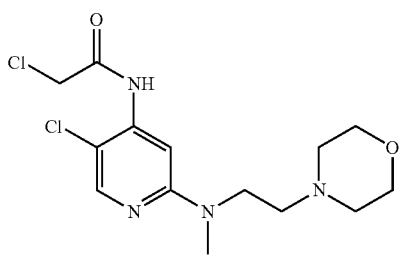 [SMILES: CN(CCN1CCOCC1)c1cc(NC(=O)CCl)c(Cl)cn1] | 2-chloro-N-(5-chloro-2-(methyl(2-morpholinoethyl)amino)pyridin-4-yl)acetamide<br>Exact Mass: 346.10 | 24% yield; LCMS [M + H]+ 347 |
| 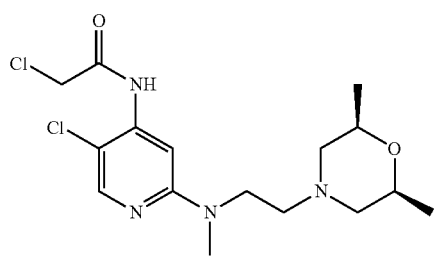 [SMILES: C[C@@H]1CN(CCN(C)c2cc(NC(=O)CCl)c(Cl)cn2)C[C@H](C)O1] | 2-chloro-N-(5-chloro-2-((2-((2S,6R)-2,6-dimethylmorpholino)ethyl)(methyl)amino)pyridin-4-yl)acetamide<br>Exact Mass: 374.13 | 26% yield; LCMS [M + H]+ 375 |
| 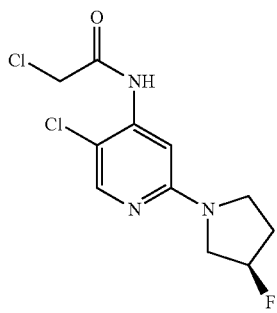 [SMILES: O=C(CCl)Nc1cc(N2CC[C@@H](F)C2)ncc1Cl] | (R)-2-chloro-N-(5-chloro-2-(3-fluoropyrrolidin-1-yl)pyridin-4-yl)acetamide<br>Exact Mass: 291.03 | 88% yield; LCMS [M + H]+ 292 |
| 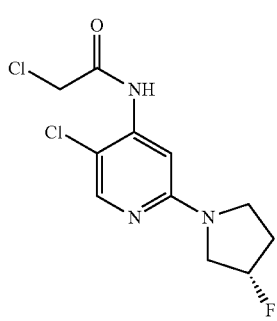 [SMILES: O=C(CCl)Nc1cc(N2CC[C@H](F)C2)ncc1Cl] | (S)-2-chloro-N-(5-chloro-2-(3-fluoropyrrolidin-1-yl)pyridin-4-yl)acetamide<br>Exact Mass: 291.03 | 50% yield; LCMS [M + H]+ 292 |

-continued

| | | |
|---|---|---|
| 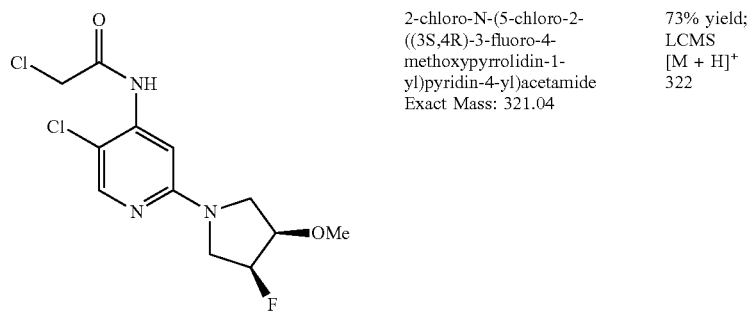 | 2-chloro-N-(5-chloro-2-((3S,4R)-3-fluoro-4-methoxypyrrolidin-1-yl)pyridin-4-yl)acetamide<br>Exact Mass: 321.04 | 73% yield;<br>LCMS [M + H]$^+$ 322 |
| 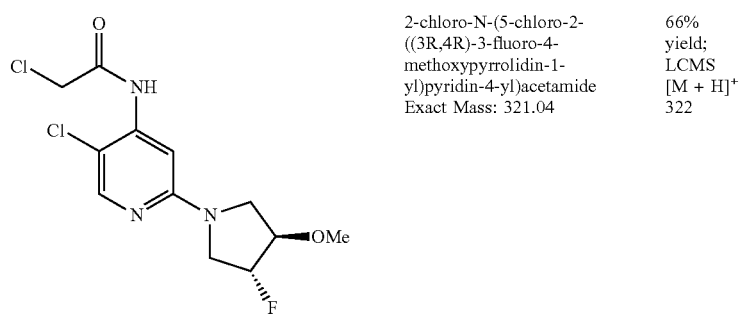 | 2-chloro-N-(5-chloro-2-((3R,4R)-3-fluoro-4-methoxypyrrolidin-1-yl)pyridin-4-yl)acetamide<br>Exact Mass: 321.04 | 66% yield;<br>LCMS [M + H]$^+$ 322 |
| 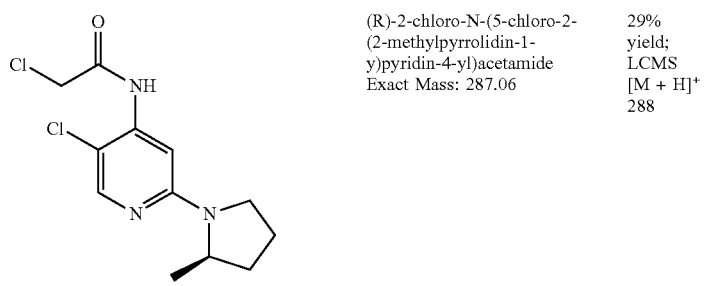 | (R)-2-chloro-N-(5-chloro-2-(2-methylpyrrolidin-1-y)pyridin-4-yl)acetamide<br>Exact Mass: 287.06 | 29% yield;<br>LCMS [M + H]$^+$ 288 |
|  | (S)-2-chloro-N-(5-chloro-2-(2-methylpyrrolidin-1-yl)pyridin-4-yl)acetamide<br>Exact Mass: 287.06 | 28% yield;<br>LCMS [M + H]$^+$ 288 |
| 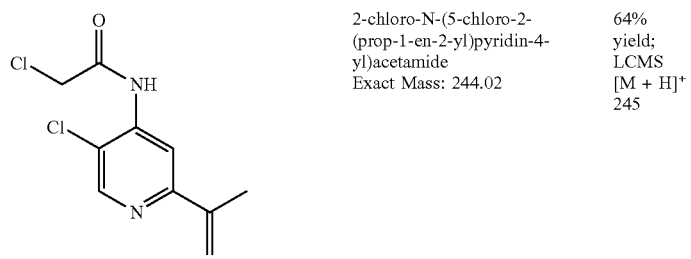 | 2-chloro-N-(5-chloro-2-(prop-1-en-2-yl)pyridin-4-yl)acetamide<br>Exact Mass: 244.02 | 64% yield;<br>LCMS [M + H]$^+$ 245 |

| | 2-chloro-N-(5-chloro-2-vinylpyridin-4-yl)acetamide Exact Mass: 230.00 | 36% yield; LCMS [M + H]+ 231 |
|---|---|---|
| 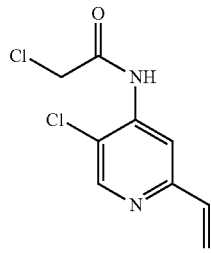 | | |

Preparation of 2-chloro-N-(2,4-dimethoxybenzyl)aniline

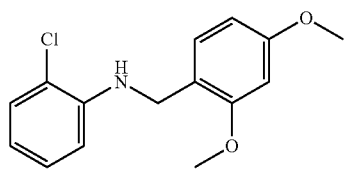 [SMILES: COc1ccc(CNc2ccccc2Cl)c(OC)c1]

A mixture of 2-chloroaniline (2.1 mL, 19.60 mmol), (2,4-dimethoxyphenyl)methanol (3.0 mL, 19.60 mmol) and tris(triphenylphosphine)ruthenium(II) dichloride (0.465 g, 0.59 mmol) in a sealed tube was heated to 140° C. overnight. The reaction mixture was concentrated onto silica gel and purified by flash chromatography (EtOAc/hexanes as eluent) to afford 2-chloro-N-(2,4-dimethoxybenzyl)aniline (4.17 g, 69% yield) as a clear colourless oil. LCMS [M+H]+ 278.03.

Preparation of 2-chloro-N-(2-chlorophenyl)-N-(2,4-dimethoxybenzyl)acetamide

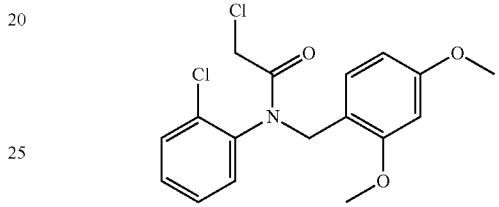

2-chloroacetyl chloride (4.6 mL, 58.0 mmol) was added dropwise to a stirring solution of 2-chloro-N-(2,4-dimethoxybenzyl)aniline (8.06 g, 29.0 mmol) and TEA (8.1 mL, 58.0 mmol) in DCM (200 mL) at room temperature. The reaction was allowed to stir at room temperature overnight. The reaction mixture was concentrated onto silica gel and purified by flash chromatography (EtOAc/hexanes as eluent) to afford 2-chloro-N-(2-chlorophenyl)-N-(2,4-dimethoxybenzyl)acetamide (10.36 g, 96% yield) as an amber oil. LCMS [M+H]+ 353.95.

Using the above described experimental procedures, the following compounds of Formula I were prepared:

TABLE 1

| Compound | Structure | Yield |
|---|---|---|
| I-1 | 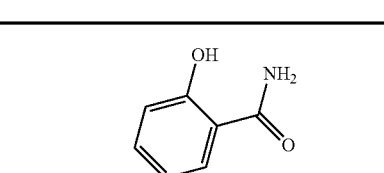 | 15% |

TABLE 1-continued

| Compound | Structure | Yield |
|---|---|---|
| I-2 | 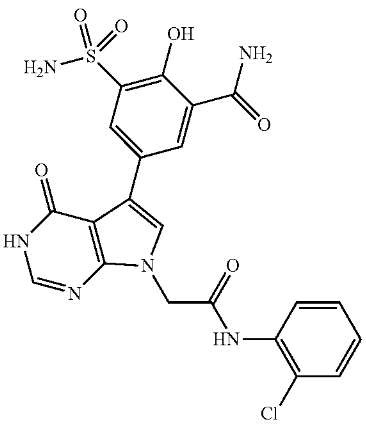 [SMILES: NC(=O)c1cc(-c2cn(CC(=O)Nc3ccccc3Cl)c3nc[nH]c(=O)c23)cc(S(N)(=O)=O)c1O] | 43% |
| I-3 | 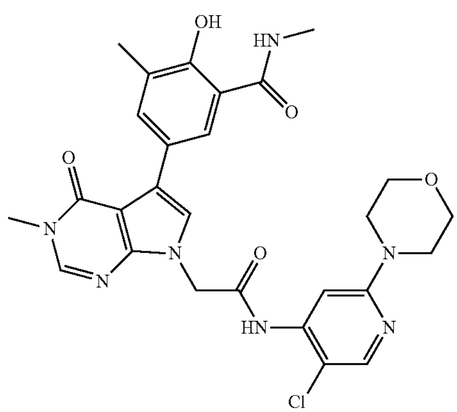 [SMILES: CNC(=O)c1cc(-c2cn(CC(=O)Nc3cc(N4CCOCC4)ncc3Cl)c3ncn(C)c(=O)c23)cc(C)c1O] | 45% |
| I-4 | 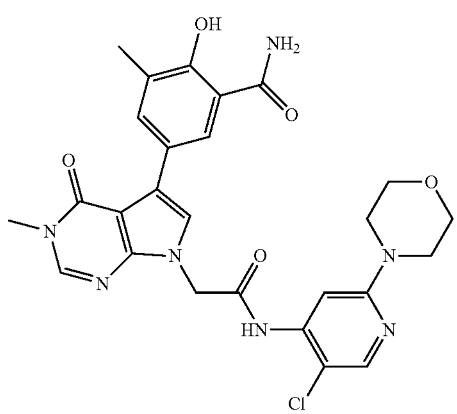 [SMILES: Cc1cc(-c2cn(CC(=O)Nc3cc(N4CCOCC4)ncc3Cl)c3ncn(C)c(=O)c23)cc(C(N)=O)c1O] | 80% |

TABLE 1-continued

| Compound | Structure | Yield |
|---|---|---|
| I-5 | 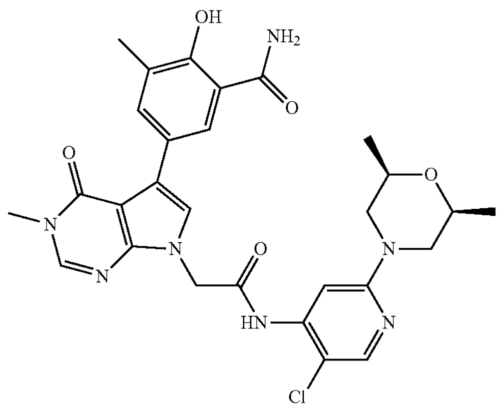 | 66% |
| I-6 | 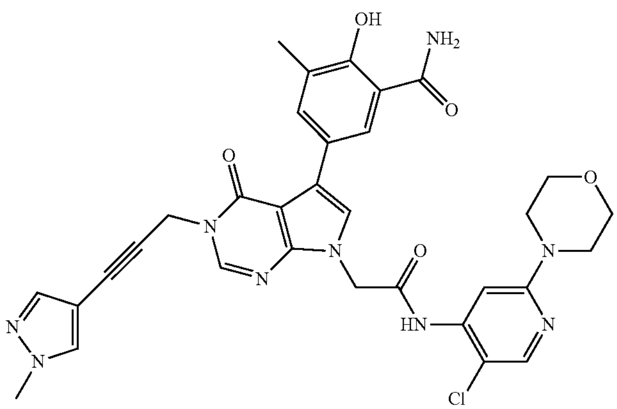 [SMILES: Cc1cc(-c2cn(CC(=O)Nc3cc(N4CCOCC4)ncc3Cl)c3ncn(CC#Cc4cnn(C)c4)c(=O)c23)cc(C(N)=O)c1O] | 42% |
| I-7 | 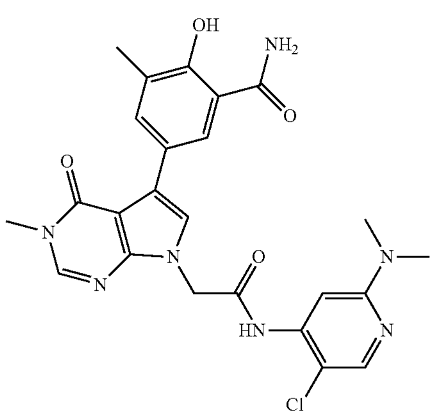 | 41% |

TABLE 1-continued

| Compound | Structure | Yield |
|---|---|---|
| I-8 | 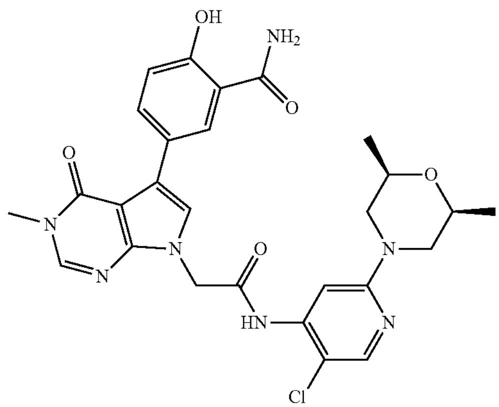 | 73% |
| I-9 | 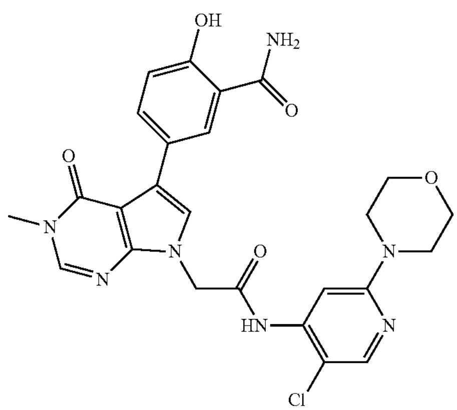 [SMILES: Cn1cnc2c(c(-c3ccc(O)c(C(N)=O)c3)cn2CC(=O)Nc2cc(N3CCOCC3)ncc2Cl)c1=O] | 92% |
| I-10 | 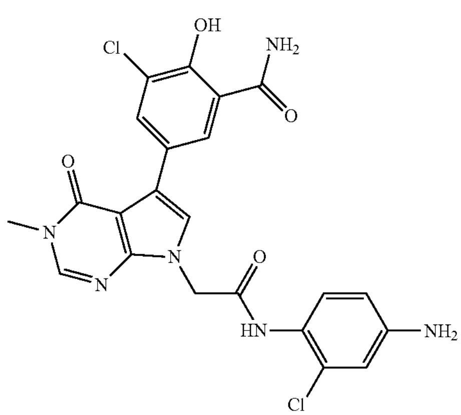 [SMILES: Cn1cnc2c(c(-c3cc(Cl)c(O)c(C(N)=O)c3)cn2CC(=O)Nc2ccc(N)cc2Cl)c1=O] | 13% |

TABLE 1-continued
| Compound | Structure | Yield |
|---|---|---|
| I-11 | 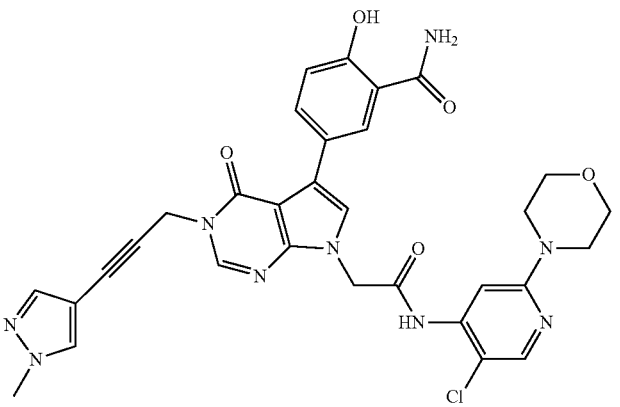 [SMILES: Cn1cc(C#CCn2cnc3c(c(-c4ccc(O)c(C(N)=O)c4)cn3CC(=O)Nc3cc(N4CCOCC4)ncc3Cl)c2=O)cn1] | 28% |
| I-12 | 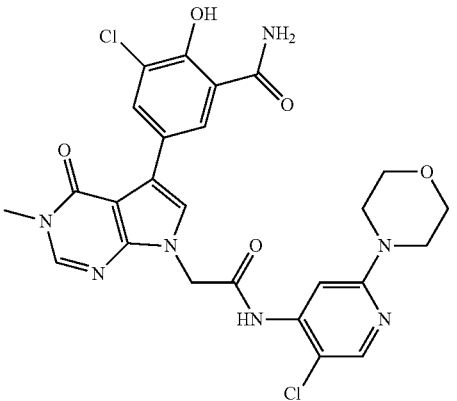 [SMILES: Cn1cnc2c(c(-c3cc(Cl)c(O)c(C(N)=O)c3)cn2CC(=O)Nc2cc(N3CCOCC3)ncc2Cl)c1=O] | 79% |
| I-13 | 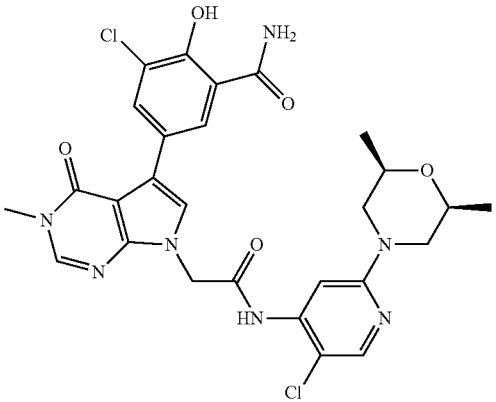 | 82% |

TABLE 1-continued

| Compound | Structure | Yield |
|---|---|---|
| I-14 | 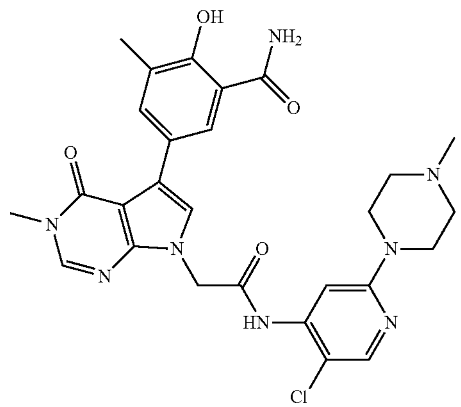 | 18% |
| I-15 | 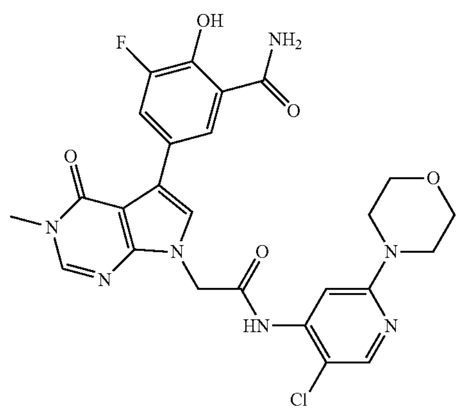 [SMILES: Cn1cnc2c(c(-c3cc(F)c(O)c(C(N)=O)c3)cn2CC(=O)Nc2cc(N3CCOCC3)ncc2Cl)c1=O] | 63% |
| I-16 | 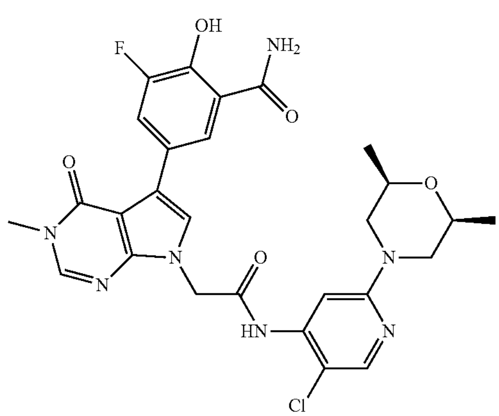 | 56% |

TABLE 1-continued
| Compound | Structure | Yield |
|---|---|---|
| I-17 | 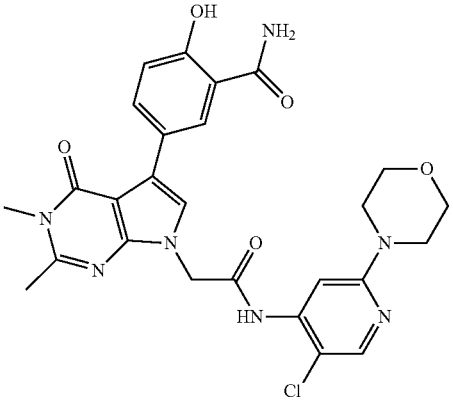 [SMILES: Cc1nc2c(c(-c3ccc(O)c(C(N)=O)c3)cn2CC(=O)Nc2cc(N3CCOCC3)ncc2Cl)c(=O)n1C] | 38% |
| I-18 | 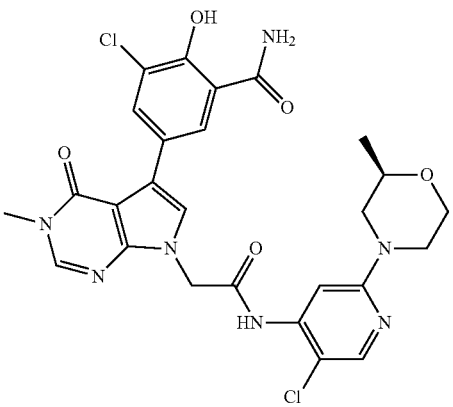 [SMILES: C[C@@H]1CN(c2cc(NC(=O)Cn3cc(-c4cc(Cl)c(O)c(C(N)=O)c4)c4c(=O)n(C)cnc43)c(Cl)cn2)CCO1] | 62% |
| I-19 | 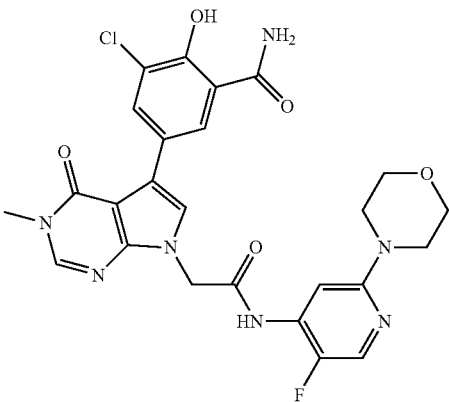 [SMILES: Cn1cnc2c(c(-c3cc(Cl)c(O)c(C(N)=O)c3)cn2CC(=O)Nc2cc(N3CCOCC3)ncc2F)c1=O] | 64% |

TABLE 1-continued

| Compound | Structure | Yield |
|---|---|---|
| I-20 | 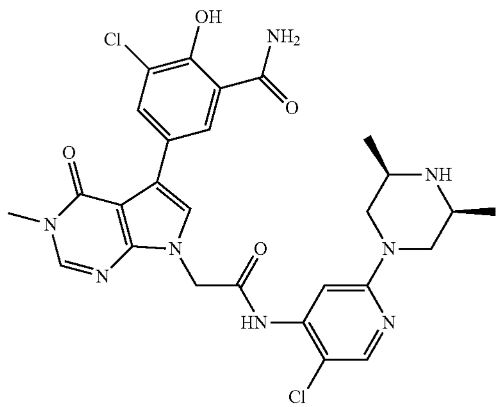 | 81% |
| I-21 | 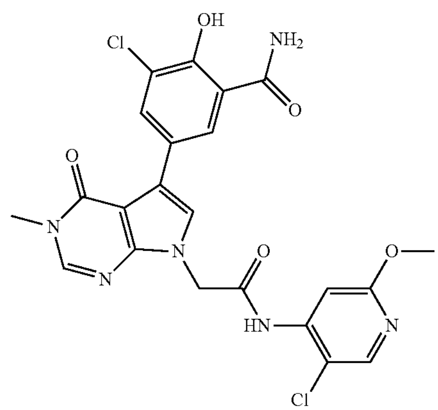 | 22% |
| I-22 | 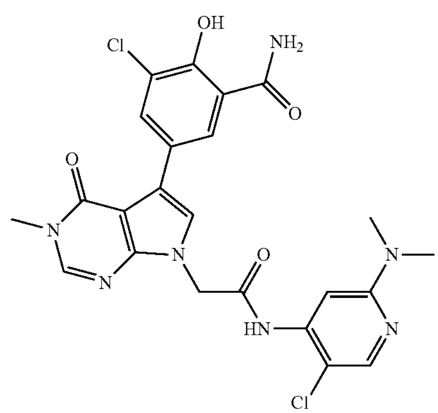 | 42% |

TABLE 1-continued

| Compound | Structure | Yield |
|---|---|---|
| I-23 | 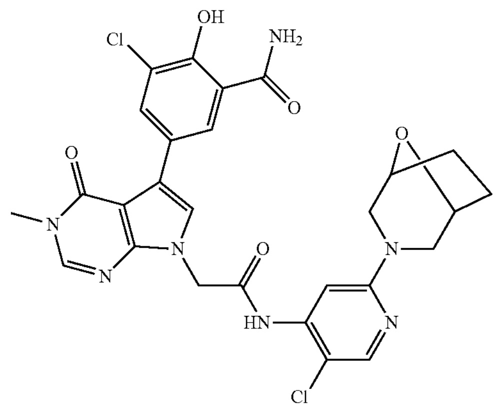 [SMILES: Cn1cnc2c(c(-c3cc(Cl)c(O)c(C(N)=O)c3)cn2CC(=O)Nc2cc(N3CC4CCC(C3)O4)ncc2Cl)c1=O] | 72% |
| I-24 | 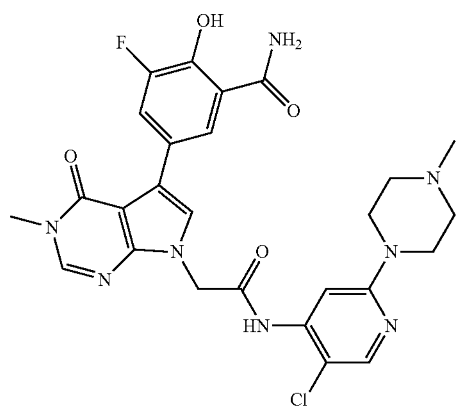 | 31% |
| I-25 | 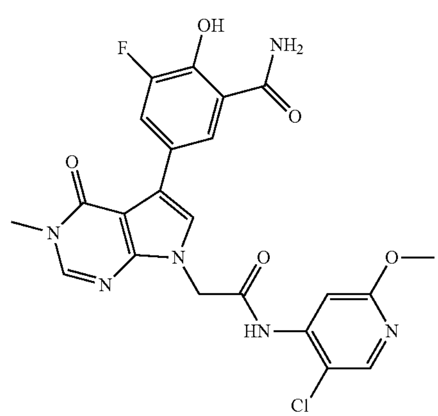 | 18% |

TABLE 1-continued

| Compound | Structure | Yield |
|---|---|---|
| I-26 | 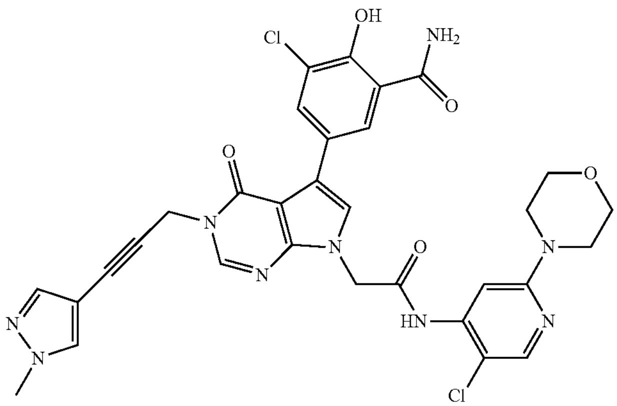 [SMILES: Cn1cc(C#CCn2cnc3c(c(-c4cc(Cl)c(O)c(C(N)=O)c4)cn3CC(=O)Nc3cc(N4CCOCC4)ncc3Cl)c2=O)cn1] | 41% |
| I-27 | 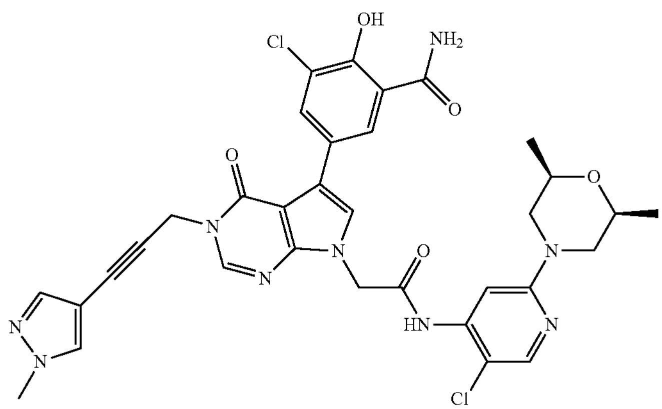 [SMILES: C[C@@H]1CN(c2cc(NC(=O)Cn3cc(-c4cc(Cl)c(O)c(C(N)=O)c4)c4c(=O)n(CC#Cc5cnn(C)c5)cnc43)c(Cl)cn2)C[C@H](C)O1] | 32% |
| I-28 | 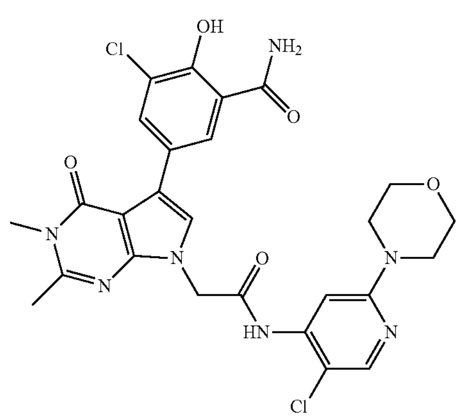 [SMILES: Cc1nc2c(c(-c3cc(Cl)c(O)c(C(N)=O)c3)cn2CC(=O)Nc2cc(N3CCOCC3)ncc2Cl)c(=O)n1C] | 39% |

TABLE 1-continued

| Compound | Structure | Yield |
|---|---|---|
| I-29 | 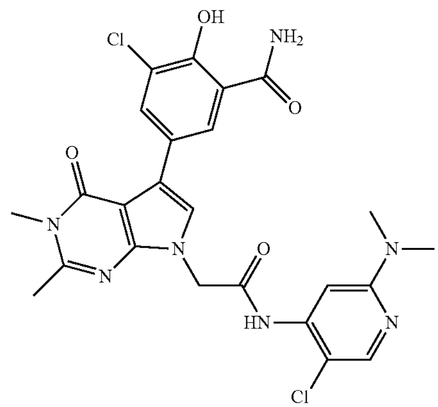 | 42% |
| I-30 | 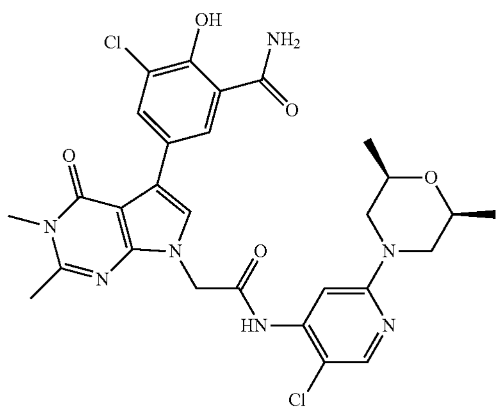 | 9% |
| I-31 | 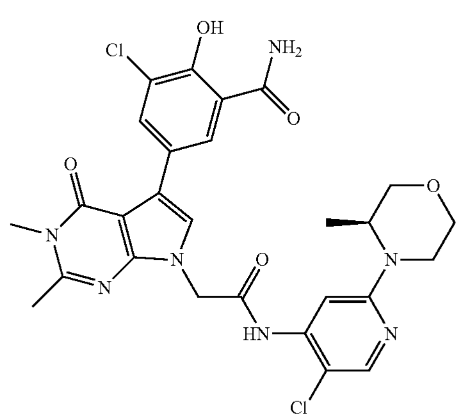 [SMILES: Cc1nc2c(c(-c3cc(Cl)c(O)c(C(N)=O)c3)cn2CC(=O)Nc2cc(N3CCOC[C@@H]3C)ncc2Cl)c(=O)n1C] | 22% |

TABLE 1-continued

| Compound | Structure | Yield |
|---|---|---|
| I-32 | 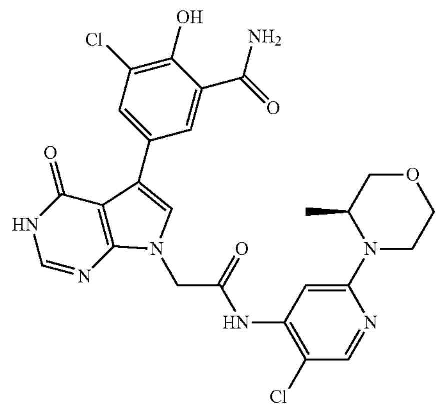 [SMILES: C[C@H]1COCCN1c1cc(NC(=O)Cn2cc(-c3cc(Cl)c(O)c(C(N)=O)c3)c3c(=O)[nH]cnc32)c(Cl)cn1] | 68% |
| I-33 | 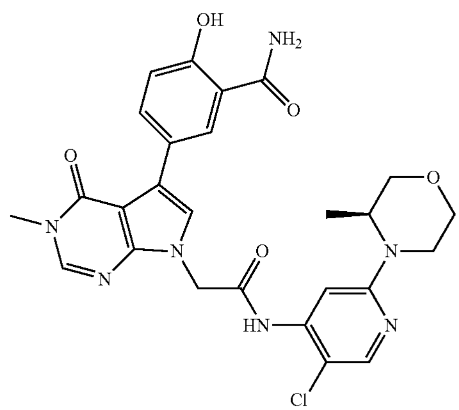 [SMILES: C[C@H]1COCCN1c1cc(NC(=O)Cn2cc(-c3ccc(O)c(C(N)=O)c3)c3c(=O)n(C)cnc32)c(Cl)cn1] | 62% |
| I-34 | 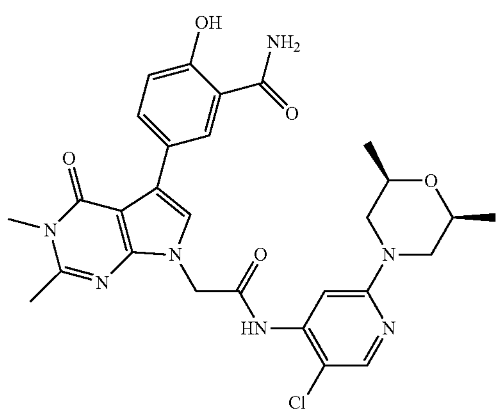 | 25% |

TABLE 1-continued
| Compound | Structure | Yield |
|---|---|---|
| I-35 | 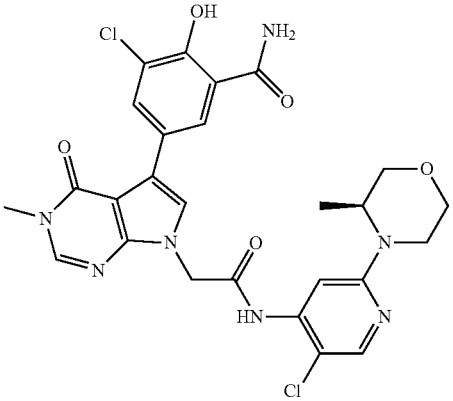 [SMILES: C[C@H]1COCCN1c1cc(NC(=O)Cn2cc(-c3cc(Cl)c(O)c(C(N)=O)c3)c3c(=O)n(C)cnc32)c(Cl)cn1] | 65% |
| I-36 | 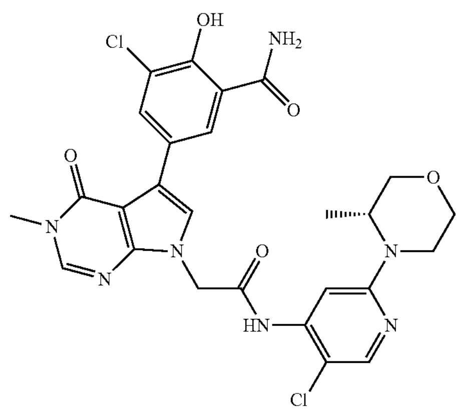 [SMILES: C[C@@H]1COCCN1c1cc(NC(=O)Cn2cc(-c3cc(Cl)c(O)c(C(N)=O)c3)c3c(=O)n(C)cnc32)c(Cl)cn1] | 26% |
| I-37 | 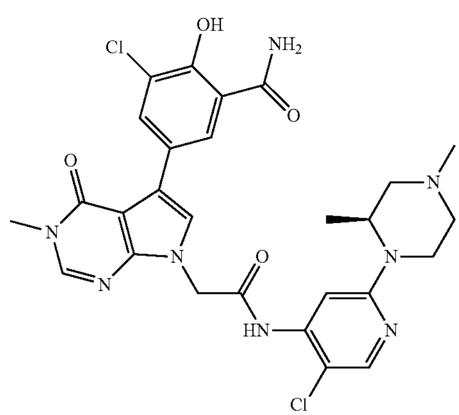 | 48% |

TABLE 1-continued
| Compound | Structure | Yield |
|---|---|---|
| I-38 | 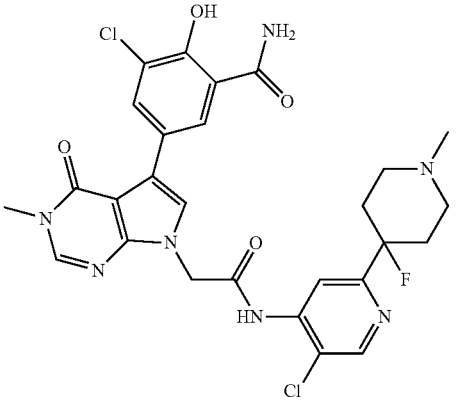 | 59% |
| I-39 | 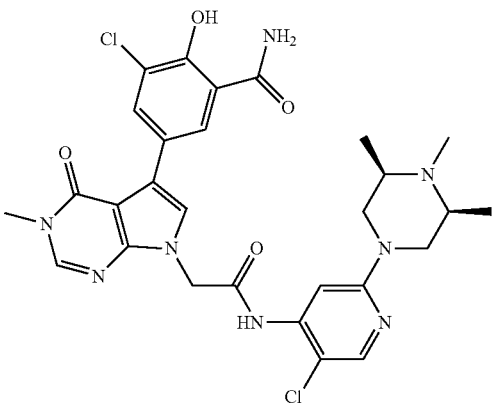 | 13% |
| I-40 | 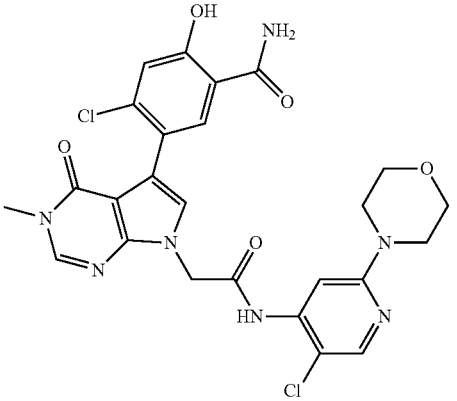 [SMILES: Cn1cnc2c(c(-c3cc(C(N)=O)c(O)cc3Cl)cn2CC(=O)Nc2cc(N3CCOCC3)ncc2Cl)c1=O] | 93% |

TABLE 1-continued

| Compound | Structure | Yield |
|---|---|---|
| I-41 | 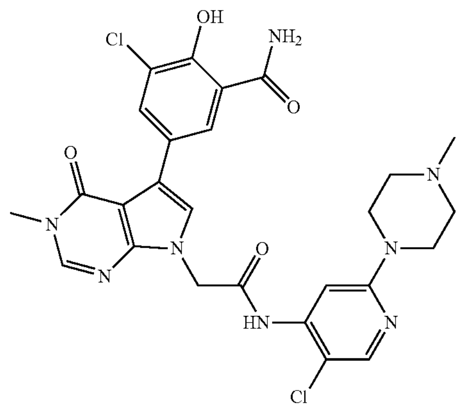 | 67% |
| I-42 | 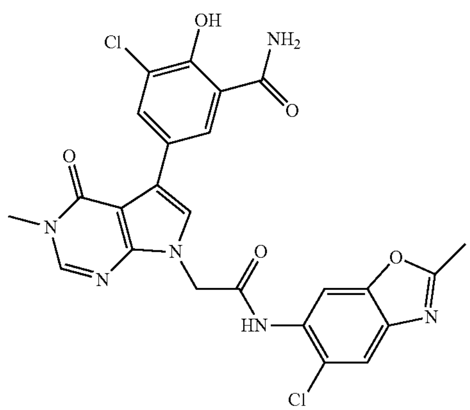 | 38% |
| I-43 | 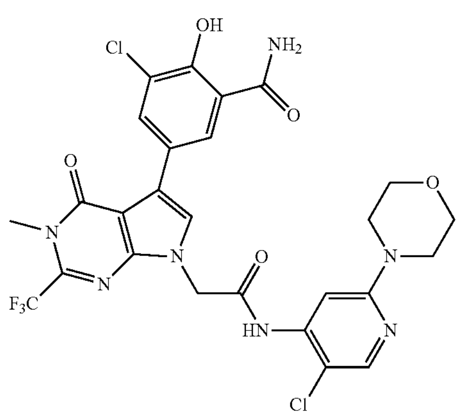 | 86% |

TABLE 1-continued

| Compound | Structure | Yield |
|---|---|---|
| I-44 | 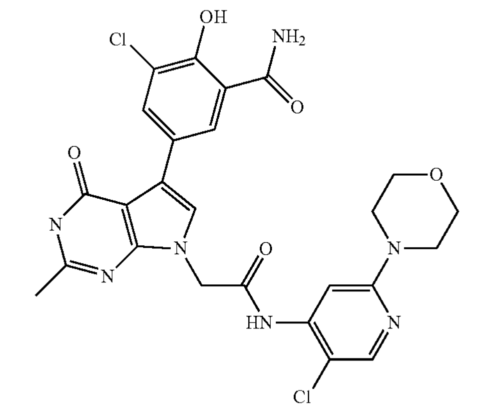 [SMILES: Cc1nc2c(c(-c3cc(Cl)c(O)c(C(N)=O)c3)cn2CC(=O)Nc2cc(N3CCOCC3)ncc2Cl)c(=O)[nH]1] | 16% |
| I-45 | 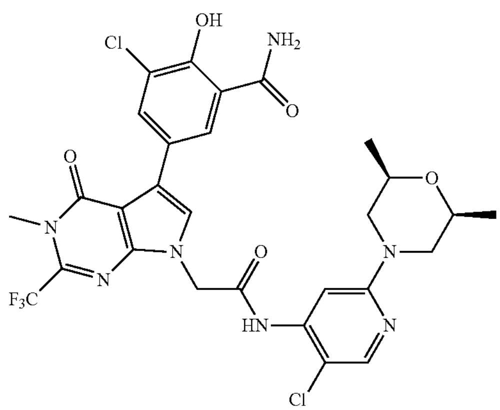 | 68% |
| I-46 | 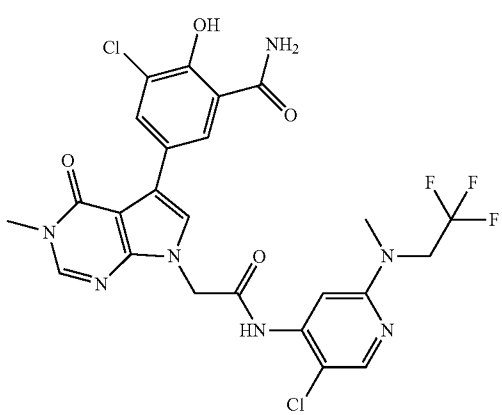 [SMILES: CN(CC(F)(F)F)c1cc(NC(=O)Cn2cc(-c3cc(Cl)c(O)c(C(N)=O)c3)c3c(=O)n(C)cnc32)c(Cl)cn1] | 97% |

TABLE 1-continued

| Compound | Structure | Yield |
|---|---|---|
| I-47 | 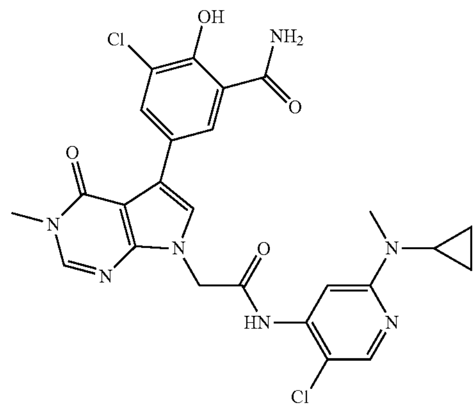 [SMILES: CN(c1cc(NC(=O)Cn2cc(-c3cc(Cl)c(O)c(C(N)=O)c3)c3c(=O)n(C)cnc32)c(Cl)cn1)C1CC1] | 100% |
| I-48 | 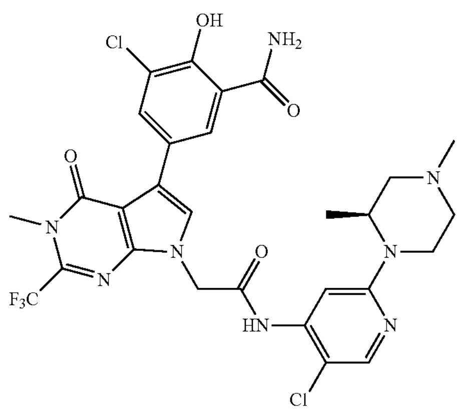 | 80% |
| I-49 | 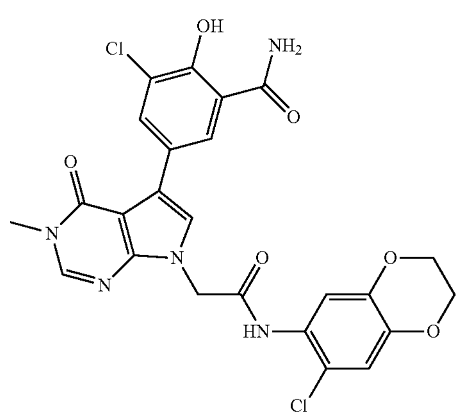 [SMILES: Cn1cnc2c(c(-c3cc(Cl)c(O)c(C(N)=O)c3)cn2CC(=O)Nc2cc3c(cc2Cl)OCCO3)c1=O] | 45% |

TABLE 1-continued

| Compound | Structure | Yield |
|---|---|---|
| I-50 | 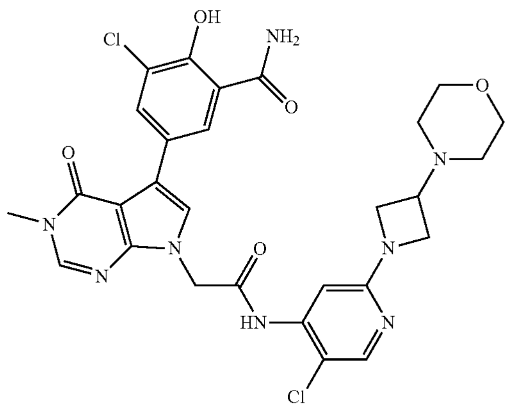 [SMILES: Cn1cnc2c(c(-c3cc(Cl)c(O)c(C(N)=O)c3)cn2CC(=O)Nc2cc(N3CC(N4CCOCC4)C3)ncc2Cl)c1=O] | 64% |
| I-51 | 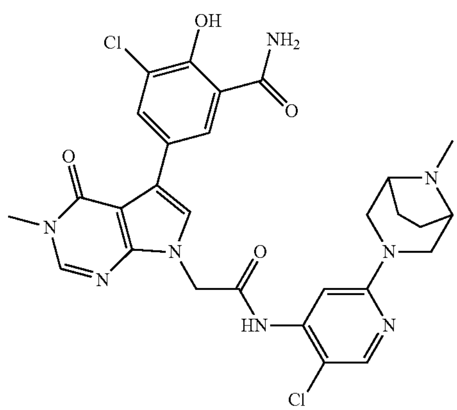 | 91% |
| I-52 | 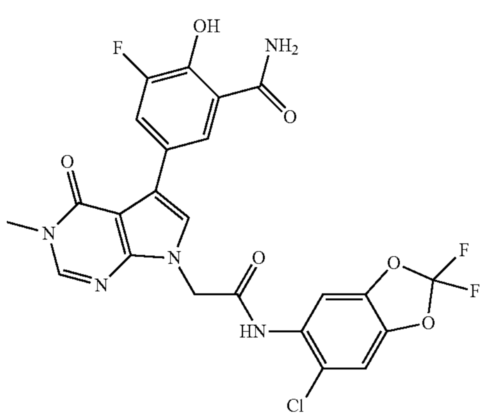 [SMILES: Cn1cnc2c(c(-c3cc(F)c(O)c(C(N)=O)c3)cn2CC(=O)Nc2cc3c(cc2Cl)OC(F)(F)O3)c1=O] | 78% |

TABLE 1-continued
| Compound | Structure | Yield |
|---|---|---|
| I-53 | 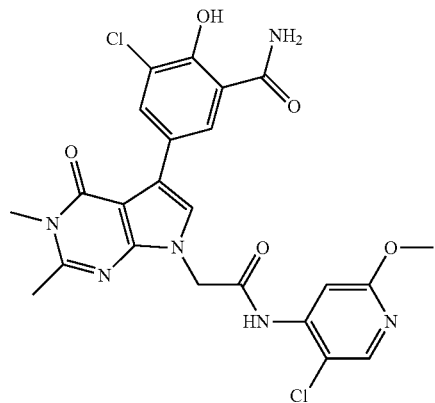 | 9% |
| I-54 | 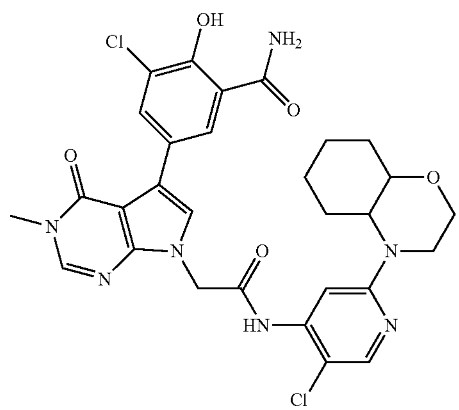 [SMILES: Cn1cnc2c(c(-c3cc(Cl)c(O)c(C(N)=O)c3)cn2CC(=O)Nc2cc(N3CCOC4CCCCC43)ncc2Cl)c1=O] | 92% |
| I-55 | 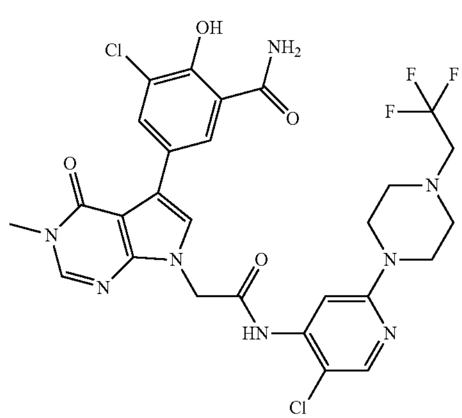 [SMILES: Cn1cnc2c(c(-c3cc(Cl)c(O)c(C(N)=O)c3)cn2CC(=O)Nc2cc(N3CCN(CC(F)(F)F)CC3)ncc2Cl)c1=O] | 89% |

TABLE 1-continued

| Compound | Structure | Yield |
|---|---|---|
| I-56 | 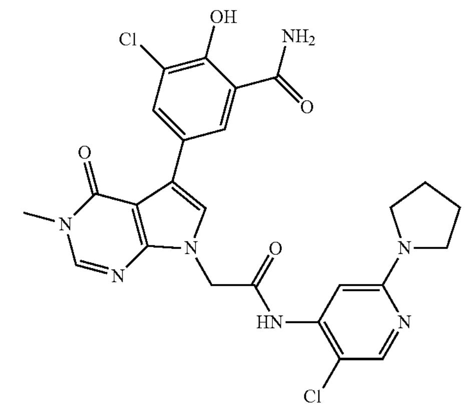 [SMILES: Cn1cnc2c(c(-c3cc(Cl)c(O)c(C(N)=O)c3)cn2CC(=O)Nc2cc(N3CCCC3)ncc2Cl)c1=O] | 89% |
| I-57 | 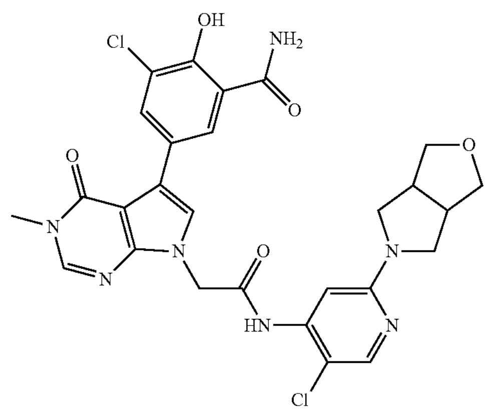 [SMILES: Cn1cnc2c(c(-c3cc(Cl)c(O)c(C(N)=O)c3)cn2CC(=O)Nc2cc(N3CC4COCC4C3)ncc2Cl)c1=O] | 54% |
| I-58 | 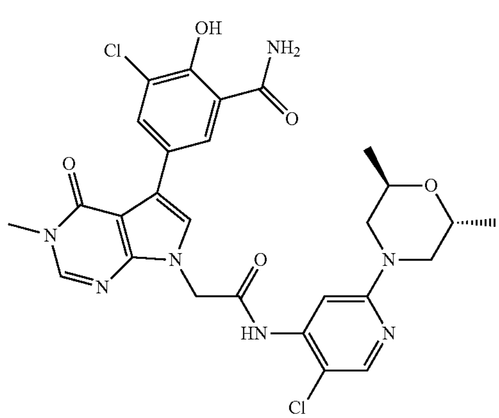 | 71% |

TABLE 1-continued

| Compound | Structure | Yield |
|---|---|---|
| I-59 | 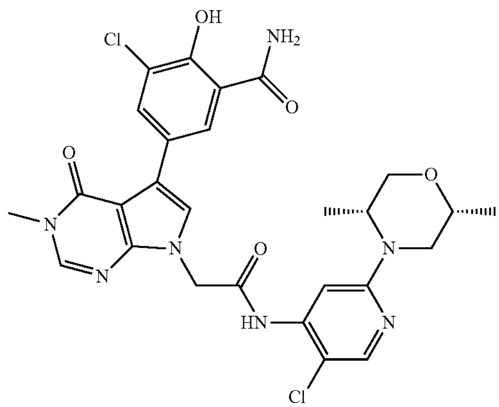 | 76% |
| I-60 | 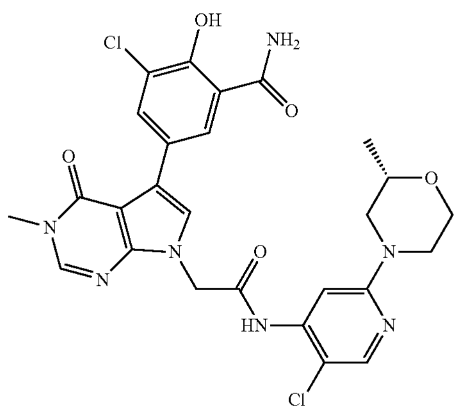 [SMILES: C[C@H]1CN(c2cc(NC(=O)Cn3cc(-c4cc(Cl)c(O)c(C(N)=O)c4)c4c(=O)n(C)cnc43)c(Cl)cn2)CCO1] | 59% |
| I-61 | 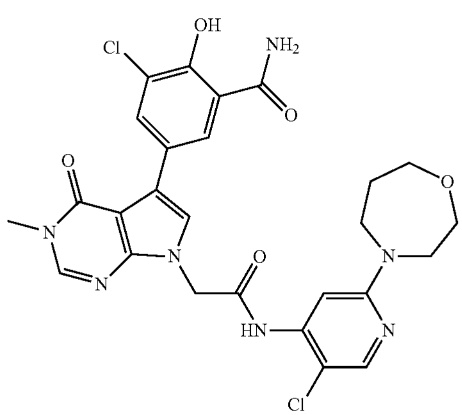 [SMILES: Cn1cnc2c(c(-c3cc(Cl)c(O)c(C(N)=O)c3)cn2CC(=O)Nc2cc(N3CCCOCC3)ncc2Cl)c1=O] | 73% |

TABLE 1-continued

| Compound | Structure | Yield |
|---|---|---|
| I-62 | 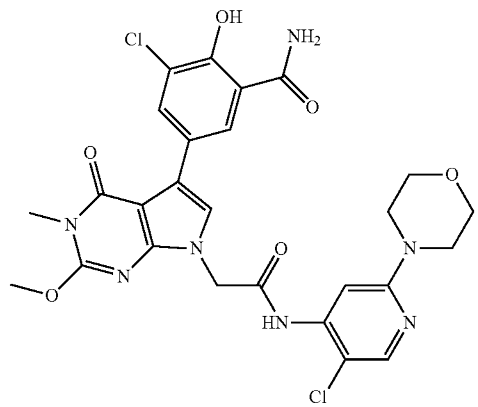 [SMILES: COc1nc2c(c(-c3cc(Cl)c(O)c(C(N)=O)c3)cn2CC(=O)Nc2cc(N3CCOCC3)ncc2Cl)c(=O)n1C] | 83% |
| I-63 | 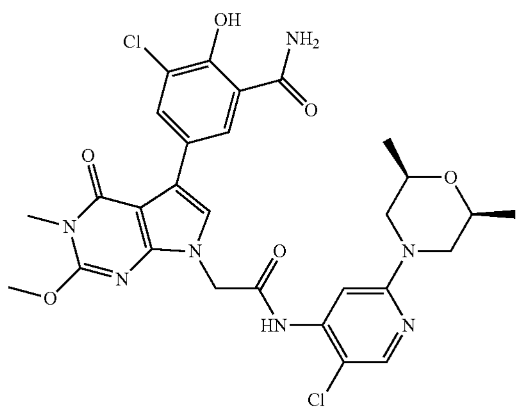 | 91% |
| I-64 | 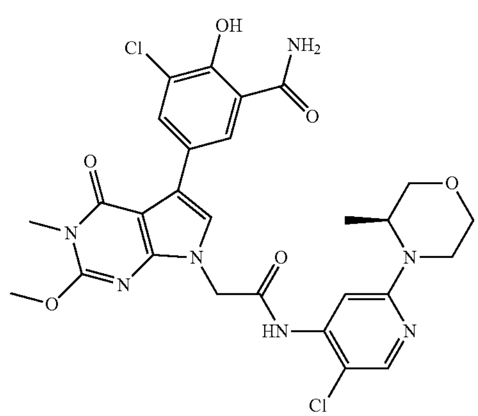 [SMILES: COc1nc2c(c(-c3cc(Cl)c(O)c(C(N)=O)c3)cn2CC(=O)Nc2cc(N3CCOC[C@@H]3C)ncc2Cl)c(=O)n1C] | 78% |

TABLE 1-continued
| Compound | Structure | Yield |
|---|---|---|
| I-65 | 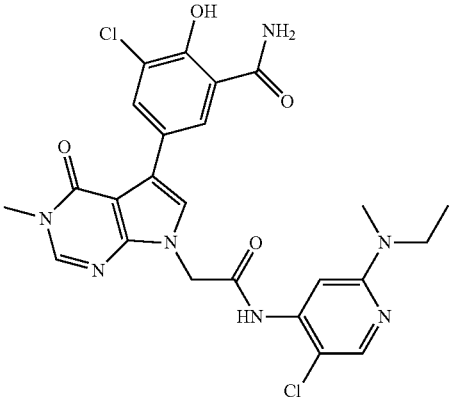 [SMILES: CCN(C)c1cc(NC(=O)Cn2cc(-c3cc(Cl)c(O)c(C(N)=O)c3)c3c(=O)n(C)cnc32)c(Cl)cn1] | 100% |
| I-66 | 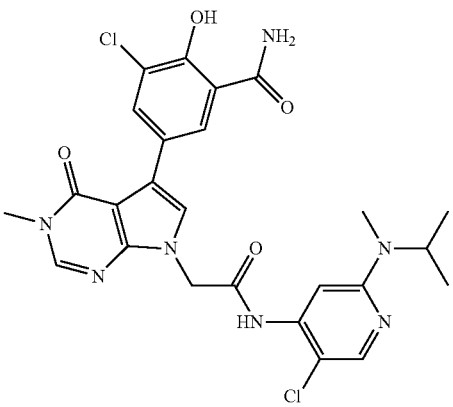 [SMILES: CC(C)N(C)c1cc(NC(=O)Cn2cc(-c3cc(Cl)c(O)c(C(N)=O)c3)c3c(=O)n(C)cnc32)c(Cl)cn1] | 100% |
| I-67 | 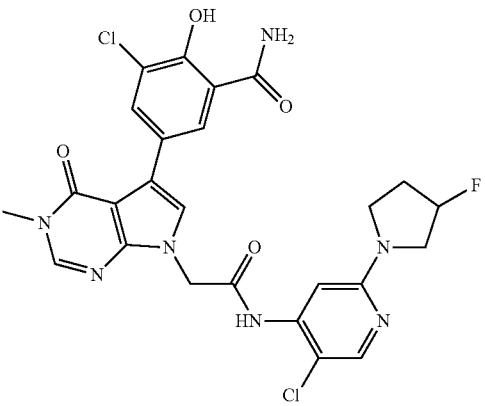 [SMILES: Cn1cnc2c(c(-c3cc(Cl)c(O)c(C(N)=O)c3)cn2CC(=O)Nc2cc(N3CCC(F)C3)ncc2Cl)c1=O] | 100% |

TABLE 1-continued
| Compound | Structure | Yield |
|---|---|---|
| I-68 | 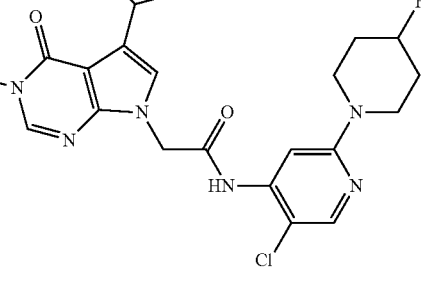 | 100% |
| I-69 | 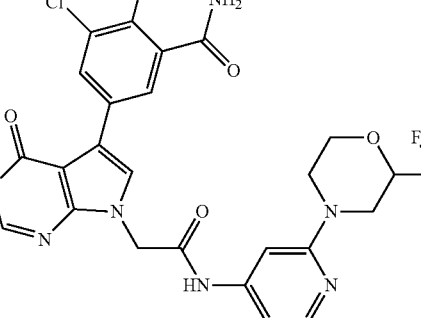 | 90% |
| I-70 | 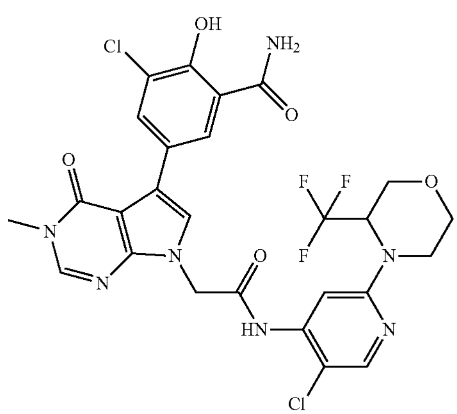 [SMILES: Cn1cnc2c(c(-c3cc(Cl)c(O)c(C(N)=O)c3)cn2CC(=O)Nc2cc(N3CCOCC3C(F)(F)F)ncc2Cl)c1=O] | 87% |
| I-71 | 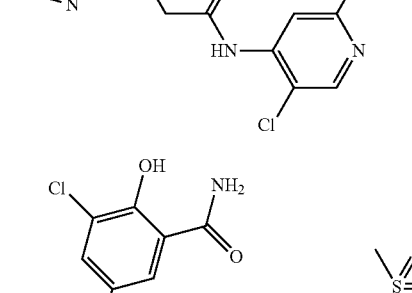 | 100% |

TABLE 1-continued

| Compound | Structure | Yield |
|---|---|---|
| I-72 | 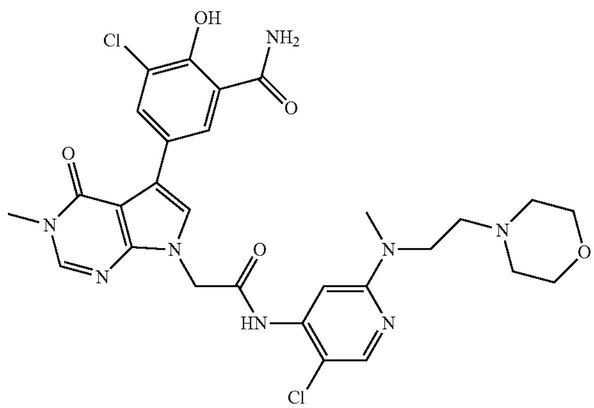 [SMILES: CN(CCN1CCOCC1)c1cc(NC(=O)Cn2cc(-c3cc(Cl)c(O)c(C(N)=O)c3)c3c(=O)n(C)cnc32)c(Cl)cn1] | 100% |
| I-73 | 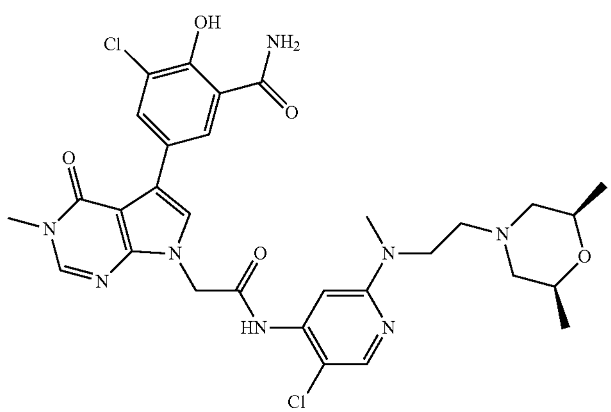 | 97% |
| I-74 | 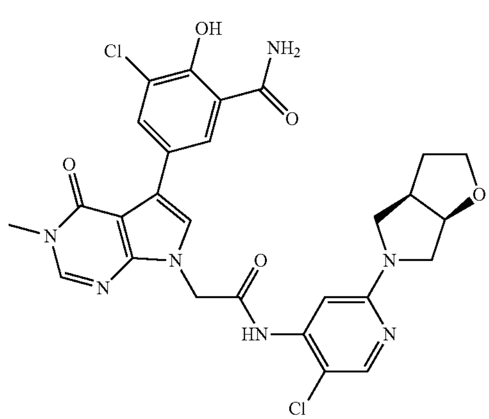 [SMILES: Cn1cnc2c(c(-c3cc(Cl)c(O)c(C(N)=O)c3)cn2CC(=O)Nc2cc(N3C[C@H]4CCO[C@H]4C3)ncc2Cl)c1=O] | 89% |

TABLE 1-continued

| Compound | Structure | Yield |
|---|---|---|
| I-75 | 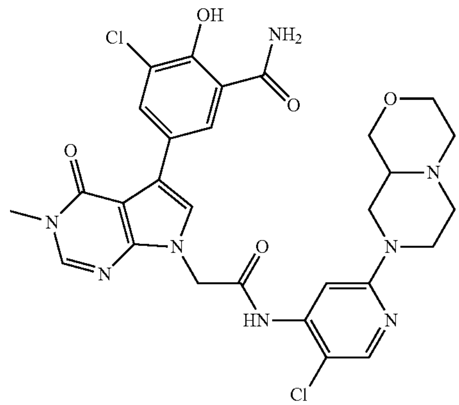 [SMILES: Cn1cnc2c(c(-c3cc(Cl)c(O)c(C(N)=O)c3)cn2CC(=O)Nc2cc(N3CCN4CCOCC4C3)ncc2Cl)c1=O] | 92% |
| I-76 | 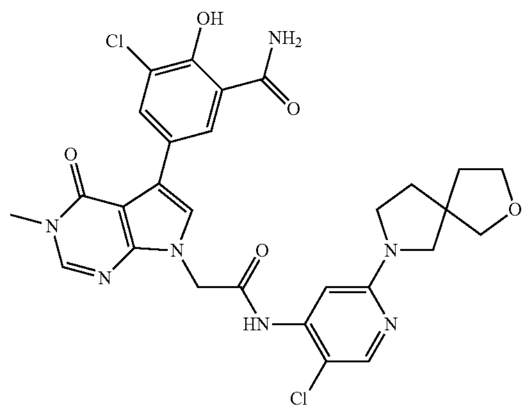 [SMILES: Cn1cnc2c(c(-c3cc(Cl)c(O)c(C(N)=O)c3)cn2CC(=O)Nc2cc(N3CCC4(CCOC4)C3)ncc2Cl)c1=O] | 90% |
| I-77 | 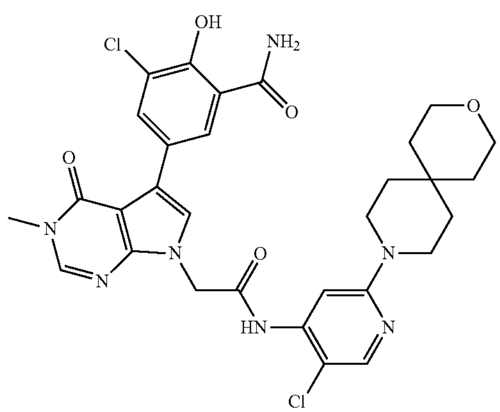 [SMILES: Cn1cnc2c(c(-c3cc(Cl)c(O)c(C(N)=O)c3)cn2CC(=O)Nc2cc(N3CCC4(CCOCC4)CC3)ncc2Cl)c1=O] | 88% |
| I-78 | 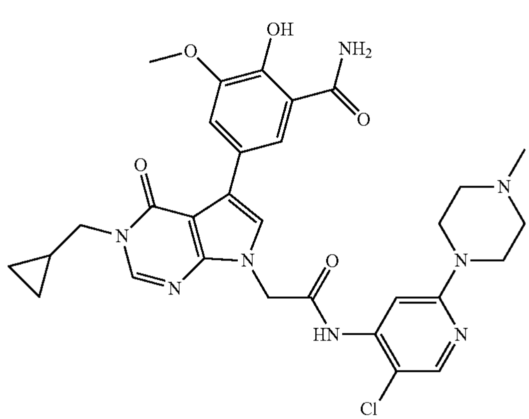 [SMILES: COc1cc(-c2cn(CC(=O)Nc3cc(N4CCN(C)CC4)ncc3Cl)c3ncn(CC4CC4)c(=O)c23)cc(C(N)=O)c1O] | 23% |

TABLE 1-continued

| Compound | Structure | Yield |
|---|---|---|
| I-79 | 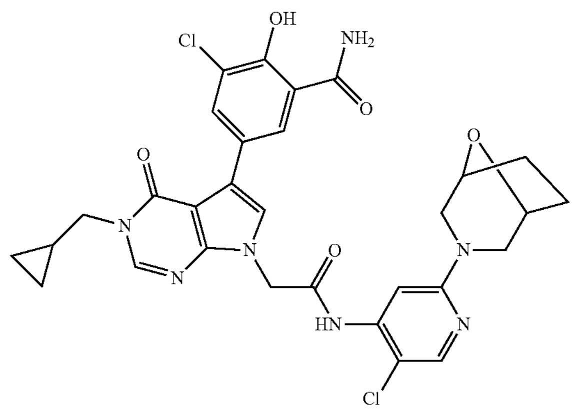 [SMILES: NC(=O)c1cc(-c2cn(CC(=O)Nc3cc(N4CC5CCC(C4)O5)ncc3Cl)c3ncn(CC4CC4)c(=O)c23)cc(Cl)c1O] | 22% |
| I-80 | 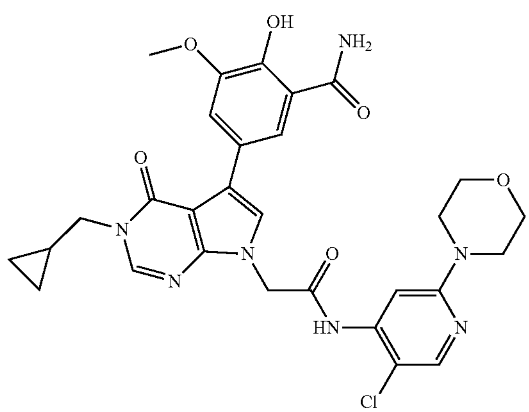 [SMILES: COc1cc(-c2cn(CC(=O)Nc3cc(N4CCOCC4)ncc3Cl)c3ncn(CC4CC4)c(=O)c23)cc(C(N)=O)c1O] | 30% |
| I-81 | 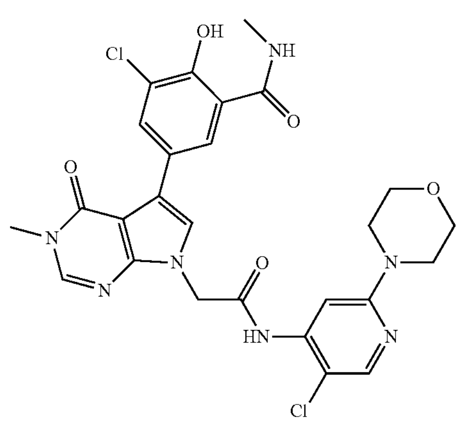 [SMILES: CNC(=O)c1cc(-c2cn(CC(=O)Nc3cc(N4CCOCC4)ncc3Cl)c3ncn(C)c(=O)c23)cc(Cl)c1O] | 20% |

TABLE 1-continued

| Compound | Structure | Yield |
|---|---|---|
| I-82 | 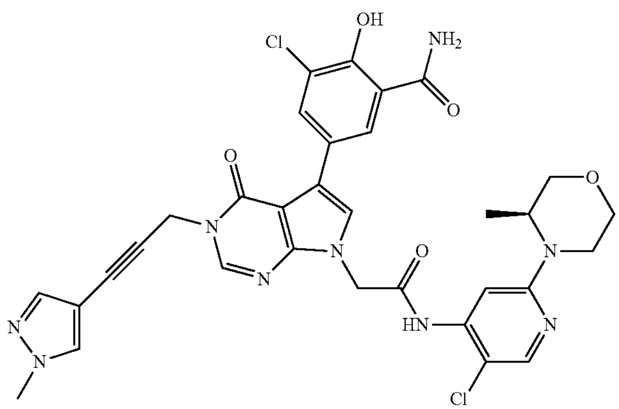 [SMILES: C[C@H]1COCCN1c1cc(NC(=O)Cn2cc(-c3cc(Cl)c(O)c(C(N)=O)c3)c3c(=O)n(CC#Cc4cnn(C)c4)cnc32)c(Cl)cn1] | 42% |
| I-83 | 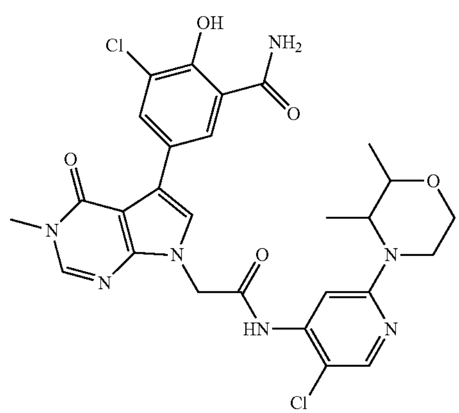 [SMILES: CC1OCCN(c2cc(NC(=O)Cn3cc(-c4cc(Cl)c(O)c(C(N)=O)c4)c4c(=O)n(C)cnc43)c(Cl)cn2)C1C] | 72% |
| I-84 | 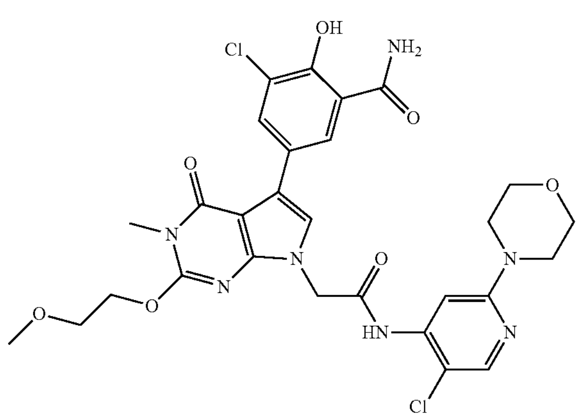 [SMILES: COCCOc1nc2c(c(-c3cc(Cl)c(O)c(C(N)=O)c3)cn2CC(=O)Nc2cc(N3CCOCC3)ncc2Cl)c(=O)n1C] | 96% |

TABLE 1-continued

| Compound | Structure | Yield |
|---|---|---|
| I-85 | 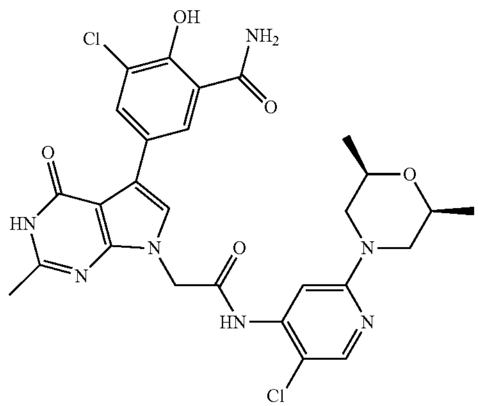 | 43% |
| I-86 | 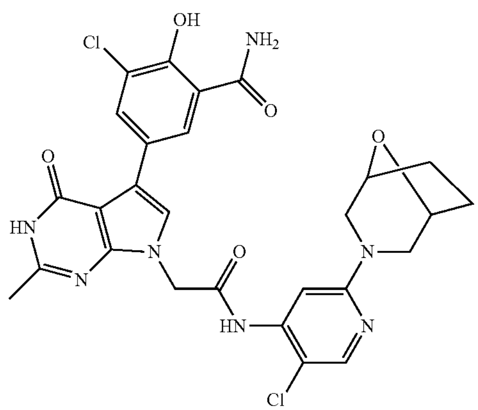 [SMILES: Cc1nc2c(c(-c3cc(Cl)c(O)c(C(N)=O)c3)cn2CC(=O)Nc2cc(N3CC4CCC(C3)O4)ncc2Cl)c(=O)[nH]1] | 34% |
| I-87 | 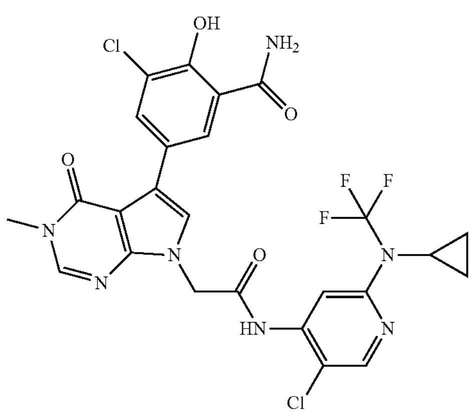 [SMILES: Cn1cnc2c(c(-c3cc(Cl)c(O)c(C(N)=O)c3)cn2CC(=O)Nc2cc(N(C3CC3)C(F)(F)F)ncc2Cl)c1=O] | 100% |
| I-88 | 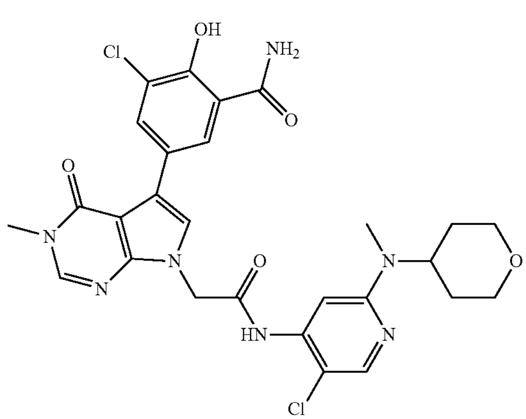 [SMILES: CN(c1cc(NC(=O)Cn2cc(-c3cc(Cl)c(O)c(C(N)=O)c3)c3c(=O)n(C)cnc32)c(Cl)cn1)C1CCOCC1] | 77% |

TABLE 1-continued

| Compound | Structure | Yield |
|---|---|---|
| I-89 | 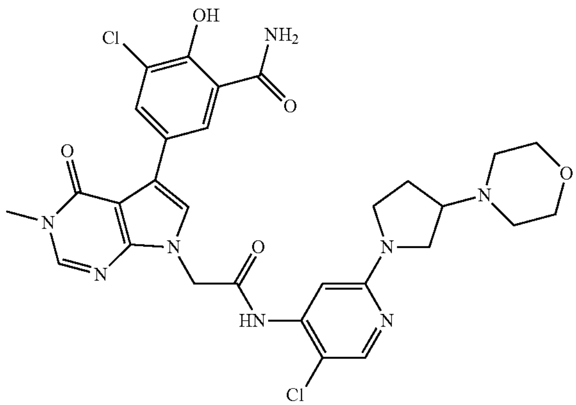 [SMILES: Cn1cnc2c(c(-c3cc(Cl)c(O)c(C(N)=O)c3)cn2CC(=O)Nc2cc(N3CCC(N4CCOCC4)C3)ncc2Cl)c1=O] | 77% |
| I-90 | 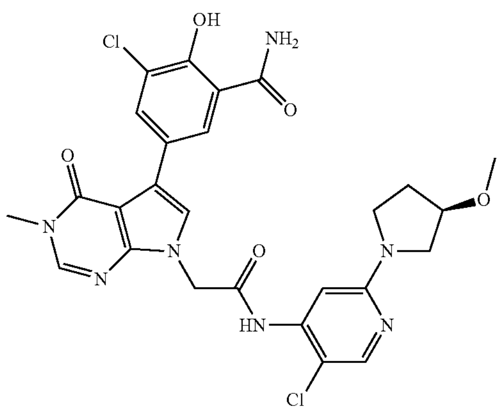 | 36% |
| I-91 | 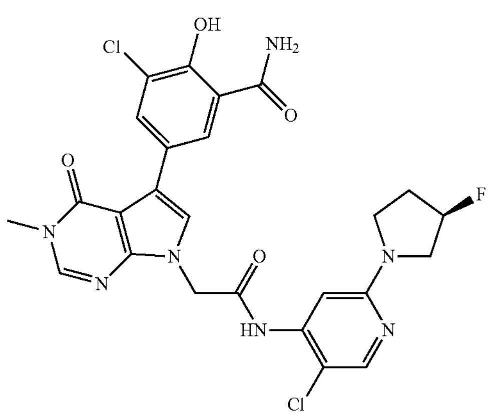 [SMILES: Cn1cnc2c(c(-c3cc(Cl)c(O)c(C(N)=O)c3)cn2CC(=O)Nc2cc(N3CC[C@@H](F)C3)ncc2Cl)c1=O] | 100% |

TABLE 1-continued

| Compound | Structure | Yield |
|---|---|---|
| I-92 | 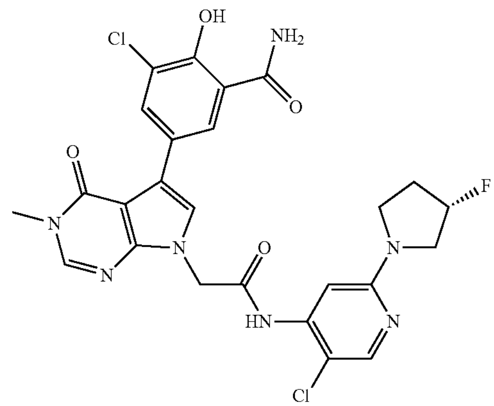 | 100% |
| I-93 | 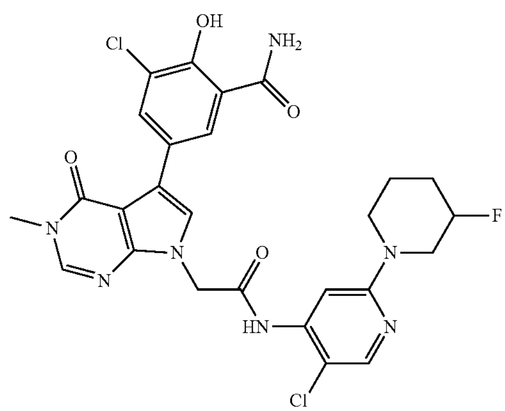 [SMILES: Cn1cnc2c(c(-c3cc(Cl)c(O)c(C(N)=O)c3)cn2CC(=O)Nc2cc(N3CCCC(F)C3)ncc2Cl)c1=O] | 100% |
| I-94 | 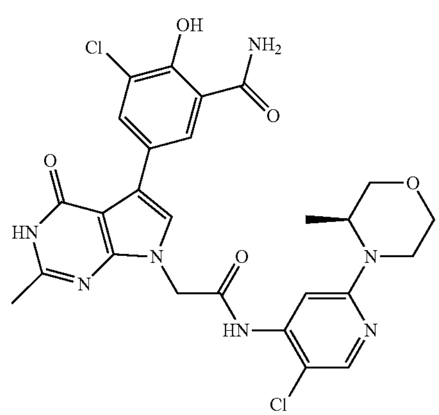 [SMILES: Cc1nc2c(c(-c3cc(Cl)c(O)c(C(N)=O)c3)cn2CC(=O)Nc2cc(N3CCOC[C@@H]3C)ncc2Cl)c(=O)[nH]1] | 39% |

TABLE 1-continued
| Compound | Structure | Yield |
|---|---|---|
| I-95 | 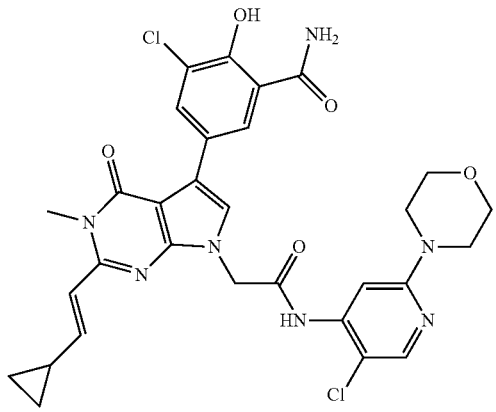 [SMILES: Cn1c(/C=C/C2CC2)nc2c(c(-c3cc(Cl)c(O)c(C(N)=O)c3)cn2CC(=O)Nc2cc(N3CCOCC3)ncc2Cl)c1=O] | 92% |
| I-96 | 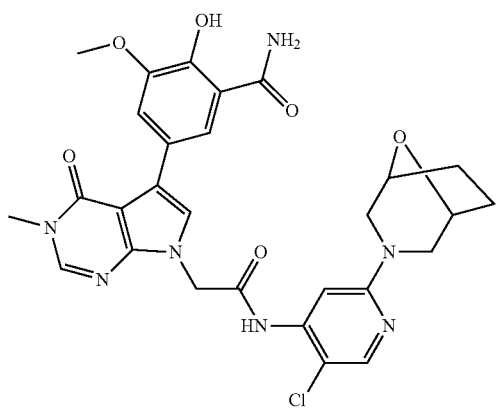 [SMILES: COc1cc(-c2cn(CC(=O)Nc3cc(N4CC5CCC(C4)O5)ncc3Cl)c3ncn(C)c(=O)c23)cc(C(N)=O)c1O] | 9% |
| I-97 | 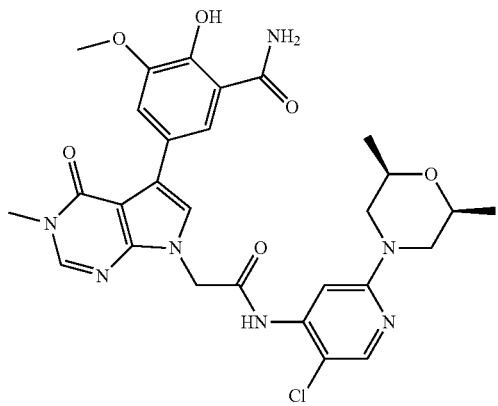 | 15% |

TABLE 1-continued

| Compound | Structure | Yield |
|---|---|---|
| I-98 | 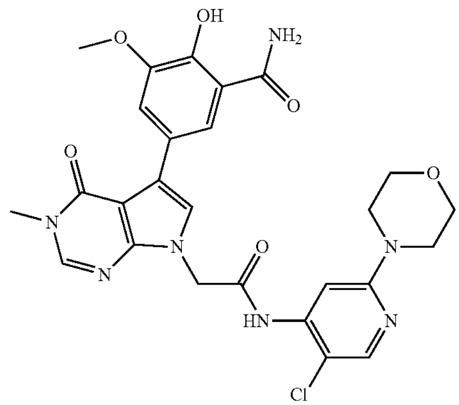 [SMILES: COc1cc(-c2cn(CC(=O)Nc3cc(N4CCOCC4)ncc3Cl)c3ncn(C)c(=O)c23)cc(C(N)=O)c1O] | 14% |
| I-99 | 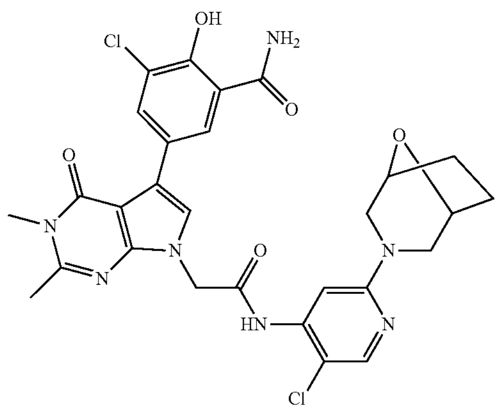 [SMILES: Cc1nc2c(c(-c3cc(Cl)c(O)c(C(N)=O)c3)cn2CC(=O)Nc2cc(N3CC4CCC(C3)O4)ncc2Cl)c(=O)n1C] | 34% |
| I-100 | 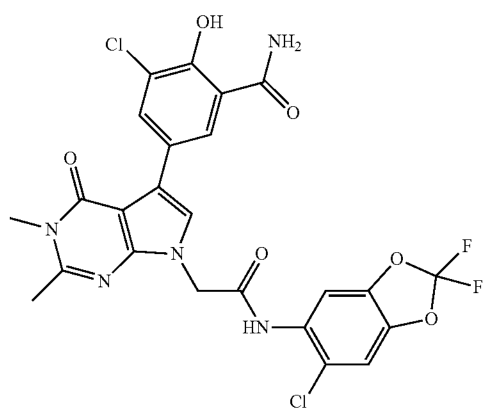 | 61% |
| I-101 | 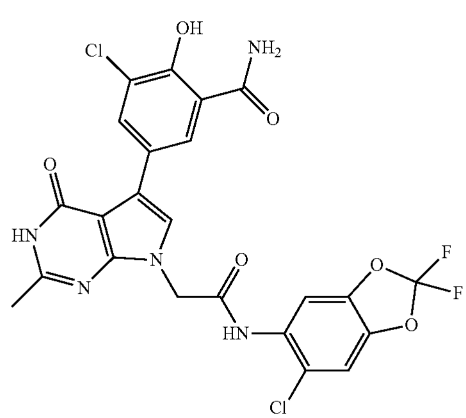 [SMILES: Cc1nc2c(c(-c3cc(Cl)c(O)c(C(N)=O)c3)cn2CC(=O)Nc2cc3c(cc2Cl)OC(F)(F)O3)c(=O)[nH]1] | 63% |

TABLE 1-continued
| Compound | Structure | Yield |
|---|---|---|
| I-102 | 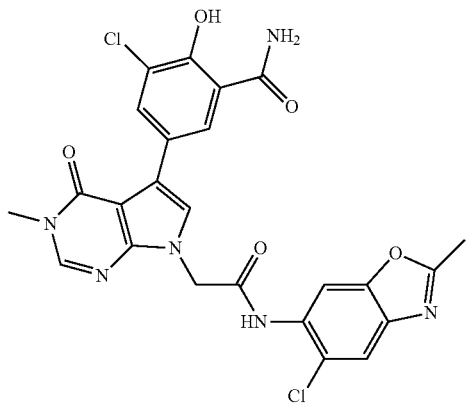 | 83% |
| I-103 | 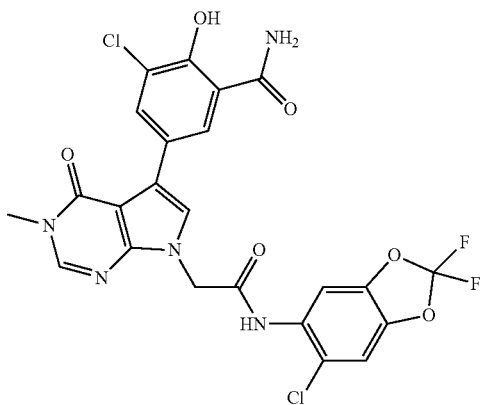 | 99% |
| I-104 | 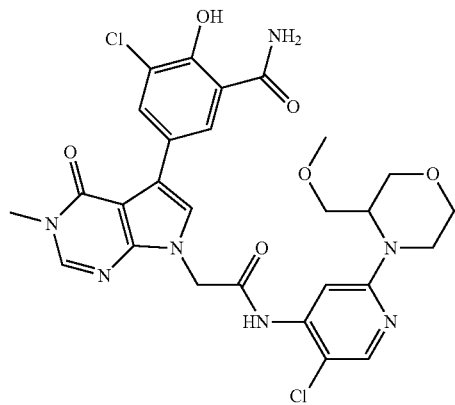 | 66% |

TABLE 1-continued

| Compound | Structure | Yield |
| --- | --- | --- |
| I-105 | 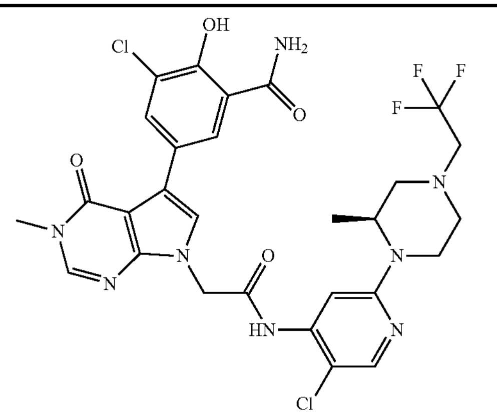 | 69% |
| I-106 | 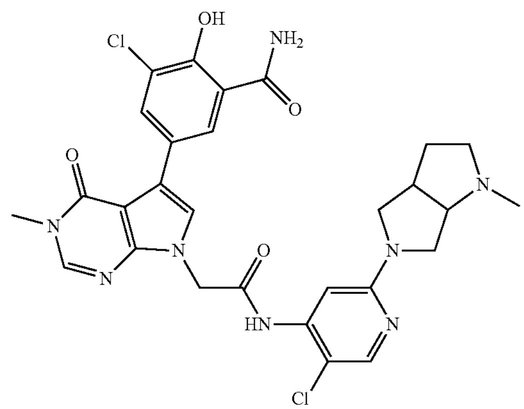 | 85% |
| I-107 | 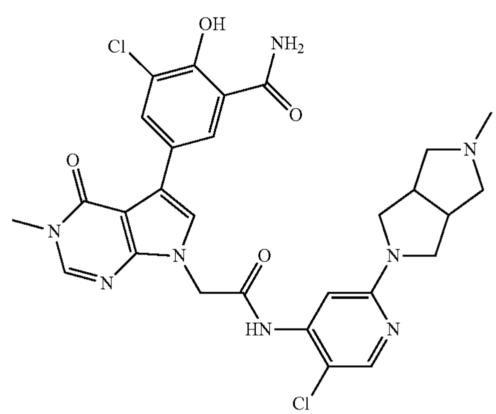 | 73% |
| I-108 | 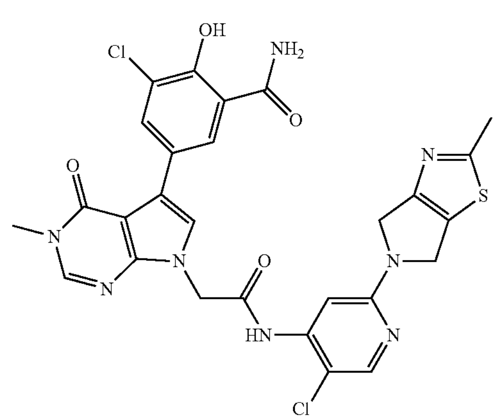 | 87% |

TABLE 1-continued

| Compound | Structure | Yield |
|---|---|---|
| I-109 | 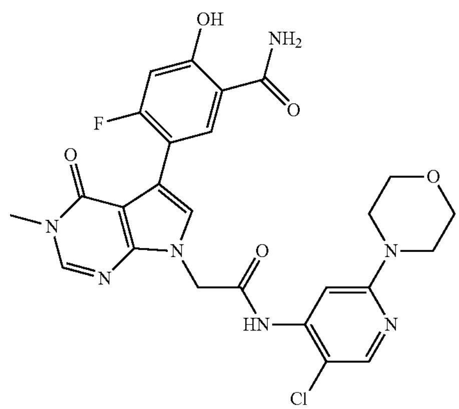 | 51% |
| I-110 | 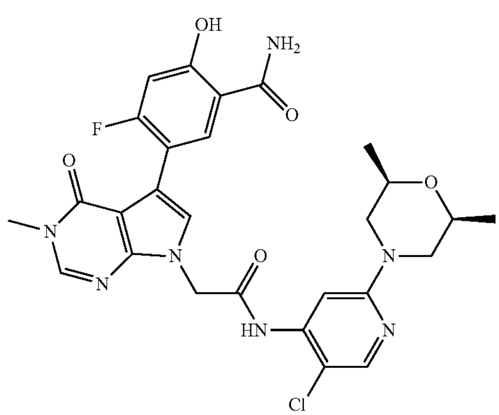 | 51% |
| I-111 | 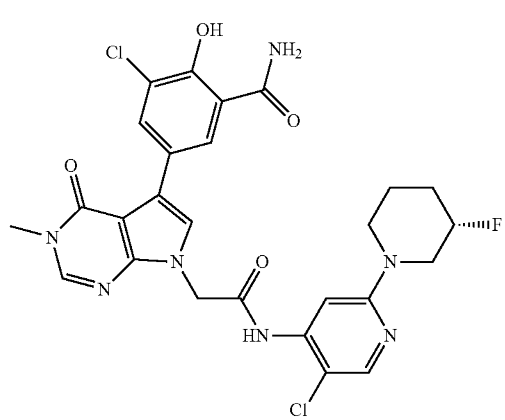 | 100% |

TABLE 1-continued

| Compound | Structure | Yield |
|---|---|---|
| I-112 | 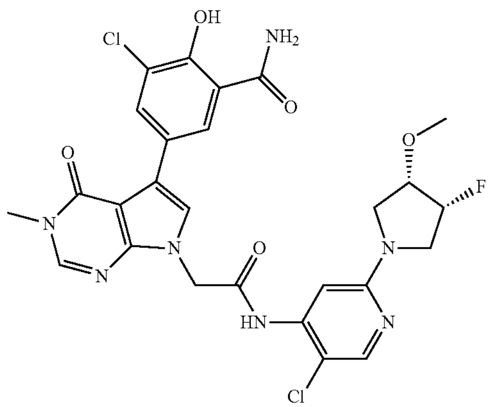 [SMILES: CO[C@H]1CN(c2cc(NC(=O)Cn3cc(-c4cc(Cl)c(O)c(C(N)=O)c4)c4c(=O)n(C)cnc43)c(Cl)cn2)C[C@H]1F] | 100% |
| I-113 | 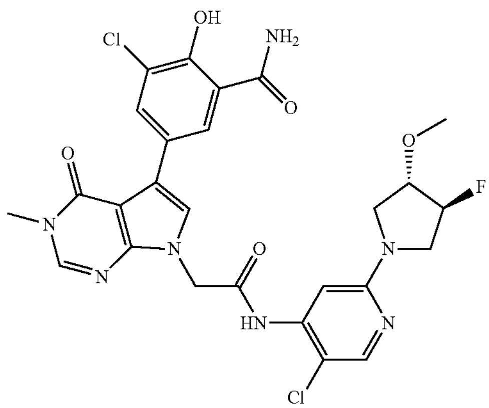 [SMILES: CO[C@H]1CN(c2cc(NC(=O)Cn3cc(-c4cc(Cl)c(O)c(C(N)=O)c4)c4c(=O)n(C)cnc43)c(Cl)cn2)C[C@@H]1F] | 100% |
| I-114 | 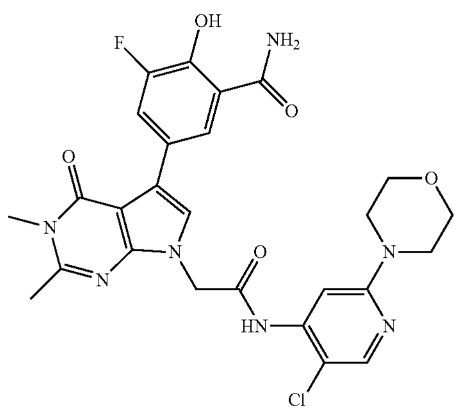 [SMILES: Cc1nc2c(c(-c3cc(F)c(O)c(C(N)=O)c3)cn2CC(=O)Nc2cc(N3CCOCC3)ncc2Cl)c(=O)n1C] | 43% |
| I-115 | 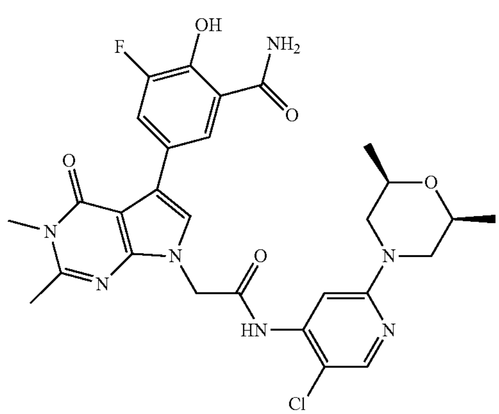 | 26% |

TABLE 1-continued
| Compound | Structure | Yield |
|---|---|---|
| I-116 | 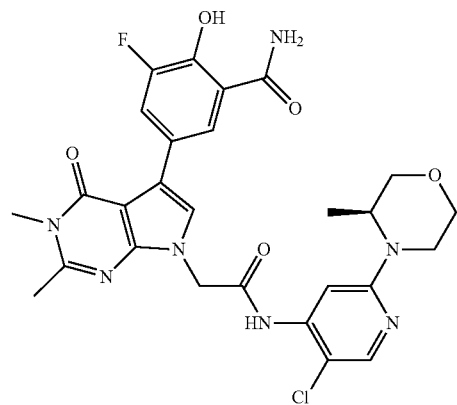 [SMILES: Cc1nc2c(c(-c3cc(F)c(O)c(C(N)=O)c3)cn2CC(=O)Nc2cc(N3CCOC[C@@H]3C)ncc2Cl)c(=O)n1C] | 38% |
| I-117 | 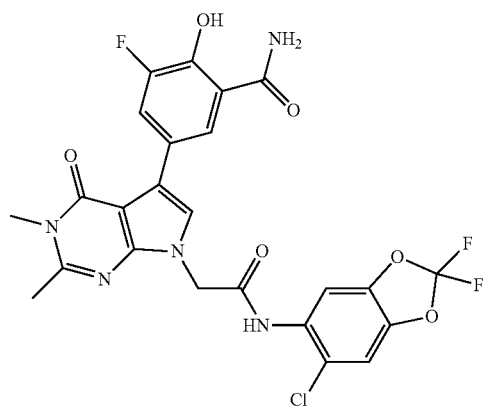 [SMILES: Cc1nc2c(c(-c3cc(F)c(O)c(C(N)=O)c3)cn2CC(=O)Nc2cc3c(cc2Cl)OC(F)(F)O3)c(=O)n1C] | 13% |
| I-118 | 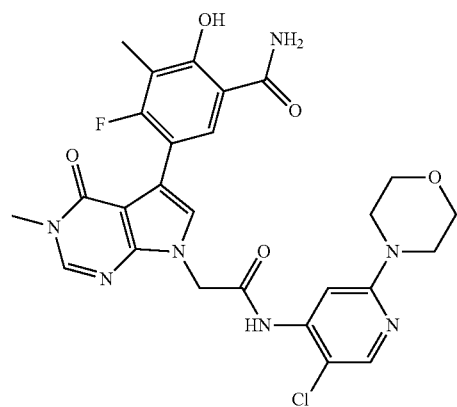 | 99% |

TABLE 1-continued

| Compound | Structure | Yield |
|---|---|---|
| I-119 | 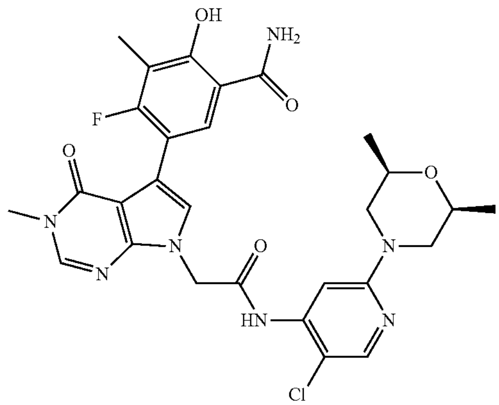 | 80% |
| I-120 | 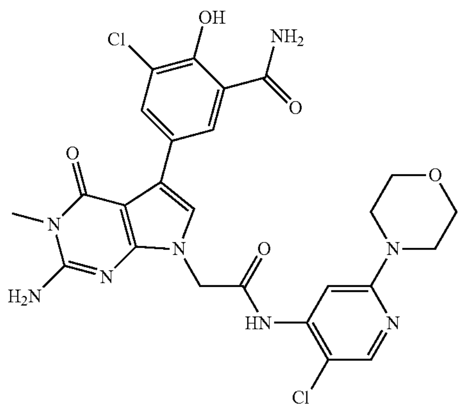 [SMILES: Cn1c(N)nc2c(c(-c3cc(Cl)c(O)c(C(N)=O)c3)cn2CC(=O)Nc2cc(N3CCOCC3)ncc2Cl)c1=O] | 72% |
| I-121 | 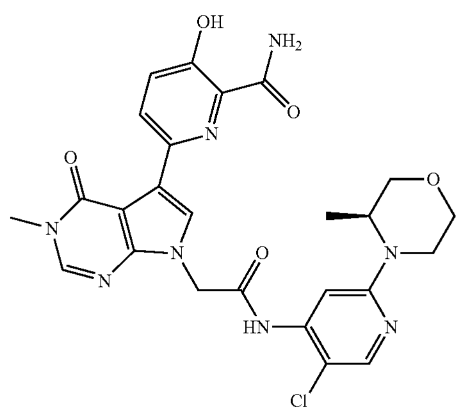 [SMILES: C[C@H]1COCCN1c1cc(NC(=O)Cn2cc(-c3ccc(O)c(C(N)=O)n3)c3c(=O)n(C)cnc32)c(Cl)cn1] | 23% |
| I-122 | 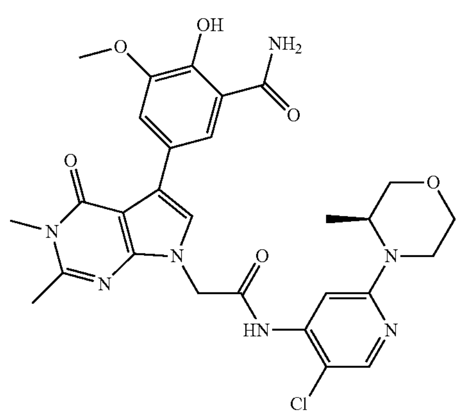 [SMILES: COc1cc(-c2cn(CC(=O)Nc3cc(N4CCOC[C@@H]4C)ncc3Cl)c3nc(C)n(C)c(=O)c23)cc(C(N)=O)c1O] | 36% |

TABLE 1-continued

| Compound | Structure | Yield |
|---|---|---|
| I-123 | 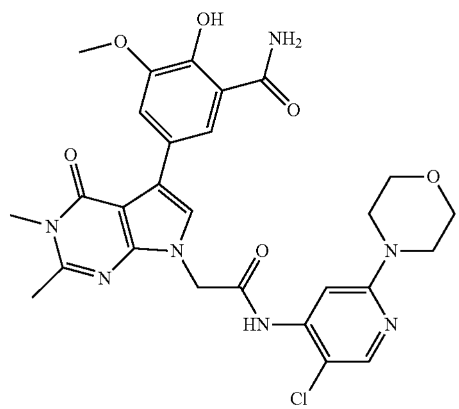 [SMILES: COc1cc(-c2cn(CC(=O)Nc3cc(N4CCOCC4)ncc3Cl)c3nc(C)n(C)c(=O)c23)cc(C(N)=O)c1O] | 32% |
| I-124 | 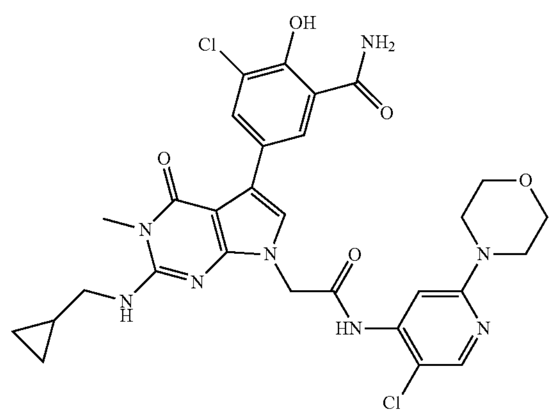 [SMILES: Cn1c(NCC2CC2)nc2c(c(-c3cc(Cl)c(O)c(C(N)=O)c3)cn2CC(=O)Nc2cc(N3CCOCC3)ncc2Cl)c1=O] | 80% |
| I-125 | 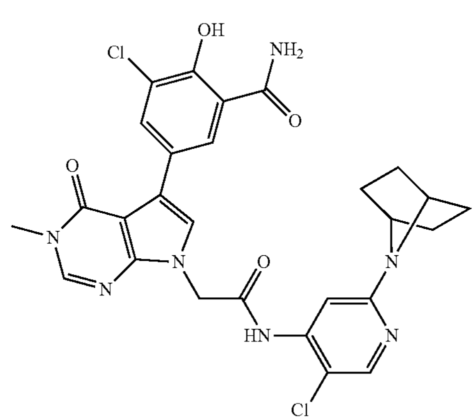 [SMILES: Cn1cnc2c(c(-c3cc(Cl)c(O)c(C(N)=O)c3)cn2CC(=O)Nc2cc(N3C4CCC3CC4)ncc2Cl)c1=O] | 82% |

TABLE 1-continued

| Compound | Structure | Yield |
|---|---|---|
| I-126 | 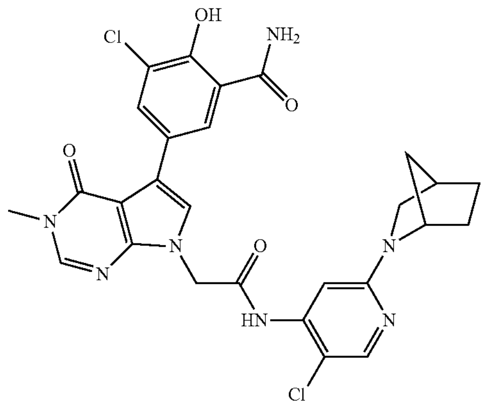 [SMILES: Cn1cnc2c(c(-c3cc(Cl)c(O)c(C(N)=O)c3)cn2CC(=O)Nc2cc(N3CC4CCC3C4)ncc2Cl)c1=O] | 52% |
| I-127 | 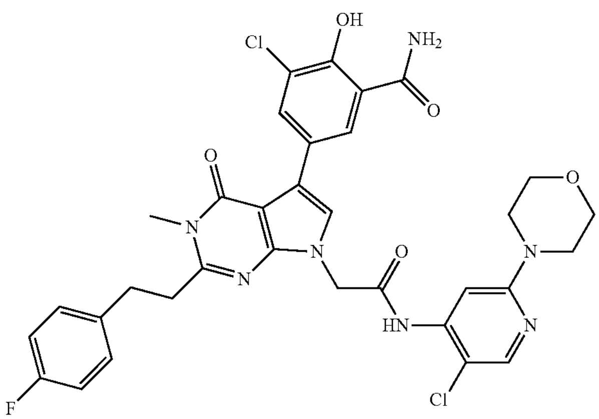 [SMILES: Cn1c(CCc2ccc(F)cc2)nc2c(c(-c3cc(Cl)c(O)c(C(N)=O)c3)cn2CC(=O)Nc2cc(N3CCOCC3)ncc2Cl)c1=O] | 77% |
| I-128 | 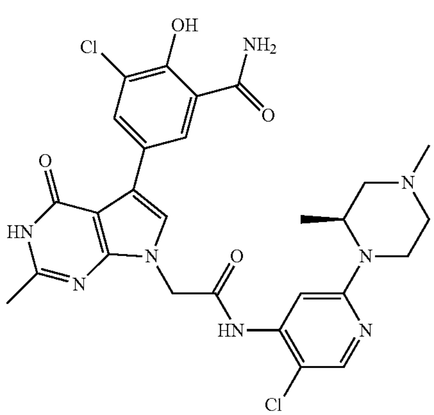 | 51% |

TABLE 1-continued

| Compound | Structure | Yield |
|---|---|---|
| I-129 | 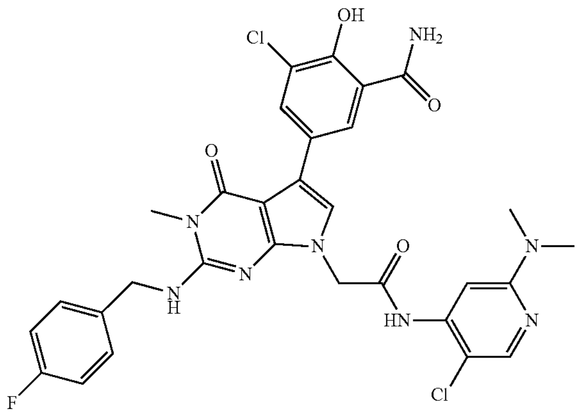 [SMILES: CN(C)c1cc(NC(=O)Cn2cc(-c3cc(Cl)c(O)c(C(N)=O)c3)c3c(=O)n(C)c(NCc4ccc(F)cc4)nc32)c(Cl)cn1] | 85% |
| I-130 | 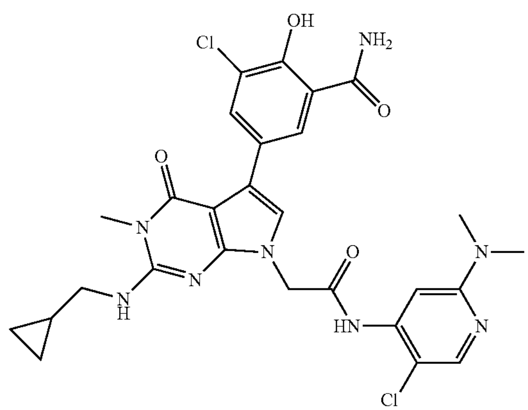 [SMILES: CN(C)c1cc(NC(=O)Cn2cc(-c3cc(Cl)c(O)c(C(N)=O)c3)c3c(=O)n(C)c(NCC4CC4)nc32)c(Cl)cn1] | 85% |
| I-131 | 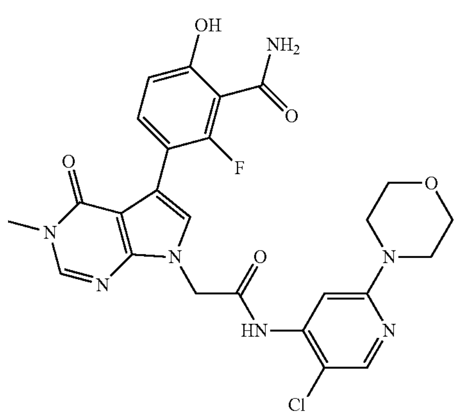 [SMILES: Cn1cnc2c(c(-c3ccc(O)c(C(N)=O)c3F)cn2CC(=O)Nc2cc(N3CCOCC3)ncc2Cl)c1=O] | 78% |

TABLE 1-continued

| Compound | Structure | Yield |
|---|---|---|
| I-132 | 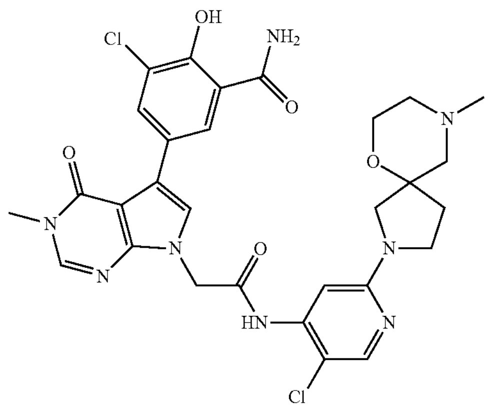 | 64% |
| I-133 | 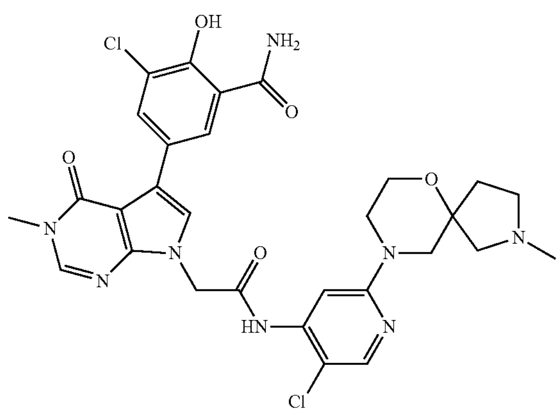 | 52% |
| I-134 | 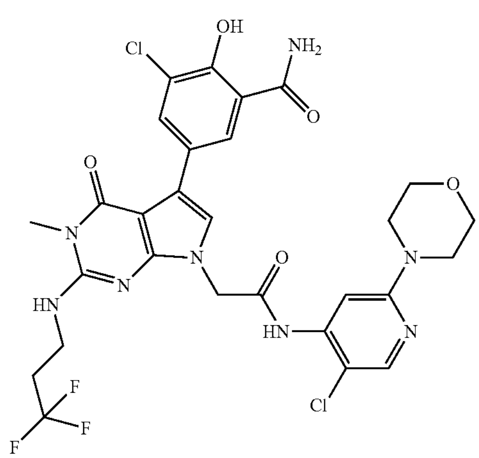 [SMILES: Cn1c(NCCC(F)(F)F)nc2c(c(-c3cc(Cl)c(O)c(C(N)=O)c3)cn2CC(=O)Nc2cc(N3CCOCC3)ncc2Cl)c1=O] | 74% |

TABLE 1-continued

| Compound | Structure | Yield |
|---|---|---|
| I-135 | 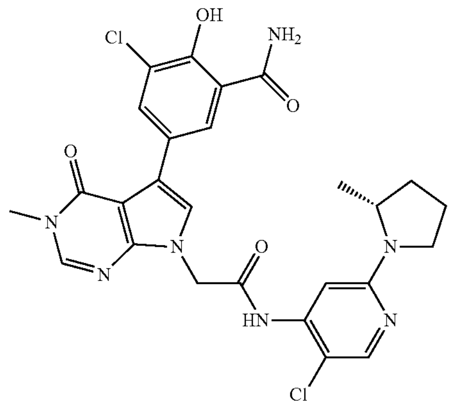 [SMILES: C[C@@H]1CCCN1c1cc(NC(=O)Cn2cc(-c3cc(Cl)c(O)c(C(N)=O)c3)c3c(=O)n(C)cnc32)c(Cl)cn1] | 100% |
| I-136 | 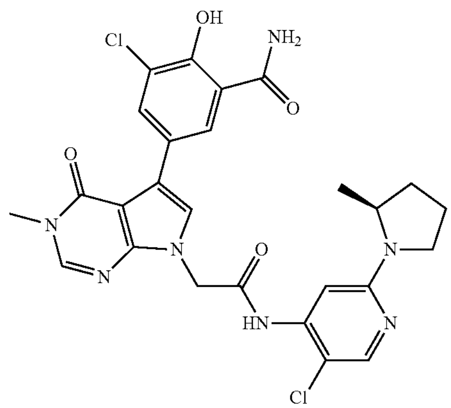 [SMILES: C[C@H]1CCCN1c1cc(NC(=O)Cn2cc(-c3cc(Cl)c(O)c(C(N)=O)c3)c3c(=O)n(C)cnc32)c(Cl)cn1] | 100% |
| I-137 | 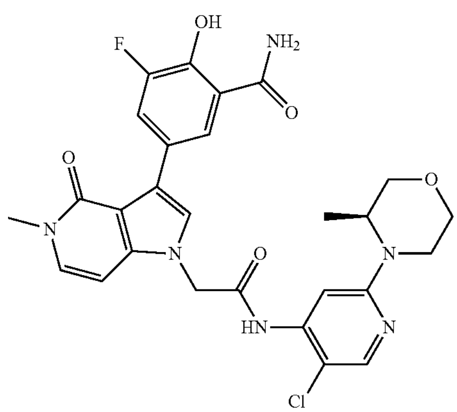 [SMILES: C[C@H]1COCCN1c1cc(NC(=O)Cn2cc(-c3cc(F)c(O)c(C(N)=O)c3)c3c(=O)n(C)ccc32)c(Cl)cn1] | 31% |
| I-138 | 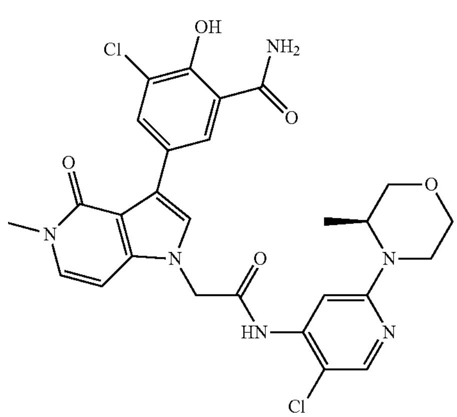 [SMILES: C[C@H]1COCCN1c1cc(NC(=O)Cn2cc(-c3cc(Cl)c(O)c(C(N)=O)c3)c3c(=O)n(C)ccc32)c(Cl)cn1] | 40% |

TABLE 1-continued

| Compound | Structure | Yield |
|---|---|---|
| I-139 | 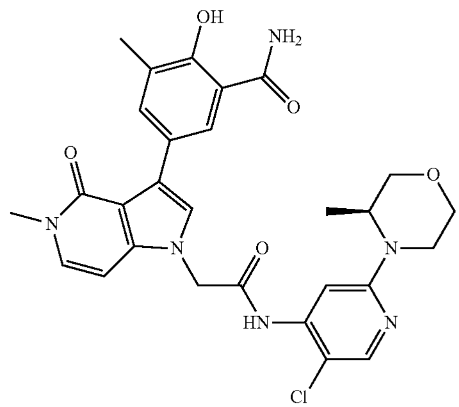 [SMILES: Cc1cc(-c2cn(CC(=O)Nc3cc(N4CCOC[C@@H]4C)ncc3Cl)c3ccn(C)c(=O)c23)cc(C(N)=O)c1O] | 6% |
| I-140 | 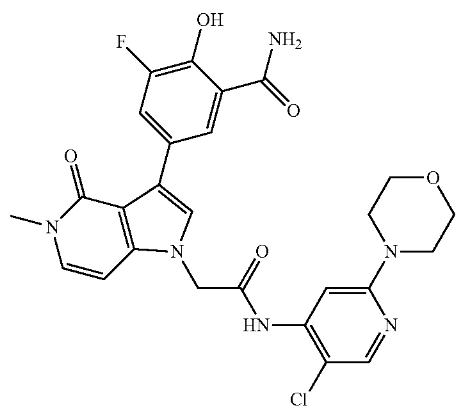 [SMILES: Cn1ccc2c(c(-c3cc(F)c(O)c(C(N)=O)c3)cn2CC(=O)Nc2cc(N3CCOCC3)ncc2Cl)c1=O] | 26% |
| I-141 | 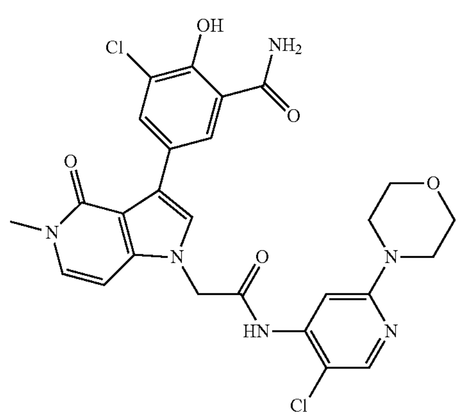 | 16% |

TABLE 1-continued

| Compound | Structure | Yield |
|---|---|---|
| I-142 | 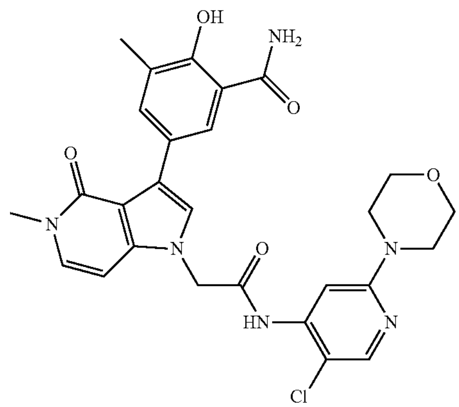 [SMILES: Cc1cc(-c2cn(CC(=O)Nc3cc(N4CCOCC4)ncc3Cl)c3ccn(C)c(=O)c23)cc(C(N)=O)c1O] | 20% |
| I-143 | 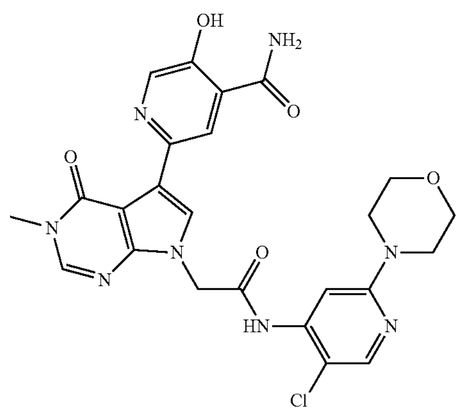 [SMILES: Cn1cnc2c(c(-c3cc(C(N)=O)c(O)cn3)cn2CC(=O)Nc2cc(N3CCOCC3)ncc2Cl)c1=O] | 68% |
| I-144 | 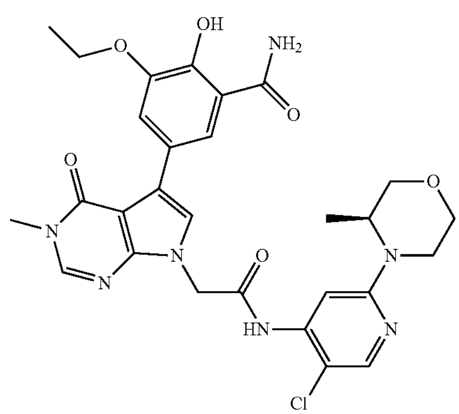 [SMILES: CCOc1cc(-c2cn(CC(=O)Nc3cc(N4CCOC[C@@H]4C)ncc3Cl)c3ncn(C)c(=O)c23)cc(C(N)=O)c1O] | 82% |
| I-145 | 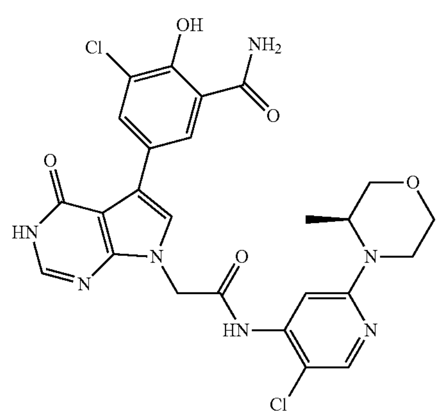 [SMILES: C[C@H]1COCCN1c1cc(NC(=O)Cn2cc(-c3cc(Cl)c(O)c(C(N)=O)c3)c3c(=O)[nH]cnc32)c(Cl)cn1] | 68% |

TABLE 1-continued

| Compound | Structure | Yield |
|---|---|---|
| I-146 | 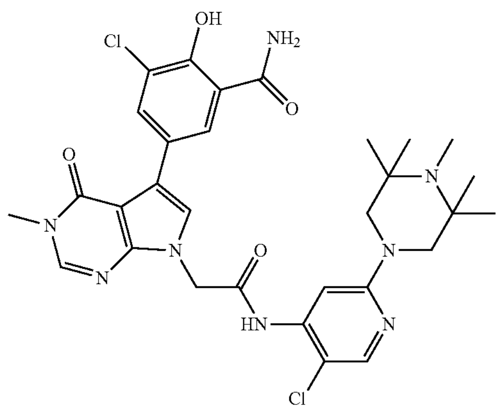 | 79% |
| I-147 | 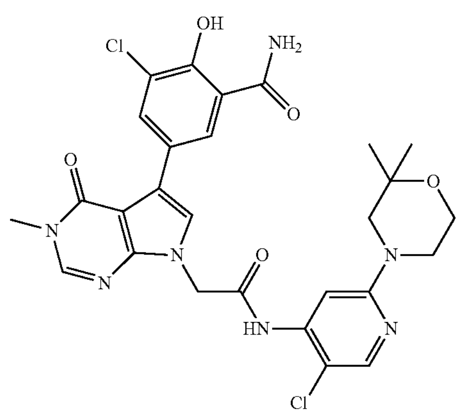 [SMILES: Cn1cnc2c(c(-c3cc(Cl)c(O)c(C(N)=O)c3)cn2CC(=O)Nc2cc(N3CCOC(C)(C)C3)ncc2Cl)c1=O] | 52% |
| I-148 | 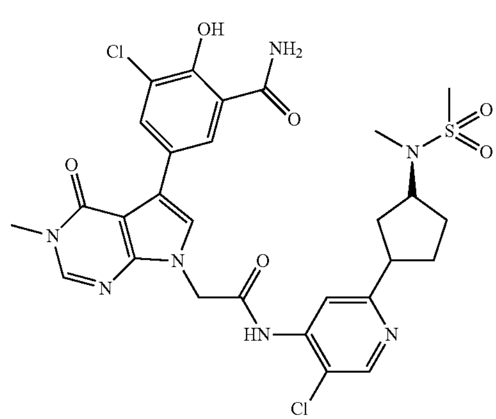 | 84% |

TABLE 1-continued
| Compound | Structure | Yield |
|---|---|---|
| I-149 | 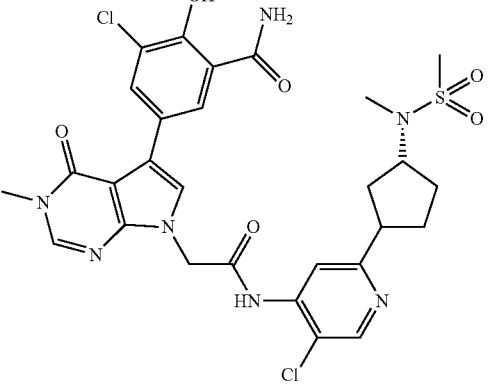 | 85% |
| I-150 | 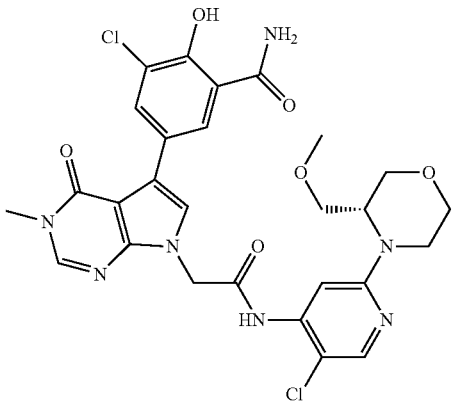 [SMILES: COC[C@@H]1COCCN1c1cc(NC(=O)Cn2cc(-c3cc(Cl)c(O)c(C(N)=O)c3)c3c(=O)n(C)cnc32)c(Cl)cn1] | 88% |
| I-151 | 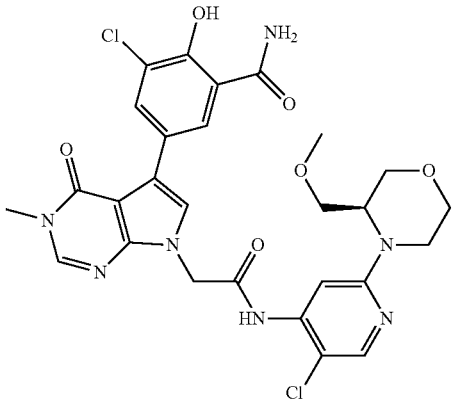 [SMILES: COC[C@H]1COCCN1c1cc(NC(=O)Cn2cc(-c3cc(Cl)c(O)c(C(N)=O)c3)c3c(=O)n(C)cnc32)c(Cl)cn1] | 44% |
| I-152 | 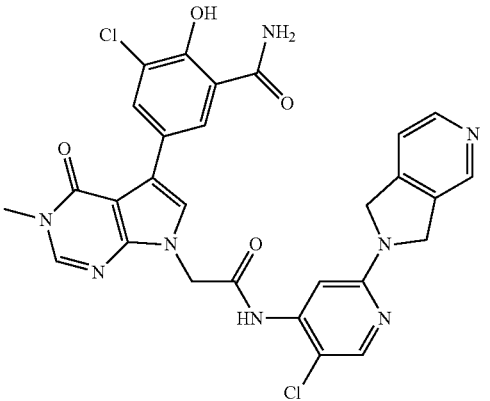 [SMILES: Cn1cnc2c(c(-c3cc(Cl)c(O)c(C(N)=O)c3)cn2CC(=O)Nc2cc(N3Cc4ccncc4C3)ncc2Cl)c1=O] | 89% |

TABLE 1-continued

| Compound | Structure | Yield |
|---|---|---|
| I-153 | 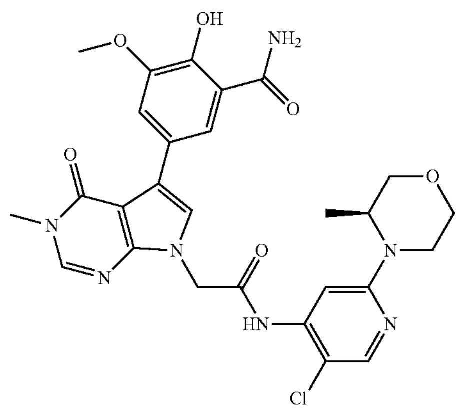 [SMILES: COc1cc(-c2cn(CC(=O)Nc3cc(N4CCOC[C@@H]4C)ncc3Cl)c3ncn(C)c(=O)c23)cc(C(N)=O)c1O] | 84% |
| I-154 | 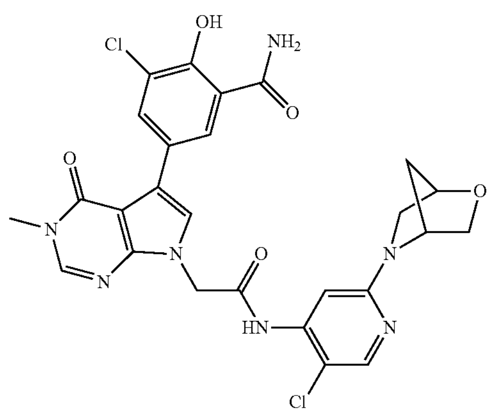 [SMILES: Cn1cnc2c(c(-c3cc(Cl)c(O)c(C(N)=O)c3)cn2CC(=O)Nc2cc(N3CC4CC3CO4)ncc2Cl)c1=O] | 92% |
| I-155 | 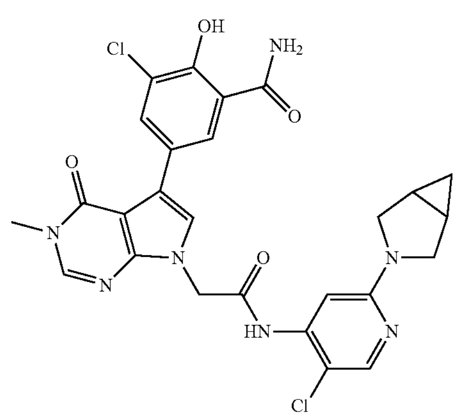 [SMILES: Cn1cnc2c(c(-c3cc(Cl)c(O)c(C(N)=O)c3)cn2CC(=O)Nc2cc(N3CC4CC4C3)ncc2Cl)c1=O] | 49% |

TABLE 1-continued

| Compound | Structure | Yield |
|---|---|---|
| I-156 | 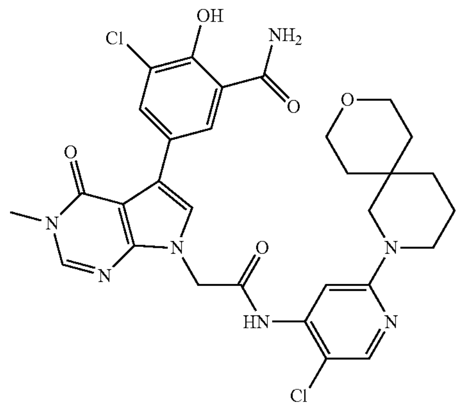 [SMILES: Cn1cnc2c(c(-c3cc(Cl)c(O)c(C(N)=O)c3)cn2CC(=O)Nc2cc(N3CCCC4(CCOCC4)C3)ncc2Cl)c1=O] | 96% |
| I-157 | 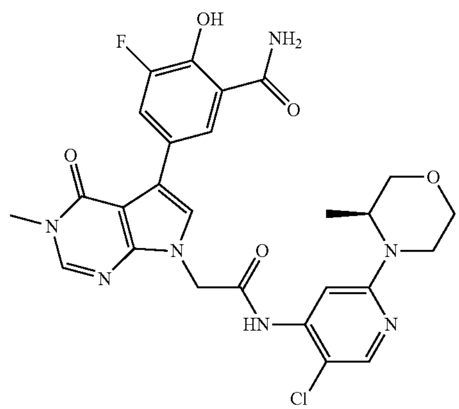 [SMILES: C[C@H]1COCCN1c1cc(NC(=O)Cn2cc(-c3cc(F)c(O)c(C(N)=O)c3)c3c(=O)n(C)cnc32)c(Cl)cn1] | 91% |
| I-158 | 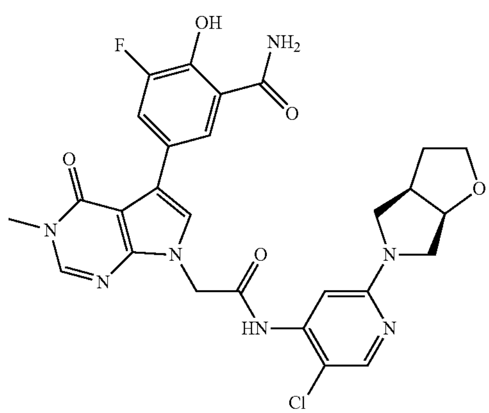 [SMILES: Cn1cnc2c(c(-c3cc(F)c(O)c(C(N)=O)c3)cn2CC(=O)Nc2cc(N3C[C@H]4CCO[C@H]4C3)ncc2Cl)c1=O] | 93% |
| I-159 | 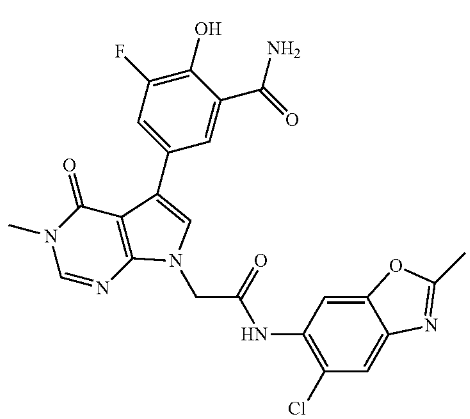 | 77% |

TABLE 1-continued
| Compound | Structure | Yield |
|---|---|---|
| I-160 | 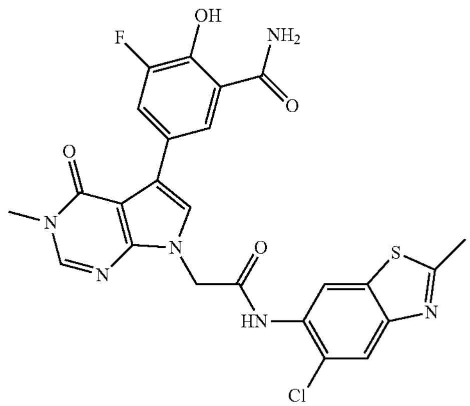 | 78% |
| I-161 | 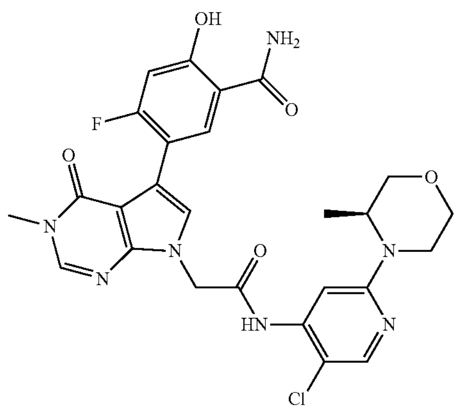 [SMILES: C[C@H]1COCCN1c1cc(NC(=O)Cn2cc(-c3cc(C(N)=O)c(O)cc3F)c3c(=O)n(C)cnc32)c(Cl)cn1] | 75% |
| I-162 | 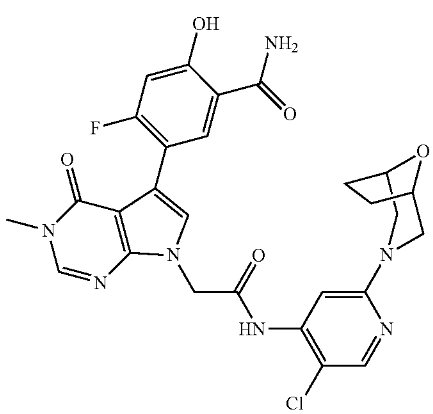 [SMILES: Cn1cnc2c(c(-c3cc(C(N)=O)c(O)cc3F)cn2CC(=O)Nc2cc(N3CC4CCC(C3)O4)ncc2Cl)c1=O] | 92% |

TABLE 1-continued
| Compound | Structure | Yield |
|---|---|---|
| I-163 | 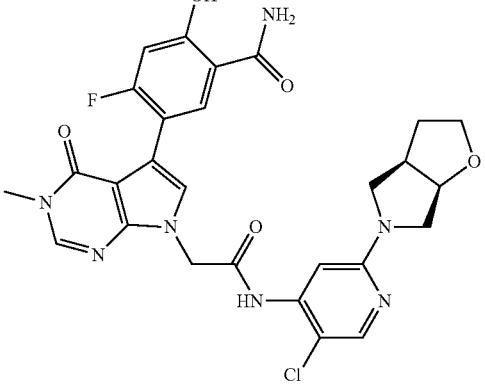 | 54% |
| I-164 | 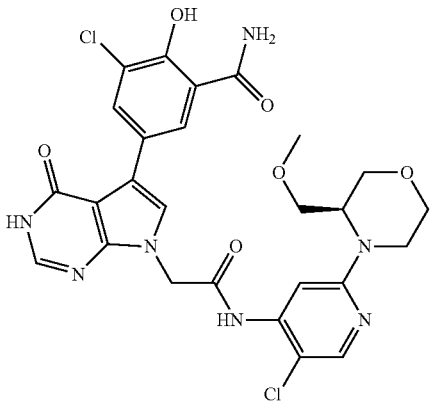 [SMILES: COC[C@H]1COCCN1c1cc(NC(=O)Cn2cc(-c3cc(Cl)c(O)c(C(N)=O)c3)c3c(=O)[nH]cnc32)c(Cl)cn1] | 92% |
| I-165 | 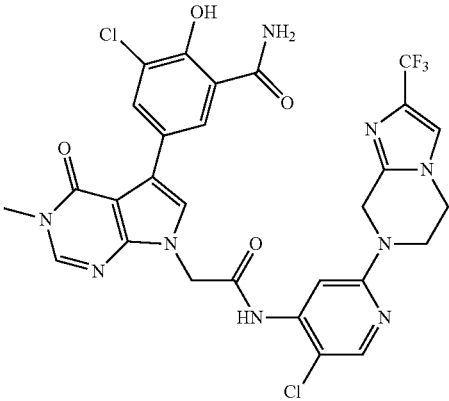 [SMILES: Cn1cnc2c(c(-c3cc(Cl)c(O)c(C(N)=O)c3)cn2CC(=O)Nc2cc(N3CCn4cc(C(F)(F)F)nc4C3)ncc2Cl)c1=O] | 95% |
| I-166 | 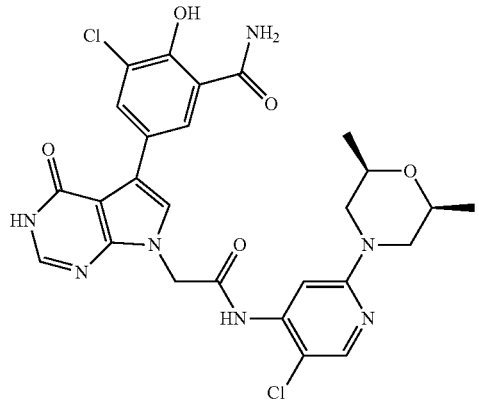 [SMILES: C[C@@H]1CN(c2cc(NC(=O)Cn3cc(-c4cc(Cl)c(O)c(C(N)=O)c4)c4c(=O)[nH]cnc43)c(Cl)cn2)C[C@H](C)O1] | 87% |

TABLE 1-continued

| Compound | Structure | Yield |
|---|---|---|
| I-167 | 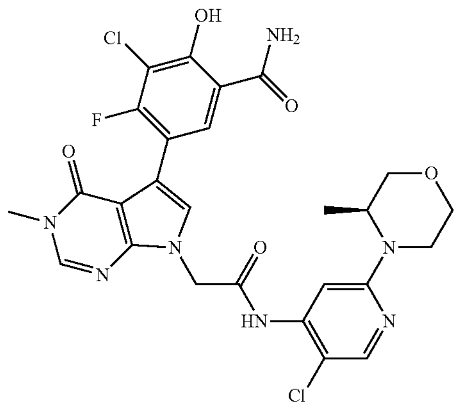 [SMILES: C[C@H]1COCCN1c1cc(NC(=O)Cn2cc(-c3cc(C(N)=O)c(O)c(Cl)c3F)c3c(=O)n(C)cnc32)c(Cl)cn1] | 90% |
| I-168 | 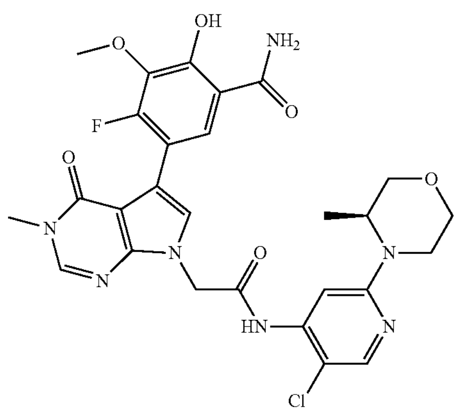 [SMILES: COc1c(O)c(C(N)=O)cc(-c2cn(CC(=O)Nc3cc(N4CCOC[C@@H]4C)ncc3Cl)c3ncn(C)c(=O)c23)c1F] | 77% |
| I-169 | 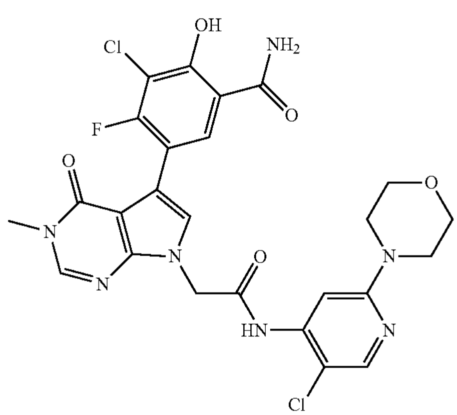 [SMILES: Cn1cnc2c(c(-c3cc(C(N)=O)c(O)c(Cl)c3F)cn2CC(=O)Nc2cc(N3CCOCC3)ncc2Cl)c1=O] | 77% |

TABLE 1-continued

| Compound | Structure | Yield |
|---|---|---|
| I-170 | 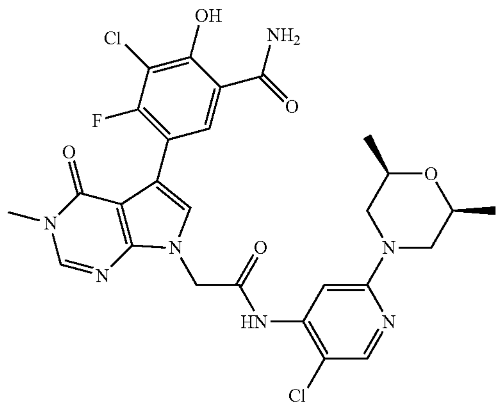 | 77% |
| I-171 | 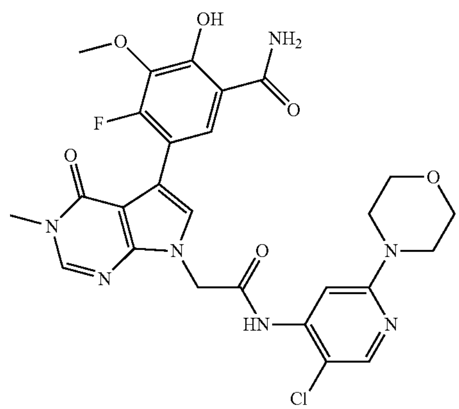 [SMILES: COc1c(O)c(C(N)=O)cc(-c2cn(CC(=O)Nc3cc(N4CCOCC4)ncc3Cl)c3ncn(C)c(=O)c23)c1F] | 82% |
| I-172 | 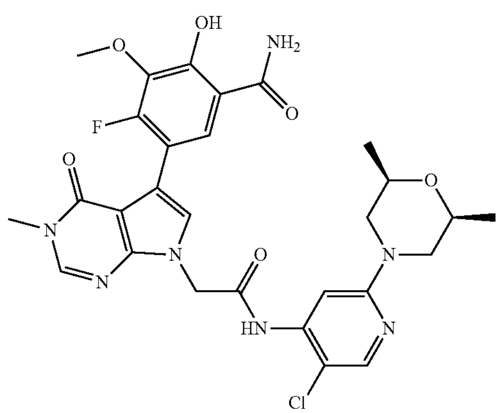 | 69% |
| I-173 | 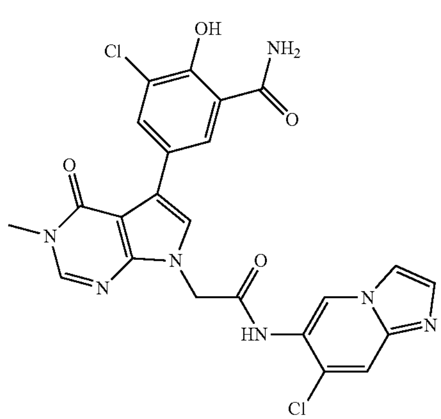 [SMILES: Cn1cnc2c(c(-c3cc(Cl)c(O)c(C(N)=O)c3)cn2CC(=O)Nc2cn3ccnc3cc2Cl)c1=O] | 90% |

TABLE 1-continued
| Compound | Structure | Yield |
|---|---|---|
| I-174 | 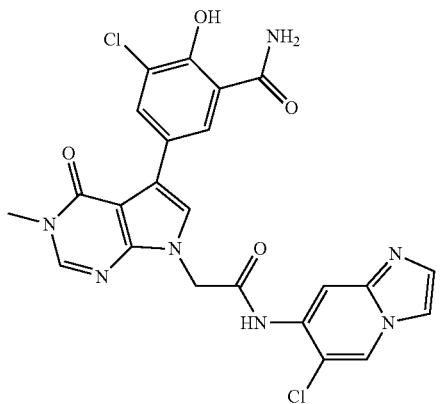 [SMILES: Cn1cnc2c(c(-c3cc(Cl)c(O)c(C(N)=O)c3)cn2CC(=O)Nc2cc3nccn3cc2Cl)c1=O] | 69% |
| I-175 | 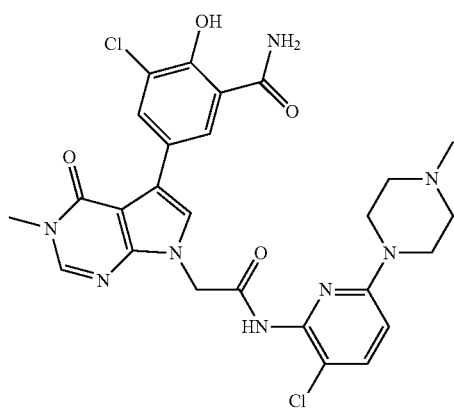 | 70% |
| I-176 | 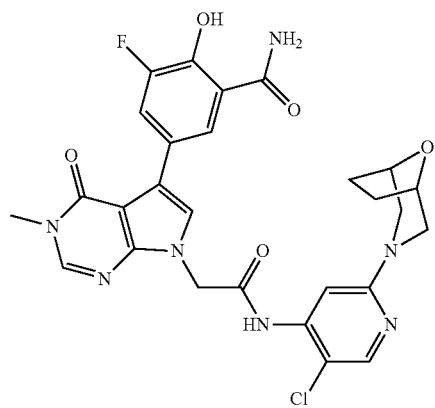 [SMILES: Cn1cnc2c(c(-c3cc(F)c(O)c(C(N)=O)c3)cn2CC(=O)Nc2cc(N3CC4CCC(C3)O4)ncc2Cl)c1=O] | 89% |

TABLE 1-continued

| Compound | Structure | Yield |
|---|---|---|
| I-177 | 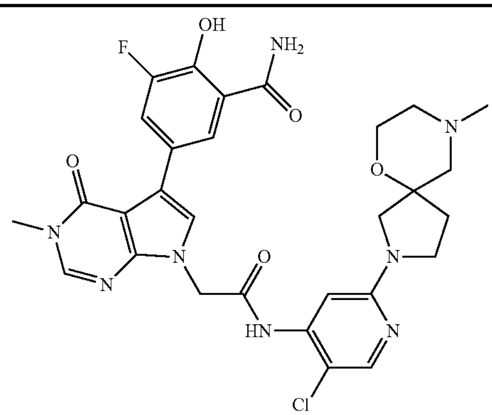 | 81% |
| I-178 | 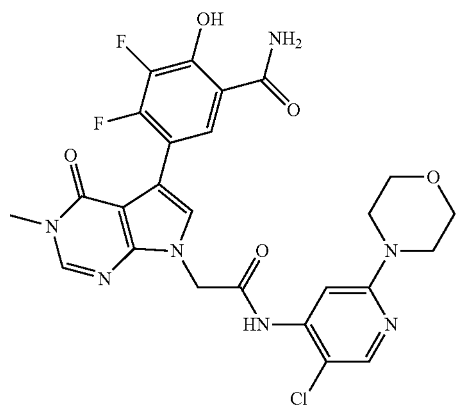 [SMILES: Cn1cnc2c(c(-c3cc(C(N)=O)c(O)c(F)c3F)cn2CC(=O)Nc2cc(N3CCOCC3)ncc2Cl)c1=O] | 89% |
| I-179 | 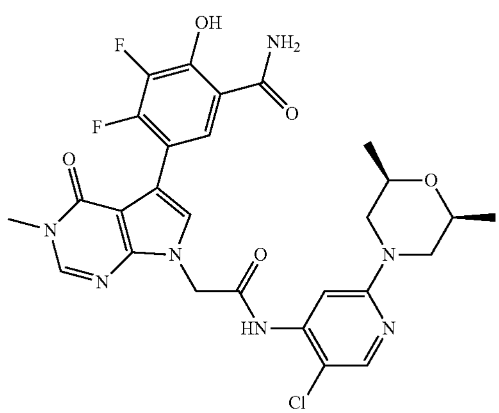 | 68% |
| I-180 | 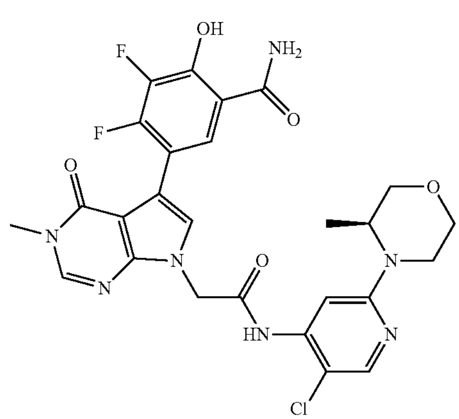 [SMILES: C[C@H]1COCCN1c1cc(NC(=O)Cn2cc(-c3cc(C(N)=O)c(O)c(F)c3F)c3c(=O)n(C)cnc32)c(Cl)cn1] | 70% |

TABLE 1-continued
| Compound | Structure | Yield |
|---|---|---|
| I-181 | 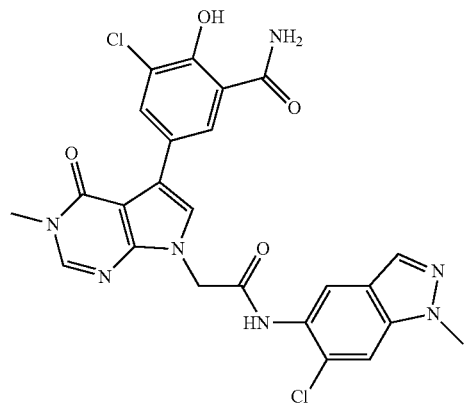 | 60% |
| I-182 | 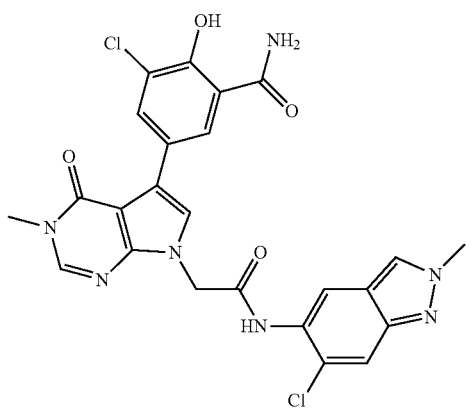 | 78% |
| I-183 | 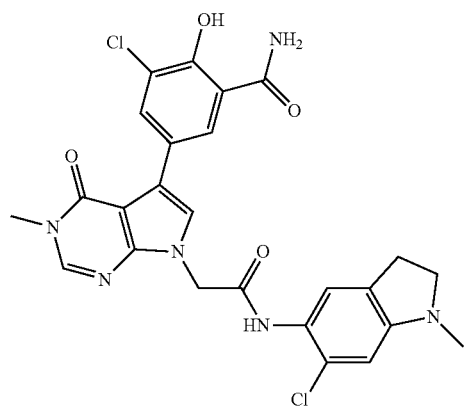 | 73% |

TABLE 1-continued
| Compound | Structure | Yield |
|---|---|---|
| I-184 | 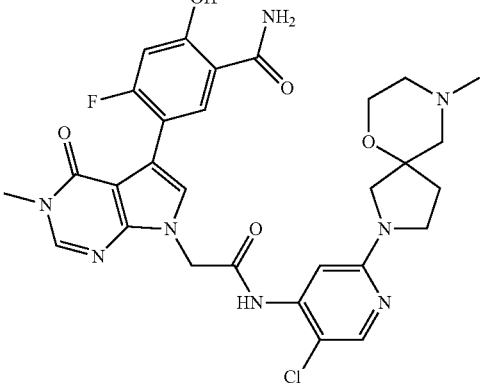 | 17% |
| I-185 | 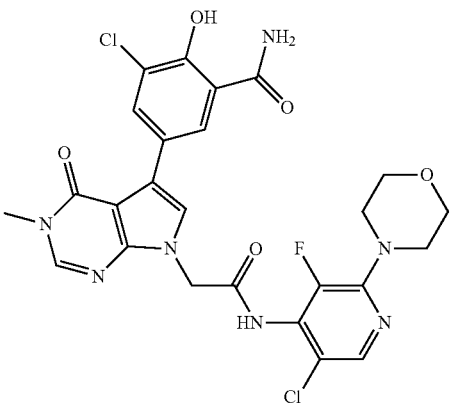 [SMILES: Cn1cnc2c(c(-c3cc(Cl)c(O)c(C(N)=O)c3)cn2CC(=O)Nc2c(Cl)cnc(N3CCOCC3)c2F)c1=O] | 100% |
| I-186 | 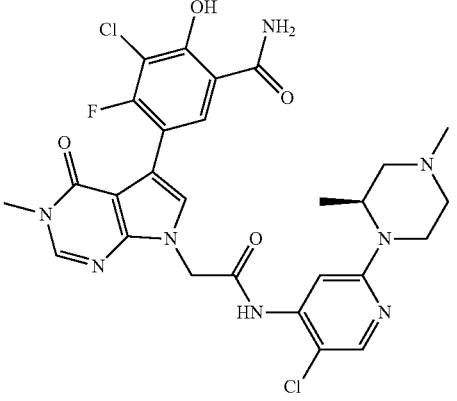 | 80% |

TABLE 1-continued

| Compound | Structure | Yield |
| --- | --- | --- |
| I-187 | 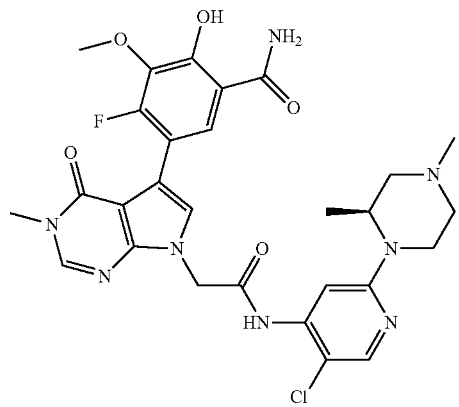 | 81% |
| I-188 | 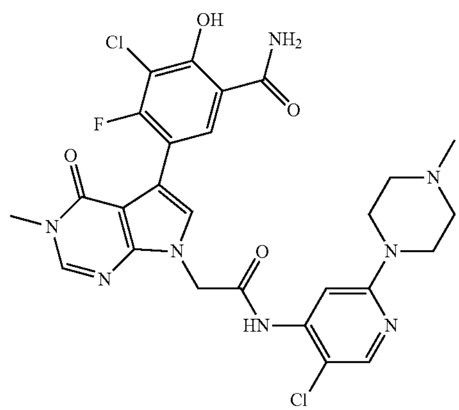 | 80% |
| I-189 | 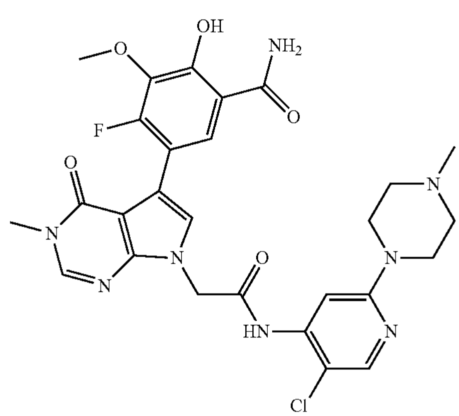 | 86% |

TABLE 1-continued
| Compound | Structure | Yield |
|---|---|---|
| I-190 | 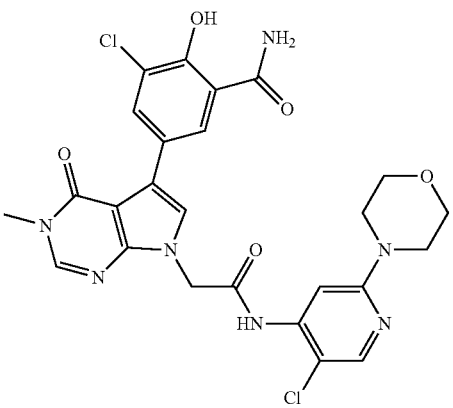 [SMILES: Cn1cnc2c(c(-c3cc(Cl)c(O)c(C(N)=O)c3)cn2CC(=O)Nc2cc(N3CCOCC3)ncc2Cl)c1=O] | 86% |
| I-191 | 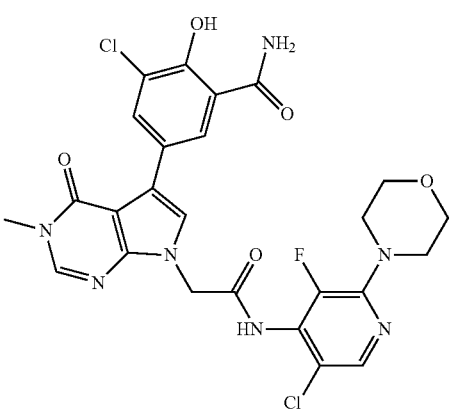 [SMILES: Cn1cnc2c(c(-c3cc(Cl)c(O)c(C(N)=O)c3)cn2CC(=O)Nc2c(Cl)cnc(N3CCOCC3)c2F)c1=O] | 100% |
| I-192 | 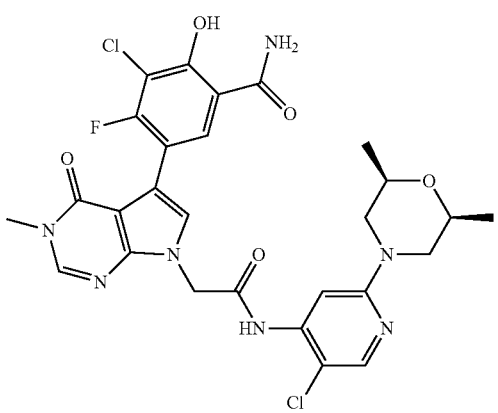 | 80% |

TABLE 1-continued
| Compound | Structure | Yield |
|---|---|---|
| I-193 | 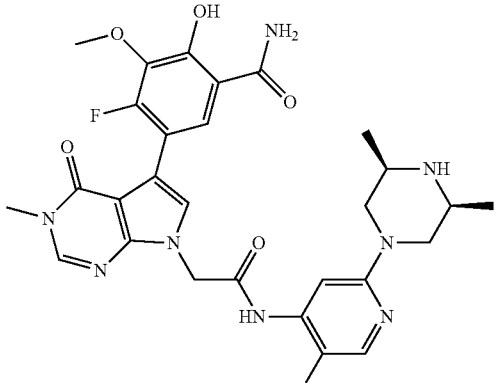 | 77% |
| I-194 | 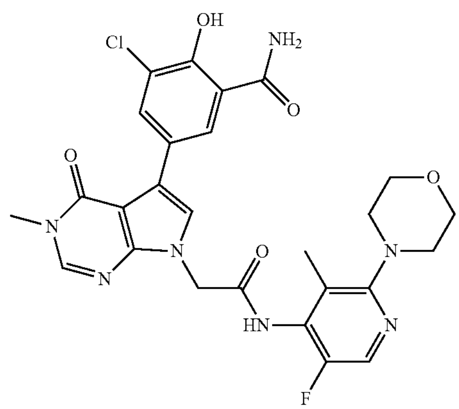 [SMILES: Cc1c(N2CCOCC2)ncc(F)c1NC(=O)Cn1cc(-c2cc(Cl)c(O)c(C(N)=O)c2)c2c(=O)n(C)cnc21] | Quant. |
| I-195 | 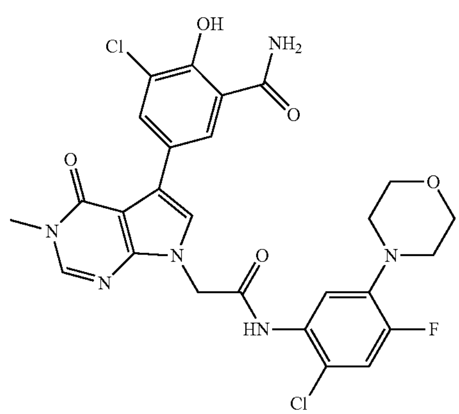 [SMILES: Cn1cnc2c(c(-c3cc(Cl)c(O)c(C(N)=O)c3)cn2CC(=O)Nc2cc(N3CCOCC3)c(F)cc2Cl)c1=O] | Quant. |

TABLE 1-continued
| Compound | Structure | Yield |
|---|---|---|
| I-196 | 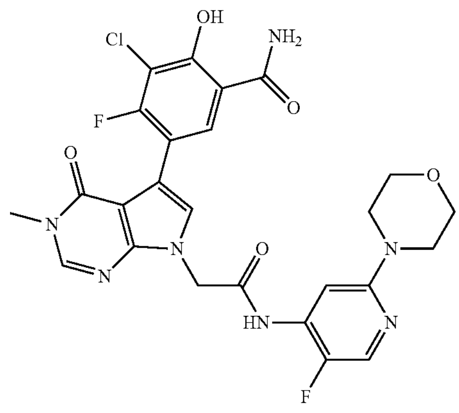 [SMILES: Cn1cnc2c(c(-c3cc(C(N)=O)c(O)c(Cl)c3F)cn2CC(=O)Nc2cc(N3CCOCC3)ncc2F)c1=O] | 89% |
| I-197 | 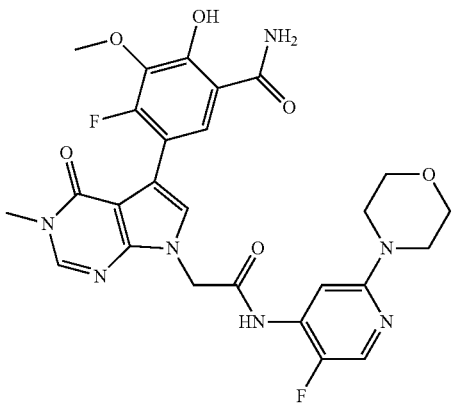 [SMILES: COc1c(O)c(C(N)=O)cc(-c2cn(CC(=O)Nc3cc(N4CCOCC4)ncc3F)c3ncn(C)c(=O)c23)c1F] | 83% |
| I-198 | 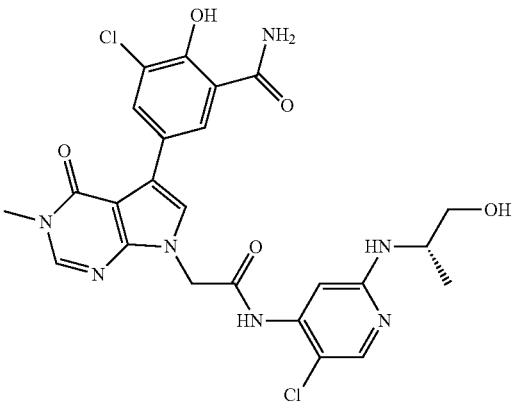 [SMILES: C[C@@H](CO)Nc1cc(NC(=O)Cn2cc(-c3cc(Cl)c(O)c(C(N)=O)c3)c3c(=O)n(C)cnc32)c(Cl)cn1] | 22% |

TABLE 1-continued

| Compound | Structure | Yield |
|---|---|---|
| I-199 | 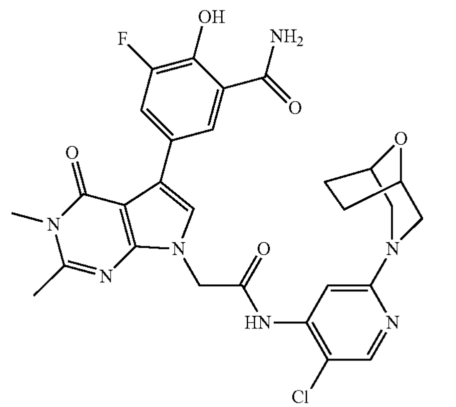 [SMILES: Cc1nc2c(c(-c3cc(F)c(O)c(C(N)=O)c3)cn2CC(=O)Nc2cc(N3CC4CCC(C3)O4)ncc2Cl)c(=O)n1C] | 44% |
| I-200 | 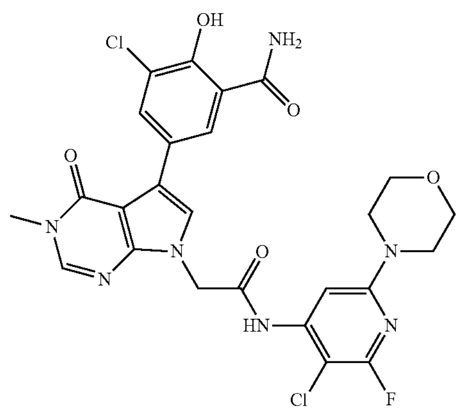 [SMILES: Cn1cnc2c(c(-c3cc(Cl)c(O)c(C(N)=O)c3)cn2CC(=O)Nc2cc(N3CCOCC3)nc(F)c2Cl)c1=O] | 93% |
| I-201 | 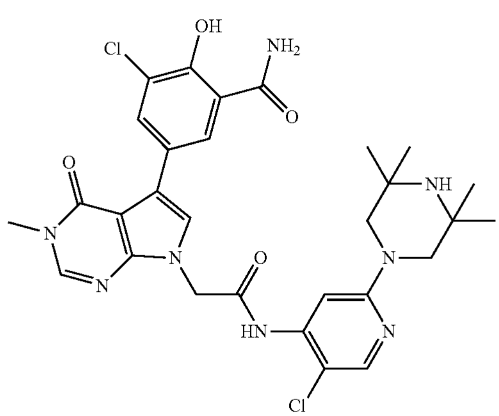 | 83% |

TABLE 1-continued

| Compound | Structure | Yield |
|---|---|---|
| I-202 | 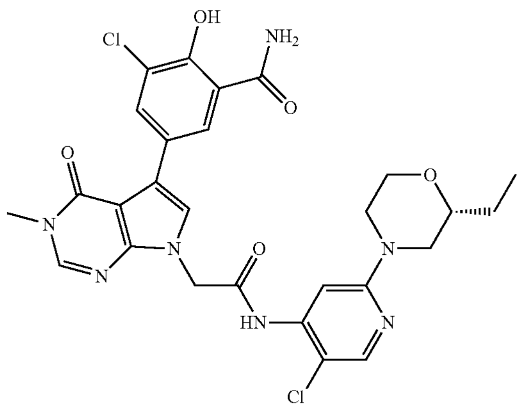 [SMILES: CC[C@@H]1CN(c2cc(NC(=O)Cn3cc(-c4cc(Cl)c(O)c(C(N)=O)c4)c4c(=O)n(C)cnc43)c(Cl)cn2)CCO1] | 77% |
| I-203 | 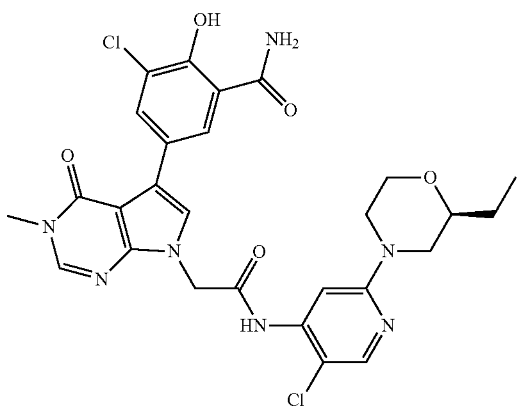 [SMILES: CC[C@H]1CN(c2cc(NC(=O)Cn3cc(-c4cc(Cl)c(O)c(C(N)=O)c4)c4c(=O)n(C)cnc43)c(Cl)cn2)CCO1] | 90% |
| I-204 | 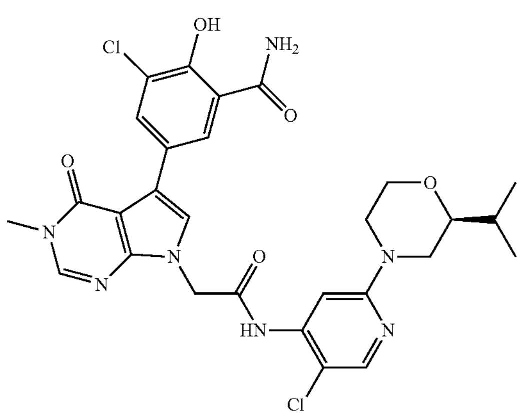 [SMILES: CC(C)[C@H]1CN(c2cc(NC(=O)Cn3cc(-c4cc(Cl)c(O)c(C(N)=O)c4)c4c(=O)n(C)cnc43)c(Cl)cn2)CCO1] | 76% |

TABLE 1-continued

| Compound | Structure | Yield |
|---|---|---|
| I-205 | 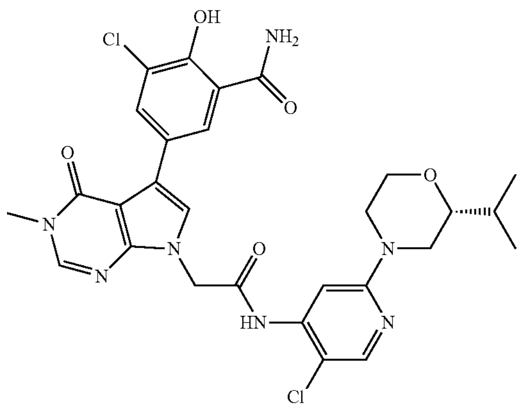 [SMILES: CC(C)[C@@H]1CN(c2cc(NC(=O)Cn3cc(-c4cc(Cl)c(O)c(C(N)=O)c4)c4c(=O)n(C)cnc43)c(Cl)cn2)CCO1] | 83% |
| I-206 | 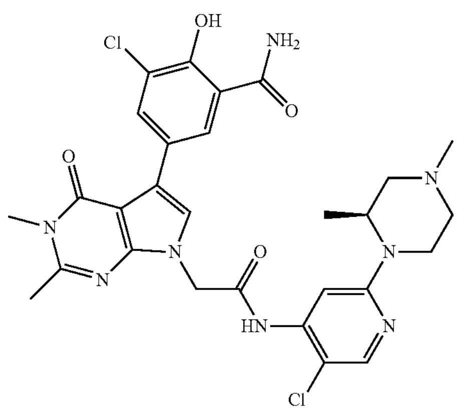 | 56% |
| I-207 | 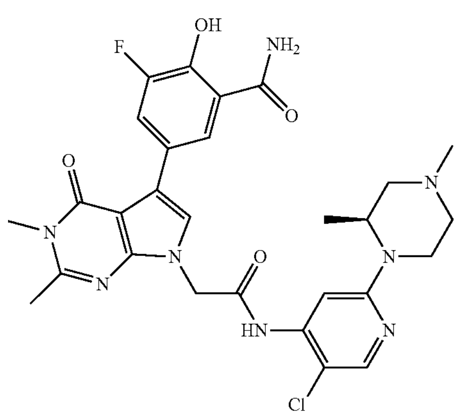 | 63% |

TABLE 1-continued

| Compound | Structure | Yield |
|---|---|---|
| I-208 | 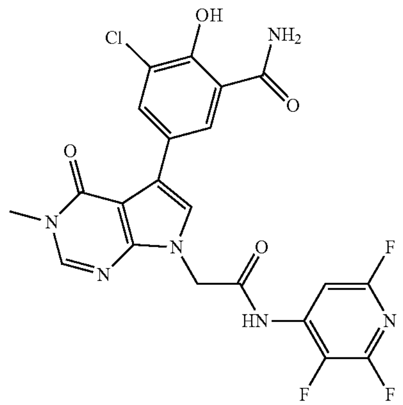 [SMILES: Cn1cnc2c(c(-c3cc(Cl)c(O)c(C(N)=O)c3)cn2CC(=O)Nc2cc(F)nc(F)c2F)c1=O] | 56% |
| I-209 | 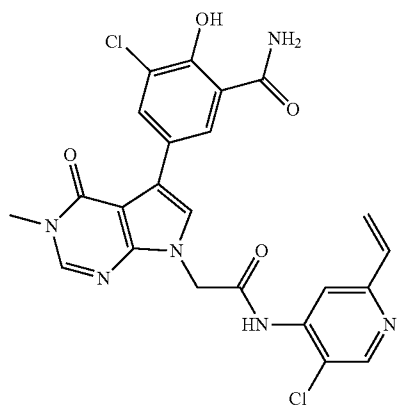 [SMILES: C=Cc1cc(NC(=O)Cn2cc(-c3cc(Cl)c(O)c(C(N)=O)c3)c3c(=O)n(C)cnc32)c(Cl)cn1] | 73% |
| I-210 | 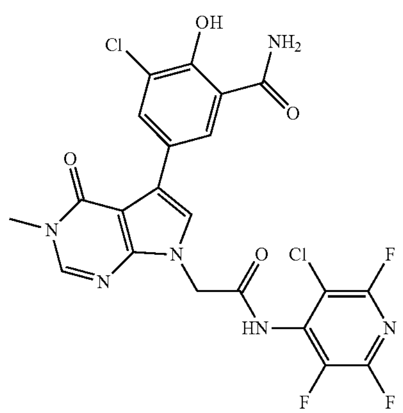 [SMILES: Cn1cnc2c(c(-c3cc(Cl)c(O)c(C(N)=O)c3)cn2CC(=O)Nc2c(F)c(F)nc(F)c2Cl)c1=O] | 74% |
| I-211 | 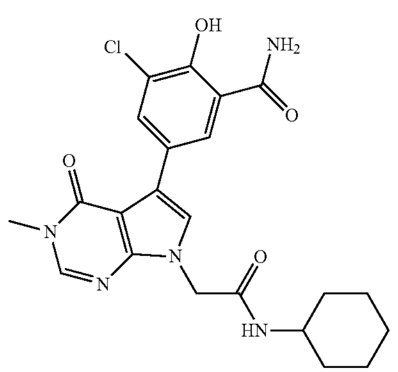 [SMILES: Cn1cnc2c(c(-c3cc(Cl)c(O)c(C(N)=O)c3)cn2CC(=O)NC2CCCCC2)c1=O] | 51% |

TABLE 1-continued

| Compound | Structure | Yield |
|---|---|---|
| I-212 | 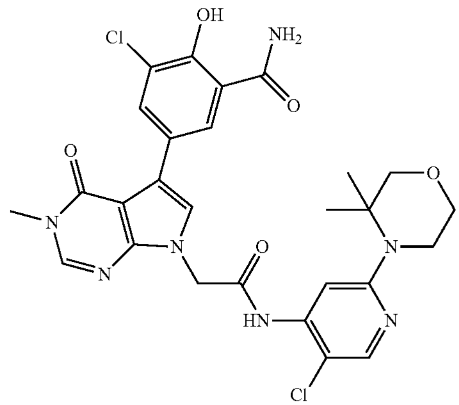 [SMILES: Cn1cnc2c(c(-c3cc(Cl)c(O)c(C(N)=O)c3)cn2CC(=O)Nc2cc(N3CCOCC3(C)C)ncc2Cl)c1=O] | 55% |
| I-213 | 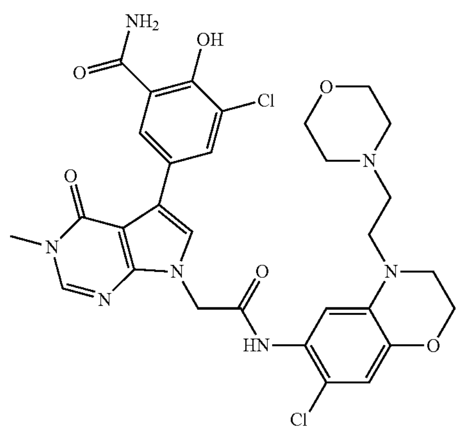 [SMILES: Cn1cnc2c(c(-c3cc(Cl)c(O)c(C(N)=O)c3)cn2CC(=O)Nc2cc3c(cc2Cl)OCCN3CCN2CCOCC2)c1=O] | 70% |
| I-214 | 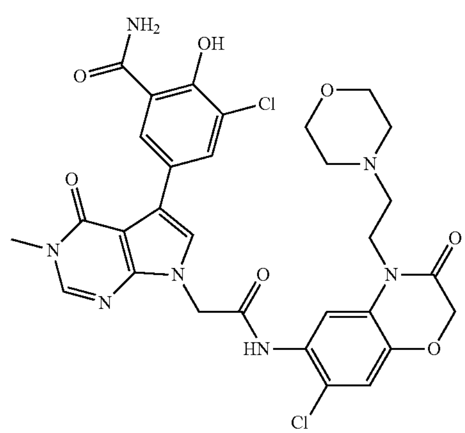 [SMILES: Cn1cnc2c(c(-c3cc(Cl)c(O)c(C(N)=O)c3)cn2CC(=O)Nc2cc3c(cc2Cl)OCC(=O)N3CCN2CCOCC2)c1=O] | 81% |

TABLE 1-continued

| Compound | Structure | Yield |
|---|---|---|
| I-215 | 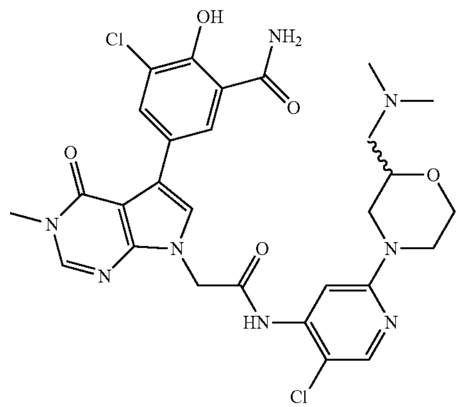 [SMILES: CN(C)CC1CN(c2cc(NC(=O)Cn3cc(-c4cc(Cl)c(O)c(C(N)=O)c4)c4c(=O)n(C)cnc43)c(Cl)cn2)CCO1] | 67% |
| I-216 | 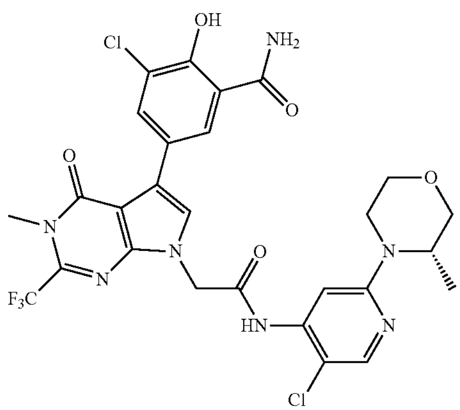 | 92% |
| I-217 | 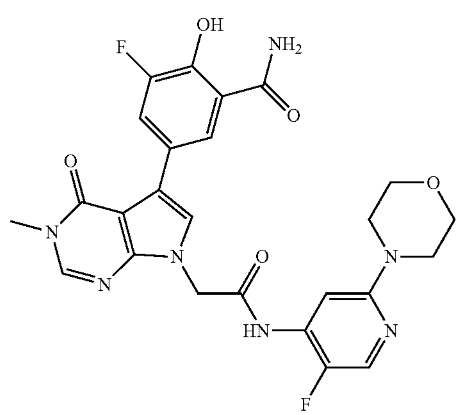 [SMILES: Cn1cnc2c(c(-c3cc(F)c(O)c(C(N)=O)c3)cn2CC(=O)Nc2cc(N3CCOCC3)ncc2F)c1=O] | 97% |

TABLE 1-continued
| Compound | Structure | Yield |
|---|---|---|
| I-218 | 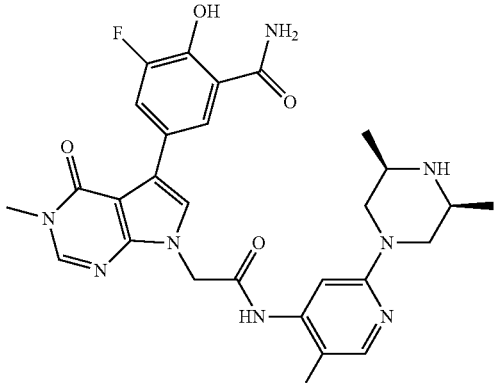 | 88% |
| I-219 | 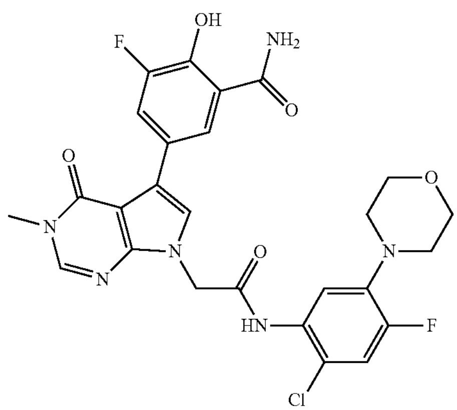 [SMILES: Cn1cnc2c(c(-c3cc(F)c(O)c(C(N)=O)c3)cn2CC(=O)Nc2cc(N3CCOCC3)c(F)cc2Cl)c1=O] | 81% |
| I-220 | 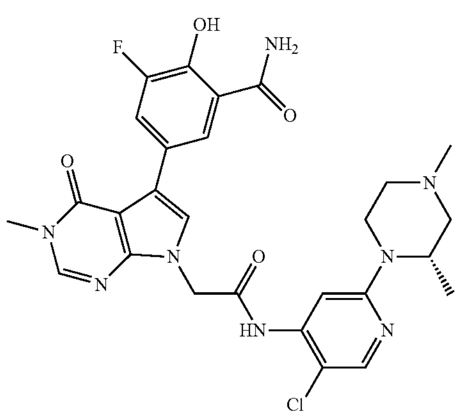 | 75% |

TABLE 1-continued

| Compound | Structure | Yield |
|---|---|---|
| I-221 | 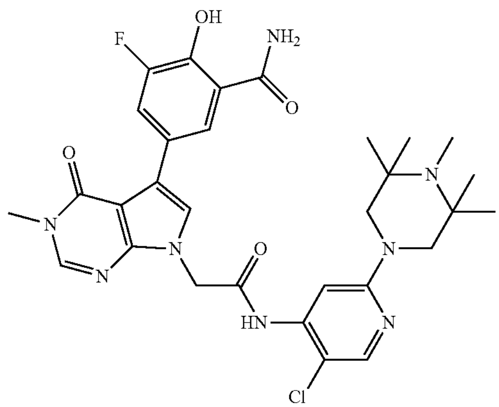 | 83% |
| I-222 | 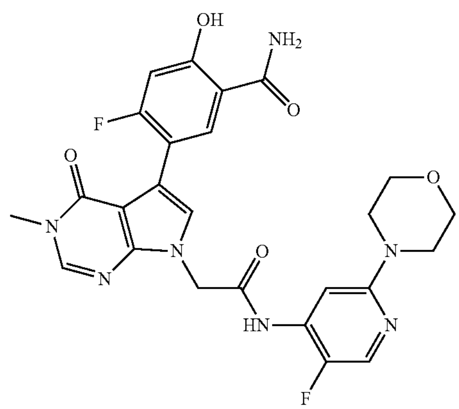 [SMILES: Cn1cnc2c(c(-c3cc(C(N)=O)c(O)cc3F)cn2CC(=O)Nc2cc(N3CCOCC3)ncc2F)c1=O] | 83% |
| I-223 | 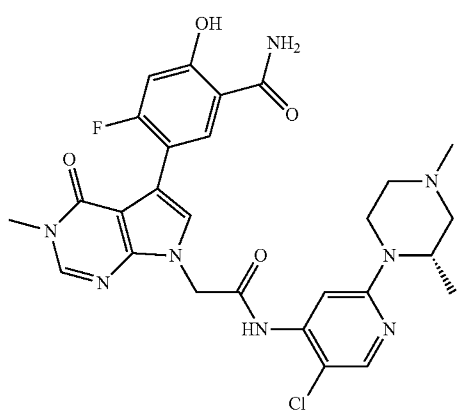 | 77% |

TABLE 1-continued

| Compound | Structure | Yield |
|---|---|---|
| I-224 | 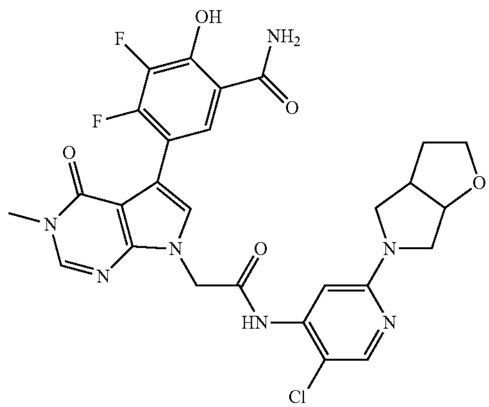 [SMILES: Cn1cnc2c(c(-c3cc(C(N)=O)c(O)c(F)c3F)cn2CC(=O)Nc2cc(N3CC4CCOC4C3)ncc2Cl)c1=O] | 85% |
| I-225 | 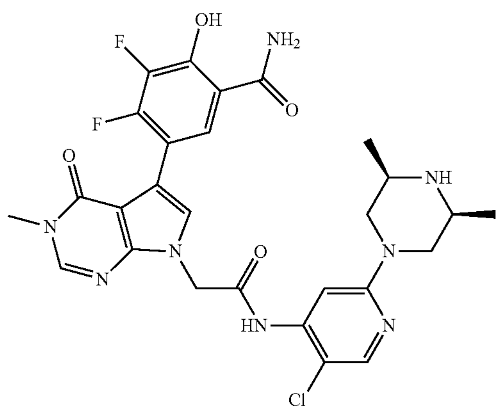 | 85% |
| I-226 | 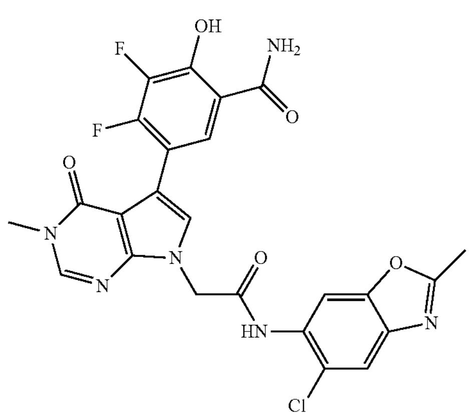 | 96% |

TABLE 1-continued
| Compound | Structure | Yield |
|---|---|---|
| I-227 | 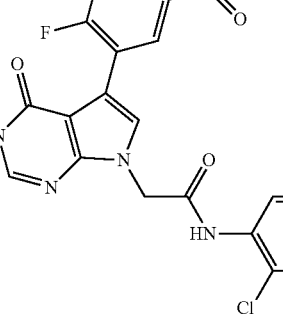 | 81% |
| I-228 | 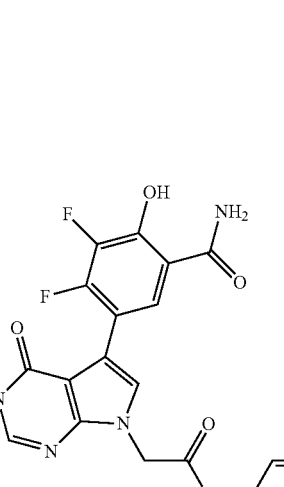 | 86% |
| I-229 | 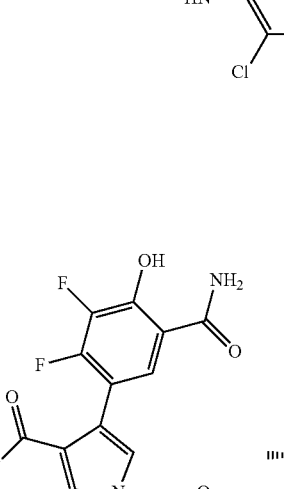 | 46% |

TABLE 1-continued

| Compound | Structure | Yield |
|---|---|---|
| I-230 | 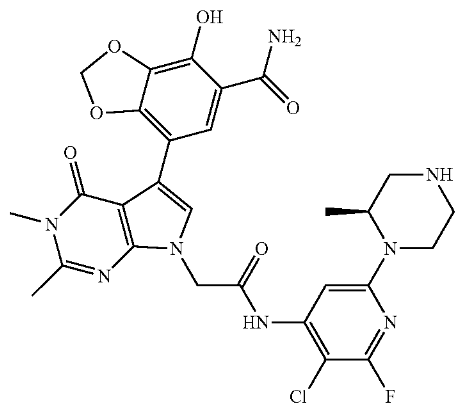 [SMILES: Cc1nc2c(c(-c3cc(C(N)=O)c(O)c4c3OCO4)cn2CC(=O)Nc2cc(N3CCNC[C@@H]3C)nc(F)c2Cl)c(=O)n1C] | 81% |
| I-231 | 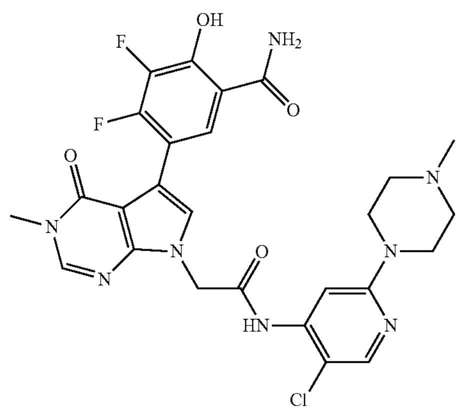 | 21% |
| I-232 | 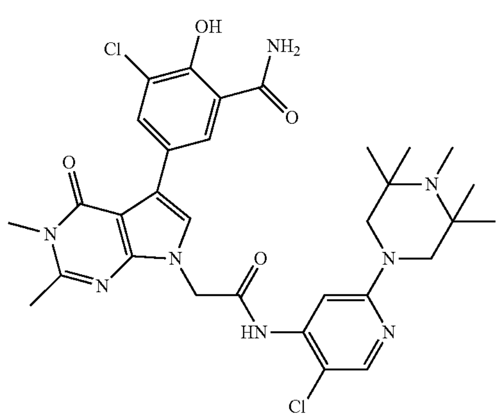 | 76% |

TABLE 1-continued
| Compound | Structure | Yield |
|---|---|---|
| I-233 | 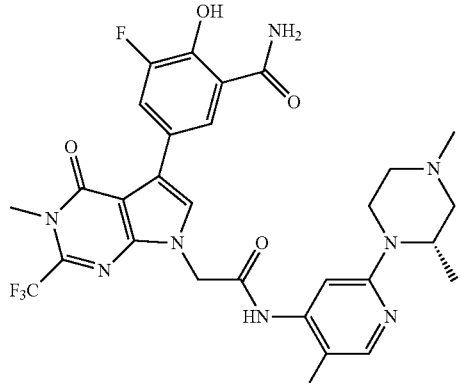 | 90% |
| I-234 | 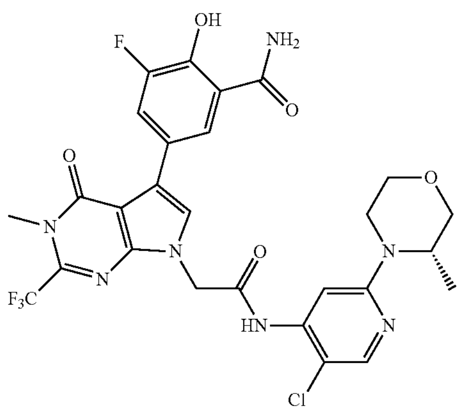 | 78% |
| I-235 | 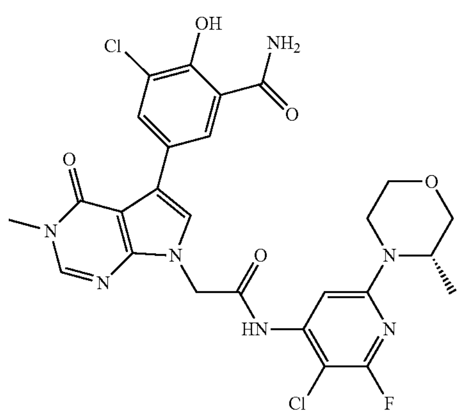 | 92% |

TABLE 1-continued
| Compound | Structure | Yield |
|---|---|---|
| I-236 | 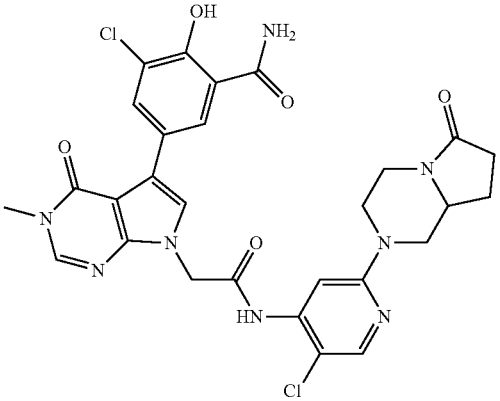 [SMILES: Cn1cnc2c(c(-c3cc(Cl)c(O)c(C(N)=O)c3)cn2CC(=O)Nc2cc(N3CCN4C(=O)CCC4C3)ncc2Cl)c1=O] | 38% |
| I-237 | 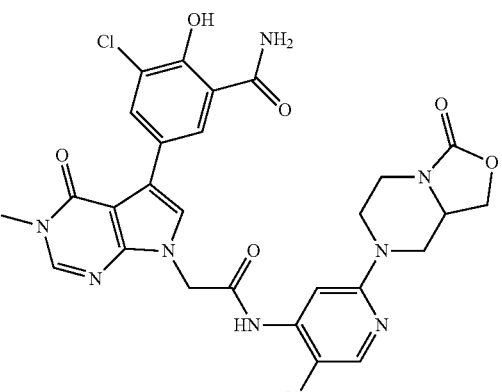 | 36% |
| I-238 | 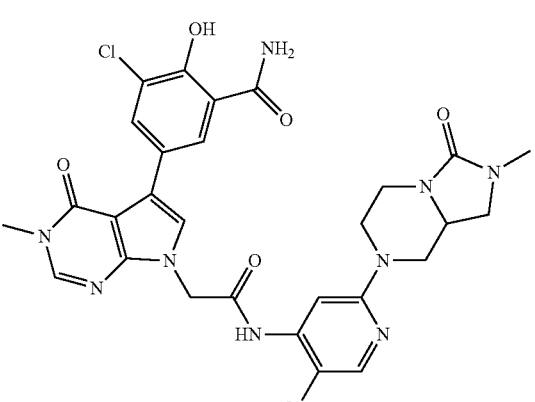 | 24% |

TABLE 1-continued
| Compound | Structure | Yield |
|---|---|---|
| I-239 | 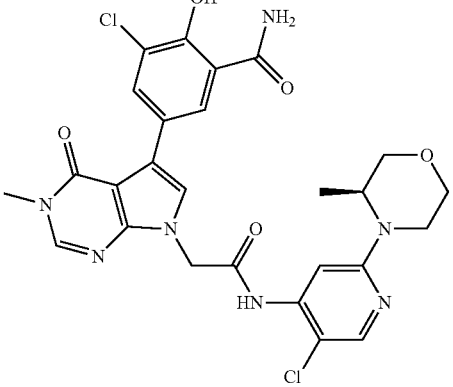 | 64% |
| I-240 | 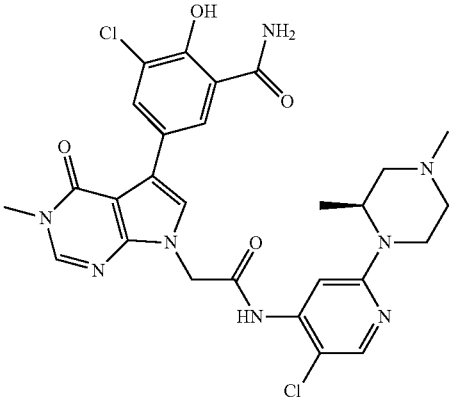 | 68% |
| I-241 | 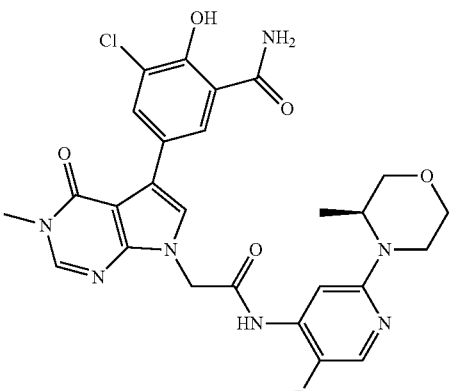 | 88% |

TABLE 1-continued
| Compound | Structure | Yield |
|---|---|---|
| I-242 | 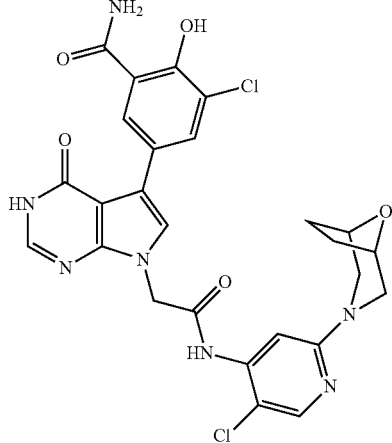 [SMILES: NC(=O)c1cc(-c2cn(CC(=O)Nc3cc(N4CC5CCC(C4)O5)ncc3Cl)c3nc[nH]c(=O)c23)cc(Cl)c1O] | 82% |
| I-243 | 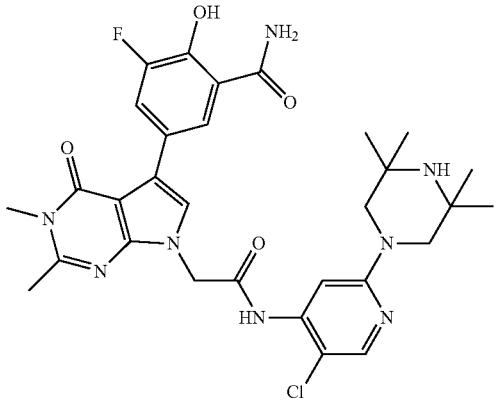 | 39% |
| I-244 | 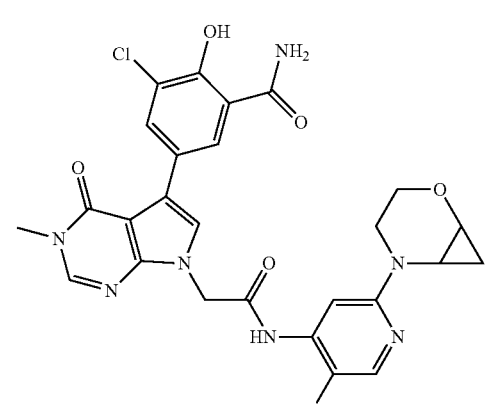 | 79% |

TABLE 1-continued

| Compound | Structure | Yield |
|---|---|---|
| I-245 | 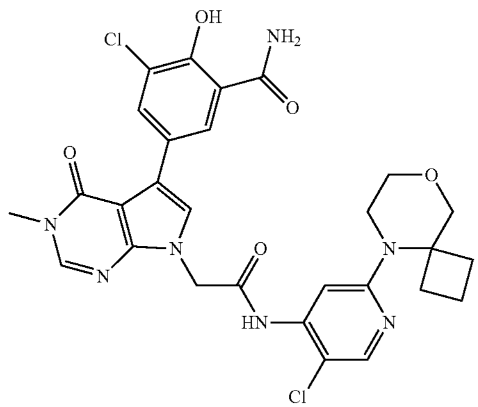 [SMILES: Cn1cnc2c(c(-c3cc(Cl)c(O)c(C(N)=O)c3)cn2CC(=O)Nc2cc(N3CCOCC34CCC4)ncc2Cl)c1=O] | 65% |
| I-246 | 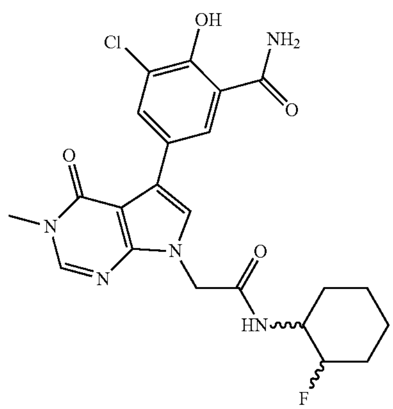 [SMILES: Cn1cnc2c(c(-c3cc(Cl)c(O)c(C(N)=O)c3)cn2CC(=O)NC2CCCCC2F)c1=O] | 55% |
| I-247 | 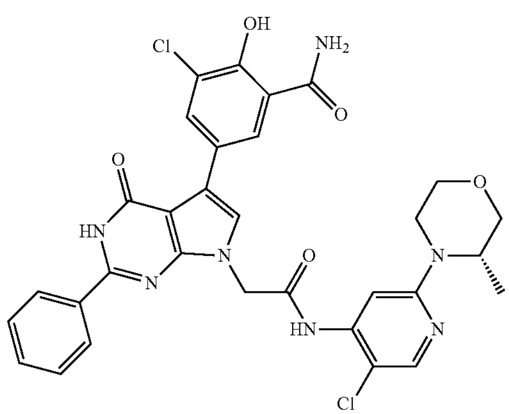 [SMILES: C[C@H]1COCCN1c1cc(NC(=O)Cn2cc(-c3cc(Cl)c(O)c(C(N)=O)c3)c3c(=O)[nH]c(-c4ccccc4)nc32)c(Cl)cn1] | 68% |

TABLE 1-continued

| Compound | Structure | Yield |
|---|---|---|
| I-248 | 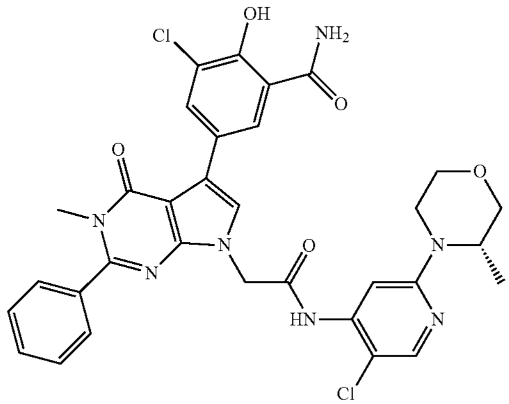 [SMILES: C[C@H]1COCCN1c1cc(NC(=O)Cn2cc(-c3cc(Cl)c(O)c(C(N)=O)c3)c3c(=O)n(C)c(-c4ccccc4)nc32)c(Cl)cn1] | 40% |
| I-249 | 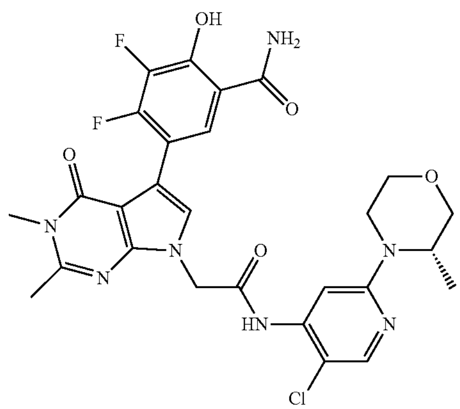 | 44% |
| I-250 | 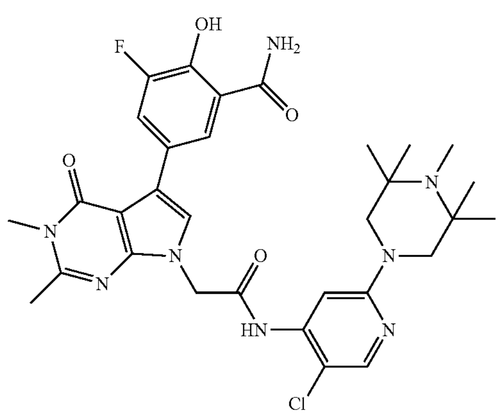 | 51% |

TABLE 1-continued
| Compound | Structure | Yield |
|---|---|---|
| I-251 | 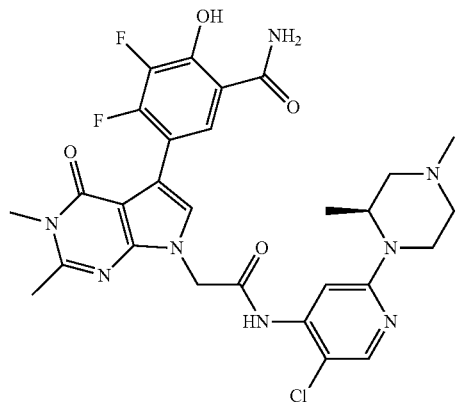 | 50% |
| I-252 | 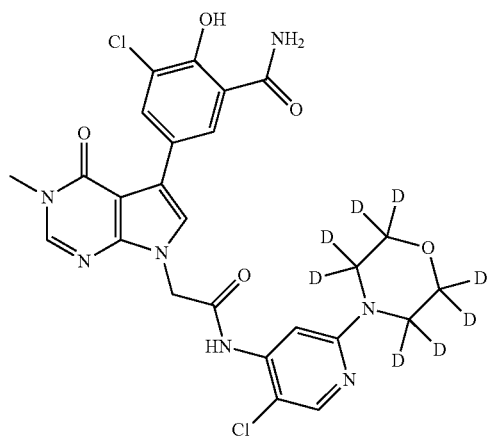 [SMILES: [2H]C1([2H])OC([2H])([2H])C([2H])([2H])N(c2cc(NC(=O)Cn3cc(-c4cc(Cl)c(O)c(C(N)=O)c4)c4c(=O)n(C)cnc43)c(Cl)cn2)C1([2H])[2H]] | 93% |
| I-253 | 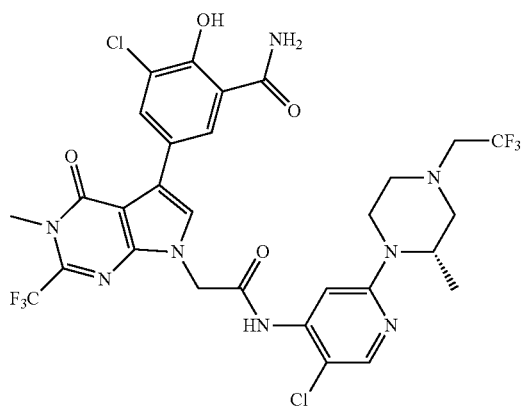 [SMILES: C[C@H]1CN(CC(F)(F)F)CCN1c1cc(NC(=O)Cn2cc(-c3cc(Cl)c(O)c(C(N)=O)c3)c3c(=O)n(C)c(C(F)(F)F)nc32)c(Cl)cn1] | 98% |

TABLE 1-continued

| Compound | Structure | Yield |
|---|---|---|
| I-254 | 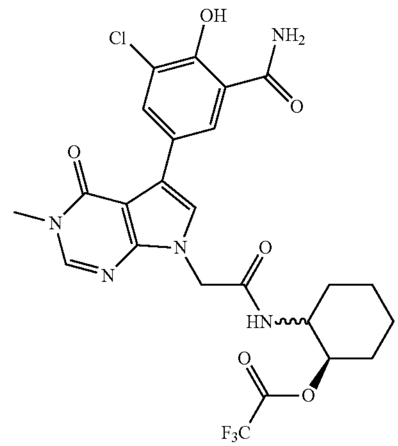 [SMILES: Cn1cnc2c(c(-c3cc(Cl)c(O)c(C(N)=O)c3)cn2CC(=O)NC2CCCC[C@H]2OC(=O)C(F)(F)F)c1=O] | 61% |
| I-255 | 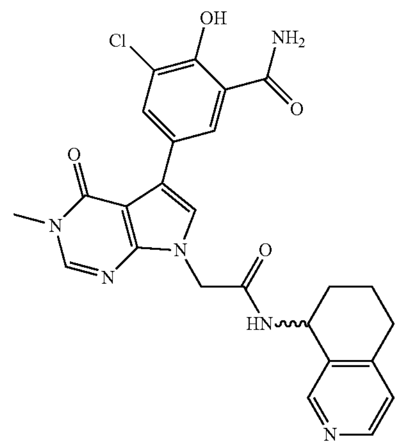 [SMILES: Cn1cnc2c(c(-c3cc(Cl)c(O)c(C(N)=O)c3)cn2CC(=O)NC2CCCc3ccncc32)c1=O] | 26% |
| I-256 | 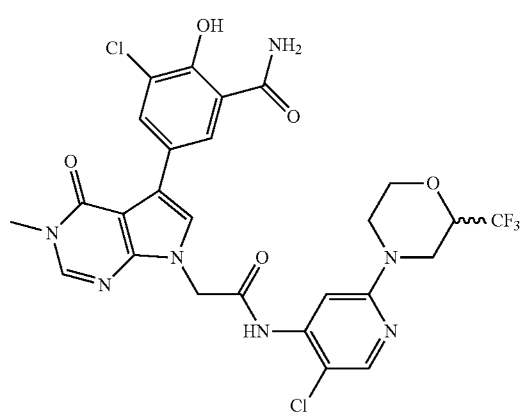 | 95% |

Enantiomer 1

TABLE 1-continued
| Compound | Structure | Yield |
|---|---|---|
| I-257 | 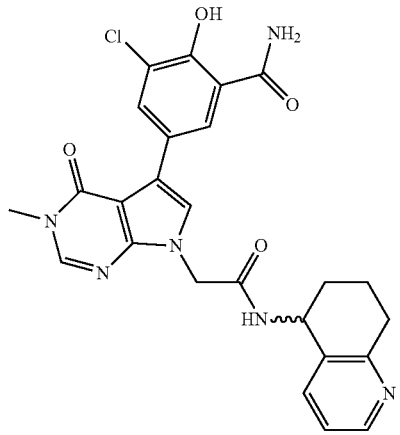 [SMILES: Cn1cnc2c(c(-c3cc(Cl)c(O)c(C(N)=O)c3)cn2CC(=O)NC2CCCc3ncccc32)c1=O] | 59% |
| I-258 | 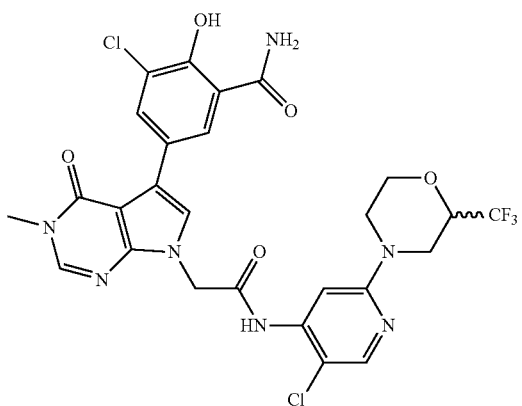<br>Enantiomer 2 | 78% |
| I-259 | 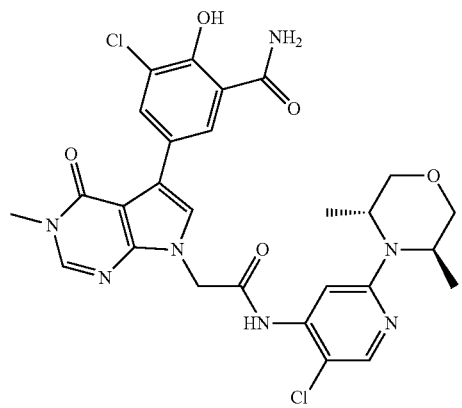 | 50% |

TABLE 1-continued

| Compound | Structure | Yield |
|---|---|---|
| I-260 | 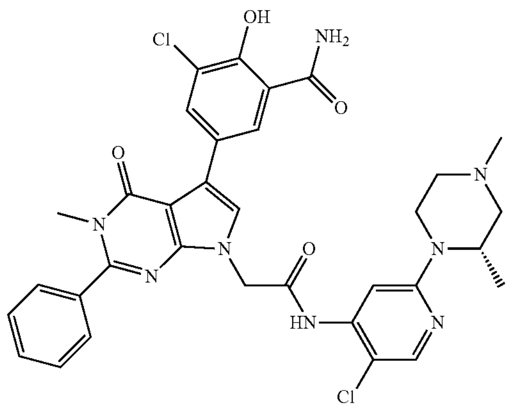 [SMILES: C[C@H]1CN(C)CCN1c1cc(NC(=O)Cn2cc(-c3cc(Cl)c(O)c(C(N)=O)c3)c3c(=O)n(C)c(-c4ccccc4)nc32)c(Cl)cn1] | Quant. |
| I-261 | 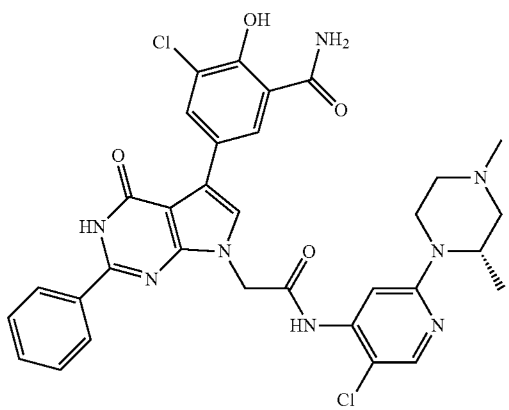 [SMILES: C[C@H]1CN(C)CCN1c1cc(NC(=O)Cn2cc(-c3cc(Cl)c(O)c(C(N)=O)c3)c3c(=O)[nH]c(-c4ccccc4)nc32)c(Cl)cn1] | 64% |
| I-262 | 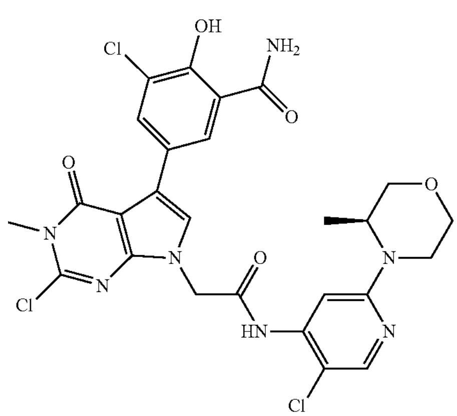 [SMILES: C[C@H]1COCCN1c1cc(NC(=O)Cn2cc(-c3cc(Cl)c(O)c(C(N)=O)c3)c3c(=O)n(C)c(Cl)nc32)c(Cl)cn1] | 49% |

TABLE 1-continued

| Compound | Structure | Yield |
|---|---|---|
| I-263 | 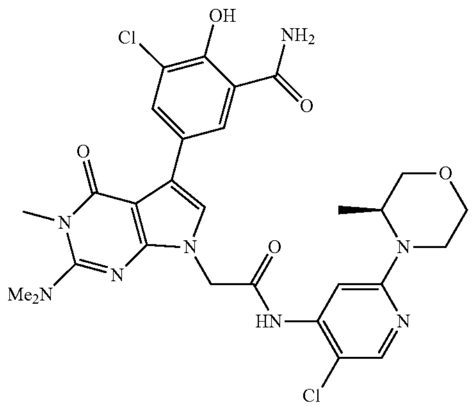 [SMILES: C[C@H]1COCCN1c1cc(NC(=O)Cn2cc(-c3cc(Cl)c(O)c(C(N)=O)c3)c3c(=O)n(C)c(N(C)C)nc32)c(Cl)cn1] | 85% |
| I-264 | 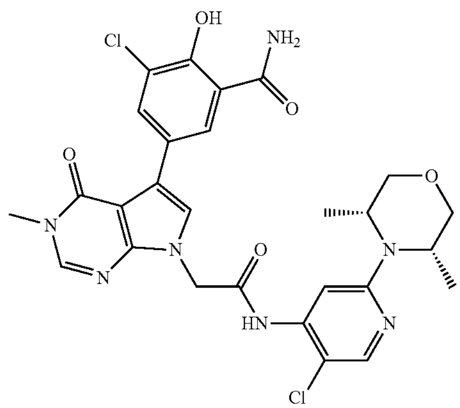 | Quant. |
| I-265 | 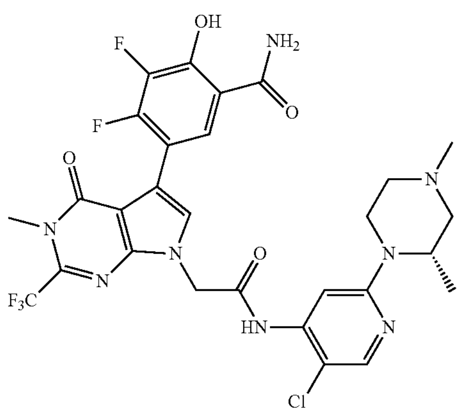 | 68% |
| I-266 | 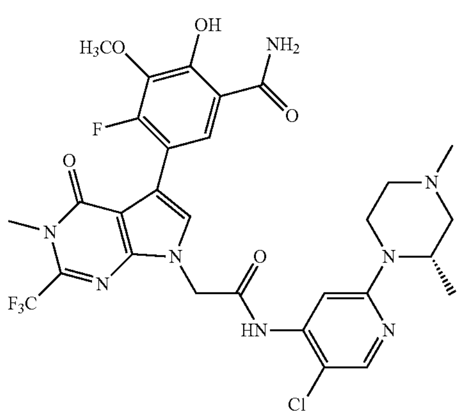 | 77% |

TABLE 1-continued
| Compound | Structure | Yield |
|---|---|---|
| I-267 | 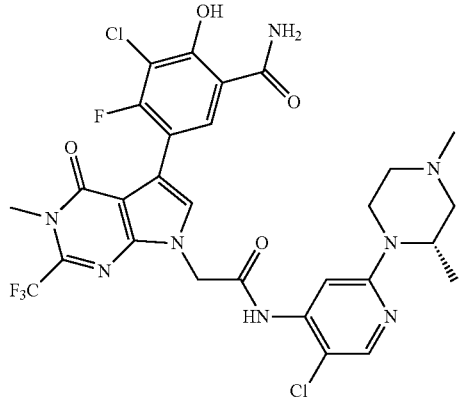 | 71% |
| I-268 | 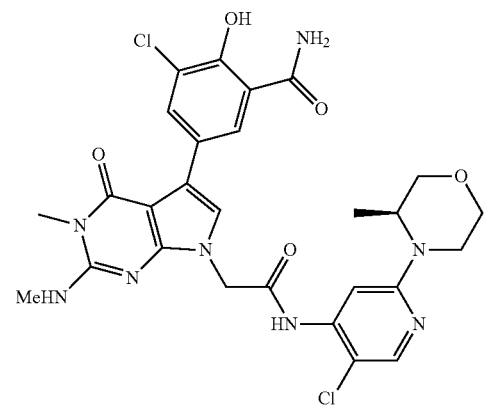 [SMILES: CNc1nc2c(c(-c3cc(Cl)c(O)c(C(N)=O)c3)cn2CC(=O)Nc2cc(N3CCOC[C@@H]3C)ncc2Cl)c(=O)n1C] | 77% |
| I-269 | 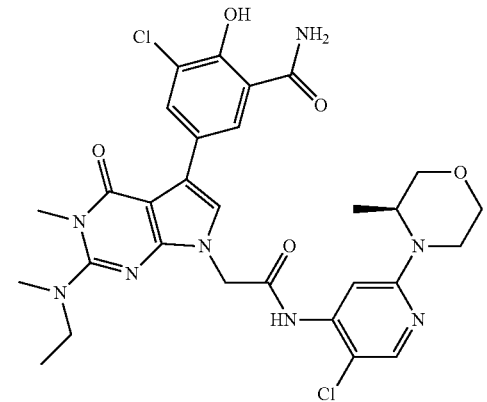 [SMILES: CCN(C)c1nc2c(c(-c3cc(Cl)c(O)c(C(N)=O)c3)cn2CC(=O)Nc2cc(N3CCOC[C@@H]3C)ncc2Cl)c(=O)n1C] | 63% |

TABLE 1-continued

| Compound | Structure | Yield |
|---|---|---|
| I-270 | 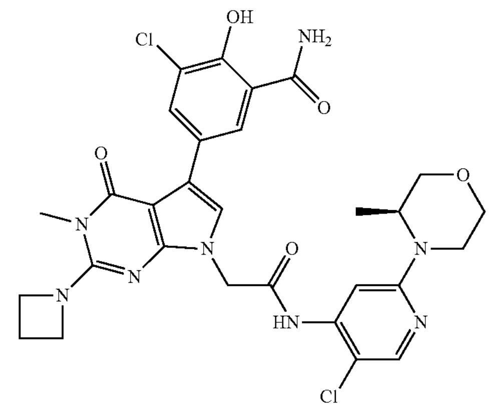 [SMILES: C[C@H]1COCCN1c1cc(NC(=O)Cn2cc(-c3cc(Cl)c(O)c(C(N)=O)c3)c3c(=O)n(C)c(N4CCC4)nc32)c(Cl)cn1] | 61% |
| I-271 | 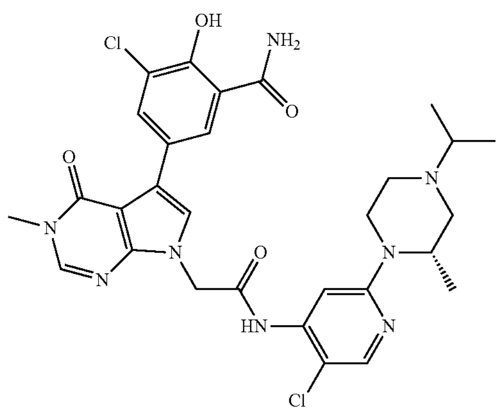 [SMILES: CC(C)N1CCN(c2cc(NC(=O)Cn3cc(-c4cc(Cl)c(O)c(C(N)=O)c4)c4c(=O)n(C)cnc43)c(Cl)cn2)[C@@H](C)C1] | 68% |
| I-272 | 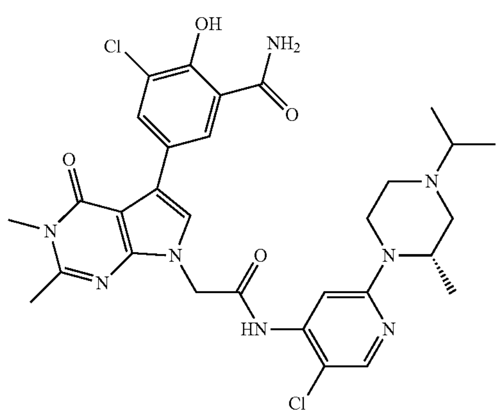 [SMILES: Cc1nc2c(c(-c3cc(Cl)c(O)c(C(N)=O)c3)cn2CC(=O)Nc2cc(N3CCN(C(C)C)C[C@@H]3C)ncc2Cl)c(=O)n1C] | 62% |
| I-273 | 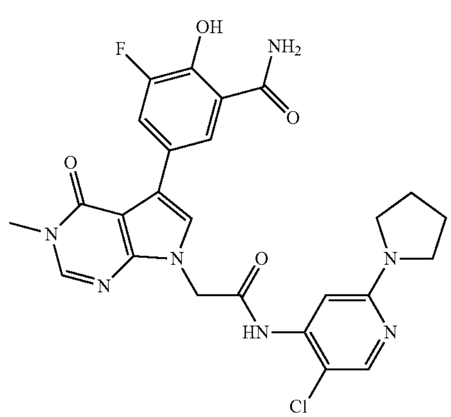 | 85% |

TABLE 1-continued
| Compound | Structure | Yield |
|---|---|---|
| I-274 | 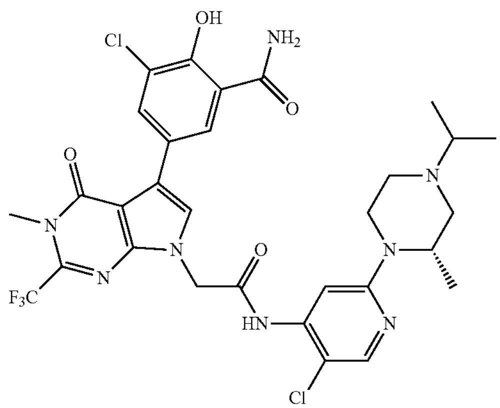 | 80% |
| I-275 | 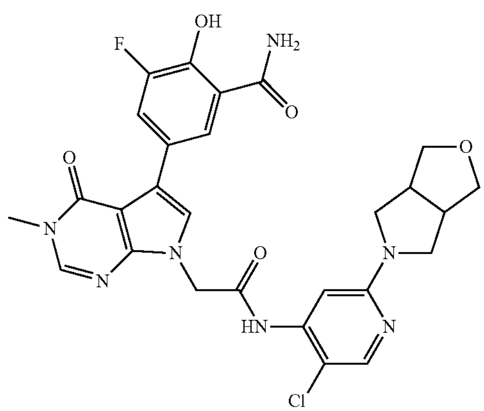 | 81% |
| I-276 | 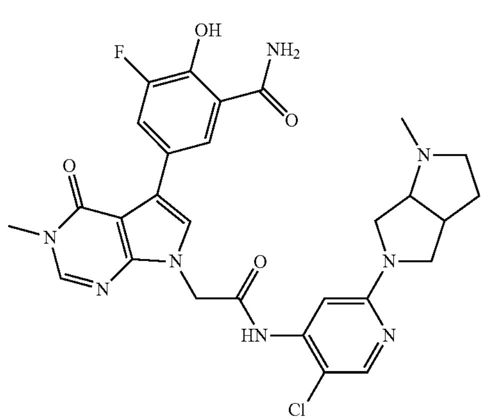 [SMILES: CN1CCC2CN(c3cc(NC(=O)Cn4cc(-c5cc(F)c(O)c(C(N)=O)c5)c5c(=O)n(C)cnc54)c(Cl)cn3)CC21] | 54% |

TABLE 1-continued

| Compound | Structure | Yield |
|---|---|---|
| I-277 | 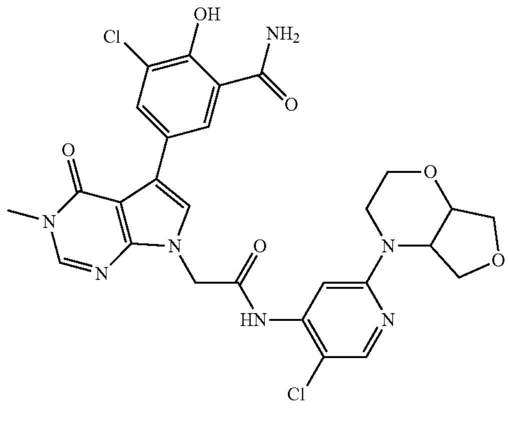 [SMILES: Cn1cnc2c(c(-c3cc(Cl)c(O)c(C(N)=O)c3)cn2CC(=O)Nc2cc(N3CCOC4COCC43)ncc2Cl)c1=O] | 99% |
| I-278 | 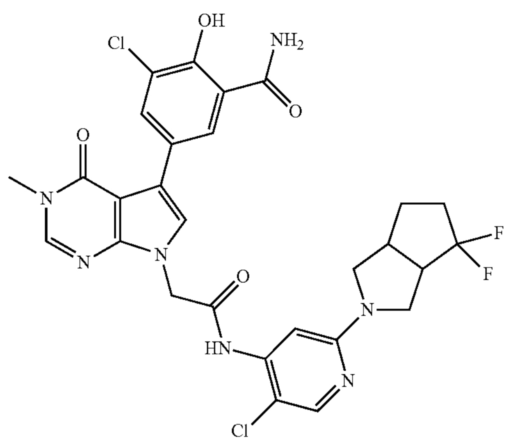 [SMILES: Cn1cnc2c(c(-c3cc(Cl)c(O)c(C(N)=O)c3)cn2CC(=O)Nc2cc(N3CC4CCC(F)(F)C4C3)ncc2Cl)c1=O] | 92% |
| I-279 | 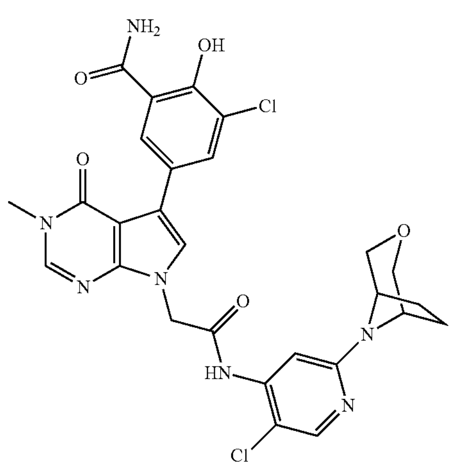 [SMILES: Cn1cnc2c(c(-c3cc(Cl)c(O)c(C(N)=O)c3)cn2CC(=O)Nc2cc(N3C4CCC3COC4)ncc2Cl)c1=O] | 99% |

TABLE 1-continued

| Compound | Structure | Yield |
|---|---|---|
| I-280 | 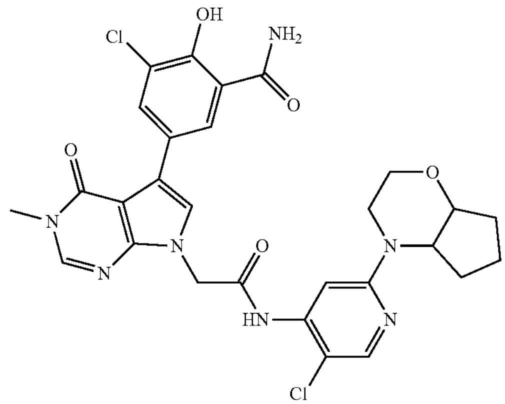 [SMILES: Cn1cnc2c(c(-c3cc(Cl)c(O)c(C(N)=O)c3)cn2CC(=O)Nc2cc(N3CCOC4CCCC43)ncc2Cl)c1=O] | 99% |
| I-281 | 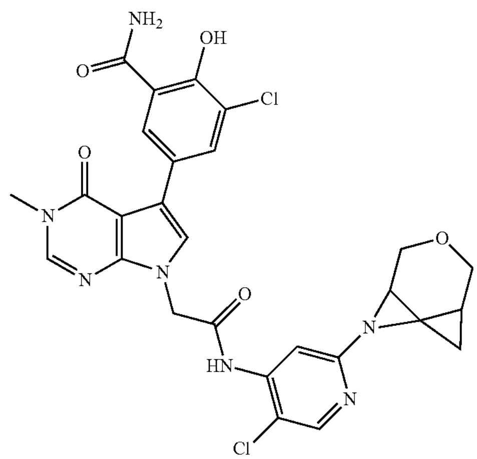 [SMILES: Cn1cnc2c(c(-c3cc(Cl)c(O)c(C(N)=O)c3)cn2CC(=O)Nc2cc(N3C4COCC5CC543)ncc2Cl)c1=O] | 76% |
| I-282 | 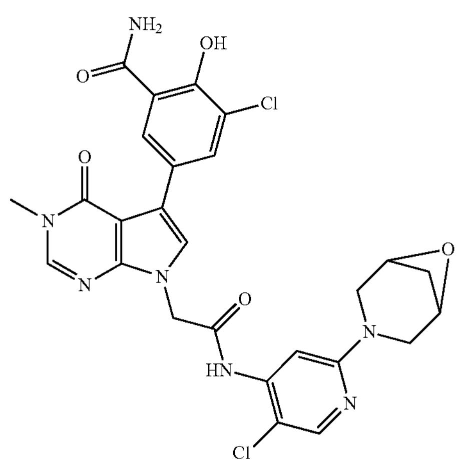 [SMILES: Cn1cnc2c(c(-c3cc(Cl)c(O)c(C(N)=O)c3)cn2CC(=O)Nc2cc(N3CC4CC(C3)O4)ncc2Cl)c1=O] | 99% |

TABLE 1-continued

| Compound | Structure | Yield |
|---|---|---|
| I-283 | 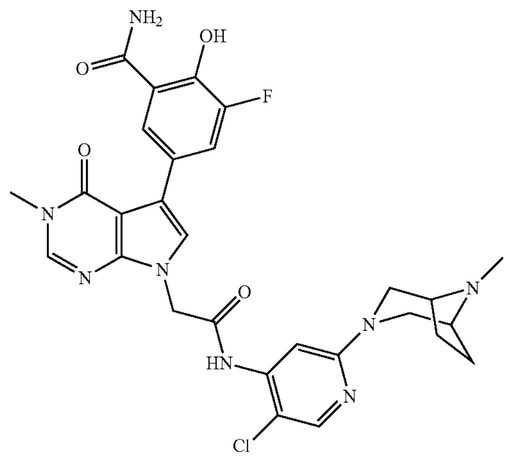 | 61% |
| I-284 | 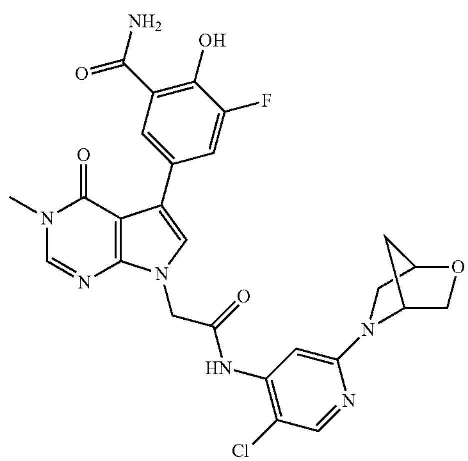 [SMILES: Cn1cnc2c(c(-c3cc(F)c(O)c(C(N)=O)c3)cn2CC(=O)Nc2cc(N3CC4CC3CO4)ncc2Cl)c1=O] | 85% |
| I-285 | 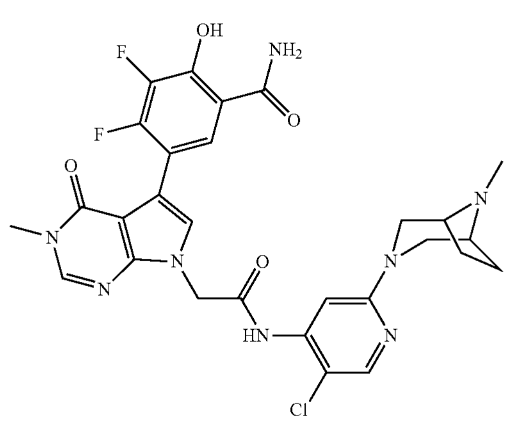 | 83% |

TABLE 1-continued

| Compound | Structure | Yield |
|---|---|---|
| I-286 | 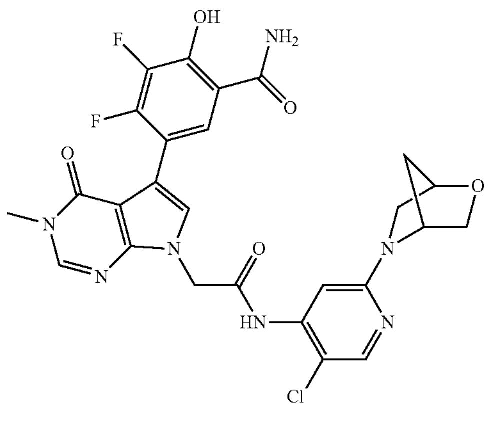 [SMILES: Cn1cnc2c(c(-c3cc(C(N)=O)c(O)c(F)c3F)cn2CC(=O)Nc2cc(N3CC4CC3CO4)ncc2Cl)c1=O] | 77% |
| I-287 | 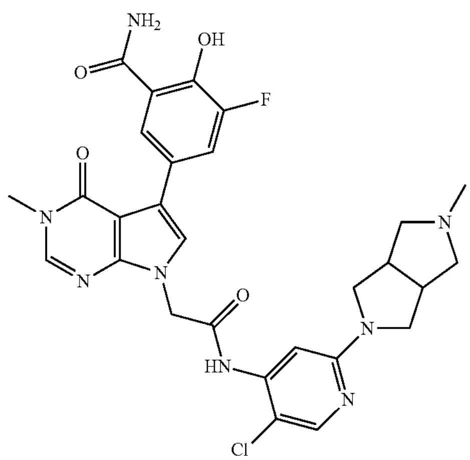 | 10% |
| I-288 | 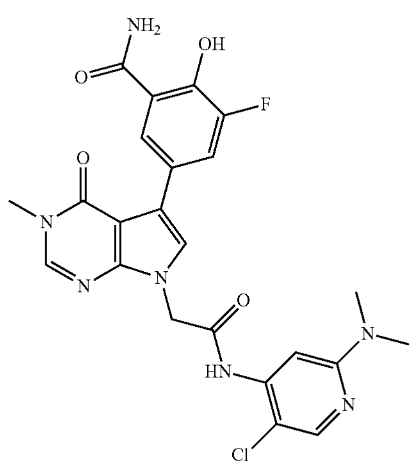 | 84% |

TABLE 1-continued
| Compound | Structure | Yield |
|---|---|---|
| I-289 | 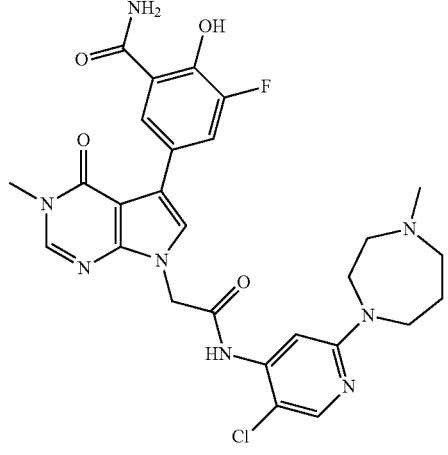 [SMILES: CN1CCCN(c2cc(NC(=O)Cn3cc(-c4cc(F)c(O)c(C(N)=O)c4)c4c(=O)n(C)cnc43)c(Cl)cn2)CC1] | 75% |
| I-290 | 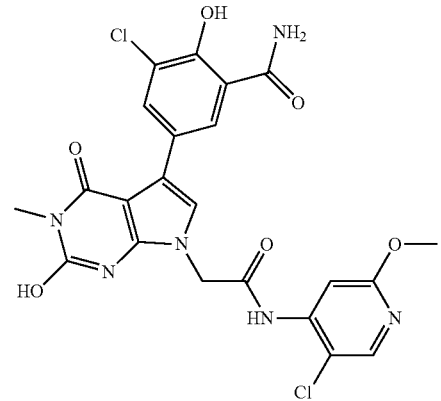 | 57% |
| I-291 | 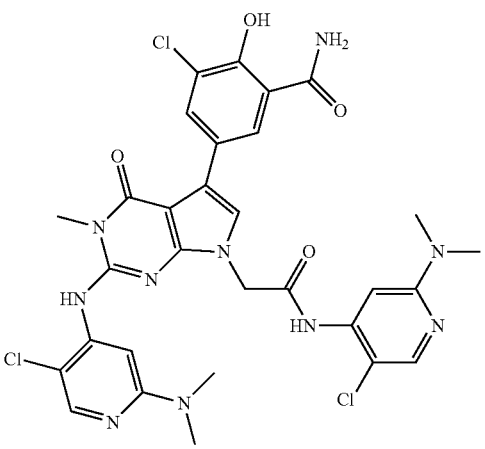 [SMILES: CN(C)c1cc(NC(=O)Cn2cc(-c3cc(Cl)c(O)c(C(N)=O)c3)c3c(=O)n(C)c(Nc4cc(N(C)C)ncc4Cl)nc32)c(Cl)cn1] | 64% |

TABLE 1-continued
| Compound | Structure | Yield |
|---|---|---|
| I-292 | 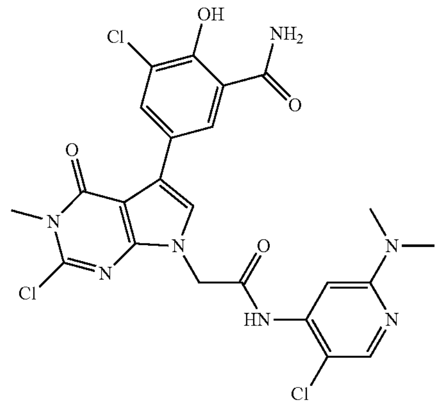 | 63% |
| I-293 | 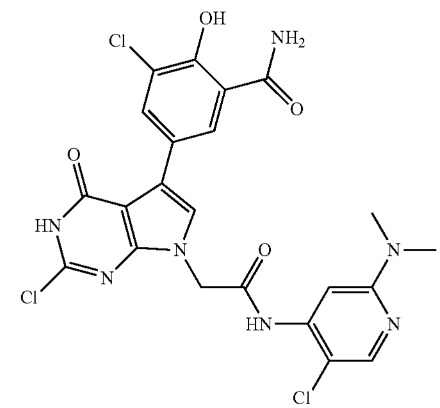 [SMILES: CN(C)c1cc(NC(=O)Cn2cc(-c3cc(Cl)c(O)c(C(N)=O)c3)c3c(=O)[nH]c(Cl)nc32)c(Cl)cn1] | 27% |
| I-294 | 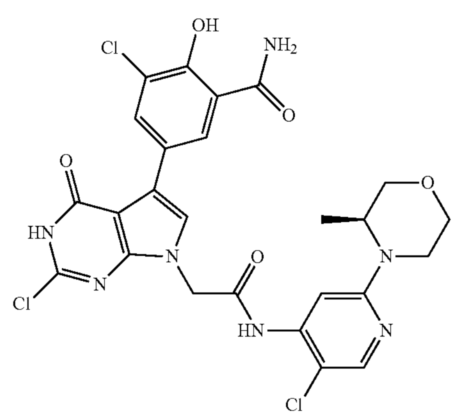 [SMILES: C[C@H]1COCCN1c1cc(NC(=O)Cn2cc(-c3cc(Cl)c(O)c(C(N)=O)c3)c3c(=O)[nH]c(Cl)nc32)c(Cl)cn1] | 20% |

TABLE 1-continued

| Compound | Structure | Yield |
|---|---|---|
| I-295 | 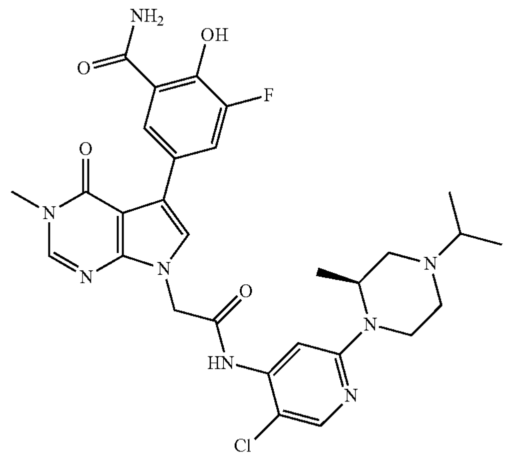 [SMILES: CC(C)N1CCN(c2cc(NC(=O)Cn3cc(-c4cc(F)c(O)c(C(N)=O)c4)c4c(=O)n(C)cnc43)c(Cl)cn2)[C@@H](C)C1] | 89% |
| I-296 | 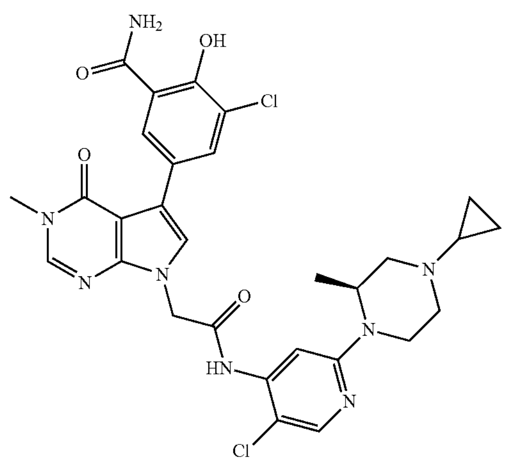 [SMILES: C[C@H]1CN(C2CC2)CCN1c1cc(NC(=O)Cn2cc(-c3cc(Cl)c(O)c(C(N)=O)c3)c3c(=O)n(C)cnc32)c(Cl)cn1] | 68% |
| I-297 | 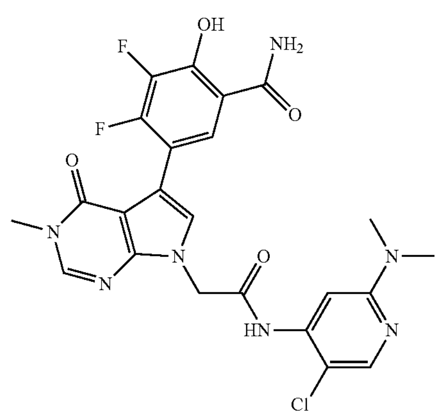 | 85% |

TABLE 1-continued

| Compound | Structure | Yield |
|---|---|---|
| I-298 | 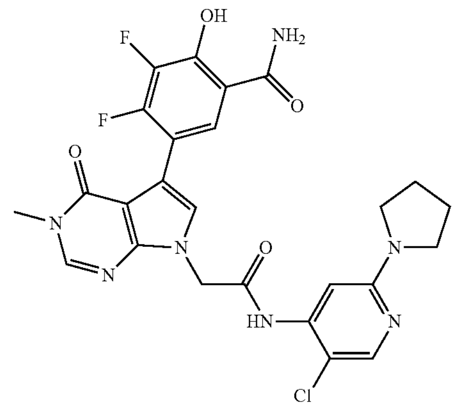 [SMILES: Cn1cnc2c(c(-c3cc(C(N)=O)c(O)c(F)c3F)cn2CC(=O)Nc2cc(N3CCCC3)ncc2Cl)c1=O] | 99% |
| I-299 | 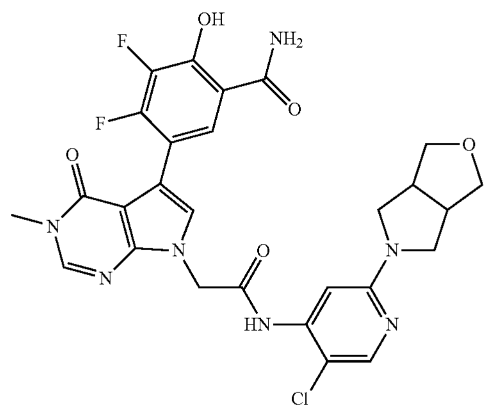 [SMILES: Cn1cnc2c(c(-c3cc(C(N)=O)c(O)c(F)c3F)cn2CC(=O)Nc2cc(N3CC4COCC4C3)ncc2Cl)c1=O] | 90% |
| I-300 | 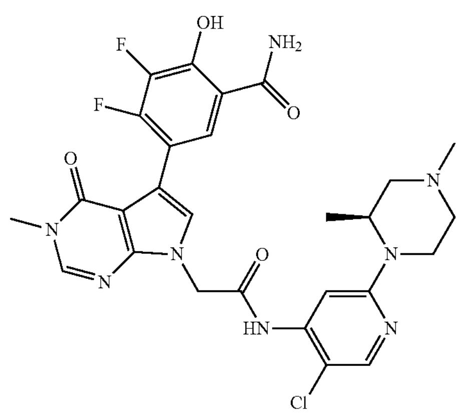 | 81% |
| I-301 | 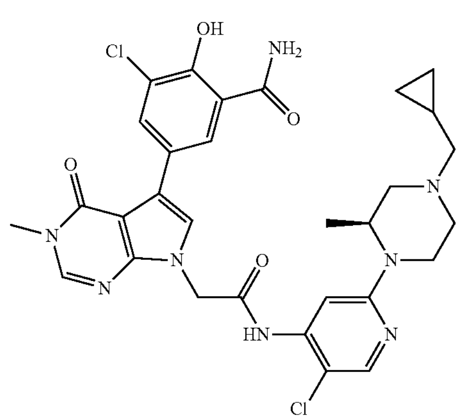 [SMILES: C[C@H]1CN(CC2CC2)CCN1c1cc(NC(=O)Cn2cc(-c3cc(Cl)c(O)c(C(N)=O)c3)c3c(=O)n(C)cnc32)c(Cl)cn1] | 57% |

TABLE 1-continued

| Compound | Structure | Yield |
|---|---|---|
| I-302 | 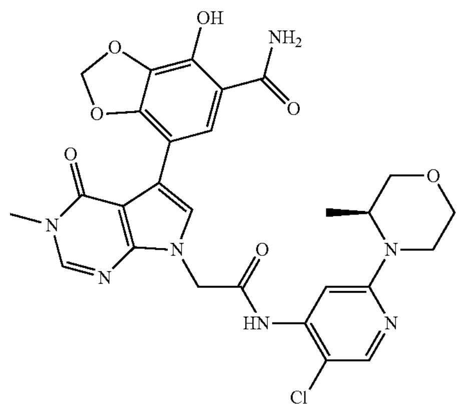 [SMILES: C[C@H]1COCCN1c1cc(NC(=O)Cn2cc(-c3cc(C(N)=O)c(O)c4c3OCO4)c3c(=O)n(C)cnc32)c(Cl)cn1] | 52% |
| I-303 | 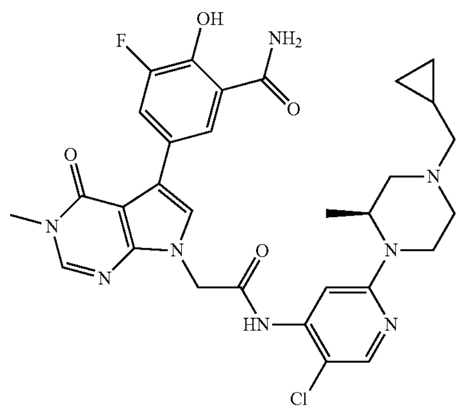 [SMILES: C[C@H]1CN(CC2CC2)CCN1c1cc(NC(=O)Cn2cc(-c3cc(F)c(O)c(C(N)=O)c3)c3c(=O)n(C)cnc32)c(Cl)cn1] | 37% |
| I-304 | 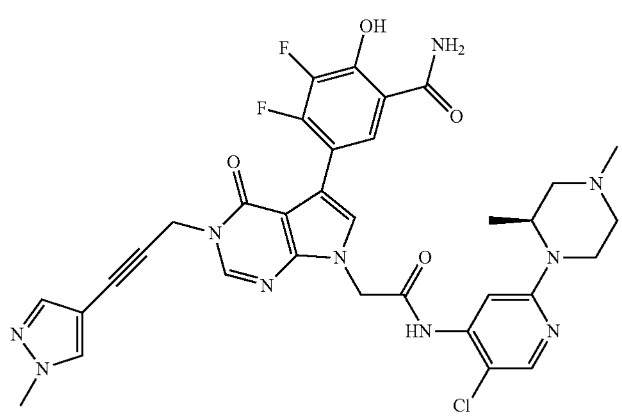 [SMILES: C[C@H]1CN(C)CCN1c1cc(NC(=O)Cn2cc(-c3cc(C(N)=O)c(O)c(F)c3F)c3c(=O)n(CC#Cc4cnn(C)c4)cnc32)c(Cl)cn1] | 6% |

TABLE 1-continued

| Compound | Structure | Yield |
|---|---|---|
| I-305 | 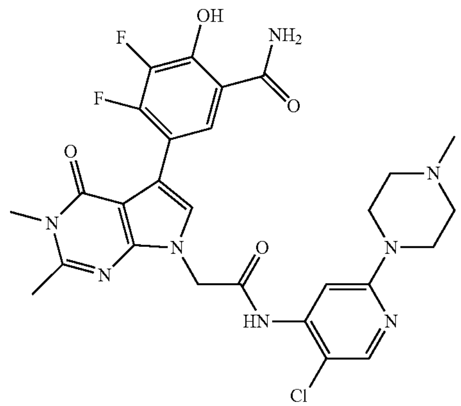 | 86% |
| I-306 | 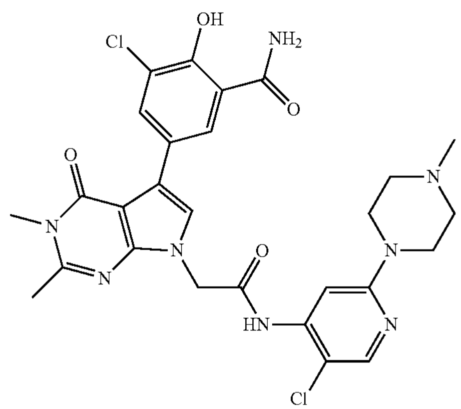 | 69% |
| I-307 | 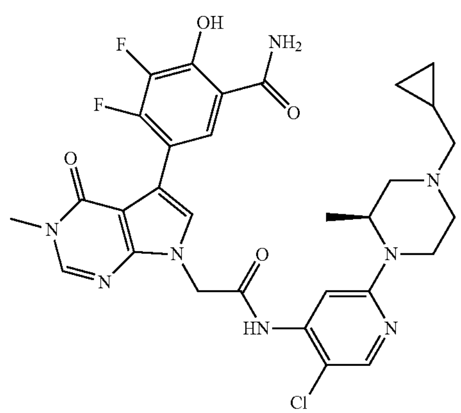 [SMILES: C[C@H]1CN(CC2CC2)CCN1c1cc(NC(=O)Cn2cc(-c3cc(C(N)=O)c(O)c(F)c3F)c3c(=O)n(C)cnc32)c(Cl)cn1] | 79% |
| I-308 | 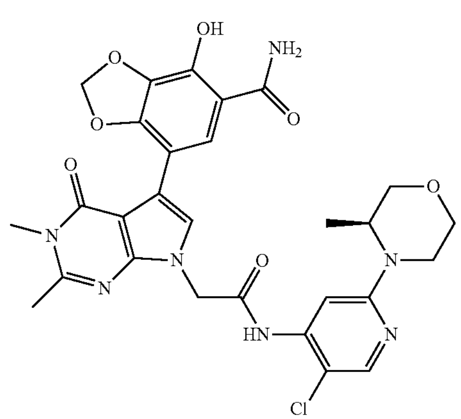 [SMILES: Cc1nc2c(c(-c3cc(C(N)=O)c(O)c4c3OCO4)cn2CC(=O)Nc2cc(N3CCOC[C@@H]3C)ncc2Cl)c(=O)n1C] | 71% |

TABLE 1-continued

| Compound | Structure | Yield |
|---|---|---|
| I-309 | 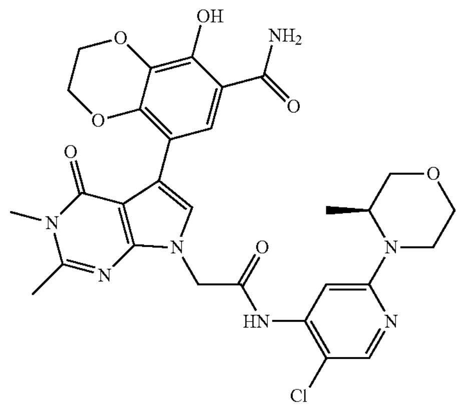 [SMILES: Cc1nc2c(c(-c3cc(C(N)=O)c(O)c4c3OCCO4)cn2CC(=O)Nc2cc(N3CCOC[C@@H]3C)ncc2Cl)c(=O)n1C] | 50% |
| I-310 | 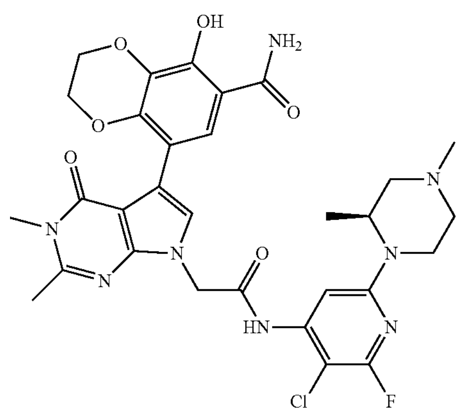 | 45% |
| I-311 | 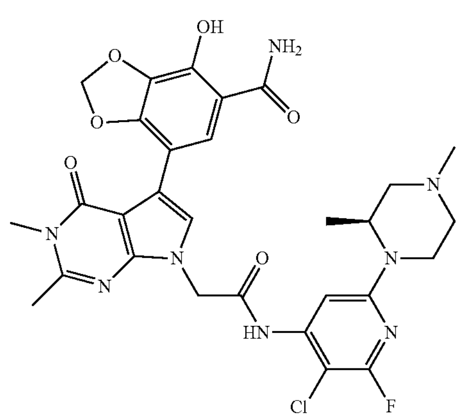 | 78% |

TABLE 1-continued

| Compound | Structure | Yield |
|---|---|---|
| I-312 | 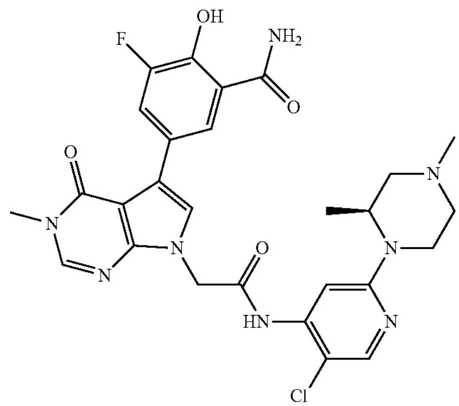 | 42% |
| I-313 | 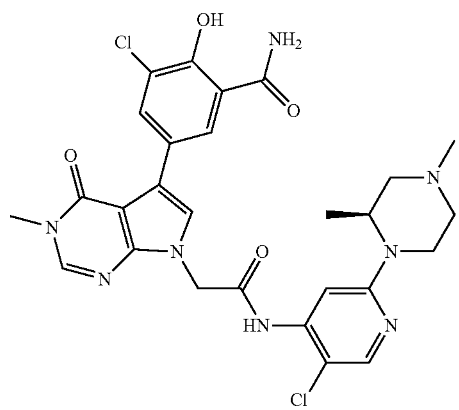 | 35% |
| I-314 | 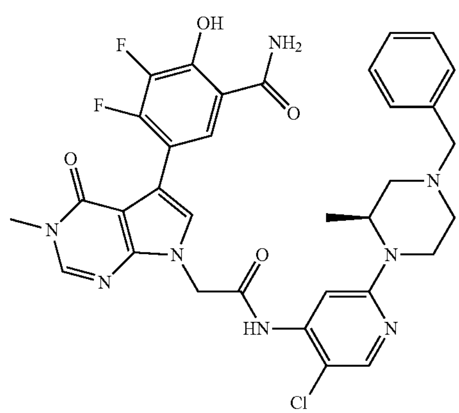 [SMILES: C[C@H]1CN(Cc2ccccc2)CCN1c1cc(NC(=O)Cn2cc(-c3cc(C(N)=O)c(O)c(F)c3F)c3c(=O)n(C)cnc32)c(Cl)cn1] | 59% |
| I-315 | 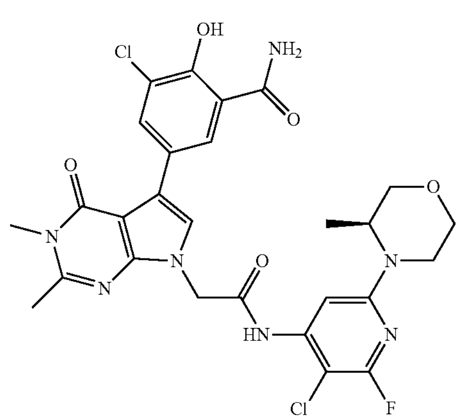 [SMILES: Cc1nc2c(c(-c3cc(Cl)c(O)c(C(N)=O)c3)cn2CC(=O)Nc2cc(N3CCOC[C@@H]3C)nc(F)c2Cl)c(=O)n1C] | 63% |

TABLE 1-continued
| Compound | Structure | Yield |
|---|---|---|
| I-316 | 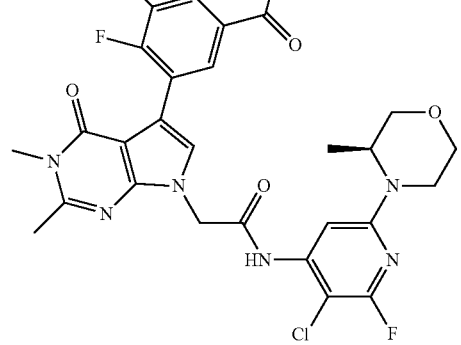 | 57% |
| I-317 | 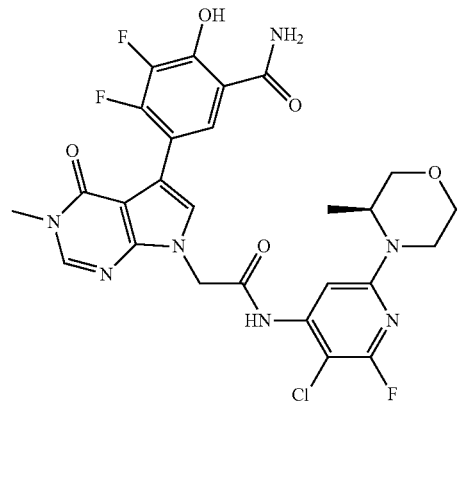 [SMILES: C[C@H]1COCCN1c1cc(NC(=O)Cn2cc(-c3cc(C(N)=O)c(O)c(F)c3F)c3c(=O)n(C)cnc32)c(Cl)c(F)n1] | 74% |
| I-318 | 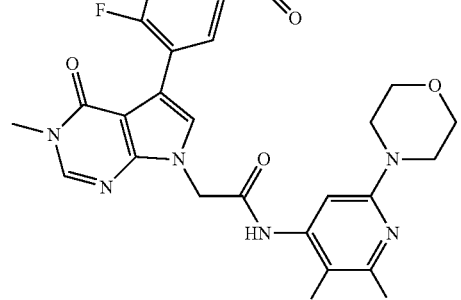 | 79% |

TABLE 1-continued
| Compound | Structure | Yield |
|---|---|---|
| I-319 | 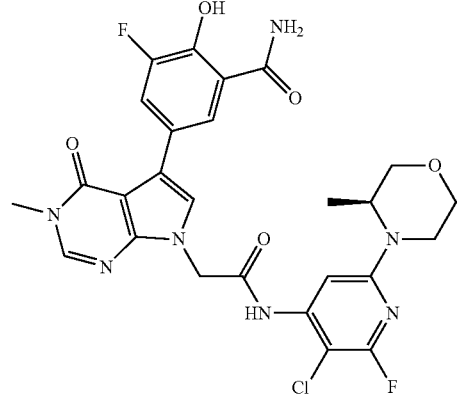 [SMILES: C[C@H]1COCCN1c1cc(NC(=O)Cn2cc(-c3cc(F)c(O)c(C(N)=O)c3)c3c(=O)n(C)cnc32)c(Cl)c(F)n1] | 85% |
| I-320 | 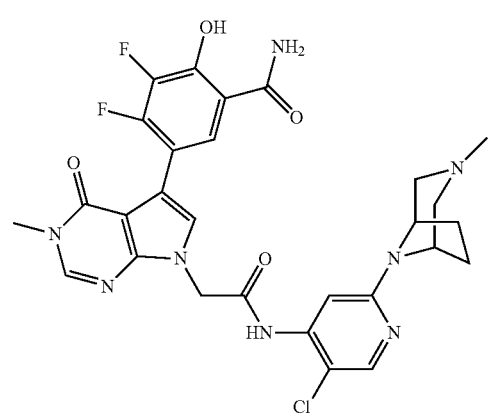 | 93% |
| I-321 | 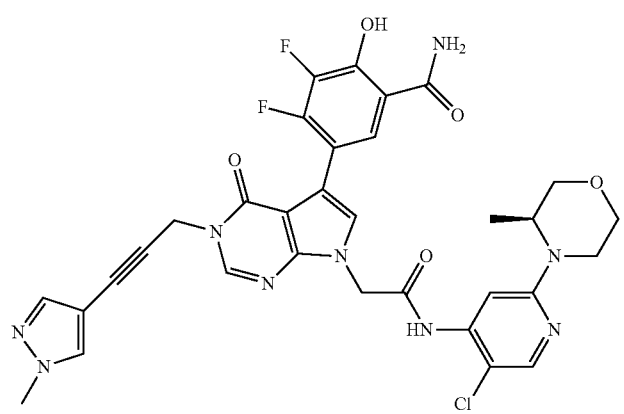 [SMILES: C[C@H]1COCCN1c1cc(NC(=O)Cn2cc(-c3cc(C(N)=O)c(O)c(F)c3F)c3c(=O)n(CC#Cc4cnn(C)c4)cnc32)c(Cl)cn1] | 24% |

TABLE 1-continued

| Compound | Structure | Yield |
|---|---|---|
| I-322 | 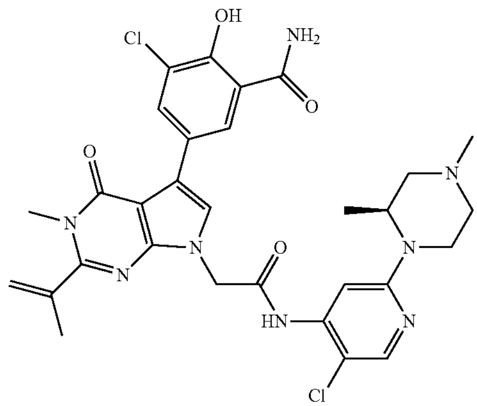 [SMILES: C=C(C)c1nc2c(c(-c3cc(Cl)c(O)c(C(N)=O)c3)cn2CC(=O)Nc2cc(N3CCN(C)C[C@@H]3C)ncc2Cl)c(=O)n1C] | 67% |
| I-323 | 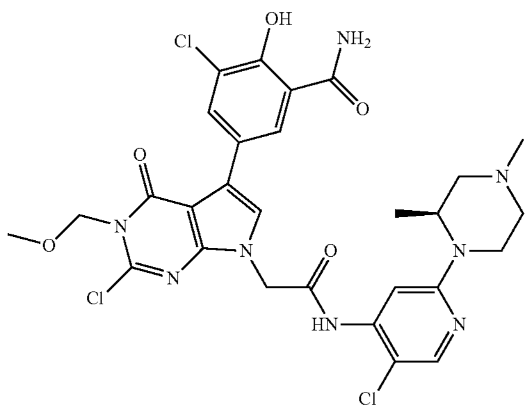 | 27% |
| I-324 | 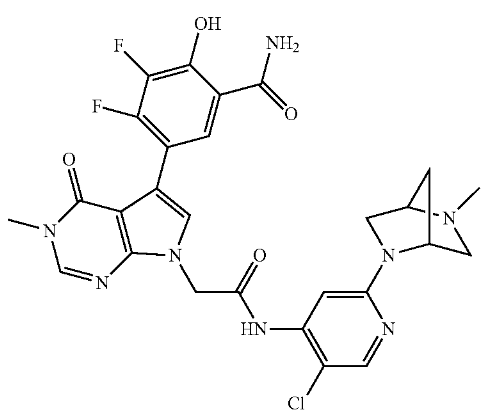 | 31% |
| I-325 | 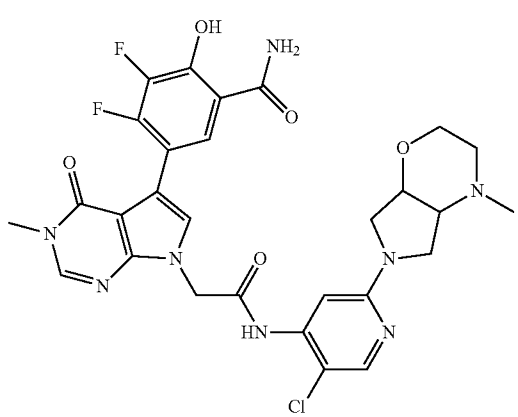 | 90% |

TABLE 1-continued
| Compound | Structure | Yield |
|---|---|---|
| I-326 | 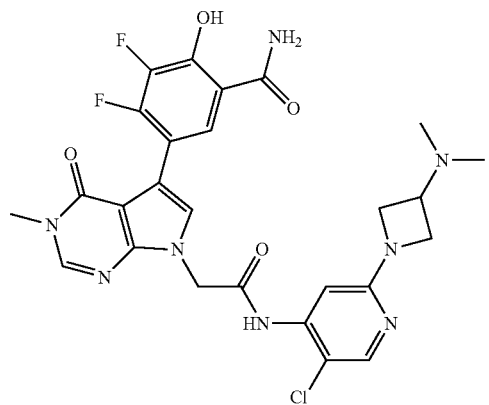 | 87% |
| I-327 | 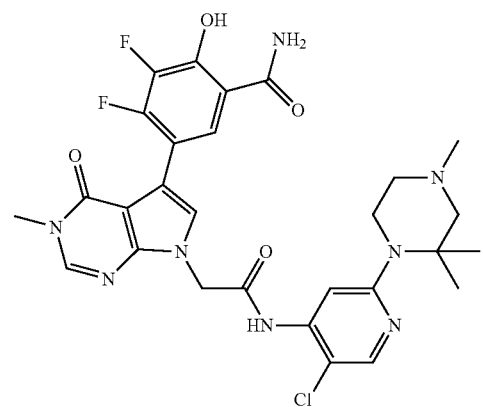 | 80% |
| I-328 | 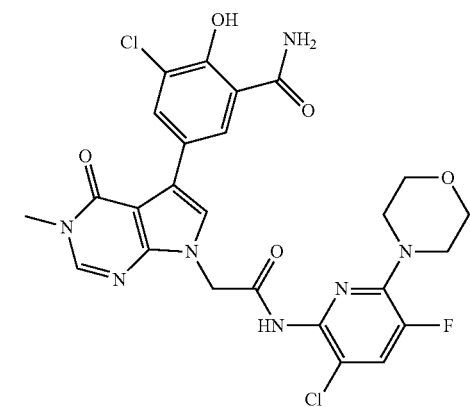 | 86% |

TABLE 1-continued

| Compound | Structure | Yield |
|---|---|---|
| I-329 | 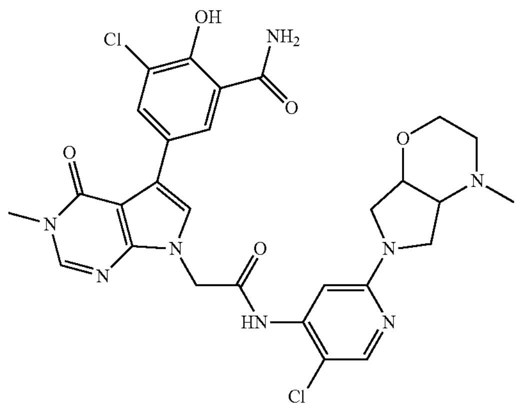 | 85% |
| I-330 | 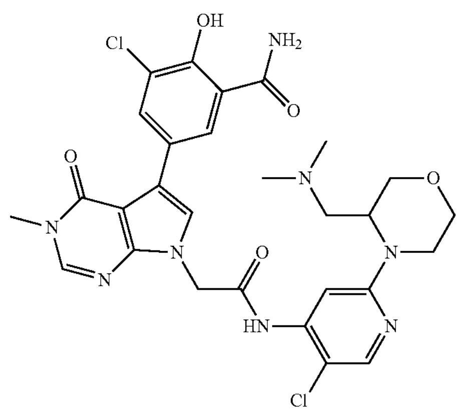 | 69% |
| I-331 | 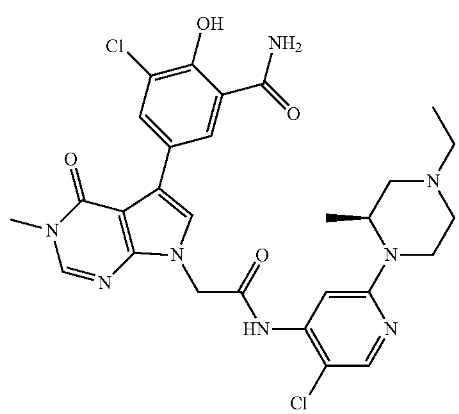 | 47% |
| I-332 | 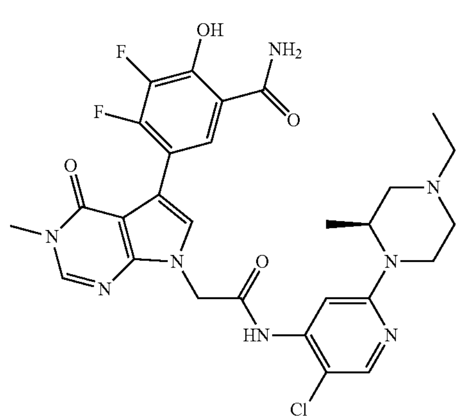 [SMILES: CCN1CCN(c2cc(NC(=O)Cn3cc(-c4cc(C(N)=O)c(O)c(F)c4F)c4c(=O)n(C)cnc43)c(Cl)cn2)[C@@H](C)C1] | 42% |

TABLE 1-continued
| Compound | Structure | Yield |
|---|---|---|
| I-333 | 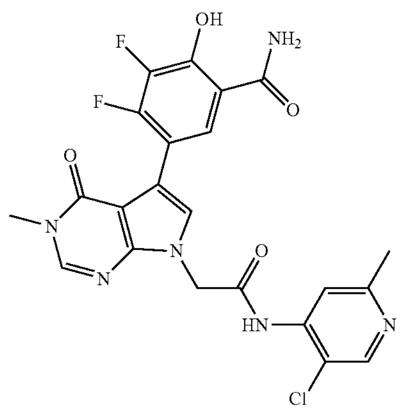 | 69% |
| I-334 | 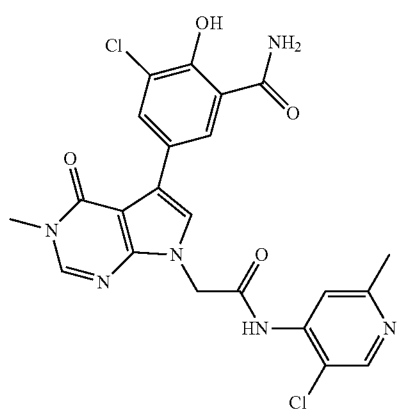 | 61% |
| I-335 | 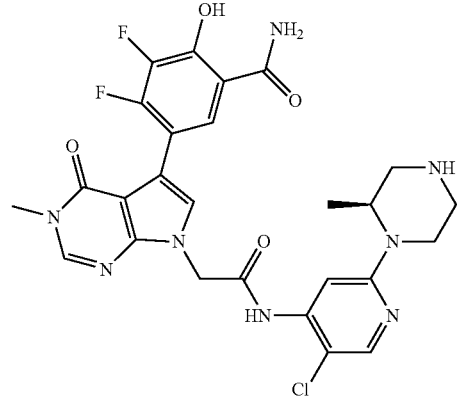 [SMILES: C[C@H]1CNCCN1c1cc(NC(=O)Cn2cc(-c3cc(C(N)=O)c(O)c(F)c3F)c3c(=O)n(C)cnc32)c(Cl)cn1] | 39% |

TABLE 1-continued

| Compound | Structure | Yield |
|---|---|---|
| I-336 | 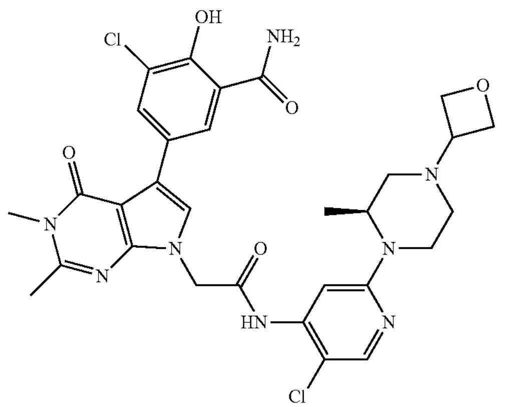 [SMILES: Cc1nc2c(c(-c3cc(Cl)c(O)c(C(N)=O)c3)cn2CC(=O)Nc2cc(N3CCN(C4COC4)C[C@@H]3C)ncc2Cl)c(=O)n1C] | 53% |
| I-337 | 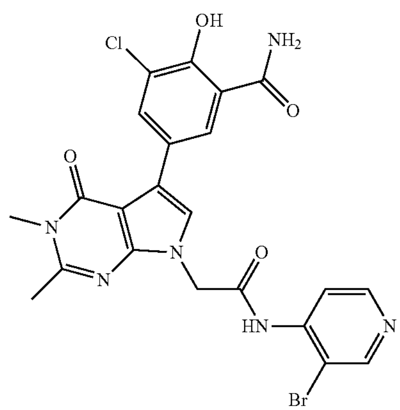 [SMILES: Cc1nc2c(c(-c3cc(Cl)c(O)c(C(N)=O)c3)cn2CC(=O)Nc2ccncc2Br)c(=O)n1C] | 75% |
| I-338 | 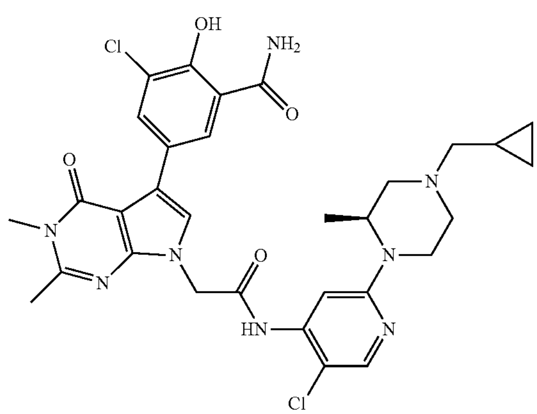 [SMILES: Cc1nc2c(c(-c3cc(Cl)c(O)c(C(N)=O)c3)cn2CC(=O)Nc2cc(N3CCN(CC4CC4)C[C@@H]3C)ncc2Cl)c(=O)n1C] | 64% |
| I-339 | 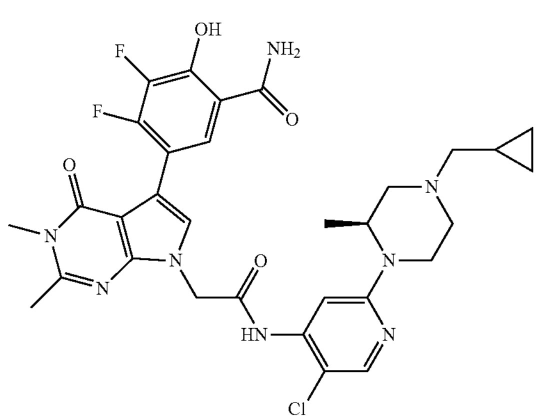 [SMILES: Cc1nc2c(c(-c3cc(C(N)=O)c(O)c(F)c3F)cn2CC(=O)Nc2cc(N3CCN(CC4CC4)C[C@@H]3C)ncc2Cl)c(=O)n1C] | 57% |

TABLE 1-continued

| Compound | Structure | Yield |
|---|---|---|
| I-340 | 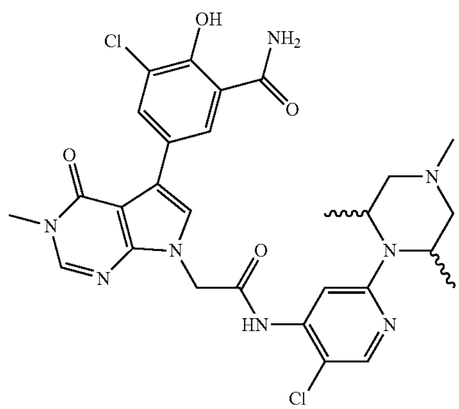 | 15% |
| I-341 | 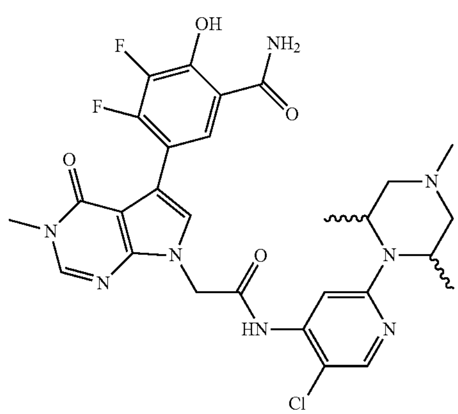 | 17% |
| I-342 | 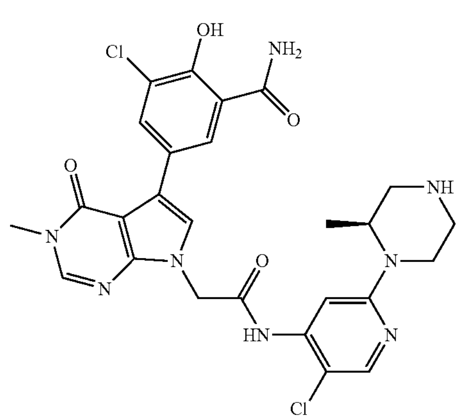 [SMILES: C[C@H]1CNCCN1c1cc(NC(=O)Cn2cc(-c3cc(Cl)c(O)c(C(N)=O)c3)c3c(=O)n(C)cnc32)c(Cl)cn1] | 50% |

TABLE 1-continued

| Compound | Structure | Yield |
|---|---|---|
| I-343 | 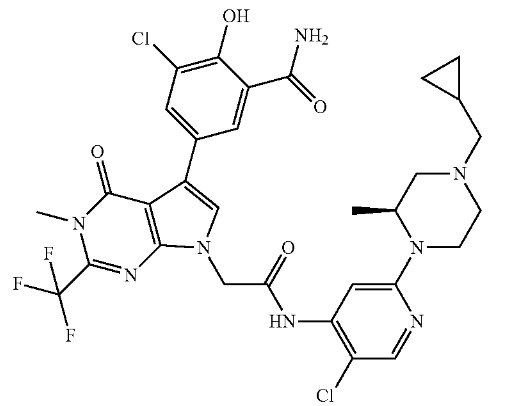 [SMILES: C[C@H]1CN(CC2CC2)CCN1c1cc(NC(=O)Cn2cc(-c3cc(Cl)c(O)c(C(N)=O)c3)c3c(=O)n(C)c(C(F)(F)F)nc32)c(Cl)cn1] | 93% |
| I-344 | 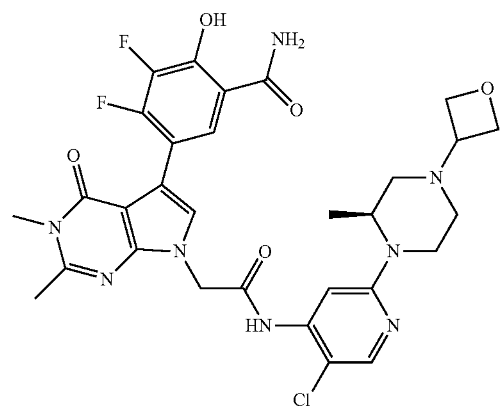 [SMILES: Cc1nc2c(c(-c3cc(C(N)=O)c(O)c(F)c3F)cn2CC(=O)Nc2cc(N3CCN(C4COC4)C[C@@H]3C)ncc2Cl)c(=O)n1C] | 25% |
| I-345 | 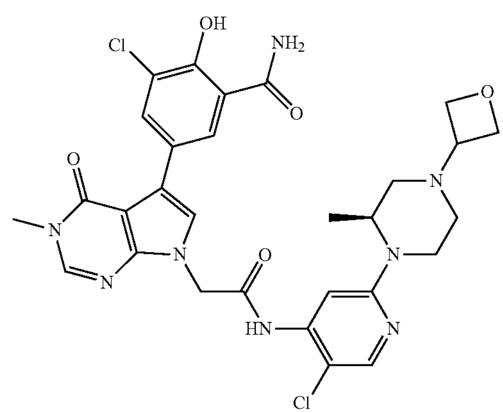 [SMILES: C[C@H]1CN(C2COC2)CCN1c1cc(NC(=O)Cn2cc(-c3cc(Cl)c(O)c(C(N)=O)c3)c3c(=O)n(C)cnc32)c(Cl)cn1] | 86% |
| I-346 | 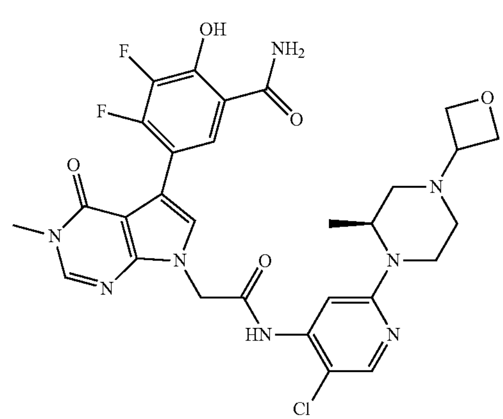 [SMILES: C[C@H]1CN(C2COC2)CCN1c1cc(NC(=O)Cn2cc(-c3cc(C(N)=O)c(O)c(F)c3F)c3c(=O)n(C)cnc32)c(Cl)cn1] | 85% |

TABLE 1-continued

| Compound | Structure | Yield |
|---|---|---|
| I-347 | 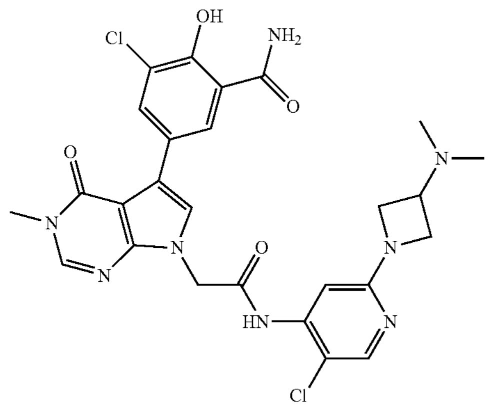 | 91% |
| I-348 | 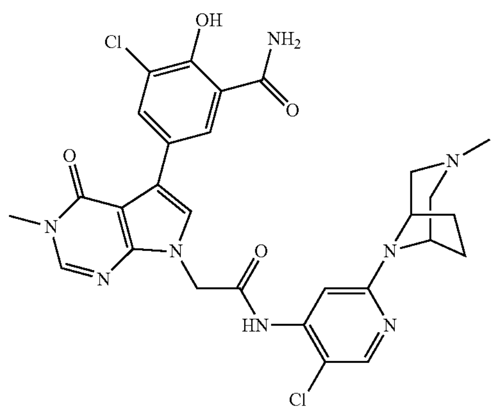 | 88% |
| I-349 | 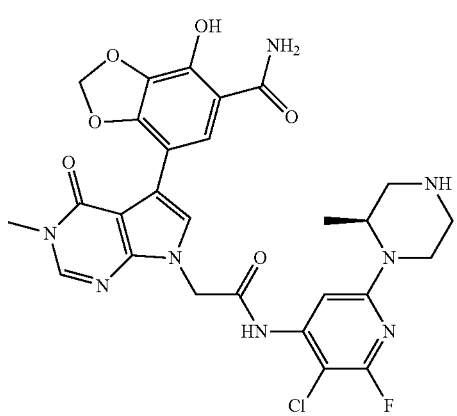 [SMILES: C[C@H]1CNCCN1c1cc(NC(=O)Cn2cc(-c3cc(C(N)=O)c(O)c4c3OCO4)c3c(=O)n(C)cnc32)c(Cl)c(F)n1] | 72% |

TABLE 1-continued

| Compound | Structure | Yield |
|---|---|---|
| I-350 | 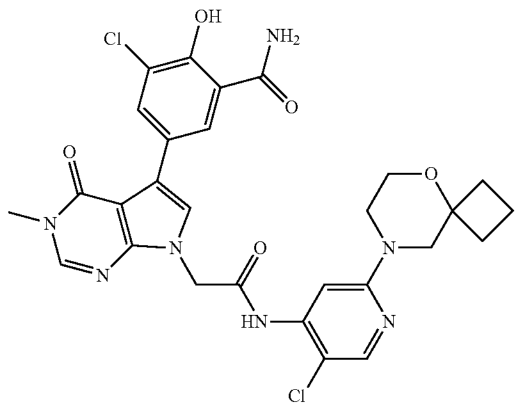 [SMILES: Cn1cnc2c(c(-c3cc(Cl)c(O)c(C(N)=O)c3)cn2CC(=O)Nc2cc(N3CCOC4(CCC4)C3)ncc2Cl)c1=O] | 84% |
| I-351 | 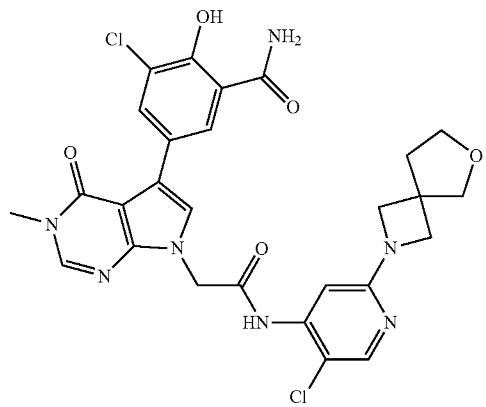 [SMILES: Cn1cnc2c(c(-c3cc(Cl)c(O)c(C(N)=O)c3)cn2CC(=O)Nc2cc(N3CC4(CCOC4)C3)ncc2Cl)c1=O] | 79% |
| I-352 | 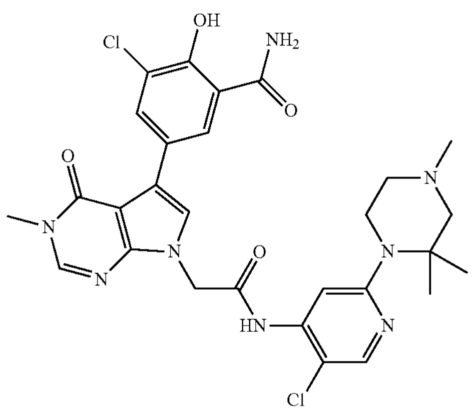 | 90% |
| I-353 | 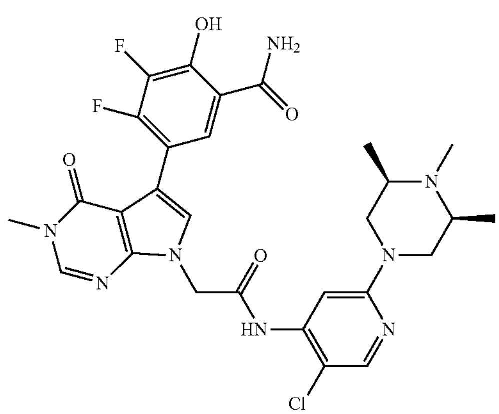 | 98% |

TABLE 1-continued
| Compound | Structure | Yield |
|---|---|---|
| I-354 | 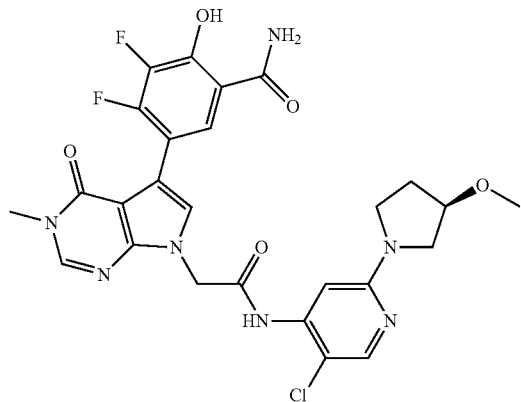 | 76% |
| I-355 | 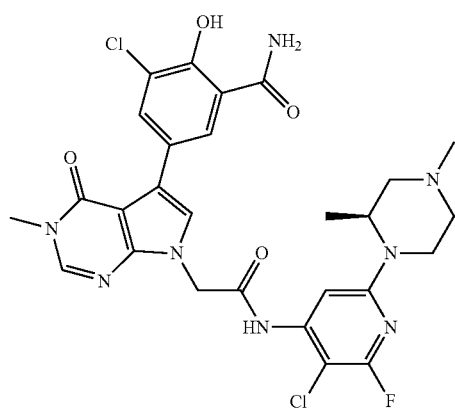 | 85% |
| I-356 | 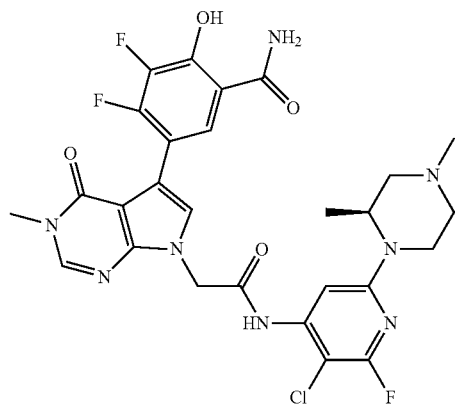 | 88% |

| Compound | Structure | Yield |
|---|---|---|
| I-357 | 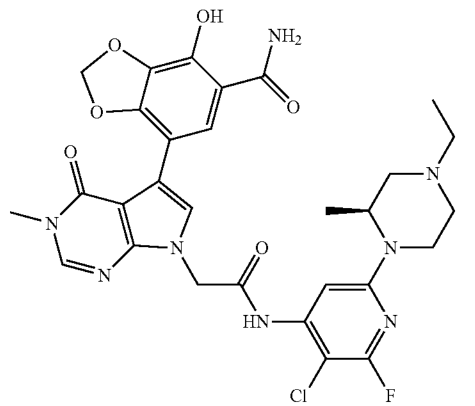 [SMILES: CCN1CCN(c2cc(NC(=O)Cn3cc(-c4cc(C(N)=O)c(O)c5c4OCO5)c4c(=O)n(C)cnc43)c(Cl)c(F)n2)[C@@H](C)C1] | 59% |
| I-358 | 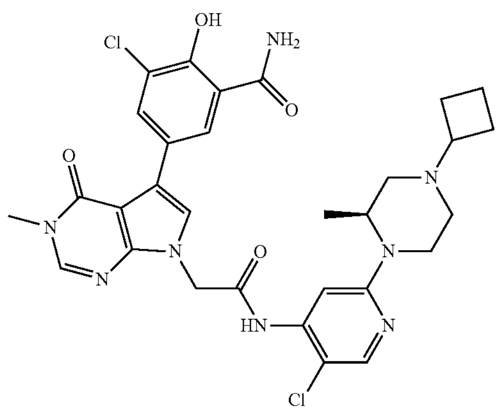 [SMILES: C[C@H]1CN(C2CCC2)CCN1c1cc(NC(=O)Cn2cc(-c3cc(Cl)c(O)c(C(N)=O)c3)c3c(=O)n(C)cnc32)c(Cl)cn1] | 88% |
| I-359 | 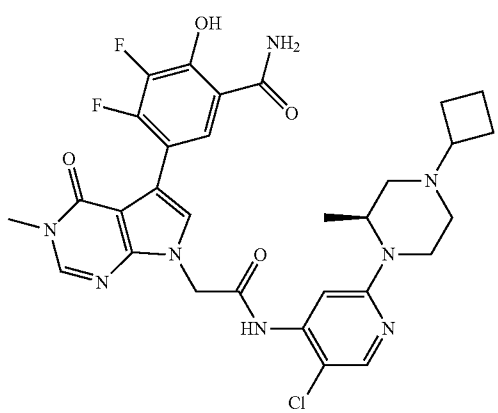 | 90% |
| I-360 | 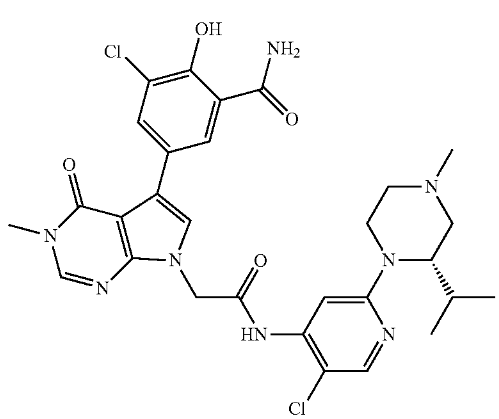 [SMILES: CC(C)[C@H]1CN(C)CCN1c1cc(NC(=O)Cn2cc(-c3cc(Cl)c(O)c(C(N)=O)c3)c3c(=O)n(C)cnc32)c(Cl)cn1] | 90% |

TABLE 1-continued

| Compound | Structure | Yield |
| --- | --- | --- |
| I-361 | 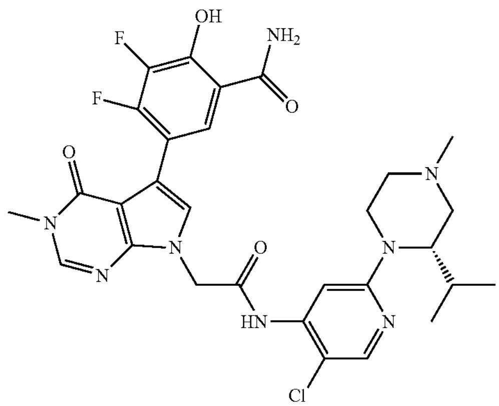 [SMILES: CC(C)[C@H]1CN(C)CCN1c1cc(NC(=O)Cn2cc(-c3cc(C(N)=O)c(O)c(F)c3F)c3c(=O)n(C)cnc32)c(Cl)cn1] | 88% |
| I-362 | 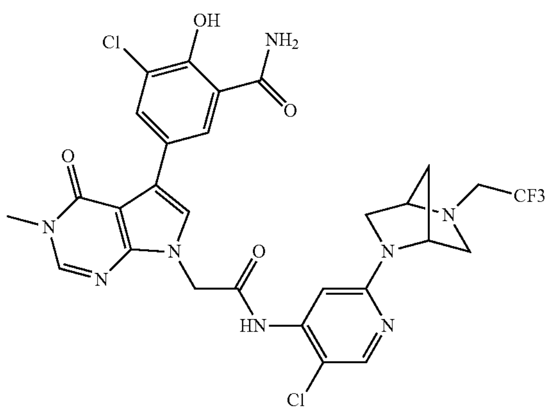 [SMILES: Cn1cnc2c(c(-c3cc(Cl)c(O)c(C(N)=O)c3)cn2CC(=O)Nc2cc(N3CC4CC3CN4CC(F)(F)F)ncc2Cl)c1=O] | 87% |
| I-363 | 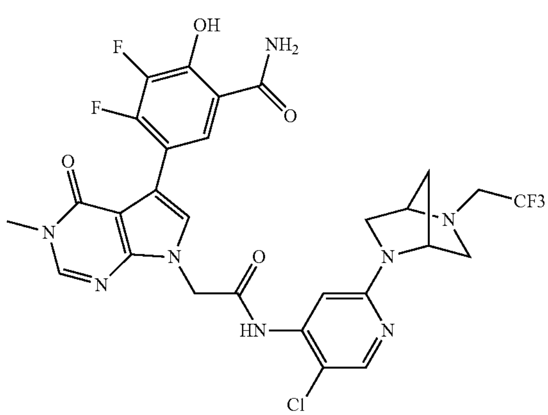 [SMILES: Cn1cnc2c(c(-c3cc(C(N)=O)c(O)c(F)c3F)cn2CC(=O)Nc2cc(N3CC4CC3CN4CC(F)(F)F)ncc2Cl)c1=O] | 84% |

TABLE 1-continued

| Compound | Structure | Yield |
|---|---|---|
| I-364 | 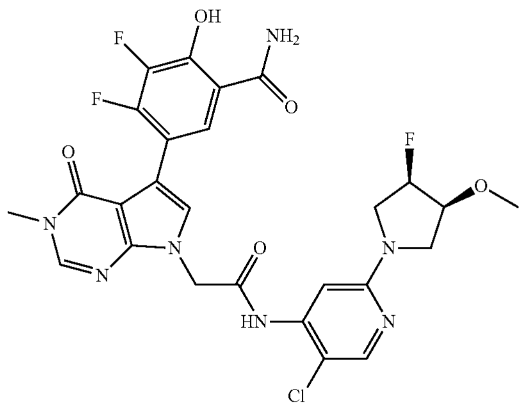 | 79% |
| I-365 | 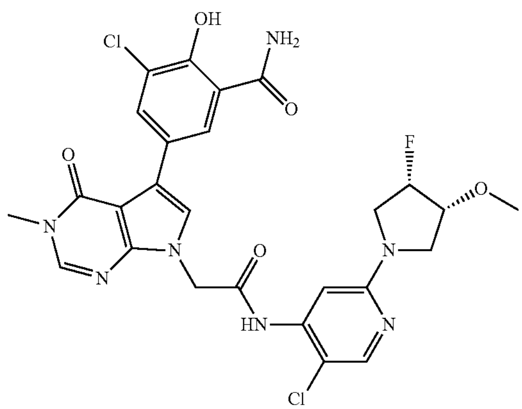 | 78% |
| I-366 | 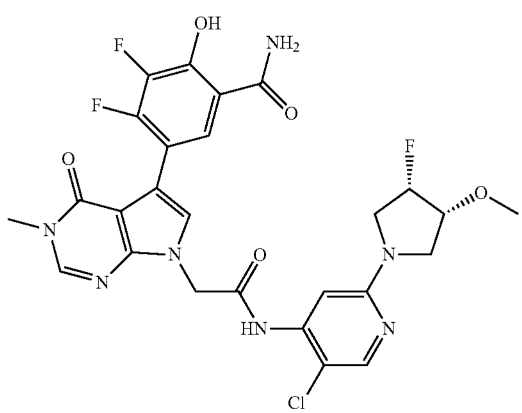 | 82% |
| I-367 | 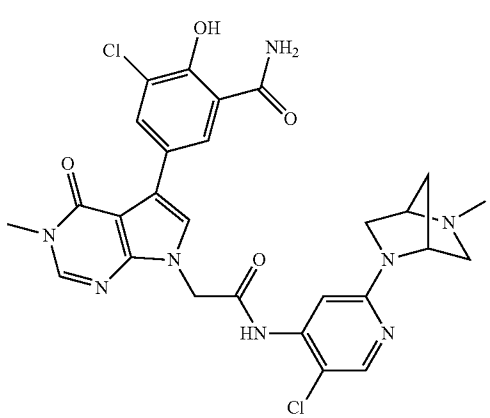 | 48% |

TABLE 1-continued
| Compound | Structure | Yield |
|---|---|---|
| I-368 | 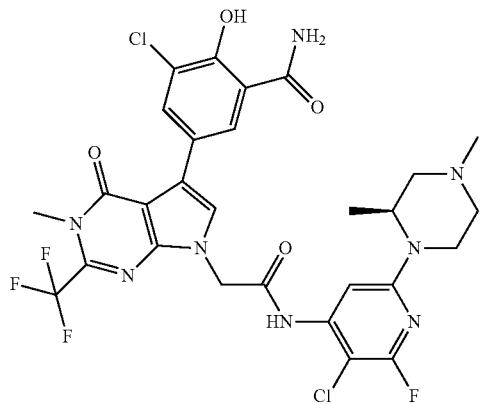 [SMILES: C[C@H]1CN(C)CCN1c1cc(NC(=O)Cn2cc(-c3cc(Cl)c(O)c(C(N)=O)c3)c3c(=O)n(C)c(C(F)(F)F)nc32)c(Cl)c(F)n1] | 90% |
| I-369 | 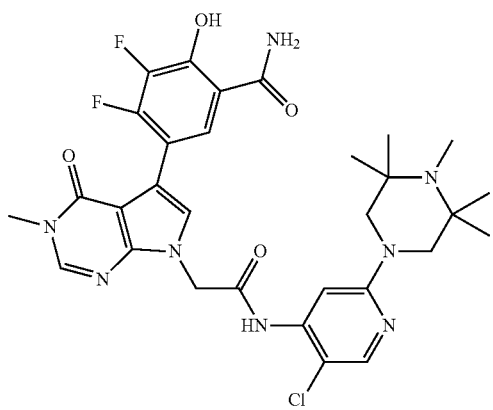 | 54% |
| I-370 | 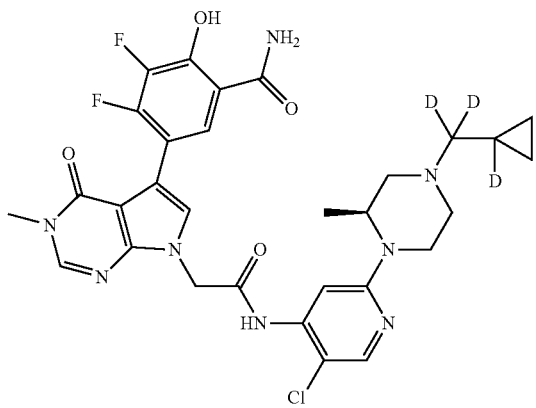 [SMILES: [2H]C1(C([2H])([2H])N2CCN(c3cc(NC(=O)Cn4cc(-c5cc(C(N)=O)c(O)c(F)c5F)c5c(=O)n(C)cnc54)c(Cl)cn3)[C@@H](C)C2)CC1] | 22% |

TABLE 1-continued

| Compound | Structure | Yield |
|---|---|---|
| I-371 | 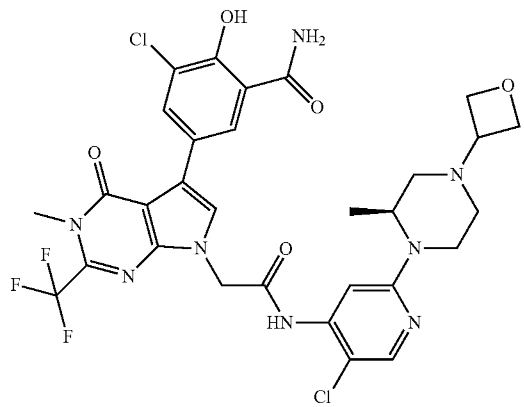 [SMILES: C[C@H]1CN(C2COC2)CCN1c1cc(NC(=O)Cn2cc(-c3cc(Cl)c(O)c(C(N)=O)c3)c3c(=O)n(C)c(C(F)(F)F)nc32)c(Cl)cn1] | 85% |
| I-372 | 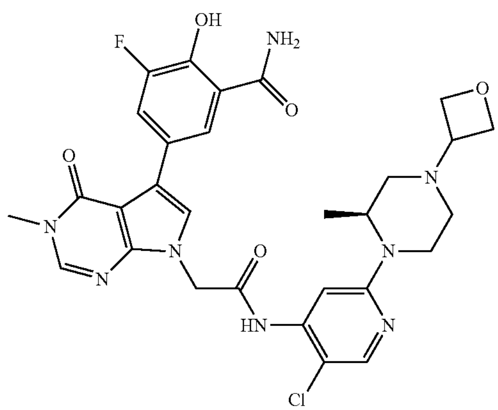 [SMILES: C[C@H]1CN(C2COC2)CCN1c1cc(NC(=O)Cn2cc(-c3cc(F)c(O)c(C(N)=O)c3)c3c(=O)n(C)cnc32)c(Cl)cn1] | 64% |
| I-373 | 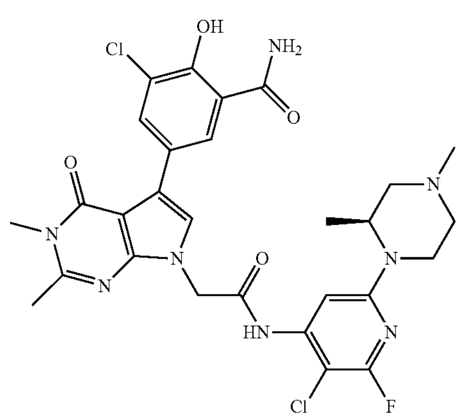 | 87% |

TABLE 1-continued

| Compound | Structure | Yield |
|---|---|---|
| I-374 | 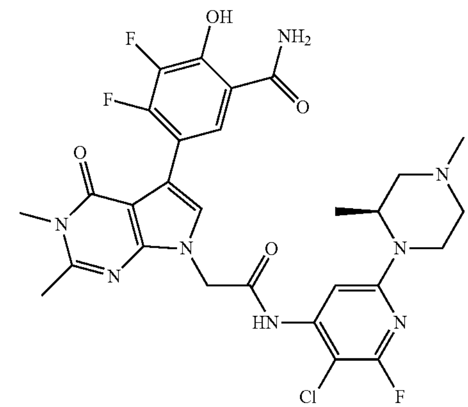 | 62% |
| I-375 | 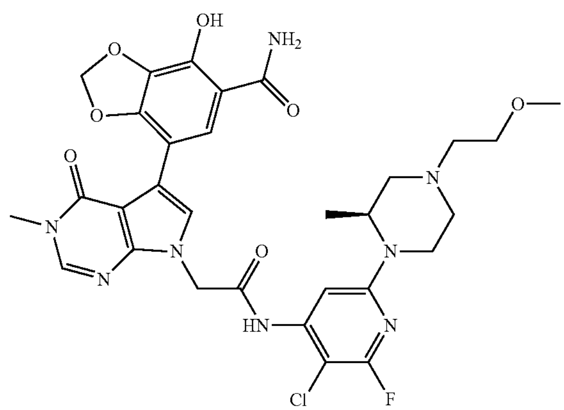 | 64% |
| I-376 | 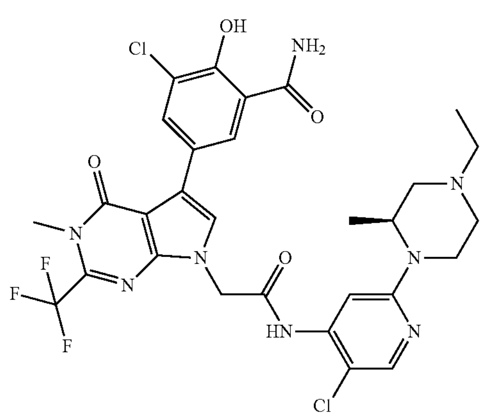 [SMILES: CCN1CCN(c2cc(NC(=O)Cn3cc(-c4cc(Cl)c(O)c(C(N)=O)c4)c4c(=O)n(C)c(C(F)(F)F)nc43)c(Cl)cn2)[C@@H](C)C1] | 84% |

TABLE 1-continued
| Compound | Structure | Yield |
|---|---|---|
| I-377 | 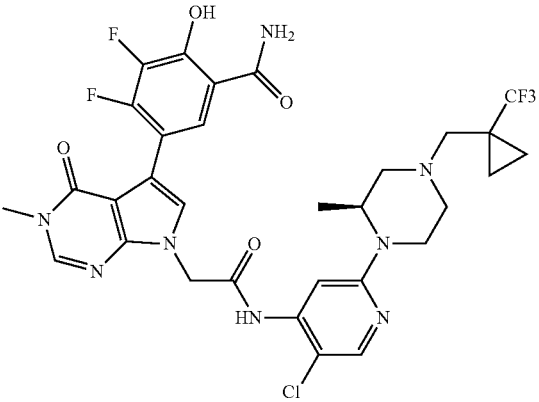 [SMILES: C[C@H]1CN(CC2(C(F)(F)F)CC2)CCN1c1cc(NC(=O)Cn2cc(-c3cc(C(N)=O)c(O)c(F)c3F)c3c(=O)n(C)cnc32)c(Cl)cn1] | 69% |
| I-378 | 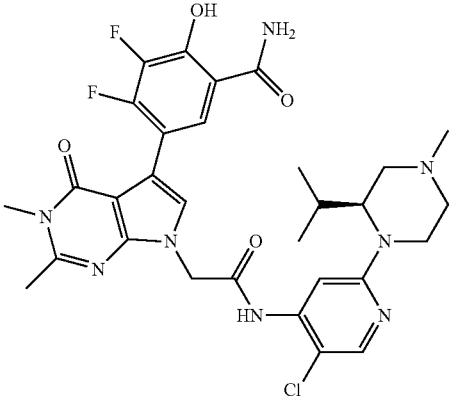 | 44% |
| I-379 | 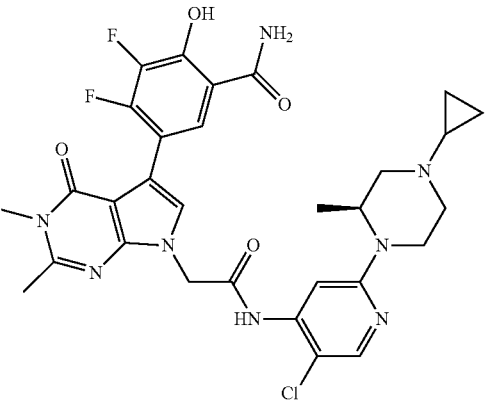 [SMILES: Cc1nc2c(c(-c3cc(C(N)=O)c(O)c(F)c3F)cn2CC(=O)Nc2cc(N3CCN(C4CC4)C[C@@H]3C)ncc2Cl)c(=O)n1C] | 84% |

TABLE 1-continued

| Compound | Structure | Yield |
|---|---|---|
| I-380 | 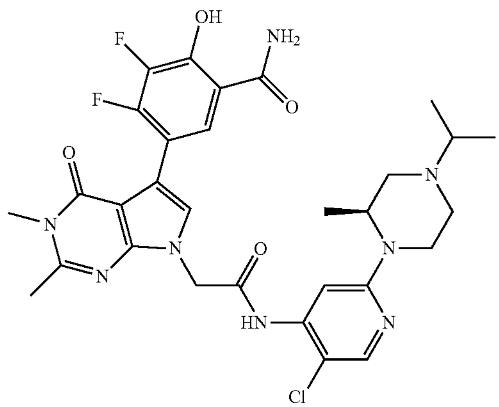 [SMILES: Cc1nc2c(c(-c3cc(C(N)=O)c(O)c(F)c3F)cn2CC(=O)Nc2cc(N3CCN(C(C)C)C[C@@H]3C)ncc2Cl)c(=O)n1C] | 90% |
| I-381 | 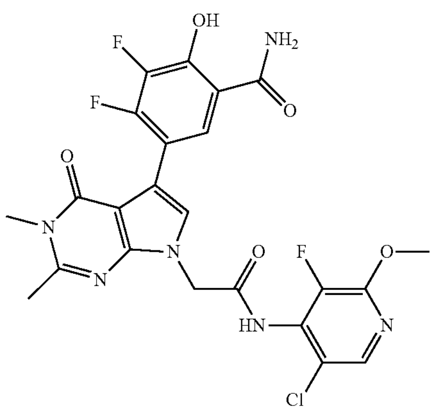 | 38% |
| I-382 | 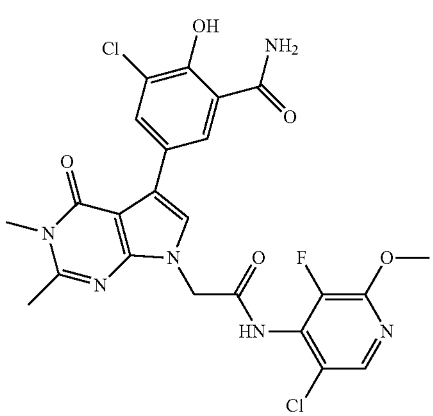 | 25% |

TABLE 1-continued

| Compound | Structure | Yield |
|---|---|---|
| I-383 | 5-(3-chloro-4-hydroxy-5-carbamoylphenyl)-3-methyl-7-[2-(2-chloro-4-fluorophenylamino)-2-oxoethyl]-3H-pyrrolo[2,3-d]pyrimidin-4(7H)-one | 28% |
| I-384 | 5-(3-chloro-4-hydroxy-5-carbamoylphenyl)-3-methyl-7-[2-(2-chloro-4-cyanophenylamino)-2-oxoethyl]-3H-pyrrolo[2,3-d]pyrimidin-4(7H)-one | 29% |
| I-385 | 5-(3-chloro-4-hydroxy-5-carbamoylphenyl)-3-methyl-7-[2-(2-chloro-4-nitrophenylamino)-2-oxoethyl]-3H-pyrrolo[2,3-d]pyrimidin-4(7H)-one | 25% |

TABLE 1-continued

| Compound | Structure | Yield |
|---|---|---|
| I-386 | 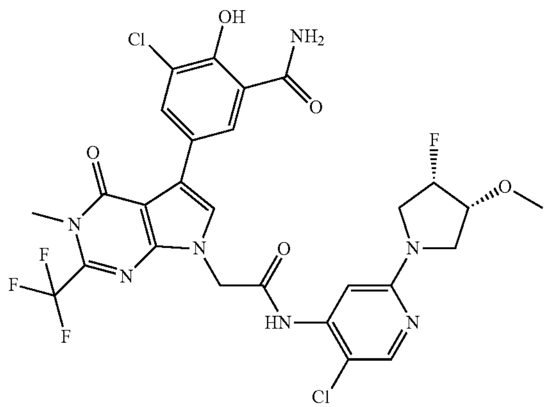 [SMILES: CO[C@@H]1CN(c2cc(NC(=O)Cn3cc(-c4cc(Cl)c(O)c(C(N)=O)c4)c4c(=O)n(C)c(C(F)(F)F)nc43)c(Cl)cn2)C[C@@H]1F] | 87% |
| I-387 | 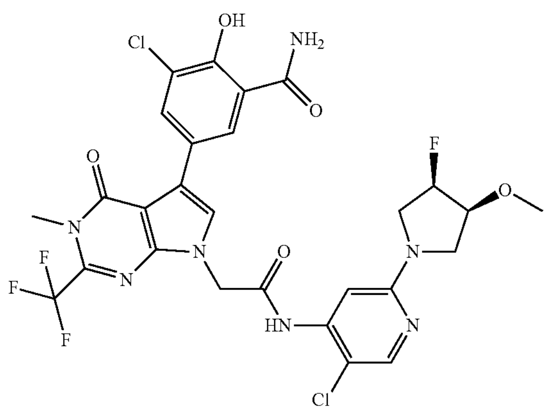 [SMILES: CO[C@H]1CN(c2cc(NC(=O)Cn3cc(-c4cc(Cl)c(O)c(C(N)=O)c4)c4c(=O)n(C)c(C(F)(F)F)nc43)c(Cl)cn2)C[C@H]1F] | 85% |
| I-388 | 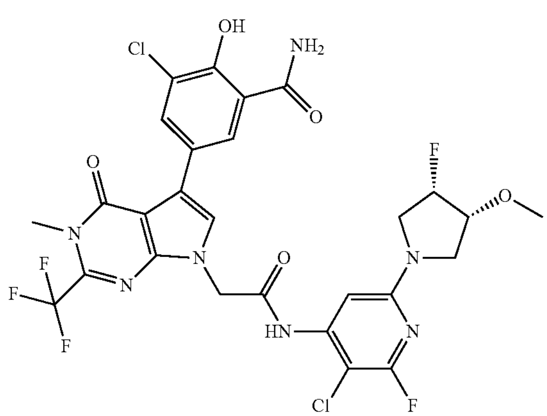 [SMILES: CO[C@@H]1CN(c2cc(NC(=O)Cn3cc(-c4cc(Cl)c(O)c(C(N)=O)c4)c4c(=O)n(C)c(C(F)(F)F)nc43)c(Cl)c(F)n2)C[C@@H]1F] | 94% |

TABLE 1-continued
| Compound | Structure | Yield |
|---|---|---|
| I-389 | 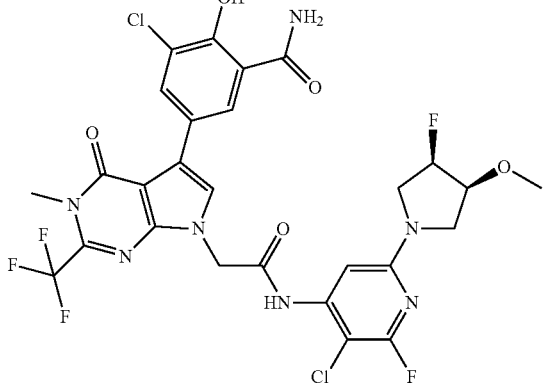 | 91% |
| I-390 | 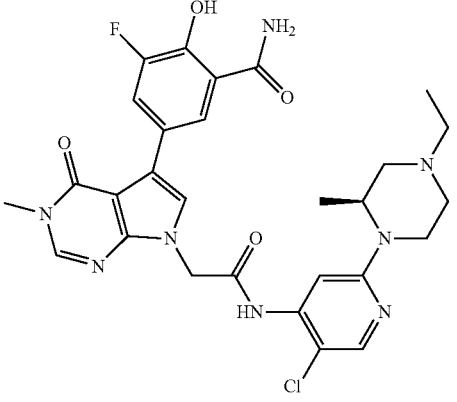 [SMILES: CCN1CCN(c2cc(NC(=O)Cn3cc(-c4cc(F)c(O)c(C(N)=O)c4)c4c(=O)n(C)cnc43)c(Cl)cn2)[C@@H](C)C1] | 7% |
| I-391 | 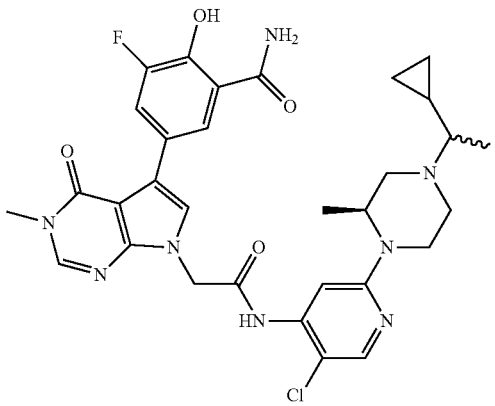 [SMILES: CC(C1CC1)N1CCN(c2cc(NC(=O)Cn3cc(-c4cc(F)c(O)c(C(N)=O)c4)c4c(=O)n(C)cnc43)c(Cl)cn2)[C@@H](C)C1] | 15% |

TABLE 1-continued

| Compound | Structure | Yield |
|---|---|---|
| I-392 | 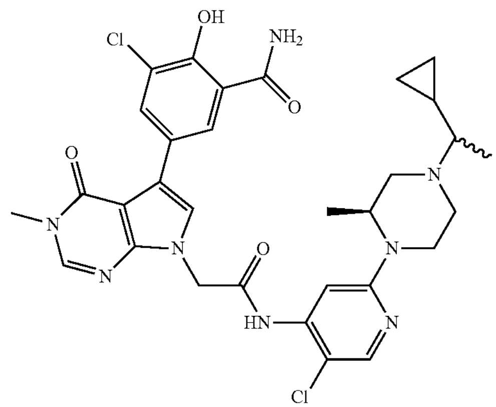 [SMILES: CC(C1CC1)N1CCN(c2cc(NC(=O)Cn3cc(-c4cc(Cl)c(O)c(C(N)=O)c4)c4c(=O)n(C)cnc43)c(Cl)cn2)[C@@H](C)C1] | 14% |
| I-393 | 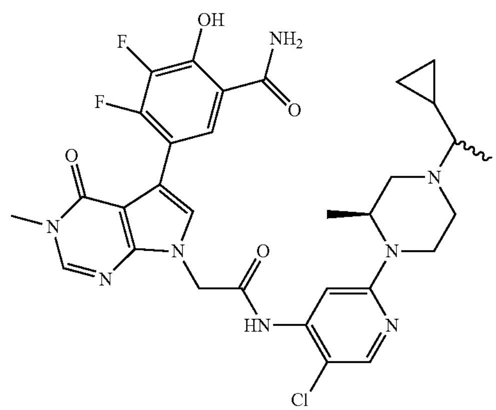 [SMILES: CC(C1CC1)N1CCN(c2cc(NC(=O)Cn3cc(-c4cc(C(N)=O)c(O)c(F)c4F)c4c(=O)n(C)cnc43)c(Cl)cn2)[C@@H](C)C1] | 9% |
| I-394 | 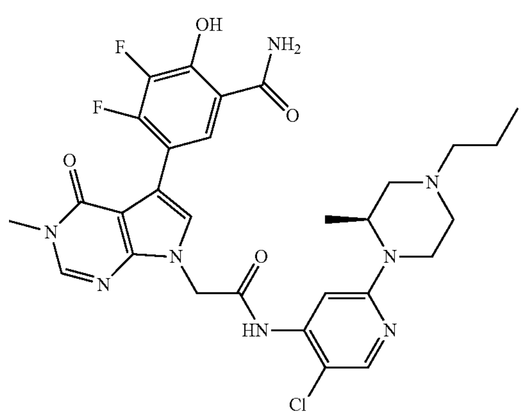 [SMILES: CCCN1CCN(c2cc(NC(=O)Cn3cc(-c4cc(C(N)=O)c(O)c(F)c4F)c4c(=O)n(C)cnc43)c(Cl)cn2)[C@@H](C)C1] | 80% |

TABLE 1-continued
| Compound | Structure | Yield |
|---|---|---|
| I-395 | 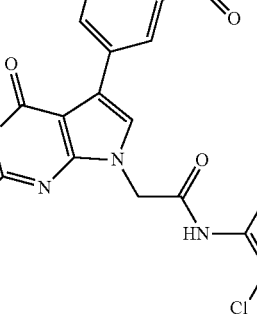 | 97% |
| I-396 | 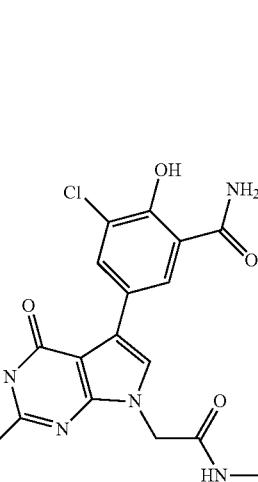 | 94% |
| I-397 | 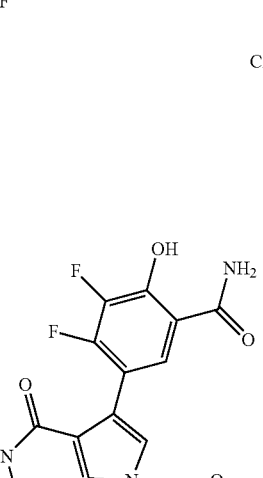 | 63% |

TABLE 1-continued
| Compound | Structure | Yield |
|---|---|---|
| I-398 | 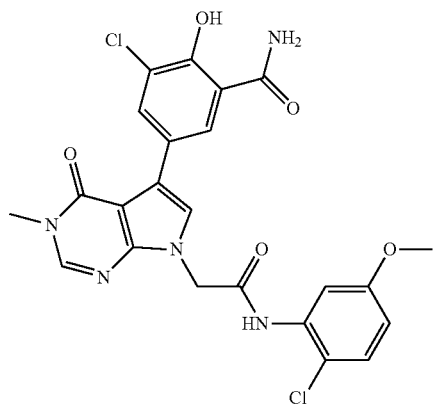 | 84% |
| I-399 | 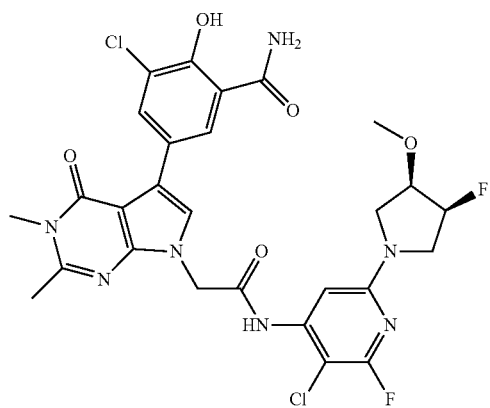 [SMILES: CO[C@@H]1CN(c2cc(NC(=O)Cn3cc(-c4cc(Cl)c(O)c(C(N)=O)c4)c4c(=O)n(C)c(C)nc43)c(Cl)c(F)n2)C[C@@H]1F] | 71% |
| I-400 | 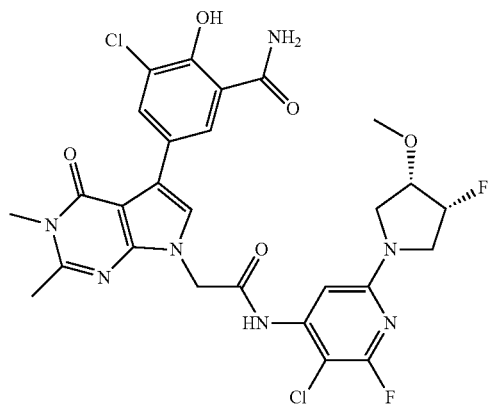 [SMILES: CO[C@H]1CN(c2cc(NC(=O)Cn3cc(-c4cc(Cl)c(O)c(C(N)=O)c4)c4c(=O)n(C)c(C)nc43)c(Cl)c(F)n2)C[C@H]1F] | 76% |

TABLE 1-continued
| Compound | Structure | Yield |
|---|---|---|
| I-401 | 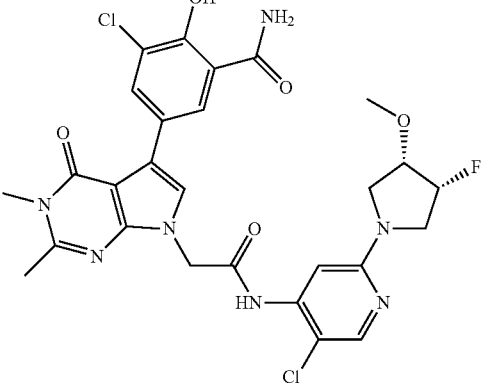 | 77% |
| I-402 | 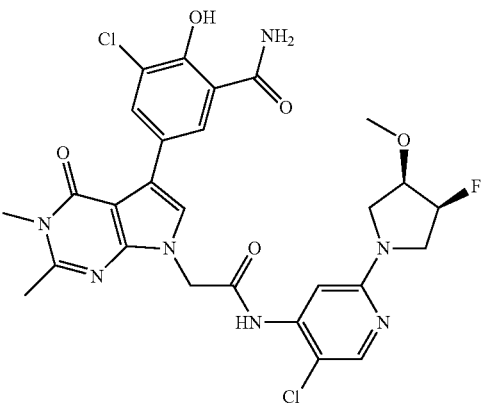 [SMILES: CO[C@@H]1CN(c2cc(NC(=O)Cn3cc(-c4cc(Cl)c(O)c(C(N)=O)c4)c4c(=O)n(C)c(C)nc43)c(Cl)cn2)C[C@@H]1F] | 85% |
| I-403 | 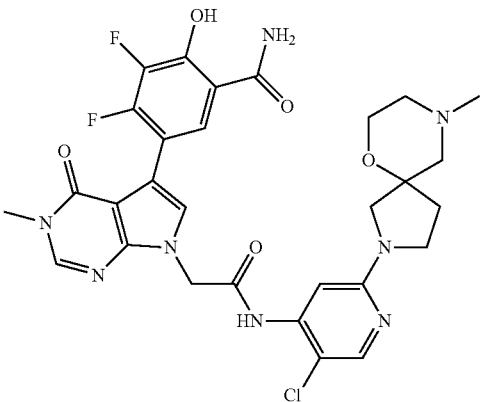 | 42% |

TABLE 1-continued

| Compound | Structure | Yield |
|---|---|---|
| I-404 | 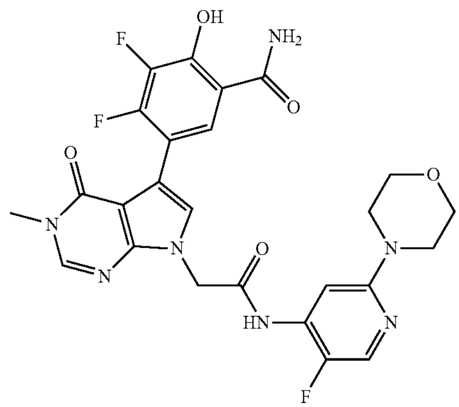 [SMILES: Cn1cnc2c(c(-c3cc(C(N)=O)c(O)c(F)c3F)cn2CC(=O)Nc2cc(N3CCOCC3)ncc2F)c1=O] | 43% |
| I-405 | 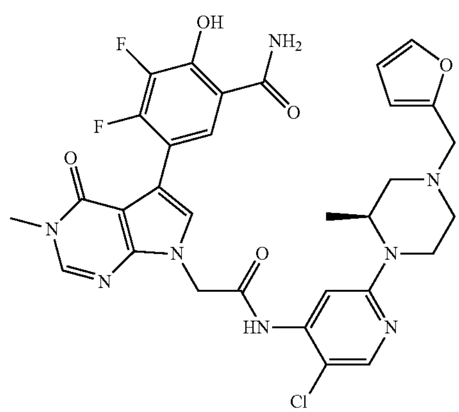 [SMILES: C[C@H]1CN(Cc2ccco2)CCN1c1cc(NC(=O)Cn2cc(-c3cc(C(N)=O)c(O)c(F)c3F)c3c(=O)n(C)cnc32)c(Cl)cn1] | 50% |
| I-406 | 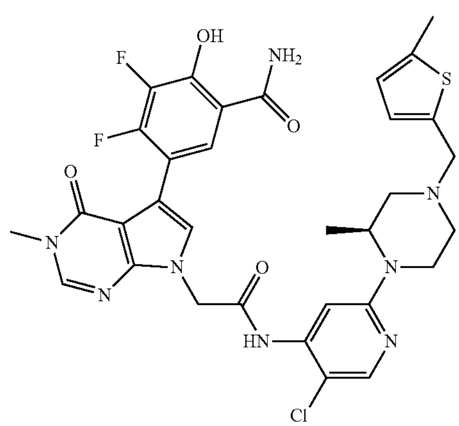 [SMILES: Cc1ccc(CN2CCN(c3cc(NC(=O)Cn4cc(-c5cc(C(N)=O)c(O)c(F)c5F)c5c(=O)n(C)cnc54)c(Cl)cn3)[C@@H](C)C2)s1] | 31% |

TABLE 1-continued

| Compound | Structure | Yield |
|---|---|---|
| I-407 | 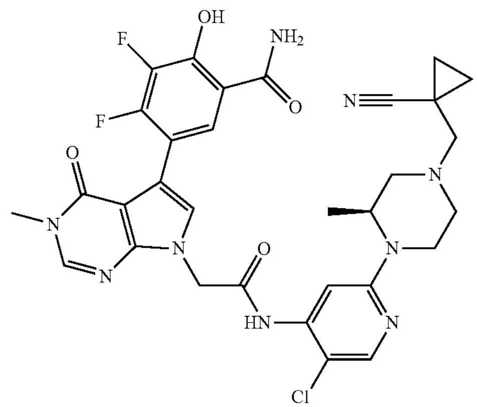 [SMILES: C[C@H]1CN(CC2(C#N)CC2)CCN1c1cc(NC(=O)Cn2cc(-c3cc(C(N)=O)c(O)c(F)c3F)c3c(=O)n(C)cnc32)c(Cl)cn1] | 46% |
| I-408 | 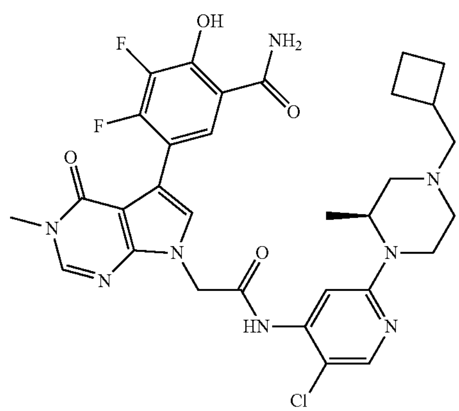 [SMILES: C[C@H]1CN(CC2CCC2)CCN1c1cc(NC(=O)Cn2cc(-c3cc(C(N)=O)c(O)c(F)c3F)c3c(=O)n(C)cnc32)c(Cl)cn1] | 48% |
| I-409 | 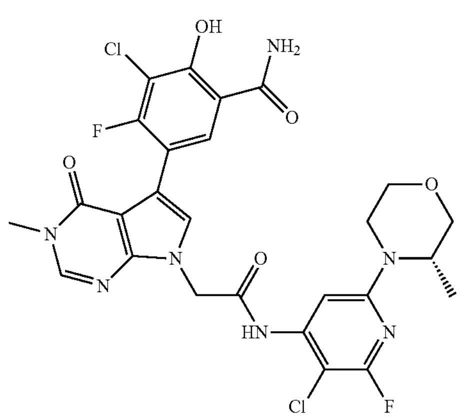 | 98% |

TABLE 1-continued

| Compound | Structure | Yield |
|---|---|---|
| I-410 | 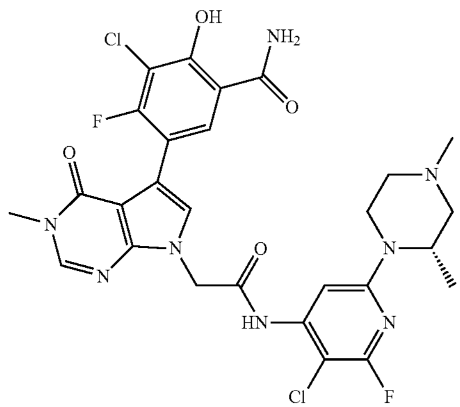 | 84% |
| I-411 | 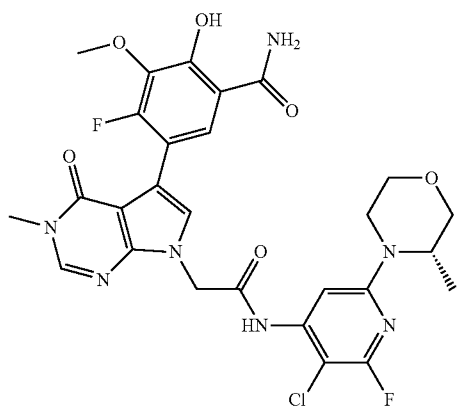 | 91% |
| I-412 | 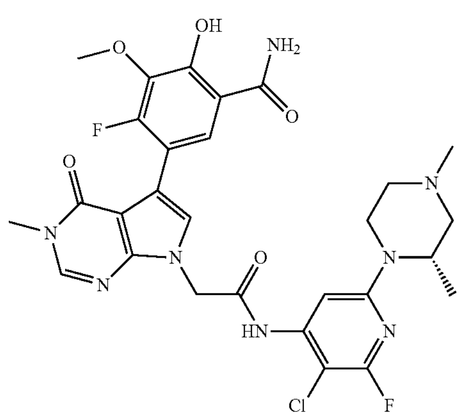 | 89% |

TABLE 1-continued
| Compound | Structure | Yield |
|---|---|---|
| I-413 | 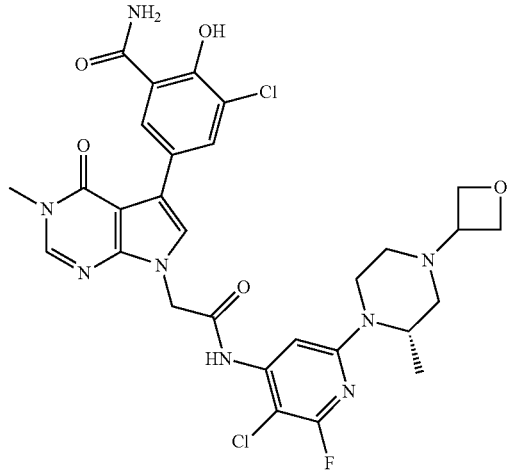 [SMILES: C[C@H]1CN(C2COC2)CCN1c1cc(NC(=O)Cn2cc(-c3cc(Cl)c(O)c(C(N)=O)c3)c3c(=O)n(C)cnc32)c(Cl)c(F)n1] | 87% |
| I-414 | 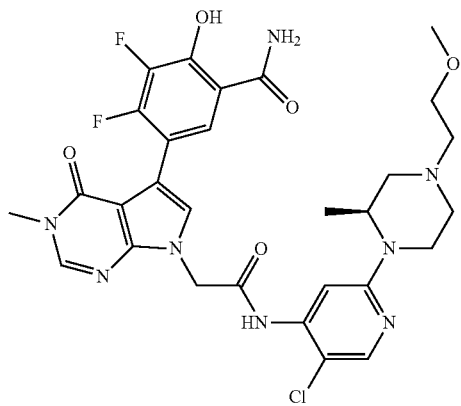 [SMILES: COCCN1CCN(c2cc(NC(=O)Cn3cc(-c4cc(C(N)=O)c(O)c(F)c4F)c4c(=O)n(C)cnc43)c(Cl)cn2)[C@@H](C)C1] | 21% |
| I-415 | 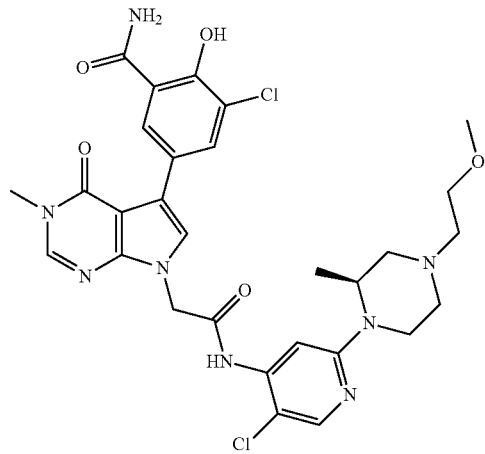 [SMILES: COCCN1CCN(c2cc(NC(=O)Cn3cc(-c4cc(Cl)c(O)c(C(N)=O)c4)c4c(=O)n(C)cnc43)c(Cl)cn2)[C@@H](C)C1] | 24% |

TABLE 1-continued

| Compound | Structure | Yield |
|---|---|---|
| I-416 | 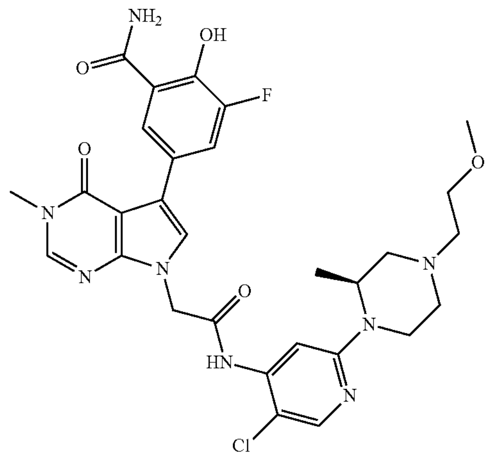 [SMILES: COCCN1CCN(c2cc(NC(=O)Cn3cc(-c4cc(F)c(O)c(C(N)=O)c4)c4c(=O)n(C)cnc43)c(Cl)cn2)[C@@H](C)C1] | 60% |
| I-417 | 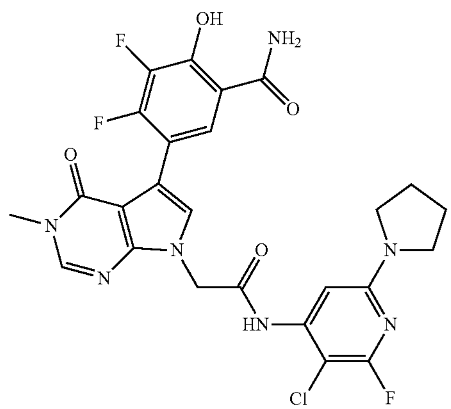 [SMILES: Cn1cnc2c(c(-c3cc(C(N)=O)c(O)c(F)c3F)cn2CC(=O)Nc2cc(N3CCCC3)nc(F)c2Cl)c1=O] | 63% |
| I-418 | 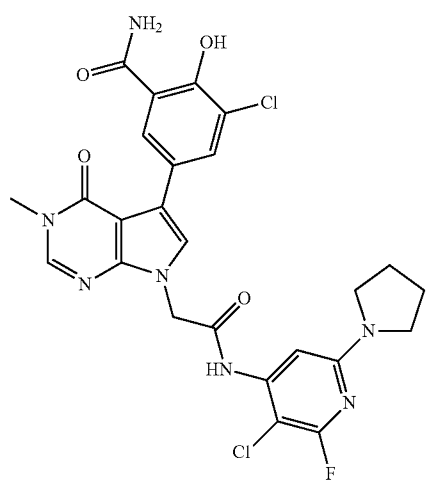 [SMILES: Cn1cnc2c(c(-c3cc(Cl)c(O)c(C(N)=O)c3)cn2CC(=O)Nc2cc(N3CCCC3)nc(F)c2Cl)c1=O] | 46% |

TABLE 1-continued
| Compound | Structure | Yield |
|---|---|---|
| I-419 | 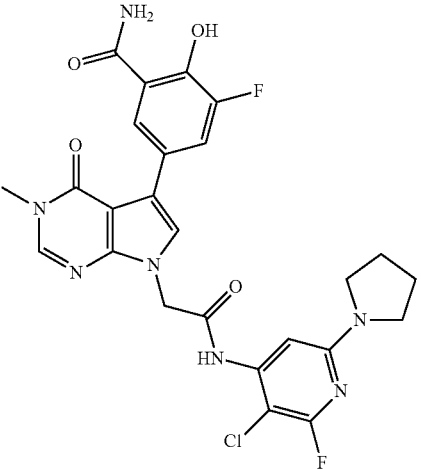 [SMILES: Cn1cnc2c(c(-c3cc(F)c(O)c(C(N)=O)c3)cn2CC(=O)Nc2cc(N3CCCC3)nc(F)c2Cl)c1=O] | 33% |
| I-420 | 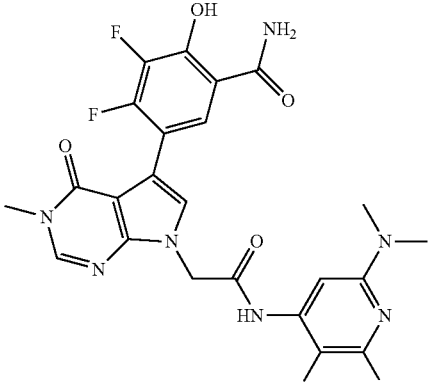 | 51% |
| I-421 | 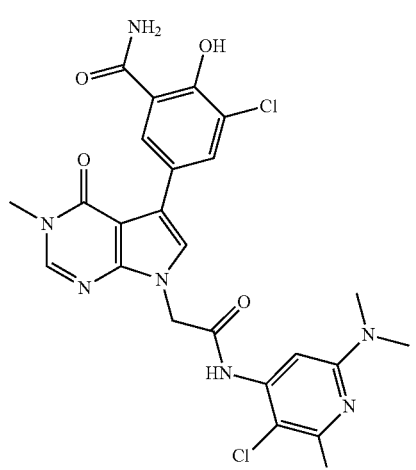 | 61% |

TABLE 1-continued

| Compound | Structure | Yield |
|---|---|---|
| I-422 | 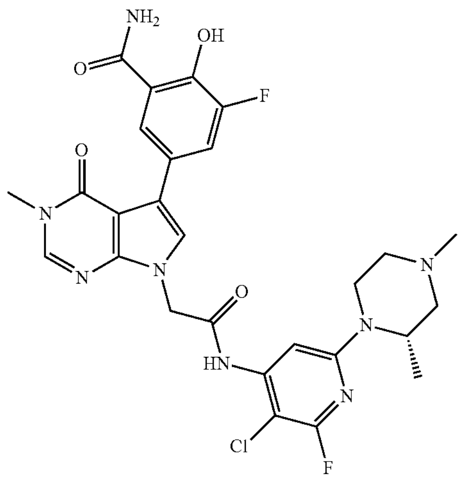 | 86% |
| I-423 | 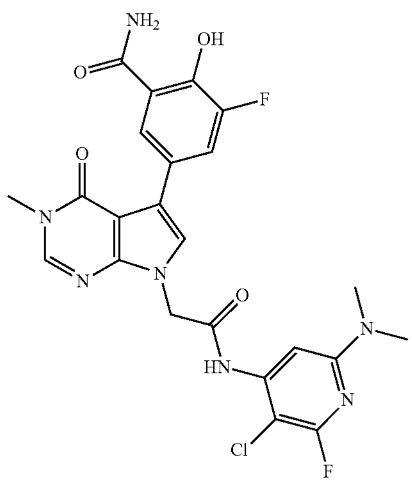 | 25% |
| I-424 | 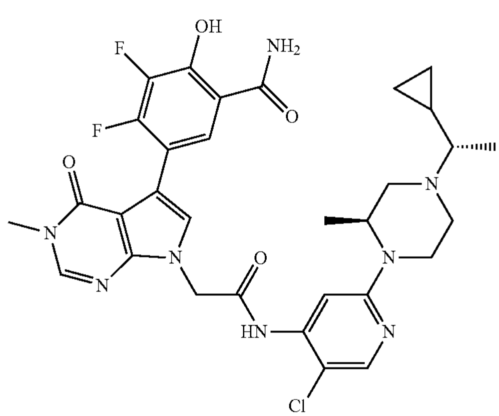 [SMILES: C[C@@H](C1CC1)N1CCN(c2cc(NC(=O)Cn3cc(-c4cc(C(N)=O)c(O)c(F)c4F)c4c(=O)n(C)cnc43)c(Cl)cn2)[C@@H](C)C1] | 56% |

TABLE 1-continued

| Compound | Structure | Yield |
|---|---|---|
| I-425 | 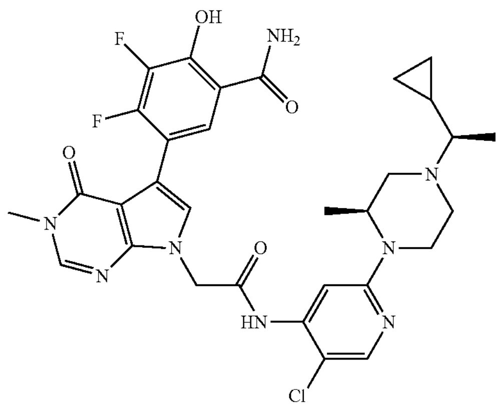 [SMILES: C[C@H](C1CC1)N1CCN(c2cc(NC(=O)Cn3cc(-c4cc(C(N)=O)c(O)c(F)c4F)c4c(=O)n(C)cnc43)c(Cl)cn2)[C@@H](C)C1] | 53% |
| I-426 | 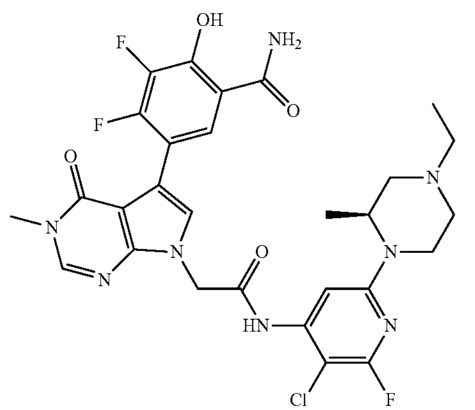 [SMILES: CCN1CCN(c2cc(NC(=O)Cn3cc(-c4cc(C(N)=O)c(O)c(F)c4F)c4c(=O)n(C)cnc43)c(Cl)c(F)n2)[C@@H](C)C1] | 61% |
| I-427 | 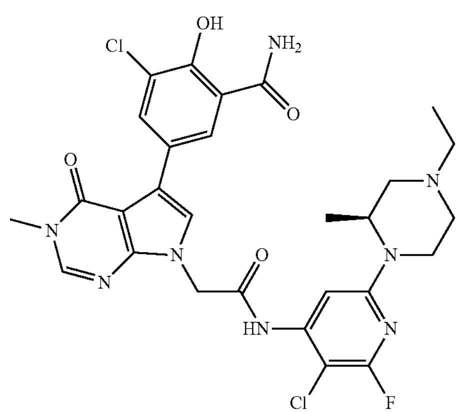 [SMILES: CCN1CCN(c2cc(NC(=O)Cn3cc(-c4cc(Cl)c(O)c(C(N)=O)c4)c4c(=O)n(C)cnc43)c(Cl)c(F)n2)[C@@H](C)C1] | 55% |
| I-428 | 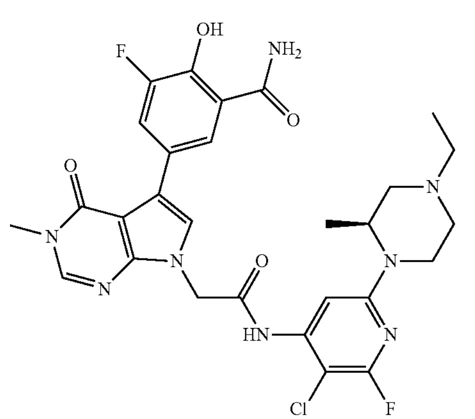 [SMILES: CCN1CCN(c2cc(NC(=O)Cn3cc(-c4cc(F)c(O)c(C(N)=O)c4)c4c(=O)n(C)cnc43)c(Cl)c(F)n2)[C@@H](C)C1] | 65% |

| Compound | Structure | Yield |
|---|---|---|
| I-429 | 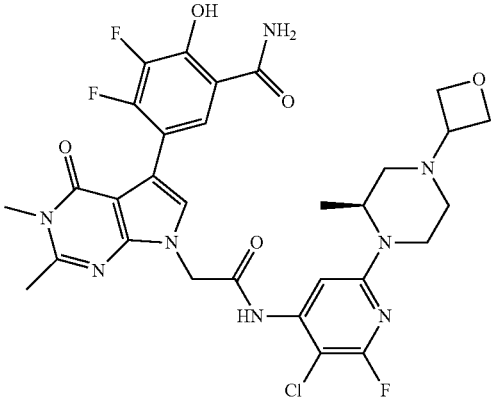 [SMILES: Cc1nc2c(c(-c3cc(C(N)=O)c(O)c(F)c3F)cn2CC(=O)Nc2cc(N3CCN(C4COC4)C[C@@H]3C)nc(F)c2Cl)c(=O)n1C] | 50% |
| I-430 | 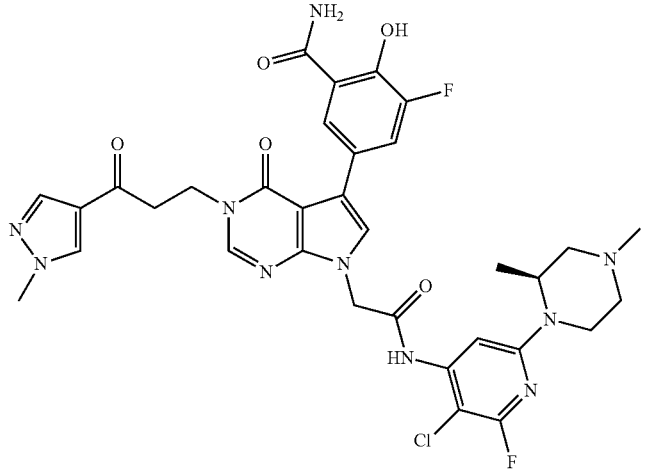 [SMILES: C[C@H]1CN(C)CCN1c1cc(NC(=O)Cn2cc(-c3cc(F)c(O)c(C(N)=O)c3)c3c(=O)n(CCC(=O)c4cnn(C)c4)cnc32)c(Cl)c(F)n1] | 9% |
| I-431 | 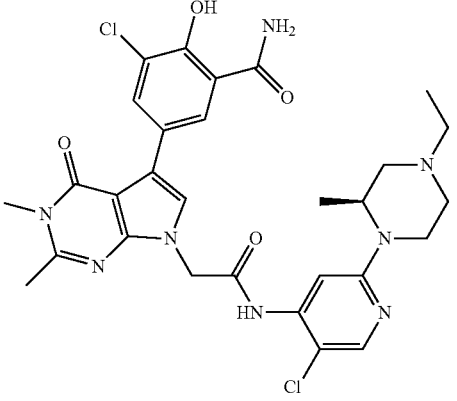 [SMILES: CCN1CCN(c2cc(NC(=O)Cn3cc(-c4cc(Cl)c(O)c(C(N)=O)c4)c4c(=O)n(C)c(C)nc43)c(Cl)cn2)[C@@H](C)C1] | 68% |

TABLE 1-continued
| Compound | Structure | Yield |
|---|---|---|
| I-432 | 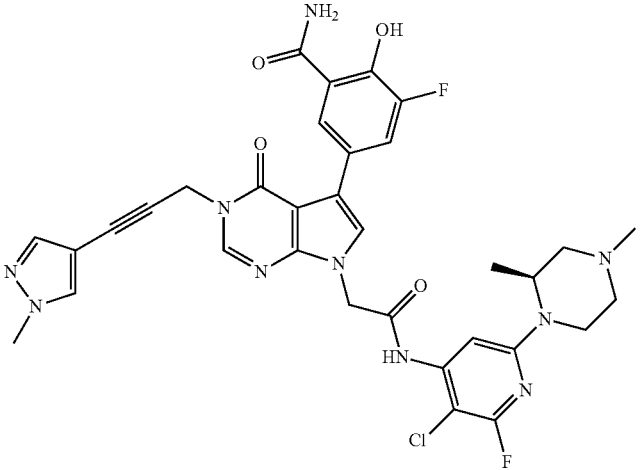 [SMILES: C[C@H]1CN(C)CCN1c1cc(NC(=O)Cn2cc(-c3cc(F)c(O)c(C(N)=O)c3)c3c(=O)n(CC#Cc4cnn(C)c4)cnc32)c(Cl)c(F)n1] | 12% |
| I-433 | 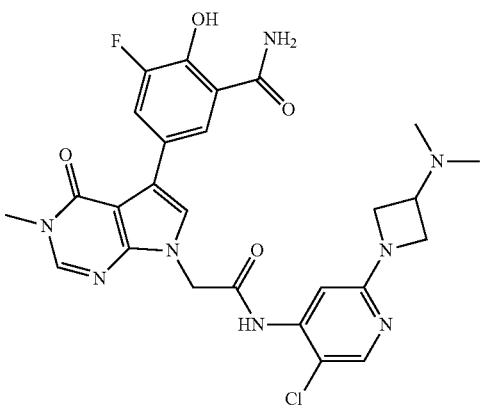 | 36% |
| I-434 | 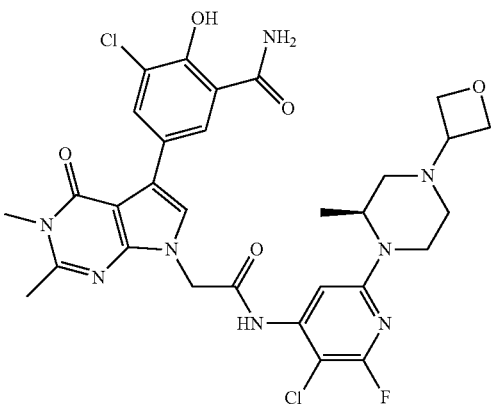 [SMILES: Cc1nc2c(c(-c3cc(Cl)c(O)c(C(N)=O)c3)cn2CC(=O)Nc2cc(N3CCN(C4COC4)C[C@@H]3C)nc(F)c2Cl)c(=O)n1C] | 37% |

TABLE 1-continued

| Compound | Structure | Yield |
|---|---|---|
| I-435 | 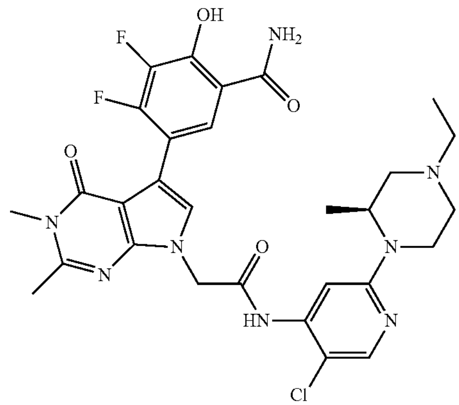 [SMILES: CCN1CCN(c2cc(NC(=O)Cn3cc(-c4cc(C(N)=O)c(O)c(F)c4F)c4c(=O)n(C)c(C)nc43)c(Cl)cn2)[C@@H](C)C1] | 89% |
| I-436 | 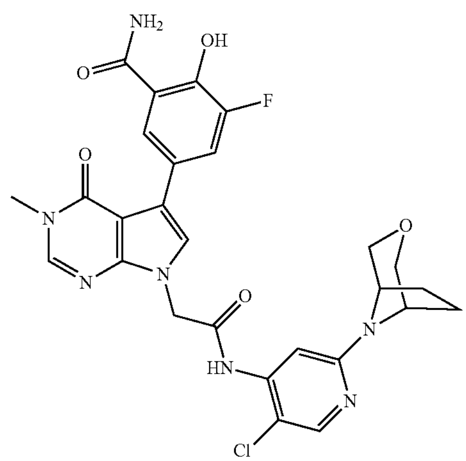 [SMILES: Cn1cnc2c(c(-c3cc(F)c(O)c(C(N)=O)c3)cn2CC(=O)Nc2cc(N3C4CCC3COC4)ncc2Cl)c1=O] | 49% |
| I-437 | 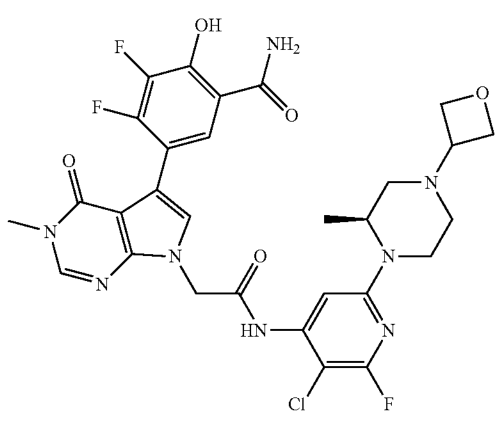 [SMILES: C[C@H]1CN(C2COC2)CCN1c1cc(NC(=O)Cn2cc(-c3cc(C(N)=O)c(O)c(F)c3F)c3c(=O)n(C)cnc32)c(Cl)c(F)n1] | 50% |

TABLE 1-continued

| Compound | Structure | Yield |
|---|---|---|
| I-438 | 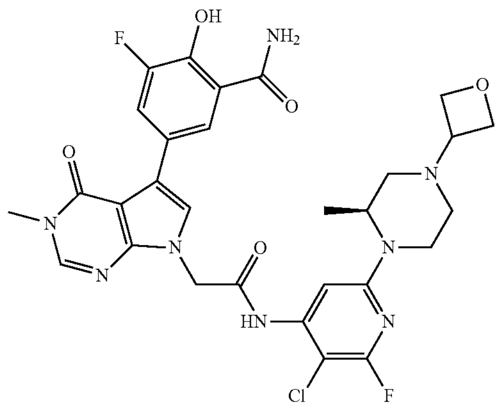 [SMILES: C[C@H]1CN(C2COC2)CCN1c1cc(NC(=O)Cn2cc(-c3cc(F)c(O)c(C(N)=O)c3)c3c(=O)n(C)cnc32)c(Cl)c(F)n1] | 45% |
| I-439 | 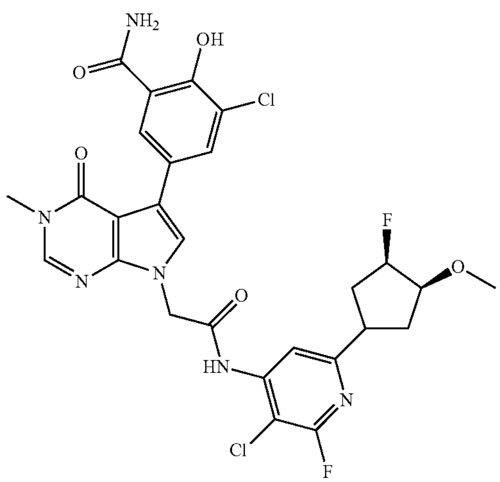 | 28% |
| I-440 | 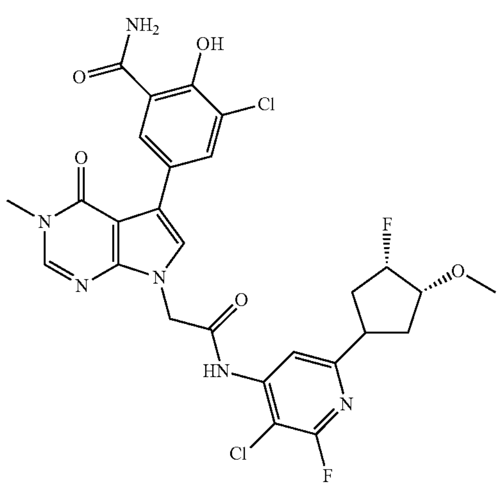 | 38% |

TABLE 1-continued

| Compound | Structure | Yield |
|---|---|---|
| I-441 | 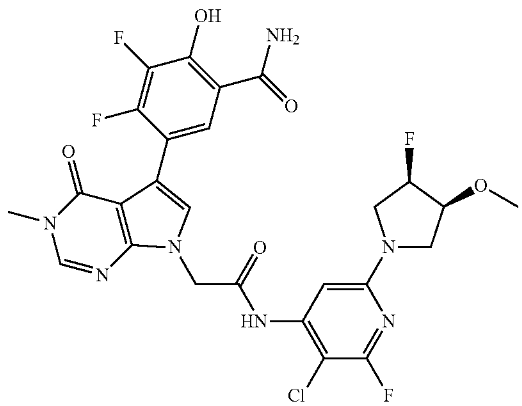 | 8% |
| I-442 | 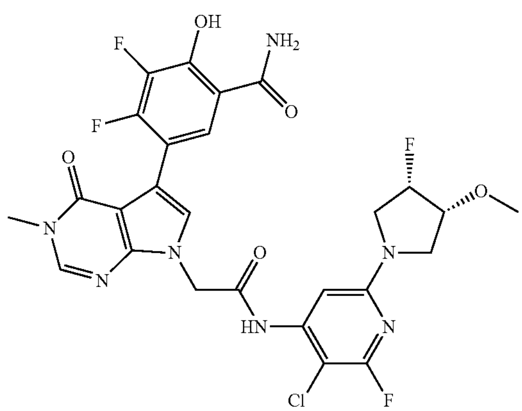 | 52% |
| I-443 | 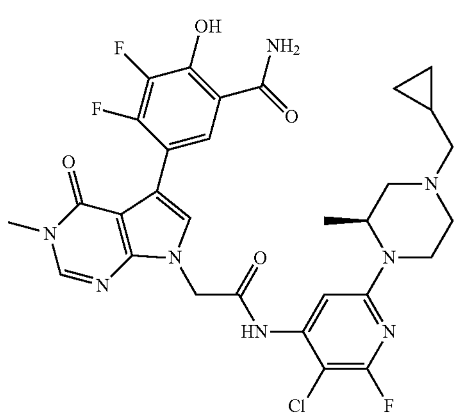 [SMILES: C[C@H]1CN(CC2CC2)CCN1c1cc(NC(=O)Cn2cc(-c3cc(C(N)=O)c(O)c(F)c3F)c3c(=O)n(C)cnc32)c(Cl)c(F)n1] | 50% |

TABLE 1-continued
| Compound | Structure | Yield |
|---|---|---|
| I-444 | 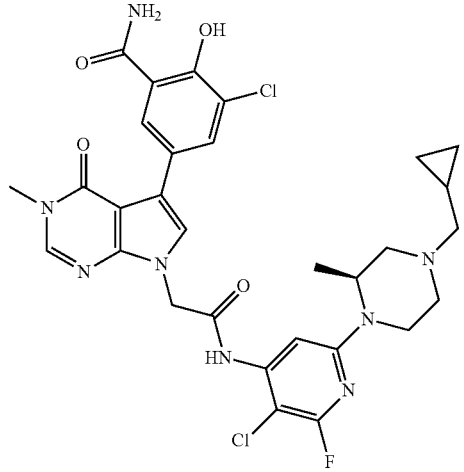 [SMILES: C[C@H]1CN(CC2CC2)CCN1c1cc(NC(=O)Cn2cc(-c3cc(Cl)c(O)c(C(N)=O)c3)c3c(=O)n(C)cnc32)c(Cl)c(F)n1] | 64% |
| I-445 | 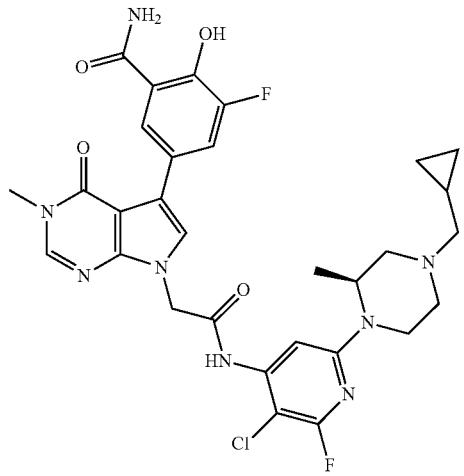 [SMILES: C[C@H]1CN(CC2CC2)CCN1c1cc(NC(=O)Cn2cc(-c3cc(F)c(O)c(C(N)=O)c3)c3c(=O)n(C)cnc32)c(Cl)c(F)n1] | 57% |
| I-446 | 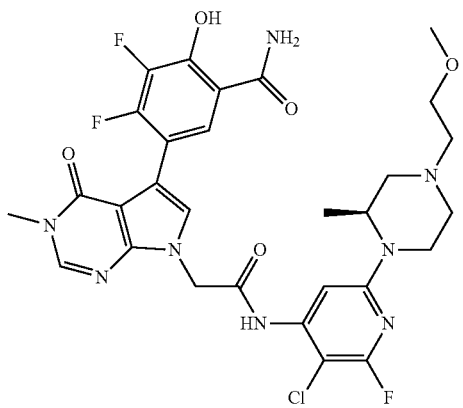 [SMILES: COCCN1CCN(c2cc(NC(=O)Cn3cc(-c4cc(C(N)=O)c(O)c(F)c4F)c4c(=O)n(C)cnc43)c(Cl)c(F)n2)[C@@H](C)C1] | 60% |

TABLE 1-continued
| Compound | Structure | Yield |
|---|---|---|
| I-447 | 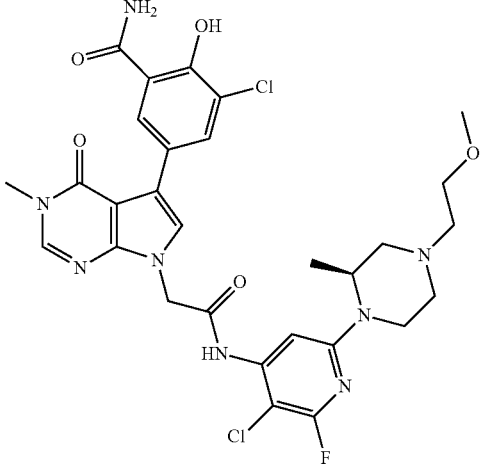 [SMILES: COCCN1CCN(c2cc(NC(=O)Cn3cc(-c4cc(Cl)c(O)c(C(N)=O)c4)c4c(=O)n(C)cnc43)c(Cl)c(F)n2)[C@@H](C)C1] | 34% |
| I-448 | 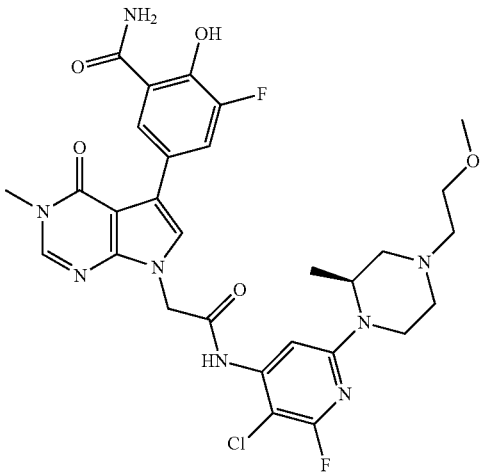 [SMILES: COCCN1CCN(c2cc(NC(=O)Cn3cc(-c4cc(F)c(O)c(C(N)=O)c4)c4c(=O)n(C)cnc43)c(Cl)c(F)n2)[C@@H](C)C1] | 62% |
| I-449 | 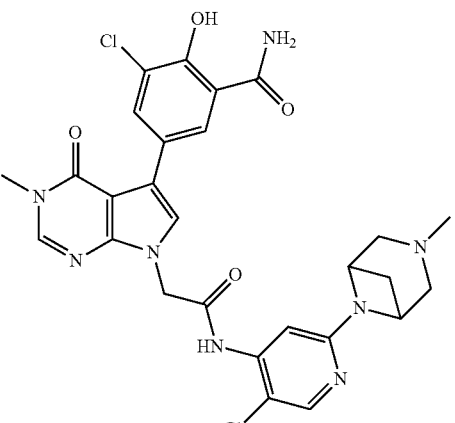 | 78% |

TABLE 1-continued
| Compound | Structure | Yield |
|----------|-----------|-------|
| I-450 | 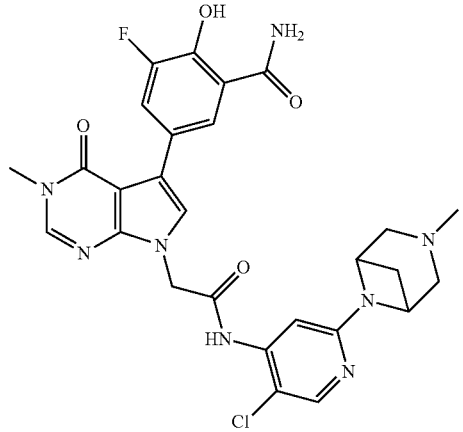 | 73% |
| I-451 | 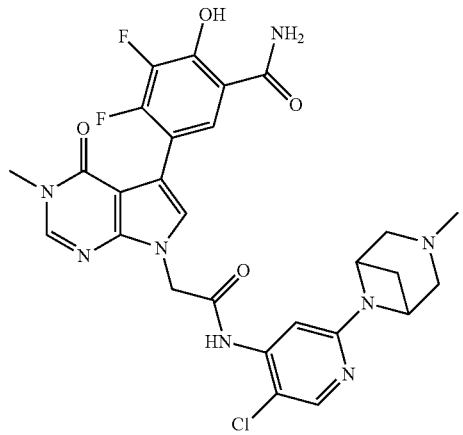 | 76% |
| I-452 | 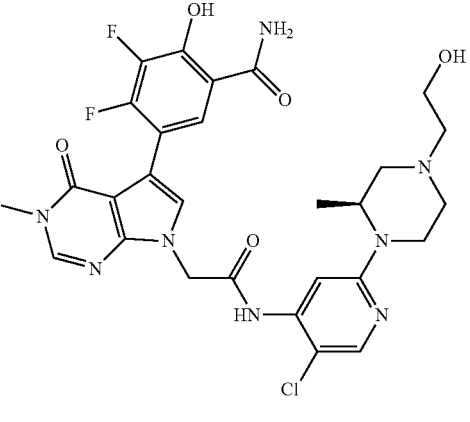 [SMILES: C[C@H]1CN(CCO)CCN1c1cc(NC(=O)Cn2cc(-c3cc(C(N)=O)c(O)c(F)c3F)c3c(=O)n(C)cnc32)c(Cl)cn1] | 67% |

TABLE 1-continued

| Compound | Structure | Yield |
|---|---|---|
| I-453 | 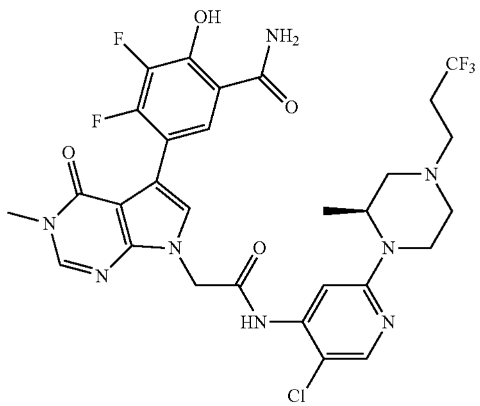 [SMILES: C[C@H]1CN(CCC(F)(F)F)CCN1c1cc(NC(=O)Cn2cc(-c3cc(C(N)=O)c(O)c(F)c3F)c3c(=O)n(C)cnc32)c(Cl)cn1] | 63% |
| I-454 | 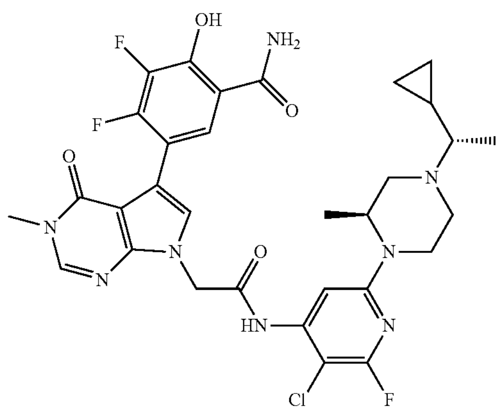 [SMILES: C[C@@H](C1CC1)N1CCN(c2cc(NC(=O)Cn3cc(-c4cc(C(N)=O)c(O)c(F)c4F)c4c(=O)n(C)cnc43)c(Cl)c(F)n2)[C@@H](C)C1] | 54% |
| I-455 | 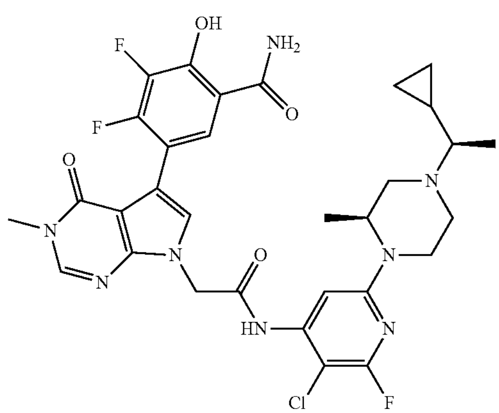 [SMILES: C[C@H](C1CC1)N1CCN(c2cc(NC(=O)Cn3cc(-c4cc(C(N)=O)c(O)c(F)c4F)c4c(=O)n(C)cnc43)c(Cl)c(F)n2)[C@@H](C)C1] | 62% |
| I-456 | 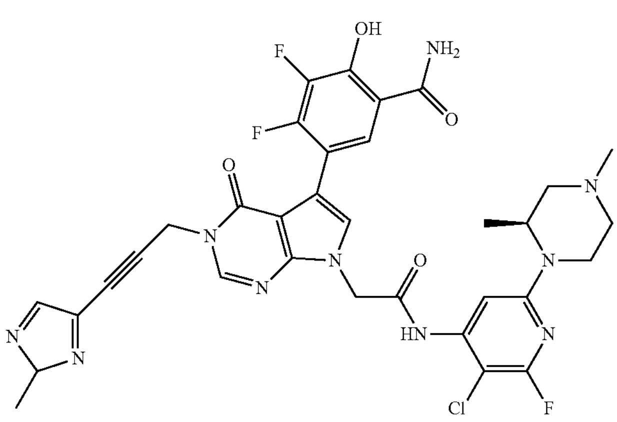 [SMILES: CC1N=CC(C#CCn2cnc3c(c(-c4cc(C(N)=O)c(O)c(F)c4F)cn3CC(=O)Nc3cc(N4CCN(C)C[C@@H]4C)nc(F)c3Cl)c2=O)=N1] | 10% |

TABLE 1-continued
| Compound | Structure | Yield |
|---|---|---|
| I-457 | 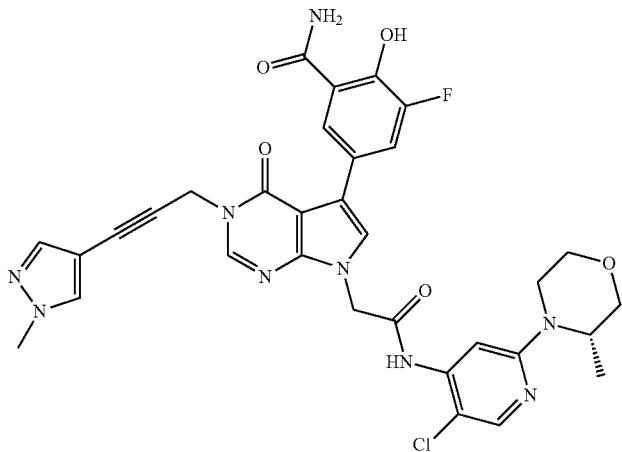 [SMILES: C[C@H]1COCCN1c1cc(NC(=O)Cn2cc(-c3cc(F)c(O)c(C(N)=O)c3)c3c(=O)n(CC#Cc4cnn(C)c4)cnc32)c(Cl)cn1] | 23% |
| I-458 | 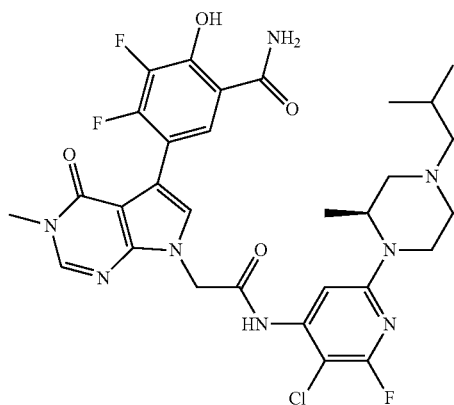 [SMILES: CC(C)CN1CCN(c2cc(NC(=O)Cn3cc(-c4cc(C(N)=O)c(O)c(F)c4F)c4c(=O)n(C)cnc43)c(Cl)c(F)n2)[C@@H](C)C1] | 60% |
| I-459 | 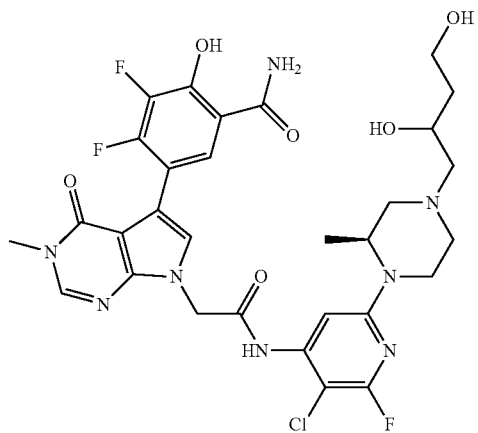 [SMILES: C[C@H]1CN(CC(O)CCO)CCN1c1cc(NC(=O)Cn2cc(-c3cc(C(N)=O)c(O)c(F)c3F)c3c(=O)n(C)cnc32)c(Cl)c(F)n1] | 8% |

TABLE 1-continued

| Compound | Structure | Yield |
|---|---|---|
| I-460 | 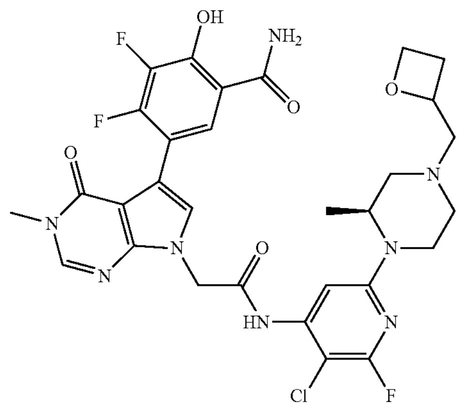 [SMILES: C[C@H]1CN(CC2CCO2)CCN1c1cc(NC(=O)Cn2cc(-c3cc(C(N)=O)c(O)c(F)c3F)c3c(=O)n(C)cnc32)c(Cl)c(F)n1] | 3% |
| I-461 | 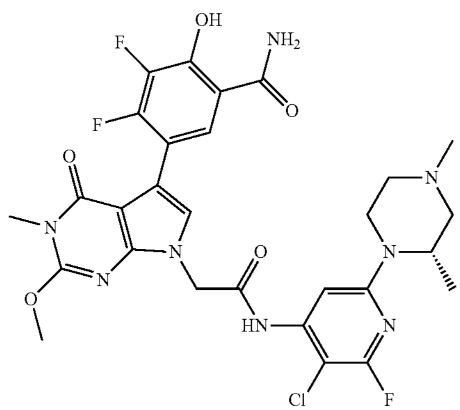 | 100% |
| I-462 | 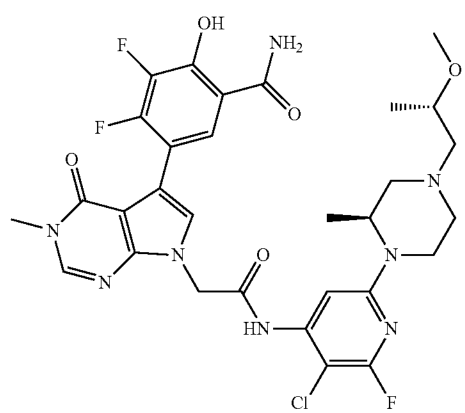 [SMILES: CO[C@@H](C)CN1CCN(c2cc(NC(=O)Cn3cc(-c4cc(C(N)=O)c(O)c(F)c4F)c4c(=O)n(C)cnc43)c(Cl)c(F)n2)[C@@H](C)C1] | 25% |
| I-463 | 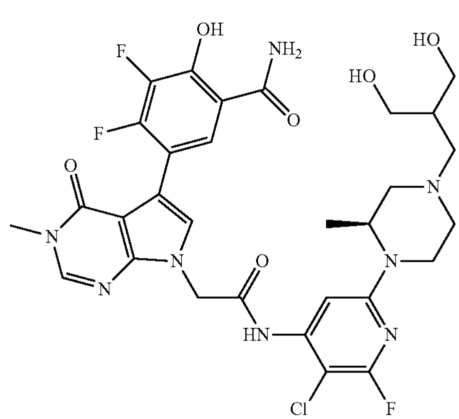 [SMILES: C[C@H]1CN(CC(CO)CO)CCN1c1cc(NC(=O)Cn2cc(-c3cc(C(N)=O)c(O)c(F)c3F)c3c(=O)n(C)cnc32)c(Cl)c(F)n1] | 4% |

TABLE 1-continued
| Compound | Structure | Yield |
|---|---|---|
| I-464 | 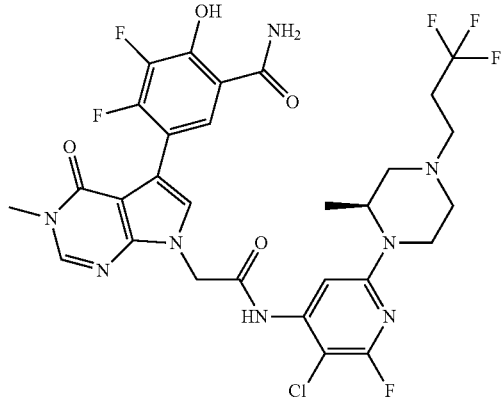 [SMILES: C[C@H]1CN(CCC(F)(F)F)CCN1c1cc(NC(=O)Cn2cc(-c3cc(C(N)=O)c(O)c(F)c3F)c3c(=O)n(C)cnc32)c(Cl)c(F)n1] | 40% |
| I-465 | 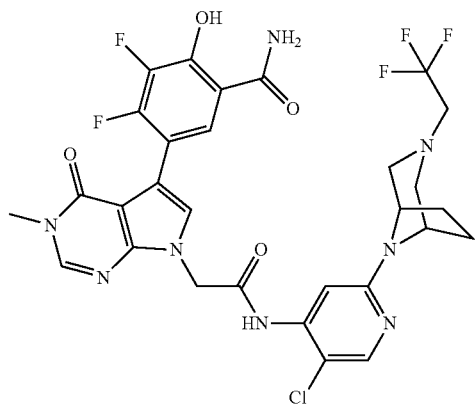 [SMILES: Cn1cnc2c(c(-c3cc(C(N)=O)c(O)c(F)c3F)cn2CC(=O)Nc2cc(N3C4CCC3CN(CC(F)(F)F)C4)ncc2Cl)c1=O] | 47% |
| I-466 | 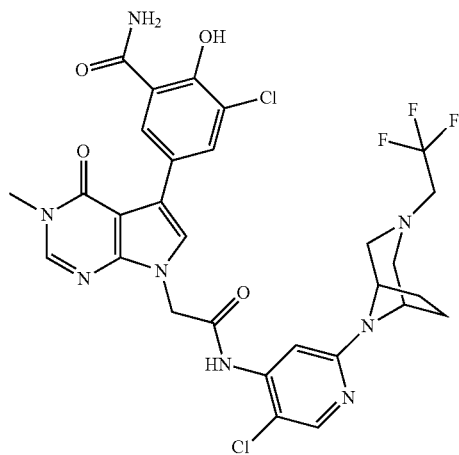 | 86% |

TABLE 1-continued
| Compound | Structure | Yield |
|---|---|---|
| I-467 | 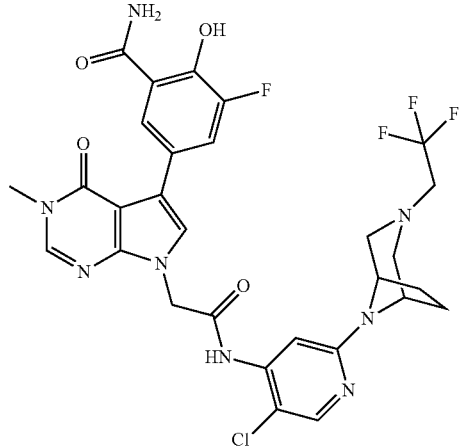 [SMILES: Cn1cnc2c(c(-c3cc(F)c(O)c(C(N)=O)c3)cn2CC(=O)Nc2cc(N3C4CCC3CN(CC(F)(F)F)C4)ncc2Cl)c1=O] | 68% |
| I-468 | 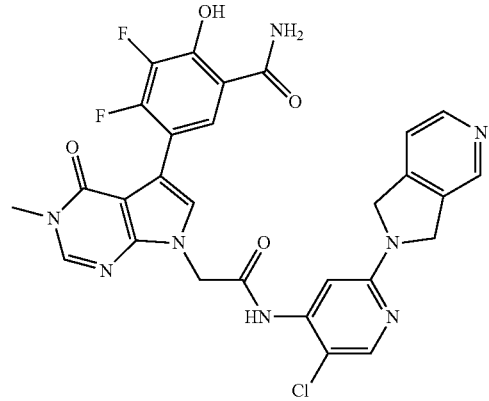 [SMILES: Cn1cnc2c(c(-c3cc(C(N)=O)c(O)c(F)c3F)cn2CC(=O)Nc2cc(N3Cc4ccncc4C3)ncc2Cl)c1=O] | 52% |
| I-469 | 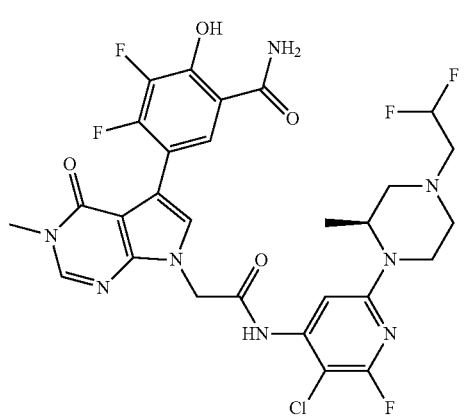 [SMILES: C[C@H]1CN(CC(F)F)CCN1c1cc(NC(=O)Cn2cc(-c3cc(C(N)=O)c(O)c(F)c3F)c3c(=O)n(C)cnc32)c(Cl)c(F)n1] | 41% |

TABLE 1-continued

| Compound | Structure | Yield |
|---|---|---|
| I-470 | 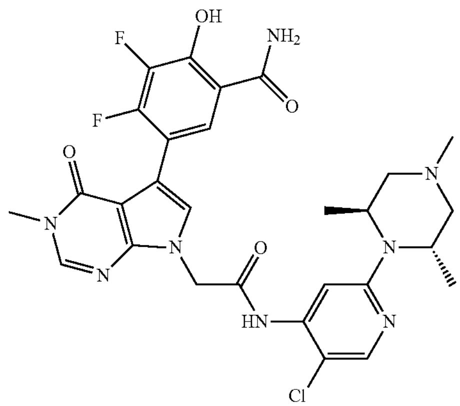 | 27% |
| I-471 | 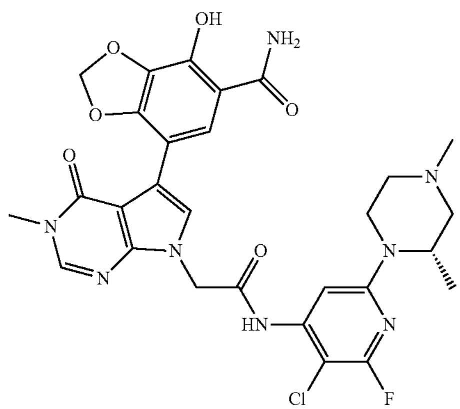 | |
| I-472 | 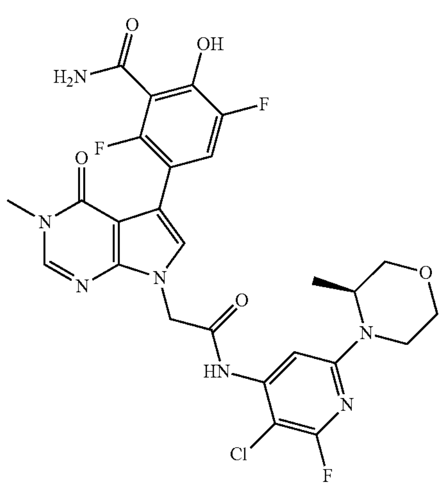 [SMILES: C[C@H]1COCCN1c1cc(NC(=O)Cn2cc(-c3cc(F)c(O)c(C(N)=O)c3F)c3c(=O)n(C)cnc32)c(Cl)c(F)n1] | 38% |

TABLE 1-continued
| Compound | Structure | Yield |
|---|---|---|
| I-473 | 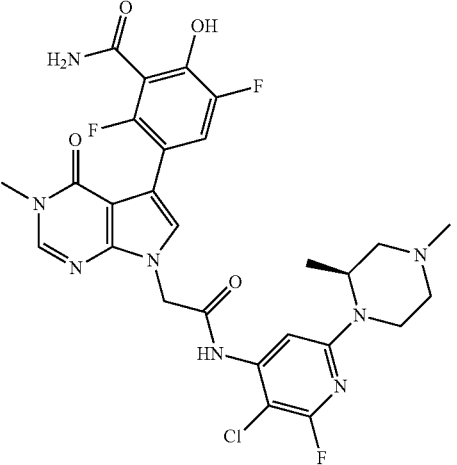 | 33% |
| I-474 | 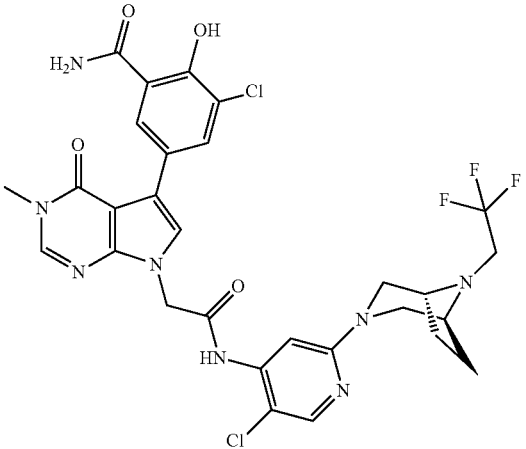 [SMILES: Cn1cnc2c(c(-c3cc(Cl)c(O)c(C(N)=O)c3)cn2CC(=O)Nc2cc(N3C[C@H]4CC[C@@H](C3)N4CC(F)(F)F)ncc2Cl)c1=O] | 77% |
| I-475 | 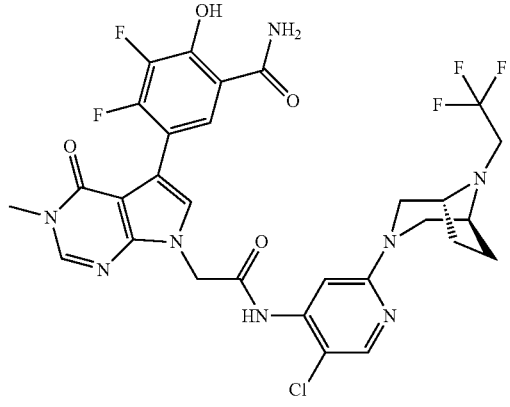 [SMILES: Cn1cnc2c(c(-c3cc(C(N)=O)c(O)c(F)c3F)cn2CC(=O)Nc2cc(N3C[C@H]4CC[C@@H](C3)N4CC(F)(F)F)ncc2Cl)c1=O] | 74% |

| Compound | Structure | Yield |
|---|---|---|
| I-476 | 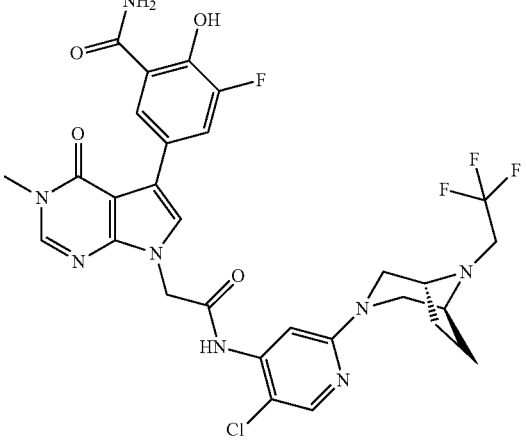 | 72% |
| I-477 | 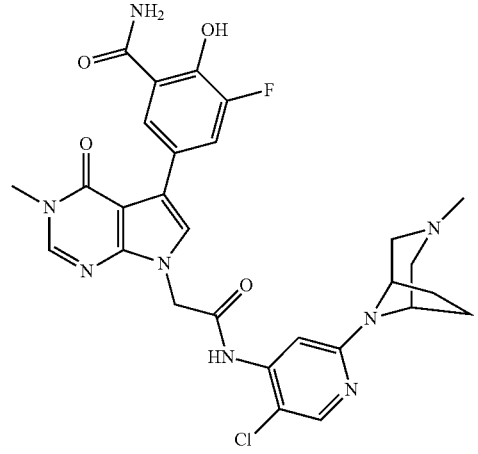 [SMILES: CN1CC2CCC(C1)N2c1cc(NC(=O)Cn2cc(-c3cc(F)c(O)c(C(N)=O)c3)c3c(=O)n(C)cnc32)c(Cl)cn1] | 34% |
| I-478 | 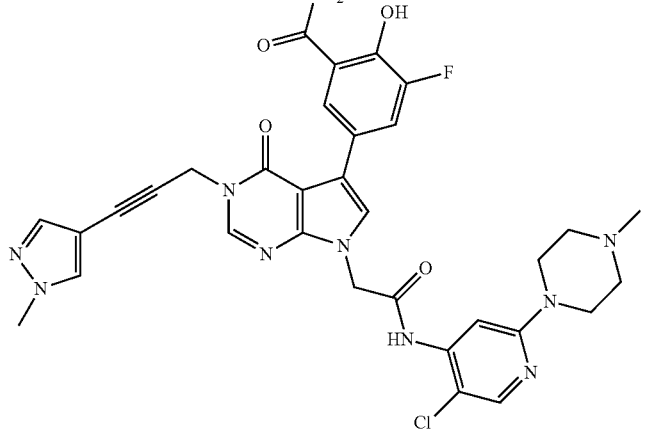 | 2% |

TABLE 1-continued
| Compound | Structure | Yield |
|---|---|---|
| I-479 | 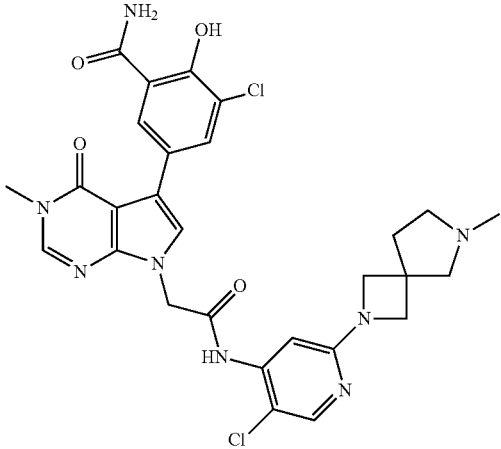 | 25% |
| I-480 | 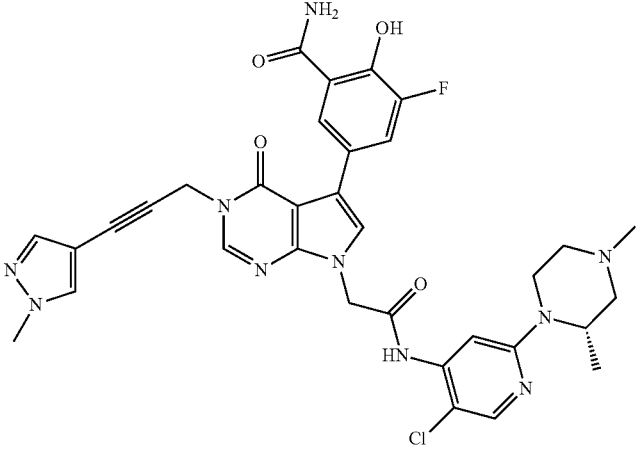 [SMILES: C[C@H]1CN(C)CCN1c1cc(NC(=O)Cn2cc(-c3cc(F)c(O)c(C(N)=O)c3)c3c(=O)n(CC#Cc4cnn(C)c4)cnc32)c(Cl)cn1] | 19% |
| I-481 | 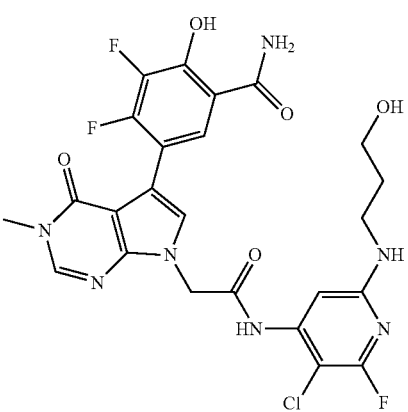 [SMILES: Cn1cnc2c(c(-c3cc(C(N)=O)c(O)c(F)c3F)cn2CC(=O)Nc2cc(NCCCO)nc(F)c2Cl)c1=O] | 19% |

TABLE 1-continued
| Compound | Structure | Yield |
|---|---|---|
| I-482 | 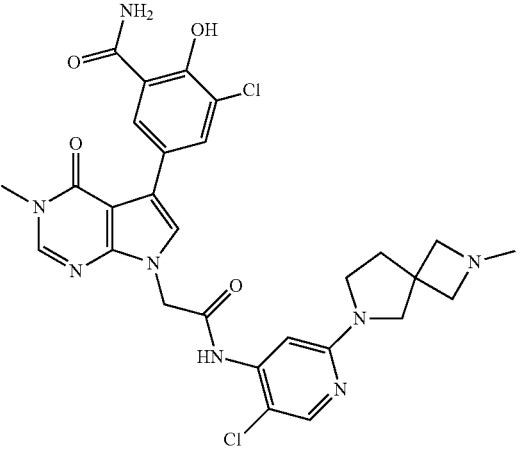 | 19% |
| I-483 | 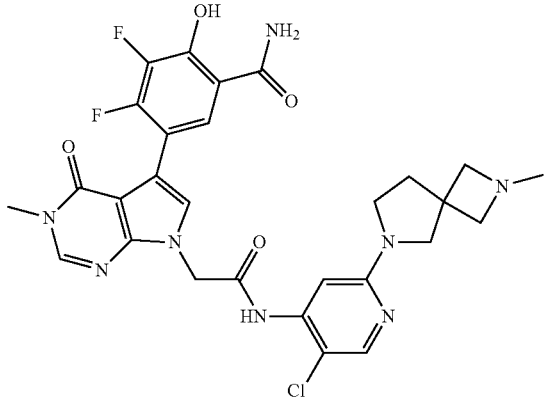 | 51% |
| I-484 | 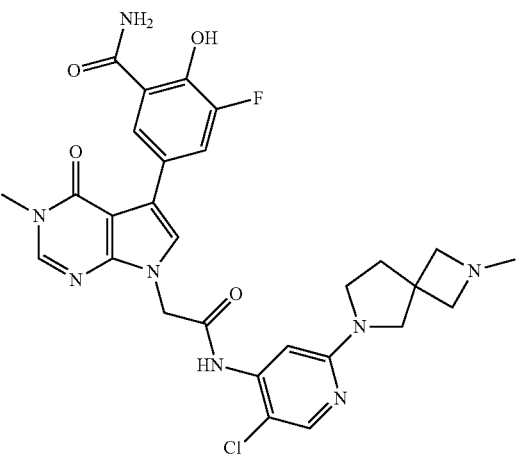 | 32% |

TABLE 1-continued

| Compound | Structure | Yield |
|---|---|---|
| I-485 | 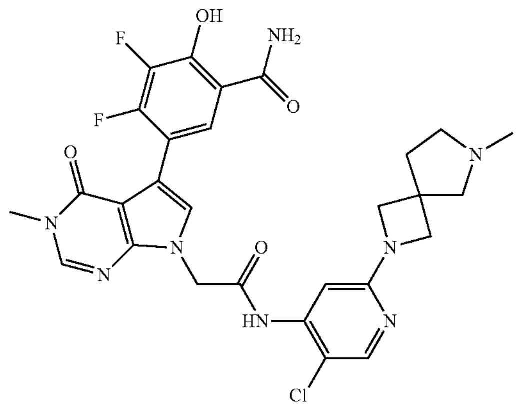 | 26% |
| I-486 | 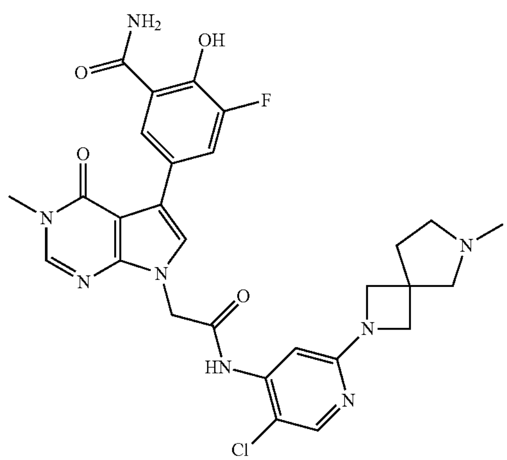 | 16% |
| I-487 | 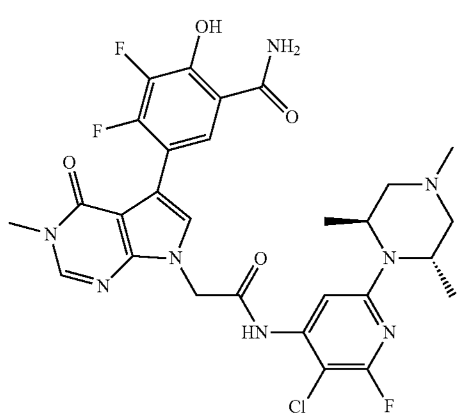 | 51% |

TABLE 1-continued

| Compound | Structure | Yield |
|---|---|---|
| I-488 | 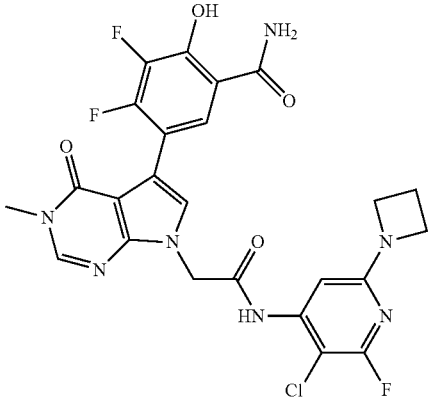 [SMILES: Cn1cnc2c(c(-c3cc(C(N)=O)c(O)c(F)c3F)cn2CC(=O)Nc2cc(N3CCC3)nc(F)c2Cl)c1=O] | 15% |

Example 2: Biological Assays

Compounds of the present invention display inhibition of the interaction between BCL6-BTB domain and SMRT/NCOR2 in the following assays.

BCL6-BTB—SMRT Peptide Inhibition Fluorescence Polarization (FP) Screen

This assay is used to determine whether compounds inhibit the interaction between the BTB domain of BCL6 and a peptide derived from the BCL6 binding domain (BBD) of the SMRT/NCOR2 corepressor protein Compounds were dissolved in 100% DMSO at 10 mM, assayed fresh, and then stored at −20° C. for repeat studies and future work. The reaction mixture consists of 1.25 uM of the 25 kd BCL6-BTB domain (Thioredoxin-His6-STag-TEV-biotinylation-thrombin-BCL6 amino acids 1-129) plus 20 nM of the peptide probe (Ac-GSLVATVKEAGRSI-HEIPA [SEQ ID NO:1]) with 16aa from the SMRT BBD (1414-1429) with a Bodipy-TMR fluorescent label on the lysine. The assay buffer was 10 mM HEPES pH7.4, 150 mM NaCl, 0.05% Tween-20, 3 mM EDTA, and had a final DMSO concentration of 5%. 20 ul of this assay mixture was added to each well of the 384 well plates with the exception of the control wells that contained no protein (for setting the minimum FP value). Compounds were directly sprayed using an HP D300 Digital Dispenser from 10 mM DMSO stocks onto black 384 well plates (greiner bio-one #781900) in a concentration range from 1 uM to 500 uM (10 points in duplicate). The assay was equilibrated for 1 hour prior to reading the FP values (Ex 540 nm/Em 580 nm) with a Perkin Elmer Envision plate reader. The results were curve fitted and $IC_{50}$ values were calculated using the BioAssay software from CambridgeSoft.

Surface Plasmon Resonance (SPR) Assay

SPR studies were performed using a Biacore™ T200 instrument (GE Health Sciences Inc.). The BCL6 BTB protein used in the FP assay was biotinylated using the site specific biotinylating enzyme BirA, and then cleaved with TEV protease to produce the BCL6 BTB domain (biotin-thrombin-BCL6 amino acids 1-129; 17 kd) that were use in SPR. This protein was stably captured (1000RU) to streptavidin coupled SA chips (BR-1005-31, GE Health Sciences Inc.) according to the manufacture's protocol. Compounds were dissolved in 100% DMSO at 10 mM and 2-fold serial dilutions were done in 100% DMSO. For SPR analysis the serially titrated compounds were diluted 1/20 into buffer (10 mM HEPES pH7.4, 150 mM NaCl, 0.05% Tween-20, 3 mM EDTA) giving a final concentration of 5% DMSO. The Biacore flow rate was set at 100 ul/min. For KD determinations, single cycle kinetic analysis was performed with an on time of 60 seconds, and an off time of 300 seconds. Curve fitting and KD calculations were done with the Biacore T200 Evaluation software (GE Health Sciences Inc).

Cell-Based Luciferase Assay

A BCL6 reporter construct containing three copies of the consensus BCL6 binding site, the TK promoter, and the firefly luciferase gene was stably expressed in SuDHL4 cells after lentivirus infection and selection with Blasticidin. SuDHL4-3×BCL6-TK-Luc cells were seeded into a Viewplate 384-well assay dish at 15,000 cells/well in 25 ul medium (Alpha-MEM high glucose containing 10% FBS, 25 mM HEPES, 200 mM GlutaMAX, 100 ug/ml Normocin, and 50 mg/ml Gentamycin, Invitrogen). A HP D300 digital dispenser was used to dose cells with DMSO or test compounds across a 10-point range of concentrations (high dose of 10 uM), and cultures were grown in a humidified 5% $CO_2$ incubator at 37° C. After two days, plates were removed from the incubator and equilibrated to room temperature. An equal volume of neolite reporter gene assay reagent was added to each well, and samples were processed according to manufacturer's instructions (Perkin Elmer). Luminescent signal was measured using an Envision plate reader equipped with a US-Luminescence detector.

Tumor Cell Growth inhibition Assay

Karpas422 cells were seeded into a 96-well plate at 2,000 cells/well in 150 ul medium (Alpha-MEM containing 10% FBS, 100 mg/ml Normocin, and 50 mg/ml Gentamycin, Invitrogen). A HP D300 digital dispenser was used to dose cells with DMSO or test compounds across a 10-point range of concentrations (high dose of 5 uM), and cultures were grown in a humidified 5% CO2 incubator at 37° C. After six days, plates were removed from incubator and equilibrated to room temperature. An equal volume of ATPlite assay reagent was added to each well, and samples were processed according to manufacturer's instructions (Perkin Elmer). Luminescent signal was measured using an Envision plate reader equipped with a US-Luminescence detector.

Table 2 summarizes the results of the biological assays for select compounds of the application.

TABLE 2

Activity of representative of compounds of the invention in the biochemical (SPR), cell-based luciferase and tumor growth inhibition assays

| Example # | SPR ($K_D$, uM) | Luciferase-Assay $EC_{50}$, uM | Tumor Growth Inhibition in Karpas-422 ($IC_{50}$, uM) |
|---|---|---|---|
| I-4 | 0.279 | 1.80 | 0.525 |
| I-9 | 0.038 | 0.257 | 0.247 |
| I-12 | 0.010 | 0.122 | 0.102 |
| I-13 | 0.022 | 0.170 | 0.180 |
| I-35 | 0.010 | 0.137 | 0.133 |
| I-67 | 0.014 | 0.296 | 0.267 |
| I-69 | 0.072 | 0.269 | 0.220 |
| I-73 | 0.019 | 0.233 | 0.165 |
| I-74 | 0.002 | 2.30 | 0.123 |
| I-75 | 0.008 | 0.132 | 0.099 |
| I-76 | 0.012 | 0.155 | 0.112 |
| I-77 | 0.027 | 0.279 | 0.115 |
| I-82 | 0.006 | 0.133 | 0.034 |
| I-83 | 0.016 | 0.148 | 0.119 |
| I-85 | 0.011 | 0.076 | 0.064 |
| I-108 | 0.030 | 0.203 | 0.408 |
| I-118 | 2.00 | >10.0 | 2.45 |
| I-119 | 4.00 | >10.0 | >10.0 |
| I-122 | 0.006 | 0.119 | 0.078 |
| I-123 | 0.007 | 0.095 | 0.216 |
| I-124 | 0.086 | 0.371 | 0.434 |
| I-125 | 0.030 | 3.76 | 0.407 |
| I-126 | 0.039 | 2.85 | 0.268 |
| I-127 | 0.201 | 0.756 | 0.276 |
| I-128 | 0.012 | 0.173 | 0.074 |
| I-129 | 0.044 | 2.62 | 0.866 |
| I-130 | 0.080 | 1.03 | 0.775 |
| I-131 | 8.00 | >10.0 | >10.0 |
| I-132 | 0.010 | 0.192 | 0.067 |
| I-133 | 0.030 | 0.137 | 0.199 |
| I-134 | 0.097 | 0.477 | 0.570 |
| I-135 | 0.069 | 3.01 | 1.43 |
| I-136 | 0.055 | 0.578 | 0.960 |
| I-137 | 0.066 | 1.34 | 1.74 |
| I-138 | 0.178 | 1.74 | 1.72 |
| I-139 | 3.27 | 8.35 | >10.0 |
| I-140 | 0.317 | 1.33 | 1.28 |
| I-141 | 0.265 | 1.83 | 1.02 |
| I-142 | 2.20 | 4.02 | >10.0 |
| I-143 | 0.250 | 6.20 | ND |
| I-144 | 41.1 | 10 | 10 |
| I-145 | 0.00609 | 0.303 | 0.551 |
| I-146 | 0.0184 | 0.182 | 0.121 |
| I-147 | 0.0196 | 0.144 | 0.0995 |
| I-148 | 0.0209 | 1.31 | 0.541 |
| I-149 | 0.0163 | 0.725 | 0.617 |
| I-150 | 0.0128 | 0.184 | 0.124 |
| I-151 | 0.0106 | 0.168 | 0.144 |
| I-152 | 0.0207 | 0.168 | 0.134 |
| I-153 | 0.00414 | 0.313 | 0.176 |
| I-154 | 0.0339 | 0.469 | 0.559 |
| I-155 | 0.0326 | 0.923 | 1.55 |
| I-156 | 0.0496 | 0.941 | 0.576 |
| I-157 | 0.0061 | 0.18 | 0.148 |
| I-158 | 0.00176 | 1.01 | 0.249 |
| I-159 | 0.0477 | 0.282 | 0.282 |
| I-160 | 0.0391 | 0.396 | 0.507 |
| I-161 | 0.115 | 0.971 | 1.29 |
| I-162 | 0.0847 | 0.676 | 0.643 |
| I-163 | 0.0505 | 0.572 | 0.93 |
| I-164 | 0.00776 | 0.601 | 0.251 |
| I-165 | 0.0149 | 0.466 | 0.102 |
| I-166 | 0.015 | 0.184 | 0.0862 |
| I-167 | 0.299 | 2.81 | 2.34 |
| I-168 | 0.074 | 1.3 | 0.769 |
| I-169 | 0.206 | 1.96 | 1.89 |
| I-170 | 0.369 | 2.14 | 10 |
| I-171 | 0.0997 | 1.2 | 1.04 |
| I-172 | 0.167 | 0.797 | 1.34 |
| I-173 | 0.2 | 44.6 | 5.72 |
| I-174 | 2.95 | 10 | 10 |
| I-175 | 0.429 |  | 4.79 |
| I-176 | 0.00606 | 0.239 | 0.137 |
| I-177 | 0.00588 | 0.629 | 0.331 |
| I-178 | 0.0621 | 0.96 | 0.877 |
| I-179 | 0.0777 | 0.612 | 0.681 |
| I-180 | 0.0454 | 1.37 | 2.18 |
| I-181 | 0.617 | 33 | 10 |
| I-182 | 0.0863 | 1.41 | 1.03 |
| I-183 | 0.221 | 3.91 | 10 |
| I-184 | 0.0374 | 0.348 | 0.26 |
| I-185 | 0.118 | 3.44 | 2.2 |
| I-186 | 0.47 | 3.08 | 3.2 |
| I-187 | 0.133 | 1.13 | 0.781 |
| I-188 | 0.435 | 4.75 | 2.95 |
| I-189 | 0.143 | 1.69 | 2.19 |
| I-190 | 0.0265 | 0.436 | 0.722 |
| I-191 | 0.122 | 5.42 | 4.72 |
| I-192 | 0.757 | 3.98 | 1.24 |
| I-193 | 0.229 | 5.39 | 2.66 |
| I-194 | 0.12 | 11 | 5.65 |
| I-195 | 0.196 | 1.5 | 1.08 |
| I-196 | 0.323 | 6.34 | 10 |
| I-197 | 0.218 | 4.01 | 10 |
| I-198 | 0.0217 | 5.82 | 3.02 |
| I-199 | 0.00818 | 0.117 | 0.0909 |
| I-200 | 0.0179 | 0.158 | 0.133 |
| I-201 | 0.0111 | 0.317 | 0.155 |
| I-202 | 0.0239 | 0.211 | 0.156 |
| I-203 | 0.0306 | 0.222 | 0.187 |
| I-204 | 0.0357 | 0.251 | 0.146 |
| I-205 | 0.0436 | 0.248 | 0.457 |
| I-206 | 0.00934 | 0.122 | 0.128 |
| I-207 | 0.00445 | 0.0429 | 0.0703 |
| I-208 | 0.567 | 5.15 | 1.2 |
| I-209 | 0.051 | 0.296 | 0.343 |
| I-210 | 1.1 | 14.9 | 6.16 |
| I-211 | 1.21 | 10 | 10 |
| I-212 | 0.0284 | 0.494 | 0.457 |
| I-213 | 0.0186 | 0.842 | 0.878 |
| I-214 | 0.0312 | 1.35 | 0.855 |
| I-215 | 0.00981 | 0.806 | 0.662 |
| I-216 | 0.0764 | 0.97 | 0.831 |
| I-217 | 0.0266 | 0.727 | 0.382 |
| I-218 | 0.0164 | 0.975 | 0.563 |
| I-219 | 0.0709 | 0.535 | 0.216 |
| I-220 | 0.0124 | 0.164 | 0.119 |
| I-221 | 0.0141 | 0.14 | 0.11 |
| I-222 | 0.228 | 1.33 | 0.371 |
| I-223 | 0.125 | 0.572 | 0.299 |
| I-224 | 0.0224 | 2.02 | 0.651 |
| I-225 | 0.115 | 20.5 | 4.34 |
| I-226 | 0.468 | 5.12 | 1.89 |
| I-227 | 0.42 | 2.5 | 2.16 |
| I-228 | 0.0319 | 0.382 | 0.407 |
| I-229 | 0.0163 | 0.102 | 0.0784 |
| I-230 | 0.00232 | 0.0625 | 0.0157 |
| I-231 | 0.0899 | 1.47 | 1.18 |
| I-232 | 0.0118 | 0.267 | 0.222 |
| I-233 | 0.0237 | 0.161 | 0.102 |
| I-234 | 0.0488 | 0.441 | 0.255 |
| I-235 | 0.014 | 0.139 | 0.138 |
| I-236 | 0.0166 | 0.739 | 0.385 |
| I-237 | 0.0176 | 1.04 | 1.25 |
| I-238 | 0.0121 | 0.588 | 0.291 |
| I-239 | 0.0102 | 0.889 | 0.316 |
| I-240 | 0.0278 | 0.399 | 0.343 |
| I-241 | 0.0195 | 0.483 | 0.281 |
| I-242 | 0.00501 | 0.483 | 0.312 |
| I-243 | 0.0124 | 0.19 | 0.134 |
| I-244 | 0.00846 | 0.279 | 0.169 |
| I-245 | 0.0204 | 0.245 | 0.182 |
| I-246 | 1.32 | 10 | 10 |
| I-247 | 0.118 | 15.2 | 0.628 |

TABLE 2-continued

Activity of representative of compounds of the invention in the biochemical (SPR), cell-based luciferase and tumor growth inhibition assays

| Example # | SPR ($K_D$, uM) | Luciferase-Assay $EC_{50}$, uM) | Tumor Growth Inhibition in Karpas-422 ($IC_{50}$, uM) |
|---|---|---|---|
| I-248 | 0.326 | 11.9 | 0.29 |
| I-249 | 0.0773 | 0.689 | 0.736 |
| I-250 | 0.0163 | 0.0822 | 0.0902 |
| I-251 | 0.0472 | 0.361 | 0.409 |
| I-252 | 0.0162 | 0.0965 | 0.262 |
| I-253 | 2.1 | ND | ND |
| I-254 | 3.88 | ND | ND |
| I-255 | 6.11 | ND | ND |
| I-256 | 0.211 | 0.509 | 0.274 |
| I-257 | 3.64 | ND | ND |
| I-258 | 0.1 | 0.549 | 0.491 |
| I-259 | 0.0385 | 0.214 | 0.652 |
| I-260 | 0.0588 | 10 | 0.238 |
| I-261 | 0.0398 | 0.65 | 0.225 |
| I-262 | 0.0228 | 0.468 | 0.389 |
| I-263 | 0.141 | 2.07 | 0.745 |
| I-264 | 0.0303 | 0.347 | 0.376 |
| I-265 | 0.116 | 0.767 | 1.3 |
| I-266 | 0.196 | 1.61 | 2.78 |
| I-267 | 0.582 | 2.27 | 3.79 |
| I-268 | 0.162 | 1.8 | 1.86 |
| I-269 | 0.157 | 8.55 | 1.7 |
| I-270 | 0.063 | 2.31 | 3.82 |
| I-271 | 0.016 | 0.208 | 0.22 |
| I-272 | 0.0148 | 0.133 | 0.145 |
| I-273 | 0.00531 | 0.416 | 0.251 |
| I-274 | 0.138 | 0.669 | 0.332 |
| I-275 | 0.00476 | 0.209 | 0.137 |
| I-276 | 0.0331 | 1.1 | 0.355 |
| I-277 | 0.021 | 0.418 | 0.255 |
| I-278 | 0.0425 | 0.622 | 1.13 |
| I-279 | 0.0102 | 0.468 | 0.197 |
| I-280 | 0.101 | 1.4 | 0.821 |
| I-281 | 0.0608 | 2.88 | 2.18 |
| I-282 | 0.0213 | 0.669 | 0.489 |
| I-283 | 0.0167 | 0.222 | 0.282 |
| I-284 | 0.0234 | 0.628 | 0.75 |
| I-285 | 0.102 | 1.6 | 1.6 |
| I-286 | 0.0837 | 1.96 | 1.54 |
| I-287 | 0.0186 | 1.71 | 1.44 |
| I-288 | 0.00947 | 0.181 | 0.128 |
| I-289 | 0.016 | 1.18 | 0.652 |
| I-290 | 18.4 | 10 | 10 |
| I-291 | 0.374 | 1.76 | 0.908 |
| I-292 | 0.0812 | 1.66 | 0.575 |
| I-293 | 0.0183 | 10 | 2.44 |
| I-294 | 0.00995 | 1.43 | 1.88 |
| I-295 | 0.00784 | 0.14 | 0.106 |
| I-296 | 0.0334 | 0.271 | 0.209 |
| I-297 | 0.0579 | 0.395 | 0.846 |
| I-298 | 0.0324 | 0.399 | 0.883 |
| I-299 | 0.0314 | 0.521 | 0.685 |
| I-300 | 0.0604 | 0.209 | 0.271 |
| I-301 | 0.0196 | 0.210 | 0.252 |
| I-302 | 0.00505 | 0.0865 | 0.0528 |
| I-303 | 0.00636 | 0.0493 | 0.0323 |
| I-304 | 0.00656 | 0.228 | 0.314 |
| I-305 | 0.0705 | 0.647 | 1.32 |
| I-306 | 0.0158 | 0.106 | 0.265 |
| I-307 | 0.0334 | 0.464 | 0.676 |
| I-308 | 0.00205 | 0.0368 | 0.0161 |
| I-309 | 0.146 | 1.02 | 2.55 |
| I-310 | 0.119 | 0.808 | 0.971 |
| I-311 | 0.00104 | 0.0155 | 0.0127 |
| I-312 | 0.0155 | 0.0652 | 0.0756 |
| I-313 | 0.0142 | 0.083 | 0.233 |
| I-314 | 0.117 | 0.901 | 6.7 |
| I-315 | 0.0142 | 0.114 | 0.147 |
| I-316 | 0.0241 | 0.243 | 0.376 |
| I-317 | 0.0549 | 0.633 | 0.467 |
| I-318 | 0.0518 | 0.228 | 0.319 |
| I-319 | 0.00396 | 0.104 | 0.0994 |
| I-320 | 0.0484 | 1.15 | 0.979 |
| I-321 | 0.00919 | 0.405 | 0.437 |
| I-322 | 0.034 | 3.09 | 1.19 |
| I-323 | 0.1 | 1.09 | 0.914 |
| I-324 | 0.264 | 10 | 10 |
| I-325 | 0.0408 | 2 | 1.13 |
| I-326 | 0.0645 | 2.35 | 2 |
| I-327 | 0.271 | 3 | 2.07 |
| I-328 | 0.239 | 3.76 | 2.66 |
| I-329 | 0.0134 | 0.345 | 0.173 |
| I-330 | 0.0394 | 0.89 | 0.56 |
| I-331 | 0.0178 | 0.254 | 0.176 |
| I-332 | 0.0287 | 0.492 | 0.207 |
| I-333 | 0.145 | 2.42 | 4.21 |
| I-334 | 0.0305 | 0.475 | 0.829 |
| I-335 | 0.0246 | 6.92 | 5.1 |
| I-336 | ND | 0.0383 | 0.0502 |
| I-337 | ND | 1.55 | 1.93 |
| I-338 | ND | 0.163 | 0.231 |
| I-339 | ND | 0.454 | 0.237 |
| I-340 | 0.0116 | 0.0724 | 0.0759 |
| I-341 | 0.0276 | 0.211 | 0.27 |
| I-342 | 0.0113 | 0.312 | 0.27 |
| I-343 | 0.18 | 0.641 | 0.383 |
| I-344 | 0.0138 | 0.317 | 0.701 |
| I-345 | 0.00615 | 0.0927 | 0.166 |
| I-346 | 0.0244 | 0.836 | 1.1 |
| I-347 | 0.0574 | 0.603 | 0.454 |
| I-348 | 0.0134 | 0.479 | 0.150 |
| I-349 | 0.00329 | 0.131 | 0.0873 |
| I-350 | 0.0639 | 0.486 | 0.897 |
| I-351 | 0.0401 | 0.591 | 1.2 |
| I-352 | 0.0597 | 0.79 | 0.346 |
| I-353 | 0.075 | 1.35 | 0.648 |
| I-354 | 0.0548 | 1.02 | 1.27 |
| I-355 | 0.011 | 0.0898 | 0.0508 |
| I-356 | 0.0105 | 0.142 | 0.166 |
| I-357 | 0.00186 | 0.0322 | 0.0288 |
| I-358 | 0.0227 | 0.256 | 0.341 |
| I-359 | 0.0422 | 0.521 | 1.34 |
| I-360 | 0.0309 | 0.659 | 0.778 |
| I-361 | 0.0708 | 1.33 | 1.37 |
| I-362 | 0.038 | 0.226 | 0.337 |
| I-363 | 0.0593 | 0.931 | 1.19 |
| I-364 | 0.025 | 0.819 | 1.04 |
| I-365 | 0.0174 | 0.281 | 0.462 |
| I-366 | 0.0352 | 0.899 | 0.978 |
| I-367 | 0.0419 | 5.3 | 3.49 |
| I-368 | 0.0835 | 0.369 | 0.407 |
| I-369 | 0.159 | 2.2 | 2.8 |
| I-370 | 0.0481 | 0.61 | 1.31 |
| I-371 | 0.0395 | 0.141 | 0.288 |
| I-372 | 0.00741 | 0.233 | 0.267 |
| I-373 | 0.00596 | 0.0803 | 0.105 |
| I-374 | 0.011 | 0.166 | 0.142 |
| I-375 | 0.00131 | 0.0114 | 0.0256 |
| I-376 | 0.0734 | 0.385 | 0.366 |
| I-377 | 0.208 | 2.97 | 8.61 |
| I-378 | 0.118 | 0.944 | 1.22 |
| I-379 | 0.0686 | 0.664 | 0.853 |
| I-380 | 0.056 | 0.59 | 0.478 |
| I-381 | 0.24 | 10 | 10 |
| I-382 | 0.342 | 3.1 | 10 |
| I-383 | 0.46 | 2.44 | 1.05 |
| I-384 | 0.115 | 1.18 | 0.8 |
| I-385 | 0.0384 | 0.312 | 0.335 |
| I-386 | 0.153 | 1.01 | 0.772 |
| I-387 | 0.189 | 1.12 | 1.04 |
| I-388 | 0.528 | 1.51 | 0.394 |
| I-389 | 0.286 | 2.01 | 1.46 |
| I-390 | 0.00618 | 0.0677 | 0.0483 |
| I-391 | 0.00726 | 0.0672 | 0.0726 |

TABLE 2-continued

Activity of representative of compounds of the invention in the biochemical (SPR), cell-based luciferase and tumor growth inhibition assays

| Example # | SPR ($K_D$, uM) | Luciferase-Assay $EC_{50}$, uM | Tumor Growth Inhibition in Karpas-422 ($IC_{50}$, uM) |
|---|---|---|---|
| I-392 | 0.0155 | 0.178 | 0.072 |
| I-393 | 0.0336 | 0.266 | 0.222 |
| I-394 | 0.0384 | 0.313 | 0.269 |
| I-395 | 0.0483 | 0.168 | 0.669 |
| I-396 | 0.226 | 0.683 | 0.749 |
| I-397 | 0.0983 | 3.31 | 2.54 |
| I-398 | 0.0827 | 2.6 | 1.3 |
| I-399 | 0.0307 | 0.268 | 0.535 |
| I-400 | 0.0278 | 0.204 | 0.408 |
| I-401 | 0.0289 | 0.427 | 1.22 |
| I-402 | 0.028 | 0.18 | 0.714 |
| I-403 | 0.0819 | 5.54 | 3.32 |
| I-404 | 0.106 | 4.06 | 10 |
| I-405 | 0.0326 | 0.459 | 0.254 |
| I-406 | 0.574 | 3.06 | 4.32 |
| I-407 | 0.0236 | 0.783 | 0.377 |
| I-408 | 0.0382 | 0.759 | 0.463 |
| I-409 | 0.0952 | 2.34 | 1.82 |
| I-410 | 0.0852 | 1.11 | 1.24 |
| I-411 | 0.0462 | 0.771 | 1.12 |
| I-412 | 0.0427 | 0.6 | 0.612 |
| I-413 | 0.00615 | 0.06 | 0.0822 |
| I-414 | 0.0179 | 0.374 | 0.455 |
| I-415 | 0.00595 | 0.0872 | 0.122 |
| I-416 | 0.00273 | 0.0787 | 0.0592 |
| I-417 | 0.0217 | 0.478 | 0.441 |
| I-418 | 0.0221 | 0.663 | 0.303 |
| I-419 | 0.00585 | 0.348 | 0.22 |
| I-420 | 0.0163 | 0.429 | 0.383 |
| I-421 | 0.0147 | 0.154 | 0.154 |
| I-422 | 0.00264 | 0.111 | 0.0653 |
| I-423 | 0.00506 | 0.143 | 0.0391 |
| I-424 | 0.0261 | 0.309 | 0.157 |
| I-425 | 0.0447 | 0.629 | 0.624 |
| I-426 | 0.0177 | 0.226 | 0.128 |
| I-427 | 0.0138 | 0.156 | 0.114 |
| I-428 | 0.00235 | 0.102 | 0.0682 |
| I-429 | 0.0109 | 0.162 | 0.154 |
| I-430 | 0.0232 | 0.622 | 0.38 |
| I-431 | 0.0307 | 0.193 | 0.175 |
| I-432 | 0.00239 | 0.0347 | 0.0181 |
| I-433 | 0.00842 | 0.548 | 0.201 |
| I-434 | 0.00545 | 0.0381 | 0.05 |
| I-435 | 0.0489 | 0.847 | 0.415 |
| I-436 | 0.0141 | 0.803 | 0.401 |
| I-437 | 0.0113 | 0.231 | 0.124 |
| I-438 | 0.0025 | 0.0686 | 0.0508 |
| I-439 | 0.0329 | 0.267 | 0.28 |
| I-440 | 0.0158 | 0.286 | 0.291 |
| I-441 | 0.0223 | 0.324 | 0.338 |
| I-442 | 0.0218 | 0.386 | 0.266 |
| I-443 | 0.0186 | 0.285 | 0.149 |
| I-444 | 0.0198 | 0.239 | 0.104 |
| I-445 | 0.00732 | 0.0854 | 0.0622 |
| I-446 | 0.00729 | 0.157 | 0.137 |
| I-447 | 0.00902 | 0.113 | 0.0709 |
| I-448 | 0.00342 | 0.0483 | 0.0446 |
| I-449 | 0.0603 | 2.48 | 1.97 |
| I-450 | 0.0436 | ND | ND |
| I-451 | 0.157 | ND | ND |
| I-452 | 0.0136 | 2.6 | 1.52 |
| I-453 | 0.0543 | 0.41 | 0.16 |
| I-454 | 0.0135 | 0.306 | 0.244 |
| I-455 | 0.0112 | 0.307 | 0.204 |
| I-456 | 0.00187 | 0.0858 | 0.0554 |
| I-457 | 0.0131 | 0.328 | 0.183 |
| I-458 | 0.0558 | 0.963 | 3.68 |
| I-459 | 0.00655 | 0.945 | 1.06 |
| I-460 | 0.00987 | 0.102 | 0.223 |
| I-461 | 0.0876 | 0.673 | 1.14 |
| I-462 | 0.0503 | 0.184 | 0.289 |
| I-463 | 0.00856 | 3.53 | 1.28 |
| I-464 | 0.0838 | 0.213 | 0.421 |
| I-465 | 0.0849 | 4.47 | 1.17 |
| I-466 | 0.519 | 3.81 | 0.773 |
| I-467 | 0.175 | 1.23 | 0.496 |
| I-468 | 0.0235 | 0.461 | 0.417 |
| I-469 | 0.0355 | 0.141 | 0.153 |
| I-470 | 0.101 | 13.7 | 10 |
| I-471 | 0.00105 | 0.0168 | 0.0148 |
| I-472 | 0.0557 | 3.8 | 10 |
| I-473 | 0.191 | 6.6 | 7.8 |
| I-474 | 0.0358 | 0.216 | 0.237 |
| I-475 | 0.0505 | 0.484 | 0.576 |
| I-476 | 0.0137 | 0.159 | 0.118 |
| I-477 | 0.0101 | 0.328 | 0.272 |
| I-478 | 0.00458 | 0.366 | 0.182 |
| I-479 | 0.0162 | 1.43 | 0.778 |
| I-480 | 0.137 | 2.21 | 0.704 |
| I-481 | 0.0192 | 19.4 | 10 |
| I-482 | 0.0343 | 4.69 | 2.32 |
| I-483 | 0.128 | 10 | 10 |
| I-484 | 0.0403 | 21.6 | 10 |
| I-485 | 0.805 | ND | ND |
| I-486 | 0.03 | 6.95 | 10 |
| I-487 | 0.122 | 1.29 | 1.8 |
| I-488 | 0.0716 | 1.28 | 0.417 |

ND: Not determined

The invention claimed is:
1. A compound of formula (I):

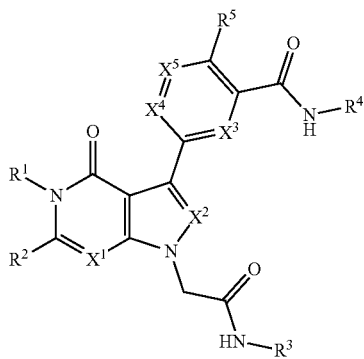

or a pharmaceutically acceptable salt or stereoisomer thereof,
wherein:

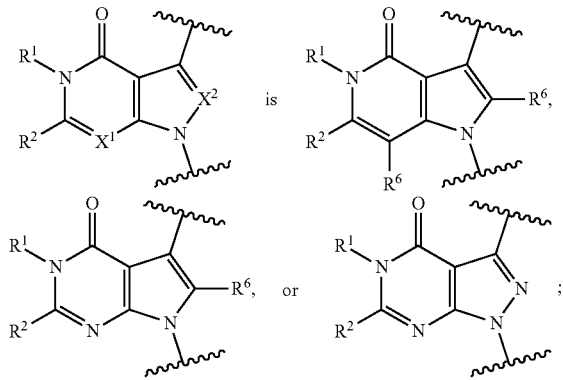

$X^3$ is $CR^6$ or N;
$X^4$ is $CR^7$ or N;
$X^5$ is $CR^8$ or N;
$R^1$ is H, $C_{1-6}$ alkyl, $C_{1-6}$ alkylene-C(O)—$C_{3-6}$ cycloalkyl, $C_{1-6}$ alkylene-C(O)—$C_{3-6}$heterocycloalkyl, $C_{1-6}$ alkylene-C(O)-phenyl, $C_{1-6}$ alkylene-C(O)—$C_{5-6}$heteroaryl, $C_{1-6}$ alkylene-O—$C_{1-6}$ alkyl, $C_{1-6}$ alkylene-$C_{3-6}$ cycloalkcyl, $C_{1-6}$ alkylene-$C_{3-6}$heterocycloalkyl, $C_{1-6}$ alkylene-phenyl, $C_{1-6}$ alkylene-$C_{5-6}$heteroaryl, $C_{2-6}$ alkenylene-O—$C_{1-6}$ alkyl, $C_{2-6}$ alkenylene-$C_{3-6}$ cycloalkyl, $C_{2-6}$ alkenylene-$C_{3-6}$heterocycloalkyl, $C_{2-6}$ alkenylene-phenyl, $C_{2-6}$ alkenylene-$C_{5-6}$heteroaryl, $C_{2-6}$ alkynylene-O—$C_{1-6}$ alkyl, $C_{2-6}$ alkynylene-$C_{3-6}$ cycloalkyl, $C_{2-6}$ alkynylene-$C_{3-6}$ heterocycloalkcyl, $C_{2-6}$ alkynylene-phenyl, or $C_{2-6}$ alkynylene-$C_{5-6}$ heteroaryl, wherein each $C_{3-6}$ cycloalkyl, $C_{3-6}$heterocycloalkyl, phenyl, or $C_{5-6}$heteroaryl is optionally substituted with 1, 2, or 3 substituents independently selected from the group consisting of halo and $C_{1-4}$ alkyl;

$R^2$ is H, halo, $C_{1-6}$ alkyl, $NH_2$, $NH_{1-6}$ alkyl, $N(C_{1-6}$ alkyl)($C_{1-6}$ alkyl), OH, $OC_{1-6}$ alkyl, SH, $Z^1$—$C_{1-6}$ alkylene-O—$C_{1-6}$ alkyl, $Z^1$—$C_{1-6}$ alkylene-$C_{3-6}$ cycloalkyl, $Z^1$—$C_{1-6}$ alkylene-$C_{3-6}$heterocycloalkyl, $Z^1$—$C_{1-6}$ alkylene-phenyl, $Z^1$—$C_{1-6}$ alkylene-$C_{5-6}$heteroaryl, $Z^1$—$C_{2-6}$ alkenylene-O—$C_{1-6}$ alkyl, $Z^1$—$C_{2-6}$ alkenylene-$C_{3-6}$ cycloalkyl, $Z^1$—$C_{2-6}$ alkenylene-$C_{3-6}$heterocycloalkyl, $Z^1$—$C_{2-6}$ alkenylene-phenyl, $Z^1$—$C_{2-6}$ alkenylene-$C_{5-6}$ heteroaryl, $Z^1$—$C_{2-6}$ alkynylene-O—$C_{1-6}$ alkyl, $Z^1$—$C_{2-6}$ alkynylene-$C_{3-6}$ cycloalkyl, $Z^1$—$C_{2-6}$ alkynylene-$C_{3-6}$heterocycloalkyl, $Z^1$—$C_{2-6}$ alkynylene-phenyl, $Z^1$—$C_{2-6}$ alkynylene-$C_{5-6}$heteroaryl, $Z^1$—$C_{3-6}$ cycloalkyl, $Z^1$—$C_{3-6}$ heterocycloalkyl, $Z^1$-phenyl, or $Z^1$—$C_{5-6}$heteroaryl, wherein each $C_{3-6}$ cycloalkyl, $C_{3-6}$heterocycloalkyl, phenyl, or $C_{5-6}$heteroaryl is optionally substituted with 1, 2, or 3 substituents independently selected from the group consisting of halo, $NH_2$, $NHC_{1-6}$ alkyl, $N(C_{1-6}$ alkyl)($C_{1-6}$ alkyl), OH, and SH;

$R^3$ is $C_{6-10}$ cycloalkyl, $C_{6-10}$ heterocycloalkyl, $C_{6-10}$ aryl, or $C_{6-10}$heteroaryl, wherein the $C_{6-10}$ cycloalkyl, $C_{6-10}$heterocycloalkyl, $C_{6-10}$ aryl, or $C_{6-10}$heteroaryl is optionally substituted with 1 $Z^2$—$R^9$ substituent, and optionally further substituted with 1, 2, 3, or 4 substituents independently selected from the group consisting of halo, CN, $NO_2$, $C_{1-6}$ alkyl, $C_{2-6}$ alkenyl, $C_{2-6}$ alkynyl, $OC_1$ alkyl, and =O;

$R^4$ is H or $C_{1-6}$ alkyl;
$R^5$ is OH;
$R^6$ is H or halo;
$R^7$ is H, halo, $C_{1-6}$ alkyl, $OC_{1-6}$ alkyl, or $S(O)_2NH_2$;
$R^8$ is H, halo, $C_{1-6}$ alkyl, $OC_{1-6}$ alkyl, or $S(O)_2NH_2$; or
$R^7$ and $R^8$, taken together with the carbon atoms to which they are attached, form a 3- to 8-membered heterocycloalkyl or heteroaryl, wherein the 3- to 8-membered heterocycloalkyl or heteroaryl contains 1 or 2 heteroatoms or heteroatomic groups independently selected from the group consisting of NH, $N(C_{1-6}$ alkyl), O, S, S(O), and $S(O)_2$;

$R^9$ is $C_{1-6}$ alkyl, $NR^{10}R^{11}$, $C_{3-10}$ cycloalkyl, $C_{3-10}$ heterocycloalkyl, $C_{6-10}$ aryl, or $C_{5-10}$heteroaryl, wherein the $C_{3-10}$ cycloalkyl, $C_{3-10}$ heterocycloalkyl, $C_{6-10}$ aryl, or $C_{5-10}$heteroaryl is optionally substituted with 1 substituent selected from the group consisting of $C_{1-6}$ alkylene-OH, $C_{1-6}$ alkylene-(diOH), $C_{1-6}$ alkylene-O—$C_{1-6}$ alkyl, $S(O)_2C_{1-4}$ alkyl, $Z^3$—$C_{3-10}$ cycloalkyl, $Z^3$—$C_{3-10}$ heterocycloalkyl, $Z^3$—$C_{6-10}$ aryl, and $Z^3$—$C_{5-10}$heteroaryl, wherein the $Z^3$—$C_{3-10}$ cycloalkyl, $Z^3$—$C_{3-10}$ heterocycloalkyl, $Z^3$—$C_{6-10}$ aryl, or $Z^3$—$C_{5-10}$ heteroaryl is optionally substituted with 1, 2, 3, or 4 substituents independently selected from the group consisting of halo and $C_{1-6}$ alkyl, and optionally further substituted with 1, 2, 3, 4, 5, or 6 substituents independently selected from the group consisting of halo, CN, $C_{1-6}$ alkyl, and $OC_{1-6}$ alkyl;

$R^{10}$ is H, $C_{1-6}$ alkyl, $C_{1-6}$ alkylene-OH, $C_{1-6}$ alkylene-(diOH), $C_{1-6}$ alkylene-O—$C_{1-6}$ alkyl, $S(O)_2C_{1-6}$ alkyl, $Z^4$—$C_{3-10}$ cycloalkyl, $Z^4$—$C_{3-10}$ heterocycloalkyl, $Z^4$—$C_{6-10}$ aryl, or $Z^4$—$C_{5-10}$heteroaryl, wherein the $Z^4$—$C_{3-10}$ cycloalkyl, $Z^4$—$C_{3-10}$ heterocycloalkyl, $Z^4$—$C_{6-10}$ aryl, or $Z^4$—$C_{5-10}$heteroaryl is optionally substituted with 1, 2, 3, 4, 5, or 6 substituents independently selected from the group consisting of halo and $C_{1-6}$ alkyl;

$R^{11}$ is H, $C_{1-6}$ alkyl, $C_{1-6}$ alkylene-OH, $C_{1-6}$ alkylene-(diOH), $C_{1-6}$ alkylene-O—$C_{1-6}$ alkyl, $S(O)_2C_{1-6}$ alkyl, $Z^4$—$C_{3-10}$ cycloalkyl, $Z^4$—$C_{3-10}$ heterocycloalkyl, $Z^4$—$C_{6-10}$ aryl, or $Z^4$—$C_{5-10}$heteroaryl, wherein the $Z^4$—$C_{3-10}$ cycloalkyl, $Z^4$—$C_{3-10}$ heterocycloalkyl, $Z^4$—$C_{6-10}$ aryl, or $Z^4$—$C_{5-10}$heteroaryl is optionally substituted with 1, 2, 3, 4, 5, or 6 substituents independently selected from the group consisting of halo and $C_{1-6}$ alkyl;

$Z^1$ is a direct bond, —NH—, —N$C_{1-6}$ alkyl-, —O—, —S(O)—, or —S(O)$_2$—;

$Z^2$ is a direct bond, —$C_{1-6}$ alkylene-, —C(O)—, —O—, —S—, —S(O)—, or —S(O)$_2$—

$Z^3$ is a direct bond or —$C_{1-6}$ alkylene-; and $Z^4$ is a direct bond or —$C_{1-6}$ alkylene-;

wherein each $C_{1-6}$ alkyl and $C_{1-6}$ alkylene is optionally and independently substituted with 1 or more substituents independently selected from the group consisting of D and F.

2. The compound of claim 1, or a pharmaceutically acceptable salt or stereoisomer thereof, wherein $R^1$ is H, $CH_3$, $CF_3$, $CH_2OCH_3$, $CH_2OCF_3$, $CH_2$—$C_{3-6}$ cycloalkyl, $CH_2$—$C_{3-6}$heterocycloalkyl, $CH_2$-phenyl, $CH_2$—$C_{5-6}$ heteroaryl, $CH_2CH_2$—C(O)—$C_{3-6}$ cycloalkyl, $CH_2CH_2$—C(O)—$C_{3-6}$heterocycloalkyl, $CH_2CH_2$—C(O)-phenyl, $CH_2CH_2$—C(O)—$C_{5-6}$heteroaryl, $CH_2C\equiv C$—$C_{3-6}$ cycloalkyl, $CH_2C\equiv C$—$C_{3-6}$heterocycloalkyl, $CH_2C\equiv C$-phenyl, and $CH_2C\equiv C$—$C_{5-6}$heteroaryl, wherein each $C_{3-6}$ cycloalkyl, $C_{3-6}$heterocycloalkyl, phenyl, or $C_{3-6}$heteroaryl is optionally substituted with 1 or 2 substituents independently selected from the group consisting of F, Cl, $CH_3$, and $CF_3$.

3. The compound of claim 1, or a pharmaceutically acceptable salt or stereoisomer thereof, wherein the heteroaryl of $R^1$ is a $C_5$heteroaryl, wherein 1 or 2 C atoms of the $C_5$heteroaryl of $R^1$ is replaced with 1 or 2 N heteroatoms, and further wherein the $C_5$heteroaryl of $R^1$ is optionally substituted with 1 or 2 $CH_3$ substituents.

4. The compound of claim 1, or a pharmaceutically acceptable salt or stereoisomer thereof, wherein $R^2$ is H, F, Cl, $CH_3$, $CF_3$, $NH_2$, $NHCH_3$, $N(CH_3)_2$, $N(CH_3)(CH_2CH_3)$, OH, $OCH_3$, $Z^1$—$C_{1-2}$ alkylene-$OCH_3$, $Z^1$—$C_{1-2}$ alkylene-$C_{3-6}$ cycloalkyl, $Z^1$—$C_{1-2}$ alkylene-$C_{3-6}$heterocycloalkyl, $Z^1$—$C_{1-4}$ alkylene-phenyl, $Z^1$—$C_{1-4}$ alkylene-$C_{5-6}$heteroaryl, $Z^1$—$C_{2-3}$ alkenylene-O—$C_{1-4}$ alkyl, $Z^1$—$C_{2-3}$ alkenylene-$C_{3-6}$ cycloalkyl, $Z^1$—$C_{2-3}$ alkenylene-$C_{3-6}$ heterocycloalkyl, $Z^1$—$C_{2-3}$ alkenylene-phenyl, $Z^1$—$C_{2-3}$ alkenylene-$C_{5-6}$heteroaryl, $Z^1$—$C_{3-6}$ cycloalkyl, $Z^1$—$C_{3-6}$ heterocycloalkyl, $Z^1$-phenyl, or $Z^1$—$C_{5-6}$heteroaryl, wherein each $C_{3-6}$ cycloalkyl, $C_{3-6}$heterocycloalkyl, phenyl, or $C_{5-6}$heteroaryl is optionally substituted with 1 or 2 substituents independently selected from the group consisting of F, Cl, and $N(CH_3)_2$.

5. The compound of claim 4, or a pharmaceutically acceptable salt or stereoisomer thereof, wherein $R^2$ is H, Cl, $CH_3$, $CF_3$, CH=CH-cyclopropyl, $NH_2$, $NHCH_3$, NH—$CH_2$-cyclopropyl, $NH_2$—$CH_2$-(p-F-phenyl), $N(CH_3)_2$, $N(CH_3)(CH_2CH_3)$, OH, $OCH_3$, O—$CH_2CH_2$—$OCH_3$, azetidin-1-yl, phenyl, or NH-[5-chloro-2-(dimethylamino)pyridin-4-yl].

6. The compound of claim 1, or a pharmaceutically acceptable salt or stereoisomer thereof, wherein $R^3$ is $C_{6-10}$ aryl or $C_{6-10}$heteroaryl, wherein the $C_{6-10}$ aryl or $C_{6-10}$heteroaryl is monocyclic or bicyclic, and further wherein the $C_{6-10}$ aryl or $C_{6-10}$heteroaryl is optionally substituted with 1 $Z^2$—$R^9$ substituent, and optionally further substituted with 1, 2, or 3 substituents independently selected from the group consisting of F, Cl, CN, $NO_2$, $C_{1-2}$ alkyl, $C_{2-4}$ alkenyl, $C_{2-4}$ alkynyl, $OC_{1-2}$ alkyl, and =O.

7. The compound of claim 1, or a pharmaceutically acceptable salt or stereoisomer thereof, wherein:

$Z^2$ is a direct bond; and $R^9$ is:

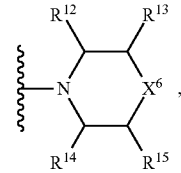

wherein:

⸺ is the point of attachment to $R^3$;

$X^6$ is —$CH_2$—, —CHF—, —$CF_2$—, —CH($C_{1-4}$ alkyl)-, —CH($C_{1-4}$ alkylene-O—$C_{1-4}$ alkyl)-, —CH($C_{1-4}$ alkylene-$C_{3-6}$ cycloalkyl)-, —CH($C_{1-4}$ alkylene-$C_{3-6}$heterocycloalkyl)-, —CH($C_{3-6}$ cycloalkyl)-, —CH($C_{3-6}$ heterocycloalkyl)-, —C($C_{1-4}$ alkyl)($C_{1-4}$ alkyl)-, —NH—, —N($C_{1-4}$ alkyl)-, —N($C_{1-4}$ alkylene-O—$C_{1-4}$ alkyl)-, —N($C_{1-4}$ alkylene-$C_{3-6}$ cycloalkyl)-, —N($C_{1-4}$ alkylene-$C_{3-6}$heterocycloalkyl)-, —N($C_{3-6}$ cycloalkyl)-, —N($C_{3-6}$ heterocycloalkyl)-, or —O—;

$R^{12}$ is H, F, $C_{1-4}$ alkyl, or $C_{1-4}$ alkylene-O—$C_{1-4}$ alkyl;

$R^{13}$ is H, F, $C_{1-4}$ alkyl, or $C_{1-4}$ alkylene-O—$C_{1-4}$ alkyl;

$R^{14}$ is H, F, $C_{1-4}$ alkyl, or $C_{1-4}$ alkylene-O—$C_{1-4}$ alkyl; and $R^{15}$ is H, F, $C_{1-4}$ alkyl, or $C_{1-4}$ alkylene-O—$C_{1-4}$ alkyl; or $R^{12}$ and $R^{14}$ form a $C_{1-3}$ alkylene bridge linking the carbon atoms to which they are attached; or $R^{13}$ and $R^{15}$ form a $C_{1-3}$ alkylene bridge linking the carbon atoms to which they are attached;

wherein each $C_{1-4}$ alkyl and $C_{1-4}$ alkylene is optionally and independently substituted with 1 or more F substituents.

8. The compound of claim 7, or a pharmaceutically acceptable salt or stereoisomer thereof, wherein:

$X^6$ is —$CH_2$—, —CHF—, —$CF_2$—, —CH($CH_2$-cyclopropyl)-, —CH($CH_2$-cyclobutyl)-, —NH—, —N($CH_3$)—, —N($CH_2CH_3$)—, —N[CH($CH_3$)$_2$]—, N($CH_2CH_2$—O—$CH_3$)—, —N($CH_2$-cyclopropyl)-, N[CH($CH_3$)-cyclopropyl]-, N($CH_2$-cyclobutyl)-, —N(cyclopropyl)-, —N(cyclobutyl)-, —N(oxetanyl)-, or —O—;

$R^{12}$ is H, F, $CH_3$, $CF_3$, or $C_{1-2}$ alkylene-O—$CH_3$;

$R^{13}$ is H, F, $CH_3$, $CF_3$, or $C_{1-2}$ alkylene-O—$CH_3$;

$R^{14}$ is H, F, $CH_3$, $CF_3$, or $C_{1-2}$ alkylene-O—$CH_3$; and $R^{15}$ is H, F, $CH_3$, $CF_3$, or $C_{1-2}$ alkylene-O—$CH_3$; or $R^{12}$ and $R^{14}$ form a —$CH_2CH_2$— bridge linking the carbon atoms to which they are attached; or $R^{13}$ and $R^{15}$ form a —$CH_2CH_2$— bridge linking the carbon atoms to which they are attached.

9. The compound of claim 1, or a pharmaceutically acceptable salt or stereoisomer thereof, wherein:

$R^7$ is H, F, Cl, $CH_3$, $CF_3$, $CH_2CH_3$, $OCH_3$, $OCF_3$, or $S(O)_2NH_2$; and $R^8$ is H, F, Cl, $CH_3$, $CF_3$, $CH_2CH_3$, $OCH_3$, $OCF_3$, or $S(O)_2NH_2$.

10. The compound of claim 1, or a pharmaceutically acceptable salt or stereoisomer thereof, wherein $R^7$ and $R^8$, taken together with the carbon atoms to which they are attached, form a 3- to 6-membered heterocycloalkyl or heteroaryl, wherein the 3- to 6-membered heterocycloalkyl or heteroaryl contains 1 or 2 heteroatoms or heteroatomic groups independently selected from the group consisting of NH, N(CH$_3$), O, and S.

11. The compound of claim 1, or a pharmaceutically acceptable salt or stereoisomer thereof, wherein $R^9$ is $C_{1-4}$ alkyl, $NR^{10}R^{11}$, $C_{3-10}$ cycloalkyl, $C_{3-10}$ heterocycloalkyl, $C_{6-10}$ aryl, or $C_{5-10}$heteroaryl, wherein the $C_{3-10}$ cycloalkyl, $C_{3-10}$ heterocycloalkyl, $C_{6-10}$ aryl, or $C_{5-10}$heteroaryl is optionally substituted with 1 substituent selected from the group consisting of $C_{1-4}$ alkylene-OH, $C_{1-4}$ alkylene-(diOH), $C_{1-4}$ alkylene-O—$C_{1-4}$ alkyl, $S(O)_2C_{1-4}$ alkyl, $Z^3$—$C_{3-10}$ cycloalkyl, $Z^3$—$C_{3-10}$ heterocycloalkyl, $Z^3$—$C_{6-10}$ aryl, and $Z^3$—$C_{5-10}$heteroaryl, wherein the $Z^3$—$C_{3-10}$ cycloalkyl, $Z^3$—$C_{3-10}$ heterocycloalkyl, $Z^3$—$C_{6-10}$ aryl, or $Z^3$—$C_{5-10}$heteroaryl is optionally substituted with 1, 2, 3, or 4 substituents independently selected from the group consisting of F, Cl, and $C_{1-4}$ alkyl, and optionally further substituted with 1, 2, 3, 4, 5, or 6 substituents independently selected from the group consisting of halo, CN, $C_{1-4}$ alkyl, and $OC_{1-4}$ alkyl.

12. The compound of claim 1, or a pharmaceutically acceptable salt or stereoisomer thereof, wherein:

$R^{10}$ is H, $C_{1-4}$ alkyl, $C_{1-4}$ alkylene-OH, $C_{1-4}$ alkylene-(diOH), $C_{1-4}$ alkylene-O—$C_{1-6}$ alkyl, $S(O)_2C_{1-4}$ alkyl, $Z^4$—$C_{3-10}$ cycloalkyl, $Z^4$—$C_{3-10}$ heterocycloalkyl, $Z^4$—$C_{6-10}$ aryl, or $Z^4$—$C_{5-10}$heteroaryl, wherein the $Z^4$—$C_{3-10}$ cycloalkyl, $Z^4$—$C_{3-10}$ heterocycloalkyl, $Z^4$—$C_{6-10}$ aryl, or $Z^4$—$C_{5-10}$heteroaryl is optionally substituted with 1, 2, 3, 4, 5, or 6 substituents independently selected from the group consisting of halo and $C_{1-6}$ alkyl; and $R^{11}$ is H, $C_{1-4}$ alkyl, $C_{1-4}$ alkylene-OH, $C_{1-4}$ alkylene-(diOH), $C_{1-4}$ alkylene-O—$C_{1-6}$ alkyl, $S(O)_2C_{1-4}$ alkyl, $Z^4$—$C_{3-10}$ cycloalkyl, $Z^4$—$C_{3-10}$ heterocycloalkyl, $Z^4$—$C_{6-10}$ aryl, or $Z^4$—$C_{5-10}$heteroaryl, wherein the $Z^4$—$C_{3-10}$ cycloalkyl, $Z^4$—$C_{3-10}$ heterocycloalkyl, $Z^4$—$C_{6-10}$ aryl, or $Z^4$—$C_{5-10}$heteroaryl is optionally substituted with 1, 2, 3, 4, 5, or 6 substituents independently selected from the group consisting of halo and $C_{1-6}$ alkyl.

13. The compound of claim 1, or a stereoisomer thereof, wherein the compound, or stereoisomer thereof, is selected from the group consisting of:

| Compound | Structure |
| --- | --- |
| I-1 | 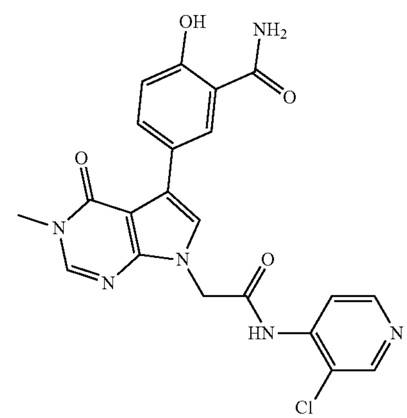 [SMILES: Cn1cnc2c(c(-c3ccc(O)c(C(N)=O)c3)cn2CC(=O)Nc2ccncc2Cl)c1=O] |
| I-2 | 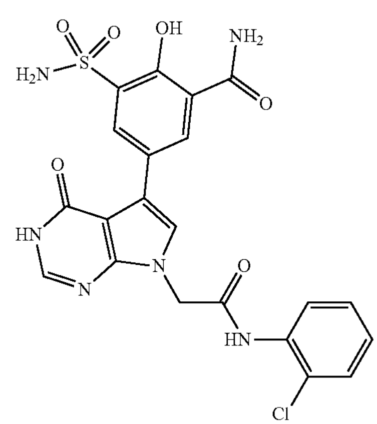 [SMILES: NC(=O)c1cc(-c2cn(CC(=O)Nc3ccccc3Cl)c3nc[nH]c(=O)c23)cc(S(N)(=O)=O)c1O] |

| Compound | Structure |
|---|---|
| I-3 | 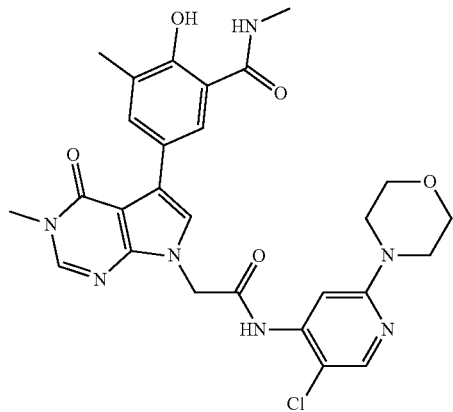 [SMILES: CNC(=O)c1cc(-c2cn(CC(=O)Nc3cc(N4CCOCC4)ncc3Cl)c3ncn(C)c(=O)c23)cc(C)c1O] |
| I-4 | 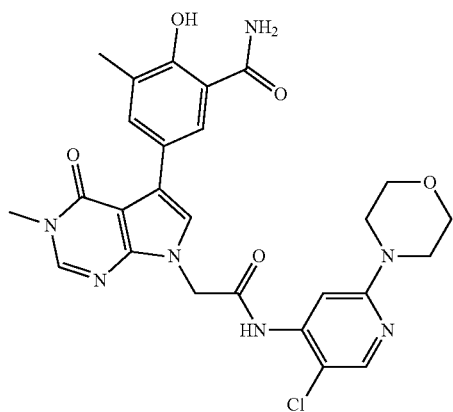 |
| I-5 | 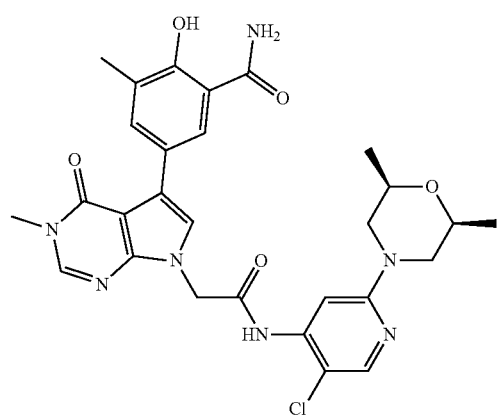 |

-continued
| Compound | Structure |
|---|---|
| I-6 | 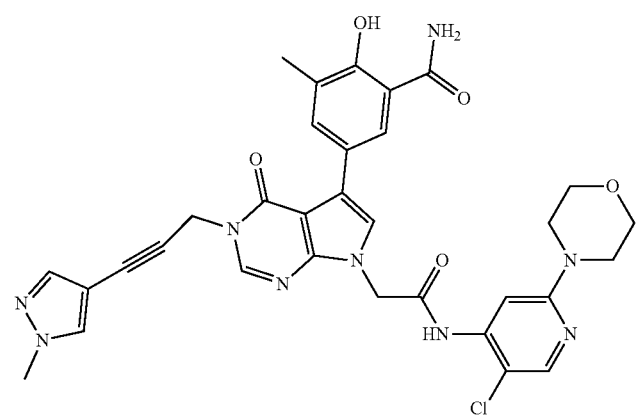 |
| I-7 | 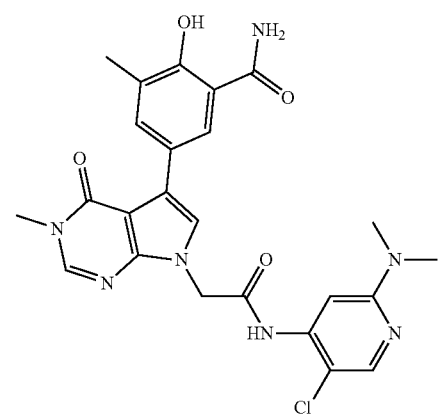 |
| I-8 | 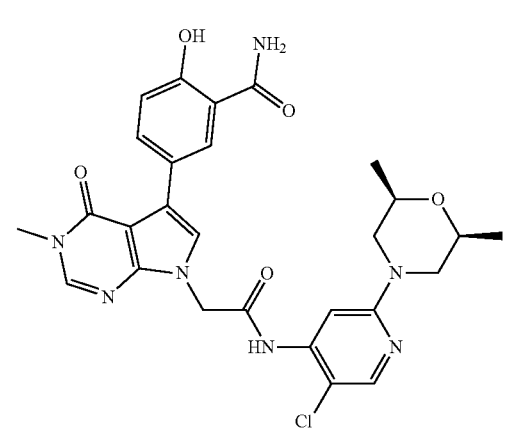 |

-continued
| Compound | Structure |
|---|---|
| I-9 | 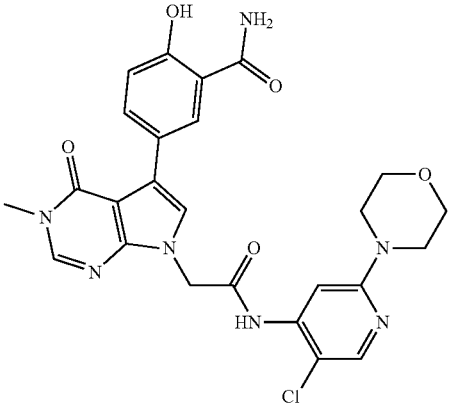 [SMILES: Cn1cnc2c(c(-c3ccc(O)c(C(N)=O)c3)cn2CC(=O)Nc2cc(N3CCOCC3)ncc2Cl)c1=O] |
| I-10 | 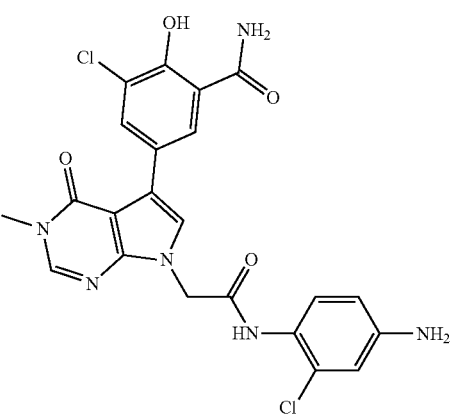 [SMILES: Cn1cnc2c(c(-c3cc(Cl)c(O)c(C(N)=O)c3)cn2CC(=O)Nc2ccc(N)cc2Cl)c1=O] |
| I-11 | 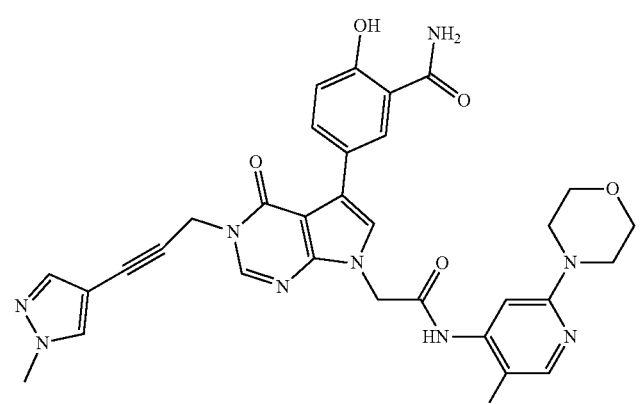 |

-continued

| Compound | Structure |
|---|---|
| I-12 | 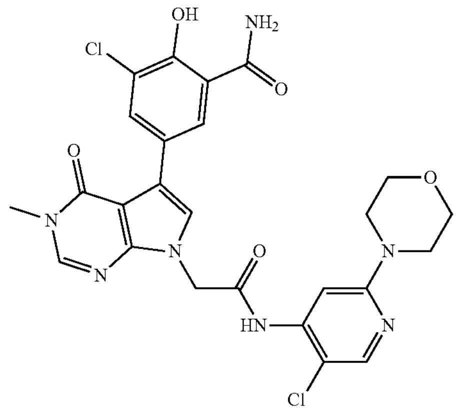 [SMILES: Cn1cnc2c(c(-c3cc(Cl)c(O)c(C(N)=O)c3)cn2CC(=O)Nc2cc(N3CCOCC3)ncc2Cl)c1=O] |
| I-13 | 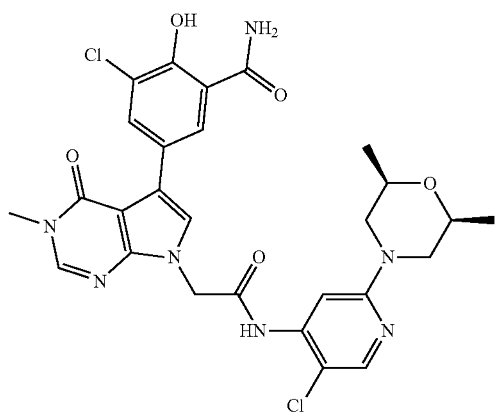 |
| I-14 | 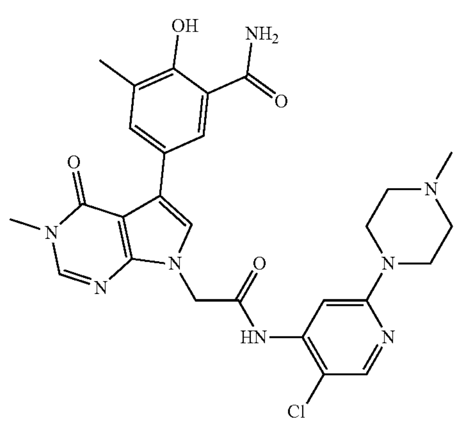 |

-continued
| Compound | Structure |
|---|---|
| I-15 | 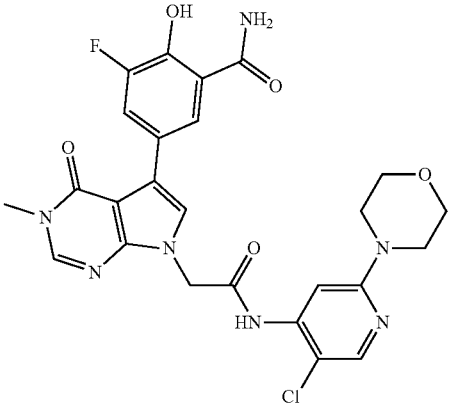 [SMILES: Cn1cnc2c(c(-c3cc(F)c(O)c(C(N)=O)c3)cn2CC(=O)Nc2cc(N3CCOCC3)ncc2Cl)c1=O] |
| I-16 | 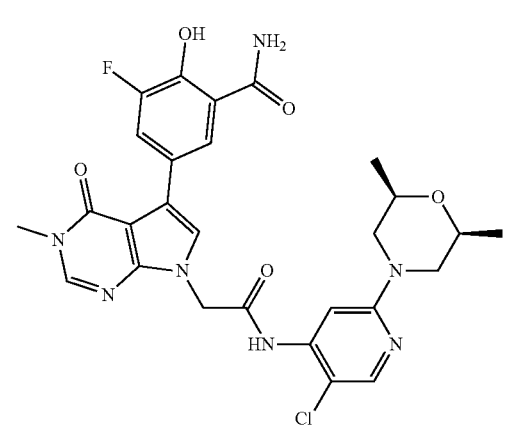 |
| I-17 | 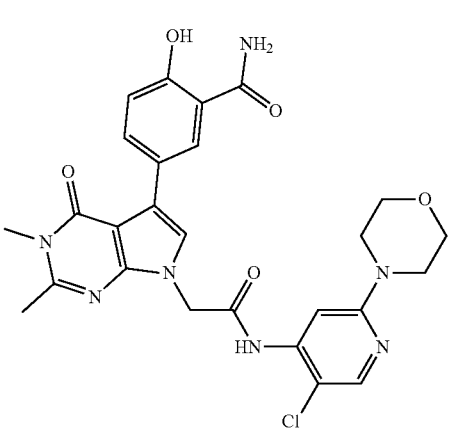 [SMILES: Cc1nc2c(c(-c3ccc(O)c(C(N)=O)c3)cn2CC(=O)Nc2cc(N3CCOCC3)ncc2Cl)c(=O)n1C] |

| Compound | Structure |
|---|---|
| I-18 | 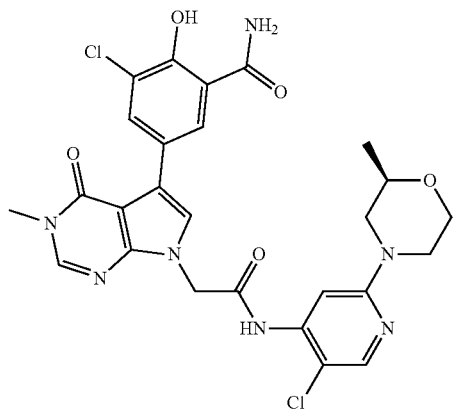 [SMILES: C[C@@H]1CN(c2cc(NC(=O)Cn3cc(-c4cc(Cl)c(O)c(C(N)=O)c4)c4c(=O)n(C)cnc43)c(Cl)cn2)CCO1] |
| I-19 | 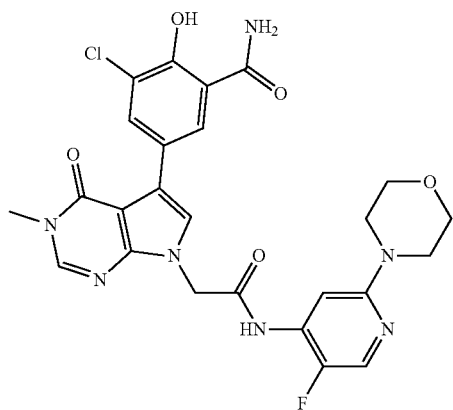 [SMILES: Cn1cnc2c(c(-c3cc(Cl)c(O)c(C(N)=O)c3)cn2CC(=O)Nc2cc(N3CCOCC3)ncc2F)c1=O] |
| I-20 | 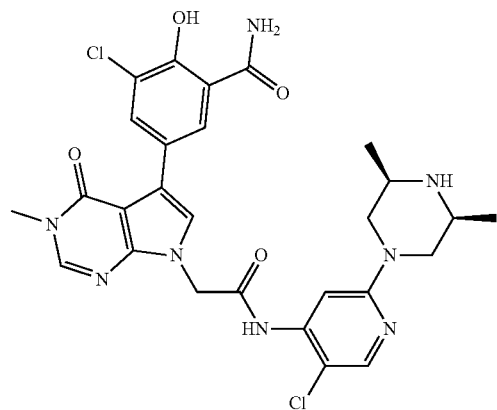 |

| Compound | Structure |
|---|---|
| I-21 | 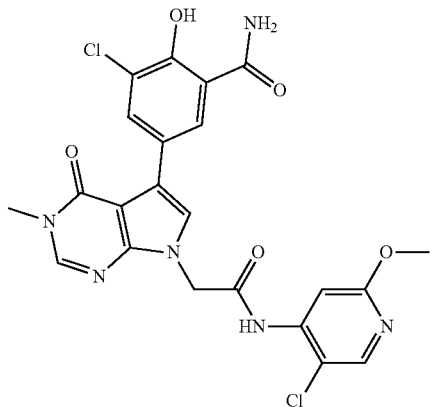 |
| I-22 | 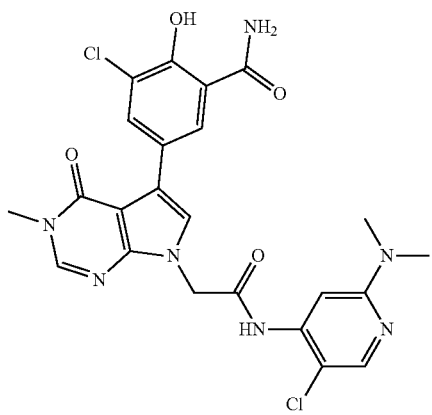 |
| I-23 | 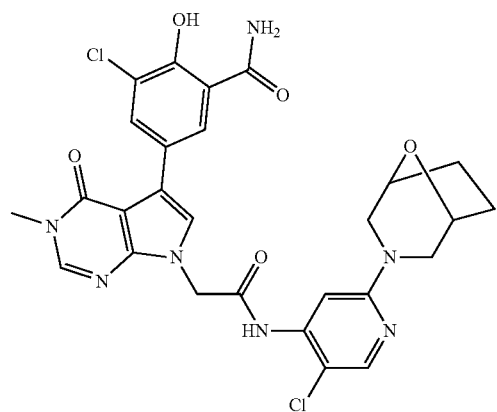 [SMILES: Cn1cnc2c(c(-c3cc(Cl)c(O)c(C(N)=O)c3)cn2CC(=O)Nc2cc(N3CC4CCC(C3)O4)ncc2Cl)c1=O] |

-continued
| Compound | Structure |
|---|---|
| I-24 | 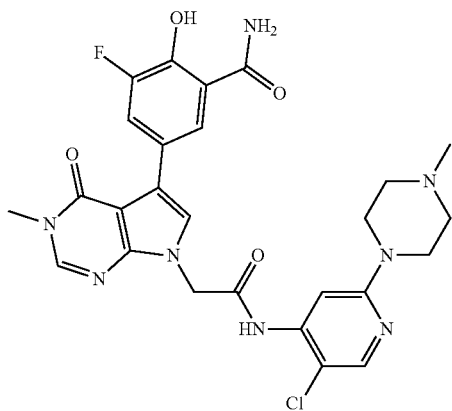 |
| I-25 | 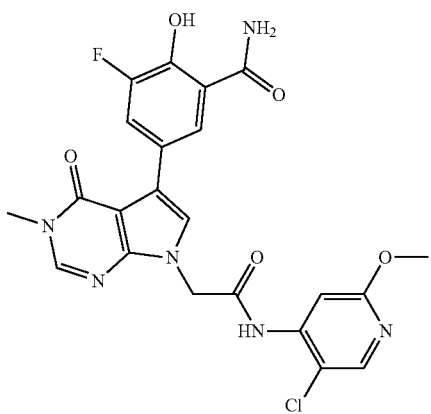 |
| I-26 | 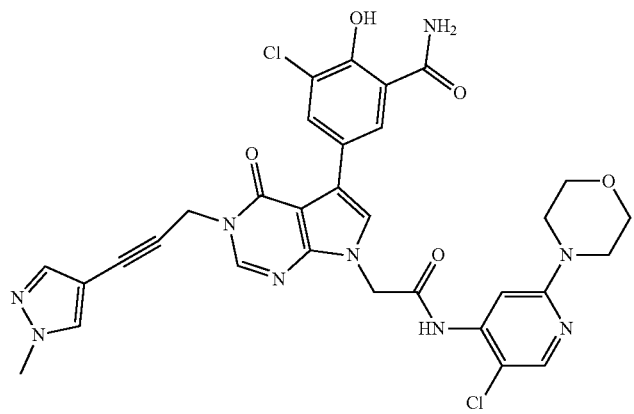 [SMILES: Cn1cc(C#CCn2cnc3c(c(-c4cc(Cl)c(O)c(C(N)=O)c4)cn3CC(=O)Nc3cc(N4CCOCC4)ncc3Cl)c2=O)cn1] |

-continued
| Compound | Structure |
|---|---|
| I-27 | 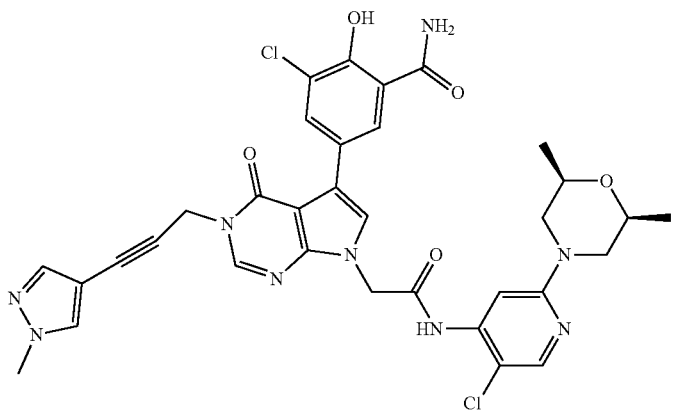 [SMILES: C[C@@H]1CN(c2cc(NC(=O)Cn3cc(-c4cc(Cl)c(O)c(C(N)=O)c4)c4c(=O)n(CC#Cc5cnn(C)c5)cnc43)c(Cl)cn2)C[C@H](C)O1] |
| I-28 | 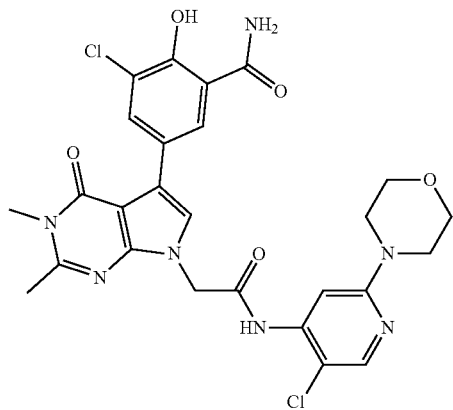 [SMILES: Cc1nc2c(c(-c3cc(Cl)c(O)c(C(N)=O)c3)cn2CC(=O)Nc2cc(N3CCOCC3)ncc2Cl)c(=O)n1C] |
| I-29 | 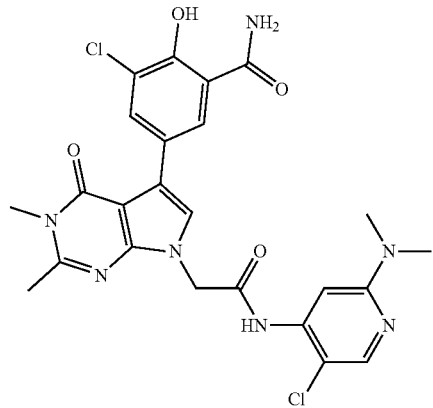 |

-continued
| Compound | Structure |
|---|---|
| I-30 | 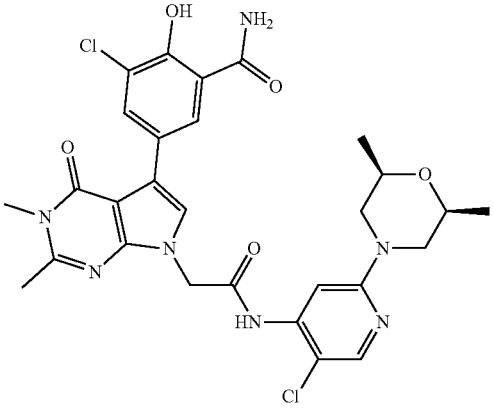 |
| I-31 | 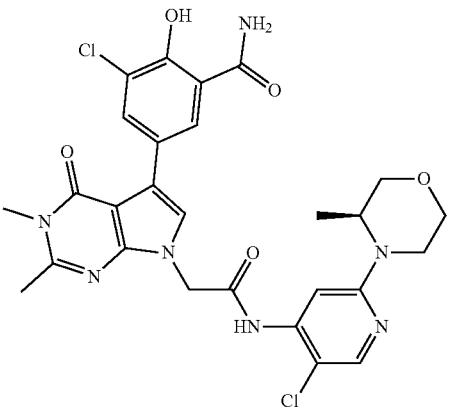 |
| I-32 | 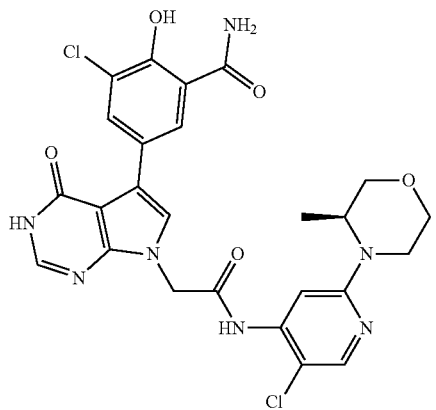 [SMILES: C[C@H]1COCCN1c1cc(NC(=O)Cn2cc(-c3cc(Cl)c(O)c(C(N)=O)c3)c3c(=O)[nH]cnc32)c(Cl)cn1] |

-continued
| Compound | Structure |
|---|---|
| I-33 | 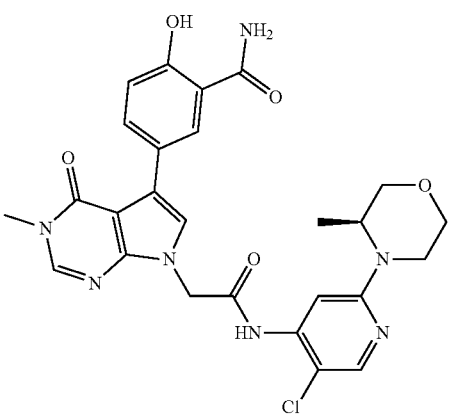 [SMILES: C[C@H]1COCCN1c1cc(NC(=O)Cn2cc(-c3ccc(O)c(C(N)=O)c3)c3c(=O)n(C)cnc32)c(Cl)cn1] |
| I-34 | 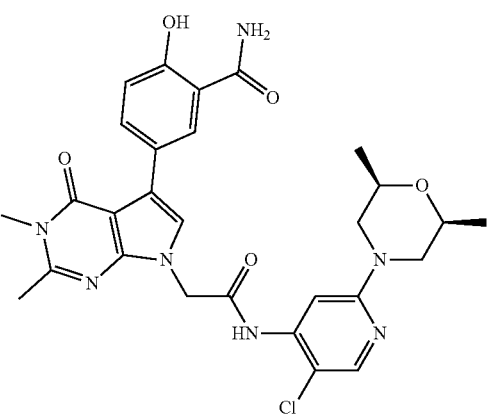 |
| I-35 | 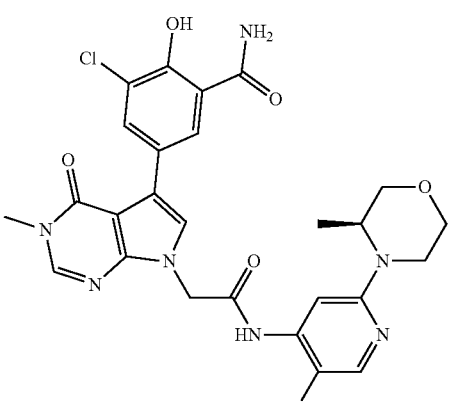 |

-continued
| Compound | Structure |
|---|---|
| I-36 | 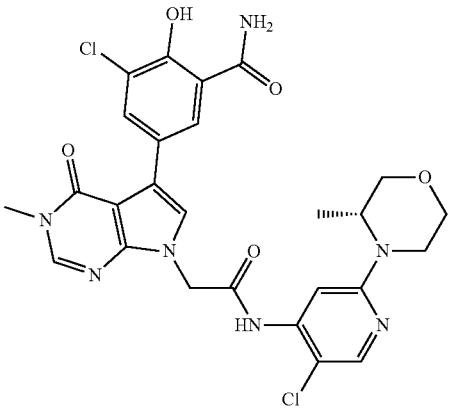 [SMILES: C[C@@H]1COCCN1c1cc(NC(=O)Cn2cc(-c3cc(Cl)c(O)c(C(N)=O)c3)c3c(=O)n(C)cnc32)c(Cl)cn1] |
| I-37 | 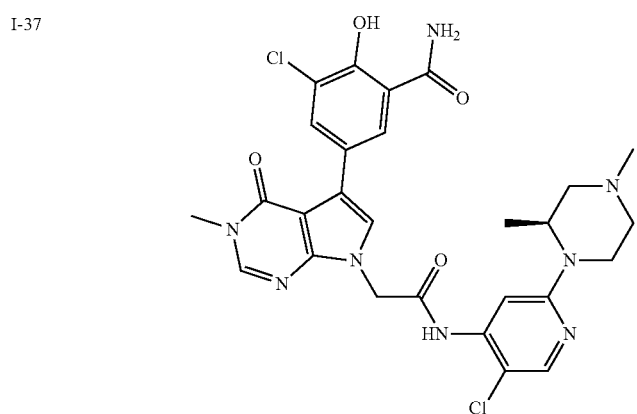 |
| I-38 | 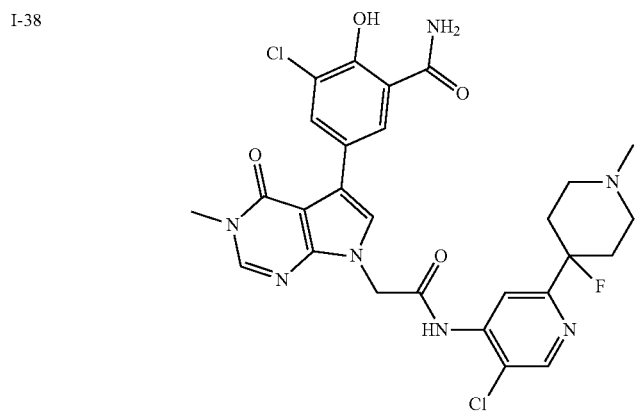 |

| Compound | Structure |
|---|---|
| I-39 | 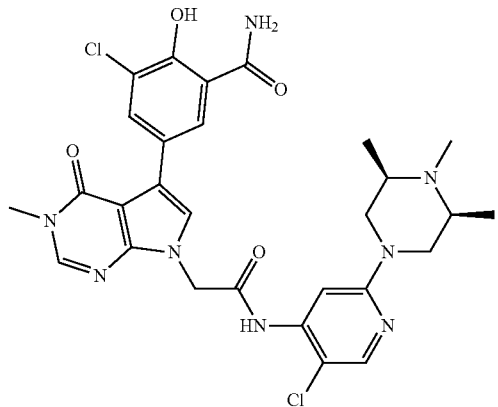 |
| I-40 | 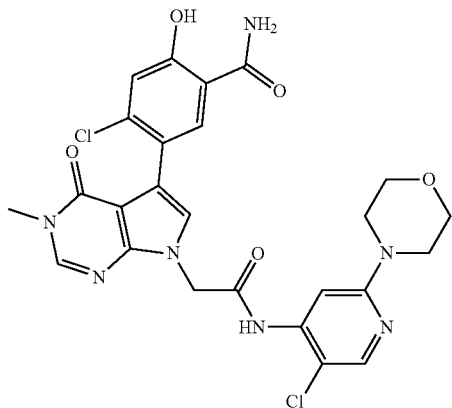 [SMILES: Cn1cnc2c(c(-c3cc(C(N)=O)c(O)cc3Cl)cn2CC(=O)Nc2cc(N3CCOCC3)ncc2Cl)c1=O] |
| I-41 | 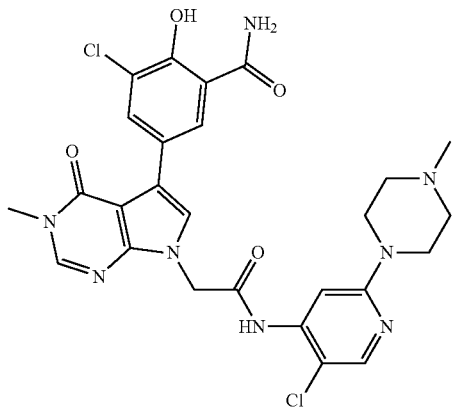 |

-continued
| Compound | Structure |
|---|---|
| I-42 | 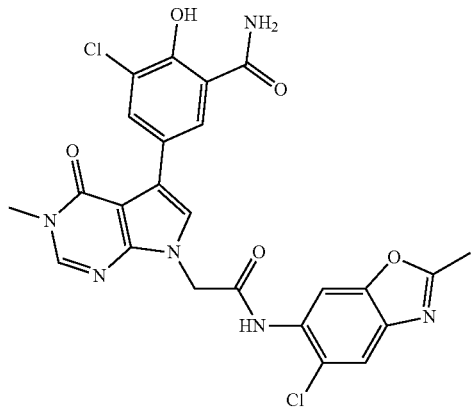 |
| I-43 | 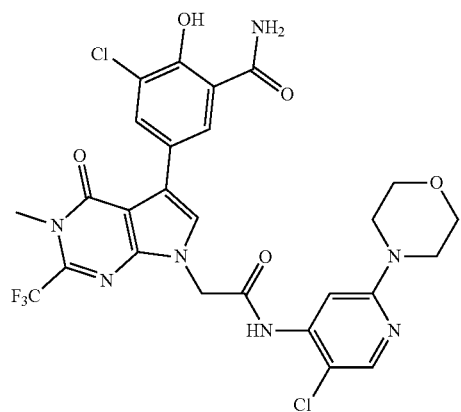 [SMILES: Cn1c(C(F)(F)F)nc2c(c(-c3cc(Cl)c(O)c(C(N)=O)c3)cn2CC(=O)Nc2cc(N3CCOCC3)ncc2Cl)c1=O] |
| I-44 | 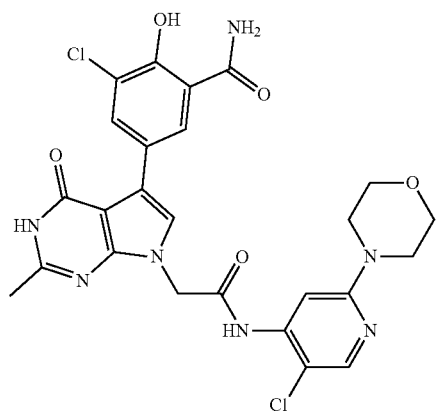 [SMILES: Cc1nc2c(c(-c3cc(Cl)c(O)c(C(N)=O)c3)cn2CC(=O)Nc2cc(N3CCOCC3)ncc2Cl)c(=O)[nH]1] |

-continued

| Compound | Structure |
|---|---|
| I-45 | 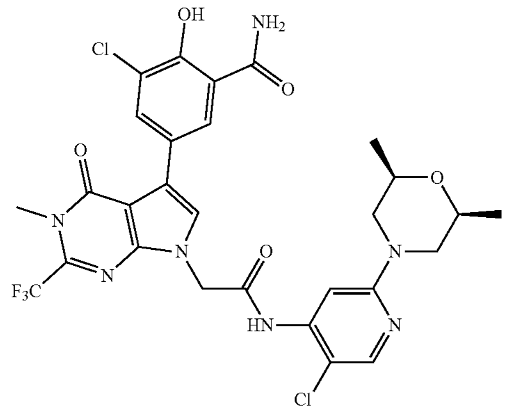 |
| I-46 | 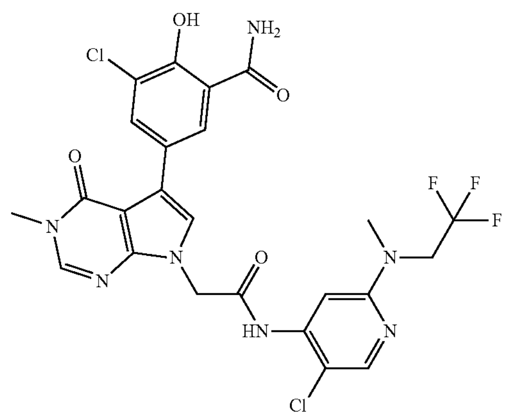 [SMILES: CN(CC(F)(F)F)c1cc(NC(=O)Cn2cc(-c3cc(Cl)c(O)c(C(N)=O)c3)c3c(=O)n(C)cnc32)c(Cl)cn1] |
| I-47 | 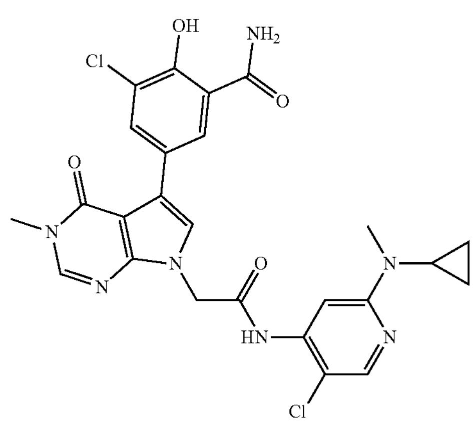 [SMILES: CN(c1cc(NC(=O)Cn2cc(-c3cc(Cl)c(O)c(C(N)=O)c3)c3c(=O)n(C)cnc32)c(Cl)cn1)C1CC1] |

| Compound | Structure |
|---|---|
| I-48 | 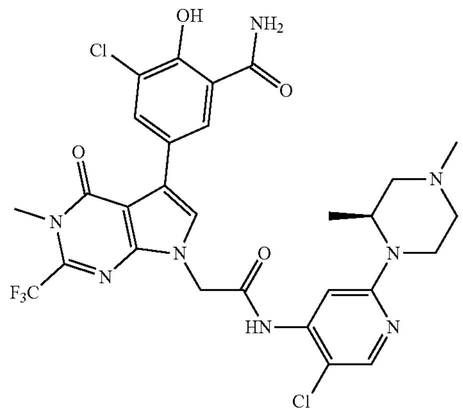 |
| I-49 | 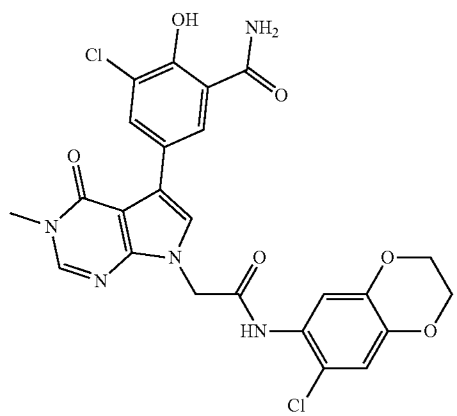 [SMILES: Cn1cnc2c(c(-c3cc(Cl)c(O)c(C(N)=O)c3)cn2CC(=O)Nc2cc3c(cc2Cl)OCCO3)c1=O] |
| I-50 | 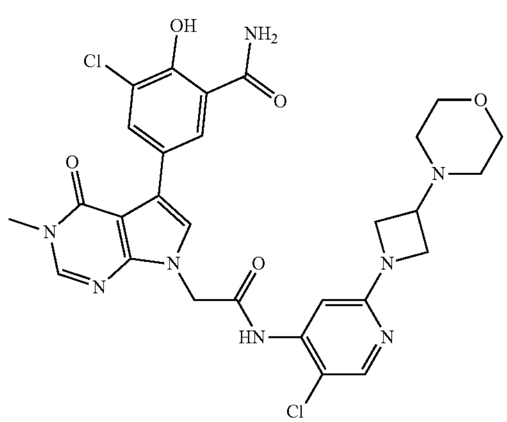 [SMILES: Cn1cnc2c(c(-c3cc(Cl)c(O)c(C(N)=O)c3)cn2CC(=O)Nc2cc(N3CC(N4CCOCC4)C3)ncc2Cl)c1=O] |

-continued
| Compound | Structure |
|---|---|
| I-51 | 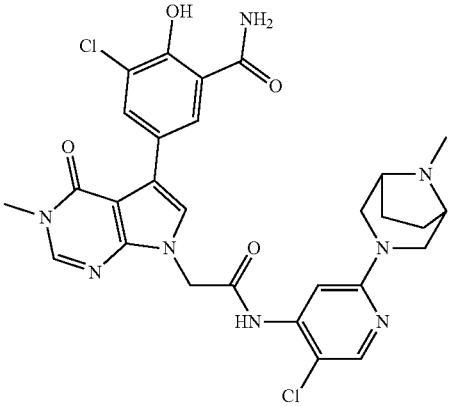 |
| I-52 | 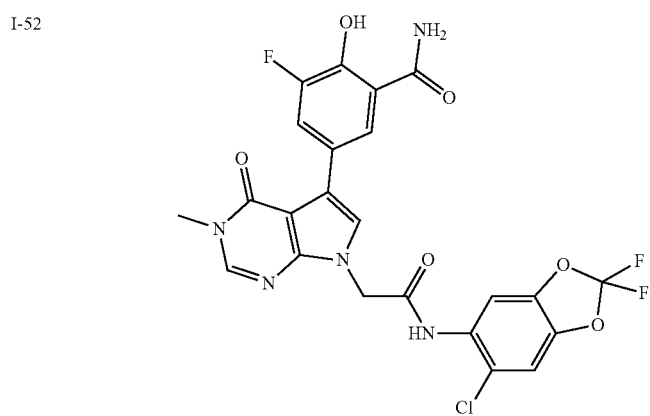 |
| I-53 | 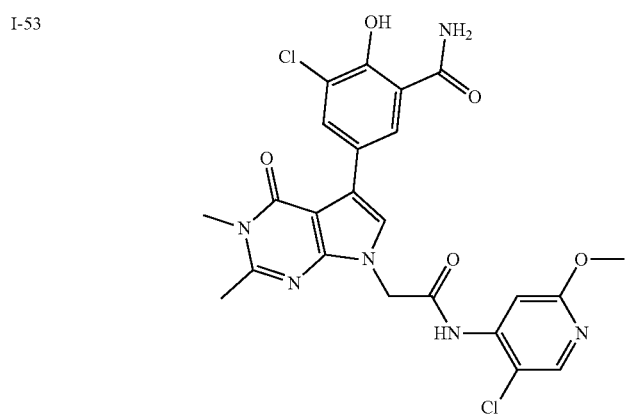 |

-continued
| Compound | Structure |
|---|---|
| I-54 | 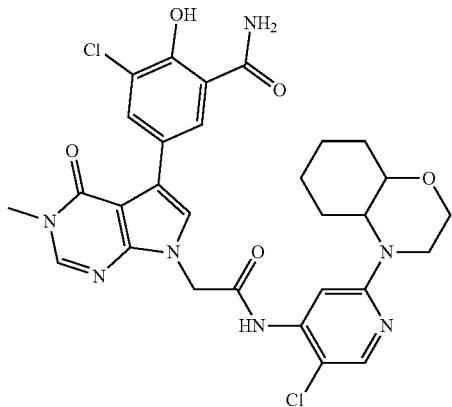 [SMILES: Cn1cnc2c(c(-c3cc(Cl)c(O)c(C(N)=O)c3)cn2CC(=O)Nc2cc(N3CCOC4CCCCC43)ncc2Cl)c1=O] |
| I-55 | 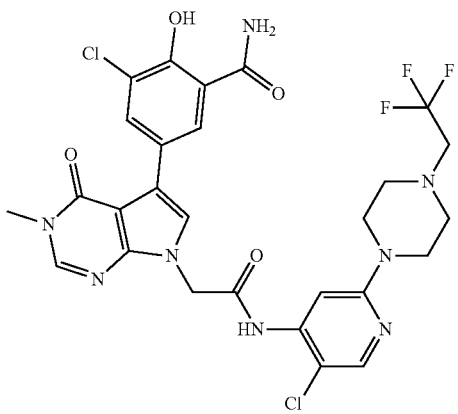 [SMILES: Cn1cnc2c(c(-c3cc(Cl)c(O)c(C(N)=O)c3)cn2CC(=O)Nc2cc(N3CCN(CC(F)(F)F)CC3)ncc2Cl)c1=O] |
| I-56 | 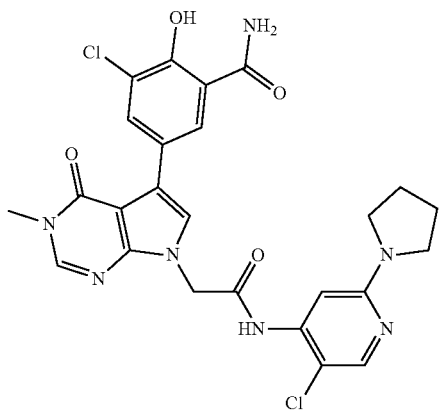 |

| Compound | Structure |
| --- | --- |
| I-57 | 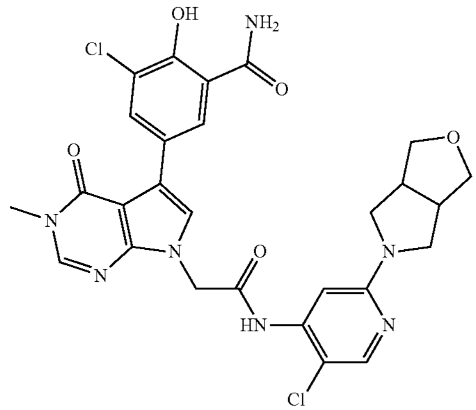 |
| I-58 | 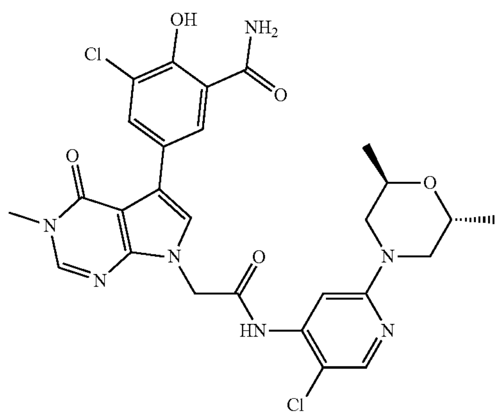 |
| I-59 | 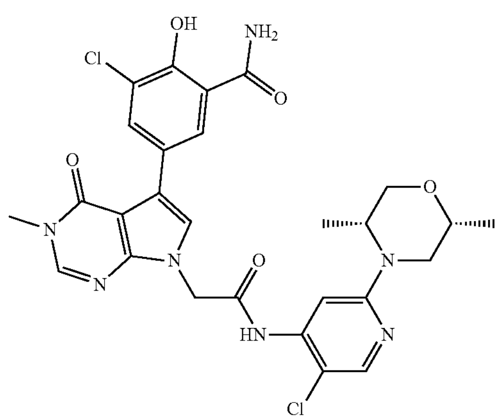 |

| Compound | Structure |
|---|---|
| I-60 | 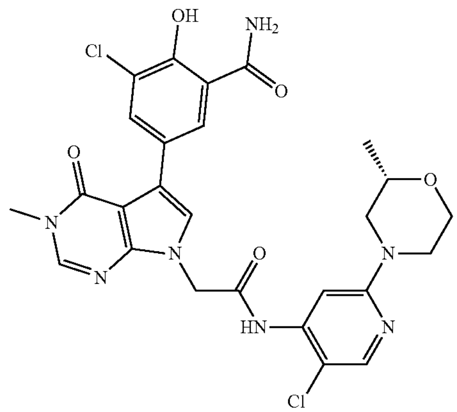 [SMILES: C[C@H]1CN(c2cc(NC(=O)Cn3cc(-c4cc(Cl)c(O)c(C(N)=O)c4)c4c(=O)n(C)cnc43)c(Cl)cn2)CCO1] |
| I-61 | 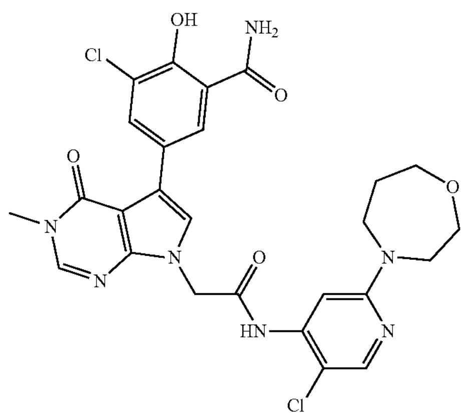 [SMILES: Cn1cnc2c(c(-c3cc(Cl)c(O)c(C(N)=O)c3)cn2CC(=O)Nc2cc(N3CCCOCC3)ncc2Cl)c1=O] |
| I-62 | 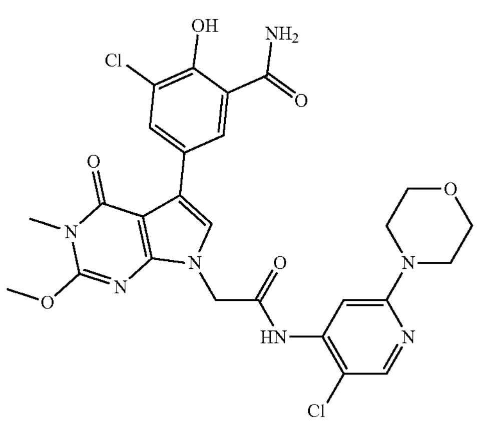 [SMILES: COc1nc2c(c(-c3cc(Cl)c(O)c(C(N)=O)c3)cn2CC(=O)Nc2cc(N3CCOCC3)ncc2Cl)c(=O)n1C] |

-continued
| Compound | Structure |
|---|---|
| I-63 | 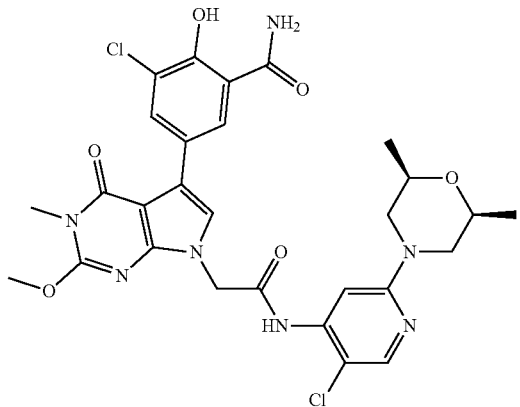 |
| I-64 | 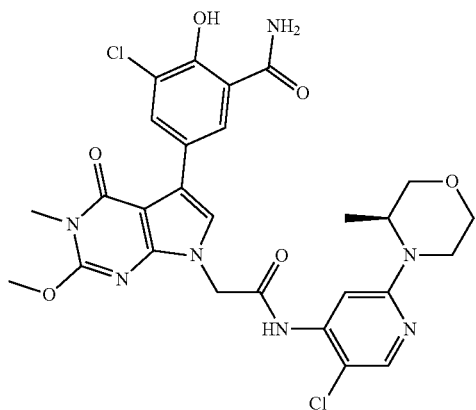 [SMILES: COc1nc2c(c(-c3cc(Cl)c(O)c(C(N)=O)c3)cn2CC(=O)Nc2cc(N3CCOC[C@@H]3C)ncc2Cl)c(=O)n1C] |
| I-65 | 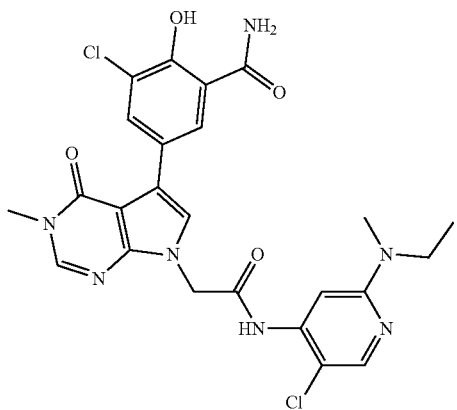 [SMILES: CCN(C)c1cc(NC(=O)Cn2cc(-c3cc(Cl)c(O)c(C(N)=O)c3)c3c(=O)n(C)cnc32)c(Cl)cn1] |

| Compound | Structure |
|---|---|
| I-66 | 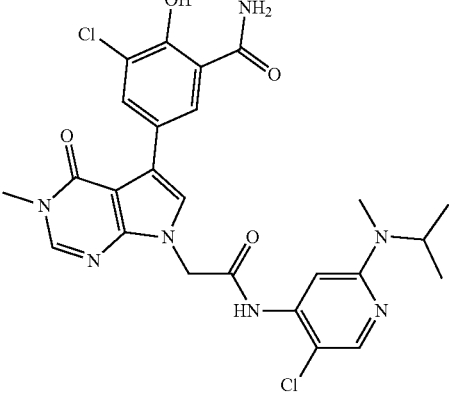 |
| I-67 | 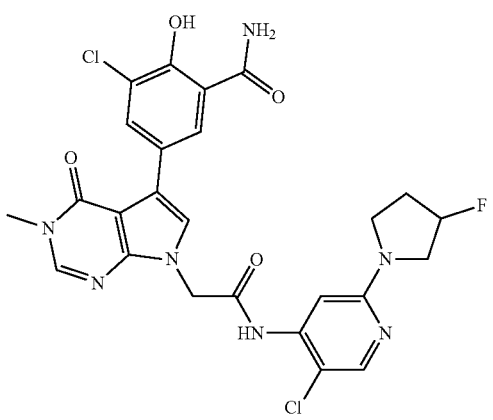 |
| I-68 | 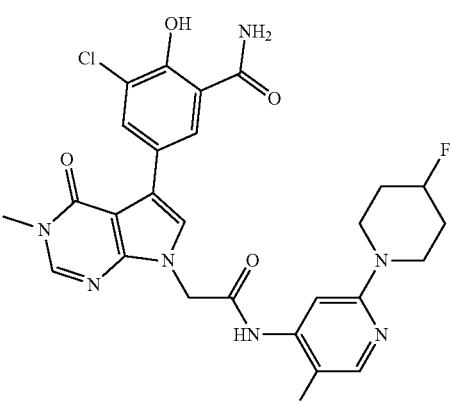 |

-continued
| Compound | Structure |
|---|---|
| I-69 | 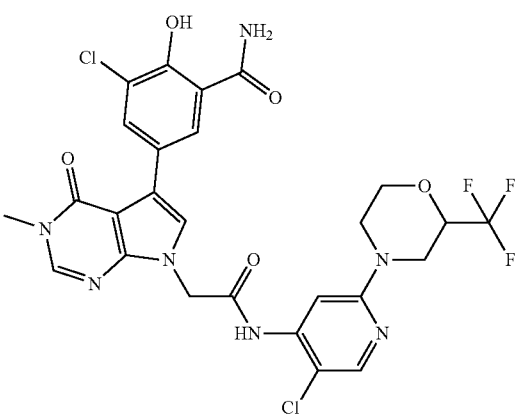 [SMILES: Cn1cnc2c(c(-c3cc(Cl)c(O)c(C(N)=O)c3)cn2CC(=O)Nc2cc(N3CCOC(C(F)(F)F)C3)ncc2Cl)c1=O] |
| I-70 | 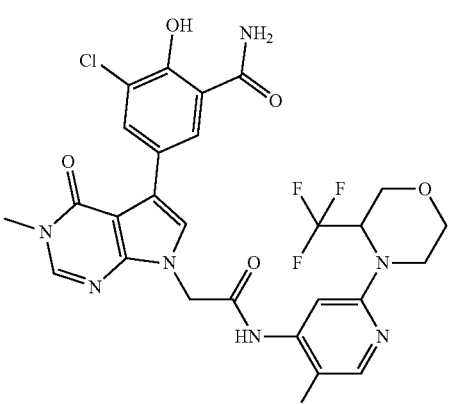 |
| I-71 | 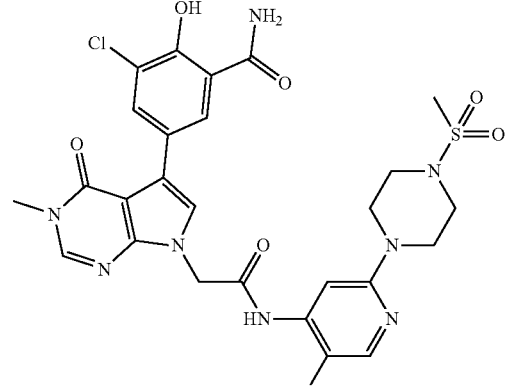 |

-continued
| Compound | Structure |
|----------|-----------|
| I-72 | 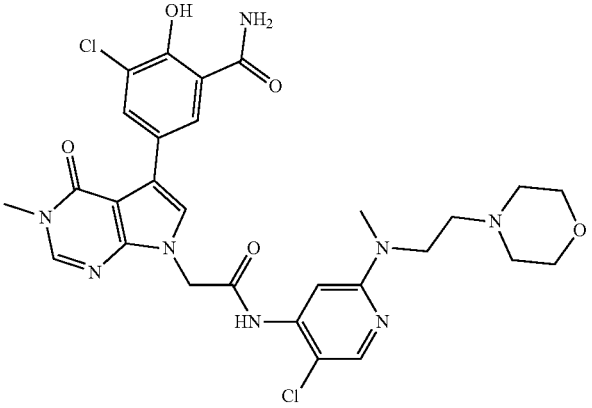 [SMILES: CN(CCN1CCOCC1)c1cc(NC(=O)Cn2cc(-c3cc(Cl)c(O)c(C(N)=O)c3)c3c(=O)n(C)cnc32)c(Cl)cn1] |
| I-73 | 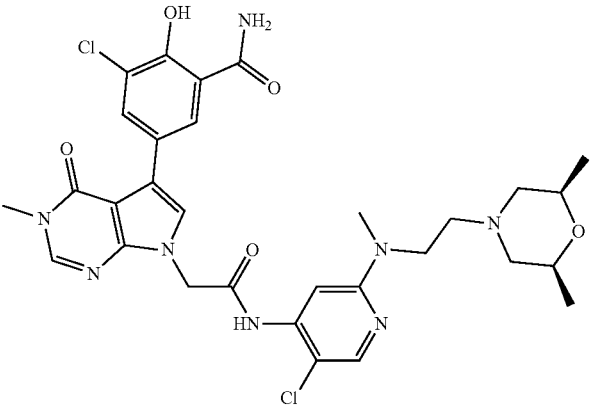 |
| I-74 | 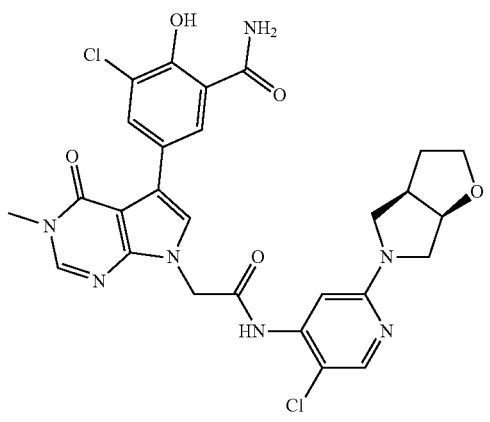 [SMILES: Cn1cnc2c(c(-c3cc(Cl)c(O)c(C(N)=O)c3)cn2CC(=O)Nc2cc(N3C[C@H]4CCO[C@H]4C3)ncc2Cl)c1=O] |

| Compound | Structure |
|---|---|
| I-75 | 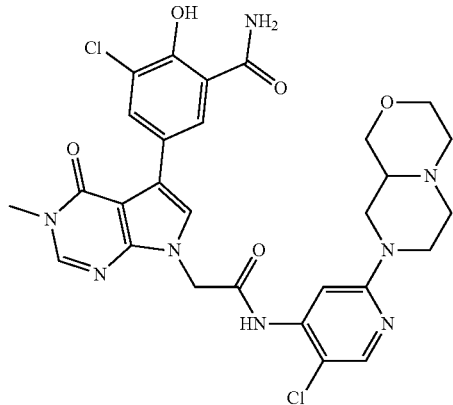 [SMILES: Cn1cnc2c(c(-c3cc(Cl)c(O)c(C(N)=O)c3)cn2CC(=O)Nc2cc(N3CCN4CCOCC4C3)ncc2Cl)c1=O] |
| I-76 | 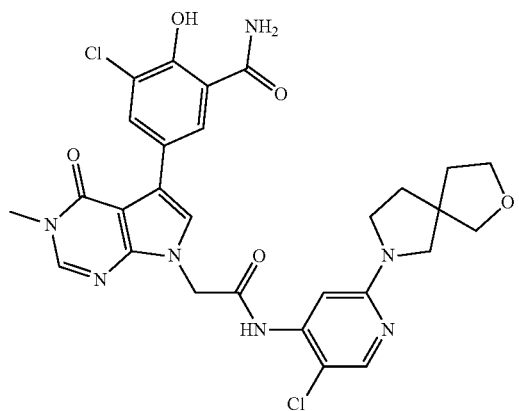 [SMILES: Cn1cnc2c(c(-c3cc(Cl)c(O)c(C(N)=O)c3)cn2CC(=O)Nc2cc(N3CCC4(CCOC4)C3)ncc2Cl)c1=O] |
| I-77 | 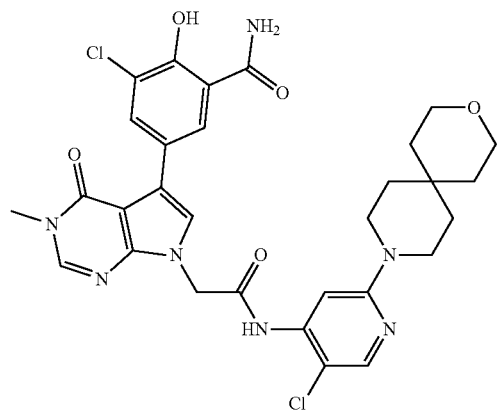 [SMILES: Cn1cnc2c(c(-c3cc(Cl)c(O)c(C(N)=O)c3)cn2CC(=O)Nc2cc(N3CCC4(CCOCC4)CC3)ncc2Cl)c1=O] |

| Compound | Structure |
|---|---|
| I-78 | 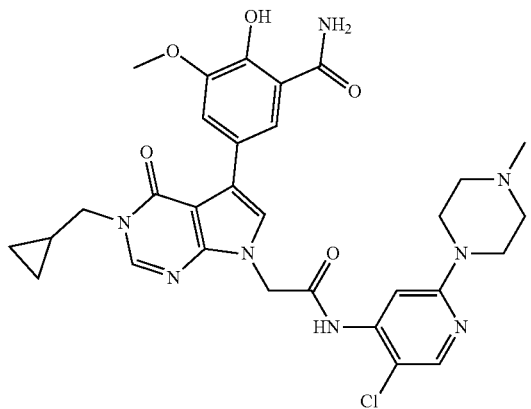 [SMILES: COc1cc(-c2cn(CC(=O)Nc3cc(N4CCN(C)CC4)ncc3Cl)c3ncn(CC4CC4)c(=O)c23)cc(C(N)=O)c1O] |
| I-79 | 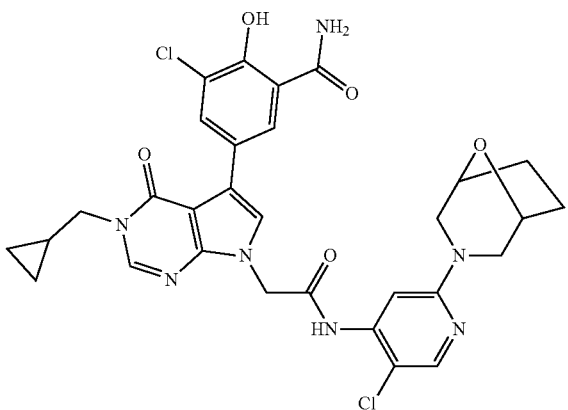 [SMILES: NC(=O)c1cc(-c2cn(CC(=O)Nc3cc(N4CC5CCC(C4)O5)ncc3Cl)c3ncn(CC4CC4)c(=O)c23)cc(Cl)c1O] |
| I-80 | 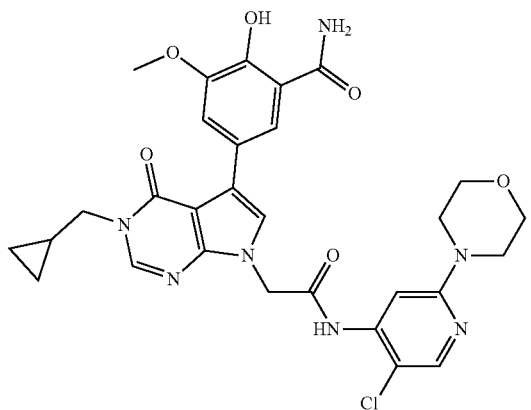 [SMILES: COc1cc(-c2cn(CC(=O)Nc3cc(N4CCOCC4)ncc3Cl)c3ncn(CC4CC4)c(=O)c23)cc(C(N)=O)c1O] |

| Compound | Structure |
|---|---|
| I-81 | 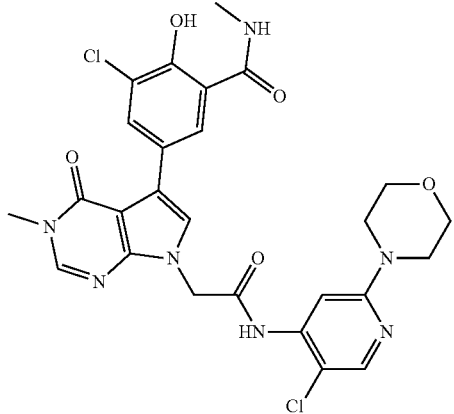 [SMILES: CNC(=O)c1cc(-c2cn(CC(=O)Nc3cc(N4CCOCC4)ncc3Cl)c3ncn(C)c(=O)c23)cc(Cl)c1O] |
| I-82 | 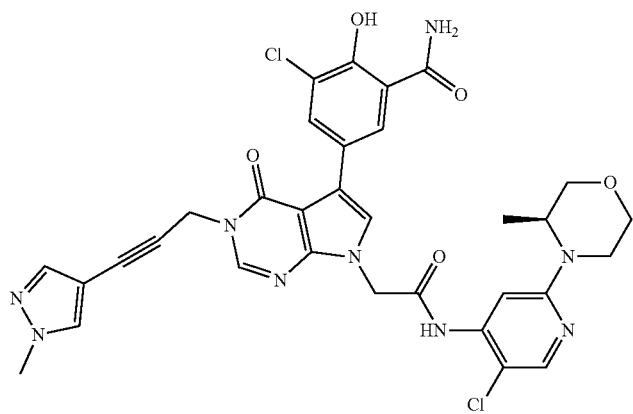 [SMILES: C[C@H]1COCCN1c1cc(NC(=O)Cn2cc(-c3cc(Cl)c(O)c(C(N)=O)c3)c3c(=O)n(CC#Cc4cnn(C)c4)cnc32)c(Cl)cn1] |
| I-83 | 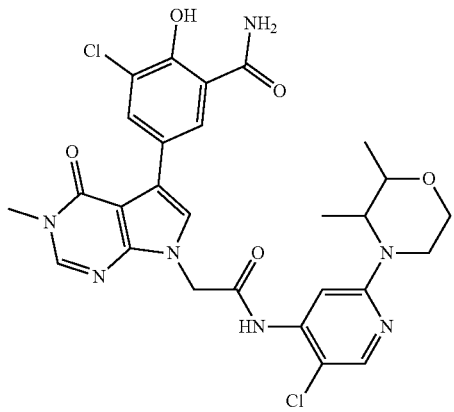 [SMILES: CC1OCCN(c2cc(NC(=O)Cn3cc(-c4cc(Cl)c(O)c(C(N)=O)c4)c4c(=O)n(C)cnc43)c(Cl)cn2)C1C] |

| Compound | Structure |
|---|---|
| I-84 | 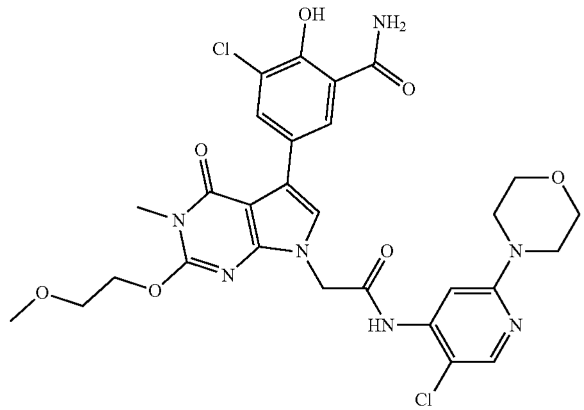 [SMILES: COCCOc1nc2c(c(-c3cc(Cl)c(O)c(C(N)=O)c3)cn2CC(=O)Nc2cc(N3CCOCC3)ncc2Cl)c(=O)n1C] |
| I-85 | 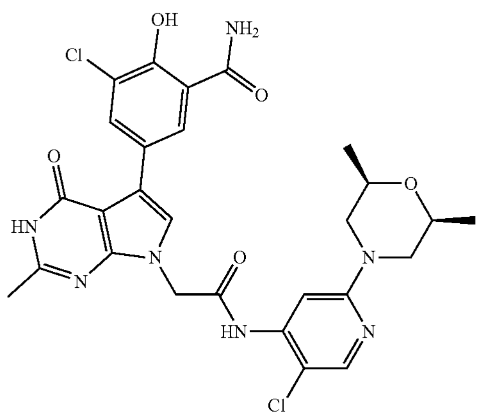 |
| I-86 | 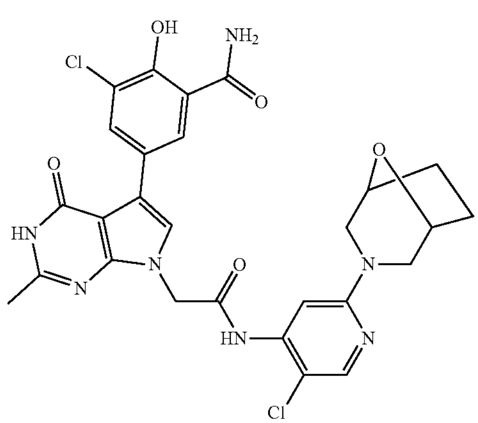 [SMILES: Cc1nc2c(c(-c3cc(Cl)c(O)c(C(N)=O)c3)cn2CC(=O)Nc2cc(N3CC4CCC(C3)O4)ncc2Cl)c(=O)[nH]1] |

| Compound | Structure |
|---|---|
| I-87 | 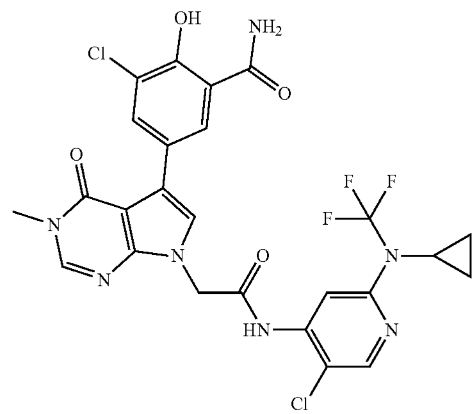 [SMILES: Cn1cnc2c(c(-c3cc(Cl)c(O)c(C(N)=O)c3)cn2CC(=O)Nc2cc(N(C3CC3)C(F)(F)F)ncc2Cl)c1=O] |
| I-88 | 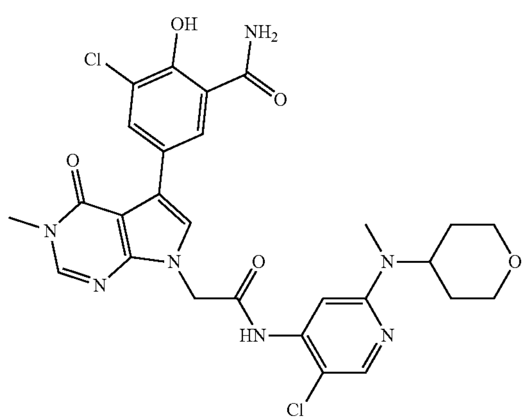 [SMILES: CN(c1cc(NC(=O)Cn2cc(-c3cc(Cl)c(O)c(C(N)=O)c3)c3c(=O)n(C)cnc32)c(Cl)cn1)C1CCOCC1] |
| I-89 | 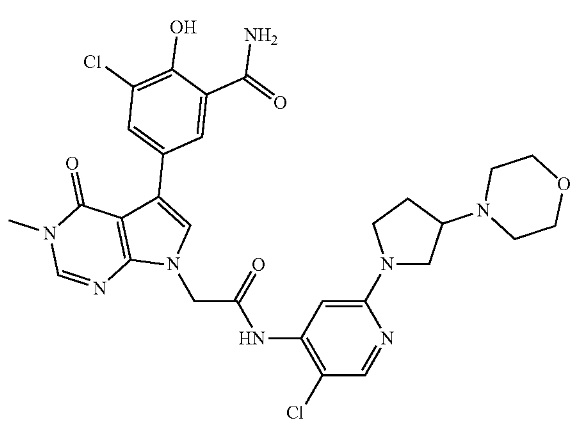 [SMILES: Cn1cnc2c(c(-c3cc(Cl)c(O)c(C(N)=O)c3)cn2CC(=O)Nc2cc(N3CCC(N4CCOCC4)C3)ncc2Cl)c1=O] |

-continued
| Compound | Structure |
|---|---|
| I-90 | 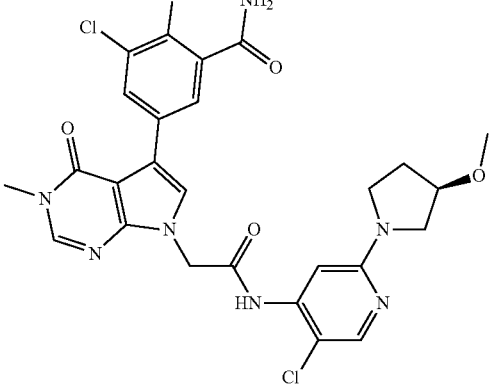 |
| I-91 | 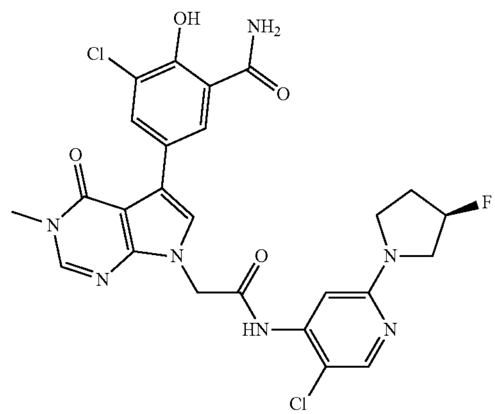 [SMILES: Cn1cnc2c(c(-c3cc(Cl)c(O)c(C(N)=O)c3)cn2CC(=O)Nc2cc(N3CC[C@@H](F)C3)ncc2Cl)c1=O] |
| I-92 | 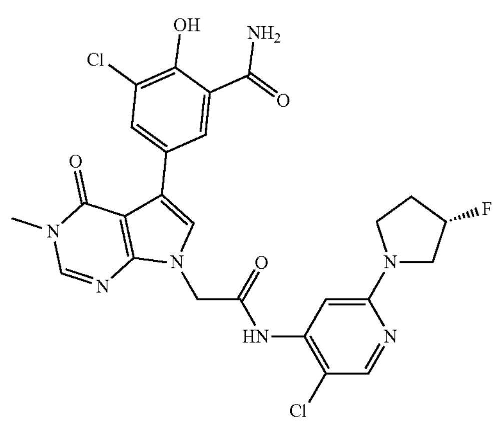 [SMILES: Cn1cnc2c(c(-c3cc(Cl)c(O)c(C(N)=O)c3)cn2CC(=O)Nc2cc(N3CC[C@H](F)C3)ncc2Cl)c1=O] |

-continued
| Compound | Structure |
|---|---|
| I-93 | 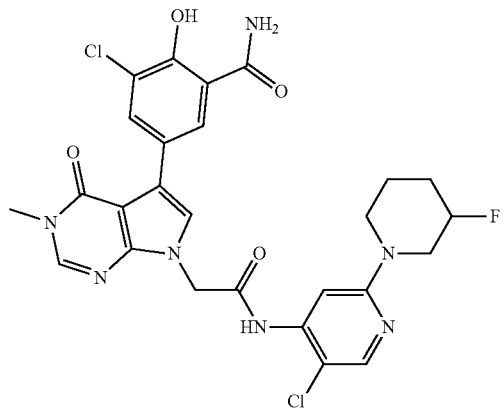 [SMILES: Cn1cnc2c(c(-c3cc(Cl)c(O)c(C(N)=O)c3)cn2CC(=O)Nc2cc(N3CCCC(F)C3)ncc2Cl)c1=O] |
| I-94 | 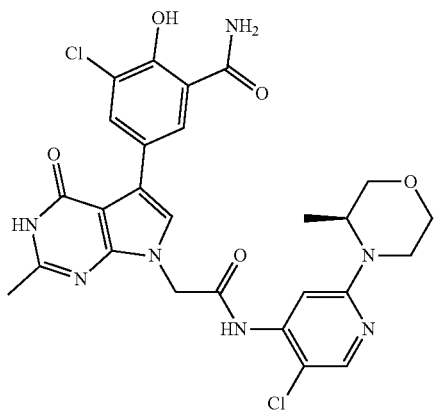 [SMILES: Cc1nc2c(c(-c3cc(Cl)c(O)c(C(N)=O)c3)cn2CC(=O)Nc2cc(N3CCOC[C@@H]3C)ncc2Cl)c(=O)[nH]1] |
| I-95 | 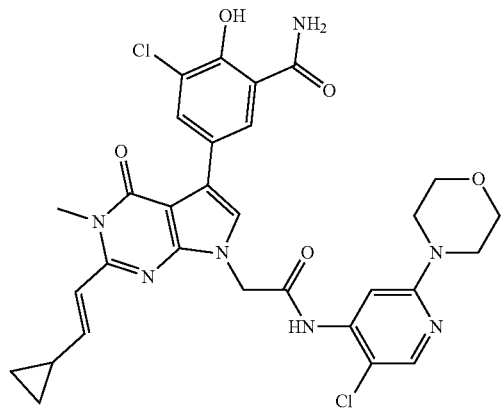 [SMILES: Cn1c(/C=C/C2CC2)nc2c(c(-c3cc(Cl)c(O)c(C(N)=O)c3)cn2CC(=O)Nc2cc(N3CCOCC3)ncc2Cl)c1=O] |

| Compound | Structure |
|---|---|
| I-96 | 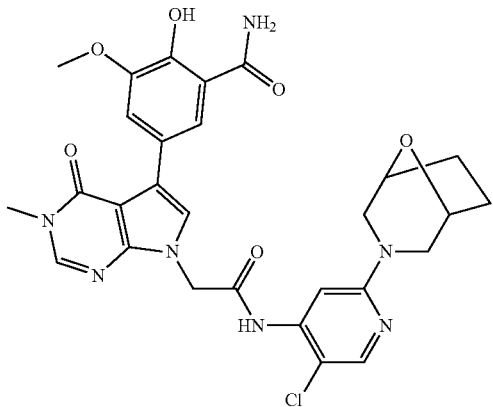 [SMILES: COc1cc(-c2cn(CC(=O)Nc3cc(N4CC5CCC(C4)O5)ncc3Cl)c3ncn(C)c(=O)c23)cc(C(N)=O)c1O] |
| I-97 | 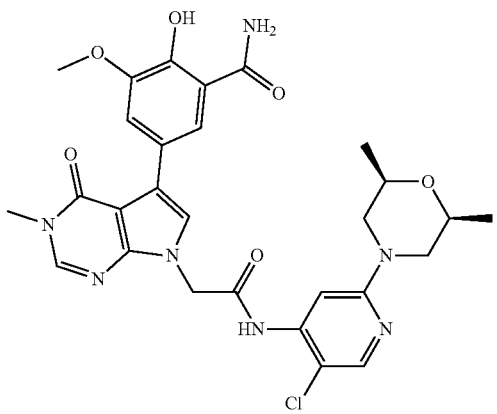 |
| I-98 | 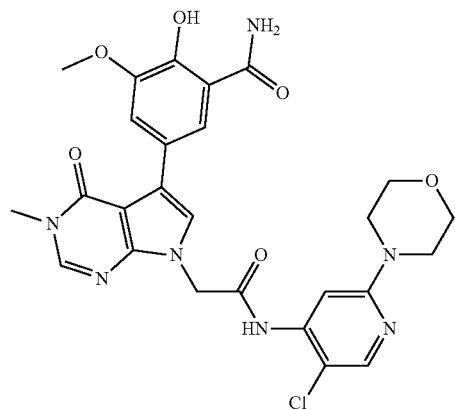 |

-continued
| Compound | Structure |
|---|---|
| I-99 | 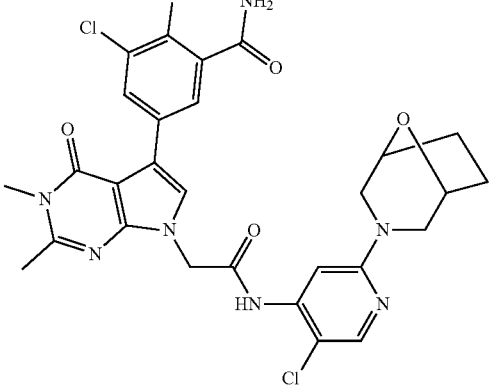 |
| I-100 | 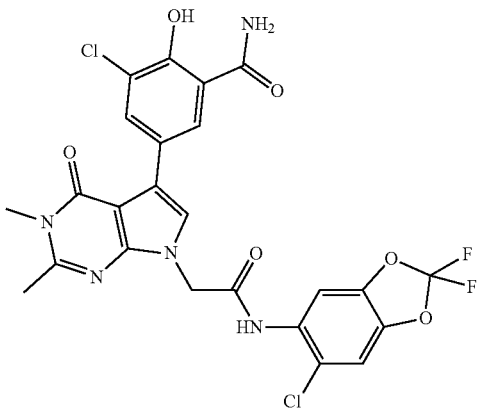 [SMILES: Cc1nc2c(c(-c3cc(Cl)c(O)c(C(N)=O)c3)cn2CC(=O)Nc2cc3c(cc2Cl)OC(F)(F)O3)c(=O)n1C] |
| I-101 | 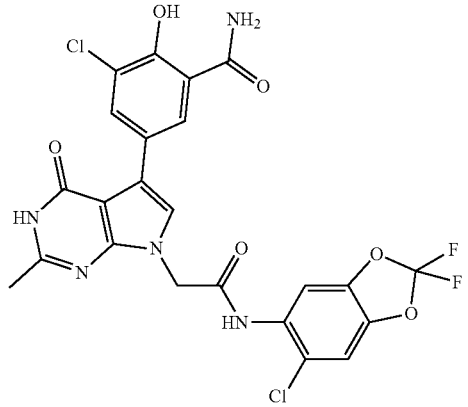 [SMILES: Cc1nc2c(c(-c3cc(Cl)c(O)c(C(N)=O)c3)cn2CC(=O)Nc2cc3c(cc2Cl)OC(F)(F)O3)c(=O)[nH]1] |

| Compound | Structure |
|---|---|
| I-102 | 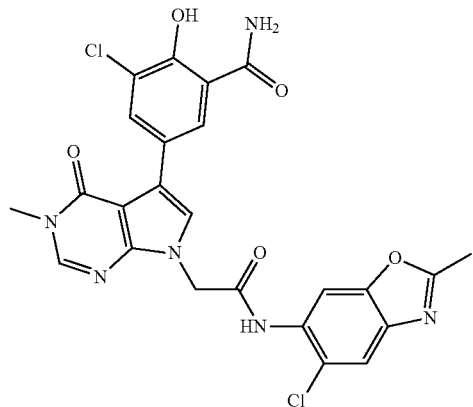 |
| I-103 | 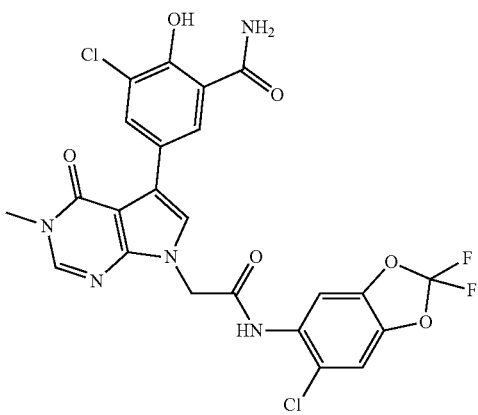 [SMILES: Cn1cnc2c(c(-c3cc(Cl)c(O)c(C(N)=O)c3)cn2CC(=O)Nc2cc3c(cc2Cl)OC(F)(F)O3)c1=O] |
| I-104 | 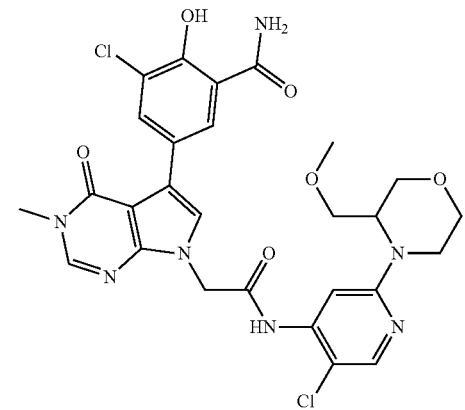 |

-continued
| Compound | Structure |
|---|---|
| I-105 | 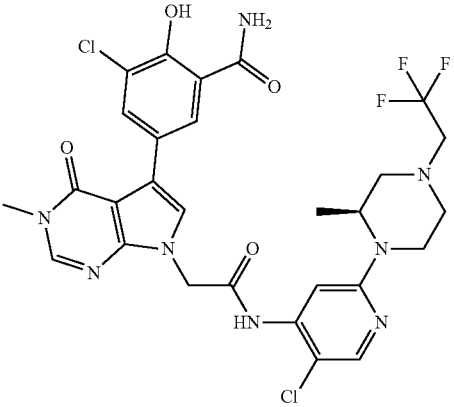 [SMILES: C[C@H]1CN(CC(F)(F)F)CCN1c1cc(NC(=O)Cn2cc(-c3cc(Cl)c(O)c(C(N)=O)c3)c3c(=O)n(C)cnc32)c(Cl)cn1] |
| I-106 | 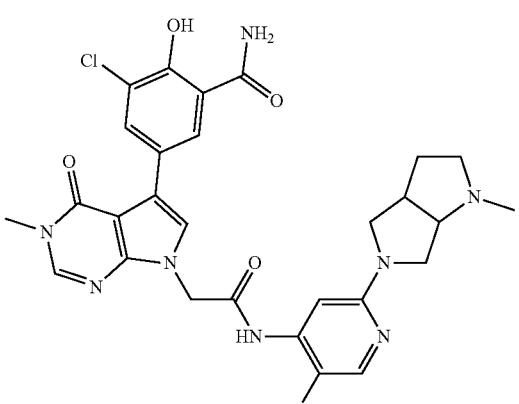 |
| I-107 | 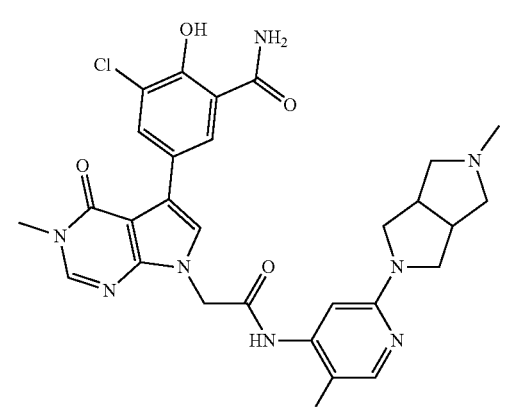 |

-continued
| Compound | Structure |
|---|---|
| I-108 | 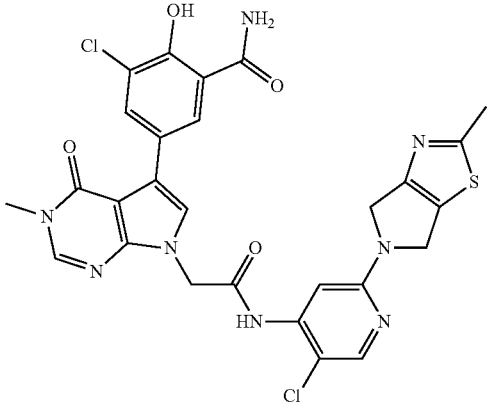 |
| I-109 | 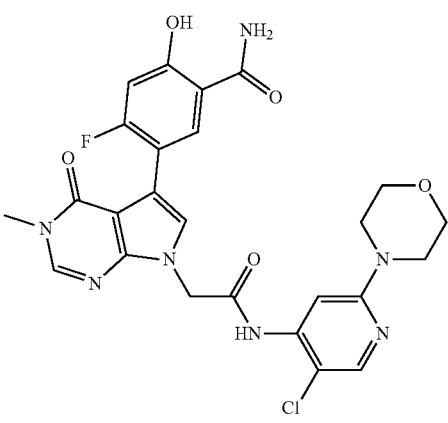 [SMILES: Cn1cnc2c(c(-c3cc(C(N)=O)c(O)cc3F)cn2CC(=O)Nc2cc(N3CCOCC3)ncc2Cl)c1=O] |
| I-110 | 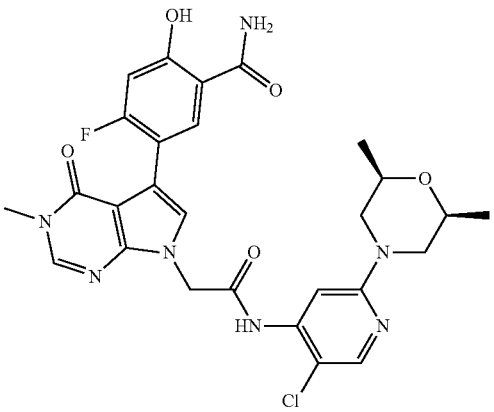 |

-continued
| Compound | Structure |
|---|---|
| I-111 | 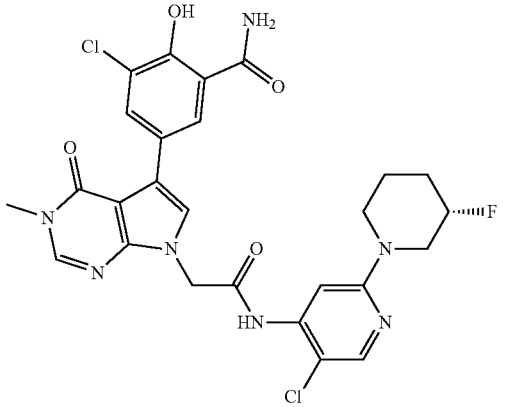 [SMILES: Cn1cnc2c(c(-c3cc(Cl)c(O)c(C(N)=O)c3)cn2CC(=O)Nc2cc(N3CCC[C@H](F)C3)ncc2Cl)c1=O] |
| I-112 | 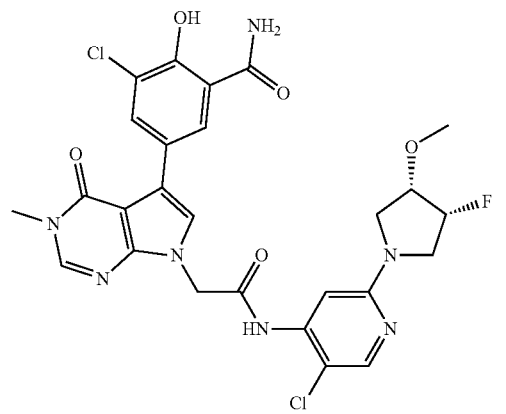 [SMILES: CO[C@H]1CN(c2cc(NC(=O)Cn3cc(-c4cc(Cl)c(O)c(C(N)=O)c4)c4c(=O)n(C)cnc43)c(Cl)cn2)C[C@H]1F] |
| I-113 | 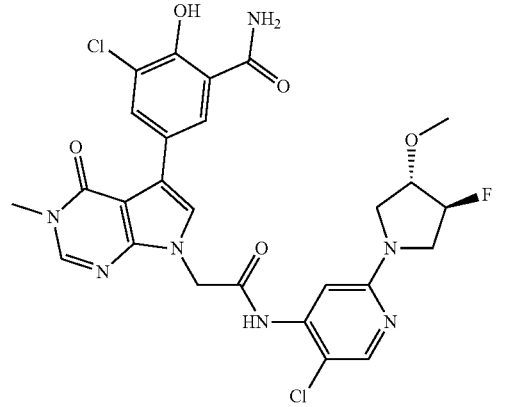 [SMILES: CO[C@H]1CN(c2cc(NC(=O)Cn3cc(-c4cc(Cl)c(O)c(C(N)=O)c4)c4c(=O)n(C)cnc43)c(Cl)cn2)C[C@@H]1F] |

-continued
| Compound | Structure |
|---|---|
| I-114 | 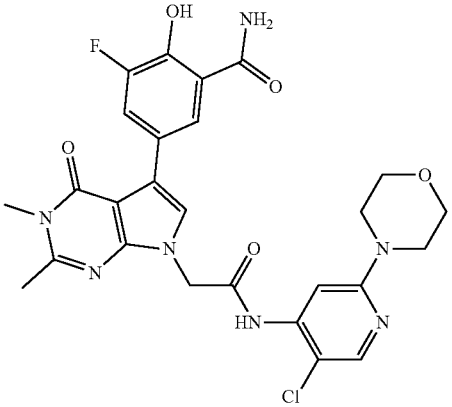 [SMILES: Cc1nc2c(c(-c3cc(F)c(O)c(C(N)=O)c3)cn2CC(=O)Nc2cc(N3CCOCC3)ncc2Cl)c(=O)n1C] |
| I-115 | 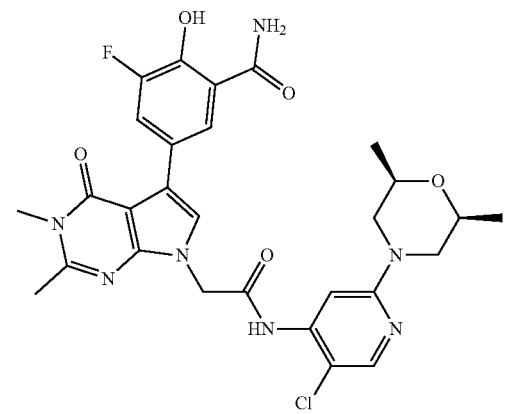 |
| I-116 | 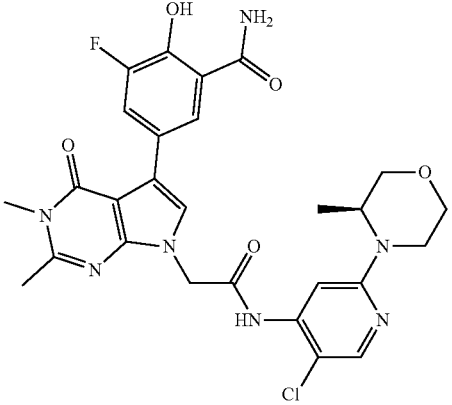 [SMILES: Cc1nc2c(c(-c3cc(F)c(O)c(C(N)=O)c3)cn2CC(=O)Nc2cc(N3CCOC[C@@H]3C)ncc2Cl)c(=O)n1C] |

| Compound | Structure |
|---|---|
| I-117 | 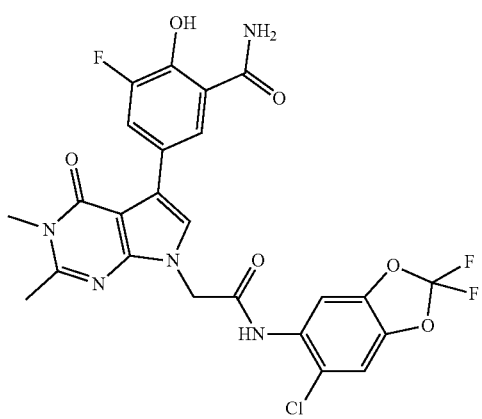 |
| I-118 | 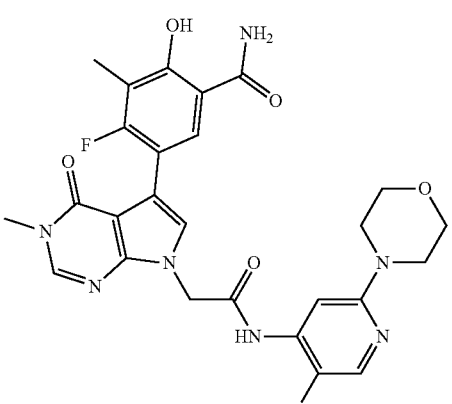 |
| I-119 | 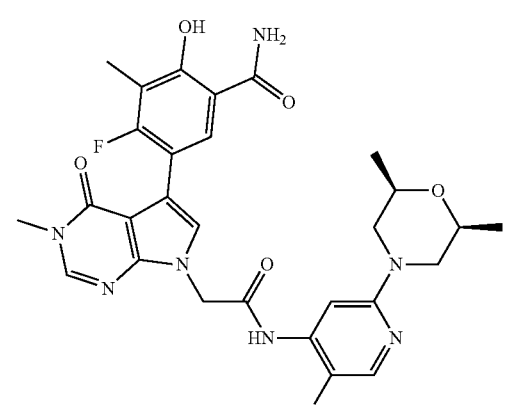 |

-continued
| Compound | Structure |
|---|---|
| I-120 | 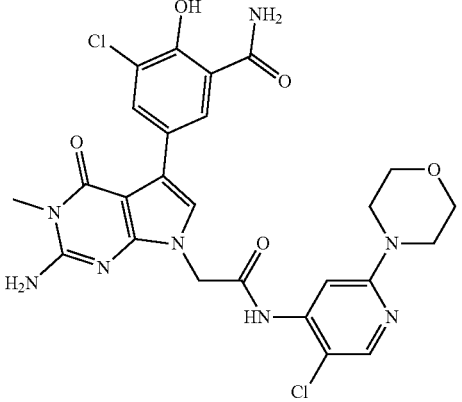 [SMILES: Cn1c(N)nc2c(c(-c3cc(Cl)c(O)c(C(N)=O)c3)cn2CC(=O)Nc2cc(N3CCOCC3)ncc2Cl)c1=O] |
| I-121 | 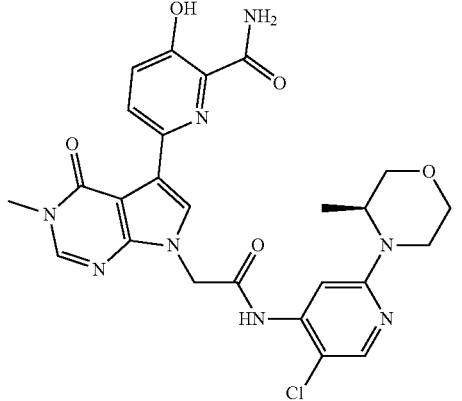 |
| I-122 | 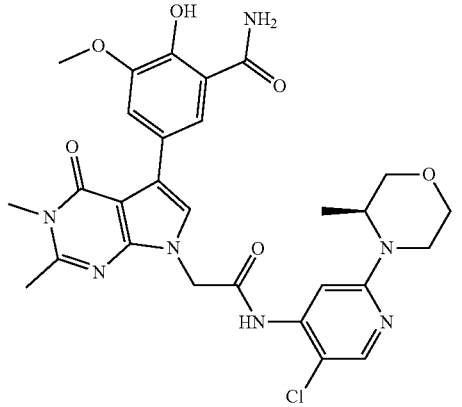 [SMILES: COc1cc(-c2cn(CC(=O)Nc3cc(N4CCOC[C@@H]4C)ncc3Cl)c3nc(C)n(C)c(=O)c23)cc(C(N)=O)c1O] |

| Compound | Structure |
|---|---|
| I-123 | 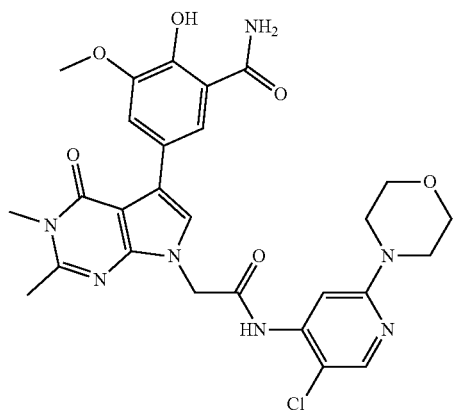 [SMILES: COc1cc(-c2cn(CC(=O)Nc3cc(N4CCOCC4)ncc3Cl)c3nc(C)n(C)c(=O)c23)cc(C(N)=O)c1O] |
| I-124 | 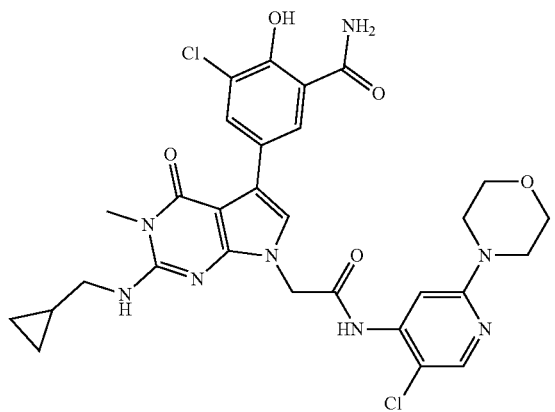 [SMILES: Cn1c(NCC2CC2)nc2c(c(-c3cc(Cl)c(O)c(C(N)=O)c3)cn2CC(=O)Nc2cc(N3CCOCC3)ncc2Cl)c1=O] |
| I-125 | 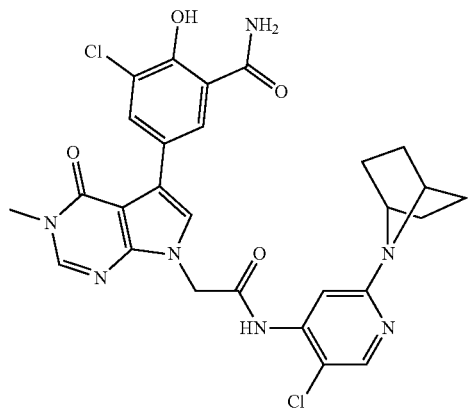 [SMILES: Cn1cnc2c(c(-c3cc(Cl)c(O)c(C(N)=O)c3)cn2CC(=O)Nc2cc(N3C4CCC3CC4)ncc2Cl)c1=O] |

-continued
| Compound | Structure |
|---|---|
| I-126 | 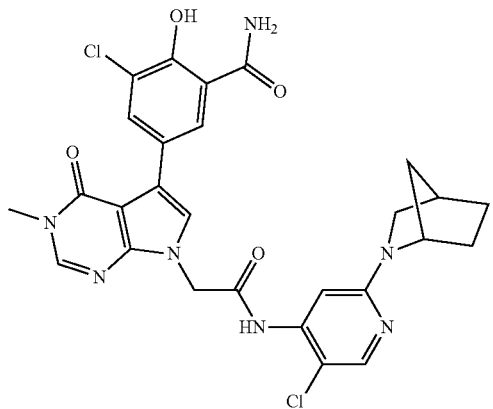 [SMILES: Cn1cnc2c(c(-c3cc(Cl)c(O)c(C(N)=O)c3)cn2CC(=O)Nc2cc(N3CC4CCC3C4)ncc2Cl)c1=O] |
| I-127 | 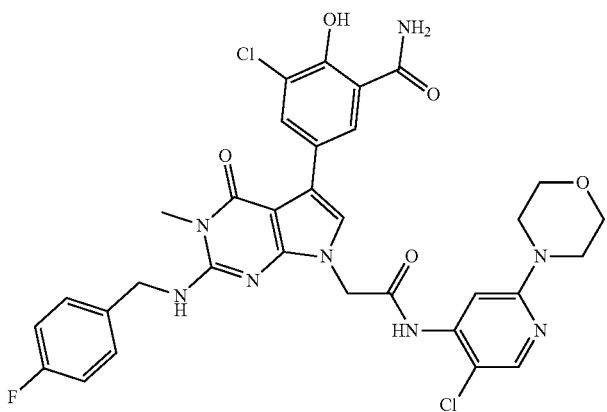 [SMILES: Cn1c(NCc2ccc(F)cc2)nc2c(c(-c3cc(Cl)c(O)c(C(N)=O)c3)cn2CC(=O)Nc2cc(N3CCOCC3)ncc2Cl)c1=O] |
| I-128 | 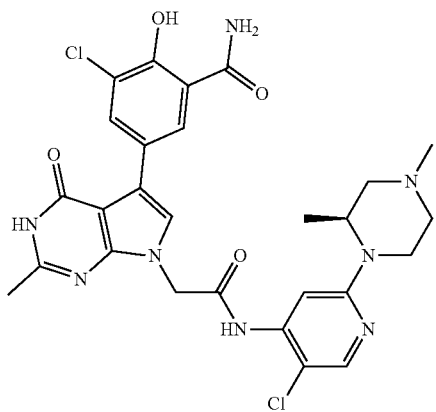 |

-continued
| Compound | Structure |
|---|---|
| I-129 | 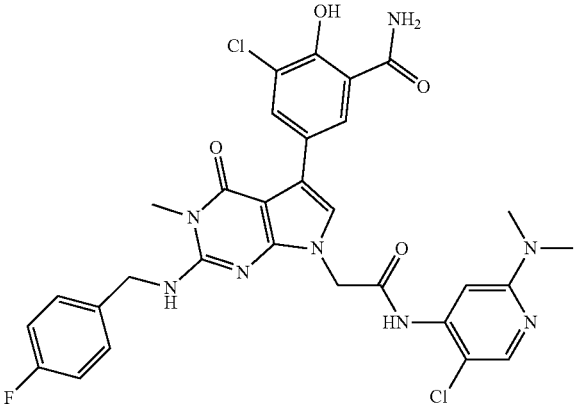 [SMILES: CN(C)c1cc(NC(=O)Cn2cc(-c3cc(Cl)c(O)c(C(N)=O)c3)c3c(=O)n(C)c(NCc4ccc(F)cc4)nc32)c(Cl)cn1] |
| I-130 | 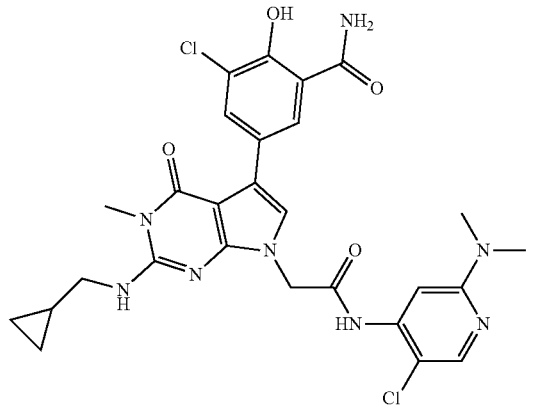 [SMILES: CN(C)c1cc(NC(=O)Cn2cc(-c3cc(Cl)c(O)c(C(N)=O)c3)c3c(=O)n(C)c(NCC4CC4)nc32)c(Cl)cn1] |
| I-131 | 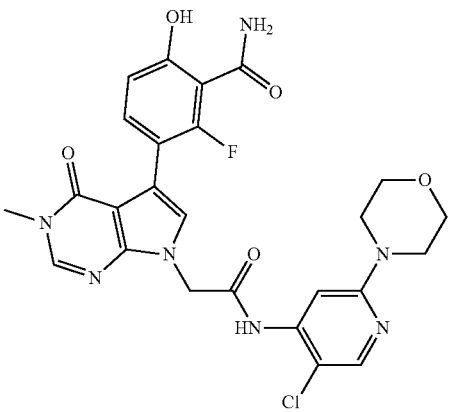 [SMILES: Cn1cnc2c(c(-c3ccc(O)c(C(N)=O)c3F)cn2CC(=O)Nc2cc(N3CCOCC3)ncc2Cl)c1=O] |

-continued

| Compound | Structure |
|---|---|
| I-132 | 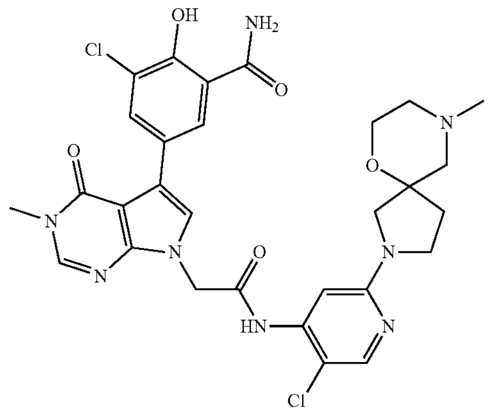 |
| I-133 | 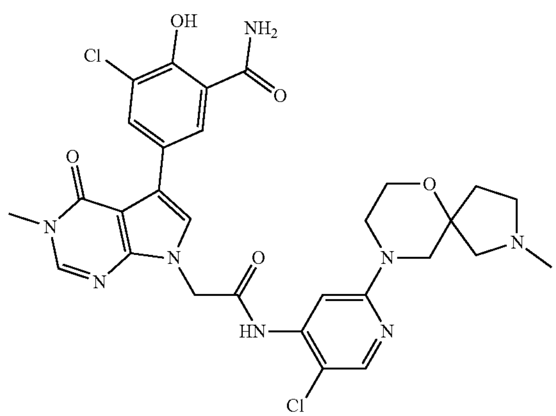 |
| I-134 | 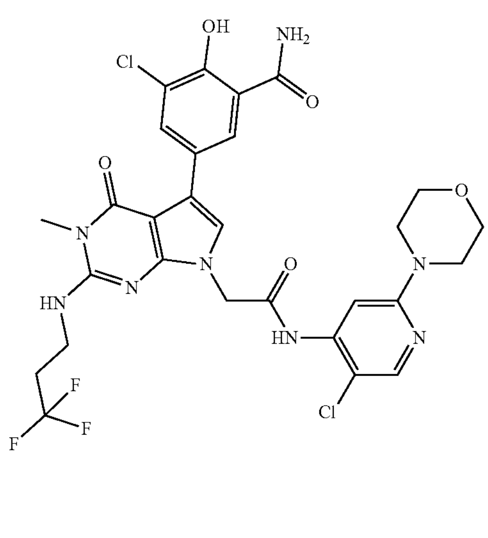 [SMILES: Cn1c(NCCC(F)(F)F)nc2c(c(-c3cc(Cl)c(O)c(C(N)=O)c3)cn2CC(=O)Nc2cc(N3CCOCC3)ncc2Cl)c1=O] |

| Compound | Structure |
|---|---|
| I-135 | 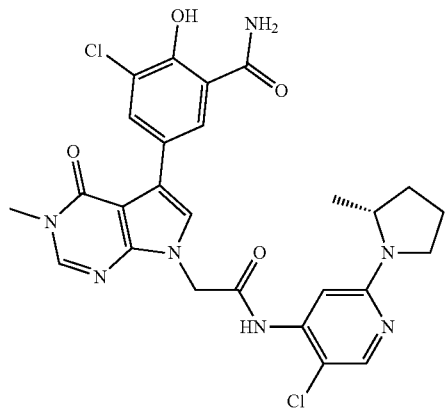 [SMILES: C[C@@H]1CCCN1c1cc(NC(=O)Cn2cc(-c3cc(Cl)c(O)c(C(N)=O)c3)c3c(=O)n(C)cnc32)c(Cl)cn1] |
| I-136 | 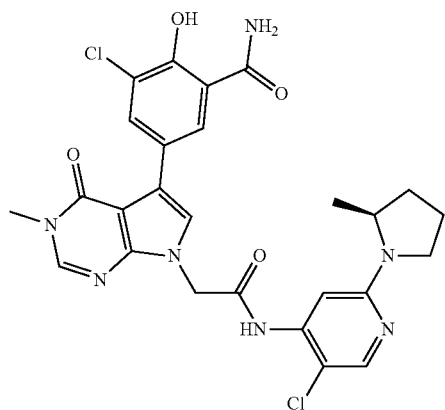 [SMILES: C[C@H]1CCCN1c1cc(NC(=O)Cn2cc(-c3cc(Cl)c(O)c(C(N)=O)c3)c3c(=O)n(C)cnc32)c(Cl)cn1] |
| I-137 | 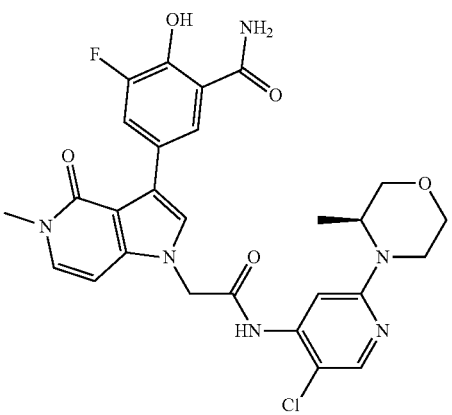 |

| Compound | Structure |
|---|---|
| I-138 | 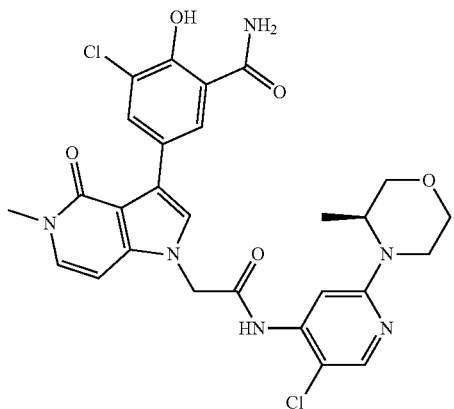 [SMILES: C[C@H]1COCCN1c1cc(NC(=O)Cn2cc(-c3cc(Cl)c(O)c(C(N)=O)c3)c3c(=O)n(C)ccc32)c(Cl)cn1] |
| I-139 | 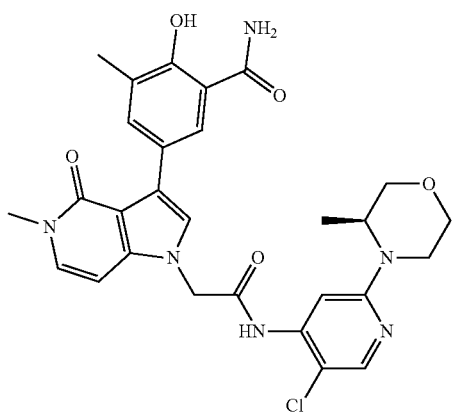 [SMILES: Cc1cc(-c2cn(CC(=O)Nc3cc(N4CCOC[C@@H]4C)ncc3Cl)c3ccn(C)c(=O)c23)cc(C(N)=O)c1O] |
| I-140 | 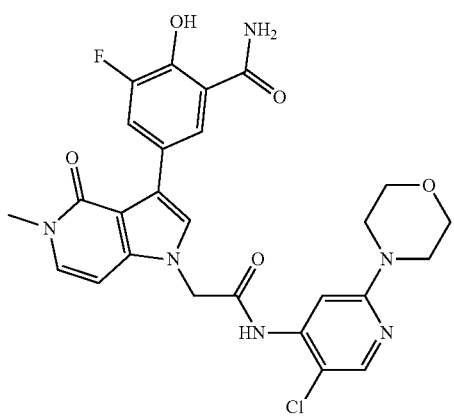 |

-continued
| Compound | Structure |
|---|---|
| I-141 | 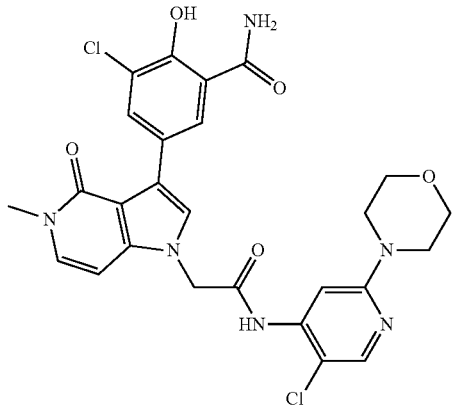 [SMILES: Cn1ccc2c(c(-c3cc(Cl)c(O)c(C(N)=O)c3)cn2CC(=O)Nc2cc(N3CCOCC3)ncc2Cl)c1=O] |
| I-142 | 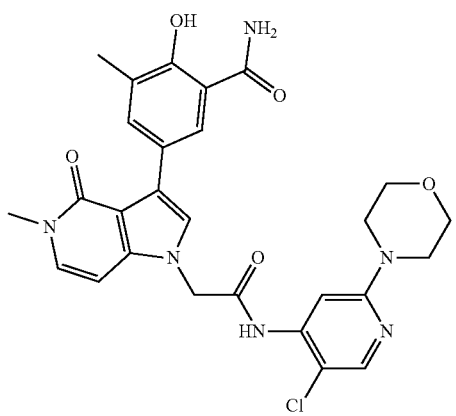 [SMILES: Cc1cc(-c2cn(CC(=O)Nc3cc(N4CCOCC4)ncc3Cl)c3ccn(C)c(=O)c23)cc(C(N)=O)c1O] |
| I-143 | 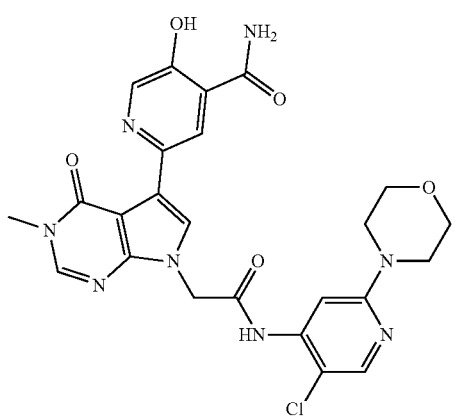 [SMILES: Cn1cnc2c(c(-c3cc(C(N)=O)c(O)cn3)cn2CC(=O)Nc2cc(N3CCOCC3)ncc2Cl)c1=O] |

-continued
| Compound | Structure |
|---|---|
| I-144 | 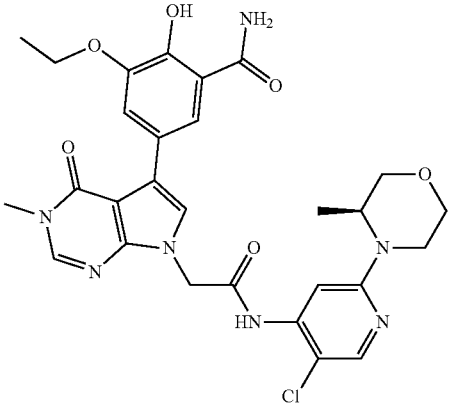 [SMILES: CCOc1cc(-c2cn(CC(=O)Nc3cc(N4CCOC[C@@H]4C)ncc3Cl)c3ncn(C)c(=O)c23)cc(C(N)=O)c1O] |
| I-145 | 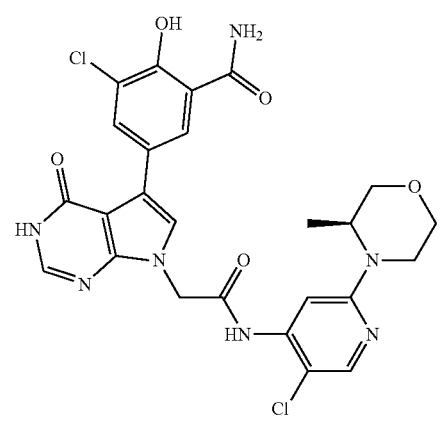 [SMILES: C[C@H]1COCCN1c1cc(NC(=O)Cn2cc(-c3cc(Cl)c(O)c(C(N)=O)c3)c3c(=O)[nH]cnc32)c(Cl)cn1] |
| I-146 | 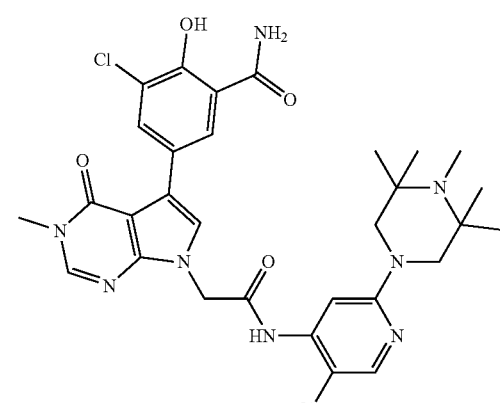 |

-continued
| Compound | Structure |
|---|---|
| I-147 | 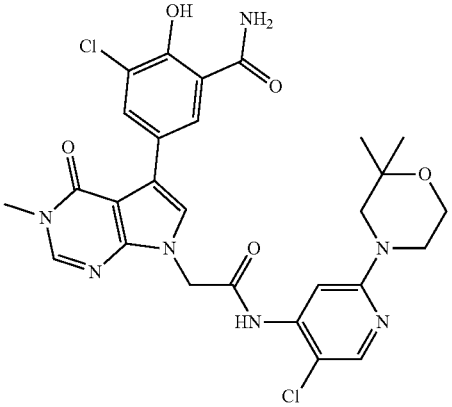 [SMILES: Cn1cnc2c(c(-c3cc(Cl)c(O)c(C(N)=O)c3)cn2CC(=O)Nc2cc(N3CCOC(C)(C)C3)ncc2Cl)c1=O] |
| I-148 | 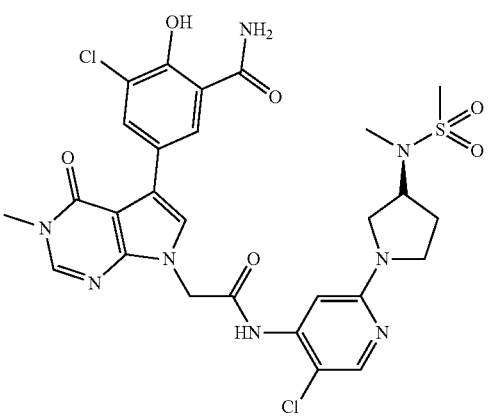 |
| I-149 | 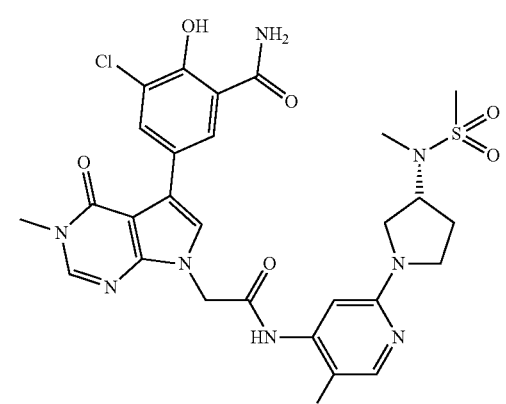 |

| Compound | Structure |
|---|---|
| I-150 | 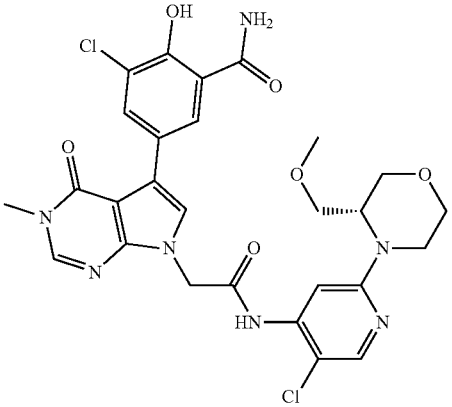 [SMILES: COC[C@@H]1COCCN1c1cc(NC(=O)Cn2cc(-c3cc(Cl)c(O)c(C(N)=O)c3)c3c(=O)n(C)cnc32)c(Cl)cn1] |
| I-151 | 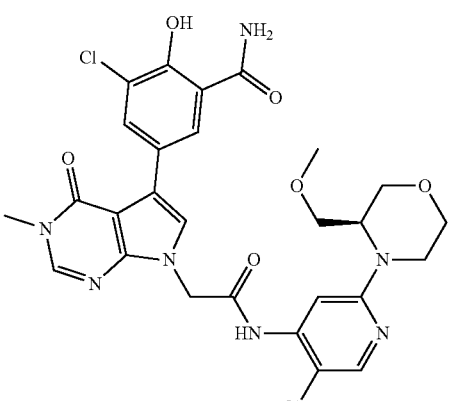 |
| I-152 | 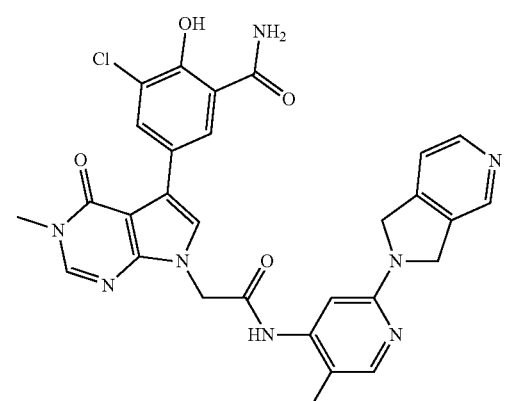 |

-continued
| Compound | Structure |
|---|---|
| I-153 | 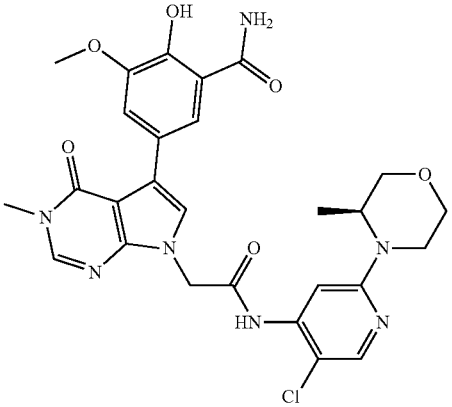 [SMILES: COc1cc(-c2cn(CC(=O)Nc3cc(N4CCOC[C@@H]4C)ncc3Cl)c3ncn(C)c(=O)c23)cc(C(N)=O)c1O] |
| I-154 | 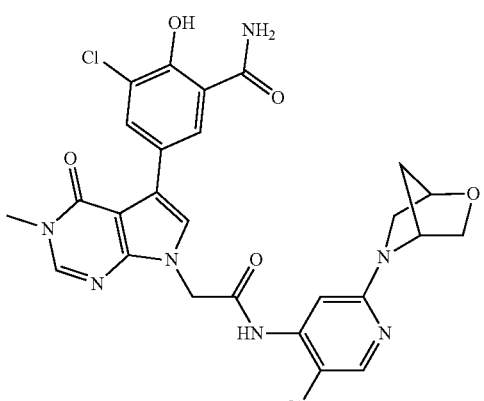 |
| I-155 | 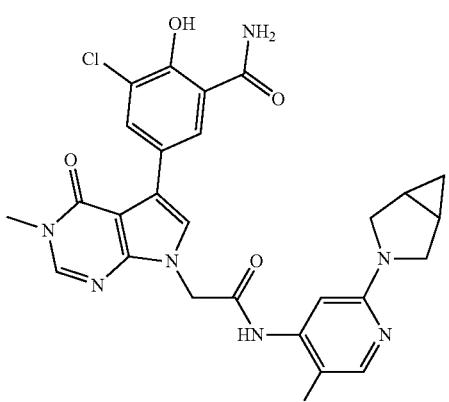 |

| Compound | Structure |
|---|---|
| I-156 | 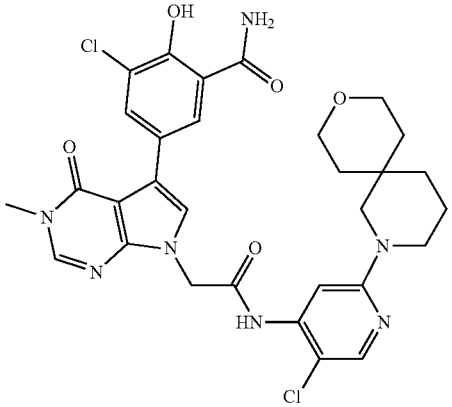 [SMILES: Cn1cnc2c(c(-c3cc(Cl)c(O)c(C(N)=O)c3)cn2CC(=O)Nc2cc(N3CCCC4(CCOCC4)C3)ncc2Cl)c1=O] |
| I-157 | 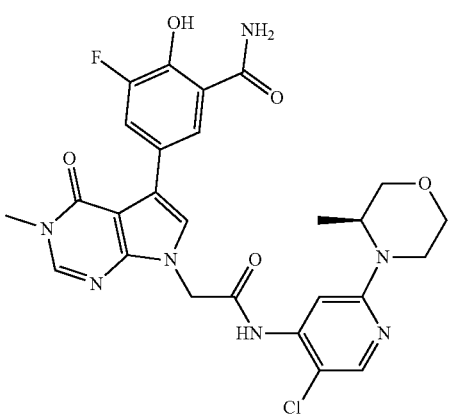 [SMILES: C[C@H]1COCCN1c1cc(NC(=O)Cn2cc(-c3cc(F)c(O)c(C(N)=O)c3)c3c(=O)n(C)cnc32)c(Cl)cn1] |
| I-158 | 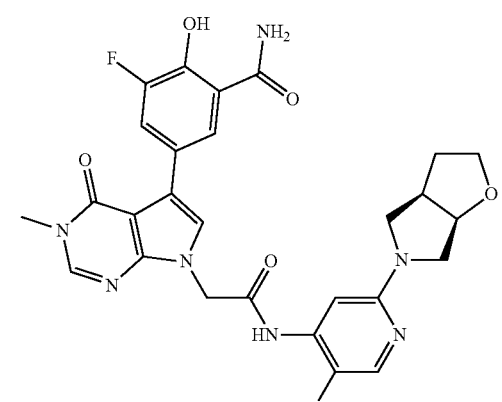 |

-continued
| Compound | Structure |
|---|---|
| I-159 | 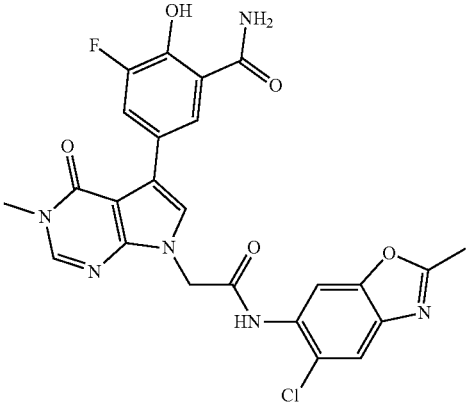 |
| I-160 | 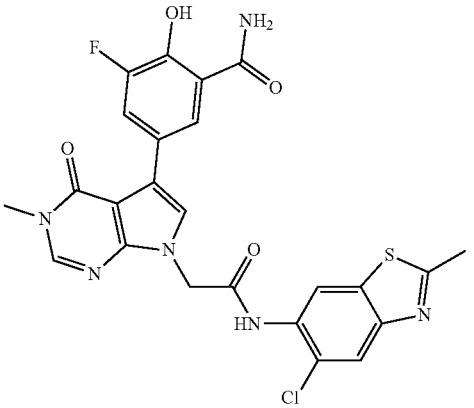 |
| I-161 | 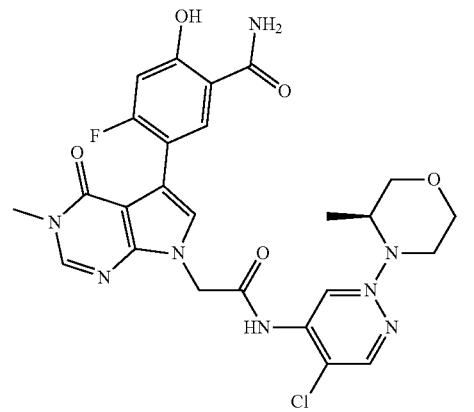 |

| Compound | Structure |
|---|---|
| I-162 | 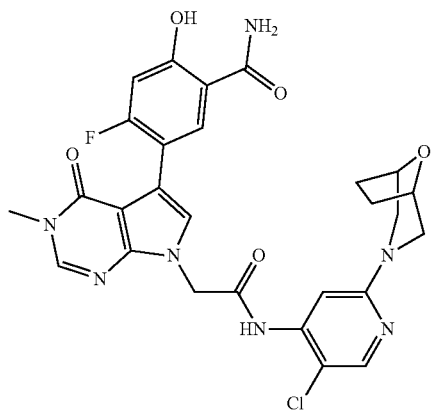 [SMILES: Cn1cnc2c(c(-c3cc(C(N)=O)c(O)cc3F)cn2CC(=O)Nc2cc(N3CC4CCC(C3)O4)ncc2Cl)c1=O] |
| I-163 | 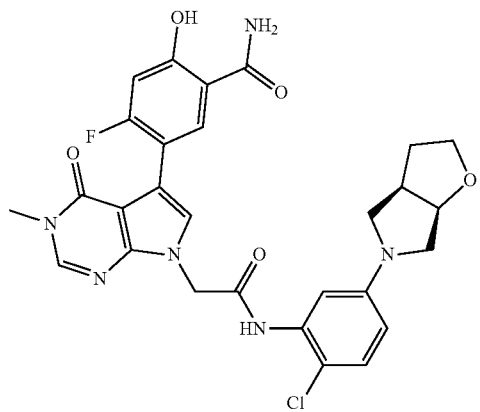 [SMILES: Cn1cnc2c(c(-c3cc(C(N)=O)c(O)cc3F)cn2CC(=O)Nc2cc(N3C[C@H]4CCO[C@H]4C3)ccc2Cl)c1=O] |
| I-164 | 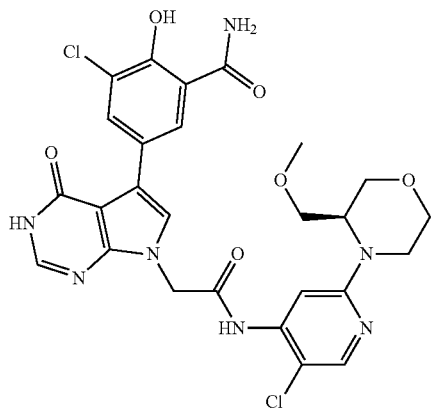 [SMILES: COC[C@H]1COCCN1c1cc(NC(=O)Cn2cc(-c3cc(Cl)c(O)c(C(N)=O)c3)c3c(=O)[nH]cnc32)c(Cl)cn1] |

-continued
| Compound | Structure |
|---|---|
| I-165 | 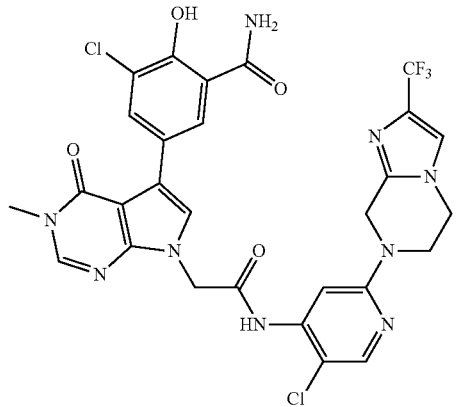 [SMILES: Cn1cnc2c(c(-c3cc(Cl)c(O)c(C(N)=O)c3)cn2CC(=O)Nc2cc(N3CCn4cc(C(F)(F)F)nc4C3)ncc2Cl)c1=O] |
| I-166 | 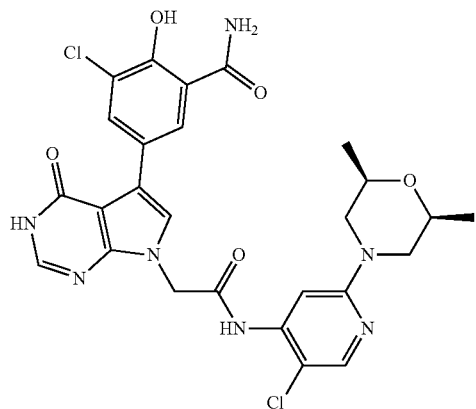 [SMILES: C[C@@H]1CN(c2cc(NC(=O)Cn3cc(-c4cc(Cl)c(O)c(C(N)=O)c4)c4c(=O)[nH]cnc43)c(Cl)cn2)C[C@H](C)O1] |
| I-167 | 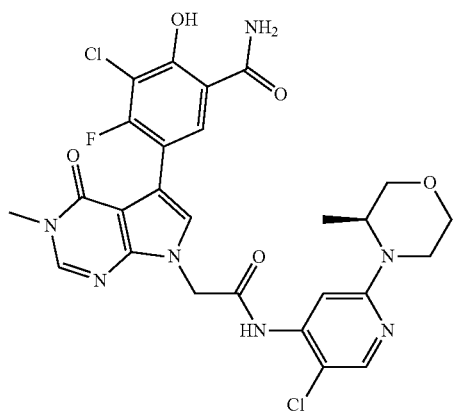 [SMILES: C[C@H]1COCCN1c1cc(NC(=O)Cn2cc(-c3cc(C(N)=O)c(O)c(Cl)c3F)c3c(=O)n(C)cnc32)c(Cl)cn1] |

| Compound | Structure |
|---|---|
| I-168 | 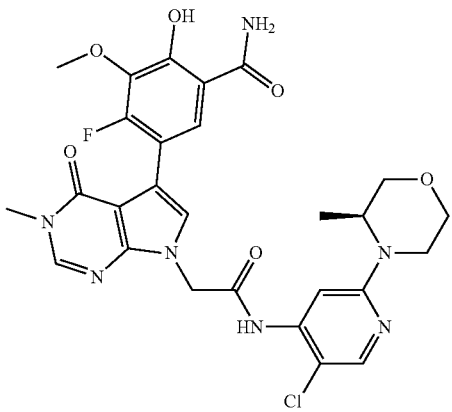 [SMILES: COc1c(O)c(C(N)=O)cc(-c2cn(CC(=O)Nc3cc(N4CCOC[C@@H]4C)ncc3Cl)c3ncn(C)c(=O)c23)c1F] |
| I-169 | 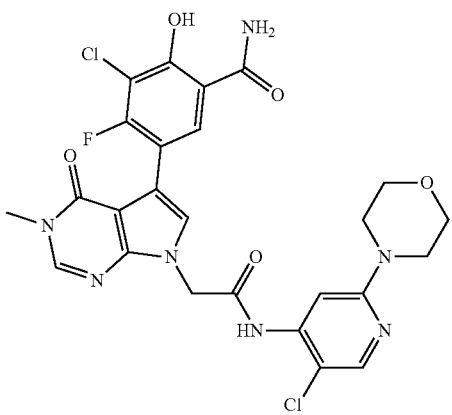 [SMILES: Cn1cnc2c(c(-c3cc(C(N)=O)c(O)c(Cl)c3F)cn2CC(=O)Nc2cc(N3CCOCC3)ncc2Cl)c1=O] |
| I-170 | 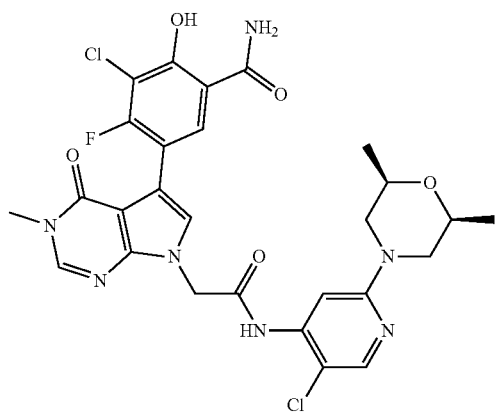 |

-continued
| Compound | Structure |
|---|---|
| I-171 | 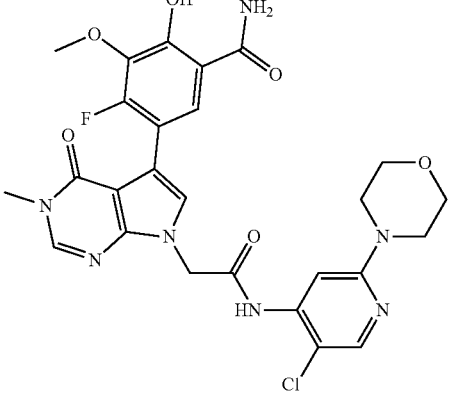 |
| I-172 | 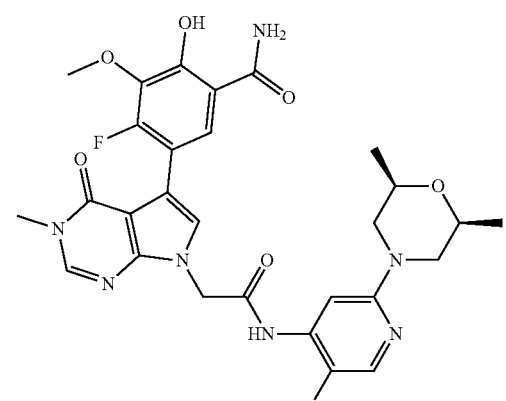 |
| I-173 | 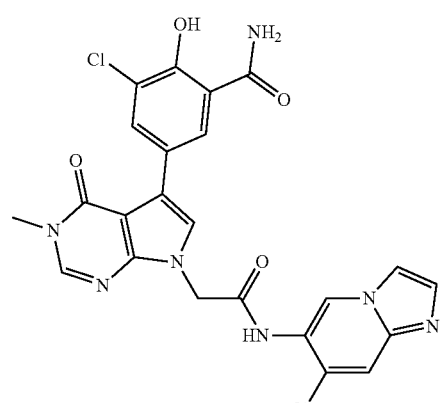 |

-continued
| Compound | Structure |
|---|---|
| I-174 | 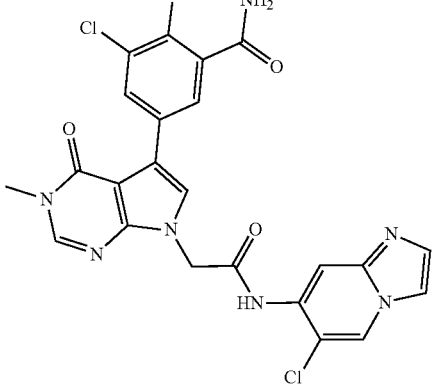 |
| I-175 | 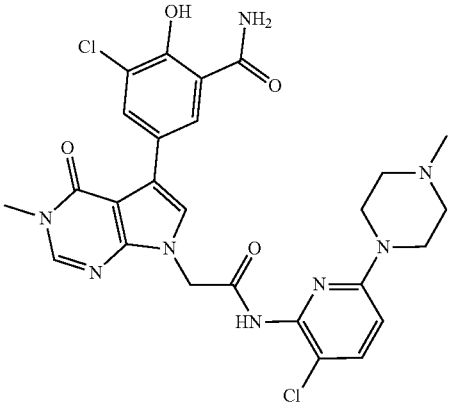 |
| I-176 | 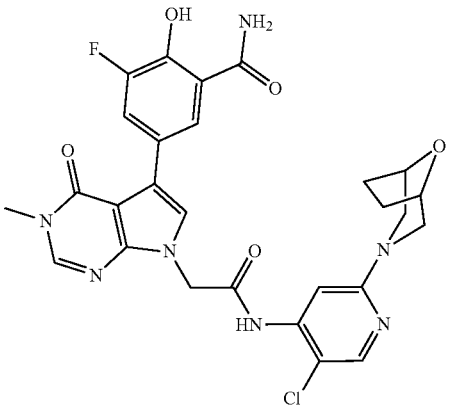 [SMILES: Cn1cnc2c(c(-c3cc(F)c(O)c(C(N)=O)c3)cn2CC(=O)Nc2cc(N3CC4CCC(C3)O4)ncc2Cl)c1=O] |

| Compound | Structure |
|---|---|
| I-177 | 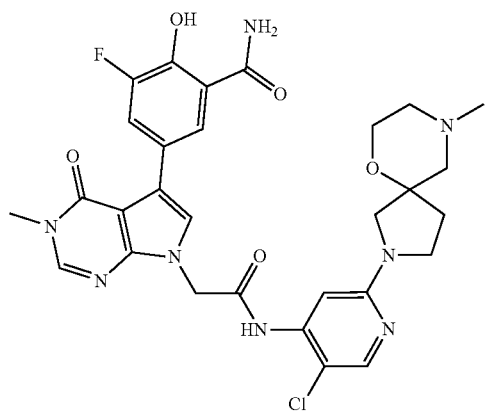 |
| I-178 | 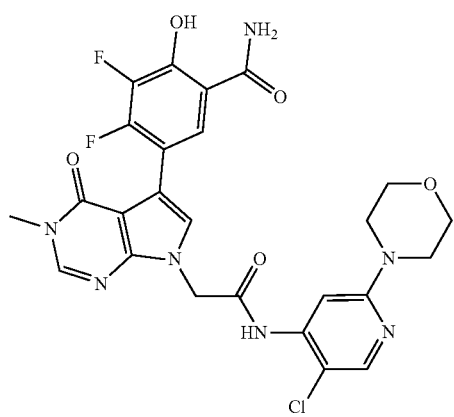 [SMILES: Cn1cnc2c(c(-c3cc(C(N)=O)c(O)c(F)c3F)cn2CC(=O)Nc2cc(N3CCOCC3)ncc2Cl)c1=O] |
| I-179 | 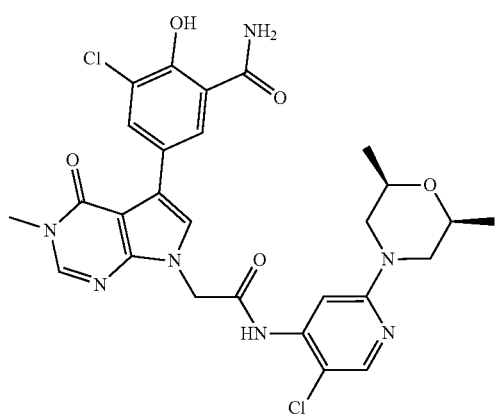 |

-continued
| Compound | Structure |
|---|---|
| I-180 | 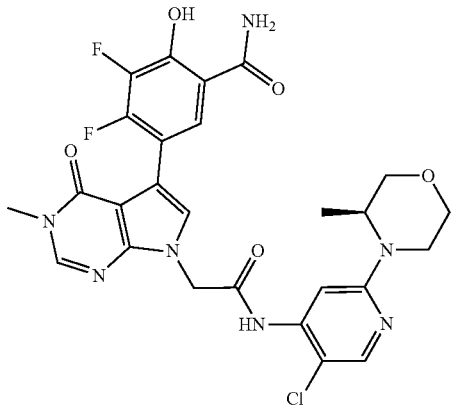 [SMILES: C[C@H]1COCCN1c1cc(NC(=O)Cn2cc(-c3cc(C(N)=O)c(O)c(F)c3F)c3c(=O)n(C)cnc32)c(Cl)cn1] |
| I-181 | 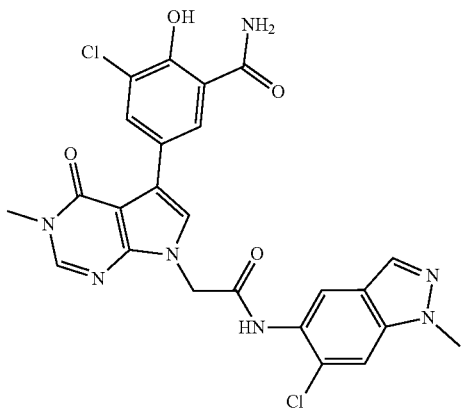 |
| I-182 | 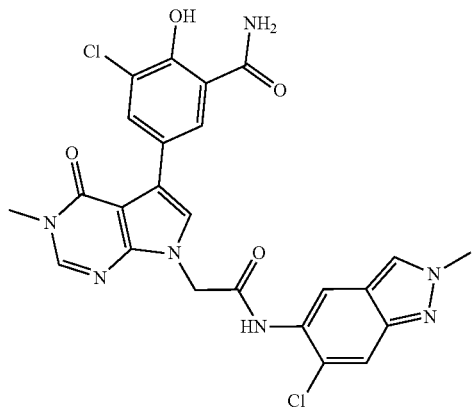 |

| Compound | Structure |
|---|---|
| I-183 | 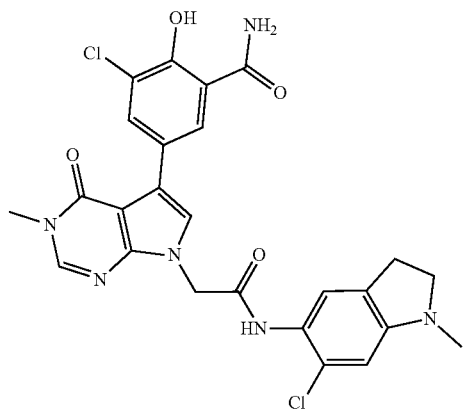 |
| I-184 | 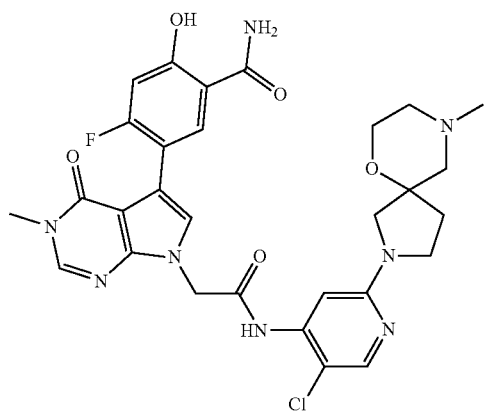 |
| I-185 | 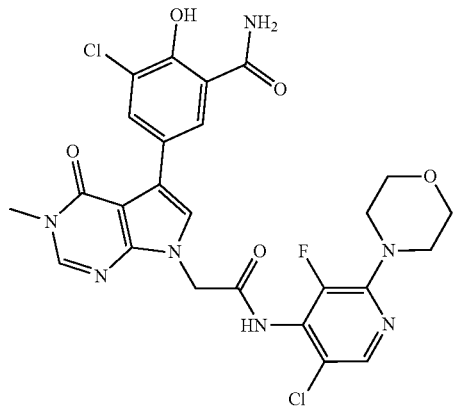 [SMILES: Cn1cnc2c(c(-c3cc(Cl)c(O)c(C(N)=O)c3)cn2CC(=O)Nc2c(Cl)cnc(N3CCOCC3)c2F)c1=O] |

-continued
| Compound | Structure |
|---|---|
| I-186 | 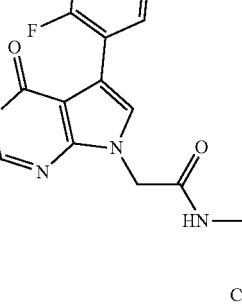 |
| I-187 | 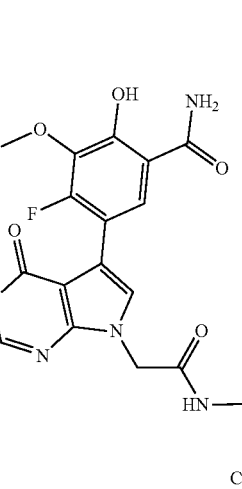 |
| I-188 | 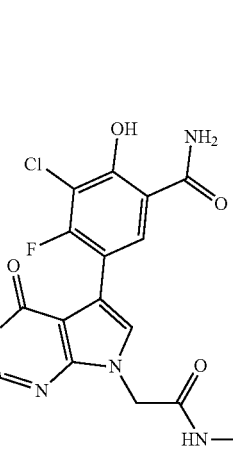 |

| Compound | Structure |
|---|---|
| I-189 | 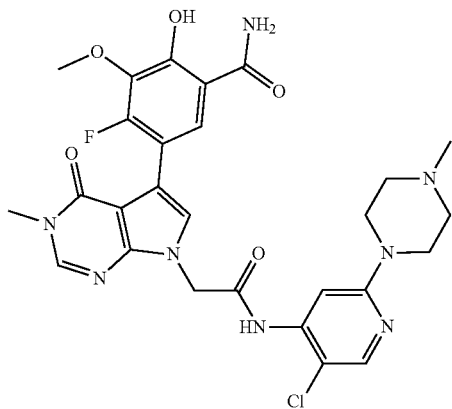 |
| I-190 | 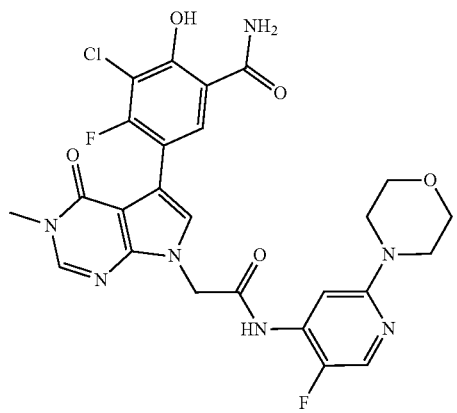 [SMILES: Cn1cnc2c(c(-c3cc(C(N)=O)c(O)c(Cl)c3F)cn2CC(=O)Nc2cc(N3CCOCC3)ncc2F)c1=O] |
| I-191 | 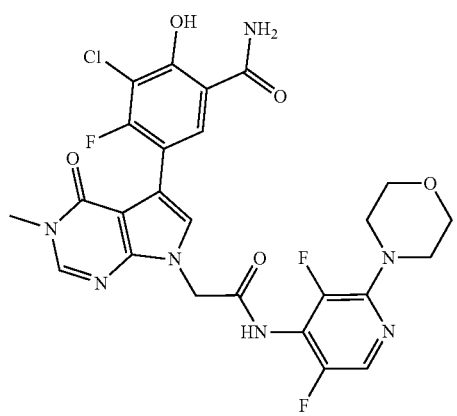 [SMILES: Cn1cnc2c(c(-c3cc(C(N)=O)c(O)c(Cl)c3F)cn2CC(=O)Nc2c(F)cnc(N3CCOCC3)c2F)c1=O] |

-continued
| Compound | Structure |
|---|---|
| I-192 | 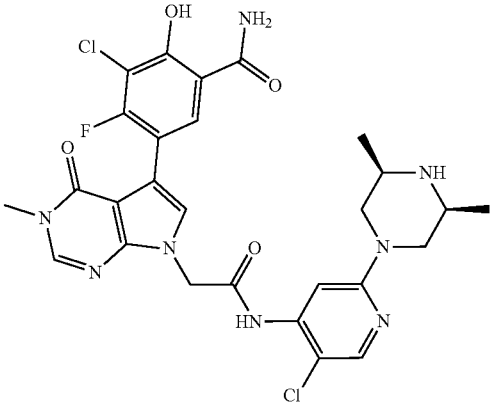 |
| I-193 | 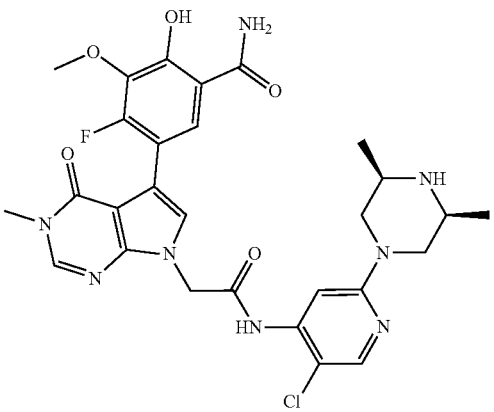 |
| I-194 | 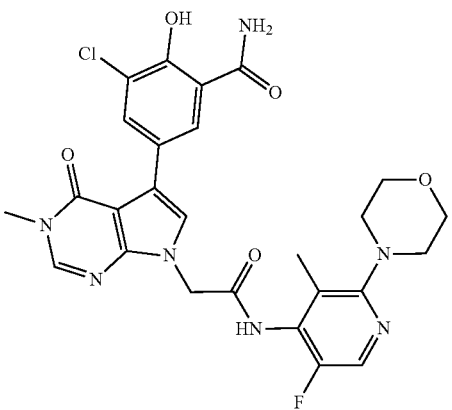 [SMILES: Cc1c(N2CCOCC2)ncc(F)c1NC(=O)Cn1cc(-c2cc(Cl)c(O)c(C(N)=O)c2)c2c(=O)n(C)cnc21] |

-continued
| Compound | Structure |
|---|---|
| I-195 | 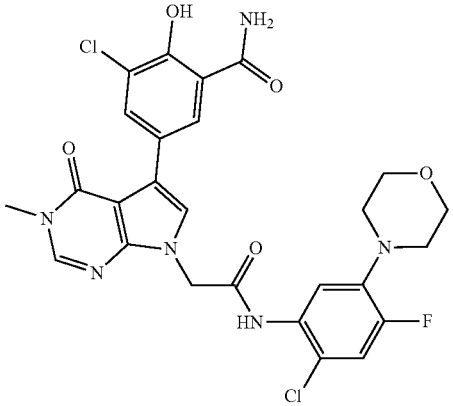 [SMILES: Cn1cnc2c(c(-c3cc(Cl)c(O)c(C(N)=O)c3)cn2CC(=O)Nc2cc(N3CCOCC3)c(F)cc2Cl)c1=O] |
| I-196 | 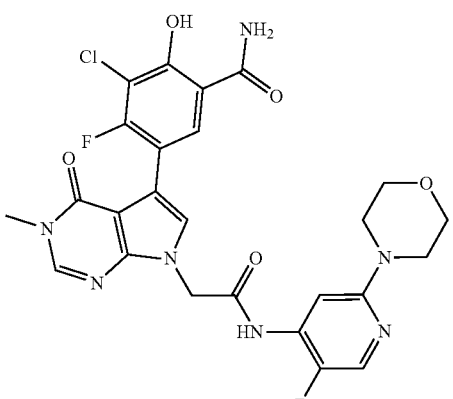 |
| I-197 | 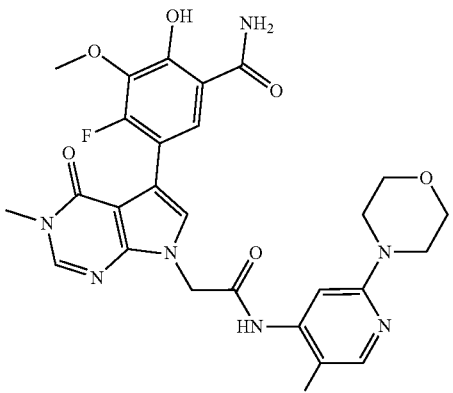 |

| Compound | Structure |
|---|---|
| I-198 | 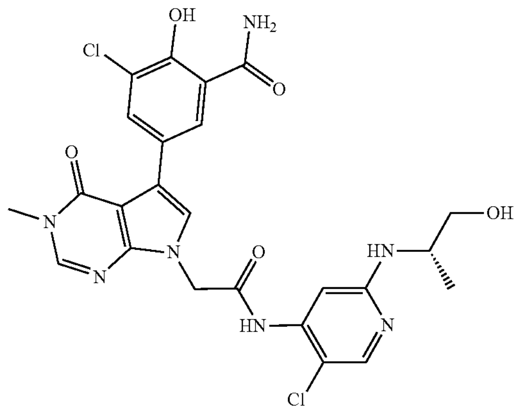 [SMILES: C[C@@H](CO)Nc1cc(NC(=O)Cn2cc(-c3cc(Cl)c(O)c(C(N)=O)c3)c3c(=O)n(C)cnc32)c(Cl)cn1] |
| I-199 | 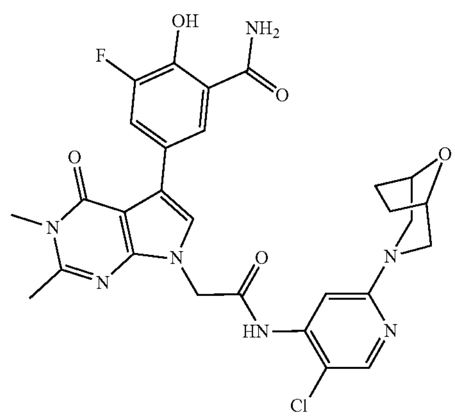 [SMILES: Cc1nc2c(c(-c3cc(F)c(O)c(C(N)=O)c3)cn2CC(=O)Nc2cc(N3CC4CCC(C3)O4)ncc2Cl)c(=O)n1C] |
| I-200 | 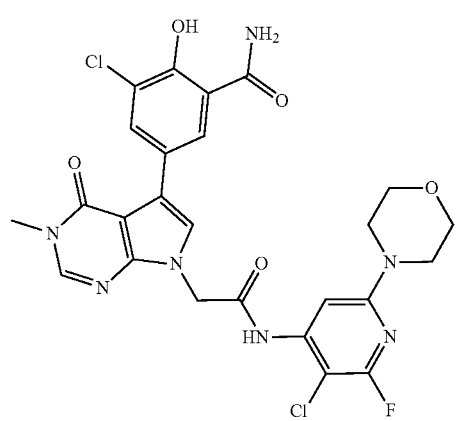 [SMILES: Cn1cnc2c(c(-c3cc(Cl)c(O)c(C(N)=O)c3)cn2CC(=O)Nc2cc(N3CCOCC3)nc(F)c2Cl)c1=O] |

-continued
| Compound | Structure |
|---|---|
| I-201 | 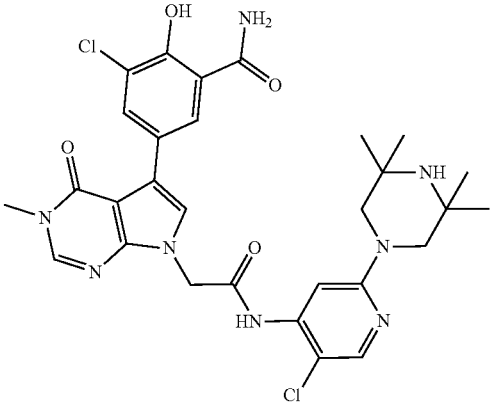 |
| I-202 | 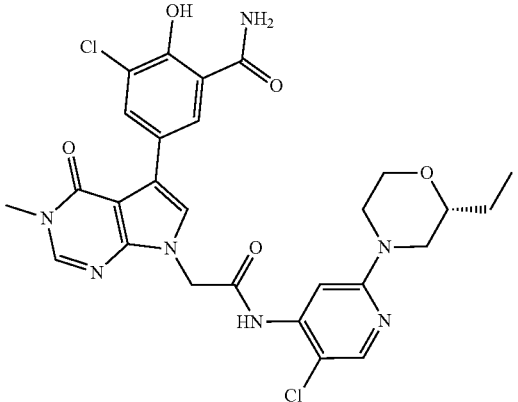 [SMILES: CC[C@@H]1CN(c2cc(NC(=O)Cn3cc(-c4cc(Cl)c(O)c(C(N)=O)c4)c4c(=O)n(C)cnc43)c(Cl)cn2)CCO1] |
| I-203 | 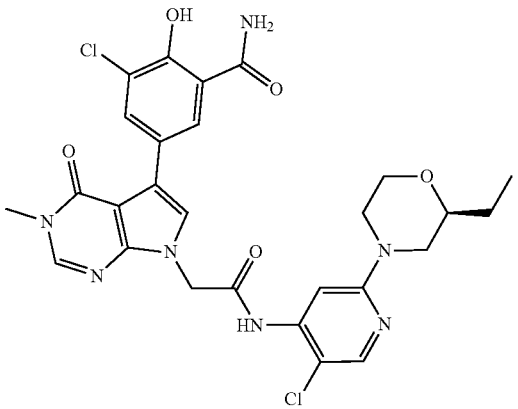 [SMILES: CC[C@H]1CN(c2cc(NC(=O)Cn3cc(-c4cc(Cl)c(O)c(C(N)=O)c4)c4c(=O)n(C)cnc43)c(Cl)cn2)CCO1] |

| Compound | Structure |
|---|---|
| I-204 | 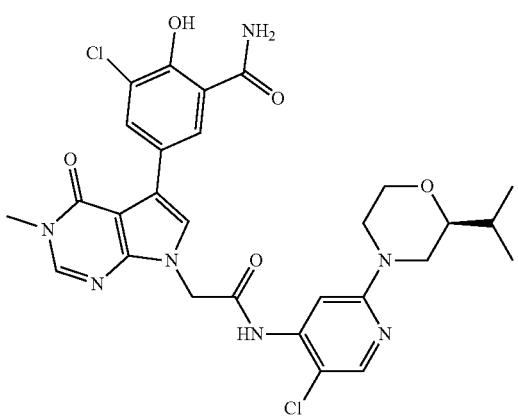 [SMILES: CC(C)[C@H]1CN(c2cc(NC(=O)Cn3cc(-c4cc(Cl)c(O)c(C(N)=O)c4)c4c(=O)n(C)cnc43)c(Cl)cn2)CCO1] |
| I-205 | 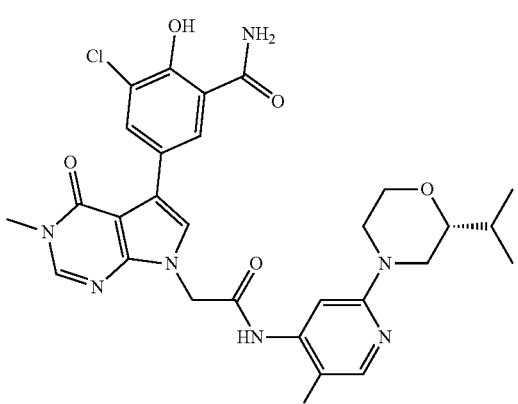 |
| I-206 | 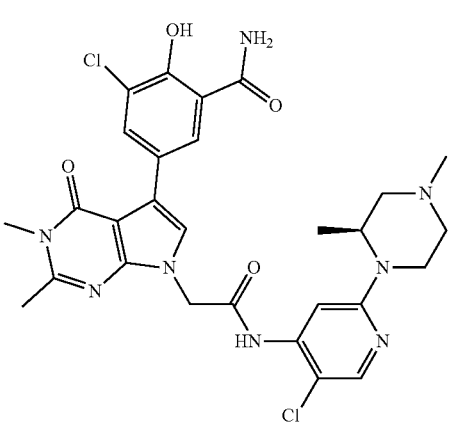 |

| Compound | Structure |
|---|---|
| I-207 | 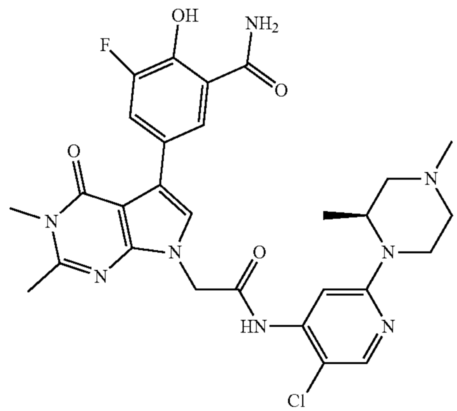 |
| I-208 | 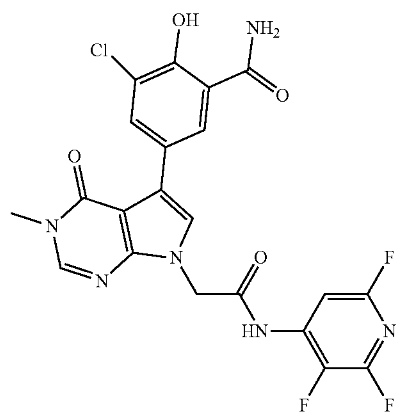 [SMILES: Cn1cnc2c(c(-c3cc(Cl)c(O)c(C(N)=O)c3)cn2CC(=O)Nc2cc(F)nc(F)c2F)c1=O] |
| I-209 | 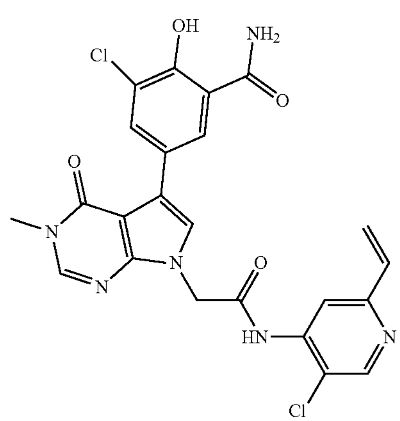 [SMILES: C=Cc1cc(NC(=O)Cn2cc(-c3cc(Cl)c(O)c(C(N)=O)c3)c3c(=O)n(C)cnc32)c(Cl)cn1] |

-continued

| Compound | Structure |
|---|---|
| I-210 | 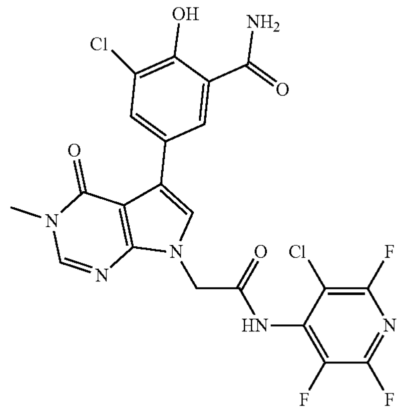 [SMILES: Cn1cnc2c(c(-c3cc(Cl)c(O)c(C(N)=O)c3)cn2CC(=O)Nc2c(F)c(F)nc(F)c2Cl)c1=O] |
| I-211 | 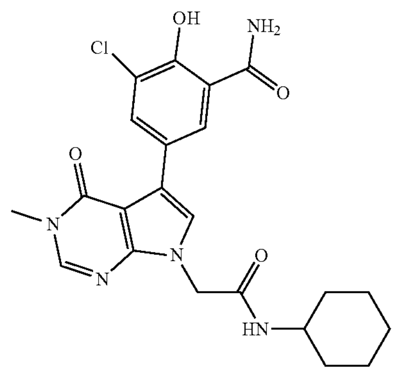 [SMILES: Cn1cnc2c(c(-c3cc(Cl)c(O)c(C(N)=O)c3)cn2CC(=O)NC2CCCCC2)c1=O] |
| I-212 | 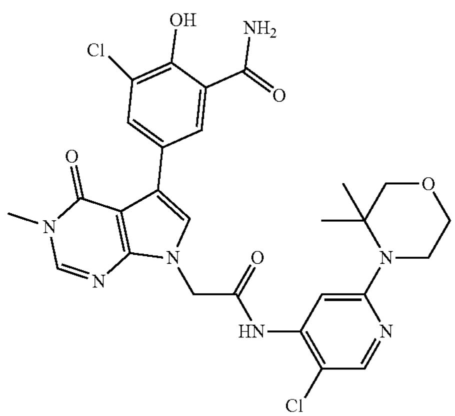 [SMILES: Cn1cnc2c(c(-c3cc(Cl)c(O)c(C(N)=O)c3)cn2CC(=O)Nc2cc(N3CCOCC3(C)C)ncc2Cl)c1=O] |
| I-213 | 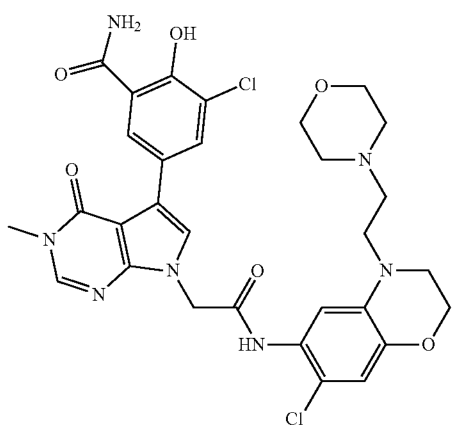 [SMILES: Cn1cnc2c(c(-c3cc(Cl)c(O)c(C(N)=O)c3)cn2CC(=O)Nc2cc3c(cc2Cl)OCCN3CCN2CCOCC2)c1=O] |

| Compound | Structure |
|---|---|
| I-214 | 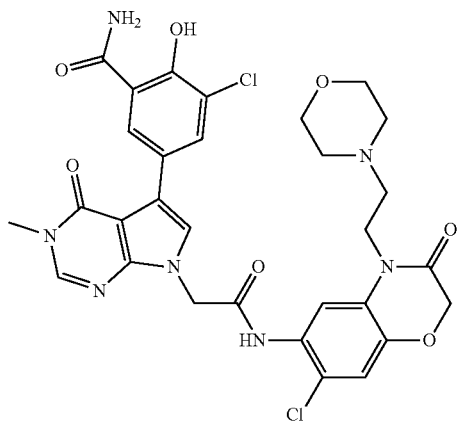 [SMILES: Cn1cnc2c(c(-c3cc(Cl)c(O)c(C(N)=O)c3)cn2CC(=O)Nc2cc3c(cc2Cl)OCC(=O)N3CCN2CCOCC2)c1=O] |
| I-215 | 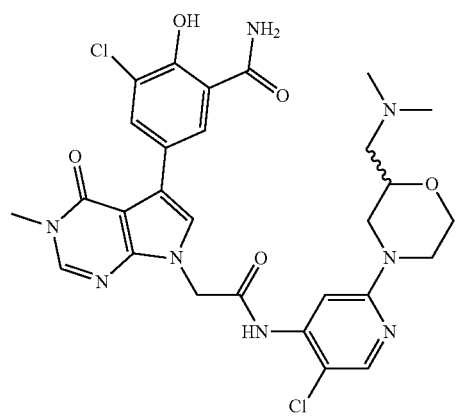 [SMILES: CN(C)CC1CN(c2cc(NC(=O)Cn3cc(-c4cc(Cl)c(O)c(C(N)=O)c4)c4c(=O)n(C)cnc43)c(Cl)cn2)CCO1] |
| I-216 | 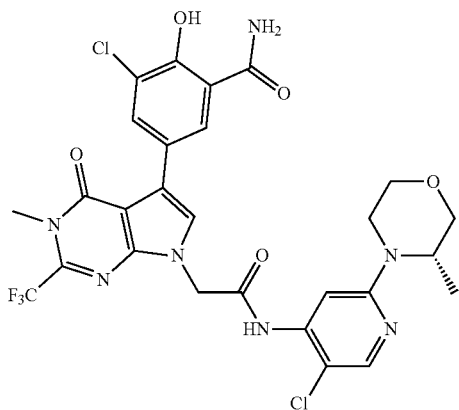 |

| Compound | Structure |
|----------|-----------|
| I-217 | 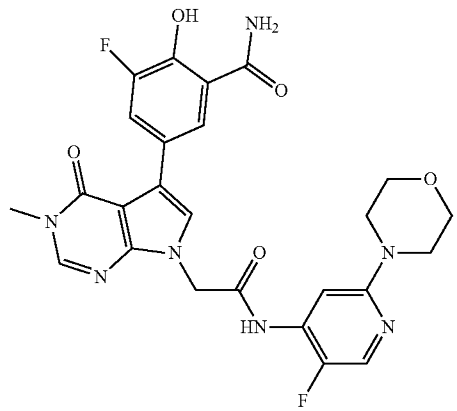 [SMILES: Cn1cnc2c(c(-c3cc(F)c(O)c(C(N)=O)c3)cn2CC(=O)Nc2cc(N3CCOCC3)ncc2F)c1=O] |
| I-218 | 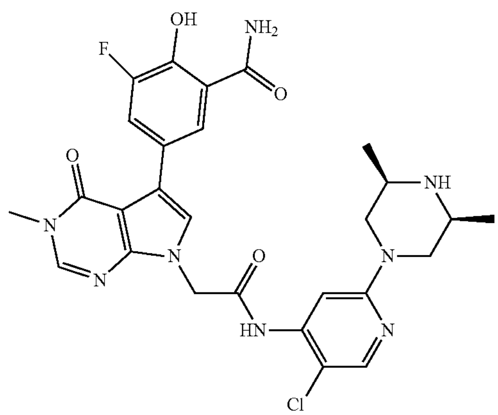 |
| I-219 | 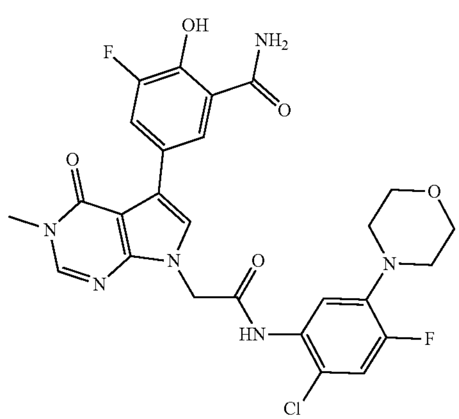 [SMILES: Cn1cnc2c(c(-c3cc(F)c(O)c(C(N)=O)c3)cn2CC(=O)Nc2cc(N3CCOCC3)c(F)cc2Cl)c1=O] |

| Compound | Structure |
|---|---|
| I-220 | 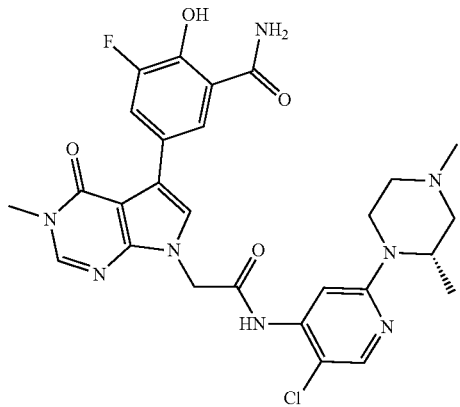 |
| I-221 | 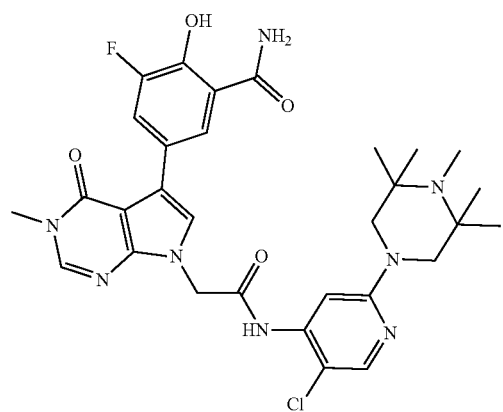 |
| I-222 | 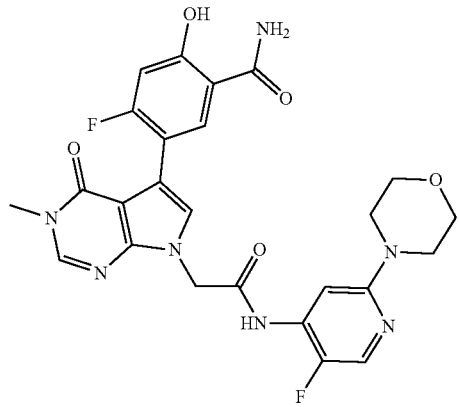 [SMILES: Cn1cnc2c(c(-c3cc(C(N)=O)c(O)cc3F)cn2CC(=O)Nc2cc(N3CCOCC3)ncc2F)c1=O] |

| Compound | Structure |
|---|---|
| I-223 | 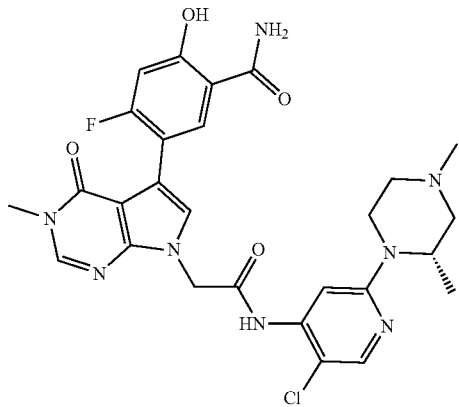 |
| I-224 | 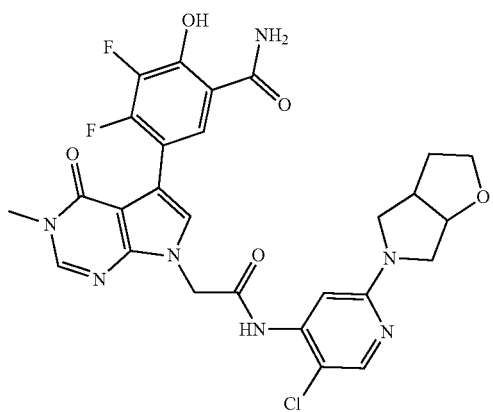 [SMILES: Cn1cnc2c(c(-c3cc(C(N)=O)c(O)c(F)c3F)cn2CC(=O)Nc2cc(N3CC4CCOC4C3)ncc2Cl)c1=O] |
| I-225 | 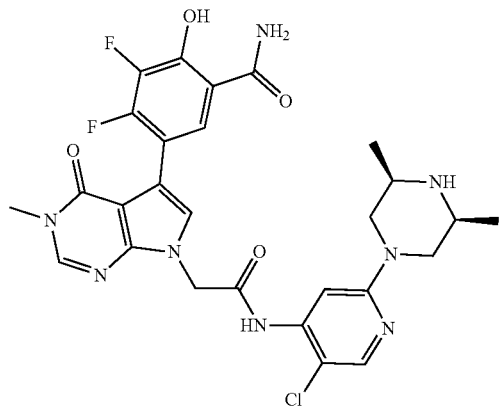 |

-continued
| Compound | Structure |
|---|---|
| I-226 | 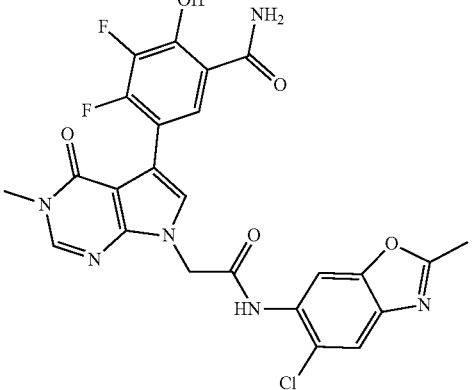 |
| I-227 | 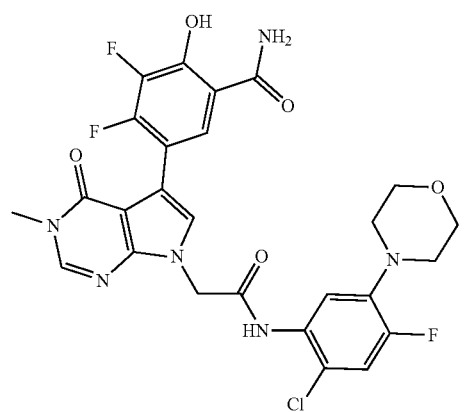 [SMILES: Cn1cnc2c(c(-c3cc(C(N)=O)c(O)c(F)c3F)cn2CC(=O)Nc2cc(N3CCOCC3)c(F)cc2Cl)c1=O] |
| I-228 | 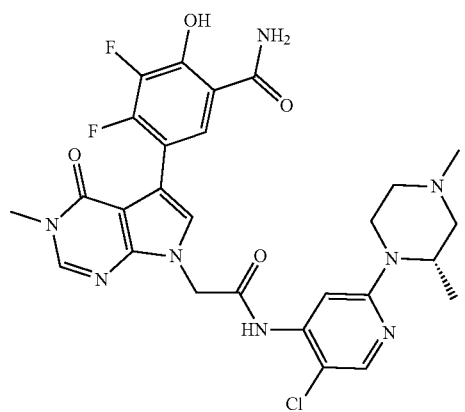 |

-continued
| Compound | Structure |
|---|---|
| I-229 | 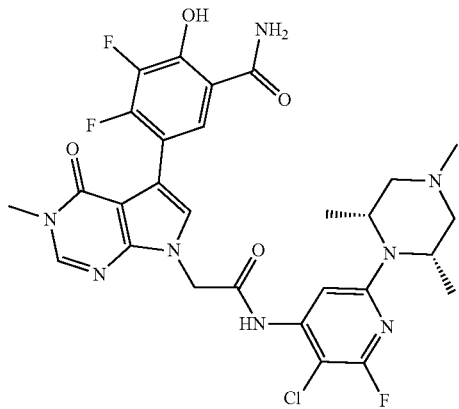 |
| I-230 | 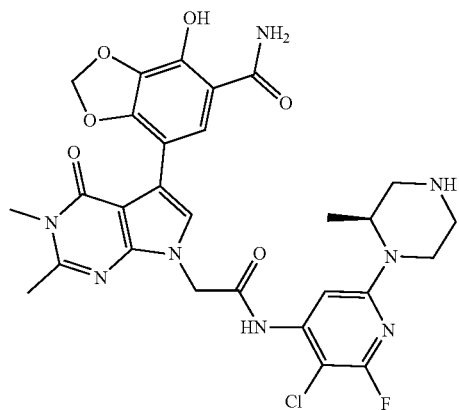 [SMILES: Cc1nc2c(c(-c3cc(C(N)=O)c(O)c4c3OCO4)cn2CC(=O)Nc2cc(N3CCNC[C@@H]3C)nc(F)c2Cl)c(=O)n1C] |
| I-231 | 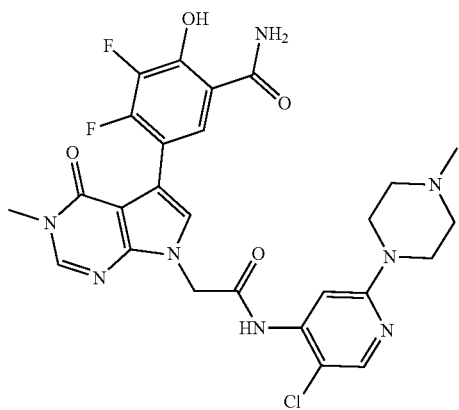 |

| Compound | Structure |
|---|---|
| I-232 | 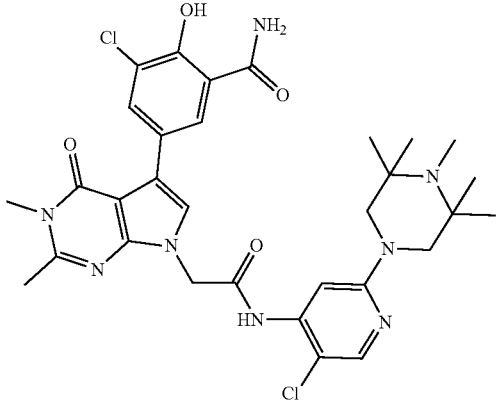 |
| I-233 | 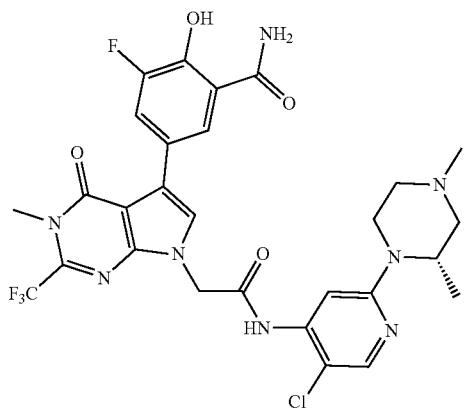 |
| I-234 | 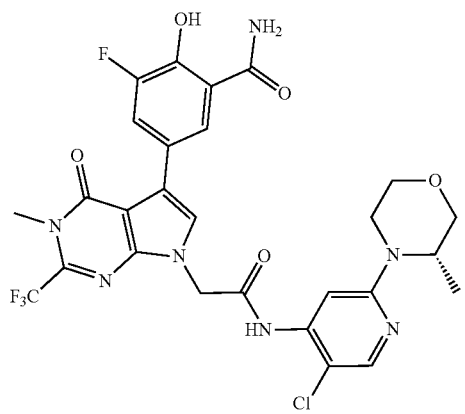 |

-continued
| Compound | Structure |
|---|---|
| I-235 | 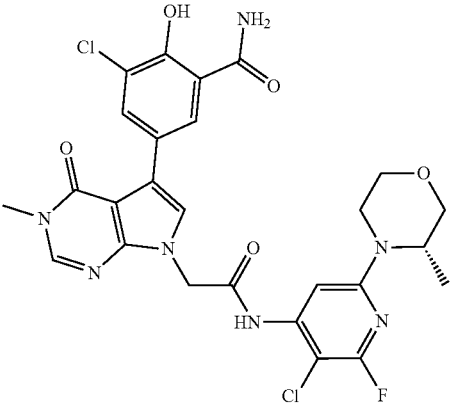 |
| I-236 | 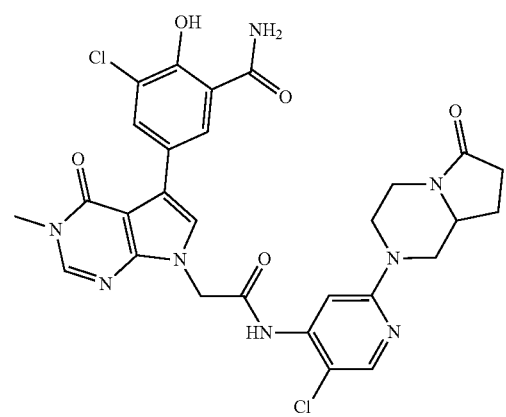 [SMILES: Cn1cnc2c(c(-c3cc(Cl)c(O)c(C(N)=O)c3)cn2CC(=O)Nc2cc(N3CCN4C(=O)CCC4C3)ncc2Cl)c1=O] |
| I-237 | 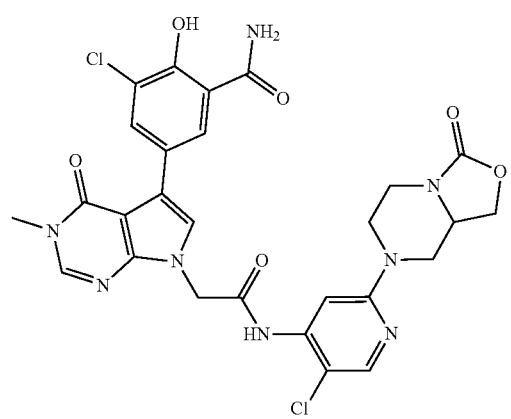 [SMILES: Cn1cnc2c(c(-c3cc(Cl)c(O)c(C(N)=O)c3)cn2CC(=O)Nc2cc(N3CCN4C(=O)OCC4C3)ncc2Cl)c1=O] |

-continued
| Compound | Structure |
| --- | --- |
| I-238 | 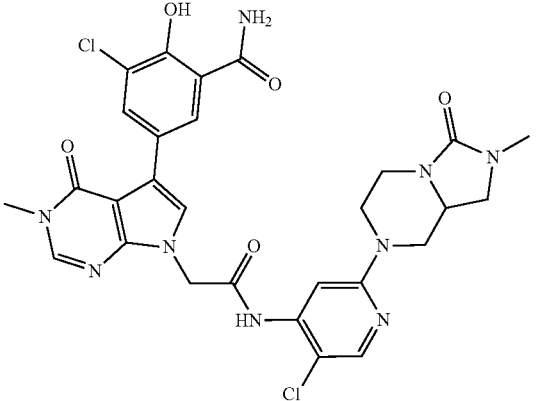 |
| I-239 | 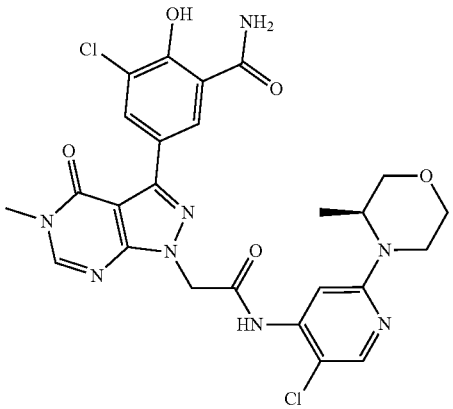 [SMILES: C[C@H]1COCCN1c1cc(NC(=O)Cn2nc(-c3cc(Cl)c(O)c(C(N)=O)c3)c3c(=O)n(C)cnc32)c(Cl)cn1] |
| I-240 | 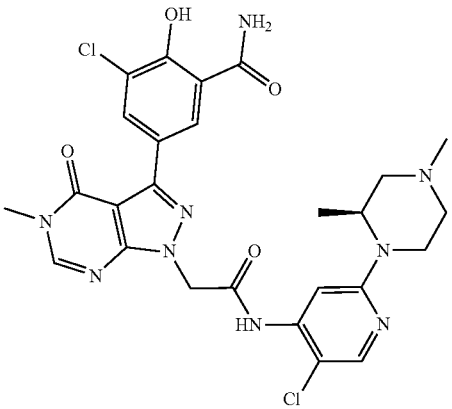 |

US 11,518,764 B2
-continued
| Compound | Structure |
|---|---|
| I-241 | 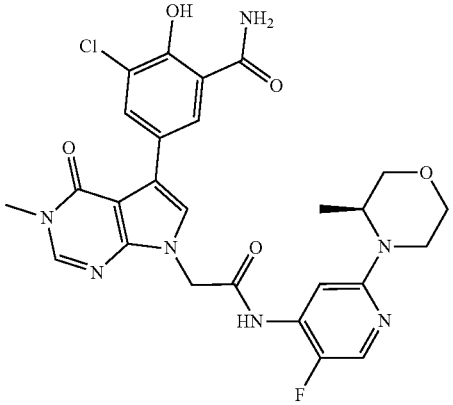 [SMILES: C[C@H]1COCCN1c1cc(NC(=O)Cn2cc(-c3cc(Cl)c(O)c(C(N)=O)c3)c3c(=O)n(C)cnc32)c(F)cn1] |
| I-242 | 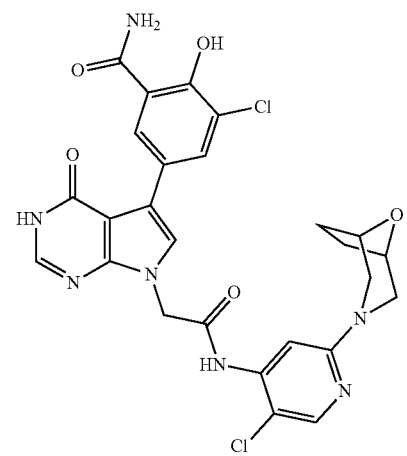 [SMILES: NC(=O)c1cc(-c2cn(CC(=O)Nc3cc(N4CC5CCC(C4)O5)ncc3Cl)c3nc[nH]c(=O)c23)cc(Cl)c1O] |
| I-243 | 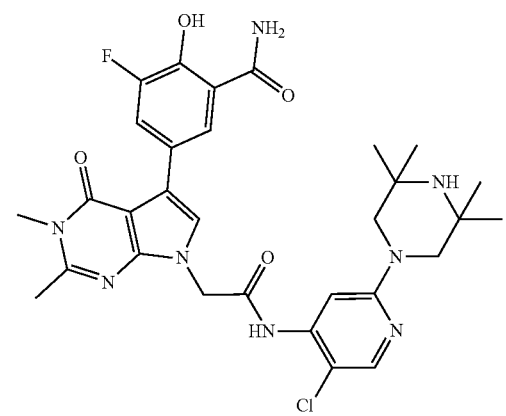 |

-continued
| Compound | Structure |
|---|---|
| I-244 | 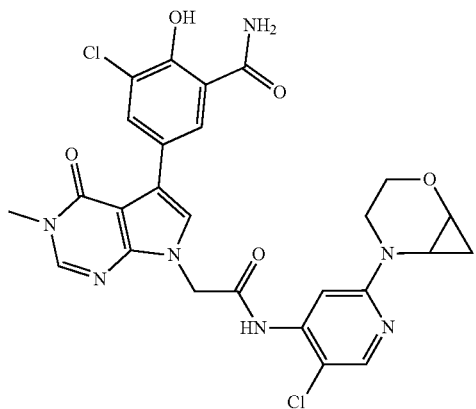 [SMILES: Cn1cnc2c(c(-c3cc(Cl)c(O)c(C(N)=O)c3)cn2CC(=O)Nc2cc(N3CCOC4CC43)ncc2Cl)c1=O] |
| I-245 | 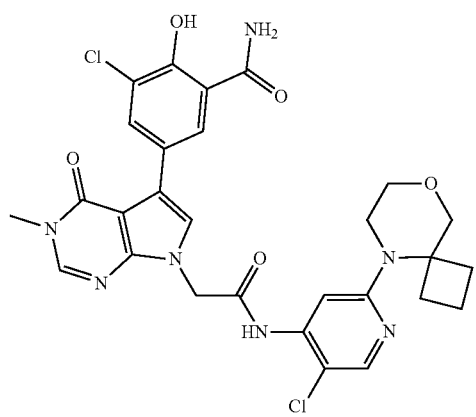 [SMILES: Cn1cnc2c(c(-c3cc(Cl)c(O)c(C(N)=O)c3)cn2CC(=O)Nc2cc(N3CCOCC34CCC4)ncc2Cl)c1=O] |
| I-246 | 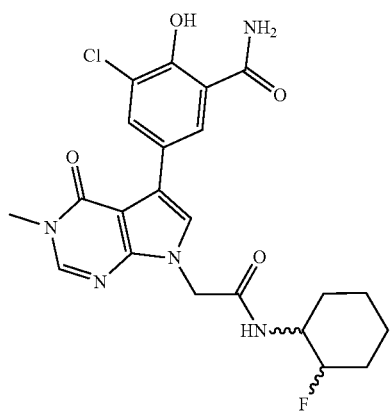 [SMILES: Cn1cnc2c(c(-c3cc(Cl)c(O)c(C(N)=O)c3)cn2CC(=O)NC2CCCCC2F)c1=O] |

| Compound | Structure |
|---|---|
| I-247 | 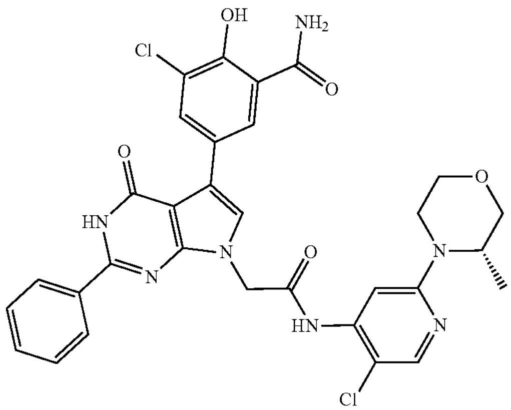 [SMILES: C[C@H]1COCCN1c1cc(NC(=O)Cn2cc(-c3cc(Cl)c(O)c(C(N)=O)c3)c3c(=O)[nH]c(-c4ccccc4)nc32)c(Cl)cn1] |
| I-248 | 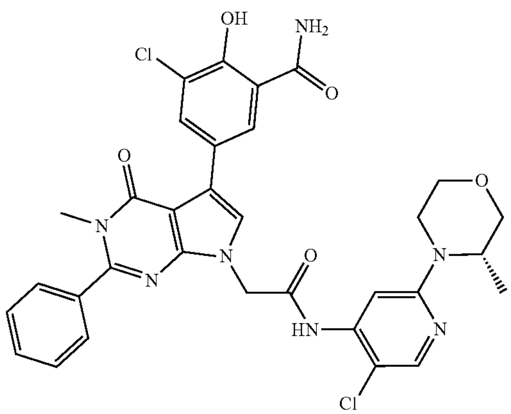 [SMILES: C[C@H]1COCCN1c1cc(NC(=O)Cn2cc(-c3cc(Cl)c(O)c(C(N)=O)c3)c3c(=O)n(C)c(-c4ccccc4)nc32)c(Cl)cn1] |
| I-249 | 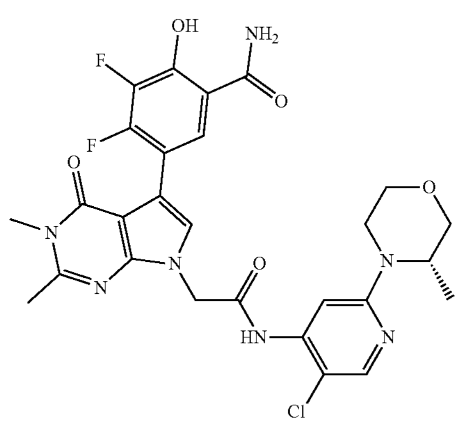 |

-continued
| Compound | Structure |
|---|---|
| I-250 | 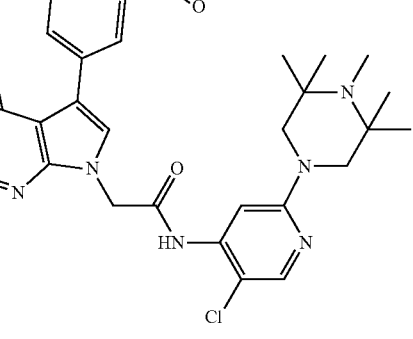 |
| I-251 | 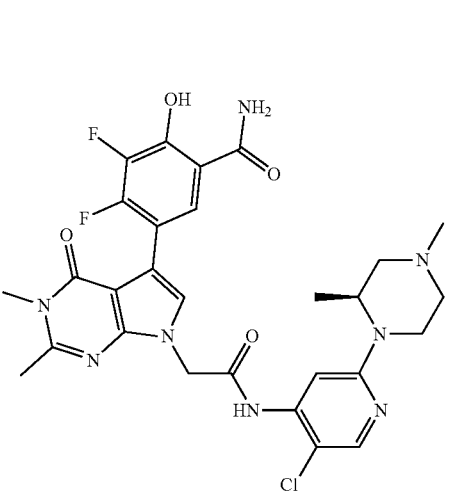 |
| I-252 | 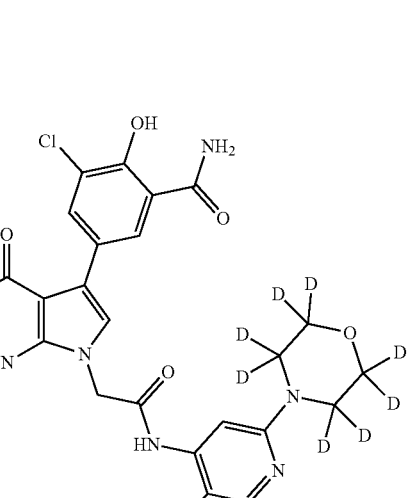 |

| Compound | Structure |
|---|---|
| I-253 | 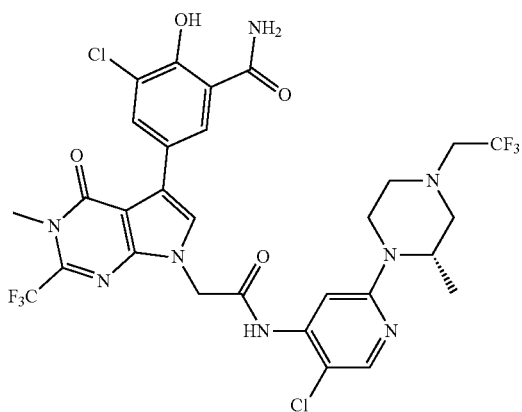 [SMILES: C[C@H]1CN(CC(F)(F)F)CCN1c1cc(NC(=O)Cn2cc(-c3cc(Cl)c(O)c(C(N)=O)c3)c3c(=O)n(C)c(C(F)(F)F)nc32)c(Cl)cn1] |
| I-254 | 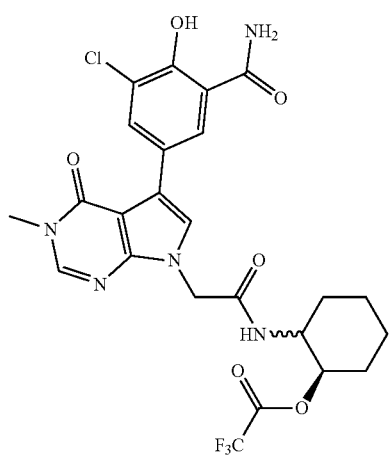 [SMILES: Cn1cnc2c(c(-c3cc(Cl)c(O)c(C(N)=O)c3)cn2CC(=O)NC2CCCC[C@H]2OC(=O)C(F)(F)F)c1=O] |
| I-255 | 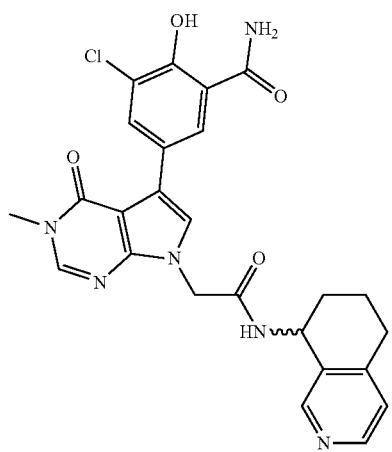 [SMILES: Cn1cnc2c(c(-c3cc(Cl)c(O)c(C(N)=O)c3)cn2CC(=O)NC2CCCc3ccncc32)c1=O] |

-continued
| Compound | Structure |
|---|---|
| I-256 | 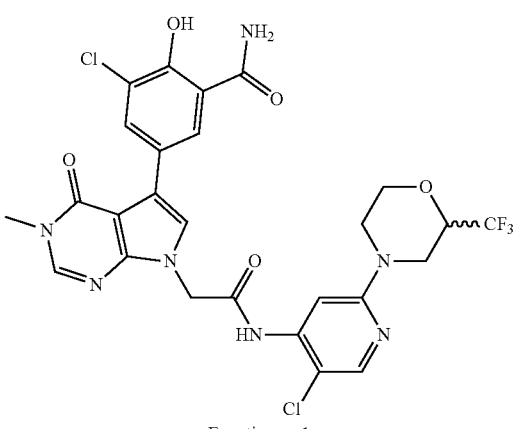<br>Enantiomer 1 |
| I-257 | 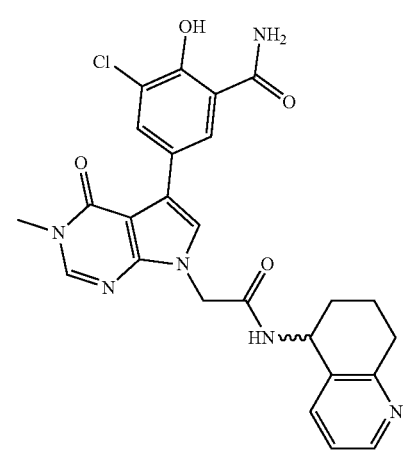 [SMILES: Cn1cnc2c(c(-c3cc(Cl)c(O)c(C(N)=O)c3)cn2CC(=O)NC2CCCc3ncccc32)c1=O] |
| I-258 | 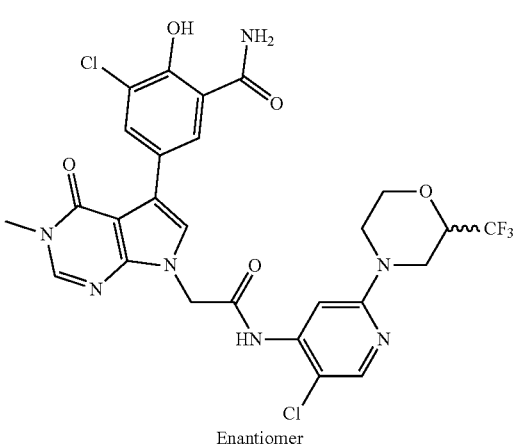<br>Enantiomer |

| Compound | Structure |
|---|---|
| I-259 | 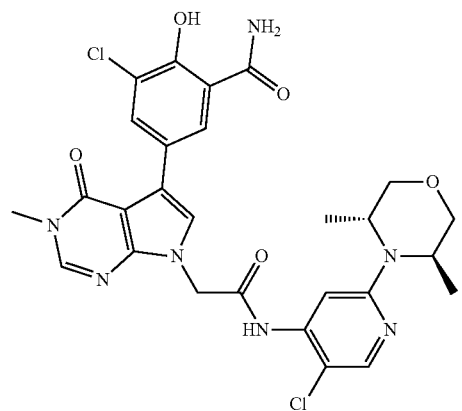 |
| I-260 | 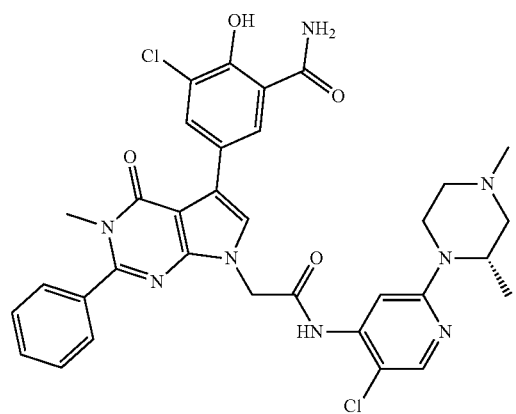 [SMILES: C[C@H]1CN(C)CCN1c1cc(NC(=O)Cn2cc(-c3cc(Cl)c(O)c(C(N)=O)c3)c3c(=O)n(C)c(-c4ccccc4)nc32)c(Cl)cn1] |
| I-261 | 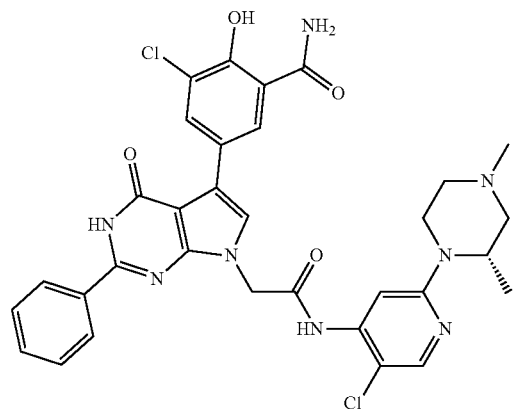 [SMILES: C[C@H]1CN(C)CCN1c1cc(NC(=O)Cn2cc(-c3cc(Cl)c(O)c(C(N)=O)c3)c3c(=O)[nH]c(-c4ccccc4)nc32)c(Cl)cn1] |

-continued
| Compound | Structure |
|---|---|
| I-262 | 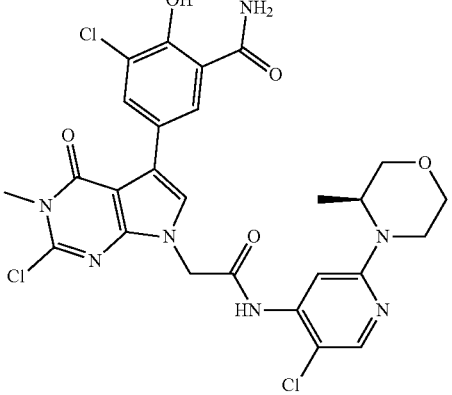 |
| I-263 | 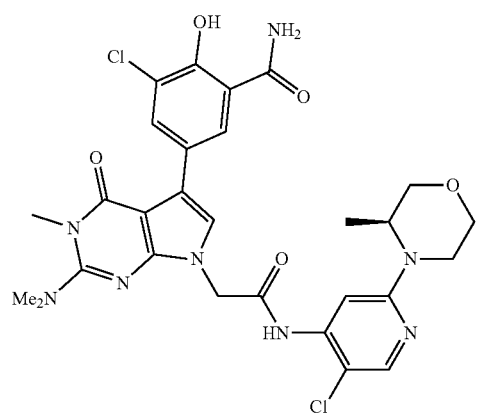 [SMILES: C[C@H]1COCCN1c1cc(NC(=O)Cn2cc(-c3cc(Cl)c(O)c(C(N)=O)c3)c3c(=O)n(C)c(N(C)C)nc32)c(Cl)cn1] |
| I-264 | 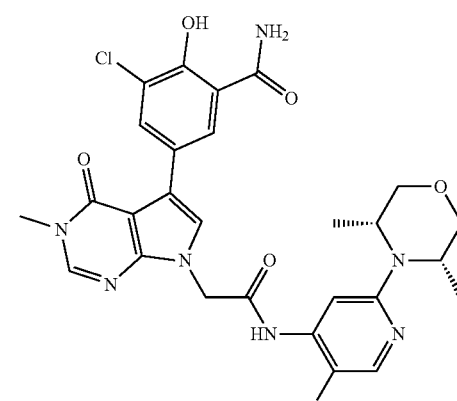 |

| Compound | Structure |
|---|---|
| I-265 | 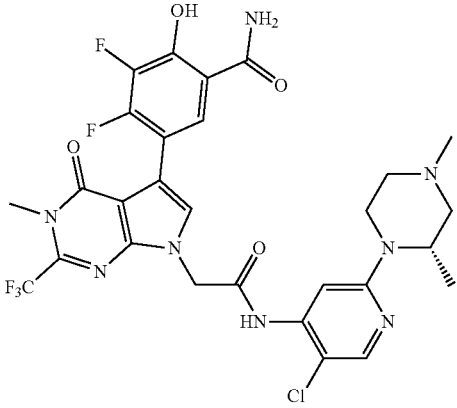 |
| I-266 | 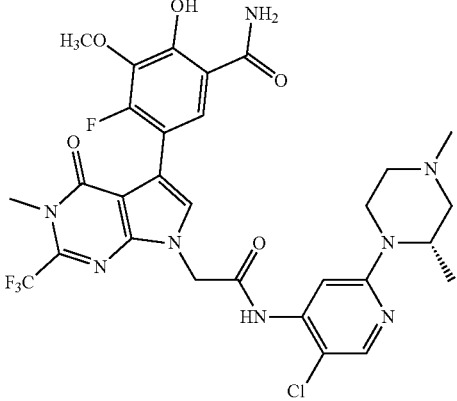 |
| I-267 | 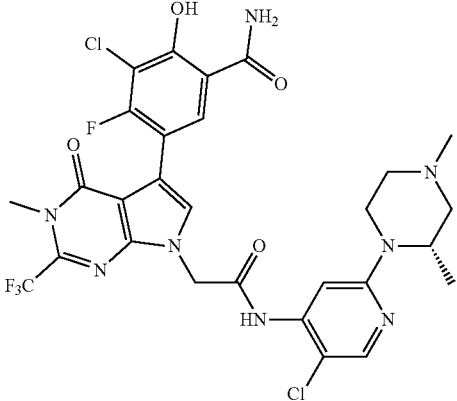 |

| Compound | Structure |
|---|---|
| I-268 | 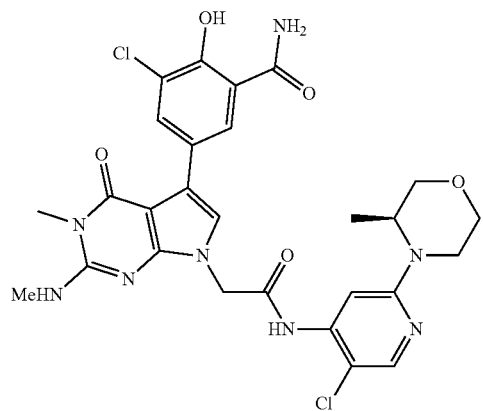 [SMILES: CNc1nc2c(c(-c3cc(Cl)c(O)c(C(N)=O)c3)cn2CC(=O)Nc2cc(N3CCOC[C@@H]3C)ncc2Cl)c(=O)n1C] |
| I-269 | 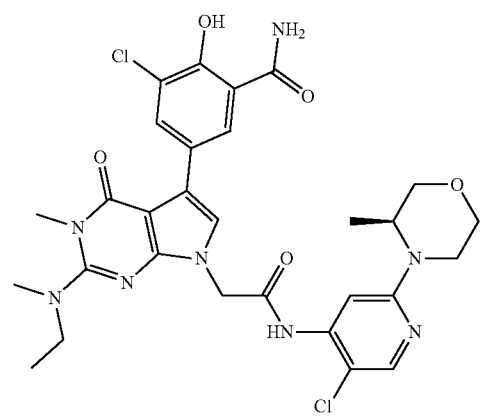 [SMILES: CCN(C)c1nc2c(c(-c3cc(Cl)c(O)c(C(N)=O)c3)cn2CC(=O)Nc2cc(N3CCOC[C@@H]3C)ncc2Cl)c(=O)n1C] |
| I-270 | 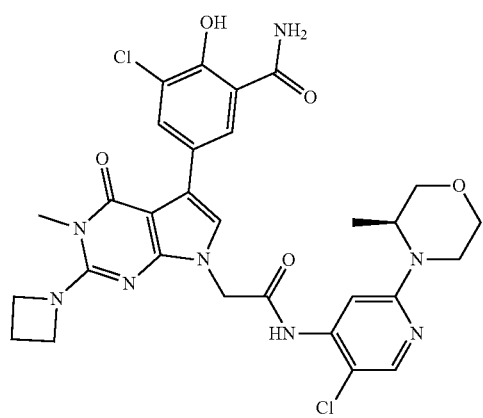 [SMILES: C[C@H]1COCCN1c1cc(NC(=O)Cn2cc(-c3cc(Cl)c(O)c(C(N)=O)c3)c3c(=O)n(C)c(N4CCC4)nc32)c(Cl)cn1] |

| Compound | Structure |
|---|---|
| I-271 | 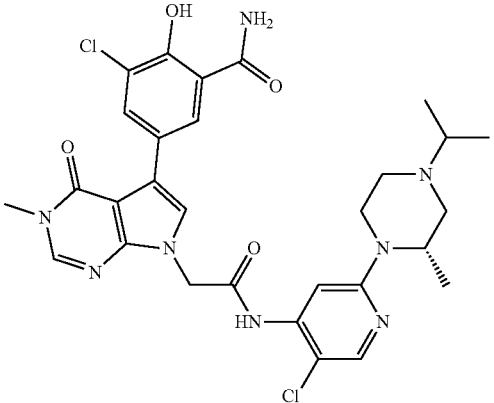 [SMILES: Cc1nc2c(c(-c3cc(Cl)c(O)c(C(N)=O)c3)cn2CC(=O)Nc2cc(N3CCN(C(C)C)C[C@@H]3C)ncc2Cl)c(=O)n1C] |
| I-272 | 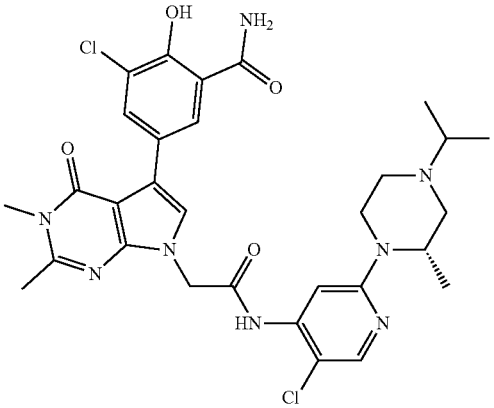 |
| I-273 | 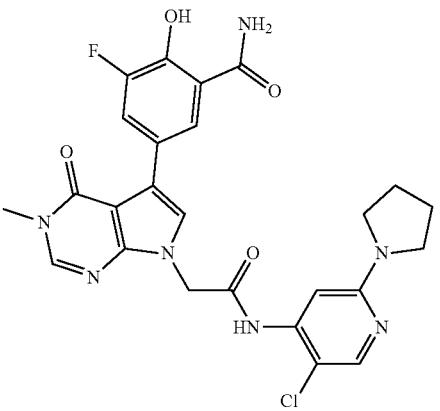 [SMILES: Cn1cnc2c(c(-c3cc(F)c(O)c(C(N)=O)c3)cn2CC(=O)Nc2cc(N3CCCC3)ncc2Cl)c1=O] |

| Compound | Structure |
|---|---|
| I-274 | 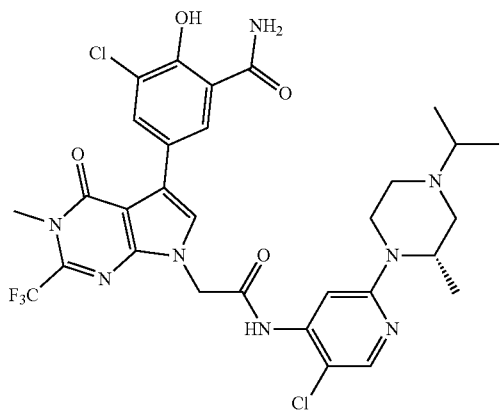 [SMILES: CC(C)N1CCN(c2cc(NC(=O)Cn3cc(-c4cc(Cl)c(O)c(C(N)=O)c4)c4c(=O)n(C)c(C(F)(F)F)nc43)c(Cl)cn2)[C@@H](C)C1] |
| I-275 | 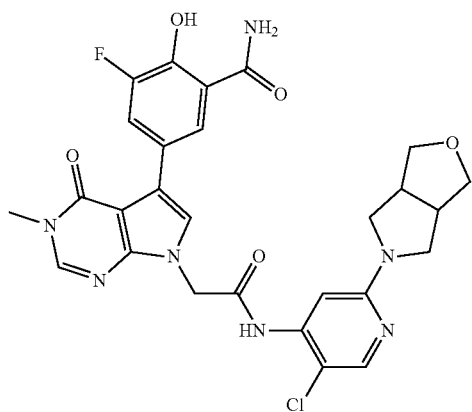 [SMILES: Cn1cnc2c(c(-c3cc(F)c(O)c(C(N)=O)c3)cn2CC(=O)Nc2cc(N3CC4COCC4C3)ncc2Cl)c1=O] |
| I-276 | 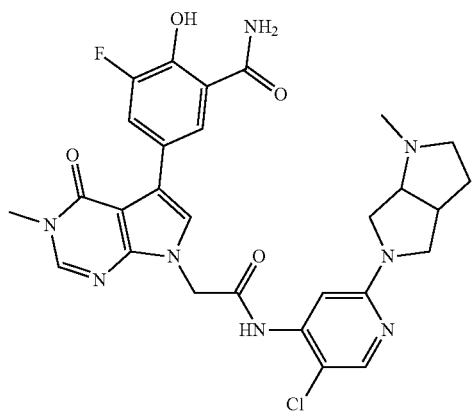 [SMILES: CN1CCC2CN(c3cc(NC(=O)Cn4cc(-c5cc(F)c(O)c(C(N)=O)c5)c5c(=O)n(C)cnc54)c(Cl)cn3)CC21] |

-continued
| Compound | Structure |
|---|---|
| I-277 | 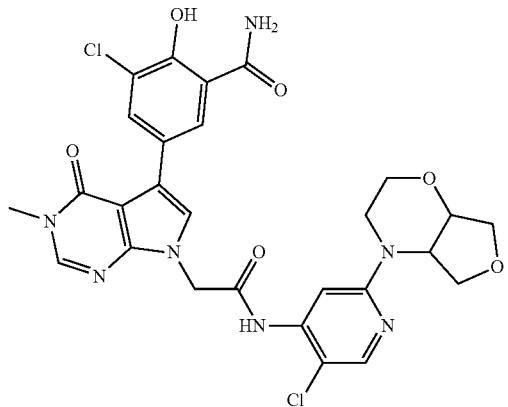 [SMILES: Cn1cnc2c(c(-c3cc(Cl)c(O)c(C(N)=O)c3)cn2CC(=O)Nc2cc(N3CCOC4COCC43)ncc2Cl)c1=O] |
| I-278 | 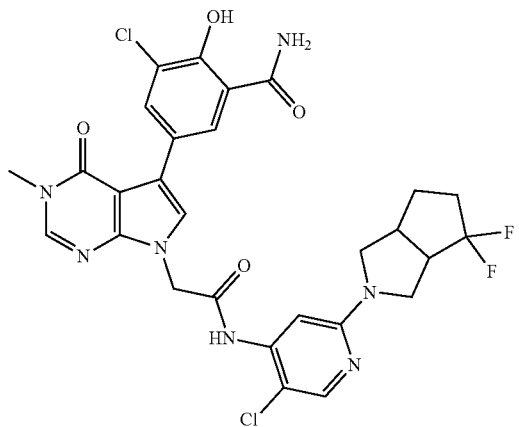 [SMILES: Cn1cnc2c(c(-c3cc(Cl)c(O)c(C(N)=O)c3)cn2CC(=O)Nc2cc(N3CC4CCC(F)(F)C4C3)ncc2Cl)c1=O] |
| I-279 | 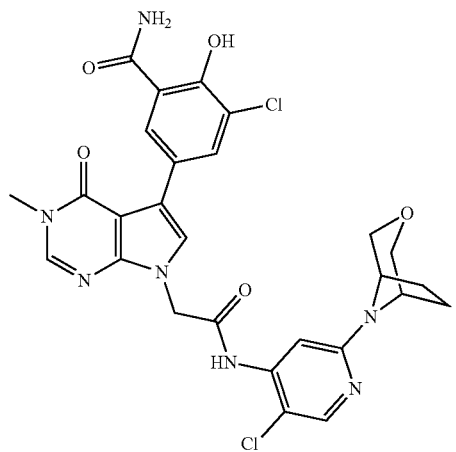 [SMILES: Cn1cnc2c(c(-c3cc(Cl)c(O)c(C(N)=O)c3)cn2CC(=O)Nc2cc(N3C4CCC3COC4)ncc2Cl)c1=O] |

-continued
| Compound | Structure |
|---|---|
| I-280 | 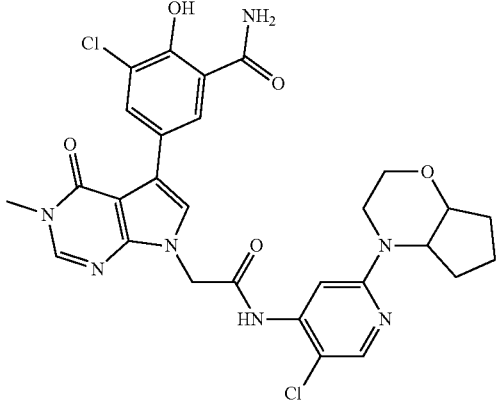 [SMILES: Cn1cnc2c(c(-c3cc(Cl)c(O)c(C(N)=O)c3)cn2CC(=O)Nc2cc(N3CCOC4CCCC43)ncc2Cl)c1=O] |
| I-281 | 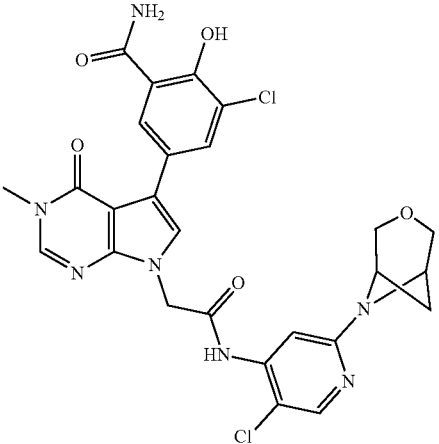 [SMILES: Cn1cnc2c(c(-c3cc(Cl)c(O)c(C(N)=O)c3)cn2CC(=O)Nc2cc(N3C4COCC3C4)ncc2Cl)c1=O] |
| I-282 | 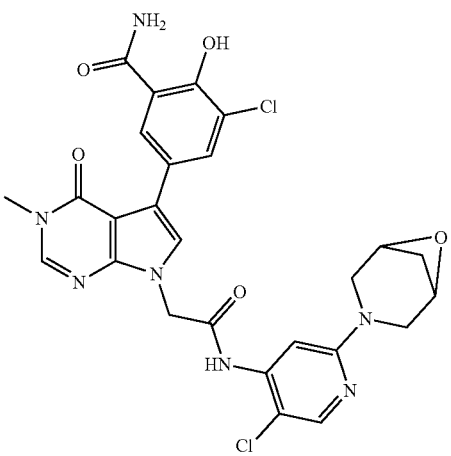 [SMILES: Cn1cnc2c(c(-c3cc(Cl)c(O)c(C(N)=O)c3)cn2CC(=O)Nc2cc(N3CC4CC(C3)O4)ncc2Cl)c1=O] |

| Compound | Structure |
|---|---|
| I-283 | 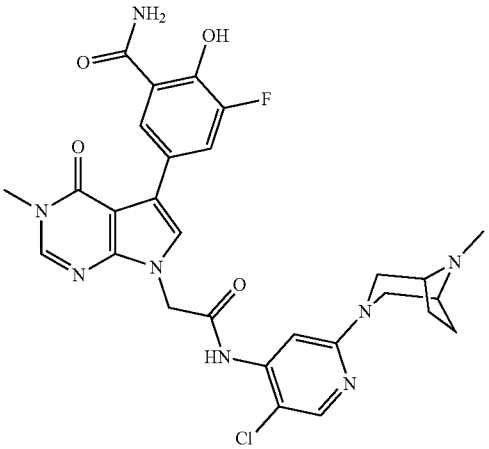 |
| I-284 | 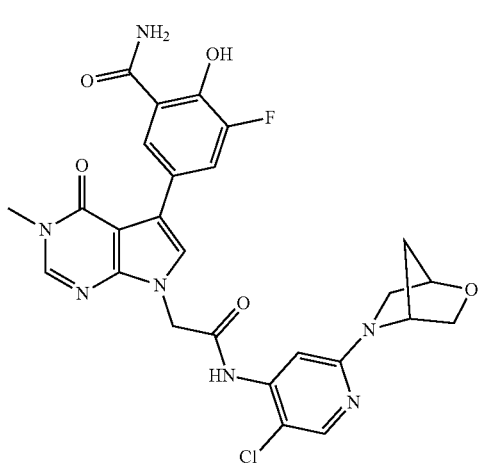 [SMILES: Cn1cnc2c(c(-c3cc(F)c(O)c(C(N)=O)c3)cn2CC(=O)Nc2cc(N3CC4CC3CO4)ncc2Cl)c1=O] |
| I-285 | 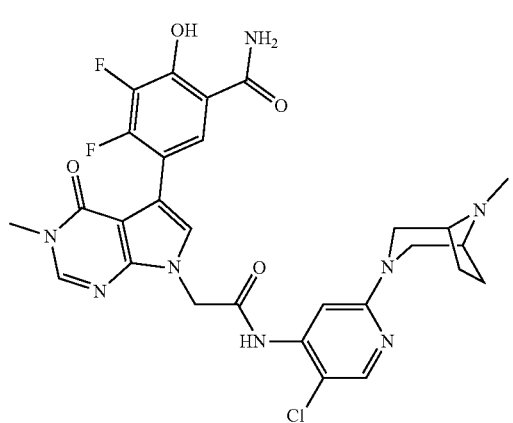 |

-continued
| Compound | Structure |
|---|---|
| I-286 | 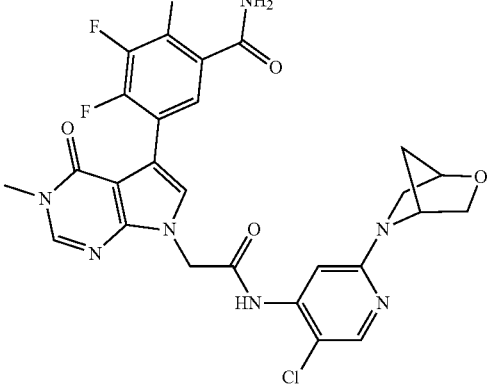 |
| I-287 | 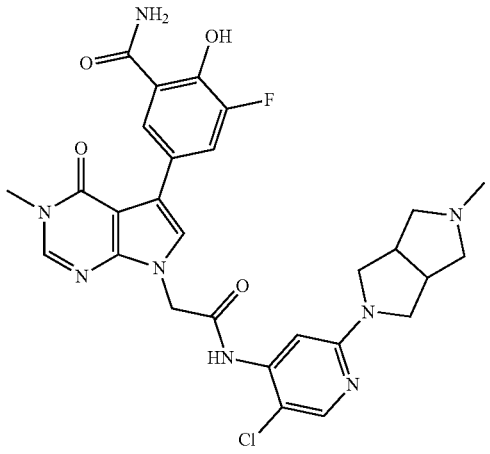 |
| I-288 | 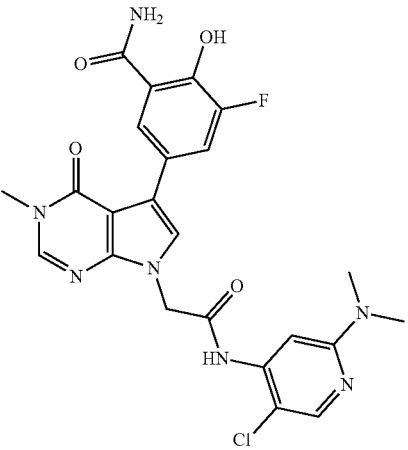 |

| Compound | Structure |
|---|---|
| I-289 | 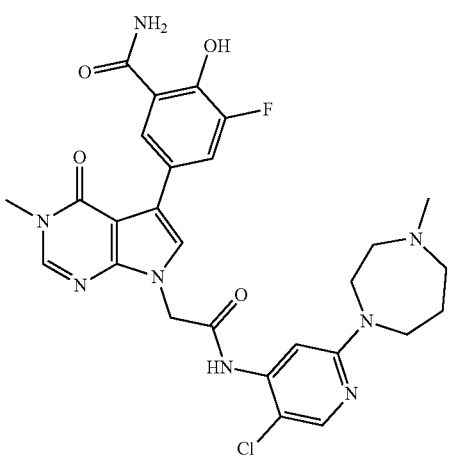 [SMILES: CN1CCCN(c2cc(NC(=O)Cn3cc(-c4cc(F)c(O)c(C(N)=O)c4)c4c(=O)n(C)cnc43)c(Cl)cn2)CC1] |
| I-290 | 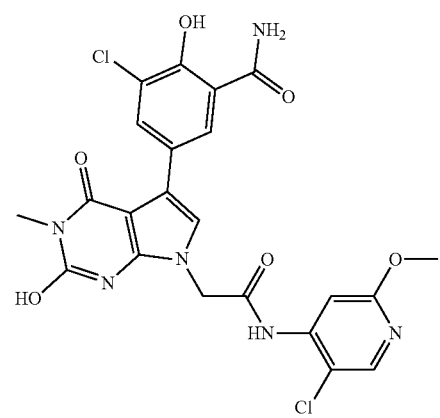 |
| I-291 | 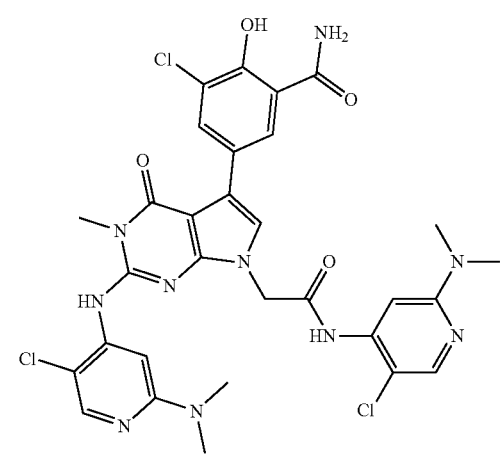 [SMILES: CN(C)c1cc(NC(=O)Cn2cc(-c3cc(Cl)c(O)c(C(N)=O)c3)c3c(=O)n(C)c(Nc4cc(N(C)C)ncc4Cl)nc32)c(Cl)cn1] |

| Compound | Structure |
|---|---|
| I-292 | 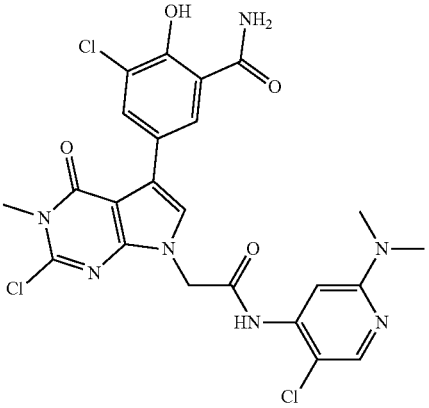 |
| I-293 | 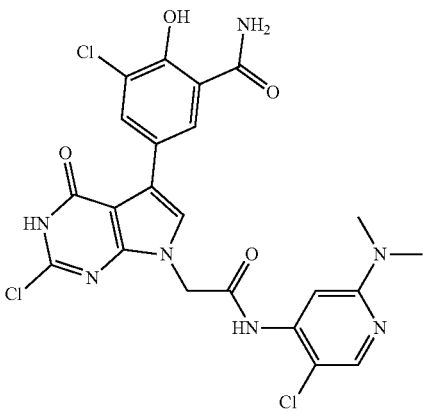 [SMILES: CN(C)c1cc(NC(=O)Cn2cc(-c3cc(Cl)c(O)c(C(N)=O)c3)c3c(=O)[nH]c(Cl)nc32)c(Cl)cn1] |
| I-294 | 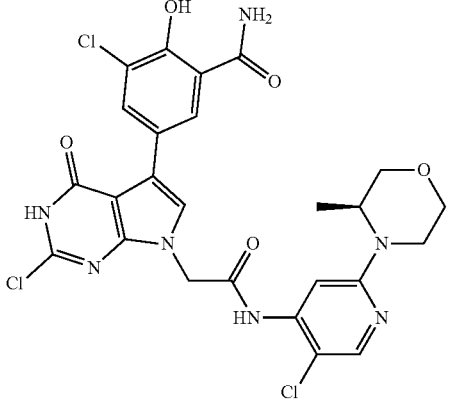 [SMILES: C[C@H]1COCCN1c1cc(NC(=O)Cn2cc(-c3cc(Cl)c(O)c(C(N)=O)c3)c3c(=O)[nH]c(Cl)nc32)c(Cl)cn1] |

| Compound | Structure |
| --- | --- |
| I-295 | 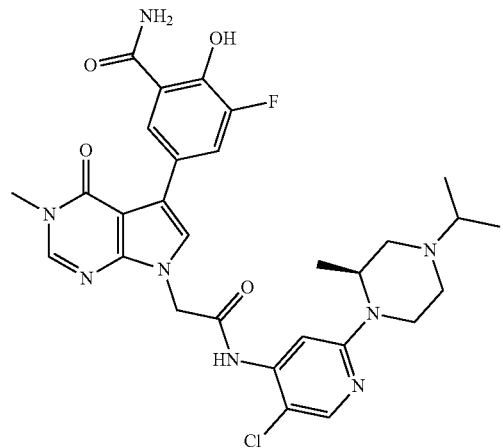 [SMILES: CC(C)N1CCN(c2cc(NC(=O)Cn3cc(-c4cc(F)c(O)c(C(N)=O)c4)c4c(=O)n(C)cnc43)c(Cl)cn2)[C@@H](C)C1] |
| I-296 | 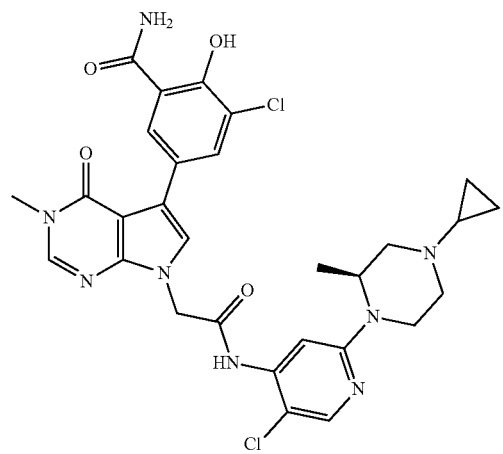 [SMILES: C[C@H]1CN(C2CC2)CCN1c1cc(NC(=O)Cn2cc(-c3cc(Cl)c(O)c(C(N)=O)c3)c3c(=O)n(C)cnc32)c(Cl)cn1] |
| I-297 | 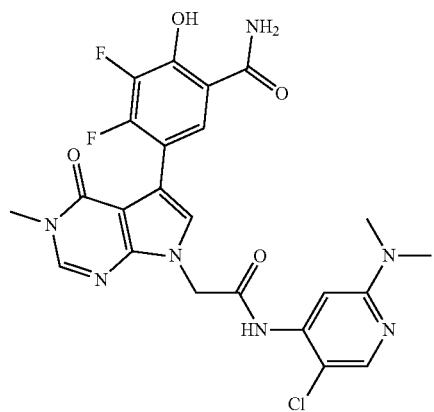 |

| Compound | Structure |
|---|---|
| I-298 | 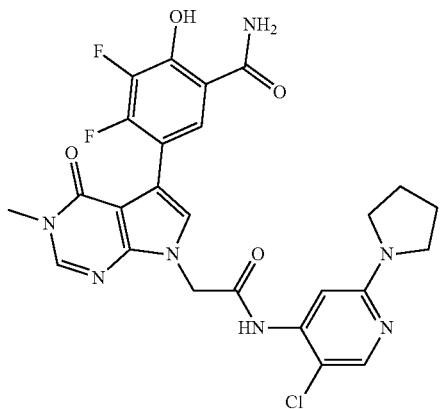 [SMILES: Cn1cnc2c(c(-c3cc(C(N)=O)c(O)c(F)c3F)cn2CC(=O)Nc2cc(N3CCCC3)ncc2Cl)c1=O] |
| I-299 | 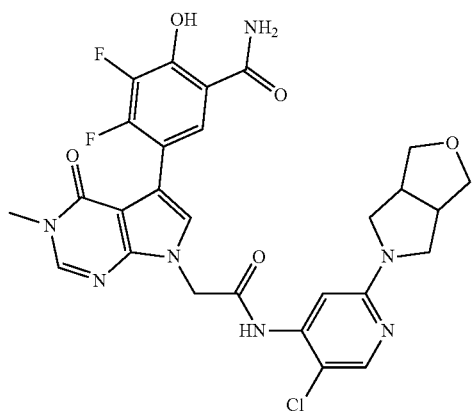 [SMILES: Cn1cnc2c(c(-c3cc(C(N)=O)c(O)c(F)c3F)cn2CC(=O)Nc2cc(N3CC4COCC4C3)ncc2Cl)c1=O] |
| I-300 | 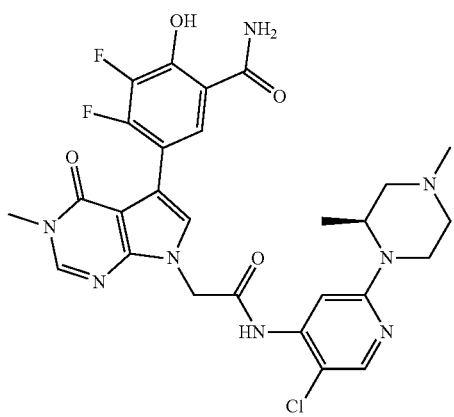 |

| Compound | Structure |
|---|---|
| I-301 | 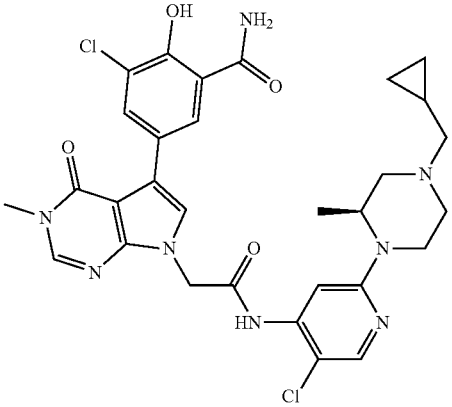 [SMILES: C[C@H]1CN(CC2CC2)CCN1c1cc(NC(=O)Cn2cc(-c3cc(Cl)c(O)c(C(N)=O)c3)c3c(=O)n(C)cnc32)c(Cl)cn1] |
| I-302 | 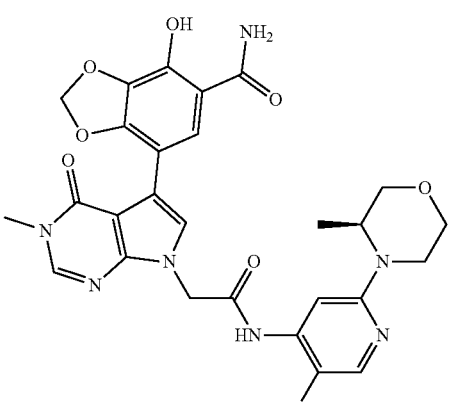 |
| I-303 | 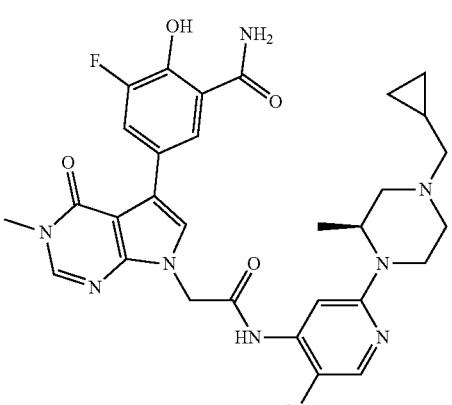 |

-continued
| Compound | Structure |
|---|---|
| I-304 | 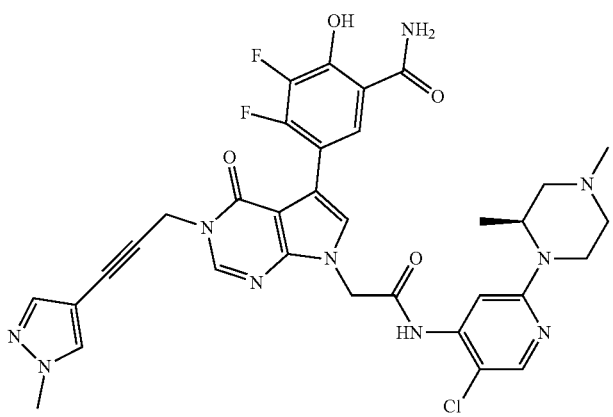 [SMILES: C[C@H]1CN(C)CCN1c1cc(NC(=O)Cn2cc(-c3cc(C(N)=O)c(O)c(F)c3F)c3c(=O)n(CC#Cc4cnn(C)c4)cnc32)c(Cl)cn1] |
| I-305 | 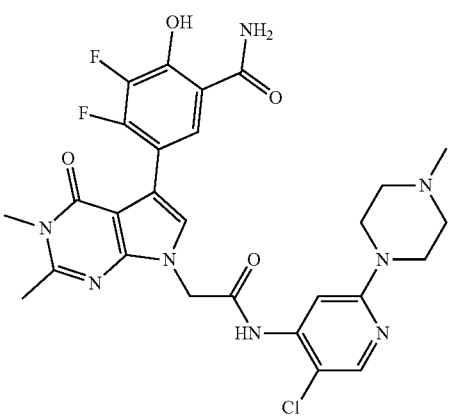 |
| I-306 | 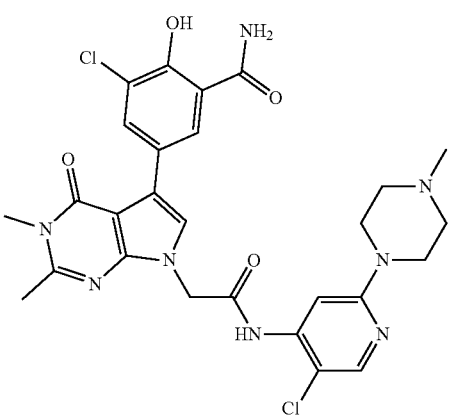 |

-continued
| Compound | Structure |
|---|---|
| I-307 | 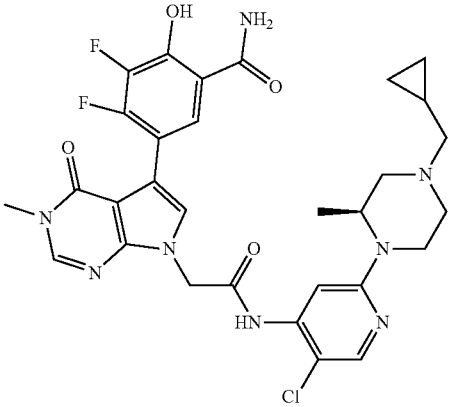 [SMILES: C[C@H]1CN(CC2CC2)CCN1c1cc(NC(=O)Cn2cc(-c3cc(C(N)=O)c(O)c(F)c3F)c3c(=O)n(C)cnc32)c(Cl)cn1] |
| I-308 | 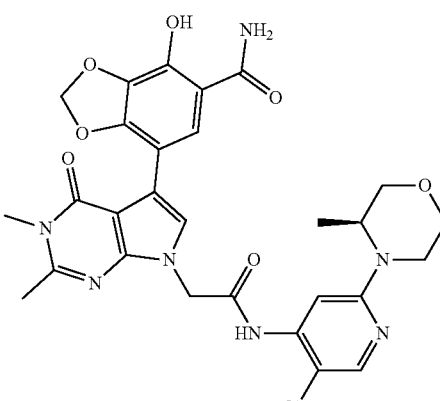 |
| I-309 | 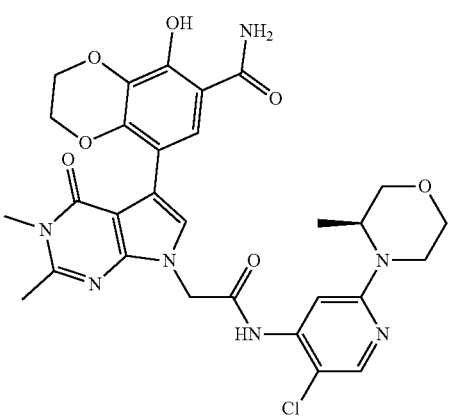 [SMILES: Cc1nc2c(c(-c3cc(C(N)=O)c(O)c4c3OCCO4)cn2CC(=O)Nc2cc(N3CCOC[C@@H]3C)ncc2Cl)c(=O)n1C] |

| Compound | Structure |
|---|---|
| I-310 | 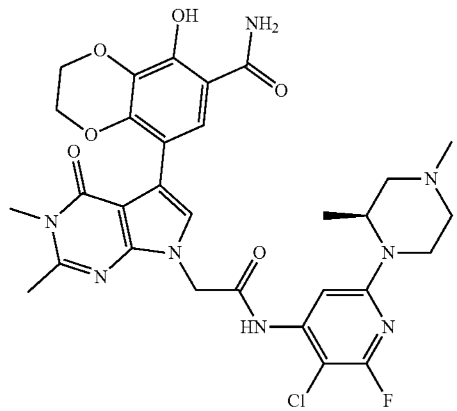 |
| I-311 | 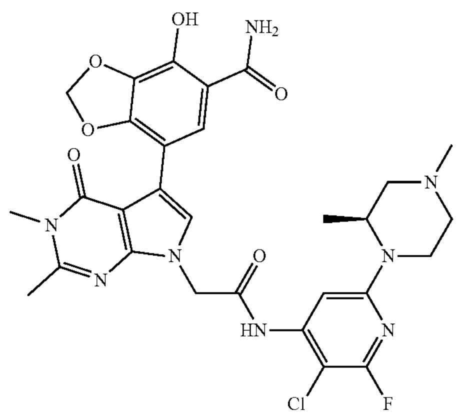 |
| I-312 | 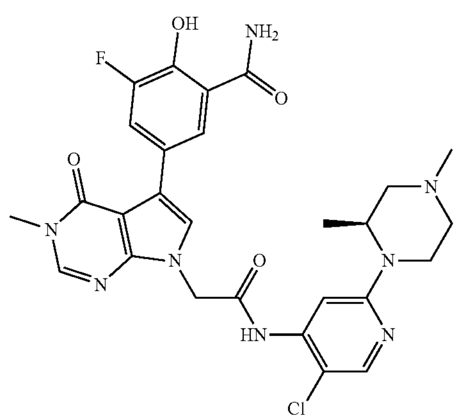 |

-continued
| Compound | Structure |
|---|---|
| I-313 | 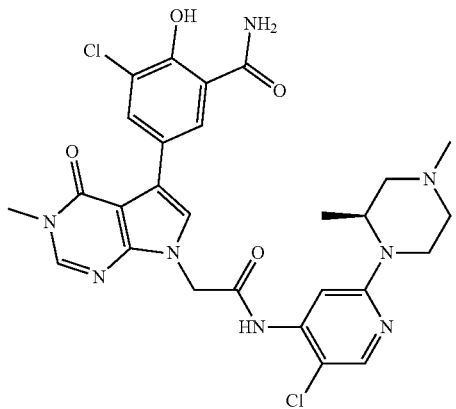 |
| I-314 | 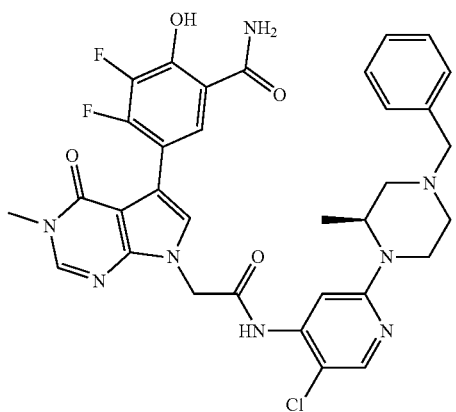 [SMILES: C[C@H]1CN(Cc2ccccc2)CCN1c1cc(NC(=O)Cn2cc(-c3cc(C(N)=O)c(O)c(F)c3F)c3c(=O)n(C)cnc32)c(Cl)cn1] |
| I-315 | 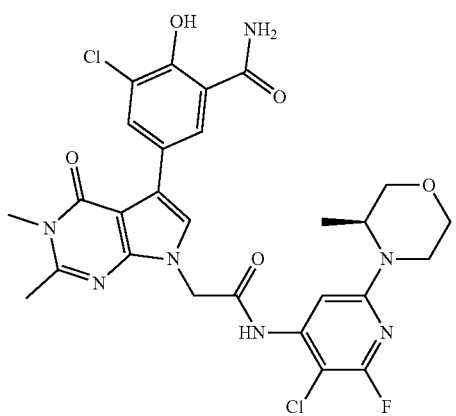 [SMILES: Cc1nc2c(c(-c3cc(Cl)c(O)c(C(N)=O)c3)cn2CC(=O)Nc2cc(N3CCOC[C@@H]3C)nc(F)c2Cl)c(=O)n1C] |

| Compound | Structure |
|---|---|
| I-316 | 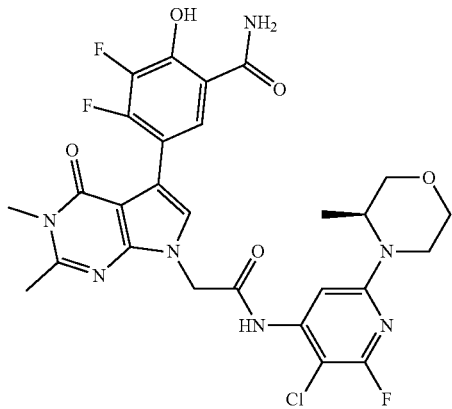 [SMILES: Cc1nc2c(c(-c3cc(C(N)=O)c(O)c(F)c3F)cn2CC(=O)Nc2cc(N3CCOC[C@@H]3C)nc(F)c2Cl)c(=O)n1C] |
| I-317 | 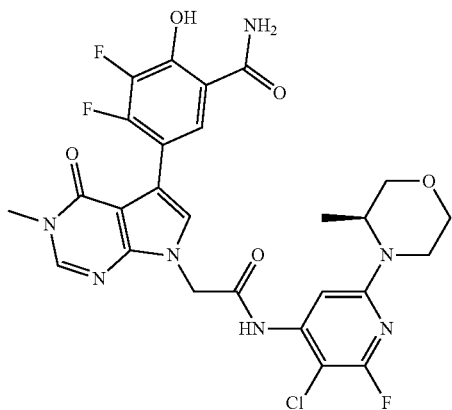 [SMILES: C[C@H]1COCCN1c1cc(NC(=O)Cn2cc(-c3cc(C(N)=O)c(O)c(F)c3F)c3c(=O)n(C)cnc32)c(Cl)c(F)n1] |
| I-318 | 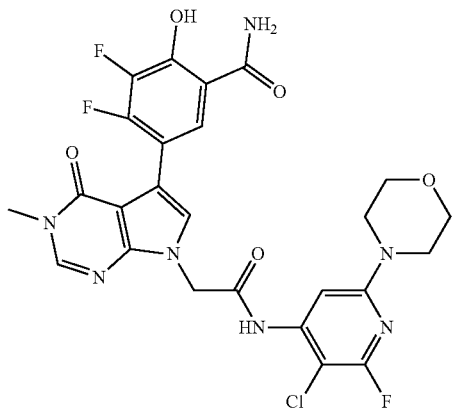 [SMILES: Cn1cnc2c(c(-c3cc(C(N)=O)c(O)c(F)c3F)cn2CC(=O)Nc2cc(N3CCOCC3)nc(F)c2Cl)c1=O] |

| Compound | Structure |
|---|---|
| I-319 | 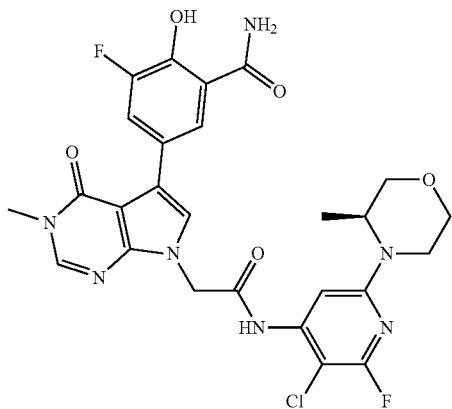 [SMILES: C[C@H]1COCCN1c1cc(NC(=O)Cn2cc(-c3cc(F)c(O)c(C(N)=O)c3)c3c(=O)n(C)cnc32)c(Cl)c(F)n1] |
| I-320 | 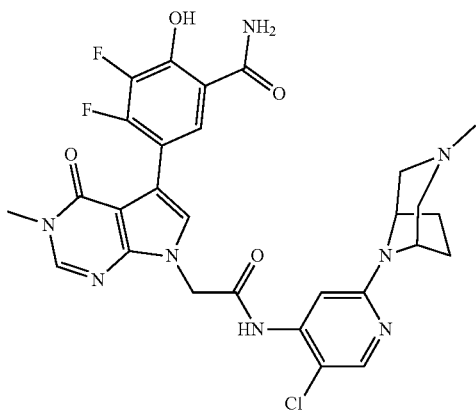 |
| I-321 | 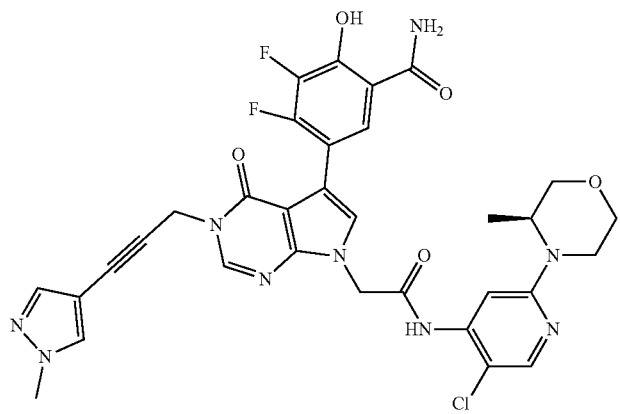 [SMILES: C[C@H]1COCCN1c1cc(NC(=O)Cn2cc(-c3cc(C(N)=O)c(O)c(F)c3F)c3c(=O)n(CC#Cc4cnn(C)c4)cnc32)c(Cl)cn1] |

-continued
| Compound | Structure |
|---|---|
| I-322 | 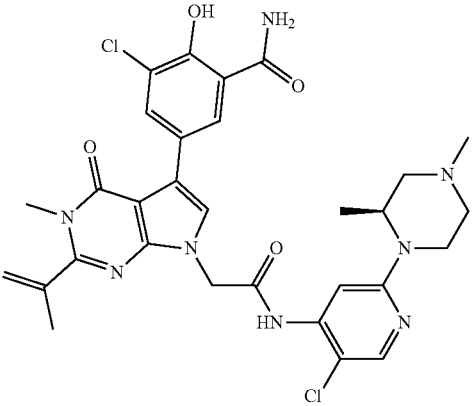 [SMILES: C=C(C)c1nc2c(c(-c3cc(Cl)c(O)c(C(N)=O)c3)cn2CC(=O)Nc2cc(N3CCN(C)C[C@@H]3C)ncc2Cl)c(=O)n1C] |
| I-323 | 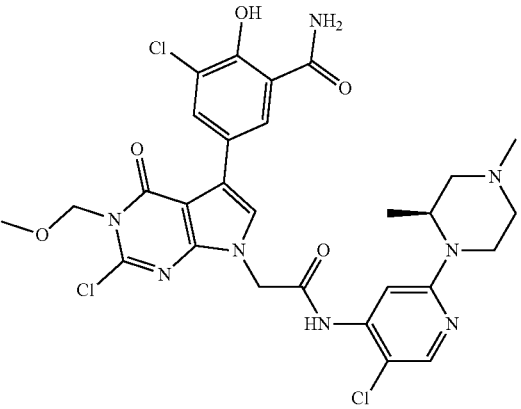 |
| I-324 | 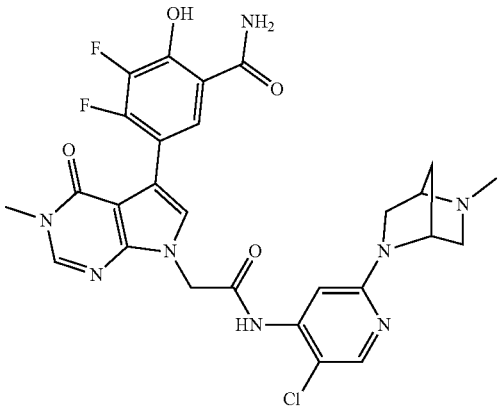 |

-continued
| Compound | Structure |
|---|---|
| I-325 | 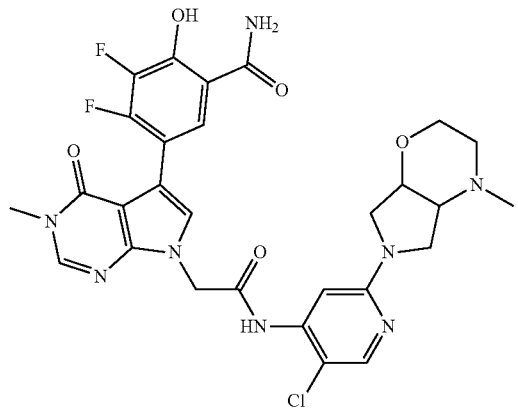 |
| I-326 | 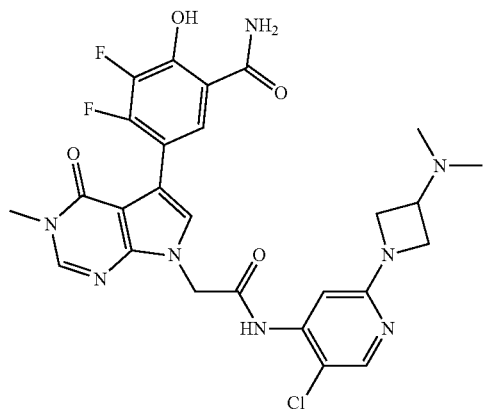 |
| I-327 | 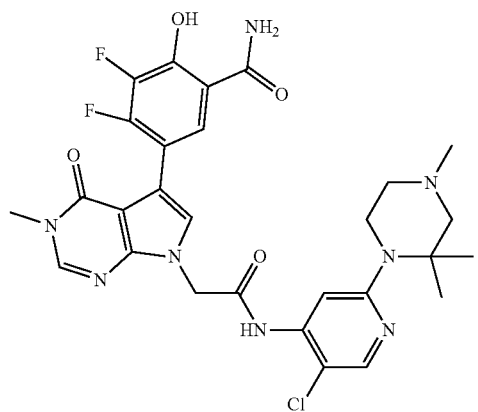 |

-continued
| Compound | Structure |
|---|---|
| I-328 | 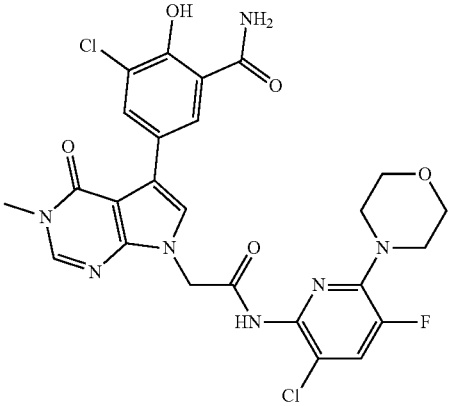 [SMILES: Cn1cnc2c(c(-c3cc(Cl)c(O)c(C(N)=O)c3)cn2CC(=O)Nc2nc(N3CCOCC3)c(F)cc2Cl)c1=O] |
| I-329 | 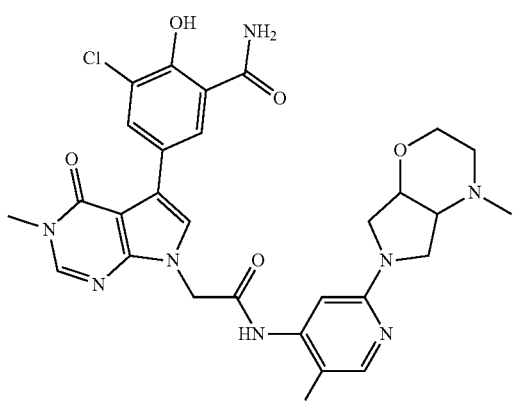 |
| I-330 | 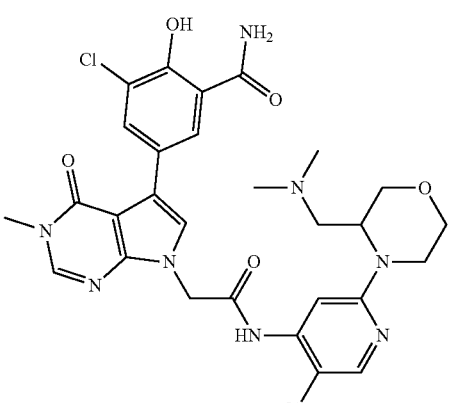 |

| Compound | Structure |
|---|---|
| I-331 | 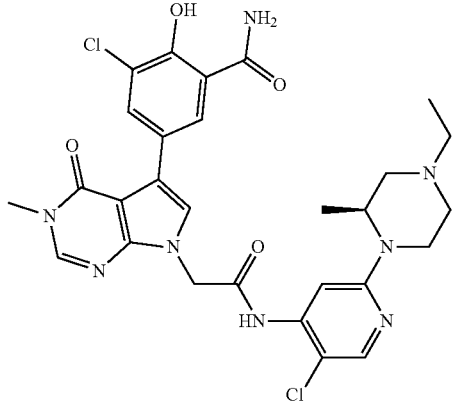 [SMILES: CCN1CCN(c2cc(NC(=O)Cn3cc(-c4cc(Cl)c(O)c(C(N)=O)c4)c4c(=O)n(C)cnc43)c(Cl)cn2)[C@@H](C)C1] |
| I-332 | 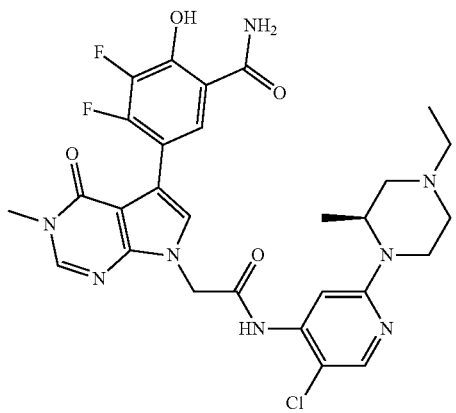 [SMILES: CCN1CCN(c2cc(NC(=O)Cn3cc(-c4cc(C(N)=O)c(O)c(F)c4F)c4c(=O)n(C)cnc43)c(Cl)cn2)[C@@H](C)C1] |
| I-333 | 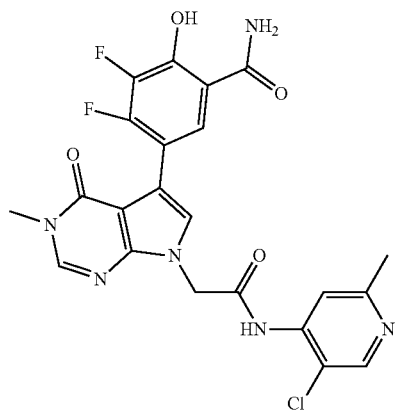 |

-continued
| Compound | Structure |
|---|---|
| I-334 | 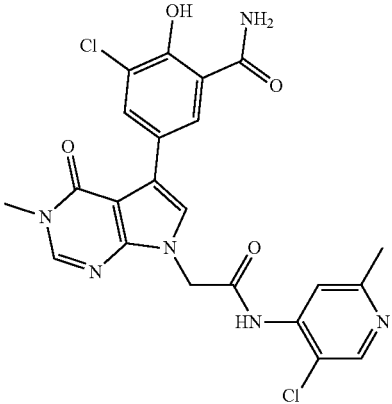 |
| I-335 | 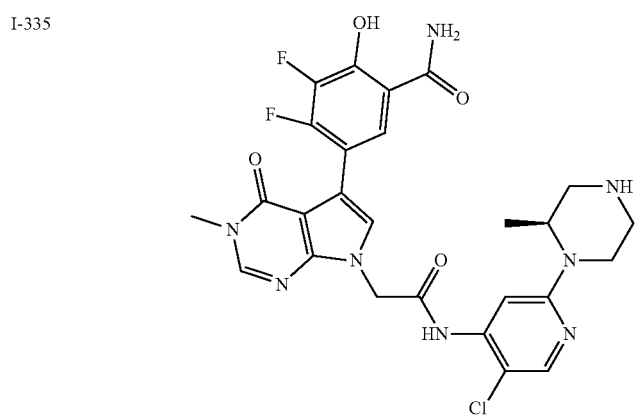 |
| I-336 | 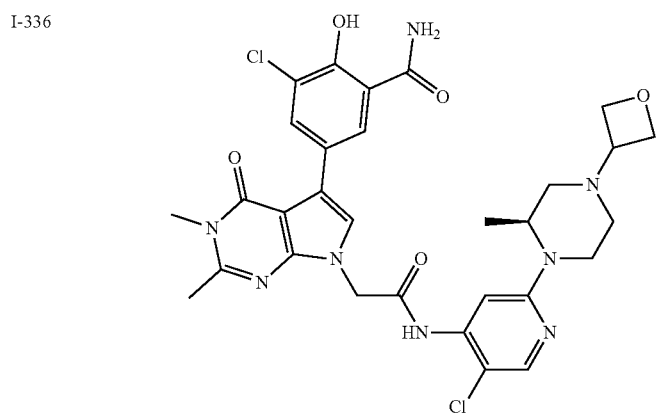 |

-continued
| Compound | Structure |
|---|---|
| I-337 | 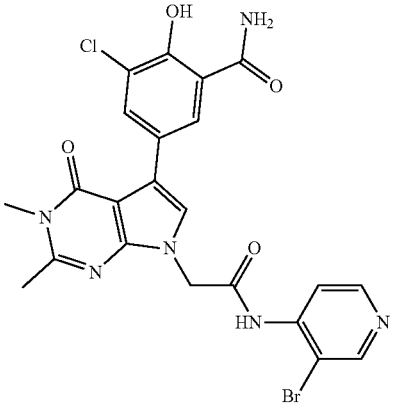 [SMILES: Cc1nc2c(c(-c3cc(Cl)c(O)c(C(N)=O)c3)cn2CC(=O)Nc2ccncc2Br)c(=O)n1C] |
| I-338 | 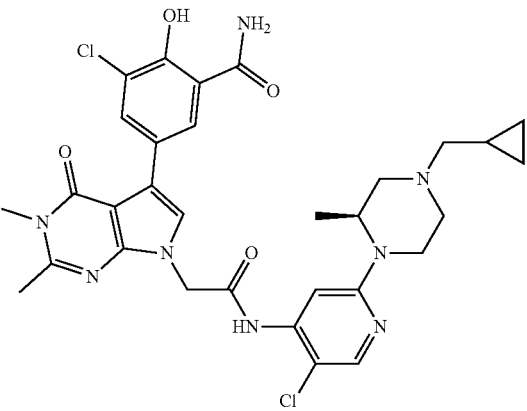 [SMILES: Cc1nc2c(c(-c3cc(Cl)c(O)c(C(N)=O)c3)cn2CC(=O)Nc2cc(N3CCN(CC4CC4)C[C@@H]3C)ncc2Cl)c(=O)n1C] |
| I-339 | 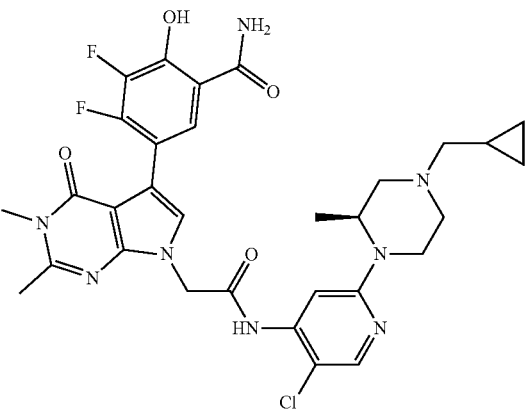 [SMILES: Cc1nc2c(c(-c3cc(C(N)=O)c(O)c(F)c3F)cn2CC(=O)Nc2cc(N3CCN(CC4CC4)C[C@@H]3C)ncc2Cl)c(=O)n1C] |

| Compound | Structure |
|---|---|
| I-340 | 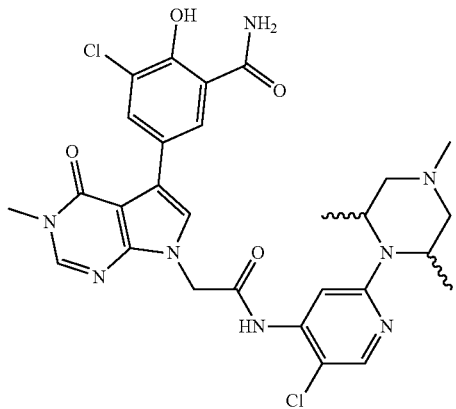 |
| I-341 | 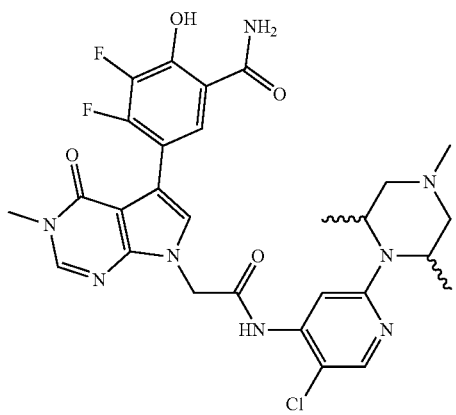 |
| I-342 | 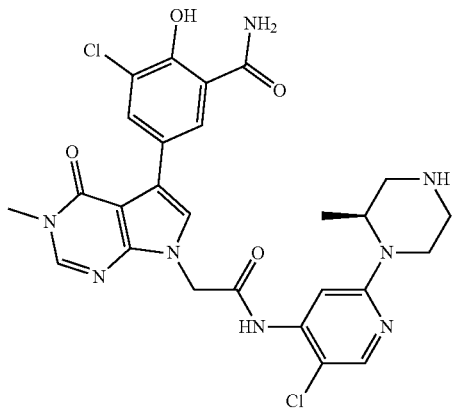 [SMILES: C[C@H]1CNCCN1c1cc(NC(=O)Cn2cc(-c3cc(Cl)c(O)c(C(N)=O)c3)c3c(=O)n(C)cnc32)c(Cl)cn1] |

| Compound | Structure |
|---|---|
| I-343 | 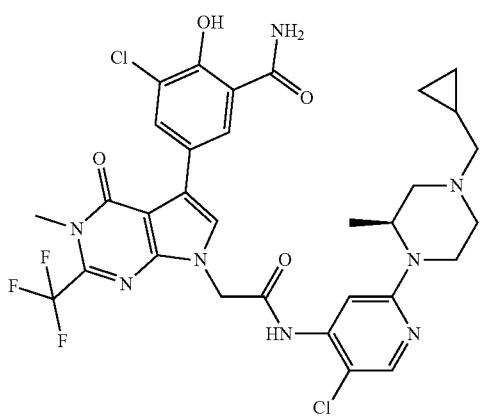 [SMILES: C[C@H]1CN(CC2CC2)CCN1c1cc(NC(=O)Cn2cc(-c3cc(Cl)c(O)c(C(N)=O)c3)c3c(=O)n(C)c(C(F)(F)F)nc32)c(Cl)cn1] |
| I-344 | 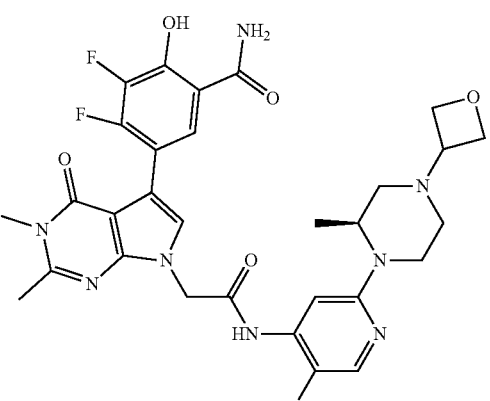 |
| I-345 | 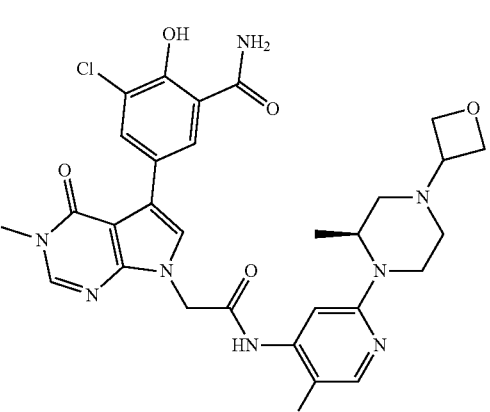 |

| Compound | Structure |
|---|---|
| I-346 | 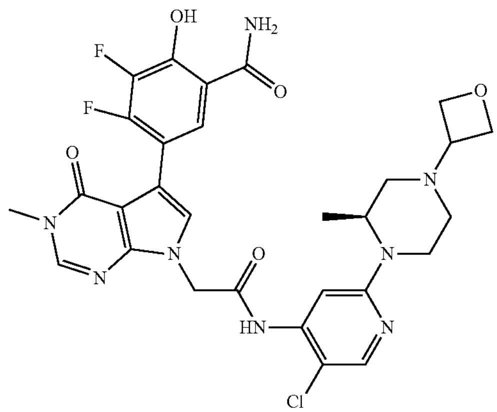 [SMILES: C[C@H]1CN(C2COC2)CCN1c1cc(NC(=O)Cn2cc(-c3cc(C(N)=O)c(O)c(F)c3F)c3c(=O)n(C)cnc32)c(Cl)cn1] |
| I-347 | 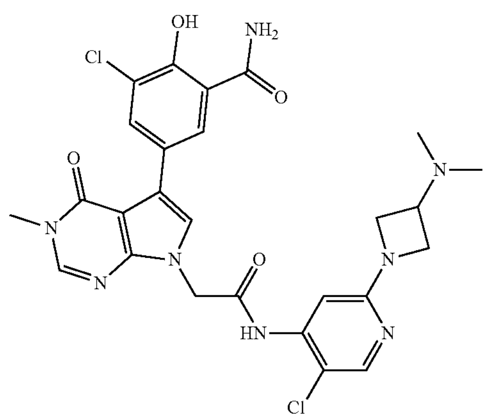 |
| I-348 | 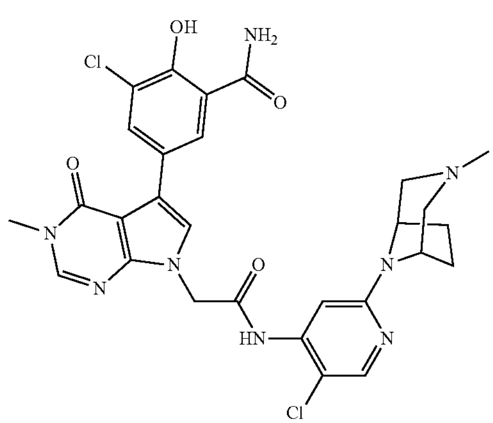 |

-continued
| Compound | Structure |
|---|---|
| I-349 | 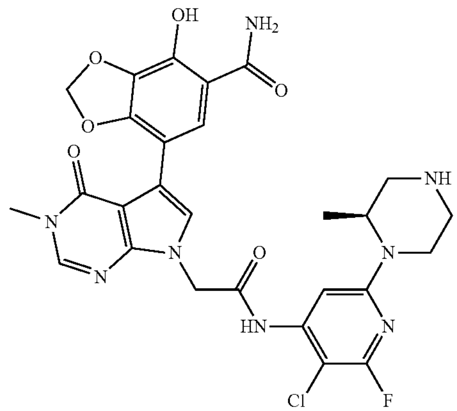 [SMILES: C[C@H]1CNCCN1c1cc(NC(=O)Cn2cc(-c3cc(C(N)=O)c(O)c4c3OCO4)c3c(=O)n(C)cnc32)c(Cl)c(F)n1] |
| I-350 | 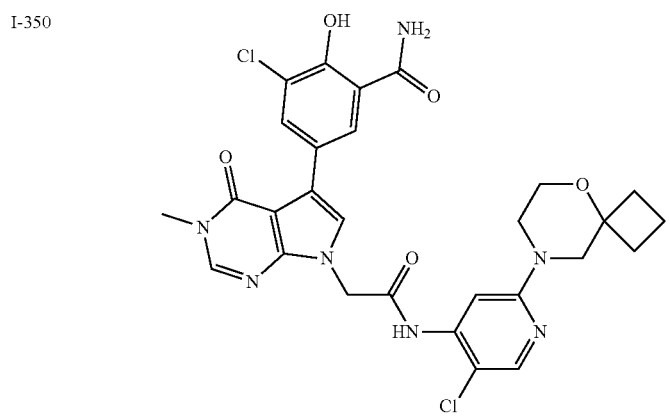 |
| I-351 | 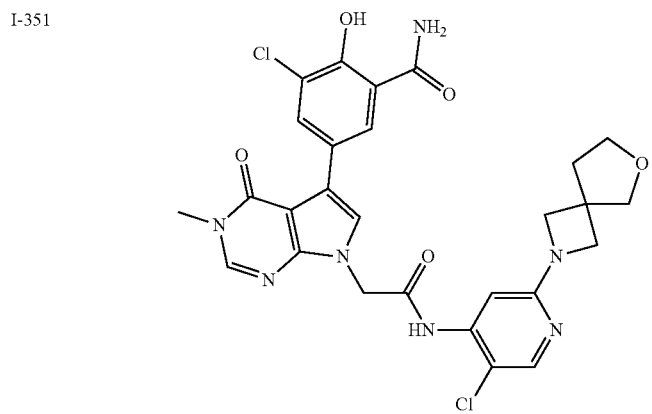 |

-continued
| Compound | Structure |
|---|---|
| I-352 | 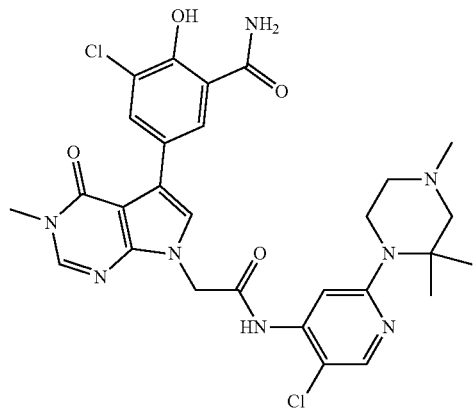 |
| I-353 | 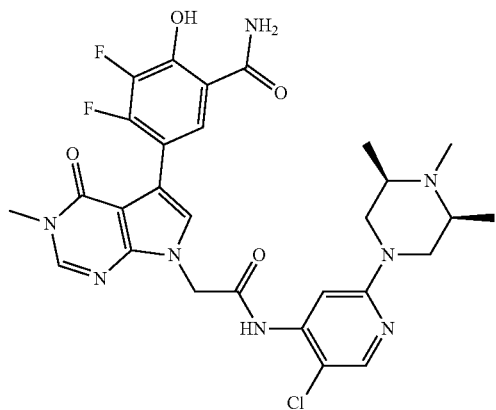 |
| I-354 | 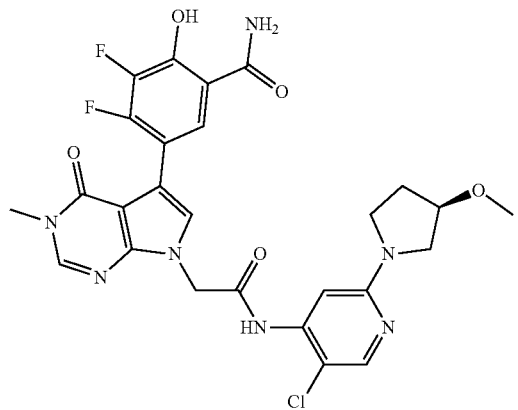 |

| Compound | Structure |
|---|---|
| I-355 | 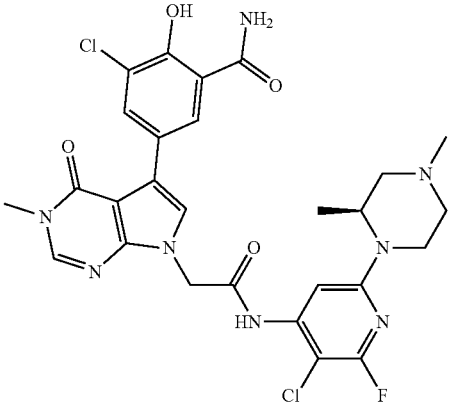 |
| I-356 | 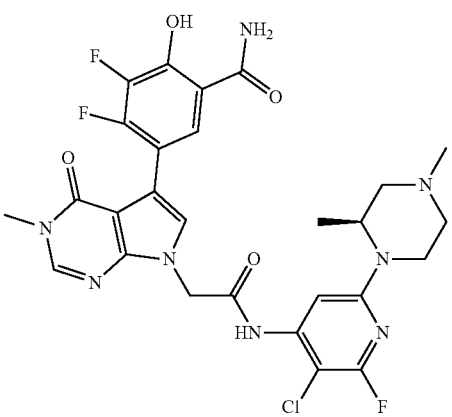 |
| I-357 | 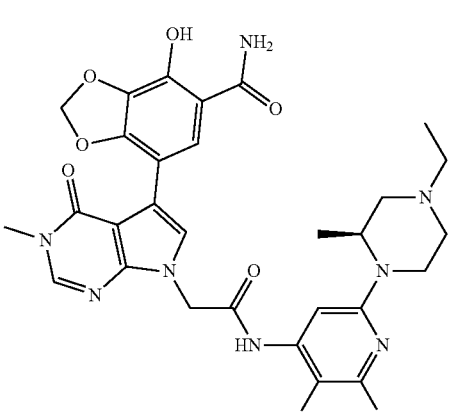 |

-continued

| Compound | Structure |
|---|---|
| I-358 | 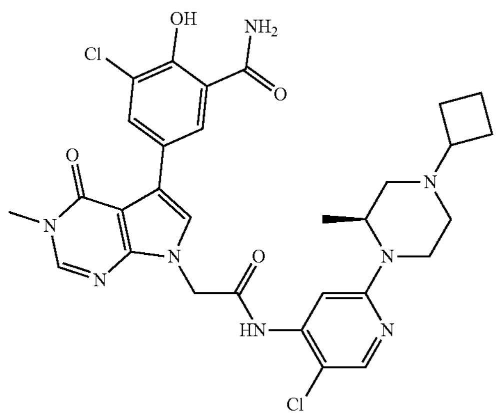 [SMILES: C[C@H]1CN(C2CCC2)CCN1c1cc(NC(=O)Cn2cc(-c3cc(Cl)c(O)c(C(N)=O)c3)c3c(=O)n(C)cnc32)c(Cl)cn1] |
| I-359 | 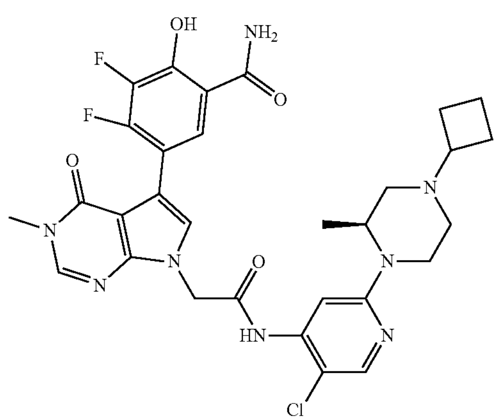 |
| I-360 | 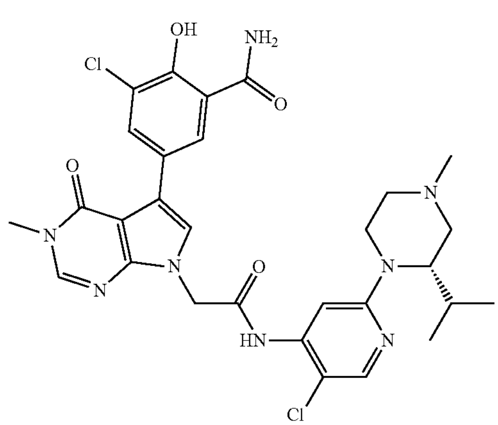 [SMILES: CC(C)[C@H]1CN(C)CCN1c1cc(NC(=O)Cn2cc(-c3cc(Cl)c(O)c(C(N)=O)c3)c3c(=O)n(C)cnc32)c(Cl)cn1] |

-continued
| Compound | Structure |
| --- | --- |
| I-361 | 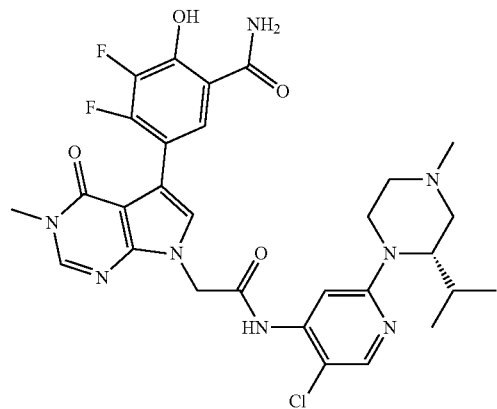 [SMILES: CC(C)[C@H]1CN(C)CCN1c1cc(NC(=O)Cn2cc(-c3cc(C(N)=O)c(O)c(F)c3F)c3c(=O)n(C)cnc32)c(Cl)cn1] |
| I-362 | 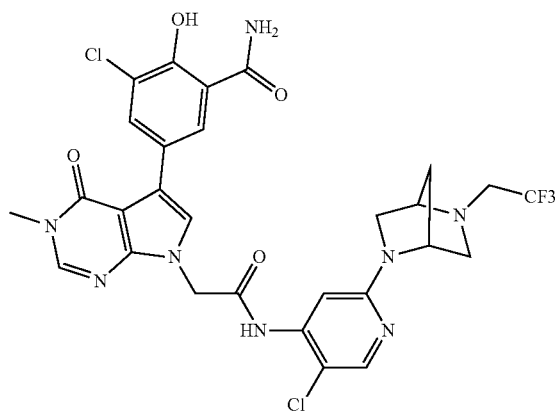 [SMILES: Cn1cnc2c(c(-c3cc(Cl)c(O)c(C(N)=O)c3)cn2CC(=O)Nc2cc(N3CC4CC3CN4CC(F)(F)F)ncc2Cl)c1=O] |
| I-363 | 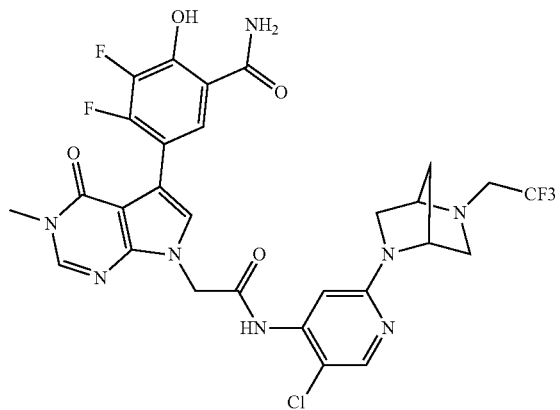 [SMILES: Cn1cnc2c(c(-c3cc(C(N)=O)c(O)c(F)c3F)cn2CC(=O)Nc2cc(N3CC4CC3CN4CC(F)(F)F)ncc2Cl)c1=O] |

| Compound | Structure |
|---|---|
| I-364 | 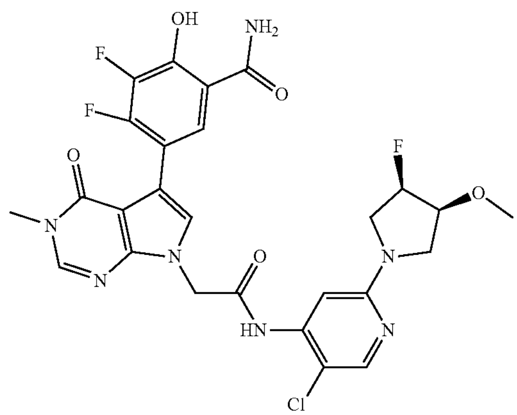 |
| I-365 | 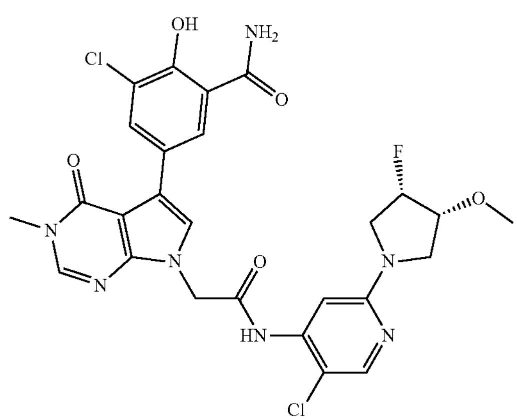 |
| I-366 | 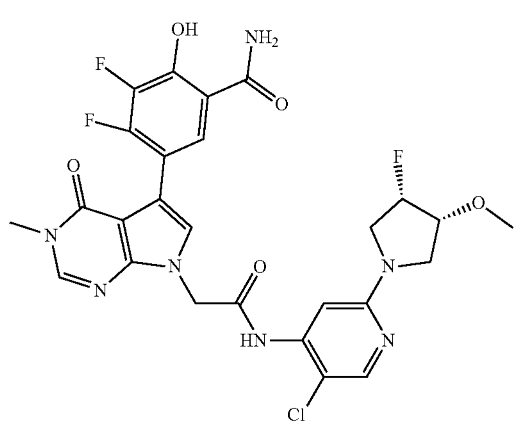 |

-continued
| Compound | Structure |
|---|---|
| I-367 | 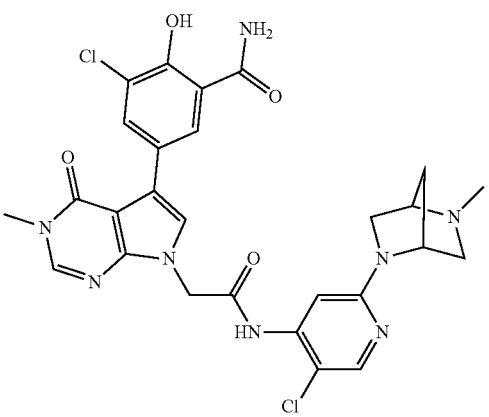 |
| I-368 | 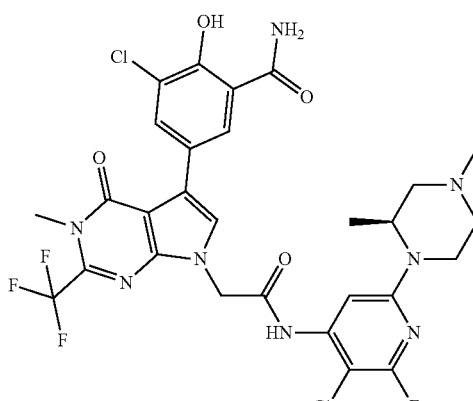 |
| I-369 | 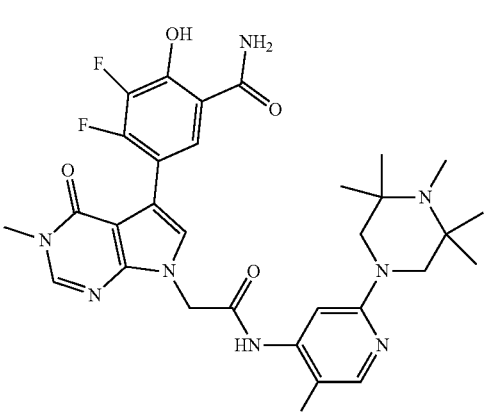 |

| Compound | Structure |
|---|---|
| I-370 | 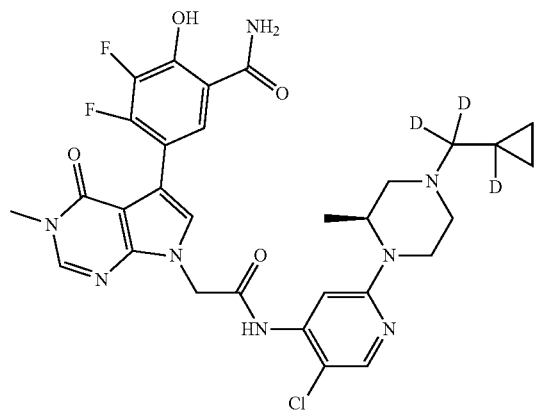 [SMILES: [2H]C1(C([2H])([2H])N2CCN(c3cc(NC(=O)Cn4cc(-c5cc(C(N)=O)c(O)c(F)c5F)c5c(=O)n(C)cnc54)c(Cl)cn3)[C@@H](C)C2)CC1] |
| I-371 | 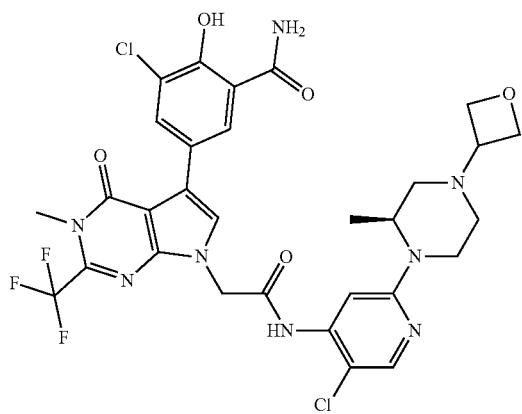 [SMILES: C[C@H]1CN(C2COC2)CCN1c1cc(NC(=O)Cn2cc(-c3cc(Cl)c(O)c(C(N)=O)c3)c3c(=O)n(C)c(C(F)(F)F)nc32)c(Cl)cn1] |
| I-372 | 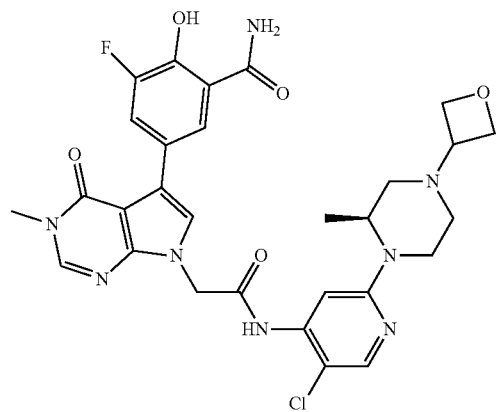 [SMILES: C[C@H]1CN(C2COC2)CCN1c1cc(NC(=O)Cn2cc(-c3cc(F)c(O)c(C(N)=O)c3)c3c(=O)n(C)cnc32)c(Cl)cn1] |

US 11,518,764 B2
891
892
-continued
| Compound | Structure |
|---|---|
| I-373 | 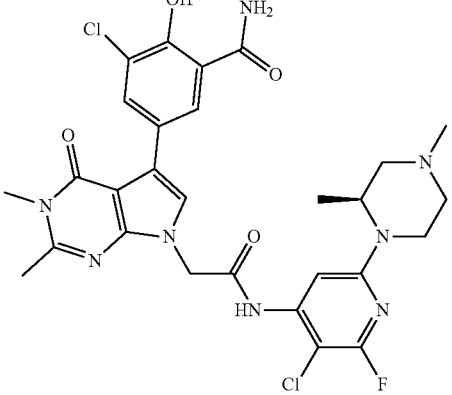 |
| I-374 | 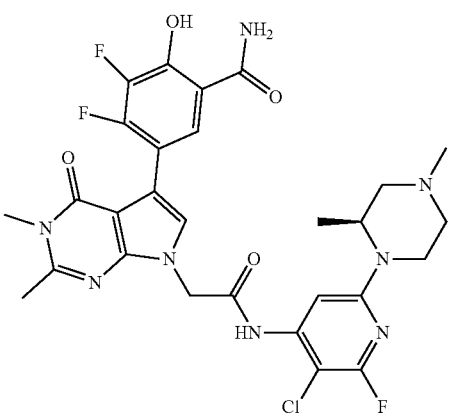 |
| I-375 | 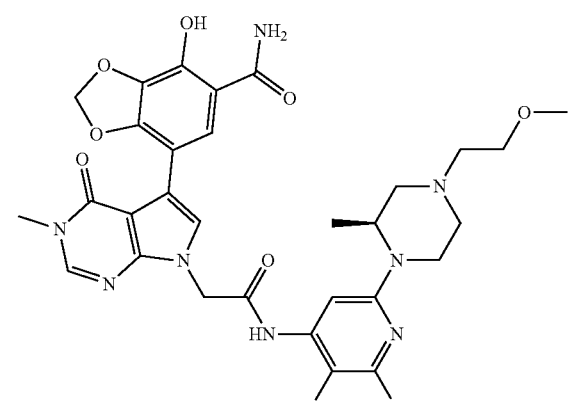 |

-continued
| Compound | Structure |
|---|---|
| I-376 | 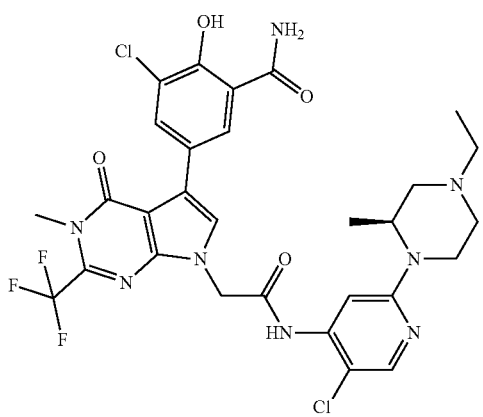 [SMILES: CCN1CCN(c2cc(NC(=O)Cn3cc(-c4cc(Cl)c(O)c(C(N)=O)c4)c4c(=O)n(C)c(C(F)(F)F)nc43)c(Cl)cn2)[C@@H](C)C1] |
| I-377 | 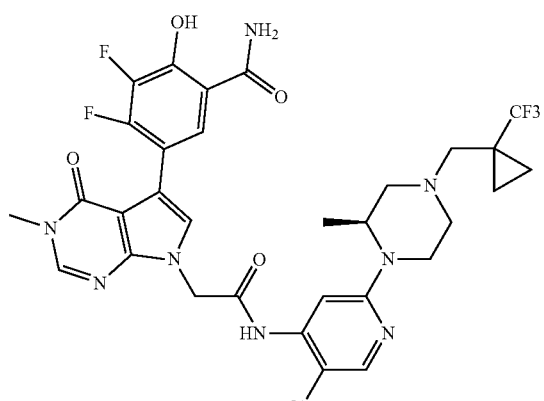 |
| I-378 | 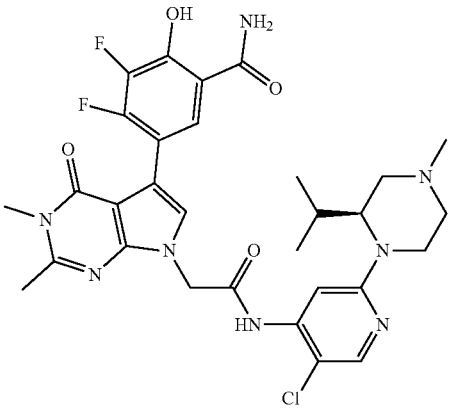 |

| Compound | Structure |
|---|---|
| I-379 | 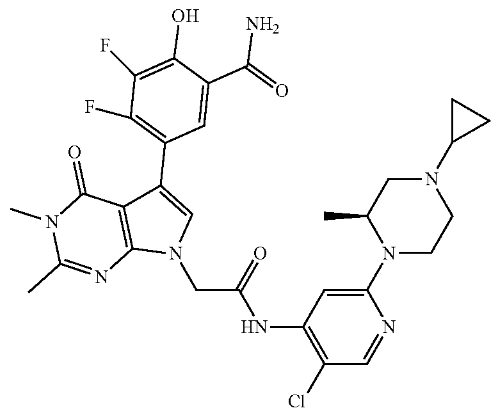 [SMILES: Cc1nc2c(c(-c3cc(C(N)=O)c(O)c(F)c3F)cn2CC(=O)Nc2cc(N3CCN(C4CC4)C[C@@H]3C)ncc2Cl)c(=O)n1C] |
| I-380 | 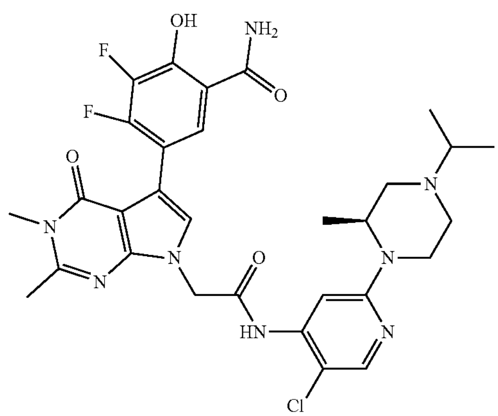 [SMILES: Cc1nc2c(c(-c3cc(C(N)=O)c(O)c(F)c3F)cn2CC(=O)Nc2cc(N3CCN(C(C)C)C[C@@H]3C)ncc2Cl)c(=O)n1C] |
| I-381 | 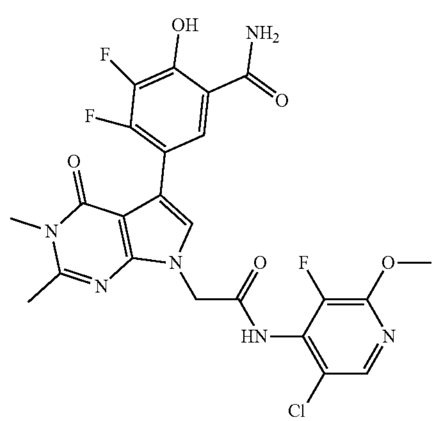 |

-continued
| Compound | Structure |
|---|---|
| I-382 | 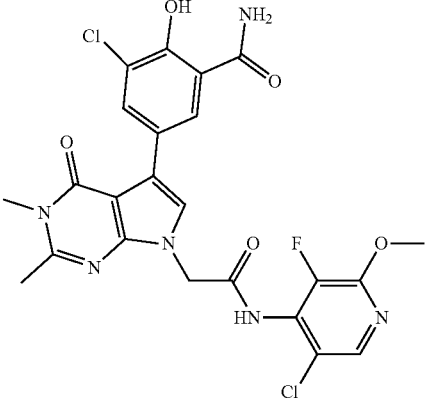 |
| I-383 | 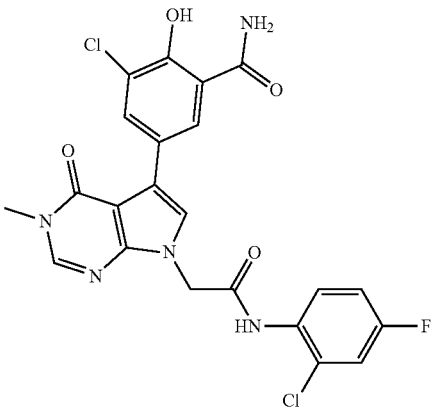 [SMILES: Cn1cnc2c(c(-c3cc(Cl)c(O)c(C(N)=O)c3)cn2CC(=O)Nc2ccc(F)cc2Cl)c1=O] |
| I-384 | 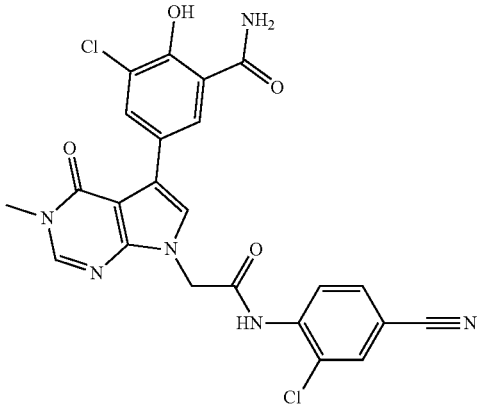 [SMILES: Cn1cnc2c(c(-c3cc(Cl)c(O)c(C(N)=O)c3)cn2CC(=O)Nc2ccc(C#N)cc2Cl)c1=O] |

| Compound | Structure |
|---|---|
| I-385 | 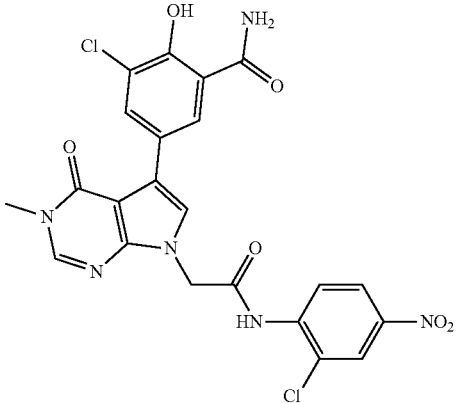 [SMILES: Cn1cnc2c(c(-c3cc(Cl)c(O)c(C(N)=O)c3)cn2CC(=O)Nc2ccc([N+](=O)[O-])cc2Cl)c1=O] |
| I-386 | 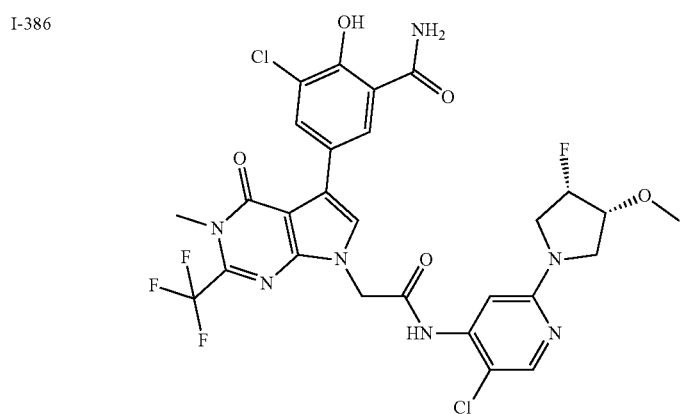 |
| I-387 | 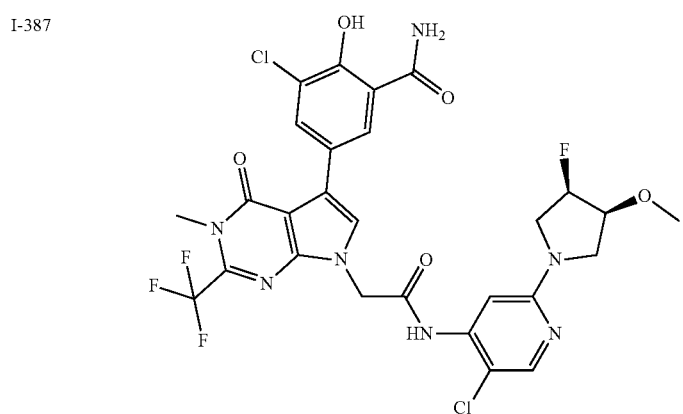 |

| Compound | Structure |
|---|---|
| I-388 | 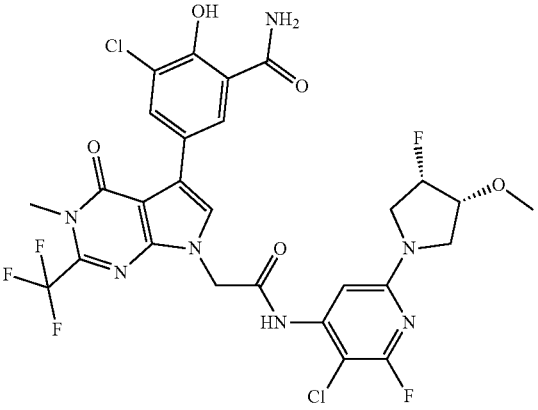 [SMILES: CO[C@@H]1CN(c2cc(NC(=O)Cn3cc(-c4cc(Cl)c(O)c(C(N)=O)c4)c4c(=O)n(C)c(C(F)(F)F)nc43)c(Cl)c(F)n2)C[C@@H]1F] |
| I-389 | 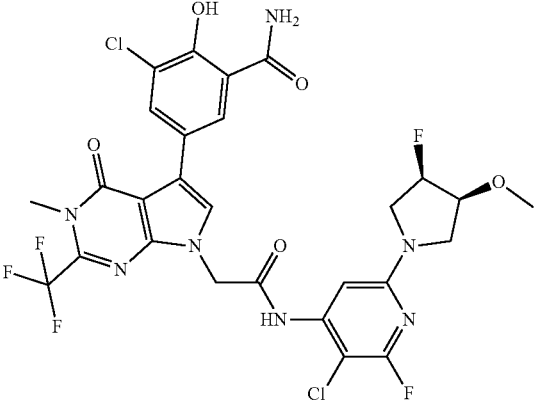 [SMILES: CO[C@H]1CN(c2cc(NC(=O)Cn3cc(-c4cc(Cl)c(O)c(C(N)=O)c4)c4c(=O)n(C)c(C(F)(F)F)nc43)c(Cl)c(F)n2)C[C@H]1F] |
| I-390 | 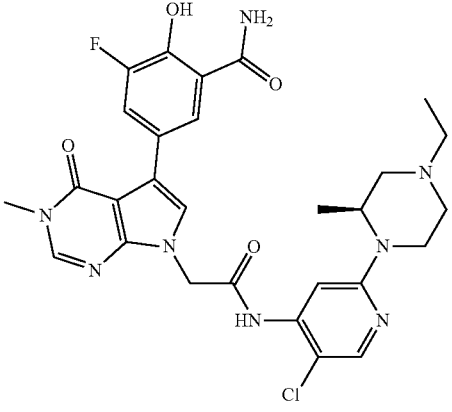 [SMILES: CCN1CCN(c2cc(NC(=O)Cn3cc(-c4cc(F)c(O)c(C(N)=O)c4)c4c(=O)n(C)cnc43)c(Cl)cn2)[C@@H](C)C1] |

| Compound | Structure |
|---|---|
| I-391 | 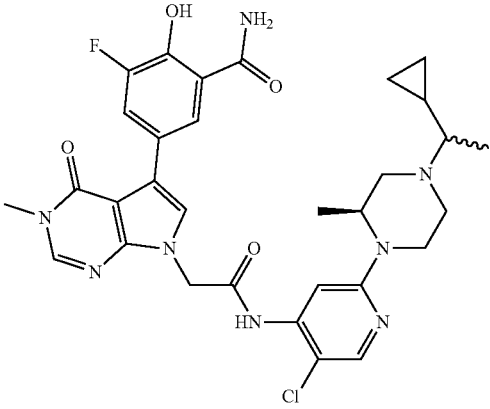 [SMILES: CC(C1CC1)N1CCN(c2cc(NC(=O)Cn3cc(-c4cc(F)c(O)c(C(N)=O)c4)c4c(=O)n(C)cnc43)c(Cl)cn2)[C@@H](C)C1] |
| I-392 | 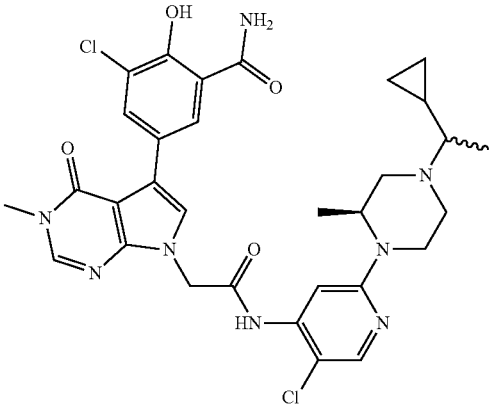 |
| I-393 | 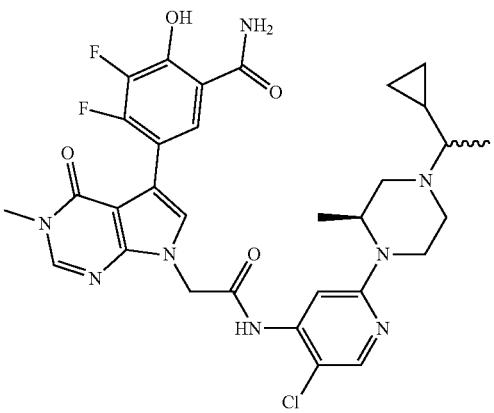 [SMILES: CC(C1CC1)N1CCN(c2cc(NC(=O)Cn3cc(-c4cc(C(N)=O)c(O)c(F)c4F)c4c(=O)n(C)cnc43)c(Cl)cn2)[C@@H](C)C1] |

-continued

| Compound | Structure |
|---|---|
| I-394 | 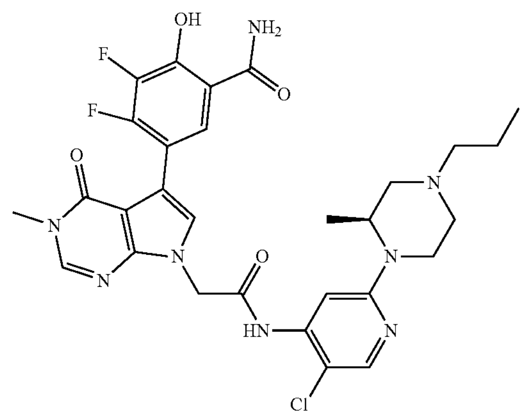 [SMILES: CCCN1CCN(c2cc(NC(=O)Cn3cc(-c4cc(C(N)=O)c(O)c(F)c4F)c4c(=O)n(C)cnc43)c(Cl)cn2)[C@@H](C)C1] |
| I-395 | 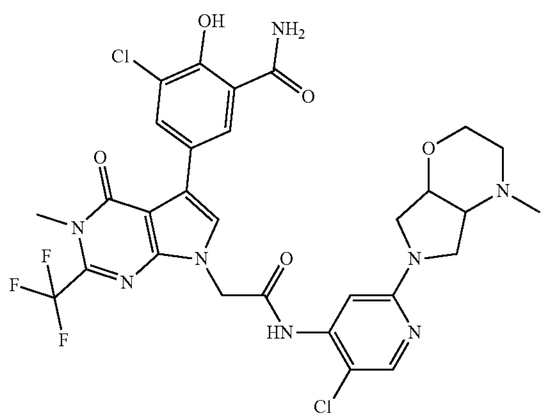 [SMILES: CN1CCOC2CN(c3cc(NC(=O)Cn4cc(-c5cc(Cl)c(O)c(C(N)=O)c5)c5c(=O)n(C)c(C(F)(F)F)nc54)c(Cl)cn3)CC21] |
| I-396 | 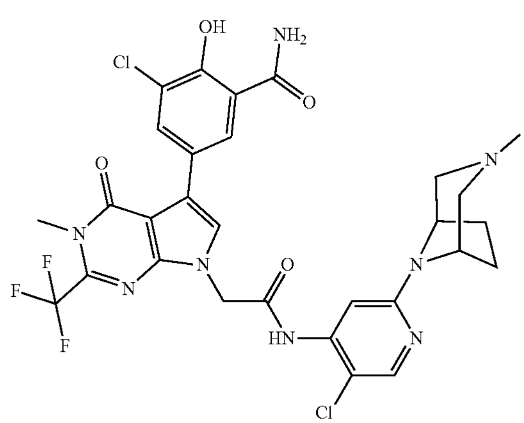 [SMILES: CN1CC2CCC(C1)N2c1cc(NC(=O)Cn2cc(-c3cc(Cl)c(O)c(C(N)=O)c3)c3c(=O)n(C)c(C(F)(F)F)nc32)c(Cl)cn1] |

| Compound | Structure |
|---|---|
| I-397 | 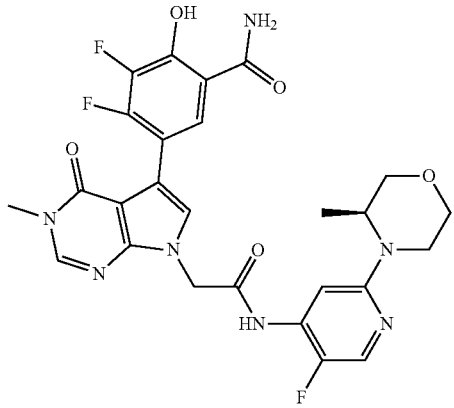 [SMILES: C[C@H]1COCCN1c1cc(NC(=O)Cn2cc(-c3cc(C(N)=O)c(O)c(F)c3F)c3c(=O)n(C)cnc32)c(F)cn1] |
| I-398 | 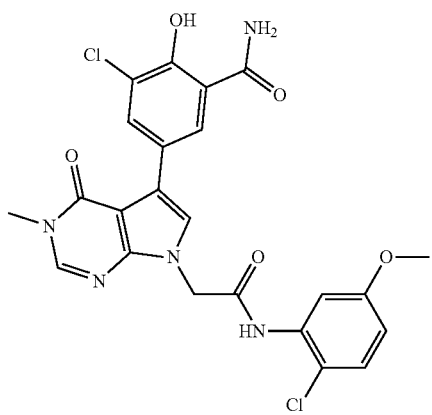 |
| I-399 | 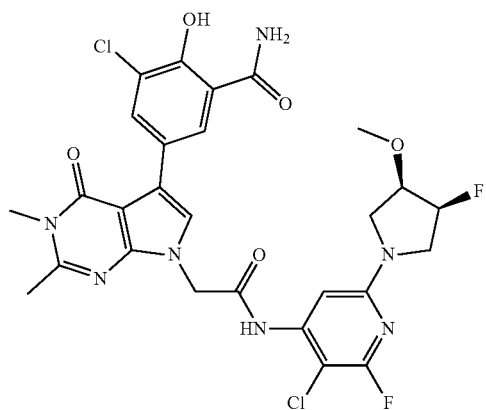 [SMILES: CO[C@@H]1CN(c2cc(NC(=O)Cn3cc(-c4cc(Cl)c(O)c(C(N)=O)c4)c4c(=O)n(C)c(C)nc43)c(Cl)c(F)n2)C[C@@H]1F] |

| Compound | Structure |
|---|---|
| I-400 | 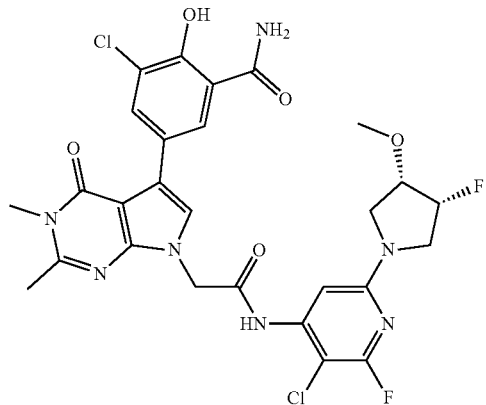 [SMILES: CO[C@H]1CN(c2cc(NC(=O)Cn3cc(-c4cc(Cl)c(O)c(C(N)=O)c4)c4c(=O)n(C)c(C)nc43)c(Cl)c(F)n2)C[C@H]1F] |
| I-401 | 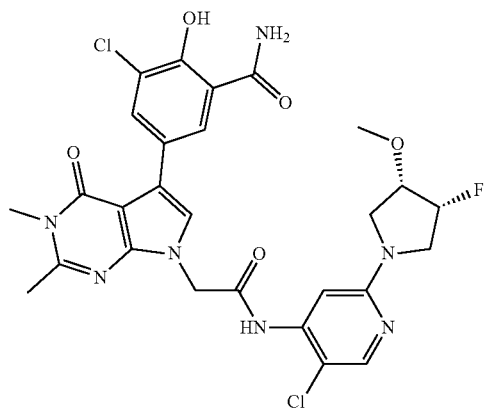 [SMILES: CO[C@H]1CN(c2cc(NC(=O)Cn3cc(-c4cc(Cl)c(O)c(C(N)=O)c4)c4c(=O)n(C)c(C)nc43)c(Cl)cn2)C[C@H]1F] |
| I-402 | 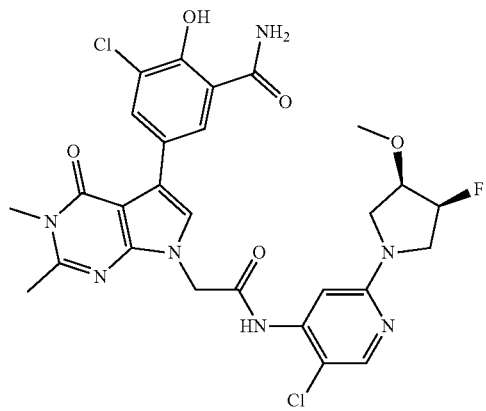 [SMILES: CO[C@@H]1CN(c2cc(NC(=O)Cn3cc(-c4cc(Cl)c(O)c(C(N)=O)c4)c4c(=O)n(C)c(C)nc43)c(Cl)cn2)C[C@@H]1F] |

-continued
| Compound | Structure |
|---|---|
| I-403 | 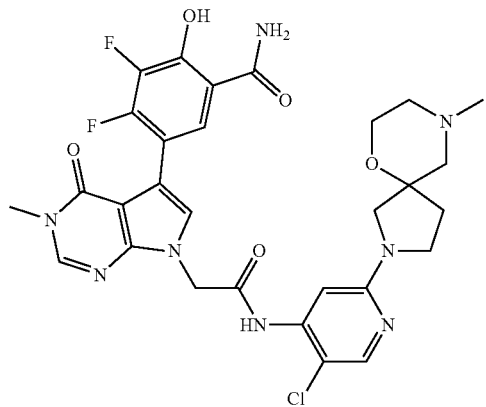 |
| I-404 | 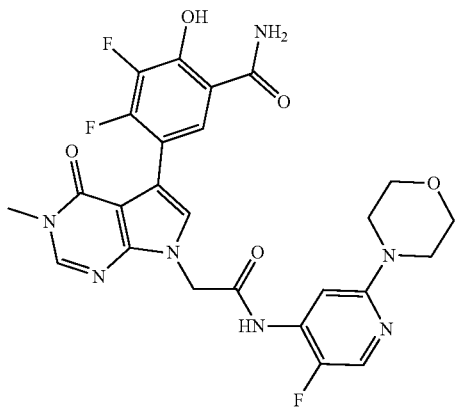 [SMILES: Cn1cnc2c(c(-c3cc(C(N)=O)c(O)c(F)c3F)cn2CC(=O)Nc2cc(N3CCOCC3)ncc2F)c1=O] |
| I-405 | 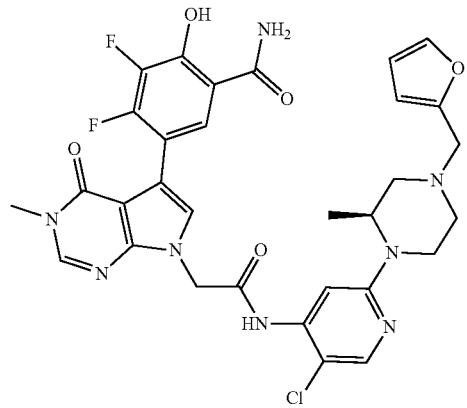 [SMILES: C[C@H]1CN(Cc2ccco2)CCN1c1cc(NC(=O)Cn2cc(-c3cc(C(N)=O)c(O)c(F)c3F)c3c(=O)n(C)cnc32)c(Cl)cn1] |

| Compound | Structure |
|---|---|
| I-406 | 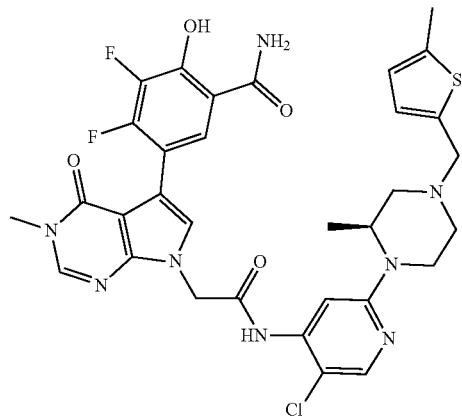 [SMILES: Cc1ccc(CN2CCN(c3cc(NC(=O)Cn4cc(-c5cc(C(N)=O)c(O)c(F)c5F)c5c(=O)n(C)cnc54)c(Cl)cn3)[C@@H](C)C2)s1] |
| I-407 | 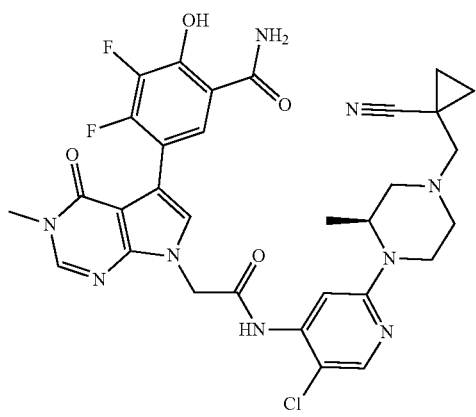 [SMILES: C[C@H]1CN(CC2(C#N)CC2)CCN1c1cc(NC(=O)Cn2cc(-c3cc(C(N)=O)c(O)c(F)c3F)c3c(=O)n(C)cnc32)c(Cl)cn1] |
| I-408 | 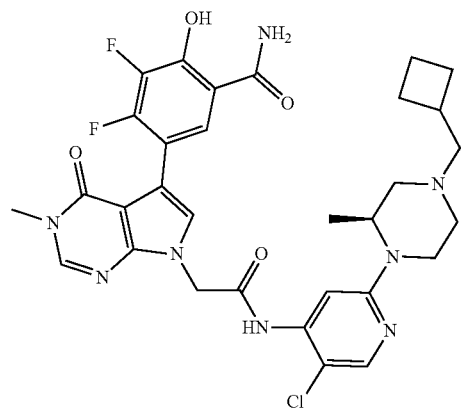 [SMILES: C[C@H]1CN(CC2CCC2)CCN1c1cc(NC(=O)Cn2cc(-c3cc(C(N)=O)c(O)c(F)c3F)c3c(=O)n(C)cnc32)c(Cl)cn1] |

| Compound | Structure |
|---|---|
| I-409 | 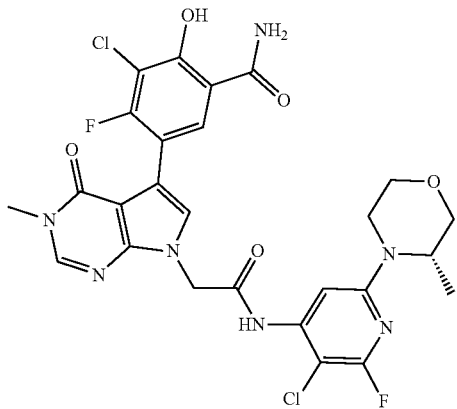 [SMILES: C[C@H]1COCCN1c1cc(NC(=O)Cn2cc(-c3cc(C(N)=O)c(O)c(Cl)c3F)c3c(=O)n(C)cnc32)c(Cl)c(F)n1] |
| I-410 | 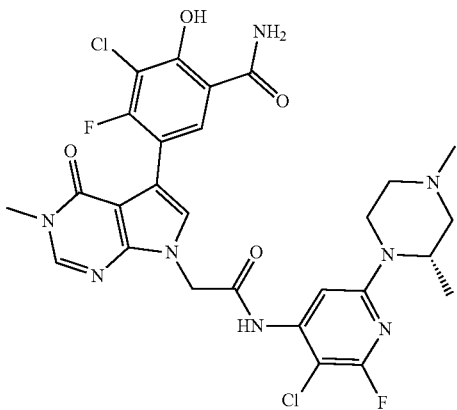 |
| I-411 | 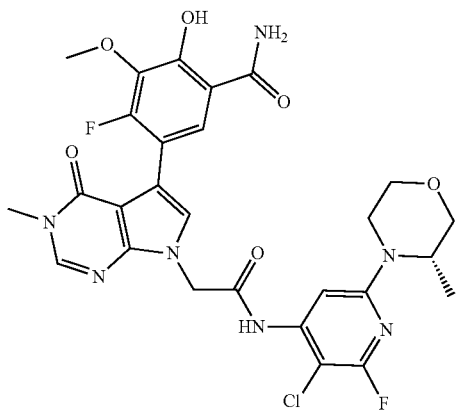 [SMILES: COc1c(O)c(C(N)=O)cc(-c2cn(CC(=O)Nc3cc(N4CCOC[C@@H]4C)nc(F)c3Cl)c3ncn(C)c(=O)c23)c1F] |

| Compound | Structure |
|---|---|
| I-412 | 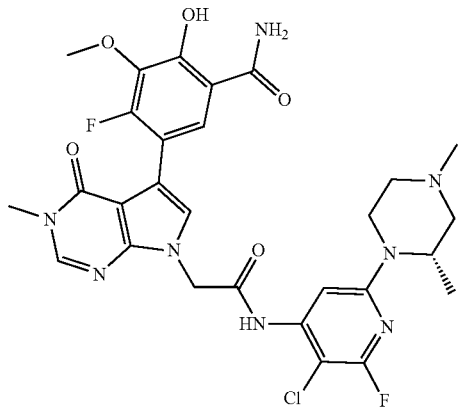 |
| I-413 | 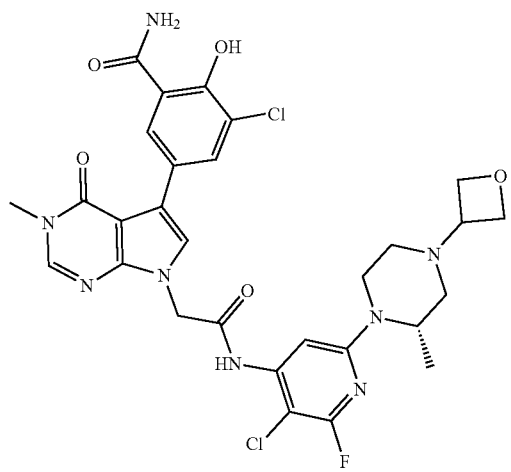 [SMILES: C[C@H]1CN(C2COC2)CCN1c1cc(NC(=O)Cn2cc(-c3cc(Cl)c(O)c(C(N)=O)c3)c3c(=O)n(C)cnc32)c(Cl)c(F)n1] |
| I-414 | 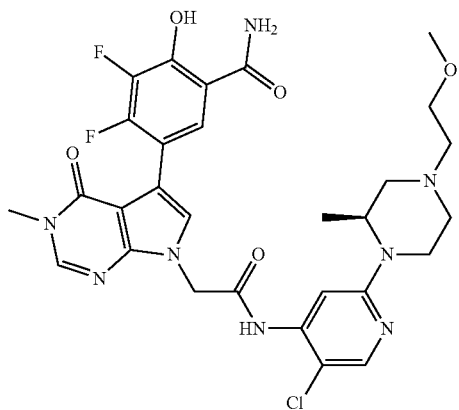 [SMILES: COCCN1CCN(c2cc(NC(=O)Cn3cc(-c4cc(C(N)=O)c(O)c(F)c4F)c4c(=O)n(C)cnc43)c(Cl)cn2)[C@@H](C)C1] |

| Compound | Structure |
|---|---|
| I-415 | 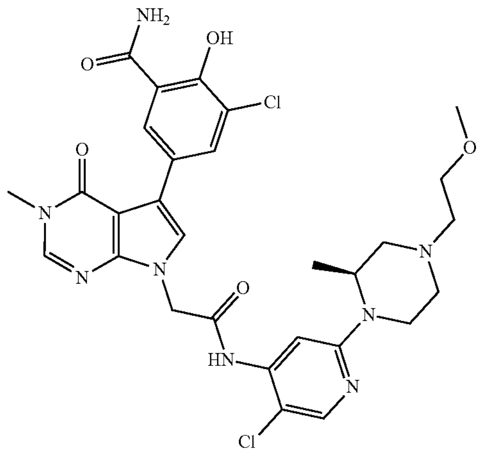 [SMILES: COCCN1CCN(c2cc(NC(=O)Cn3cc(-c4cc(Cl)c(O)c(C(N)=O)c4)c4c(=O)n(C)cnc43)c(Cl)cn2)[C@@H](C)C1] |
| I-416 | 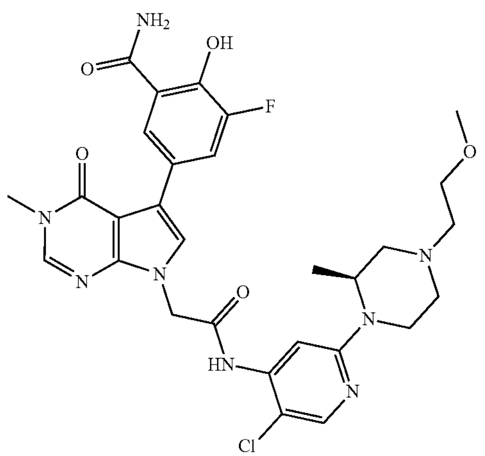 [SMILES: COCCN1CCN(c2cc(NC(=O)Cn3cc(-c4cc(F)c(O)c(C(N)=O)c4)c4c(=O)n(C)cnc43)c(Cl)cn2)[C@@H](C)C1] |
| I-417 | 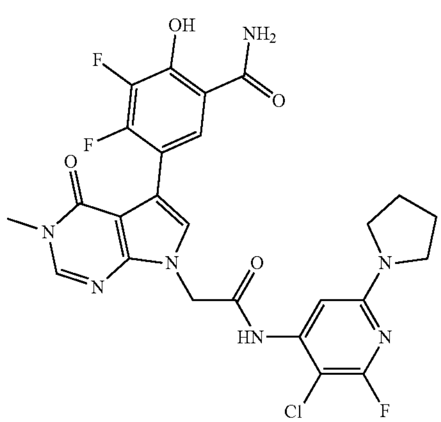 [SMILES: Cn1cnc2c(c(-c3cc(C(N)=O)c(O)c(F)c3F)cn2CC(=O)Nc2cc(N3CCCC3)nc(F)c2Cl)c1=O] |

-continued
| Compound | Structure |
|---|---|
| I-418 | 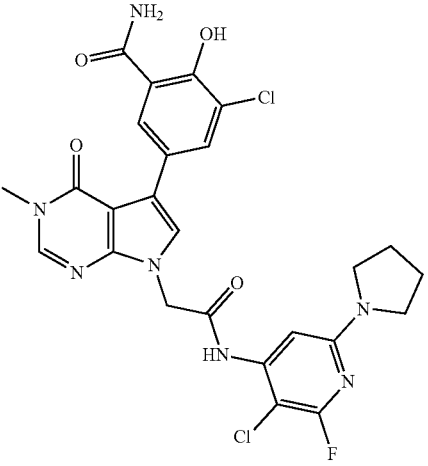 [SMILES: Cn1cnc2c(c(-c3cc(Cl)c(O)c(C(N)=O)c3)cn2CC(=O)Nc2cc(N3CCCC3)nc(F)c2Cl)c1=O] |
| I-419 | 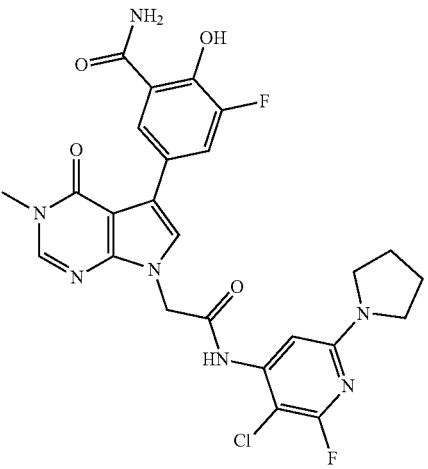 |
| I-420 | 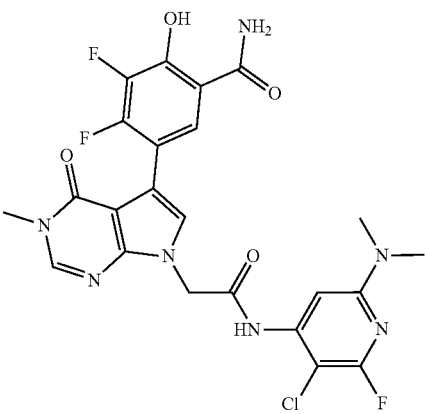 |

-continued
| Compound | Structure |
|---|---|
| I-421 | 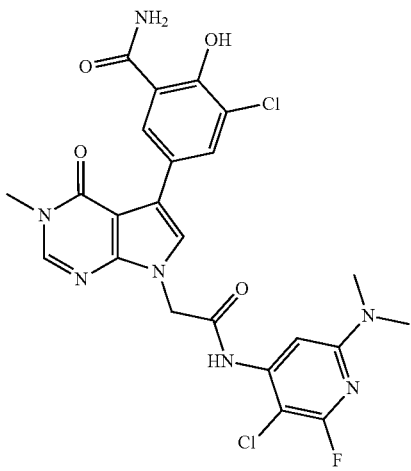 |
| lp;2.4p I-422 | 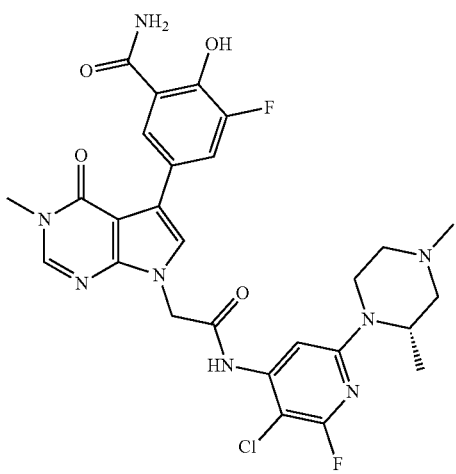 |
| I-423 | 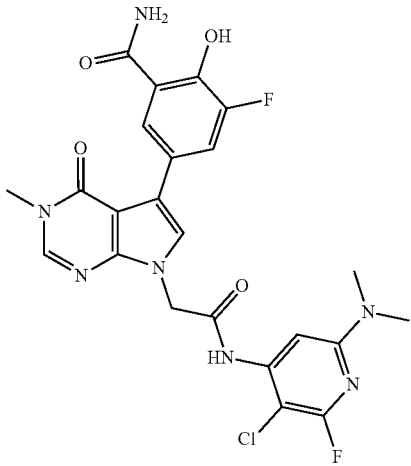 |

-continued
| Compound | Structure |
|---|---|
| I-424 | 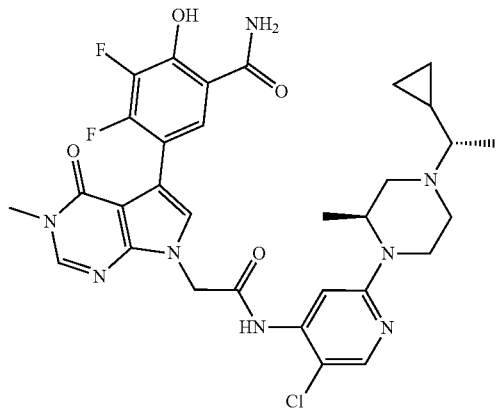 [SMILES: C[C@@H](C1CC1)N1CCN(c2cc(NC(=O)Cn3cc(-c4cc(C(N)=O)c(O)c(F)c4F)c4c(=O)n(C)cnc43)c(Cl)cn2)[C@@H](C)C1] |
| I-425 | 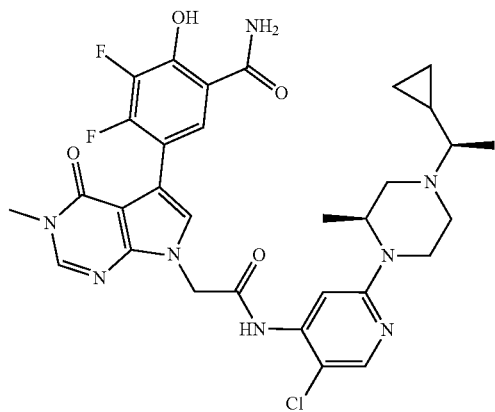 [SMILES: C[C@H](C1CC1)N1CCN(c2cc(NC(=O)Cn3cc(-c4cc(C(N)=O)c(O)c(F)c4F)c4c(=O)n(C)cnc43)c(Cl)cn2)[C@@H](C)C1] |
| I-426 | 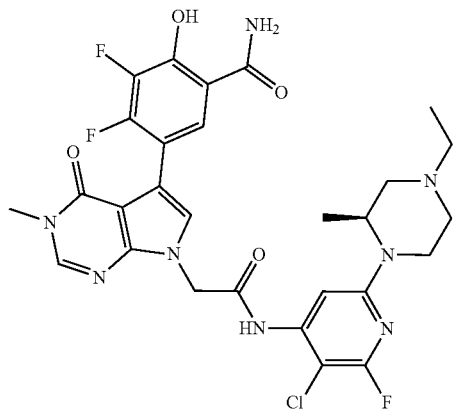 [SMILES: CCN1CCN(c2cc(NC(=O)Cn3cc(-c4cc(C(N)=O)c(O)c(F)c4F)c4c(=O)n(C)cnc43)c(Cl)c(F)n2)[C@@H](C)C1] |

-continued
| Compound | Structure |
|---|---|
| I-427 | 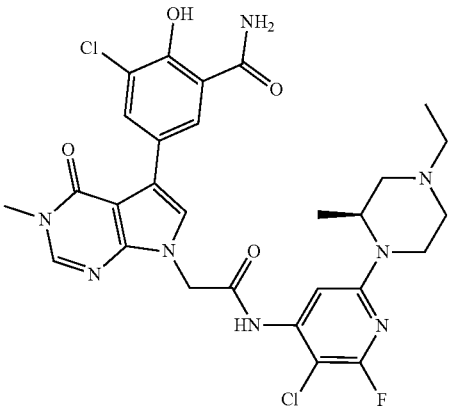 |
| I-428 | 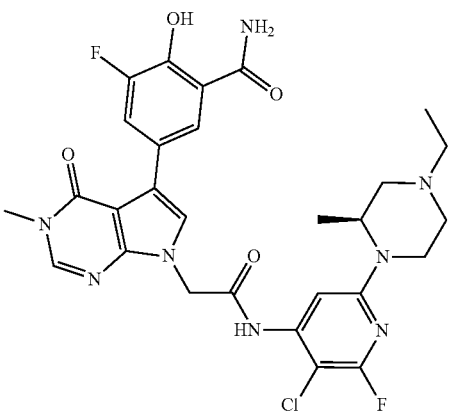 [SMILES: CCN1CCN(c2cc(NC(=O)Cn3cc(-c4cc(F)c(O)c(C(N)=O)c4)c4c(=O)n(C)cnc43)c(Cl)c(F)n2)[C@@H](C)C1] |
| I-429 | 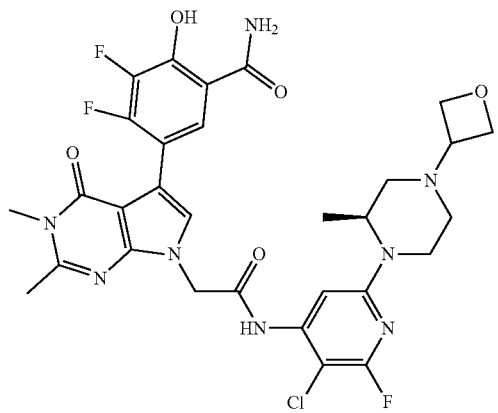 [SMILES: Cc1nc2c(c(-c3cc(C(N)=O)c(O)c(F)c3F)cn2CC(=O)Nc2cc(N3CCN(C4COC4)C[C@@H]3C)nc(F)c2Cl)c(=O)n1C] |

-continued
| Compound | Structure |
|---|---|
| I-430 | 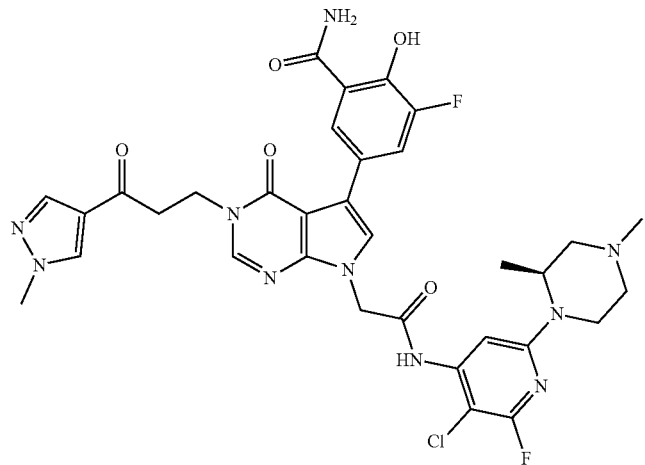 [SMILES: C[C@H]1CN(C)CCN1c1cc(NC(=O)Cn2cc(-c3cc(F)c(O)c(C(N)=O)c3)c3c(=O)n(CCC(=O)c4cnn(C)c4)cnc32)c(Cl)c(F)n1] |
| I-431 | 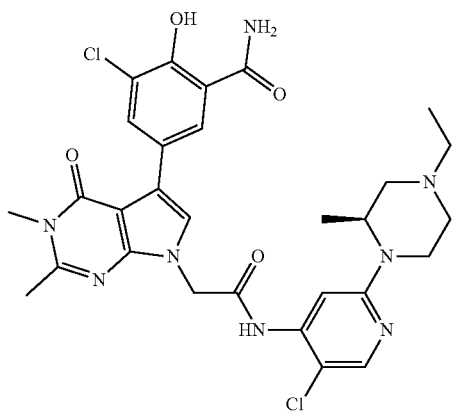 [SMILES: CCN1CCN(c2cc(NC(=O)Cn3cc(-c4cc(Cl)c(O)c(C(N)=O)c4)c4c(=O)n(C)c(C)nc43)c(Cl)cn2)[C@@H](C)C1] |
| I-432 | 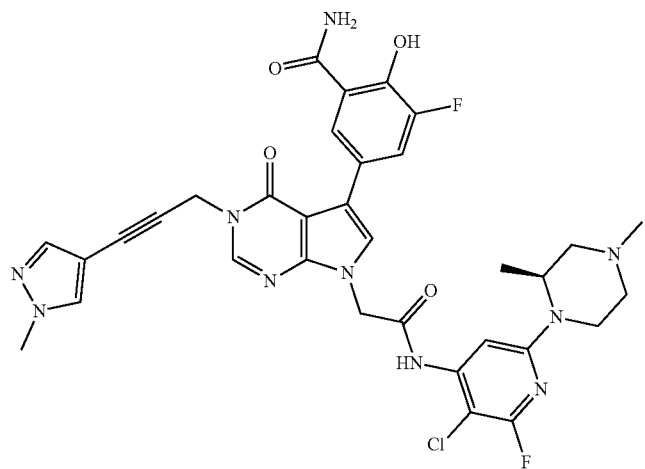 [SMILES: C[C@H]1CN(C)CCN1c1cc(NC(=O)Cn2cc(-c3cc(F)c(O)c(C(N)=O)c3)c3c(=O)n(CC#Cc4cnn(C)c4)cnc32)c(Cl)c(F)n1] |

| Compound | Structure |
|---|---|
| I-433 | 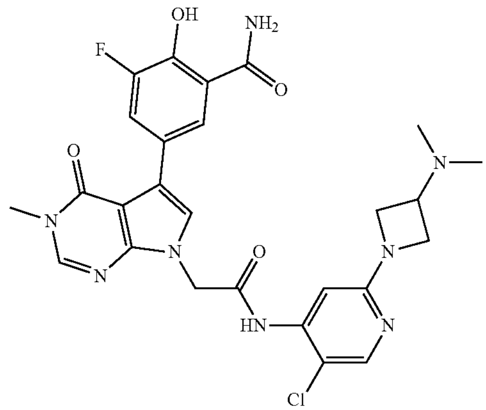 |
| I-434 | 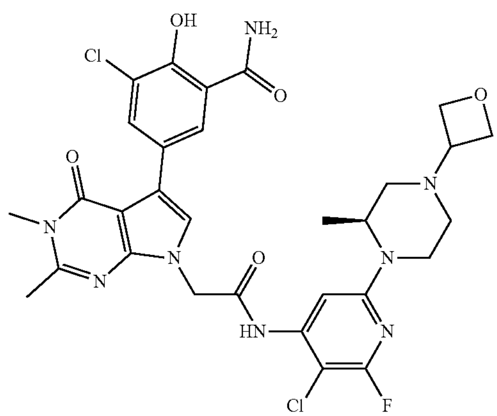 [SMILES: Cc1nc2c(c(-c3cc(Cl)c(O)c(C(N)=O)c3)cn2CC(=O)Nc2cc(N3CCN(C4COC4)C[C@@H]3C)nc(F)c2Cl)c(=O)n1C] |
| I-435 | 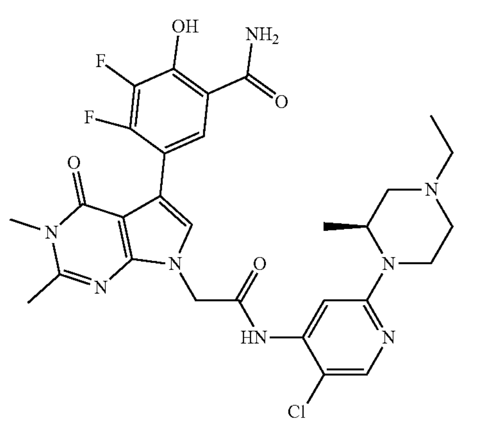 [SMILES: CCN1CCN(c2cc(NC(=O)Cn3cc(-c4cc(C(N)=O)c(O)c(F)c4F)c4c(=O)n(C)c(C)nc43)c(Cl)cn2)[C@@H](C)C1] |

| Compound | Structure |
|---|---|
| I-436 | 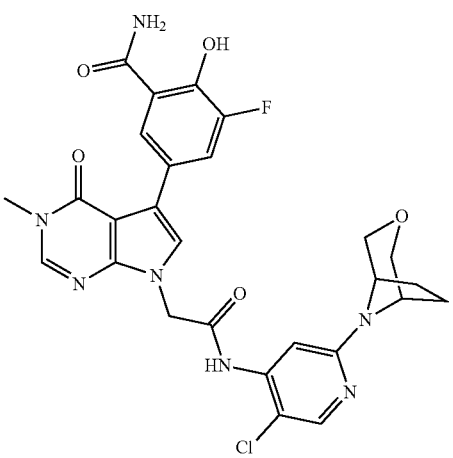 [SMILES: Cn1cnc2c(c(-c3cc(F)c(O)c(C(N)=O)c3)cn2CC(=O)Nc2cc(N3C4CCC3COC4)ncc2Cl)c1=O] |
| I-437 | 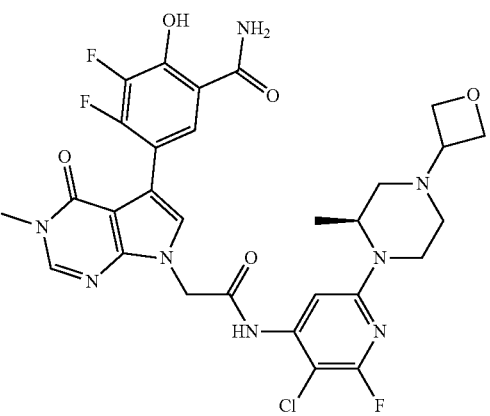 [SMILES: C[C@H]1CN(C2COC2)CCN1c1cc(NC(=O)Cn2cc(-c3cc(C(N)=O)c(O)c(F)c3F)c3c(=O)n(C)cnc32)c(Cl)c(F)n1] |
| I-438 | 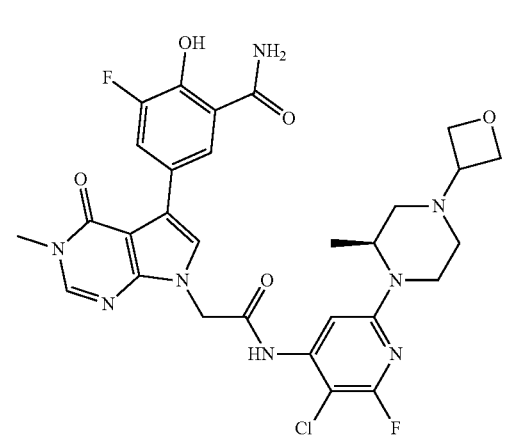 [SMILES: C[C@H]1CN(C2COC2)CCN1c1cc(NC(=O)Cn2cc(-c3cc(F)c(O)c(C(N)=O)c3)c3c(=O)n(C)cnc32)c(Cl)c(F)n1] |

| Compound | Structure |
|---|---|
| I-439 | 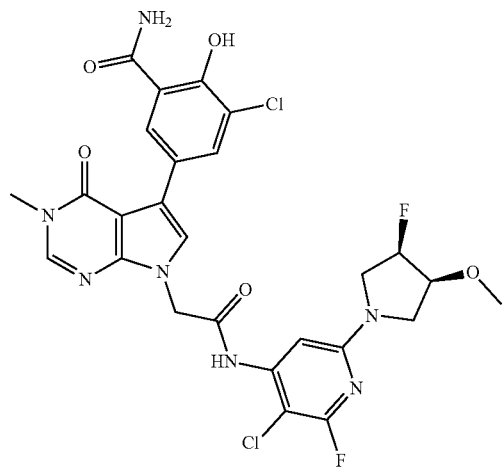 |
| I-440 | 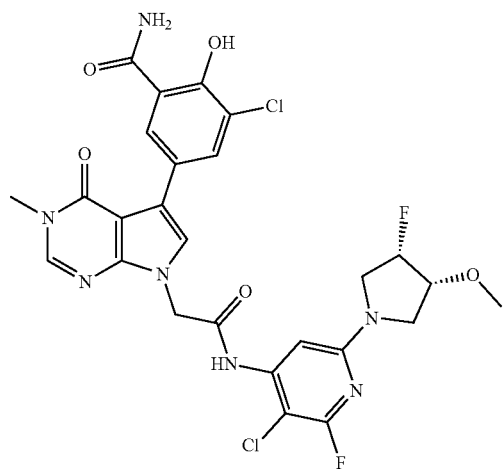 |
| I-441 | 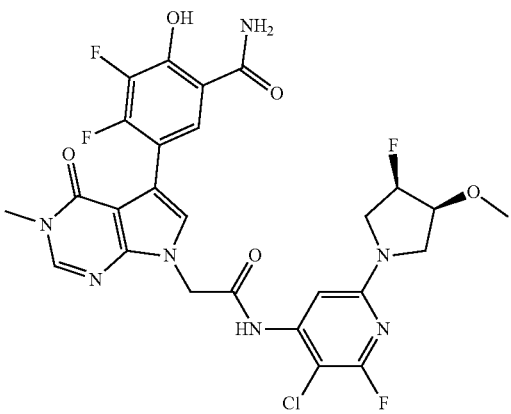 |

| Compound | Structure |
|---|---|
| I-442 | 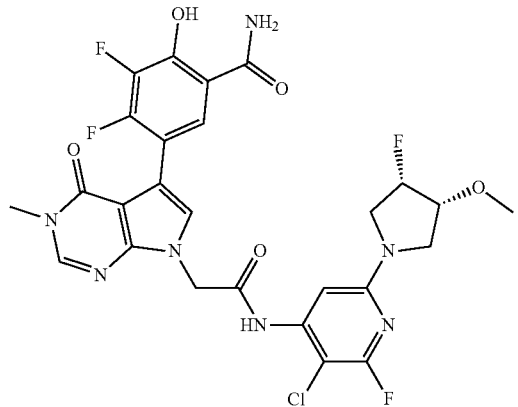 |
| I-443 | 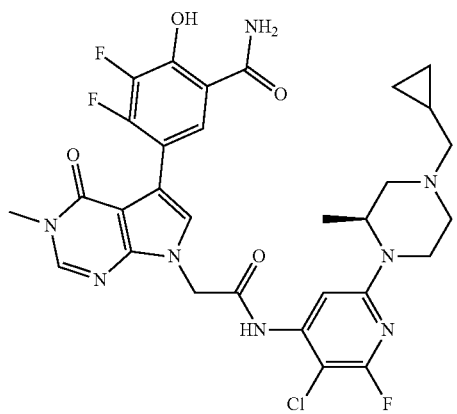 [SMILES: C[C@H]1CN(CC2CC2)CCN1c1cc(NC(=O)Cn2cc(-c3cc(C(N)=O)c(O)c(F)c3F)c3c(=O)n(C)cnc32)c(Cl)c(F)n1] |
| I-444 | 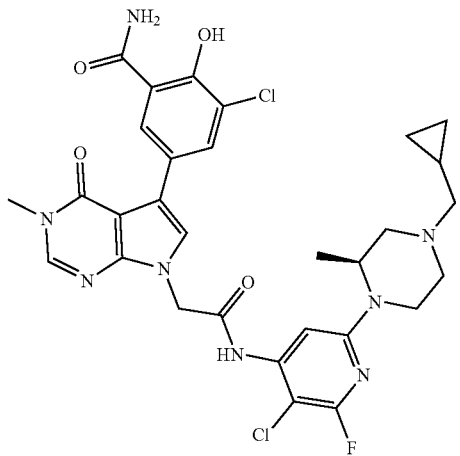 [SMILES: C[C@H]1CN(CC2CC2)CCN1c1cc(NC(=O)Cn2cc(-c3cc(Cl)c(O)c(C(N)=O)c3)c3c(=O)n(C)cnc32)c(Cl)c(F)n1] |

| Compound | Structure |
|---|---|
| I-445 | 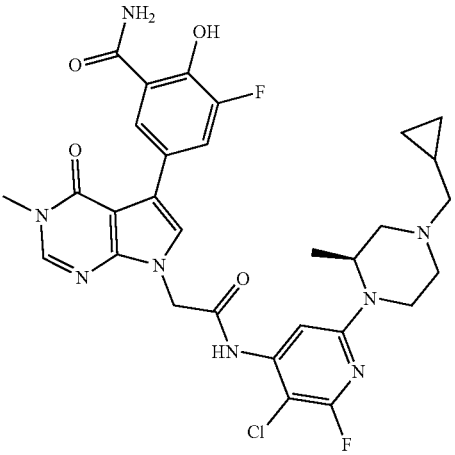 [SMILES: C[C@H]1CN(CC2CC2)CCN1c1cc(NC(=O)Cn2cc(-c3cc(F)c(O)c(C(N)=O)c3)c3c(=O)n(C)cnc32)c(Cl)c(F)n1] |
| I-446 | 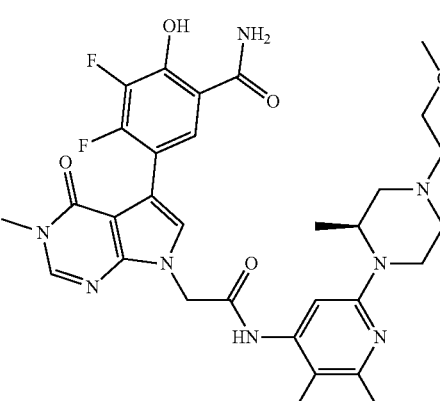 |
| I-447 | 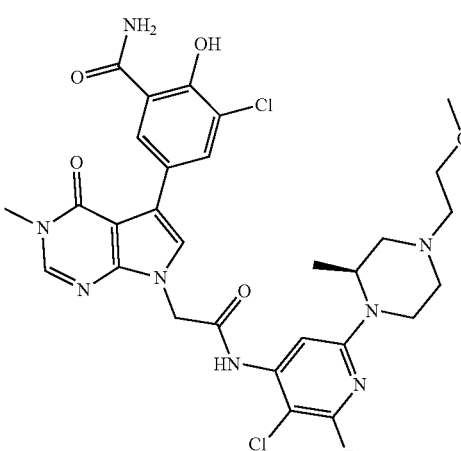 |

-continued
| Compound | Structure |
|---|---|
| I-448 | 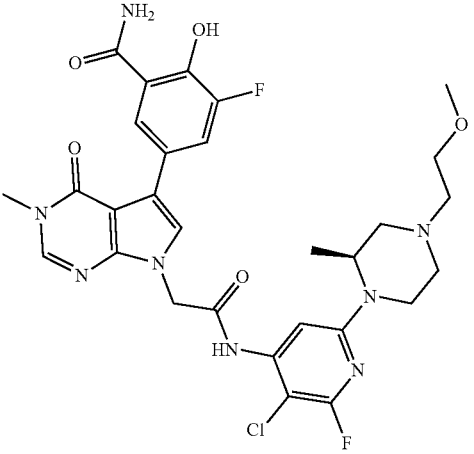 [SMILES: COCCN1CCN(c2cc(NC(=O)Cn3cc(-c4cc(F)c(O)c(C(N)=O)c4)c4c(=O)n(C)cnc43)c(Cl)c(F)n2)[C@@H](C)C1] |
| I-449 | 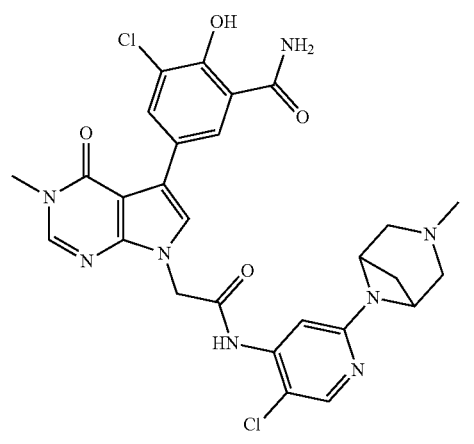 |
| I-450 | 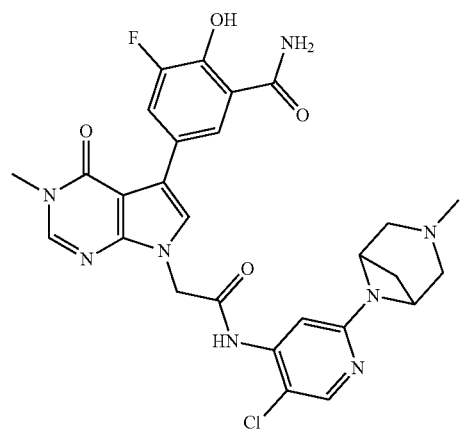 |

| Compound | Structure |
|---|---|
| I-451 | 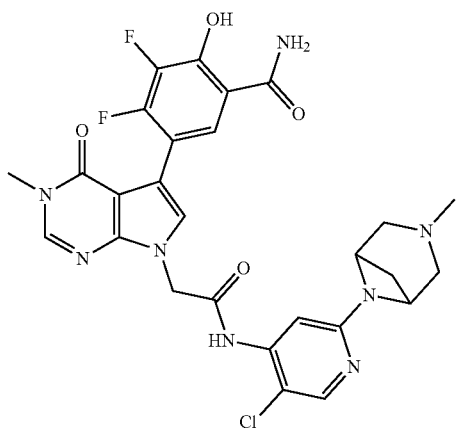 |
| I-452 | 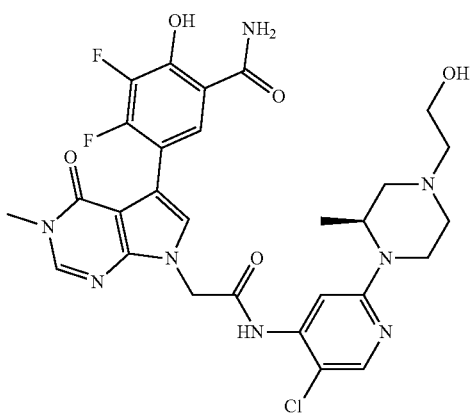 [SMILES: C[C@H]1CN(CCO)CCN1c1cc(NC(=O)Cn2cc(-c3cc(C(N)=O)c(O)c(F)c3F)c3c(=O)n(C)cnc32)c(Cl)cn1] |
| I-453 | 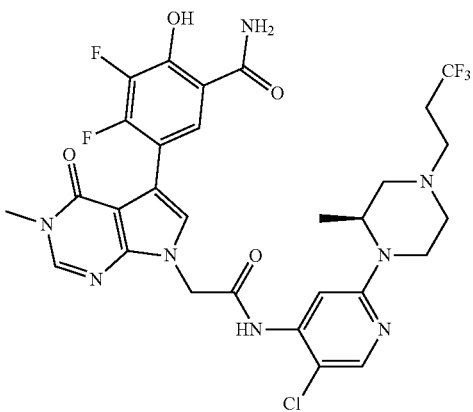 [SMILES: C[C@H]1CN(CCC(F)(F)F)CCN1c1cc(NC(=O)Cn2cc(-c3cc(C(N)=O)c(O)c(F)c3F)c3c(=O)n(C)cnc32)c(Cl)cn1] |

| Compound | Structure |
|---|---|
| I-454 | 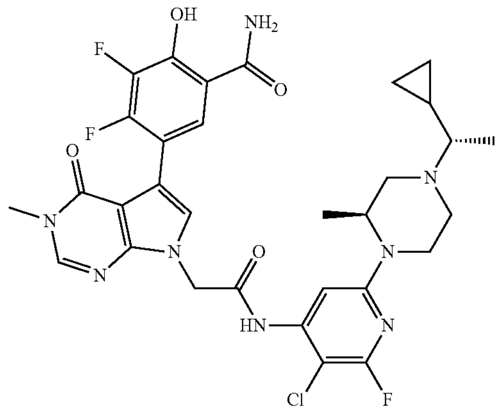 [SMILES: C[C@@H](C1CC1)N1CCN(c2cc(NC(=O)Cn3cc(-c4cc(C(N)=O)c(O)c(F)c4F)c4c(=O)n(C)cnc43)c(Cl)c(F)n2)[C@@H](C)C1] |
| I-455 | 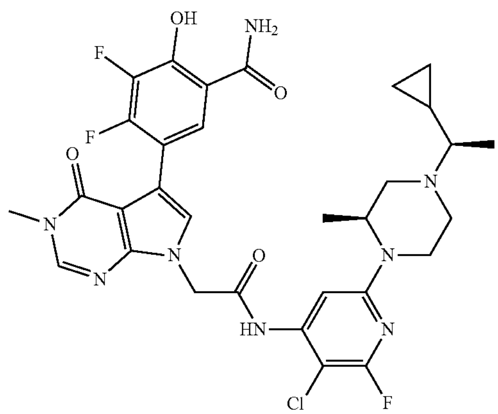 [SMILES: C[C@H](C1CC1)N1CCN(c2cc(NC(=O)Cn3cc(-c4cc(C(N)=O)c(O)c(F)c4F)c4c(=O)n(C)cnc43)c(Cl)c(F)n2)[C@@H](C)C1] |
| I-456 | 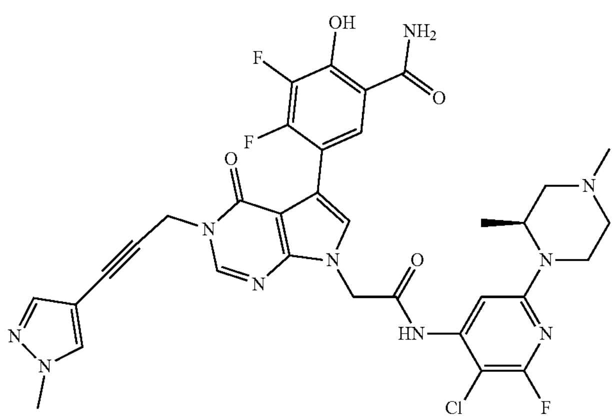 [SMILES: C[C@H]1CN(C)CCN1c1cc(NC(=O)Cn2cc(-c3cc(C(N)=O)c(O)c(F)c3F)c3c(=O)n(CC#Cc4cnn(C)c4)cnc32)c(Cl)c(F)n1] |

| Compound | Structure |
|---|---|
| I-457 | 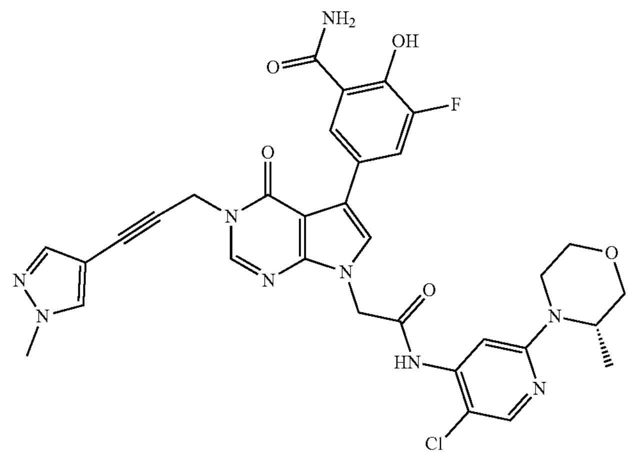 [SMILES: C[C@H]1COCCN1c1cc(NC(=O)Cn2cc(-c3cc(F)c(O)c(C(N)=O)c3)c3c(=O)n(CC#Cc4cnn(C)c4)cnc32)c(Cl)cn1] |
| I-458 | 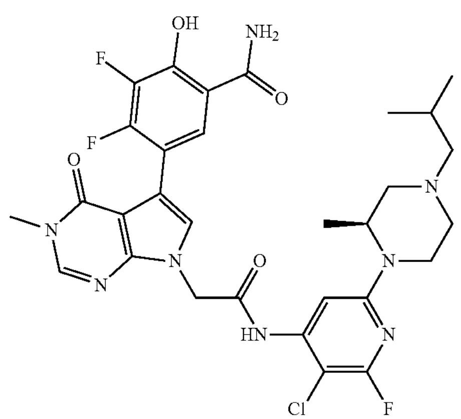 [SMILES: CC(C)CN1CCN(c2cc(NC(=O)Cn3cc(-c4cc(C(N)=O)c(O)c(F)c4F)c4c(=O)n(C)cnc43)c(Cl)c(F)n2)[C@@H](C)C1] |
| I-459 | 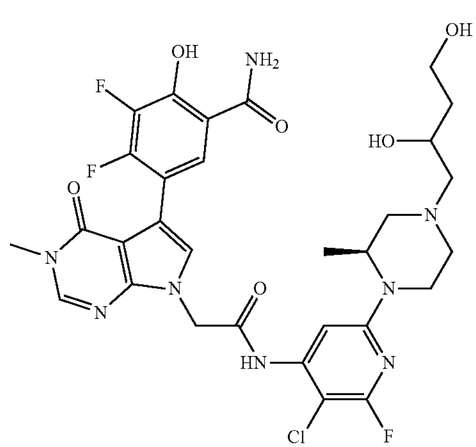 [SMILES: C[C@H]1CN(CC(O)CCO)CCN1c1cc(NC(=O)Cn2cc(-c3cc(C(N)=O)c(O)c(F)c3F)c3c(=O)n(C)cnc32)c(Cl)c(F)n1] |

| Compound | Structure |
|---|---|
| I-460 | 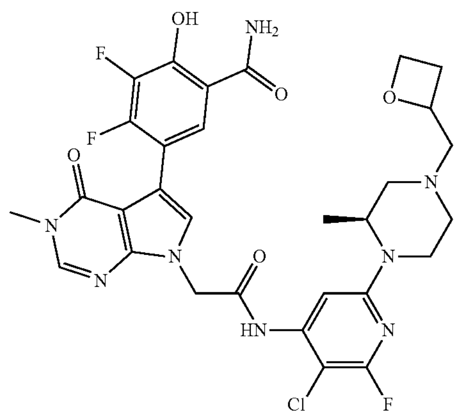 [SMILES: C[C@H]1CN(CC2CCO2)CCN1c1cc(NC(=O)Cn2cc(-c3cc(C(N)=O)c(O)c(F)c3F)c3c(=O)n(C)cnc32)c(Cl)c(F)n1] |
| I-461 | 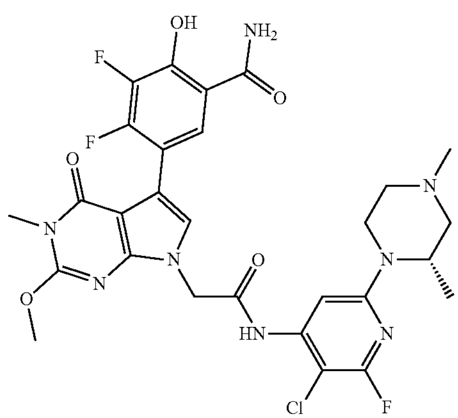 |
| I-462 | 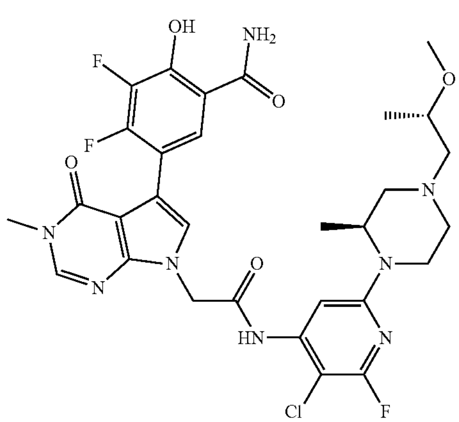 [SMILES: CO[C@@H](C)CN1CCN(c2cc(NC(=O)Cn3cc(-c4cc(C(N)=O)c(O)c(F)c4F)c4c(=O)n(C)cnc43)c(Cl)c(F)n2)[C@@H](C)C1] |

-continued
| Compound | Structure |
|---|---|
| I-463 | 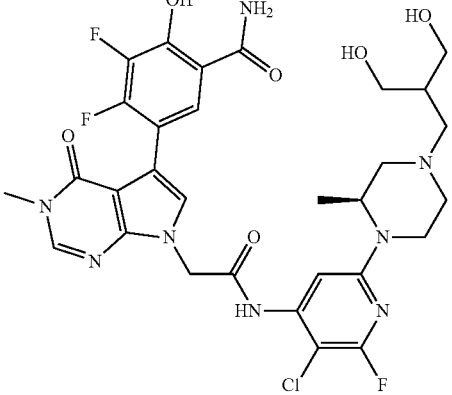 |
| I-464 | 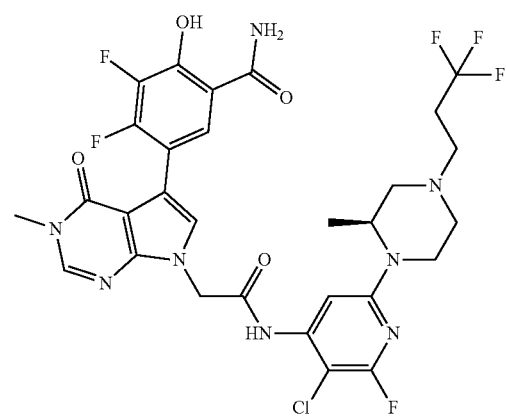 [SMILES: C[C@H]1CN(CCC(F)(F)F)CCN1c1cc(NC(=O)Cn2cc(-c3cc(C(N)=O)c(O)c(F)c3F)c3c(=O)n(C)cnc32)c(Cl)c(F)n1] |
| I-465 | 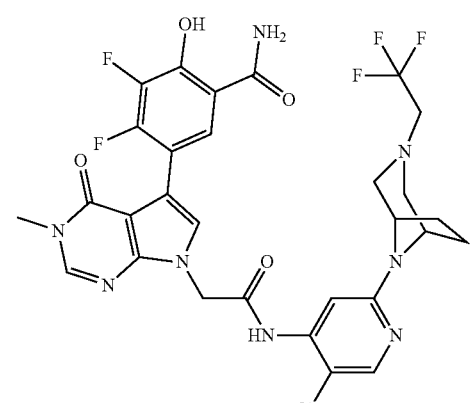 |

| Compound | Structure |
|---|---|
| I-466 | 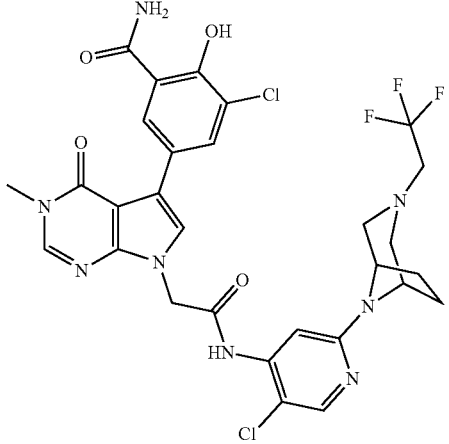 [SMILES: Cn1cnc2c(c(-c3cc(Cl)c(O)c(C(N)=O)c3)cn2CC(=O)Nc2cc(N3C4CCC3CN(CC(F)(F)F)C4)ncc2Cl)c1=O] |
| I-467 | 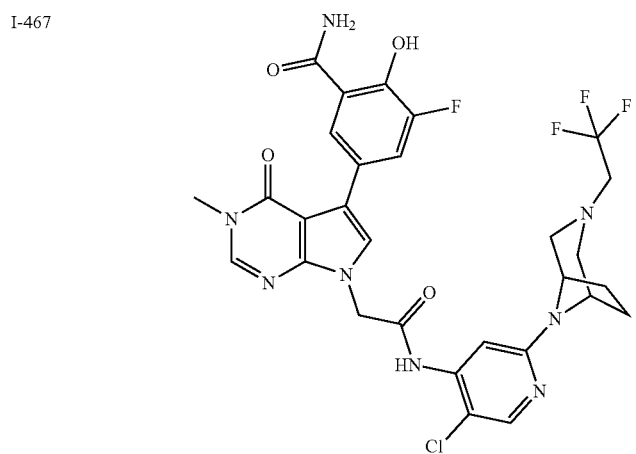 |
| I-468 | 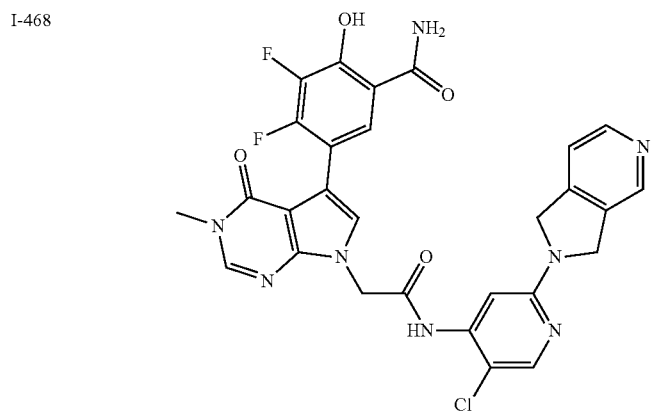 |

| Compound | Structure |
|---|---|
| I-469 | 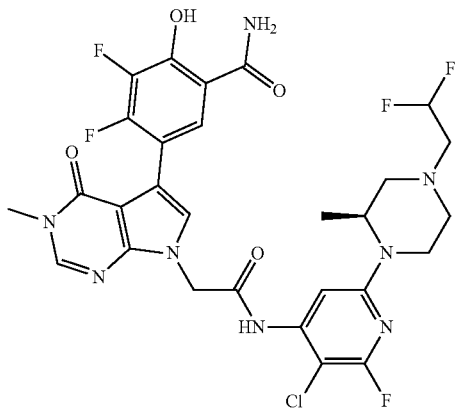 [SMILES: C[C@H]1CN(CC(F)F)CCN1c1cc(NC(=O)Cn2cc(-c3cc(C(N)=O)c(O)c(F)c3F)c3c(=O)n(C)cnc32)c(Cl)c(F)n1] |
| I-470 | 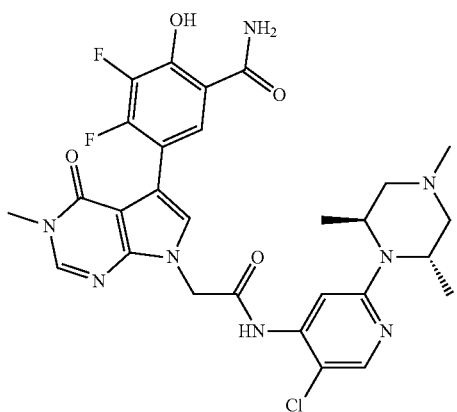 |
| I-471 | 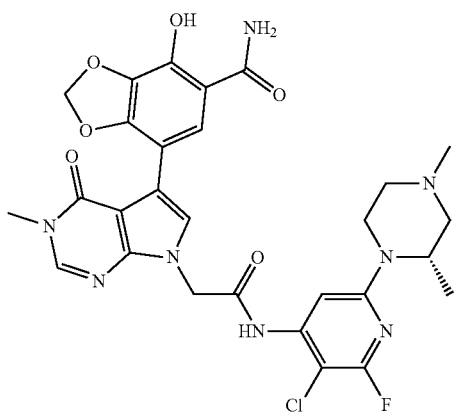 |

| Compound | Structure |
|---|---|
| I-472 | 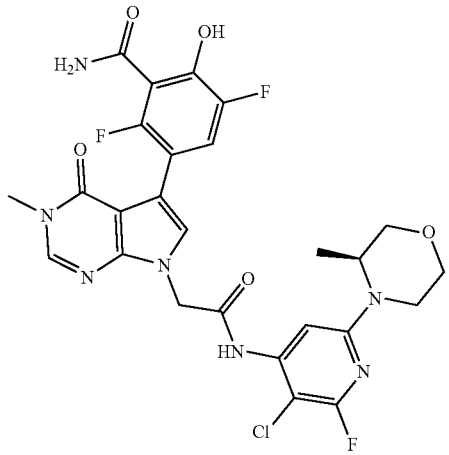 [SMILES: C[C@H]1COCCN1c1cc(NC(=O)Cn2cc(-c3cc(F)c(O)c(C(N)=O)c3F)c3c(=O)n(C)cnc32)c(Cl)c(F)n1] |
| I-473 | 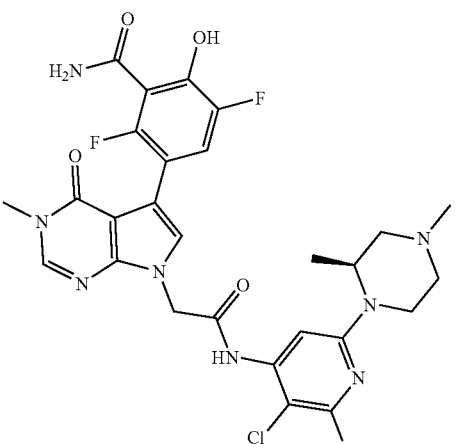 |
| I-474 | 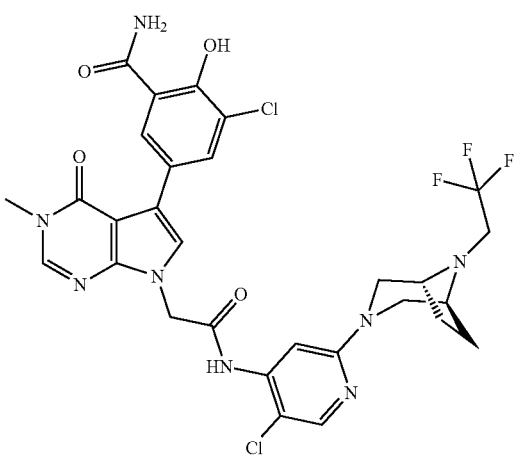 [SMILES: Cn1cnc2c(c(-c3cc(Cl)c(O)c(C(N)=O)c3)cn2CC(=O)Nc2cc(N3C[C@H]4CC[C@@H](C3)N4CC(F)(F)F)ncc2Cl)c1=O] |

| Compound | Structure |
|---|---|
| I-475 | 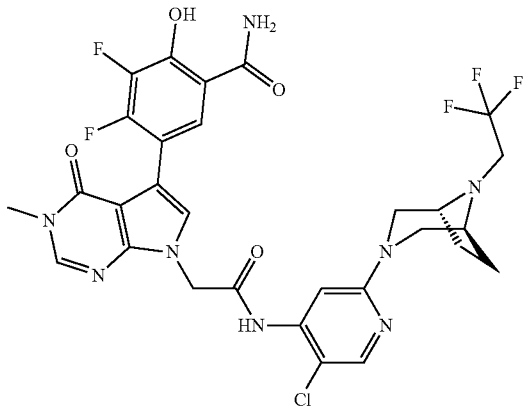 [SMILES: Cn1cnc2c(c(-c3cc(C(N)=O)c(O)c(F)c3F)cn2CC(=O)Nc2cc(N3C[C@H]4CC[C@@H](C3)N4CC(F)(F)F)ncc2Cl)c1=O] |
| I-476 | 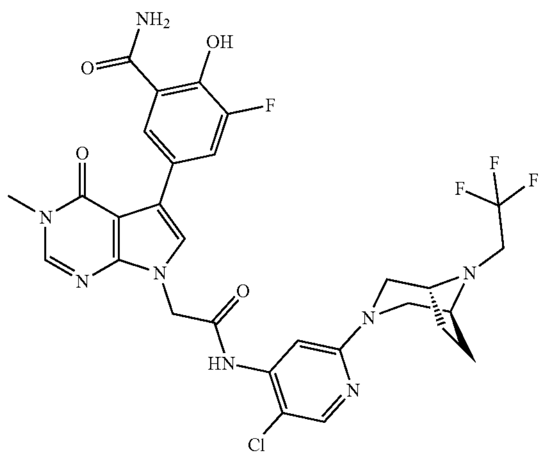 [SMILES: Cn1cnc2c(c(-c3cc(F)c(O)c(C(N)=O)c3)cn2CC(=O)Nc2cc(N3C[C@H]4CC[C@@H](C3)N4CC(F)(F)F)ncc2Cl)c1=O] |
| I-477 | 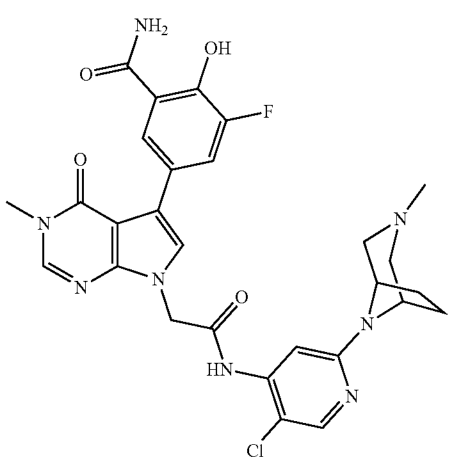 [SMILES: CN1CC2CCC(C1)N2c1cc(NC(=O)Cn2cc(-c3cc(F)c(O)c(C(N)=O)c3)c3c(=O)n(C)cnc32)c(Cl)cn1] |

| Compound | Structure |
|---|---|
| I-478 | 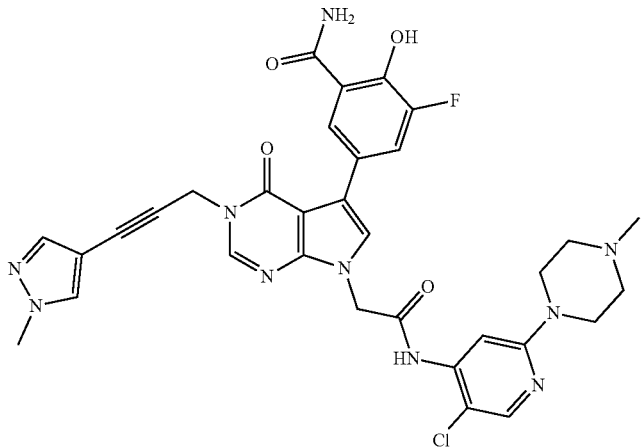 [SMILES: CN1CCN(c2cc(NC(=O)Cn3cc(-c4cc(F)c(O)c(C(N)=O)c4)c4c(=O)n(CC#Cc5cnn(C)c5)cnc43)c(Cl)cn2)CC1] |
| I-479 | 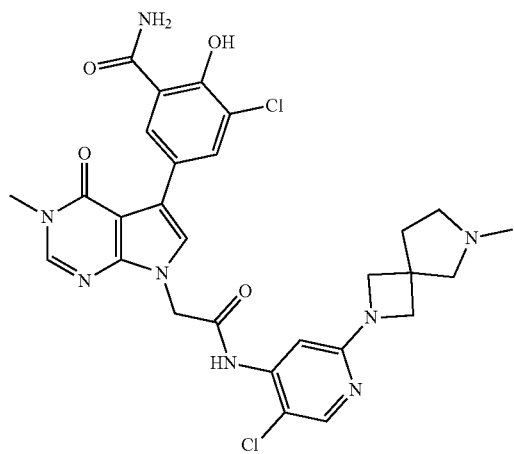 |
| I-480 | 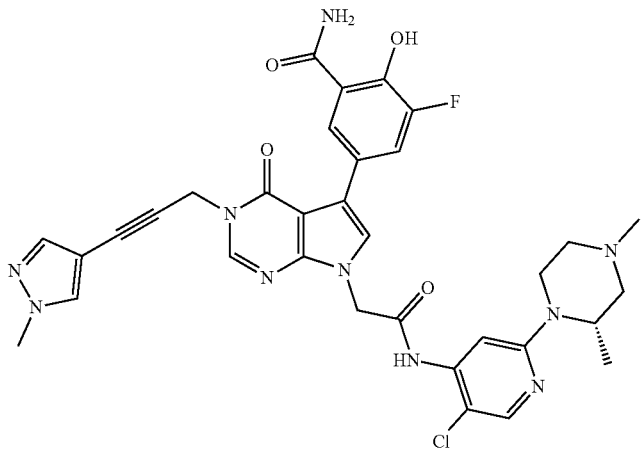 [SMILES: C[C@H]1CN(C)CCN1c1cc(NC(=O)Cn2cc(-c3cc(F)c(O)c(C(N)=O)c3)c3c(=O)n(CC#Cc4cnn(C)c4)cnc32)c(Cl)cn1] |

| Compound | Structure |
|---|---|
| I-481 | 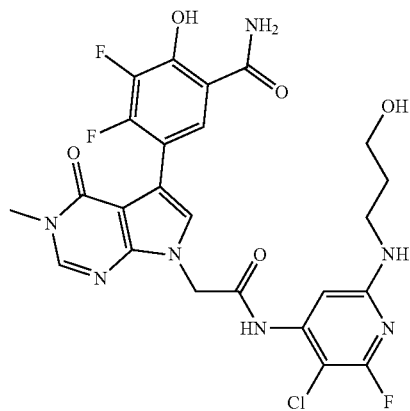 [SMILES: Cn1cnc2c(c(-c3cc(C(N)=O)c(O)c(F)c3F)cn2CC(=O)Nc2cc(NCCCO)nc(F)c2Cl)c1=O] |
| I-482 | 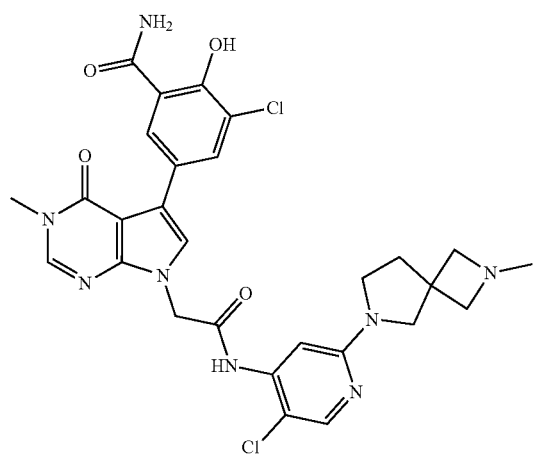 |
| I-483 | 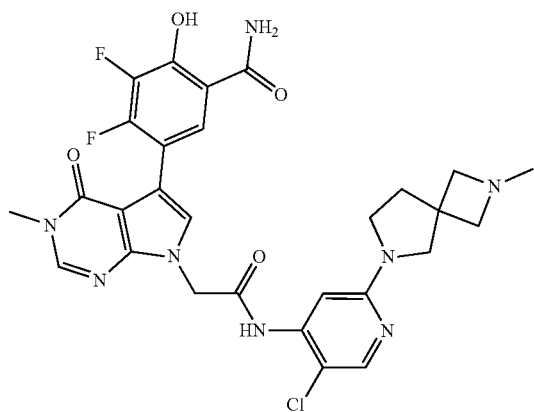 |

| Compound | Structure |
|---|---|
| I-484 | 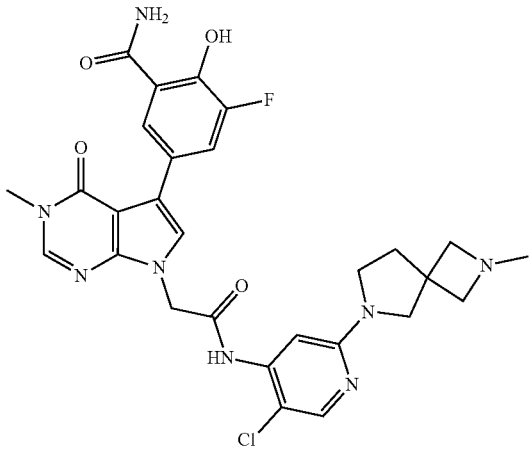 |
| I-485 | 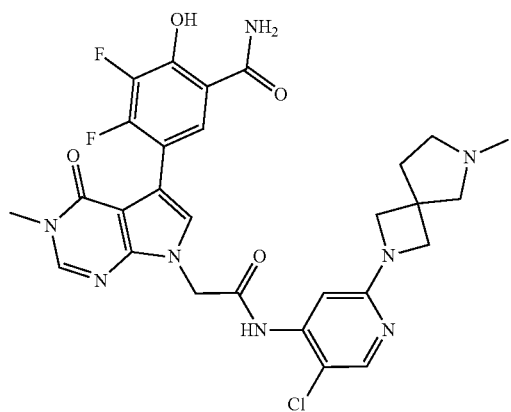 |
| I-486 | 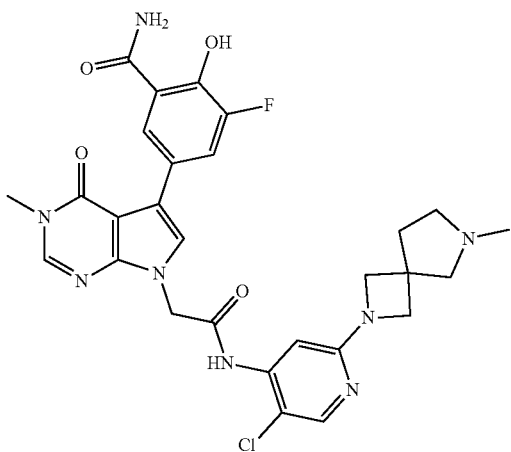 |

| Compound | Structure |
|---|---|
| I-487 | 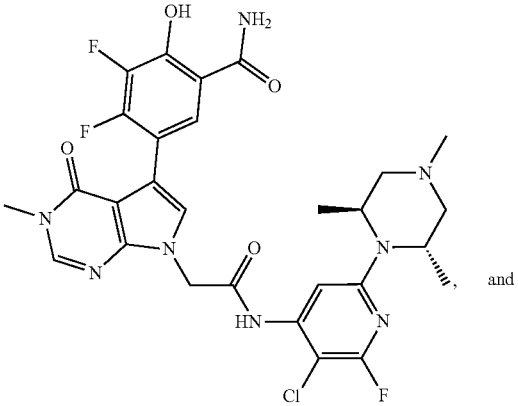 and |
| I-488 | 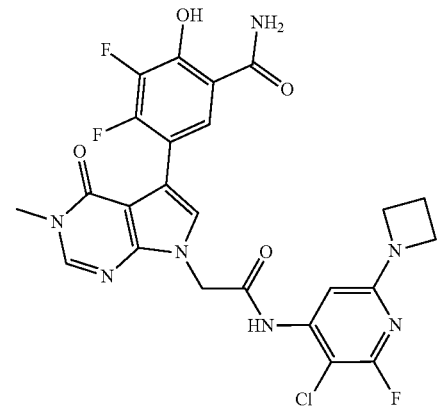 [SMILES: Cn1cnc2c(c(-c3cc(C(N)=O)c(O)c(F)c3F)cn2CC(=O)Nc2cc(N3CCC3)nc(F)c2Cl)c1=O] | or a pharmaceutically acceptable salt thereof.

14. A pharmaceutical composition comprising a pharmaceutically acceptable carrier and at least one compound of claim 1, or a pharmaceutically acceptable salt or stereoisomer thereof.

15. A method for treating lymphoma in a subject, wherein the method comprises administering to the subject in need thereof a therapeutically effective amount of at least one compound of claim 1, or a pharmaceutically acceptable salt or stereoisomer thereof.

16. The method of claim 15, wherein the lymphoma is selected from the group consisting of a B-cell lymphoma, a follicular lymphoma, and a non-Hodgkins lymphoma.

17. The method of claim 16, wherein the B-cell lymphoma is diffuse large B-cell lymphoma (DLBCL).

18. The method of claim 15, wherein the method further comprises administering to the subject in need thereof a therapeutically effective amount of at least one compound of claim 1, or a pharmaceutically acceptable salt or stereoisomer thereof, in combination with at least one additional lymphoma treatment.

* * * * *

UNITED STATES PATENT AND TRADEMARK OFFICE
CERTIFICATE OF CORRECTION

PATENT NO. : 11,518,764 B2
APPLICATION NO. : 16/960924
DATED : December 6, 2022
INVENTOR(S) : Rima Al-awar et al.

Page 1 of 6

It is certified that error appears in the above-identified patent and that said Letters Patent is hereby corrected as shown below:

In the Claims

Claim 1, Column 640, Line 9:
"$R_2$ is H, halo, C1-6 alkyl, $NH_2$, NH1-6..."
Should read:
"$R_2$ is H, halo, C1-6 alkyl, $NH_2$, NHC1-6...".

Claim 13, Column 749, compound I-161:

"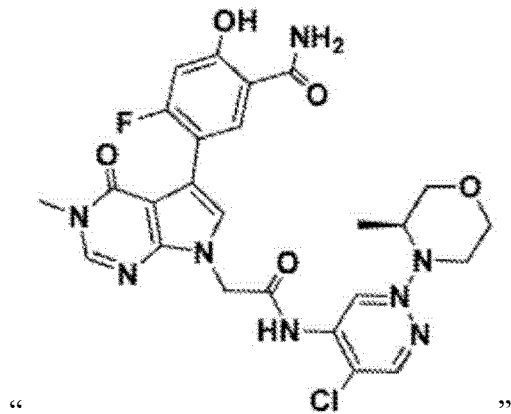"

Signed and Sealed this
Fourth Day of June, 2024

Katherine Kelly Vidal
*Director of the United States Patent and Trademark Office*

CERTIFICATE OF CORRECTION (continued)
U.S. Pat. No. 11,518,764 B2

Page 2 of 6

Should read:

I-161

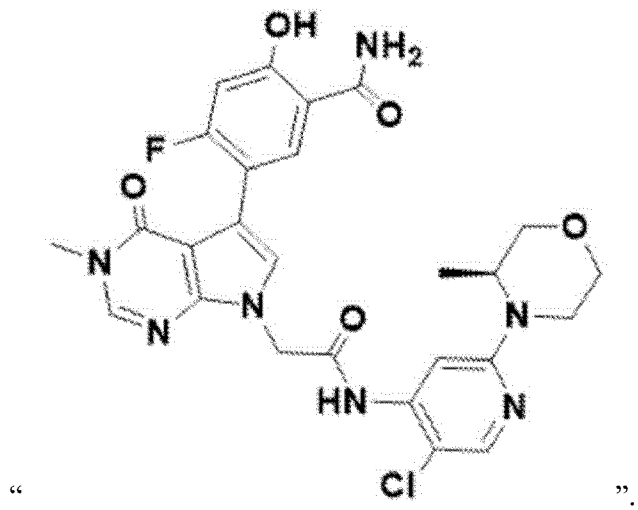

"                                                    ".

Claim 13, Column 813, compound I-258:

I-258

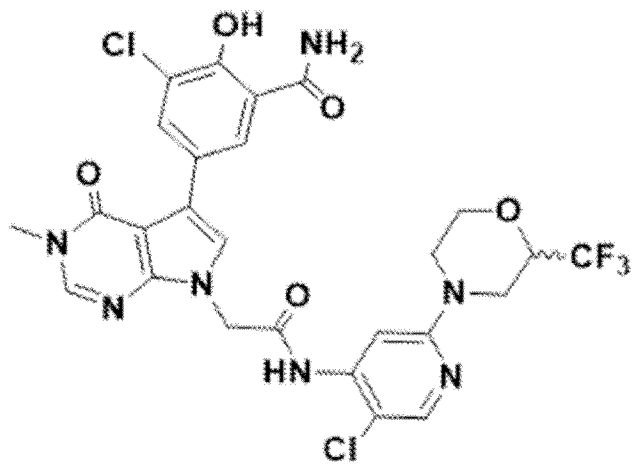

"            Enantiomer                  "

CERTIFICATE OF CORRECTION (continued)
U.S. Pat. No. 11,518,764 B2

Should read:

I-258

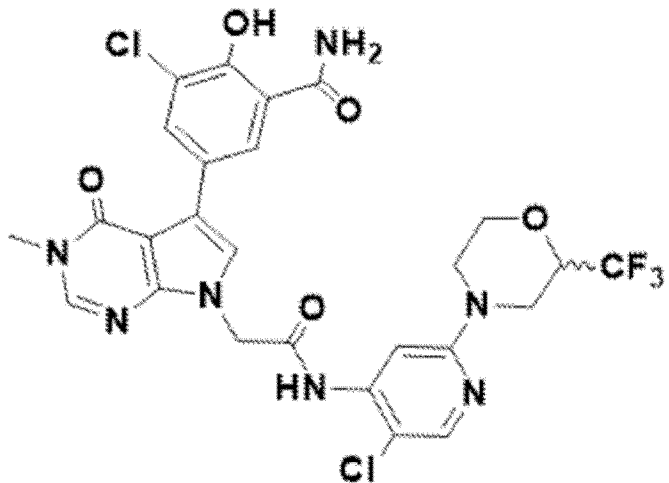

" Enantiomer 2 ".

Claim 13, Column 883, compound I-362:

I-362

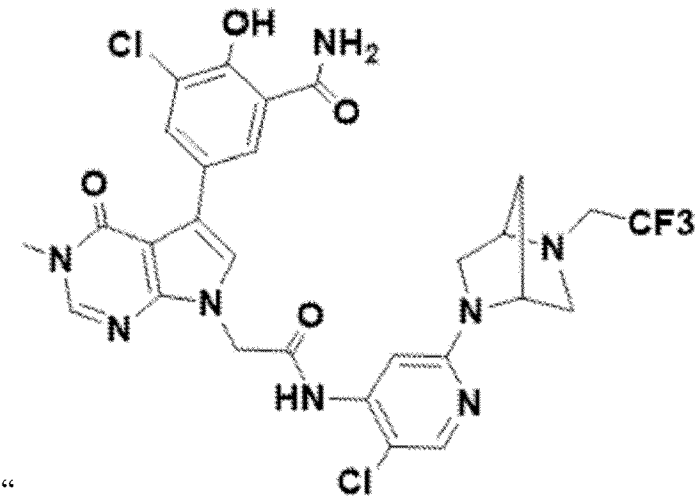

" "

CERTIFICATE OF CORRECTION (continued)
U.S. Pat. No. 11,518,764 B2

Should read:

I-362

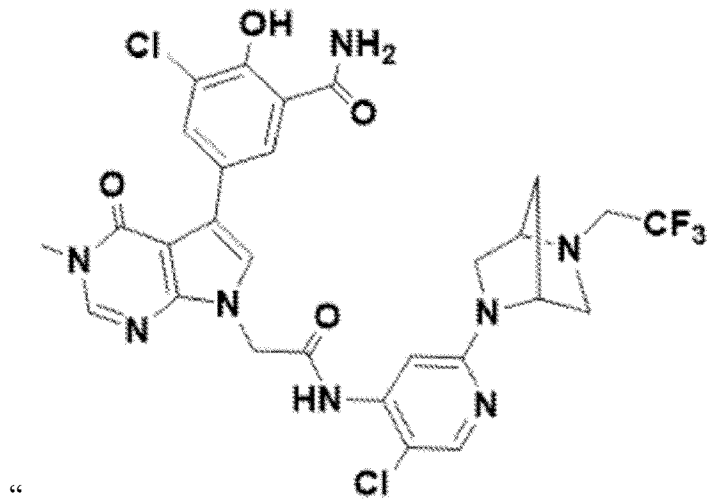

"                    ".

Claim 13, Column 883, compound I-363:

I-363

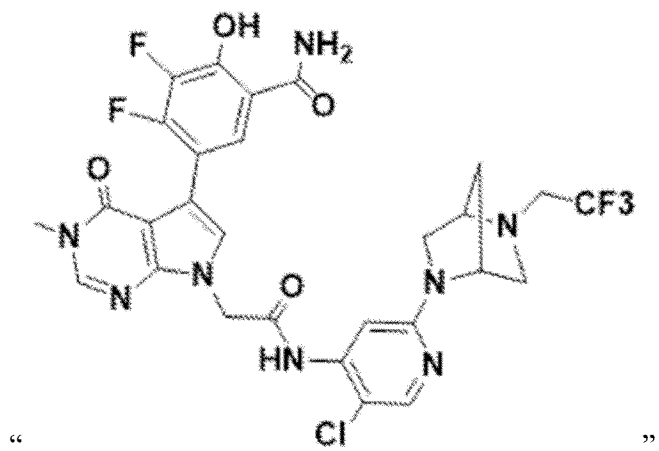

"                    "

Should read:
I-363
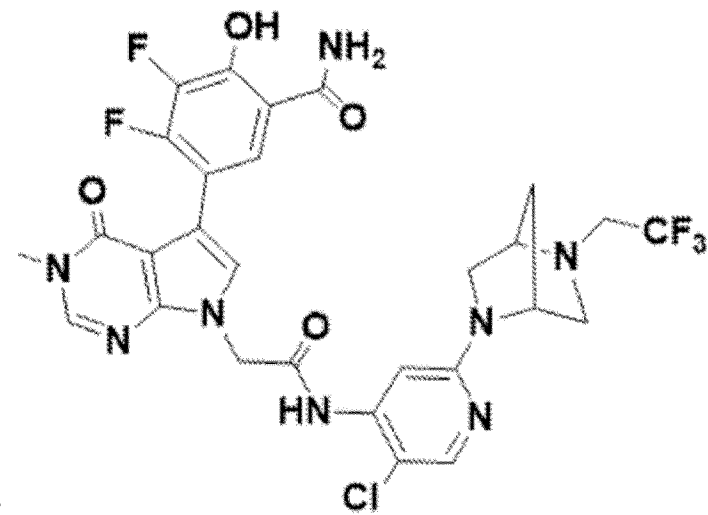
"          ".
Claim 13, Column 893, compound I-377:
I-377
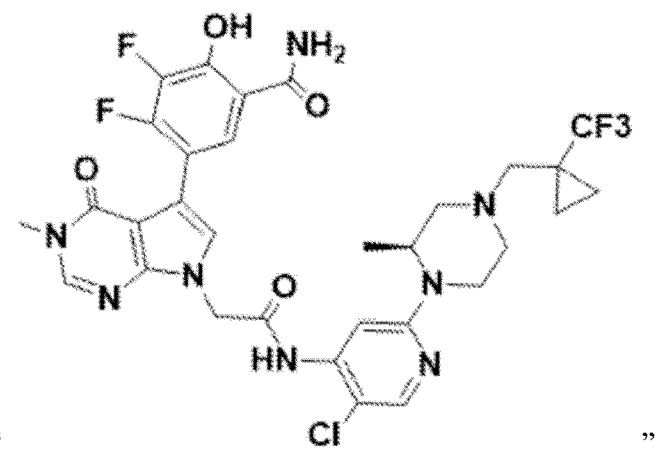
"          "

CERTIFICATE OF CORRECTION (continued)
U.S. Pat. No. 11,518,764 B2

Should read:

I-377

"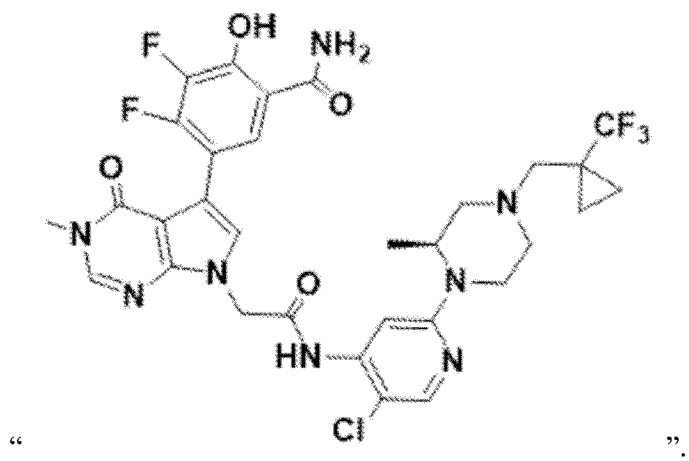".